US011655235B2

(12) United States Patent
Dong et al.

(10) Patent No.: US 11,655,235 B2
(45) Date of Patent: May 23, 2023

(54) PYRROLIDINE AND PIPERIDINE COMPOUNDS

(71) Applicant: YUHAN CORPORATION, Seoul (KR)

(72) Inventors: Tae Han Dong, Yongin-si (KR); Yoo Hoi Park, Suwon-si (KR); Tae Kyun Kim, Hwaseong-si (KR); Jae Eun Joo, Yongin-si (KR); Eun Hye Jung, Yongin-si (KR); Jae Won Jeong, Hwaseong-si (KR); Hyun Seung Lee, Yongin-si (KR); Do Hoon Kim, Yongin-si (KR); Ji Eun Yang, Yongin-si (KR); Jun Chui Park, Yongin-si (KR); Sang Myoun Lim, Seoul (KR); Na Ry Ha, Seoul (KR); Da In Chung, Seoul (KR); Ji Yeong Gal, Suwon-si (KR)

(73) Assignee: YUHAN CORPORATION, Seoul (KR)

( * ) Notice: Subject to any disclaimer, the term of this patent is extended or adjusted under 35 U.S.C. 154(b) by 134 days.

(21) Appl. No.: 17/090,552

(22) Filed: Nov. 5, 2020

(65) Prior Publication Data

US 2021/0147386 A1 May 20, 2021

Related U.S. Application Data

(60) Provisional application No. 62/931,554, filed on Nov. 6, 2019.

(51) Int. Cl.
| | | |
|---|---|---|
| *A61P 1/16* | (2006.01) | |
| *A61P 35/00* | (2006.01) | |
| *C07D 207/16* | (2006.01) | |
| *C07D 401/14* | (2006.01) | |
| *C07D 403/14* | (2006.01) | |
| *C07D 405/14* | (2006.01) | |
| *C07D 409/14* | (2006.01) | |
| *C07D 413/14* | (2006.01) | |
| *C07D 471/04* | (2006.01) | |
| *C07D 491/048* | (2006.01) | |
| *C07D 495/04* | (2006.01) | |
| *A61K 31/4545* | (2006.01) | |
| *A61K 31/4709* | (2006.01) | |
| *A61K 31/5377* | (2006.01) | |
| *A61K 31/4725* | (2006.01) | |
| *A61K 31/519* | (2006.01) | |
| *A61K 31/423* | (2006.01) | |
| *A61K 31/517* | (2006.01) | |
| *A61K 31/4365* | (2006.01) | |
| *A61K 31/4025* | (2006.01) | |
| *A61K 31/4355* | (2006.01) | |

(52) U.S. Cl.
CPC ........ *C07D 401/14* (2013.01); *C07D 207/16* (2013.01); *C07D 403/14* (2013.01); *C07D 405/14* (2013.01); *C07D 409/14* (2013.01); *C07D 413/14* (2013.01); *C07D 471/04* (2013.01); *C07D 491/048* (2013.01); *C07D 495/04* (2013.01); *A61K 31/4025* (2013.01); *A61K 31/423* (2013.01); *A61K 31/4355* (2013.01); *A61K 31/4365* (2013.01); *A61K 31/4545* (2013.01); *A61K 31/4709* (2013.01); *A61K 31/4725* (2013.01); *A61K 31/517* (2013.01); *A61K 31/519* (2013.01); *A61K 31/5377* (2013.01); *A61P 1/16* (2018.01); *A61P 35/00* (2018.01)

(58) Field of Classification Search
None
See application file for complete search history.

(56) References Cited

U.S. PATENT DOCUMENTS

| | | |
|---|---|---|
| 6,924,285 B2 | 8/2005 | Himmelsbach et al. |
| 7,115,634 B2 | 10/2006 | Thurieau et al. |
| 7,205,323 B2 | 4/2007 | Thomas et al. |
| 7,456,189 B2 | 11/2008 | Himmelsbach et al. |
| 7,524,844 B2 | 4/2009 | Thomas et al. |
| 7,538,128 B2 | 5/2009 | Thomas et al. |
| 7,858,789 B2 | 12/2010 | Thurieau et al. |
| 8,110,574 B2 | 2/2012 | Thurieau et al. |
| 8,183,280 B2 | 5/2012 | Evans et al. |
| 8,299,055 B2 | 10/2012 | Kaneko et al. |
| 9,000,175 B2 | 4/2015 | Thotapally et al. |
| 9,340,554 B2 | 5/2016 | Romero et al. |

(Continued)

FOREIGN PATENT DOCUMENTS

| | | |
|---|---|---|
| CN | 101284810 | 10/2008 |
| CN | 101284810 A * | 10/2008 |

(Continued)

OTHER PUBLICATIONS

Chen et al. CN 108689905 A English machine translation [online] Retrieved from <https://worldwide.espacenet.com> [downloaded on Aug. 5, 2022]. (Year: 2022).*

(Continued)

*Primary Examiner* — Amanda L. Aguirre
(74) *Attorney, Agent, or Firm* — Sheppard Mullin Richter & Hampton LLP

(57) ABSTRACT

The present technology provides pyrrolidine and piperidine compounds or pharmaceutically acceptable salts thereof, preparation processes thereof, pharmaceutical compositions comprising the same, and uses thereof. In particular, said compounds may be usefully applied in the treatment and prevention of FAP-mediated diseases.

28 Claims, No Drawings

(56) References Cited

U.S. PATENT DOCUMENTS

| | | |
|---|---|---|
| 9,434,722 B2 | 9/2016 | Griffioen et al. |
| 9,598,398 B2 | 3/2017 | Koike et al. |
| 10,118,904 B2 | 11/2018 | Davies et al. |
| 2009/0182140 A1* | 7/2009 | Furukubo ............ C07D 239/95 544/254 |

FOREIGN PATENT DOCUMENTS

| | | | |
|---|---|---|---|
| CN | 101337920 | | 1/2009 |
| CN | 108689905 A | * | 10/2018 ........... C07D 207/16 |
| EP | 1 667 992 B1 | | 1/2007 |
| EP | 1 492 536 B1 | | 5/2012 |
| EP | 2 366 699 B1 | | 8/2013 |
| EP | 3 190 109 B1 | | 2/2020 |
| EP | 3 265 456 B1 | | 11/2020 |
| WO | WO-2017/172802 A1 | | 10/2017 |
| WO | WO-2018/109202 A1 | | 6/2018 |
| WO | WO-2018/154133 A1 | | 8/2018 |

OTHER PUBLICATIONS

International Search Report and Written Opinion for International Application No. PCT/IB2020/060436 dated Feb. 15, 2021. 17 pages.

Jansen et al., Extended structure-activity relationship and pharmacokinetic investigation of (4-quinolinoyl)glycyl-2-cyanopyrrolidine inhibitors of fibroblast activation protein (FAP). Journal of Medicinal Chemistry 2014, 57, pp. 3053-3074.

Villhauer et al., 1-[[(3-Hydroxy-1-adamantyl)amino]acetyl]-2-cyano-(S)-pyrrolidine: A Potent, Selective, and Orally Bioavailable Dipeptidyl Peptidase IV Inhibitor with Antihyperglycemic Properties. Journal of Medicinal Chemistry 2003, vol. 46, No. 13, pp. 2774-2789.

Yeh et al., (2S,4S)-1-[2-(1,1-Dimethyl-3-oxo-3-pyrrolidin-1-yl-propylamino)acetyl]-4-fluoro-pyrrolidine-2-carbonitrile: A potent, selective, and orally bioavailable dipeptide-derived inhibitor of dipeptidyl peptidase IV. Bioorganic & Medicinal Chemistry Letters 2010, vol. 20, No. 12, pp. 3596-3600.

* cited by examiner

PYRROLIDINE AND PIPERIDINE COMPOUNDS

CROSS-REFERENCE TO RELATED APPLICATIONS

This application claims the benefit under 35 U.S.C. § 119(e) of U.S. Provisional Application No. 62/931,554, filed Nov. 6, 2019.

FIELD

The present technology relates to pyrrolidine and piperidine compounds, stereoisomers, and pharmaceutically acceptable salts thereof having inhibitory activity on fibroblast activation protein (FAP). Processes for the preparation, pharmaceutical compositions, and methods of use are also provided.

BACKGROUND

The fibroblast activation protein (FAP) is a homodimeric type II integral membrane serine protease belonging to the dipeptidyl peptidase-4 (dipeptidyl peptidase IV, DPP4) group. This protein group includes other subtype proteins such as DPP7, 8, 9, etc. FAP and DPP4 have about 50% amino acid sequence similarity. However, unlike DPP4 which is expressed in most biological tissues, FAP is expressed in tissue remodeling sites including, but not limited to, malignant tumor, fibrosis, atherosclerosis, and arthritis.

FAP, like DPP4, has dipeptidyl peptidase activities capable of cleaving the post-proline bond at two or more residues from the N-terminus but, unlike DPP4, FAP also has specific enzymatic activities of endopeptidase activities capable of cleaving the glycine-proline bond present in the substrate (Aertgeerts et al., J. Biol. Chem., 2005, 280, 19441). Moreover, FAP has collagenase activities capable of degrading gelatin and type 1 collagen (CN-1) (Fuming Zi et al., Molecular Medicine Reports, November 2015, 3203).

FAP is expressed where tissue remodeling is in progress, for example, liver fibrosis (Levy et al., Hepatol., 1999, 29:1768). It was found that patients suffering from fibrosis as a result of alcohol abuse or viral infection have a great quantity of FAP expressed in cells associated with excessive scarring and liver diseases. As an example, it was reported that the expression of FAP increases in activated hepatic stellate cells (hereinafter, "aHSC") and myofibroblasts, which play important roles in liver fibrosis or liver fibrosis (Levy et al., Hepatol., 1999, 29, 1768; Lay A J et al., Front. Biosci. [Landmark Ed] 2019, 24, 1-17).

The substrates degraded by FAP include a2-antiplasmin, Sprouty-2 protein, and gelatin and type 1 collagen (CN-1). Recently, it was reported that fibroblast growth factor-21 (FGF21) which is one of non-mitogenic hepatokines is also a substrate degraded by FAP (D. R. Dunshee et al., J. Biol. Chem., 2016, 291, 5986).

Accordingly, there is a need for FAP inhibitors, which may be usefully applied for the prophylaxis and treatment of diseases.

SUMMARY

Provided herein, in one aspect is a compound of Formula 1:

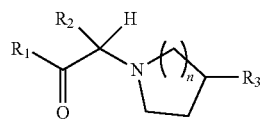

(Formula 1)

wherein
n is 1 or 2;
$R_1$ is selected from the group consisting of Formulas I, II, III, IV, and IV;

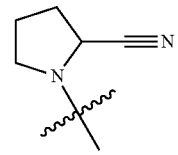

I

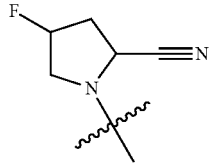

II

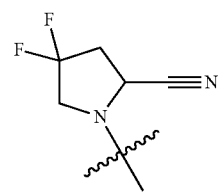

III

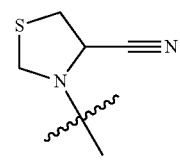

IV

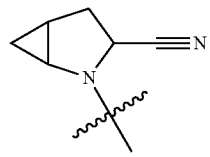

V $R_2$ is a hydrogen or a $C_{1-3}$alkyl;
$R_3$ is a 5- to 12-membered heteroaryl, wherein said heteroaryl contains 1 to 3 heteroatoms selected from O, N, and S and is optionally substituted by 1 to 3 Z,
 a 3- to 12-membered non-aromatic heterocycle, wherein said heterocycle contains 1 to 3 heteroatoms selected from O, N, and S and is optionally substituted by 1 to 3 Z,
 —$NR_4R_5$, —$OR_4$, —$C(O)NHR_4$, —$NHC(O)(CH_2)_mR_4$, —$NHS(O)_2R_4$, —$(CH_2)_mCH_2R_4$, or —$(CH_2)_mNHR_4$, wherein m is 0 or 1;

R$_4$ is a phenyl substituted with 1 to 3 Z,
a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl, wherein said heterocycle is optionally substituted with 1 to 3 Z,
a naphthyl optionally substituted with 1 to 3 Z, or
a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z;

R$_5$ is a hydrogen or a C$_{1-3}$alkyl; and each Z is independently selected from the group consisting of hydroxy, amino, halogen, cyano, nitro, carboxylic acid, C$_{1-5}$alkyl optionally substituted by 1 to 3 Z$^1$, C$_{2-6}$alkenyl optionally substituted by Z$^1$, C$_{2-6}$alkynyl optionally substituted by Z$^1$, C$_{1-5}$alkoxy optionally substituted by 1 to 3 Z$^1$, C$_{1-5}$alkylthio optionally substituted by Z$^1$, mono- or di-C$_{1-5}$alkylamino optionally substituted by Z$^1$, piperazinyl optionally substituted by Z$^1$, C$_{1-5}$alkylsulfonylamino optionally substituted by Z$^1$, C$_{1-5}$alkylcarbonylamino optionally substituted by Z$^1$, aminosulfonyl optionally substituted by Z$^1$, aminocarbonyl optionally substituted by Z$^1$, C$_{1-5}$alkylaminocarbonyl optionally substituted by Z$^1$, phenyl optionally substituted by Z$^1$, phenoxy optionally substituted by Z$^1$, benzyl optionally substituted by Z$^1$, benzoyl optionally substituted by Z$^1$, phenylaminocarbonyl optionally substituted by Z$^1$, pyrazolyl optionally substituted by Z$^1$, benzoxazolyl optionally substituted by Z$^1$, C$_{1-5}$ alkoxycarbonyl optionally substituted by Z$^1$, benzyloxy optionally substituted by Z$^1$, C$_{1-5}$ alkylsulfonyl optionally substituted by Z$^1$, acetyl, morpholinyl optionally substituted by Z$^1$, —NR$_6$C(O)R$_7$, and —C(O)NR$_6$R$_7$;

wherein each Z$^1$ is independently chosen from halogen, hydroxyl, amino, C$_{1-5}$alkylamino, cyano, acetyl, C$_{1-5}$ alkyl, C$_{1-5}$ haloalkyl, C$_{3-6}$ carbocycle, C$_{3-6}$ heterocycle, wherein said C$_{3-6}$ carbocycle and said C$_{3-6}$ heterocycle are optionally substituted with halogen, hydroxyl, C$_{1-5}$alkyl or C$_{1-5}$ haloalkyl;

R$_6$ is hydrogen or a C$_{1-3}$alkyl group;

R$_7$ is a C$_{1-3}$alkyl group optionally substituted with phenyl, a phenyl optionally substituted with 1 to 3 Z$^2$, or
a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z$^2$; and each Z$^2$ is independently selected from the group consisting of hydroxy, amino, halogen, cyano, nitro, hydroxycarbonyl, C$_{1-5}$alkyl optionally substituted by 1 to 3 Z$^3$, C$_{2-6}$alkenyl, C$_{2-6}$alkynyl, C$_{1-5}$alkoxy optionally substituted by 1 to 3 Z$^3$, C$_{1-5}$alkylthio, mono- or di-C$_{1-5}$alkylamino, piperazinyl optionally substituted by Z$^3$, C$_{1-5}$alkylsulfonylamino, C$_{1-5}$alkylcarbonylamino, aminosulfonyl, aminocarbonyl, C$_{1-5}$alkylaminocarbonyl, phenyl, phenoxy, benzyl, benzoyl, phenylaminocarbonyl, pyrazolyl, and benzoxazolyl;

wherein each Z$^3$ is independently chosen from halogen, amino, or acetyl;

or a stereoisomer or a mixture of stereoisomers, or a pharmaceutically acceptable salt thereof.

In some embodiments, R$_1$ is selected from the group consisting of compounds of Formulas I, II, III, and V:

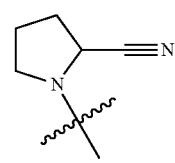

I

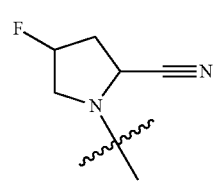

II

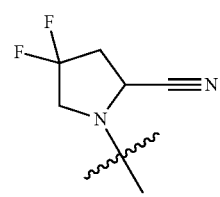

III

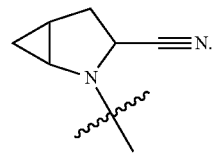

V

In some embodiments, R$_1$ is a compound of Formula I:

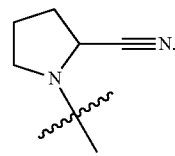

I

In some embodiments, R$_1$ is a compound of Formula II:

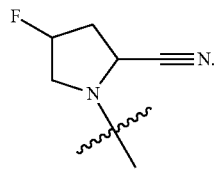

II

In some embodiments, $R_1$ is a compound of Formula III:

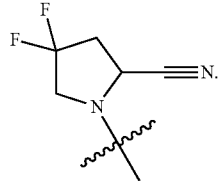

III

In some embodiments, $R_1$ is a compound of Formula IV:

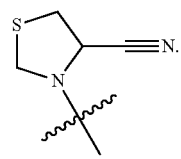

IV

In some embodiments, $R_1$ is a compound of Formula V:

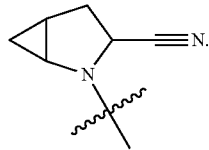

V

In some embodiments, $R_1$ is a substituent selected from the group consisting of compounds of Formulas Ia-Va,

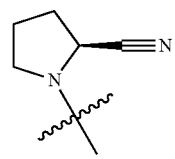

Ia

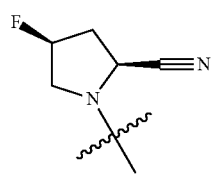

IIa

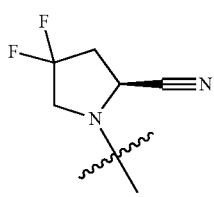

IIIa

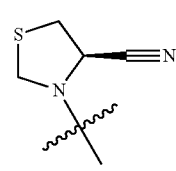

IVa

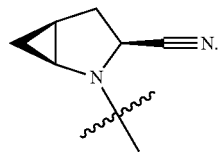

Va

In some embodiments, $R_1$ is a substituent selected from the group consisting of compounds of Formulas Ia, IIa, IIIa, and Va:

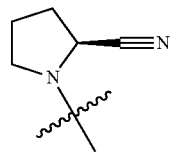

Ia

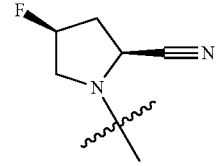

IIa

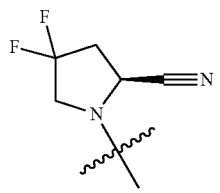

IIIa

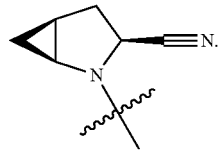

Va

In some embodiments, $R_1$ is a compound of Formula Ia:

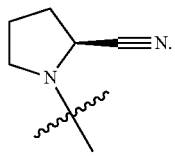

Ia

In some embodiments, $R_1$ is a compound of Formula IIa:

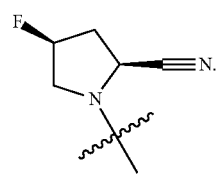

IIa

In some embodiments, R₁ is a compound of Formula IIIa:

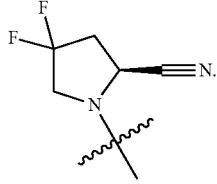

IIIa

In some embodiments, R₁ is a compound of Formula IVa:

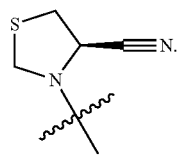

IVa

In some embodiments, R₁ is a compound of Formula Va:

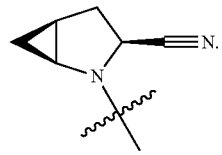

Va

In some embodiments, R₂ is hydrogen. In some embodiments, R₂ is a $C_{1-3}$alkyl.

In some embodiments, the compound, or its stereoisomer or mixture of stereoisomers, or its pharmaceutically acceptable salt has a structure of Formula 1a:

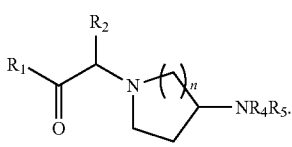

(Formula 1a)

In further embodiments, R₅ is hydrogen. In other embodiments, R₅ is a $C_{1-3}$alkyl.

In some embodiments, the compound, or its stereoisomer or mixture of stereoisomers, or its pharmaceutically acceptable salt has a structure of Formula 1b:

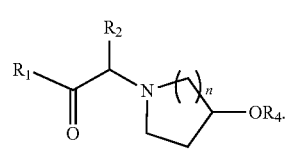

(Formula 1b)

In some embodiments, the compound, or its stereoisomer or mixture of stereoisomers, or its pharmaceutically acceptable salt has a structure of Formula 1c:

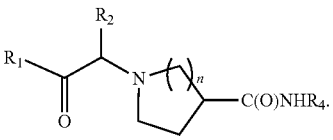

(Formula 1c)

In some embodiments, the compound, or its stereoisomer or mixture of stereoisomers, or its pharmaceutically acceptable salt has a structure of Formula 1d:

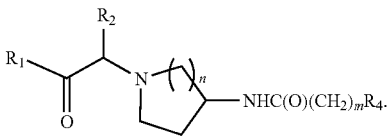

(Formula 1d)

In further embodiments, m is 0. In other embodiments, m is 1.

In some embodiments, the compound, or its stereoisomer or mixture of stereoisomers, or its pharmaceutically acceptable salt has a structure of Formula 1e:

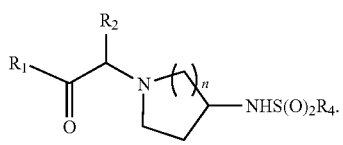

(Formula 1e)

In some embodiments, R₃ is a substituent selected from the group consisting of —NR₄R₅, —OR₄, —C(O)NHR₄, —NHC(O)(CH₂)ₘR₄, and —NHS(O)₂R₄. In some embodiments, R₃ is a substituent selected from the group consisting of —NR₄R₅, —OR₄, and —NHC(O)(CH₂)ₘR₄. In some embodiments, R₃ is a substituent selected from the group consisting of —NR₄R₅ and —OR₄.

In some embodiments, R₄ is a phenyl substituted with 1 to 3 Z, wherein each Z is independently selected from the group consisting of hydroxy, amino, halogen, cyano, nitro, carboxylic acid, $C_{1-5}$alkyl optionally substituted with 1 to 3 halogens or amino, $C_{2-6}$alkenyl, $C_{2-6}$alkynyl, $C_{1-5}$alkoxy, $C_{1-5}$alkylthio, mono- or di-$C_{1-5}$alkylamino, piperazinyl optionally substituted with acetyl, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl. In further embodiments, R₄ is a phenyl substituted with a substituent selected from the group consisting of piperazinyl optionally substituted with acetyl, phenyl, phenoxy, benzyl, benzoyl, phenylaminocarbonyl, pyrazolyl, and benzoxazolyl.

In some embodiments, R₄ is a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl, wherein said heterocycle is optionally substituted with 1 to 3 Z. In further embodiments, R₄ is a heterocycle selected from the group consisting of benzo[d][1,3]dioxolyl, 2,3-dihydrobenzofuranyl, 2-oxo-1,2-dihydroquinolinyl, and 2-oxo-1,2,3,4-tetrahydroquinolinyl.

In some embodiments, $R_4$ is a naphthyl optionally substituted with halogen.

In some embodiments, $R_4$ is a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —C(O)$NR_6R_7$. In further embodiments, $R_4$ is a heteroaryl selected from the group consisting of pyridinyl, quinolinyl, isoquinolinyl, chromenonyl, quinazolinyl, benzofuranyl, indolinyl, benzimidazolyl, benzothiophenyl, benzothiazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z, wherein each Z is independently selected from the group consisting of hydroxy, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, acetyl, morpholinyl, —$NR_6C(O)R_7$, —C(O)$NR_6R_7$, and phenyl optionally substituted with halogen; wherein $R_6$ is hydrogen or a $C_{1-3}$alkyl group; and $R_7$ is a $C_{1-3}$alkyl group optionally substituted with phenyl, a phenyl, or a heteroaryl selected from the group consisting of pyridinyl, pyrimidinyl, and isoxazolyl.

In some embodiments, $R_4$ is a phenyl substituted with a substituent selected from the group consisting of piperazinyl optionally substituted with acetyl, phenyl, phenoxy, benzyl, benzoyl, phenylaminocarbonyl, pyrazolyl, and benzoxazolyl;
a heterocycle selected from the group consisting of benzo[d][1,3]dioxolyl, 2,3-dihydrobenzofuranyl, 2-oxo-1,2-dihydroquinolinyl, and 2-oxo-1,2,3,4-tetrahydroquinolinyl;
a naphthyl optionally substituted with halogen; or
a heteroaryl selected from the group consisting of pyridinyl, quinolinyl, isoquinolinyl, chromenonyl, quinazolinyl, benzofuranyl, indolinyl, benzimidazolyl, benzothiophenyl, benzothiazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z, wherein each Z is independently selected from the group consisting of hydroxy, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, acetyl, morpholinyl, —$NR_6C(O)R_7$, —C(O)$NR_6R_7$, and phenyl optionally substituted with halogen; wherein $R_6$ is hydrogen or a $C_{1-3}$alkyl group; and $R_7$ is a $C_{1-3}$alkyl group optionally substituted with phenyl, a phenyl, or a heteroaryl selected from the group consisting of pyridinyl, pyrimidinyl, and isoxazolyl.

In some embodiments, $R_4$ is a phenyl substituted with phenyl; a naphthyl; or a heteroaryl selected from the group consisting of pyridinyl, quinolinyl, isoquinolinyl, chromenonyl, quinazolinyl, benzofuranyl, indolinyl, benzimidazolyl, benzothiophenyl, benzothiazolyl, furo[3,2-c]pyridinyl, and naphthyridinyl, wherein said heteroaryl is optionally substituted with 1 to 3 Z, wherein each Z is independently selected from the group consisting of hydroxy, cyano, nitro, halogen, $C_{1-5}$alkyl optionally substituted with 1 to 3 halogens, $C_{1-5}$alkoxy optionally substituted with 1 to 3 halogens, benzyloxy, acetyl, morpholinyl, —$NR_6C(O)R_7$, and —C(O)$NR_6R_7$. In further embodiments, $R_4$ is a phenyl substituted with phenyl. In other embodiments, $R_4$ is a naphthyl. In still other embodiments, $R_4$ is a heteroaryl selected from the group consisting of pyridinyl, quinolinyl, isoquinolinyl, chromenonyl, quinazolinyl, benzofuranyl, indolinyl, benzimidazolyl, benzothiophenyl, benzothiazolyl, furo[3,2-c]pyridinyl, and naphthyridinyl, wherein said heteroaryl is optionally substituted with 1 to 3 Z, wherein each Z is independently selected from the group consisting of hydroxy, cyano, nitro, halogen, $C_{1-5}$alkyl optionally substituted with 1 to 3 halogens, $C_{1-5}$alkoxy optionally substituted with 1 to 3 halogens, benzyloxy, acetyl, morpholinyl, —$NR_6C(O)R_7$, and —C(O)$NR_6R_7$; $R_6$ is hydrogen or a $C_{1-3}$alkyl group; and $R_7$ is a $C_{1-3}$alkyl group optionally substituted with phenyl, a phenyl, or a heteroaryl selected from the group consisting of pyridinyl, pyrimidinyl, and isoxazolyl. In further embodiments, $R_4$ is quinolinyl or isoquinolinyl, each of which is optionally substituted with 1 to 3 Z, wherein each Z is independently selected from the group consisting of hydroxy, cyano, nitro, halogen, $C_{1-5}$alkyl optionally substituted with 1 to 3 halogens, $C_{1-5}$alkoxy optionally substituted with 1 to 3 halogens, benzyloxy, acetyl, morpholinyl, —$NR_6C(O)R_7$, and —C(O)$NR_6R_7$. In still further embodiments, $R_4$ is quinolinyl, optionally substituted with 1 to 3 Z, wherein each Z is independently selected from the group consisting of hydroxy, cyano, nitro, halogen, $C_{1-5}$alkyl optionally substituted with 1 to 3 halogens, $C_{1-5}$alkoxy optionally substituted with 1 to 3 halogens, benzyloxy, acetyl, morpholinyl, —$NR_6C(O)R_7$, and —C(O)$NR_6R_7$. In other embodiments, $R_4$ is benzofuranyl, benzothiophenyl, or furo[3,2-c]pyridinyl, each of which is optionally substituted with 1 to 3 Z, wherein each Z is independently selected from the group consisting of halogen, $C_{1-5}$alkyl, and $C_{1-5}$alkoxy. In further embodiments, $R_4$ is benzofuranyl or benzothiophenyl, each of which is optionally substituted with 1 to 3 Z, wherein each Z is independently selected from the group consisting of halogen, $C_{1-5}$alkyl, and $C_{1-5}$alkoxy.

In some embodiments, $R_4$ is a phenyl substituted with a substituent selected from the group consisting of piperazinyl optionally substituted with acetyl, phenyl, phenoxy, benzyl, benzoyl, phenylaminocarbonyl, pyrazolyl, and benzoxazolyl;
a heterocycle selected from the group consisting of benzo[d][1,3]dioxolyl, 2,3-dihydrobenzofuranyl, 2-oxo-1,2-dihydroquinolinyl, and 2-oxo-1,2,3,4-tetrahydroquinolinyl;
a naphthyl optionally substituted with halogen; or
a heteroaryl selected from the group consisting of pyridinyl, quinolinyl, isoquinolinyl, quinazolinyl, thieno[2,3-d]pyrimidinyl, isoxazolyl, and acridinyl wherein said heteroaryl is optionally substituted with 1 to 3 Z, wherein each Z is independently selected from the group consisting of cyano, halogen, $C_{1-5}$alkyl optionally substituted with 1 to 3 halogens, $C_{1-5}$alkoxy optionally substituted with 1 to 3 halogens, benzyloxy, and phenyl optionally substituted with halogen. In further embodiments, $R_4$ is a phenyl substituted with a substituent selected from the group consisting of piperazinyl optionally substituted with acetyl, phenyl, phenoxy, benzyl, benzoyl, phenylaminocarbonyl, pyrazolyl, and benzoxazolyl. In other embodiments, $R_4$ is a heterocycle selected from the group consisting of benzo[d][1,3]dioxolyl, 2,3-dihydrobenzofuranyl, 2-oxo-1,2-dihydroquinolinyl, and 2-oxo-1,2,3,4-tetrahydroquinolinyl. In other embodiments, $R_4$ is a naphthyl optionally substituted with halogen. In other embodiments, $R_4$ is a heteroaryl selected from the group consisting of pyridinyl, quinolinyl, isoquinolinyl, quinazolinyl, thieno[2,3-d]pyrimidinyl, isoxazolyl, and acridinyl wherein said heteroaryl is optionally substituted with 1 to 3 Z, wherein each Z is independently selected from the group consisting of cyano, halogen, $C_{1-5}$alkyl optionally substituted with 1 to 3 halogens, $C_{1-5}$alkoxy optionally substituted with 1 to 3 halogens, benzyloxy, and phenyl optionally substituted with halogen. In further embodiments, $R_4$ is quinolinyl, isoquinolinyl, or quinazolinyl, each of which is optionally substituted with 1 to 3 Z, wherein each Z is independently selected from the group consisting of cyano, halogen, $C_{1-5}$alkyl optionally substituted with 1 to 3 halogens, and $C_{1-5}$alkoxy optionally substituted with 1 to 3 halogens.

In some embodiments, $R_4$ is quinolinyl.

In some embodiments, $R_4$ is a phenyl substituted with phenyl; a naphthyl; or a heteroaryl selected from the group consisting of quinolinyl, isoquinolinyl, benzofuranyl, and benzothiophenyl, wherein said heteroaryl is optionally substituted with 1 to 3 Z, wherein each Z is independently selected from the group consisting of hydroxy, halogen, $C_{1-5}$alkyl, and $C_{1-5}$alkoxy. In further embodiments, $R_4$ is a phenyl substituted with phenyl. In other embodiments, $R_4$ is a naphthyl. In other embodiments, $R_4$ is a heteroaryl selected from the group consisting of quinolinyl, isoquinolinyl, benzofuranyl, and benzothiophenyl, wherein said heteroaryl is optionally substituted with 1 to 3 Z, wherein each Z is independently selected from the group consisting of hydroxy, halogen, $C_{1-5}$alkyl, and $C_{1-5}$alkoxy. In further embodiments, $R_4$ is benzofuranyl, optionally substituted with 1 to 3 Z, wherein each Z is independently selected from the group consisting of hydroxy, halogen, $C_{1-5}$alkyl, and $C_{1-5}$alkoxy. In other embodiments, $R_4$ is quinolinyl or isoquinolinyl, each of which is optionally substituted with 1 to 3 Z, wherein each Z is independently selected from the group consisting of hydroxy, halogen, $C_{1-5}$alkyl, and $C_{1-5}$alkoxy.

In some embodiments, $R_4$ is benzofuranyl or benzothiophenyl.

In some embodiments, $R_3$ is a 3- to 12-membered non-aromatic heterocycle comprising nitrogen, wherein said heterocycle is optionally substituted by 1 to 3 Z. In some embodiments, $R_3$ is a 5- to 12-membered heteroaryl optionally substituted by 1 to 3 Z. In some embodiments, $R_3$ is 2-oxo-2,3-dihydro-1H-benzo[d]imidazol-1-yl.

In some embodiments, n is 1 or 2; $R_1$ is a substituent selected from the group consisting of compounds of Formulas I, II, III, and V; $R_2$ is hydrogen; $R_3$ is a substituent selected from the group consisting of —$NR_4R_5$, —$OR_4$, —$C(O)NHR_4$, —$NHC(O)(CH_2)_mR_4$, and —$NHS(O)_2R_4$; wherein m is 0 or 1; wherein $R_4$ is a phenyl substituted with a substituent selected from the group consisting of piperazinyl optionally substituted with acetyl, phenyl, phenoxy, benzyl, benzoyl, phenylaminocarbonyl, pyrazolyl, and benzoxazolyl; a heterocycle selected from the group consisting of benzo[d][1,3]dioxolyl, 2,3-dihydrobenzofuranyl, 2-oxo-1,2-dihydroquinolinyl, and 2-oxo-1,2,3,4-tetrahydroquinolinyl; a naphthyl optionally substituted with halogen; or a heteroaryl selected from the group consisting of pyridinyl, quinolinyl, isoquinolinyl, quinazolinyl, benzofuranyl, benzothiophenyl, furo[3,2-c]pyridinyl, thieno[2,3-d]pyrimidinyl, thieno[3,2-c]pyridinyl, isoxazolyl, and acridinyl, wherein said heteroaryl is optionally substituted with 1 to 3 Z, wherein each Z is independently selected from the group consisting of hydroxy, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, and phenyl optionally substituted with halogen; and $R_5$ is hydrogen.

In some embodiments, n is 1. In some embodiments, n is 2.

In some embodiments, the compound, or its stereoisomer or mixture of stereoisomers, or its pharmaceutically acceptable salt is selected from Table 1, or a stereoisomer or mixture of stereoisomers thereof, or a pharmaceutically acceptable salt thereof.

Provided herein, in another aspect, is a pharmaceutical composition comprising a compound described herein, or a stereoisomer or mixture of stereoisomers thereof, or a pharmaceutically acceptable salt thereof, and at least one pharmaceutically acceptable excipient.

Provided herein, in another aspect, is a method of inhibiting fibroblast activation protein in a mammal, comprising administering, to the mammal, a therapeutically effective amount of a compound, or its stereoisomer or mixture of stereoisomers, or its pharmaceutically acceptable salt described herein.

Provided herein, in another aspect, is a method of treating NASH in a subject in need thereof, the method comprising administering to the subject a therapeutically effective amount of a compound described herein, or a stereoisomer or mixture of stereoisomers thereof, or a pharmaceutically acceptable salt thereof, or a therapeutically effective amount of a pharmaceutical composition described herein.

Provided herein, in another aspect, is a use of a compound described herein, or a stereoisomer or mixture of stereoisomers thereof, or a pharmaceutically acceptable salt thereof, for the manufacture of a medicament for the treatment of NASH.

Provided herein, in another aspect, is a compound described herein, or a stereoisomer or mixture of stereoisomers thereof, or a pharmaceutically acceptable salt thereof, for use in treating NASH.

Provided herein, in another aspect, is a composition described herein for use in treating NASH.

Provided herein, in another aspect, is a compound described herein, or a stereoisomer or mixture of stereoisomers thereof, or a pharmaceutically acceptable salt thereof, for use in inhibiting fibroblast activation protein.

Provided herein, in another aspect, is a composition described herein for use in inhibiting fibroblast activation protein.

Provided herein, in another aspect, is a method of treating a disease mediated by fibroblast activation protein in a subject in need thereof, the method comprising administering to the subject a therapeutically effective amount of a compound described herein, or a stereoisomer or mixture of stereoisomers thereof, or a pharmaceutically acceptable salt thereof, or a therapeutically effective amount of a pharmaceutical composition described herein. In some embodiments, the disease mediated by fibroblast activation protein is selected from the group consisting of lipid and lipoprotein disorders, conditions and diseases which result from chronic fatty and fibrotic degeneration of organs due to accumulated lipid and specifically triglyceride accumulation and subsequent activation of profibrotic pathways, Type I or Type II Diabetes and clinical complications of Type I and Type II Diabetes, chronic intrahepatic or some forms of extrahepatic cholestatic conditions, liver fibrosis, acute intraheptic cholestatic conditions, obstructive or chronic inflammatory disorders that arise out of improper bile composition, gastrointestinal conditions with a reduced uptake of dietary fat and fat-soluble dietary vitamins, inflammatory bowel diseases, obesity and metabolic syndrome (combined conditions of dyslipidemia, diabetes and abnormally high body-mass index), persistent infections by intracellular bacteria or parasitic protozoae, non-malignant hyperproliferative disorders, malignant hyperproliferative disorders, colon adenocarcinoma and hepatocellular carcinoma in particular, liver steatosis and associated syndromes, Hepatitis B infection, Hepatitis C infection and/or of cholestatic and fibrotic effects that are associated with alcohol-induced cirrhosis or with viral-borne forms of hepatitis, liver failure or liver malfunction as an outcome of chronic liver diseases or of surgical liver resection, acute myocardial infarction, acute stroke, thrombosis which occurs as an endpoint of chronic obstructive atherosclerosis, osteoarthritis, rheumatoid arthritis, psoriasis, and cerebral infarction, individually or any combination thereof.

Provided herein, in another aspect, is a compound described herein, or a stereoisomer or mixture of stereoisomers thereof, or a pharmaceutically acceptable salt thereof, for use in treating a disease mediated by fibroblast activation protein. In some embodiments, the the disease mediated by fibroblast activation protein is selected from the group consisting of lipid and lipoprotein disorders, conditions and diseases which result from chronic fatty and fibrotic degeneration of organs due to accumulated lipid and specifically triglyceride accumulation and subsequent activation of pro-fibrotic pathways, Type I or Type II Diabetes and clinical complications of Type I and Type II Diabetes, chronic intrahepatic or some forms of extrahepatic cholestatic conditions, liver fibrosis, acute intraheptic cholestatic conditions, obstructive or chronic inflammatory disorders that arise out of improper bile composition, gastrointestinal conditions with a reduced uptake of dietary fat and fat-soluble dietary vitamins, inflammatory bowel diseases, obesity and metabolic syndrome (combined conditions of dyslipidemia, diabetes and abnormally high body-mass index), persistent infections by intracellular bacteria or parasitic protozoae, non-malignant hyperproliferative disorders, malignant hyperproliferative disorders, colon adenocarcinoma and hepatocellular carcinoma in particular, liver steatosis and associated syndromes, Hepatitis B infection, Hepatitis C infection and/or of cholestatic and fibrotic effects that are associated with alcohol-induced cirrhosis or with viral-borne forms of hepatitis, liver failure or liver malfunction as an outcome of chronic liver diseases or of surgical liver resection, acute myocardial infarction, acute stroke, thrombosis which occurs as an endpoint of chronic obstructive atherosclerosis, osteoarthritis, rheumatoid arthritis, psoriasis, and cerebral infarction, individually or any combination thereof.

Provided herein, in another aspect, is a method of treating cancer in a subject in need thereof, the method comprising administering to the subject a therapeutically effective amount of a compound described herein, or a stereoisomer or mixture of stereoisomers thereof, or a pharmaceutically acceptable salt thereof, or a therapeutically effective amount of a pharmaceutical composition described herein.

Provided herein, in another aspect, is a compound described herein, or a stereoisomer or mixture of stereoisomers thereof, or a pharmaceutically acceptable salt thereof, for use in treating cancer.

Provided herein, in another aspect, is a method of inhibiting degradation of fibroblast growth factor-21 in a subject, the method comprising administering, to the subject, a therapeutically effective amount of the compound, or its stereoisomer or mixture of stereoisomers, or its pharmaceutically acceptable salt described herein.

Provided herein, in another aspect, is a compound described herein, or a stereoisomer or mixture of stereoisomers thereof, or a pharmaceutically acceptable salt thereof, for use in inhibiting degradation of fibroblast growth factor-21.

Provided herein, in another aspect, is a method of preparing a compound of Formula 1a,

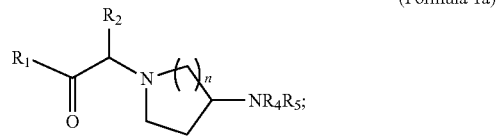

(Formula 1a)

or a stereoisomer or mixture of stereoisomers thereof, or a pharmaceutically acceptable salt thereof, the method comprising reacting a compound of Formula 2a with a compound of Formula 2aa under metal-mediated conditions to obtain a compound of Formula 3a:

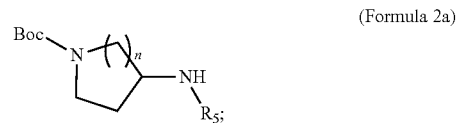

(Formula 2a)

$R_4X$            (Formula 2aa);

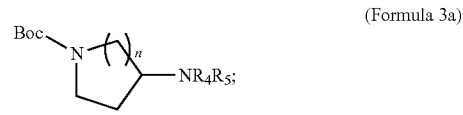

(Formula 3a)

removing Boc from the compound of Formula 3a under reaction conditions to obtain the compound of Formula 4a:

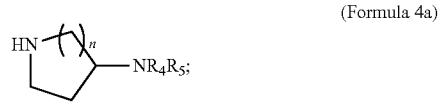

(Formula 4a)

and reacting the compound of Formula 4a with a compound of Formula 5 to obtain the compound of Formula 1a, or the isomer thereof, or the pharmaceutically acceptable salt thereof:

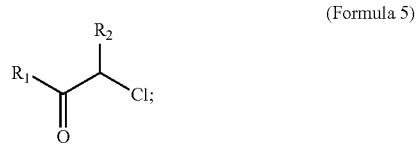

(Formula 5)

wherein n is 1 or 2,
wherein X is halogen,
wherein $R_1$ is a substituent selected from the group consisting of compounds of Formulas I-V,

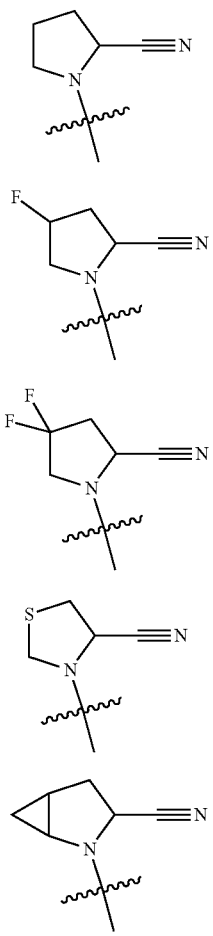

wherein $R_2$ is hydrogen or a $C_{1-3}$alkyl,
wherein $R_4$ is a phenyl substituted with 1 to 3 Z, wherein each Z is independently selected from the group consisting of hydroxy, amino, halogen, cyano, nitro, carboxylic acid, $C_{1-5}$alkyl optionally substituted with 1 to 3 halogens or amino, $C_{2-6}$alkenyl, $C_{2-6}$alkynyl, $C_{1-5}$alkoxy, $C_{1-5}$alkylthio, mono- or di-$C_{1-5}$alkylamino, piperazinyl optionally substituted with acetyl, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl;
a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl;
a naphthyl optionally substituted with halogen; or
a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$;
wherein $R_5$ is hydrogen or a $C_{1-3}$alkyl;
wherein $R_6$ is hydrogen or a $C_{1-3}$alkyl group; and
wherein $R_7$ is a $C_{1-3}$alkyl group optionally substituted with phenyl; a phenyl; or a heteroaryl selected from the group consisting of pyridinyl, pyrimidinyl, and isoxazolyl.

Provided herein, in another aspect, is a method of preparing a compound of Formula 1a,

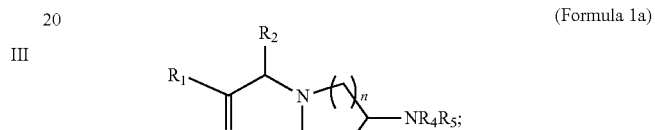

(Formula 1a)

or a stereoisomer or mixture of stereoisomers thereof, or a pharmaceutically acceptable salt thereof, the method comprising reacting a compound of Formula 2a with a compound of Formula 2aa under metal-mediated conditions to obtain a compound of Formula 3a:

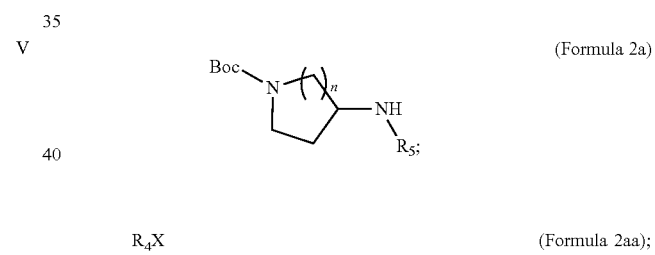

(Formula 2a)

$R_4X$ (Formula 2aa);

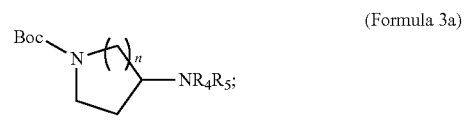

(Formula 3a)

removing Boc from the compound of Formula 3a under reaction conditions to obtain the compound of Formula 4a:

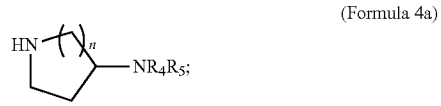

(Formula 4a)

and reacting the compound of Formula 4a with a compound of Formula 5 to obtain the compound of Formula 1a, or the isomer thereof, or the pharmaceutically acceptable salt thereof:

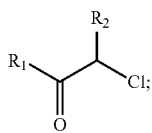

(Formula 5)

wherein n is 1 or 2,
wherein X is halogen,
wherein $R_1$ is a substituent selected from the group consisting of compounds of Formulas I-V,

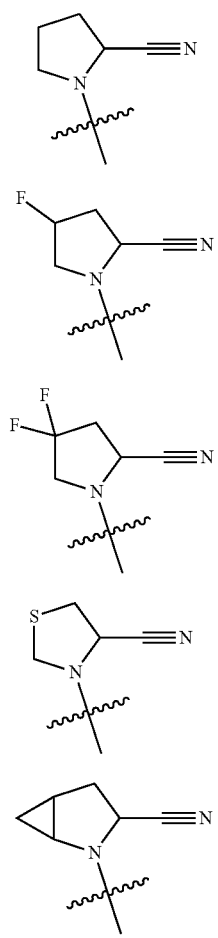

wherein $R_2$ is hydrogen or a $C_{1-3}$alkyl,
wherein $R_4$ is a phenyl substituted with 1 to 3 Z, wherein each Z is independently selected from the group consisting of hydroxy, amino, halogen, cyano, nitro, carboxylic acid, $C_{1-5}$alkyl optionally substituted with 1 to 3 halogens or amino, $C_{2-6}$alkenyl, $C_{2-6}$alkynyl, $C_{1-5}$alkoxy, $C_{1-5}$alkylthio, mono- or di-$C_{1-5}$alkylamino, piperazinyl optionally substituted with acetyl, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl;
a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl;
a naphthyl optionally substituted with halogen; or
a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, and acridinyl, wherein said heteroaryl is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy, $C_{1-5}$alkoxycarbonyl, benzyloxy, phenyl optionally substituted with halogen, acetyl, and $C_{1-5}$alkylsulfonyl, and
wherein $R_5$ is hydrogen or a $C_{1-3}$alkyl.

In some embodiments, the metal-mediated conditions comprise a palladium catalyst, a ligand, and base at a reaction temperature ranging from 50° C. to 150° C.

Provided herein, in another aspect, is a method of preparing a compound of Formula 1b,

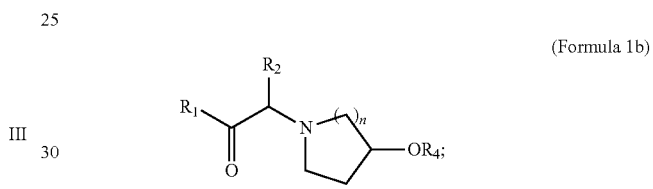

(Formula 1b)

or a stereoisomer or mixture of stereoisomers thereof, or a pharmaceutically acceptable salt thereof, the method comprising
reacting a compound of Formula 2b with a compound of Formula 2ba under Mitsunobu reaction conditions to obtain a compound of Formula 3b:

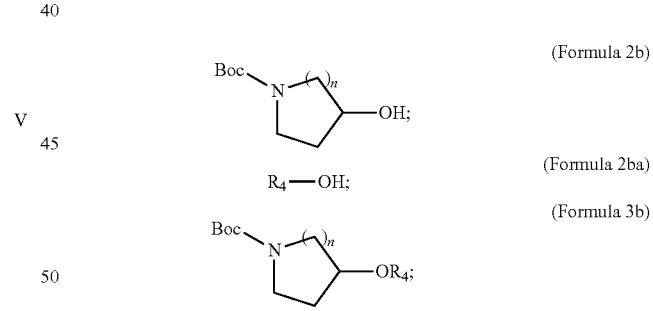

(Formula 2b)

(Formula 2ba)

(Formula 3b)

removing Boc from the compound of Formula 3b under reaction conditions to obtain the compound of Formula 4b:

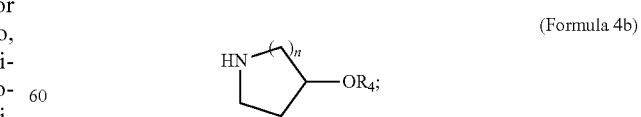

(Formula 4b)

and
reacting the compound of Formula 4b with a compound of Formula 5 to obtain the compound of Formula 1b, or the isomer thereof, or the pharmaceutically acceptable salt thereof:

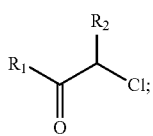

(Formula 5)

wherein n is 1 or 2, wherein $R_1$ is a substituent selected from the group consisting of compounds of Formulas I-V,

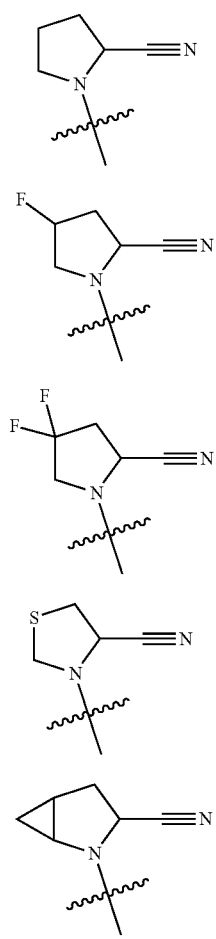

wherein $R_2$ is hydrogen or a $C_{1-3}$alkyl, and wherein $R_4$ is a phenyl substituted with 1 to 3 Z, wherein each Z is independently selected from the group consisting of hydroxy, amino, halogen, cyano, nitro, carboxylic acid, $C_{1-5}$alkyl optionally substituted with 1 to 3 halogens or amino, $C_{2-6}$alkenyl, $C_{2-6}$alkynyl, $C_{1-5}$alkoxy, $C_{1-5}$alkylthio, mono- or di-$C_{1-5}$alkylamino, piperazinyl optionally substituted with acetyl, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl;

a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl;

a naphthyl optionally substituted with halogen; or a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy, $C_{1-5}$alkoxycarbonyl, benzyloxy, phenyl optionally substituted with halogen, acetyl, $C_{1-5}$alkylsulfonyl, morpholinyl, $-NR_6C(O)R_7$, and $-C(O)NR_6R_7$;

wherein $R_6$ is hydrogen or a $C_{1-3}$alkyl group; and wherein $R_7$ is a $C_{1-3}$alkyl group optionally substituted with phenyl; a phenyl; or a heteroaryl selected from the group consisting of pyridinyl, pyrimidinyl, and isoxazolyl.

Provided herein, in another aspect, is a method of preparing a compound of Formula 1b,

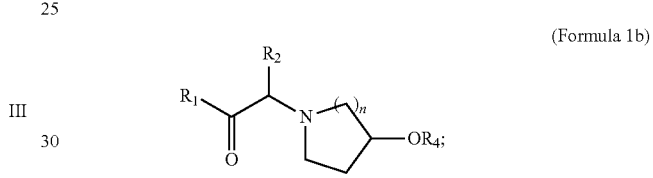

(Formula 1b)

or a stereoisomer or mixture of stereoisomers thereof, or a pharmaceutically acceptable salt thereof, the method comprising reacting a compound of Formula 2b with a compound of Formula 2ba under Mitsunobu reaction conditions to obtain a compound of Formula 3b:

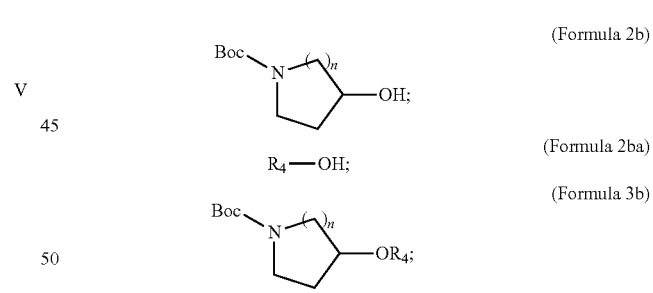

(Formula 2b)

(Formula 2ba)

(Formula 3b)

removing Boc from the compound of Formula 3b under reaction conditions to obtain the compound of Formula 4b:

(Formula 4b)

and reacting the compound of Formula 4b with a compound of Formula 5 to obtain the compound of Formula 1b, or the isomer thereof, or the pharmaceutically acceptable salt thereof:

(Formula 5)

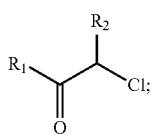

wherein n is 1 or 2, wherein $R_1$ is a substituent selected from the group consisting of compounds of Formulas I-V,

I

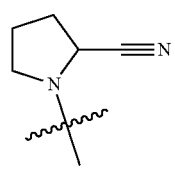

II

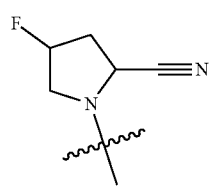

III

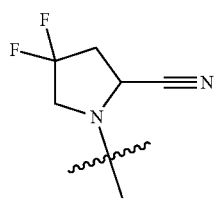

IV

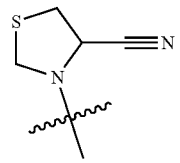

V

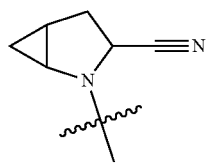

wherein $R_2$ is hydrogen or a $C_{1-3}$alkyl, and wherein $R_4$ is a phenyl substituted with 1 to 3 Z, wherein each Z is independently selected from the group consisting of hydroxy, amino, halogen, cyano, nitro, carboxylic acid, $C_{1-5}$alkyl optionally substituted with 1 to 3 halogens or amino, $C_{2-6}$alkenyl, $C_{2-6}$alkynyl, $C_{1-5}$alkoxy, $C_{1-5}$alkylthio, mono- or di-$C_{1-5}$alkylamino, piperazinyl optionally substituted with acetyl, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl;

a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl;

a naphthyl optionally substituted with halogen; or a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, and acridinyl, wherein said heteroaryl is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy, $C_{1-5}$alkoxycarbonyl, benzyloxy, phenyl optionally substituted with halogen, acetyl, and $C_{1-5}$alkylsulfonyl.

Provided herein, in another aspect, is a method of preparing a compound of Formula 1c, (Formula 1c)

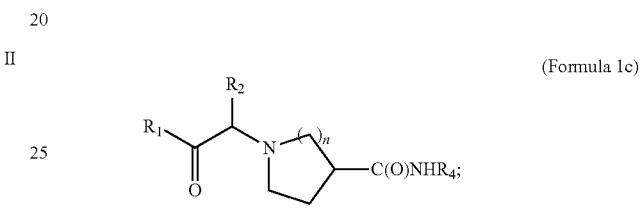

or a stereoisomer or mixture of stereoisomers thereof, or a pharmaceutically acceptable salt thereof, the method comprising reacting a compound of Formula 2c with a compound of Formula 2ca under amide coupling conditions to obtain a compound of Formula 3c:

(Formula 2c)

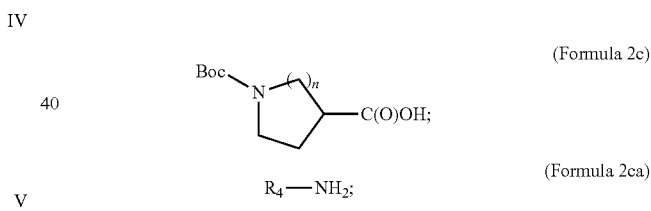

(Formula 2ca)

$R_4$—$NH_2$;

(Formula 3c)

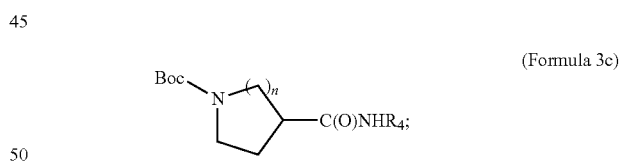

removing Boc from the compound of Formula 3c under reaction conditions to obtain the compound of Formula 4c:

(Formula 4c)

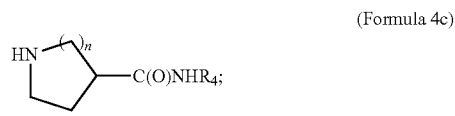

and reacting the compound of Formula 4c with a compound of Formula 5 to obtain the compound of Formula 1c, or the isomer thereof, or the pharmaceutically acceptable salt thereof:

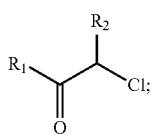
(Formula 5)

wherein n is 1 or 2, wherein $R_1$ is a substituent selected from the group consisting of compounds of Formulas I-V,

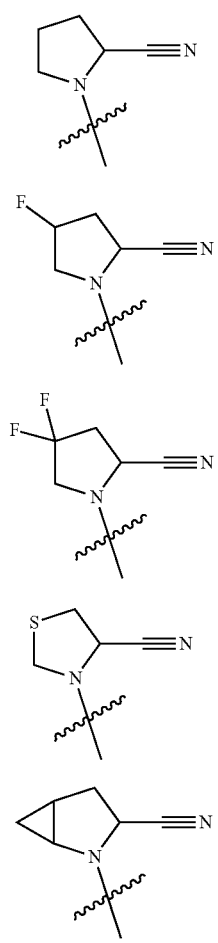

wherein $R_2$ is hydrogen or a $C_{1-3}$alkyl, and wherein $R_4$ is a phenyl substituted with 1 to 3 Z, wherein each Z is independently selected from the group consisting of hydroxy, amino, halogen, cyano, nitro, carboxylic acid, $C_{1-5}$alkyl optionally substituted with 1 to 3 halogens or amino, $C_{2-6}$alkenyl, $C_{2-6}$alkynyl, $C_{1-5}$alkoxy, $C_{1-5}$alkylthio, mono- or di-$C_{1-5}$alkylamino, piperazinyl optionally substituted with acetyl, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl;

a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl;

a naphthyl optionally substituted with halogen; or a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$;

wherein $R_6$ is hydrogen or a $C_{1-3}$alkyl group; and wherein $R_7$ is a $C_{1-3}$alkyl group optionally substituted with phenyl; a phenyl; or a heteroaryl selected from the group consisting of pyridinyl, pyrimidinyl, and isoxazolyl.

Provided herein, in another aspect, is a method of preparing a compound of Formula 1c,

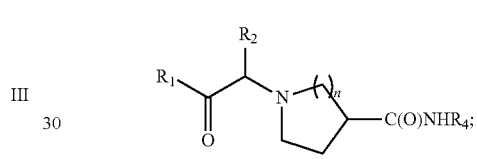
(Formula 1c)

or a stereoisomer or mixture of stereoisomers thereof, or a pharmaceutically acceptable salt thereof, the method comprising reacting a compound of Formula 2c with a compound of Formula 2ca under amide coupling conditions to obtain a compound of Formula 3c:

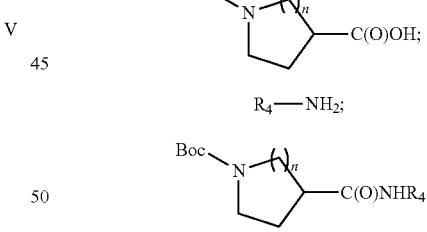

(Formula 2c)

(Formula 2ca)

(Formula 3c)

removing Boc from the compound of Formula 3c under reaction conditions to obtain the compound of Formula 4c:

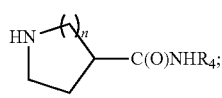
(Formula 4c)

and reacting the compound of Formula 4c with a compound of Formula 5 to obtain the compound of Formula 1c, or the isomer thereof, or the pharmaceutically acceptable salt thereof:

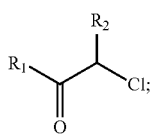
(Formula 5)

wherein n is 1 or 2, wherein $R_1$ is a substituent selected from the group consisting of compounds of Formulas I-V,

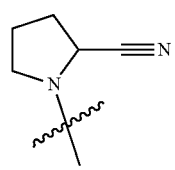
I

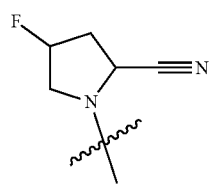
II

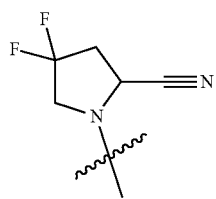
III

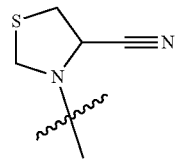
IV

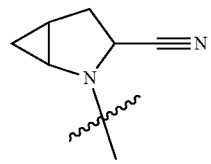
V wherein $R_2$ is hydrogen or a $C_{1-3}$alkyl, and wherein $R_4$ is a phenyl substituted with 1 to 3 Z, wherein each Z is independently selected from the group consisting of hydroxy, amino, halogen, cyano, nitro, carboxylic acid, $C_{1-5}$alkyl optionally substituted with 1 to 3 halogens or amino, $C_{2-6}$alkenyl, $C_{2-6}$alkynyl, $C_{1-5}$alkoxy, $C_{1-5}$alkylthio, mono- or di-$C_{1-5}$alkylamino, piperazinyl optionally substituted with acetyl, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl;

a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl;

a naphthyl optionally substituted with halogen; or a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, and acridinyl, wherein said heteroaryl is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy, $C_{1-5}$alkoxycarbonyl, benzyloxy, phenyl optionally substituted with halogen, acetyl, and $C_{1-5}$alkylsulfonyl.

Provided herein, in another aspect, is a method of preparing a compound of Formula 1d,

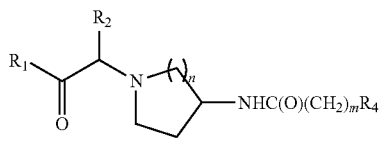
(Formula 1d)

or a stereoisomer or mixture of stereoisomers thereof, or a pharmaceutically acceptable salt thereof, the method comprising reacting a compound of Formula 5 with a compound of Formula 9 to obtain a compound of Formula 10:

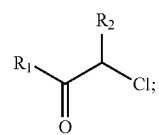
(Formula 5)

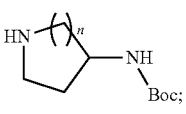
(Formula 9)

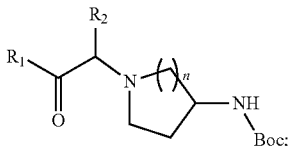
(Formula 10)

removing Boc from the compound of Formula 10 under reaction conditions to obtain the compound of Formula 11:

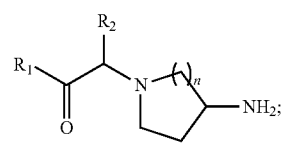
(Formula 11)

and reacting the compound of Formula 11 with a compound of Formula 11a to obtain the compound of Formula 1d, the isomer thereof, or the pharmaceutically acceptable salt thereof:

R₄—(CH₂)$_m$COOH    (Formula 11a);

wherein n is 1 or 2, wherein $R_1$ is a substituent selected from the group consisting of compounds of Formulas I-V,

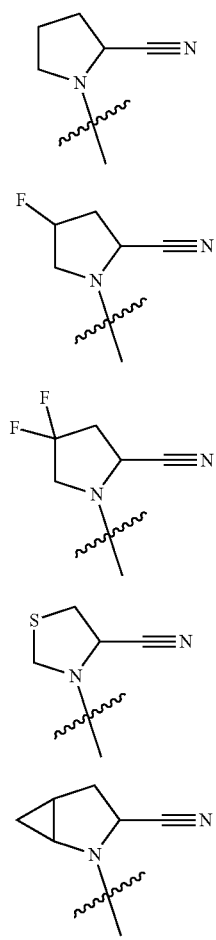

wherein $R_2$ is hydrogen or a $C_{1-3}$alkyl, wherein m is 0 or 1, and wherein $R_4$ is a phenyl substituted with 1 to 3 Z, wherein each Z is independently selected from the group consisting of hydroxy, amino, halogen, cyano, nitro, carboxylic acid, $C_{1-5}$alkyl optionally substituted with 1 to 3 halogens or amino, $C_{2-6}$alkenyl, $C_{2-6}$alkynyl, $C_{1-5}$alkoxy, $C_{1-5}$alkylthio, mono- or di-$C_{1-5}$alkylamino, piperazinyl optionally substituted with acetyl, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl;

a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl;

a naphthyl optionally substituted with halogen; or a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy, $C_{1-5}$alkoxycarbonyl, benzyloxy, phenyl optionally substituted with halogen, acetyl, $C_{1-5}$alkylsulfonyl, morpholinyl, —NR₆C(O)R₇, and —C(O)NR₆R₇;

wherein $R_6$ is hydrogen or a $C_{1-3}$alkyl group; and wherein $R_7$ is a $C_{1-3}$alkyl group optionally substituted with phenyl; a phenyl; or a heteroaryl selected from the group consisting of pyridinyl, pyrimidinyl, and isoxazolyl.

Provided herein, in another aspect, is a method of preparing a compound of Formula 1d,

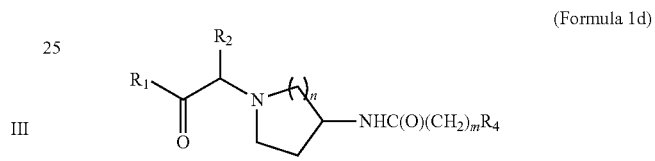
(Formula 1d)

or a stereoisomer or mixture of stereoisomers thereof, or a pharmaceutically acceptable salt thereof, the method comprising reacting a compound of Formula 5 with a compound of Formula 9 to obtain a compound of Formula 10:

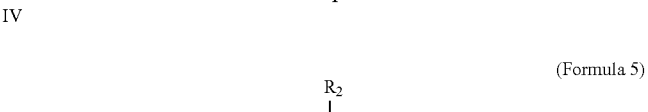
(Formula 5)

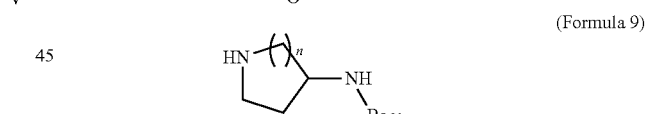
(Formula 9)

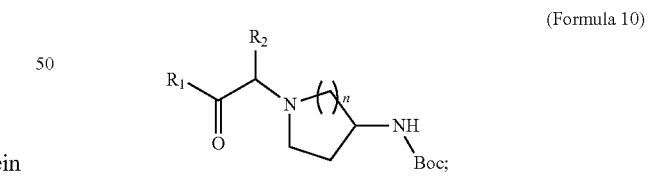
(Formula 10)

removing Boc from the compound of Formula 10 under reaction conditions to obtain the compound of Formula 11:

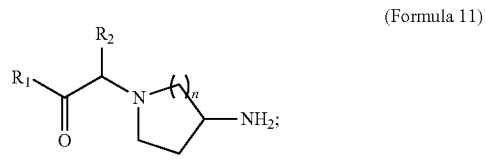
(Formula 11)

and reacting the compound of Formula 11 with a compound of Formula 11a to obtain the compound of Formula 1d, or the isomer thereof, or the pharmaceutically acceptable salt thereof:

R$_4$—(CH$_2$)$_m$COOH    (Formula 11a);

wherein n is 1 or 2, wherein R$_1$ is a substituent selected from the group consisting of compounds of Formulas I-V,

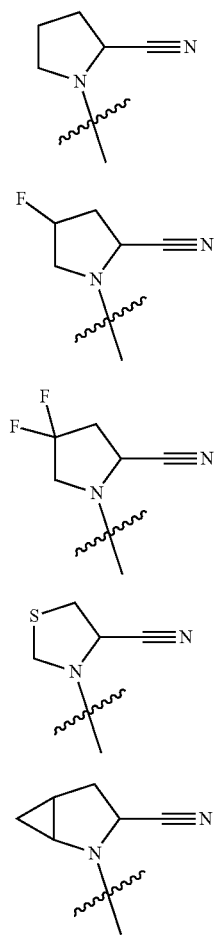

wherein R$_2$ is hydrogen or a C$_{1-3}$alkyl, wherein m is 0 or 1, and wherein R$_4$ is a phenyl substituted with 1 to 3 Z, wherein each Z is independently selected from the group consisting of hydroxy, amino, halogen, cyano, nitro, carboxylic acid, C$_{1-5}$alkyl optionally substituted with 1 to 3 halogens or amino, C$_{2-6}$alkenyl, C$_{2-6}$alkynyl, C$_{1-5}$alkoxy, C$_{1-5}$alkylthio, mono- or di-C$_{1-5}$alkylamino, piperazinyl optionally substituted with acetyl, C$_{1-5}$alkylsulfonylamino, C$_{1-5}$alkylcarbonylamino, aminosulfonyl, aminocarbonyl, C$_{1-5}$alkylaminocarbonyl, phenyl, phenoxy, benzyl, benzoyl, phenylaminocarbonyl, pyrazolyl, and benzoxazolyl;

a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl;

a naphthyl optionally substituted with halogen; or a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, and acridinyl, wherein said heteroaryl is optionally substituted with 1 to 3 Z, wherein each Z is independently selected from the group consisting of hydroxy, amino, di-C$_{1-5}$alkylamino, cyano, nitro, halogen, C$_{1-5}$alkyl optionally substituted with 1 to 3 halogens, C$_{1-5}$alkoxy, C$_{1-5}$alkoxycarbonyl, benzyloxy, phenyl optionally substituted with halogen, acetyl, and C$_{1-5}$alkylsulfonyl.

Provided herein, in another aspect, is a method of preparing a compound of Formula 1e,

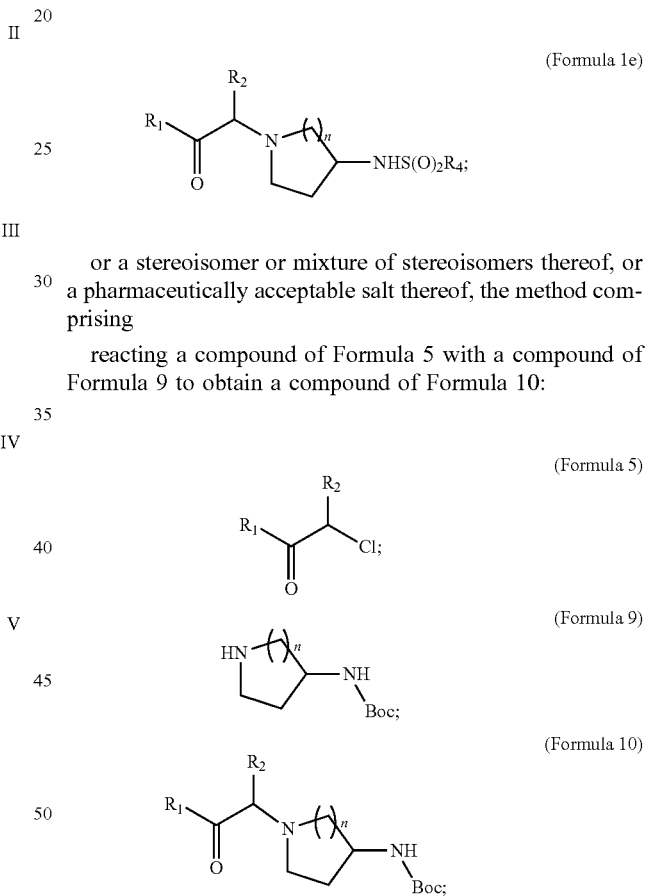

or a stereoisomer or mixture of stereoisomers thereof, or a pharmaceutically acceptable salt thereof, the method comprising reacting a compound of Formula 5 with a compound of Formula 9 to obtain a compound of Formula 10:

removing Boc from the compound of Formula 10 under reaction conditions to obtain the compound of Formula 11:

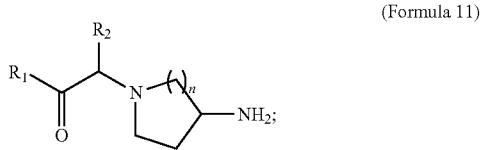

and reacting the compound of Formula 11 with a compound of Formula 11b to obtain the compound of Formula 1d, or the isomer thereof, or the pharmaceutically acceptable salt thereof:

R₄—S(O)₂Cl    (Formula 11b);

wherein n is 1 or 2, wherein R₁ is a substituent selected from the group consisting of compounds of Formulas I-V,

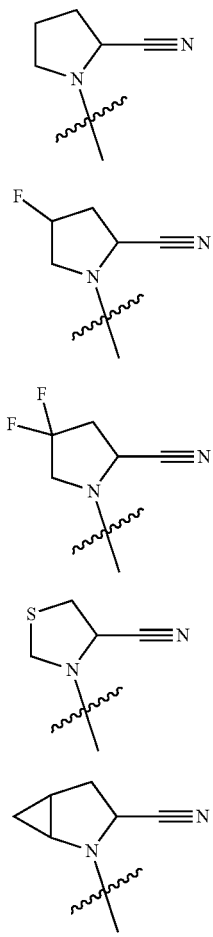

wherein R₂ is hydrogen or a $C_{1-3}$alkyl, and wherein R₄ is a phenyl substituted with 1 to 3 Z, wherein each Z is independently selected from the group consisting of hydroxy, amino, halogen, cyano, nitro, carboxylic acid, $C_{1-5}$alkyl optionally substituted with 1 to 3 halogens or amino, $C_{2-6}$alkenyl, $C_{2-6}$alkynyl, $C_{1-5}$alkoxy, $C_{1-5}$alkylthio, mono- or di-$C_{1-5}$alkylamino, piperazinyl optionally substituted with acetyl, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl;

a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl;

a naphthyl optionally substituted with halogen; or a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy, $C_{1-5}$alkoxycarbonyl, benzyloxy, phenyl optionally substituted with halogen, acetyl, $C_{1-5}$alkylsulfonyl, morpholinyl, —NR₆C(O)R₇, and —C(O)NR₆R₇;

wherein R₆ is hydrogen or a $C_{1-3}$alkyl group; and wherein R₇ is a $C_{1-3}$alkyl group optionally substituted with phenyl; a phenyl; or a heteroaryl selected from the group consisting of pyridinyl, pyrimidinyl, and isoxazolyl.

Provided herein, in another aspect, is a method of preparing a compound of Formula 1e,

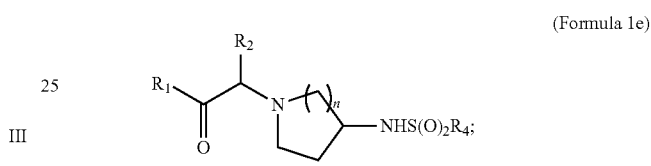
(Formula 1e)

or a stereoisomer or mixture of stereoisomers thereof, or a pharmaceutically acceptable salt thereof, the method comprising reacting a compound of Formula 5 with a compound of Formula 9 to obtain a compound of Formula 10:

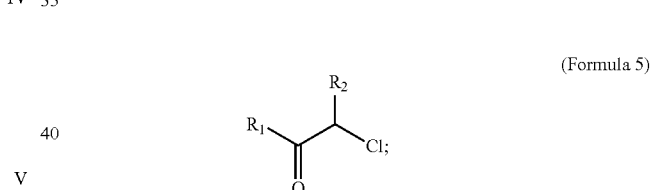
(Formula 5)

(Formula 9)

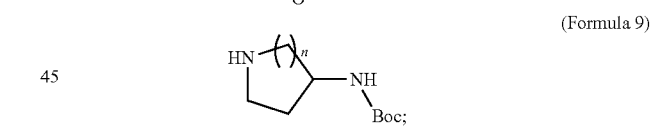
(Formula 10)

removing Boc from the compound of Formula 10 under reaction conditions to obtain the compound of Formula 11:

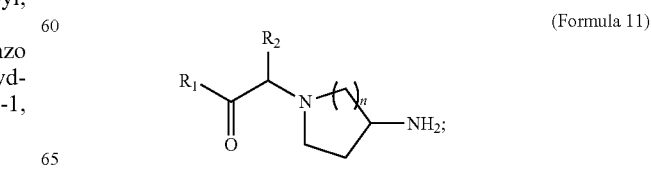
(Formula 11)

and reacting the compound of Formula 11 with a compound of Formula 11b to obtain the compound of Formula 1d, or the isomer thereof, or the pharmaceutically acceptable salt thereof:

$$R_4\text{—}S(O)_2Cl \qquad \text{(Formula 11b);}$$

wherein n is 1 or 2, wherein $R_1$ is a substituent selected from the group consisting of compounds of Formulas I-V,

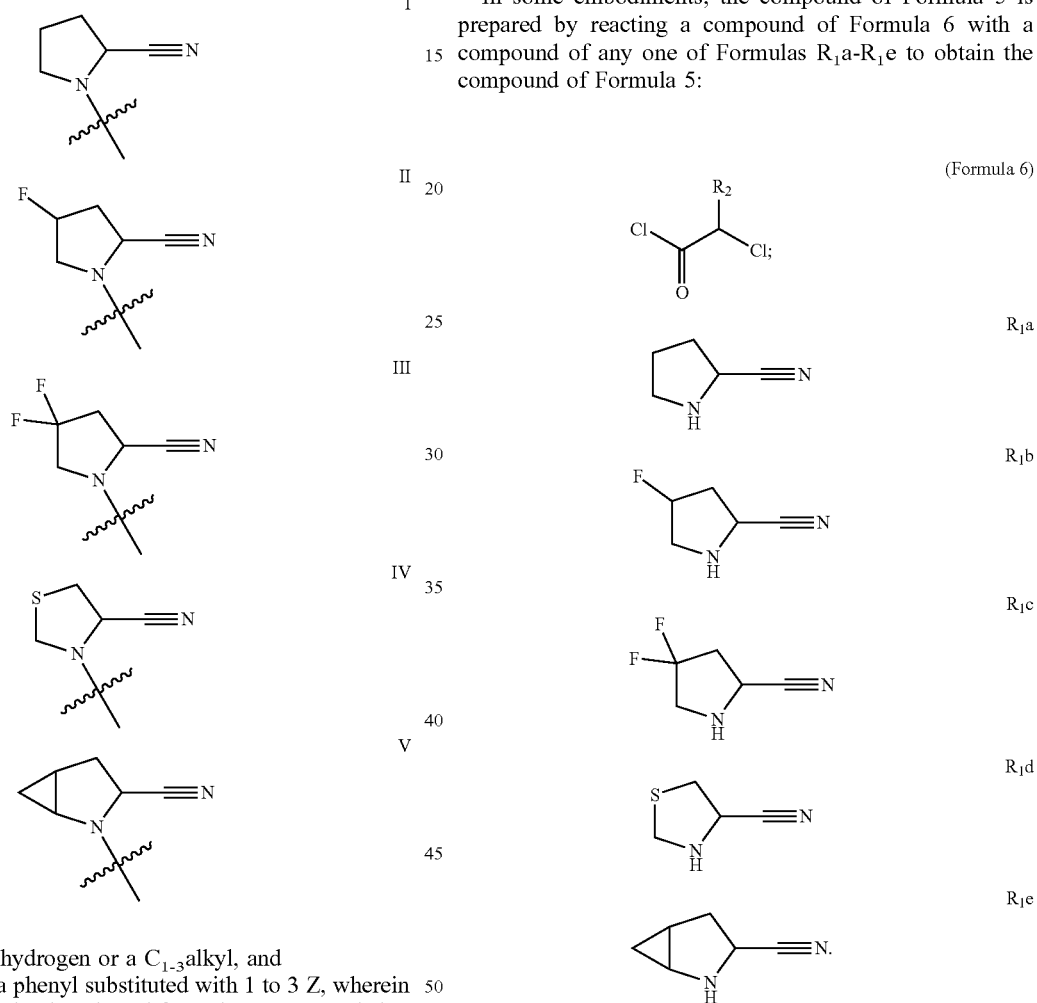

wherein $R_2$ is hydrogen or a $C_{1-3}$alkyl, and wherein $R_4$ is a phenyl substituted with 1 to 3 Z, wherein each Z is independently selected from the group consisting of hydroxy, amino, halogen, cyano, nitro, carboxylic acid, $C_{1-5}$alkyl optionally substituted with 1 to 3 halogens or amino, $C_{2-6}$alkenyl, $C_{2-6}$alkynyl, $C_{1-5}$alkoxy, $C_{1-5}$alkylthio, mono- or di-$C_{1-5}$alkylamino, piperazinyl optionally substituted with acetyl, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl;

a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl;

a naphthyl optionally substituted with halogen; or a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, and acridinyl, wherein said heteroaryl is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy, $C_{1-5}$alkoxycarbonyl, benzyloxy, phenyl optionally substituted with halogen, acetyl, and $C_{1-5}$alkylsulfonyl.

In some embodiments, the compound of Formula 5 is prepared by reacting a compound of Formula 6 with a compound of any one of Formulas $R_1a$-$R_1e$ to obtain the compound of Formula 5:

Provided herein, in another aspect, is a method of preparing a compound of Formula 1b,

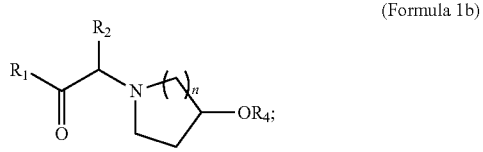

or a stereoisomer or mixture of stereoisomers thereof, or a pharmaceutically acceptable salt thereof, the method comprising reacting a compound of Formula 5 with a compound of Formula 7 to obtain a compound of Formula 8:

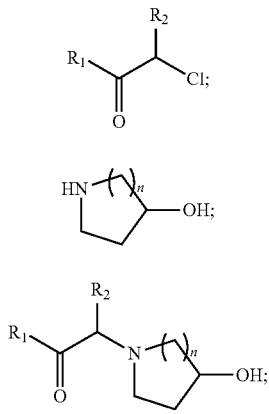

(Formula 5)

(Formula 7)

(Formula 8)

and reacting the compound of Formula 8 with a compound of Formula 2ba under Mitsunobu reaction conditions to obtain the compound of Formula 1b, or the isomer thereof, or the pharmaceutically acceptable salt thereof:

$R_4$—OH  (Formula 2ba);

wherein n is 1 or 2, wherein $R_1$ is a substituent selected from the group consisting of compounds of Formulas I-V,

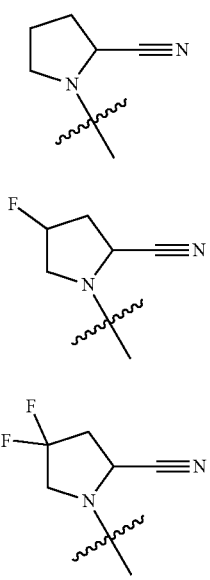

I

II

III

IV

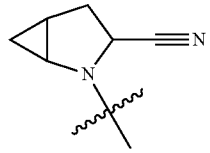

V wherein $R_2$ is hydrogen or a $C_{1-3}$alkyl, wherein $R_4$ is a phenyl substituted with 1 to 3 Z, wherein each Z is independently selected from the group consisting of hydroxy, amino, halogen, cyano, nitro, carboxylic acid, $C_{1-5}$alkyl optionally substituted with 1 to 3 halogens or amino, $C_{2-6}$alkenyl, $C_{2-6}$alkynyl, $C_{1-5}$alkoxy, $C_{1-5}$alkylthio, mono- or di-$C_{1-5}$alkylamino, piperazinyl optionally substituted with acetyl, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl;

a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl;

a naphthyl optionally substituted with halogen; or a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy, $C_{1-5}$alkoxycarbonyl, benzyloxy, phenyl optionally substituted with halogen, acetyl, $C_{1-5}$alkylsulfonyl, morpholinyl, —NR$_6$C(O)R$_7$, and —C(O)NR$_6$R$_7$;

wherein $R_6$ is hydrogen or a $C_{1-3}$alkyl group; and wherein $R_7$ is a $C_{1-3}$alkyl group optionally substituted with phenyl; a phenyl; or a heteroaryl selected from the group consisting of pyridinyl, pyrimidinyl, and isoxazolyl.

Provided herein, in another aspect, is a method of preparing a compound of Formula 1b, (Formula 1b)

or a stereoisomer or mixture of stereoisomers thereof, or a pharmaceutically acceptable salt thereof, the method comprising reacting a compound of Formula 5 with a compound of Formula 7 to obtain a compound of Formula 8:

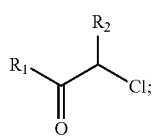

(Formula 5)

-continued

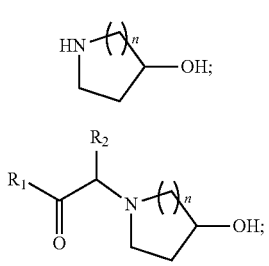

(Formula 7)

(Formula 8)

and reacting the compound of Formula 8 with a compound of Formula 2ba under Mitsunobu reaction conditions to obtain the compound of Formula 1b, or the isomer thereof, or the pharmaceutically acceptable salt thereof:

R₄—OH    (Formula 2ba);

wherein n is 1 or 2, wherein $R_1$ is a substituent selected from the group consisting of compounds of Formulas I-V,

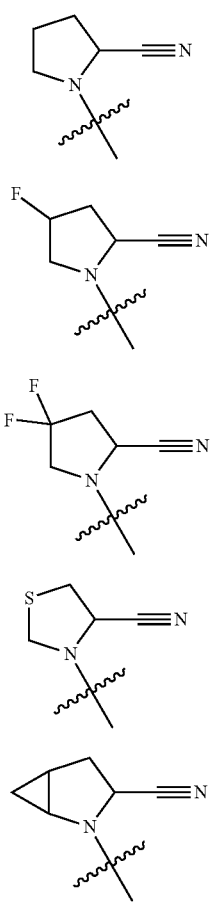

wherein $R_2$ is hydrogen or a $C_{1-3}$alkyl, wherein $R_4$ is a phenyl substituted with 1 to 3 Z, wherein each Z is independently selected from the group consisting of hydroxy, amino, halogen, cyano, nitro, carboxylic acid, $C_{1-5}$alkyl optionally substituted with 1 to 3 halogens or amino, $C_{2-6}$alkenyl, $C_{2-6}$alkynyl, $C_{1-5}$alkoxy, $C_{1-5}$alkylthio, mono- or di-$C_{1-5}$alkylamino, piperazinyl optionally substituted with acetyl, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl;

a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl;

a naphthyl optionally substituted with halogen; or a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, and acridinyl, wherein said heteroaryl is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy, $C_{1-5}$alkoxycarbonyl, benzyloxy, phenyl optionally substituted with halogen, acetyl, and $C_{1-5}$alkylsulfonyl.

DETAILED DESCRIPTIONS

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As used herein, the term "comprising" or "comprises" is intended to mean that the compositions and methods include the recited elements, but not excluding others. A composition or method "consisting essentially" of the elements as defined herein would not exclude other materials or steps that do not materially affect the basic and novel characteristic(s) of the claimed technology. "Consisting of" shall mean excluding more than trace elements of other ingredients and substantial method steps. Embodiments defined by each of these transition terms are within the scope of this technology. When an embodiment is defined by one of these terms (e.g., "comprising") it should be understood that this disclosure also includes alternative embodiments, such as "consisting essentially of" and "consisting of" for said embodiment.

"Substantially" or "essentially" means nearly totally or completely, for instance, 95%, 96%, 97%, 98%, 99%, or greater of some given quantity.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Where a range of values is provided, it is understood that each intervening value, to the tenth of the unit of the lower limit unless the context clearly dictates otherwise, between the upper and lower limit of that range and any other stated or intervening value in that stated range, is encompassed within the present technology. The upper and lower limits of these smaller ranges may independently be included in the smaller ranges and are also encompassed within the present technology, subject to any specifically excluded limit in the stated range. Where the stated range includes one or both of the limits, ranges excluding either or both of those included limits are also included in the present technology.

In general, "substituted" refers to an organic group (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. The present disclosure is understood to include embodiments where, for instance a "substituted alkyl" optionally contains one or more alkene and/or alkyne. A substituted group will be substituted with one or more substituents, unless otherwise specified. In some embodiments, a substituted group is substituted with 1, 2, 3, 4, 5, or 6 substituents. Examples of substituent groups include: alkyls, haloalkyls, halogens (i.e., F, Cl, Br, and I); hydroxyls; alkoxy, alkenoxy, alkynoxy, aryloxy, aralkyloxy, heterocyclyloxy, and heterocyclylalkoxy groups; aryl groups; heteroaryl groups; cycloalkyl groups; heterocyclyl groups; carbonyls (oxo); carboxyls; esters; carbamates; urethanes; ureas; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like. As used herein, an "optionally substituted" group refers to a group that is substituted or unsubstituted. As such, "optionally substituted" and "substituted or unsubstituted" may be used interchangeably.

Substituted ring groups such as substituted carbocyclic, substituted cycloalkyl, substituted aryl, substituted heterocyclic and substituted heteroaryl groups also include rings and fused ring systems in which a bond to a hydrogen atom is replaced with a bond to a carbon atom. Therefore, substituted carbocyclic, substituted cycloalkyl, substituted aryl, substituted heterocyclic and substituted heteroaryl groups may also be substituted with substituted or unsubstituted alkyl, alkenyl, and alkynyl groups as defined below.

As used herein, the term "carbocyclic group" or "carbocycle" includes aromatic (also referred to as aryl) and non-aromatic ring compounds (such as cycloalkyl) containing 3 or more ring members and that do not contain any heteroatom ring members. In some embodiments, a carbocycle includes 3 to 20 ring members, whereas other such groups have 3 to 6, 3 to 10, 3 to 12, 3 to 15, or 5 to 12 ring members.

As used herein, an "aryl group" refers to a cyclic aromatic hydrocarbon that does not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

As used herein, the term "cycloalkyl group" refers to a cyclic alkyl group such as, but not limited to, cyclopropyl, cyclobutyl, cyclopentyl, cyclohexyl, cycloheptyl, and cyclooctyl groups. In some embodiments, the cycloalkyl group has 3 to 8 carbon ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-di-substituted cyclohexyl groups, which may be substituted with substituents such as those listed above. In some embodiments, a cycloalkyl group has one or more alkene bonds, but is not aromatic.

As used herein, the term "heterocyclic group" or "heterocycle" includes aromatic (also referred to as heteroaryl) and non-aromatic ring compounds containing 3 or more ring members, of which one or more is a heteroatom such as, but not limited to, N, O, S or B. In some embodiments, heterocyclic groups include 3 to 20 ring members, whereas other such groups have 3 to 6, 3 to 10, 3 to 12, 3 to 15, or 5 to 12 ring members. Heterocyclic groups encompass unsaturated, partially saturated and saturated ring systems, such as, for example, imidazolyl, imidazolinyl and imidazolidinyl groups. The phrase "heterocyclic group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclic groups that have other groups, such as alkyl, oxo or halo groups, bonded to one of the ring members. Rather, these are referred to as "substituted heterocyclic groups". Heterocyclic groups include, but are not limited to, acridinyl, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, chromenonyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, dihydrobenzo[1,4]dioxinyl, 2,3-dihydrobenzofuranyl, 2-oxo-1,2-dihydroquinolinyl, 2-oxo-1,2,3,4-tetrahydroquinolinyl, pyrazolopyridyl, imidazopyridyl (azabenzimidazolyl), triazolopyridyl, isoxazolopyridyl, furo[3,2-c]pyridinyl, thieno[2,3-d]pyrimidinyl, thieno[3,2-c]pyridinyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclic groups may be mono-substituted or substituted more than once, such as, but not limited to, pyridyl or piperazinyl groups, which are 2-, 3-, 4-, 5-, or 6-substituted, or disubstituted with various substituents such as those listed above. In some embodiments, the term "naphthyridinyl" refers to 1,8-naphthyridinyl; 2,6-naphthyridinyl; or 1,5-naphthyridinyl, or any combination of two or more thereof.

As used herein, the term "heteroaryl group" refers to an aromatic ring compound containing 5 or more ring members, of which, one or more is a heteroatom such as, but not limited to, N, O, S or B. In some embodiments, one or more heteroatoms are independently chosen from N, O, or S. In some embodiments, 1 to 4 heteroatoms are independently chosen from N, O, or S. In some embodiments, 1 to 5 heteroatoms are independently chosen from N, O, or S. In some embodiments, heteroaryl groups include 5 to 14 ring members, whereas other such groups have 5 to 6, 5 to 9, 5 to 10, 6 to 9, 6 to 10, or 6 to 14 ring members. For example, a 5-membered heteroaryl group has 5 ring members; a 6-membered heteroaryl group has 6 ring members; and a 9-membered heteroaryl group has 9 ring members (such as, but not limited to, benzothiophene). Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, naphthyridinyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above. An azolyl group is a 5-membered heteroaryl group containing a nitrogen atom and at least one other atom selected from nitrogen, sulfur, and oxygen as part of the ring. Azolyl groups include imidazole, pyrazole, 1,2,3-triazole, 1,2,4-triazole, tetrazole, pentazole, oxazole, isoxazole, 1,2,4-oxadiazole, 1,2,5-oxadiazole, 1,3,4-oxadiazole, thiazole, isothiazole, 1,2,3-thiadiazole, 1,2,4-thiadiazole, 1,2,5-thiadiazole, and 1,3,4-thiadiazole.

As used herein, the term "alkyl" refers to an aliphatic hydrocarbon radical, which encompasses both straight and branched hydrocarbon radicals. In some embodiments, alkyl has from 1 to about 20 carbon atoms, from 1 to 12 carbons, from 1 to 8 carbons, 1 to 6 carbons, or 1 to 4 carbon atoms. For example, $C_{1-6}$alkyl refers to an aliphatic hydrocarbon having 1 to 6 carbons, which includes methyl, ethyl, propyl, n-butyl, n-pentyl, n-hexyl, isopropyl, isobutyl, sec-butyl, tert-butyl, neopentyl, isopentyl, and the like.

In addition, as used herein, the term "hydroxy" is defined as —OH.

As used herein, the term "alkoxy," unless particularly defined herein, refers to a radical formed by substituting the hydrogen atom of a hydroxyl group with an alkyl, as defined above. For example, $C_{1-5}$alkoxy includes methoxy, ethoxy, propoxy, n-butoxy, n-pentyloxy, isopropoxy, sec-butoxy, tert-butoxy, neopentyloxy, isopentyloxy, and the like.

In addition, as used herein, the term "halogen" refers to fluorine, bromine, chlorine, and iodine.

In addition, as used herein, the term "amino" is defined as —NH$_2$, and the term "alkylamino" refers to a mono- or di-alkyl substituted amino. For example, $C_{1-6}$alkylamino includes mono- or di-$C_{1-6}$alkyl substituted amino.

In addition, as used herein, the term "alkylthio" is defined as —SR* (wherein R* is alkyl), and the term "cyano" is defined as —CN.

Those of skill in the art will appreciate that compounds of the present technology may exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the present technology encompasses any tautomeric, conformational isomeric, optical isomeric and/or geometric isomeric forms of the compounds having one or more of the utilities described herein, as well as mixtures of these various different forms. As used herein, "isomer" refers to a tautomer, conformation isomer, optical isomer, geometric isomer, or any combination thereof, of a compound.

As readily understood by one skilled in the art, a wide variety of functional groups and other structures may exhibit tautomerism, and all tautomers of compounds as described herein are within the scope of the present technology.

Stereoisomers of compounds, also known as "optical isomers," include all chiral, diastereomeric, and racemic forms of a structure, unless the specific stereochemistry is expressly indicated. Thus, compounds used in the present technology include enriched or resolved optical isomers at any or all stereogenic atoms as are apparent from the depictions. Both racemic and diastereomeric mixtures, as well as the individual optical isomers can be isolated or synthesized so as to be substantially free of their enantiomeric or diastereomeric partners, and these are all within the scope of the present technology.

By "pharmaceutically acceptable" is meant a material that is not biologically or otherwise undesirable, e.g., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

Generally, reference to a certain moiety capable of being protected (such as hydroxy, amine, carbonyl, etc.) includes the protected groups in some embodiments of the disclosure. For example, in some embodiments, an —OH moiety as included herein also includes —OP, where P is a protecting group. Protecting groups, as referred to herein may be selected by one of ordinary skill in the art, and include the groups and strategies set forth in the art, for example, those such as described in R. Larock, *Comprehensive Organic Transformations*, VCH Publishers (1989); T. W. Greene and P. G. M. Wuts, *Greene's protective groups in organic synthesis*, John Wiley & Sons (2006); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

"Subject" refers to an animal, such as a mammal (including a human), that has been or will be the object of treatment, observation or experiment. "Subject" and "patient" may be used interchangeably, unless otherwise indicated. The methods described herein may be useful in human therapy and/or veterinary applications. In some embodiments, the subject is a mammal. In some embodiments, the subject is a human.

The terms "therapeutically effective amount" and "effective amount" are used interchangibly and refer to an amount of a compound that is sufficient to effect treatment as defined below, when administered to a patient (e.g., a human) in need of such treatment in one or more doses. The therapeutically effective amount will vary depending upon the patient, the disease being treated, the weight and/or age of the patient, the severity of the disease, or the manner of administration as determined by a qualified prescriber or care giver.

The term "treatment" or "treating" means administering a compound disclosed herein for the purpose of: (i) delaying the onset of a disease, that is, causing the clinical symptoms of the disease not to develop or delaying the development thereof, (ii) inhibiting the disease, that is, arresting the development of clinical symptoms; and/or (iii) relieving the disease, that is, causing the regression of clinical symptoms or the severity thereof.

Unless defined otherwise, all technical and scientific terms used herein have the same meaning as commonly understood by one of ordinary skill in the art to which this present technology belongs. Although any methods and materials similar or equivalent to those described herein can also be used in the practice or testing of the present technology, representative illustrative methods and materials are described herein.

The present inventors found that specific pyrrolidine or piperidine compounds, while exhibiting low inhibitory activity on other DPP family enzymes (DPP4, DPP7, DPP8, DPP9, PREP), exhibit selective inhibitory activity on FAP. Therefore, the pyrrolidine or piperidine compounds or their salts can be usefully used in the treatment and prophylaxis of various FAP-mediated diseases, for example, cancer, wound healing, obesity, diabetes, steatosis, nonalcoholic steatohepatitis (NASH), and liver cirrhosis.

Therefore, the present technology provides the pyrrolidine and piperidine compounds, their stereoisomers, or their pharmaceutically acceptable salts, preparation processes thereof, pharmaceutical compositions comprising the same, and the use thereof.

In accordance with one aspect of the present technology, there is provided a pyrrolidine or piperidine compound, its stereoisomer or mixture of stereoisomers, or its pharmaceutically acceptable salt.

In accordance with another aspect of the present technology, there is provided a preparation process of the pyrrolidine or piperidine compound.

In accordance with another aspect of the present technology, there is provided a pharmaceutical composition comprising the pyrrolidine or piperidine compound as an active ingredient.

In accordance with another aspect of the present technology, there is provided a method of treatment comprising administering the pyrrolidine or piperidine compound described herein.

In accordance with another aspect of the present technology, there is provided the use of the pyrrolidine or piperidine compound or its stereoisomer or mixture of stereoisomers, or its pharmaceutically acceptable salt in the manufacture of a medicament for inhibition of fibroblast activation proteins.

It was found by the present technology that the compounds according to the present technology, i.e., the pyrrolidine or piperidine compounds, or their stereoisomers, or their pharmaceutically acceptable salts, exhibit inhibitory activity on FAP. Therefore, the compounds according to the present technology, or stereoisomers thereof, or pharmaceutically acceptable salts thereof can be usefully applied for the treatment and prophylaxis of FAP-mediated various diseases, for example, cancer, wound healing, obesity, diabetes, steatosis, nonalcoholic steatohepatitis (NASH), and liver cirrhosis.

In one aspect, provided herein is a compound of Formula X, or a stereoisomer or mixture of stereoisomers thereof, or a pharmaceutically acceptable salt thereof:

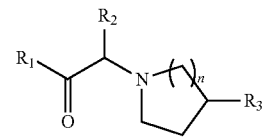

(Figure X)

wherein n is 1 or 2;

$R_1$ is a substituent selected from the group consisting of compounds of Formulas I-V:

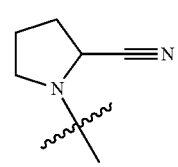

I

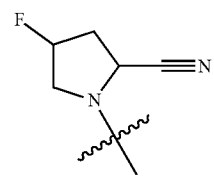

II

-continued

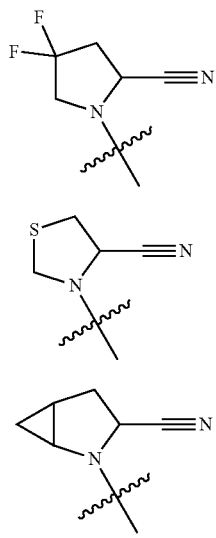

R$_2$ is hydrogen or a C$_{1-3}$alkyl;

R$_3$ is a 5- to 12-membered substituted or unsubstituted heteroaryl, wherein said heteroaryl contains 1 to 3 heteroatoms independently selected from O, N, and S,
  a 3- to 12-membered substituted or unsubstituted non-aromatic heterocycle, wherein said heterocycle contains 1 to 3 heteroatoms independently selected from O, N, and S,
  —NR$_4$R$_5$, —OR$_4$, —C(O)NHR$_4$, —NHC(O)(CH$_2$)$_m$R$_4$, or —NHS(O)$_2$R$_4$,
  wherein m is 0 or 1;

R$_4$ is a substituted phenyl; a substituted or unsubstituted naphthyl; a substituted or unsubstituted non-aromatic heterocycle; or a substituted or unsubstituted heteroaryl; and R$_5$ is hydrogen or a C$_{1-3}$alkyl.

In another aspect, provided herein is a compound of Formula Xa, or a stereoisomer or mixture of stereoisomers thereof, or a pharmaceutically acceptable salt thereof:

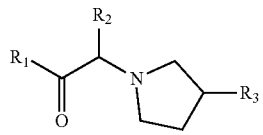

(Formula Xa)

wherein n is 1 or 2,

R$_1$ is a substituent selected from the group consisting of compounds of Formulas I-V:

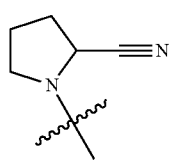

-continued

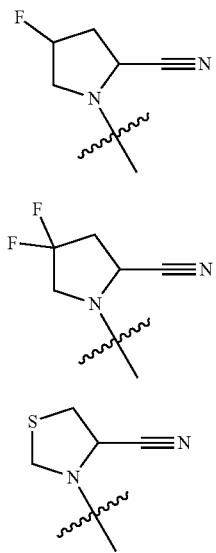

R$_2$ is hydrogen or a C$_{1-3}$alkyl;

R$_3$ is a 5- to 12-membered substituted or unsubstituted heteroaryl, wherein said heteroaryl contains 1 to 3 heteroatoms independently selected from O, N, and S,
  a 3- to 12-membered substituted or unsubstituted non-aromatic heterocycle, wherein said heterocycle contains 1 to 3 heteroatoms independently selected from O, N, and S,
  —NR$_4$R$_5$, —OR$_4$, —C(O)NHR$_4$, —NHC(O)(CH$_2$)$_m$R$_4$, or —NHS(O)$_2$R$_4$,
  wherein m is 0 or 1;

R$_4$ is a substituted phenyl; a substituted or unsubstituted naphthyl; a substituted or unsubstituted non-aromatic heterocycle; or a substituted or unsubstituted heteroaryl; and R$_5$ is hydrogen or a C$_{1-3}$alkyl.

In another aspect, provided herein is a compound of Formula Xb, or a stereoisomer or mixture of stereoisomers thereof, or a pharmaceutically acceptable salt thereof:

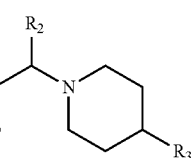

(Formula Xb)

wherein n is 1 or 2;

R$_1$ is a substituent selected from the group consisting of compounds of Formulas I-V,

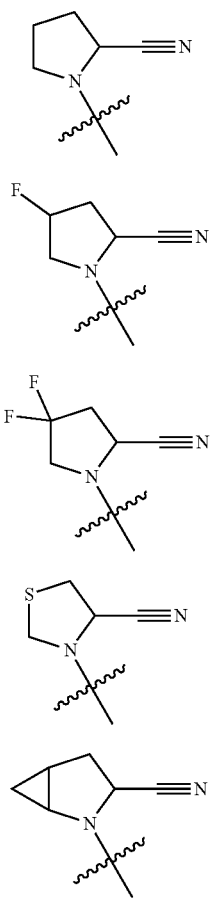

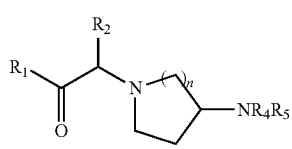

$R_2$ is hydrogen or a $C_{1-3}$alkyl;

$R_3$ is a 5- to 12-membered substituted or unsubstituted heteroaryl, wherein said heteroaryl contains 1 to 3 heteroatoms independently selected from O, N, and S,
 a 3- to 12-membered substituted or unsubstituted non-aromatic heterocycle, wherein said heterocycle contains 1 to 3 heteroatoms independently selected from O, N, and S,
 —$NR_4R_5$, —$OR_4$, —$C(O)NHR_4$, —$NHC(O)(CH_2)_mR_4$, or —$NHS(O)_2R_4$,
 wherein m is 0 or 1;

$R_4$ is a substituted phenyl; a substituted or unsubstituted naphthyl; a substituted or unsubstituted non-aromatic heterocycle; or a substituted or unsubstituted heteroaryl; and $R_5$ is hydrogen or a $C_{1-3}$alkyl.

In another aspect, provided herein is a compound of Formula 1a, or a stereoisomer or mixture of stereoisomers thereof, or a pharmaceutically acceptable salt thereof:

(Formula 1a)

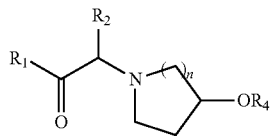

wherein $R_1$, $R_2$, $R_4$, $R_5$, and n are as defined in the embodiments above or below.

In another aspect, provided herein is a compound of Formula 1b, or a stereoisomer or mixture of stereoisomers thereof, or a pharmaceutically acceptable salt thereof:

(Formula 1b)

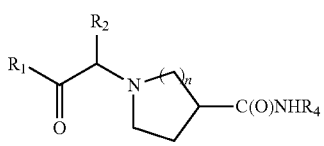

wherein $R_1$, $R_2$, $R_4$, and n are as defined in the embodiments above or below.

In another aspect, provided herein is a compound of Formula 1c, or a stereoisomer or mixture of stereoisomers thereof, or a pharmaceutically acceptable salt thereof:

(Formula 1c)

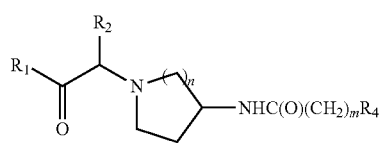

wherein $R_1$, $R_2$, $R_4$, and n are as defined in the embodiments above or below.

In another aspect, provided herein is a compound of Formula 1d, or a stereoisomer or mixture of stereoisomers thereof, or a pharmaceutically acceptable salt thereof:

(Formula 1d)

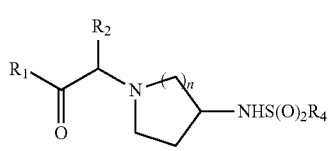

wherein $R_1$, $R_2$, $R_4$, m, and n are as defined in the embodiments above or below.

In another aspect, provided herein is a compound of Formula 1e, or a stereoisomer or mixture of stereoisomers thereof, or a pharmaceutically acceptable salt thereof:

(Formula 1e)

wherein $R_1$, $R_2$, $R_4$, and n are as defined in the embodiments above or below.

In some embodiments of Formulas X, Xa, Xb, 1a, 1b, 1c, 1d, and 1e, $R_4$ is
 a phenyl substituted with 1 to 3 Z; a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl, wherein said heterocycle is optionally substituted with 1 to 3 Z;

a naphthyl optionally substituted with 1 to 3 Z, or a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, and acridinyl, wherein said heteroaryl is optionally substituted with 1 to 3 Z; and each Z is independently selected from the group consisting of hydroxy, amino, halogen, cyano, nitro, carboxylic acid, $C_{1-5}$alkyl optionally substituted by 1 to 3 $Z^1$, $C_{2-6}$alkenyl optionally substituted by $Z^1$, $C_{2-6}$alkynyl optionally substituted by $Z^1$, $C_{1-5}$alkoxy optionally substituted by 1 to 3 $Z^1$, $C_{1-5}$alkylthio optionally substituted by $Z^1$, mono- or di-$C_{1-5}$alkylamino optionally substituted by $Z^1$, piperazinyl optionally substituted by $Z^1$, $C_{1-5}$alkylsulfonylamino optionally substituted by $Z^1$, $C_{1-5}$alkylcarbonylamino optionally substituted by $Z^1$, aminosulfonyl optionally substituted by $Z^1$, aminocarbonyl optionally substituted by $Z^1$, $C_{1-5}$alkylaminocarbonyl optionally substituted by $Z^1$, phenyl optionally substituted by $Z^1$, phenoxy optionally substituted by $Z^1$, benzyl optionally substituted by $Z^1$, benzoyl optionally substituted by $Z^1$, phenylaminocarbonyl optionally substituted by $Z^1$, pyrazolyl optionally substituted by $Z^1$, benzoxazolyl optionally substituted by $Z^1$, $C_{1-5}$ alkoxycarbonyl optionally substituted by $Z^1$, benzyloxy optionally substituted by $Z^1$, and $C_{1-5}$ alkylsulfonyl optionally substituted by $Z^1$;

wherein each $Z^1$ is independently chosen from halogen, hydroxyl, amino, $C_{1-5}$alkylamino, cyano, acetyl, $C_{1-5}$ alkyl, $C_{1-5}$ haloalkyl, $C_{3-6}$ carbocycle, $C_{3-6}$ heterocycle, wherein said $C_{3-6}$ carbocycle and said $C_{3-6}$ heterocycle are optionally substituted with halogen, hydroxyl, $C_{1-5}$alkyl or $C_{1-5}$ haloalkyl.

In some embodiments of Formulas X, Xa, Xb, 1a, 1b, 1c, 1d, and 1e, $R_4$ is a phenyl substituted with 1 to 3 Z, wherein each Z is independently selected from the group consisting of hydroxy, amino, halogen, cyano, nitro, carboxylic acid, $C_{1-5}$alkyl optionally substituted with 1 to 3 halogens or amino, $C_{2-6}$alkenyl, $C_{2-6}$alkynyl, $C_{1-5}$alkoxy, $C_{1-5}$alkylthio, mono- or di-$C_{1-5}$alkylamino, piperazinyl optionally substituted with acetyl, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl; or $R_4$ is a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl; or $R_4$ is a naphthyl optionally substituted with halogen; or $R_4$ is a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl and acridinyl, wherein the heteroaryl is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, and $C_{1-5}$alkylsulfonyl.

In another aspect, the present technology provides a compound having inhibitory activity on FAP or its salt, that is, a compound of Formula 1, or its stereoisomer or mixture of stereoisomers, or its pharmaceutically acceptable salt:

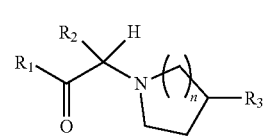

(Formula 1)

wherein n is 1 or 2;

$R_1$ is selected from the group consisting of Formulas I, II, III, IV, and IV;

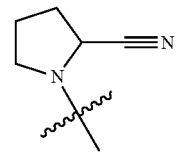

I

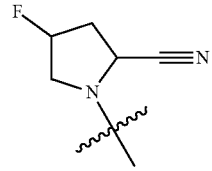

II

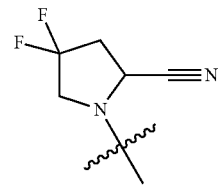

III

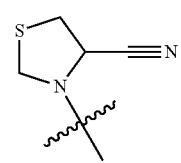

IV

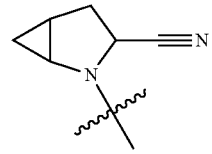

V $R_2$ is a hydrogen or a $C_{1-3}$alkyl;

$R_3$ is a 5- to 12-membered heteroaryl, wherein said heteroaryl contains 1 to 3 heteroatoms independently selected from O, N, and S and is optionally substituted by 1 to 3 Z, a 3- to 12-membered non-aromatic heterocycle, wherein said heterocycle contains 1 to 3 heteroatoms independently selected from O, N, and S and is optionally substituted by 1 to 3 Z, —$NR_4R_5$, —$OR_4$, —$C(O)NHR_4$, —$NHC(O)(CH_2)_mR_4$, —$NHS(O)_2R_4$, —$(CH_2)_mCH_2R_4$, or —$(CH_2)_mNHR_4$, wherein m is 0 or 1;
$R_4$ is a phenyl substituted with 1 to 3 Z,
  a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl, wherein said heterocycle is optionally substituted with 1 to 3 Z,
  a naphthyl optionally substituted with 1 to 3 Z, or
  a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z;
$R_5$ is a hydrogen or a $C_{1-3}$alkyl; and
each Z is independently selected from the group consisting of hydroxy, amino, halogen, cyano, nitro, carboxylic acid, $C_{1-5}$alkyl optionally substituted by 1 to 3 $Z^1$, $C_{2-6}$alkenyl optionally substituted by $Z^1$, $C_{2-6}$alkynyl optionally substituted by $Z^1$, $C_{1-5}$alkoxy optionally substituted by 1 to 3 $Z^1$, $C_{1-5}$alkylthio optionally substituted by $Z^1$, mono- or di-$C_{1-5}$alkylamino optionally substituted by $Z^1$, piperazinyl optionally substituted by $Z^1$, $C_{1-5}$alkylsulfonylamino optionally substituted by $Z^1$, $C_{1-5}$alkylcarbonylamino optionally substituted by $Z^1$, aminosulfonyl optionally substituted by $Z^1$, aminocarbonyl optionally substituted by $Z^1$, $C_{1-5}$alkylaminocarbonyl optionally substituted by $Z^1$, phenyl optionally substituted by $Z^1$, phenoxy optionally substituted by $Z^1$, benzyl optionally substituted by $Z^1$, benzoyl optionally substituted by $Z^1$, phenylaminocarbonyl optionally substituted by $Z^1$, pyrazolyl optionally substituted by $Z^1$, benzoxazolyl optionally substituted by $Z^1$, $C_{1-5}$ alkoxycarbonyl optionally substituted by $Z^1$, benzyloxy optionally substituted by $Z^1$, $C_{1-5}$ alkylsulfonyl optionally substituted by $Z^1$, acetyl, morpholinyl optionally substituted by $Z^1$, —$NR_6C(O)R_7$, and —$C(O)NR_6R_7$;
  wherein each $Z^1$ is independently chosen from halogen, hydroxyl, amino, $C_{1-5}$alkylamino, cyano, acetyl, $C_{1-5}$ alkyl, $C_{1-5}$ haloalkyl, $C_{3-6}$ carbocycle, $C_{3-6}$ heterocycle, wherein said $C_{3-6}$ carbocycle and said $C_{3-6}$ heterocycle are optionally substituted with halogen, hydroxyl, $C_{1-5}$alkyl, or $C_{1-5}$ haloalkyl;
$R_6$ is hydrogen or a $C_{1-3}$alkyl group;
$R_7$ is a $C_{1-3}$alkyl group optionally substituted with phenyl, a phenyl optionally substituted with 1 to 3 $Z^2$, or
  a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 $Z^2$; and
each $Z^2$ is independently selected from the group consisting of hydroxy, amino, halogen, cyano, nitro, hydroxycarbonyl, $C_{1-5}$alkyl optionally substituted by 1 to 3 $Z^3$, $C_{2-6}$alkenyl, $C_{2-6}$alkynyl, $C_{1-5}$alkoxy optionally substituted by 1 to 3 $Z^3$, $C_{1-5}$alkylthio, mono- or di-$C_{1-5}$alkylamino, piperazinyl optionally substituted by $Z^3$, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl;
  wherein each $Z^3$ is independently chosen from halogen, amino, or acetyl.

In some embodiments of a compound of Formula 1, or its stereoisomer or mixture of stereoisomers, or its pharmaceutically acceptable salt:
n is 1 or 2;
$R_1$ is selected from the group consisting of Formulas I, II, III, IV, and IV;

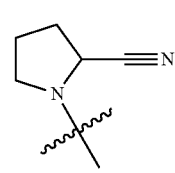

I

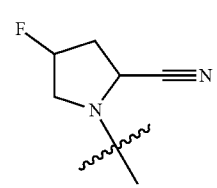

II

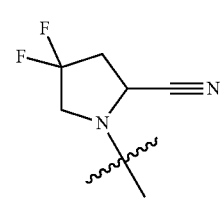

III

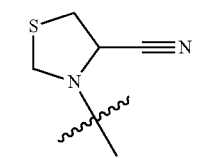

IV

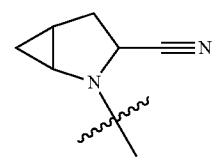

V $R_2$ is a hydrogen or a $C_{1-3}$alkyl;
$R_3$ is a 5- to 12-membered heteroaryl, wherein said heteroaryl contains 1 to 3 heteroatoms independently selected from O, N, and S and is optionally substituted by 1 to 3 Z,
  a 3- to 12-membered non-aromatic heterocycle, wherein said heterocycle contains 1 to 3 heteroatoms independently selected from O, N, and S and is optionally substituted by 1 to 3 Z,
  —$NR_4R_5$, —$OR_4$, —$C(O)NHR_4$, —$NHC(O)(CH_2)_mR_4$, or —$NHS(O)_2R_4$,
  wherein m is 0 or 1;
$R_4$ is a phenyl substituted with 1 to 3 Z,
  a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl, wherein said heterocycle is optionally substituted with 1 to 3 Z, a naphthyl optionally substituted with 1 to 3 Z, or a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, and acridinyl, wherein said heteroaryl is optionally substituted with 1 to 3 Z;

$R_5$ is a hydrogen or a $C_{1-3}$alkyl; and each Z is independently selected from the group consisting of hydroxy, amino, halogen, cyano, nitro, carboxylic acid, $C_{1-5}$alkyl optionally substituted by 1 to 3 $Z^1$, $C_{2-6}$alkenyl optionally substituted by $Z^1$, $C_{2-6}$alkynyl optionally substituted by $Z^1$, $C_{1-5}$alkoxy optionally substituted by 1 to 3 $Z^1$, $C_{1-5}$alkylthio optionally substituted by $Z^1$, mono- or di-$C_{1-5}$alkylamino optionally substituted by $Z^1$, piperazinyl optionally substituted by $Z^1$, $C_{1-5}$alkylsulfonylamino optionally substituted by $Z^1$, $C_{1-5}$alkylcarbonylamino optionally substituted by $Z^1$, aminosulfonyl optionally substituted by $Z^1$, aminocarbonyl optionally substituted by $Z^1$, $C_{1-5}$alkylaminocarbonyl optionally substituted by $Z^1$, phenyl optionally substituted by $Z^1$, phenoxy optionally substituted by $Z^1$, benzyl optionally substituted by $Z^1$, benzoyl optionally substituted by $Z^1$, phenylaminocarbonyl optionally substituted by $Z^1$, pyrazolyl optionally substituted by $Z^1$, benzoxazolyl optionally substituted by $Z^1$, $C_{1-5}$ alkoxycarbonyl optionally substituted by $Z^1$, benzyloxy optionally substituted by $Z^1$, and $C_{1-5}$ alkylsulfonyl optionally substituted by $Z^1$;

wherein each $Z^1$ is independently chosen from halogen, hydroxyl, amino, $C_{1-5}$alkylamino, cyano, acetyl, $C_{1-5}$ alkyl, $C_{1-5}$ haloalkyl, $C_{3-6}$ carbocycle, $C_{3-6}$ heterocycle, wherein said $C_{3-6}$ carbocycle and said $C_{3-6}$ heterocycle are optionally substituted with halogen, hydroxyl, $C_{1-5}$alkyl or $C_{1-5}$ haloalkyl.

In some embodiments, $R_1$ is selected from the group consisting of compounds of Formulas I, II, III, and V:

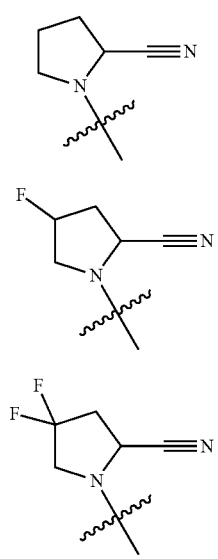

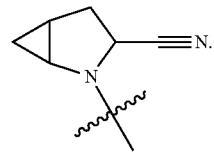

In some embodiments, $R_1$ is a substituent of Formula I. In some embodiments, $R_1$ is a substituent of Formula II. In some embodiments, $R_1$ is a substituent of Formula III. In some embodiments, $R_1$ is a substituent of Formula IV. In some embodiments, $R_1$ is a substituent of Formula V.

In some embodiments, $R_1$ is a substituent selected from the group consisting of compounds of Formulas Ia-Va,

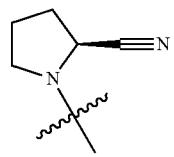

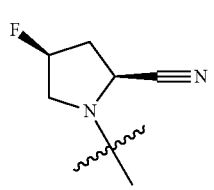

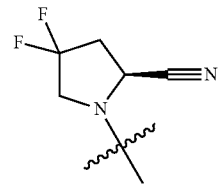

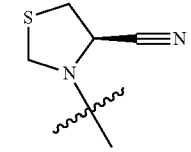

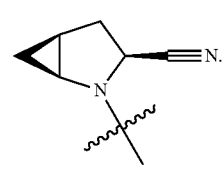

In some embodiments, $R_1$ is a substituent selected from the group consisting of compounds of Formulas Ia, IIa, IIIa, and Va:

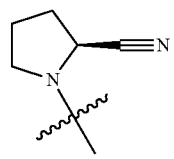

In some embodiments, R$_1$ is a compound of Formula IIa:

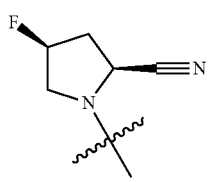

In some embodiments, R$_1$ is a compound of Formula IIIa:

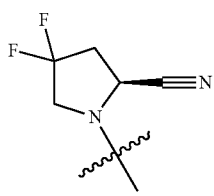

In some embodiments, R$_1$ is a compound of Formula Va:

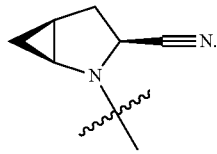

In some embodiments, R$_1$ is a compound of Formula Ia:

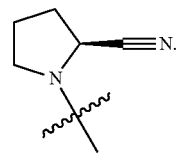

In some embodiments, R$_1$ is a compound of Formula IIa:

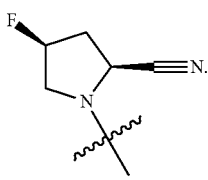

In some embodiments, R$_1$ is a compound of Formula IIIa:

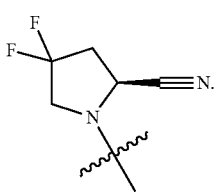

In some embodiments, R$_1$ is a compound of Formula IVa:

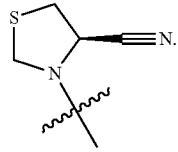

In some embodiments, R$_1$ is a compound of Formula Va:

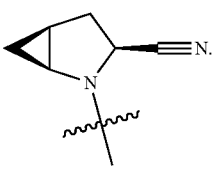

In some embodiments, R$_2$ is hydrogen. In some embodiments, R$_2$ is a C$_{1-3}$alkyl.

In some embodiments, m is 0. In some embodiments, m is 1.

In some embodiments, n is 1. In some embodiments, n is 2.

In some embodiments, R$_3$ is a substituent selected from the group consisting of —NR$_4$R$_5$, —OR$_4$, —C(O)NHR$_4$, —NHC(O)(CH$_2$)$_m$R$_4$, and —NHS(O)$_2$R$_4$. In some embodiments, R$_3$ is a substituent selected from the group consisting of —NR$_4$R$_5$, —OR$_4$, and —NHC(O)(CH$_2$)$_m$R$_4$. In some embodiments, R$_3$ is a substituent selected from the group consisting of —NR$_4$R$_5$ and —OR$_4$. In some embodiments, R$_3$ is —NR$_4$R$_5$. In some embodiments, R$_3$ is —OR$_4$. In some embodiments, R$_3$ is —C(O)NHR$_4$. In some embodiments, R$_3$ is —NHC(O)(CH$_2$)$_m$R$_4$. In some embodiments, R$_3$ is —NHS(O)$_2$R$_4$.

In some embodiments, R$_3$ is a 3- to 12-membered non-aromatic heterocycle containing 1-3 nitrogens, wherein said heterocycle is optionally substituted by 1 to 3 Z. In some embodiments, R$_3$ is a 5- to 12-membered heteroaryl optionally substituted by 1 to 3 Z. In some embodiments, R$_3$ is 2-oxo-2,3-dihydro-1H-benzo[d]imidazol-1-yl.

In some embodiments, R$_4$ is a phenyl substituted with a substituent selected from the group consisting of piperazinyl optionally substituted with acetyl, phenyl, phenoxy, benzyl, benzoyl, phenylaminocarbonyl, pyrazolyl, and benzoxazolyl; or R$_4$ is a heterocycle selected from the group consisting of benzo[d][1,3]dioxolyl, 2,3-dihydrobenzofuranyl, 2-oxo-1,2-dihydroquinolinyl, and 2-oxo-1,2,3,4-tetrahydroquinolinyl; or R$_4$ is a naphthyl optionally substituted with halogen; or or R$_4$ is a heteroaryl selected from the group consisting of pyridinyl, quinolinyl, isoquinolinyl, quinazolinyl, benzofuranyl, benzothiophenyl, furo[3,2-c]pyridinyl, thieno[2,3-d]pyrimidinyl, thieno[3,2-c]pyridinyl, isoxazolyl, and acridinyl, wherein said heteroaryl is optionally substituted with 1 to 3 Z, wherein each Z is independently selected from the group consisting of hydroxy, halogen, C$_{1-5}$alkyl optionally substituted 1 to 3 halogens, C$_{1-5}$alkoxy optionally substituted with 1 to 3 halogens, C$_{1-5}$alkoxycarbonyl, benzyloxy, and phenyl optionally substituted with halogen.

In some embodiments, R$_4$ is a phenyl substituted with phenyl; or R$_4$ is a naphthyl; or or R is a heteroaryl selected from the group consisting of quinolinyl, isoquinolinyl, benzofuranyl, benzothiophenyl, and furo[3,2-c]pyridinyl, wherein said heteroaryl is optionally substituted with 1 to 3 Z, wherein each Z is independently selected from the group consisting of halogen, $C_{1-5}$alkyl optionally substituted with 1 to 3 halogens, and $C_{1-5}$alkoxy optionally substituted with 1 to 3 halogens.

In some embodiments, $R_4$ is a phenyl substituted with phenyl; or $R_4$ is a naphthyl; or or R is a heteroaryl selected from the group consisting of quinolinyl, isoquinolinyl, benzofuranyl, and benzothiophenyl, wherein said heteroaryl is optionally substituted with 1 to 3 Z, wherein each Z is independently selected from the group consisting of hydroxy, halogen, $C_{1-5}$alkyl, and $C_{1-5}$alkoxy.

In some embodiments, $R_4$ is a phenyl substituted with a substituent selected from the group consisting of piperazinyl optionally substituted with acetyl, phenyl, phenoxy, benzyl, benzoyl, phenylaminocarbonyl, pyrazolyl, and benzoxazolyl; or $R_4$ is a heterocycle selected from the group consisting of benzo[d][1,3]dioxolyl, 2,3-dihydrobenzofuranyl, 2-oxo-1,2-dihydroquinolinyl, and 2-oxo-1,2,3,4-tetrahydroquinolinyl; or $R_4$ is a naphthyl optionally substituted with halogen; or or $R_4$ is a heteroaryl selected from the group consisting of pyridinyl, quinolinyl, isoquinolinyl, quinazolinyl, thieno[2,3-d]pyrimidinyl, isoxazolyl, and acridinyl wherein said heteroaryl is optionally substituted with 1 to 3 Z, wherein each Z is independently selected from the group consisting of halogen, $C_{1-5}$alkyl optionally substituted with 1 to 3 halogens, $C_{1-5}$alkoxy optionally substituted with 1 to 3 halogens, benzyloxy, and phenyl optionally substituted with halogen.

In some embodiments, $R_4$ is a phenyl substituted with 1 to 3 Z, wherein each Z is independently selected from the group consisting of hydroxy, amino, halogen, cyano, nitro, carboxylic acid, $C_{1-5}$alkyl optionally substituted with 1 to 3 halogens or amino, $C_{2-6}$alkenyl, $C_{2-6}$alkynyl, $C_{1-5}$alkoxy, $C_{1-5}$alkylthio, mono- or di-$C_{1-5}$alkylamino, piperazinyl optionally substituted with acetyl, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl.

In some embodiments, $R_4$ is a phenyl substituted with a substituent selected from the group consisting of piperazinyl optionally substituted with acetyl, phenyl, phenoxy, benzyl, benzoyl, phenylaminocarbonyl, pyrazolyl, and benzoxazolyl. In some embodiments, $R_4$ is a phenyl substituted with phenyl.

In some embodiments, $R_4$ is a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl. In some embodiments, $R_4$ is a heterocycle selected from the group consisting of benzo[d][1,3]dioxolyl, 2,3-dihydrobenzofuranyl, 2-oxo-1,2-dihydroquinolinyl, and 2-oxo-1,2,3,4-tetrahydroquinolinyl.

In some embodiments, $R_4$ is a naphthyl optionally substituted with halogen. In some embodiments, $R_4$ is a naphthyl.

In some embodiments, $R_4$ is a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$. In some embodiments, $R_4$ is a heteroaryl selected from the group consisting of pyridinyl, quinolinyl, isoquinolinyl, chromenonyl, quinazolinyl, benzofuranyl, indolinyl, benzimidazolyl, benzothiophenyl, benzothiazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z, wherein each Z is independently selected from the group consisting of hydroxy, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, acetyl, morpholinyl, —$NR_6C(O)R_7$, —$C(O)NR_6R_7$, and phenyl optionally substituted with halogen; $R_6$ is hydrogen or a $C_{1-3}$alkyl group; and $R_7$ is a $C_{1-3}$alkyl group optionally substituted with phenyl, a phenyl, or a heteroaryl selected from the group consisting of pyridinyl, pyrimidinyl, and isoxazolyl. In some embodiments, $R_4$ is a heteroaryl selected from the group consisting of pyridinyl, quinolinyl, isoquinolinyl, chromenonyl, quinazolinyl, benzofuranyl, indolinyl, benzimidazolyl, benzothiophenyl, benzothiazolyl, furo[3,2-c]pyridinyl, and naphthyridinyl, wherein said heteroaryl is optionally substituted with 1 to 3 Z, wherein each Z is independently selected from the group consisting of hydroxy, cyano, nitro, halogen, $C_{1-5}$alkyl optionally substituted with 1 to 3 halogens, $C_{1-5}$alkoxy optionally substituted with 1 to 3 halogens, benzyloxy, acetyl, morpholinyl, —$NR_6C(O)R_7$, and —$C(O)NR_6R_7$. In some embodiments, $R_4$ is a heteroaryl selected from the group consisting of pyridinyl, quinolinyl, isoquinolinyl, chromenonyl, quinazolinyl, benzofuranyl, indolinyl, benzimidazolyl, benzothiophenyl, benzothiazolyl, furo[3,2-c]pyridinyl, and naphthyridinyl, wherein said heteroaryl is optionally substituted with 1 to 3 Z, wherein each Z is independently selected from the group consisting of hydroxy, cyano, nitro, halogen, $C_{1-5}$alkyl optionally substituted with 1 to 3 halogens, $C_{1-5}$alkoxy optionally substituted with 1 to 3 halogens, benzyloxy, acetyl, morpholinyl, —$NR_6C(O)R_7$, and —$C(O)NR_6R_7$; $R_6$ is hydrogen or a $C_{1-3}$alkyl group; and $R_7$ is a $C_{1-3}$alkyl group optionally substituted with phenyl, a phenyl, or a heteroaryl selected from the group consisting of pyridinyl, pyrimidinyl, and isoxazolyl.

In some embodiments, $R_4$ is quinolinyl or isoquinolinyl, each of which is optionally substituted with 1 to 3 Z, wherein each Z is independently selected from the group consisting of hydroxy, cyano, nitro, halogen, $C_{1-5}$alkyl optionally substituted with 1 to 3 halogens, $C_{1-5}$alkoxy optionally substituted with 1 to 3 halogens, benzyloxy, acetyl, morpholinyl, —$NR_6C(O)R_7$, and —$C(O)NR_6R_7$; $R_6$ is hydrogen or a $C_{1-3}$alkyl group; and $R_7$ is a $C_{1-3}$alkyl group optionally substituted with phenyl, a phenyl, or a heteroaryl selected from the group consisting of pyridinyl, pyrimidinyl, and isoxazolyl. In some embodiments, $R_4$ is quinolinyl, optionally substituted with 1 to 3 Z, wherein each Z is independently selected from the group consisting of hydroxy, cyano, nitro, halogen, $C_{1-5}$alkyl optionally substituted with 1 to 3 halogens, $C_{1-5}$alkoxy optionally substituted with 1 to 3 halogens, benzyloxy, acetyl, morpholinyl, —$NR_6C(O)R_7$, and —$C(O)NR_6R_7$; $R_6$ is hydrogen or a $C_{1-3}$alkyl group; and $R_7$ is a $C_{1-3}$alkyl group optionally substituted with phenyl, a phenyl, or a heteroaryl selected from the group consisting of pyridinyl, pyrimidinyl, and isoxazolyl.

In some embodiments, $R_4$ is a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, and acridinyl, wherein said heteroaryl is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, and $C_{1-5}$alkylsulfonyl. In some embodiments, $R_4$ is a heteroaryl selected from the group consisting of pyridinyl, quinolinyl, isoquinolinyl, quinazolinyl, benzofuranyl, benzothiophenyl, furo[3,2-c]pyridinyl, thieno[2,3-d]pyrimidinyl, thieno[3,2-c]pyridinyl, isoxazolyl, and acridinyl, wherein said heteroaryl is optionally substituted with 1 to 3 Z, wherein each Z is independently selected from the group consisting of hydroxy, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, and phenyl optionally substituted with halogen. In some embodiments, $R_4$ is a heteroaryl selected from the group consisting of quinolinyl, isoquinolinyl, benzofuranyl, benzothiophenyl, and furo[3,2-c]pyridinyl, wherein said heteroaryl is optionally substituted with 1 to 3 Z, wherein each Z is independently selected from the group consisting of halogen, $C_{1-5}$alkyl optionally substituted with 1 to 3 halogens, and $C_{1-5}$alkoxy optionally substituted with 1 to 3 halogens.

In some embodiments, $R_4$ is a heteroaryl selected from the group consisting of quinolinyl, isoquinolinyl, benzofuranyl, and benzothiophenyl, wherein said heteroaryl is optionally substituted with 1 to 3 Z, wherein each Z is independently selected from the group consisting of hydroxy, halogen, $C_{1-5}$alkyl, and $C_{1-5}$alkoxy.

In some embodiments, $R_4$ is a heteroaryl selected from the group consisting of pyridinyl, quinolinyl, isoquinolinyl, quinazolinyl, thieno[2,3-d]pyrimidinyl, isoxazolyl, and acridinyl wherein said heteroaryl is optionally substituted with 1 to 3 Z, wherein each Z is independently selected from the group consisting of cyano, halogen, $C_{1-5}$alkyl optionally substituted with 1 to 3 halogens, $C_{1-5}$alkoxy optionally substituted with 1 to 3 halogens, benzyloxy, and phenyl optionally substituted with halogen. In some embodiments, $R_4$ is a heteroaryl selected from the group consisting of pyridinyl, quinolinyl, isoquinolinyl, quinazolinyl, thieno[2,3-d]pyrimidinyl, isoxazolyl, and acridinyl wherein said heteroaryl is optionally substituted with 1 to 3 Z, wherein each Z is independently selected from the group consisting of halogen, $C_{1-5}$alkyl optionally substituted with 1 to 3 halogens, $C_{1-5}$alkoxy optionally substituted with 1 to 3 halogens, benzyloxy, and phenyl optionally substituted with halogen.

In some embodiments, $R_4$ is quinolinyl, isoquinolinyl, or quinazolinyl, each of which is optionally substituted with 1 to 3 Z, wherein each Z is independently selected from the group consisting of cyano, halogen, $C_{1-5}$alkyl optionally substituted with 1 to 3 halogens, and $C_{1-5}$alkoxy optionally substituted with 1 to 3 halogens. In some embodiments, $R_4$ is quinolinyl, isoquinolinyl, or quinazolinyl, each of which is optionally substituted with 1 to 3 Z, wherein each Z is independently selected from the group consisting of halogen, $C_{1-5}$alkyl optionally substituted with 1 to 3 halogens, and $C_{1-5}$alkoxy optionally substituted with 1 to 3 halogens.

In some embodiments, $R_4$ is quinolinyl or isoquinolinyl, each of which is optionally substituted with 1 to 3 Z, wherein each Z is independently selected from the group consisting of halogen, $C_{1-5}$alkyl optionally substituted with 1 to 3 halogens, and $C_{1-5}$alkoxy optionally substituted with 1 to 3 halogens.

In some embodiments, $R_4$ is quinolinyl or isoquinolinyl, each of which is optionally substituted with 1 to 3 Z, wherein each Z is independently selected from the group consisting of hydroxy, halogen, $C_{1-5}$alkyl, and $C_{1-5}$alkoxy. In some embodiments, $R_4$ is quinolinyl, optionally substituted with 1 to 3 Z, wherein each Z is independently selected from the group consisting of halogen, $C_{1-5}$alkyl optionally substituted with 1 to 3 halogens, and $C_{1-5}$alkoxy optionally substituted with 1 to 3 halogens.

In some embodiments, $R_4$ is benzofuranyl, benzothiophenyl, or furo[3,2-c]pyridinyl, each of which is optionally substituted with 1 to 3 Z, wherein each Z is independently selected from the group consisting of halogen, $C_{1-5}$alkyl, and $C_{1-5}$alkoxy. In some embodiments, $R_4$ is benzofuranyl or benzothiophenyl, each of which is optionally substituted with 1 to 3 Z, wherein each Z is independently selected from the group consisting of halogen, $C_{1-5}$alkyl, and $C_{1-5}$alkoxy. In some embodiments, $R_4$ is benzofuranyl, optionally substituted with 1 to 3 Z, wherein each Z is independently selected from the group consisting of hydroxy, halogen, $C_{1-5}$alkyl, and $C_{1-5}$alkoxy. In some embodiments, $R_4$ is benzofuranyl or benzothiophenyl.

In some embodiments, $R_4$ is pyridinyl, wherein said $R_4$ is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$. In some embodiments, $R_4$ is pyridinyl, wherein said $R_4$ is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$; $R_6$ is hydrogen or a $C_{1-3}$alkyl group; and $R_7$ is a $C_{1-3}$alkyl group optionally substituted with phenyl, a phenyl, or a heteroaryl selected from the group consisting of pyridinyl, pyrimidinyl, and isoxazolyl.

In some embodiments, $R_4$ is chromenonyl, wherein said $R_4$ is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$. In some embodiments, $R_4$ is chromenonyl, wherein said $R_4$ is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$; $R_6$ is hydrogen or a $C_{1-3}$alkyl group; and $R_7$ is a $C_{1-3}$alkyl group optionally substituted with phenyl, a phenyl, or a heteroaryl selected from the group consisting of pyridinyl, pyrimidinyl, and isoxazolyl.

In some embodiments, $R_4$ is quinazolinyl, wherein said $R_4$ is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$. In some embodiments, $R_4$ is quinazolinyl, wherein said $R_4$ is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$; $R_6$ is hydrogen or a $C_{1-3}$alkyl group; and $R_7$ is a $C_{1-3}$alkyl group optionally substituted with phenyl, a phenyl, or a heteroaryl selected from the group consisting of pyridinyl, pyrimidinyl, and isoxazolyl.

In some embodiments, $R_4$ is benzothiophenyl, wherein said $R_4$ is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$. In some embodiments, $R_4$ is benzothiophenyl, wherein said $R_4$ is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$; $R_6$ is hydrogen or a $C_{1-3}$alkyl group; and $R_7$ is a $C_{1-3}$alkyl group optionally substituted with phenyl, a phenyl, or a heteroaryl selected from the group consisting of pyridinyl, pyrimidinyl, and isoxazolyl.

In some embodiments, $R_4$ is indolinyl, wherein said $R_4$ is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$. In some embodiments, $R_4$ is indolinyl, wherein said $R_4$ is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$; $R_6$ is hydrogen or a $C_{1-3}$alkyl group; and $R_7$ is a $C_{1-3}$alkyl group optionally substituted with phenyl, a phenyl, or a heteroaryl selected from the group consisting of pyridinyl, pyrimidinyl, and isoxazolyl.

In some embodiments, $R_4$ is benzothiazolyl, wherein said $R_4$ is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$. In some embodiments, $R_4$ is benzothiazolyl, wherein said $R_4$ is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$; $R_6$ is hydrogen or a $C_{1-3}$alkyl group; and $R_7$ is a $C_{1-3}$alkyl group optionally substituted with phenyl, a phenyl, or a heteroaryl selected from the group consisting of pyridinyl, pyrimidinyl, and isoxazolyl.

In some embodiments, $R_4$ is furo[3,2-c]pyridinyl, wherein said $R_4$ is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$. In some embodiments, $R_4$ is furo[3,2-c]pyridinyl, wherein said $R_4$ is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$; $R_6$ is hydrogen or a $C_{1-3}$alkyl group; and $R_7$ is a $C_{1-3}$alkyl group optionally substituted with phenyl, a phenyl, or a heteroaryl selected from the group consisting of pyridinyl, pyrimidinyl, and isoxazolyl.

In some embodiments, $R_4$ is naphthyridinyl, wherein said $R_4$ is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$. In some embodiments, $R_4$ is naphthyridinyl, wherein said $R_4$ is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, phenyl optionally substituted with halogen, acetyl, $C_{1-5}$alkylsulfonyl, morpholinyl, —$NR_6C(O)R_7$, and —$C(O)NR_6R_7$; $R_6$ is hydrogen or a $C_{1-3}$alkyl group; and $R_7$ is a $C_{1-3}$alkyl group optionally substituted with phenyl, a phenyl, or a heteroaryl selected from the group consisting of pyridinyl, pyrimidinyl, and isoxazolyl.

In some embodiments, $R_4$ is substituted or unsubstituted pyridinyl. In some embodiments, $R_4$ is substituted or unsubstituted pyrimidinyl. In some embodiments, $R_4$ is substituted or unsubstituted pyrazinyl. In some embodiments, $R_4$ is substituted or unsubstituted imidazolyl. In some embodiments, $R_4$ is substituted or unsubstituted pyrazolyl. In some embodiments, $R_4$ is substituted or unsubstituted triazolyl. In some embodiments, $R_4$ is substituted or unsubstituted oxazolyl. In some embodiments, $R_4$ is substituted or unsubstituted thiazolyl. In some embodiments, $R_4$ is substituted or unsubstituted furanyl. In some embodiments, $R_4$ is substituted or unsubstituted pyrrolyl. In some embodiments, $R_4$ is substituted or unsubstituted thiophenyl. In some embodiments, $R_4$ is substituted or unsubstituted quinolinyl. In some embodiments, $R_4$ is substituted or unsubstituted isoquinolinyl. In some embodiments, $R_4$ is substituted or unsubstituted chromenonyl. In some embodiments, $R_4$ is substituted or unsubstituted quinazolinyl. In some embodiments, $R_4$ is substituted or unsubstituted benzoxazolyl. In some embodiments, $R_4$ is substituted or unsubstituted benzofuranyl. In some embodiments, $R_4$ is substituted or unsubstituted benzothiophenyl. In some embodiments, $R_4$ is substituted or unsubstituted indolyl. In some embodiments, $R_4$ is substituted or unsubstituted indolinyl. In some embodiments, $R_4$ is substituted or unsubstituted benzimidazolyl. In some embodiments, $R_4$ is substituted or unsubstituted benzoxazolyl. In some embodiments, $R_4$ is substituted or unsubstituted benzothiazolyl. In some embodiments, $R_4$ is substituted or unsubstituted indazolyl. In some embodiments, $R_4$ is substituted or unsubstituted furo[3,2-c]pyridinyl. In some embodiments, $R_4$ is substituted or unsubstituted thieno[2,3-d]pyrimidinyl. In some embodiments, $R_4$ is substituted or unsubstituted thieno[3,2-c]pyridinyl. In some embodiments, $R_4$ is substituted or unsubstituted isoxazolyl. In some embodiments, $R_4$ is substituted or unsubstituted acridinyl. In some embodiments, $R_4$ is substituted or unsubstituted naphthyridinyl.

In some embodiments, $R_4$ is a phenyl substituted with a substituent selected from the group consisting of piperazinyl optionally substituted with acetyl, phenyl, phenoxy, benzyl, benzoyl, phenylaminocarbonyl, pyrazolyl, and benzoxazolyl;
a heterocycle selected from the group consisting of benzo[d][1,3]dioxolyl, 2,3-dihydrobenzofuranyl, 2-oxo-1,2-dihydroquinolinyl, and 2-oxo-1,2,3,4-tetrahydroquinolinyl;
a naphthyl optionally substituted with halogen; or
a heteroaryl selected from the group consisting of pyridinyl, quinolinyl, isoquinolinyl, chromenonyl, quinazolinyl, benzofuranyl, indolinyl, benzimidazolyl, benzothiophenyl, benzothiazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z, wherein each Z is independently selected from the group consisting of hydroxy, cyano, nitro, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, acetyl, morpholinyl, —$NR_6C(O)R_7$, —$C(O)NR_6R_7$, and phenyl optionally substituted with halogen;
wherein $R_6$ is hydrogen or a $C_{1-3}$alkyl group; and
$R_7$ is a $C_{1-3}$alkyl group optionally substituted with phenyl,
a phenyl, or
a heteroaryl selected from the group consisting of pyridinyl, pyrimidinyl, and isoxazolyl.

In some embodiments, $R_4$ is a phenyl substituted with a substituent selected from the group consisting of piperazinyl optionally substituted with acetyl, phenyl, phenoxy, benzyl, benzoyl, phenylaminocarbonyl, pyrazolyl, and benzoxazolyl;
a heterocycle selected from the group consisting of benzo[d][1,3]dioxolyl, 2,3-dihydrobenzofuranyl, 2-oxo-1,2-dihydroquinolinyl, and 2-oxo-1,2,3,4-tetrahydroquinolinyl; a naphthyl optionally substituted with halogen; or
a heteroaryl selected from the group consisting of pyridinyl, quinolinyl, isoquinolinyl, quinazolinyl, benzofuranyl, benzothiophenyl, furo[3,2-c]pyridinyl, thieno[2,3-d]pyrimidinyl, thieno[3,2-c]pyridinyl, isoxazolyl, and acridinyl, wherein said heteroaryl is optionally substituted with 1 to 3 Z, wherein each Z is independently selected from the group consisting of hydroxy, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, and phenyl optionally substituted with halogen.

In some embodiments, $R_4$ is a phenyl substituted with phenyl;
a naphthyl; or
a heteroaryl selected from the group consisting of pyridinyl, quinolinyl, isoquinolinyl, chromenonyl, quinazolinyl, benzofuranyl, indolinyl, benzimidazolyl, benzothiophenyl, benzothiazolyl, furo[3,2-c]pyridinyl, and naphthyridinyl, wherein said heteroaryl is optionally substituted with 1 to 3 Z, wherein each Z is independently selected from the group consisting of hydroxy, cyano, nitro, halogen, $C_{1-5}$alkyl optionally substituted 1 to 3 halogens, $C_{1-5}$alkoxy optionally substituted with 1 to 3 halogens, benzyloxy, acetyl, morpholinyl, —$NR_6C(O)R_7$, and —$C(O)NR_6R_7$.

In some embodiments, $R_4$ is a phenyl substituted with phenyl;
a naphthyl; or
a heteroaryl selected from the group consisting of quinolinyl, isoquinolinyl, benzofuranyl, benzothiophenyl, and furo[3,2-c]pyridinyl, wherein said heteroaryl is optionally substituted with 1 to 3 Z, wherein each Z is independently selected from the group consisting of halogen, $C_{1-5}$alkyl optionally substituted 1 to 3 halogens, and $C_{1-5}$alkoxy optionally substituted with 1 to 3 halogens.

In some embodiments, $R_5$ is hydrogen. In some embodiments, $R_5$ is a $C_{1-3}$alkyl.

In some embodiments, $R_6$ is hydrogen. In some embodiments, $R_6$ is a $C_{1-3}$alkyl group.

In some embodiments, $R_7$ is a $C_{1-3}$alkyl group optionally substituted with phenyl.

In some embodiments, $R_7$ is a phenyl optionally substituted with 1 to 3 $Z^2$;
wherein each $Z^2$ is independently selected from the group consisting of hydroxy, amino, halogen, cyano, nitro, hydroxycarbonyl, $C_{1-5}$alkyl optionally substituted by 1 to 3 $Z^3$, $C_{2-6}$alkenyl, $C_{2-6}$alkynyl, $C_{1-5}$alkoxy optionally substituted by 1 to 3 $Z^3$, $C_{1-5}$alkylthio, mono- or di-$C_{1-5}$alkylamino, piperazinyl optionally substituted by $Z^3$, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl; wherein each $Z^3$ is independently chosen from halogen, amino, or acetyl In some embodiments, $R_7$ is a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3- d]pyrimidinyl, thieno[3,2-c]pyridinyl, isoxazolyl, acridinyl, and naphthyridinyl, wherein said heteroaryl is optionally substituted with 1 to 3 $Z^2$;

wherein each $Z^2$ is independently selected from the group consisting of hydroxy, amino, halogen, cyano, nitro, hydroxycarbonyl, $C_{1-5}$alkyl optionally substituted by 1 to 3 $Z^3$, $C_{2-6}$alkenyl, $C_{2-6}$alkynyl, $C_{1-5}$alkoxy optionally substituted by 1 to 3 $Z^3$, $C_{1-5}$alkylthio, mono- or di-$C_{1-5}$alkylamino, piperazinyl optionally substituted by $Z^3$, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl; wherein each $Z^3$ is independently chosen from halogen, amino, or acetyl.

In some embodiments, $R_6$ is hydrogen or a $C_{1-3}$alkyl group; and $R_7$ is a $C_{1-3}$alkyl group optionally substituted with phenyl, a phenyl, or a heteroaryl selected from the group consisting of pyridinyl, pyrimidinyl, and isoxazolyl.

In one embodiment of the present technology, there is provided a compound of Formulas X, Xa, Xb, 1, 1a, 1b, 1c, 1d, or 1e, or a stereoisomer or mixture of stereoisomers thereof, or a pharmaceutically acceptable salt thereof, wherein n is 1 or 2;

$R_1$ is a substituent selected from the group consisting of Formulas I, II, III, and V;

$R_2$ is hydrogen;

$R_3$ is a substituent selected from the group consisting of —$NR_4R_5$, —$OR_4$, —$C(O)NHR_4$, —$NHC(O)(CH_2)_mR_4$, and —$NHS(O)_2R_4$, wherein m is 0 or 1;

$R_4$ is a phenyl substituted with a substituent selected from the group consisting of piperazinyl optionally substituted with acetyl, phenyl, phenoxy, benzyl, benzoyl, phenylaminocarbonyl, pyrazolyl, and benzoxazolyl;

a naphthyl optionally substituted with halogen; or a heteroaryl selected from the group consisting of pyridinyl, quinolinyl, isoquinolinyl, 2-oxo-1,2-dihydroquinolinyl, 2-oxo-1,2,3,4-tetrahydroquinolinyl, quinazolinyl, benzofuranyl, 2,3-dihydrobenzofuranyl, benzothiophenyl, benzo[d][1,3]dioxolyl, furo[3,2-c]pyridinyl, thieno[2,3-d]pyrimidinyl, thieno[3,2-c]pyridinyl, isoxazolyl, and acridinyl, wherein said heteroaryl is optionally substituted with 1 to 3 Z, wherein each Z is independently selected from the group consisting of hydroxy, halogen, $C_{1-5}$alkyl optionally substituted with 1 to 3 halogens, $C_{1-5}$alkoxy optionally substituted with 1 to 3 halogens, $C_{1-5}$alkoxycarbonyl, benzyloxy, and phenyl optionally substituted with halogen), and $R_5$ is hydrogen.

In another aspect, a compound of Formulas X, Xa, Xb, 1, 1, 1a, 1b, 1c, 1d, or 1e, or a stereoisomer or mixture of stereoisomers thereof, or a pharmaceutically acceptable salt thereof is selected from the following compounds, or stereoisomers thereof, or a pharmaceutically acceptable salt thereof:

(R)-1-(2-((S)-2-cyanopyrrolidin-1-yl)-2-oxoethyl)-N-(quinolin-3-yl)pyrrolidine-3-carboxamide;
(R)-1-(2-((S)-2-cyanopyrrolidin-1-yl)-2-oxoethyl)-N-(quinolin-4-yl)pyrrolidine-3-carboxamide;
(S)-1-(2-((S)-2-cyanopyrrolidin-1-yl)-2-oxoethyl)-N-(quinolin-3-yl)pyrrolidine-3-carboxamide;
(S)-1-(2-((S)-2-cyanopyrrolidin-1-yl)-2-oxoethyl)-N-(quinolin-4-yl)pyrrolidine-3-carboxamide;
(S)-1-(2-((S)-3-(quinolin-4-ylamino)pyrrolidin-1-yl)acetyl)pyrrolidine-2-carbonitrile;
(S)-4,4-difluoro-1-(2-((S)-3-(quinolin-3-ylamino)pyrrolidin-1-yl)acetyl)pyrrolidine-2-carbonitrile;
(S)-4,4-difluoro-1-(2-((S)-3-(quinolin-4-ylamino)pyrrolidin-1-yl)acetyl)pyrrolidine-2-carbonitrile;
(S)-4,4-difluoro-1-(2-((S)-3-(isoquinolin-4-ylamino)pyrrolidin-1-yl)acetyl)pyrrolidine-2-carbonitrile;
(S)-1-(2-((S)-3-(benzo[b]thiophen-4-ylamino)pyrrolidin-1-yl)acetyl)-4,4-difluoropyrrolidine-2-carbonitrile;
(S)-1-(2-((S)-3-(benzo[b]thiophen-7-ylamino)pyrrolidin-1-yl)acetyl)-4,4-difluoropyrrolidine-2-carbonitrile;
(S)-1-(2-((S)-3-(benzofuran-7-ylamino)pyrrolidin-1-yl)acetyl)-4,4-difluoropyrrolidine-2-carbonitrile;
(S)-4,4-difluoro-1-(2-((S)-3-(furo[3,2-c]pyridin-7-ylamino)pyrrolidin-1-yl)acetyl)pyrrolidine-2-carbonitrile;
(S)-1-(2-((S)-3-([1,1'-biphenyl]-2-ylamino)pyrrolidin-1-yl)acetyl)-4,4-difluoropyrrolidine-2-carbonitrile;
(S)-1-(2-((S)-3-([1,1'-biphenyl]-4-ylamino)pyrrolidin-1-yl)acetyl)-4,4-difluoropyrrolidine-2-carbonitrile;
(S)-4,4-difluoro-1-(2-((S)-3-(naphthalen-2-ylamino)pyrrolidin-1-yl)acetyl)pyrrolidine-2-carbonitrile;
(S)-1-(2-((S)-3-([1,1'-biphenyl]-3-ylamino)pyrrolidin-1-yl)acetyl)-4,4-difluoropyrrolidine-2-carbonitrile;
(S)-1-(2-(R)-3-(quinolin-3-ylamino)pyrrolidin-1-yl)acetyl)pyrrolidine-2-carbonitrile;
(S)-1-(2-((R)-3-([1,1'-biphenyl]-3-ylamino)pyrrolidin-1-yl)acetyl)pyrrolidine-2-carbonitrile;
(S)-1-(2-((S)-3-(isoquinolin-4-ylamino)pyrrolidin-1-yl)acetyl)pyrrolidine-2-carbonitrile;
(S)-1-(2-((S)-3-(benzo[b]thiophen-4-ylamino)pyrrolidin-1-yl)acetyl)pyrrolidine-2-carbonitrile;
(S)-1-(2-((S)-3-(benzo[b]thiophen-7-ylamino)pyrrolidin-1-yl)acetyl)pyrrolidine-2-carbonitrile;
(S)-1-(2-((S)-3-(benzofuran-7-ylamino)pyrrolidin-1-yl)acetyl)pyrrolidine-2-carbonitrile;
(S)-1-(2-((S)-3-(furo[3,2-c]pyridin-7-ylamino)pyrrolidin-1-yl)acetyl)pyrrolidine-2-carbonitrile;
(S)-1-(2-((R)-3-(isoquinolin-4-ylamino)pyrrolidin-1-yl)acetyl)pyrrolidine-2-carbonitrile;
(S)-1-(2-((R)-3-(benzo[b]thiophen-7-ylamino)pyrrolidin-1-yl)acetyl)pyrrolidine-2-carbonitrile;
(1S,3S,5S)-2-(2-((S)-3-(furo[3,2-c]pyridin-7-ylamino)pyrrolidin-1-yl)acetyl)-2-azabicyclo[3.1.0]hexane-3-carbonitrile;
(S)-1-(2-((S)-3-(quinolin-5-ylamino)pyrrolidin-1-yl)acetyl)pyrrolidine-2-carbonitrile; (2S,4S)-4-fluoro-1-(2-((S)-3-(furo[3,2-c]pyridin-7-ylamino)pyrrolidin-1-yl)acetyl)pyrrolidin-2-carbonitrile;
N—((S)-1-(2-((2S,4S)-2-cyano-4-fluoropyrrolidin-1-yl)-2-oxoethyl)pyrrolidin-3-yl)-6-fluorobenzofuran-3-carboxamide;
N—((S)-1-(2-((S)-2-cyanopyrrolidin-1-yl)-2-oxoethyl)pyrrolidin-3-yl)quinoline-4-carboxamide;
N—((S)-1-(2-((S)-2-cyanopyrrolidin-1-yl)-2-oxoethyl)pyrrolidin-3-yl)quinoline-3-carboxamide;
N—((S)-1-(2-((S)-2-cyanopyrrolidin-1-yl)-2-oxoethyl)pyrrolidin-3-yl)quinoline-5-carboxamide;
N—((S)-1-(2-((S)-2-cyanopyrrolidin-1-yl)-2-oxoethyl)pyrrolidin-3-yl)quinoline-2-carboxamide;
N—((S)-1-(2-((S)-2-cyanopyrrolidin-1-yl)-2-oxoethyl)pyrrolidin-3-yl)quinoline-8-carboxamide;
N—((S)-1-(2-((S)-2-cyanopyrrolidin-1-yl)-2-oxoethyl)pyrrolidin-3-yl)isoquinoline-1-carboxamide;
N—((S)-1-(2-((S)-2-cyanopyrrolidin-1-yl)-2-oxoethyl)pyrrolidin-3-yl)benzo[b]thiophene-2-carboxamide;
N—((S)-1-(2-((S)-2-cyanopyrrolidin-1-yl)-2-oxoethyl)pyrrolidin-3-yl)benzofuran-3-carboxamide;

N—((S)-1-(2-((S)-2-cyanopyrrolidin-1-yl)-2-oxoethyl)pyrrolidin-3-yl)-2-(naphthalen-1-yl)acetamide;
N—((S)-1-(2-((S)-2-cyanopyrrolidin-1-yl)-2-oxoethyl)pyrrolidin-3-yl)-[1,1'-biphenyl]-2-carboxamide;
N—((S)-1-(2-((S)-2-cyanopyrrolidin-1-yl)-2-oxoethyl)pyrrolidin-3-yl)benzofuran-2-carboxamide;
N—((S)-1-(2-((S)-2-cyanopyrrolidin-1-yl)-2-oxoethyl)pyrrolidin-3-yl)benzo[b]thiophene-3-carboxamide;
N—((S)-1-(2-((S)-2-cyanopyrrolidin-1-yl)-2-oxoethyl)pyrrolidin-3-yl)-2-methylbenzofuran-3-carboxamide;
N—((S)-1-(2-((S)-2-cyanopyrrolidin-1-yl)-2-oxoethyl)pyrrolidin-3-yl)-5-fluorobenzofuran-3-carboxamide;
N—((S)-1-(2-((S)-2-cyanopyrrolidin-1-yl)-2-oxoethyl)pyrrolidin-3-yl)-6-fluorobenzofuran-3-carboxamide;
N—((S)-1-(2-((S)-2-cyanopyrrolidin-1-yl)-2-oxoethyl)pyrrolidin-3-yl)-7-methylbenzofuran-3-carboxamide;
N—((S)-1-(2-((S)-2-cyanopyrrolidin-1-yl)-2-oxoethyl)pyrrolidin-3-yl)-5-methoxybenzofuran-3-carboxamide;
N—((S)-1-(2-((S)-2-cyanopyrrolidin-1-yl)-2-oxoethyl)pyrrolidin-3-yl)-7-methoxybenzofuran-3-carboxamide;
N—((S)-1-(2-((S)-2-cyanopyrrolidin-1-yl)-2-oxoethyl)pyrrolidin-3-yl)-4-hydroxybenzofuran-3-carboxamide;
N—((S)-1-(2-((S)-2-cyanopyrrolidin-1-yl)-2-oxoethyl)pyrrolidin-3-yl)-6-hydroxybenzofuran-3-carboxamide;
N—((S)-1-(2-((S)-2-cyanopyrrolidin-1-yl)-2-oxoethyl)pyrrolidin-3-yl)-7-fluorobenzofuran-3-carboxamide;
N—((S)-1-(2-((S)-2-cyanopyrrolidin-1-yl)-2-oxoethyl)pyrrolidin-3-yl)-5,7-difluorobenzofuran-3-carboxamide;
N—((S)-1-(2-((S)-2-cyanopyrrolidin-1-yl)-2-oxoethyl)pyrrolidin-3-yl)-5-methylbenzofuran-3-carboxamide;
N—((S)-1-(2-((S)-2-cyanopyrrolidin-1-yl)-2-oxoethyl)pyrrolidin-3-yl)-6-methylbenzofuran-3-carboxamide;
N—((S)-1-(2-((S)-2-cyanopyrrolidin-1-yl)-2-oxoethyl)pyrrolidin-3-yl)-6-methoxybenzofuran-3-carboxamide;
N—((S)-1-(2-((S)-2-cyanopyrrolidin-1-yl)-2-oxoethyl)pyrrolidin-3-yl)benzofuran-4-carboxamide;
N—((S)-1-(2-((S)-2-cyanopyrrolidin-1-yl)-2-oxoethyl)pyrrolidin-3-yl)benzofuran-5-carboxamide;
N—((S)-1-(2-((S)-2-cyanopyrrolidin-1-yl)-2-oxoethyl)pyrrolidin-3-yl)benzofuran-6-carboxamide;
N—((S)-1-(2-((S)-2-cyanopyrrolidin-1-yl)-2-oxoethyl)pyrrolidin-3-yl)benzofuran-7-carboxamide;
N—((S)-1-(2-((S)-2-cyanopyrrolidin-1-yl)-2-oxoethyl)pyrrolidin-3-yl)benzofuran-2-sulfonamide;
N—((S)-1-(2-((S)-2-cyanopyrrolidin-1-yl)-2-oxoethyl)pyrrolidin-3-yl)benzo[b]thiophene-2-sulfonamide;
(S)-1-(2-((S)-3-(quinolin-4-yloxy)pyrrolidin-1-yl)acetyl)pyrrolidine-2-carbonitrile;
(S)-1-(2-((S)-3-(naphthalen-1-yloxy)pyrrolidin-1-yl)acetyl)pyrrolidine-2-carbonitrile;
(S)-1-(2-((S)-3-(quinolin-6-yloxy)pyrrolidin-1-yl)acetyl)pyrrolidine-2-carbonitrile;
(S)-1-(2-((S)-3-(quinolin-8-yloxy)pyrrolidin-1-yl)acetyl)pyrrolidine-2-carbonitrile;
(S)-1-(2-((S)-3-(isoquinolin-5-yloxy)pyrrolidin-1-yl)acetyl)pyrrolidine-2-carbonitrile;
(S)-1-(2-((S)-3-(quinolin-5-yloxy)pyrrolidin-1-yl)acetyl)pyrrolidine-2-carbonitrile;
(S)-1-(2-((S)-3-(benzo[d][1,3]dioxol-5-yloxy)pyrrolidin-1-yl)acetyl)pyrrolidine-2-carbonitrile;
(S)-1-(2-((S)-3-(thieno[2,3-d]pyrimidin-4-yloxy)pyrrolidin-1-yl)acetyl)pyrrolidine-2-carbonitrile;
(S)-1-(2-((S)-3-(isoquinolin-3-yloxy)pyrrolidin-1-yl)acetyl)pyrrolidine-2-carbonitrile;
(S)-1-(2-((S)-3-((3-bromothieno[3,2-c]pyridin-4-yl)oxy)pyrrolidin-1-yl)acetyl)pyrrolidine-2-carbonitrile;
(S)-1-(2-((S)-3-((4-chloronaphthalen-1-yl)oxy)pyrrolidin-1-yl)acetyl)pyrrolidine-2-carbonitrile;
(S)-1-(2-((S)-3-(2-(1H-pyrazol-3-yl)phenoxy)pyrrolidin-1-yl)acetyl)pyrrolidine-2-carbonitrile;
(S)-1-(2-((S)-3-((4-chloroquinazolin-8-yl)oxy)pyrrolidin-1-yl)acetyl)pyrrolidine-2-carbonitrile;
(S)-1-(2-((S)-3-((4-chloroquinazolin-6-yl)oxy)pyrrolidin-1-yl)acetyl)pyrrolidine-2-carbonitrile;
(S)-1-(2-((S)-3-((2-oxo-1,2-dihydroquinolin-5-yl)oxy)pyrrolidin-1-yl)acetyl)pyrrolidine-2-carbonitrile;
(S)-1-(2-((S)-3-((2-oxo-1,2,3,4-tetrahydroquinolin-5-yl)oxy)pyrrolidin-1-yl)acetyl)pyrrolidine-2-carbonitrile;
(S)-1-(2-((S)-3-((2-oxo-1,2,3,4-tetrahydroquinolin-6-yl)oxy)pyrrolidin-1-yl)acetyl)pyrrolidine-2-carbonitrile;
(S)-1-(2-((S)-3-((2-methylquinolin-8-yl)oxy)pyrrolidin-1-yl)acetyl)pyrrolidine-2-carbonitrile;
(S)-1-(2-((S)-3-((7-chloroquinolin-4-yl)oxy)pyrrolidin-1-yl)acetyl)pyrrolidine-2-carbonitrile;
(S)-1-(2-((S)-3-((7-bromoquinolin-4-yl)oxy)pyrrolidin-1-yl)acetyl)pyrrolidine-2-carbonitrile;
(S)-1-(2-((S)-3-((5-chloroquinolin-8-yl)oxy)pyrrolidin-1-yl)acetyl)pyrrolidine-2-carbonitrile;
(S)-1-(2-((S)-3-([1,1'-biphenyl]-3-yloxy)pyrrolidin-1-yl)acetyl)pyrrolidine-2-carbonitrile;
(S)-1-(2-((S)-3-([1,1'-biphenyl]-4-yloxy)pyrrolidin-1-yl)acetyl)pyrrolidine-2-carbonitrile;
(S)-1-(2-((S)-3-((6-methoxyquinolin-4-yl)oxy)pyrrolidin-1-yl)acetyl)pyrrolidine-2-carbonitrile;
(S)-1-(2-((S)-3-((7,8-difluoroquinolin-4-yl)oxy)pyrrolidin-1-yl)acetyl)pyrrolidine-2-carbonitrile;
methyl 6-(((S)-1-(2-((S)-2-cyanopyrrolidin-1-yl)-2-oxoethyl)pyrrolidin-3-yl)oxy)-2,3-dihydrobenzofuran-2-carboxylate;
(S)-1-(2-((S)-3-(4-phenoxyphenoxy)pyrrolidin-1-yl)acetyl)pyrrolidine-2-carbonitrile;
(S)-1-(2-((S)-3-(3-phenoxyphenoxy)pyrrolidin-1-yl)acetyl)pyrrolidine-2-carbonitrile;
(S)-1-(2-((S)-3-(4-benzylphenoxy)pyrrolidin-1-yl)acetyl)pyrrolidine-2-carbonitrile;
(S)-1-(2-((S)-3-(2-benzylphenoxy)pyrrolidin-1-yl)acetyl)pyrrolidine-2-carbonitrile;
(S)-1-(2-((S)-3-(3-benzoylphenoxy)pyrrolidin-1-yl)acetyl)pyrrolidine-2-carbonitrile;
(S)-1-(2-((S)-3-(4-benzoylphenoxy)pyrrolidin-1-yl)acetyl)pyrrolidine-2-carbonitrile;
(S)-1-(2-((S)-3-((4-(benzyloxy)pyridin-2-yl)oxy)pyrrolidin-1-yl)acetyl)pyrrolidine-2-carbonitrile;
(S)-1-(2-((S)-3-((7-(trifluoromethyl)quinolin-4-yl)oxy)pyrrolidin-1-yl)acetyl)pyrrolidine-2-carbonitrile;
(S)-1-(2-((S)-3-((8-(trifluoromethyl)quinolin-4-yl)oxy)pyrrolidin-1-yl)acetyl)pyrrolidine-2-carbonitrile;
(S)-1-(2-((S)-3-(acridin-4-yloxy)pyrrolidin-1-yl)acetyl)pyrrolidine-2-carbonitrile;
(S)-1-(2-((S)-3-(2-(benzo[d]oxazol-2-yl)phenoxy)pyrrolidin-1-yl)acetyl)pyrrolidine-2-carbonitrile;
(S)-1-(2-((S)-3-(4-(4-acetylpiperazin-1-yl)phenoxy)pyrrolidin-1-yl)acetyl)pyrrolidine-2-carbonitrile;
2-(((S)-1-(2-((S)-2-cyanopyrrolidin-1-yl)-2-oxoethyl)pyrrolidin-3-yl)oxy)-N-phenylbenzamide;
(S)-1-(2-((S)-3-((7-methoxyquinolin-4-yl)oxy)pyrrolidin-1-yl)acetyl)pyrrolidine-2-carbonitrile;
(S)-1-(2-((S)-3-((6,7-dimethoxyquinolin-4-yl)oxy)pyrrolidin-1-yl)acetyl)pyrrolidine-2-carbonitrile;
(S)-1-(2-((S)-3-((3-(4-bromophenyl)isoxazol-5-yl)oxy)pyrrolidin-1-yl)acetyl)pyrrolidine-2-carbonitrile;
(S)-4,4-difluoro-1-(2-((S)-3-((6-methoxyquinolin-4-yl)oxy)pyrrolidin-1-yl)acetyl)pyrrolidine-2-carbonitrile;

(S)-4,4-difluoro-1-(2-((S)-3-((8-(trifluoromethyl)quinolin-4-yl)oxy)pyrrolidin-1-yl)acetyl)pyrrolidine-2-carbonitrile;

(S)-4,4-difluoro-1-(2-((S)-3-(quinolin-5-yloxy)pyrrolidin-1-yl)acetyl)pyrrolidine-2-carbonitrile;

(S)-4,4-difluoro-1-(2-((S)-3-(isoquinolin-5-yloxy)pyrrolidin-1-yl)acetyl)pyrrolidine-2-carbonitrile;

(S)-1-(2-((S)-3-((7-chloroquinolin-4-yl)oxy)pyrrolidin-1-yl)acetyl)-4,4-difluoropyrrolidine-2-carbonitrile;

(S)-4,4-difluoro-1-(2-((S)-3-((2-oxo-1,2-dihydroquinolin-5-yl)oxy)pyrrolidin-1-yl)acetyl)pyrrolidine-2-carbonitrile;

(S)-1-(2-((S)-3-((5-chloroquinolin-8-yl)oxy)pyrrolidin-1-yl)acetyl)-4,4-difluoropyrrolidine-2-carbonitrile;

(S)-1-(2-(4-(quinolin-5-ylamino)piperidin-1-yl)acetyl)pyrrolidine-2-carbonitrile;

(S)-1-(2-(4-(quinolin-4-ylamino)piperidin-1-yl)acetyl)pyrrolidine-2-carbonitrile;

(1S,3S,5S)-2-(2-(4-(quinolin-4-ylamino)piperidin-1-yl)acetyl)-2-azabicyclo[3.1.0]hexane-3-carbonitrile;

(2S,4S)-4-fluoro-1-(2-(4-(quinolin-5-ylamino)piperidin-1-yl)acetyl)pyrrolidine-2-carbonitrile;

(S)-4,4-difluoro-1-(2-(4-(quinolin-5-ylamino)piperidin-1-yl)acetyl)pyrrolidine-2-carbonitrile;

(1S,3S,5S)-2-(2-(4-(quinolin-5-ylamino)piperidin-1-yl)acetyl)-2-azabicyclo[3.1.0]hexane-3-carbonitrile;

(S)-1-(2-(4-(furo[3,2-c]pyridin-7-ylamino)piperidin-1-yl)acetyl)pyrrolidine-2-carbonitrile;

(S)-1-(2-(4-(quinolin-3-yloxy)piperidin-1-yl)acetyl)pyrrolidine-2-carbonitrile;

(S)-1-(2-(4-(quinolin-4-yloxy)piperidin-1-yl)acetyl)pyrrolidine-2-carbonitrile;

(S)-1-(2-(4-(quinolin-5-yloxy)piperidin-1-yl)acetyl)pyrrolidine-2-carbonitrile;

(S)-1-(2-(4-(quinolin-6-yloxy)piperidin-1-yl)acetyl)pyrrolidine-2-carbonitrile;

(S)-1-(2-(4-((3-methylquinolin-5-yl)amino)piperidin-1-yl)acetyl)pyrrolidine-2-carbonitrile;

(S)-1-(2-(4-((6-methylquinolin-5-yl)amino)piperidin-1-yl)acetyl)pyrrolidine-2-carbonitrile;

(S)-1-(2-(4-((7-fluoroquinolin-5-yl)amino)piperidin-1-yl)acetyl)pyrrolidine-2-carbonitrile;

(S)-1-(2-(4-((7-methoxyquinolin-5-yl)amino)piperidin-1-yl)acetyl)pyrrolidine-2-carbonitrile;

(S)-1-(2-(4-((8-methoxyquinolin-5-yl)amino)piperidin-1-yl)acetyl)pyrrolidine-2-carbonitrile;

(2S,4S)-4-fluoro-1-(2-(4-((6-fluoroquinolin-4-yl)oxy)piperidin-1-yl)acetyl)pyrrolidine-2-carbonitrile;

(2S,4S)-1-(2-(4-((6-chloroquinolin-4-yl)oxy)piperidin-1-yl)acetyl)-4-fluoropyrrolidine-2-carbonitrile;

(2S,4S)-4-fluoro-1-(2-(4-((6-methoxyquinolin-4-yl)oxy)piperidin-1-yl)acetyl)pyrrolidine-2-carbonitrile;

(2S,4S)-4-fluoro-1-(2-(4-((7-methoxyquinolin-4-yl)oxy)piperidin-1-yl)acetyl)pyrrolidine-2-carbonitrile;

(2S,4S)-1-(2-(4-((6,7-dimethoxyquinolin-4-yl)oxy)piperidin-1-yl)acetyl)-4-fluoropyrrolidine-2-carbonitrile;

(2S,4S)-4-fluoro-1-(2-(4-((3-methylquinolin-5-yl)amino)piperidin-1-yl)acetyl)pyrrolidine-2-carbonitrile;

(2S,4S)-4-fluoro-1-(2-(4-((7-fluoroquinolin-5-yl)amino)piperidin-1-yl)acetyl)pyrrolidine-2-carbonitrile;

(2S,4S)-4-fluoro-1-(2-(4-((7-methoxyquinolin-5-yl)amino)piperidin-1-yl)acetyl)pyrrolidine-2-carbonitrile;

(2S,4S)-4-fluoro-1-(2-(4-((6-methylquinolin-5-yl)amino)piperidin-1-yl)acetyl)pyrrolidine-2-carbonitrile; and (2S,4S)-4-fluoro-1-(2-(4-((8-methoxyquinolin-5-yl)amino)piperidin-1-yl)acetyl)pyrrolidine-2-carbonitrile.

In another aspect, a compound of Formulas X, Xa, Xb, 1, 1, 1a, 1b, 1c, 1d, or 1e, or a stereoisomer or mixture of stereoisomers thereof, or a pharmaceutically acceptable salt thereof is selected from the compounds listed in Table 1, or a stereoisomer or mixture of stereoisomers thereof, or a pharmaceutically acceptable salt thereof.

The compound of Formulas X, Xa, Xb, 1, 1a, 1b, 1c, 1d, or 1e, or the pharmaceutically acceptable salt thereof can have a substituent comprising asymmetric carbon (e.g., a substituent of $R_2$). In this case, the compound of Formula 1 or a salt thereof may exist as an optical isomer, such as (R) or (S), or a racemate (RS). Thus, unless indicated otherwise, the compound of Formula 1 or a salt thereof comprises both an optical isomer, such as (R) or (S), and a racemate (RS). Further, in some embodiments, the compound of Formula 1 or a salt thereof may exist as the geometric isomer of a double-bond cis- or trans-structure depending on the substituent. Thus, in some embodiments, unless indicated otherwise, the compound of Formula 1 or salt thereof comprises both geometric isomers of cis- and trans-structures. Further, the compound of Formula 1 or a salt thereof may exist as a diastereomer and, unless indicated otherwise, comprises both diastereomers and mixtures thereof.

The compounds provided in the description are inhibitors of FAP. FAP inhibition may be measured, for example, by determining the half maximal inhibitory concentration ($IC_{50}$). One method for determining an $IC_{50}$ for FAP is provided in the experimental section.

In some embodiments, the compounds are selective inhibitors of FAP. Selectivity may be determined, for example, by comparing inhibition of FAP to inhibition to other DPP families such as DPP7 (dipeptidyl peptidase 7), DPP8 (dipeptidyl peptidase 8), DPP9 (dipeptidyl peptidase 9), or PREP (prolyl oligopeptidase). In one embodiment, "selective inhibitory activity" means $IC_{50}$ for FAP obtained from the in vitro enzyme analysis (in vitro enzyme assay) test is at least 100 times lower than $IC_{50}$ of DPP7, at least 100 times lower than $IC_{50}$ of DPP8, at least 100 times lower than $IC_{50}$ of DPP9, or at least 100 times lower than $IC_{50}$ of PREP. In an alternative embodiment, "selective inhibitory activity" means the $IC_{50}$ for FAP obtained from the in vitro enzyme analysis (in vitro enzyme assay) test is at least 100 times lower than $IC_{50}$ of DPP7, at least 100 times lower than $IC_{50}$ of DPP8, at least 100 times lower than $IC_{50}$ of DPP9, and at least 100 times lower than $IC_{50}$ of PREP.

The compound of Formula 1 of the present technology can be in the form of a pharmaceutically acceptable salt. The term "pharmaceutically acceptable salt," as used herein, represents salts or zwitterionic forms of the compounds of the present technology which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by, for example, reacting the appropriate compound in the form of the free base with a suitable acid. Such salts include conventional acid addition salts, e.g., a salt derived from inorganic acid such as hydrochloric acid, bromic acid, sulfuric acid, sulfamic acid, phosphoric acid, or nitric acid and a salt derived from organic acid such as acetic acid, propionic acid, succinic acid, glycolic acid, stearic acid, citric acid, maleic acid, malonic acid, methanesulfonic acid, tartaric acid, malic acid, phenylacetic acid, glutamic acid, benzoic acid, salicylic acid, 2-acetoxybenzoic acid, fumaric acid, p-toluenesulfonic acid, oxalic acid or trifluoroacetic acid. Further, said salts include conventional metal salt types, e.g. a salt derived from a metal such as lithium, sodium, potassium, magnesium, or calcium. Said acid addition salt or metal salt can be prepared according to conventional methods.

The compound of Formula 1 or a salt thereof according to the technology may be prepared by various methods. For example, a compound of Formula 1a wherein $R_3$ of Formula 1 is —$NR_4R_5$, or a salt thereof can be prepared by a preparation process comprising the step of reacting a compound of Formula 2a with $R_4X$ to prepare a compound of Formula 3a; the step of conducting deprotection reaction of the compound of Formula 3a above to prepare a compound of Formula 4a or a salt thereof, and the step of reacting the compound of Formula 4a above or a salt thereof with a compound of Formula 5 to form a compound of Formula 1a.

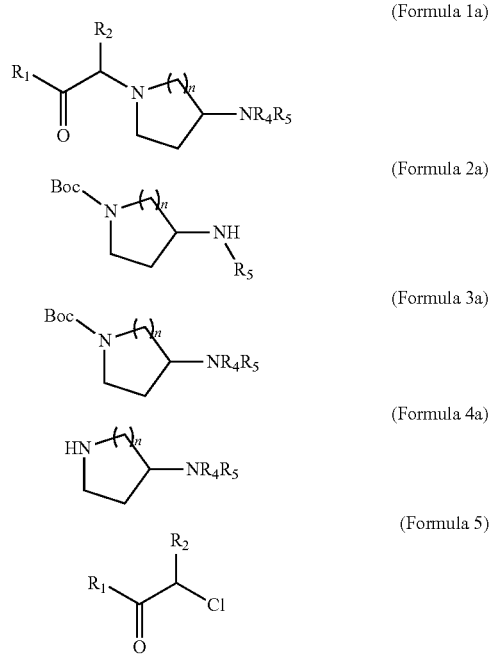

In said Formulas 1a, 2a, 3a, 4a, and 5, X is a halogen (e.g., Br, F, Cl, Br, or I), Boc is an amine protecting group (e.g., tert-butoxycarbonyl, 9-fluorenylmethyloxycarbonyl (FMOC), benzyloxycarbonyl (CBZ), triphenylmethyl(trityl), etc.), and $R_1$, $R_2$, $R_4$, $R_5$, and n are the same as defined above.

The compound of Formula 2a is commercially available. The reaction of the compound of Formula 2a above with $R_4X$ may be carried out by using a palladium catalyst via Buchwald-Hartwig reaction. The palladium catalyst includes palladium diacetate ($Pd(OAc)_2$), tris(dibenzylideneacetone)dipalladium ($Pd_2(dba)_3$), tetrakis(triphenylphosphine)palladium ($Pd(PPh_3)_4$) or palladiumdi[1,1'-bis(diphenylphosphino)ferrocene]dichloride ($PdCl_2(dppf)_2$), etc. Further, a ligand and a base can be added in addition to the palladium catalyst. Said ligand includes (S)-2,2-bis(diphenylphospino)-1,1-binaphthyl (BINAP), 1,1'-bis(diphenylphospino)ferrocene(dppf) or (tri-O-tolyl)phosphine(P(O-Tol)$_3$), etc., and said base includes an inorganic base such as cesium carbonate ($Cs_2CO_3$), sodium carbonate ($Na_2CO_3$), potassium carbonate ($K_2CO_3$), potassium fluoride (KF), cesium fluoride (CsF), sodium hydroxide (NaOH), potassium phosphonate ($K_3PO_4$), sodium tert-butoxide (tert-BuONa), potassium tert-butoxide (tert-BuOK), or the like. The reaction may be carried out, in a non-polar organic solvent such as benzene or toluene, or a polar organic solvent such as dioxane, tetrahydrofuran, acetonitrile, 1,2-dimethoxyethane, N,N-dimethylformamide, or the like, at a temperature ranging from 50° C. to 150° C., preferably from 80° C. to 110° C. Other reaction conditions, including e.g., reaction time, may be determined according to known methods for the Buchwald-Hartwig reaction (Barbara Czako et al, STRATEGIC APPLICATIONS of NAMED REACTIONS in ORGANIC SYNTHESIS, 2005).

In some embodiments, the reaction of the compound of Formula 2a with $R_4X$ is carried out via nucleophilic substitution. The nucleophilic substitution reaction may be carried out at room temperature or reflux conditions (20° C. to 120° C.) by using a base such as cesium carbonate, potassium carbonate, etc., in a solvent such as acetonitrile, dichloromethane, or the like.

Deprotection of the compound of Formula 3a can be carried out by conventional methods of removing an amine protecting group. For example, said amine protecting group in an organic solvent such as dichloromethane, etc. can be removed by using an acid such as trifluoroacetic acid or can be removed in the form of a hydrochloride salt by using hydrogen chloride dissolved in the organic solvents, such as diethyl ether, 1,4-dioxane, etc.

The reaction of the compound of Formula 4a above or a salt thereof with a compound of Formula 5 may be carried out via nucleophilic substitution. The nucleophilic substitution reaction can be carried out at room temperature or warm temperature conditions (20° C. to 60° C.) by using a base such as cesium carbonate, potassium carbonate, etc., in a solvent such as acetonitrile, dichloromethane, or the like.

The compound of Formula 5 above can be prepared by reacting the compound of Formula 6 with the compounds of Formulas $R_1a$-$R_1e$, respectively.

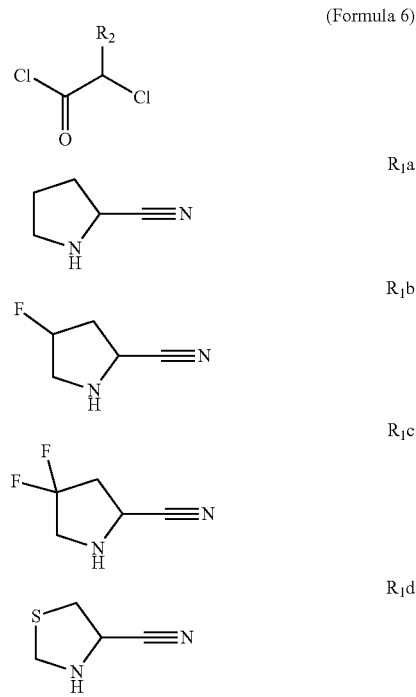

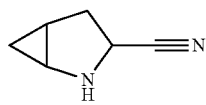

In said Formula 6, $R_2$ is the same as defined in the above.

The compound of Formula 6 and the compounds of Formulas $R_1a$ to $R_1e$ are commercially available. The reaction of the compound of Formula 6 with the compounds of Formulas $R_1a$-$R_1e$ can be converted to a compound of Formula 5 via nucleophilic acylsubstitution. The nucleophilic acyl-substitution reaction can be carried out by using cesium carbonate, potassium carbonate, etc., in a solvent such as acetonitrile, dichloromethane, or the like, and can be carried out at 0° C. to room temperature.

Further, the present technology includes a preparation process of a compound of Formula 1b wherein $R_3$ is —$OR_4$, or a stereoisomer or mixture of stereoisomers thereof, or a pharmaceutically acceptable salt thereof. That is, the present technology includes a preparation process of a compound of Formula 1b, or a stereoisomer or mixture of stereoisomers thereof, or a pharmaceutically acceptable salt thereof, comprising the step of reacting a compound of Formula 2b with $R_4$—OH to prepare a compound of Formula 3b; the step of carrying out deprotection reaction of the compound of Formula 3b above to prepare a compound of Formula 4b or a salt thereof; and the step of reacting a compound of Formula 4b or a salt thereof with a compound of Formula 5 to give a compound of Formula 1b.

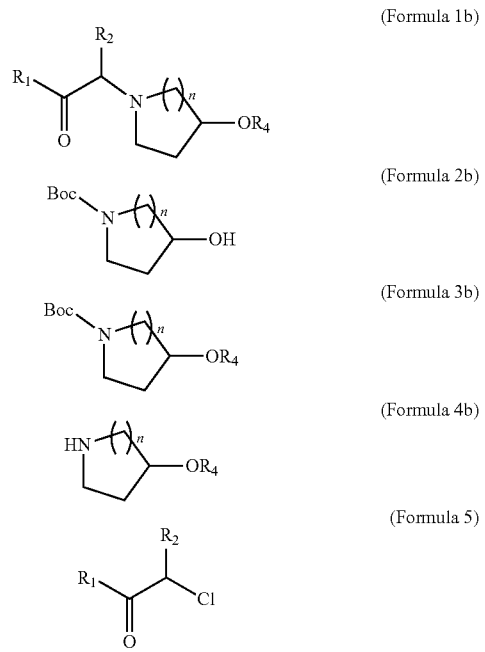

In said Formulas 1b, 2b, 3b, 4b, and 5, Boc is an amine protecting group (e.g., tert-butoxycarbonyl, 9-fluorenylmethyloxycarbonyl (FMOC), benzyloxycarbonyl(CBZ), triphenylmethyl(trityl), etc.) and $R_1$, $R_2$, $R_4$ and n are the same as defined in the above.

The compound of Formula 2b is commercially available. The reaction of the compound of Formula 2b above with $R_4$—OH may be carried out via Mitsunobu reaction. The Mitsunobu reaction can be carried out at room temperature or warm temperature conditions (20° C. to 60° C.) by using dialkyl azodicarboxylate such as diethyl azodicarboxylate (DEAD), diisopropyl azodicarboxylate (DIAD), di-2-methoxyethyl azodicarboxylate (DMEAD), 1,1'-(azodicarbonyl)dipiperidine, etc. and trialkylphosphine or triarylphosphine such as triphenylphosphine ($PPh_3$), tributylphosphine ($PBu_3$), etc. Other reaction conditions, including e.g., reaction time, may be determined according to known methods for the Mitsunobu reaction (Barbara Czako and Laszlo Kurti, STRATEGIC APPLICATIONS of NAMED REACTIONS in ORGANIC SYNTHESIS, 2005).

Deprotection of the compound of Formula 3b can be carried out by conventional methods of removing an amine protecting group. For example, said amine protecting group in an organic solvent such as dichloromethane, etc. can be removed by using an acid such as trifluoroacetic acid or can be removed in the form of a hydrochloride salt by using hydrogen chloride dissolved in the organic solvents, such as diethyl ether, 1,4-dioxane, etc.

The reaction of the compound of Formula 4b above or a salt thereof with a compound of Formula 5 may be carried out via nucleophilic substitution. The nucleophilic substitution reaction can be carried out at room temperature or warm temperature conditions (20° C. to 60° C.) by using a base such as cesium carbonate, potassium carbonate, etc., in a solvent such as acetonitrile, dichloromethane, or the like.

The present technology includes a preparation process of a compound of Formula 1b, or a stereoisomer or mixture of stereoisomers thereof, or a pharmaceutically acceptable salt thereof, comprising the step of reacting a compound of Formula 5 with a compound of Formula 7 to prepare a compound of Formula 8; the step of reacting the compound of Formula 8 above with $R_4$—OH to prepare a compound of Formula 1b.

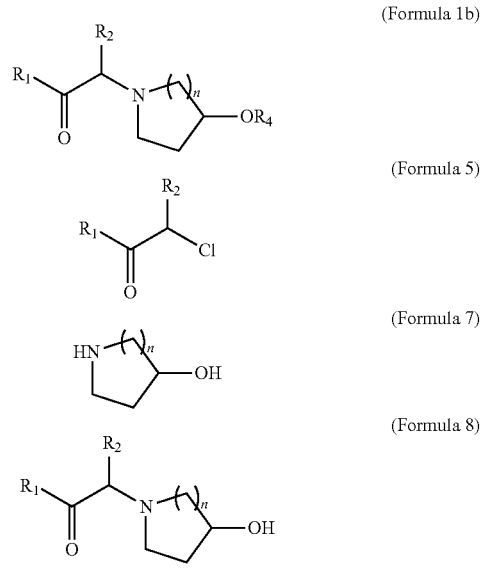

In said Formulas 1b, 5, 7, and 8, $R_1$, $R_2$, $R_4$, and n are the same as defined in the above.

The compound of Formula 7 is commercially available. The reaction of the compound of Formula 5 above with the compound of Formula 7 may be carried out via nucleophilic substitution. The nucleophilic substitution reaction can be carried out at room temperature or warm temperature conditions (20° C. to 60° C.) by using a base such as cesium carbonate, potassium carbonate, etc., in a solvent such as acetonitrile, dichloromethane, or the like.

The reaction of the compound of Formula 8 above with $R_4$—OH may be carried out via the Mitsunobu reaction.

Further, the present technology includes a preparation process of a compound of Formula 1c wherein $R_3$ of Formula 1 is —C(O)NHR$_4$, or a stereoisomer or mixture of stereoisomers thereof, or a pharmaceutically acceptable salt thereof. That is, the present technology includes a preparation process of a compound of Formula 1c, or a stereoisomer or mixture of stereoisomers thereof, or a pharmaceutically acceptable salt thereof, comprising the step of reacting a compound of Formula 2c with $R_4$—NH$_2$ to prepare a compound of Formula 3c; the step of carrying out deprotection reaction of the compound of Formula 3c above to prepare a compound of Formula 4c or a salt thereof, and the step of reacting the compound of Formula 4c or a salt thereof with a compound of Formula 5 to give a compound of Formula 1c.

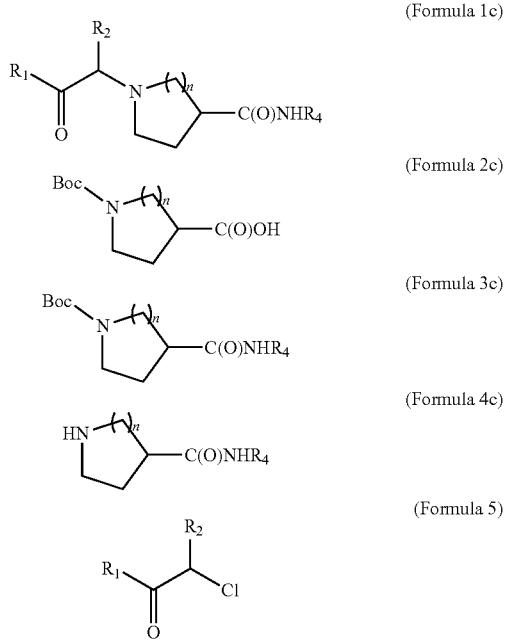

(Formula 1c)

(Formula 2c)

(Formula 3c)

(Formula 4c)

(Formula 5)

In said Formulas 1c, 2c, 3c, 4c, and 5, Boc is an amine protecting group (e.g., tert-butoxycarbonyl, 9-fluorenylmethyloxycarbonyl (FMOC), benzyloxycarbonyl (CBZ), triphenylmethyl(trityl), etc.) and $R_1$, $R_2$, $R_4$, and n are the same as defined in the above.

The compound of Formula 2c is commercially available. The reaction of the compound of Formula 2c above with $R_4$—NH$_2$ can be carried out via amide coupling reaction. Said amide coupling reaction can be performed using a base such as diisopropylamine, diisopropylethylamine, triethylamine, etc., and a coupling reagent such as O-(7-azabenzotriazol-1-yl)-N,N,N',N'-tetramethylurinium hexafluorophosphate (HATU), O-(benzotriazol-1-yl)-N,N,N',N'-tetramethyluronium hexafluorophosphate (HBTU), etc. Said coupling reaction can be performed in organic solvents such as dichloromethane, N,N-dimethylformamide, etc., and can be carried out at room temperature or warm temperature conditions (20° C. to 60° C.).

Deprotection of the compound of Formula 3c can be carried out by conventional methods of removing an amine protecting group. For example, said amine protecting group in an organic solvent such as dichloromethane, etc. can be removed by using an acid such as trifluoroacetic acid or can be removed in the form of a hydrochloride salt by using hydrogen chloride dissolved in the organic solvents, such as diethyl ether, 1,4-dioxane, etc.

The reaction of the compound of Formula 4c above or a salt thereof with a compound of Formula 5 can be carried out via nucleophilic substitution. The nucleophilic substitution reaction can be carried out at room temperature or warm temperature conditions (20° C. to 60° C.) by using a base such as cesium carbonate, potassium carbonate, etc., in a solvent such as acetonitrile, dichloromethane, or the like.

Further, the present technology includes a preparation process of a compound of Formula 1d, wherein $R_3$ in Formula 1 is —NHC(O)(CH$_2$)$_m$R$_4$, or a stereoisomer or mixture of stereoisomers thereof, or a pharmaceutically acceptable salt thereof. That is, the present technology includes a preparation process of a compound of Formula 1d, or a stereoisomer or mixture of stereoisomers thereof, or a pharmaceutically acceptable salt thereof, comprising the step of reacting a compound of Formula 5 with a compound of Formula 9 to prepare a compound of Formula 10; the step of carrying out deprotection reaction of the compound of Formula 10 above to prepare a compound of Formula 11 or a salt thereof, and the step of reacting the compound of Formula 11 with $R_4$—(CH$_2$)$_m$COOH to give a compound of Formula 1d.

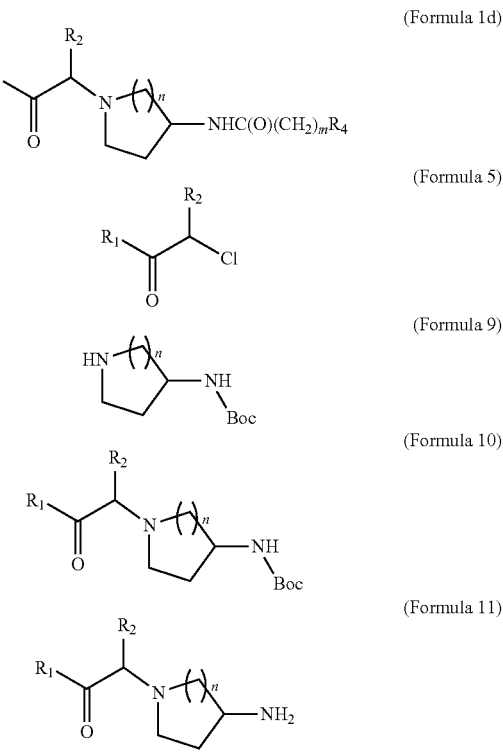

(Formula 1d)

(Formula 5)

(Formula 9)

(Formula 10)

(Formula 11)

In said Formulas 1d, 5, 9, 10, and 11, Boc is an amine protecting group (e.g., tert-butoxycarbonyl, 9-fluorenylmethyloxycarbonyl (FMOC), benzyloxycarbonyl (CBZ), triphenylmethyl(trityl), etc.) and $R_1$, $R_2$, $R_4$, n, and m are the same as defined in the above.

The compound of Formula 9 is commercially available. The reaction of the compound of Formula 5 above with the compound of Formula 9 can be carried out via nucleophilic substitution. The nucleophilic substitution reaction can be carried out at room temperature or warm temperature conditions (20° C. to 60° C.) by using a base such as cesium carbonate, potassium carbonate, etc., in a solvent such as acetonitrile, dichloromethane, or the like.

Deprotection of the compound of Formula 10 can be carried out by conventional methods of removing an amine protecting group. For example, said amine protecting group in an organic solvent such as dichloromethane, etc. can be removed by using an acid such as trifluoroacetic acid or can be removed in the form of a hydrochloride salt by using hydrogen chloride dissolved in the organic solvents, such as diethyl ether, 1,4-dioxane, etc.

The reaction of the compound of Formula 11 above with $R_4$—$(CH_2)_m$COOH can be carried out via amide coupling reaction. Said amide coupling reaction can be performed using a base such as diisopropylamine, diisopropylethylamine, triethylamine, etc., and a coupling reagent such as O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU), etc. Said coupling reaction can be performed in organic solvents such as dichloromethane, N,N-dimethylformamide, etc., and can be carried out at room temperature or warm temperature conditions (20° C. to 60° C.).

Further, the present technology includes a preparation process of a compound of Formula 1e, wherein $R_3$ in Formula 1 is —NHS(O)$_2$R$_4$, or a stereoisomer or mixture of stereoisomers thereof, or a pharmaceutically acceptable salt thereof. That is, the present technology includes a preparation process of a compound of Formula 1e, or a stereoisomer or mixture of stereoisomers thereof, or a pharmaceutically acceptable salt thereof, comprising the step of reacting a compound of Formula 11 or a salt thereof with $R_4$—S(O)$_2$Cl to prepare a compound of Formula 1e.

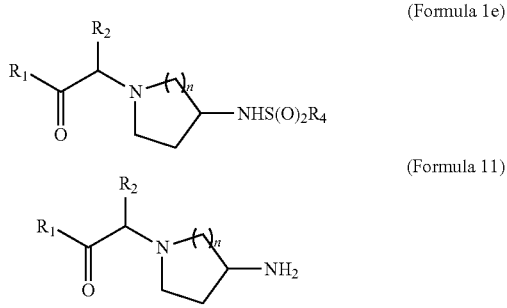

(Formula 1e)

(Formula 11)

In said Formulas 1e and 11, $R_1$, $R_2$, $R_4$, and n are the same as defined in the above.

The reaction of the compound of Formula 11 above or a salt thereof with $R_4$—S(O)$_2$Cl may be carried out via nucleophilic substitution. The nucleophilic substitution reaction can be carried out at room temperature or warm temperature conditions (20° C. to 60° C.) by using a base such as cesium carbonate, potassium carbonate, etc., in a solvent such as acetonitrile, dichloromethane, or the like.

Generally, FAP is not expressed in normal tissues but its expression increases in stromal fibroblasts of malignant tumors such as breast cancer, colorectal cancer, ovarian cancer, and the like (Garin-Chesa et al., Proc. Natl. Acad. Sci., 1990, 87: 7235). Accordingly, the inhibition of FAP can be a target of treatment of a malignant tumor. In fact, it was reported that ValboroPro (PT-100, Talobostat) known as an FAP inhibitor, when orally administered, exhibits anticancer activities in mice by delaying the proliferation of tumors and inducing the degeneration of tumors (Adams et al., Cancer Res., 2004, 64:5471). However, Val-boroPro (PT-100, talabostat) known as an FAP inhibitor also has DPP4, PREP inhibitory activity, etc. Thus, the low selectivity for FAP needs to be improved (O. Ryabtsova et al. Bioorg. Med. Chem. Lett., 2012, 3412-3417).

In addition, since FAP regulates the metabolic functions and is expressed in activated hepatic stellate cells (aHSC) and tissue remodeling sites associated with liver fibrosis, the FAP inhibition may be useful for the treatment of nonalcoholic fatty liver disease (NAFLD). Nonalcoholic fatty liver disease (NAFLD), histologically, encompasses simple steatosis, nonalcoholic steatohepatitis (NASH), and liver cirrhosis. Among these, unlike simple steatosis (non-alcoholic fatty liver, NAFL), NASH may potentially progress to liver cirrhosis and hepatocellular carcinoma. In addition to insulin resistance, oxidative stress, inflammatory cascade, and fibrosis are known to play important roles in the progress of NASH. Thus, the inhibition of FAP may improve insulin resistance which is one of the key factors of NASH and may regulate the hepatoprotective effect and the function of activated hepatic stellate cells (aHSC) by FGF21 regulation and thereby may have the potential for treating NASH (Lay A J et al., Front. Biosci. (Landmark Ed), 2019, 24, 1-17).

The pyrrolidine and piperidine compounds according to the present technology, i.e., the compound of Formulas X, Xa, Xb, 1, 1a, 1b, 1c, 1d, or 1e, or a stereoisomer or mixture of stereoisomers thereof, or a pharmaceutically acceptable salt thereof, have a inhibitory activity on FAP and thus can be usefully applied in the prevention or treatment of a disease mediated by fibroblast activation protein (FAP). Preferably, the compound of Formula 1 according to the present technology, or a stereoisomer or mixture of stereoisomers thereof, or a pharmaceutically acceptable salt thereof can be usefully applied for the prevention or treatment of obesity, diabetes, steatosis, and nonalcoholic steatohepatitis (NASH).

In some embodiments, provided herein is the use of the pyrrolidine and piperidine compounds according to the present technology, i.e., the compound of Formulas X, Xa, Xb, 1, 1a, 1b, 1c, 1d, or 1e, or a stereoisomer or mixture of stereoisomers thereof, or a pharmaceutically acceptable salt thereof, in the preparation of a medicament for the prophylaxis and/or treatment of lipid and lipoprotein disorders (such as, but not limited to, hypercholesterolemia, hypertriglyceridemia, and atherosclerosis), of conditions and diseases which result from chronic fatty and fibrotic degeneration of organs due to accumulated lipid and specifically triglyceride accumulation and subsequent activation of profibrotic pathways (such as, but not limited to, NASH and chronic cholestatic conditions in the liver, Glomerulosclerosis and Diabetic Nephropathy in the kidney, Macular Degeneration and Diabetic Retinopathy in the eye and neurodegenerative diseases, such as Alzheimer's Disease in the brain, or Diabetic Neuropathies in the peripheral nervous system), of Type I or Type II Diabetes and clinical complications of Type I and Type II Diabetes (such as, but not limited to, Diabetic Nephropathy, Diabetic Retinopathy, Diabetic Neuropathies, or Peripheral Arterial Occlusive Disease (PAOD)), of chronic intrahepatic or some forms of extrahepatic cholestatic conditions, of liver fibrosis, of acute intraheptic cholestatic conditions, of obstructive or chronic inflammatory disorders that arise out of improper bile composition (such as, but not limited to, cholelithiasis also known as cholesterol gallstones), of gastrointestinal conditions with a reduced uptake of dietary fat and fat-soluble dietary vitamins, of inflammatory bowel diseases, of obesity and metabolic syndrome (combined conditions of dyslipidemia, diabetes and abnormally high body-mass index), of persistent infections by intracellular bacteria or parasitic protozoae, of non-malignant hyperproliferative disorders, of malignant hyperproliferative disorders (such as, but not limited to, different forms of cancer, specifically certain forms of breast, liver or colon cancer, or a disorder selected from the group consisting of hepatocellular carcinoma, colon adenoma, and polyposis), of colon adenocarcinoma and hepatocellular carcinoma in particular, of liver steatosis and associated syndromes, of Hepatitis B infection, of Hepatitis C infection and/or of cholestatic and fibrotic effects that are associated with alcohol-induced cirrhosis or with viral-borne forms of hepatitis, of liver failure or liver malfunction as an outcome of chronic liver diseases or of surgical liver resection, of acute myocardial infarction, of acute stroke, of thrombosis which occurs as an endpoint of chronic obstructive atherosclerosis, of osteoarthritis, of rheumatoid arthritis, of psoriasis, or of cerebral infarction, individually or of any combination thereof.

In some embodiments, the compounds and/or pharmaceutical compositions disclosed herein are used for prophylaxis and/or treatment of chronic intrahepatic conditions, such as Primary Biliary Cirrhosis (PBC), Primary Sclerosing Cholangitis (PSC), progressive familiar cholestasis (PFIC), alcohol-induced cirrhosis and associated cholestasis, and some forms of extrahepatic cholestatic conditions, or liver fibrosis.

In some embodiments, provided herein is a method to treat chronic intrahepatic conditions and/or some forms of extrahepatic cholestatic conditions in a patient in need thereof, the method comprising, consisting essentially of, or consisting of administering to the patient a therapeutically effective amount of a compound or a composition disclosed herein. In some embodiments, the chronic intrahepatic conditions are selected from PBC, PSC, PFIC, and alcohol-induced cirrhosis and associated cholestasis.

In some embodiments, provided herein is a method to treat liver fibrosis in a patient in need thereof, the method comprising, consisting essentially of, or consisting of administering to the patient a therapeutically effective amount of a compound or a composition disclosed herein.

In some embodiments, provided herein is a method to treat a lipid and lipoprotein disorder in a patient in need thereof, the method comprising, consisting essentially of, or consisting of administering to the patient a therapeutically effective amount of a compound or a composition disclosed herein. In some embodiments, the lipid and lipoprotein disorder is selected from hypercholesterolemia, hypertriglyceridemia, and atherosclerosis.

In some embodiments, provided herein is a method to treat a condition or disease which results from chronic fatty and fibrotic degeneration of organs due to accumulated lipid and specifically triglyceride accumulation and subsequent activation of profibrotic pathways in a patient in need thereof, the method comprising, consisting essentially of, or consisting of administering to the patient a therapeutically effective amount of a compound or a composition disclosed herein. In some embodiments, the condition or disease which results from chronic fatty and fibrotic degeneration of organs due to accumulated lipid and specifically triglyceride accumulation and subsequent activation of profibrotic pathways is selected from NASH and chronic cholestatic conditions in the liver, Glomerulosclerosis and Diabetic Nephropathy in the kidney, Macular Degeneration and Diabetic Retinopathy in the eye, and neurodegenerative diseases. In some further embodiments, neurodegenerative diseases are selected from Alzheimer's Disease in the brain, and Diabetic Neuropathies in the peripheral nervous system.

In some embodiments, provided herein is a method to treat Type I or Type II Diabetes and clinical complications of Type I and Type II Diabetes in a patient in need thereof, the method comprising, consisting essentially of, or consisting of administering to the patient a therapeutically effective amount of a compound or a composition disclosed herein. In some embodiments, provided herein is a method to treat Type I Diabetes in a patient in need thereof, the method comprising, consisting essentially of, or consisting of administering to the patient a therapeutically effective amount of a compound or a composition disclosed herein. In some embodiments, provided herein is a method to treat Type II Diabetes in a patient in need thereof, the method comprising, consisting essentially of, or consisting of administering to the patient a therapeutically effective amount of a compound or a composition disclosed herein. In some embodiments, provided herein is a method to treat one or more clinical complications of Type I and Type II Diabetes in a patient in need thereof, the method comprising, consisting essentially of, or consisting of administering to the patient a therapeutically effective amount of a compound or a composition disclosed herein. In some embodiments, the clinical complications of Type I and Type II Diabetes are selected from Diabetic Nephropathy, Diabetic Retinopathy, Diabetic Neuropathies, and Peripheral Arterial Occlusive Disease (PAOD), or any combination thereof.

In some embodiments, provided herein is a method to treat acute intraheptic cholestatic conditions in a patient in need thereof, the method comprising, consisting essentially of, or consisting of administering to the patient a therapeutically effective amount of a compound or a composition disclosed herein.

In some embodiments, provided herein is a method to treat obstructive or chronic inflammatory disorders that arise out of improper bile composition in a patient in need thereof, the method comprising, consisting essentially of, or consisting of administering to the patient a therapeutically effective amount of a compound or a composition disclosed herein. In some embodiments, the obstructive or chronic inflammatory disorders that arise out of improper bile composition is cholelithiasis also known as cholesterol gallstones.

In some embodiments, provided herein is a method to treat gastrointestinal conditions with a reduced uptake of dietary fat and fat-soluble dietary vitamins in a patient in need thereof, the method comprising, consisting essentially of, or consisting of administering to the patient a therapeutically effective amount of a compound or a composition disclosed herein.

In some embodiments, provided herein is a method to treat inflammatory bowel diseases in a patient in need thereof, the method comprising, consisting essentially of, or consisting of administering to the patient a therapeutically effective amount of a compound or a composition disclosed herein.

In some embodiments, provided herein is a method to treat obesity and metabolic syndrome in a patient in need thereof, the method comprising, consisting essentially of, or consisting of administering to the patient a therapeutically effective amount of a compound or a composition disclosed herein.

In some embodiments, provided herein is a method to treat persistent infections by intracellular bacteria or parasitic protozoae in a patient in need thereof, the method comprising, consisting essentially of, or consisting of administering to the patient a therapeutically effective amount of a compound or a composition disclosed herein.

In some embodiments, provided herein is a method to treat non-malignant hyperproliferative disorders in a patient in need thereof, the method comprising, consisting essentially of, or consisting of administering to the patient a therapeutically effective amount of a compound or a composition disclosed herein.

In some embodiments, provided herein is a method to treat malignant hyperproliferative disorders in a patient in need thereof, the method comprising, consisting essentially of, or consisting of administering to the patient a therapeutically effective amount of a compound or a composition disclosed herein. In some embodiments, malignant hyperproliferative disorders are selected from different forms of cancer, specifically certain forms of breast, liver or colon cancer, or a disorder selected from the group consisting of hepatocellular carcinoma, colon adenoma, and polyposis.

In some embodiments, provided herein is a method to treat colon adenocarcinoma in a patient in need thereof, the method comprising, consisting essentially of, or consisting of administering to the patient a therapeutically effective amount of a compound or a composition disclosed herein.

In some embodiments, provided herein is a method to treat hepatocellular carcinoma in a patient in need thereof, the method comprising, consisting essentially of, or consisting of administering to the patient a therapeutically effective amount of a compound or a composition disclosed herein.

In some embodiments, provided herein is a method to treat liver steatosis and associated syndromes in a patient in need thereof, the method comprising, consisting essentially of, or consisting of administering to the patient a therapeutically effective amount of a compound or a composition disclosed herein.

In some embodiments, provided herein is a method to treat Hepatitis B infection in a patient in need thereof, the method comprising, consisting essentially of, or consisting of administering to the patient a therapeutically effective amount of a compound or a composition disclosed herein.

In some embodiments, provided herein is a method to treat Hepatitis C infection in a patient in need thereof, the method comprising, consisting essentially of, or consisting of administering to the patient a therapeutically effective amount of a compound or a composition disclosed herein.

In some embodiments, provided herein is a method to treat cholestatic and fibrotic effects that are associated with alcohol-induced cirrhosis or with viral-borne forms of hepatitis in a patient in need thereof, the method comprising, consisting essentially of, or consisting of administering to the patient a therapeutically effective amount of a compound or a composition disclosed herein.

In some embodiments, provided herein is a method to treat liver failure or liver malfunction as an outcome of chronic liver diseases or of surgical liver resection in a patient in need thereof, the method comprising, consisting essentially of, or consisting of administering to the patient a therapeutically effective amount of a compound or a composition disclosed herein.

In some embodiments, provided herein is a method to treat acute myocardial infarction in a patient in need thereof, the method comprising, consisting essentially of, or consisting of administering to the patient a therapeutically effective amount of a compound or a composition disclosed herein.

In some embodiments, provided herein is a method to treat acute stroke in a patient in need thereof, the method comprising, consisting essentially of, or consisting of administering to the patient a therapeutically effective amount of a compound or a composition disclosed herein.

In some embodiments, provided herein is a method to treat thrombosis which occurs as an endpoint of chronic obstructive atherosclerosis in a patient in need thereof, the method comprising, consisting essentially of, or consisting of administering to the patient a therapeutically effective amount of a compound or a composition disclosed herein.

In some embodiments, provided herein is a method to treat osteoarthritis in a patient in need thereof, the method comprising, consisting essentially of, or consisting of administering to the patient a therapeutically effective amount of a compound or a composition disclosed herein.

In some embodiments, provided herein is a method to treat rheumatoid arthritis in a patient in need thereof, the method comprising, consisting essentially of, or consisting of administering to the patient a therapeutically effective amount of a compound or a composition disclosed herein.

In some embodiments, provided herein is a method to treat psoriasis in a patient in need thereof, the method comprising, consisting essentially of, or consisting of administering to the patient a therapeutically effective amount of a compound or a composition disclosed herein.

In some embodiments, provided herein is a method to treat cerebral infarction in a patient in need thereof, the method comprising, consisting essentially of, or consisting of administering to the patient a therapeutically effective amount of a compound or a composition disclosed herein.

FAP is expressed not only in the form of being attached to a cell membrane but also in the form of being secreted from a cell and circulated in blood (circulating FAP, hereinafter, "c-FAP") and the two forms have the same enzymatic activity. c-FAP can be quantified at antigen levels using an enzyme-linked immunosorbent assay (ELISA) or can be quantified at enzymatic activity levels using an FAP-specific substrate, and this FAP quantitative analysis revealed that said levels correlate with the degree of induction of said diseases (Ultte de Willige S et al., PLoS One, Jun. 5, 2017, 12). That is, c-FAP can be utilized as an indicator for diagnosis of a disease such as chronic liver disease, malignant tumor, etc. Accordingly, in another aspect, provided herein are methods of using the compounds disclosed herein with c-FAP detection. In some embodiments, provided herein are methods of diagnosing a disease described herein in a subject, the method comprising contacting blood from the subject with a compound described herein and ascertaining a concentration of c-FAP from the blood.

FGF21 is known to have anti-obesity and anti-diabetic effects (M. J. Potthoff et al., Nature Reviews Endocrinology, 2017, 13, and 74), lipid metabolic regulation effect (Murata Y et al. J Nutr Metab. 2011; 2011: 981315), and is known to have a potent hepatoprotective effect (Y. Yu et al, Molecular & Cellular Biochemistry, 2015, 403, 287). Thus, the inhibition of FAP activity may regulate the degradation of FGF-21 by FAP and may be useful for the treatment of metabolic syndromes such as obesity, diabetes, etc.

Accordingly, in another aspect, provided herein are methods of regulating the degradation of FGF-21 by the inhibition of FAP using a compound described herein.

Thus, the present technology includes a pharmaceutical composition for inhibiting FAP, comprising a therapeutically effective amount of a compound of Formulas X, Xa, Xb, 1, 1a, 1b, 1c, 1d, or 1e, or a stereoisomer or mixture of stereoisomers thereof, or a pharmaceutically acceptable salt thereof as an active ingredient. In one embodiment, the present technology provides a pharmaceutical composition for preventing or treating obesity, diabetes, steatosis, and nonalcoholic steatohepatitis (NASH), comprising a therapeutically effective amount of a compound of Formulas X, Xa, Xb, 1, 1a, 1b, 1c, 1d, or 1e, or a stereoisomer or mixture of stereoisomers thereof, or a pharmaceutically acceptable salt thereof as an active ingredient.

In some embodiments, the compounds of the present disclosure may be combined with one or more additional therapies for the prevention or treatment of a disease or condition amenable to treatment by inhibition of FAP.

In some embodiments, the compositions disclosed herein contain at least one additional active agent.

Exemplary additional active agents include, but are not limited to, one or more of a(n) ACE inhibitor, Acetyl CoA carboxylase inhibitor (e.g., firsocostat), Adenosine A3 receptor agonist, Adiponectin receptor agonist, AKT protein kinase inhibitor, AMP-activated protein kinases (AMPK), Amylin receptor agonist, Angiotensin II AT-1 receptor antagonist, Apoptosis Signaling Kinase 1 inhibitor, Autotaxin inhibitors, Bioactive lipid, Calcitonin agonist, Caspase inhibitor, Caspase-3 stimulator, Cathepsin inhibitor, Caveolin 1 inhibitor, CCR2 chemokine antagonist, CCR3 chemokine antagonist, CCR5 chemokine antagonist, CCR2/CCR5 dual antagonist (e.g., cenicriviroc), Chloride channel stimulator, CNR1 inhibitor, Cyclin D1 inhibitor, Cytochrome P450 7A1 inhibitor, DGAT1/2 inhibitor, Dipeptidyl peptidase IV inhibitor, Endosialin modulator, Eotaxin ligand inhibitor, Extracellular matrix protein modulator, Farnesoid X receptor agonist (e.g., obeticholic acid, tropofexor, or cilofexor), Fatty acid synthase inhibitors, FGF1 receptor agonists, Pegylated FGF21, Fibroblast growth factor (FGF-15, FGF-19, FGF-21) ligands, Galectin-3 inhibitor, Glucagon receptor agonist, Glucagon-like peptide 1 agonist, G-protein coupled bile acid receptor 1 agonist, Hedgehog (Hh) modulator, Hepatitis C virus NS3 protease inhibitor, Hepatocyte nuclear factor 4 alpha modulator (HNF4A), Hepatocyte growth factor modulator, HMG CoA reductase inhibitor, IL-10 agonist, IL-17 antagonist, Ileal sodium bile acid cotransporter inhibitor, Insulin sensitizer, integrin modulator, intereukin-1 receptor-associated kinase 4 (IRAK4) inhibitor, Jak2 tyrosine kinase inhibitor, ketohexokinase inhibitors, Klotho beta stimulator, 5-Lipoxygenase inhibitor, Lipoprotein lipase inhibitor, Liver X receptor, LPL gene stimulator, Lysophosphatidate-1 receptor antagonist, Lysyl oxidase homolog 2 inhibitor, Matrix metalloproteinases (MMPs) inhibitor, MEKK-5 protein kinase inhibitor, Membrane copper amine oxidase (VAP-1) inhibitor, Methionine aminopeptidase-2 inhibitor, Methyl CpG binding protein 2 modulator, MicroRNA-21(miR-21) inhibitor, Mitochondrial uncoupler, Myelin basic protein stimulator, NACHT LRR PYD domain protein 3 (NLRP3) inhibitor, NAD-dependent deacetylase sirtuin stimulator, NADPH oxidase inhibitor (NOX), Nicotinic acid receptor 1 agonist, P2Y13 purinoceptor stimulator, PDE 3 inhibitor, PDE 4 inhibitor, PDE 5 inhibitor, PDGF receptor beta modulator, Phospholipase C inhibitor, PPAR alpha agonist, PPAR delta agonist, PPAR gamma agonist, PPAR gamma modulator (e.g., elafibrinor), Protease-activated receptor-2 antagonist, Protein kinase modulator, Rho associated protein kinase inhibitor, Sodium glucose transporter-2 inhibitor, SREBP transcription factor inhibitor, STAT-1 inhibitor, Stearoyl CoA desaturase-1 inhibitor, Suppressor of cytokine signalling-1 stimulator, Suppressor of cytokine signalling-3 stimulator, Thyroid hormone Receptor β-selective agonists such as MGL-3196, Transforming growth factor β (TGF-β), Transforming growth factor β activated Kinase 1 (TAK1), Thyroid hormone receptor beta agonist, TLR-4 antagonist, Transglutaminase inhibitor, Tyrosine kinase receptor modulator, GPCR modulator, nuclear hormone receptor modulator, WNT modulators, and YAP/TAZ modulator. Examples of JAK inhibitors include, but are not limited to, filgotonib and tofacitinib. A non-limiting example of an apoptosis signal kinase inhibitor is selonsertib.

The compound of Formulas X, Xa, Xb, 1, 1a, 1b, 1c, 1d, or 1e, or the stereoisomer or mixture of stereoisomers thereof, or the pharmaceutically acceptable salt thereof, and at least one additional active agent may be administered in any order or even simultaneously. The multiple active agents may be provided in a single, unified form, or in multiple forms (by way of example only, either as a single pill or as two separate pills). One of the active agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

The pharmaceutical composition of the present technology may comprise a pharmaceutically acceptable carrier, such as diluents, disintegrants, sweetening agents, glidants, or flavoring agents and may be formulated into an oral dosage form such as tablets, capsules, powders, granules, suspensions, emulsions, or syrups; or a parenteral dosage form such as liquids for external use, suspensions for external use, emulsions for external use, gels (ointments or the like), inhaling agents, spraying agents, injections, etc. Said dosage forms may be formulated in various forms, e.g., a dosage form for single administration or for multiple administrations.

The pharmaceutical composition of the present technology may comprise excipients such as lactose, corn starch, or the like, glidants such as magnesium stearate, etc., emulsifying agents, suspending agents, stabilizers, and isotonic agents, etc. If desired, a sweetening agent and/or a flavoring agent may be added. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Inorganic salt or buffers include, but are not limited to, citric acid, sodium chloride, potassium chloride, sodium sulfate, potassium nitrate, sodium phosphate monobasic, sodium phosphate dibasic, and combinations thereof.

Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition disclosed herein may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition.

Generally, however, the excipient will be present in the composition in an amount of about 1% to about 99% by weight, preferably from about 5% to about 98% by weight, more preferably from about 15 to about 95% by weight of the excipient. In general, the amount of excipient present in a composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

The composition of the present technology can be administered orally or parenterally, including inhalation, intravenous, intraperitoneal, subcutaneous, rectal and topical administration routes. Therefore, the composition of the present technology can be formulated into various forms such as tablets, capsules, aqueous solutions, suspensions, or the like. In the case of tablets for oral administration, carriers such as lactose, corn starch, and lubricating agents, e.g. magnesium stearate, can be conventionally added thereto. In the case of capsules for oral administration, lactose and/or dried corn starch can be used as a diluent. When an aqueous suspension is required for oral administration, the active ingredient can be combined with emulsifying and/or suspending agents. If desired, certain sweetening agents and/or flavoring agents can be added thereto. For intramuscular, intraperitoneal, subcutaneous and intravenous administration, sterile solutions of the active ingredient are usually prepared, and the pH of the solutions should be suitably adjusted and buffered. For intravenous administration, the total concentration of solutes should be controlled in order to render the preparation isotonic. The composition of the present technology may be in the form of an aqueous solution containing pharmaceutically acceptable carriers, e.g., saline having a pH level of 7.4. The solutions may be introduced into a patient's intramuscular blood-stream by local bolus injection.

Said pyrrolidine or piperidine compound, i.e., the compound of Formulas X, Xa, Xb, 1, 1a, 1b, 1c, 1d, or 1e, or its stereoisomer or mixture of stereoisomers, or its pharmaceutically acceptable salt, can be administered to a patient in an effective amount ranging from about 0.001 mg/kg to about 100 mg/kg per day. Of course, the dosage may be changed according to the patient's age, weight, susceptibility, symptom, or the efficacy of the compound. This includes 0.001, 0.0025, 0.005, 0.0075, 0.01, 0.025, 0.05, 0.075, 0.1, 0.25, 0.5, 0.75, 1, 2, 3, 4, 5, 6, 7, 8, 9, 10, 15, 20, 25, 30, 35, 40, 45, 50, 55, 60, 65, 70, 75, 80, 85, 90, 95, or 100 mg/kg.

Generally, a therapeutically effective amount of the compound of Formulas X, Xa, Xb, 1, 1a, 1b, 1c, 1d, or 1e, or a stereoisomer or mixture of stereoisomers thereof, or a pharmaceutically acceptable salt thereof, will range from a total daily dosage of about 0.1 mg/day to 1000 mg/day, about 30-720 mg/day, about 60-600 mg/day, or about 100-480 mg/day, or more. In some embodiments, a therapeutically effective amount of the compound of Formulas X, Xa, Xb, 1, 1a, 1b, 1c, 1d, or 1e, or a stereoisomer or mixture of stereoisomers thereof, or a pharmaceutically acceptable salt thereof, will range from about 1-240 mg/day, about 30-240 mg/day, about 30-200 mg/day, about 30-120 mg/day, about 1-120 mg/day, about 50-150 mg/day, about 60-150 mg/day, about 60-120 mg/day, or about 60-100 mg/day, administered as either a single dosage or as multiple dosages. In some embodiments, multiple dosages include two, three, or four doses per day.

In some embodiments, the therapeutically effective amount of the compound of Formulas X, Xa, Xb, 1, 1a, 1b, 1c, 1d, or 1e, or a stereoisomer or mixture of stereoisomers thereof, or a pharmaceutically acceptable salt thereof, is at least 0.1 mg/day, at least 0.5 mg/day, at least 1 mg/day, at least 5 mg/day, at least 10 mg/day, at least 20 mg/day, at least 30 mg/day, at least 40 mg/day, at least 50 mg/day, at least 60 mg/day, at least 70 mg/day, at least 80 mg/day, at least 90 mg/day, at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 225 mg/day, at least 250 mg/day, at least 275 mg/day, at least 300 mg/day, at least 325 mg/day, at least 350 mg/day, at least 375 mg/day, at least 400 mg/day, at least 425 mg/day, at least 450 mg/day, at least 475 mg/day, at least 500 mg/day, at least 525 mg/day, at least 550 mg/day, at least 575 mg/day, at least 600 mg/day, at least 625 mg/day, at least 650 mg/day, at least 675 mg/day, at least 700 mg/day, at least 725 mg/day, at least 750 mg/day, at least 775 mg/day, at least 800 mg/day, at least 825 mg/day, at least 850 mg/day, at least 875 mg/day, at least 900 mg/day, at least 925 mg/day, at least 950 mg/day, at least 975 mg/day, or at least 1000 mg/day.

The present technology also includes a method of inhibiting a fibroblast activation protein (FAP) in a mammal, comprising administering to the mammal a therapeutically effective amount of the compound of Formulas X, Xa, Xb, 1, 1a, 1b, 1c, 1d, or 1e, or a stereoisomer or mixture of stereoisomers thereof, or a pharmaceutically acceptable salt thereof. In one embodiment, the present technology provides a method for treating obesity, diabetes, steatosis, and non-alcoholic steatohepatitis (NASH), comprising administering, to a mammal, a therapeutically effective amount of the compound of Formulas X, Xa, Xb, 1, 1a, 1b, 1c, 1d, or 1e, or a stereoisomer or mixture of stereoisomers thereof, or a pharmaceutically acceptable salt thereof. In some embodiments, provided herein is a method for treating NASH in a subject in need thereof, the method comprising, consisting essentially of, or consisting of administering to the subject a therapeutically effective amount of a compound of Formulas X, Xa, Xb, 1, 1a, 1b, 1c, 1d, or 1e, or a stereoisomer or mixture of stereoisomers thereof, or a pharmaceutically acceptable salt thereof. Mammals include, but are not limited to, mice, rodents, rats, simians, humans, farm animals, dogs, cats, sport animals, and pets.

The present technology provides a use of the compound of Formulas X, Xa, Xb, 1, 1a, 1b, 1c, 1d, or 1e, or a stereoisomer or mixture of stereoisomers thereof, or a pharmaceutically acceptable salt thereof for use in the manufacture of a medicament for inhibiting a fibroblast activation protein (FAP) in mammals. In one embodiment, the present technology provides a use of the compound of Formulas X, Xa, Xb, 1, 1a, 1b, 1c, 1d, or 1e, or a stereoisomer or mixture of stereoisomers thereof, or a pharmaceutically acceptable salt thereof for use in the manufacture of a medicament for treating or preventing obesity, diabetes, steatosis, and non-alcoholic steatohepatitis (NASH).

Hereinafter, the present technology is further elaborated through Examples and Experimental Examples. However, the following examples and experimental examples are provided for illustration purposes only, and are not intended to limit the scope of the invention.

As will be apparent to those of skill in the art upon reading this disclosure, each of the individual embodiments described and illustrated herein has discrete components and features which may be readily separated from or combined with the features of any of the other several embodiments without departing from the scope or spirit of the present technology. Any recited method can be carried out in the order of events recited or in any other order which is logically possible.

EXAMPLES

The analyses of the compounds prepared in the following examples were carried out as follows: Nuclear magnetic resonance (NMR) spectrum analysis was carried out using Bruker 400 MHz spectrometer and Agilent 600 MHz spectrometer and chemical shifts thereof were analyzed in ppm. Further, the indicated molecular weights were measured by using liquid chromatography/mass selective detector (MSD) of Agilent 1260 Infinity series equipped with an electrostatic spray interface (by using Single Quadrupole, it indicates a value of m/z in ESI+(ESI-MS (cation), which is represented by the [M+H]+peak). Column chromatography was carried out on silica gel (Merck, 70-230 mesh). (W. C. Still, J. Org. Chem., 43, 2923, 1978). Further, the abbreviations used in the following examples are as follows: methyl is abbreviated to Me, ethyl is abbreviated to Et, phenyl is abbreviated to Ph, and tert-butyloxycarbonyl is abbreviated to Boc. Further, the starting materials in each example are known compounds, which were synthesized according to literatures or obtained from the market such as Sigma-Aldrich.

Reference Example 1.
(S)-1-(2-chloroacetyl)pyrrolidine-2-carbonitrile (S)-Pyrrolidine-2-carbonitrile hydrochloride (7 g, 52.8 mmol) was dissolved in dichloromethane (264 mL). The resulting solution was dropwise added with triethylamine (22.1 mL, 158.3 mmol) and then cooled to 0° C. The solution in which 2-chloroacetylchloride (4.63 mL, 58.1 mmol) was dissolved in dichloromethane (10 mL) was slowly added dropwise to the reaction mixture. The reaction mixture was stirred for 2 hours at 0° C. and then added with water to extract an aqueous layer with dichloromethane. The extracted organic layer was dried and filtered over anhydrous magnesium sulfate. The filtered solution was concentrated and then purified with silica gel column chromatography (ethyl acetate/n-hexane=2/1, v/v) to give the title compound (7.6 g). $^1$H-NMR (CDCl$_3$, 400 MHz) δ 4.81 (d, 1H), 4.24-4.11 (m, 2H), 3.73 (s, 2H), 3.61 (s, 1H), 3.61 (s, 1H) 2.42-2.05 (m, 4H)

Reference Example 2. (2S,4S)-1-(2-chloroacetyl)-4-fluoro-pyrrolidine-2-carbonitrile The title compound as a solid (6.31 g) was prepared in the same fashion as Reference Example 1 except that (2S,4S)-4-fluoro-pyrrolidine-2-carbonitrile hydrochloride (7.95 g, 52.8 mmol) was used instead of (S)-pyrrolidine-2-carbonitrile hydrochloride. $^1$H-NMR (CDCl$_3$, 400 MHz) δ 5.52-5.31 (m, 1H), 5.06-4.94 (m, 1H), 4.26-3.84 (m, 3H) 2.80-2.68 (m, 1H), 2.42-2.32 (m, 1H)

Reference Example 3. (2S)-1-(2-chloroacetyl)-4,4-difluoro-pyrrolidine-2-carbonitrile The title compound as a solid (8.57 g) was prepared in the same fashion as Reference Example 1 except that (2S)-4,4-difluoropyrrolidine-2-carbonitrile 4-methylbenzenesulfonate (16.1 g, 52.8 mmol) was used instead of (S)-pyrrolidine-2-carbonitrile hydrochloride. $^1$H-NMR (CDCl$_3$, 400 MHz) δ 4.97 (s, 1H), 4.04 (s, 3H), 2.79 (s, 2H), 1.55 (s, 1H)

Reference Example 4. (1S,3S,5S)-2-(2-chloroacetyl)-2-azabicyclo[3.1.0]hexane-3-carbonitrile The title compound as a liquid (8 g) was prepared in the same fashion as Reference Example 1 except that (1S,3S,5S)-2-azabicyclo[3.1.0]hexane-3-carbonitrile 4-methylbenzenesulfonate (14.8 g, 52.8 mmol) was used instead of (S)-pyrrolidine-2-carbonitrile hydrochloride. $^1$H-NMR (CDCl$_3$, 400 MHz) δ 4.96 (d, 1H), 4.25-4.14 (m, 2H), 3.62-3.58 (m, 1H), 2.65-2.58 (m, 1H), 2.42 (d, 1H), 1.94-1.90 (m, 1H), 1.16-1.05 (m, 2H)

Reference Example 5.
(S)—N-(pyrrolidin-3-yl)quinolin-4-amine hydrochloride

Step 1: tert-butyl (S)-3-(quinolin-4-ylamino)pyrrolidine-1-carboxylate

Tert-butyl (S)-3-aminopyrrolidine-1-carboxylate (500 mg, 2.68 mmol) was dissolved in anhydrous toluene. To the resulting solution, 4-bromoquinoline (670.2 mg, 3.22 mmol), cesium carbonate (1.31 g, 4.02 mmol), tris(dibenzylideneacetone)dipalladium(0) (245.8 mg, 0.27 mmol), and (+/−)-2,2'-bis(diphenylphospino)-1,1'-binaphthalene (167.1 mg, 0.27 mmol) were added. The reaction mixture was refluxed and stirred at 100° C. overnight. After the completion of the reaction, the reaction mixture was cooled to room temperature and then added with water to extract an aqueous layer with ethyl acetate. The extracted organic layer was dried and filtered over anhydrous magnesium sulfate. The filtered solution was concentrated and then purified with silica gel column chromatography (ethyl acetate/n-hexane=1/1, v/v) to give the title compound (633.5 mg). $^1$H-NMR (CDCl$_3$, 400 MHz) δ 8.53 (d, 1H), 8.14 (d, 1H), 7.99 (d, 1H), 7.60 (t, 1H), 7.36 (t, 1H), 6.47 (d, 1H), 4.80 (m, 1H), 4.39 (m, 1H), 3.89-3.98 (m, 1H), 3.79-3.89 (m, 1H), 3.63-3.74 (m, 1H), 3.51-3.63 (m, 1H), 2.21-2.30 (m, 1H), 1.96-2.08 (m, 1H), 1.46 (s, 9H)

Step 2: (S)—N-(pyrrolidin-3-yl)quinolin-4-amine hydrochloride

Tert-butyl (S)-3-(quinolin-4-ylamino)pyrrolidine-1-carboxylate (472 mg, 1.51 mmol) prepared in Step 1 was dissolved in dichloromethane (8.4 ml) and then 4.0 M of hydrochloric acid dissolved in 1,4-dioxane was added thereto in excess drops. The reaction mixture was stirred overnight at room temperature. After the completion of the reaction, the solid compound obtained therefrom was filtered, washed, and vacuum dried to prepare the title compound (394.5 mg). $^1$H-NMR ((CD$_3$)$_2$SO, 400 MHz) δ 14.6 (s, 1H), 9.75 (s, 1H), 9.46 (d, 1H), 8.98 (d, 1H), 8.66 (d, 1H), 8.08 (d, 1H), 8.00 (dd, 1H), 7.74 (dd, 1H), 6.98 (d, 1H), 4.74-4.82 (m, 1H), 3.35-3.59 (m, 2H), 2.23-2.32 (m, 1H), 2.18-2.28 (m, 1H)

Reference Example 6. (S)—N-(pyrrolidin-3-yl)quinolin-3-amine hydrochloride

Step 1: tert-butyl (S)-3-(quinolin-3-ylamino)pyrrolidine-1-carboxylate

The title compound (576.3 mg) was prepared in the same fashion as Step 1 of Reference Example 5, except that 3-bromoquinoline (670.2 mg, 3.22 mmol) was used instead of 4-bromoquinoline. $^1$H-NMR (CDCl$_3$, 400 MHz) δ 8.40-8.53 (m, 1H), 7.88-8.02 (m, 1H), 7.60-7.74 (m, 1H), 7.34-7.55 (m, 2H), 6.95-7.09 (m, 1H), 4.17-4.33 (m, 1H), 3.80 (m, 1H), 3.42-3.64 (m, 2H), 3.21-3.41 (m, 1H), 2.13-2.42 (m, 2H), 1.87-2.02 (m, 1H), 1.34-1.60 (m, 9H)

Step 2: (S)—N-(pyrrolidin-3-yl)quinolin-3-amine hydrochloride

The title compound (473.5 mg) was prepared in the same fashion as Step 2 of Reference Example 5 and used in the next step without any further purification.

Reference Example 7. (S)—N-(pyrrolidin-3-yl)isoquinolin-4-amine hydrochloride

Step 1: tert-butyl (S)-3-(isoquinolin-4-ylamino)pyrrolidine-1-carboxylate

The title compound (457.9 mg) was prepared in the same fashion as Step 1 of Reference Example 5, except that 4-bromoisoquinoline (670.2 mg, 3.22 mmol) was used instead of 4-bromoquinoline. $^1$H-NMR (CDCl$_3$, 400 MHz) δ 8.85 (s, 1H), 8.11 (d, 1H), 8.01-8.15 (m, 1H), 7.93 (d, 1H), 7.54-7.68 (m, 2H), 4.91-4.94 (m, 1H), 4.39-4.48 (m, 1H), 3.62-3.86 (m, 2H), 3.29-3.43 (m, 2H), 2.31-2.41 (m, 1H), 1.90-1.99 (m, 1H), 1.47 (s, 9H)

Step 2: (S)—N-(pyrrolidin-3-yl)isoquinolin-4-amine hydrochloride

The title compound (343.2 mg) was prepared in the same fashion as Step 2 of Reference Example 5 and used in the next step without any further purification.

Reference Example 8. (S)—N-(benzo[b]thiophen-4-yl)pyrrolidin-3-amine hydrochloride

Step 1: tert-butyl (S)-3-(benzo[b]thiophen-4-ylamino)pyrrolidine-1-carboxylate The title compound (351.6 mg) was prepared in the same fashion as Step 1 of Reference Example 5, except that 4-bromobenzo[b]thiophene (686.2 mg, 3.22 mmol) was used instead of 4-bromoquinoline. $^1$H-NMR (CDCl$_3$, 400 MHz) δ 7.26-7.37 (m, 2H), 7.15-7.24 (m, 2H), 6.53 (d, 1H), 4.07-4.25 (m, 2H), 3.77-3.82 (m, 1H), 3.43-3.63 (m, 2H), 3.26-3.42 (m, 1H), 2.25-2.35 (m, 1H), 1.93-2.07 (m, 1H), 1.42-1.52 (m, 9H)

Step 2: (S)—N-(benzo[b]thiophen-4-yl)pyrrolidin-3-amine hydrochloride

The title compound (200.3 mg) was prepared in the same fashion as Step 2 of Reference Example 5 and used in the next step without any further purification.

Reference Example 9. (S)—N-(benzo[b]thiophen-7-yl)pyrrolidin-3-amine hydrochloride

Step 1: tert-butyl (S)-3-(benzo[b]thiophen-7-ylamino)pyrrolidine-1-carboxylate The title compound (264.5 mg) was prepared in the same fashion as Step 1 of Reference Example 5, except that 7-bromobenzo[b]thiophene (686.2 mg, 3.22 mmol) was used instead of 4-bromoquinoline. $^1$H-NMR (CDCl$_3$, 400 MHz) δ 7.34-7.40 (m, 1H), 7.26-7.33 (m, 3H), 6.59 (d, 1H), 4.23-4.32 (m, 1H), 3.79-3.88 (m, 1H), 3.70-3.82 (m, 1H), 3.46-3.61 (m, 2H), 3.24-3.42 (m, 1H), 2.24-2.32 (m, 1H), 1.90-2.04 (m, 1H), 1.47 (s, 9H)

Step 2: (S)—N-(benzo[b]thiophen-7-yl)pyrrolidin-3-amine hydrochloride

The title compound (172 mg) was prepared in the same fashion as Step 2 of Reference Example 5 and used in the next step without any further purification.

Reference Example 10. (S)—N-(benzofuran-7-yl)pyrrolidin-3-amine hydrochloride

Step 1: tert-butyl (S)-3-(benzofuran-7-ylamino)pyrrolidine-1-carboxylate

The title compound (555.9 mg) was prepared in the same fashion as Step 1 of Reference Example 5, except that 7-bromobenzofuran (641.2 mg, 3.22 mmol) was used instead of 4-bromoquinoline. $^1$H-NMR (CDCl$_3$, 400 MHz) δ 7.55-7.67 (m, 1H), 7.10-7.35 (m, 1H), 6.99-7.05 (m, 1H), 6.72-6.85 (m, 1H), 6.54 (d, 1H), 4.19-4.31 (m, 2H), 3.69-3.82 (m, 1H), 3.48-3.62 (m, 2H), 3.27-3.43 (m, 1H), 2.18-2.27 (m, 1H), 1.97-2.03 (m, 1H), 1.46 (s, 9H)

Step 2: (S)—N-(benzofuran-7-yl)pyrrolidin-3-amine hydrochloride

The title compound (342.8 mg) was prepared in the same fashion as Step 2 of [0286] Reference Example 5 and used in the next step without any further purification.

Reference Example 11. (S)—N-(pyrrolidin-3-yl)furo[3,2-c]pyridin-7-amine hydrochloride

Step 1: tert-butyl (S)-3-(furo[3,2-c]pyridin-7-ylamino)pyrrolidine-1-carboxylate The title compound (171.5 mg) was prepared in the same fashion as Step 1 of Reference Example 5, except that 7-bromofuro[3,2-c]pyridine (640.2 mg, 3.22 mmol) was used instead of 4-bromoquinoline. $^1$H-NMR (CDCl$_3$, 400 MHz) δ 8.40 (s, 1H), 7.91 (s, 1H), 7.60 (d, 1H), 6.81 (d, 1H), 4.30-4.45 (m, 1H), 4.07-4.29 (m, 1H), 3.76-3.89 (m, 1H), 3.47-3.60 (m, 2H), 3.28-3.44 (m, 1H), 2.43- 2.65 (m, 1H), 2.19-2.34 (m, 11H), 1.94-2.03 (m, 1H), 1.46 (s, 9H)

Step 2: (S)—N-(pyrrolidin-3-yl)furo[3,2-c]pyridin-7-amine hydrochloride

The title compound (100.9 mg) was prepared in the same fashion as Step 2 of Reference Example 5 and used in the next step without any further purification.

Reference Example 12. (S)—N-([1,1'-biphenyl]-2-yl)pyrrolidin-3-amine hydrochloride Step 1: tert-butyl (S)-3-([1,1'-biphenyl]-2-ylamino)pyrrolidine-1-carboxylate The title compound (836.3 mg) was prepared in the same fashion as Step 1 of Reference Example 5, except that 2-bromobiphenyl (750.0 mg, 3.22 mmol) was used instead of 4-bromoquinoline. $^1$H-NMR (CDCl$_3$, 400 MHz) δ 7.40-7.58 (m, 2H), 7.32-7.40 (m, 3H), 7.18-7.24 (m, 1H), 7.04-7.13 (m, 1H), 6.75-6.86 (m, 1H), 6.66-6.72 (m, 1H), 4.03-4.10 (m, 1H), 3.93-4.01 (m, 1H), 3.67-3.75 (m, 1H), 3.27-3.47 (m, 2H), 3.11-3.25 (m, 1H), 2.09-2.19 (m, 1H), 1.48-1.58 (m, 1H), 1.38- 1.47 (s, 9H)

Step 2: (S)—N-([1,1'-biphenyl]-2-yl)pyrrolidin-3-amine hydrochloride

The title compound (562 mg) was prepared in the same fashion as Step 2 of Reference Example 5 and used in the next step without any further purification.

Reference Example 13. (S)—N-([1,1'-biphenyl]-4-yl)pyrrolidin-3-amine hydrochloride Step 1: tert-butyl (S)-3-([1,1'-biphenyl]-4-ylamino)pyrrolidine-1-carboxylate The title compound (756.5 mg) was prepared in the same fashion as Step 1 of Reference Example 5, except that 4-bromobiphenyl (750.0 mg, 3.22 mmol) was used instead of 4-bromoquinoline. $^1$H-NMR (CDCl$_3$, 400 MHz) δ 7.47-7.56 (m, 2H), 7.40-7.46 (m, 2H), 7.35-7.40 (m, 2H), 7.22-7.29 (m, 2H), 6.66-6.68 (m, 1H), 3.99-4.08 (m, 1H), 3.87-3.91 (m, 1H), 3.70-3.85 (m, 1H), 3.42-3.54 (m, 2H), 3.18-3.32 (m, 1H), 2.13-2.21 (m, 1H), 1.42-1.51 (m, 9H)

Step 2: (S)—N-([1,1'-biphenyl]-4-yl)pyrrolidin-3-amine hydrochloride

The title compound (414 mg) was prepared in the same fashion as Step 2 of Reference Example 5 and used in the next step without any further purification.

Reference Example 14. (S)—N-(naphthalen-2-yl)pyrrolidin-3-amine

Step 1: tert-butyl (S)-3-(naphthalen-2-ylamino)pyrrolidine-1-carboxylate

Tert-butyl (S)-3-aminopyrrolidine-1-carboxylate (500 mg, 2.68 mmol) was dissolved in anhydrous toluene. To the resulting solution, 2-bromonaphthalene (665.2 mg, 3.22 mmol), cesium carbonate (1.31 g, 4.02 mmol), tris(dibenzylideneacetone)dipalladium(0) (245.8 mg, 0.27 mmol), and (+/−)-2,2'-bis(diphenylphospino)-1,1'-binaphthalene (167.1 mg, 0.27 mmol) were added. The reaction mixture was refluxed and stirred at 100° C. overnight. After the completion of the reaction, the reaction mixture was cooled to room temperature and then added with water to extract an aqueous layer with ethyl acetate. The extracted organic layer was dried and filtered over anhydrous magnesium sulfate. The filtered solution was concentrated and then purified with silica gel column chromatography (ethyl acetate/n-hexane=1/1, v/v) to give the title compound (633.5 mg). MS (ESI) m/z=312.4 (M+H)+

Step 2: (S)—N-(naphthalen-2-yl)pyrrolidin-3-amine

Tert-butyl (S)-3-(naphthalen-2-ylamino)pyrrolidine-1-carboxylate (633.5 mg, 2.02 mmol) prepared in Step 1 was dissolved in dichloromethane (11.2 ml) and then 4.0 M hydrochloric acid dissolved in 1,4-dioxane was added thereto in excess drops. The reaction mixture was stirred overnight at room temperature. After the completion of the reaction, the residue obtained by concentration under reduced pressure was dissolved in dichloromethane, and the solution was washed with an 1N sodium hydroxide aqueous solution and brine, dried over anhydrous magnesium sulfate, and then concentrated under reduced pressure to produce the title compound (318.6 mg). $^1$H-NMR (CDCl$_3$, 400 MHz) δ 7.58-7.71 (m, 3H), 7.36 (dd, 1H), 7.19 (dd, 1H), 6.84 (dd, 1H), 6.74-6.82 (m, 1H), 4.01-4.12 (m, 1H), 3.88-3.98 (m, 0.9H), 3.73-3.79 (m, 0.2H), 3.57-3.65 (m, 0.3H), 3.04-3.30 (m, 2H), 2.81-3.00 (m, 2H), 2.16-2.28 (m, 1H), 1.64-1.78 (m, 1H)

Reference Example 15. (S)—N-([1,1'-biphenyl]-3-yl)pyrrolidin-3-amine hydrochloride Step 1: tert-butyl (S)-3-([1,1'-biphenyl]-3-ylamino)pyrrolidine-1-carboxylate The title compound (562.4 mg) was prepared in the same fashion as Step 1 of Reference Example 5, except that 3-bromobiphenyl (750.0 mg, 3.22 mmol) was used instead of 4-bromoquinoline. $^1$H-NMR (CDCl$_3$, 400 MHz) δ 7.52-7.60 (m, 2H), 7.36-7.47 (m, 3H), 7.31-7.35 (m, 1H), 6.96-7.05 (m, 1H), 6.80-6.93 (m, 1H), 6.60-6.75 (m, 1H), 4.03-4.15 (m, 1H), 3.84-3.95 (m, 1H), 3.65-3.77 (m, 1H), 3.47-3.52 (m, 1H), 3.18-3.35 (m, 1H), 2.15-2.25 (m, 1H), 1.86-1.98 (m, 1H), 1.40- 1.52 (m, 9H)

Step 2: (S)—N-([1,1'-biphenyl]-3-yl)pyrrolidin-3-amine hydrochloride

The title compound (342.2 mg) was prepared in the same fashion as Step 2 of Reference Example 5 and used in the next step without any further purification.

Reference Example 16. (S)—N-(pyrrolidin-3-yl)quinolin-5-amine hydrochloride

Step 1: tert-butyl (S)-3-(quinolin-5-ylamino)pyrrolidine-1-carboxylate

The title compound (297.4 mg) was prepared in the same fashion as Step 1 of Reference Example 5, except that 5-bromoquinoline (670.2 mg, 3.22 mmol) was used instead of 4-bromoquinoline. $^1$H-NMR (CD$_3$OD, 400 MHz) δ 9.67-9.72 (m, 1H), 9.06-9.21 (m, 1H), 7.90-8.00 (m, 2H), 7.46-7.52 (m, 1H), 7.01-7.11 (m, 1H), 4.58 (m, 1H), 3.60-3.75 (m, 2H), 3.53-3.59 (m, 2H), 2.45-2.52 (m, 1H), 2.37-2.42 (m, 1H)

Step 2: (S)—N-(pyrrolidin-3-yl)quinolin-5-amine hydrochloride

The title compound (342.2 mg) was prepared in the same fashion as Step 2 of Reference Example 5 and used in the next step without any further purification.

Reference Example 17. (R)—N-(pyrrolidin-3-yl)quinolin-3-amine hydrochloride

Step 1: tert-butyl (R)-3-(quinolin-3-ylamino)pyrrolidine-1-carboxylate

Tert-butyl (R)-3-aminopyrrolidine-1-carboxylate (500 mg, 2.68 mmol) was dissolved in anhydrous toluene. To the resulting solution, 3-bromoquinoline (670.2 mg, 3.22 mmol), cesium carbonate (1.31 g, 4.02 mmol), tris(dibenzylideneacetone)dipalladium(0) (245.8 mg, 0.27 mmol), and (+/−)-2,2'-bis(diphenylphospino)-1,1'-binaphthalene (167.1 mg, 0.27 mmol) were added. The reaction mixture was refluxed and stirred at 100° C. overnight. After the completion of the reaction, the reaction mixture was cooled to room temperature and then added with water to extract an aqueous layer with ethyl acetate. The extracted organic layer was dried and filtered over anhydrous magnesium sulfate. The filtered solution was concentrated and then purified with silica gel column chromatography (ethyl acetate/n-hexane=1/1, v/v) to give the title compound (472 mg). $^1$H-NMR (CDCl$_3$, 400 MHz) δ 8.41-8.52 (m, 1H), 7.94-8.11 (m, 1H), 7.57-7.68 (m, 1H), 7.38-7.51 (m, 2H), 7.02-7.13 (m, 1H), 4.27 (m, 1H), 3.89-3.92 (m, 1H), 3.51-3.75 (m, 2H), 3.32-3.42 (m, 1H), 2.26-2.31 (m, 1H), 1.90-2.13 (m, 2H), 1.40-1.60 (m, 9H)

Step 2: (R)—N-(pyrrolidin-3-yl)quinolin-3-amine hydrochloride

The title compound (344.7 mg) was prepared in the same fashion as Step 2 of Reference Example 5 and used in the next step without any further purification.

Reference Example 18. (R)—N-([1,1'-biphenyl]-3-yl)pyrrolidin-3-amine hydrochloride

Step 1: tert-butyl (R)-3-([1,1'-biphenyl]-3-yl)pyrrolidine-1-carboxylate

The title compound (621.3 mg) was prepared in the same fashion as Step 1 of Reference Example 17, except that 3-bromobiphenyl (750.0 mg, 3.22 mmol) was used instead of 3-bromoquinoline. $^1$H-NMR (CDCl$_3$, 400 MHz) δ 7.55-7.68 (m, 2H), 7.38-7.53 (m, 2H), 7.30-7.35 (m, 1H), 7.23-7.28 (m, 1H), 6.94-7.08 (m, 1H), 6.79-6.84 (m, 1H), 6.58-6.63 (m, 1H), 4.04-4.12 (m, 1H), 3.90-4.03 (m, 1H), 3.71-3.85 (m, 2H), 3.46-3.52 (m, 2H), 3.15-3.35 (m, 1H), 2.16-2.20 (m, 1H), 1.82-1.98 (m, 1H), 1.46-1.58 (m, 9H)

Step 2: (R)—N-([1,1'-biphenyl]-3-yl)pyrrolidin-3-amine hydrochloride

The title compound (383.7 mg) was prepared in the same fashion as Step 2 of Reference Example 5 and used in the next step without any further purification.

Reference Example 19. (R)—N-(pyrrolidin-3-yl)isoquinolin-4-amine hydrochloride

Step 1: tert-butyl (R)-3-(isoquinolin-4-ylamino)pyrrolidine-1-carboxylate

The title compound (447.7 mg) was prepared in the same fashion as Step 1 of Reference Example 17, except that 4-bromoisoquinoline (670.2 mg, 3.22 mmol) was used instead of 3-bromoquinoline. MS (ESI) m/z=314.2 (M+H)+

Step 2: (R)—N-(pyrrolidin-3-yl)isoquinolin-4-amine hydrochloride

The title compound (299.7 mg) was prepared in the same fashion as Step 2 of Reference Example 5. MS (ESI) m/z=214.2 (M+H)+

Reference Example 20. (R)—N-(benzo[b]thiophen-7-yl)pyrrolidin-3-amine hydrochloride

Step 1: tert-butyl (R)-3-(benzo[b]thiophen-7-ylamino)pyrrolidine-1-carboxylate The title compound (128 mg) was prepared in the same fashion as Step 1 of Reference Example 17, except that 7-bromobenzo[b]thiophene (685.0 mg, 3.22 mmol) was used instead of 3-bromoquinoline. $^1$H-NMR (CDCl$_3$, 400 MHz) δ 7.21-7.45 (m, 4H), 6.57-6.62 (m, 1H), 4.21-4.31 (m, 1H), 3.73-3.82 (m, 2H), 3.44-3.60 (m, 2H), 3.26-3.40 (m, 1H), 2.23-2.25 (m, 1H), 1.97-2.21 (m, 1H), 1.40-1.56 (m, 9H)

Step 2: (R)—N-(benzo[b]thiophen-7-yl)pyrrolidin-3-amine hydrochloride

The title compound (79.0 mg) was prepared in the same fashion as Step 2 of Reference Example 5 and used in the next step without any further purification.

Reference Example 21. (S)—N-(quinolin-4-yl)pyrrolidine-3-carboxamide hydrochloride

Step 1: tert-butyl (S)-3-(quinolin-4-ylcabamoyl)pyrrolidine-1-carboxylate (S)-1-(Tert-butoxycarbonyl)pyrrolidine-3-carboxylic acid (300 mg, 1.39 mmol) was dissolved in dichloromethane. To the resulting solution, 4-aminoquinoline (200.9 mg, 1.39 mmol), HATU (O-(7-azabenzotriazol-1-yl)-N,N,N',N'-tetramethyluranium hexafluorophosphate) (794.9 mg, 2.09 mmol), and diisopropylethylamine (0.49 mL, 2.79 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=20/1, v/v) to give the title compound (250 mg). $^1$H-NMR (CDCl$_3$, 400 MHz) δ 9.05 (s, 1H), 8.80 (s, 1H), 8.63 (s, 1H), 8.38 (s, 1H), 7.95 (d, 2H), 7.71 (s, 1H), 3.71-3.46 (m, 5H), 2.83 (s, 10H), 2.32-2.18 (m, 2H), 1.50-1.43 (d, 9H)

Step 2: (S)—N-(quinolin-4-yl)pyrrolidine-3-carboxamide hydrochloride

Tert-butyl (S)-3-(quinolin-4-ylcabamoyl)pyrrolidine-1-carboxylate (450 mg, 1.32 mmol) prepared in Step 1 was dissolved in dichloromethane (7.3 ml) and then 4.0 M of hydrochloric acid dissolved in 1,4-dioxane was added thereto in excess drops. The reaction mixture was stirred overnight at room temperature. After the completion of the reaction, the solid produced therefrom was filtered and dried to give the title compound (220 mg). The title compound was used in the next step without any further purification.

Reference Example 22. (S)—N-(quinolin-3-yl)pyrrolidine-3-carboxamide hydrochloride Step 1: tert-butyl (S)-3-(quinolin-3-ylcabamoyl)pyrrolidine-1-carboxylate The title compound (100 mg) was prepared in the same fashion as Step 1 of Reference Example 21, except that 3-aminoquinoline (200.9 mg, 1.39 mmol) was used instead of 4-aminoquinoline. MS (ESI) m/z=342.4 (M+H)+

Step 2: (S)—N-(quinolin-3-yl)pyrrolidine-3-carboxamide hydrochloride

The title compound (190.7 mg) was prepared in the same fashion as Step 2 of Reference Example 21 and used in the next step without any further purification.

Reference Example 23. (R)—N-(quinolin-4-yl)pyrrolidine-3-carboxamide hydrochloride Step 1: tert-butyl (R)-3-(quinolin-4-ylcabamoyl)pyrrolidine-1-carboxylate The title compound (340 mg) was prepared in the same fashion as Step 1 of Reference Example 21 except that (R)-1-(tert-butoxycarbonyl)pyrrolidine-3-carboxylic acid (300 mg, 1.39 mmol) was used instead of (S)-1-(tert-butoxycarbonyl)pyrrolidine-3-carboxylic acid. $^1$H-NMR (CDCl$_3$, 400 MHz) δ 9.05 (s, 1H), 8.80 (s, 1H), 8.63 (s, 1H), 8.38 (s, 1H), 7.95 (d, 2H), 7.71 (s, 1H), 3.71-3.46 (m, 5H), 2.83 (s, 10H), 2.32-2.18 (m, 2H), 1.50-1.43 (d, 9H)

Step 2: (R)—N-(quinolin-4-yl)pyrrolidine-3-carboxamide hydrochloride

The title compound (260 mg) was prepared in the same fashion as Step 2 of Reference Example 21 and used in the next step without any further purification.

Reference Example 24. (R)—N-(quinolin-3-yl)pyrrolidine-3-carboxamide hydrochloride Step 1: tert-butyl (R)-3-(quinolin-3-ylcabamoyl)pyrrolidine-1-carboxylate The title compound (450 mg) was prepared in the same fashion as Step 1 of Reference Example 21, except that 3-aminoquinoline (200.9 mg, 1.39 mmol) was used instead of 4-aminoquinoline. MS (ESI) m/z=342.4 (M+H)+

Step 2: (R)—N-(quinolin-3-yl)pyrrolidine-3-carboxamide hydrochloride

The title compound (310.7 mg) was prepared in the same fashion as Step 2 of Reference Example 21 and used in the next step without any further purification.

Reference Example 25. (S)-1-(2-((S)-3-aminopyrrolidin-1-yl)acetyl)pyrrolidine-2-carbonitrile trifluoroacetate Step 1: tert-butyl ((S)-1-(2-((S)-2-cyanopyrrolidin-1-yl)-2-oxoethyl)pyrrolidin-3-yl)carbamate (S)-1-(2-Chloroacetyl)pyrrolidine-2-carbonitrile (3 g, 17.4 mmol) prepared in Reference Example 1 was dissolved in anhydrous dichloromethane (34.8 ml). To the resulting solution, (3S)-(−)-3-(tert-butoxycarbonylamino)pyrrolidine (3.56 g, 19.1 mmol), and potassium carbonate (4.8 g, 34.8 mmol) was added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (ethyl acetate/n-hexane=4/1, v/v) to give the title compound (2.33 g). $^1$H-NMR (CDCl$_3$, 400 MHz) δ 4.77-4.82 (m, 1H), 3.60-3.74 (m, 1H), 3.30-3.55 (m, 6H), 3.05-3.28 (m, 1H), 2.10-2.44 (m, 4H), 1.68-1.86 (m, 4H), 1.41-1.54 (m, 9H)

Step 2: (S)-1-(2-((S)-3-aminopyrrolidin-1-yl)acetyl)pyrrolidine-2-carbonitrile trifluoroacetate Tert-butyl ((S)-1-(2-((S)-2-cyanopyrrolidin-1-yl)-2-oxoethyl)pyrrolidin-3-yl)carbamate (2.6 g, 8.06 mmol) prepared in Step 1 was dissolved in dichloromethane (44.8 ml) and trifluoroacetic acid was added thereto in excess drops. The reaction mixture was stirred overnight at room temperature and concentrated to give the title compound (1.3 g). $^1$H-NMR (CD$_3$OD, 400 MHz) δ 4.79-4.91 (m, 1H), 4.41 (q, 2H), 4.09-4.21 (m, 1H), 3.96-4.05 (m, 1H), 3.54-3.81 (m, 5H), 2.55-2.67 (m, 1H), 2.10-2.31 (m, 5H)

Reference Example 26. (S)-1-(2-((R)-3-hydroxypyrrolidin-1-yl)acetyl)pyrrolidine-2-carbonitrile (S)-1-(2-Chloroacetyl)pyrrolidine-2-carbonitrile (2 g, 11.6 mmol) prepared in Reference Example 1 was dissolved in anhydrous acetonitrile (23.2 ml). To the resulting solution, (R)-3-pyrrolidinol (1.12 mL, 13.9 mmol) and potassium carbonate (4 g, 28.9 mmol) were added. The reaction mixture was stirred overnight at room temperature. After the completion of the reaction, the reaction mixture was filtered. The filtered solution was concentrated and then purified with silica gel column chromatography (ethyl acetate/n-hexane=1/1, v/v) to give the title compound (2.42 g). $^1$H-NMR (CDCl$_3$, 400 MHz) δ 4.74 (d, 1H), 4.35 (s, 1H), 3.65-3.63 (m, 1H), 3.51-3.33 (m, 3H), 3.11-2.96 (m, 2H), 2.88-2.80 (m, 2H), 2.55-2.47 (m, 1H), 2.35-2.16 (m, 5H), 1.90-1.75 (m, 1H)

Reference Example 27. (S)-4,4-difluoro-1-(2-((R)-3-hydroxypyrrolidin-1-yl)-2-oxoethyl)pyrrolidine-2-carbonitrile The title compound (2.52 g) was prepared in the same fashion as Reference Example 26, except that (2S)-1-(2-chloroacetyl)-4,4-difluoro-pyrrolidine-2-carbonitrile (1.4 g, 11.6 mmol) prepared in Reference Example 3 was used instead of (S)-1-(2-chloroacetyl)pyrrolidine-2-carbonitrile. MS (ESI) m/z=260.2 (M+H)+

Reference Example 28. N-(piperidin-4-yl)quinolin-4-amine hydrochloride

Step 1: tert-butyl 4-(quinolin-4-ylamino)piperidine-1-carboxylate

Tert-butyl 4-aminopiperidine-1-carboxylate (500 mg, 2.68 mmol) was dissolved in anhydrous toluene. To the resulting solution, 4-bromoquinoline (670.2 mg, 3.22 mmol), cesium carbonate (1.31 g, 4.02 mmol), tris(dibenzylideneacetone)dipalladium(0) (245.8 mg, 0.27 mmol), and (+/−)-2,2'-bis(diphenylphospino)-1,1'-binaphthalene (167.1 mg, 0.27 mmol) were added. The reaction mixture was refluxed and stirred at 100° C. overnight. After the completion of the reaction, the reaction mixture was cooled to room temperature and then added with water to extract an aqueous layer with ethyl acetate. The extracted organic layer was dried and filtered over anhydrous magnesium sulfate. The filtered solution was concentrated and then purified with silica gel column chromatography (ethyl acetate/n-hexane=1/1, v/v) to give the title compound (720 mg). $^1$H-NMR (CDCl$_3$, 400 MHz) δ 8.56 (d, 1H), 7.99 (d, 1H), 7.72 (d, 1H), 7.63 (t, 1H), 7.43 (t, 1H), 6.47 (d, 1H), 4.93 (d, 1H), 4.12 (d, 2H), 3.68 (s, 1H), 3.00 (t, 1H), 2.17-2.14 (m, 2H), 1.53-1.44 (m, 12H)

Step 2: N-(piperidin-4-yl)quinolin-4-amine hydrochloride

Tert-butyl 4-(quinolin-4-ylamino)piperidine-1-carboxylate (720 mg, 2.20 mmol) prepared in Step 1 was dissolved in dichloromethane (12.2 ml). To the resulting solution, 4.0 M of hydrochloric acid dissolved in 1,4-dioxane was added in excess drops. The reaction mixture was stirred overnight at room temperature. After the completion of the reaction, the solid produced therefrom was filtered and dried to give the title compound (320 mg). The title compound was used in the next step without any further purification.

Reference Example 29. N-(piperidin-4-yl)quinolin-5-amine hydrochloride

Step 1: tert-butyl 4-(quinolin-5-ylamino)piperidine-1-carboxylate

The title compound (500 mg) was prepared in the same fashion as Step 1 of Reference Example 28, except that 5-bromoquinoline (500 mg, 2.50 mmol) was used instead of 4-bromoquinoline. $^1$H-NMR (CDCl$_3$, 400 MHz) δ 8.87 (s, 1H), 8.15 (d, 1H), 7.58-7.49 (m, 2H), 7.34-7.32 (m, 1H), 6.69 (d, 1H), 4.17 (d, 3H), 3.64 (s, 1H), 3.02 (t, 2H), 2.18-2.15 (m, 2H), 1.49-1.45 (m, 11H)

Step 2: N-(piperidin-4-yl)quinolin-5-amine hydrochloride

The title compound (390 mg) was prepared in the same fashion as Step 2 of Reference Example 28 and used in the next step without any further purification.

Reference Example 30. N-(piperidin-4-yl)furo[3,2-c]pyridin-7-amine hydrochloride The title compound (324 mg) was prepared in the same fashion as Reference Example 28, except that 7-bromofuro[3,2-c]pyridine (495.1 mg, 2.50 mmol) was used instead of 4-bromoquinoline in Step 1. $^1$H-NMR (CD$_3$OD, 400 MHz) δ 8.6 (s, 1H), 8.26 (s, 1H), 8.17 (s, 1H), 7.29 (s, 1H), 4.00 (s, 1H), 3.52 (d, 2H), 3.24 (t, 2H), 2.32 (d, 2H), 1.91 (q, 2H)

Reference Example 31. 3-(piperidin-4-yloxy)quinoline hydrochloride

Step 1: tert-butyl 4-(quinolin-3-yloxy)piperidine-1-carboxylate

Tert-butyl 4-hydroxypiperidine-1-carboxylate (200 mg, 1.0 mmol) was dissolved in tetrahydrofuran (4.97 ml). To the resulting solution, 3-quinolinol (144.25 mg, 1.0 mmol) and triphenylphosphine (391 mg, 1.5 mmol) were added. The mixture solution was cooled to 0° C. and then, DIAD (diisopropyl azodicarboxylate) (0.29 mL, 1.5 mmol) was slowly added thereto dropwise for 15 minutes. The reaction mixture was stirred for 12 hours at room temperature. After the completion of the reaction, a saturated ammonium chloride solution and a saturated sodium hydrogen carbonate solution were added to the reaction mixture. The aqueous layer of the reaction mixture was extracted with ethyl acetate. The extracted organic layer was dried and filtered over anhydrous magnesium sulfate. The filtered solution was concentrated and then purified with silica gel column chromatography (dichloromethane/methanol=10/1, v/v) to give the title compound (280 mg). MS (ESI) m/z=330.2 (M+H)+

Step 2: 3-(piperidin-4-yloxy)quinoline hydrochloride

Tert-butyl 4-(quinolin-3-yloxy)piperidine-1-carboxylate (280 mg, 0.85 mmol) was dissolved in dichloromethane (4.7 ml). To the resulting solution, 4.0 M of hydrochloric acid dissolved in 1,4-dioxane was added in excess drops. The reaction mixture was stirred overnight at room temperature. After the completion of the reaction, the solid produced therefrom was filtered and dried to give the title compound (47 mg). The title compound was used in the next step without any further purification. MS (ESI) m/z=230.1 (M+H)+

Reference Example 32. 4-(piperidin-4-yloxy)quinoline hydrochloride

The title compound (100 mg) was prepared in the same fashion as Reference Example 31, except that 4-quinolinol (144.25 mg, 1.0 mmol) was used instead of 3-quinolinol in Step 1. MS (ESI) m/z=230.1 (M+H)+

Reference Example 33.
5-(piperidin-4-yloxy)quinoline hydrochloride

The title compound (60 mg) was prepared in the same fashion as Reference Example 31, except that 5-quinolinol (144.25 mg, 1.0 mmol) was used instead of 3-quinolinol in Step 1. The title compound was used in the next step without any further purification. MS (ESI) m/z=230.1 (M+H)+

Reference Example 34.
6-(piperidin-4-yloxy)quinoline hydrochloride

The title compound (40 mg) was prepared in the same fashion as Reference Example 31, except that 6-quinolinol (144.25 mg, 1.0 mmol) was used instead of 3-quinolinol in Step 1. The title compound was used in the next step without any further purification. MS (ESI) m/z=230.1 (M+H)+

Reference Example 35.
3-methyl-N-(piperidin-4-yl)quinolin-5-amine hydrochloride The title compound (81.8 mg) was prepared in the same fashion as Reference Example 28, except that 5-bromo-3-methylquinoline (554.4 mg, 2.50 mmol) was used instead of 4-bromoquinoline in Step 1. The title compound was used in the next step without any further purification. MS (ESI) m/z=242.3 (M+H)+

Reference Example 36.
6-methyl-N-(piperidin-4-yl)quinolin-5-amine hydrochloride The title compound (40.2 mg) was prepared in the same fashion as Reference Example 28, except that 5-bromo-6-methylquinoline (554.4 mg, 2.50 mmol) was used instead of 4-bromoquinoline in Step 1. The title compound was used in the next step without any further purification. MS (ESI) m/z=242.3 (M+H)+

Reference Example 37.
7-fluoro-N-(piperidin-4-yl)quinolin-5-amine hydrochloride The title compound (251 mg) was prepared in the same fashion as Reference Example 28, except that 5-bromo-7-fluoroquinoline (564 mg, 2.50 mmol) was used instead of 4-bromoquinoline in Step 1. The title compound was used in the next step without any further purification. MS (ESI) m/z=246.3 (M+H)+

Reference Example 38.
7-methoxy-N-(piperidin-4-yl)quinolin-5-amine hydrochloride The title compound (106 mg) was prepared in the same fashion as Reference Example 28, except that 5-bromo-7-methoxyquinoline (594 mg, 2.50 mmol) was used instead of 4-bromoquinoline in Step 1. The title compound was used in the next step without any further purification. MS (ESI) m/z=258.3 (M+H)+

Reference Example 39.
8-methoxy-N-(piperidin-4-yl)quinolin-5-amine hydrochloride The title compound (27 mg) was prepared in the same fashion as Reference Example 28, except that 5-bromo-8-methoxyquinoline (594 mg, 2.50 mmol) was used instead of 4-bromoquinoline in Step 1. The title compound was used in the next step without any further purification. MS (ESI) m/z=258.3 (M+H)+

Reference Example 40.
6-fluoro-4-(piperidin-4-yloxy)quinoline hydrochloride

The title compound (214 mg) was prepared in the same fashion as Reference Example 31, except that 6-fluoroquinolin-4-ol (202.6 mg, 1.2 mmol) was used instead of 3-quinolinol in Step 1. The title compound was used in the next step without any further purification. MS (ESI) m/z=246.3 (M+H)+

Reference Example 41.
6-chloro-4-(piperidin-4-yloxy)quinoline hydrochloride

The title compound (197 mg) was prepared in the same fashion as Reference Example 31, except that 6-chloroquinolin-4-ol (223.1 mg, 1.2 mmol) was used instead of 3-quinolinol in Step 1. The title compound was used in the next step without any further purification. MS (ESI) m/z=262.8 (M+H)+

Reference Example 42.
6-methoxy-4-(piperidin-4-yloxy)quinoline hydrochloride The title compound (108.6 mg) was prepared in the same fashion as Reference Example 31, except that 6-methoxyquinolin-4-ol (217.6 mg, 1.2 mmol) was used instead of 3-quinolinol in Step 1. The title compound was used in the next step without any further purification. MS (ESI) m/z=258.3 (M+H)+

Reference Example 43.
7-methoxy-4-(piperidin-4-yloxy)quinoline hydrochloride The title compound (39.2 mg) was prepared in the same fashion as Reference Example 31, except that 7-methoxyquinolin-4-ol (217.6 mg, 1.2 mmol) was used instead of 3-quinolinol in Step 1. The title compound was used in the next step without any further purification. MS (ESI) m/z=258.3 (M+H)+

Reference Example 44.
6,7-dimethoxy-4-(piperidin-4-yloxy)quinoline hydrochloride The title compound (24.7 mg) was prepared in the same fashion as Reference Example 31, except that 6,7-dimethoxyquinolin-4-ol (254.9 mg, 1.2 mmol) was used instead of 3-quinolinol in Step 1. The title compound was used in the next step without any further purification. MS (ESI) m/z=288.3 (M+H)+

Reference Example 45. (S)-6-fluoro-N-(pyrrolidin-3-yl)benzofuran-3-carboxamide hydrochloride Step 1: tert-butyl (S)-3-(6-fluorobenzofuran-3-carboxamido)pyrrolidin-1-carboxylate Tert-butyl (S)-3-aminopyrrolidin-1-carboxylate (500 mg, 2.68 mmol) was dissolved in dimethylformamide (5.4 ml).

To the resulting solution, 6-fluorobenzofuran-3-carboxylic acid (725.4 mg, 4.02 mmol), HATU(O-(7-azabenzotriazol-1-yl)-N,N,N',N'-tetramethyluronium hexafluorophosphate) (1541.4 mg, 4.05 mmol) and diisopropylethylamine (4.67 mL, 26.8 mmol) were added. The reaction mixture was stirred overnight at room temperature. After the completion of the reaction, water was added to the reaction mixture. The aqueous layer of the reaction mixture was extracted with ethyl acetate. The extracted organic layer was dried and filtered over anhydrous magnesium sulfate. The filtered solution was concentrated and then purified with silica gel column chromatography (hexane/ethyl acetate=1/4, v/v) to give the title compound (766 mg). 1H NMR (CDCl3, 400 MHz) δ 8.17 (s, 1H), 7.95 (s, 1H), 7.22 (d, 1H), 7.10 (t, 1H), 6.73-6.52 (m, 1H), 4.67 (s, 1H), 3.70 (d, 1H), 3.47 (d, 2H), 3.32 (s, 1H), 2.23 (s, 1H), 2.00 (d, 1H), 1.46 (s, 9H)

Step 2: (S)-6-fluoro-N-(pyrrolidin-3-yl)benzofuran-3-carboxamide hydrochloride

Tert-butyl (S)-3-(6-fluorobenzofuran-3-carboxamido)pyrrolidin-1-carboxylate (280 mg, 0.85 mmol) was dissolved in dichloromethane (4.7 ml) and then 4.0 M of hydrochloric acid dissolved in 1,4-dioxane was added thereto in excess drops. The reaction mixture was stirred overnight at room temperature. After the completion of the reaction, the solid produced therefrom was filtered and dried to give the title compound (47 mg). The title compound was used in the next step without any further purification. MS (ESI) m/z=249.2 (M+H)+

Reference Example 46. (S)-6-methoxy-N-(pyrrolidin-3-yl)benzofuran-3-carboxamide hydrochloride Step 1: tert-butyl (S)-3-(6-methoxybenzofuran-3-carboxamido)pyrrolidine-1-carboxylate The title compound (399.3 mg, 41.3%) was prepared in the same fashion as Step 1 of Reference Example 45, except that 6-methoxybenzofuran-3-carboxylic acid (772.5 mg, 4.02 mmol) was used instead of 6-fluorobenzofuran-3-carboxyl acid. $^1$H NMR (CDCl$_3$, 400 MHz) δ 8.06 (s, 1H), 7.78 (d, 1H), 7.03 (s, 1H), 6.97 (d, 1H), 4.68 (s, 1H), 3.86 (s, 3H), 3.72 (s, 1H), 3.51-3.32 (m, 3H), 2.26-2.25 (m, 1H), 1.98-1.83 (m, 2H), 1.47 (s, 9H).

Step 2: (S)-6-methoxy-N-(pyrrolidin-3-yl)benzofuran-3-carboxamide hydrochloride

The title compound (295.9 mg, 90.0%) was prepared in the same fashion as Step 2 of Reference Example 5 and used in the next step without any further purification. $^1$H NMR (MeOD$_4$, 400 MHz) δ 8.35 (s, 1H), 7.90 (d, 1H), 7.14 (s, 1H), 697 (d, 1H), 4.63-4.62 (m, 1H), 3.85 (s, 3H), 3.61-3.58 (m, 2H), 3.43-3.41 (m, 2H), 2.45-2.40 (m, 1H), 2.23-2.22 (m, 1H).

Reference Example 47. (R)—N-methyl-N-(pyrrolidin-3-yl)quinolin-2-amine hydrochloride Step 1: tert-butyl (R)-3-(methyl(quinolin-2-yl)amino)pyrrolidine-1-carboxylate (R)-tert-butyl 3-(methylamino)pyrrolidine-1-carboxylate (250.0 mg, 1.25 mmol) was dissolved in anhydrous toluene. To the resulting solution, 2-bromoquinoline (259.7 mg, 1.25 mmol), cesium carbonate (488.1 mg, 1.50 mmol), tris(dibenzylideneacetone)dipalladium(0) (114.3 mg, 0.13 mmol), and (+/−)-2,2'-bis(diphenylphospino)-1,1'-binaphthalene (93.3 mg, 0.15 mmol) were added. The reaction mixture was refluxed and stirred at 100° C. overnight. After the completion of the reaction, the reaction mixture was cooled to room temperature and then added with water to extract an aqueous layer with ethyl acetate. The extracted organic layer was dried and filtered over anhydrous magnesium sulfate. The filtered solution was concentrated and then purified with silica gel column chromatography (ethyl acetate/n-hexane=1/1, v/v) to give a title compound (56.4 mg, 13.8%). MS (ESI) m/z=328.2 (M+H)+

Step 2: (R)—N-methyl-N-(pyrrolidin-3-yl)quinolin-2-amine hydrochloride

The title compound (25.5 mg, 100.0%) was prepared in the same fashion as Step 2 of Reference Example 5 and used in the next step without any further purification.

Reference Example 48. (R)—N-methyl-N-(pyrrolidin-3-yl)quinolin-3-amine hydrochloride Step 1: tert-butyl (R)-3-(methyl(quinolin-3-yl)amino)pyrrolidine-1-carboxylate The title compound (220.4 mg, 53.9%) was prepared in the same fashion as Step 1 of Reference Example 47, except that 3-bromoquinoline (259.7 mg, 1.25 mmol) was used instead of 2-bromoquinoline. MS (ESI) m/z=328.2 (M+H)+

Step 2: (R)—N-methyl-N-(pyrrolidin-3-yl)quinolin-3-amine hydrochloride

The title compound (168.8 mg, 100.0%) was prepared in the same fashion as Step 2 of Reference Example 5 and used in the next step without any further purification.

Reference Example 49. (R)—N-methyl-N-(pyrrolidin-3-yl)quinolin-5-amine hydrochloride Step 1: tert-butyl (R)-3-(methyl(quinolin-5-yl)amino)pyrrolidine-1-carboxylate The title compound (109.4 mg, 26.8%) was prepared in the same fashion as Step 1 of Reference Example 47, except that 5-bromoquinoline (259.7 mg, 1.25 mmol) was used instead of 2-bromoquinoline. MS (ESI) m/z=328.1 (M+H)+

Step 2: (R)—N-methyl-N-(pyrrolidin-3-yl)quinolin-5-amine hydrochloride

The title compound (88.1 mg, 100.0%) was prepared in the same fashion as Step 2 of Reference Example 5 and used in the next step without any further purification.

Reference Example 50. (R)—N-methyl-N-(pyrrolidin-3-yl)quinolin-6-amine hydrochloride Step 1: tert-butyl (R)-3-(methyl(quinolin-6-yl)amino)pyrrolidine-1-carboxylate The title compound (73.9 mg, 18.1%) was prepared in the same fashion as Step 1 of Reference Example 47, except that 6-bromoquinoline (259.7 mg, 1.25 mmol) was used instead of 2-bromoquinoline. MS (ESI) m/z=328.3 (M+H)+

Step 2: (R)—N-methyl-N-(pyrrolidin-3-yl)quinolin-6-amine hydrochloride

The title compound (59.5 mg, 100.0%) was prepared in the same fashion as Step 2 of Reference Example 5 and used in the next step without any further purification.

Reference Example 51. (R)—N-methyl-N-(pyrrolidin-3-yl)quinolin-7-amine hydrochloride Step 1: tert-butyl (R)-3-(methyl(quinolin-7-yl)amino)pyrrolidine-1-carboxylate The title compound (131.9 mg, 32.3%) was prepared in the same fashion as Step 1 of Reference Example 47, except that 7-bromoquinoline (259.7 mg, 1.25 mmol) was used instead of 2-bromoquinoline. MS (ESI) m/z=358.2 (M+H)+

Step 2: (R)—N-methyl-N-(pyrrolidin-3-yl)quinolin-7-amine hydrochloride

The title compound (106.3 mg, 100.0%) was prepared in the same fashion as Step 2 of Reference Example 5 and used in the next step without any further purification.

Reference Example 52. (S)—N-methyl-N-(pyrrolidin-3-yl)quinolin-3-amine hydrochloride Step 1: tert-butyl (S)-3-(methyl(quinolin-3-yl)amino)pyrrolidine-1-carboxylate (S)-tert-butyl 3-(methylamino)pyrrolidine-1-carboxylate (250.0 mg, 1.25 mmol) was dissolved in anhydrous toluene. To the resulting solution, 3-bromoquinoline (259.7 mg, 1.25 mmol), cesium carbonate (488.1 mg, 1.50 mmol), tris(dibenzylideneacetone)dipalladium(0) (114.3 mg, 0.13 mmol), and (+/−)-2,2'-bis(diphenylphospino)-1,1'-binaphthalene (93.3 mg, 0.15 mmol) were added. The reaction mixture was refluxed and stirred at 100° C. overnight. After the completion of the reaction, the reaction mixture was cooled to room temperature and then added with water to extract an aqueous layer with ethyl acetate. The extracted organic layer was dried and filtered over anhydrous magnesium sulfate. The filtered solution was concentrated and then purified with silica gel column chromatography (ethyl acetate/n-hexane=1/1, v/v) to give a title compound (252.5 mg, 61.8%). MS (ESI) m/z=328.3 (M+H)+

Step 2: (S)—N-methyl-N-(pyrrolidin-3-yl)quinolin-3-amine hydrochloride

The title compound (203.4 mg, 100.0%) was prepared in the same fashion as Step 2 of Reference Example 5 and used in the next step without any further purification.

Reference Example 53. (S)—N-methyl-N-(pyrrolidin-3-yl)quinolin-4-amine hydrochloride Step 1: tert-butyl (S)-3-(methyl(quinolin-4-yl)amino)pyrrolidine-1-carboxylate The title compound (74.2 mg, 18.2%) was prepared in the same fashion as Step 1 of Reference Example 52, except that 4-bromoquinoline (259.7 mg, 1.25 mmol) was used instead of 3-bromoquinoline. MS (ESI) m/z=328.3 (M+H)+

Step 2: (S)—N-methyl-N-(pyrrolidin-3-yl)quinolin-4-amine hydrochloride

The title compound (59.8 mg, 100.0%) was prepared in the same fashion as Step 2 of Reference Example 5 and used in the next step without any further purification.

Reference Example 54. (S)—N-methyl-N-(pyrrolidin-3-yl)quinolin-5-amine hydrochloride Step 1: tert-butyl (S)-3-(methyl(quinolin-5-yl)amino)pyrrolidine-1-carboxylate The title compound (124.2 mg, 30.4%) was prepared in the same fashion as Step 1 of Reference Example 52, except that 5-bromoquinoline (259.7 mg, 1.25 mmol) was used instead of 3-bromoquinoline. MS (ESI) m/z=328.2 (M+H)+

Step 2: (S)—N-methyl-N-(pyrrolidin-3-yl)quinolin-5-amine hydrochloride

The title compound (100.1 mg, 100.0%) was prepared in the same fashion as Step 2 of Reference Example 5 and used in the next step without any further purification.

Reference Example 55. (S)—N-methyl-N-(pyrrolidin-3-yl)quinolin-6-amine hydrochloride Step 1: tert-butyl (S)-3-(methyl(quinolin-6-yl)amino)pyrrolidine-1-carboxylate The title compound (120.5 mg, 29.5%) was prepared in the same fashion as Step 1 of Reference Example 52, except that 6-bromoquinoline (259.7 mg, 1.25 mmol) was used instead of 3-bromoquinoline. MS (ESI) m/z=328.3 (M+H)+

Step 2: (S)—N-methyl-N-(pyrrolidin-3-yl)quinolin-6-amine hydrochloride

The title compound (97.1 mg, 100.0%) was prepared in the same fashion as Step 2 of Reference Example 5 and used in the next step without any further purification.

Reference Example 56. (S)—N-methyl-N-(pyrrolidin-3-yl)quinolin-7-amine hydrochloride Step 1: tert-butyl (S)-3-(methyl(quinolin-7-yl)amino)pyrrolidine-1-carboxylate The title compound (260.0 mg, 63.6%) was prepared in the same fashion as Step 1 of Reference Example 52, except that 7-bromoquinoline (259.7 mg, 1.25 mmol) was used instead of 3-bromoquinoline. MS (ESI) m/z=328.2 (M+H)+

Step 2: (S)—N-methyl-N-(pyrrolidin-3-yl)quinolin-7-amine hydrochloride

The title compound (209.5 mg, 100.0%) was prepared in the same fashion as Step 2 of Reference Example 5 and used in the next step without any further purification.

Reference Example 57. (S)—N-methyl-N-(pyrrolidin-3-yl)isoquinolin-4-amine hydrochloride Step 1: tert-butyl (S)-3-(isoquinolin-4-yl(methyl)amino)pyrrolidine-1-carboxylate The title compound (69.0 mg, 16.9%) was prepared in the same fashion as Step 1 of Reference Example 52, except that 4-bromoisoquinoline (259.7 mg, 1.25 mmol) was used instead of 3-bromoquinoline. MS (ESI) m/z=328.3 (M+H)+

Step 2: (S)—N-methyl-N-(pyrrolidin-3-yl)isoquinolin-4-amine hydrochloride

The title compound (55.6 mg, 100.0%) was prepared in the same fashion as Step 2 of Reference Example 5 and used in the next step without any further purification.

Reference Example 58. (S)—N-methyl-N-(pyrrolidin-3-yl)isoquinolin-5-amine hydrochloride Step 1: tert-butyl (S)-3-(isoquinolin-5-yl(methyl)amino)pyrrolidine-1-carboxylate The title compound (87.8 mg, 21.5%) was prepared in the same fashion as Step 1 of Reference Example 52, except that 5-bromoisoquinoline (259.7 mg, 1.25 mmol) was used instead of 3-bromoquinoline. MS (ESI) m/z=328.3 (M+H)+

Step 2: (S)—N-methyl-N-(pyrrolidin-3-yl)isoquinolin-5-amine hydrochloride

The title compound (70.7 mg, 100.0%) was prepared in the same fashion as Step 2 of Reference Example 5 and used in the next step without any further purification.

Reference Example 59. (S)—N,4-dimethyl-N-(pyrrolidin-3-yl)quinolin-3-amine hydrochloride Step 1: tert-butyl (S)-3-(methyl(4-methylquinolin-3-yl)amino)pyrrolidine-1-carboxylate The title compound (60.4 mg, 14.2%) was prepared in the same fashion as Step 1 of Reference Example 52, except that 3-bromo-4-methylquinoline (277.2 mg, 1.25 mmol) was used instead of 3-bromoquinoline. MS (ESI) m/z=342.2 (M+H)+

Step 2: (S)—N,4-dimethyl-N-(pyrrolidin-3-yl)quinolin-3-amine hydrochloride

The title compound (49.1 mg, 100.0%) was prepared in the same fashion as Step 2 of Reference Example 5 and used in the next step without any further purification.

Reference Example 60. (S)—N,6-dimethyl-N-(pyrrolidin-3-yl)quinolin-3-amine hydrochloride Step 1: tert-butyl (S)-3-(methyl(6-methylquinolin-3-yl)amino)pyrrolidine-1-carboxylate The title compound (244.0 mg, 57.3%) was prepared in the same fashion as Step 1 of Reference Example 52, except that 3-bromo-6-methylquinoline (277.2 mg, 1.25 mmol) was used instead of 3-bromoquinoline. MS (ESI) m/z=342.2 (M+H)+

Step 2: (S)—N,6-dimethyl-N-(pyrrolidin-3-yl)quinolin-3-amine hydrochloride

The title compound (198.5 mg, 100.0%) was prepared in the same fashion as Step 2 of Reference Example 5 and used in the next step without any further purification.

Reference Example 61. (S)-6-fluoro-N-methyl-N-(pyrrolidin-3-yl)quinolin-3-amine hydrochloride Step 1: tert-butyl (S)-3-((6-fluoroquinolin-3-yl)(methyl)amino)pyrrolidine-1-carboxylate The title compound (314.7 mg, 73.0%) was prepared in the same fashion as Step 1 of Reference Example 52, except that 3-bromo-6-fluoroquinoline (282.2 mg, 1.25 mmol) was used instead of 3-bromoquinoline. MS (ESI) m/z=346.3 (M+H)+

Step 2: (S)-6-fluoro-N-methyl-N-(pyrrolidin-3-yl)quinolin-3-amine hydrochloride

The title compound (256.7 mg, 100.0%) was prepared in the same fashion as Step 2 of Reference Example 5 and used in the next step without any further purification.

Reference Example 62. (S)-6-methoxy-N-methyl-N-(pyrrolidin-3-yl)quinolin-3-amine hydrochloride Step 1: tert-butyl (S)-3-((6-methoxyquinolin-3-yl)(methyl)amino)pyrrolidine-1-carboxylate The title compound (264.3 mg, 59.2%) was prepared in the same fashion as Step 1 of Reference Example 52, except that 3-bromo-6-methoxyquinoline (297.2 mg, 1.25 mmol) was used instead of 3-bromoquinoline. MS (ESI) m/z=358.2 (M+H)+

Step 2: (S)-6-methoxy-N-methyl-N-(pyrrolidin-3-yl)quinolin-3-amine hydrochloride The title compound (217.2 mg, 100.0%) was prepared in the same fashion as Step 2 of Reference Example 5 and used in the next step without any further purification.

Reference Example 63. (S)-7-methoxy-N-methyl-N-(pyrrolidin-3-yl)quinolin-3-amine hydrochloride Step 1: tert-butyl (S)-3-((7-methoxyquinolin-3-yl)(methyl)amino)pyrrolidine-1-carboxylate The title compound (177.0 mg, 39.7%) was prepared in the same fashion as Step 1 of Reference Example 52, except that 3-bromo-7-methoxyquinoline (297.2 mg, 1.25 mmol) was used instead of 3-bromoquinoline. MS (ESI) m/z=358.2 (M+H)+

Step 2: (S)-7-methoxy-N-methyl-N-(pyrrolidin-3-yl)quinolin-3-amine hydrochloride The title compound (145.5 mg, 100.0%) was prepared in the same fashion as Step 2 of Reference Example 5 and used in the next step without any further purification.

Reference Example 64. (S)-8-methoxy-N-methyl-N-(pyrrolidin-3-yl)quinolin-3-amine hydrochloride Step 1: tert-butyl (S)-3-((8-methoxyquinolin-3-yl)(methyl)amino)pyrrolidine-1-carboxylate The title compound (359.9 mg, 80.7%) was prepared in the same fashion as Step 1 of Reference Example 52, except that 3-bromo-8-methoxyquinoline (297.2 mg, 1.25 mmol) was used instead of 3-bromoquinoline. MS (ESI) m/z=358.2 (M+H)+

Step 2: (S)-8-methoxy-N-methyl-N-(pyrrolidin-3-yl)quinolin-3-amine hydrochloride The title compound (295.8 mg, 100.0%) was prepared in the same fashion as Step 2 of Reference Example 5 and used in the next step without any further purification.

Reference Example 65. (S)—N,3-dimethyl-N-(pyrrolidin-3-yl)quinolin-5-amine hydrochloride Step 1: tert-butyl (S)-3-(methyl(3-methylquinolin-5-yl)amino)pyrrolidine-1-carboxylate The title compound (115.1 mg, 27.0%) was prepared in the same fashion as Step 1 of Reference Example 52, except that 5-bromo-3-methylquinoline (277.2 mg, 1.25 mmol) was used instead of 3-bromoquinoline. MS (ESI) m/z=342.2 (M+H)+

Step 2: (S)—N,3-dimethyl-N-(pyrrolidin-3-yl)quinolin-5-amine hydrochloride

The title compound (93.6 mg, 100.0%) was prepared in the same fashion as Step 2 of Reference Example 5 and used in the next step without any further purification.

Reference Example 66. (S)-3-fluoro-N-methyl-N-(pyrrolidin-3-yl)quinolin-5-amine hydrochloride Step 1: tert-butyl (S)-3-((3-fluoroquinolin-5-yl)(methyl)amino)pyrrolidine-1-carboxylate The title compound (286.6 mg, 66.5%) was prepared in the same fashion as Step 1 of Reference Example 52, except that 5-bromo-3-fluoro-quinoline (282.2 mg, 1.25 mmol) was used instead of 3-bromoquinoline. MS (ESI) m/z=346.2 (M+H)+

Step 2: (S)-3-fluoro-N-methyl-N-(pyrrolidin-3-yl)quinolin-5-amine hydrochloride

The title compound (233.8 mg, 100.0%) was prepared in the same fashion as Step 2 of Reference Example 5 and used in the next step without any further purification.

Reference Example 67. (S)-7-fluoro-N-methyl-N-(pyrrolidin-3-yl)quinolin-5-amine hydrochloride Step 1: tert-butyl (S)-3-((7-fluoroquinolin-5-yl)(methyl)amino)pyrrolidine-1-carboxylate The title compound (223.7 mg, 51.9%) was prepared in the same fashion as Step 1 of Reference Example 52, except that 5-bromo-7-fluoro-quinoline (282.2 mg, 1.25 mmol) was used instead of 3-bromoquinoline. MS (ESI) m/z=346.2 (M+H)+

Step 2: (S)-7-fluoro-N-methyl-N-(pyrrolidin-3-yl)quinolin-5-amine hydrochloride

The title compound (182.5 mg, 100.0%) was prepared in the same fashion as Step 2 of Reference Example 5 and used in the next step without any further purification.

Reference Example 68. (S)-8-fluoro-N-methyl-N-(pyrrolidin-3-yl)quinolin-5-amine hydrochloride Step 1: tert-butyl (S)-3-((8-fluoroquinolin-5-yl)(methyl)amino)pyrrolidine-1-carboxylate The title compound (209.9 mg, 48.7%) was prepared in the same fashion as Step 1 of Reference Example 52, except that 5-bromo-8-fluoro-quinoline (282.2 mg, 1.25 mmol) was used instead of 3-bromoquinoline. MS (ESI) m/z=346.2 (M+H)+

Step 2: (S)-8-fluoro-N-methyl-N-(pyrrolidin-3-yl)quinolin-5-amine hydrochloride

The title compound (171.2 mg, 100.0%) was prepared in the same fashion as Step 2 of Reference Example 5 and used in the next step without any further purification.

Reference Example 69. (S)—N-methyl-N-(pyrrolidin-3-yl)-8-(trifluoromethyl)quinolin-5-amine hydrochloride Step 1: tert-butyl (S)-3-(methyl(8-(trifluoromethyl)quinolin-5-yl)amino)pyrrolidine-1-carboxylate The title compound (416.4 mg, 84.4%) was prepared in the same fashion as Step 1 of Reference Example 52, except that 5-bromo-8-(trifluoromethyl)quinoline (344.6 mg, 1.25 mmol) was used instead of 3-bromoquinoline. MS (ESI) m/z=396.2 (M+H)+

Step 2: (S)—N-methyl-N-(pyrrolidin-3-yl)-8-(trifluoromethyl)quinolin-5-amine hydrochloride The title compound (349.4 mg, 100.0%) was prepared in the same fashion as Step 2 of Reference Example 5 and used in the next step without any further purification.

Reference Example 70. (S)—N-methyl-N-(pyrrolidin-3-yl)-8-(trifluoromethoxy)quinolin-5-amine hydrochloride Step 1: tert-butyl (S)-3-(methyl(8-(trifluoromethoxy)quinolin-5-yl)amino)pyrrolidine-1-carboxylate The title compound (432.5 mg, 84.2%) was prepared in the same fashion as Step 1 of Reference Example 52, except that 5-bromo-8-trifluoromethoxyquinoline (364.6 mg, 1.25 mmol) was used instead of 3-bromoquinoline. MS (ESI) m/z=412.2 (M+H)+

Step 2: (S)—N-methyl-N-(pyrrolidin-3-yl)-8-(trifluoromethoxy)quinolin-5-amine hydrochloride The title compound (365.6 mg, 100.0%) was prepared in the same fashion as Step 2 of Reference Example 5 and used in the next step without any further purification.

Reference Example 71. (R)—N-(pyrrolidin-3-yl)quinolin-5-amine hydrochloride

Step 1: tert-butyl (R)-3-(quinolin-5-ylamino)pyrrolidine-1-carboxylate

The title compound (589.6 mg, 70.0%) was prepared in the same fashion as Step 1 of Reference Example 17, except that 5-bromoquinoline (558.5 mg, 2.68 mmol) was used instead of 3-bromoquinoline. MS (ESI) m/z=314.2 (M+H)+

Step 2: (R)—N-(pyrrolidin-3-yl)quinolin-5-amine hydrochloride

The title compound (466.5 mg, 86.6%) was prepared in the same fashion as Step 2 of Reference Example 5. MS (ESI) m/z=214.2 (M+H)+

Reference Example 72. (R)—N-(pyrrolidin-3-yl)quinolin-6-amine hydrochloride

Step 1: tert-butyl (R)-3-(quinolin-6-ylamino)pyrrolidine-1-carboxylate

The title compound (389.3 mg, 46.3%) was prepared in the same fashion as Step 1 of Reference Example 17, except that 6-bromoquinoline (558.5 mg, 2.68 mmol) was used instead of 3-bromoquinoline. MS (ESI) m/z=314.2 (M+H)+

Step 2: (R)—N-(pyrrolidin-3-yl)quinolin-6-amine hydrochloride

The title compound (298.1 mg, 94.1%) was prepared in the same fashion as Step 2 of Reference Example 5. MS (ESI) m/z=214.2 (M+H)+

Reference Example 73. (R)—N-(pyrrolidin-3-yl)quinolin-7-amine hydrochloride

Step 1: tert-butyl (R)-3-(quinolin-7-ylamino)pyrrolidine-1-carboxylate

The title compound (356.5 mg, 42.4%) was prepared in the same fashion as Step 1 of Reference Example 17, except that 7-bromoquinoline (558.5 mg, 2.68 mmol) was used instead of 3-bromoquinoline. MS (ESI) m/z=314.2 (M+H)+

Step 2: (R)—N-(pyrrolidin-3-yl)quinolin-7-amine hydrochloride

The title compound (261.9 mg, 82.6%) was prepared in the same fashion as Step 2 of Reference Example 5. MS (ESI) m/z=214.2 (M+H)+

Reference Example 74. (R)—N-(pyrrolidin-3-yl)quinolin-8-amine hydrochloride

Step 1: tert-butyl (R)-3-(quinolin-8-ylamino)pyrrolidine-1-carboxylate

The title compound (692.6 mg, 82.3%) was prepared in the same fashion as Step 1 of Reference Example 17, except that 8-bromoquinoline (558.5 mg, 2.68 mmol) was used instead of 3-bromoquinoline. MS (ESI) m/z=314.2 (M+H)+

Step 2: (R)—N-(pyrrolidin-3-yl)quinolin-8-amine hydrochloride

The title compound (589.4 mg, 93.1%) was prepared in the same fashion as Step 2 of Reference Example 5. MS (ESI) m/z=214.2 (M+H)+

Reference Example 75. (R)—N-(pyrrolidin-3-yl)quinolin-4-amine hydrochloride

Step 1: tert-butyl (R)-3-(quinolin-4-ylamino)pyrrolidine-1-carboxylate

The title compound (490.9 mg, 58.4%) was prepared in the same fashion as Step 1 of Reference Example 17, except that 4-bromoquinoline (558.5 mg, 2.68 mmol) was used instead of 3-bromoquinoline. MS (ESI) m/z=314.2 (M+H)+

Step 2: (R)—N-(pyrrolidin-3-yl)quinolin-4-amine hydrochloride

The title compound (195.4 mg, 43.6%) was prepared in the same fashion as Step 2 of Reference Example 5. MS (ESI) m/z=214.2 (M+H)+

Reference Example 76. (R)—N-(pyrrolidin-3-yl)-1,8-naphthyridin-3-amine hydrochloride Step 1: tert-butyl (R)-3-((1,8-naphthyridin-3-yl)amino)pyrrolidine-1-carboxylate The title compound (278.2 mg, 65.9%) was prepared in the same fashion as Step 1 of Reference Example 17, except that 3-bromo-1,8-naphthyridine (280.6 mg, 1.34 mmol) was used instead of 3-bromoquinoline. MS (ESI) m/z=315.1 (M+H)+

Step 2: (R)—N-(pyrrolidin-3-yl)-1,8-naphthyridin-3-amine hydrochloride

The title compound (254.2 mg, 100.0%) was prepared in the same fashion as Step 2 of Reference Example 5 and used in the next step without any further purification.

Reference Example 77. (R)-7-chloro-N-(pyrrolidin-3-yl)-1,8-naphthyridin-3-amine hydrochloride Step 1: tert-butyl (R)-3-((7-chloro-1,8-naphthyridin-3-yl)amino)pyrrolidine-1-carboxylate The title compound (174.8 mg, 37.3%) was prepared in the same fashion as Step 1 of Reference Example 17, except that 6-bromo-2-chloro-1,8-naphthyridine (326.8 mg, 1.34 mmol) was used instead of 3-bromoquinoline. MS (ESI) m/z=349.1 (M+H)+

Step 2: (R)-7-chloro-N-(pyrrolidin-3-yl)-1,8-naphthyridin-3-amine hydrochloride

The title compound (161.2 mg, 100.0%) was prepared in the same fashion as Step 2 of Reference Example 5 and used in the next step without any further purification.

Reference Example 78. (R)-6-fluoro-N-(pyrrolidin-3-yl)quinolin-5-amine hydrochloride Step 1: tert-butyl (R)-3-((6-fluoroquinolin-5-yl)amino)pyrrolidine-1-carboxylate The title compound (187.1 mg, 42.1%) was prepared in the same fashion as Step 1 of Reference Example 17, except that 5-bromo-6-fluoroquinoline (303.4 mg, 1.34 mmol) was used instead of 3-bromoquinoline. MS (ESI) m/z=332.2 (M+H)+

Step 2: (R)-6-fluoro-N-(pyrrolidin-3-yl)quinolin-5-amine hydrochloride

The title compound (171.9 mg, 100.0%) was prepared in the same fashion as Step 2 of Reference Example 5 and used in the next step without any further purification.

Reference Example 79. (R)-7-fluoro-N-(pyrrolidin-3-yl)quinolin-5-amine hydrochloride Step 1: tert-butyl (R)-3-((7-fluoroquinolin-5-yl)amino)pyrrolidine-1-carboxylate The title compound (129.4 mg, 29.1%) was prepared in the same fashion as Step 1 of Reference Example 17, except that 5-bromo-7-fluoroquinoline (303.4 mg, 1.34 mmol) was used instead of 3-bromoquinoline. MS (ESI) m/z=332.2 (M+H)+

Step 2: (R)-7-fluoro-N-(pyrrolidin-3-yl)quinolin-5-amine hydrochloride

The title compound (118.6 mg, 100.0%) was prepared in the same fashion as Step 2 of Reference Example 5 and used in the next step without any further purification.

Reference Example 80. (R)-8-fluoro-N-(pyrrolidin-3-yl)quinolin-5-amine hydrochloride Step 1: tert-butyl (R)-3-((8-fluoroquinolin-5-yl)amino)pyrrolidine-1-carboxylate The title compound (330.4 mg, 74.3%) was prepared in the same fashion as Step 1 of Reference Example 17, except that 5-bromo-8-fluoroquinoline (303.4 mg, 1.34 mmol) was used instead of 3-bromoquinoline. MS (ESI) m/z=332.2 (M+H)+

Step 2: (R)-8-fluoro-N-(pyrrolidin-3-yl)quinolin-5-amine hydrochloride

The title compound (303.3 mg, 100.0%) was prepared in the same fashion as Step 2 of Reference Example 5 and used in the next step without any further purification.

Reference Example 81. (R)-6-methoxy-N-(pyrrolidin-3-yl)quinolin-5-amine hydrochloride Step 1: tert-butyl (R)-3-((6-methoxyquinolin-5-yl)amino)pyrrolidine-1-carboxylate The title compound (427.4 mg, 92.7%) was prepared in the same fashion as Step 1 of Reference Example 17, except that 5-bromo-6-methoxyquinoline (319.6 mg, 1.34 mmol) was used instead of 3-bromoquinoline. MS (ESI) m/z=344.2 (M+H)+

Step 2: (R)-6-methoxy-N-(pyrrolidin-3-yl)quinolin-5-amine hydrochloride

The title compound (393.7 mg, 100.0%) was prepared in the same fashion as Step 2 of Reference Example 5 and used in the next step without any further purification.

Reference Example 82. (R)-7-methoxy-N-(pyrrolidin-3-yl)quinolin-5-amine hydrochloride Step 1: tert-butyl (R)-3-((7-methoxyquinolin-5-yl)amino)pyrrolidine-1-carboxylate The title compound (460.9 mg, 100.0%) was prepared in the same fashion as Step 1 of Reference Example 17, except that 5-bromo-7-methoxyquinoline (319.6 mg, 1.34 mmol) was used instead of 3-bromoquinoline. MS (ESI) m/z=344.2 (M+H)+

Step 2: (R)-7-methoxy-N-(pyrrolidin-3-yl)quinolin-5-amine hydrochloride

The title compound (424.4 mg, 100.0%) was prepared in the same fashion as Step 2 of Reference Example 5 and used in the next step without any further purification.

Reference Example 83. (R)-8-methoxy-N-(pyrrolidin-3-yl)quinolin-5-amine hydrochloride Step 1: tert-butyl (R)-3-((8-methoxyquinolin-5-yl)amino)pyrrolidine-1-carboxylate The title compound (180.0 mg, 39.1%) was prepared in the same fashion as Step 1 of Reference Example 17, except that 5-bromo-8-methoxyquinoline (319.6 mg, 1.34 mmol) was used instead of 3-bromoquinoline. MS (ESI) m/z=344.2 (M+H)+

Step 2: (R)-8-methoxy-N-(pyrrolidin-3-yl)quinolin-5-amine hydrochloride

The title compound (165.7 mg, 100.0%) was prepared in the same fashion as Step 2 of Reference Example 5 and used in the next step without any further purification.

Reference Example 84. (R)-3-methyl-N-(pyrrolidin-3-yl)quinolin-5-amine hydrochloride Step 1: tert-butyl (R)-3-((3-methylquinolin-5-yl)amino)pyrrolidine-1-carboxylate The title compound (314.2 mg, 71.5%) was prepared in the same fashion as Step 1 of Reference Example 17, except that 5-bromo-3-methylquinoline (298.1 mg, 1.34 mmol) was used instead of 3-bromoquinoline. MS (ESI) m/z=328.2 (M+H)+

Step 2: (R)-3-methyl-N-(pyrrolidin-3-yl)quinolin-5-amine hydrochloride

The title compound (288.2 mg, 100.0%) was prepared in the same fashion as Step 2 of Reference Example 5 and used in the next step without any further purification.

Reference Example 85. (R)-6-methyl-N-(pyrrolidin-3-yl)quinolin-5-amine hydrochloride Step 1: tert-butyl (R)-3-((6-methylquinolin-5-yl)amino)pyrrolidine-1-carboxylate The title compound (419.0 mg, 95.3%) was prepared in the same fashion as Step 1 of Reference Example 17, except that 5-bromo-6-methylquinoline (298.1 mg, 1.34 mmol) was used instead of 3-bromoquinoline. MS (ESI) m/z=328.2 (M+H)+

Step 2: (R)-6-methyl-N-(pyrrolidin-3-yl)quinolin-5-amine hydrochloride

The title compound (384.3 mg, 100.0%) was prepared in the same fashion as Step 2 of Reference Example 5 and used in the next step without any further purification.

Reference Example 86. (R)-8-methyl-N-(pyrrolidin-3-yl)quinolin-5-amine hydrochloride Step 1: tert-butyl (R)-3-((8-methylquinolin-5-yl)amino)pyrrolidine-1-carboxylate The title compound (290.5 mg, 66.1%) was prepared in the same fashion as Step 1 of Reference Example 17, except that 5-bromo-8-methylquinoline (298.1 mg, 1.34 mmol) was used instead of 3-bromoquinoline. MS (ESI) m/z=328.2 (M+H)+

Step 2: (R)-8-methyl-N-(pyrrolidin-3-yl)quinolin-5-amine hydrochloride

The title compound (266.3 mg, 100.0%) was prepared in the same fashion as Step 2 of Reference Example 5 and used in the next step without any further purification.

Reference Example 87. (R)—N-(pyrrolidin-3-yl)-7-(trifluoromethyl)quinolin-5-amine hydrochloride Step 1: tert-butyl (R)-3-((7-(trifluoromethyl)quinolin-5-yl)amino)pyrrolidine-1-carboxylate The title compound (424.1 mg, 82.8%) was prepared in the same fashion as Step 1 of Reference Example 17, except that 5-bromo-7-(trifluoromethyl)quinoline (370.5 mg, 1.34 mmol) was used instead of 3-bromoquinoline. MS (ESI) m/z=382.2 (M+H)+

Step 2: (R)—N-(pyrrolidin-3-yl)-7-(trifluoromethyl)quinolin-5-amine hydrochloride The title compound (393.9 mg, 100.0%) was prepared in the same fashion as Step 2 of Reference Example 5 and used in the next step without any further purification.

Reference Example 88. (R)—N-(pyrrolidin-3-yl)-8-(trifluoromethyl)quinolin-5-amine hydrochloride Step 1: tert-butyl (R)-3-((8-(trifluoromethyl)quinolin-5-yl)amino)pyrrolidine-1-carboxylate The title compound (186.5 mg, 36.4%) was prepared in the same fashion as Step 1 of Reference Example 17, except that 5-bromo-8-(trifluoromethyl)quinoline (370.5 mg, 1.34 mmol) was used instead of 3-bromoquinoline. MS (ESI) m/z=382.2 (M+H)+

Step 2: (R)—N-(pyrrolidin-3-yl)-8-(trifluoromethyl)quinolin-5-amine hydrochloride The title compound (173.2 mg, 100.0%) was prepared in the same fashion as Step 2 of Reference Example 5 and used in the next step without any further purification.

Reference Example 89. (R)-3-fluoro-N-(pyrrolidin-3-yl)quinolin-5-amine hydrochloride Step 1: tert-butyl (R)-3-((3-fluoroquinolin-5-yl)amino)pyrrolidine-1-carboxylate The title compound (251.6 mg, 56.6%) was prepared in the same fashion as Step 1 of Reference Example 17, except that 5-bromo-3-fluoro-quinoline (303.4 mg, 1.34 mmol) was used instead of 3-bromoquinoline. MS (ESI) m/z=332.2 (M+H)+

Step 2: (R)-3-fluoro-N-(pyrrolidin-3-yl)quinolin-5-amine hydrochloride

The title compound (230.9 mg, 100.0%) was prepared in the same fashion as Step 2 of Reference Example 5 and used in the next step without any further purification.

Reference Example 90. (R)-3-chloro-N-(pyrrolidin-3-yl)quinolin-5-amine hydrochloride Step 1: tert-butyl (R)-3-((3-chloroquinolin-5-yl)amino)pyrrolidine-1-carboxylate The title compound (320.1 mg, 68.6%) was prepared in the same fashion as Step 1 of Reference Example 17, except that 5-bromo-3-chloro-quinoline (325.5 mg, 1.34 mmol) was used instead of 3-bromoquinoline. MS (ESI) m/z=348.2 (M+H)+

Step 2: (R)-3-chloro-N-(pyrrolidin-3-yl)quinolin-5-amine hydrochloride

The title compound (295.0 mg, 100.0%) was prepared in the same fashion as Step 2 of Reference Example 5 and used in the next step without any further purification.

Reference Example 91. (R)—N-(pyrrolidin-3-yl)-8-(trifluoromethoxy)quinolin-5-amine hydrochloride Step 1: tert-butyl (R)-3-((8-(trifluoromethoxy)quinolin-5-yl)amino)pyrrolidine-1-carboxylate The title compound (470.2 mg, 88.2%) was prepared in the same fashion as Step 1 of Reference Example 17, except that 5-bromo-8-trifluoromethoxyquinoline (392.0 mg, 1.34 mmol) was used instead of 3-bromoquinoline. MS (ESI) m/z=398.2 (M+H)+

Step 2: (R)—N-(pyrrolidin-3-yl)-8-(trifluoromethoxy)quinolin-5-amine hydrochloride The title compound (438.0 mg, 100.0%) was prepared in the same fashion as Step 2 of Reference Example 5 and used in the next step without any further purification.

Reference Example 92. (R)-6-methyl-N-(pyrrolidin-3-yl)quinolin-4-amine hydrochloride Step 1: tert-butyl (R)-3-((6-methylquinolin-4-yl)amino)pyrrolidine-1-carboxylate The title compound (47.1 mg, 10.7%) was prepared in the same fashion as Step 1 of Reference Example 17, except that 4-bromo-6-methylquinoline (298.1 mg, 1.34 mmol) was used instead of 3-bromoquinoline. MS (ESI) m/z=328.2 (M+H)+

Step 2: (R)-6-methyl-N-(pyrrolidin-3-yl)quinolin-4-amine hydrochloride

The title compound (43.2 mg, 100.0%) was prepared in the same fashion as Step 2 of Reference Example 5 and used in the next step without any further purification.

Reference Example 93. (R)-6-methoxy-N-(pyrrolidin-3-yl)quinolin-4-amine hydrochloride Step 1: tert-butyl (R)-3-((6-methoxyquinolin-4-yl)amino)pyrrolidine-1-carboxylate The title compound (326.8 mg, 70.9%) was prepared in the same fashion as Step 1 of Reference Example 17, except that 4-bromo-6-methoxyquinoline (319.6 mg, 1.34 mmol) was used instead of 3-bromoquinoline. MS (ESI) m/z=344.1 (M+H)+

Step 2: (R)-6-methoxy-N-(pyrrolidin-3-yl)quinolin-4-amine hydrochloride

The title compound (301.1 mg, 100.0%) was prepared in the same fashion as Step 2 of Reference Example 5 and used in the next step without any further purification.

Reference Example 94. (R)-8-chloro-N-(pyrrolidin-3-yl)quinolin-4-amine hydrochloride Step 1: tert-butyl (R)-3-((8-chloroquinolin-4-yl)amino)pyrrolidine-1-carboxylate The title compound (126.9 mg, 27.2%) was prepared in the same fashion as Step 1 of Reference Example 17, except that 4-bromo-8-chloroquinoline (325.5 mg, 1.34 mmol) was used instead of 3-bromoquinoline. MS (ESI) m/z=348.2 (M+H)+

Step 2: (R)-8-chloro-N-(pyrrolidin-3-yl)quinolin-4-amine hydrochloride

The title compound (117.0 mg, 100.0%) was prepared in the same fashion as Step 2 of Reference Example 5 and used in the next step without any further purification.

Reference Example 95. (R)-8-methyl-N-(pyrrolidin-3-yl)quinolin-4-amine hydrochloride Step 1: tert-butyl (R)-3-((8-methylquinolin-4-yl)amino)pyrrolidine-1-carboxylate The title compound (425.0 mg, 96.7%) was prepared in the same fashion as Step 1 of Reference Example 17, except that 4-bromo-8-methylquinoline (298.1 mg, 1.34 mmol) was used instead of 3-bromoquinoline. MS (ESI) m/z=328.2 (M+H)+

Step 2: (R)-8-methyl-N-(pyrrolidin-3-yl)quinolin-4-amine hydrochloride

The title compound (406.2 mg, 100.0%) was prepared in the same fashion as Step 2 of Reference Example 5 and used in the next step without any further purification.

Reference Example 96. (R)-6-fluoro-N-(pyrrolidin-3-yl)quinolin-4-amine hydrochloride Step 1: tert-butyl (R)-3-((6-fluoroquinolin-4-yl)amino)pyrrolidine-1-carboxylate The title compound (367.7.0 mg, 82.7%) was prepared in the same fashion as Step 1 of Reference Example 17, except that 4-bromo-6-fluoro-quinoline (303.4 mg, 1.34 mmol) was used instead of 3-bromoquinoline. MS (ESI) m/z=332.2 (M+H)+

Step 2: (R)-6-fluoro-N-(pyrrolidin-3-yl)quinolin-4-amine hydrochloride

The title compound (337.7 mg, 100.0%) was prepared in the same fashion as Step 2 of Reference Example 5 and used in the next step without any further purification.

Reference Example 97. (R)-6-chloro-N-(pyrrolidin-3-yl)quinolin-4-amine hydrochloride Step 1: tert-butyl (R)-3-((6-chloroquinolin-4-yl)amino)pyrrolidine-1-carboxylate The title compound (298.1 mg, 63.9%) was prepared in the same fashion as Step 1 of Reference Example 17, except that 4-bromo-6-chloro-quinoline (325.5 mg, 1.34 mmol) was used instead of 3-bromoquinoline. MS (ESI) m/z=348.1 (M+H)+

Step 2: (R)-6-chloro-N-(pyrrolidin-3-yl)quinolin-4-amine hydrochloride

The title compound (274.8 mg, 100.0%) was prepared in the same fashion as Step 2 of Reference Example 5 and used in the next step without any further purification.

Reference Example 98. (R)-7-methoxy-N-(pyrrolidin-3-yl)quinolin-4-amine hydrochloride Step 1: tert-butyl (R)-3-((7-methoxyquinolin-4-yl)amino)pyrrolidine-1-carboxylate The title compound (423.5 mg, 91.9%) was prepared in the same fashion as Step 1 of Reference Example 17, except that 4-bromo-7-methoxy-quinoline (319.6 mg, 1.34 mmol) was used instead of 3-bromoquinoline. MS (ESI) m/z=344.2 (M+H)+

Step 2: (R)-7-methoxy-N-(pyrrolidin-3-yl)quinolin-4-amine hydrochloride

The title compound (358.2 mg, 100.0%) was prepared in the same fashion as Step 2 of Reference Example 5 and used in the next step without any further purification.

Reference Example 99. (R)-8-fluoro-N-(pyrrolidin-3-yl)quinolin-4-amine hydrochloride Step 1: tert-butyl (R)-3-((8-fluoroquinolin-4-yl)amino)pyrrolidine-1-carboxylate The title compound (444.7 mg, 100.0%) was prepared in the same fashion as Step 1 of Reference Example 17, except that 4-bromo-8-fluoroquinoline (303.4 mg, 1.34 mmol) was used instead of 3-bromoquinoline. MS (ESI) m/z=332.2 (M+H)+

Step 2: (R)-8-fluoro-N-(pyrrolidin-3-yl)quinolin-4-amine hydrochloride

The title compound (418.0 mg, 100.0%) was prepared in the same fashion as Step 2 of Reference Example 5 and used in the next step without any further purification.

Reference Example 100. (R)-8-methoxy-N-(pyrrolidin-3-yl)quinolin-4-amine hydrochloride Step 1: tert-butyl (R)-3-((8-methoxyquinolin-4-yl)amino)pyrrolidine-1-carboxylate The title compound (348.5 mg, 75.6%) was prepared in the same fashion as Step 1 of Reference Example 17, except that 4-bromo-8-methoxyquinoline (319.6 mg, 1.34 mmol) was used instead of 3-bromoquinoline. MS (ESI) m/z=344.2 (M+H)+

Step 2: (R)-8-methoxy-N-(pyrrolidin-3-yl)quinolin-4-amine hydrochloride

The title compound (316.4 mg, 100.0%) was prepared in the same fashion as Step 2 of Reference Example 5 and used in the next step without any further purification.

Reference Example 101. (R)—N-(pyrrolidin-3-yl)-8-(trifluoromethyl)quinolin-4-amine hydrochloride Step 1: tert-butyl (R)-3-((8-(trifluoromethyl)quinolin-4-yl)amino)pyrrolidine-1-carboxylate The title compound (511.8 mg, 100.0%) was prepared in the same fashion as Step 1 of Reference Example 17, except that 4-bromo-8-(trifluoromethyl)quinoline (370.5 mg, 1.34 mmol) was used instead of 3-bromoquinoline. MS (ESI) m/z=382.2 (M+H)+

Step 2: (R)—N-(pyrrolidin-3-yl)-8-(trifluoromethyl)quinolin-4-amine hydrochloride The title compound (499.4 mg, 100.0%) was prepared in the same fashion as Step 2 of Reference Example 5 and used in the next step without any further purification.

Reference Example 102. (R)-3-methoxy-N-(pyrrolidin-3-yl)quinolin-5-amine hydrochloride Step 1: tert-butyl (R)-3-((3-methoxyquinolin-5-yl)amino)pyrrolidine-1-carboxylate The title compound (662.7 mg, 71.9%) was prepared in the same fashion as Step 1 of Reference Example 17, except that 5-bromo-3-methoxyquinoline (639.1 mg, 2.69 mmol) was used instead of 3-bromoquinoline. MS (ESI) m/z=344.2 (M+H)+

Step 2: (R)-3-methoxy-N-(pyrrolidin-3-yl)quinolin-5-amine hydrochloride

The title compound (610.3 mg, 100.0%) was prepared in the same fashion as Step 2 of Reference Example 5 and used in the next step without any further purification.

Reference Example 103. (R)-2-chloro-N-(pyrrolidin-3-yl)quinolin-6-amine hydrochloride Step 1: tert-butyl (R)-3-((2-chloroquinolin-6-yl)amino)pyrrolidine-1-carboxylate The title compound (720.5 mg, 77.2%) was prepared in the same fashion as Step 1 of Reference Example 17, except that 2-chloro-6-bromoquinoline (651.0 mg, 2.69 mmol) was used instead of 3-bromoquinoline. MS (ESI) m/z=348.2 (M+H)+

Step 2: (R)-2-chloro-N-(pyrrolidin-3-yl)quinolin-6-amine hydrochloride

The title compound (618.5 mg, 100.0%) was prepared in the same fashion as Step 2 of Reference Example 5 and used in the next step without any further purification.

Reference Example 104. (R)—N-(pyrrolidin-3-yl)-2-(trifluoromethyl)quinolin-6-amine hydrochloride Step 1: tert-butyl (R)-3-((2-(trifluoromethyl)quinolin-6-yl)amino)pyrrolidine-1-carboxylate The title compound (408.1 mg, 79.7%) was prepared in the same fashion as Step 1 of Reference Example 17, except that 6-bromo-2-(trifluoromethyl)quinoline (370.5 mg, 1.34 mmol) was used instead of 3-bromoquinoline. MS (ESI) m/z=382.2 (M+H)+

Step 2: (R)—N-(pyrrolidin-3-yl)-2-(trifluoromethyl)quinolin-6-amine hydrochloride The title compound (379.0 mg, 100.0%) was prepared in the same fashion as Step 2 of Reference Example 5 and used in the next step without any further purification.

Reference Example 105. (R)-3-methyl-N-(pyrrolidin-3-yl)quinolin-6-amine hydrochloride Step 1: tert-butyl (R)-3-((3-methylquinolin-6-yl)amino)pyrrolidine-1-carboxylate The title compound (328.0 mg, 74.6%) was prepared in the same fashion as Step 1 of Reference Example 17, except that 6-bromo-3-methylquinoline (298.1 mg, 1.34 mmol) was used instead of 3-bromoquinoline. MS (ESI) m/z=328.2 (M+H)+

Step 2: (R)-3-methyl-N-(pyrrolidin-3-yl)quinolin-6-amine hydrochloride

The title compound (300.8 mg, 100.0%) was prepared in the same fashion as Step 2 of Reference Example 5 and used in the next step without any further purification.

Reference Example 106. (R)-4-methoxy-N-(pyrrolidin-3-yl)quinolin-6-amine hydrochloride Step 1: tert-butyl (R)-3-((4-methoxyquinolin-7-yl)amino)pyrrolidine-1-carboxylate The title compound (239.7 mg, 52.0%) was prepared in the same fashion as Step 1 of Reference Example 17, except that 6-bromo-4-methoxy-quinoline (319.6 mg, 1.34 mmol) was used instead of 3-bromoquinoline. MS (ESI) m/z=344.2 (M+H)+

Step 2: (R)-4-methoxy-N-(pyrrolidin-3-yl)quinolin-6-amine hydrochloride

The title compound (220.7 mg, 100.0%) was prepared in the same fashion as Step 2 of Reference Example 5 and used in the next step without any further purification.

Reference Example 107. (R)-8-methyl-N-(pyrrolidin-3-yl)quinolin-6-amine hydrochloride Step 1: tert-butyl (R)-3-((8-methylquinolin-6-yl)amino)pyrrolidine-1-carboxylate The title compound (258.6 mg, 58.8%) was prepared in the same fashion as Step 1 of Reference Example 17, except that 6-bromo-8-methylquinoline (298.1 mg, 1.34 mmol) was used instead of 3-bromoquinoline. MS (ESI) m/z=328.2 (M+H)+

Step 2: (R)-8-methyl-N-(pyrrolidin-3-yl)quinolin-6-amine hydrochloride

The title compound (238.2 mg, 100.0%) was prepared in the same fashion as Step 2 of Reference Example 5 and used in the next step without any further purification.

Reference Example 108. (R)-8-chloro-N-(pyrrolidin-3-yl)quinolin-6-amine hydrochloride Step 1: tert-butyl (R)-3-((8-chloroquinolin-6-yl)amino)pyrrolidine-1-carboxylate The title compound (311.9 mg, 66.8%) was prepared in the same fashion as Step 1 of Reference Example 17, except that 6-bromo-8-chloro-quinoline (325.5 mg, 1.34 mmol) was used instead of 3-bromoquinoline. MS (ESI) m/z=348.1 (M+H)+

Step 2: (R)-8-chloro-N-(pyrrolidin-3-yl)quinolin-6-amine hydrochloride

The title compound (287.6 mg, 100.0%) was prepared in the same fashion as Step 2 of Reference Example 5 and used in the next step without any further purification.

Reference Example 109. (R)—N-(pyrrolidin-3-yl)-8-(trifluoromethyl)quinolin-6-amine hydrochloride Step 1: tert-butyl (R)-3-((8-(trifluoromethyl)quinolin-6-yl)amino)pyrrolidine-1-carboxylate The title compound (424.5 mg, 82.9%) was prepared in the same fashion as Step 1 of Reference Example 17, except that 6-bromo-8-(trifluoromethyl)quinoline (370.5 mg, 1.34 mmol) was used instead of 3-bromoquinoline. MS (ESI) m/z=382.1 (M+H)+

Step 2: (R)—N-(pyrrolidin-3-yl)-8-(trifluoromethyl)quinolin-6-amine hydrochloride The title compound (394.2 mg, 100.0%) was prepared in the same fashion as Step 2 of Reference Example 5 and used in the next step without any further purification.

Reference Example 110. (R)-8-fluoro-N-(pyrrolidin-3-yl)quinolin-6-amine hydrochloride Step 1: tert-butyl (R)-3-((8-fluoroquinolin-6-yl)amino)pyrrolidine-1-carboxylate The title compound (167.0 mg, 37.5%) was prepared in the same fashion as Step 1 of Reference Example 17, except that 6-bromo-8-fluoroquinoline (303.4 mg, 1.34 mmol) was used instead of 3-bromoquinoline. MS (ESI) m/z=332.2 (M+H)+

Step 2: (R)-8-fluoro-N-(pyrrolidin-3-yl)quinolin-6-amine hydrochloride

The title compound (153.3 mg, 100.0%) was prepared in the same fashion as Step 2 of Reference Example 5 and used in the next step without any further purification.

Reference Example 111. (S)—N-(pyrrolidin-3-yl)quinolin-6-amine hydrochloride

Step 1: tert-butyl (S)-3-(quinolin-6-ylamino)pyrrolidin-1-carboxylate

The title compound (610.0 mg, 72.5%) was prepared in the same fashion as Step 1 of Reference Example 5, except that 6-bromoquinoline (558.5 mg, 2.68 mmol) was used instead of 4-bromoquinoline. MS (ESI) m/z=314.2 (M+H)+

Step 2: (S)—N-(pyrrolidin-3-yl)quinolin-6-amine hydrochloride

The title compound (102.0 mg, 61.3%) was prepared in the same fashion as Step 2 of Reference Example 5 and used in the next step without any further purification. MS (ESI) m/z=214.2 (M+H)+

Reference Example 112. (S)-5-(pyrrolidin-3-ylamino)quinolin-2-carbonitrile hydrochloride Step 1: tert-butyl (S)-3-((2-cyanoquinolin-5-yl)amino)pyrrolidine-1-carboxylate The title compound (818 mg, 90.0%) was prepared in the same fashion as Step 1 of Reference Example 5, except that 5-bromoquinoline-2-carbonitrile (625.6 mg, 2.68 mmol) was used instead of 4-bromoquinoline. MS (ESI) m/z=339.2 (M+H)+

Step 2: (S)-5-(pyrrolidin-3-ylamino)quinolin-2-carbonitrile hydrochloride

The title compound (200.2 mg, 66.5%) was prepared in the same fashion as Step 2 of Reference Example 5 and used in the next step without any further purification.

Reference Example 113. (S)-5-(pyrrolidin-3-ylamino)quinolin-3-carbonitrile hydrochloride Step 1: tert-butyl (S)-3-((3-cyanoquinolin-5-yl)amino)pyrrolidine-1-carboxylate The title compound (698.0 mg, 76.8%) was prepared in the same fashion as Step 1 of Reference Example 5, except that 5-bromoquinoline-3-carbonitrile (625.6 mg, 2.68 mmol) was used instead of 4-bromoquinoline. MS (ESI) m/z=339.2 (M+H)+

Step 2: (S)-5-(pyrrolidin-3-ylamino)quinolin-3-carbonitrile hydrochloride

The title compound (143.2 mg, 47.9%) was prepared in the same fashion as Step 2 of Reference Example 5 and used in the next step without any further purification Reference Example 114. (S)-3-methoxy-N-(pyrrolidin-3-yl)quinolin-5-amine hydrochloride Step 1: tert-butyl (S)-3-((3-methoxyquinolin-5-yl)amino)pyrrolidine-1-carboxylate The title compound (446.2 mg, 48.4%) was prepared in the same fashion as Step 1 of Reference Example 5, except that 5-bromo-3-methoxyquinoline (639.2 mg, 2.68 mmol) was used instead of 4-bromoquinoline. MS (ESI) m/z=344.2 (M+H)+

Step 2: (S)-3-methoxy-N-(pyrrolidin-3-yl)quinolin-5-amine hydrochloride

The title compound (187.5 mg, 59.3%) was prepared in the same fashion as Step 2 of Reference Example 5 and used in the next step without any further purification Reference Example 115. (S)-3-fluoro-N-(pyrrolidin-3-yl)quinolin-5-amine hydrochloride Step 1: tert-butyl (S)-3-((3-fluoroquinolin-5-yl)amino)pyrrolidine-1-carboxylate The title compound (668.7 mg, 75.1%) was prepared in the same fashion as Step 1 of Reference Example 5, except that 5-bromo-3-fluoroquinoline (606.8 mg, 2.68 mmol) was used instead of 4-bromoquinoline. MS (ESI) m/z=333.1 (M+H)+

Step 2: (S)-3-fluoro-N-(pyrrolidin-3-yl)quinolin-5-amine hydrochloride

The title compound (392.5 mg, 63.9%) was prepared in the same fashion as Step 2 of Reference Example 5 and used in the next step without any further purification Reference Example 116. (S)-3-chloro-N-(pyrrolidin-3-yl)quinolin-5-amine hydrochloride Step 1: tert-butyl (S)-3-((3-chloroquinolin-5-yl)amino)pyrrolidine-1-carboxylate The title compound (613.0 mg, 65.6%) was prepared in the same fashion as Step 1 of Reference Example 5, except that 5-bromo-3-chloroquinoline (651.0 mg, 2.68 mmol) was used instead of 4-bromoquinoline. MS (ESI) m/z=348.2 (M+H)+

Step 2: (S)-3-chloro-N-(pyrrolidin-3-yl)quinolin-5-amine hydrochloride

The title compound (163.7 mg, 28.9%) was prepared in the same fashion as Step 2 of Reference Example 5 and used in the next step without any further purification Reference Example 117. (S)-7-fluoro-N-(pyrrolidin-3-yl)quinolin-5-amine hydrochloride Step 1: tert-butyl (S)-3-((7-fluoroquinolin-5-yl)amino)pyrrolidine-1-carboxylate The title compound (875.0 mg, 98.3%) was prepared in the same fashion as Step 1 of Reference Example 5, except that 5-bromo-7-fluoroquinoline (606.8 mg, 2.68 mmol) was used instead of 4-bromoquinoline. MS (ESI) m/z=333.1 (M+H)+

Step 2: (S)-7-fluoro-N-(pyrrolidin-3-yl)quinolin-5-amine hydrochloride

The title compound (250.0 mg, 38.3%) was prepared in the same fashion as Step 2 of Reference Example 5 and used in the next step without any further purification Reference Example 118. (S)-7-methoxy-N-(pyrrolidin-3-yl)quinolin-5-amine hydrochloride Step 1: tert-butyl (S)-3-((7-methoxyquinolin-5-yl)amino)pyrrolidine-1-carboxylate The title compound (848.2 mg, 92.0%) was prepared in the same fashion as Step 1 of Reference Example 5, except that 5-bromo-7-methoxyquinoline (639.2 mg, 2.68 mmol) was used instead of 4-bromoquinoline. $^1$H-NMR (CDCl$_3$, 400 MHz) δ 8.78 (d, 1H), 8.02 (d, 1H), 7.19 (dd, 1H), 6.89 (s, 1H), 6.28 (s, 1H), 4.43 (d, 1H), 4.15 (s, 1H), 3.93 (s, 3H), 3.79 (s, 1H), 3.56-3.36 (m, 3H), 2.27 (s, 1H), 2.05-1.93 (m, 1H), 1.47 (s, 9H).

Step 2: (S)-7-methoxy-N-(pyrrolidin-3-yl)quinolin-5-amine hydrochloride

The title compound (485.0 mg, 62.0%) was prepared in the same fashion as Step 2 of Reference Example 5 and used in the next step without any further purification Reference Example 119. (S)—N-(pyrrolidin-3-yl)-7-(trifluoromethyl)quinolin-5-amine hydrochloride Step 1: tert-butyl (S)-3-((7-(trifluoromethyl)quinolin-5-yl)amino)pyrrolidine-1-carboxylate The title compound (888.5 mg, 86.7%) was prepared in the same fashion as Step 1 of Reference Example 5, except that 5-bromo-7-(trifluoromethyl)quinoline (741.1 mg, 2.68 mmol) was used instead of 4-bromoquinoline. $^1$H-NMR (CDCl$_3$, 400 MHz) δ 8.97 (d, 1H), 8.19 (d, 1H), 7.80 (s, 1H), 7.47-7.44 (m, 1H), 6.73 (s, 1H), 4.63 (s, 1H), 4.26 (s, 1H), 3.83 (s, 1H), 3.59-3.39 (m, 3H), 2.37-2.29 (m, 1H) 2.07-2.05 (m, 1H), 1.49 (s, 9H).

Step 2: (S)—N-(pyrrolidin-3-yl)-7-(trifluoromethyl)quinolin-5-amine hydrochloride The title compound (325.0 mg, 39.3%) was prepared in the same fashion as Step 2 of Reference Example 5 and used in the next step without any further purification

Reference Example 120. (S)-6-methyl-N-(pyrrolidin-3-yl)quinolin-5-amine hydrochloride

Step 1: tert-butyl (S)-3-((6-methylquinolin-5-yl)amino)pyrrolidine-1-carboxylate The title compound (683.2 mg, 77.7%) was prepared in the same fashion as Step 1 of Reference Example 5, except that 5-bromo-6-methylquinoline (596.2 mg, 2.68 mmol) was used instead of 4-bromoquinoline. $^1$H-NMR (CDCl$_3$, 400 MHz) δ 8.84 (d, 1H), 8.39 (d, 1H), 7.75 (d, 1H), 7.52 (d, 1H), 7.37 (d, 1H), 3.97 (s, 1H), 3.64-3.29 (m, 5H), 2.43 (s, 3H), 2.15-1.97 (m, 2H), 1.48-1.45 (s, 9H)

Step 2: (S)-6-methyl-N-(pyrrolidin-3-yl)quinolin-5-amine hydrochloride

The title compound (495.0 mg, 79.0%) was prepared in the same fashion as Step 2 of Reference Example 5 and used in the next step without any further purification

Reference Example 121. (S)-6-methoxy-N-(pyrrolidin-3-yl)quinolin-5-amine hydrochloride

Step 1: tert-butyl (S)-3-((6-methoxyquinolin-5-yl)amino)pyrrolidine-1-carboxylate The title compound (378.5 mg, 41.0%) was prepared in the same fashion as Step 1 of Reference Example 5, except that 5-bromo-6-methoxyquinoline (639.2 mg, 2.68 mmol) was used instead of 4-bromoquinoline. $^1$H-NMR (CDCl$_3$, 400 MHz) δ 8.78 (s, 1H), 8.39 (d, 1H), 7.83 (d, 1H), 7.48 (d, 1H), 7.35-7.33 (m, 1H), 4.00-3.97 (m, 4H), 3.61-3.31 (m, 5H), 2.05-1.90 (m, 2H), 1.48-1.46 (s, 9H).

Step 2: (S)-6-methoxy-N-(pyrrolidin-3-yl)quinolin-5-amine hydrochloride

The title compound (248.5 mg, 71.2%) was prepared in the same fashion as Step 2 of Reference Example 5 and used in the next step without any further purification

Reference Example 122. (S)-6-fluoro-N-(pyrrolidin-3-yl)quinolin-5-amine hydrochloride

Step 1: tert-butyl (S)-3-((6-fluoroquinolin-5-yl)amino)pyrrolidine-1-carboxylate The title compound (344.7 mg, 38.7%) was prepared in the same fashion as Step 1 of Reference Example 5, except that 5-bromo-6-fluoroquinoline (606.8 mg, 2.68 mmol) was used instead of 4-bromoquinoline. $^1$H-NMR (CDCl$_3$, 400 MHz) δ 8.88 (s, 1H), 8.37 (d, 1H), 7.75 (s, 1H), 7.49 (t, 1H), 7.41 (dd, 1H), 4.14 (d, 1H), 3.69-3.36 (m, 5H), 2.16-2.08 (m, 1H), 1.93 (s, 1H), 1.48-1.46 (m, 9H).

Step 2: (S)-6-fluoro-N-(pyrrolidin-3-yl)quinolin-5-amine hydrochloride

The title compound (251.7 mg, 79.5%) was prepared in the same fashion as Step 2 of Reference Example 5 and used in the next step without any further purification

Reference Example 123. (S)-8-methyl-N-(pyrrolidin-3-yl)quinolin-5-amine hydrochloride

Step 1: tert-butyl (S)-3-((8-methylquinolin-5-yl)amino)pyrrolidine-1-carboxylate The title compound (631.0 mg, 71.7%) was prepared in the same fashion as Step 1 of Reference Example 5, except that 5-bromo-8-methylquinoline (596.2 mg, 2.68 mmol) was used instead of 4-bromoquinoline. $^1$H-NMR (CDCl$_3$, 400 MHz) δ 8.94 (d, 1H), 8.17 (d, 1H), 7.41 (s, 1H), 7.36 (dd, 1H), 6.60 (d, 1H), 4.19 (s, 2H), 3.83-3.78 (m, 1H), 3.56-3.48 (m, 2H), 3.40-3.32 (m, 1H), 2.69 (s, 3H), 2.27 (m, 1H), 2.04 (s, 1H), 1.47 (s, 9H).

Step 2: (S)-8-methyl-N-(pyrrolidin-3-yl)quinolin-5-amine hydrochloride

The title compound (489.3 mg, 84.5%) was prepared in the same fashion as Step 2 of Reference Example 5 and used in the next step without any further purification

Reference Example 124. (S)-8-methoxy-N-(pyrrolidin-3-yl)quinolin-5-amine hydrochloride

Step 1: tert-butyl (S)-3-((8-methoxyquinolin-5-yl)amino)pyrrolidine-1-carboxylate The title compound (712.0 mg, 77.2%) was prepared in the same fashion as Step 1 of Reference Example 5, except that 5-bromo-8-methoxyquinoline (639.2 mg, 2.68 mmol) was used instead of 4-bromoquinoline. $^1$H-NMR (CDCl$_3$, 400 MHz) δ 8.94 (d, 1H), 8.20 (d, 1H), 7.42 (dd, 1H), 6.96 (s, 1H), 6.64 (d, 1H), 4.15-4.13 (m, 1H), 4.04 (s, 3H), 3.88-3.76 (m, 2H), 3.49-3.33 (m, 3H), 2.29-2.24 (m, 1H), 2.05-2.02 (m, 1H), 1.47 (s, 9H).

Step 2: (S)-8-methoxy-N-(pyrrolidin-3-yl)quinolin-5-amine hydrochloride

The title compound (505.5 mg, 77.0%) was prepared in the same fashion as Step 2 of Reference Example 5 and used in the next step without any further purification

Reference Example 125. (S)-8-fluoro-N-(pyrrolidin-3-yl)quinolin-5-amine hydrochloride

Step 1: tert-butyl (S)-3-((8-fluoroquinolin-5-yl)amino)pyrrolidine-1-carboxylate The title compound (852.0 mg, 95.7%) was prepared in the same fashion as Step 1 of Reference Example 5, except that 5-bromo-8-fluoroquinoline (606.8 mg, 2.68 mmol) was used instead of 4-bromoquinoline. $^1$H-NMR (CDCl$_3$, 400 MHz) δ 8.95 (d, 1H), 8.20 (d, 1H), 7.43 (dd, 1H), 7.29 (t, 1H), 6.55 (dd, 1H), 4.17 (s, 2H), 3.81 (s, 1H), 3.56-3.35 (m, 3H), 2.28 (s, 1H), 2.04 (s, 1H), 1.47 (s, 9H).

Step 2: (S)-8-fluoro-N-(pyrrolidin-3-yl)quinolin-5-amine hydrochloride

The title compound (556.6 mg, 71.2%) was prepared in the same fashion as Step 2 of Reference Example 5 and used in the next step without any further purification

Reference Example 126. (S)—N-(pyrrolidin-3-yl)-8-(trifluoromethyl)quinolin-5-amine hydrochloride

Step 1: tert-butyl (S)-3-((8-(trifluoromethyl)quinolin-5-yl)amino)pyrrolidine-1-carboxylate The title compound (318.0 mg, 31.0%) was prepared in the same fashion as Step 1 of Reference Example 5, except that 5-bromo-8-(trifluoromethyl)quinoline (741.1 mg, 2.68 mmol) was used instead of 4-bromoquinoline. $^1$H-NMR (CDCl$_3$, 400 MHz) δ 9.04 (d, 1H), 8.16 (d, 1H), 7.92 (d, 1H), 7.43 (dd, 1H), 6.59 (d, 1H), 4.78 (s, 1H), 4.26 (s, 1H), 3.84 (s, 1H), 3.59-3.37 (m, 3H), 2.37-2.32 (m, 1H), 2.07-2.05 (m, 1H), 1.48 (s, 9H).

Step 2: (S)—N-(pyrrolidin-3-yl)-8-(trifluoromethyl)quinolin-5-amine hydrochloride The title compound (175.0 mg, 59.3%) was prepared in the same fashion as Step 2 of Reference Example 5 and used in the next step without any further purification

Reference Example 127. (S)—N-(pyrrolidin-3-yl)-8-(trifluoromethoxy)quinolin-5-amine hydrochloride

Step 1: tert-butyl (S)-3-((8-(trifluoromethoxy)quinolin-5-yl)amino)pyrrolidine-1-carboxylate The title compound (844.5 mg, 79.1%) was prepared in the same fashion as Step 1 of Reference Example 5, except that 5-bromo-8-(trifluoromethoxy)quinoline (784.0 mg, 2.68 mmol) was used instead of 4-bromoquinoline. $^1$H-NMR (CDCl$_3$, 400 MHz) δ 8.99 (d, 1H), 8.19 (d, 1H), 7.51 (d, 1H), 7.42 (dd, 1H), 6.56 (d, 1H), 4.50 (s, 1H), 4.19 (s, 1H), 3.81 (s, 1H), 3.56-3.36 (m, 2H), 2.35-2.25 (m, 1H), 2.05 (s, 1H), 1.48 (s, 9H).

Step 2: (S)—N-(pyrrolidin-3-yl)-8-(trifluoromethoxy)quinolin-5-amine hydrochloride The title compound (505.3 mg, 64.2%) was prepared in the same fashion as Step 2 of Reference Example 5 and used in the next step without any further purification

Reference Example 128. (S)-5-(pyrrolidin-3-ylamino)quinoline-8-carbonitrile hydrochloride

Step 1: tert-butyl (S)-3-((8-cyanoquinolin-5-yl)amino)pyrrolidine-1-carboxylate The title compound (800.0 mg, 88.0%) was prepared in the same fashion as Step 1 of Reference Example 5, except that 5-bromoquinoline-8-carbonitrile (625.6 mg, 2.68 mmol) was used instead of 4-bromoquinoline. $^1$H-NMR (CDCl$_3$, 400 MHz) δ 9.01 (d, 1H), 8.26 (d, 1H), 7.94 (d, 1H), 7.42 (dd, 1H), 6.60 (d, 1H), 5.30-5.25 (m, 1H), 4.27 (s, 1H), 3.83 (s, 1H), 3.57-3.40 (m, 3H), 2.38-2.31 (m, 1H), 2.11 (s, 1H), 1.48 (s, 9H).

Step 2: (S)-5-(pyrrolidin-3-ylamino)quinoline-8-carbonitrile hydrochloride

The title compound (525.0 mg, 71.3%) was prepared in the same fashion as Step 2 of Reference Example 5 and used in the next step without any further purification

Reference Example 129. (S)-8-(benzyloxy)-N-(pyrrolidin-3-yl)quinolin-5-amine hydrochloride

Step 1: tert-butyl (S)-3-((8-(benzyloxy)quinolin-5-yl)amino)pyrrolidine-1-carboxylate The title compound (1120.0 mg, 99.6%) was prepared in the same fashion as Step 1 of Reference Example 5, except that 8-(benzyloxy)-5-bromoquinoline (843.4 mg, 2.68 mmol) was used instead of 4-bromoquinoline. $^1$H-NMR (CDCl$_3$, 400 MHz) δ 8.97 (d, 1H), 8.19 (d, 1H), 7.50 (d, 2H), 7.41 (dd, 1H), 7.35 (t, 2H), 7.29 (d, 1H), 6.93 (d, 1H), 6.51 (d, 1H), 5.38 (s, 2H), 4.13-4.08 (m, 1H), 3.93 (s, 1H), 3.76-3.72 (m, 1H), 3.53-3.47 (m, 2H), 3.39-3.28 (m, 1H), 2.25-2.20 (m, 1H), 1.99 (s, 1H), 1.46 (s, 9H).

Step 2: (S)-8-(benzyloxy)-N-(pyrrolidin-3-yl)quinolin-5-amine hydrochloride The title compound (1000.0 mg, 79.7%) was prepared in the same fashion as Step 2 of Reference Example 5 and used in the next step without any further purification

Reference Example 130. (S)—N-(pyrrolidin-3-yl)quinolin-7-amine hydrochloride

Step 1: tert-butyl (S)-3-(quinolin-7-ylamino)pyrrolidin-1-carboxylate

The title compound (631.5 mg, 75.0%) was prepared in the same fashion as Step 1 of Reference Example 5, except that 7-bromoquinoline (558.5 mg, 2.68 mmol) was used instead of 4-bromoquinoline. MS (ESI) m/z=314.2 (M+H)+

Step 2: (S)—N-(pyrrolidin-3-yl)quinolin-7-amine hydrochloride

The title compound (110.0 mg, 64.1%) was prepared in the same fashion as Step 2 of Reference Example 5 and used in the next step without any further purification. MS (ESI) m/z=214.2 (M+H)+

Reference Example 131. (S)—N-(pyrrolidin-3-yl)-8-(trifluoromethyl)quinolin-4-amine hydrochloride

Step 1: tert-butyl (S)-3-((8-(trifluoromethyl)quinolin-4-yl)amino)pyrrolidin-1-carboxylate The title compound (384.0 mg, 37.5%) was prepared in the same fashion as Step 1 of Reference Example 5, except that 4-bromo-8-(trifluoromethyl)quinoline (741.0 mg, 2.68 mmol) was used instead of 4-bromoquinoline. MS (ESI) m/z=382.2 (M+H)+

Step 2: (S)—N-(pyrrolidin-3-yl)-8-(trifluoromethyl)quinolin-4-amine hydrochloride The title compound (254.0 mg, 71.2%) was prepared in the same fashion as Step 2 of Reference Example 5 and used in the next step without any further purification. MS (ESI) m/z=282.2 (M+H)+

Reference Example 132. (S)—N-(pyrrolidin-3-yl)-1,8-naphthyridin-3-amine hydrochloride

Step 1: tert-butyl (S)-3-((1,8-naphthyridin-3-yl)amino)pyrrolidine-1-carboxylate The title compound (215.3 mg, 51.0%) was prepared in the same fashion as Step 1 of Reference Example 5, except that 3-bromo-1,8-naphthyridine (280.6 mg, 1.34 mmol) was used instead of 4-bromoquinoline. MS (ESI) m/z=315.1 (M+H)+

Step 2: (S)—N-(pyrrolidin-3-yl)-1,8-naphthyridin-3-amine hydrochloride

The title compound (196.7 mg, 100.0%) was prepared in the same fashion as Step 2 of Reference Example 5 and used in the next step without any further purification.

Reference Example 133. (S)-7-chloro-N-(pyrrolidin-3-yl)-1,8-naphthyridin-3-amine hydrochloride

Step 1: tert-butyl (S)-3-((7-chloro-1,8-naphthyridin-3-yl)amino)pyrrolidine-1-carboxylate The title compound (168.8 mg, 36.1%) was prepared in the same fashion as Step 1 of Reference Example 5, except that 6-bromo-2-chloro-1,8-naphthyridine (326.8 mg, 1.34 mmol) was used instead of 4-bromoquinoline. MS (ESI) m/z=349.2 (M+H)+

Step 2: (S)-7-chloro-N-(pyrrolidin-3-yl)-1,8-naphthyridin-3-amine hydrochloride The title compound (155.6 mg, 100.0%) was prepared in the same fashion as Step 2 of Reference Example 5 and used in the next step without any further purification.

Reference Example 134. (S)-8-ethoxy-N-(pyrrolidin-3-yl)quinolin-5-amine hydrochloride

Step 1: tert-butyl (S)-3-((8-ethoxyquinolin-5-yl)amino)pyrrolidin-1-carboxylate The title compound (561.0 mg, 58.4%) was prepared in the same fashion as Step 1 of Reference Example 5, except that 5-bromo-8-ethoxyquinoline (676.8 mg, 2.68 mmol) was used instead of 4-bromoquinoline. MS (ESI) m/z=358.2 (M+H)+

Step 2: (S)-8-ethoxy-N-(pyrrolidin-3-yl)quinolin-5-amine hydrochloride

The title compound (321.0 mg, 61.9%) was prepared in the same fashion as Step 2 of Reference Example 5 and used in the next step without any further purification. MS (ESI) m/z=258.2 (M+H)+

Reference Example 135. (S)-5-(pyrrolidin-3-ylamino)quinolin-8-ol hydrochloride

Step 1: 5-bromo-8-((tert-butyldimethylsilyl)oxy)quinoline

5-Bromoquinolin-8-ol (1 g, 4.46 mmol) was dissolved in anhydrous dichloromethane. To the resulting solution, tert-butyldimethylsilyl chloride (0.74 g, 4.91 mmol), and imidazole (0.67 g, 9.819 mmol) were added. The reaction mixture was stirred overnight at room temperature. After the completion of the reaction, the reaction mixture was was diluted with dichloromethane, and then added with water to extract an aqueous layer. The extracted organic layer was dried and filtered over anhydrous magnesium sulfate. The filtered solution was concentrated and then purified with silica gel column chromatography (n-hexane only) to give a title compound (1.16 g, 76.8%). $^1$H-NMR (CDCl$_3$, 400 MHz) δ 8.88 (dd, 1H), 8.47 (dd, 1H), 7.68 (d, 1H), 7.49 (q, 1H), 7.07 (d, 1H), 1.07 (s, 9H), 0.27 (s, 6H)

Step 2: tert-butyl (S)-3-((8-((tert-butyldimethylsilyl)oxy)quinolin-5-yl)amino)pyrrolidine-1-carboxylate 5-Bromo-8-((tert-butyldimethylsilyl)oxy)quinoline (500 mg, 1.47 mmol) prepared in Step 1 was dissolved in anhydrous toluene. To the resulting solution, tert-butyl (S)-3-aminopyrrolidine-1-carboxylate (275.3 mg, 1.47 mmol), cesium carbonate (578 mg, 1.77 mmol), tris(dibenzylideneacetone)dipalladium(0) (162.4 mg, 0.17 mmol), and Ruphos (82.7 mg, 0.17 mmol) were added. The reaction mixture was refluxed and stirred at 100° C. overnight. After the completion of the reaction, the reaction mixture was cooled to room temperature and then added with water to extract an aqueous layer with ethyl acetate. The extracted organic layer was dried and filtered over anhydrous magnesium sulfate. The filtered solution was concentrated and then purified with silica gel column chromatography (ethyl acetate/n-hexane=1/1, v/v) to give a title compound (655.3 mg, 99.9%). MS (ESI) m/z=444.3 (M+H)+

Step 3: (S)-5-(pyrrolidin-3-ylamino)quinolin-8-ol hydrochloride tert-Butyl (S)-3-((8-((tert-butyldimethylsilyl)oxy)quinolin-5-yl)amino)pyrrolidine-1-carboxylate (655.3 mg, 1.47 mmol) prepared in Step 2 was dissolved in dichloromethane (8.4 ml) and then 4.0 M of hydrochloric acid dissolved in 1,4-dioxane was added thereto in excess drops. The reaction mixture was stirred overnight at room temperature. After the completion of the reaction, the solid compound obtained therefrom was filtered, washed, and vacuum dried to prepare a title compound (405.2 mg, 91.2%). $^1$H-NMR ((CD$_3$)$_2$SO, 400 MHz) δ 9.55 (d, 1H), 8.99 (d, 1H), 7.98 (q, 1H), 7.43 (d, 1H), 6.96 (d, 1H), 4.48-4.46 (m, 1H), 3.67-3.61 (m, 2H), 3.53-3.47 (m, 2H), 2.53-2.44 (m, 1H), 2.36-2.29 (m, 1H).

Reference Example 136. (S)-8-methyl-N-(pyrrolidin-3-yl)quinolin-6-amine hydrochloride

Step 1: tert-butyl (S)-3-((8-methylquinolin-6-yl)amino)pyrrolidine-1-carboxylate The title compound (261.6 mg, 59.5%) was prepared in the same fashion as Step 1 of Reference Example 5, except that 6-bromo-8-methylquinoline (298.1 mg, 1.34 mmol) was used instead of 4-bromoquinoline. MS (ESI) m/z=328.2 (M+H)+

Step 2: (S)-8-methyl-N-(pyrrolidin-3-yl)quinolin-6-amine hydrochloride

The title compound (238.2 mg, 100.0%) was prepared in the same fashion as Step 2 of Reference Example 5 and used in the next step without any further purification.

Reference Example 137. (S)-8-fluoro-N-(pyrrolidin-3-yl)quinolin-6-amine hydrochloride

Step 1: tert-butyl (S)-3-((8-fluoroquinolin-6-yl)amino)pyrrolidine-1-carboxylate The title compound (391.1 mg, 87.9%) was prepared in the same fashion as Step 1 of Reference Example 5, except that 6-bromo-8-fluoroquinoline (303.4 mg, 1.34 mmol) was used instead of 4-bromoquinoline. MS (ESI) m/z=332.2 (M+H)+

Step 2: (S)-8-fluoro-N-(pyrrolidin-3-yl)quinolin-6-amine hydrochloride

The title compound (294.2 mg, 100.0%) was prepared in the same fashion as Step 2 of Reference Example 5 and used in the next step without any further purification.

Reference Example 138. (S)-8-chloro-N-(pyrrolidin-3-yl)quinolin-6-amine hydrochloride

Step 1: tert-butyl (S)-3-((8-chloroquinolin-6-yl)amino)pyrrolidine-1-carboxylate The title compound (316.5 mg, 67.8%) was prepared in the same fashion as Step 1 of Reference Example 5, except that 6-bromo-8-chloro-quinoline (325.5 mg, 1.34 mmol) was used instead of 4-bromoquinoline. MS (ESI) m/z=348.1 (M+H)+

Step 2: (S)-8-chloro-N-(pyrrolidin-3-yl)quinolin-6-amine hydrochloride

The title compound (287.6 mg, 100.0%) was prepared in the same fashion as Step 2 of Reference Example 5 and used in the next step without any further purification.

Reference Example 139. (S)—N-(pyrrolidin-3-yl)-8-(trifluoromethyl)quinolin-6-amine hydrochloride

Step 1: tert-butyl (S)-3-((8-(trifluoromethyl)quinolin-6-yl)amino)pyrrolidine-1-carboxylate The title compound (232.4 mg, 45.4%) was prepared in the same fashion as Step 1 of Reference Example 5, except that 6-bromo-8-(trifluoromethyl)quinoline (370.5 mg, 1.34 mmol) was used instead of 4-bromoquinoline. MS (ESI) m/z=382.1 (M+H)+

Step 2: (S)—N-(pyrrolidin-3-yl)-8-(trifluoromethyl)quinolin-6-amine hydrochloride The title compound (394.2 mg, 100.0%) was prepared in the same fashion as Step 2 of Reference Example 5 and used in the next step without any further purification.

Reference Example 140. (S)—N-methyl-5-(pyrrolidin-3-ylamino)quinoline-8-carboxamide hydrochloride

Step 1: 5-bromo-N-methylquinoline-8-carboxamide

5-Bromoquinolin-8-carboxylic acid (300 mg, 1.19 mmol) was dissolved in dimethylformamide. To the resulting solution, methanamine (0.06 ml, 1.42 mmol), HATU (0-(7-azabenzotriazol-1-yl)-N,N,N',N'-tetramethyluranium hexafluorophosphate) (633.6 mg, 1.67 mmol), and diisopropylethylamine (769.16 mg, 5.95 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (ethyl acetate/n-hexane=1/1, v/v) to give a title compound (229.8 mg, 72.8%). $^1$H-NMR (CDCl$_3$, 400 MHz) δ 8.96 (dd, 1H), 8.74 (d, 1H), 8.72 (dd, 1H), 7.99 (d, 1H), 7.60 (q, 1H), 3.16 (d, 3H).

Step 2: tert-butyl (S)-3-((8-(methylcarbamoyl)quinolin-5-yl)amino)pyrrolidine-1-carboxylate 5-Bromo-N-methylquinoline-8-carboxamide (192 mg, 0.72 mmol) prepared in Step 1 was dissolved in anhydrous toluene. To the resulting solution, tert-butyl (S)-3-aminopyrrolidine-1-carboxylate (135.0 mg, 0.72 mmol), cesium carbonate (192.4 mg, 0.591 mmol), tris(dibenzylideneacetone)dipalladium(0) (49.2 mg, 0.05 mmol), and (+/−)-2,2'-bis(diphenylphospino)-1,1'-binaphthalene (40.1 mg, 0.06 mmol) were added. The reaction mixture was refluxed and stirred at 100° C. overnight. After the completion of the reaction, the reaction mixture was cooled to room temperature and then added with water to extract an aqueous layer with ethyl acetate. The extracted organic layer was dried and filtered over anhydrous magnesium sulfate. The filtered solution was concentrated and then purified with silica gel column chromatography (ethyl acetate/n-hexane=1/1, v/v) to give a title compound (106.3 mg, 39.6%). MS (ESI) m/z=371.2 (M+H)+

Step 3: (S)—N-methyl-5-(pyrrolidin-3-ylamino)quinoline-8-carboxamide hydrochloride tert-Butyl (S)-3-((8-(methylcarbamoyl)quinolin-5-yl)amino)pyrrolidine-1-carboxylate (106.3 mg, 0.287 mmol) prepared in Step 2 was dissolved in dichloromethane (8.4 ml) and then 4.0 M of hydrochloric acid dissolved in 1,4-dioxane was added thereto in excess drops. The reaction mixture was stirred overnight at room temperature. After the completion of the reaction, the solid compound obtained therefrom was filtered, washed, and vacuum dried to prepare a title compound (12.5 mg, 16.1%). MS (ESI) m/z=271.1 (M+H)+

Reference Example 141. (S)—N,N-dimethyl-5-(pyrrolidin-3-ylamino)quinoline-8-carboxamide hydrochloride

Step 1: 5-bromo-N,N-dimethylquinoline-8-carboxamide

The title compound (179.1 mg, 53.9%) was prepared in the same fashion as Step 1 of Reference Example 140, except that dimethylamine (64.1 mg, 1.42 mmol) was used instead of methanamine. $^1$H-NMR (CDCl$_3$, 400 MHz) δ 8.95 (dd, 1H), 8.55 (dd, 1H), 7.86 (d, 1H), 7.56-7.52 (m, 2H), 3.24 (s, 3H), 2.77 (s, 3H).

Step 2: tert-butyl (S)-3-((8-(dimethylcarbamoyl)quinolin-5-yl)amino)pyrrolidine-1-carboxylate The title compound (86.2 mg, 23.2%) was prepared in the same fashion as Step 2 of Reference Example 140. MS (ESI) m/z=385.2 (M+H)+

Step 3: (S)—N,N-dimethyl-5-(pyrrolidin-3-ylamino) quinoline-8-carboxamide hydrochloride The title compound (57.0 mg, 71.4%) was prepared in the same fashion as Step 3 of Reference Example 140 and used in the next step without any further purification. MS (ESI) m/z=285.1 (M+H)+

Reference Example 142. (S)—N-phenyl-5-(pyrrolidin-3-ylamino)quinoline-8-carboxamide hydrochloride

Step 1: 5-bromo-N-phenylquinoline-8-carboxamide

The title compound (348.12 mg, 89.4%) was prepared in the same fashion as Step 1 of Reference Example 140, except that aniline (132.2 mg, 1.42 mmol) was used instead of methanamine. 1H-NMR (CDCl3, 400 MHz) δ 13.41 (s, 1H), 9.03 (d, 1H), 8.80 (d, 1H), 8.75 (d, 1H), 8.02 (d, 1H), 7.87 (d, 2H), 7.64 (q, 1H), 7.42 (t, 2H), 7.16 (t, 1H).

Step 2: tert-butyl (S)-3-((8-(phenylcarbamoyl)quinolin-5-yl)amino)pyrrolidine-1-carboxylate The title compound (54.0 mg, 38.3%) was prepared in the same fashion as Step 2 of Reference Example 140. MS (ESI) m/z=433.2 (M+H)+

Step 3: (S)—N-phenyl-5-(pyrrolidin-3-ylamino) quinoline-8-carboxamide hydrochloride The title compound (47.4 mg, 93.6%) was prepared in the same fashion as Step 3 of Reference Example 140 and used in the next step without any further purification. MS (ESI) m/z=333.2 (M+H)+

Reference Example 143. (S)—N-methyl-N-phenyl-5-(pyrrolidin-3-ylamino)quinoline-8-carboxamide hydrochloride

Step 1: 5-bromo-N-methyl-N-phenylquinoline-8-carboxamide

The title compound (365.2 mg, 89.9%) was prepared in the same fashion as Step 1 of Reference Example 140, except that N-methylaniline (152.2 mg, 1.42 mmol) was used instead of methanamine. $^1$H-NMR (CDCl$_3$, 400 MHz) δ 8.95 (dd, 1H), 8.35 (dd, 1H), 7.56 (d, 1H), 7.41 (q, 1H), 7.30 (d, 1H), 7.05 (d, 2H), 6.97-6.91 (m, 3H), 3.59 (s, 3H)

Step 2: tert-butyl (S)-3-((8-(methyl(phenyl)carbamoyl)quinolin-5-yl)amino)pyrrolidine-1-carboxylate The title compound (92.2 mg, 36.4%) was prepared in the same fashion as Step 2 of Reference Example 140. MS (ESI) m/z=447.2 (M+H)+

Step 3: (S)—N-methyl-N-phenyl-5-(pyrrolidin-3-ylamino)quinoline-8-carboxamide hydrochloride The title compound (85 mg, 98.5%) was prepared in the same fashion as Step 3 of Reference Example 140 and used in the next step without any further purification. MS (ESI) m/z=347.2 (M+H)+

Reference Example 144. (S)—N-benzyl-N-methyl-5-(pyrrolidin-3-ylamino)quinoline-8-carboxamide hydrochloride

Step 1: N-benzyl-5-bromo-N-methylquinoline-8-carboxamide

The title compound (382.5 mg, 90.4%) was prepared in the same fashion as Step 1 of Reference Example 140, except that N-methyl-1-phenylmethanamine (172.0 mg, 1.42 mmol) was used instead of methanamine. $^1$H-NMR (CDCl$_3$, 400 MHz) δ 8.99-8.98 (m, 1H), 8.54-8.49 (m, 1H), 7.86-7.78 (m, 1H), 7.59-7.50 (m, 3H), 7.41-7.37 (m, 1H), 7.31-7.19 (m, 3H), 4.93 (s, 1H), 4.29 (s, 1H), 3.15 (s, 1.5H), 2.65 (s, 1.5H)

Step 2: tert-butyl (S)-3-((8-(benzyl(methyl)carbamoyl)quinolin-5-yl)amino)pyrrolidine-1-carboxylate The title compound (90.1 mg, 31.2%) was prepared in the same fashion as Step 2 of Reference Example 140. MS (ESI) m/z=461.2 (M+H)+

Step 3: (S)—N-benzyl-N-methyl-5-(pyrrolidin-3-ylamino)quinoline-8-carboxamide hydrochloride The title compound (76.0 mg, 89.2%) was prepared in the same fashion as Step 3 of Reference Example 140 and used in the next step without any further purification. MS (ESI) m/z=361.2 (M+H)+

Reference Example 145. (S)—N-(pyridin-3-yl)-5-(pyrrolidin-3-ylamino)quinoline-8-carboxamide hydrochloride

Step 1: 5-bromo-N-(pyrid-3-yl)quinoline-8-carboxamide

The title compound (259.5 mg, 66.4%) was prepared in the same fashion as Step 1 of Reference Example 140, except that 3-aminopyridine (123.2 mg, 1.42 mmol) was used instead of methanamine. $^1$H-NMR (CDCl$_3$, 400 MHz) δ 9.09 (dd, 1H), 8.88 (d, 1H), 8.83-8.79 (m, 2H), 8.51 (dt, 1H), 8.41 (dd, 1H), 8.07 (d, 1H), 7.70 (dd, 1H), 7.36 (dd, 1H).

Step 2: tert-butyl (S)-3-((8-(pyridin-3-ylcarbamoyl) quinolin-5-yl)amino)pyrrolidine-1-carboxylate The title compound (273.9 mg, 79.9%) was prepared in the same fashion as Step 2 of Reference Example 140. MS (ESI) m/z=434.2 (M+H)+

Step 3: (S)—N-(pyridin-3-yl)-5-(pyrrolidin-3-ylamino)quinoline-8-carboxamide hydrochloride The title compound (221.4 mg, 86.2%) was prepared in the same fashion as Step 3 of Reference Example 140 and used in the next step without any further purification.

Reference Example 146. (S)—N-(pyridin-4-yl)-5-(pyrrolidin-3-ylamino)quinoline-8-carboxamide hydrochloride

Step 1: 5-bromo-N-(pyrid-4-yl)quinoline-8-carboxamide

The title compound (325.5 mg, 83.3%) was prepared in the same fashion as Step 1 of Reference Example 140, except that 4-aminopyridine (123.2 mg, 1.42 mmol) was used instead of methanamine. $^1$H-NMR (CDCl$_3$, 400 MHz) δ 9.07 (dd, 1H), 8.81 (d, 2H), 8.59 (d, 2H), 8.07 (d, 1H), 7.79 (d, 2H), 7.71 (dd, 1H).

Step 2: tert-butyl (S)-3-((8-(pyridin-4-ylcarbamoyl) quinolin-5-yl)amino)pyrrolidine-1-carboxylate The title compound (363.6 mg, 84.5%) was prepared in the same fashion as Step 2 of Reference Example 140. MS (ESI) m/z=434.2 (M+H)+

Step 3: (S)—N-(pyridin-4-yl)-5-(pyrrolidin-3-ylamino)quinoline-8-carboxamide hydrochloride The title compound (330.0 mg, 96.7%) was prepared in the same fashion as Step 3 of Reference Example 140 and used in the next step without any further purification.

Reference Example 147. (S)—N-(pyridin-2-yl)-5-(pyrrolidin-3-ylamino)quinoline-8-carboxamide hydrochloride Step 1: 5-bromo-N-(pyrid-2-yl)quinoline-8-carboxamide The title compound (262.5 mg, 67.2%) was prepared in the same fashion as Step 1 of Reference Example 140, except that 2-aminopyridine (123.2 mg, 1.42 mmol) was used instead of methanamine. $^1$H-NMR (CDCl$_3$, 400 MHz) δ 9.19 (dd, 1H), 8.82 (d, 1H), 8.77 (dd, 1H), 8.52 (d, 1H), 8.44 (dd, 1H), 8.05 (d, 1H), 7.78 (td, 1H), 7.68 (dd, 1H), 7.10 (dd, 1H).

Step 2: tert-butyl (S)-3-((8-(pyridin-2-ylcarbamoyl) quinolin-5-yl)amino)pyrrolidine-1-carboxylate The title compound (318.9 mg, 91.9%) was prepared in the same fashion as Step 2 of Reference Example 140. MS (ESI) m/z=434.2 (M+H)+

Step 3: (S)—N-(pyridin-2-yl)-5-(pyrrolidin-3-ylamino)quinoline-8-carboxamide hydrochloride The title compound (287.1 mg, 96.0%) was prepared in the same fashion as Step 3 of Reference Example 140 and used in the next step without any further purification.

Reference Example 148. (S)—N-(5-(pyrrolidin-3-ylamino)quinolin-8-yl)acetamide hydrochloride Step 1: tert-butyl (S)-3-((8-acetamidoquinolin-5-yl) amino)pyrrolidin-1-carboxylate The title compound (434.0 mg, 43.6%) was prepared in the same fashion as Step 1 of Reference Example 5, except that N-(5-bromoquinolin-8-yl)acetamide (711.7 mg, 2.68 mmol) was used instead of 4-bromoquinoline. MS (ESI) m/z=371.2 (M+H)+

Step 2: (S)—N-(5-(pyrrolidin-3-ylamino)quinolin-8-yl)acetamide hydrochloride

The title compound (300.5 mg, 74.6%) was prepared in the same fashion as Step 2 of Reference Example 5 and used in the next step without any further purification. MS (ESI) m/z=271.2 (M+H)+

Reference Example 149. (S)—N-(5-(pyrrolidin-3-ylamino)quinolin-8-yl)benzamide hydrochloride Step 1: N-(5-bromo-quinolin-8-yl)benzamide 5-Bromoquinolin-8-amine (500 mg, 2.24 mmol) was dissolved in dimethylformamide. To the resulting solution, benzoic acid (355.8 mg, 2.91 mmol), HATU (0-(7-azabenzotriazol-1-yl)-N,N,N',N'-tetramethyluranium hexafluorophosphate) (1278.4 mg, 8.96 mmol), and diisopropylethylamine (11158.83 mg, 8.96 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (ethyl acetate/n-hexane=1/1, v/v) to give a title compound (88.3 mg, 12.0%). MS (ESI) m/z=327.0 (M+H)+

Step 2: tert-butyl (S)-3-((8-(phenylcarbamoyl)quinolin-5-yl)amino)pyrrolidine-1-carboxylate The title compound (72.4 mg, 31.1%) was prepared in the same fashion as Step 2 of Reference Example 140 except that N-(5-bromo-quinolin-8-yl)benzamide (192 mg, 0.58 mmol) was used instead of 5-bromo-N-methylquinoline-8-carboxamide. MS (ESI) m/z=433.2 (M+H)+

Step 3: (S)—N-(5-(pyrrolidin-3-ylamino)quinolin-8-yl)benzamide hydrochloride

The title compound (60.1 mg, 88.6%) was prepared in the same fashion as Step 3 of Reference Example 140 and used in the next step without any further purification. MS (ESI) m/z=333.1 (M+H)+

Reference Example 150. (S)-6-methoxy-4-(pyrrolidin-3-yloxy)quinoline hydrochloride Step 1: tert-butyl (S)-3-((6-methoxyquinolin-4-yl) oxy)pyrrolidine-1-carboxylate tert-Butyl (R)-3-hydroxypyrrolidine-1-carboxylate (187 mg, 1.0 mmol) was dissolved in tetrahydrofuran (5.0 mL). To the resulting solution, 4-hydroxy-6-methoxyquinoline (175 mg, 1.0 mmol) and triphenylphosphine (393 mg, 1.5 mmol) were added. The mixture solution was cooled to 0° C. And then, DIAD (diisopropyl azodicarboxylate) (0.29 mL, 1.5 mmol) was slowly added dropwise for 15 minutes. The reaction mixture was stirred for 12 hours at room temperature. After the completion of the reaction, the reaction mixture was evaporated in vacuo and then purified with silica gel column chromatography (ethyl acetate/methanol=10/1, v/v) to give a title compound (275 mg, 80%). MS (ESI) m/z=345.2 (M+H)+

Step 2: (S)-6-methoxy-4-(pyrrolidin-3-yloxy)quinoline hydrochloride tert-Butyl (S)-3-((6-methoxyquinolin-4-yl)oxy)pyrrolidine-1-carboxylate (275 mg, 0.80 mmol) prepared in Step 1 was dissolved in dichloromethane (2.4 mL) and methanol (0.2 mL). To the resulting solution, 4.0 M of hydrochloric acid dissolved in 1,4-dioxane was added in excess drops. The reaction mixture was stirred overnight at room temperature. After the completion of the reaction, the solid produced therefrom was filtered and dried to give a title compound (224 mg, 100%). The title compound was used in the next step without any further purification.

Reference Example 151.
(S)-6,7-dimethoxy-4-(pyrrolidin-3-yloxy)quinoline hydrochloride Step 1: tert-butyl (S)-3-((6,7-dimethoxyquinolin-4-yl)oxy)pyrrolidine-1-carboxylate tert-Butyl (R)-3-hydroxypyrrolidine-1-carboxylate (187 mg, 1.0 mmol) was dissolved in tetrahydrofuran (5.0 mL). To the resulting solution, 4-hydroxy-6,7-dimethoxyquinoline (205 mg, 1.0 mmol) and triphenylphosphine (393 mg, 1.5 mmol) were added. The mixture solution was cooled to 0° C. And then, DIAD (diisopropyl azodicarboxylate) (0.29 mL, 1.5 mmol) was slowly added dropwise for 15 minutes. The reaction mixture was stirred for 12 hours at room temperature. After the completion of the reaction, the reaction mixture was evaporated in vacuo and then purified with silica gel column chromatography (ethyl acetate/methanol=10/1, v/v) to give a title compound (138 mg, 37%). MS (ESI) m/z=375.2 (M+H)+

Step 2: (S)-6,7-dimethoxy-4-(pyrrolidin-3-yloxy)quinoline hydrochloride tert-Butyl (S)-3-((6,7-dimethoxyquinolin-4-yl)oxy)pyrrolidine-1-carboxylate (138 mg, 0.37 mmol) prepared in Step 1 was dissolved in dichloromethane (1.0 mL) and methanol (0.1 mL). To the resulting solution, 4.0 M of hydrochloric acid dissolved in 1,4-dioxane was added in excess drops. The reaction mixture was stirred overnight at room temperature. After the completion of the reaction, the solid produced therefrom was filtered and dried to give a title compound (114 mg, 100%). The title compound was used in the next step without any further purification.

Reference Example 152.
N-(piperidin-4-yl)quinoline-8-carboxamide hydrochloride Step 1: tert-butyl 4-(quinoline-8-carboxamido)piperidine-1-carboxylate 4-Amino-1-tert-butoxycarbonylpiperidine (250.0 mg, 1.25 mmol) was dissolved in dichloromethane. To the resulting solution, 8-quinolinecarboxylic acid (216.2 mg, 1.25 mmol), 1-hydroxybenzotriazole hydrate (337.3 mg, 2.50 mmol), EDAC (N-(3-dimethylaminopropyl)-N'-ethylcarbodiimide hydrochloride) (478.6 mg, 2.50 mmol), and triethylamine (0.35 ml, 2.50 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (ethyl acetate/n-hexane=1/1, v/v) to give a title compound (443.6 mg, 99.9%). MS (ESI) m/z=356.2 (M+H)+

Step 2: N-(piperidin-4-yl)quinoline-8-carboxamide hydrochloride tert-Butyl 4-(quinoline-8-carboxamido)piperidine-1-carboxylate (443.6 mg, 1.25 mmol) prepared in Step 1 was dissolved in dichloromethane (5.0 ml) and then 4.0 M of hydrochloric acid dissolved in 1,4-dioxane was added thereto in excess drops. The reaction mixture was stirred overnight at room temperature. After the completion of the reaction, the solid produced therefrom was filtered and dried to give a title compound (409.7 mg, 100.0%). The title compound was used in the next step without any further purification.

Reference Example 153.
N-ethyl-N-(piperidin-4-yl)quinolin-3-amine hydrochloride Step 1: tert-butyl 4-(ethyl(quinolin-3-yl)amino)piperidine-1-carboxylate tert-Butyl 4-(ethylamino)piperidine-1-carboxylate (109.7 mg, 0.48 mmol) was dissolved in anhydrous toluene. To the resulting solution, 3-bromoquinoline (100.0 mg, 0.48 mmol), cesium carbonate (187.9 mg, 0.58 mmol), tris(dibenzylideneacetone)dipalladium(0) (44.0 mg, 0.04 mmol), and (+/−)-2,2'-bis(diphenylphospino)-1,1'-binaphthalene (29.9 mg, 0.27 mmol) were added. The reaction mixture was refluxed and stirred at 100° C. overnight. After the completion of the reaction, the reaction mixture was cooled to room temperature and then added with water to extract an aqueous layer with ethyl acetate. The extracted organic layer was dried and filtered over anhydrous magnesium sulfate. The filtered solution was concentrated and then purified with silica gel column chromatography (ethyl acetate/n-hexane=1/1, v/v) to give a title compound (120.0 mg, 70.2%). MS (ESI) m/z=356.2 (M+H)+

Step 2: N-ethyl-N-(piperidin-4-yl)quinolin-3-amine hydrochloride tert-Butyl 4-(ethyl(quinolin-3-yl)amino)piperidine-1-carboxylate (120 mg, 0.34 mmol) prepared in Step 1 was dissolved in dichloromethane (2.2 ml) and then 4.0 M of hydrochloric acid dissolved in 1,4-dioxane was added thereto in excess drops. The reaction mixture was stirred overnight at room temperature. After the completion of the reaction, the solid compound obtained therefrom was filtered, washed, and vacuum dried to prepare a title compound (72.7 mg, 65.6%) and used in the next step without any further purification.

Reference Example 154.
N-ethyl-N-(piperidin-4-yl)quinolin-6-amine hydrochloride Step 1: tert-butyl 4-(ethyl(quinolin-6-yl)amino)piperidine-1-carboxylate The title compound (97.3 mg, 56.9%) was prepared in the same fashion as Step 1 of Reference Example 153, except that 6-bromoquinoline (100.0 mg, 0.48 mmol) was used instead of 3-bromoquinoline. MS (ESI) m/z=356.2 (M+H)+

Step 2: N-ethyl-N-(piperidin-4-yl)quinolin-6-amine hydrochloride

The title compound (67.0 mg, 77.8%) was prepared in the same fashion as Step 2 of Reference Example 153 and used in the next step without any further purification.

Reference Example 155.
N-ethyl-N-(piperidin-4-yl)quinolin-5-amine hydrochloride

Step 1: tert-butyl 4-(ethyl(quinolin-5-yl)amino)piperidine-1-carboxylate

The title compound (93.1 mg, 54.4%) was prepared in the same fashion as Step 1 of Reference Example 153, except that 5-bromoquinoline (100.0 mg, 0.48 mmol) was used instead of 3-bromoquinoline. MS (ESI) m/z=356.2 (M+H)+

Step 2: N-ethyl-N-(piperidin-4-yl)quinolin-5-amine hydrochloride

The title compound (68.6 mg, 76.5%) was prepared in the same fashion as Step 2 of Reference Example 153 and used in the next step without any further purification.

Reference Example 156.
N-methyl-N-(piperidin-4-yl)quinolin-2-amine hydrochloride Step 1: tert-butyl 4-(methyl(quinolin-2-yl)amino) piperidine-1-carboxylate tert-Butyl 4-(methylamino)piperidine-1-carboxylate (500.0 mg, 2.33 mmol) was dissolved in anhydrous toluene. To the resulting solution, 2-bromoquinoline (485.4 mg, 2.33 mmol), cesium carbonate (910 mg, 2.80 mmol), tris(dibenzylideneacetone)dipalladium(0) (210.0 mg, 0.23 mmol), and (+/−)-2,2'-bis(diphenylphospino)-1,1'-binaphthalene (170.0 mg, 0.28 mmol) were added. The reaction mixture was refluxed and stirred at 100° C. overnight. After the completion of the reaction, the reaction mixture was cooled to room temperature and then added with water to extract an aqueous layer with ethyl acetate. The extracted organic layer was dried and filtered over anhydrous magnesium sulfate. The filtered solution was concentrated and then purified with silica gel column chromatography (ethyl acetate/n-hexane=1/1, v/v) to give a title compound (203.8 mg, 25.5%). MS (ESI) m/z=342.3 (M+H)+

Step 2:
N-methyl-N-(piperidin-4-yl)quinolin-2-amine hydrochloride tert-Butyl 4-(methyl(quinolin-2-yl)amino)piperidine-1-carboxylate (203.8 mg, 0.34 mmol) prepared in Step 1 was dissolved in dichloromethane (3.1 ml) and then 4.0 M of hydrochloric acid dissolved in 1,4-dioxane was added thereto in excess drops. The reaction mixture was stirred overnight at room temperature. After the completion of the reaction, the solid compound obtained therefrom was filtered, washed, and vacuum dried to prepare a title compound (128.8 mg, 68.6%) and used in the next step without any further purification.

Reference Example 157.
N-methyl-N-(piperidin-4-yl)quinolin-4-amine hydrochloride Step 1: tert-butyl 4-(methyl(quinolin-4-yl)amino) piperidine-1-carboxylate The title compound (85.2 mg, 15.5%) was prepared in the same fashion as Step 1 of Reference Example 156, except that 4-bromoquinoline (485.4 mg, 2.33 mmol) was used instead of 2-bromoquinoline. MS (ESI) m/z=342.3 (M+H)+

Step 2:
N-methyl-N-(piperidin-4-yl)quinolin-4-amine hydrochloride

The title compound (85.2 mg, 74.6%) was prepared in the same fashion as Step 2 of Reference Example 156 and used in the next step without any further purification.

Reference Example 158.
N-methyl-N-(piperidin-4-yl)quinolin-5-amine hydrochloride Step 1: tert-butyl 4-(methyl(quinolin-5-yl)amino) piperidine-1-carboxylate The title compound (154.7 mg, 19.4%) was prepared in the same fashion as Step 1 of Reference Example 156, except that 5-bromoquinoline (485.4 mg, 2.33 mmol) was used instead of 2-bromoquinoline. MS (ESI) m/z=342.3 (M+H)+

Step 2:
N-methyl-N-(piperidin-4-yl)quinolin-5-amine hydrochloride

The title compound (141.0 mg, 99.1%) was prepared in the same fashion as Step 2 of Reference Example 156 and used in the next step without any further purification.

Reference Example 159.
N-methyl-N-(piperidin-4-yl)quinolin-6-amine hydrochloride Step 1: tert-butyl 4-(methyl(quinolin-6-yl)amino) piperidine-1-carboxylate The title compound (184.2 mg, 23.1%) was prepared in the same fashion as Step 1 of Reference Example 156, except that 6-bromoquinoline (485.4 mg, 2.33 mmol) was used instead of 2-bromoquinoline. MS (ESI) m/z=342.3 (M+H)+

Step 2:
N-methyl-N-(piperidin-4-yl)quinolin-6-amine hydrochloride

The title compound (155.4 mg, 91.6%) was prepared in the same fashion as Step 2 of Reference Example 156 and used in the next step without any further purification.

Reference Example 160.
N-methyl-N-(piperidin-4-yl)quinolin-7-amine hydrochloride Step 1: tert-butyl 4-(methyl(quinolin-7-yl)amino) piperidine-1-carboxylate The title compound (220.4 mg, 27.6%) was prepared in the same fashion as Step 1 of Reference Example 156, except that 7-bromoquinoline (485.4 mg, 2.33 mmol) was used instead of 2-bromoquinoline. MS (ESI) m/z=342.3 (M+H)+

Step 2: N-methyl-N-(piperidin-4-yl)quinolin-7-amine hydrochloride

The title compound (198.0 mg, 97.6%) was prepared in the same fashion as Step 2 of Reference Example 156 and used in the next step without any further purification.

Reference Example 161. N-methyl-N-(piperidin-4-yl)furo[3,2-c]pyridin-7-amine hydrochloride Step 1: tert-butyl 4-(furo[3,2-c]pyridin-7-yl(methyl)amino)piperidine-1-carboxylate The title compound (230.8 mg, 29.8%) was prepared in the same fashion as Step 1 of Reference Example 156, except that 7-bromofuro[3,2-c]pyridine (462.0 mg, 2.33 mmol) was used instead of 2-bromoquinoline. MS (ESI) m/z=332.3 (M+H)+

Step 2: N-methyl-N-(piperidin-4-yl)furo[3,2-c]pyridin-7-amine hydrochloride

The title compound (153.7 mg, 72.5%) was prepared in the same fashion as Step 2 of Reference Example 156 and used in the next step without any further purification.

Reference Example 162.
N-methyl-N-(piperidin-4-yl)isoquinolin-5-amine hydrochloride Step 1: tert-butyl 4-(methyl(isoquinolin-5-yl)amino) piperidine-1-carboxylate The title compound (228.0 mg, 28.6%) was prepared in the same fashion as Step 1 of Reference Example 156, except that 5-bromoisoquinoline (485.4 mg, 2.33 mmol) was used instead of 2-bromoquinoline. MS (ESI) m/z=342.3 (M+H)+

Step 2: N-methyl-N-(piperidin-4-yl)isoquinolin-5-amine hydrochloride

The title compound (126.6 mg, 60.4%) was prepared in the same fashion as Step 2 of Reference Example 156 and used in the next step without any further purification.

Reference Example 163.
N-methyl-N-(piperidin-4-yl)isoquinolin-6-amine hydrochloride Step 1: tert-butyl 4-(methyl(isoquinolin-6-yl)amino) piperidine-1-carboxylate The title compound (165.0 mg, 20.7%) was prepared in the same fashion as Step 1 of Reference Example 156, except that 6-bromoisoquinoline (485.4 mg, 2.33 mmol) was used instead of 2-bromoquinoline. MS (ESI) m/z=342.3 (M+H)+

Step 2: N-methyl-N-(piperidin-4-yl)isoquinolin-6-amine hydrochloride

The title compound (119.0 mg, 47.6%) was prepared in the same fashion as Step 2 of Reference Example 156 and used in the next step without any further purification.

Reference Example 164.
N-methyl-N-(piperidin-4-yl)quinolin-3-amine hydrochloride Step 1: tert-butyl 4-(methyl(quinolin-3-yl)amino) piperidine-1-carboxylate The title compound (124.0 mg, 15.5%) was prepared in the same fashion as Step 1 of Reference Example 156, except that 3-bromoquinoline (485.4 mg, 2.33 mmol) was used instead of 2-bromoquinoline. MS (ESI) m/z=342.3 (M+H)+

Step 2: N-methyl-N-(piperidin-4-yl)quinolin-3-amine hydrochloride

The title compound (69.5 mg, 60.9%) was prepared in the same fashion as Step 2 of Reference Example 156 and used in the next step without any further purification.

Reference Example 165.
N-methyl-N-(piperidin-4-yl)isoquinolin-3-amine hydrochloride Step 1: tert-butyl 4-(methyl(isoquinolin-3-yl)amino) piperidine-1-carboxylate The title compound (406.5 mg, 51.0%) was prepared in the same fashion as Step 1 of Reference Example 156, except that 3-bromoisoquinoline (485.4 mg, 2.33 mmol) was used instead of 2-bromoquinoline. MS (ESI) m/z=342.3 (M+H)+

Step 2: N-methyl-N-(piperidin-4-yl)isoquinolin-3-amine hydrochloride

The title compound (238.6 mg, 63.8%) was prepared in the same fashion as Step 2 of Reference Example 156 and used in the next step without any further purification.

Reference Example 166.
N-methyl-N-(piperidin-4-yl)isoquinolin-7-amine hydrochloride Step 1: tert-butyl 4-(methyl(isoquinolin-7-yl)amino) piperidine-1-carboxylate The title compound (245.0 mg, 30.7%) was prepared in the same fashion as Step 1 of Reference Example 156, except that 7-bromoisoquinoline (485.4 mg, 2.33 mmol) was used instead of 2-bromoquinoline. MS (ESI) m/z=342.3 (M+H)+

Step 2: N-methyl-N-(piperidin-4-yl)isoquinolin-7-amine hydrochloride

The title compound (132.7 mg, 58.3%) was prepared in the same fashion as Step 2 of Reference Example 156 and used in the next step without any further purification.

Reference Example 167. N-methyl-N-(piperidin-4-yl)isoquinolin-8-amine hydrochloride Step 1: tert-butyl 4-(methyl(isoquinolin-8-yl)amino)piperidine-1-carboxylate The title compound (514.5 mg, 64.6%) was prepared in the same fashion as Step 1 of Reference Example 156, except that 8-bromoisoquinoline (485.4 mg, 2.33 mmol) was used instead of 2-bromoquinoline. MS (ESI) m/z=342.3 (M+H)+

Step 2: N-methyl-N-(piperidin-4-yl)isoquinolin-8-amine hydrochloride

The title compound (303.3 mg, 64.1%) was prepared in the same fashion as Step 2 of Reference Example 156 and used in the next step without any further purification.

Reference Example 168. N,6-dimethyl-N-(piperidin-4-yl)quinolin-3-amine hydrochloride Step 1: tert-butyl 4-(methyl(6-methylquinolin-3-yl)amino)piperidine-1-carboxylate The title compound (750.3 mg, 45.2%) was prepared in the same fashion as Step 1 of Reference Example 156, except that 3-bromo-6-methylquinoline (518.1 mg, 2.33 mmol) was used instead of 2-bromoquinoline. MS (ESI) m/z=356.2 (M+H)+

Step 2: N,6-dimethyl-N-(piperidin-4-yl)quinolin-3-amine hydrochloride

The title compound (525.6 mg, 75.8%) was prepared in the same fashion as Step 2 of Reference Example 156 and used in the next step without any further purification. MS (ESI) m/z=256.2 (M+H)+

Reference Example 169. 6-methoxy-N-methyl-N-(piperidin-4-yl)quinolin-3-amine hydrochloride Step 1: tert-butyl 4-(methyl(6-methyoxyquinolin-3-yl)amino)piperidine-1-carboxylate The title compound (781.3 mg, 45.2%) was prepared in the same fashion as Step 1 of Reference Example 156, except that 3-bromo-6-methoxylquinoline (555.5 mg, 2.33 mmol) was used instead of 2-bromoquinoline. MS (ESI) m/z=372.2 (M+H)+

Step 2: 6-methoxy-N-methyl-N-(piperidin-4-yl)quinolin-3-amine hydrochloride

The title compound (420.3 mg, 57.8%) was prepared in the same fashion as Step 2 of Reference Example 156 and used in the next step without any further purification. MS (ESI) m/z=272.1 (M+H)+

Reference Example 170. 7-methoxy-N-methyl-N-(piperidin-4-yl)quinolin-3-amine hydrochloride Step 1: tert-butyl 4-(methyl(7-methyoxyquinolin-3-yl)amino)piperidine-1-carboxylate The title compound (778.3 mg, 44.9%) was prepared in the same fashion as Step 1 of Reference Example 156, except that 3-bromo-7-methoxylquinoline (555.5 mg, 2.33 mmol) was used instead of 2-bromoquinoline. MS (ESI) m/z=372.2 (M+H)+

Step 2: 7-methoxy-N-methyl-N-(piperidin-4-yl)quinolin-3-amine hydrochloride

The title compound (303.3 mg, 41.7%) was prepared in the same fashion as Step 2 of Reference Example 156 and used in the next step without any further purification. MS (ESI) m/z=272.2 (M+H)+

Reference Example 171. 8-methoxy-N-methyl-N-(piperidin-4-yl)quinolin-3-amine hydrochloride Step 1: tert-butyl 4-(methyl(8-methyoxyquinolin-3-yl)amino)piperidine-1-carboxylate The title compound (780.0 mg, 45.0%) was prepared in the same fashion as Step 1 of Reference Example 156, except that 3-bromo-8-methoxylquinoline (555.5 mg, 2.33 mmol) was used instead of 2-bromoquinoline. MS (ESI) m/z=372.2 (M+H)+

Step 2: 8-methoxy-N-methyl-N-(piperidin-4-yl)quinolin-3-amine hydrochloride

The title compound (645.5 mg, 88.8%) was prepared in the same fashion as Step 2 of Reference Example 156 and used in the next step without any further purification. MS (ESI) m/z=272.2 (M+H)+

Reference Example 172. 8-fluoro-N-(piperidin-4-yl)quinolin-5-amine hydrochloride Step 1: tert-butyl 4-((8-fluoroquinolin-5-yl)amino)piperidine-1-carboxylate The title compound (163.9 mg, 38.0%) was prepared in the same fashion as Step 1 of Reference Example 28, except that 5-bromo-8-fluoroquinoline (282.2 mg, 1.25 mmol) was used instead of 4-bromoquinoline. MS (ESI) m/z=293.1 (M+H)+

Step 2: 8-fluoro-N-(piperidin-4-yl)quinolin-5-amine hydrochloride

The title compound (151.0 mg, 100.0%) was prepared in the same fashion as Step 2 of Reference Example 28 and used in the next step without any further purification.

Reference Example 173.
8-methyl-N-(piperidin-4-yl)quinolin-5-amine hydrochloride Step 1: tert-butyl 4-((8-methylquinolin-5-yl)amino)piperidine-1-carboxylate The title compound (66.5 mg, 15.6%) was prepared in the same fashion as Step 1 of Reference Example 28, except that 5-bromo-8-methylquinoline (277.2 mg, 1.25 mmol) was used instead of 4-bromoquinoline. MS (ESI) m/z=342.3 (M+H)+

Step 2: 8-methyl-N-(piperidin-4-yl)quinolin-5-amine hydrochloride

The title compound (61.2 mg, 100.0%) was prepared in the same fashion as Step 2 of Reference Example 28 and used in the next step without any further purification.

Reference Example 174. 8-(benzyloxy)-N-(piperidin-4-yl)quinolin-5-amine hydrochloride Step 1: tert-butyl 4-((8-(benzyloxy)quinolin-5-yl)amino)piperidine-1-carboxylate The title compound (143.2 mg, 26.5%) was prepared in the same fashion as Step 1 of Reference Example 28, except that 8-(benzyloxy)-5-bromoquinoline (392.2 mg, 1.25 mmol) was used instead of 4-bromoquinoline. MS (ESI) m/z=434.3 (M+H)+

Step 2: 8-(benzyloxy)-N-(piperidin-4-yl)quinolin-5-amine hydrochloride

The title compound (134.2 mg, 100.0%) was prepared in the same fashion as Step 2 of Reference Example 28 and used in the next step without any further purification.

Reference Example 175.
3-chloro-N-(piperidin-4-yl)quinolin-5-amine hydrochloride Step 1: tert-butyl 4-((3-chloroquinolin-5-yl)amino)piperidine-1-carboxylate The title compound (261.0 mg, 57.8%) was prepared in the same fashion as Step 1 of Reference Example 28, except that 5-bromo-3-chloro-quinoline (302.7 mg, 1.25 mmol) was used instead of 4-bromoquinoline. MS (ESI) m/z=262.1 (M+H)+

Step 2: 3-chloro-N-(piperidin-4-yl)quinolin-5-amine hydrochloride

The title compound (241.4 mg, 100.0%) was prepared in the same fashion as Step 2 of Reference Example 28 and used in the next step without any further purification.

Reference Example 176. N-(piperidin-4-yl)-8-(trifluoromethyl)quinolin-5-amine hydrochloride Step 1: tert-butyl 4-((8-(trifluoromethyl)quinolin-5-yl)amino)piperidine-1-carboxylate The title compound (147.6 mg, 29.9%) was prepared in the same fashion as Step 1 of Reference Example 28, except that 5-bromo-8-(trifluoromethyl)quinoline (344.6 mg, 1.25 mmol) was used instead of 4-bromoquinoline. MS (ESI) m/z=396.2 (M+H)+

Step 2: N-(piperidin-4-yl)-8-(trifluoromethyl)quinolin-5-amine hydrochloride

The title compound (137.5 mg, 100.0%) was prepared in the same fashion as Step 2 of Reference Example 28 and used in the next step without any further purification.

Reference Example 177.
5-(piperidin-4-ylamino)quinoline-2-carbonitrile hydrochloride Step 1: tert-butyl 4-((8-(trifluoromethyl)quinolin-5-yl)amino)piperidine-1-carboxylate The title compound (324.8 mg, 73.8%) was prepared in the same fashion as Step 1 of Reference Example 28, except that 5-bromoquinoline-2-carbonitrile (290.9 mg, 1.25 mmol) was used instead of 4-bromoquinoline. MS (ESI) m/z=353.2 (M+H)+

Step 2: 5-(piperidin-4-ylamino)quinoline-2-carbonitrile hydrochloride

The title compound (299.7 mg, 100.0%) was prepared in the same fashion as Step 2 of Reference Example 28 and used in the next step without any further purification.

Reference Example 178. N-(benzo[b]thiophen-4-yl)piperidin-4-amine hydrochloride Step 1: tert-butyl 4-(benzo[b]thiophen-4-ylamino)piperidine-1-carboxylate The title compound (220.4 mg, 53.1%) was prepared in the same fashion as Step 1 of Reference Example 28, except that 4-bromobenzo[b]thiophene (266.0 mg, 1.25 mmol) was used instead of 4-bromoquinoline. MS (ESI) m/z=333.1 (M+H)+

Step 2: N-(benzo[b]thiophen-4-yl)piperidin-4-amine hydrochloride

The title compound (220.4 mg, 100.0%) was prepared in the same fashion as Step 2 of Reference Example 28 and used in the next step without any further purification.

Reference Example 179.
6-fluoro-N-(piperidin-4-yl)quinolin-4-amine hydrochloride Step 1: tert-butyl 4-((6-fluoroquinolin-4-yl)amino)piperidine-1-carboxylate The title compound (167.7 mg, 38.9%) was prepared in the same fashion as Step 1 of Reference Example 28, except that 4-bromo-6-fluoroquinoline (282.2 mg, 1.25 mmol) was used instead of 4-bromoquinoline. MS (ESI) m/z=346.2 (M+H)+

Step 2: 6-fluoro-N-(piperidin-4-yl)quinolin-4-amine hydrochloride

The title compound (154.5 mg, 100.0%) was prepared in the same fashion as Step 2 of Reference Example 28 and used in the next step without any further purification.

Reference Example 180.
6-chloro-N-(piperidin-4-yl)quinolin-4-amine hydrochloride Step 1: tert-butyl 4-((6-chloroquinolin-4-yl)amino)piperidine-1-carboxylate The title compound (210.0 mg, 46.5%) was prepared in the same fashion as Step 1 of Reference Example 28, except that 4-bromo-6-chloroquinoline (302.7 mg, 1.25 mmol) was used instead of 4-bromoquinoline. MS (ESI) m/z=362.2 (M+H)+

Step 2: 6-chloro-N-(piperidin-4-yl)quinolin-4-amine hydrochloride

The title compound (194.2 mg, 100.0%) was prepared in the same fashion as Step 2 of Reference Example 28 and used in the next step without any further purification.

Reference Example 181.
N-(piperidin-4-yl)isoquinolin-4-amine hydrochloride

Step 1: tert-butyl 4-(isoquinolin-4-ylamino)piperidine-1-carboxylate

The title compound (381.7 mg, 93.4%) was prepared in the same fashion as Step 1 of Reference Example 28, except that 4-bromoisoquinoline (259.7 mg, 1.25 mmol) was used instead of 4-bromoquinoline. MS (ESI) m/z=328.2 (M+H)+

Step 2: N-(piperidin-4-yl)isoquinolin-4-amine hydrochloride

The title compound (350.0 mg, 100.0%) was prepared in the same fashion as Step 2 of Reference Example 28 and used in the next step without any further purification.

Reference Example 182.
N-(piperidin-4-yl)isoquinolin-5-amine hydrochloride

Step 1: tert-butyl 4-(isoquinolin-5-ylamino)piperidine-1-carboxylate

The title compound (333.6 mg, 81.6%) was prepared in the same fashion as Step 1 of Reference Example 28, except that 5-bromoisoquinoline (259.7 mg, 1.25 mmol) was used instead of 4-bromoquinoline. MS (ESI) m/z=328.2 (M+H)+

Step 2: N-(piperidin-4-yl)isoquinolin-5-amine hydrochloride

The title compound (305.9 mg, 100.0%) was prepared in the same fashion as Step 2 of Reference Example 28 and used in the next step without any further purification.

Reference Example 183.
N-(piperidin-4-yl)isoquinolin-6-amine hydrochloride

Step 1: tert-butyl 4-(isoquinolin-6-ylamino)piperidine-1-carboxylate

The title compound (150.1 mg, 36.7%) was prepared in the same fashion as Step 1 of Reference Example 28, except that 6-bromoisoquinoline (259.7 mg, 1.25 mmol) was used instead of 4-bromoquinoline. MS (ESI) m/z=328.2 (M+H)+

Step 2: N-(piperidin-4-yl)isoquinolin-6-amine hydrochloride

The title compound (137.6 mg, 100.0%) was prepared in the same fashion as Step 2 of Reference Example 28 and used in the next step without any further purification.

Reference Example 184.
N-(piperidin-4-yl)isoquinolin-8-amine hydrochloride

Step 1: tert-butyl 4-(isoquinolin-8-ylamino)piperidine-1-carboxylate

The title compound (408.7 mg, 99.9%) was prepared in the same fashion as Step 1 of Reference Example 28, except that 8-bromoisoquinoline (259.7 mg, 1.25 mmol) was used instead of 4-bromoquinoline. MS (ESI) m/z=328.2 (M+H)+

Step 2: N-(piperidin-4-yl)isoquinolin-8-amine hydrochloride

The title compound (374.8 mg, 100.0%) was prepared in the same fashion as Step 2 of Reference Example 28 and used in the next step without any further purification.

Reference Example 185.
8-methyl-N-(piperidin-4-yl)quinolin-4-amine hydrochloride Step 1: tert-butyl 4-((8-methylquinolin-4-yl)amino)piperidine-1-carboxylate The title compound (336.4 mg, 78.9%) was prepared in the same fashion as Step 1 of Reference Example 28, except that 4-bromo-8-methyl-quinoline (277.2 mg, 1.25 mmol) was used instead of 4-bromoquinoline. MS (ESI) m/z=342.2 (M+H)+

Step 2: 8-methyl-N-(piperidin-4-yl)quinolin-4-amine hydrochloride

The title compound (309.6 mg, 100.0%) was prepared in the same fashion as Step 2 of Reference Example 28 and used in the next step without any further purification.

Reference Example 186.
8-chloro-N-(piperidin-4-yl)quinolin-4-amine hydrochloride Step 1: tert-butyl 4-((8-chloroquinolin-4-yl)amino)piperidine-1-carboxylate The title compound (75.8 mg, 16.8%) was prepared in the same fashion as Step 1 of Reference Example 28, except that 4-bromo-8-chloro-quinoline (302.7 mg, 1.25 mmol) was used instead of 4-bromoquinoline. MS (ESI) m/z=362.2 (M+H)+

Step 2: 8-chloro-N-(piperidin-4-yl)quinolin-4-amine hydrochloride

The title compound (70.1 mg, 100.0%) was prepared in the same fashion as Step 2 of Reference Example 28 and used in the next step without any further purification.

Reference Example 187. 8-fluoro-N-(piperidin-4-yl)quinolin-4-amine hydrochloride

Step 1: tert-butyl 4-((8-fluoroquinolin-4-yl)amino)piperidine-1-carboxylate The title compound (209.4 mg, 48.6%) was prepared in the same fashion as Step 1 of Reference Example 28, except that 4-bromo-8-fluoro-quinoline (282.2 mg, 1.25 mmol) was used instead of 4-bromoquinoline. MS (ESI) m/z=346.2 (M+H)+

Step 2: 8-fluoro-N-(piperidin-4-yl)quinolin-4-amine hydrochloride

The title compound (192.9 mg, 100.0%) was prepared in the same fashion as Step 2 of Reference Example 28 and used in the next step without any further purification.

Reference Example 188. N-(piperidin-4-yl)-8-(trifluoromethyl)quinolin-4-amine hydrochloride

Step 1: tert-butyl 4-((8-(trifluoromethyl)quinolin-4-yl)amino)piperidine-1-carboxylate The title compound (366.5 mg, 74.3%) was prepared in the same fashion as Step 1 of Reference Example 28, except that 4-bromo-8-(trifluoromethyl)quinoline (344.6 mg, 1.25 mmol) was used instead of 4-bromoquinoline. MS (ESI) m/z=396.2 (M+H)+

Step 2: N-(piperidin-4-yl)-8-(trifluoromethyl)quinolin-4-amine hydrochloride The title compound (341.3 mg, 100.0%) was prepared in the same fashion as Step 2 of Reference Example 28 and used in the next step without any further purification.

Reference Example 189. N-(piperidin-4-yl)-8-(trifluoromethoxy)quinolin-5-amine hydrochloride

Step 1: tert-butyl 4-((8-(trifluoromethoxy)quinolin-5-yl)amino)piperidine-1-carboxylate The title compound (437.1 mg, 85.1%) was prepared in the same fashion as Step 1 of Reference Example 28, except that 5-bromo-8-trifluoromethoxyquinoline (364.6 mg, 1.25 mmol) was used instead of 4-bromoquinoline. MS (ESI) m/z=412.2 (M+H)+

Step 2: N-(piperidin-4-yl)-8-(trifluoromethoxy)quinolin-5-amine hydrochloride The title compound (408.2 mg, 100.0%) was prepared in the same fashion as Step 2 of Reference Example 28 and used in the next step without any further purification.

Reference Example 190. 3-methoxy-N-(piperidin-4-yl)quinolin-5-amine hydrochloride

Step 1: tert-butyl 4-((3-methoxyquinolin-5-yl)amino)piperidine-1-carboxylate The title compound (327.6 mg, 73.4%) was prepared in the same fashion as Step 1 of Reference Example 28, except that 5-bromo-3-methoxyquinoline (297.2 mg, 1.25 mmol) was used instead of 4-bromoquinoline. MS (ESI) m/z=358.2 (M+H)+

Step 2: 3-methoxy-N-(piperidin-4-yl)quinolin-5-amine hydrochloride

The title compound (302.7 mg, 100.0%) was prepared in the same fashion as Step 2 of Reference Example 28 and used in the next step without any further purification.

Reference Example 191. 3-fluoro-N-(piperidin-4-yl)quinolin-5-amine hydrochloride

Step 1: tert-butyl 4-((3-fluoroquinolin-5-yl)amino)piperidine-1-carboxylate The title compound (343.7 mg, 79.7%) was prepared in the same fashion as Step 1 of Reference Example 28, except that 5-bromo-3-fluoro-quinoline (282.2 mg, 1.25 mmol) was used instead of 4-bromoquinoline. MS (ESI) m/z=346.2 (M+H)+

Step 2: 3-fluoro-N-(piperidin-4-yl)quinolin-5-amine hydrochloride

The title compound (316.6 mg, 100.0%) was prepared in the same fashion as Step 2 of Reference Example 28 and used in the next step without any further purification.

Reference Example 192. 1-chloro-N-(piperidin-4-yl)isoquinolin-5-amine hydrochloride

Step 1: tert-butyl 4-((1-chloroisoquinolin-5-yl)amino)piperidine-1-carboxylate The title compound (49.5 mg, 11.0%) was prepared in the same fashion as Step 1 of Reference Example 28, except that 5-bromo-1-chloro-isoquinoline (302.7 mg, 1.25 mmol) was used instead of 4-bromoquinoline. MS (ESI) m/z=362.2 (M+H)+

Step 2: 1-chloro-N-(piperidin-4-yl)isoquinolin-5-amine hydrochloride

The title compound (45.8 mg, 100.0%) was prepared in the same fashion as Step 2 of Reference Example 28 and used in the next step without any further purification.

Reference Example 193.
3-chloro-N-(piperidin-4-yl)isoquinolin-5-amine hydrochloride

Step 1: tert-butyl 4-((3-chloroisoquinolin-5-yl)amino)piperidine-1-carboxylate The title compound (332.2 mg, 73.5%) was prepared in the same fashion as Step 1 of Reference Example 28, except that 5-bromo-3-chloro-isoquinoline (302.7 mg, 1.25 mmol) was used instead of 4-bromoquinoline. MS (ESI) m/z=362.2 (M+H)+

Step 2: 3-chloro-N-(piperidin-4-yl)isoquinolin-5-amine hydrochloride

The title compound (307.2 mg, 100.0%) was prepared in the same fashion as Step 2 of Reference Example 28 and used in the next step without any further purification.

Reference Example 194.
8-chloro-N-(piperidin-4-yl)isoquinolin-5-amine hydrochloride

Step 1: tert-butyl 4-((8-chloroisoquinolin-5-yl)amino)piperidine-1-carboxylate The title compound (265.1 mg, 58.7%) was prepared in the same fashion as Step 1 of Reference Example 28, except that 5-bromo-8-chloro-isoquinoline (302.7 mg, 1.25 mmol) was used instead of 4-bromoquinoline. MS (ESI) m/z=362.2 (M+H)+

Step 2: 8-chloro-N-(piperidin-4-yl)isoquinolin-5-amine hydrochloride

The title compound (245.2 mg, 100.0%) was prepared in the same fashion as Step 2 of Reference Example 28 and used in the next step without any further purification.

Reference Example 195.
4-methyl-N-(piperidin-4-yl)isoquinolin-5-amine hydrochloride

Step 1: tert-butyl 4-((4-methylisoquinolin-5-yl)amino)piperidine-1-carboxylate The title compound (284.3 mg, 66.7%) was prepared in the same fashion as Step 1 of Reference Example 28, except that 5-bromo-4-methyl-isoquinoline (277.2 mg, 1.25 mmol) was used instead of 4-bromoquinoline. MS (ESI) m/z=342.2 (M+H)+

Step 2: 4-methyl-N-(piperidin-4-yl)isoquinolin-5-amine hydrochloride

The title compound (261.6 mg, 100.0%) was prepared in the same fashion as Step 2 of Reference Example 28 and used in the next step without any further purification.

Reference Example 196.
3-methoxy-N-(piperidin-4-yl)isoquinolin-5-amine hydrochloride

Step 1: tert-butyl 4-((3-methoxyisoquinolin-5-yl)amino)piperidine-1-carboxylate The title compound (407.0 mg, 91.2%) was prepared in the same fashion as Step 1 of Reference Example 28, except that 5-bromo-3-methoxy-isoquinoline (297.2 mg, 1.25 mmol) was used instead of 4-bromoquinoline. MS (ESI) m/z=358.2 (M+H)+

Step 2: 3-methoxy-N-(piperidin-4-yl)isoquinolin-5-amine hydrochloride

The title compound (376.0 mg, 100.0%) was prepared in the same fashion as Step 2 of Reference Example 28 and used in the next step without any further purification.

Reference Example 197.
8-nitro-N-(piperidin-4-yl)isoquinolin-5-amine hydrochloride

Step 1: tert-butyl 4-((8-nitroisoquinolin-5-yl)amino)piperidine-1-carboxylate The title compound (178.1 mg, 38.2%) was prepared in the same fashion as Step 1 of Reference Example 28, except that 5-bromo-8-nitro-isoquinoline (315.9 mg, 1.25 mmol) was used instead of 4-bromoquinoline. MS (ESI) m/z=373.2 (M+H)+

Step 2: 8-nitro-N-(piperidin-4-yl)isoquinolin-5-amine hydrochloride

The title compound (165.1 mg, 100.0%) was prepared in the same fashion as Step 2 of Reference Example 28 and used in the next step without any further purification.

Reference Example 198.
8-fluoro-N-(piperidin-4-yl)isoquinolin-5-amine hydrochloride

Step 1: tert-butyl 4-((8-fluoroisoquinolin-5-yl)amino)piperidine-1-carboxylate The title compound (377.9 mg, 87.7%) was prepared in the same fashion as Step 1 of Reference Example 28, except that 5-bromo-8-fluoro-isoquinoline (282.2 mg, 1.25 mmol) was used instead of 4-bromoquinoline. MS (ESI) m/z=346.2 (M+H)+

Step 2: 8-fluoro-N-(piperidin-4-yl)isoquinolin-5-amine hydrochloride

The title compound (348.2 mg, 100.0%) was prepared in the same fashion as Step 2 of Reference Example 28 and used in the next step without any further purification.

Reference Example 199. 2-chloro-6,7-dimethoxy-N-(piperidin-4-yl)quinazolin-4-amine hydrochloride

Step 1: tert-butyl 4-((2-chloro-6,7-dimethoxyquinazolin-4-yl)amino)piperidine-1-carboxylate tert-Butyl 4-aminopiperidine-1-carboxylate (250.0 mg, 1.25 mmol) was dissolved in anhydrous dichloromethane. To the resulting solution, 2,4-dichloro-6,7-dimethoxyquinazoline (291.1 mg, 1.12 mmol), and triethylamine (0.35 ml, 2.50 mmol) were added. The reaction mixture was stirred overnight at room temperature. After the completion of the reaction, saturated $NH_4Cl$ aqueous solution was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (ethyl acetate/n-hexane=1/1, v/v) to give a title compound (204.0 mg, 38.6%). MS (ESI) m/z=423.2 (M+H)+

Step 2: 2-chloro-6,7-dimethoxy-N-(piperidin-4-yl)quinazolin-4-amine hydrochloride tert-Butyl 4-((2-chloro-6,7-dimethoxyquinazolin-4-yl)amino)piperidine-1-carboxylate (204.0 mg, 0.48 mmol) prepared in Step 1 was dissolved in dichloromethane (5.0 ml). To the resulting solution, 4.0 M of hydrochloric acid dissolved in 1,4-dioxane was added in excess drops. The reaction mixture was stirred overnight at room temperature. After the completion of the reaction, the solid produced therefrom was filtered and dried to give a title compound (190.9 mg, 100.0%). The title compound was used in the next step without any further purification.

Reference Example 200. 2-chloro-8-methyl-N-(piperidin-4-yl)quinazolin-4-amine hydrochloride

Step 1: tert-butyl 4-((2-chloro-8-methylquinazolin-4-yl)amino)piperidine-1-carboxylate The title compound (138.7 mg, 29.5%) was prepared in the same fashion as Step 1 of Reference Example 199, except that 2,4-dichloro-8-methylquinazoline (239.4 mg, 1.25 mmol) was used instead of 2,4-dichloro-6,7-dimethoxyquinazoline. MS (ESI) m/z=377.2 (M+H)+

Step 2: 2-chloro-8-methyl-N-(piperidin-4-yl)quinazolin-4-amine hydrochloride The title compound (128.7 mg, 100.0%) was prepared in the same fashion as Step 2 of Reference Example 199 and used in the next step without any further purification.

Reference Example 201. N-(piperidin-4-yl)-2,6-naphthyridin-4-amine hydrochloride

Step 1: tert-butyl 4-((2,6-naphthyridin-4-yl)amino)piperidine-1-carboxylate The title compound (113.5 mg, 27.7%) was prepared in the same fashion as Step 1 of Reference Example 28, except that 4-bromo-2,6-naphthyridine (260.9 mg, 1.25 mmol) was used instead of 4-bromoquinoline. MS (ESI) m/z=329.2 (M+H)+

Step 2: N-(piperidin-4-yl)-2,6-naphthyridin-4-amine hydrochloride

The title compound (104.1 mg, 100.0%) was prepared in the same fashion as Step 2 of Reference Example 28 and used in the next step without any further purification.

Reference Example 202. 8-chloro-N-(piperidin-4-yl)isoquinolin-4-amine hydrochloride

Step 1: tert-butyl 4-((8-chloroisoquinolin-4-yl)amino)piperidine-1-carboxylate The title compound (102.8 mg, 22.8%) was prepared in the same fashion as Step 1 of Reference Example 28, except that 4-bromo-8-chloro-isoquinoline (302.7 mg, 1.25 mmol) was used instead of 4-bromoquinoline. MS (ESI) m/z=362.2 (M+H)+

Step 2: 8-chloro-N-(piperidin-4-yl)isoquinolin-4-amine hydrochloride

The title compound (95.1 mg, 100.0%) was prepared in the same fashion as Step 2 of Reference Example 28 and used in the next step without any further purification.

Reference Example 203. N-(piperidin-4-yl)quinolin-3-amine hydrochloride

Step 1: tert-butyl 4-(quinolin-3-ylamino)piperidine-1-carboxylate

The title compound (212.5 mg, 99.9%) was prepared in the same fashion as Step 1 of Reference Example 28, except that 3-bromoquinoline (135.0 mg, 0.65 mmol) was used instead of 4-bromoquinoline. MS (ESI) m/z=328.2 (M+H)+

Step 2: N-(piperidin-4-yl)quinolin-3-amine hydrochloride

The title compound (202.9 mg, 100.0%) was prepared in the same fashion as Step 2 of Reference Example 28 and used in the next step without any further purification.

Reference Example 204. 6-methyl-N-(piperidin-4-yl)quinolin-3-amine hydrochloride

Step 1: tert-butyl 4-((6-methylquinolin-3-yl)amino)piperidine-1-carboxylate The title compound (143.3 mg, 64.7%) was prepared in the same fashion as Step 1 of Reference Example 28, except that 3-bromo-6-methylquinoline (144.2 mg, 0.65 mmol) was used instead of 4-bromoquinoline. MS (ESI) m/z=342.3 (M+H)+

Step 2: 6-methyl-N-(piperidin-4-yl)quinolin-3-amine hydrochloride

The title compound (131.9 mg, 100.0%) was prepared in the same fashion as Step 2 of Reference Example 28 and used in the next step without any further purification.

Reference Example 205.
6-fluoro-N-(piperidin-4-yl)quinolin-3-amine hydrochloride Step 1: tert-butyl 4-((6-fluoroquinolin-3-yl)amino) piperidine-1-carboxylate The title compound (218.3 mg, 64.7%) was prepared in the same fashion as Step 1 of Reference Example 28, except that 3-bromo-6-fluoroquinoline (146.7 mg, 0.65 mmol) was used instead of 4-bromoquinoline. MS (ESI) m/z=346.2 (M+H)+

Step 2: 6-fluoro-N-(piperidin-4-yl)quinolin-3-amine hydrochloride

The title compound (201.1 mg, 100.0%) was prepared in the same fashion as Step 2 of Reference Example 28 and used in the next step without any further purification.

Reference Example 206.
6-methoxy-N-(piperidin-4-yl)quinolin-3-amine hydrochloride Step 1: tert-butyl 4-((6-methoxyquinolin-3-yl) amino)piperidine-1-carboxylate The title compound (194.2 mg, 83.7%) was prepared in the same fashion as Step 1 of Reference Example 28, except that 3-bromo-6-methoxyquinoline (154.5 mg, 0.65 mmol) was used instead of 4-bromoquinoline. MS (ESI) m/z=358.2 (M+H)+

Step 2: 6-methoxy-N-(piperidin-4-yl)quinolin-3-amine hydrochloride

The title compound (179.4 mg, 100.0%) was prepared in the same fashion as Step 2 of Reference Example 28 and used in the next step without any further purification.

Reference Example 207.
7-methoxy-N-(piperidin-4-yl)quinolin-3-amine hydrochloride Step 1: tert-butyl 4-((7-methoxyquinolin-3-yl) amino)piperidine-1-carboxylate The title compound (66.0 mg, 28.5%) was prepared in the same fashion as Step 1 of Reference Example 28, except that 3-bromo-7-methoxyquinoline (154.5 mg, 0.65 mmol) was used instead of 4-bromoquinoline. MS (ESI) m/z=358.2 (M+H)+

Step 2: 7-methoxy-N-(piperidin-4-yl)quinolin-3-amine hydrochloride

The title compound (61.0 mg, 100.0%) was prepared in the same fashion as Step 2 of Reference Example 28 and used in the next step without any further purification.

Reference Example 208.
8-methoxy-N-(piperidin-4-yl)quinolin-3-amine hydrochloride Step 1: tert-butyl 4-((8-methoxyquinolin-3-yl) amino)piperidine-1-carboxylate The title compound (78.5 mg, 33.8%) was prepared in the same fashion as Step 1 of Reference Example 28, except that 3-bromo-8-methoxyquinoline (154.5 mg, 0.65 mmol) was used instead of 4-bromoquinoline. MS (ESI) m/z=358.1 (M+H)+

Step 2: 8-methoxy-N-(piperidin-4-yl)quinolin-3-amine hydrochloride

The title compound (72.5 mg, 100.0%) was prepared in the same fashion as Step 2 of Reference Example 28 and used in the next step without any further purification.

Reference Example 209.
N-(piperidin-4-yl)-1,8-naphthyridin-3-amine hydrochloride Step 1: tert-butyl 4-((1,8-naphthyridin-3-yl)amino) piperidine-1-carboxylate The title compound (189.1 mg, 46.1%) was prepared in the same fashion as Step 1 of Reference Example 28, except that 3-bromo-1,8-naphthyridine (260.9 mg, 1.25 mmol) was used instead of 4-bromoquinoline. MS (ESI) m/z=329.2 (M+H)+

Step 2: N-(piperidin-4-yl)-1,8-naphthyridin-3-amine hydrochloride

The title compound (173.4 mg, 100.0%) was prepared in the same fashion as Step 2 of Reference Example 28 and used in the next step without any further purification.

Reference Example 210. 7-chloro-N-(piperidin-4-yl)-1,8-naphthyridin-3-amine hydrochloride Step 1: tert-butyl 4-((7-chloro-1,8-naphthyridin-3-yl)amino)piperidine-1-carboxylate The title compound (57.9 mg, 12.8%) was prepared in the same fashion as Step 1 of Reference Example 28, except that 6-bromo-2-chloro-1,8-naphthyridine (303.9 mg, 1.25 mmol) was used instead of 4-bromoquinoline. MS (ESI) m/z=363.2 (M+H)+

Step 2: 7-chloro-N-(piperidin-4-yl)-1,8-naphthyridin-3-amine hydrochloride

The title compound (53.6 mg, 100.0%) was prepared in the same fashion as Step 2 of Reference Example 28 and used in the next step without any further purification.

Reference Example 211.
8-ethoxy-N-(piperidin-4-yl)quinolin-5-amine hydrochloride Step 1: tert-butyl 4-((8-ethoxyquinolin-5-yl)amino) piperidine-1-carboxylate The title compound (776.4 mg, 83.7%) was prepared in the same fashion as Step 1 of Reference Example 28, except that 5-bromo-8-ethoxyquinoline (629.4 mg, 2.49 mmol) was used instead of 4-bromoquinoline. MS (ESI) m/z=372.2 (M+H)+

Step 2: 8-ethoxy-N-(piperidin-4-yl)quinolin-5-amine hydrochloride

The title compound (432.6 mg, 60.1%) was prepared in the same fashion as Step 2 of Reference Example 28 and used in the next step without any further purification. MS (ESI) m/z=272.2 (M+H)+

Reference Example 212. N-(piperidin-4-yl)benzo[d]thiazol-7-amine hydrochloride

Step 1: tert-butyl 4-(1,3-benzothiazol-7-ylamino)piperidine-1-carboxylate

1-Boc-4-piperidone (250.0 mg, 1.26 mmol) was dissolved in anhydrous dichloromethane. To the resulting solution, benzo[d]thiazol-7-amine (188.5 mg, 1.26 mmol), acetic acid (0.15 ml), and sodium triacetoxyborohydride (265.9 mg, 1.26 mmol) were added. The reaction mixture was stirred overnight at room temperature. After the completion of the reaction, saturated sodium carbonate aqueous solution was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (ethyl acetate/n-hexane=1/1, v/v) to give a title compound (375.3 mg, 89.7%). MS (ESI) m/z=334.2 (M+H)+

Step 2: N-(piperidin-4-yl)benzo[d]thiazol-7-amine hydrochloride tert-butyl 4-(1,3-benzothiazol-7-ylamino)piperidine-1-carboxylate (375.3 mg, 1.13 mmol) prepared in Step 1 was dissolved in dichloromethane (5.0 ml). To the resulting solution, 4.0 M of hydrochloric acid dissolved in 1,4-dioxane was added in excess drops. The reaction mixture was stirred overnight at room temperature. After the completion of the reaction, the solid produced therefrom was filtered and dried to give a title compound (344.8 mg, 100.0%). The title compound was used in the next step without any further purification.

Reference Example 213. 1-(4-(piperidin-4-ylamino)indolin-1-yl)ethan-1-one hydrochloride Step 1: tert-butyl 4-[(1-acetylindolin-4-yl)amino]piperidine-1-carboxylate The title compound (310.2 mg, 68.8%) was prepared in the same fashion as Step 1 of Reference Example 212, except that 1-(4-aminoindolin-1-yl)ethanone (221.1 mg, 1.26 mmol) was used instead of benzo[d]thiazol-7-amine. MS (ESI) m/z=360.2 (M+H)+

Step 2: 1-(4-(piperidin-4-ylamino)indolin-1-yl)ethan-1-one hydrochloride

The title compound (286.8 mg, 100.0%) was prepared in the same fashion as Step 2 of Reference Example 212 and used in the next step without any further purification.

Reference Example 214. 8-methyl-N-(piperidin-4-yl)quinolin-6-amine hydrochloride Step 1: tert-butyl 4-((8-methylquinolin-6-yl)amino)piperidine-1-carboxylate The title compound (196.4 mg, 50.1%) was prepared in the same fashion as Step 1 of Reference Example 28, except that 6-bromo-8-methylquinoline (255.0 mg, 1.15 mmol) was used instead of 4-bromoquinoline. MS (ESI) m/z=342.2 (M+H)+

Step 2: 8-methyl-N-(piperidin-4-yl)quinolin-6-amine hydrochloride

The title compound (180.7 mg, 100.0%) was prepared in the same fashion as Step 2 of Reference Example 28 and used in the next step without any further purification.

Reference Example 215. 8-fluoro-N-(piperidin-4-yl)quinolin-6-amine hydrochloride Step 1: tert-butyl 4-((8-fluoroquinolin-6-yl)amino)piperidine-1-carboxylate The title compound (317.3 mg, 80.0%) was prepared in the same fashion as Step 1 of Reference Example 28, except that 6-bromo-8-fluoroquinoline (259.6 mg, 1.15 mmol) was used instead of 4-bromoquinoline. MS (ESI) m/z=346.2 (M+H)+

Step 2: 8-fluoro-N-(piperidin-4-yl)quinolin-6-amine hydrochloride

The title compound (292.4 mg, 100.0%) was prepared in the same fashion as Step 2 of Reference Example 28 and used in the next step without any further purification.

Reference Example 216. 8-chloro-N-(piperidin-4-yl)quinolin-6-amine hydrochloride Step 1: tert-butyl 4-((8-chloroquinolin-6-yl)amino)piperidine-1-carboxylate The title compound (369.5 mg, 88.9%) was prepared in the same fashion as Step 1 of Reference Example 28, except that 6-bromo-8-chloro-quinoline (278.5 mg, 1.15 mmol) was used instead of 4-bromoquinoline. MS (ESI) m/z=362.2 (M+H)+

Step 2: 8-chloro-N-(piperidin-4-yl)quinolin-6-amine hydrochloride

The title compound (341.7 mg, 100.0%) was prepared in the same fashion as Step 2 of Reference Example 28 and used in the next step without any further purification.

Reference Example 217. N-(piperidin-4-yl)-8-(trifluoromethyl)quinolin-6-amine hydrochloride Step 1: tert-butyl 4-((8-(trifluoromethyl)quinolin-6-yl)amino)piperidine-1-carboxylate The title compound (284.3 mg, 62.6%) was prepared in the same fashion as Step 1 of Reference Example 28, except that 6-bromo-8-(trifluoromethyl)quinoline (317.0 mg, 1.15 mmol) was used instead of 4-bromoquinoline. MS (ESI) m/z=396.2 (M+H)+

Step 2: N-(piperidin-4-yl)-8-(trifluoromethyl)quinolin-6-amine hydrochloride

The title compound (264.8 mg, 100.0%) was prepared in the same fashion as Step 2 of Reference Example 28 and used in the next step without any further purification.

Reference Example 218.
4-(piperidin-4-ylamino)-2H-chromen-2-one hydrochloride

Step 1: tert-butyl 4-((2-oxo-2H-chromen-4-yl)amino)piperidine-1-carboxylate

Tert-butyl 4-aminopiperidine-1-carboxylate (300 mg, 1.4 mmol) was dissolved in anhydrous DMF. To the resulting solution, 4-bromo-2H-chromen-2-one (337.1 mg, 1.49 mmol) and potassium carbonate (414.0 mg, 2.996 mmol) were added. The reaction mixture was stirred at 100° C. overnight. After the completion of the reaction, the reaction mixture was cooled to room temperature and then added with water to extract an aqueous layer with ethyl acetate. The extracted organic layer was dried and filtered over anhydrous magnesium sulfate. The filtered solution was concentrated and then purified with silica gel column chromatography (ethyl acetate/n-hexane=1/1, v/v) to give a title compound (300 mg, 58.1%). $^1$H-NMR (MeOD$_4$, 400 MHz) δ 8.01 (dd, 1H), 7.61 (td, 1H), 7.36-7.32 (m, 2H), 5.41 (s, 1H), 4.16 (d, 2H), 3.77-3.75 (m, 1H), 2.97 (s, 2H), 2.07-2.02 (m, 2H), 1.60-1.53 (m, 2H), 1.49 (s, 9H).

Step 2: 4-(piperidin-4-ylamino)-2H-chromen-2-one hydrochloride

The title compound (210.0 mg, 76.0%) was prepared in the same fashion as Step 2 of Reference Example 28 and used in the next step without any further purification. $^1$H-NMR (MeOD$_4$, 400 MHz) δ 8.05 (dd, 1H), 7.63 (td, 1H), 7.38-7.33 (m, 2H), 5.45 (s, 1H), 3.95-3.89 (m, 1H), 3.53 (d, 2H), 3.22 (td, 2H), 2.33 (d, 2H), 2.00-1.89 (m, 2H).

Reference Example 219. N-(piperidin-4-yl)-1,5-naphthyridin-4-aminehydrochloride

Step 1: tert-butyl 4-((1,5-naphthyridin-4-yl)amino)piperidine-1-carboxylate

The title compound (700.0 mg, 85.4%) was prepared in the same fashion as Step 1 of Reference Example 28, except that 4-bromo-1,5-naphthyridine (521.8 mg, 2.49 mmol) was used instead of 4-bromoquinoline. MS (ESI) m/z=329.2 (M+H)+

Step 2: N-(piperidin-4-yl)-1,5-naphthyridin-4-aminehydrochloride

The title compound (321.0 mg, 80.6%) was prepared in the same fashion as Step 2 of Reference Example 28 and used in the next step without any further purification. MS (ESI) m/z=229.2 (M+H)+

Reference Example 220. N-(piperidin-4-yl)-2-(trifluoromethyl)quinolin-6-amine hydrochloride Step 1: tert-butyl 4-((2-(trifluoromethyl)quinolin-6-yl)amino)piperidine-1-carboxylate The title compound (462.5 mg, 93.7%) was prepared in the same fashion as Step 1 of Reference Example 28, except that 6-bromo-2-(trifluoromethyl)quinoline (344.6 mg, 1.25 mmol) was used instead of 4-bromoquinoline. MS (ESI) m/z=396.2 (M+H)+

Step 2: N-(piperidin-4-yl)-2-(trifluoromethyl)quinolin-6-amine hydrochloride

The title compound (430.8 mg, 100.0%) was prepared in the same fashion as Step 2 of Reference Example 28 and used in the next step without any further purification.

Reference Example 221.
4-methoxy-N-(piperidin-4-yl)quinolin-6-amine hydrochloride Step 1: tert-butyl 4-((4-methoxyquinolin-6-yl)amino)piperidine-1-carboxylate The title compound (110.2 mg, 24.7%) was prepared in the same fashion as Step 1 of Reference Example 28, except that 6-bromo-4-methoxy-quinoline (297.2 mg, 1.25 mmol) was used instead of 4-bromoquinoline. MS (ESI) m/z=358.2 (M+H)+

Step 2:
4-methoxy-N-(piperidin-4-yl)quinolin-6-amine hydrochloride

The title compound (101.7 mg, 100.0%) was prepared in the same fashion as Step 2 of Reference Example 28 and used in the next step without any further purification.

Reference Example 222.
2-bromo-N-(piperidin-4-yl)pyridin-4-amine hydrochloride

Step 1: tert-butyl 4-[(2-bromo-4-pyridyl)amino]piperidine-1-carboxylate

The title compound (257.0 mg, 57.5%) was prepared in the same fashion as Step 1 of Reference Example 212, except that 4-amino-2-bromopyridine (217.1 mg, 1.26 mmol) was used instead of benzo[d]thiazol-7-amine. MS (ESI) m/z=358.1 (M+H)+

Step 2: 2-bromo-N-(piperidin-4-yl)pyridin-4-amine hydrochloride

The title compound (237.3 mg, 100.0%) was prepared in the same fashion as Step 2 of Reference Example 212 and used in the next step without any further purification.

Reference Example 223. N-(piperidin-4-yl)-1H-benzo[d]imidazol-7-amine hydrochloride Step 1: tert-butyl 4-((1H-benzo[d]imidazol-7-yl)amino)piperidine-1-carboxylate The title compound (319.6 mg, 80.5%) was prepared in the same fashion as Step 1 of Reference Example 212, except that 3H-benzo[d]imidazol-4-amine (167.1 mg, 1.26 mmol) was used instead of benzo[d]thiazol-7-amine. MS (ESI) m/z=317.2 (M+H)+

Step 2: N-(piperidin-4-yl)-1H-benzo[d]imidazol-7-amine hydrochloride

The title compound (292.1 mg, 100.0%) was prepared in the same fashion as Step 2 of Reference Example 212 and used in the next step without any further purification.

Reference Example 224. 2-chloro-6-morpholino-N-(piperidin-4-yl)pyridin-4-amine hydrochloride Step 1: tert-butyl 4-((2-chloro-6-morpholinopyridin-4-yl)amino)piperidine-1-carboxylate The title compound (463.1 mg, 93.0%) was prepared in the same fashion as Step 1 of Reference Example 212, except that 4-amino-2-chloro-6-morpholinopyridine (268.1 mg, 1.26 mmol) was used instead of benzo[d]thiazol-7-amine. MS (ESI) m/z=397.2 (M+H)+

Step 2: 2-chloro-6-morpholino-N-(piperidin-4-yl)pyridin-4-amine hydrochloride

The title compound (431.5 mg, 100.0%) was prepared in the same fashion as Step 2 of Reference Example 212 and used in the next step without any further purification.

Reference Example 225. N-(piperidin-4-yl)-3-(trifluoromethyl)quinolin-5-amine hydrochloride Step 1: tert-butyl 4-((3-(trifluoromethyl)quinolin-5-yl)amino)piperidine-1-carboxylate The title compound (853.9 mg, 86.5%) was prepared in the same fashion as Step 1 of Reference Example 28, except that 5-bromo-3-(trifluoromethyl)quinoline (689.2 mg, 2.50 mmol) was used instead of 4-bromoquinoline. MS (ESI) m/z=396.1 (M+H)+

Step 2: N-(piperidin-4-yl)-3-(trifluoromethyl)quinolin-5-amine hydrochloride

The title compound (795.0 mg, 100.0%) was prepared in the same fashion as Step 2 of Reference Example 28 and used in the next step without any further purification.

Reference Example 226. N-phenyl-5-(piperidin-4-ylamino)quinoline-3-carboxamide hydrochloride Step 1: 5-bromo-N-phenylquinoline-3-carboxamide 5-Bromoquinolin-3-carboxylic acid (300 mg, 1.19 mmol) was dissolved in dimethylformamide. To the resulting solution, aniline (133.0 mg, 1.42 mmol), HATU (0-(7-azabenzotriazol-1-yl)-N,N,N',N'-tetramethyluranium hexafluorophosphate) (633.6 mg, 1.67 mmol), and diisopropylethylamine (769.16 mg, 5.95 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (ethyl acetate/n-hexane=1/1, v/v) to give a title compound (144.0 mg, 36.9%). $^1$H-NMR (CDCl$_3$, 400 MHz) δ 9.40 (dd, 1H), 8.97 (d, 1H), 8.16 (d, 1H), 7.99 (s, 1H), 7.94 (d, 1H), 7.73-7.68 (m, 3H), 7.44 (t, 2H), 7.23 (t, 1H).

Step 2: tert-butyl 4-((3-(phenylcarbamoyl)quinolin-5-yl)amino)piperidine-1-carboxylate 5-Bromo-N-phenylquinoline-3-carboxamide (144.0 mg, 0.44 mmol) prepared in Step 1 was dissolved in anhydrous toluene. To the resulting solution, tert-butyl 4-aminopiperidine-1-carboxylate (88.2 mg, 0.44 mmol), cesium carbonate (103.1 mg, 0.53 mmol), tris(dibenzylideneacetone)dipalladium(0) (36.6 mg, 0.04 mmol), and (+/−)-2,2'-bis(diphenylphospino)-1,1'-binaphthalene (32.9 mg, 0.05 mmol) were added. The reaction mixture was refluxed and stirred at 100° C. overnight. After the completion of the reaction, the reaction mixture was cooled to room temperature and then added with water to extract an aqueous layer with ethyl acetate. The extracted organic layer was dried and filtered over anhydrous magnesium sulfate. The filtered solution was concentrated and then purified with silica gel column chromatography (ethyl acetate/n-hexane=1/1, v/v) to give a title compound (81.4 mg, 41.4%). MS (ESI) m/z=447.2 (M+H)+

Step 3: N-phenyl-5-(piperidin-4-ylamino)quinoline-3-carboxamide hydrochloride

Tert-butyl 4-((3-(phenylcarbamoyl)quinolin-5-yl)amino)piperidine-1-carboxylate (81.4 mg, 0.18 mmol) prepared in Step 2 was dissolved in dichloromethane (8.4 ml) and then 4.0 M of hydrochloric acid dissolved in 1,4-dioxane was added thereto in excess drops. The reaction mixture was stirred overnight at room temperature. After the completion of the reaction, the solid compound obtained therefrom was filtered, washed, and vacuum dried to prepare a title compound (5.4 mg, 7.2%).

Reference Example 227. N-benzyl-N-methyl-5-(piperidin-4-ylamino)quinoline-3-carboxamide hydrochloride Step 1: N-benzyl-5-bromo-N-methylquinoline-3-carboxamide The title compound (172.2 mg, 40.7%) was prepared in the same fashion as Step 1 of Reference Example 226, except that N-methyl-1-phenylmethanamine (173.0 mg, 1.42 mmol) was used instead of aniline. $^1$H-NMR (CDCl$_3$, 400 MHz) δ 9.04 (s, 1H), 8.64 (s, 1H), 8.11 (s, 1H), 7.89.7.86 (m, 1H), 7.64-7.62 (m, 1H), 7.43-7.35 (m, 4H), 7.24-7.23 (m, 1H), 4.73 (d, 2H), 3.08 (d, 3H).

Step 2: tert-butyl 4-((3-(benzyl(methyl)carbamoyl)quinolin-5-yl)amino)piperidine-1-carboxylate The title compound (120.8 mg, 52.4%) was prepared in the same fashion as Step 2 of Reference Example 226. MS (ESI) m/z=475.3 (M+H)+

Step 3: N-benzyl-N-methyl-5-(piperidin-4-ylamino)quinoline-3-carboxamide hydrochloride The title compound (105.3 mg, 92.4%) was prepared in the same fashion as Step 3 of Reference Example 226 and used in the next step without any further purification.

Reference Example 228. N-methyl-5-(piperidin-4-ylamino)quinoline-8-carboxamide hydrochloride Step 1: tert-butyl 4-((8-(methylcarbamoyl)quinolin-5-yl)amino)piperidine-1-carboxylate The title compound (116.9 mg, 42.0%) was prepared in the same fashion as Step 2 of Example 140, except that tert-butyl 4-aminopiperidine-1-carboxylate (144.2 mg, 0.72 mmol) was used instead of tert-butyl (S)-3-aminopyrrolidine-1-carboxylate. MS (ESI) m/z=385.2 (M+H)+

Step 2: N-methyl-5-(piperidin-4-ylamino)quinoline-8-carboxamide hydrochloride

The title compound (71.3 mg, 85.6%) was prepared in the same fashion as Step 3 of Reference Example 140 and used in the next step without any further purification.

Reference Example 229. N,N-dimethyl-5-(piperidin-4-ylamino)quinoline-8-carboxamide hydrochloride Step 1: tert-butyl 4-((8-(dimethylcarbamoyl)quinolin-5-yl)amino)piperidine-1-carboxylate The title compound (84.9 mg, 32.9%) was prepared in the same fashion as Step 2 of Example 141, except that tert-butyl 4-aminopiperidine-1-carboxylate (128.0 mg, 0.64 mmol) was used instead of tert-butyl (S)-3-aminopyrrolidine-1-carboxylate. MS (ESI) m/z=399.2 (M+H)+

Step 2: N,N-dimethyl-5-(piperidin-4-ylamino)quinoline-8-carboxamide hydrochloride The title compound (60.1 mg, 23.4%) was prepared in the same fashion as Step 3 of Reference Example 141 and used in the next step without any further purification

Reference Example 230. N-methyl-N-phenyl-5-(piperidin-4-ylamino)quinoline-8-carboxamide hydrochloride Step 1: tert-butyl 4-((8-(methyl(phenyl)carbamoyl)quinolin-5-yl)amino)piperidine-1-carboxylate The title compound (196.6 mg, 39.9%) was prepared in the same fashion as Step 2 of Example 143, except that tert-butyl 4-aminopiperidine-1-carboxylate (128.0 mg, 0.64 mmol) was used instead of tert-butyl (S)-3-aminopyrrolidine-1-carboxylate. MS (ESI) m/z=461.3 (M+H)+

Step 2: N-methyl-N-phenyl-5-(piperidin-4-ylamino)quinoline-8-carboxamide hydrochloride The title compound (134.2 mg, 72.6%) was prepared in the same fashion as Step 3 of Reference Example 143 and used in the next step without any further purification

Reference Example 231. N-benzyl-N-methyl-5-(piperidin-4-ylamino)quinoline-8-carboxamide hydrochloride Step 1: tert-butyl 4-((8-(benzyl(methyl)carbamoyl)quinolin-5-yl)amino)piperidine-1-carboxylate The title compound (218.1 mg, 32.4%) was prepared in the same fashion as Step 2 of Example 144, except that tert-butyl 4-aminopiperidine-1-carboxylate (215.0 mg, 1.07 mmol) was used instead of tert-butyl (S)-3-aminopyrrolidine-1-carboxylate. MS (ESI) m/z=475.3 (M+H)+

Step 2: N-methyl-N-phenyl-5-(piperidin-4-ylamino)quinoline-8-carboxamide hydrochloride The title compound (179.2 mg, 87.1%) was prepared in the same fashion as Step 3 of Reference Example 144 and used in the next step without any further purification

Reference Example 232. N-phenyl-5-(piperidin-4-ylamino)quinoline-8-carboxamide hydrochloride Step 1: tert-butyl 4-((8-(phenylcarbamoyl)quinolin-5-yl)amino)piperidine-1-carboxylate The title compound (196.9 mg, 41.6%) was prepared in the same fashion as Step 2 of Example 142, except that tert-butyl 4-aminopiperidine-1-carboxylate (213.0 mg, 1.06 mmol) was used instead of tert-butyl (S)-3-aminopyrrolidine-1-carboxylate. MS (ESI) m/z=447.2 (M+H)+

Step 2: N-phenyl-5-(piperidin-4-ylamino)quinoline-8-carboxamide hydrochloride

The title compound (100.8 mg, 54.4%) was prepared in the same fashion as Step 3 of Reference Example 142 and used in the next step without any further purification

Reference Example 233. 5-(piperidin-4-ylamino)-N-(pyridin-2-yl)quinoline-8-carboxamide hydrochloride Step 1: tert-butyl 4-((8-(pyridin-2-ylcarbamoyl)quinolin-5-yl)amino)piperidine-1-carboxylate The title compound (100.6 mg, 45.0%) was prepared in the same fashion as Step 2 of Example 147, except that tert-butyl 4-aminopiperidine-1-carboxylate (100.0 mg, 0.50 mmol) was used instead of tert-butyl (S)-3-aminopyrrolidine-1-carboxylate. MS (ESI) m/z=448.2 (M+H)+

Step 2: 5-(piperidin-4-ylamino)-N-(pyridin-2-yl)quinoline-8-carboxamide hydrochloride The title compound (63.5 mg, 67.6%) was prepared in the same fashion as Step 3 of Reference Example 147 and used in the next step without any further purification. $^1$H-NMR (MeOD$_4$, 400 MHz) δ 9.40 (s, 1H), 9.18 (dd, 1H), 8.84 (d, 1H), 8.53-8.49 (m, 2H), 8.02 (d, 1H), 7.89 (dd, 1H), 7.67 (t, 1H), 7.17 (d, 1H), 4.22-4.17 (m, 1H), 3.58 (d, 2H), 3.30-3.26 (m, 2H), 2.39 (d, 2H), 2.12-2.02 (m, 2H).

Reference Example 234. 5-(piperidin-4-ylamino)-N-(pyridin-3-yl)quinoline-8-carboxamide hydrochloride Step 1: tert-butyl 4-((8-(pyridin-3-ylcarbamoyl)quinolin-5-yl)amino)piperidine-1-carboxylate The title compound (210.3 mg, 94.1%) was prepared in the same fashion as Step 2 of Example 145, except that tert-butyl 4-aminopiperidine-1-carboxylate (100.0 mg, 0.50 mmol) was used instead of tert-butyl (S)-3-aminopyrrolidine-1-carboxylate. MS (ESI) m/z=448.2 (M+H)+

Step 2: 5-(piperidin-4-ylamino)-N-(pyridin-3-yl)quinoline-8-carboxamide hydrochloride The title compound (195.3 mg, 98.9%) was prepared in the same fashion as Step 3 of Reference Example 145 and used in the next step without any further purification. $^1$H-NMR (MeOD$_4$, 400 MHz) δ 9.66 (d, 1H), 9.16 (dd, 1H), 8.88 (d, 1H), 8.80 (d, 1H), 8.73-8.71 (m, 1H), 8.63 (d, 1H), 8.14-8.11 (m, 1H), 7.94-7.88 (m, 1H), 7.17 (d, 1H), 4.22-4.17 (m, 1H), 3.58 (d, 2H), 3.27 (d, 2H), 2.40 (d, 2H), 2.03 (d, 2H).

Reference Example 235. 5-(piperidin-4-ylamino)-N-(pyridin-4-yl)quinoline-8-carboxamide hydrochloride

Step 1: tert-butyl 4-((8-(pyridin-4-ylcarbamoyl)quinolin-5-yl)amino)piperidine-1-carboxylate The title compound (130.1 mg, 58.2%) was prepared in the same fashion as Step 2 of Example 146, except that tert-butyl 4-aminopiperidine-1-carboxylate (100.0 mg, 0.50 mmol) was used instead of tert-butyl (S)-3-aminopyrrolidine-1-carboxylate. MS (ESI) m/z=448.2 (M+H)+

Step 2: 5-(piperidin-4-ylamino)-N-(pyridin-4-yl)quinoline-8-carboxamide hydrochloride The title compound (68.6 mg, 56.0%) was prepared in the same fashion as Step 3 of Reference Example 146 and used in the next step without any further purification. $^1$H-NMR (MeOD$_4$, 400 MHz) δ 9.34-9.24 (m, 1H), 9.15 (d, 1H), 8.79 (d, 1H), 8.67 (d, 2H), 8.47 (d, 2H), 7.84 (s, 1H), 7.12 (d, 1H), 4.18-4.12 (m, 1H), 3.57 (d, 2H), 3.26 (d, 2H), 2.40 (d, 2H), 2.07-1.96 (m, 2H).

Reference Example 236. 5-(piperidin-4-ylamino)-N-(pyrimidin-2-yl)quinoline-8-carboxamide hydrochloride

Step 1: 5-bromo-N-(pyrimidin-2-yl)quinoline-8-carboxamide

The title compound (140.1 mg, 21.4%) was prepared in the same fashion as Step 1 of Reference Example 140, except that pyrimidin-2-amine (188.6 mg, 1.98 mmol) was used instead of methanamine. $^1$H-NMR (CDCl$_3$, 400 MHz) δ 9.16 (dd, 1H), 8.87 (d, 1H), 8.79 (dd, 1H), 8.76 (d, 2H), 8.07 (d, 1H), 7.69 (dd, 1H), 7.08 (t, 1H).

Step 2: tert-butyl 4-((8-(pyrimidin-2-ylcarbamoyl)quinolin-5-yl)amino)piperidine-1-carboxylate The title compound (144.4 mg, 75.8%) was prepared in the same fashion as Step 1 of Reference Example 233, except 5-bromo-N-(pyrimidin-2-yl)quinoline-8-carboxamide (140.3 mg, 0.43 mmol) prepared in Step 1 was used instead of 5-bromo-N-(pyridin-2-yl)quinoline-8-carboxamide. MS (ESI) m/z=449.2 (M+H)+

Step 3: (S)—N-(pyridin-4-yl)-5-(pyrrolidin-3-ylamino)quinoline-8-carboxamide hydrochloride The title compound (63.6 mg, 46.9%) was prepared in the same fashion as Step 2 of Reference Example 233 and used in the next step without any further purification. $^1$H-NMR (MeOD$_4$, 400 MHz) δ 9.32 (d, 1H), 9.13 (d, 1H), 9.01 (d, 2H), 8.78 (d, 1H), 7.85 (dd, 1H), 7.61 (t, 1H), 7.14 (d, 1H), 4.20-4.14 (m, 1H), 3.58 (d, 2H), 3.27 (d, 2H), 2.40 (d, 2H), 2.10-2.00 (m, 2H).

Reference Example 237. N-(isoxazol-3-yl)-5-(piperidin-4-ylamino)quinoline-8-carboxamide hydrochloride

Step 1: 5-bromo-N-(isoxazol-3-yl)quinoline-8-carboxamide

The title compound (158.8 mg, 41.9%) was prepared in the same fashion as Step 1 of Reference Example 140, except that isoxazol-3-amine (118.0 mg, 1.42 mmol) was used instead of methanamine. $^1$H-NMR (CDCl$_3$, 400 MHz) δ 9.09 (dd, 1H), 8.78 (dd, 2H), 8.38 (dd, 1H), 8.05 (dd, 1H), 7.69 (dd, 1H), 7.29 (d, 1H).

Step 2: tert-butyl 4-((8-(isoxazol-3-ylcarbamoyl)quinolin-5-yl)amino)piperidine-1-carboxylate The title compound (84.9 mg, 38.8%) was prepared in the same fashion as Step 1 of Reference Example 233, except 5-bromo-N-(isoxazol-3-yl)quinoline-8-carboxamide (158.8 mg, 0.5 mmol) prepared in Step 1 was used instead of 5-bromo-N-(pyridin-2-yl)quinoline-8-carboxamide. MS (ESI) m/z=438.2 (M+H)+

Step 3: N-(isoxazol-3-yl)-5-(piperidin-4-ylamino)quinoline-8-carboxamide hydrochloride The title compound (21.6 mg, 27.3%) was prepared in the same fashion as Step 2 of Reference Example 233 and used in the next step without any further purification.

Reference Example 238. N-(5-(piperidin-4-ylamino)quinolin-8-yl)acetamide hydrochloride

Step 1: tert-butyl 4-((8-acetamidoquinolin-5-yl)amino)piperidine-1-carboxylate The title compound (264.2 mg, 27.5%) was prepared in the same fashion as Step 1 of Reference Example 28, except that N-(5-bromoquinolin-8-yl)acetamide (661.8 mg, 2.49 mmol) was used instead of 4-bromoquinoline. MS (ESI) m/z=385.2 (M+H)+

Step 2: N-(5-(piperidin-4-ylamino)quinolin-8-yl)acetamide hydrochloride

The title compound (204.2 mg, 83.1%) was prepared in the same fashion as Step 2 of Reference Example 28 and used in the next step without any further purification. $^1$H-NMR (MeOD$_4$, 400 MHz) δ 9.54 (dd, 1H), 9.00 (dd, 1H), 7.95 (dd, 1H), 7.79 (d, 1H), 7.08 (d, 1H), 4.02-3.05 (m, 1H), 3.55 (m, 2H), 3.25 (td, 2H), 2.39 (d, 2H), 2.30 (s, 3H), 2.00-1.89 (m, 2H).

Reference Example 239. 6-methyl-4-(piperidin-4-yloxy)quinoline hydrochloride

Step 1: tert-butyl 4-((6-methylquinolin-4-yl)oxy)piperidine-1-carboxylate

The title compound (425.3 mg, 100.0%) was prepared in the same fashion as Step 1 of Reference Example 31, except that 4-hydroxy-6-methyl quinoline (197.7 mg, 1.24 mmol) was used instead of 3-quinolinol. MS (ESI) m/z=343.2 (M+H)+

Step 2: 6-methyl-4-(piperidin-4-yloxy)quinoline hydrochloride

The title compound (346.3 mg, 100.0%) was prepared in the same fashion as Step 2 of Reference Example 31 and used in the next step without any further purification.

Reference Example 240. 4-(piperidin-4-yloxy)-6-(trifluoromethyl)quinoline hydrochloride

Step 1: tert-butyl 4-((6-(trifluoromethyl)quinolin-4-yl)oxy)piperidine-1-carboxylate The title compound (492.3 mg, 100.0%) was prepared in the same fashion as Step 1 of Reference Example 31, except that 6-(trifluoromethyl)quinolin-4-ol (264.8 mg, 1.24 mmol) was used instead of 3-quinolinol. MS (ESI) m/z=397.1 (M+H)+

Step 2: 4-(piperidin-4-yloxy)-6-(trifluoromethyl)quinoline hydrochloride

The title compound (413.3 mg, 100.0%) was prepared in the same fashion as Step 2 of Reference Example 31 and used in the next step without any further purification.

Reference Example 241. 4-(piperidin-4-yloxy)-2-(trifluoromethyl)quinoline hydrochloride

Step 1: tert-butyl 4-((2-(trifluoromethyl)quinolin-4-yl)oxy)piperidine-1-carboxylate The title compound (347.0 mg, 70.5%) was prepared in the same fashion as Step 1 of Reference Example 31, except that 4-hydroxy-2-trifluoromethylquinoline (264.8 mg, 1.24 mmol) was used instead of 3-quinolinol. MS (ESI) m/z=397.1 (M+H)+

Step 2: 4-(piperidin-4-yloxy)-2-(trifluoromethyl)quinoline hydrochloride

The title compound (291.3 mg, 100.0%) was prepared in the same fashion as Step 2 of Reference Example 31 and used in the next step without any further purification.

Reference Example 242. 6-fluoro-4-(piperidin-4-yloxy)-2-(trifluoromethyl)quinoline hydrochloride

Step 1: tert-butyl 4-((6-fluoro-2-(trifluoromethyl)quinolin-4-yl)oxy)piperidine-1-carboxylate The title compound (302.0 mg, 58.7%) was prepared in the same fashion as Step 1 of Reference Example 31, except that 6-fluoro-2-(trifluoromethyl)quinolin-4-ol (287.1 mg, 1.24 mmol) was used instead of 3-quinolinol. MS (ESI) m/z=415.2 (M+H)+

Step 2: 6-fluoro-4-(piperidin-4-yloxy)-2-(trifluoromethyl)quinoline hydrochloride The title compound (255.6 mg, 100.0%) was prepared in the same fashion as Step 2 of Reference Example 31 and used in the next step without any further purification.

Reference Example 243. 6-methoxy-4-(piperidin-4-yloxy)-2-(trifluoromethyl)quinoline hydrochloride

Step 1: tert-butyl 4-((6-methoxy-2-(trifluoromethyl)quinolin-4-yl)oxy)piperidine-1-carboxylate The title compound (357.1 mg, 67.4%) was prepared in the same fashion as Step 1 of Reference Example 31, except that 6-methoxy-2-(trifluoromethyl)quinolin-4-ol (302.1 mg, 1.24 mmol) was used instead of 3-quinolinol. MS (ESI) m/z=427.2 (M+H)+

Step 2: 6-methoxy-4-(piperidin-4-yloxy)-2-(trifluoromethyl)quinoline hydrochloride The title compound (303.8 mg, 100.0%) was prepared in the same fashion as Step 2 of Reference Example 31 and used in the next step without any further purification.

Reference Example 244. 8-methoxy-4-(piperidin-4-yloxy)-2-(trifluoromethyl)quinoline hydrochloride

Step 1: tert-butyl 4-((8-methoxy-2-(trifluoromethyl)quinolin-4-yl)oxy)piperidine-1-carboxylate The title compound (487.7 mg, 92.1%) was prepared in the same fashion as Step 1 of Reference Example 31, except that 8-methoxy-2-(trifluoromethyl)quinolin-4-ol (302.1 mg, 1.24 mmol) was used instead of 3-quinolinol. MS (ESI) m/z=427.2 (M+H)+

Step 2: 8-methoxy-4-(piperidin-4-yloxy)-2-(trifluoromethyl)quinoline hydrochloride The title compound (414.9 mg, 100.0%) was prepared in the same fashion as Step 2 of Reference Example 31 and used in the next step without any further purification.

Reference Example 245. 3-fluoro-5-(piperidin-4-yloxy)quinoline hydrochloride

Step 1: tert-butyl 4-((3-fluoroquinolin-5-yl)oxy)piperidine-1-carboxylate

The title compound (430.2 mg, 100.0%) was prepared in the same fashion as Step 1 of Reference Example 31, except that 3-fluoroquinolin-5-ol (202.7 mg, 1.24 mmol) was used instead of 3-quinolinol. MS (ESI) m/z=347.2 (M+H)+

Step 2: 3-fluoro-5-(piperidin-4-yloxy)quinoline hydrochloride

The title compound (442.2 mg, 100.0%) was prepared in the same fashion as Step 2 of Reference Example 31 and used in the next step without any further purification.

Reference Example 246.
5-(piperidin-4-yloxy)quinoline-2-carbonitrile hydrochloride Step 1: tert-butyl 4-((2-cyanoquinolin-5-yl)oxy)piperidine-1-carboxylate The title compound (438.9 mg, 100.0%) was prepared in the same fashion as Step 1 of Reference Example 31, except that 5-hydroxyquinoline-2-carbonitrile (211.4 mg, 1.24 mmol) was used instead of 3-quinolinol. MS (ESI) m/z=354.2 (M+H)+

Step 2: 5-(piperidin-4-yloxy)quinoline-2-carbonitrile hydrochloride

The title compound (381.6 mg, 100.0%) was prepared in the same fashion as Step 2 of Reference Example 31 and used in the next step without any further purification.

Reference Example 247.
8-chloro-5-(piperidin-4-yloxy)quinoline hydrochloride Step 1: tert-butyl 4-((8-chloroquinolin-5-yl)oxy)piperidine-1-carboxylate The title compound (450.7 mg, 100.0%) was prepared in the same fashion as Step 1 of Reference Example 31, except that 8-chloroquinolin-5-ol (223.1 mg, 1.24 mmol) was used instead of 3-quinolinol. MS (ESI) m/z=363.2 (M+H)+

Step 2: 8-chloro-5-(piperidin-4-yloxy)quinoline hydrochloride

The title compound (660.6 mg, 100.0%) was prepared in the same fashion as Step 2 of Reference Example 31 and used in the next step without any further purification.

Reference Example 248.
1-(piperidin-4-yloxy)isoquinoline hydrochloride

Step 1: tert-butyl 4-(isoquinolin-1-yloxy)piperidine-1-carboxylate

The title compound (155.8 mg, 38.2%) was prepared in the same fashion as Step 1 of Reference Example 31, except that 1-hydroxyisoquinoline (180.3 mg, 1.24 mmol) was used instead of 3-quinolinol. MS (ESI) m/z=329.2 (M+H)+

Step 2: 1-(piperidin-4-yloxy)isoquinoline hydrochloride

The title compound (125.6 mg, 100.0%) was prepared in the same fashion as Step 2 of Reference Example 31 and used in the next step without any further purification.

Reference Example 249.
4-(piperidin-4-yloxy)isoquinoline hydrochloride

Step 1: tert-butyl 4-(isoquinolin-4-yloxy)piperidine-1-carboxylate

The title compound (407.9 mg, 100.0%) was prepared in the same fashion as Step 1 of Reference Example 31, except that 4-hydroxyisoquinoline (180.3 mg, 1.24 mmol) was used instead of 3-quinolinol. MS (ESI) m/z=329.1 (M+H)+

Step 2: 4-(piperidin-4-yloxy)isoquinoline hydrochloride

The title compound (328.8 mg, 100.0%) was prepared in the same fashion as Step 2 of Reference Example 31 and used in the next step without any further purification.

Reference Example 250.
5-(piperidin-4-yloxy)isoquinoline hydrochloride

Step 1: tert-butyl 4-(isoquinolin-5-yloxy)piperidine-1-carboxylate

The title compound (194.1 mg, 47.6%) was prepared in the same fashion as Step 1 of Reference Example 31, except that 5-hydroxyisoquinoline (180.3 mg, 1.24 mmol) was used instead of 3-quinolinol. MS (ESI) m/z=329.1 (M+H)+

Step 2: 5-(piperidin-4-yloxy)isoquinoline hydrochloride

The title compound (156.5 mg, 100.0%) was prepared in the same fashion as Step 2 of Reference Example 31 and used in the next step without any further purification.

Reference Example 251.
6-(piperidin-4-yloxy)isoquinoline hydrochloride

Step 1: tert-butyl 4-(isoquinolin-6-yloxy)piperidine-1-carboxylate

The title compound (407.9 mg, 100.0%) was prepared in the same fashion as Step 1 of Reference Example 31, except that 6-hydroxyisoquinoline (180.3 mg, 1.24 mmol) was used instead of 3-quinolinol. MS (ESI) m/z=329.2 (M+H)+

Step 2: 6-(piperidin-4-yloxy)isoquinoline hydrochloride

The title compound (328.9 mg, 100.0%) was prepared in the same fashion as Step 2 of Reference Example 31 and used in the next step without any further purification.

Reference Example 252.
7-(piperidin-4-yloxy)isoquinoline hydrochloride

Step 1: tert-butyl 4-(isoquinolin-7-yloxy)piperidine-1-carboxylate

The title compound (407.9 mg, 100.0%) was prepared in the same fashion as Step 1 of Reference Example 31, except that 7-hydroxyisoquinoline (180.3 mg, 1.24 mmol) was used instead of 3-quinolinol. MS (ESI) m/z=329.2 (M+H)+

Step 2: 7-(piperidin-4-yloxy)isoquinoline hydrochloride

The title compound (328.9 mg, 100.0%) was prepared in the same fashion as Step 2 of Reference Example 31 and used in the next step without any further purification.

Reference Example 253.
6-methoxy-2-methyl-4-(piperidin-4-yloxy)quinoline hydrochloride Step 1: tert-butyl 4-((6-methoxy-2-methylquinolin-4-yl)oxy)piperidine-1-carboxylate The title compound (462.6 mg, 100.0%) was prepared in the same fashion as Step 1 of Reference Example 31, except that 6-methoxy-2-methylquinolin-4-ol (235.0 mg, 1.24 mmol) was used instead of 3-quinolinol. MS (ESI) m/z=373.2 (M+H)+

Step 2: 6-methoxy-2-methyl-4-(piperidin-4-yloxy)quinoline hydrochloride

The title compound (383.6 mg, 100.0%) was prepared in the same fashion as Step 2 of Reference Example 31 and used in the next step without any further purification.

Reference Example 254.
7-chloro-4-(piperidin-4-yloxy)quinoline hydrochloride Step 1: tert-butyl 4-((7-chloroquinolin-4-yl)oxy)piperidine-1-carboxylate The title compound (450.7 mg, 99.9%) was prepared in the same fashion as Step 1 of Reference Example 31, except that 7-chloroquinolin-4-ol (223.1 mg, 1.24 mmol) was used instead of 3-quinolinol. MS (ESI) m/z=363.2 (M+H)+

Step 2: 7-chloro-4-(piperidin-4-yloxy)quinoline hydrochloride

The title compound (371.6 mg, 100.0%) was prepared in the same fashion as Step 2 of Reference Example 31 and used in the next step without any further purification.

Reference Example 255.
7-methyl-4-(piperidin-4-yloxy)quinoline hydrochloride Step 1: tert-butyl 4-((7-methylquinolin-4-yl)oxy)piperidine-1-carboxylate The title compound (500.0 mg, 98.0%) was prepared in the same fashion as Step 1 of Reference Example 31, except that 7-methylquinolin-4-ol (237.3 mg, 1.49 mmol) was used instead of 3-quinolinol. MS (ESI) m/z=343.3 (M+H)+

Step 2: 7-methyl-4-(piperidin-4-yloxy)quinoline hydrochloride

The title compound (407.0 mg, 100.0%) was prepared in the same fashion as Step 2 of Reference Example 31 and used in the next step without any further purification.

Reference Example 256.
7-fluoro-4-(piperidin-4-yloxy)quinoline hydrochloride Step 1: tert-butyl 4-((7-fluoroquinolin-4-yl)oxy)piperidine-1-carboxylate The title compound (516.0 mg, 99.9%) was prepared in the same fashion as Step 1 of Reference Example 31, except that 7-fluoroquinolin-4-ol (243.2 mg, 1.49 mmol) was used instead of 3-quinolinol. MS (ESI) m/z=347.2 (M+H)+

Step 2: 7-fluoro-4-(piperidin-4-yloxy)quinoline hydrochloride

The title compound (421.3 mg, 100.0%) was prepared in the same fashion as Step 2 of Reference Example 31 and used in the next step without any further purification.

Reference Example 257.
4-(piperidin-4-yloxy)quinoline-8-carbonitrile hydrochloride Step 1: tert-butyl 4-((8-cyanoquinolin-4-yl)oxy)piperidine-1-carboxylate The title compound (505.4 mg, 95.9%) was prepared in the same fashion as Step 1 of Reference Example 31, except that 4-hydroxyquinoline-8-carbonitrile (253.7 mg, 1.49 mmol) was used instead of 3-quinolinol. MS (ESI) m/z=354.2 (M+H)+

Step 2: 4-(piperidin-4-yloxy)quinoline-8-carbonitrile hydrochloride

The title compound (414.4 mg, 100.0%) was prepared in the same fashion as Step 2 of Reference Example 31 and used in the next step without any further purification.

Reference Example 258.
8-fluoro-4-(piperidin-4-yloxy)quinoline hydrochloride Step 1: tert-butyl 4-((8-fluoroquinolin-4-yl)oxy)piperidine-1-carboxylate The title compound (516.0 mg, 99.9%) was prepared in the same fashion as Step 1 of Reference Example 31, except that 8-fluoro-4-hydroxyquinoline (243.2 mg, 1.49 mmol) was used instead of 3-quinolinol. MS (ESI) m/z=347.1 (M+H)+

Step 2: 8-fluoro-4-(piperidin-4-yloxy)quinoline hydrochloride

The title compound (421.3 mg, 100.0%) was prepared in the same fashion as Step 2 of Reference Example 31 and used in the next step without any further purification.

Reference Example 259.
2-methyl-4-(piperidin-4-yloxy)quinoline hydrochloride Step 1: tert-butyl 4-((2-methylquinolin-4-yl)oxy)piperidine-1-carboxylate The title compound (510.0 mg, 99.9%) was prepared in the same fashion as Step 1 of Reference Example 31, except that 4-hydroxy-2-methyl-quinoline (237.3 mg, 1.49 mmol) was used instead of 3-quinolinol. MS (ESI) m/z=343.2 (M+H)+

Step 2: 2-methyl-4-(piperidin-4-yloxy)quinoline hydrochloride

The title compound (415.4 mg, 100.0%) was prepared in the same fashion as Step 2 of Reference Example 31 and used in the next step without any further purification.

Reference Example 260.
6-fluoro-2-methyl-4-(piperidin-4-yloxy)quinoline hydrochloride

Step 1: tert-butyl 4-((6-fluoro-2-methylquinolin-4-yl)oxy)piperidine-1-carboxylate The title compound (537.0 mg, 99.9%) was prepared in the same fashion as Step 1 of Reference Example 31, except that 6-fluoro-2-methyl-quinolin-4-ol (264.1 mg, 1.49 mmol) was used instead of 3-quinolinol. MS (ESI) m/z=361.2 (M+H)+

Step 2: 6-fluoro-2-methyl-4-(piperidin-4-yloxy)quinoline hydrochloride

The title compound (442.2 mg, 100.0%) was prepared in the same fashion as Step 2 of Reference Example 31 and used in the next step without any further purification.

Reference Example 261.
8-methoxy-4-(piperidin-4-yloxy)quinoline hydrochloride

Step 1: tert-butyl 4-((8-methoxyquinolin-4-yl)oxy) piperidine-1-carboxylate The title compound (118.7 mg, 22.2%) was prepared in the same fashion as Step 1 of Reference Example 31, except that 4-hydroxy-8-methoxyquinoline (261.1 mg, 1.49 mmol) was used instead of 3-quinolinol. MS (ESI) m/z=359.2 (M+H)+

Step 2: 8-methoxy-4-(piperidin-4-yloxy)quinoline hydrochloride

The title compound (97.6 mg, 100.0%) was prepared in the same fashion as Step 2 of Reference Example 31 and used in the next step without any further purification.

Reference Example 262.
8-methyl-4-(piperidin-4-yloxy)quinoline hydrochloride

Step 1: tert-butyl 4-((8-methylquinolin-4-yl)oxy) piperidine-1-carboxylate

The title compound (510.0 mg, 99.9%) was prepared in the same fashion as Step 1 of Reference Example 31, except that 8-methylquinolin-4-ol (237.3 mg, 1.49 mmol) was used instead of 3-quinolinol. MS (ESI) m/z=343.2 (M+H)+

Step 2: 8-methyl-4-(piperidin-4-yloxy)quinoline hydrochloride

The title compound (415.4 mg, 100.0%) was prepared in the same fashion as Step 2 of Reference Example 31 and used in the next step without any further purification.

Example 1. (R)-1-(2-((S)-2-cyanopyrrolidin-1-yl)-2-oxoethyl)-N-(quinolin-3-yl)pyrrolidine-3-carboxamide (S)-1-(2-Chloroacetyl)pyrrolidine-2-carbonitrile (30 mg, 0.17 mmol) prepared in Reference Example 1 was dissolved in anhydrous dichloromethane (1.2 ml). To the resulting solution, (R)—N-(quinolin-3-yl)pyrrolidine-3-carboxamide hydrochloride (54.6 mg, 0.19 mmol) prepared in Reference Example 24 and potassium carbonate (96.0 mg, 0.69 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (ethyl acetate/methanol=10/1, v/v) to give the title compound (31.6 mg). $^1$H-NMR (CDCl$_3$, 400 MHz) δ 10.45 (s, 1H), 9.12 (s, 1H), 8.75 (s, 1H), 7.97 (d, 1H), 7.73 (d, 1H), 7.55-7.46 (m, 2H), 4.78 (s, 1H), 3.74-3.18 (m, 7H), 2.82 (s, 1H), 2.59-2.18 (m, 8H)

Example 2. (R)-1-(2-((S)-2-cyanopyrrolidin-1-yl)-2-oxoethyl)-N-(quinolin-4-yl)pyrrolidine-3-carboxamide The title compound (33.3 mg) was prepared in the same fashion as Example 1, except that (R)—N-(quinolin-4-yl) pyrrolidine-3-carboxamide hydrochloride (54.6 mg, 0.19 mmol) prepared in Reference Example 23 was used instead of (R)—N-(quinolin-3-yl)pyrrolidine-3-carboxamide hydrochloride. $^1$H-NMR (CDCl$_3$, 400 MHz) δ 10.62 (s, 1H), 8.78 (s, 1H), 8.31-8.26 (m, 2H), 8.05 (d, 1H), 7.71-7.62 (m, 2H), 4.78 (d, 1H), 3.71-3.19 (m, 8H), 2.82 (s, 1H), 2.62-2.05 (m, 8H)

Example 3. (S)-1-(2-((S)-2-cyanopyrrolidin-1-yl)-2-oxoethyl)-N-(quinolin-3-yl)pyrrolidine-3-carboxamide The title compound (6.3 mg) was prepared in the same fashion as Example 1, except that (S)—N-(quinolin-3-yl) pyrrolidine-3-carboxamide hydrochloride (54.6 mg, 0.19 mmol) prepared in Reference Example 22 was used instead of (R)—N-(quinolin-3-yl)pyrrolidine-3-carboxamide hydrochloride. $^1$H-NMR (CDCl$_3$, 400 MHz) δ 10.36 (d, 1H), 9.11 (d, 1H), 8.84 (d, 1H), 8.02 (t, 1H), 7.81 (d, 1H), 7.60-7.47 (m, 2H), 4.83 (d, 1H), 3.69-3.04 (m, 7H), 2.56-2.05 (m, 10H)

Example 4. (S)-1-(2-((S)-2-cyanopyrrolidin-1-yl)-2-oxoethyl)-N-(quinolin-4-yl)pyrrolidine-3-carboxamide The title compound (14.3 mg) was prepared in the same fashion as Example 1, except that (S)—N-(quinolin-4-yl) pyrrolidine-3-carboxamide hydrochloride (54.6 mg, 0.19 mmol) prepared in Reference Example 21 was used instead of (R)—N-(quinolin-3-yl)pyrrolidine-3-carboxamide hydrochloride. $^1$H-NMR (CDCl$_3$, 400 MHz) δ 10.42 (s, 1H), 8.77 (d, 1H), 8.35-8.03 (m, 3H), 7.71-7.58 (m, 2H), 4.79 (d, 1H), 3.70-3.35 (m, 6H), 3.22 (s, 1H), 2.48-2.05 (m, 9H)

Example 5. (S)-1-(2-((S)-3-(quinolin-4-ylamino) pyrrolidin-1-yl)acetyl)pyrrolidine-2-carbonitrile (S)-1-(2-Chloroacetyl)pyrrolidine-2-carbonitrile (20 mg, 0.12 mmol) prepared in Reference Example 1 was dissolved in anhydrous dichloromethane (4 ml). To the resulting solution, (S)—N-(pyrrolidin-3-yl)quinolin-4-amine hydrochloride (39.8 mg, 0.14 mmol) prepared in Reference Example 5 and potassium carbonate (48.0 mg, 0.35 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=10/1, v/v) to give the title compound (11.4 mg). $^1$H-NMR (CDCl$_3$, 400 MHz) δ 8.65-8.72 (m, 1H), 8.00 (d, 1H), 7.87-7.93 (m, 1H), 7.77-7.82 (m, 1H), 7.67-7.75 (m, 1H), 7.58-7.62 (m, 1H), 4.75-4.82 (m, 1H), 4.25-4.31 (m, 1H), 3.63-3.70 (m, 1H), 3.44-3.52 (m, 2H), 3.12- 3.22 (m, 1H), 3.08 (d, 1H), 2.80 (dd, 0.3H), 2.64-2.71 (m, 0.5H), 2.26-2.36 (m, 2H), 2.13-2.25 (m, 2H)

Example 6. (S)-4,4-difluoro-1-(2-((S)-3-(quinolin-3-ylamino)pyrrolidin-1-yl)acetyl)pyrrolidine-2-carbonitrile (2S)-1-(2-Chloroacetyl)-4,4-difluoro-pyrrolidine-2-carbonitrile (25.0 mg 0.12 mmol) prepared in Reference Example 3 was dissolved in anhydrous dichloromethane (4 ml). To the resulting solution, (S)—N-(pyrrolidin-3-yl)quinolin-3-amine hydrochloride (34.3 mg 0.12 mmol) prepared in Reference Example 6 and potassium carbonate (48.0 mg, 0.35 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=10/1, v/v) to give the title compound (6.1 mg). $^1$H-NMR (CDCl$_3$, 400 MHz) δ 8.42 (s, 1H), 7.85-7.96 (m, 1H), 7.50-7.64 (m, 1H), 7.36-7.46 (m, 2H), 6.96 (s, 1H), 5.17-5.28 (m, 0.4H), 4.89-5.01 (m, 0.6H), 4.32-4.56 (m, 1H), 4.05-4.19 (m, 2H), 3.37-3.55 (m, 1H), 3.30-3.36 (m, 1H), 2.91-3.11 (m, 2H), 2.68-2.86 (m, 3H), 2.33-2.53 (m, 2H), 1.78-1.99 (m, 2H)

Example 7. (S)-4,4-difluoro-1-(2-((S)-3-(quinolin-4-ylamino)pyrrolidin-1-yl)acetyl)pyrrolidine-2-carbonitrile The title compound (5.3 mg) was prepared in the same fashion as Example 6, except that (S)—N-(pyrrolidin-3-yl)quinolin-4-amine hydrochloride (34.3 mg 0.12 mmol) prepared in Reference Example 5 was used instead of (S)—N-(pyrrolidin-3-yl)quinolin-3-amine hydrochloride. $^1$H-NMR (CDCl$_3$, 400 MHz) δ 8.68 (s, 1H), 7.90 (d, 1H), 7.85 (d, 1H), 7.76-7.83 (m, 1H), 7.62-7.72 (m, 1H), 7.54-7.62 (m, 1H), 5.13-5.21 (m, 0.4H), 4.91-5.02 (m, 0.6H), 4.65-4.80 (m, 1H), 4.26 (m, 1H), 3.98-4.15 (m, 2H), 3.78-3.91 (m, 0.5H), 3.47-3.59 (m, 0.5H), 3.34-3.43 (m, 1.5H), 2.87-3.14 (m, 3H), 2.59-2.81 (m, 3H), 2.35-2.59 (m, 1.5H)

Example 8. (S)-4,4-difluoro-1-(2-((S)-3-(isoquinolin-4-ylamino)pyrrolidin-1-yl)acetyl)pyrrolidine-2-carbonitrile The title compound (16.3 mg) was prepared in the same fashion as Example 6, except that (S)—N-(pyrrolidin-3-yl)isoquinolin-4-amine hydrochloride (34.3 mg, 0.12 mmol) prepared in Reference Example 7 was used instead of (S)—N-(pyrrolidin-3-yl)quinolin-3-amine hydrochloride. $^1$H-NMR (CDCl$_3$, 400 MHz) δ 8.51 (d, 1H), 7.96 (d, 1H), 7.83-7.91 (m, 1H), 7.59-7.65 (m, 1H), 7.42 (t, 1H), 5.92 (d, 0.6H), 5.69 (d, 0.4H), 5.11 (dd, 0.4H), 4.91 (t, 0.6H), 4.16-4.28 (m, 1H), 3.72-4.12 (m, 2H), 3.59 (d, 0.5H), 3.37 (s, 1H), 3.31 (d, 0.5H), 3.07-3.18 (m, 0.5H), 2.99-3.07 (m, 1H), 2.89-2.95 (m, 1H), 2.55-2.76 (m, 5H), 2.44-2.55 (m, 0.5H), 2.30-2.41 (m, 1H), 1.92 (m, 1H)

Example 9. (S)-1-(2-((S)-3-(benzo[b]thiophen-4-ylamino)pyrrolidin-1-yl)acetyl)-4,4-difluoropyrrolidine-2-carbonitrile The title compound (5.62 mg) was prepared in the same fashion as Example 6, except that (S)—N-(benzo[b]thiophen-4-yl)pyrrolidin-3-amine hydrochloride (26.2 mg, 0.12 mmol) prepared in Reference Example 8 was used instead of (S)—N-(pyrrolidin-3-yl)quinolin-3-amine hydrochloride. $^1$H-NMR (CDCl$_3$, 400 MHz) δ 7.23-7.36 (m, 3H), 7.16-7.23 (m, 1H), 6.35 (s, 1H), 5.15 (d, 0.4H), 4.88 (t, 0.6H), 4.18 (s, 1H), 3.94-4.05 (m, 1.6H), 3.81-3.91 (m, 0.5H), 3.44-3.53 (m, 0.5H), 3.31-3.40 (m, 0.5H), 3.25-3.31 (m, 1H), 3.03-3.11 (m, 0.4H), 2.86-2.99 (m, 1.6H), 2.76-2.82 (m, 0.5H), 2.29-2.72 (m, 5H), 1.79-1.98 (m, 1H)

Example 10. (S)-1-(2-((S)-3-(benzo[b]thiophen-7-ylamino)pyrrolidin-1-yl)acetyl)-4,4-difluoropyrrolidine-2-carbonitrile The title compound (10.9 mg) was prepared in the same fashion as Example 6, except that (S)—N-(benzo[b]thiophen-7-yl)pyrrolidin-3-amine hydrochloride (26.2 mg, 0.12 mmol) prepared in Reference Example 9 was used instead of (S)—N-(pyrrolidin-3-yl)quinolin-3-amine hydrochloride. $^1$H-NMR (CDCl$_3$, 400 MHz) δ 7.34-7.41 (m, 1H), 7.20-7.34 (m, 4H), 6.47-6.57 (m, 1H), 5.37 (d, 0.5H), 4.89 (t, 0.7H), 4.17-4.28 (m, 1H), 3.75-4.08 (m, 3H), 3.35-3.55 (m, 1H), 3.21-3.35 (m, 1H), 2.78-3.13 (m, 2H), 2.55-2.73 (m, 4H), 2.31-2.53 (m, 2H), 1.78-1.97 (m, 1H)

Example 11. (S)-1-(2-((S)-3-(benzofuran-7-ylamino)pyrrolidin-1-yl)acetyl)-4,4-difluoropyrrolidine-2-carbonitrile The title compound (6.91 mg) was prepared in the same fashion as Example 6, except that (S)—N-(benzofuran-7-yl)pyrrolidin-3-amine hydrochloride (24.27 mg, 0.12 mmol) prepared in Reference Example 10 was used instead of (S)—N-(pyrrolidin-3-yl)quinolin-3-amine hydrochloride. $^1$H-NMR (CDCl$_3$, 400 MHz) δ 7.55 (s, 1H), 7.08 (t, 1H), 6.97 (d, 1H), 6.72 (s, 1H), 6.45-6.50 (m, 1H), 5.44 (d, 0.3H), 4.90 (dd, 0.6H), 4.13-4.29 (m, 1H), 3.75-4.08 (m, 2H), 3.32-3.59 (m, 1H), 3.23-3.32 (m, 1H), 2.85-3.08 (m, 2H), 2.55-2.78 (m, 4H), 2.32-2.53 (m, 1H), 1.72-1.93 (m, 1H)

Example 12. (S)-4,4-difluoro-1-(2-((S)-3-(furo[3,2-c]pyridin-7-ylamino)pyrrolidin-1-yl)acetyl)pyrrolidine-2-carbonitrile The title compound (4.59 mg) was prepared in the same fashion as Example 6, except that (S)—N-(pyrrolidin-3-yl)furo[3,2-c]pyridin-7-amine hydrochloride (24.4 mg, 0.12 mmol) prepared in Reference Example 11 was used instead of (S)—N-(pyrrolidin-3-yl)quinolin-3-amine hydrochloride. $^1$H-NMR (CDCl$_3$, 400 MHz) δ 8.39 (s, 1H), 7.87 (s, 1H), 7.61-7.72 (m, 1H), 6.82-6.98 (m, 1H), 5.31-5.41 (m, 0.4H), 4.92-5.03 (m, 0.7H), 4.21-4.45 (m, 2H), 3.49-3.62 (m, 1H), 3.33-3.40 (m, 1H), 2.94-3.12 (m, 2H), 2.58-2.87 (m, 6H), 2.37-2.54 (m, 2H), 1.77-2.00 (m, 1H)

Example 13. (S)-1-(2-((S)-3-([1,1'-biphenyl]-2-ylamino)pyrrolidin-1-yl)acetyl)-4,4-difluoropyrrolidine-2-carbonitrile The title compound (14.9 mg) was prepared in the same fashion as Example 6, except that (S)—N-([1,1'-biphenyl]-2-yl)pyrrolidin-3-amine hydrochloride (28.6 mg, 0.12 mmol) prepared in Reference Example 12 was used instead of (S)—N-(pyrrolidin-3-yl)quinolin-3-amine hydrochloride. $^1$H-NMR (CDCl$_3$, 400 MHz) δ 7.32-7.48 (m, 5H), 7.19-7.26 (m, 1H), 7.09 (d, 1H), 6.78 (br t, 1H), 6.64 (d, 1H), 5.36 (br d, 0.3H), 4.87-4.92 (m, 0.6H), 3.75-4.22 (m, 4H), 3.57 (br d, 0.5H), 3.20-3.30 (m, 1.6H), 2.79-2.93 (m, 1H), 2.62-2.76 (m, 2H), 2.43-2.61 (m, 2H), 2.24-2.35 (m, 1H), 1.56-1.70 (m, 1H)

Example 14. (S)-1-(2-((S)-3-([1,1'-biphenyl]-4-ylamino)pyrrolidin-1-yl)acetyl)-4,4-difluoropyrrolidine-2-carbonitrile The title compound (13.3 mg) was prepared in the same fashion as Example 6, except that (S)—N-([1,1'-biphenyl]-4-yl)pyrrolidin-3-amine hydrochloride (28.6 mg, 0.12 mmol) prepared in Reference Example 13 was used instead of (S)—N-(pyrrolidin-3-yl)quinolin-3-amine hydrochloride. $^1$H-NMR (CDCl$_3$, 400 MHz) δ 7.53 (d, 2H), 7.41-7.51 (m, 2H), 7.39 (t, 2H), 7.22-7.30 (m, 1H), 6.65 (d, 2H), 5.31-5.48 (s, 0.4H), 4.95-5.12 (m, 0.6H), 3.96-4.17 (m, 3H), 3.33-3.52 (m, 1H), 2.84-3.08 (m, 2H), 2.56-2.81 (m, 4H), 2.27-2.53 (m, 2H), 1.78-1.85 (m, 1H)

Example 15. (S)-4,4-difluoro-1-(2-((S)-3-(naphthalen-2-ylamino)pyrrolidin-1-yl)acetyl)pyrrolidine-2-carbonitrile The title compound (13.8 mg) was prepared in the same fashion as Example 6, except that (S)—N-(naphthalen-2-yl)pyrrolidin-3-amine (25.5 mg, 0.12 mmol) prepared in Reference Example 14 was used instead of (S)—N-(pyrrolidin-3-yl)quinolin-3-amine hydrochloride. $^1$H-NMR (CDCl$_3$, 400 MHz) δ 7.58-7.68 (m, 3H), 7.36 (t, 1H), 7.16-7.26 (m, 1H), 6.85 (d, 1H), 6.73-6.81 (m, 1H), 5.26 (d, 0.3H), 4.89 (t, 0.6H), 4.08-4.19 (m, 1H), 3.82-3.92 (m, 0.5H), 3.37-3.57 (m, 1H), 3.23-3.33 (m, 1H), 2.87-3.04 (m, 1.5H), 2.55-2.83 (m, 4H), 2.30-2.47 (m, 1H), 1.81-1.93 (m, 1H)

Example 16. (S)-1-(2-((S)-3-([1,1'-biphenyl]-3-ylamino)pyrrolidin-1-yl)acetyl)-4,4-difluoropyrrolidine-2-carbonitrile The title compound (8.3 mg) was prepared in the same fashion as Example 6, except that (S)—N-([1,1'-biphenyl]-3-yl)pyrrolidin-3-amine hydrochloride (28.6 mg, 0.12 mmol) prepared in Reference Example 15 was used instead of (S)—N-(pyrrolidin-3-yl)quinolin-3-amine hydrochloride. $^1$H-NMR (CDCl$_3$, 400 MHz) δ 7.55 (d, 2H), 7.41 (t, 2H), 7.30-7.35 (m, 1H), 7.20-7.25 (m, 1H), 6.93 (d, 1H), 6.77 (s, 1H), 6.54-6.62 (m, 1H), 5.28 (m, 0.3H), 4.90 (m, 0.6H), 3.95-4.14 (m, 3H), 3.77-3.87 (m, 0.4H), 3.42-3.52 (m, 0.6H), 3.23-3.29 (m, 1H), 2.84-3.01 (m, 1H), 2.54-2.78 (m, 4H), 2.29-2.44 (m, 1H), 1.68-1.84 (m, 1H)

Example 17. (S)-1-(2-((R)-3-(quinolin-3-ylamino)pyrrolidin-1-yl)acetyl)pyrrolidine-2-carbonitrile (S)-1-(2-Chloroacetyl)pyrrolidine-2-carbonitrile (25.0 mg 0.12 mmol) prepared in Reference Example 1 was dissolved in anhydrous dichloromethane (4 ml). To the resulting solution, (R)—N-(pyrrolidin-3-yl)quinolin-3-amine hydrochloride (34.3 mg 0.12 mmol) prepared in Reference Example 17 and potassium carbonate (48.0 mg, 0.35 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=10/1, v/v) to give the title compound (6.1 mg). $^1$H-NMR (CDCl$_3$, 400 MHz) δ 8.39-8.54 (m, 1H), 7.93 (d, 1H), 7.60-7.72 (m, 1H), 7.37-7.44 (m, 2.0H), 6.96 (s, 1H), 4.83-4.91 (m, 0.4H), 4.76-4.81 (m, 1H), 4.50 (m, 0.6H), 3.67-3.81 (m, 1H), 3.46-3.56 (m, 1H), 3.28-3.43 (m, 2H), 3.02-3.12 (m, 2H), 2.80-2.90 (m, 1H), 2.52-2.73 (m, 1H), 2.10-2.48 (m, 5H), 1.81 (m, 2H)

Example 18. (S)-1-(2-((R)-3-([1,1'-biphenyl]-3-ylamino)pyrrolidin-1-yl)acetyl)pyrrolidine-2-carbonitrile The title compound (6.92 mg) was prepared in the same fashion as Example 17, except that (R)—N-([1,1'-biphenyl]-3-yl)pyrrolidin-3-amine hydrochloride (28.6 mg, 0.12 mmol) prepared in Reference Example 18 was used instead of (R)—N-(pyrrolidin-3-yl)quinolin-3-amine hydrochloride. $^1$H-NMR (CDCl$_3$, 400 MHz) δ 7.56 (d, 2H), 7.41 (t, 2H), 7.33 (d, 1H), 7.20-7.32 (m, 1H), 6.92 (d, 1H), 6.79 (s, 1H), 6.58 (d, 1H), 4.89-4.96 (m, 0.3H), 4.74 (m, 0.7H), 4.11-4.24 (m, 1H), 3.65-3.72 (m, 1H), 3.29-3.56 (m, 4H), 2.88-3.02 (m, 2H), 2.79-2.85 (m, 1H), 2.63-2.71 (m, 1H), 2.04-2.45 (m, 5H), 1.78-1.85 (m, 1H)

Example 19. (S)-1-(2-((S)-3-(isoquinolin-4-ylamino)pyrrolidin-1-yl)acetyl)pyrrolidine-2-carbonitrile The title compound (4.78 mg) was prepared in the same fashion as Example 5, except that (S)—N-(pyrrolidin-3-yl)isoquinolin-4-amine hydrochloride (25.6 mg, 0.12 mmol) prepared in Reference Example 7 was used instead of (S)—N-(pyrrolidin-3-yl)quinolin-4-amine hydrochloride. $^1$H-NMR (CDCl$_3$, 400 MHz) δ 8.41-8.54 (m, 1H), 7.93-8.22 (m, 2H), 7.65-7.75 (m, 1H), 7.39-7.53 (m, 1H), 7.36-7.41 (m, 0.5H), 6.34-6.44 (m, 1H), 6.22-6.32 (m, 0.4H), 4.72-4.86 (m, 1H), 4.24-4.34 (m, 1H), 3.43-3.72 (m, 4H), 3.24-3.36 (m, 1H), 2.98-3.17 (m, 2H), 2.83-2.94 (m, 1H), 1.93-2.54 (m, 7H)

Example 20. (S)-1-(2-((S)-3-(benzo[b]thiophen-4-ylamino)pyrrolidin-1-yl)acetyl)pyrrolidine-2-carbonitrile The title compound (8.46 mg) was prepared in the same fashion as Example 5, except that (S)—N-(benzo[b]thiophen-4-yl)pyrrolidin-3-amine hydrochloride (26.2 mg, 0.12 mmol) prepared in Reference Example 8 was used instead of (S)—N-(pyrrolidin-3-yl)quinolin-4-amine hydrochloride. $^1$H-NMR (CDCl$_3$, 400 MHz) δ 7.33-7.42 (m, 1H), 7.28-7.32

(m, 1H), 7.20-7.25 (m, 1H), 7.17-7.20 (m, 1H), 6.44 (dd, 1H), 4.63-4.88 (m, 1H), 4.19-4.24 (m, 1H), 3.26-3.69 (m, 4H), 2.98-3.18 (m, 1H), 2.82-2.95 (m, 1H), 2.62-2.76 (m, 1H), 1.83-2.52 (m, 7H)

Example 21. (S)-1-(2-((S)-3-(benzo[b]thiophen-7-ylamino)pyrrolidin-1-yl)acetyl)pyrrolidine-2-carbonitrile The title compound (6.55 mg) was prepared in the same fashion as Example 5, except that (S)—N-(benzo[b]thiophen-7-yl)pyrrolidin-3-amine hydrochloride (26.2 mg, 0.12 mmol) prepared in Reference Example 9 was used instead of (S)—N-(pyrrolidin-3-yl)quinolin-4-amine hydrochloride. $^1$H-NMR (CDCl$_3$, 400 MHz) δ 7.24-7.37 (m, 4H), 6.50-6.72 (m, 1H), 4.99-5.02 (m, 0.4H), 4.74-4.82 (m, 0.6H), 4.24-4.32 (m, 1H), 3.97-4.13 (m, 1H), 3.57-3.68 (m, 1H), 3.24-3.52 (m, 3H), 3.03-3.10 (m, 1H), 2.95-3.01 (m, 0.6H), 2.75-2.84 (m, 1H), 2.62-2.71 (m, 0.6H), 2.34-2.46 (m, 1H), 1.75-2.28 (m, 5H)

Example 22. (S)-1-(2-((S)-3-(benzofuran-7-ylamino)pyrrolidin-1-yl)acetyl)pyrrolidine-2-carbonitrile The title compound (22.5 mg) was prepared in the same fashion as Example 5, except that (S)—N-(benzofuran-7-yl)pyrrolidin-3-amine hydrochloride (24.27 mg, 0.12 mmol) prepared in Reference Example 10 was used instead of (S)—N-(pyrrolidin-3-yl)quinolin-4-amine hydrochloride. $^1$H-NMR (CDCl$_3$, 400 MHz) δ 7.54-7.65 (m, 1H), 7.08 (t, 1H), 6.96 (d, 1H), 6.72 (s, 1H), 6.47-6.52 (m, 1H), 5.06-5.12 (m, 0.3H), 4.74-4.85 (m, 0.6H), 4.18-4.30 (m, 1H), 3.58-3.68 (m, 1H), 3.44-3.56 (m, 1H), 3.24-3.42 (m, 2H), 2.89-3.14 (m, 2H), 2.65-2.87 (m, 2H), 2.33-2.51 (m, 1H), 1.94-2.29 (m, 4H), 1.78-1.91 (m, 1H)

Example 23. (S)-1-(2-((S)-3-(furo[3,2-c]pyridin-7-ylamino)pyrrolidin-1-yl)acetyl)pyrrolidine-2-carbonitrile The title compound (14.0 mg) was prepared in the same fashion as Example 5, except that (S)—N-(pyrrolidin-3-yl)furo[3,2-c]pyridin-7-amine hydrochloride (24.4 mg, 0.12 mmol) prepared in Reference Example 11 was used instead of (S)—N-(pyrrolidin-3-yl)quinolin-4-amine hydrochloride. $^1$H-NMR (CDCl$_3$, 400 MHz) δ 8.37 (s, 1H), 7.87 (s, 1H), 7.60-7.71 (m, 1H), 6.80-6.95 (m, 1H), 4.96-5.02 (m, 0.3H), 4.77-4.88 (m, 0.7H), 4.37-4.51 (m, 1H), 4.30-4.35 (m, 1H), 3.59-3.72 (m, 1H), 3.40-3.55 (m, 1H), 2.97-3.11 (m, 2H), 2.80-2.89 (m, 1.4H), 2.60-2.68 (m, 0.6H), 2.04-2.55 (m, 6H), 1.81-1.95 (m, 1H)

Example 24. (S)-1-(2-((R)-3-(isoquinolin-4-ylamino)pyrrolidin-1-yl)acetyl)pyrrolidine-2-carbonitrile The title compound (12.4 mg) was prepared in the same fashion as Example 17, except that (R)—N-(pyrrolidin-3-yl)isoquinolin-4-amine hydrochloride prepared in Reference Example 19 was used instead of (R)—N-(pyrrolidin-3-yl)quinolin-3-amine hydrochloride. $^1$H-NMR (CDCl$_3$, 400 MHz) δ 8.52-8.62 (m, 1H), 7.94-8.01 (m, 2H), 7.59-7.65 (m, 1H), 7.39-7.47 (m, 1H), 6.38-6.54 (m, 1H), 4.76-4.84 (m, 1H), 4.14-4.35 (m, 1H), 3.60-3.68 (m, 1H), 3.33-3.58 (m, 3H), 3.13-3.23 (m, 1H), 2.90- 3.10 (m, 2H), 2.58-2.78 (m, 1H), 2.08-2.50 (m, 5H), 1.87-2.00 (m, 1H)

Example 25. (S)-1-(2-((R)-3-(benzo[b]thiophen-7-ylamino)pyrrolidin-1-yl)acetyl)pyrrolidine-2-carbonitrile The title compound (4.5 mg) was prepared in the same fashion as Example 17, except that (R)—N-(benzo[b]thiophen-7-yl)pyrrolidin-3-amine hydrochloride (26.2 mg, 0.12 mmol) prepared in Reference Example 20 was used instead of (R)—N-(pyrrolidin-3-yl)quinolin-3-amine hydrochloride. $^1$H-NMR (CDCl$_3$, 400 MHz) δ 7.24-7.38 (m, 4H), 6.54-6.72 (m, 1H), 5.02-5.12 (m, 0.4H), 4.75-4.82 (m, 0.7H), 4.25-4.32 (m, 1H), 3.61-3.88 (m, 1H), 3.47-3.58 (m, 1H), 3.28-3.46 (m, 2H), 2.87-3.10 (m, 2H), 2.79-2.87 (m, 1H), 2.59-2.73 (m, 1H), 2.32-2.50 (m, 1H), 2.04-2.30 (m, 4H), 1.79-1.93 (m, 1H)

Example 26. (1S,3S,5S)-2-(2-((S)-3-(furo[3,2-c]pyridin-7-ylamino)pyrrolidin-1-yl)acetyl)-2-azabicyclo[3.1.0]hexane-3-carbonitrile (1S,3S,5S)-2-(2-Chloroacetyl)-2-azabicyclo[3.1.0]hexane-3-carbonitrile (22.2 mg, 0.12 mmol) prepared in Reference Example 4 was dissolved in anhydrous acetonitrile (4 ml). To the resulting solution, (S)—N-(pyrrolidin-3-yl)furo[3,2-c]pyridin-7-amine hydrochloride (33.1 mg, 0.12 mmol) prepared in Reference Example 11 and potassium carbonate (48.0 mg, 0.35 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=10/1, v/v) to give the title compound (1.8 mg). $^1$H-NMR (CDCl$_3$, 400 MHz) δ 8.84 (m, 1H), 8.37 (d, 0.6H), 8.28 (d, 0.4H), 7.54-7.72 (m, 1H), 7.46-7.52 (m, 1H), 7.33-7.42 (m, 1H), 6.56-6.72 (m, 1H), 5.42-5.51 (m, 0.6H), 5.09-5.24 (m, 0.4H), 4.75-4.92 (m, 1H), 4.20-4.31 (m, 1H), 3.62-3.78 (m, 1H), 3.24-3.57 (m, 3H), 2.92-3.20 (m, 3H), 2.59-2.76 (m, 1H), 1.86-2.49 (m, 6H)

Example 27. (S)-1-(2-((S)-3-(quinolin-5-ylamino)pyrrolidin-1-yl)acetyl)pyrrolidine-2-carbonitrile The title compound (18.1 mg) was prepared in the same fashion as Example 5, except that (S)—N-(pyrrolidin-3-yl)quinolin-5-amine hydrochloride (34.3 mg, 0.12 mmol) prepared in Reference Example 16 was used instead of (S)—N-(pyrrolidin-3-yl)quinolin-4-amine hydrochloride. $^1$H-NMR (CDCl$_3$, 400 MHz) δ 8.84 (m, 1H), 8.37 (d, 0.6H), 8.28 (d, 0.4H), 7.54-7.72 (m, 1H), 7.46-7.52 (m, 1H), 7.33-7.42 (m, 1H), 6.56-6.72 (m, 1H), 5.42-5.51 (m, 0.6H), 5.09-5.24 (m, 0.4H), 4.75-4.92 (m, 1H), 4.20-4.31 (m, 1H), 3.62-3.78 (m, 1H), 3.24-3.57 (m, 3H), 2.92-3.20 (m, 3H), 2.59-2.76 (m, 1H), 1.86-2.49 (m, 6H)

Example 28. (2S,4S)-4-fluoro-1-(2-((S)-3-(furo[3,2-c]pyridin-7-ylamino)pyrrolidin-1-yl)acetyl)pyrrolidin-2-carbonitrile (2S,4S)-1-(2-Chloroacetyl)-4-fluoro-pyrrolidin-2-carbonitrile (20.0 mg, 0.10 mmol) prepared in Reference Example 2 was dissolved in anhydrous dichloromethane (4 ml). To the resulting solution, (S)—N-(pyrrolidin-3-yl)furo[3,2-c]pyridin-7-amine hydrochloride (31.8 mg 0.12 mmol) prepared in Reference Example 11 and potassium carbonate (29.0 mg, 0.21 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=10/1, v/v) to give the title compound (27.7 mg). $^{1}$H NMR (CD$_{3}$OD, 400 MHz) δ 8.36 (s, 1H), 7.89 (d, 1H), 7.13 (s, 1H), 6.98 (d, 1H), 5.51-5.38 (m, 1H), 5.00 (dd, 1H), 4.60 (s, 1H), 4.03 (dd, 1H), 3.85-3.73 (m, 1H), 3.58-3.39 (m, 2H), 3.07-3.04 (m, 1H) 2.92-2.84 (m, 2H), 2.69-2.31 (m, 4H), 1.88-1.86 (m, 1H)

Example 29. N—((S)-1-(2-((2S,4S)-2-cyano-4-fluoropyrrolidin-1-yl)-2-oxoethyl)pyrrolidin-3-yl)-6-fluorobenzofuran-3-carboxamide (2S,4S)-1-(2-Chloroacetyl)-4-fluoro-pyrrolidin-2-carbonitrile (20.0 mg, 0.10 mmol) prepared in Reference Example 2 was dissolved in anhydrous acetonitrile (1 ml). To the resulting solution, (S)-6-fluoro-N-(pyrrolidin-3-yl)benzofuran-3-carboxamide hydrochloride (32.8 mg 0.12 mmol) prepared in Reference Example 45 and potassium carbonate (29.0 mg, 0.21 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=10/1, v/v) to give the title compound (4.3 mg). $^{1}$H NMR (CD$_{3}$OD, 400 MHz) δ 8.36 (s, 1H), 8.03 (s, 1H), 7.35 (d, 1H), 7.15 (t, 1H), 5.51-5.38 (m, 1H), 5.00 (dd, 1H), 4.60 (s, 1H), 4.03 (dd, 1H), 3.85-3.73 (m, 1H), 3.64-3.36 (m, 2H), 3.07-3.04 (m, 1H) 2.92-2.86 (m, 2H), 2.69-2.32 (m, 4H), 1.88-1.86 (m, 1H)

Example 30. N—((S)-1-(2-((S)-2-cyanopyrrolidin-1-yl)-2-oxoethyl)pyrrolidin-3-yl)quinoline-4-carboxamide (S)-1-(2-((S)-3-Aminopyrrolidin-1-yl)acetyl)pyrrolidine-2-carbonitrile trifluoroacetate (20 mg, 0.09 mmol) prepared in Reference Example 25 was dissolved in dimethylformamide (2 ml). To the resulting solution, quinoline-4-carboxylic acid (31.2 mg, 0.18 mmol), HATU (0-(7-azabenzotriazol-1-yl)-N,N,N',N'-tetramethyluranium hexafluorophosphate) (24.9 mg, 0.18 mmol), and diisopropylethylamine (47 uL, 0.27 mmol) were added. The reaction mixture was stirred overnight at room temperature. After the completion of the reaction, water was added to the reaction mixture. The aqueous layer of the reaction mixture was extracted with ethyl acetate. The extracted organic layer was dried and filtered over anhydrous magnesium sulfate. The filtered solution was concentrated and then purified with silica gel column chromatography (dichloromethane/methanol=20/1, v/v) to give the title compound (7 mg). $^{1}$H-NMR (CDCl$_{3}$, 400 MHz) δ 8.92-9.01 (m, 1H), 8.33 (d, 1H), 8.14 (d, 1H), 7.76 (t, 1H), 7.49-7.69 (m, 2H), 4.77-7.89 (m, 1H), 4.68-4.75 (m, 1H), 3.55-3.67 (m, 1H), 3.43 (q, 2H), 3.18 (m, 1H), 2.99 (m, 2H), 2.58-2.83 (m, 1H), 2.07-2.51 (m, 5H), 1.78-2.02 (m, 3H)

Example 31. N—((S)-1-(2-((S)-2-cyanopyrrolidin-1-yl)-2-oxoethyl)pyrrolidin-3-yl)quinoline-3-carboxamide The title compound (7.23 mg) was prepared in the same fashion as Example 30, except that quinoline-3-carboxylic acid (31.2 mg, 0.18 mmol) was used instead of quinoline-4-carboxylic acid. $^{1}$H-NMR (CDCl$_{3}$, 400 MHz) δ 9.41-9.50 (m, 1H), 8.73-8.85 (m, 1H), 8.12-8.21 (m, 1H), 7.97-8.11 (m, 1H), 7.78-7.95 (m, 1H), 7.60-7.72 (m, 1H), 4.74-4.88 (m, 2H), 3.36-3.78 (m, 4H), 3.26-3.32 (m, 2H), 3.02-3.12 (m, 1H), 2.73-2.82 (m, 1H), 2.13-2.45 (m, 5H), 2.05-2.12 (m, 2H)

Example 32. N—((S)-1-(2-((S)-2-cyanopyrrolidin-1-yl)-2-oxoethyl)pyrrolidin-3-yl)quinoline-5-carboxamide The title compound (11.7 mg) was prepared in the same fashion as Example 30, except that quinoline-5-carboxylic acid (31.2 mg, 0.18 mmol) was used instead of quinoline-4-carboxylic acid. $^{1}$H-NMR (CD$_{3}$OD, 400 MHz): Shift=9.23 (d, 0.3H), 8.83-8.94 (m, 1H), 8.76 (d, 0.7H), 8.12 (d, 1H), 7.81-7.92 (m, 2H), 7.61-7.80 (m, 1H), 5.07-5.15 (m, 0.2H), 4.78-4.87 (m, 0.5H), 4.67-4.77 (m, 0.7H), 3.66-3.75 (m, 1H), 3.46-3.65 (m, 2H), 3.33-3.42 (m, 1H), 2.72-3.23 (m, 4H), 2.44-2.52 (m, 1H), 1.89-2.26 (m, 4H), 1.24-1.40 (m, 2H)

Example 33. N—((S)-1-(2-((S)-2-cyanopyrrolidin-1-yl)-2-oxoethyl)pyrrolidin-3-yl)quinoline-2-carboxamide The title compound (14.4 mg) was prepared in the same fashion as Example 30, except that quinoline-2-carboxylic acid (31.2 mg, 0.18 mmol) was used instead of quinoline-4-carboxylic acid. $^{1}$H-NMR (CDCl$_{3}$, 400 MHz) δ 8.67-8.81 (m, 1H), 8.29-8.42 (m, 2H), 8.12-8.24 (m, 1H), 7.87-8.10 (m, 1H), 7.77-7.86 (m, 1H), 7.62-7.72 (m, 1H), 5.11-5.19 (m, 0.3H), 4.78-7.85 (m, 1.7H), 3.60-3.77 (m, 1H), 3.54-3.59 (m, 1H), 3.42-3.51 (m, 2H), 3.27-3.42 (m, 1H), 3.01-3.11 (m, 1H), 2.82-2.92 (m, 1H), 2.62-2.72 (m, 1H), 2.54-2.60 (m, 1H), 2.17-2.42 (m, 4H), 1.94-2.02 (m, 1H), 1.44-1.59 (m, 1H)

Example 34. N—((S)-1-(2-((S)-2-cyanopyrrolidin-1-yl)-2-oxoethyl)pyrrolidin-3-yl)quinoline-8-carboxamide The title compound (4.82 mg) was prepared in the same fashion as Example 30, except that quinoline-8-carboxylic acid (31.2 mg, 0.18 mmol) was used instead of quinoline-4-carboxylic acid. $^{1}$H-NMR (CDCl$_{3}$, 400 MHz) δ 8.92-9.02 (m, 1H), 8.75-8.88 (m, 1H), 8.21-8.34 (m, 1H), 7.92-8.03 (m, 1H), 7.61-7.73 (m, 1H), 7.45-7.59 (m, 1H), 4.61-4.91 (m, 1.7H), 3.33-3.82 (m, 4H), 2.73-3.24 (m, 3H), 2.41-2.63 (m, 1H), 1.87-2.34 (m, 6H)

Example 35. N—((S)-1-(2-((S)-2-cyanopyrrolidin-1-yl)-2-oxoethyl)pyrrolidin-3-yl)isoquinoline-1-carboxamide The title compound (4.9 mg) was prepared in the same fashion as Example 30, except that isoquinoline-1-carboxylic acid (31.2 mg, 0.18 mmol) was used instead of quinoline-4-carboxylic acid. $^1$H-NMR (CDCl$_3$, 400 MHz) δ 9.55-9.68 (m, 1H), 8.45-8.58 (m, 2H), 7.83-7.98 (m, 1H), 7.75-7.81 (m, 1H), 7.61-7.74 (m, 2H), 5.18-5.26 (m, 0.3H), 4.77-4.87 (m, 0.7H), 4.64-4.74 (m, 1H), 3.57-3.71 (m, 2H), 3.40-3.55 (m, 1H), 3.10-3.28 (m, 1H), 2.85-2.96 (m, 2H), 2.39-2.72 (m, 2H), 2.17-2.35 (m, 3H), 1.84-2.10 (m, 2H)

Example 36. N—((S)-1-(2-((S)-2-cyanopyrrolidin-1-yl)-2-oxoethyl)pyrrolidin-3-yl)benzo[b]thiophene-2-carboxamide The title compound (8.0 mg) was prepared in the same fashion as Example 30, except that benzo[b]thiophene-2-carboxylic acid (32.6 mg, 0.18 mmol) was used instead of quinoline-4-carboxylic acid. $^1$H-NMR (CDCl$_3$, 400 MHz) δ 8.20-8.29 (m, 0.5H), 7.97-8.12 (m, 0.6H), 7.80-7.89 (m, 2H), 7.39-7.52 (m, 2H), 4.77-4.89 (m, 1H), 4.67-4.72 (m, 1H), 3.39-3.73 (m, 3H), 3.06-3.25 (m, 2H), 2.93-3.00 (m, 1H), 2.71-2.82 (m, 1H), 2.13-2.47 (m, 5H), 1.95 (m, 1H)

Example 37. N—((S)-1-(2-((S)-2-cyanopyrrolidin-1-yl)-2-oxoethyl)pyrrolidin-3-yl)benzofuran-3-carboxamide The title compound (6.4 mg) was prepared in the same fashion as Example 30, except that benzofuran-3-carboxylic acid (29.2 mg, 0.18 mmol) was used instead of quinoline-4-carboxylic acid. $^1$H-NMR (CDCl$_3$, 400 MHz) δ 8.26-8.36 (m, 0.7H), 8.14-8.21 (m, 1.4H), 7.81-7.92 (m, 0.6H), 7.52-7.68 (m, 1H), 7.35-7.51 (m, 2H), 7.05-7.13 (m, 0.3H), 4.75-4.82 (m, 2H), 3.64-3.82 (m, 2H), 3.39-3.52 (m, 3H), 3.00-3.26 (m, 2H), 2.94-3.00 (m, 1H), 2.69-2.85 (m, 1H), 2.11-2.46 (m, 6H), 1.87-2.02 (m, 1H)

Example 38. N—((S)-1-(2-((S)-2-cyanopyrrolidin-1-yl)-2-oxoethyl)pyrrolidin-3-yl)-2-(naphthalen-1-yl)acetamide The title compound (6.6 mg) was prepared in the same fashion as Example 30, except that 2-(naphthalen-1-yl)acetic acid (31.2 mg, 0.18 mmol) was used instead of quinoline-4-carboxylic acid. $^1$H-NMR (CDCl$_3$, 400 MHz) δ 7.95-8.03 (m, 1H), 7.79-7.90 (m, 2H), 7.41-7.57 (m, 4H), 6.06-6.33 (m, 1H), 4.62 (m, 0.6H), 4.45 (m, 1H), 3.92-4.07 (m, 2H), 3.36-3.52 (m, 1H), 3.18-3.30 (m, 2H), 2.64-3.08 (m, 2H), 2.32-2.55 (m, 2H), 2.07-2.30 (m, 4H), 1.48-1.58 (m, 1H)

Example 39. N—((S)-1-(2-((S)-2-cyanopyrrolidin-1-yl)-2-oxoethyl)pyrrolidin-3-yl)-[1,1'-biphenyl]-2-carboxamide The title compound (7.6 mg) was prepared in the same fashion as Example 30, except that [1,1'-biphenyl]-2-carboxylic acid (35.7 mg, 0.18 mmol) was used instead of quinoline-4-carboxylic acid. $^1$H-NMR (CDCl$_3$, 400 MHz) δ 7.66-7.76 (m, 1H), 7.34-7.50 (m, 8H), 5.87-6.07 (m, 1H), 4.40-4.78 (m, 2H), 3.56-3.72 (m, 2H), 3.06-3.30 (m, 2H), 2.65-2.81 (m, 1H), 2.58-2.64 (m, 1H), 2.19-2.39 (m, 3H), 2.03-2.18 (m, 4H), 1.25-1.35 (m, 2H)

Example 40. N—((S)-1-(2-((S)-2-cyanopyrrolidin-1-yl)-2-oxoethyl)pyrrolidin-3-yl)benzofuran-2-carboxamide The title compound (8.4 mg) was prepared in the same fashion as Example 30, except that benzofuran-2-carboxylic acid (29.2 mg, 0.18 mmol) was used instead of quinoline-4-carboxylic acid. $^1$H-NMR (CDCl$_3$, 400 MHz) δ 7.66-7.75 (m, 1H), 7.49-7.59 (m, 1H), 7.37-7.49 (m, 2H), 7.27-7.33 (m, 1H), 4.91 (m, 0.3H), 4.79 (m, 0.7H), 4.71-4.78 (m, 1H), 3.62-3.71 (m, 1H), 3.41-3.60 (m, 2H), 3.08-3.28 (m, 1H), 2.88-2.98 (m, 2H), 2.52-2.83 (m, 1H), 2.03-2.42 (m, 5H), 1.79-1.98 (m, 1H)

Example 41. N—((S)-1-(2-((S)-2-cyanopyrrolidin-1-yl)-2-oxoethyl)pyrrolidin-3-yl)benzo[b]thiophene-3-carboxamide The title compound (10.4 mg) was prepared in the same fashion as Example 30, except that benzo[b]thiophene-3-carboxylic acid (32.1 mg, 0.18 mmol) was used instead of quinoline-4-carboxylic acid. $^1$H-NMR (CDCl$_3$, 400 MHz) δ 8.49-8.58 (m, 1H), 8.08 (s, 0.6H), 7.96 (s, 0.4H), 7.85-7.95 (m, 1H), 7.68-7.82 (m, 0.6H), 7.34-7.48 (m, 2H), 7.10 (m, 0.4H), 4.72-4.82 (m, 2H), 3.39-3.75 (m, 4H), 3.10-3.26 (m, 1H), 2.88-3.07 (m, 2H), 2.56-2.77 (m, 1H), 2.09-2.50 (m, 5H), 1.86-2.02 (m, 1H)

Example 42. N—((S)-1-(2-((S)-2-cyanopyrrolidin-1-yl)-2-oxoethyl)pyrrolidin-3-yl)-2-methylbenzofuran-3-carboxamide The title compound (14.4 mg) was prepared in the same fashion as Example 30, except that 2-methylbenzofuran-3-carboxylic acid (31.7 mg, 0.18 mmol) was used instead of quinoline-4-carboxylic acid. $^1$H-NMR (CDCl$_3$, 400 MHz) δ 7.68-7.82 (m, 1H), 7.43-7.52 (m, 1H), 7.27-7.33 (m, 1H), 6.97-7.12 (m, 0.7H), 6.58-6.71 (m, 0.3H), 4.69-4.91 (m, 2H), 3.60-3.73 (m, 1H), 3.32-3.59 (m, 3H), 3.08-3.24 (m, 1H), 2.92-3.05 (m, 2H), 2.78-2.90 (m, 1H), 2.71-2.75 (m, 3H), 2.65-2.71 (m, 1H), 2.08-2.49 (m, 5H), 1.86-2.00 (m, 1H)

Example 43. N—((S)-1-(2-((S)-2-cyanopyrrolidin-1-yl)-2-oxoethyl)pyrrolidin-3-yl)-5-fluorobenzofuran-3-carboxamide The title compound (6.5 mg) was prepared in the same fashion as Example 30, except that 5-fluorobenzofuran-3-carboxylic acid (32.4 mg, 0.18 mmol) was used instead of quinoline-4-carboxylic acid. $^1$H-NMR (CDCl$_3$, 400 MHz) δ 8.33 (s, 0.6H), 8.16-8.22 (m, 0.3H), 8.12-8.14 (m, 0.7H), 7.74-7.92 (m, 1H), 7.43-7.52 (m, 1H), 6.95-7.17 (m, 1H), 4.64-4.86 (m, 2H), 3.49-3.72 (m, 3H), 3.43 (m, 1H), 3.21-3.35 (m, 1H), 3.16 (m, 1H), 2.91-3.10 (m, 1H), 2.69-2.86 (m, 1H), 2.13-2.40 (m, 5H)

Example 44. N—((S)-1-(2-((S)-2-cyanopyrrolidin-1-yl)-2-oxoethyl)pyrrolidin-3-yl)-6-fluorobenzofuran-3-carboxamide The title compound (9.8 mg) was prepared in the same fashion as Example 30, except that 6-fluorobenzofuran-3-carboxylic acid (32.4 mg, 0.18 mmol) was used instead of quinoline-4-carboxylic acid. $^1$H-NMR (CDCl$_3$, 400 MHz) δ 8.29 (s, 1H), 8.01-8.18 (m, 2H), 7.21-7.40 (m, 1H), 7.05-7.17 (m, 1H), 4.73-4.85 (m, 2H), 3.48-3.71 (m, 3H), 3.36-3.47 (m, 1H), 3.06-3.29 (m, 2H), 2.94-3.05 (m, 1H), 2.66-2.80 (m, 1H), 2.11-2.39 (m, 5H), 1.84-2.03 (m, 1H)

Example 45. N—((S)-1-(2-((S)-2-cyanopyrrolidin-1-yl)-2-oxoethyl)pyrrolidin-3-yl)-7-methylbenzofuran-3-carboxamide The title compound (8.5 mg) was prepared in the same fashion as Example 30, except that 7-methylbenzofuran-3- carboxylic acid (31.7 mg, 0.18 mmol) was used instead of quinoline-4-carboxylic acid. $^1$H-NMR (CDCl$_3$, 400 MHz) δ 8.29 (s, 0.7H), 8.17 (s, 0.4H), 7.80-8.00 (m, 2H), 7.20-7.25 (m, 1H), 7.14-7.18 (m, 1H), 4.69-4.84 (m, 2H), 3.53-3.69 (m, 3H), 3.27-3.49 (m, 2H), 3.11- 3.25 (m, 1H), 2.77-2.97 (m, 1H), 2.52-2.62 (s, 3H), 2.10-2.42 (m, 5H), 1.99-2.04 (m, 1H)

Example 46. N—((S)-1-(2-((S)-2-cyanopyrrolidin-1-yl)-2-oxoethyl)pyrrolidin-3-yl)-5-methoxybenzofuran-3-carboxamide The title compound (5.9 mg) was prepared in the same fashion as Example 30, except that 5-methoxybenzofuran-3-carboxylic acid (34.6 mg, 0.18 mmol) was used instead of quinoline-4-carboxylic acid. $^1$H-NMR (CDCl$_3$, 400 MHz) δ 8.27 (s, 0.7H), 8.12 (s, 0.4H), 8.00 (d, 0.7H), 7.60-7.69 (m, 1H), 7.38 (d, 1H), 7.09-7.24 (m, 0.4H), 6.93 (d, J=9.1, 1H), 4.68-4.81 (m, 2H), 3.88 (s, 3H), 3.50-3.70 (m, 3H), 3.25-3.49 (m, 2H), 2.98-3.23 (m, 2H), 2.68-2.79 (m, 1H), 2.11-2.41 (m, 5H), 1.97- 2.03 (m, 1H)

Example 47. N—((S)-1-(2-((S)-2-cyanopyrrolidin-1-yl)-2-oxoethyl)pyrrolidin-3-yl)-7-methoxybenzofuran-3-carboxamide The title compound (1.1 mg) was prepared in the same fashion as Example 30, except that 7-methoxybenzofuran-3-carboxylic acid (34.6 mg, 0.18 mmol) was used instead of quinoline-4-carboxylic acid. $^1$H-NMR (CDCl$_3$, 400 MHz) δ 8.28 (s, 0.6H), 8.16 (s, 0.5H), 7.79-8.15 (m, 0.5H), 7.61-7.74 (m, 1H), 7.28-7.33 (m, 0.6H), 6.86 (d, 1), 4.76-4.87 (m, 2H), 4.01-4.21 (s, 3H), 3.52-3.72 (m, 3H), 3.44-3.51 (m, 1H), 3.33-3.42 (m, 1H), 3.16-3.32 (m, 1H), 3.08-3.15 (m, 1H), 2.73-2.86 (m, 1H), 2.11-2.45 (m, 5H), 1.90-2.04 (m, 1H)

Example 48. N—((S)-1-(2-((S)-2-cyanopyrrolidin-1-yl)-2-oxoethyl)pyrrolidin-3-yl)-4-hydroxybenzofuran-3-carboxamide The title compound (1.8 mg) was prepared in the same fashion as Example 30, except that 4-hydroxybenzofuran-3-carboxylic acid (32.1 mg, 0.18 mmol) was used instead of quinoline-4-carboxylic acid. $^1$H-NMR (CDCl$_3$, 400 MHz) δ 9.15-9.21 (m, 0.8H), 8.36 (s, 0.7H), 8.13 (s, 0.3H), 7.88 (m, 0.2H), 7.19-7.25 (m, 1H), 6.98-7.12 (m, 1H), 6.76 (d, 1H), 4.77-4.88 (m, 1H), 4.67-4.76 (m, 1H), 3.54-3.75 (m, 3H), 3.35-3.51 (m, 1H), 3.15-3.28 (m, 2H), 3.02 (m, 1H), 2.67-2.90 (m, 1H), 2.14- 2.42 (m, 5H), 2.05 (s, 1H)

Example 49. N—((S)-1-(2-((S)-2-cyanopyrrolidin-1-yl)-2-oxoethyl)pyrrolidin-3-yl)-6-hydroxybenzofuran-3-carboxamide The title compound (7.6 mg) was prepared in the same fashion as Example 30, except that 6-hydroxybenzofuran-3-carboxylic acid (32.1 mg, 0.18 mmol) was used instead of quinoline-4-carboxylic acid. $^1$H-NMR (CDCl$_3$, 400 MHz) δ 8.05-8.12 (m, 1H), 7.80-7.98 (m, 1H), 7.64-7.78 (m, 1H), 6.99-7.12 (m, 1H), 6.82-6.98 (m, 1H), 4.76-4.82 (m, 2H), 3.48-3.84 (m, 3H), 3.41-3.47 (m, 1H), 3.31-3.40 (m, 1H), 2.91-3.23 (m, 2H), 2.62-2.81 (m, 1H), 2.11-2.40 (m, 5H), 1.86-2.01 (m, 1H)

Example 50. N—((S)-1-(2-((S)-2-cyanopyrrolidin-1-yl)-2-oxoethyl)pyrrolidin-3-yl)-7-fluorobenzofuran-3-carboxamide The title compound (9.6 mg) was prepared in the same fashion as Example 30, except that 7-fluorobenzofuran-3-carboxylic acid (32.4 mg, 0.18 mmol) was used instead of quinoline-4-carboxylic acid. $^1$H-NMR (CDCl$_3$, 400 MHz) δ 8.32 (s, 0.6H), 8.18 (s, 0.3H), 8.04-8.12 (m, 0.6H), 7.88-7.98 (m, 1.0H), 7.18-7.34 (m, 1.4H), 7.03-7.14 (m, 1H), 4.67-4.85 (m, 2H), 3.35-3.78 (m, 4H), 3.05-3.27 (m, 2H), 2.98-3.03 (m, 1H), 2.66-2.79 (m, 1H), 2.12-2.48 (m, 5H), 1.87-2.03 (m, 1H)

Example 51. N—((S)-1-(2-((S)-2-cyanopyrrolidin-1-yl)-2-oxoethyl)pyrrolidin-3-yl)-5,7-difluorobenzofuran-3-carboxamide The title compound (12 mg) was prepared in the same fashion as Example 30, except that 5,7-difluorobenzofuran-3-carboxylic acid (35.6 mg, 0.18 mmol) was used instead of quinoline-4-carboxylic acid. $^1$H-NMR (CDCl$_3$, 400 MHz) δ 8.38 (s, 0.7H), 8.31 (d, 0.6H), 8.21 (s, 0.3H), 7.67-7.77 (m, 1H), 7.36 (d, 0.3H), 6.88 (t, 1H), 4.77-4.89 (m, 1H), 4.65-4.73 (m, 1H), 3.36-3.74 (m, 4H), 3.08-3.28 (m, 2H), 3.00-3.07 (m, 1H), 2.69-2.82 (m, 1H), 2.13-2.41 (m, 5H), 1.86-2.05 (m, 1H)

Example 52. N—((S)-1-(2-((S)-2-cyanopyrrolidin-1-yl)-2-oxoethyl)pyrrolidin-3-yl)-5-methylbenzofuran-3-carboxamide The title compound (6.2 mg) was prepared in the same fashion as Example 30, except that 5-methylbenzofuran-3-carboxylic acid (31.7 mg, 0.18 mmol) was used instead of quinoline-4-carboxylic acid. $^1$H-NMR (CDCl$_3$, 400 MHz) δ 8.22 (s, 0.6H), 8.10 (s, 0.4H), 7.91 (s, 1H), 7.69 (m, 0.7H), 7.38 (d, 1H), 7.15 (d, 1H), 7.03 (m, 0.3H), 4.67-4.82 (m, 2H), 3.37-3.77 (m, 4H), 2.89-3.32 (m, 3H), 2.63-2.85 (m, 1H), 2.45-2.50 (m, 3H), 2.12-2.39 (m, 5H), 1.97-2.11 (m, 1H)

Example 53. N—((S)-1-(2-((S)-2-cyanopyrrolidin-1-yl)-2-oxoethyl)pyrrolidin-3-yl)-6-methylbenzofuran-3-carboxamide The title compound (3.3 mg) was prepared in the same fashion as Example 30, except that 6-methylbenzofuran-3-carboxylic acid (31.7 mg, 0.18 mmol) was used instead of quinoline-4-carboxylic acid. $^1$H-NMR (CDCl$_3$, 400 MHz) δ 8.20 (s, 0.7H), 8.08 (s, 0.3H), 7.88-8.04 (m, 1H), 7.75 (m, 0.7H), 7.28-7.36 (m, 1H), 7.10-7.21 (m, 1H), 7.04 (m, 0.3H), 4.67-4.81 (m, 2H), 3.52-3.74 (m, 3H), 3.38-3.52 (m, 1H), 3.22-3.36 (m, 1H), 2.96-3.21 (m, 2H), 2.72-2.83 (m, 1H), 2.48 (s, 3H), 2.12-2.39 (m, 5H), 2.00-2.11 (m, 1H)

Example 54. N—((S)-1-(2-((S)-2-cyanopyrrolidin-1-yl)-2-oxoethyl)pyrrolidin-3-yl)-6-methoxybenzofuran-3-carboxamide The title compound (1.8 mg) was prepared in the same fashion as Example 30, except that 6-methoxybenzofuran-3-carboxylic acid (34.6 mg, 0.18 mmol) was used instead of quinoline-4-carboxylic acid. $^1$H-NMR (CDCl$_3$, 400 MHz) δ 8.16 (s, 0.7H), 7.93-8.08 (m, 1.4H), 7.75 (m, 0.7H), 6.94-7.08 (m, 2.4H), 4.67-4.83 (m, 2H), 3.86 (s, 3H), 3.50-3.71 (m, 3H), 3.44-3.49 (m, 1H), 2.94-3.32 (m, 3H), 2.73-2.91 (m, 1H), 2.12-2.40 (m, 5H), 1.99-2.11 (m, 1H)

Example 55. N—((S)-1-(2-((S)-2-cyanopyrrolidin-1-yl)-2-oxoethyl)pyrrolidin-3-yl)benzofuran-4-carboxamide The title compound (7.0 mg) was prepared in the same fashion as Example 30, except that benzofuran-4-carboxylic acid (29.2 mg, 0.18 mmol) was used instead of quinoline-4-carboxylic acid of Example 28. ¹H-NMR (CDCl₃, 400 MHz) δ 7.50-7.74 (m, 3H), 7.29-7.44 (m, 2H), 4.75-4.86 (m, 2H), 3.35-3.71 (m, 4H), 2.93-3.34 (m, 3H), 2.62-2.80 (m, 1H), 2.32-2.52 (m, 3H), 2.17-2.31 (m, 3H), 1.95-2.13 (m, 2H)

Example 56. N—((S)-1-(2-((S)-2-cyanopyrrolidin-1-yl)-2-oxoethyl)pyrrolidin-3-yl)benzofuran-5-carboxamide The title compound (10.6 mg) was prepared in the same fashion as Example 30, except that benzofuran-5-carboxylic acid (29.2 mg, 0.18 mmol) was used instead of quinoline-4-carboxylic acid. ¹H-NMR (CDCl₃, 400 MHz) δ 8.11-8.24 (m, 1H), 7.76-7.99 (m, 1.7H), 7.66-7.75 (m, 1H), 7.53-7.62 (m, 1H), 7.06-7.24 (m, 0.4H), 6.80-6.90 (m, 1H), 4.75 (m, 2H), 3.39-3.73 (m, 4H), 2.84-3.31 (m, 4H), 2.70-2.82 (m, 1H), 2.09-2.47 (m, 5H), 1.94-2.08 (m, 1H)

Example 57. N—((S)-1-(2-((S)-2-cyanopyrrolidin-1-yl)-2-oxoethyl)pyrrolidin-3-yl)benzofuran-6-carboxamide The title compound (15.0 mg) was prepared in the same fashion as Example 30, except that benzofuran-6-carboxylic acid (29.2 mg, 0.18 mmol) was used instead of quinoline-4-carboxylic acid. ¹H-NMR (CDCl₃, 400 MHz) δ 8.00-8.15 (m, 1H), 7.57-7.87 (m, 3.7H), 7.15-7.24 (m, 0.4H), 6.80-6.92 (m, 1H), 4.76-4.86 (m, 2H), 3.38-3.75 (m, 4H), 3.10-3.27 (m, 1H), 2.80-3.05 (m, 2H), 2.56- 2.78 (m, 1H), 2.07-2.47 (m, 6H), 1.93-2.05 (m, 1H)

Example 58. N—((S)-1-(2-((S)-2-cyanopyrrolidin-1-yl)-2-oxoethyl)pyrrolidin-3-yl)benzofuran-7-carboxamide The title compound (11.2 mg) was prepared in the same fashion as Example 30, except that benzofuran-7-carboxylic acid (29.2 mg, 0.18 mmol) was used instead of quinoline-4-carboxylic acid. ¹H-NMR (CDCl₃, 400 MHz) δ 8.08 (m, 1H), 7.68-7.95 (m, 3H), 7.30-7.41 (m, 1H), 6.87 (s, 1H), 5.06 (m, 0.4H), 4.78-4.89 (m, 1.6H), 3.59-3.78 (m, 1H), 3.30-3.55 (m, 3H), 3.14-3.28 (m, 1H), 2.77-3.03 (m, 2H), 2.38-2.69 (m, 2H), 2.01-2.35 (m, 5H), 1.93-2.00 (m, 1H)

Example 59. N—((S)-1-(2-((S)-2-cyanopyrrolidin-1-yl)-2-oxoethyl)pyrrolidin-3-yl)benzofuran-2-sulfonamide (S)-1-(2-((S)-3-Aminopyrrolidin-1-yl)acetyl)pyrrolidine-2-carbonitrile trifluoroacetate (30 mg, 0.13 mmol) prepared in Reference Example 25 was dissolved in anhydrous dichloromethane (2 ml). To the resulting solution, triethylamine (60 uL, 0.40 mmol) and benzofuran 2-sulfonyl chloride (32.2 mg, 0.15 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (ethyl acetate/methanol=20/1, v/v) to give the title compound (7.3 mg). ¹H-NMR (CDCl₃, 400 MHz) δ 7.68-7.79 (m, 1H), 7.56-7.62 (m, 1H), 7.46-7.55 (m, 1H), 7.31-7.40 (m, 2H), 4.68-4.80 (m, 1H), 4.09-4.12 (m, 1H), 3.55-3.77 (m, 1H), 3.21-3.53 (m, 3H), 2.74- 3.16 (m, 3H), 2.42-2.69 (m, 1H), 2.02-2.40 (m, 7H), 1.76-1.86 (m, 1H)

Example 60. N—((S)-1-(2-((S)-2-cyanopyrrolidin-1-yl)-2-oxoethyl)pyrrolidin-3-yl)benzo[b]thiophene-2-sulfonamide The title compound (8.7 mg) was prepared in the same fashion as Example 59, except that benzo[b]thiophene-2-sulfonyl chloride (34.6 mg, 0.15 mmol) was used instead of benzofuran 2-sulfonyl chloride. ¹H-NMR (CDCl₃, 400 MHz) δ 7.87-7.99 (m, 3H), 7.46-7.58 (m, 2H), 4.73-4.82 (m, 1H), 4.03-4.12 (m, 1H), 3.57-3.62 (m, 1H), 3.24-3.42 (m, 2H), 3.09-3.21 (m, 1H), 2.53-2.88 (m, 2H), 2.41-2.51 (m, 1H), 2.09-2.31 (m, 6H), 1.67-1.85 (m, 1H)

Example 61. (S)-1-(2-((S)-3-(quinolin-4-yloxy)pyrrolidin-1-yl)acetyl)pyrrolidine-2-carbonitrile (S)-1-(2-((R)-3-Hydroxypyrrolidin-1-yl)acetyl)pyrrolidine-2-carbonitrile (242 mg, 1.08 mmol) prepared in Reference Example 26 was dissolved in tetrahydrofuran (9.03 ml). To the resulting solution, 4-quinolinol (157.34 mg, 1.08 mmol) and triphenylphosphine (568.6 mg, 2.17 mmol) were added. The mixture solution was cooled to 0° C. And then, DIAD (diisopropyl azodicarboxylate) (0.43 mL, 2.17 mmol) was slowly added dropwise for 15 minutes. The reaction mixture was stirred for 12 hours at room temperature. After the completion of the reaction, a saturated ammonium chloride solution and a saturated sodium hydrogen carbonate solution were added to the reaction mixture. The aqueous layer of the reaction mixture was extracted with ethyl acetate. The extracted organic layer was dried and filtered over anhydrous magnesium sulfate. The filtered solution was concentrated and then purified with silica gel column chromatography (dichloromethane/methanol=10/1, v/v) to give the title compound (18.5 mg). ¹H-NMR (CDCl₃, 400 MHz) δ 8.73 (d, 1H), 8.19 (t, 1H), 8.04 (d, 1H), 7.70 (t, 1H), 7.51 (m, 1H), 6.64 (d, 1H), 5.16-5.09 (m, 1.3H), 4.76 (d, 0.7H), 3.71-3.63 (m, 2H), 3.53-3.51 (m, 1H), 3.41-3.37 (m, 1H), 3.15-2.72 (m, 3H), 2.46-2.29 (m, 1H), 2.27-1.98 (m, 6H)

Example 62. (S)-1-(2-((S)-3-(naphthalen-1-yloxy)pyrrolidin-1-yl)acetyl)pyrrolidine-2-carbonitrile The title compound (68 mg) was prepared in the same fashion as Example 61, except that naphthalen-1-ol (160 mg, 1.08 mmol) was used instead of 4-quinolinol. ¹H-NMR (CDCl₃, 400 MHz) δ 8.23 (t, 1H), 7.80 (d, 1H), 7.46-7.40 (m, 3H), 7.32 (t, 1H), 6.72 (d, 1H), 5.27 (d, 0.3H), 5.05 (m, 1H), 4.76 (m, 0.7H), 3.72-3.31 (m, 5H), 3.05-3.03 (m, 1H), 2.95-2.91 (m, 2H), 2.41-2.38 (m, 1H), 2.25-2.14 (m, 4H), 2.02-1.98 (m, 1H), 1.89 (m, 1H)

Example 63. (S)-1-(2-((S)-3-(quinolin-6-yloxy)pyrrolidin-1-yl)acetyl)pyrrolidine-2-carbonitrile The title compound (87 mg) was prepared in the same fashion as Example 61, except that 6-quinolinol (160 mg, 1.08 mmol) was used instead of 4-quinolinol. ¹H-NMR (CDCl₃, 400 MHz) δ 8.76 (s, 1H), 8.04-7.98 (m, 2H), 7.35-7.27 (m, 2H), 6.97 (s, 1H), 5.24-4.76 (m, 2H), 3.68-3.34 (m, 5H), 3.01-2.89 (m, 3H), 2.44-2.10 (m, 7H)

Example 64. (S)-1-(2-((S)-3-(quinolin-8-yloxy)pyrrolidin-1-yl)acetyl)pyrrolidine-2-carbonitrile The title compound (57 mg) was prepared in the same fashion as Example 61, except that 8-quinolinol (160 mg, 1.08 mmol) was used instead of 4-quinolinol. $^1$H-NMR (CDCl$_3$, 400 MHz) δ 8.93 (s, 1H), 8.14 (d, 1H), 7.44-7.38 (m, 3H), 7.00-6.96 (m, 1H), 5.47 (d, 0.4H), 5.14 (s, 1H), 4.75 (d, 0.6H), 3.79-3.66 (m, 2H), 3.64-3.30 (m, 3H), 3.09-2.84 (m, 3H), 2.47-2.43 (m, 1H), 2.28-2.03 (m, 6H)

Example 65. (S)-1-(2-((S)-3-(isoquinolin-5-yloxy)pyrrolidin-1-yl)acetyl)pyrrolidine-2-carbonitrile The title compound (62 mg) was prepared in the same fashion as Example 61, except that 5-isoquinolinol (160 mg, 1.08 mmol) was used instead of 4-quinolinol. $^1$H-NMR (CDCl$_3$, 400 MHz) δ 9.20 (s, 1H), 8.51 (s, 1H), 8.00-7.99 (m, 1H), 7.54-7.46 (m, 2H), 6.91 (d, 1H), 5.19 (d, 0.3H), 5.05 (s, 1H), 4.76 (d, 0.7H), 3.71-3.63 (m, 2H), 3.53-3.51 (m, 1H), 3.42-3.38 (m, 2H), 3.13-2.91 (m, 3H), 2.48-2.41 (m, 1H), 2.34-1.99 (m, 6H)

Example 66. (S)-1-(2-((S)-3-(quinolin-5-yloxy)pyrrolidin-1-yl)acetyl)pyrrolidine-2-carbonitrile The title compound (89 mg) was prepared in the same fashion as Example 61, except that 5-quinolinol (160 mg, 1.08 mmol) was used instead of 4-quinolinol. $^1$H-NMR (CDCl$_3$, 400 MHz) δ 8.90 (s, 1H), 8.59 (t, 1H), 7.69 (d, 1H), 7.58 (t, 1H), 7.37 (s, 1H), 6.76 (d, 1H), 5.15 (m, 0.3H), 5.05 (m, 1H), 4.76 (m, 0.7H), 3.71-3.61 (m, 2H), 3.50 (m, 1H), 3.41-3.37 (m, 1H), 3.00-2.86 (m, 3H), 2.45-2.40 (m, 1H), 2.28-2.07 (m, 6H)

Example 67. (S)-1-(2-((S)-3-(benzo[d][1,3]dioxol-5-yloxy)pyrrolidin-1-yl)acetyl)pyrrolidine-2-carbonitrile The title compound (76 mg) was prepared in the same fashion as Example 61, except that benzo[d][1,3]dioxol-5-ol (150 mg, 1.08 mmol) was used instead of 4-quinolinol. $^1$H-NMR (CDCl$_3$, 400 MHz) δ 6.69 (d, 1H), 6.44 (d, 1H), 6.24 (t, 1H), 5.90 (s, 2H), 5.28 (d, 0.3H), 4.94-4.92 (m, 1H), 4.75 (m, 0.7H), 3.72-3.63 (m, 2H), 3.52-3.50 (m, 1H), 3.37-3.21 (m, 1H), 2.94-2.74 (m, 3H), 2.33-2.00 (m, 7H)

Example 68. (S)-1-(2-((S)-3-(thieno[2,3-d]pyrimidin-4-yloxy)pyrrolidin-1-yl)acetyl)pyrrolidine-2-carbonitrile The title compound (63 mg) was prepared in the same fashion as Example 61, except that thieno[2,3-d]pyrimidin-4-ol (160 mg, 1.08 mmol) was used instead of 4-quinolinol. $^1$H-NMR (CDCl$_3$, 400 MHz) δ 8.62 (s, 1H), 7.38 (s, 2H), 5.72 (m, 1H), 5.20 (d, 0.3H), 4.76 (m, 0.7H), 3.71-3.62 (m, 2H), 3.53-3.52 (m, 1H), 3.45-3.35 (m, 1H), 3.27-3.22 (m, 1H), 3.04 (d, 2H), 2.49-2.44 (m, 1H), 2.42-2.04 (m, 6H)

Example 69. (S)-1-(2-((S)-3-(isoquinolin-3-yloxy)pyrrolidin-1-yl)acetyl)pyrrolidine-2-carbonitrile The title compound (123 mg) was prepared in the same fashion as Example 61, except that 3-isoquinolinol (151 mg, 1.08 mmol) was used instead of 4-quinolinol. $^1$H-NMR (CDCl$_3$, 400 MHz) δ 8.89 (s, 1H), 7.84 (m, 1H), 7.65 (d, 1H), 7.54 (m, 1H), 7.34 (m, 1H), 6.96 (m, 1H), 5.47 (m, 1H), 4.71 (m, 1H), 3.68-3.37 (m, 4H), 3.07-2.89 (m, 3H), 2.41-2.01 (m, 7H)

Example 70. (S)-1-(2-((S)-3-((3-bromothieno[3,2-c]pyridin-4-yl)oxy)pyrrolidin-1-yl)acetyl)pyrrolidine-2-carbonitrile The title compound (70.2 mg) was prepared in the same fashion as Example 61, except that 3-bromothieno[3,2-c]pyridin-4-ol (151 mg, 1.08 mmol) was used instead of 4-quinolinol. 1H-NMR (CDCl$_3$, 400 MHz) δ 7.92 (s, 1H), 7.34 (m, 2H), 5.62 (m, 1H), 4.75 (m, 1H), 3.72-3.39 (m, 4H), 3.04-2.91 (m, 3H), 2.42 (m, 1H), 2.27-2.19 (m, 6H)

Example 71. (S)-1-(2-((S)-3-((4-chloronaphthalen-1-yl)oxy)pyrrolidin-1-yl)acetyl)pyrrolidine-2-carbonitrile The title compound (94.0 mg) was prepared in the same fashion as Example 61, except that 4-chloronaphthalen-1-ol (194 mg, 1.08 mmol) was used instead of 4-quinolinol. $^1$H-NMR (CDCl$_3$, 400 MHz) δ 8.27 (d, 1H), 8.16 (d, 1H), 7.58 (m, 1H), 7.52 (m, 1H), 7.40 (d, 1H), 6.60 (d, 1H), 4.90 (m, 1H), 4.70 (m, 1H), 3.61-3.27 (m, 4H), 2.97-2.69 (m, 3H), 2.39-1.93 (m, 7H)

Example 72. (S)-1-(2-((S)-3-(2-(1H-pyrazol-3-yl)phenoxy)pyrrolidin-1-yl)acetyl)pyrrolidine-2-carbonitrile The title compound (81 mg) was prepared in the same fashion as Example 61, except that 2-(1H-pyrazol-3-yl)phenol (173 mg, 1.08 mmol) was used instead of 4-quinolinol. $^1$H-NMR (CDCl$_3$, 400 MHz) δ 7.63 (d, 1H), 7.56 (s, 1H), 7.25 (m, 1H), 7.04 (m, 1H), 6.97 (d, 1H), 6.58 (s, 1H), 5.03 (s, 1H), 4.72 (s, 1H), 3.59 (d, 2H), 3.44-3.40 (m, 2H), 3.22-3.02 (m, 3H), 2.31-2.30 (m, 1H), 2.20-1.98 (m, 6H)

Example 73. (S)-1-(2-((S)-3-((4-chloroquinazolin-8-yl)oxy)pyrrolidin-1-yl)acetyl)pyrrolidine-2-carbonitrile The title compound (72 mg) was prepared in the same fashion as Example 61, except that 4-chloroquinazolin-8-ol (194 mg, 1.08 mmol) was used instead of 4-quinolinol of Example 59. $^1$H-NMR (CDCl$_3$, 400 MHz) δ 7.85-7.47 (m, 3H), 7.20 (m, 1H), 5.03 (s, 1H), 4.76 (s, 1H), 3.66-3.54 (m, 4H), 3.18-2.96 (m, 4H), 2.49-2.05 (m, 6H)

Example 74. (S)-1-(2-((S)-3-((4-chloroquinazolin-6-yl)oxy)pyrrolidin-1-yl)acetyl)pyrrolidine-2-carbonitrile The title compound (90.7 mg) was prepared in the same fashion as Example 61, except that 4-chloroquinazolin-6-ol (194 mg, 1.08 mmol) was used instead of 4-quinolinol. $^1$H-NMR (CDCl$_3$, 400 MHz) δ 7.97 (m, 1H), 7.62-7.54 (m, 2H), 7.37 (d, 1H), 5.06 (s, 1H), 4.75 (s, 1H), 3.69-3.36 (m, 4H), 3.10-2.92 (m, 4H), 2.49-2.18 (m, 6H)

Example 75. (S)-1-(2-((S)-3-((2-oxo-1,2-dihydroquinolin-5-yl)oxy)pyrrolidin-1-yl)acetyl)pyrrolidine-2-carbonitrile The title compound (93.9 mg) was prepared in the same fashion as Example 61, except that 5-hydroxyquinolin-2

(1H)-one (176 mg, 1.08 mmol) was used instead of 4-quinolinol. $^1$H-NMR (CDCl$_3$, 400 MHz) δ 11.68 (m, 1H), 8.17 (m, 1H), 7.37-7.26 (m, 1H), 6.61 (m, 1H), 6.49 (m, 1H), 5.10 (s, 2H), 3.70-3.30 (m, 4H), 2.96-2.85 (m, 3H), 2.38-1.92 (m, 7H)

Example 76. (S)-1-(2-((S)-3-((2-oxo-1,2,3,4-tetrahydroquinolin-5-yl)oxy)pyrrolidin-1-yl)acetyl)pyrrolidine-2-carbonitrile The title compound (112.3 mg) was prepared in the same fashion as Example 61, except that 5-hydroxy-3,4-dihydroquinolin-2(1H)-one (176 mg, 1.08 mmol) was used instead of 4-quinolinol. $^1$H-NMR (CDCl$_3$, 400 MHz) δ 9.71 (s, 0.5H), 8.49 (s, 0.5H), 7.07 (t, 1H), 6.44 (m, 2H), 4.87 (s, 1H), 4.76 (s, 1H), 3.69-3.30 (m, 4H), 2.92-2.79 (m, 5H), 2.70-2.57 (m, 2H), 2.33-2.06 (m, 7H)

Example 77. (S)-1-(2-((S)-3-((2-oxo-1,2,3,4-tetrahydroquinolin-6-yl)oxy)pyrrolidin-1-yl)acetyl)pyrrolidine-2-carbonitrile The title compound (94.0 mg) was prepared in the same fashion as Example 61, except that 6-hydroxy-3,4-dihydroquinolin-2(1H)-one (176 mg, 1.08 mmol) was used instead of 4-quinolinol. $^1$H-NMR (CDCl$_3$, 400 MHz) δ 9.02 (s, 1H), 6.76 (d, 1H), 6.64 (m, 2H), 4.79-4.75 (m, 2H), 3.68-3.24 (m, 5H), 2.90-2.59 (m, 7H), 2.27-2.02 (m, 6H)

Example 78. (S)-1-(2-((S)-3-((2-methylquinolin-8-yl)oxy)pyrrolidin-1-yl)acetyl)pyrrolidine-2-carbonitrile The title compound (74.5 mg) was prepared in the same fashion as Example 61, except that 2-methylquinolin-8-ol (171.7 mg, 1.08 mmol) was used instead of 4-quinolinol. $^1$H-NMR (CDCl$_3$, 400 MHz) δ 8.28 (s, 1H), 7.52 (s, 1H), 7.34 (d, 2H), 6.89 (d, 1H), 5.09 (s, 1H), 4.98 (s, 1H), 3.78-3.53 (m, 4H), 3.42-3.16 (m, 3H), 2.80-2.75 (m, 4H), 2.43-2.04 (m, 6H)

Example 79. (S)-1-(2-((S)-3-((7-chloroquinolin-4-yl)oxy)pyrrolidin-1-yl)acetyl)pyrrolidine-2-carbonitrile The title compound (50.7 mg) was prepared in the same fashion as Example 61, except that 7-chloroquinolin-4-ol (194 mg, 1.08 mmol) was used instead of 4-quinolinol. $^1$H-NMR (CDCl$_3$, 400 MHz) δ 8.69 (s, 1H), 8.13 (d, 1H), 8.00 (s, 1H), 7.43 (d, 1H), 6.62 (s, 1H), 5.07 (s, 1.3H), 4.75 (s, 0.7H), 3.69-3.27 (m, 4H), 3.09-2.86 (m, 3H), 2.46-2.45 (m, 1H), 2.28-2.00 (m, 6H)

Example 80. (S)-1-(2-((S)-3-((7-bromoquinolin-4-yl)oxy)pyrrolidin-1-yl)acetyl)pyrrolidine-2-carbonitrile The title compound (48.6 mg) was prepared in the same fashion as Example 61, except that 7-bromoquinolin-4-ol (237 mg, 1.08 mmol) was used instead of 4-quinolinol. $^1$H-NMR (CDCl$_3$, 400 MHz) δ 8.67 (s, 1H), 8.17 (s, 1H), 8.05 (d, 1H), 7.55 (d, 1H), 6.63 (s, 1H), 5.06 (s, 1.3H), 4.75 (s, 0.7H), 3.71-3.26 (m, 4H), 3.03-2.85 (m, 3H), 2.45-2.44 (m, 1H), 2.31-1.99 (m, 6H)

Example 81. (S)-1-(2-((S)-3-((5-chloroquinolin-8-yl)oxy)pyrrolidin-1-yl)acetyl)pyrrolidine-2-carbonitrile The title compound (41 mg) was prepared in the same fashion as Example 61, except that 5-chloroquinolin-8-ol (194 mg, 1.08 mmol) was used instead of 4-quinolinol. $^1$H-NMR (CDCl$_3$, 400 MHz) δ 8.95 (s, 1H), 8.53 (d, 1H), 7.53-7.49 (m, 2H), 6.92 (d, 1H), 5.11 (s, 1H), 4.75 (s, 1H), 3.79-3.35 (m, 5H), 3.16-2.93 (m, 2H), 2.45 (m, 1H), 2.22-2.04 (m, 6H)

Example 82. (S)-1-(2-((S)-3-([1,1'-biphenyl]-3-yloxy)pyrrolidin-1-yl)acetyl)pyrrolidine-2-carbonitrile The title compound (81 mg) was prepared in the same fashion as Example 61, except that [1,1'-biphenyl]-3-ol (184 mg, 1.08 mmol) was used instead of 4-quinolinol. $^1$H-NMR (CDCl$_3$, 400 MHz) δ 7.56-7.48 (m, 2H), 7.42-7.27 (m, 4H), 7.17-7.06 (m, 2H), 6.90-6.67 (m, 1H), 4.91 (s, 1H), 4.72 (s, 1H), 3.74-3.27 (m, 5H), 2.88-2.83 (m, 2H), 2.31 (m, 1H), 2.30-2.11 (m, 6H)

Example 83. (S)-1-(2-((S)-3-([1,1'-biphenyl]-4-yloxy)pyrrolidin-1-yl)acetyl)pyrrolidine-2-carbonitrile The title compound (63.7 mg) was prepared in the same fashion as Example 61, except that [1,1'-biphenyl]-4-ol (184 mg, 1.08 mmol) was used instead of 4-quinolinol. $^1$H-NMR (CDCl$_3$, 400 MHz) δ 7.53-7.48 (m, 4H), 7.39 (t, 2H), 7.28 (t, 1H), 6.90 (d, 2H), 4.88 (s, 1H), 4.72 (s, 1H), 3.74-3.28 (m, 5H), 2.87-2.80 (m, 2H), 2.31 (m, 1H), 2.12-1.97 (m, 6H)

Example 84. (S)-1-(2-((S)-3-((6-methoxyquinolin-4-yl)oxy)pyrrolidin-1-yl)acetyl)pyrrolidine-2-carbonitrile The title compound (70.2 mg) was prepared in the same fashion as Example 61, except that 6-methoxyquinolin-4-ol (183 mg, 1.08 mmol) was used instead of 4-quinolinol. $^1$H-NMR (CDCl$_3$, 400 MHz) δ 8.57 (s, 1H), 7.94 (d, 1H), 7.43 (s, 1H), 7.34 (d, 1H), 6.60 (s, 1H), 5.06 (s, 1.4H), 4.75 (s, 0.6H), 3.93 (s, 3H), 3.71-3.69 (m, 2H), 3.63-3.25 (m, 3H), 3.04-2.84 (m, 2H), 2.45 (m, 1H), 2.27-1.98 (m, 6H)

Example 85. (S)-1-(2-((S)-3-((7,8-difluoroquinolin-4-yl)oxy)pyrrolidin-1-yl)acetyl)pyrrolidine-2-carbonitrile The title compound (62.6 mg) was prepared in the same fashion as Example 61, except that 7,8-difluoroquinolin-4-ol (194 mg, 1.08 mmol) was used instead of 4-quinolinol. $^1$H-NMR (CDCl$_3$, 400 MHz) δ 8.75 (s, 1H), 7.94 (s, 1H), 7.33 (d, 1H), 6.67 (s, 1H), 5.09 (s, 1.4H), 4.76 (s, 0.6H), 3.93 (s, 3H), 3.71-3.66 (m, 2H), 3.56-3.27 (m, 3H), 3.06-2.86 (m, 2H), 2.48-2.45 (m, 1H), 2.29-2.00 (m, 6H)

Example 86. Methyl 6-(((S)-1-(2-((S)-2-cyanopyrrolidin-1-yl)-2-oxoethyl)pyrrolidin-3-yl)oxy)-2,3-dihydrobenzofuran-2-carboxylate The title compound (85.3 mg) was prepared in the same fashion as Example 61, except that methyl 6-hydroxy-2,3-dihydrobenzofuran-2-carboxylate (205 mg, 1.08 mmol) was used instead of 4-quinolinol. $^1$H-NMR (CDCl$_3$, 400 MHz) δ

7.02 (d, 1H), 6.41-6.36 (m, 2H), 5.23 (t, 1H), 4.80 (s, 1H), 4.72 (s, 1H), 4.08 (m, 1H), 3.80 (s, 3H), 3.74-3.65 (m, 2H), 3.51-3.39 (m, 3H), 3.33-3.25 (m, 2H), 2.91-2.86 (m, 2H), 2.25-2.04 (m, 6H)

Example 87. (S)-1-(2-((S)-3-(4-phenoxyphenoxy)pyrrolidin-1-yl)acetyl)pyrrolidine-2-carbonitrile The title compound (50.7 mg) was prepared in the same fashion as Example 61, except that 4-phenoxyphenol (205 mg, 1.08 mmol) was used instead of 4-quinolinol. $^1$H-NMR (CDCl$_3$, 400 MHz) δ 7.29-2.27 (m, 2H), 7.03 (s, 1H), 6.94 (s, 4H), 6.82 (d, 2H), 4.81-4.69 (m, 2H), 3.74-3.62 (m, 2H), 3.51-3.43 (m, 1H), 3.39-3.35 (m, 1H), 3.32-3.24 (m, 1H), 2.87-2.82 (t, 2H), 2.29-2.04 (m, 7H)

Example 88. (S)-1-(2-((S)-3-(3-phenoxyphenoxy)pyrrolidin-1-yl)acetyl)pyrrolidine-2-carbonitrile The title compound (95 mg) was prepared in the same fashion as Example 61, except that 3-phenoxyphenol (205 mg, 1.08 mmol) was used instead of 4-quinolinol. $^1$H-NMR (CDCl$_3$, 400 MHz) δ 7.34 (t, 2H), 7.19 (t, 1H), 7.13 (t, 1H), 7.02 (d, 2H), 6.57 (d, 2H), 6.49 (s, 1H), 4.81 (s, 1H), 4.74 (s, 1H), 3.71-3.63 (m, 1H), 3.51-3.49 (m, 1H), 3.38-3.23 (m, 2H), 2.86-2.62 (m, 3H), 2.27- 2.02 (m, 7H)

Example 89. (S)-1-(2-((S)-3-(4-benzylphenoxy)pyrrolidin-1-yl)acetyl)pyrrolidine-2-carbonitrile The title compound (96.1 mg) was prepared in the same fashion as Example 61, except that 4-benzylphenol (194 mg, 1.08 mmol) was used instead of 4-quinolinol. $^1$H-NMR (CDCl$_3$, 400 MHz) δ 7.26 (s, 2H), 7.17 (t, 3H), 7.08 (d, 2H), 6.76 (d, 2H), 4.81 (s, 1H), 4.74 (s, 1H), 3.90 (s, 2H), 3.73-3.67 (m, 2H), 3.51-3.27 (m, 2H), 2.85-2.76 (m, 3H), 2.26-2.02 (m, 7H)

Example 90. (S)-1-(2-((S)-3-(2-benzylphenoxy)pyrrolidin-1-yl)acetyl)pyrrolidine-2-carbonitrile The title compound (69.1 mg) was prepared in the same fashion as Example 61, except that 2-benzylphenol (194 mg, 1.08 mmol) was used instead of 4-quinolinol. $^1$H-NMR (CDCl$_3$, 400 MHz) δ 7.26-7.09 (m, 7H), 6.87 (t, 1H), 6.74 (d, 1H), 4.93 (s, 1H), 4.73 (s, 1H), 3.94 (s, 2H), 3.71-3.64 (m, 1H), 3.57-3.48 (m, 1H), 3.32-3.24 (m, 2H), 2.84-2.64 (m, 3H), 2.23-1.97 (m, 7H)

Example 91. (S)-1-(2-((S)-3-(3-benzoylphenoxy)pyrrolidin-1-yl)acetyl)pyrrolidine-2-carbonitrile The title compound (93.9 mg) was prepared in the same fashion as Example 61, except that 3-hydroxybenzophenone (216 mg, 1.08 mmol) was used instead of 4-quinolinol. $^1$H-NMR (CDCl$_3$, 400 MHz) δ 7.79 (d, 2H), 7.59 (d, 1H), 7.50 (t, 2H), 7.37-7.27 (m, 3H), 7.09 (d, 1H), 4.93 (s, 1H), 4.47 (s, 1H), 3.73-3.65 (m, 2H), 3.56-3.30 (m, 2H), 2.97-2.86 (m, 3H), 2.34-1.98 (m, 7H)

Example 92. (S)-1-(2-((S)-3-(4-benzoylphenoxy)pyrrolidin-1-yl)acetyl)pyrrolidine-2-carbonitrile The title compound (49.7 mg) was prepared in the same fashion as Example 61, except that 4-hydroxybenzophenone (216 mg, 1.08 mmol) was used instead of 4-quinolinol. $^1$H-NMR (CDCl$_3$, 400 MHz) δ 7.80 (d, 2H), 7.74 (d, 2H), 7.56 (d, 1H), 7.48 (d, 2H), 6.91 (d, 2H), 4.97 (s, 1H), 4.73 (s, 1H), 3.75-3.65 (m, 2H), 3.57-3.40 (m, 2H), 3.00-2.88 (m, 3H), 2.38-2.36 (m, 1H), 2.18-1.99 (m, 6H)

Example 93. (S)-1-(2-((S)-3-((4-(benzyloxy)pyridin-2-yl)oxy)pyrrolidin-1-yl)acetyl)pyrrolidine-2-carbonitrile The title compound (95.0 mg) was prepared in the same fashion as Example 61, except that 4-(benzyloxy)pyridin-2-ol (216 mg, 1.08 mmol) was used instead of 4-quinolinol. $^1$H-NMR (CDCl$_3$, 400 MHz) δ 7.92 (d, 1H), 7.38-7.34 (m, 6H), 6.51 (s, 1H), 5.43 (s, 1H), 5.03 (s, 2H), 4.72 (s, 1H), 3.72-3.44 (m, 2H), 3.38-3.28 (m, 2H), 3.17-3.13 (m, 1H), 2.96-2.87 (m, 1H), 2.80-2.71 (m, 1H), 2.35-2.30 (m, 1H), 2.19-1.97 (m, 6H)

Example 94. (S)-1-(2-((S)-3-((7-(trifluoromethyl)quinolin-4-yl)oxy)pyrrolidin-1-yl)acetyl)pyrrolidine-2-carbonitrile The title compound (97.2 mg) was prepared in the same fashion as Example 61, except that 7-(trifluoromethyl)quinolin-4-ol (227 mg, 1.08 mmol) was used instead of 4-quinolinol. $^1$H-NMR (CDCl$_3$, 400 MHz) δ 8.78 (s, 1H), 8.30 (s, 2H), 7.64 (d, 1H), 6.74 (d, 1H), 5.10 (s, 1H), 4.76 (s, 1H), 3.72-3.24 (m, 4H), 3.13-2.96 (m, 2H), 2.86 (m, 1H), 2.50-2.45 (m, 1H), 2.18-1.99 (m, 6H)

Example 95. (S)-1-(2-((S)-3-((8-(trifluoromethyl)quinolin-4-yl)oxy)pyrrolidin-1-yl)acetyl)pyrrolidine-2-carbonitrile The title compound (57.2 mg) was prepared in the same fashion as Example 61, except that 8-(trifluoromethyl)quinolin-4-ol (227 mg, 1.08 mmol) was used instead of 4-quinolinol. $^1$H-NMR (CDCl$_3$, 400 MHz) δ 8.84 (d, 1H), 8.43 (d, 1H), 8.03 (d, 1H), 7.53 (t, 1H), 6.74 (s, 1H), 5.08 (s, 1H), 4.75 (s, 1H), 3.72-3.38 (m, 4H), 3.29-2.82 (m, 3H), 2.47-2.45 (m, 1H), 2.26-1.98 (m, 6H)

Example 96. (S)-1-(2-((S)-3-(acridin-4-yloxy)pyrrolidin-1-yl)acetyl)pyrrolidine-2-carbonitrile The title compound (51.8 mg) was prepared in the same fashion as Example 61, except that acridin-4-ol (205 mg, 1.08 mmol) was used instead of 4-quinolinol. $^1$H-NMR (CDCl$_3$, 400 MHz) δ 8.67 (s, 1H), 8.31 (d, 1H), 7.92 (d, 1H), 7.69 (m, 1H), 7.52-7.48 (t, 2H), 7.36 (t, 1H), 6.92 (d, 1H), 5.01 (s, 1H), 4.76 (s, 1H), 3.76-3.27 (m, 6H), 2.85 (m, 1H), 2.45 (m, 1H), 2.21-1.96 (m, 6H)

Example 97. (S)-1-(2-((S)-3-(2-(benzo[d]oxazol-2-yl)phenoxy)pyrrolidin-1-yl)acetyl)pyrrolidine-2-carbonitrile The title compound (71.3 mg) was prepared in the same fashion as Example 61, except that 2-(benzo[d]oxazol-2-yl)-phenol (227 mg, 1.08 mmol) was used instead of 4-quinolinol of Example 61. $^1$H-NMR (CDCl$_3$, 400 MHz) δ 8.09 (d, 1H), 7.77 (s, 1H), 7.58 (s, 1H), 7.44 (t, 1H), 7.34 (m, 2H), 7.06 (t, 1H), 6.96 (d, 1H), 4.99 (s, 1H), 4.69 (s, 1H), 3.69-3.54 (m, 1H), 3.48-3.27 (m, 3H), 3.03-2.84 (m, 3H), 2.37-2.32 (m, 1H), 2.17-1.88 (m, 6H)

Example 98. (S)-1-(2-((S)-3-(4-(4-acetylpiperazin-1-yl)phenoxy)pyrrolidin-1-yl)acetyl)pyrrolidine-2-carbonitrile The title compound (85.3 mg) was prepared in the same fashion as Example 61, except that 4-(4-acetylpiperazin-1-yl)phenol (238 mg, 1.08 mmol) was used instead of 4-quinolinol. $^1$H-NMR (CDCl$_3$, 400 MHz) δ 6.88 (d, 2H), 6.79 (d, 2H), 4.78 (s, 1.4H), 4.47 (s, 0.6H), 3.74-3.68 (m, 3H), 3.60-3.50 (m, 3H), 3.36-3.34 (m, 1H), 3.17-3.15 (m, 1H), 3.04-3.01 (m, 5H), 2.84-2.77 (m, 2H), 2.28-1.99 (m, 10H)

Example 99. 2-(((S)-1-(2-((S)-2-cyanopyrrolidin-1-yl)-2-oxoethyl)pyrrolidin-3-yl)oxy)-N-phenylbenzamide The title compound (40.0 mg) was prepared in the same fashion as Example 61, except that 2-hydroxy-N-phenylbenzamide (227 mg, 1.08 mmol) was used instead of 4-quinolinol. $^1$H-NMR (CDCl$_3$, 400 MHz) δ 10.06-9.94 (m, 1H), 8.21 (d, 1H), 7.73 (d, 2H), 7.41 (t, 1H), 7.33 (m, 2H), 7.09 (d, 2H), 6.91 (d, 1H), 5.06 (s, 1H), 4.58 (s, 1H), 3.61-3.26 (m, 4H), 3.07-2.99 (m, 2H), 2.69-2.67 (m, 1H), 2.40-2.38 (m, 1H), 2.10-1.80 (m, 6H)

Example 100. (S)-1-(2-((S)-3-((7-methoxyquinolin-4-yl)oxy)pyrrolidin-1-yl)acetyl)pyrrolidine-2-carbonitrile The title compound (58.3 mg) was prepared in the same fashion as Example 61, except that 7-methoxyquinolin-4-ol (183 mg, 1.08 mmol) was used instead of 4-quinolinol. $^1$H-NMR (CDCl$_3$, 400 MHz) δ 8.60 (s, 1H), 8.07 (d, 1H), 7.34 (s, 1H), 7.12 (d, 1H), 6.51 (s, 1H), 5.02 (m, 1.2H), 4.72 (s, 0.8H), 3.91 (s, 4H), 3.64-3.57 (m, 1H), 3.46-3.28 (m, 3H), 2.99-2.80 (m, 2H), 2.40 (m, 1H), 2.12-2.10 (m, 6H)

Example 101. (S)-1-(2-((S)-3-((6,7-dimethoxyquinolin-4-yl)oxy)pyrrolidin-1-yl)acetyl)pyrrolidine-2-carbonitrile The title compound (73.4 mg) was prepared in the same fashion as Example 61, except that 6,7-dimethoxyquinolin-4-ol (216 mg, 1.08 mmol) was used instead of 4-quinolinol. $^1$H-NMR (CDCl$_3$, 400 MHz) δ 8.52 (d, 1H), 7.40 (s, 1H), 7.35 (s, 1H), 6.54 (s, 1H), 5.04-5.03 (m, 1H), 4.73 (s, 1H), 4.02 (d, 6H), 3.80-3.51 (m, 1H), 3.48-3.26 (m, 3H), 3.05-2.93 (m, 2H), 2.80-2.79 (m, 1H), 2.47- 2.42 (m, 1H), 2.24-1.99 (m, 6H)

Example 102. (S)-1-(2-((S)-3-((3-(4-bromophenyl)isoxazol-5-yl)oxy)pyrrolidin-1-yl)acetyl)pyrrolidine-2-carbonitrile The title compound (79.9 mg) was prepared in the same fashion as Example 61, except that (3-(4-bromophenyl)isoxazol-5-ol (258 mg, 1.08 mmol) was used instead of 4-quinolinol. $^1$H-NMR (CDCl$_3$, 400 MHz) δ 7.61-7.50 (m, 5H), 5.04 (s, 1H), 4.74 (s, 1H), 3.65-3.61 (m, 1H), 3.50-3.41 (m, 2H), 3.17-2.86 (m, 4H), 2.38 (m, 1H), 2.26-2.08 (m, 6H)

Example 103. (S)-4,4-difluoro-1-(2-((S)-3-((6-methoxyquinolin-4-yl)oxy)pyrrolidin-1-yl)acetyl)pyrrolidine-2-carbonitrile (S)-4,4-Difluoro-1-(2-((R)-3-hydroxypyrrolidin-1-yl)-2-oxoethyl)pyrrolidine-2-carbonitrile (260 mg, 1.00 mmol) prepared in Reference Example 27 was dissolved in tetrahydrofuran (10 ml). To the resulting solution, 6-methoxyquinolin-4-ol (180 mg, 1.0 mmol) and triphenylphosphine (520 mg, 2.0 mmol) were added. The mixture solution was cooled to 0° C. And then, DIAD (diisopropyl azodicarboxylate) (0.39 mL, 2.0 mmol) was slowly added dropwise for 15 minutes. The reaction mixture was stirred for 12 hours at room temperature. After the completion of the reaction, a saturated ammonium chloride solution and a saturated sodium hydrogen carbonate solution were added to the reaction mixture. The aqueous layer of the reaction mixture was extracted with ethyl acetate. The extracted organic layer was dried and filtered over anhydrous magnesium sulfate. The filtered solution was concentrated and then purified with silica gel column chromatography (dichloromethane/methanol=10/1, v/v) to give the title compound (45 mg). $^1$H-NMR (CDCl$_3$, 400 MHz) δ 8.54 (d, 1H), 7.92 (d, 1H), 7.43-7.38 (m, 1H), 7.33-7.26 (m, 1H), 6.55 (s, 1H), 4.99-4.95 (m, 2H), 4.13-0.98 (m, 1H), 3.91-3.85 (m, 4H), 3.70-3.58 (m, 1H), 3.50-3.35 (m, 1H), 3.11-2.96 (m, 3H), 2.70-2.66 (m, 3H), 2.44-0.40 (m, 1H), 2.12-2.09 (m 1H)

Example 104. (S)-4,4-difluoro-1-(2-((S)-3-((8-(trifluoromethyl)quinolin-4-yl)oxy)pyrrolidin-1-yl)acetyl)pyrrolidine-2-carbonitrile The title compound (87 mg) was prepared in the same fashion as Example 103, except that 8-(trifluoromethyl)quinolin-4-ol (210 mg, 1.0 mmol) was used instead of 6-methoxyquinolin-4-ol. $^1$H-NMR (CDCl$_3$, 400 MHz) δ 8.82 (s, 1H), 8.41 (d, 1H), 8.02 (d, 1H), 6.71 (s, 1H), 5.11-4.98 (m, 2H), 4.16-4.06 (m, 2H), 3.65-3.42 (m, 2H), 3.16-2.99 (m, 3H), 2.73-2.72 (m, 3H), 2.43 (m, 1H), 2.12-2.01 (m, 1H)

Example 105. (S)-4,4-difluoro-1-(2-((S)-3-(quinolin-5-yloxy)pyrrolidin-1-yl)acetyl)pyrrolidine-2-carbonitrile The title compound (68 mg) was prepared in the same fashion as Example 103, except that quinolin-5-ol (150 mg, 1.0 mmol) was used instead of 6-methoxyquinolin-4-ol. $^1$H-NMR (CDCl$_3$, 400 MHz) δ 8.87 (s, 1H), 8.55 (d, 1H), 7.68 (d, 1H), 7.56 (t, 1H), 7.36 (s, 1H), 6.73 (d, 1H), 4.97 (m, 2H), 4.13-3.97 (m, 2H), 3.68-3.36 (m, 2H), 3.09 (m, 1H), 2.99-2.91 (m, 2H), 2.68 (m, 3H), 2.39-2.36 (m, 1H), 2.21-2.03 (m, 1H)

Example 106. (S)-4,4-difluoro-1-(2-((S)-3-(isoquinolin-5-yloxy)pyrrolidin-1-yl)acetyl)pyrrolidine-2-carbonitrile The title compound (59 mg) was prepared in the same fashion as Example 103, except that isoquinolin-5-ol (150 mg, 1.0 mmol) was used instead of 6-methoxyquinolin-4-ol. $^1$H-NMR (CDCl$_3$, 400 MHz) δ 9.17 (s, 1H), 8.49 (d, 1H), 7.98 (d, 1H), 7.50-7.44 (m, 2H), 6.89 (d, 1H), 4.99 (m, 2H), 4.12-3.69 (m, 2H), 3.44-3.39 (m, 2H), 3.16-2.93 (m, 3H), 2.72-2.70 (m, 3H), 2.41-2.38 (m, 1H), 2.24- 2.13 (m, 1H)

Example 107. (S)-1-(2-((S)-3-((7-chloroquinolin-4-yl)oxy)pyrrolidin-1-yl)acetyl)-4,4-difluoropyrrolidine-2-carbonitrile The title compound (37 mg) was prepared in the same fashion as Example 103, except that 7-chloroquinolin-4-ol (180 mg, 1.0 mmol) was used instead of 6-methoxyquinolin- 4-ol. ¹H-NMR (CDCl₃, 400 MHz) δ 8.65 (s, 1H), 8.06 (d, 1H), 7.96 (s, 1H), 7.47-7.31 (m, 1H), 6.58 (d, 1H), 5.01-4.97 (m, 2H), 4.17-3.99 (m, 2H), 3.86-3.35 (m, 2H), 3.12-3.11 (m, 1H), 3.02-2.97 (m, 2H), 2.77-2.71 (m, 3H), 2.42-2.41 (m, 1H), 2.12-2.10 (m, 1H)

Example 108. (S)-4,4-difluoro-1-(2-((S)-3-((2-oxo-1,2-dihydroquinolin-5-yl)oxy)pyrrolidin-1-yl)acetyl)pyrrolidine-2-carbonitrile The title compound (64 mg) was prepared in the same fashion as Example 103, except that 5-hydroxyquinolin-2(1H)-one (160 mg, 1.0 mmol) was used instead of 6-methoxyquinolin-4-ol. ¹H-NMR (CDCl₃, 400 MHz) δ 12.24 (s, 1H), 8.18 (d, 1H), 7.37 (m, 1H), 7.01 (s, 1H), 6.62 (d, 1H), 6.50 (d, 1H), 4.97 (s, 2H), 4.15-4.00 (m, 2H), 3.39 (m, 2H), 3.12-3.03 (m, 3H), 2.92-2.72 (m, 3H), 2.53-2.36 (m, 1H), 2.09 (m, 1H)

Example 109. (S)-1-(2-((S)-3-((5-chloroquinolin-8-yl)oxy)pyrrolidin-1-yl)acetyl)-4,4-difluoropyrrolidine-2-carbonitrile The title compound (81 mg) was prepared in the same fashion as Example 103, except that 5-chloroquinolin-8-ol (180 mg, 1.0 mmol) was used instead of 6-methoxyquinolin-4-ol. ¹H-NMR (CDCl₃, 400 MHz) δ 8.91 (s, 1H), 8.50 (d, 1H), 7.52-7.46 (m, 2H), 6.86 (d, 1H), 5.06-4.99 (m, 2H), 4.10-3.84 (m, 3H), 3.51-3.32 (m, 1H), 3.09-3.07 (m, 3H), 2.87-2.57 (m, 3H), 2.39 (m, 1H), 2.21 (m, 1H)

Example 110. (S)-1-(2-(4-(quinolin-5-ylamino)piperidin-1-yl)acetyl)pyrrolidine-2-carbonitrile (S)-1-(2-Chloroacetyl)pyrrolidine-2-carbonitrile (28.75 mg, 0.16 mmol) prepared in Reference Example 1 was dissolved in anhydrous dichloromethane (4 ml). To the resulting solution, N-(piperidin-4-yl)quinolin-5-amine hydrochloride (50.0 mg, 0.16 mmol) prepared in Reference Example 29 and potassium carbonate (115.0 mg, 0.83 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=10/1, v/v) to give the title compound (12 mg). ¹H-NMR (CDCl₃, 400 MHz) δ 8.83 (d, 1H), 8.25 (d, 1H), 7.54-7.42 (m, 2H), 7.28 (s, 1H), 6.52 (d, 1H), 5.15 (d, 0.3H), 4.80 (s, 0.7H), 4.12 (d, 1H), 3.69-2.90 (m, 8H), 2.37-2.04 (m, 8H), 1.79-1.64 (m, 2H)

Example 111. (S)-1-(2-(4-(quinolin-4-ylamino)piperidin-1-yl)acetyl)pyrrolidine-2-carbonitrile The title compound (19.8 mg) was prepared in the same fashion as Example 110, except that N-(piperidin-4-yl)quinolin-4-amine hydrochloride (50.0 mg, 0.16 mmol) prepared in Reference Example 28 was used instead of N-(piperidin-4-yl)quinolin-5-amine hydrochloride. ¹H-NMR (CD₃OD, 400 MHz) δ 8.35-8.32 (m, 2H), 7.81 (s, 2H), 7.59 (s, 1H), 6.79 (d, 1H), 4.80 (s, 1H), 3.78 (s, 2H), 3.60-3.35 (m, 2H), 3.08 (d, 2H), 2.42-1.82 (m, 11H), 1.28 (s, 1H)

Example 112. (1S,3S,5S)-2-(2-(4-(quinolin-4-ylamino)piperidin-1-yl)acetyl)-2-azabicyclo[3.1.0]hexane-3-carbonitrile (1S,3S,5S)-2-(2-Chloroacetyl)-2-azabicyclo[3.1.0]hexane-3-carbonitrile (25 mg, 0.14 mmol) prepared in Reference Example 4 was dissolved in anhydrous acetonitrile (3.5 ml). To the resulting solution, N-(piperidin-4-yl)quinolin-4-amine hydrochloride (50.0 mg, 0.16 mmol) prepared in Reference Example 28 and potassium carbonate (115.0 mg, 0.83 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=10/1, v/v) to give the title compound (11.9 mg). ¹H-NMR (CD₃OD, 400 MHz) δ 8.39 (d, 2H), 7.84 (s, 2H), 7.64 (s, 1H), 6.88 (s, 1H), 5.04 (s, 1H), 3.84 (s, 2H), 3.57-3.46 (m, 2H), 3.10 (s, 2H), 2.63 (s, 1H), 2.43 (d, 2H), 2.30 (d, 1H), 2.03-2.18 (m, 1H), 2.10-1.75 (m, 4H), 1.25-0.92 (s, 3H)

Example 113. (2S,4S)-4-fluoro-1-(2-(4-(quinolin-5-ylamino)piperidin-1-yl)acetyl)pyrrolidine-2-carbonitrile The title compound (29.9 mg) was prepared in the same fashion as Example 110, except that (2S,4S)-1-(2-chloroacetyl)-4-fluoro-pyrrolidine-2-carbonitrile (25.4 mg, 0.14 mmol) prepared in Reference Example 2 was used instead of (S)-1-(2-chloroacetyl)pyrrolidine-2-carbonitrile. ¹H-NMR (CD₃OD, 400 MHz) δ 8.72 (s, 1H), 8.63 (d, 1H), 7.56 (t, 1H), 7.42 (s, 1H), 7.28 (d, 1H), 6.73 (d, 1H), 5.45 (d, 1H), 4.99 (d, 1H), 3.91-3.78 (m, 1H), 3.61-3.43 (m, 3H), 3.16-3.08 (m, 2H), 2.61-2.45 (m, 4H), 2.18 (q, 2H), 2.01-1.78 (m, 4H)

Example 114. (S)-4,4-difluoro-1-(2-(4-(quinolin-5-ylamino)piperidin-1-yl)acetyl)pyrrolidine-2-carbonitrile The title compound (12.6 mg) was prepared in the same fashion as Example 110, except that (2S)-1-(2-chloroacetyl)-4,4-difluoro-pyrrolidine-2-carbonitrile (27.8 mg, 0.14 mmol) prepared in Reference Example 3 was used instead of (S)-1-(2-chloroacetyl)pyrrolidine-2-carbonitrile. ¹H-NMR (CD₃OD, 400 MHz) δ 8.72 (d, 1H), 8.62 (d, 1H), 7.54 (t, 1H), 7.40 (d, 1H), 7.27 (d, 1H), 6.71 (d, 1H), 5.58-5.05 (m, 1H), 4.25-4.09 (m, 2H), 3.53-3.24 (m, 3H), 3.00 (d, 2H), 2.90-2.74 (m, 2H), 2.39 (t, 2H), 2.13 (d, 2H), 1.72 (d, 2H), 1.28 (s, 1H)

Example 115. (1S,3S,5S)-2-(2-(4-(quinolin-5-ylamino)piperidin-1-yl)acetyl)-2-azabicyclo[3.1.0]hexane-3-carbonitrile The title compound (33.6 mg) was prepared in the same fashion as Example 112, except that N-(piperidin-4-yl)quinolin-5-amine hydrochloride (50.0 mg, 0.16 mmol) prepared in Reference Example 29 was used instead of N-(piperidin-4-yl)quinolin-4-amine hydrochloride. ¹H-NMR (CD₃OD, 400 MHz) δ 8.72 (s, 1H), 8.66 (d, 1H), 7.56 (t, 1H), 7.41 (d, 1H), 7.29 (d, 1H), 6.73 (d, 1H), 5.56-5.05 (m, 1H), 3.81 (s, 1H), 3.77 (s, 1H), 3.65 (d, 2H), 3.22-3.06 (m, 2H), 2.64 (t, 3H), 2.47-1.81 (m, 7H), 1.28-1.07 (m, 2H)

Example 116. (S)-1-(2-(4-(furo[3,2-c]pyridin-7-ylamino)piperidin-1-yl)acetyl)pyrrolidine-2-carbonitrile The title compound (21.6 mg) was prepared in the same fashion as Example 110, except that N-(piperidin-4-yl)furo[3,2-c]pyridin-7-amine hydrochloride (40.6 g, 0.16 mmol) prepared in Reference Example 30 was used instead of N-(piperidin-4-yl)quinolin-5-amine hydrochloride. $^1$H-NMR (CDCl$_3$, 400 MHz) δ 8.35 (s, 1H), 7.91 (s, 1H), 7.61 (s, 1H), 6.81 (s, 1H), 4.76 (s, 1H), 3.94 (s, 1H), 3.74 (s, 1H), 3.57 (d, 2H), 3.43-3.36 (m, 1H), 3.24 (s, 1H), 2.84-3.03 (m, 2H), 2.44-2.14 (m, 7H), 1.87-1.52 (m, 2H)

Example 117. (S)-1-(2-(4-(quinolin-3-yloxy)piperidin-1-yl)acetyl)pyrrolidine-2-carbonitrile (S)-1-(2-Chloroacetyl)pyrrolidine-2-carbonitrile (60 mg, 0.35 mmol) prepared in Reference Example 1 was dissolved in anhydrous dichloromethane (2.4 ml). To the resulting solution, 3-(piperidin-4-yloxy)quinoline hydrochloride (104.7 mg, 0.35 mmol) prepared in Reference Example 31 and potassium carbonate (192.2 mg, 1.39 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=10/1, v/v) to give the title compound (22.1 mg). $^1$H-NMR (CDCl$_3$, 400 MHz) δ 8.66 (d, 1H), 8.04 (d, 1H), 7.71 (d, 1H), 7.57-7.49 (m, 2H), 7.40 (s, 1H), 5.20 (d, 0.3H), 4.76 (d, 0.6H), 4.52 (s, 1H), 3.75-3.54 (m, 2H), 3.44-3.24 (m, 2H) 2. 82-2.51 (m, 5H) 2.28-1.94 (m, 8H)

Example 118. (S)-1-(2-(4-(quinolin-4-yloxy)piperidin-1-yl)acetyl)pyrrolidine-2-carbonitrile The title compound (23.6 mg) was prepared in the same fashion as Example 117, except that 4-(piperidin-4-yloxy)quinoline hydrochloride (104.7 mg, 0.35 mmol) prepared in Reference Example 32 was used instead of 3-(piperidin-4-yloxy)quinoline hydrochloride. $^1$H-NMR (CDCl$_3$, 400 MHz) δ 8.72 (d, 1H), 8.23 (d, 1H), 8.03 (d, 1H), 7.70 (t, 1H), 7.52 (t, 1H), 6.72 (d, 1H) 5.17 (d, 0.3H), 4.76 (d, 0.6H), 4.69 (s, 1H), 3.75-3.55 (m, 2H), 3.43-3.24 (m, 2H) 2. 93-2.36 (m, 5H) 2.28-2.05 (m, 8H)

Example 119. (S)-1-(2-(4-(quinolin-5-yloxy)piperidin-1-yl)acetyl)pyrrolidine-2-carbonitrile The title compound (20.2 mg) was prepared in the same fashion as Example 117, except that 5-(piperidin-4-yloxy)quinoline hydrochloride (104.7 mg, 0.35 mmol) prepared in Reference Example 33 was used instead of 3-(piperidin-4-yloxy)quinoline hydrochloride. $^1$H-NMR (CDCl$_3$, 400 MHz) δ 8.90 (s, 1H), 8.61 (d, 1H), 7.68 (d, 1H), 7.60 (t, 1H), 7.39 (q, 1H), 6.88 (d, 1H) 5.21 (d, 0.3H), 4.76 (s, 0.6H), 4.61 (s, 1H), 3.76-3.54 (m, 2H), 3.44-3.23 (m, 2H) 2. 83-2.58 (m, 5H) 2.28-2.01 (m, 8H)

Example 120. (S)-1-(2-(4-(quinolin-6-yloxy)piperidin-1-yl)acetyl)pyrrolidine-2-carbonitrile The title compound (24.4 mg) was prepared in the same fashion as Example 117, except that 6-(piperidin-4-yloxy)quinoline hydrochloride (104.7 mg, 0.35 mmol) prepared in Reference Example 34 was used instead of 3-(piperidin-4-yloxy)quinoline hydrochloride. $^1$H-NMR (CDCl$_3$, 400 MHz) δ 8.76 (d, 1H), 8.05-8.00 (m, 2H), 7.38-7.34 (m, 2H), 7.10 (s, 1H), 5.24 (d, 0.3H), 4.76 (s, 0.6H), 4.53 (s, 1H), 3.75-3.54 (m, 2H), 3.46-3.23 (m, 2H) 2. 86 (S, 2H) 2.62-2.50 (m, 3H), 2.35-1.96 (m, 8H)

Example 121. (S)-1-(2-(4-((3-methylquinolin-5-yl)amino)piperidin-1-yl)acetyl)pyrrolidine-2-carbonitrile (S)-1-(2-Chloroacetyl)pyrrolidine-2-carbonitrile (152.05 mg, 0.88 mmol) prepared in Reference Example 1 was dissolved in anhydrous acetonitrile (4.4 ml). To the resulting solution, 3-methyl-N-(piperidin-4-yl)quinolin-5-amine hydrochloride (308.94 mg, 0.88 mmol) prepared in Reference Example 35, potassium carbonate (487.0 mg, 3.52 mmol), and potassium iodide (1.46 mg, 0.01 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=10/1, v/v) to give the title compound (72 mg). $^1$H-NMR (CDCl$_3$, 400 MHz) δ 8.70 (s, 1H), 7.93 (s, 1H), 7.47-7.41 (m, 2H), 6.62 (d, 1H), 5.15 (d, 1H), 4.74 (s, 1H), 3.72-3.18 (m, 4H), 2.98-2.89 (m, 2H), 2.65 (s, 1H), 2.50 (s, 3H), 2.39-2.04 (m, 8H), 1.68-1.66 (m, 2H)

Example 122. (S)-1-(2-(4-((6-methylquinolin-5-yl)amino)piperidin-1-yl)acetyl)pyrrolidine-2-carbonitrile The title compound (21.8 mg) was prepared in the same fashion as Example 121, except that 6-methyl-N-(piperidin-4-yl)quinolin-5-amine hydrochloride (268.4 mg, 0.96 mmol) prepared in Reference Example 36 was used instead of 3-methyl-N-(piperidin-4-yl)quinolin-5-amine hydrochloride. $^1$H-NMR (CDCl$_3$, 400 MHz) δ 8.82 (s, 1H), 8.38 (d, 1H), 7.70 (d, 1H), 7.49 (d, 1H), 7.35 (s, 1H), 4.74 (s, 1H), 3.72-3.52 (m, 2H), 3.34-2.93 (m, 5H), 2.44 (s, 3H), 2.27-1.63 (m, 9H), 1.26 (m, 2H)

Example 123. (S)-1-(2-(4-((7-fluoroquinolin-5-yl)amino)piperidin-1-yl)acetyl)pyrrolidine-2-carbonitrile The title compound (36.4 mg) was prepared in the same fashion as Example 121, except that 7-fluoro-N-(piperidin-4-yl)quinolin-5-amine hydrochloride (329.36 mg, 0.93 mmol) prepared in Reference Example 37 was used instead of 3-methyl-N-(piperidin-4-yl)quinolin-5-amine hydrochloride. $^1$H-NMR (CDCl$_3$, 400 MHz) δ 8.82 (s, 1H), 8.10 (d, 1H), 7.26 (s, 1H), 7.05 (d, 1H), 6.37 (d, 1H), 4.75 (s, 1H), 4.59 (s, 1H), 3.74-3.22 (m, 5H), 3.00-2.90 (m, 2H), 2.39-1.67 (m, 8H), 1.26 (m, 2H)

Example 124. (S)-1-(2-(4-((7-methoxyquinolin-5-yl)amino)piperidin-1-yl)acetyl)pyrrolidine-2-carbonitrile The title compound (4.6 mg) was prepared in the same fashion as Example 121, except that 7-methoxy-N-(piperidin-4-yl)quinolin-5-amine hydrochloride (291.0 mg, 0.88 mmol) prepared in Reference Example 38 was used instead of 3-methyl-N-(piperidin-4-yl)quinolin-5-amine hydrochloride. $^1$H-NMR (CDCl$_3$, 400 MHz) δ 8.76 (s, 1H), 8.04 (s, 1H), 7.19 (s, 1H), 6.87 (s, 1H), 6.28 (s, 1H), 4.77 (s, 1H), 3.75 (s, 3H), 3.65-3.15 (m, 5H), 2.99-2.90 (m, 2H), 2.40-1.46 (m, 9H), 1.26 (m, 2H)

Example 125. (S)-1-(2-(4-((8-methoxyquinolin-5-yl)amino)piperidin-1-yl)acetyl)pyrrolidine-2-carbonitrile The title compound (6.1 mg) was prepared in the same fashion as Example 121, except that 8-methoxy-N-(piperidin-4-yl)quinolin-5-amine hydrochloride (291.0 mg, 0.88 mmol) prepared in Reference Example 39 was used instead of 3-methyl-N-(piperidin-4-yl)quinolin-5-amine hydrochloride. $^1$H-NMR (CDCl$_3$, 400 MHz) δ 8.93 (s, 1H), 8.24 (s, 1H), 7.41 (s, 1H), 6.94 (s, 1H), 6.65 (s, 1H), 4.76 (s, 1H), 4.03 (s, 3H), 3.73-3.14 (m, 7H), 3.02-2.05 (m, 9H), 1.63 (m, 2H)

Example 126. (2S,4S)-4-fluoro-1-(2-(4-((6-fluoroquinolin-4-yl)oxy)piperidin-1-yl)acetyl)pyrrolidine-2-carbonitrile (2S,4S)-1-(2-Chloroacetyl)-4-fluoro-pyrrolidine-2-carbonitrile (214 mg, 1.12 mmol) prepared in Reference Example 2 was dissolved in anhydrous acetonitrile (4 ml). To the resulting solution, 6-fluoro-4-(piperidin-4-yloxy)quinoline hydrochloride (400 mg, 1.12 mmol) prepared in Reference Example 40, potassium carbonate (621.8 mg, 5.00 mmol), and potassium iodide (1.87 mg, 0.011 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=10/1, v/v) to give the title compound (20 mg). $^1$H-NMR (CDCl$_3$, 400 MHz) δ 8.69 (s, 1H), 8.02 (d, 1H), 7.80 (d, 1H), 7.47 (t, 1H), 6.73 (s, 1H), 5.50-5.30 (m, 1H), 4.95 (d, 1H), 4.69 (s, 1H), 4.24-3.77 (m, 2H), 3.51-3.22 (m, 2H), 2.80-2.15 (m, 10H)

Example 127. (2S,4S)-1-(2-(4-((6-chloroquinolin-4-yl)oxy)piperidin-1-yl)acetyl)-4-fluoropyrrolidine-2-carbonitrile The title compound (17.0 mg) was prepared in the same fashion as Example 126, except that 6-chloro-4-(piperidin-4-yloxy)quinoline hydrochloride (336.7 mg, 1.12 mmol) prepared in Reference Example 41 was used instead of 6-fluoro-4-(piperidin-4-yloxy)quinoline hydrochloride. $^1$H-NMR (CDCl$_3$, 400 MHz) δ 8.71 (s, 1H), 8.17 (s, 1H), 7.96 (s, 1H), 7.62 (s, 1H), 6.74 (s, 1H), 5.43 (t, 1H), 4.95 (s, 1H), 4.68 (s, 1H), 4.24-3.70 (m, 2H), 3.53-3.27 (m, 2H), 2.82-1.84 (m, 10H)

Example 128. (2S,4S)-4-fluoro-1-(2-(4-((6-methoxyquinolin-4-yl)oxy)piperidin-1-yl)acetyl)pyrrolidine-2-carbonitrile The title compound (24.1 mg) was prepared in the same fashion as Example 126, except that 6-methoxy-4-(piperidin-4-yloxy)quinoline hydrochloride (410.0 mg, 1.12 mmol) prepared in Reference Example 42 was used instead of 6-fluoro-4-(piperidin-4-yloxy)quinoline hydrochloride. $^1$H-NMR (CDCl$_3$, 400 MHz) δ 8.95 (d, 1H), 7.94 (d, 1H), 7.47 (s, 1H), 7.35 (d, 1H), 6.70 (d, 1H), 5.49-5.30 (m, 1H), 4.94 (d, 1H), 4.68 (s, 1H), 4.25-4.10 (m, 1H), 3.95 (s, 3H), 3.92-3.21 (m, 3H), 2.86-2.13 (m, 10H)

Example 129. (2S,4S)-4-fluoro-1-(2-(4-((7-methoxyquinolin-4-yl)oxy)piperidin-1-yl)acetyl)pyrrolidine-2-carbonitrile The title compound (4.5 mg) was prepared in the same fashion as Example 126, except that 7-methoxy-4-(piperidin-4-yloxy)quinoline hydrochloride (331.7 mg, 1.12 mmol) prepared in Reference Example 43 was used instead of 6-fluoro-4-(piperidin-4-yloxy)quinoline hydrochloride. $^1$H-NMR (CDCl$_3$, 400 MHz) δ 8.64 (s, 1H), 8.10 (d, 1H), 7.37 (s, 1H), 7.15 (d, 1H), 6.62 (s, 1H), 5.49-5.30 (m, 1H), 4.95 (d, 1H), 4.68 (s, 1H), 4.25-4.11 (m, 1H), 3.95 (s, 3H), 3.89-3.71 (m, 1H), 3.52-3.25 (m, 2H), 2.80-2.05 (m, 10H)

Example 130. (2S,4S)-1-(2-(4-((6,7-dimethoxyquinolin-4-yl)oxy)piperidin-1-yl)acetyl)-4-fluoropyrrolidine-2-carbonitrile The title compound (4.7 mg) was prepared in the same fashion as Example 126, except that 6,7-dimethoxy-4-(piperidin-4-yloxy)quinoline hydrochloride (407.1 mg, 1.12 mmol) prepared in Reference Example 44 was used instead of 6-fluoro-4-(piperidin-4-yloxy)quinoline hydrochloride. $^1$H-NMR (CDCl$_3$, 400 MHz) δ 8.55 (s, 1H), 7.43 (d, 1H), 7.39 (s, 1H), 6.65 (s, 1H), 5.49-5.37 (m, 1H), 4.95 (d, 1H), 4.68 (s, 1H), 4.28-4.11 (m, 1H), 4.00 (s, 6H), 3.87-3.78 (m, 1H), 3.52-3.22 (m, 2H), 2.88-2.01 (m, 10H)

Example 131. (2S,4S)-4-fluoro-1-(2-(4-((3-methylquinolin-5-yl)amino)piperidin-1-yl)acetyl)pyrrolidine-2-carbonitrile (2S,4S)-1-(2-Chloroacetyl)-4-fluoro-pyrrolidine-2-carbonitrile (20.5 mg, 0.11 mmol) prepared in Reference Example 2 was dissolved in anhydrous acetonitrile (4 ml). To the resulting solution, 3-methyl-N-(piperidin-4-yl)quinolin-5-amine hydrochloride (37.7 mg, 0.11 mmol) prepared in Reference Example 35, potassium carbonate (59.38 mg, 0.43 mmol), and potassium iodide (0.18 mg, 0.001 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=10/1, v/v) to give the title compound (3 mg). $^1$H-NMR (CDCl$_3$, 400 MHz) δ 8.73 (s, 1H), 7.89 (s, 1H), 7.48-7.45 (m, 2H), 6.63 (d, 1H), 5.49-5.29 (m, 1H), 4.96 (d, 1H), 4.28-3.25 (m, 5H), 2.98-2.65 (m, 3H), 2.54 (s, 3H), 2.41-2.05 (m, 5H), 1.88-1.26 (m, 3H)

Example 132. (2S,4S)-4-fluoro-1-(2-(4-((7-fluoro-quinolin-5-yl)amino)piperidin-1-yl)acetyl)pyrrolidine-2-carbonitrile The title compound (14 mg) was prepared in the same fashion as Example 131, except that 7-fluoro-N-(piperidin-4-yl)quinolin-5-amine hydrochloride (30.12 mg, 0.11 mmol) prepared in Reference Example 37 was used instead of 3-methyl-N-(piperidin-4-yl)quinolin-5-amine hydrochloride. $^1$H-NMR (CDCl$_3$, 400 MHz) δ 8.85 (s, 1H), 8.08 (d, 1H), 7.07 (d, 1H), 6.39 (d, 1H), 5.49-5.37 (m, 1H), 4.95 (d, 1H), 4.50-3.74 (m, 3H), 3.47-3.20 (m, 3H), 3.00-2.64 (m, 3H), 2.44-2.05 (m, 6H), 1.85-1.64 (m, 2H)

Example 133. (2S,4S)-4-fluoro-1-(2-(4-((7-methoxyquinolin-5-yl)amino)piperidin-1-yl)acetyl)pyrrolidine-2-carbonitrile The title compound (4 mg) was prepared in the same fashion as Example 131, except that 7-methoxy-N-(piperidin-4-yl)quinolin-5-amine hydrochloride (35.3 mg, 0.11 mmol) prepared in Reference Example 38 was used instead of 3-methyl-N-(piperidin-4-yl)quinolin-5-amine hydrochloride. $^1$H-NMR (CDCl$_3$, 400 MHz) δ 8.78 (s, 1H), 8.01 (d, 1H), 7.20-7.18 (m, 1H), 6.86 (s, 1H), 6.27 (s, 1H), 5.49-5.36 (m, 1H), 4.95 (d, 1H), 4.26-3.98 (m, 1H), 3.93 (s, 3H), 3.87-3.70 (m, 1H), 3.38-3.16 (m, 3H), 2.94-2.64 (m, 3H), 2.39-2.05 (m, 6H), 1.82-1.64 (m, 2H)

Example 134. (2S,4S)-4-fluoro-1-(2-(4-((6-methylquinolin-5-yl)amino)piperidin-1-yl)acetyl)pyrrolidine-2-carbonitrile The title compound (14.1 mg) was prepared in the same fashion as Example 131, except that 6-methyl-N-(piperidin-4-yl)quinolin-5-amine (34.6 mg, 0.11 mmol) prepared in Reference Example 36 was used instead of 3-methyl-N-(piperidin-4-yl)quinolin-5-amine hydrochloride. $^1$H-NMR (CDCl$_3$, 400 MHz) δ 8.83 (s, 1H), 8.38 (d, 1H), 7.71 (d, 1H), 7.50 (d, 1H), 7.37-7.35 (m, 1H), 5.48-5.35 (m, 1H), 4.93 (d, 1H), 4.22-3.72 (m, 2H), 3.42-3.15 (m, 3H), 2.96-2.63 (m, 3H), 2.44 (s, 3H), 2.36-1.26 (m, 8H)

Example 135. (2S,4S)-4-fluoro-1-(2-(4-((8-methoxyquinolin-5-yl)amino)piperidin-1-yl)acetyl)pyrrolidine-2-carbonitrile The title compound (1.67 mg) was prepared in the same fashion as Example 131, except that 8-methoxy-N-(piperidin-4-yl)quinolin-5-amine hydrochloride (35.3 mg, 0.11 mmol) prepared in Reference Example 39 was used instead of 3-methyl-N-(piperidin-4-yl)quinolin-5-amine hydrochloride. $^1$H-NMR (CDCl$_3$, 400 MHz) δ 8.94 (s, 1H), 8.20 (d, 1H), 7.42 (d, 1H), 6.96 (d, 1H), 6.65 (d, 1H), 5.48-5.36 (m, 1H), 4.95 (d, 1H), 4.27-4.13 (m, 1H), 4.03 (s, 3H), 3.99-3.77 (m, 1H), 3.49-2.64 (m, 7H), 2.38-1.26 (m, 7H).

Example 136. 6-methoxy-N-[(3S)-1-[2-oxo-2-[(2S,4S)-2-cyano-4-fluoro-pyrrolidin-1-yl]ethyl]pyrrolidin-3-yl]benzofuran-3-carboxamide The title compound (10.0 mg, 23.1%) was prepared in the same fashion as Example 29, except that (S)-6-methoxy-N-(pyrrolidin-3-yl)benzofuran-3-carboxamide hydrochloride (37.9 mg, 0.12 mmol) in Reference Example 46 was used instead of (S)-6-fluoro-N-(pyrrolidin-3-yl)benzofuran-3-carboxamide hydrochloride. $^1$H-NMR (CDCl$_3$, 400 MHz) δ 8.24 (s, 1H), 7.89 (d, 1H), 7.13 (s, 1H), 6.97 (d, 1H), 5.51-4.98 (m, 2H), 4.60 (s, 1H), 4.07-3.99 (m, 1H), 3.85 (s, 3H), 3.82-3.39 (m, 3H), 3.07 (s, 1H), 2.87 (s, 2H), 2.61-2.36 (m, 3H), 1.87 (s, 1H)

Example 137. (2S)-1-[2-[(3R)-3-[methyl(2-quinolyl)amino]pyrrolidin-1-yl]acetyl]pyrrolidine-2-carbonitrile The title compound (24.0 mg, 38.3%) was prepared in the same fashion as Example 17, except that (R)—N-methyl-N-(pyrrolidin-3-yl)quinolin-2-amine hydrochloride (45.5 mg, 0.17 mmol) prepared in Reference Example 47 was used instead of (R)—N-(pyrrolidin-3-yl)quinoline-3-amine hydrochloride. $^1$H-NMR (CDCl$_3$, 400 MHz) δ 7.88 (d, 1H), 7.68 (d, 1H), 7.60 (d, 1H), 7.53 (t, 1H), 7.19 (t, 1H), 6.91 (d, 1H), 5.70-5.50 (m, 1H), 5.25-4.79 (m, 1H), 3.76-3.56 (m, 2H), 3.44-3.28 (m, 2H), 3.16 (s, 3H), 3.13-2.97 (m, 2H), 2.88-2.58 (m, 2H), 2.40-2.20 (m, 3H), 2.20-2.13 (m, 2H), 1.94-1.89 (m, 1H)

Example 138. (2S)-1-[2-[(3R)-3-[methyl(3-quinolyl)amino]pyrrolidin-1-yl]acetyl]pyrrolidine-2-carbonitrile The title compound (109.3 mg, 47.0%) was prepared in the same fashion as Example 17, except that (R)—N-methyl-N-(pyrrolidin-3-yl)quinolin-3-amine hydrochloride (168.8 mg, 0.64 mmol) prepared in Reference Example 48 was used instead of (R)—N-(pyrrolidin-3-yl)quinoline-3-amine hydrochloride. $^1$H-NMR (CDCl$_3$, 400 MHz) δ 8.77 (s, 1H), 7.96 (d, 1H), 7.64 (d, 1H), 7.45-7.28 (m, 2H), 7.23 (s, 1H), 5.15-4.77 (m, 1H), 4.70-4.50 (m, 1H), 3.73-3.70 (m, 1H), 3.60-3.52 (m, 1H), 3.48-3.26 (m, 2H), 3.04 (s, 3H), 3.03-2.88 (m, 1H), 2.86-2.77 (m, 2H), 2.64 (dd, 1H), 2.40-2.20 (m, 3H), 2.20-2.05 (m, 2H), 1.97-1.91 (m, 1H)

Example 139. (2S)-1-[2-[(3R)-3-[methyl(5-quinolyl)amino]pyrrolidin-1-yl]acetyl]pyrrolidine-2-carbonitrile The title compound (1.5 mg, 12.0%) was prepared in the same fashion as Example 17, except that (R)—N-methyl-N-(pyrrolidin-3-yl)quinolin-5-amine hydrochloride (88.1 mg, 0.33 mmol) prepared in Reference Example 49 was used instead of (R)—N-(pyrrolidin-3-yl)quinoline-3-amine hydrochloride. $^1$H-NMR (CDCl$_3$, 400 MHz) δ 8.91 (d, 1H), 8.63 (d, 1H), 7.84 (d, 1H), 7.64 (t, 1H), 7.41 (t, 1H), 7.21 (d, 1H), 5.20-4.70 (m, 1H), 4.10-3.90 (m, 1H), 3.80-3.66 (m, 1H), 3.60-3.40 (m, 2H), 3.38-3.20 (m, 2H), 3.00-2.88 (m, 1H), 2.81 (s, 3H), 2.81-2.70 (m, 2H), 2.40-2.20 (m, 2H), 2.20-2.00 (m, 3H), 2.00-1.80 (m, 1H)

Example 140. (2S)-1-[2-[(3R)-3-[methyl(6-quinolyl)amino]pyrrolidin-1-yl]acetyl]pyrrolidine-2-carbonitrile The title compound (16.5 mg, 19.9%) was prepared in the same fashion as Example 17, except that (R)—N-methyl-N-(pyrrolidin-3-yl)quinolin-6-amine hydrochloride (59.5 mg, 0.23 mmol) prepared in Reference Example 50 was used instead of (R)—N-(pyrrolidin-3-yl)quinoline-3-amine hydrochloride. $^1$H-NMR (CDCl$_3$, 400 MHz) δ 8.64 (d, 1H), 8.00-7.94 (m, 2H), 7.44 (d, 1H), 7.30-7.20 (m, 1H), 6.88 (d, 1H), 5.15-4.73 (m, 1H), 4.73-4.58 (m, 1H), 3.80-3.62 (m, 1H), 3.62-3.45 (m, 2H), 3.46-3.20 (m, 2H), 3.04 (s, 3H), 3.03-2.78 (m, 2H), 2.78-2.58 (m, 1H), 2.48-2.22 (m, 3H), 2.22-2.10 (m, 2H), 2.01-1.82 (m, 1H)

Example 141. (2S)-1-[2-[(3R)-3-[methyl(7-quinolyl)amino]pyrrolidin-1-yl]acetyl]pyrrolidine-2-carbonitrile The title compound (74.9 mg, 51.1%) was prepared in the same fashion as Example 17, except that (R)—N-methyl-N-(pyrrolidin-3-yl)quinolin-7-amine hydrochloride (106.3 mg, 0.40 mmol) prepared in Reference Example 51 was used instead of (R)—N-(pyrrolidin-3-yl)quinoline-3-amine hydrochloride. $^1$H-NMR (CDCl$_3$, 400 MHz) δ 8.75 (s, 1H), 7.97 (d, 1H), 7.65 (d, 1H), 7.28-7.23 (m, 2H), 7.12 (t, 1H), 5.20-4.74 (m, 1H), 4.74-4.61 (m, 1H), 3.82-3.64 (m, 1H), 3.64-3.50 (m, 1H), 3.46-3.24 (m, 2H), 3.07 (s, 3H), 3.07-2.83 (m, 2H), 2.83-2.66 (m, 1H), 2.60 (q, 1H), 2.46-2.22 (m, 3H), 2.22-2.10 (m, 2H), 2.00-1.92 (m, 1H)

Example 142. (2S)-1-[2-[(3S)-3-[methyl(3-quinolyl)amino]pyrrolidin-1-yl]acetyl]pyrrolidine-2-carbonitrile The title compound (165.8 mg, 59.1%) was prepared in the same fashion as Example 5, except that (S)—N-methyl-N-(pyrrolidin-3-yl)quinolin-3-amine hydrochloride (203.4 mg, 0.77 mmol) prepared in Reference Example 52 was used instead of (S)—N-(pyrrolidin-3-yl)quinoline-4-amine hydrochloride. $^1$H-NMR (CDCl$_3$, 400 MHz) δ 8.75 (s, 1H), 7.94 (d 1H), 7.63 (t, 1H), 7.44-7.41 (m, 2H), 7.22 (s, 1H), 5.16-4.70 (m, 1H), 4.70-4.52 (m, 1H), 3.80-3.60 (m, 1H), 3.60-3.48 (m, 1H), 3.48- 3.18 (m, 2H), 3.02 (s, 3H), 3.02-2.70 (m, 2H), 2.60 (dd, 1H), 2.50-2.34 (m, 1H), 2.34-2.20 (m, 3H), 2.20-2.04 (m, 2H), 2.04-1.88 (m, 1H)

Example 143. (2S)-1-[2-[(3S)-3-[methyl(4-quinolyl)amino]pyrrolidin-1-yl]acetyl]pyrrolidine-2-carbonitrile The title compound (60.3 mg, 73.1%) was prepared in the same fashion as Example 5, except that (S)—N-methyl-N-(pyrrolidin-3-yl)quinolin-4-amine hydrochloride (59.8 mg, 0.23 mmol) prepared in Reference Example 53 was used instead of (S)—N-(pyrrolidin-3-yl)quinoline-4-amine hydrochloride. $^1$H-NMR (CDCl$_3$, 400 MHz) δ 8.69 (d, 1H), 8.06-8.04 (m, 2H), 7.66 (t, 1H), 7.48 (t, 1H), 6.84 (d, 1H), 5.18-4.76 (m, 1H), 4.48-4.30 (m, 1H), 3.82-3.60 (m, 1H), 3.60-3.44 (m, 1H), 3.44- 3.20 (m, 2H), 3.01 (s, 3H), 3.01-2.90 (m, 2H), 2.90-2.80 (m, 1H), 2.70-2.58 (m, 1H), 2.40-2.30 (m, 1H), 2.30-2.20 (m, 3H), 2.20-1.94 (m, 2H)

Example 144. (2S)-1-[2-[(3S)-3-[methyl(5-quinolyl)amino]pyrrolidin-1-yl]acetyl]pyrrolidine-2-carbonitrile The title compound (22.9 mg, 16.6%) was prepared in the same fashion as Example 5, except that (S)—N-methyl-N-(pyrrolidin-3-yl)quinolin-5-amine hydrochloride (100.1 mg, 0.38 mmol) prepared in Reference Example 54 was used instead of (S)—N-(pyrrolidin-3-yl)quinoline-4-amine hydrochloride. $^1$H-NMR (CDCl$_3$, 400 MHz) δ 8.90 (d, 1H), 8.62 (d, 1H), 7.83 (d, 1H), 7.63 (t, 1H), 7.41 (t, 1H), 7.21 (d, 1H), 5.20-4.70 (m, 1H), 4.12-3.98 (m, 1H), 3.80-3.60 (m, 1H), 3.60-3.40 (m, 1H), 3.40-3.20 (m, 2H), 3.02-2.90 (m, 1H), 2.79 (s, 3H), 2.78-2.60 (m, 3H), 2.40-2.20 (m, 2H), 2.20- 2.00 (m, 3H), 2.00-1.84 (m, 1H)

Example 145. (2S)-1-[2-[(3S)-3-[methyl(6-quinolyl)amino]pyrrolidin-1-yl]acetyl]pyrrolidine-2-carbonitrile The title compound (85.9 mg, 64.1%) was prepared in the same fashion as Example 5, except that (S)—N-methyl-N-(pyrrolidin-3-yl)quinolin-6-amine hydrochloride (97.1 mg, 0.37 mmol) prepared in Reference Example 55 was used instead of (S)—N-(pyrrolidin-3-yl)quinoline-4-amine hydrochloride. $^1$H-NMR (CDCl$_3$, 400 MHz) δ 8.62 (d, 1H), 8.08-7.90 (m, 2H), 7.42 (d, 1H), 7.28-7.25 (m, 1H), 6.87 (d, 1H), 5.20-4.74 (m, 1H), 4.74-4.50 (m, 1H), 3.80-3.60 (m, 1H), 3.60-3.48 (m, 1H), 3.48-3.20 (m, 2H), 3.10 (s, 3H), 3.10-2.90 (m, 2H), 2.90-2.72 (m, 1H), 2.70-2.50 (m, 1H), 2.50-2.23 (m, 2H), 2.23-2.05 (m, 3H), 2.05-1.80 (m, 1H)

Example 146. (2S)-1-[2-[(3S)-3-[methyl(7-quinolyl)amino]pyrrolidin-1-yl]acetyl]pyrrolidine-2-carbonitrile The title compound (142.4 mg, 49.4%) was prepared in the same fashion as Example 5, except that (S)—N-methyl-N-(pyrrolidin-3-yl)quinolin-7-amine hydrochloride (209.5 mg, 0.79 mmol) prepared in Reference Example 56 was used instead of (S)—N-(pyrrolidin-3-yl)quinoline-4-amine hydrochloride. $^1$H-NMR (CDCl$_3$, 400 MHz) δ 8.73 (s, 1H), 7.98 (d, 1H), 7.65 (d, 1H), 7.28-7.23 (m, 2H), 7.14-7.10 (m, 1H), 5.20-4.74 (m, 1H), 4.74-4.60 (m, 1H), 3.80-3.60 (m, 1H), 3.60-3.48 (m, 1H), 3.48-3.20 (m, 2H), 3.07 (s, 3H), 3.07-2.90 (m, 1H), 2.90-2.72 (m, 1H), 2.70-2.50 (m, 1H), 2.50-2.20 (m, 3H), 2.20-2.00 (m, 3H), 2.00-1.85 (m, 1H)

Example 147. (2S)-1-[2-[(3S)-3-[4-isoquinolyl(methyl)amino]pyrrolidin-1-yl]acetyl]pyrrolidine-2-carbonitrile The title compound (2.4 mg, 3.3%) was prepared in the same fashion as Example 5, except that (S)—N-methyl-N-(pyrrolidin-3-yl)isoquinolin-4-amine hydrochloride (55.6 mg, 0.21 mmol) prepared in Reference Example 57 was used instead of (S)—N-(pyrrolidin-3-yl)quinoline-4-amine hydrochloride. $^1$H-NMR (CDCl$_3$, 400 MHz) δ 8.98 (s, 1H), 8.24 (s, 1H), 8.19 (d, 1H), 7.97 (d, 1H), 7.70 (t, 1H), 7.61 (t, 1H), 5.25-4.74 (m, 1H), 4.23-4.10 (m, 1H), 3.80-3.60 (m, 1H), 3.60-3.40 (m, 1H), 3.40-3.20 (m, 2H), 3.05-2.90 (m, 1H), 2.86 (s, 3H), 2.86-2.78 (m, 2H), 2.78-2.66 (m, 1H), 2.40- 2.24 (m, 2H), 2.24-2.10 (m, 3H), 2.05-1.90 (m, 1H)

Example 148. (2S)-1-[2-[(3S)-3-[5-isoquinolyl(methyl)amino]pyrrolidin-1-yl]acetyl]pyrrolidine-2-carbonitrile The title compound (10.9 mg, 11.2%) was prepared in the same fashion as Example 5, except that (S)—N-methyl-N-(pyrrolidin-3-yl)isoquinolin-5-amine hydrochloride (70.7 mg, 0.27 mmol) prepared in Reference Example 58 was used instead of (S)—N-(pyrrolidin-3-yl)quinoline-4-amine hydrochloride. $^1$H-NMR (CDCl$_3$, 400 MHz) δ 9.22 (s, 1H), 8.53 (d, 1H), 8.00 (d, 1H), 7.68 (d, 1H), 7.52 (t, 1H), 7.33 (d, 1H), 5.20-4.70 (m, 1H), 4.18-4.00 (m, 1H), 3.80-3.60 (m, 1H), 3.60-3.42 (m, 1H), 3.42-3.20 (m, 2H), 3.00-2.88 (m, 1H), 2.80 (s, 3H), 2.80-2.70 (m, 2H), 2.70-2.60 (m, 1H), 2.40- 2.20 (m, 2H), 2.20-2.05 (m, 3H), 2.00-1.85 (m, 1H)

Example 149. (2S)-1-[2-[(3S)-3-[methyl-(4-methyl-3-quinolyl)amino]pyrrolidin-1-yl]acetyl]pyrrolidine-2-carbonitrile The title compound (37.4 mg, 55.9%) was prepared in the same fashion as Example 5, except that (S)—N,4-dimethyl- N-(pyrrolidin-3-yl)quinolin-3-amine hydrochloride (49.1 mg, 0.18 mmol) prepared in Reference Example 59 was used instead of (S)—N-(pyrrolidin-3-yl)quinoline-4-amine hydrochloride. $^1$H-NMR (CDCl$_3$, 400 MHz) δ 8.79 (s, 1H), 8.05 (d, 1H), 7.99 (d, 1H), 7.64 (t, 1H), 7.55 (t, 1H), 5.20-4.70 (m, 1H), 4.10-3.96 (m, 1H), 3.78-3.60 (m, 1H), 3.60-3.44 (m, 1H), 3.40- 3.20 (m, 2H), 3.04-2.90 (m, 1H), 2.90-2.78 (m, 1H), 2.74 (s, 3H), 2.74-2.70 (m, 1H), 2.68 (s, 3H), 2.68-2.50 (m, 1H), 2.34-2.20 (m, 2H), 2.20-2.00 (m, 3H), 2.00-1.74 (m, 1H)

Example 150. (2S)-1-[2-[(3S)-3-[methyl-(6-methyl-3-quinolyl)amino]pyrrolidin-1-yl]acetyl]pyrrolidine-2-carbonitrile The title compound (224.5 mg, 83.2%) was prepared in the same fashion as Example 5, except that (S)—N,6-dimethyl-N-(pyrrolidin-3-yl)quinolin-3-amine hydrochloride (198.5 mg, 0.72 mmol) prepared in Reference Example 60 was used instead of (S)—N-(pyrrolidin-3-yl)quinoline-4-amine hydrochloride. $^1$H-NMR (CDCl$_3$, 400 MHz) δ 8.67 (s, 1H), 7.83 (d, 1H), 7.40 (s, 1H), 7.28 (d, 1H), 7.15 (s, 1H), 5.18-4.74 (m, 1H), 4.70-4.50 (m, 1H), 3.80-3.60 (m, 1H), 3.60-3.48 (m, 1H), 3.48- 3.20 (m, 2H), 3.01 (s, 3H), 3.01-2.90 (m, 2H), 2.90-2.72 (m, 1H), 2.68-2.52 (m, 1H), 2.50 (s, 3H), 2.45-2.24 (m, 2H), 2.24-2.08 (m, 3H), 2.08-1.88 (m, 1H)

Example 151. (S)-1-(2-((S)-3-((6-fluoroquinolin-3-yl)(methyl)amino)pyrrolidin-1-yl)acetyl)pyrrolidine-2-carbonitrile The title compound (273.7 mg, 78.8%) was prepared in the same fashion as Example 5, except that (S)-6-fluoro-N-methyl-N-(pyrrolidin-3-yl)quinolin-3-amine hydrochloride (256.7 mg, 0.91 mmol) prepared in Reference Example 61 was used instead of (S)—N-(pyrrolidin-3-yl)quinoline-4-amine hydrochloride. $^1$H-NMR (CDCl$_3$, 400 MHz) δ 8.69 (s, 1H), 7.91 (d, 1H), 7.22-7.13 (m, 2H), 7.10 (s, 1H), 5.12-4.72 (m, 1H), 4.72-4.58 (m, 1H), 3.82-3.60 (m, 1H), 3.60-3.48 (m, 1H), 3.48-3.20 (m, 2H), 3.04 (s, 3H), 3.04-2.90 (m, 2H), 2.90-2.70 (m, 1H), 2.68-2.52 (m, 1H), 2.45-2.24 (m, 2H), 2.24-2.06 (m, 3H), 2.06-1.85 (m, 1H)

Example 152. (S)-1-(2-((S)-3-((6-methoxyquinolin-3-yl)(methyl)amino)pyrrolidin-1-yl)acetyl)pyrrolidine-2-carbonitrile The title compound (196.9 mg, 67.7%) was prepared in the same fashion as Example 5, except that (S)-6-methoxy-N-methyl-N-(pyrrolidin-3-yl)quinolin-3-amine hydrochloride (217.2 mg, 0.74 mmol) prepared in Reference Example 62 was used instead of (S)—N-(pyrrolidin-3-yl)quinoline-4-amine hydrochloride. $^1$H-NMR (CDCl$_3$, 400 MHz) δ 8.59 (s, 1H), 7.83 (d, 1H), 7.14 (s, 1H), 7.08 (d, 1H), 6.93 (s, 1H), 5.16-4.74 (m, 1H), 4.70-4.55 (m, 1H), 3.91 (s, 3H), 3.88-3.62 (m, 1H), 3.62-3.48 (m, 1H), 3.48-3.20 (m, 2H), 3.02 (s, 3H), 3.02-2.90 (m, 2H), 2.90-2.73 (m, 1H), 2.68-2.55 (m, 1H), 2.42-2.24 (m, 2H), 2.24-2.08 (m, 3H), 2.08-1.86 (m, 1H)

Example 153. (S)-1-(2-((S)-3-((7-methoxyquinolin-3-yl)(methyl)amino)pyrrolidin-1-yl)acetyl)pyrrolidine-2-carbonitrile The title compound (61.5 mg, 31.5%) was prepared in the same fashion as Example 5, except that (S)-7-methoxy-N-methyl-N-(pyrrolidin-3-yl)quinolin-3-amine hydrochloride (145.5 mg, 0.50 mmol) prepared in Reference Example 63 was used instead of (S)—N-(pyrrolidin-3-yl)quinoline-4-amine hydrochloride. $^1$H-NMR (CDCl$_3$, 400 MHz) δ 8.70 (s, 1H), 7.55 (d, 1H), 7.33 (s, 1H), 7.28 (s, 1H), 7.14 (d, 1H), 5.20-4.72 (m, 1H), 4.62-4.49 (m, 1H), 3.93 (s, 3H), 3.88-3.62 (m, 1H), 3.62-3.50 (m, 1H), 3.50-3.20 (m, 2H), 2.99 (s, 3H), 2.99-2.90 (m, 2H), 2.90-2.73 (m, 1H), 2.73-2.56 (m, 1H), 2.46-2.05 (m, 5H), 2.05-1.82 (m, 1H)

Example 154. (S)-1-(2-((S)-3-((8-methoxyquinolin-3-yl)(methyl)amino)pyrrolidin-1-yl)acetyl)pyrrolidine-2-carbonitrile The title compound (180.2 mg, 45.5%) was prepared in the same fashion as Example 5, except that (S)-8-methoxy-N-methyl-N-(pyrrolidin-3-yl)quinolin-3-amine hydrochloride (295.8 mg, 1.01 mmol) prepared in Reference Example 64 was used instead of (S)—N-(pyrrolidin-3-yl)quinoline-4-amine hydrochloride. $^1$H-NMR (CDCl$_3$, 400 MHz) δ 8.73 (s, 1H), 7.35 (t, 1H), 7.22-7.19 (m, 2H), 6.79 (d, 1H), 5.18-4.72 (m, 1H), 4.70-4.50 (m, 1H), 4.06 (s, 3H), 3.82-3.60 (m, 1H), 3.60-3.49 (m, 1H), 3.49-3.18 (m, 2H), 3.03 (s, 3H), 3.03-2.90 (m, 2H), 2.90-2.70 (m, 1H), 2.66-2.52 (m, 1H), 2.40- 2.22 (m, 2H), 2.22-2.08 (m, 3H), 2.05-1.82 (m, 1H)

Example 155. (2S,4S)-4-fluoro-1-[2-[(3S)-3-[methyl-(3-methyl-5-quinolyl)amino]pyrrolidin-1-yl]acetyl]pyrrolidine-2-carbonitrile The title compound (38.9 mg, 29.1%) was prepared in the same fashion as Example 28, except that (S)—N,3-dimethyl-N-(pyrrolidin-3-yl)quinolin-5-amine hydrochloride (93.6 mg, 0.34 mmol) prepared in Reference Example 65 was used instead of (S)—N-(pyrrolidin-3-yl)furo[3,2-c]pyridin-7-amine hydrochloride. $^1$H-NMR (CDCl$_3$, 600 MHz) δ 8.72 (s, 1H), 8.34 (s, 1H), 7.77 (d, 1H), 7.53 (t, 1H), 7.15 (d, 1H), 5.46-4.90 (m, 2H), 4.20-3.98 (m, 2H), 3.80-3.60 (m, 1H), 3.40-3.25 (m, 2H), 3.02-2.90 (m, 1H), 2.90-2.75 (m, 1H), 2.75 (s, 3H), 2.75-2.60 (m, 3H), 2.53 (s, 3H), 2.40-2.20 (m, 1H), 2.15-2.05 (m, 1H), 1.98-1.80 (m, 1H)

Example 156. (2S,4S)-4-fluoro-1-(2-((S)-3-((3-fluoroquinolin-5-yl)(methyl)amino)pyrrolidin-1-yl)acetyl)pyrrolidine-2-carbonitrile The title compound (264.4 mg, 79.8%) was prepared in the same fashion as Example 28, except that (S)-3-fluoro-N-methyl-N-(pyrrolidin-3-yl)quinolin-5-amine hydrochloride (233.8 mg, 0.83 mmol) prepared in Reference Example 66 was used instead of (S)—N-(pyrrolidin-3-yl)furo[3,2-c]pyridin-7-amine hydrochloride. $^1$H-NMR (CDCl$_3$, 600 MHz) δ 8.77 (s, 1H), 8.20 (d, 1H), 7.82 (d, 1H), 7.58 (t, 1H), 7.24 (d, 1H), 5.50-4.90 (m, 2H), 4.20-3.98 (m, 2H), 3.80-3.68 (m, 1H), 3.60-3.18 (m, 2H), 2.98-2.76 (m, 2H), 2.76 (s, 3H), 2.76-2.50 (m, 3H), 2.40-2.20 (m, 1H), 2.18-2.05 (m, 1H), 1.94-1.78 (m, 1H)

Example 157. (2S,4S)-4-fluoro-1-(2-((S)-3-((7-fluoroquinolin-5-yl)(methyl)amino)pyrrolidin-1-yl)acetyl)pyrrolidine-2-carbonitrile The title compound (238.2 mg, 92.0%) was prepared in the same fashion as Example 28, except that (S)-7-fluoro-N-methyl-N-(pyrrolidin-3-yl)quinolin-5-amine hydrochloride (182.5 mg, 0.65 mmol) prepared in Reference Example 67 was used instead of (S)—N-(pyrrolidin-3-yl)furo[3,2-c]pyridin-7-amine hydrochloride. ¹H-NMR (CDCl₃, 600 MHz) δ 8.85 (d, 1H), 8.47 (d, 1H), 7.39 (t, 1H), 7.33 (s, 1H), 6.92 (s, 1H), 5.48-4.90 (m, 2H), 4.20-3.88 (m, 2H), 3.80-3.68 (m, 1H), 3.60-3.18 (m, 2H), 2.98-2.80 (m, 2H), 2.76 (s, 3H), 2.76-2.60 (m, 3H), 2.40-2.20 (m, 1H), 2.18-2.08 (m, 1H), 2.00-1.88 (m, 1H)

Example 158. (2S,4S)-4-fluoro-1-(2-((S)-3-((8-fluoroquinolin-5-yl)(methyl)amino)pyrrolidin-1-yl)acetyl)pyrrolidine-2-carbonitrile The title compound (196.6 mg, 80.9%) was prepared in the same fashion as Example 28, except that (S)-8-fluoro-N-methyl-N-(pyrrolidin-3-yl)quinolin-5-amine hydrochloride (171.2 mg, 0.61 mmol) prepared in Reference Example 68 was used instead of (S)—N-(pyrrolidin-3-yl)furo[3,2-c]pyridin-7-amine hydrochloride. ¹H-NMR (CDCl₃, 600 MHz) δ 8.92 (s, 1H), 8.61 (d, 1H), 7.45 (d, 1H), 7.29 (t, 1H), 7.12 (d, 1H), 5.48-4.90 (m, 2H), 4.20-3.84 (m, 2H), 3.78-3.64 (m, 1H), 3.60-3.14 (m, 2H), 3.00-2.72 (m, 2H), 2.72 (s, 3H), 2.72-2.50 (m, 3H), 2.38-2.20 (m, 1H), 2.12-2.00 (m, 1H), 1.90-1.80 (m, 1H)

Example 159. (2S,4S)-4-fluoro-1-[2-[(3S)-3-[methyl-[8-(trifluoromethyl)-5-quinolyl]amino]pyrrolidin-1-yl]acetyl]pyrrolidine-2-carbonitrile The title compound (324.1 mg, 68.5%) was prepared in the same fashion as Example 28, except that (S)—N-methyl-N-(pyrrolidin-3-yl)-8-(trifluoromethyl)quinolin-5-amine hydrochloride (349.4 mg, 1.05 mmol) prepared in Reference Example 69 was used instead of (S)—N-(pyrrolidin-3-yl)furo[3,2-c]pyridin-7-amine hydrochloride. ¹H-NMR (CDCl₃, 600 MHz) δ 9.02 (d, 1H), 8.54 (d, 1H), 7.95 (d, 1H), 7.46 (t, 1H), 7.10 (d, 1H), 5.50-4.90 (m, 2H), 4.26-3.90 (m, 2H), 3.82-3.68 (m, 1H), 3.70-3.16 (m, 2H), 3.00-2.85 (m, 1H), 2.85 (s, 3H), 2.85-2.78 (m, 2H), 2.78-2.60 (m, 2H), 2.40-2.24 (m, 1H), 2.20-2.10 (m, 1H), 2.00-1.90 (m, 1H)

Example 160. (2S,4S)-4-fluoro-1-[2-[(3S)-3-[methyl-[8-(trifluoromethoxy)-5-quinolyl]amino]pyrrolidin-1-yl]acetyl]pyrrolidine-2-carbonitrile The title compound (271.0 mg, 55.4%) was prepared in the same fashion as Example 28, except that (S)—N-methyl-N-(pyrrolidin-3-yl)-8-(trifluoromethoxy)quinolin-5-amine hydrochloride (365.6 mg, 1.05 mmol) prepared in Reference Example 70 was used instead of S)—N-(pyrrolidin-3-yl)furo[3,2-c]pyridin-7-amine hydrochloride. ¹H-NMR (CDCl₃, 600 MHz) δ 9.00 (d, 1H), 8.59 (d, 1H), 7.52 (d, 1H), 7.47 (t, 1H), 7.13 (d, 1H), 5.48-4.90 (m, 2H), 4.24-3.88 (m, 2H), 3.80-3.68 (m, 1H), 3.60-3.16 (m, 2H), 3.05-2.78 (m, 2H), 2.78 (s, 3H), 2.78-2.60 (m, 3H), 2.40-2.22 (m, 1H), 2.20-2.10 (m, 1H), 1.98-1.85 (m, 1H)

Example 161. (S)-1-(2-((R)-3-(quinolin-5-ylamino)pyrrolidin-1-yl)acetyl)pyrrolidine-2-carbonitrile The title compound (2.5 mg, 5.19%) was prepared in the same fashion as Example 17, except that (R)—N-(pyrrolidin-3-yl)quinolin-5-amine hydrochloride prepared (25.6 mg, 0.12 mmol) in Reference Example 71 was used instead of (R)—N-(pyrrolidin-3-yl)quinoline-3-amine hydrochloride. ¹H-NMR (CDCl₃, 400 MHz) δ 8.87 (s, 1H), 8.31 (dd, 1H), 7.55 (t, 1H), 7.47 (d, 1H), 7.36-7.30 (m, 1H), 6.57 (d, 1H), 4.82 (dd, 1H), 4.21 (s, 1H), 3.69-3.35 (m, 4H), 3.14-2.47 (m, 4H), 2.41-1.90 (m, 7H)

Example 162. (2S)-1-[2-[(3R)-3-(6-quinolylamino)pyrrolidin-1-yl]acetyl]pyrrolidine-2-carbonitrile The title compound (11.4 mg, 22.5%) was prepared in the same fashion as Example 17, except that (R)—N-(pyrrolidin-3-yl)quinolin-6-amine hydrochloride (25.6 mg, 0.12 mmol) prepared in Reference Example 72 was used instead of (R)—N-(pyrrolidin-3-yl)quinoline-3-amine hydrochloride. ¹H-NMR (CDCl₃, 400 MHz) δ 8.57 (d, 1H), 7.86 (dd, 2H), 7.25-7.22 (m, 1H), 7.07 (dd, 1H), 6.62 (s, 1H), 4.87-4.62 (m, 2H), 4.11 (s, 1H), 3.66-3.28 (m, 4H), 3.01-2.82 (m, 3H), 2.64-2.09 (m, 6H), 1.83-1.79 (m, 1H)

Example 163. (2S)-1-[2-[(3R)-3-(7-quinolylamino)pyrrolidin-1-yl]acetyl]pyrrolidine-2-carbonitrile The title compound (3.4 mg, 6.72%) was prepared in the same fashion as Example 17, except that (R)—N-(pyrrolidin-3-yl)quinolin-7-amine hydrochloride (25.6 mg, 0.12 mmol) prepared in Reference Example 73 was used instead of (R)—N-(pyrrolidin-3-yl)quinoline-3-amine hydrochloride. ¹H-NMR (CDCl₃, 400 MHz) δ 8.71 (d, 1H), 7.94 (d, 1H), 7.57-7.54 (m, 1H), 7.10 (q, 1H), 6.99 (d, 1H), 6.93-6.90 (m, 1H), 4.93-4.73 (m, 2H), 4.18 (s, 1H), 3.69-3.31 (m, 4H), 3.09-2.85 (m, 3H), 2.60-2.16 (m, 6H), 1.86 (m, 1H)

Example 164. (2S)-1-[2-[(3R)-3-(8-quinolylamino)pyrrolidin-1-yl]acetyl]pyrrolidine-2-carbonitrile The title compound (9.5 mg, 18.7%) was prepared in the same fashion as Example 17, except that (R)—N-(pyrrolidin-3-yl)quinolin-8-amine hydrochloride (25.6 mg, 0.12 mmol) prepared in Reference Example 74 was used instead of (R)—N-(pyrrolidin-3-yl)quinoline-3-amine hydrochloride. ¹H-NMR (CDCl₃, 400 MHz) δ 8.70-8.69 (m, 1H), 8.05 (d, 1H), 7.39-7.35 (m, 2H), 7.08-7.05 (m, 1H), 6.64 (d, 1H), 6.29 (d, 1H), 5.24-4.71 (m, 1H), 4.23 (s, 1H), 3.75-3.52 (m, 2.3H), 3.36-3.28 (m, 1.7H), 3.15-3.11 (m, 1H), 2.91-2.74 (m, 3H), 2.49-2.07 (m, 5H), 1.93-1.190 (m, 1H)

Example 165. (2S,4S)-4-fluoro-1-[2-[(3R)-3-(3-quinolylamino)pyrrolidin-1-yl]acetyl]pyrrolidine-2-carbonitrile The title compound (15.3 mg, 39.7%) was prepared in the same fashion as Example 28, except that (R)—N-(pyrrolidin-3-yl)quinoline-3-amine hydrochloride (25.6 mg, 0.12 mmol) prepared in Reference Example 17 was used instead of (S)—N-(pyrrolidin-3-yl)furo[3,2-c]pyridin-7-amine hydrochloride. ¹H-NMR (CDCl₃, 400 MHz) δ 8.42-8.39 (m, 1H), 7.88 (d, 1H), 7.57 (d, 1H), 7.40-7.34 (m, 2H), 6.90-6.89 (m, 1H), 5.36-5.20 (m, 1H), 5.06-4.83 (m, 2H), 4.07-3.54 (m, 3H), 3.40-3.23 (m, 1H), 2.96-2.95 (m, 2H), 2.88-2.80 (m, 2H), 2.67-2.51 (m, 2H), 2.40-2.10 (m, 2H), 1.77-1.76 (m, 1H)

Example 166. (2S,4S)-4-fluoro-1-[2-[(3R)-3-(5-quinolylamino)pyrrolidin-1-yl]acetyl]pyrrolidine-2-carbonitrile The title compound (16.9 mg, 44.0%) was prepared in the same fashion as Example 28, except that (R)—N-(pyrrolidin-3-yl)quinolin-5-amine hydrochloride (25.6 mg, 0.12 mmol) prepared in Reference Example 71 was used instead of (S)—N-(pyrrolidin-3-yl)furo[3,2-c]pyridin-7-amine hydrochloride. ¹H-NMR (CDCl₃, 400 MHz) δ 8.53 (d, 1H), 7.85 (d, 1H), 7.79 (d, 1H), 7.21-7.18 (m, 1H), 7.05-7.03 (m, 1H), 6.58-6.56 (m, 1H), 5.34-5.18 (m, 1H), 5.07-4.72 (m, 2H), 4.09-3.20 (m, 5H), 2.90-2.73 (m, 3H), 2.64-2.47 (m, 2H), 2.37-2.09 (m, 2H), 1.73-1.70 (m, 1H)

Example 167. (2S,4S)-4-fluoro-1-[2-[(3R)-3-(6-quinolylamino)pyrrolidin-1-yl]acetyl]pyrrolidine-2-carbonitrile The title compound (1.2 mg, 3.1%) was prepared in the same fashion as Example 28, except that (R)—N-(pyrrolidin-3-yl)quinolin-6-amine hydrochloride (25.6 mg, 0.12 mmol) prepared in Reference Example 72 was used instead of (S)—N-(pyrrolidin-3-yl)furo[3,2-c]pyridin-7-amine hydrochloride. ¹H NMR (CD₃OD, 400 MHz) δ 8.75 (dd, 1H), 8.67-8.60 (m, 1H), 7.60-7.56 (m, 1H), 7.46-7.43 (m, 1H), 7.33-7.31 (d, 1H), 6.69-6.66 (m, 1H), 5.51 (s, 1H), 5.39-5.31 (m, 1H), 5.00 (d, 1H), 4.25-4.24 (m, 1H), 4.09-4.00 (m, 1H), 3.87-3.74 (m, 1H), 3.59-3.42 (m, 1H), 3.09-3.04 (m, 2H), 2.95-2.88 (m, 1H), 2.71-2.39 (m, 4H), 1.97-1.91 (m, 1H).

Example 168. (2S,4S)-4-fluoro-1-[2-[(3R)-3-(7-quinolylamino)pyrrolidin-1-yl]acetyl]pyrrolidine-2-carbonitrile The title compound (1.5 mg, 3.9%) was prepared in the same fashion as Example 28, except that (R)—N-(pyrrolidin-3-yl)quinolin-7-amine hydrochloride (25.6 mg, 0.12 mmol) prepared in Reference Example 73 was used instead of (S)—N-(pyrrolidin-3-yl)furo[3,2-c]pyridin-7-amine hydrochloride. ¹H-NMR (CDCl₃, 400 MHz) δ 8.72-8.71 (m, 1H), 7.96 (d, 1H), 7.58-7.55 (m, 1H), 7.13-7.10 (m, 1H), 6.99 (s, 1H), 6.92-6.90 (m, 1H), 5.48-5.29 (m, 1H), 5.18-4.93 (m, 1H), 4.77-4.61 (m, 1H), 4.23-4.18 (m, 1H), 4.11-3.79 (m, 2H), 3.48-3.32 (m, 2H), 3.04-2.22 (m, 7H), 1.90-1.85 (m, 1H)

Example 169. (2S,4S)-4-fluoro-1-[2-[(3R)-3-(8-quinolylamino)pyrrolidin-1-yl]acetyl]pyrrolidine-2-carbonitrile The title compound (16.7 mg, 43.2%) was prepared in the same fashion as Example 28, except that (R)—N-(pyrrolidin-3-yl)quinolin-8-amine hydrochloride (25.6 mg, 0.12 mmol) prepared in Reference Example 74 was used instead of (S)—N-(pyrrolidin-3-yl)furo[3,2-c]pyridin-7-amine hydrochloride. ¹H-NMR (CDCl₃, 400 MHz) δ 8.69-8.67 (m, 1H), 8.05-8.03 (m, 1H), 7.39-7.34 (m, 2H), 7.08-7.04 (m, 1H), 6.64-6.61 (m, 1H), 6.25 (d, 1H), 5.44-5.19 (m, 1.3H), 4.83 (d, 0.7H), 4.19-4.17 (m, 1H), 4.05-3.65 (m, 2H), 3.39-3.07 (m, 2H), 3.00-2.02 (m, 7H), 1.92-1.85 (m, 1H)

Example 170. (2S,4S)-4-fluoro-1-[2-[(3R)-3-(4-quinolylamino)pyrrolidin-1-yl]acetyl]pyrrolidine-2-carbonitrile The title compound (1.1 mg, 2.91%) was prepared in the same fashion as Example 28, except that (R)—N-(pyrrolidin-3-yl)quinolin-4-amine hydrochloride (25.6 mg, 0.12 mmol) prepared in Reference Example 75 was used instead of (S)—N-(pyrrolidin-3-yl)furo[3,2-c]pyridin-7-amine hydrochloride. ¹H NMR (CDOD₃, 400 MHz) δ 8.38 (dd, 1H), 8.22-8.15 (m, 1H), 7.83 (d, 1H), 7.66 (t, 1H), 7.49-7.45 (m, 1H), 6.53 (d, 1H), 5.51-5.00 (m, 2H), 4.35-4.31 (m, 1H), 4.08-4.00 (m, 1H), 3.86-3.74 (m, 1H), 3.62-3.57 (m, 1H), 3.45 (d, 1H), 3.13-2.92 (m, 3H), 2.67-2.36 (m, 4H), 1.97-1.90 (m, 1H)

Example 171. (2S,4S)-4-fluoro-1-[2-[(3R)-3-(1,8-naphthyridin-3-ylamino)pyrrolidin-1-yl]acetyl]pyrrolidine-2-carbonitrile (2S)-1-(2-chloroacetyl)-4-fluoro-pyrrolidin-2-carbonitrile (168.7 mg, 0.89 mmol) prepared in Reference Example 2 was dissolved in anhydrous dichloromethane (4 ml). To the resulting solution, (R)—N-(pyrrolidin-3-yl)-1,8-naphthyridin-3-amine hydrochloride (254.1 mg 0.89 mmol) prepared in Reference Example 76 and potassium carbonate (492.0 mg, 3.56 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=10/1, v/v) to give a title compound (50.1 mg, 15.4%). ¹H-NMR (CDCl₃, 600 MHz) δ 8.79 (s, 1H), 8.61 (d, 1H), 7.96 (d, 1H), 7.35 (t, 1H), 6.90 (d, 1H), 5.50-5.28 (m, 1H), 5.10-4.70 (m, 1H), 4.20-4.00 (m, 2H), 3.98-3.70 (m, 1H), 3.60-3.30 (m, 2H), 3.10-2.98 (m, 2H), 2.95-2.82 (m, 2H), 2.80-2.55 (m, 2H), 2.50-2.20 (m, 2H), 1.90-1.80 (m, 1H)

Example 172. (2S,4S)-4-fluoro-1-[2-[(3R)-3-[(7-chloro-1,8-naphthyridin-3-yl)amino]pyrrolidin-1-yl]acetyl]pyrrolidine-2-carbonitrile The title compound (8.5 mg, 4.2%) was prepared in the same fashion as Example 171, except that (R)-7-chloro-N-(pyrrolidin-3-yl)-1,8-naphthyridin-3-amine hydrochloride (161.2 mg, 0.50 mmol) prepared in Reference Example 77 was used instead of (R)—N-(pyrrolidin-3-yl)-1,8-naphthyridin-3-amine hydrochloride. ¹H-NMR (CDCl₃, 600 MHz) δ 8.58 (s, 1H), 7.91 (d, 1H), 7.35 (d, 1H), 6.91 (s, 1H), 5.50-5.30 (m, 1H), 5.08-4.75 (m, 1H), 4.20-4.00 (m, 2H), 3.96-3.68 (m, 1H), 3.65-3.30 (m, 2H), 3.14-3.00 (m, 2H), 2.98-2.72 (m, 2H), 2.72-2.50 (m, 2H), 2.50-2.25 (m, 2H), 1.90-1.80 (m, 1H)

Example 173. (2S,4S)-4-fluoro-1-[2-[(3R)-3-[(6-fluoro-5-quinolyl)amino]pyrrolidin-1-yl]acetyl]pyrrolidine-2-carbonitrile The title compound (138.8 mg, 63.7%) was prepared in the same fashion as Example 171, except that (R)-6-fluoro-N-(pyrrolidin-3-yl)quinolin-5-amine hydrochloride (171.9 mg, 0.57 mmol) prepared in Reference Example 78 was used instead of (R)—N-(pyrrolidin-3-yl)-1,8-naphthyridin-3-amine hydrochloride. ¹H-NMR (CDCl₃, 400 MHz) δ 8.86 (d, 1H), 8.43 (d, 1H), 7.68 (d, 1H), 7.47-7.39 (m, 2H), 5.52-5.35 (m, 1H), 5.35-4.94 (m, 1H), 4.30-4.06 (m, 2H), 4.04-3.70 (m, 1H), 3.70-3.38 (m, 2H), 3.18-3.00 (m, 1H), 2.98-2.85 (m, 1H), 2.82-2.60 (m, 2H), 2.60-2.40 (m, 2H), 2.40-2.20 (m, 2H), 2.00-1.85 (m, 1H)

Example 174. (2S,4S)-4-fluoro-1-[2-[(3R)-3-[(7-fluoro-5-quinolyl)amino]pyrrolidin-1-yl]acetyl]pyrrolidine-2-carbonitrile The title compound (54.9 mg, 36.4%) was prepared in the same fashion as Example 171, except that (R)-7-fluoro-N-

(pyrrolidin-3-yl)quinolin-5-amine hydrochloride (118.6 mg, 0.39 mmol) prepared in Reference Example 79 was used instead of (R)—N-(pyrrolidin-3-yl)-1,8-naphthyridin-3-amine hydrochloride. $^1$H-NMR (CDCl$_3$, 400 MHz) δ 8.84 (d, 1H), 8.29 (d, 1H), 7.31-7.25 (m, 1H), 7.08 (s, 1H), 6.33 (s, 1H), 5.70-5.34 (m, 1H), 5.10-4.93 (m, 1H), 4.30-3.70 (m, 3H), 3.70-3.40 (m, 2H), 3.20-3.00 (m, 2H), 2.98-2.42 (m, 4H), 2.42-2.22 (m, 2H), 2.00-1.85 (m, 1H)

Example 175. (2S,4S)-4-fluoro-1-[2-[(3R)-3-[(8-fluoro-5-quinolyl)amino]pyrrolidin-1-yl]acetyl]pyrrolidine-2-carbonitrile The title compound (45.6 mg, 11.8%) was prepared in the same fashion as Example 171, except that (R)-8-fluoro-N-(pyrrolidin-3-yl)quinolin-5-amine hydrochloride (303.3 mg, 1.00 mmol) prepared in Reference Example 80 was used instead of (R)—N-(pyrrolidin-3-yl)-1,8-naphthyridin-3-amine hydrochloride. $^1$H-NMR (CDCl$_3$, 400 MHz) δ 8.95 (d, 1H), 8.32 (d, 1H), 7.42 (t, 1H), 7.32-7.22 (m, 1H), 6.46 (d, 1H), 5.50-5.30 (m, 1H), 5.10-4.90 (m, 1H), 4.30-3.74 (m, 3H), 3.74-3.35 (m, 2H), 3.15-2.85 (m, 2H), 2.80-2.58 (m, 4H), 2.58-2.20 (m, 2H), 2.00-1.85 (m, 1H)

Example 176. (2S,4S)-4-fluoro-1-[2-[(3R)-3-[(6-methoxy-5-quinolyl)amino]pyrrolidin-1-yl]acetyl]pyrrolidine-2-carbonitrile The title compound (132.2 mg, 26.7%) was prepared in the same fashion as Example 171, except that (R)-6-methoxy-N-(pyrrolidin-3-yl)quinolin-5-amine hydrochloride (393.7 mg, 1.25 mmol) prepared in Reference Example 81 was used instead of (R)—N-(pyrrolidin-3-yl)-1,8-naphthyridin-3-amine hydrochloride. $^1$H-NMR (CDCl$_3$, 400 MHz) δ 8.76 (d, 1H), 8.39 (d, 1H), 7.79 (d, 1H), 7.46 (d, 1H), 7.33 (t, 1H), 5.50-5.24 (m, 1H), 5.24-4.90 (m, 1H), 4.25-4.00 (m, 2H), 3.96 (s, 3H), 3.96-3.70 (m, 1H), 3.70-3.30 (m, 2H), 3.10-3.00 (m, 1H), 3.00-2.82 (m, 1H), 2.80-2.32 (m, 4H), 2.32-1.95 (m, 2H), 1.90-1.78 (m, 1H)

Example 177. (2S,4S)-4-fluoro-1-[2-[(3R)-3-[(7-methoxy-5-quinolyl)amino]pyrrolidin-1-yl]acetyl]pyrrolidine-2-carbonitrile The title compound (107.8 mg, 20.2%) was prepared in the same fashion as Example 171, except that (R)-7-methoxy-N-(pyrrolidin-3-yl)quinolin-5-amine hydrochloride (424.4 mg, 1.34 mmol) prepared in Reference Example 82 was used instead of (R)—N-(pyrrolidin-3-yl)-1,8-naphthyridin-3-amine hydrochloride. $^1$H-NMR (CDCl$_3$, 400 MHz) δ 8.78 (d, 1H), 8.14 (d, 1H), 7.19 (t, 1H), 6.86 (s, 1H), 6.21 (s, 1H), 5.50-5.28 (m, 1H), 5.12-4.92 (m, 1H), 4.28-3.95 (m, 2H), 3.93 (s, 3H), 3.90-3.62 (m, 1H), 3.50-3.33 (m, 2H), 3.10-2.90 (m, 2H), 2.80-2.42 (m, 4H), 2.42-2.20 (m, 2H), 2.00-1.85 (m, 1H)

Example 178. (2S,4S)-4-fluoro-1-[2-[(3R)-3-[(8-methoxy-5-quinolyl)amino]pyrrolidin-1-yl]acetyl]pyrrolidine-2-carbonitrile The title compound (11.1 mg, 5.3%) was prepared in the same fashion as Example 171, except that (R)-8-methoxy-N-(pyrrolidin-3-yl)quinolin-5-amine hydrochloride (165.7 mg, 0.52 mmol) prepared in Reference Example 83 was used instead of (R)—N-(pyrrolidin-3-yl)-1,8-naphthyridin-3-amine hydrochloride. $^1$H-NMR (CDCl$_3$, 400 MHz) δ 8.94 (d, 1H), 8.27 (d, 1H), 7.43 (t, 1H), 6.96 (d, 1H), 6.54 (d, 1H), 5.49-5.28 (m, 1H), 5.19-4.92 (m, 1H), 4.28-4.10 (m, 2H), 4.06 (s, 3H), 4.00-3.80 (m, 1H), 3.78-3.33 (m, 2H), 3.10-3.00 (m, 2H), 3.00-2.96 (m, 1H), 2.96-2.60 (m, 3H), 2.60-2.30 (m, 2H), 1.95-1.85 (m, 1H)

Example 179. (2S,4S)-4-fluoro-1-[2-[(3R)-3-[(3-methyl-5-quinolyl)amino]pyrrolidin-1-yl]acetyl]pyrrolidine-2-carbonitrile The title compound (258.9 mg, 70.7%) was prepared in the same fashion as Example 171, except that (R)-3-methyl-N-(pyrrolidin-3-yl)quinolin-5-amine hydrochloride (288.2 mg, 0.96 mmol) prepared in Reference Example 84 was used instead of (R)—N-(pyrrolidin-3-yl)-1,8-naphthyridin-3-amine hydrochloride. $^1$H-NMR (CDCl$_3$, 400 MHz) δ 8.72 (d, 1H), 8.06 (s, 1H), 7.50-7.42 (m, 2H), 6.54 (d, 1H), 5.48-5.28 (m, 1H), 5.15-4.98 (m, 1H), 4.30-3.62 (m, 3H), 3.60-3.32 (m, 2H), 3.12-3.00 (m, 2H), 3.00-2.90 (m, 1H), 2.80-2.60 (m, 2H), 2.53 (s, 3H), 2.53-2.40 (m, 1H), 2.40-2.18 (m, 2H), 2.00-1.85 (m, 1H)

Example 180. (2S,4S)-4-fluoro-1-[2-[(3R)-3-[(6-methyl-5-quinolyl)amino]pyrrolidin-1-yl]acetyl]pyrrolidine-2-carbonitrile The title compound (206.3 mg, 42.3%) was prepared in the same fashion as Example 171, except that (R)-6-methyl-N-(pyrrolidin-3-yl)quinolin-5-amine hydrochloride (384.3 mg, 1.28 mmol) prepared in Reference Example 85 was used instead of (R)—N-(pyrrolidin-3-yl)-1,8-naphthyridin-3-amine hydrochloride. $^1$H-NMR (CDCl$_3$, 400 MHz) δ 8.82 (d, 1H), 8.43 (d, 1H), 7.70 (d, 1H), 7.50 (d, 1H), 7.37 (t, 1H), 5.50-5.28 (m, 1H), 5.20-4.90 (m, 1H), 4.20-4.00 (m, 2H), 4.00-3.70 (m, 2H), 3.54- 3.28 (m, 2H), 3.20-3.00 (m, 1H), 2.90-2.64 (m, 2H), 2.64-2.50 (m, 2H), 2.46 (s, 3H), 2.46-2.15 (m, 2H), 1.98-1.80 (m, 1H)

Example 181. (2S,4S)-4-fluoro-1-[2-[(3R)-3-[(8-methyl-5-quinolyl)amino]pyrrolidin-1-yl]acetyl]pyrrolidine-2-carbonitrile The title compound (106.3 mg, 31.5%) was prepared in the same fashion as Example 171, except that (R)-8-methyl-N-(pyrrolidin-3-yl)quinolin-5-amine hydrochloride (266.3 mg, 0.89 mmol) prepared in Reference Example 86 was used instead of (R)—N-(pyrrolidin-3-yl)-1,8-naphthyridin-3-amine hydrochloride. $^1$H-NMR (CDCl$_3$, 400 MHz) δ 8.93 (d, 1H), 8.25 (d, 1H), 7.42-7.33 (m, 2H), 6.51 (d, 1H), 5.49-5.28 (m, 1H), 5.18-4.90 (m, 1H), 4.30-4.00 (m, 2H), 4.00-3.64 (m, 2H), 3.60-3.34 (m, 2H), 3.10-3.00 (m, 2H), 3.00-2.90 (m, 1H), 2.80-2.69 (m, 1H), 2.69 (s, 3H), 2.69-2.18 (m, 3H), 1.98-1.85 (m, 1H)

Example 182. (2S,4S)-4-fluoro-1-[2-[(3R)-3-[[7-(trifluoromethyl)-5-quinolyl]amino]pyrrolidin-1-yl]acetyl]pyrrolidine-2-carbonitrile The title compound (184.3 mg, 38.0%) was prepared in the same fashion as Example 171, except that (R)—N-(pyrrolidin-3-yl)-7-(trifluoromethyl)quinolin-5-amine hydrochloride (393.9 mg, 1.11 mmol) prepared in Reference Example 87 was used instead of (R)—N-(pyrrolidin-3-yl)-1,8-naphthyridin-3-amine hydrochloride. $^1$H-NMR (CDCl$_3$, 400 MHz) δ 8.95 (d, 1H), 8.40 (d, 1H), 7.74 (s, 1H), 7.44 (t, 1H), 6.64 (s, 1H), 5.78-5.40 (m, 1H), 5.03-4.97 (m, 1H), 4.38-4.20 (m, 1H), 4.10-3.74 (m, 2H), 3.70-3.35 (m, 2H), 3.22-2.85 (m, 3H), 2.82-2.42 (m, 3H), 2.42-2.22 (m, 2H), 2.05-1.88 (m, 1H)

Example 183. (2S,4S)-4-fluoro-1-[2-[(3R)-3-[[8-(trifluoromethyl)-5-quinolyl]amino]pyrrolidin-1-yl]acetyl]pyrrolidine-2-carbonitrile The title compound (116.0 mg, 54.4%) was prepared in the same fashion as Example 171, except that (R)—N-(pyrrolidin-3-yl)-8-(trifluoromethyl)quinolin-5-amine hydrochloride (173.2 mg, 0.49 mmol) prepared in Reference Example 88 was used instead of (R)—N-(pyrrolidin-3-yl)-1,8-naphthyridin-3-amine hydrochloride. $^1$H-NMR (CDCl$_3$, 400 MHz) δ 9.01 (d, 1H), 8.41 (d, 1H), 7.90 (d, 1H), 7.41 (t, 1H), 6.49 (d, 1H), 5.52-5.28 (m, 1H), 5.05-4.93 (m, 1H), 4.38-4.20 (m, 1H), 4.10-3.94 (m, 1H), 3.94-3.70 (m, 1H), 3.70-3.35 (m, 2H), 3.25-2.95 (m, 3H), 2.95-2.55 (m, 3H), 2.55-2.22 (m, 2H), 2.05-1.85 (m, 1H)

Example 184. (2S,4S)-4-fluoro-1-[2-[(3R)-3-[(3-fluoro-5-quinolyl)amino]pyrrolidin-1-yl]acetyl]pyrrolidine-2-carbonitrile The title compound (255.8 mg, 87.5%) was prepared in the same fashion as Example 171, except that (R)-3-fluoro-N-(pyrrolidin-3-yl)quinolin-5-amine hydrochloride (230.9 mg, 0.76 mmol) prepared in Reference Example 89 was used instead of (R)—N-(pyrrolidin-3-yl)-1,8-naphthyridin-3-amine hydrochloride. $^1$H-NMR (CDCl$_3$, 400 MHz) δ 8.77 (s, 1H), 7.99 (d, 1H), 7.52-7.49 (m, 2H), 6.61 (d, 1H), 5.54-5.28 (m, 1H), 5.10-4.95 (m, 1H), 4.30-4.14 (m, 1H), 4.10-3.94 (m, 1H), 3.94-3.65 (m, 1H), 3.65-3.37 (m, 2H), 3.18-2.88 (m, 3H), 2.85-2.58 (m, 2H), 2.55-2.20 (m, 3H), 2.00-1.95 (m, 1H)

Example 185. (2S,4S)-4-fluoro-1-[2-[(3R)-3-[(3-chloro-5-quinolyl)amino]pyrrolidin-1-yl]acetyl]pyrrolidine-2-carbonitrile The title compound (27.4 mg, 7.4%) was prepared in the same fashion as Example 171, except that (R)-3-chloro-N-(pyrrolidin-3-yl)quinolin-5-amine hydrochloride (295.0 mg, 0.92 mmol) prepared in Reference Example 90 was used instead of (R)—N-(pyrrolidin-3-yl)-1,8-naphthyridin-3-amine hydrochloride. $^1$H-NMR (CDCl$_3$, 400 MHz) δ 8.78 (s, 1H), 8.36 (s, 1H), 7.54 (t, 1H), 7.45 (d, 1H), 6.61 (d, 1H), 5.54-5.25 (m, 1H), 5.10-4.95 (m, 1H), 4.30-4.15 (m, 1H), 4.10-3.84 (m, 1H), 3.84- 3.65 (m, 1H), 3.65-3.40 (m, 2H), 3.20-2.90 (m, 3H), 2.84-2.40 (m, 3H), 2.40-2.20 (m, 2H), 2.00-1.86 (m, 1H)

Example 186. (2S,4S)-4-fluoro-1-[2-[(3R)-3-[[8-(trifluoromethoxy)-5-quinolyl]amino]pyrrolidin-1-yl]acetyl]pyrrolidine-2-carbonitrile The title compound (200.3 mg, 37.5%) was prepared in the same fashion as Example 171, except that (R)—N-(pyrrolidin-3-yl)-8-(trifluoromethoxy)quinolin-5-amine hydrochloride (438.0 mg, 1.18 mmol) prepared in Reference Example 91 was used instead of (R)—N-(pyrrolidin-3-yl)-1,8-naphthyridin-3-amine hydrochloride. $^1$H-NMR (CDCl$_3$, 400 MHz) δ 9.00 (d, 1H), 8.35 (d, 1H), 7.50-7.41 (m, 2H), 6.48 (d, 1H), 5.52-5.24 (m, 1H), 5.10-4.92 (m, 1H), 4.30-4.15 (m, 1H), 4.15-3.98 (m, 1H), 3.98-3.70 (m, 1H), 3.70-3.38 (m, 2H), 3.20-2.88 (m, 3H), 2.84-2.40 (m, 3H), 2.40-2.20 (m, 2H), 2.00-1.85 (m, 1H)

Example 187. (2S,4S)-4-fluoro-1-[2-[(3R)-3-[(6-methyl-4-quinolyl)amino]pyrrolidin-1-yl]acetyl]pyrrolidine-2-carbonitrile The title compound (3.7 mg, 6.7%) was prepared in the same fashion as Example 171, except that (R)-6-methyl-N-(pyrrolidin-3-yl)quinolin-4-amine hydrochloride (43.2 mg, 0.14 mmol) prepared in Reference Example 92 was used instead of (R)—N-(pyrrolidin-3-yl)-1,8-naphthyridin-3-amine hydrochloride. $^1$H-NMR (CDCl$_3$, 400 MHz) δ 8.27-8.23 (m, 3H), 7.57 (d, 1H), 6.43 (d, 1H), 5.60-5.40 (m, 1H), 5.14-5.06 (m, 1H), 4.30-4.20 (m, 1H), 4.05-3.90 (m, 1H), 3.90-3.80 (m, 1H), 3.80- 3.60 (m, 2H), 3.54-3.45 (m, 1H), 3.32-3.05 (m, 3H), 3.05-2.70 (m, 2H), 2.59 (s, 3H), 2.59-2.38 (m, 1H), 2.28-2.16 (m, 1H), 2.08-1.98 (m, 1H)

Example 188. (2S,4S)-4-fluoro-1-[2-[(3R)-3-[(6-methoxy-4-quinolyl)amino]pyrrolidin-1-yl]acetyl]pyrrolidine-2-carbonitrile The title compound (37.8 mg, 10.0%) was prepared in the same fashion as Example 171, except that (R)-6-methoxy-N-(pyrrolidin-3-yl)quinolin-4-amine hydrochloride (301.1 mg, 0.95 mmol) prepared in Reference Example 93 was used instead of (R)—N-(pyrrolidin-3-yl)-1,8-naphthyridin-3-amine hydrochloride. $^1$H-NMR (CDCl$_3$, 400 MHz) δ 8.19 (d, 1H), 8.13 (d, 1H), 7.48 (s, 1H), 7.30-7.20 (m, 1H), 6.39 (d, 1H), 5.58-5.40 (m, 1H), 5.20-5.10 (m, 1H), 4.34-4.20 (m, 1H), 4.06 (s, 3H), 4.00-3.88 (m, 1H), 3.88-3.70 (m, 1H), 3.70-3.60 (m, 2H), 3.49-3.40 (m, 1H), 3.38-3.00 (m, 3H), 3.00- 2.84 (m, 1H), 2.84-2.72 (m, 1H), 2.72-2.30 (m, 1H), 2.30-2.10 (m, 1H), 2.10-1.95 (m, 1H)

Example 189. (2S,4S)-4-fluoro-1-[2-[(3R)-3-[(8-chloro-4-quinolyl)amino]pyrrolidin-1-yl]acetyl]pyrrolidine-2-carbonitrile The title compound (60.4 mg, 41.1%) was prepared in the same fashion as Example 171, except that (R)-8-chloro-N-(pyrrolidin-3-yl)quinolin-4-amine hydrochloride (117.0 mg, 0.37 mmol) prepared in Reference Example 94 was used instead of (R)—N-(pyrrolidin-3-yl)-1,8-naphthyridin-3-amine hydrochloride. $^1$H-NMR (CDCl$_3$, 400 MHz) δ 8.55 (d, 1H), 7.48-7.41 (m, 3H), 6.67 (d, 1H), 5.54-5.38 (m, 1H), 5.30-4.88 (m, 1H), 4.30-4.18 (m, 1H), 4.18-3.90 (m, 1H), 3.90-3.70 (m, 1H), 3.50- 3.30 (m, 2H), 3.20-3.00 (m, 1H), 3.00-2.85 (m, 1H), 2.85-2.58 (m, 3H), 2.58-2.30 (m, 2H), 2.30-2.10 (m, 1H), 2.00-1.86 (m, 1H)

Example 190. (2S,4S)-4-fluoro-1-[2-[(3R)-3-[(8-methyl-4-quinolyl)amino]pyrrolidin-1-yl]acetyl]pyrrolidine-2-carbonitrile The title compound (140.6 mg, 27.3%) was prepared in the same fashion as Example 171, except that (R)-8-methyl-N-(pyrrolidin-3-yl)quinolin-4-amine hydrochloride (406.2 mg, 1.35 mmol) prepared in Reference Example 95 was used instead of (R)—N-(pyrrolidin-3-yl)-1,8-naphthyridin-3-amine hydrochloride. $^1$H-NMR (CDCl$_3$, 400 MHz) δ 8.61 (d, 1H), 7.74 (d, 1H), 7.50 (d, 1H), 7.35 (t, 1H), 6.41 (d, 1H), 5.50-5.30 (m, 1H), 5.10-4.90 (m, 1H), 4.34-4.18 (m, 1H), 4.18-3.82 (m, 1H), 3.82- 3.60 (m, 1H), 3.60-3.40 (m, 2H), 3.18-2.94 (m, 3H), 2.77 (s, 3H), 2.77-2.42 (m, 3H), 2.42-2.18 (m, 2H), 2.00-1.88 (m, 1H)

Example 191. (2S,4S)-4-fluoro-1-[2-[(3R)-3-[(6-fluoro-4-quinolyl)amino]pyrrolidin-1-yl]acetyl]pyrrolidine-2-carbonitrile The title compound (65.2 mg, 15.2%) was prepared in the same fashion as Example 171, except that (R)-6-fluoro-N-(pyrrolidin-3-yl)quinolin-4-amine hydrochloride (337.7 mg, 1.11 mmol) prepared in Reference Example 96 was used instead of (R)—N-(pyrrolidin-3-yl)-1,8-naphthyridin-3-amine hydrochloride. $^1$H-NMR (CDCl$_3$, 400 MHz) δ 8.51 (s, 1H), 7.96 (d, 1H), 7.66 (d, 1H), 7.40 (d, 1H), 6.40 (d, 1H), 5.52-5.30 (m, 1H), 5.05-4.95 (m, 1H), 4.34-4.18 (m, 1H), 4.10-3.94 (m, 1H), 3.94- 3.74 (m, 1H), 3.70-3.40 (m, 2H), 3.25-3.10 (m, 1H), 3.10-2.95 (m, 2H), 2.85-2.60 (m, 2H), 2.52-2.24 (m, 3H), 2.00-1.90 (m, 1H)

Example 192. (2S,4S)-4-fluoro-1-[2-[(3R)-3-[(6-chloro-4-quinolyl)amino]pyrrolidin-1-yl]acetyl]pyrrolidine-2-carbonitrile The title compound (109.4 mg, 31.7%) was prepared in the same fashion as Example 171, except that (R)-6-chloro-N-(pyrrolidin-3-yl)quinolin-4-amine hydrochloride (274.8 mg, 0.86 mmol) prepared in Reference Example 97 was used instead of (R)—N-(pyrrolidin-3-yl)-1,8-naphthyridin-3-amine hydrochloride. $^1$H-NMR (CDCl$_3$, 400 MHz) δ 8.51 (d, 1H), 8.07 (s, 1H), 7.90 (d, 1H), 7.55 (d, 1H), 6.38 (d, 1H), 5.55-5.30 (m, 1H), 5.08-4.95 (m, 1H), 4.30-4.15 (m, 1H), 4.08-3.70 (m, 1H), 3.70- 3.40 (m, 2H), 3.30-3.20 (m, 1H), 3.15-3.00 (m, 2H), 2.85-2.65 (m, 2H), 2.52-2.20 (m, 3H), 2.00-1.90 (m, 1H)

Example 193. (2S,4S)-4-fluoro-1-[2-[(3R)-3-[(7-methoxy-4-quinolyl)amino]pyrrolidin-1-yl]acetyl]pyrrolidine-2-carbonitrile The title compound (159.2 mg, 35.4%) was prepared in the same fashion as Example 171, except that (R)-7-methoxy-N-(pyrrolidin-3-yl)quinolin-4-amine hydrochloride (358.2 mg, 1.13 mmol) prepared in Reference Example 98 was used instead of (R)—N-(pyrrolidin-3-yl)-1,8-naphthyridin-3-amine hydrochloride. $^1$H-NMR (CDCl$_3$, 400 MHz) δ 8.47 (d, 1H), 7.81 (d, 1H), 7.33 (s, 1H), 7.11 (d, 1H), 6.31 (d, 1H), 5.50-5.30 (m, 1H), 5.10-4.94 (m, 1H), 4.35-4.20 (m, 1H), 4.10-3.94 (m, 1H), 3.94 (s, 3H), 3.94-3.66 (m, 2H), 3.66-3.40 (m, 2H), 3.15-2.90 (m, 2H), 2.80-2.40 (m, 2H), 2.40-2.20 (m, 3H), 2.00-1.85 (m, 1H)

Example 194. (2S,4S)-4-fluoro-1-[2-[(3R)-3-[(8-fluoro-4-quinolyl)amino]pyrrolidin-1-yl]acetyl]pyrrolidine-2-carbonitrile The title compound (29.9 mg, 5.7%) was prepared in the same fashion as Example 171, except that (R)-8-fluoro-N-(pyrrolidin-3-yl)quinolin-4-amine hydrochloride (418.0 mg, 1.37 mmol) prepared in Reference Example 99 was used instead of (R)—N-(pyrrolidin-3-yl)-1,8-naphthyridin-3-amine hydrochloride. $^1$H-NMR (MeOD, 400 MHz) δ 8.41 (d, 1H), 8.03 (d, 1H), 7.44-7.39 (m, 2H), 6.62 (d, 1H), 5.55-5.30 (m, 1H), 5.05-4.96 (m, 1H), 4.40-4.30 (m, 1H), 4.10-4.00 (m, 1H), 3.90-3.70 (m, 1H), 3.65-3.40 (m, 2H), 3.16-3.00 (m, 3H), 2.75-2.60 (m, 2H), 2.60-2.35 (m, 3H), 2.05-1.90 (m, 1H)

Example 195. (2S,4S)-4-fluoro-1-[2-[(3R)-3-[(8-methoxy-4-quinolyl)amino]pyrrolidin-1-yl]acetyl]pyrrolidine-2-carbonitrile The title compound (13.2 mg, 3.3%) was prepared in the same fashion as Example 171, except that (R)-8-methoxy-N-(pyrrolidin-3-yl)quinolin-4-amine hydrochloride (316.4 mg, 1.00 mmol) prepared in Reference Example 100 was used instead of (R)—N-(pyrrolidin-3-yl)-1,8-naphthyridin-3-amine hydrochloride. $^1$H-NMR (CDCl$_3$, 400 MHz) δ 8.57 (d, 1H), 7.67 (d, 1H), 7.41 (t, 1H), 7.05 (d, 1H), 6.44 (d, 1H), 5.55-5.30 (m, 1H), 5.20-5.00 (m, 1H), 4.35-4.20 (m, 1H), 4.07 (s, 3H), 4.07-3.90 (m, 1H), 3.90-3.70 (m, 1H), 3.70-3.45 (m, 2H), 3.25-3.15 (m, 1H), 3.15-2.90 (m, 3H), 2.84-2.50 (m, 2H), 2.50-2.25 (m, 2H), 2.06-1.90 (m, 1H)

Example 196. (2S,4S)-4-fluoro-1-[2-[(3R)-3-[[8-(trifluoromethyl)-4-quinolyl]amino]pyrrolidin-1-yl]acetyl]pyrrolidine-2-carbonitrile The title compound (30.8 mg, 5.0%) was prepared in the same fashion as Example 171, except that (R)—N-(pyrrolidin-3-yl)-8-(trifluoromethyl)quinolin-4-amine hydrochloride (499.4 mg, 1.41 mmol) prepared in Reference Example 101 was used instead of (R)—N-(pyrrolidin-3-yl)-1,8-naphthyridin-3-amine hydrochloride. $^1$H-NMR (CDCl$_3$, 400 MHz) δ 8.64 (d, 1H), 8.22 (d, 1H), 7.97 (d, 1H), 7.44 (t, 1H), 6.43 (d, 1H), 5.52-5.28 (m, 1H), 5.00-4.90 (m, 1H), 4.30-4.15 (m, 1H), 4.04-3.84 (m, 1H), 3.80- 3.60 (m, 1H), 3.60-3.35 (m, 2H), 3.20-2.85 (m, 3H), 2.80-2.40 (m, 3H), 2.40-2.30 (m, 1H), 2.30-2.20 (m, 1H), 2.00-1.85 (m, 1H)

Example 197. (2S)-1-[2-[(3R)-3-[(7-fluoro-5-quinolyl)amino]pyrrolidin-1-yl]acetyl]pyrrolidine-2-carbonitrile The title compound (207.1 mg, 90.3%) was prepared in the same fashion as Example 17, except that (R)-7-fluoro-N-(pyrrolidin-3-yl)quinolin-5-amine hydrochloride (189.8 mg, 0.62 mmol) prepared in Reference Example 79 was used instead of (R)—N-(pyrrolidin-3-yl)quinoline-3-amine hydrochloride. $^1$H-NMR (CDCl$_3$, 400 MHz) δ 8.81 (d, 1H), 8.33 (d, 1H), 7.27 (t, 1H), 7.04 (s, 1H), 6.31 (s, 1H), 5.95-5.50 (m, 1H), 4.85-4.75 (m, 1H), 4.24-4.08 (m, 1H), 3.70-3.55 (m, 2H), 3.55-3.30 (m, 2H), 3.20-2.80 (m, 3H), 2.75-2.50 (m, 1H), 2.50-2.20 (m, 4H), 2.20-2.00 (m, 2H), 2.00-1.85 (m, 1H)

Example 198. (2S)-1-[2-[(3R)-3-[(7-methoxy-5-quinolyl)amino]pyrrolidin-1-yl]acetyl]pyrrolidine-2-carbonitrile The title compound (287.5 mg, 59.0%) was prepared in the same fashion as Example 17, except that (R)-7-methoxy-N-(pyrrolidin-3-yl)quinolin-5-amine hydrochloride (406.4 mg, 1.29 mmol) prepared in Reference Example 82 was used instead of (R)—N-(pyrrolidin-3-yl)quinoline-3-amine hydrochloride. $^1$H-NMR (CDCl$_3$, 400 MHz) δ 8.76 (d, 1H), 8.20 (d, 1H), 7.18 (t, 1H), 6.84 (s, 1H), 6.20 (s, 1H), 5.35-5.10 (m, 1H), 4.90-4.70 (m, 1H), 4.25-4.10 (m, 1H), 3.92 (s, 3H), 3.70-3.60 (m, 1H), 3.60-3.30 (m, 3H), 3.15-2.85 (m, 3H), 2.70-2.40 (m, 1H), 2.40-2.20 (m, 2H), 2.20-2.00 (m, 2H), 2.00-1.85 (m, 1H)

Example 199. (2S)-1-[2-[(3R)-3-[(8-fluoro-5-quinolyl)amino]pyrrolidin-1-yl]acetyl]pyrrolidine-2-carbonitrile The title compound (91.5 mg, 23.6%) was prepared in the same fashion as Example 17, except that (R)-8-fluoro-N-

(pyrrolidin-3-yl)quinolin-5-amine hydrochloride (320.6 mg, 1.05 mmol) prepared in Reference Example 80 was used instead of (R)—N-(pyrrolidin-3-yl)quinoline-3-amine hydrochloride. $^1$H-NMR (CDCl$_3$, 400 MHz) δ 8.93 (d, 1H), 8.36 (d, 1H), 7.42 (d, 1H), 7.29-7.24 (m, 1H), 6.44 (s, 1H), 5.18-4.90 (m, 1H), 4.90-4.70 (m, 1H), 4.30-4.10 (m, 1H), 3.70-3.60 (m, 1H), 3.60- 3.30 (m, 3H), 3.20-2.80 (m, 3H), 2.75-2.50 (m, 1H), 2.50-2.10 (m, 4H), 2.00-1.80 (m, 1H)

Example 200. (2S)-1-[2-[(3R)-3-[(8-methyl-5-quinolyl)amino]pyrrolidin-1-yl]acetyl]pyrrolidine-2-carbonitrile The title compound (172.5 mg, 51.9%) was prepared in the same fashion as Example 17, except that (R)-8-methyl-N-(pyrrolidin-3-yl)quinolin-5-amine hydrochloride (275.0 mg, 0.92 mmol) prepared in Reference Example 86 was used instead of (R)—N-(pyrrolidin-3-yl)quinoline-3-amine hydrochloride. $^1$H-NMR (CDCl$_3$, 400 MHz) δ 8.92 (d, 1H), 8.31 (d, 1H), 7.40 (d, 1H), 7.35 (t, 1H), 6.51 (d, 1H), 4.95-4.74 (m, 1H), 4.30-4.15 (m, 1H), 3.70-3.60 (m, 1H), 3.60-3.35 (m, 3H), 3.15-2.85 (m, 3H), 2.68 (s, 3H), 2.68-2.40 (m, 2H), 2.40-2.30 (m, 1H), 2.30-2.20 (m, 1H), 2.20-2.00 (m, 2H), 2.00-1.80 (m, 1H)

Example 201. (2S)-1-[2-[(3R)-3-[[8-(trifluoromethyl)-5-quinolyl]amino]pyrrolidin-1-yl]acetyl]pyrrolidine-2-carbonitrile The title compound (118.4 mg, 62.7%) was prepared in the same fashion as Example 17, except that (R)—N-(pyrrolidin-3-yl)-8-(trifluoromethyl)quinolin-5-amine hydrochloride (160.5 mg, 0.45 mmol) prepared in Reference Example 88 was used instead of (R)—N-(pyrrolidin-3-yl)quinoline-3-amine hydrochloride. $^1$H-NMR (CDCl$_3$, 400 MHz) δ 9.00 (d, 1H), 8.48 (d, 1H), 7.88 (d, 1H), 7.42 (t, 1H), 6.47 (d, 1H), 6.30-5.70 (m, 1H), 4.85-4.75 (m, 1H), 4.30-4.15 (m, 1H), 3.70-3.60 (m, 1H), 3.60- 3.30 (m, 3H), 3.28-3.15 (m, 1H), 3.15-2.80 (m, 2H), 2.80-2.50 (m, 1H), 2.50-2.10 (m, 4H), 2.10-1.85 (m, 1H)

Example 202. (2S)-1-[2-[(3R)-3-[[8-(trifluoromethoxy)-5-quinolyl]amino]pyrrolidin-1-yl]acetyl]pyrrolidine-2-carbonitrile The title compound (97.5 mg, 17.9%) was prepared in the same fashion as Example 17, except that (R)—N-(pyrrolidin-3-yl)-8-(trifluoromethoxy)quinolin-5-amine hydrochloride (464.2 mg, 1.25 mmol) prepared in Reference Example 91 was used instead of (R)—N-(pyrrolidin-3-yl)quinoline-3-amine hydrochloride. $^1$H-NMR (CDCl$_3$, 400 MHz) δ 8.98 (d, 1H), 8.42 (d, 1H), 7.49 (d, 1H), 7.43 (t, 1H), 6.45 (d, 1H), 5.70-5.30 (m, 1H), 4.85-4.75 (m, 1H), 4.30-4.15 (m, 1H), 3.70-3.56 (m, 1H), 3.56- 3.30 (m, 3H), 3.20-3.00 (m, 3H), 2.90-2.70 (m, 1H), 2.60-2.40 (m, 1H), 2.40-2.08 (m, 3H), 2.05-1.88 (m, 1H)

Example 203. (2S)-1-[2-[(3R)-3-[(3-chloro-5-quinolyl)amino]pyrrolidin-1-yl]acetyl]pyrrolidine-2-carbonitrile The title compound (265.9 mg, 76.4%) was prepared in the same fashion as Example 17, except that (R)-3-chloro-N-(pyrrolidin-3-yl)quinolin-5-amine hydrochloride (290.8 mg, 0.91 mmol) prepared in Reference Example 90 was used instead of (R)—N-(pyrrolidin-3-yl)quinoline-3-amine hydrochloride. $^1$H-NMR (CDCl$_3$, 400 MHz) δ 8.75 (d, 1H), 8.43 (s, 1H), 7.53 (d, 1H), 7.43 (t, 1H), 6.59 (s, 1H), 5.60-5.20 (m, 1H), 4.85-4.75 (m, 1H), 4.30-4.15 (m, 1H), 3.70-3.60 (m, 1H), 3.60-3.30 (m, 3H), 3.20-3.10 (m, 1H), 3.10-2.95 (m, 2H), 2.80-2.50 (m, 1H), 2.50-2.20 (m, 3H), 2.20-2.00 (m, 1H), 2.00-1.85 (m, 1H)

Example 204. (2S)-1-[2-[(3R)-3-[(3-methoxy-5-quinolyl)amino]pyrrolidin-1-yl]acetyl]pyrrolidine-2-carbonitrile The title compound (338.5 mg, 92.4%) was prepared in the same fashion as Example 17, except that (R)-3-methoxy-N-(pyrrolidin-3-yl)quinolin-5-amine hydrochloride (305.2 mg, 0.97 mmol) prepared in Reference Example 102 was used instead of (R)—N-(pyrrolidin-3-yl)quinoline-3-amine hydrochloride. $^1$H-NMR (CDCl$_3$, 400 MHz) δ 8.62 (d, 1H), 7.65 (s, 1H), 7.42-7.38 (m, 2H), 6.57 (d, 1H), 5.55-5.10 (m, 1H), 4.85-4.70 (m, 1H), 4.30-4.15 (m, 1H), 4.01 (s, 3H), 3.65-3.55 (m, 1H), 3.55- 3.40 (m, 3H), 3.35-3.15 (m, 1H), 3.10-2.95 (m, 2H), 2.85-2.60 (m, 1H), 2.40-2.20 (m, 2H), 2.20-2.05 (m, 2H), 2.05-1.85 (m, 1H)

Example 205. (2S,4S)-4-fluoro-1-[2-[(3R)-3-[(3-methoxy-5-quinolyl)amino]pyrrolidin-1-yl]acetyl]pyrrolidine-2-carbonitrile The title compound (349.0 mg, 91.0%) was prepared in the same fashion as Example 171, except that (R)-3-methoxy-N-(pyrrolidin-3-yl)quinolin-5-amine hydrochloride (305.2 mg, 0.97 mmol) prepared in Reference Example 102 was used instead of (R)—N-(pyrrolidin-3-yl)-1,8-naphthyridin-3-amine hydrochloride. $^1$H-NMR (CDCl$_3$, 400 MHz) δ 8.65 (d, 1H), 7.59 (s, 1H), 7.46-7.38 (m, 2H), 6.59 (d, 1H), 5.55-5.25 (m, 1H), 5.10-4.90 (m, 1H), 4.35-4.20 (m, 1H), 4.02 (s, 3H), 4.00-3.80 (m, 3H), 3.80-3.60 (m, 1H), 3.60-3.35 (m, 2H), 3.25-3.00 (m, 2H), 2.90-2.60 (m, 2H), 2.60-2.20 (m, 2H), 2.05-1.90 (m, 1H)

Example 206. (2S)-1-[2-[(3R)-3-[(2-chloro-6-quinolyl)amino]pyrrolidin-1-yl]acetyl]pyrrolidine-2-carbonitrile The title compound (61.1 mg, 20.3%) was prepared in the same fashion as Example 17, except that (R)-2-chloro-N-(pyrrolidin-3-yl)quinolin-6-amine hydrochloride (251.8 mg, 0.79 mmol) prepared in Reference Example 103 was used instead of (R)—N-(pyrrolidin-3-yl)quinoline-3-amine hydrochloride. $^1$H-NMR (CDCl$_3$, 400 MHz) δ 7.86 (d, 1H), 7.78 (d, 1H), 7.27-7.23 (m, 1H), 7.09 (d, 1H), 6.64 (s, 1H), 4.90-4.75 (m, 1H), 4.20-4.10 (m, 1H), 3.75-3.60 (m, 1H), 3.60-3.30 (m, 3H), 3.10- 3.00 (m, 2H), 2.90-2.65 (m, 2H), 2.60-2.20 (m, 3H), 2.20-2.10 (m, 2H), 1.88-1.78 (m, 1H)

Example 207. (2S,4S)-4-fluoro-1-[2-[(3R)-3-[(2-chloro-6-quinolyl)amino]pyrrolidin-1-yl]acetyl]pyrrolidine-2-carbonitrile The title compound (54.3 mg, 17.2%) was prepared in the same fashion as Example 171, except that (R)-2-chloro-N-(pyrrolidin-3-yl)quinolin-6-amine hydrochloride (251.8 mg, 0.79 mmol) prepared in Reference Example 103 was used instead of (R)—N-(pyrrolidin-3-yl)-1,8-naphthyridin-3-amine hydrochloride. $^1$H-NMR (CDCl$_3$, 400 MHz) δ 7.86 (d, 1H), 7.79 (d, 1H), 7.27-7.23 (m, 1H), 7.09 (d, 1H), 6.64 (s, 1H), 5.54-5.30 (m, 1H), 5.10-4.90 (m, 1H), 4.22-4.04 (m, 1H), 4.00-3.70 (m, 1H), 3.60-3.30 (m, 3H), 3.10-2.90 (m, 2H), 2.90-2.58 (m, 3H), 2.55-2.20 (m, 3H), 1.90-1.75 (m, 1H)

Example 208. (2S)-1-[2-[(3R)-3-[(3-methyl-5-quinolyl)amino]pyrrolidin-1-yl]acetyl]pyrrolidine-2-carbonitrile The title compound (4.3 mg, 4.0%) was prepared in the same fashion as Example 17, except that (R)-3-methyl-N-(pyrrolidin-3-yl)quinolin-5-amine hydrochloride (89.8 mg, 0.30 mmol) prepared in Reference Example 84 was used instead of (R)—N-(pyrrolidin-3-yl)quinoline-3-amine hydrochloride. $^1$H-NMR (CDCl$_3$, 400 MHz) δ 8.73 (s, 1H), 8.10 (s, 1H), 7.50-7.42 (m, 2H), 6.56 (d, 1H), 5.25-4.90 (m, 1H), 4.90-4.75 (m, 1H), 4.30-4.15 (m, 1H), 3.74-3.60 (m, 1H), 3.60-3.38 (m, 3H), 3.20-2.90 (m, 3H), 2.75-2.60 (m, 1H), 2.72 (s, 3H), 2.40-2.26 (m, 2H), 2.26-2.00 (m, 2H), 2.00-1.85 (m, 1H)

Example 209. (2S)-1-[2-[(3R)-3-[(3-fluoro-5-quinolyl)amino]pyrrolidin-1-yl]acetyl]pyrrolidine-2-carbonitrile The title compound (73.0 mg, 66.5%) was prepared in the same fashion as Example 17, except that (R)-3-fluoro-N-(pyrrolidin-3-yl)quinolin-5-amine hydrochloride (120.5 mg, 0.40 mmol) prepared in Reference Example 89 was used instead of (R)—N-(pyrrolidin-3-yl)quinoline-3-amine hydrochloride. $^1$H-NMR (CDCl$_3$, 400 MHz) δ 8.77 (s, 1H), 8.04 (d, 1H), 7.52-7.46 (m, 2H), 6.62 (d, 1H), 5.30-5.05 (m, 1H), 4.88-4.78 (m, 1H), 4.30-4.15 (m, 1H), 3.74-3.60 (m, 1H), 3.60-3.30 (m, 3H), 3.20-2.85 (m, 3H), 2.80-2.50 (m, 1H), 2.40-2.24 (m, 2H), 2.24-2.10 (m, 2H), 2.00-1.85 (m, 1H)

Example 210. (2S,4S)-4-fluoro-1-[2-[(3R)-3-[[2-(trifluoromethyl)-6-quinolyl]amino]pyrrolidin-1-yl]acetyl]pyrrolidine-2-carbonitrile The title compound (84.0 mg, 18.0%) was prepared in the same fashion as Example 171, except that (R)—N-(pyrrolidin-3-yl)-2-(trifluoromethyl)quinolin-6-amine hydrochloride (379.0 mg, 1.07 mmol) prepared in Reference Example 104 was used instead of (R)—N-(pyrrolidin-3-yl)-1,8-naphthyridin-3-amine hydrochloride. $^1$H-NMR (CDCl$_3$, 400 MHz) δ 8.03 (d, 1H), 7.96 (d, 1H), 7.58 (d, 1H), 7.16 (d, 1H), 6.66 (s, 1H), 5.52-5.30 (m, 1H), 5.10-4.90 (m, 1H), 4.30-4.10 (m, 1H), 4.10-3.65 (m, 3H), 3.65-3.34 (m, 2H), 3.12-3.00 (m, 2H), 3.00-2.80 (m, 1H), 2.80-2.58 (m, 2H), 2.54-2.20 (m, 2H), 1.98-1.80 (m, 1H)

Example 211. (2S,4S)-4-fluoro-1-[2-[(3R)-3-[(3-methyl-6-quinolyl)amino]pyrrolidin-1-yl]acetyl]pyrrolidine-2-carbonitrile The title compound (98.8 mg, 25.9%) was prepared in the same fashion as Example 171, except that (R)-3-methyl-N-(pyrrolidin-3-yl)quinolin-6-amine hydrochloride (300.8 mg, 1.00 mmol) prepared in Reference Example 105 was used instead of (R)—N-(pyrrolidin-3-yl)-1,8-naphthyridin-3-amine hydrochloride. $^1$H-NMR (CDCl$_3$, 400 MHz) δ 8.47 (s, 1H), 7.82 (d, 1H), 7.68 (s, 1H), 7.00 (d, 1H), 6.59 (s, 1H), 5.50-5.25 (m, 1H), 5.15-4.90 (m, 1H), 4.40-4.15 (m, 1H), 4.15-3.70 (m, 3H), 3.54- 3.30 (m, 2H), 3.05-2.94 (m, 2H), 2.94-2.60 (m, 3H), 2.45 (s, 3H), 2.45-2.20 (m, 2H), 1.90-1.75 (m, 1H)

Example 212. (2S,4S)-4-fluoro-1-[2-[(3R)-3-[(4-methoxy-6-quinolyl)amino]pyrrolidin-1-yl]acetyl]pyrrolidine-2-carbonitrile The title compound (44.8 mg, 16.2%) was prepared in the same fashion as Example 171, except that (R)-4-methoxy-N-(pyrrolidin-3-yl)quinolin-6-amine hydrochloride (220.7 mg, 0.70 mmol) prepared in Reference Example 106 was used instead of (R)—N-(pyrrolidin-3-yl)-1,8-naphthyridin-3-amine hydrochloride. $^1$H-NMR (CDCl$_3$, 400 MHz) δ 8.50 (d, 1H), 7.82 (d, 1H), 7.08-7.03 (m, 2H), 6.66 (d, 1H), 5.50-5.30 (m, 1H), 5.20-4.90 (m, 1H), 4.30-4.18 (m, 1H), 4.18-4.05 (m, 1H), 4.03 (s, 3H), 4.03-3.70 (m, 2H), 3.05-2.95 (m, 2H), 2.95-2.80 (m, 2H), 2.80-2.58 (m, 2H), 2.55-2.20 (m, 3H), 1.90-1.75 (m, 1H)

Example 213. (2S,4S)-4-fluoro-1-[2-[(3R)-3-[(8-methyl-6-quinolyl)amino]pyrrolidin-1-yl]acetyl]pyrrolidine-2-carbonitrile The title compound (95.3 mg, 31.6%) was prepared in the same fashion as Example 171, except that (R)-8-methyl-N-(pyrrolidin-3-yl)quinolin-6-amine hydrochloride (237.2 mg, 0.79 mmol) prepared in Reference Example 107 was used instead of (R)—N-(pyrrolidin-3-yl)-1,8-naphthyridin-3-amine hydrochloride. $^1$H-NMR (CDCl$_3$, 400 MHz) δ 8.65 (d, 1H), 7.88 (d, 1H), 7.29-7.24 (m, 1H), 6.96 (s, 1H), 6.52 (s, 1H), 5.50-5.28 (m, 1H), 5.20-4.90 (m, 1H), 4.25-4.15 (m, 1H), 4.15-3.70 (m, 3H), 3.55-3.30 (m, 2H), 3.05-2.95 (m, 2H), 2.95-2.75 (m, 2H), 2.72 (s, 3H), 2.72-2.55 (m, 1H), 2.50- 2.20 (m, 2H), 1.90-1.75 (m, 1H)

Example 214. (2S,4S)-4-fluoro-1-[2-[(3R)-3-[(8-fluoro-6-quinolyl)amino]pyrrolidin-1-yl]acetyl]pyrrolidine-2-carbonitrile The title compound (220.7 mg, 59.3%) was prepared in the same fashion as Example 171, except that (R)-8-fluoro-N-(pyrrolidin-3-yl)quinolin-6-amine hydrochloride (294.2 mg, 0.97 mmol) prepared in Reference Example 110 was used instead of (R)—N-(pyrrolidin-3-yl)-1,8-naphthyridin-3-amine hydrochloride. $^1$H-NMR (CDCl$_3$, 400 MHz) δ 8.63 (s, 1H), 7.90 (d, 1H), 7.32-7.27 (m, 1H), 6.82 (d, 1H), 6.45 (s, 1H), 5.50-5.30 (m, 1H), 5.14-4.90 (m, 1H), 4.20-4.00 (m, 2H), 4.00-3.65 (m, 2H), 3.60-3.30 (m, 2H), 3.10-2.90 (m, 2H), 2.90-2.70 (m, 2H), 2.70-2.50 (m, 1H), 2.50-2.20 (m, 2H), 1.90-1.70 (m, 1H)

Example 215. (2S,4S)-4-fluoro-1-[2-[(3R)-3-[(8-chloro-6-quinolyl)amino]pyrrolidin-1-yl]acetyl]pyrrolidine-2-carbonitrile The title compound (59.4 mg, 16.5%) was prepared in the same fashion as Example 171, except that (R)-8-chloro-N-(pyrrolidin-3-yl)quinolin-6-amine hydrochloride (287.6 mg, 0.90 mmol) prepared in Reference Example 108 was used instead of (R)—N-(pyrrolidin-3-yl)-1,8-naphthyridin-3-amine hydrochloride. $^1$H-NMR (CDCl$_3$, 400 MHz) δ 8.73 (s, 1H), 7.92 (d, 1H), 7.32 (t, 1H), 7.27-7.25 (m, 1H), 6.59 (s, 1H), 5.52-5.28 (m, 1H), 5.10-4.90 (m, 1H), 4.25-4.00 (m, 2H), 4.00-3.68 (m, 2H), 3.60-3.30 (m, 2H), 3.10-3.00 (m, 2H), 2.95-2.55 (m, 3H), 2.50-2.20 (m, 2H), 1.90-1.70 (m, 1H)

Example 216. (2S,4S)-4-fluoro-1-[2-[(3R)-3-[[8-(trifluoromethyl)-6-quinolyl]amino]pyrrolidin-1-yl]acetyl]pyrrolidine-2-carbonitrile The title compound (18.0 mg, 3.7%) was prepared in the same fashion as Example 171, except that (R)—N-(pyrrolidin-3-yl)-8-(trifluoromethyl)quinolin-6-amine hydrochloride (394.2 mg, 1.11 mmol) prepared in Reference Example 109 was used instead of (R)—N-(pyrrolidin-3-yl)-1,8-naphthyridin-3-amine hydrochloride. $^1$H-NMR (CDCl$_3$, 400 MHz) δ 8.77 (d, 1H), 7.95 (d, 1H), 7.46 (s, 1H), 7.35 (t, 1H), 6.79 (s, 1H), 5.55-5.30 (m, 1H), 5.10-4.90 (m, 1H), 4.30-4.02 (m, 2H), 4.02-3.65 (m, 2H), 3.60-3.30 (m, 2H), 3.12-2.98 (m, 2H), 2.95-2.60 (m, 3H), 2.55-2.20 (m, 2H), 1.90-1.80 (m, 1H)

Example 217. (2S)-1-[2-[(3R)-3-[[2-(trifluoromethyl)-6-quinolyl]amino]pyrrolidin-1-yl]acetyl]pyrrolidine-2-carbonitrile The title compound (17.6 mg, 4.6%) was prepared in the same fashion as Example 17, except that (R)—N-(pyrrolidin-3-yl)-2-(trifluoromethyl)quinolin-6-amine hydrochloride (324.5 mg, 0.92 mmol) prepared in Reference Example 104 was used instead of (R)—N-(pyrrolidin-3-yl)quinolin-3-amine hydrochloride. $^1$H-NMR (CDCl$_3$, 400 MHz) δ 8.04 (d, 1H), 7.96 (d, 1H), 7.58 (d, 1H), 7.17 (d, 1H), 6.67 (s, 1H), 4.90-4.75 (m, 1H), 4.25-4.15 (m, 1H), 3.75-3.60 (m, 1H), 3.60-3.45 (m, 2H), 3.45-3.30 (m, 2H), 3.10-3.00 (m, 2H), 2.95-2.55 (m, 2H), 2.50-2.10 (m, 4H), 1.95-1.80 (m, 1H)

Example 218. (2S)-1-[2-[(3R)-3-[(3-methyl-6-quinolyl)amino]pyrrolidin-1-yl]acetyl]pyrrolidine-2-carbonitrile The title compound (224.2 mg, 55.4%) was prepared in the same fashion as Example 17, except that (R)-3-methyl-N-(pyrrolidin-3-yl)quinolin-6-amine hydrochloride (334.2 mg, 1.11 mmol) prepared in Reference Example 105 was used instead of (R)—N-(pyrrolidin-3-yl)quinolin-3-amine hydrochloride. $^1$H-NMR (CDCl$_3$, 400 MHz) δ 8.45 (s, 1H), 7.82 (d, 1H), 7.67 (s, 1H), 7.01 (d, 1H), 6.58 (s, 1H), 4.95-4.70 (m, 1H), 4.25-4.10 (m, 1H), 3.75-3.40 (m, 3H), 3.40-3.30 (m, 2H), 3.10-2.95 (m, 2H), 2.90-2.55 (m, 2H), 2.44 (s, 3H), 2.44-2.20 (m, 2H), 2.20-1.90 (m, 2H), 1.90-1.75 (m, 1H)

Example 219. (2S)-1-[2-[(3R)-3-[(4-methoxy-6-quinolyl)amino]pyrrolidin-1-yl]acetyl]pyrrolidine-2-carbonitrile The title compound (143.4 mg, 44.5%) was prepared in the same fashion as Example 17, except that (R)-4-methoxy-N-(pyrrolidin-3-yl)quinolin-6-amine hydrochloride (268.8 mg, 0.85 mmol) prepared in Reference Example 106 was used instead of (R)—N-(pyrrolidin-3-yl)quinolin-3-amine hydrochloride. $^1$H-NMR (CDCl$_3$, 400 MHz) δ 8.48 (d, 1H), 7.81 (d, 1H), 7.07-7.02 (m, 2H), 6.65 (d, 1H), 4.95-4.75 (m, 1H), 4.30-4.15 (m, 1H), 4.02 (s, 3H), 3.75-3.45 (m, 3H), 3.45-3.30 (m, 2H), 3.10- 2.95 (m, 2H), 2.90-2.50 (m, 2H), 2.50-2.30 (m, 2H), 2.30-2.00 (m, 2H), 1.90-1.75 (m, 1H)

Example 220. (2S)-1-[2-[(3R)-3-[(8-methyl-6-quinolyl)amino]pyrrolidin-1-yl]acetyl]pyrrolidine-2-carbonitrile The title compound (200.6 mg, 97.0%) was prepared in the same fashion as Example 17, except that (R)-8-methyl-N-(pyrrolidin-3-yl)quinolin-6-amine hydrochloride (170.8 mg, 0.57 mmol) prepared in Reference Example 107 was used instead of (R)—N-(pyrrolidin-3-yl)quinolin-3-amine hydrochloride. $^1$H-NMR (CDCl$_3$, 400 MHz) δ 8.64 (d, 1H), 7.88 (d, 1H), 7.26-7.24 (m, 1H), 6.95 (s, 1H), 6.52 (s, 1H), 4.95-4.75 (m, 1H), 4.25-4.10 (m, 1H), 3.75-3.45 (m, 3H), 3.45-3.30 (m, 2H), 3.10- 2.95 (m, 2H), 2.90-2.80 (m, 1H), 2.72 (s, 3H), 2.70-2.50 (m, 1H), 2.50-2.30 (m, 1H), 2.30-2.10 (m, 3H), 1.90-1.75 (m, 1H)

Example 221. (2S)-1-[2-[(3R)-3-[(8-fluoro-6-quinolyl)amino]pyrrolidin-1-yl]acetyl]pyrrolidine-2-carbonitrile The title compound (121.2 mg, 65.5%) was prepared in the same fashion as Example 17, except that (R)-8-fluoro-N-(pyrrolidin-3-yl)quinolin-6-amine hydrochloride (153.3 mg, 0.50 mmol) prepared in Reference Example 110 was used instead of (R)—N-(pyrrolidin-3-yl)quinolin-3-amine hydrochloride. $^1$H-NMR (CDCl$_3$, 400 MHz) δ 8.62 (s, 1H), 7.89 (d, 1H), 7.29 (t, 1H), 6.82 (d, 1H), 6.45 (s, 1H), 4.90-4.75 (m, 1H), 4.25-4.05 (m, 1H), 3.75-3.60 (m, 1H), 3.60-3.44 (m, 2H), 3.44-3.30 (m, 2H), 3.10-2.95 (m, 2H), 2.95-2.50 (m, 2H), 2.50-2.10 (m, 4H), 1.90-1.75 (m, 1H)

Example 222. (2S)-1-[2-[(3R)-3-[(8-chloro-6-quinolyl)amino]pyrrolidin-1-yl]acetyl]pyrrolidine-2-carbonitrile The title compound (77.7 mg, 57.4%) was prepared in the same fashion as Example 17, except that (R)-8-chloro-N-(pyrrolidin-3-yl)quinolin-6-amine hydrochloride (112.9 mg, 0.35 mmol) prepared in Reference Example 108 was used instead of (R)—N-(pyrrolidin-3-yl)quinolin-3-amine hydrochloride. $^1$H-NMR (CDCl$_3$, 400 MHz) δ 8.72 (d, 1H), 7.91 (d, 1H), 7.33-7.25 (m, 2H), 6.58 (s, 1H), 4.90-4.75 (m, 1H), 4.20-4.10 (m, 1H), 3.74-3.60 (m, 1H), 3.60-3.42 (m, 2H), 3.42-3.30 (m, 2H), 3.10-2.95 (m, 2H), 2.90-2.50 (m, 2H), 2.50-2.20 (m, 2H), 2.20-2.05 (m, 2H), 1.90-1.75 (m, 1H)

Example 223. (2S)-1-[2-[(3R)-3-[(6-methyl-4-quinolyl)amino]pyrrolidin-1-yl]acetyl]pyrrolidine-2-carbonitrile The title compound (233.0 mg, 64.8%) was prepared in the same fashion as Example 17, except that (R)-6-methyl-N-(pyrrolidin-3-yl)quinolin-4-amine hydrochloride (297.2 mg, 0.99 mmol) prepared in Reference Example 92 was used instead of (R)—N-(pyrrolidin-3-yl)quinolin-3-amine hydrochloride. $^1$H-NMR (CDCl$_3$, 400 MHz) δ 8.43 (d, 1H), 7.99 (d, 1H), 7.91 (s, 1H), 7.50 (d, 1H), 6.38 (d, 1H), 4.90-4.75 (m, 1H), 4.35-4.20 (m, 1H), 3.72-3.60 (m, 2H), 3.60-3.40 (m, 3H), 3.35-3.25 (m, 1H), 3.20-2.98 (m, 2H), 2.85-2.75 (m, 1H), 2.57 (s, 3H), 2.50-2.10 (m, 4H), 2.10-1.90 (m, 1H)

Example 224. (2S)-1-[2-[(3R)-3-[(6-methoxy-4-quinolyl)amino]pyrrolidin-1-yl]acetyl]pyrrolidine-2-carbonitrile The title compound (340.7 mg, 73.1%) was prepared in the same fashion as Example 17, except that (R)-6-methoxy-N-(pyrrolidin-3-yl)quinolin-4-amine hydrochloride (388.7 mg, 1.23 mmol) prepared in Reference Example 93 was used instead of (R)—N-(pyrrolidin-3-yl)quinolin-3-amine hydrochloride. $^1$H-NMR (CDCl$_3$, 400 MHz) δ 8.39 (d, 1H), 7.99 (d, 1H), 7.42 (s, 1H), 7.32 (d, 1H), 6.39 (d, 1H), 4.85-4.75 (m, 1H), 4.35-4.20 (m, 1H), 4.04 (s, 3H), 3.75-3.50 (m, 3H), 3.50-3.30 (m, 2H), 3.25-2.85 (m, 3H), 2.85-2.60 (m, 1H), 2.50-2.10 (m, 4H), 2.10-1.90 (m, 1H)

Example 225. (2S)-1-[2-[(3R)-3-[(6-fluoro-4-quinolyl)amino]pyrrolidin-1-yl]acetyl]pyrrolidine-2-carbonitrile The title compound (267.8 mg, 64.0%) was prepared in the same fashion as Example 17, except that (R)-6-fluoro-N-(pyrrolidin-3-yl)quinolin-4-amine hydrochloride (346.5 mg, 1.14 mmol) prepared in Reference Example 96 was used instead of (R)—N-(pyrrolidin-3-yl)quinolin-3-amine hydrochloride. $^1$H-NMR (CDCl$_3$, 400 MHz) δ 8.50 (d, 1H), 7.95 (d, 1H), 7.72 (d, 1H), 7.38 (s, 1H), 6.39 (d, 1H), 4.90-4.75 (m, 1H), 4.35-4.15 (m, 1H), 3.75-3.60 (m, 1H), 3.60-3.35 (m, 3H), 3.25-3.15 (m, 1H), 3.15-2.90 (m, 2H), 2.80-2.60 (m, 1H), 2.50-2.35 (m, 1H), 2.35-2.10 (m, 4H), 2.00-1.85 (m, 1H)

Example 226. (2S)-1-[2-[(3R)-3-[(6-chloro-4-quinolyl)amino]pyrrolidin-1-yl]acetyl]pyrrolidine-2-carbonitrile The title compound (335.8 mg, 70.7%) was prepared in the same fashion as Example 17, except that (R)-6-chloro-N-(pyrrolidin-3-yl)quinolin-4-amine hydrochloride (397.0 mg, 1.24 mmol) prepared in Reference Example 97 was used instead of (R)—N-(pyrrolidin-3-yl)quinolin-3-amine hydrochloride. $^1$H-NMR (CDCl$_3$, 400 MHz) δ 8.50 (d, 1H), 8.14 (s, 1H), 7.88 (d, 1H), 7.54 (d, 1H), 6.38 (d, 1H), 4.90-4.75 (m, 1H), 4.30-4.15 (m, 1H), 3.75-3.55 (m, 2H), 3.55-3.35 (m, 3H), 3.30-3.20 (m, 1H), 3.18-2.90 (m, 2H), 2.85-2.60 (m, 1H), 2.50-2.10 (m, 4H), 2.00-1.85 (m, 1H)

Example 227. (2S)-1-[2-[(3R)-3-[(8-fluoro-4-quinolyl)amino]pyrrolidin-1-yl]acetyl]pyrrolidine-2-carbonitrile The title compound (59.4 mg, 12.1%) was prepared in the same fashion as Example 17, except that (R)-8-fluoro-N-(pyrrolidin-3-yl)quinolin-4-amine hydrochloride (407.6 mg, 1.34 mmol) prepared in Reference Example 99 was used instead of (R)—N-(pyrrolidin-3-yl)quinolin-3-amine hydrochloride. $^1$H-NMR (CDCl$_3$, 400 MHz) δ 8.59 (d, 1H), 7.81 (d, 1H), 7.38-7.31 (m, 2H), 6.44 (d, 1H), 4.85-4.75 (m, 1H), 4.40-4.20 (m, 1H), 3.75-3.60 (m, 2H), 3.60-3.35 (m, 3H), 3.30-3.20 (m, 1H), 3.18-2.90 (m, 2H), 2.85-2.60 (m, 1H), 2.55-2.15 (m, 4H), 2.00-1.85 (m, 1H)

Example 228. (2S,4S)-4-fluoro-1-[2-[(3S)-3-(5-quinolylamino)pyrrolidin-1-yl]acetyl]pyrrolidine-2-carbonitrile (2S,4S)-1-(2-chloroacetyl)-4-fluoro-pyrrolidine-2-carbonitrile (20.0 mg, 0.10 mmol) prepared in Reference Example 2 was dissolved in anhydrous dichloromethane (4 ml). To the resulting solution, (S)—N-(pyrrolidin-3-yl)quinoline-5-amine hydrochloride (36.0 mg 0.12 mmol) prepared in Reference Example 16 and potassium carbonate (29.0 mg, 0.21 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=10/1, v/v) to give a title compound (5.3 mg, 13.7%). $^1$H-NMR (CDCl$_3$, 400 MHz) δ 8.86 (m, 1H), 8.30 (m, 1H), 7.48-7.54 (m, 2H), 7.33 (m, 1H), 6.55 (m, 1H), 5.25-5.49 (m, 1H), 4.97 (m, 1H), 4.31 (m, 1H), 3.82-3.92 (m, 1H), 3.62-3.80 (m, 1H), 3.32-3.60 (m, 2H), 3.01-3.25 (m, 2H), 2.62-2.82 (m, 2H), 2.21-2.42 (m, 2H), 1.96-2.19 (m, 3H)

Example 229. (2S)-1-[2-[(3S)-3-(3-quinolylamino)pyrrolidin-1-yl]acetyl]pyrrolidine-2-carbonitrile The title compound (7.7 mg, 38.3%) was prepared in the same fashion as Example 5, except that (S)—N-(pyrrolidin-3-yl)quinolin-3-amine hydrochloride (25.6 mg, 0.12 mmol) prepared in Reference Example 6 was used instead of (S)—N-(pyrrolidin-3-yl)quinoline-4-amine hydrochloride. $^1$H-NMR (CDCl$_3$, 400 MHz) δ 8.44 (d, 1H), 7.93 (d, 1H), 7.60 (d, 1H), 7.41-7.39 (m, 2H), 6.96 (d, 1H), 4.87-4.67 (m, 2H), 4.12-4.11 (m, 1H), 3.65-3.62 (m, 1H), 3.55-3.41 (m, 2H), 3.09-3.00 (m, 2H), 2.86-2.79 (m, 1H), 2.67-2.05 (m, 7H), 1.88-1.79 (m, 1H).

Example 230. (2S)-1-[2-[(3S)-3-(6-quinolylamino)pyrrolidin-1-yl]acetyl]pyrrolidine-2-carbonitrile The title compound (11.4 mg, 56.5%) was prepared in the same fashion as Example 5, except that (S)—N-(pyrrolidin-3-yl)quinolin-6-amine hydrochloride (25.6 mg, 0.12 mmol) prepared in Reference Example 111 was used instead of (S)—N-(pyrrolidin-3-yl)quinoline-4-amine hydrochloride. $^1$H-NMR (CDCl$_3$, 400 MHz) δ 8.58 (d, 1H), 7.90 (d, 1H), 7.84 (d, 1H), 7.26-7.23 (m, 1H), 7.10-7.08 (m, 1H), 6.63 (s, 1H), 4.90-4.65 (m, 2H), 4.12-4.11 (m, 1H), 3.62-3.32 (m, 3H), 3.02-3.01 (m, 2H), 2.82-2.79 (m, 2H), 2.66-2.04 (m, 6H), 1.85-1.80 (m, 1H).

Example 231. 5-[[(3S)-1-[2-oxo-2-[(2S)-2-cyanopyrrolidin-1-yl]ethyl]pyrrolidin-3-yl]amino]quinoline-2-carbonitrile The title compound (3.0 mg, 13.8%) was prepared in the same fashion as Example 5, except that (S)-5-(pyrrolidin-3-ylamino)quinoline-2-carbonitrile hydrochloride (37.3 mg, 0.12 mmol) prepared in Reference Example 112 was used instead of (S)—N-(pyrrolidin-3-yl)quinoline-4-amine hydrochloride. $^1$H-NMR (CDCl$_3$, 400 MHz) δ 8.62-8.42 (m, 1H), 7.66-7.58 (m, 2H), 7.49-7.43 (m, 1H), 6.67-6.63 (m, 1H), 6.06 (d, 0.6H), 5.34 (d, 0.4H), 4.79-4.71 (m, 1H), 4.25-4.20 (m, 1H), 3.70-3.43 (m, 3H), 3.28-2.99 (m, 3H), 2.79-2.73 (m, 1H), 2.48-2.13 (m, 5H), 2.05-1.95 (m, 2H).

Example 232. 5-[[(3S)-1-[2-oxo-2-[(2S)-2-cyanopyrrolidin-1-yl]ethyl]pyrrolidin-3-yl]amino]quinoline-3-carbonitrile The title compound (1.9 mg, 13.8%) was prepared in the same fashion as Example 5, except that (S)-5-(pyrrolidin-3-ylamino)quinoline-3-carbonitrile hydrochloride (37.3 mg, 0.12 mmol) prepared in Reference Example 113 was used instead of (S)—N-(pyrrolidin-3-yl)quinoline-4-amine hydrochloride. $^1$H-NMR (CDCl$_3$, 400 MHz) δ 8.95-8.93 (m, 1.6H), 8.79 (s, 0.4H), 7.71-7.65 (m, 1H), 7.45-7.39 (m, 1H), 6.64-6.61 (m, 1H), 6.45 (d, 0.7H), 5.79 (d, 0.3H), 4.87-4.70 (m, 1H), 4.25-4.16 (m, 1H), 3.72-3.64 (m, 1H), 3.58-3.54 (m, 1.3H), 3.49-3.43 (m, 0.7H), 3.35-3.28 (m, 1H), 3.15-3.09 (m, 1H), 3.05-3.00 (m, 1H), 2.93-2.77 (m, 1H), 2.42-2.11 (m, 5H), 2.03-1.96 (m, 1H), 1.85-1.82 (m, 1H).

Example 233. (2S)-1-[2-[(3S)-3-[(3-methoxy-5-quinolyl)amino]pyrrolidin-1-yl]acetyl]pyrrolidine-2-carbonitrile The title compound (10.6 mg, 24.2%) was prepared in the same fashion as Example 5, except that (S)-3-methoxy-N-

(pyrrolidin-3-yl)quinolin-5-amine hydrochloride (37.9 mg, 0.12 mmol) prepared in Reference Example 114 was used instead of (S)—N-(pyrrolidin-3-yl)quinoline-4-amine hydrochloride. $^1$H-NMR (CDCl$_3$, 400 MHz) δ 8.63 (d, 1H), 7.64-7.53 (m, 1H), 7.45-7.37 (m, 2H), 6.57 (q, 1H), 5.39-5.38 (m, 0.5H), 5.02-5.00 (m, 0.5H), 4.72 (t, 1H), 4.21 (s, 1H), 4.01 (s, 1.7H), 3.94 (s, 1.3H), 3.64-3.39 (m, 3H), 3.23-3.14 (m, 2H), 3.03-2.98 (m, 1H), 2.73-2.68 (m, 1H), 2.48-2.00 (m, 7H).

Example 234. (2S)-1-[2-[(3S)-3-[(3-fluoro-5-quinolyl)amino]pyrrolidin-1-yl]acetyl]pyrrolidine-2-carbonitrile The title compound (5.7 mg, 13.3%) was prepared in the same fashion as Example 5, except that (S)-3-fluoro-N-(pyrrolidin-3-yl)quinolin-5-amine hydrochloride (36.5 mg, 0.12 mmol) prepared in Reference Example 115 was used instead of (S)—N-(pyrrolidin-3-yl)quinoline-4-amine hydrochloride. $^1$H-NMR (CDCl$_3$, 400 MHz) δ 8.76 (s, 1H), 7.99 (dd, 1H), 7.52-7.46 (m, 2H), 6.60 (t, 1H), 4.97-4.79 (m, 1H), 4.21-4.19 (m, 1H), 3.67-3.43 (m, 4H), 3.31-3.07 (m, 2H), 2.96 (d, 1H), 2.81- 2.71 (m, 1H), 2.48-1.94 (m, 7H).

Example 235. (2S)-1-[2-[(3S)-3-[(3-chloro-5-quinolyl)amino]pyrrolidin-1-yl]acetyl]pyrrolidine-2-carbonitrile The title compound (13.7 mg, 34.4%) was prepared in the same fashion as Example 5, except that (S)-3-chloro-N-(pyrrolidin-3-yl)quinolin-5-amine hydrochloride (38.4 mg, 0.12 mmol) prepared in Reference Example 116 was used instead of (S)—N-(pyrrolidin-3-yl)quinoline-4-amine hydrochloride. $^1$H-NMR (CDCl$_3$, 400 MHz) δ 8.75 (s, 1H), 8.41-8.30 (m, 1H), 7.55-7.50 (m, 1H), 7.44-7.40 (m, 1H), 6.57 (d, 1H), 5.53 (d, 0.7H), 5.12 (d, 0.3H), 4.79 (d, 1H), 4.21-4.16 (m, 1H), 3.67-3.41 (m, 3H), 3.34-3.08 (m, 2H), 2.94 (d, 1H), 2.84-2.68 (m, 1H), 2.45-1.92 (m, 7H).

Example 236. (2S)-1-[2-[(3S)-3-[(7-fluoro-5-quinolyl)amino]pyrrolidin-1-yl]acetyl]pyrrolidine-2-carbonitrile The title compound (6.8 mg, 16.1%) was prepared in the same fashion as Example 5, except that (S)-7-fluoro-N-(pyrrolidin-3-yl)quinolin-5-amine hydrochloride (36.5 mg, 0.12 mmol) prepared in Reference Example 117 was used instead of (S)—N-(pyrrolidin-3-yl)quinoline-4-amine hydrochloride. $^1$H-NMR (CDCl$_3$, 400 MHz) δ 8.82 (s, 1H), 8.37-8.21 (m, 1H), 7.30-7.24 (m, 1H), 7.06-7.02 (m, 1H), 6.32-6.27 (m, 1H), 5.94 (d, 0.7H), 5.40 (d, 0.3H), 4.75 (dd, 1H), 4.18-4.13 (m, 1H), 3.67-3.43 (m, 3H), 3.28-2.98 (m, 3H), 2.77-2.67 (m, 1H), 2.52-1.92 (m, 7H).

Example 237. (2S)-1-[2-[(3S)-3-[(7-methoxy-5-quinolyl)amino]pyrrolidin-1-yl]acetyl]pyrrolidine-2-carbonitrile The title compound (10.1 mg, 16.1%) was prepared in the same fashion as Example 5, except that (S)-7-methoxy-N-(pyrrolidin-3-yl)quinolin-5-amine hydrochloride (37.9 mg, 0.12 mmol) prepared in Reference Example 118 was used instead of (S)—N-(pyrrolidin-3-yl)quinoline-4-amine hydrochloride. $^1$H-NMR (CDCl$_3$, 400 MHz) δ 8.75 (s, 1H), 8.25-8.14 (m, 1H), 7.20-7.16 (m, 1H), 6.83 (s, 1H), 6.18 (d, 1H), 5.45 (d, 0.6H), 5.11 (d, 0.3H), 4.78-4.75 (m, 1H), 4.14-4.13 (m, 1H), 3.92 (s, 3H), 3.65-3.27 (m, 4H), 3.13-2.95 (m, 2H), 2.74-2.60 (m, 1H), 2.37-1.94 (m, 7H).

Example 238. (2S)-1-[2-[(3S)-3-[[7-(trifluoromethyl)-5-quinolyl]amino]pyrrolidin-1-yl]acetyl]pyrrolidine-2-carbonitrile The title compound (15.0 mg, 31.0%) was prepared in the same fashion as Example 5, except that (S)—N-(pyrrolidin-3-yl)-7-(trifluoromethyl)quinolin-5-amine hydrochloride (42.5 mg, 0.12 mmol) prepared in Reference Example 119 was used instead of (S)—N-(pyrrolidin-3-yl)quinoline-4-amine hydrochloride. $^1$H-NMR (CDCl$_3$, 400 MHz) δ 8.93-8.90 (m, 1H), 8.51-8.33 (m, 1H), 7.70 (d, 1H), 7.45-7.40 (m, 1H), 6.61 (d, 1H), 6.15 (d, 0.7H), 5.51 (d, 0.3H), 4.77-4.72 (m, 1H), 4.25-4.20 (m, 1H), 3.69-3.24 (m, 4H), 3.18-3.01 (m, 2H), 2.79-2.65 (m, 1H), 2.57-1.95 (m, 7H).

Example 239. (2S)-1-[2-[(3S)-3-[(6-methyl-5-quinolyl)amino]pyrrolidin-1-yl]acetyl]pyrrolidine-2-carbonitrile The title compound (3.3 mg, 7.9%) was prepared in the same fashion as Example 5, except that (S)-6-methyl-N-(pyrrolidin-3-yl)quinolin-5-amine hydrochloride (36.0 mg, 0.12 mmol) prepared in Reference Example 120 was used instead of (S)—N-(pyrrolidin-3-yl)quinoline-4-amine hydrochloride. $^1$H-NMR (CDCl$_3$, 400 MHz) δ 8.82 (s, 1H), 8.47-8.41 (m, 1H), 7.69 (d, 1H), 7.50 (d, 1H), 7.36 (q, 1H), 4.98-4.77 (m, 1H), 4.02 (s, 1H), 3.73-3.66 (m, 1H), 3.57-3.29 (m, 3H), 3.19-3.11 (m, 1H), 2.87-2.79 (m, 1H), 2.60-2.39 (m, 5H), 2.29-2.15 (m, 5H), 1.93-1.84 (m, 2H).

Example 240. (2S)-1-[2-[(3S)-3-[(6-methoxy-5-quinolyl)amino]pyrrolidin-1-yl]acetyl]pyrrolidine-2-carbonitrile The title compound (5.1 mg, 11.6%) was prepared in the same fashion as Example 5, except that (S)-6-methoxy-N-(pyrrolidin-3-yl)quinolin-5-amine hydrochloride (37.9 mg, 0.12 mmol) prepared in Reference Example 121 was used instead of (S)—N-(pyrrolidin-3-yl)quinoline-4-amine hydrochloride. $^1$H-NMR (CDCl$_3$, 400 MHz) δ 8.77 (s, 1H), 8.43-8.38 (m, 1H), 7.77 (d, 1H), 7.47 (d, 1H), 7.34 (q, 1H), 5.13-4.76 (m, 1H), 4.11-4.05 (m, 1H), 3.98 (s, 3H), 3.75-3.65 (m, 1H), 3.58-3.35 (m, 3H), 3.04-2.98 (m, 1H), 2.81-2.78 (m, 1H), 2.70-2.36 (m, 2H), 2.32-2.05 (m, 5H), 1.97-1.82 (m, 2H).

Example 241. (2S)-1-[2-[(3S)-3-[(6-fluoro-5-quinolyl)amino]pyrrolidin-1-yl]acetyl]pyrrolidine-2-carbonitrile The title compound (12.8 mg, 30.1%) was prepared in the same fashion as Example 5, except that (S)-6-fluoro-N-(pyrrolidin-3-yl)quinolin-5-amine hydrochloride (36.5 mg, 0.12 mmol) prepared in Reference Example 122 was used instead of (S)—N-(pyrrolidin-3-yl)quinoline-4-amine hydrochloride. $^1$H-NMR (CDCl$_3$, 400 MHz) δ 8.86-8.83 (m, 1H), 8.55-8.42 (m, 1H), 7.70-7.63 (m, 1H), 7.48-7.38 (m, 2H), 5.03-4.76 (m, 1H), 4.65-4.17 (m, 2H), 3.73-3.64 (m, 1H), 3.58-3.37 (m, 3H), 3.16-3.09 (m, 1H), 2.94-2.81 (m, 1H), 2.59-2.47 (m, 1H), 2.38-2.11 (m, 6H), 2.02-1.83 (m, 1H).

Example 242. (2S)-1-[2-[(3S)-3-[(8-methyl-5-quinolyl)amino]pyrrolidin-1-yl]acetyl]pyrrolidine-2-carbonitrile The title compound (15.6 mg, 37.2%) was prepared in the same fashion as Example 5, except that (S)-8-methyl-N-(pyrrolidin-3-yl)quinolin-5-amine hydrochloride (36.0 mg, 0.12 mmol) prepared in Reference Example 123 was used instead of (S)—N-(pyrrolidin-3-yl)quinoline-4-amine hydrochloride. $^1$H-NMR (CDCl$_3$, 400 MHz) δ 8.91 (s, 1H), 8.34-8.26 (m, 1H), 7.40-7.33 (m, 2H), 6.51-6.47 (m, 1H), 5.03-4.74 (m, 2H), 4.22-4.14 (m, 1H), 3.69-3.28 (m, 4H), 3.10-3.05 (m, 1H), 2.94-2.92 (m, 1H), 2.76-2.63 (m, 4H), 2.47-1.91 (m, 7H)

Example 243. (2S)-1-[2-[(3S)-3-[(8-methoxy-5-quinolyl)amino]pyrrolidin-1-yl]acetyl]pyrrolidine-2-carbonitrile The title compound (3.7 mg, 8.5%) was prepared in the same fashion as Example 5, except that (S)-8-methoxy-N-(pyrrolidin-3-yl)quinolin-5-amine hydrochloride (37.9 mg, 0.12 mmol) prepared in Reference Example 124 was used instead of (S)—N-(pyrrolidin-3-yl)quinoline-4-amine hydrochloride. $^1$H-NMR (CDCl$_3$, 400 MHz) δ 8.93 (s, 1H), 8.34-8.27 (m, 1H), 7.43-7.40 (m, 1H), 6.95 (d, 1H), 6.55-6.50 (m, 1H), 4.86-4.77 (m, 1H), 4.20-4.13 (m, 1H), 4.02 (s, 3H), 3.69-3.32 (m, 4H), 3.14-3.11 (m, 1H), 2.95-2.92 (m, 1H), 2.79-2.68 (m, 1H), 2.43-1.83 (m, 8H)

Example 244. (2S)-1-[2-[(3S)-3-[(8-fluoro-5-quinolyl)amino]pyrrolidin-1-yl]acetyl]pyrrolidine-2-carbonitrile The title compound (1.9 mg, 4.3%) was prepared in the same fashion as Example 5, except that (S)-8-fluoro-N-(pyrrolidin-3-yl)quinolin-5-amine hydrochloride (36.5 mg, 0.12 mmol) prepared in Reference Example 125 was used instead of (S)—N-(pyrrolidin-3-yl)quinoline-4-amine hydrochloride. $^1$H-NMR (CDCl$_3$, 400 MHz) δ 8.93 (s, 1H), 8.42-8.29 (m, 1H), 7.44-7.41 (m, 1H), 7.29-7.24 (m, 1H), 6.46-6.41 (m, 1H), 4.79-4.77 (m, 1H), 4.17 (s, 1H), 3.74-3.31 (m, 4H), 3.31-3.11 (m, 2H), 3.03-2.95 (m, 1H), 2.78-2.73 (m, 1H), 2.49-1.92 (m, 7H)

Example 245. (2S)-1-[2-[(3S)-3-[[8-(trifluoromethyl)-5-quinolyl]amino]pyrrolidin-1-yl]acetyl]pyrrolidine-2-carbonitrile The title compound (9.9 mg, 20.4%) was prepared in the same fashion as Example 5, except that (S)—N-(pyrrolidin-3-yl)-8-(trifluoromethyl)quinolin-5-amine hydrochloride (42.5 mg, 0.12 mmol) prepared in Reference Example 126 was used instead of (S)—N-(pyrrolidin-3-yl)quinoline-4-amine hydrochloride. $^1$H-NMR (CDCl$_3$, 400 MHz) δ 8.99 (d, 1H), 8.51-8.31 (m, 1H), 7.89-7.86 (m, 1H), 7.44-7.38 (m, 1H), 6.49-6.45 (m, 1H), 6.37 (d, 0.6H), 6.65 (d, 0.4H), 4.78-4.69 (m, 1H), 4.25-4.19 (m, 1H), 3.68-3.41 (m, 3H), 3.28-2.98 (m, 3H), 2.79-2.71 (m, 1H), 2.49-1.92 (m, 7H)

Example 246. (2S)-1-[2-[(3S)-3-[[8-(trifluoromethoxy)-5-quinolyl]amino]pyrrolidin-1-yl]acetyl]pyrrolidine-2-carbonitrile The title compound (23.6 mg, 46.9%) was prepared in the same fashion as Example 5, except that (S)—N-(pyrrolidin-3-yl)-8-(trifluoromethoxy)quinolin-5-amine hydrochloride (44.4 mg, 0.12 mmol) prepared in Reference Example 127 was used instead of (S)—N-(pyrrolidin-3-yl)quinoline-4-amine hydrochloride. $^1$H-NMR (CDCl$_3$, 400 MHz) δ 8.97-8.95 (m, 1H), 8.45-8.30 (m, 1H), 7.46 (d, 1H), 7.42-7.38 (m, 1H), 6.43 (t, 1H), 5.76 (d, 0.6H), 5.25 (d, 0.4H), 4.76 (s, 1H), 4.17 (s, 1H), 3.63-3.24 (m, 3H), 3.13-2.95 (m, 3H), 2.77-2.66 (m, 1H), 2.47-1.92 (m, 7H)

Example 247. 5-[[(3S)-1-[2-oxo-2-[(2S)-2-cyanopyrrolidin-1-yl]ethyl]pyrrolidin-3-yl]amino]quinoline-8-carbonitrile The title compound (1.2 mg, 2.8%) was prepared in the same fashion as Example 5, except that (S)-5-(pyrrolidin-3-ylamino)quinoline-8-carbonitrile hydrochloride (37.3 mg, 0.12 mmol) prepared in Reference Example 128 was used instead of (S)—N-(pyrrolidin-3-yl)quinoline-4-amine hydrochloride. $^1$H-NMR (CDCl$_3$, 400 MHz) δ 9.02-9.00 (m, 1H), 8.62-8.34 (m, 1H), 7.92 (t, 1H), 7.14 (d, 1H), 6.51-6.48 (m, 1H), 4.80-4.67 (m, 1H), 4.26-4.22 (m, 1H), 3.75-3.43 (m, 4H), 3.31-3.14 (m, 3H), 2.85-2.80 (m, 1H), 2.44-2.01 (m, 7H)

Example 248. (2S)-1-[2-[(3S)-3-[(8-benzyloxy-5-quinolyl)amino]pyrrolidin-1-yl]acetyl]pyrrolidine-2-carbonitrile The title compound (19.5 mg, 29.3%) was prepared in the same fashion as Example 5, except that (S)-8-(benzyloxy)-N-(pyrrolidin-3-yl)quinolin-5-amine hydrochloride (47.1 mg, 0.12 mmol) prepared in Reference Example 129 was used instead of (S)—N-(pyrrolidin-3-yl)quinoline-4-amine hydrochloride. $^1$H-NMR (CDCl$_3$, 400 MHz) δ 8.95 (s, 1H), 8.33-8.26 (m, 1H), 7.50 (d, 2H), 7.41-7.33 (m, 3H), 7.29-7.26 (m, 1H), 6.91 (d, 1H), 6.42-6.37 (m, 1H), 5.35 (s, 2H), 4.82-4.73 (m, 1H), 4.08 (s, 1H), 3.61-3.60 (m, 1H), 3.50-3.27 (m, 3H), 3.05-3.01 (m, 1.6H), 2.89-2.86 (m, 1H), 2.72-2.61 (m, 1H), 2.42-1.86 (m, 7.4H)

Example 249. (2S,4S)-4-fluoro-1-[2-[(3S)-3-(3-quinolylamino)pyrrolidin-1-yl]acetyl]pyrrolidine-2-carbonitrile The title compound (10.2 mg, 26.6%) was prepared in the same fashion as Example 28, except that (S)—N-(pyrrolidin-3-yl)quinolin-4-amine hydrochloride (25.6 mg, 0.12 mmol) prepared in Reference Example 5 was used instead of (S)—N-(pyrrolidin-3-yl)furo[3,2-c]pyridin-7-amine hydrochloride. $^1$H NMR (MeOD$_4$, 400 MHz) δ 8.40 (d, 1H), 7.80 (d, 1H), 7.67 (d, 1H), 7.43-7.38 (m, 2H), 7.12 (s, 1H), 5.49-4.96 (m, 2H), 4.17-3.73 (m, 3H), 3.61-3.37 (m, 2H), 3.10-2.91 (m, 2H), 2.74-2.35 (m, 5H), 1.84-1.76 (m, 1H).

Example 250. (2S,4S)-4-fluoro-1-[2-[(3S)-3-(6-quinolylamino)pyrrolidin-1-yl]acetyl]pyrrolidine-2-carbonitrile The title compound (4.9 mg, 12.8%) was prepared in the same fashion as Example 28, except that (S)—N-(pyrrolidin-3-yl)quinolin-6-amine hydrochloride (25.6 mg, 0.12 mmol) prepared in Reference Example 111 was used instead of (S)—N-(pyrrolidin-3-yl)furo[3,2-c]pyridin-7-amine hydrochloride. $^1$H-NMR (CDCl$_3$, 400 MHz) δ 8.60 (d, 1H), 7.91-7.84 (m, 2H), 7.27-7.25 (m, 1H), 7.09 (t, 1H), 6.63 (s, 1H), 5.46-5.13 (m, 1H), 5.15=4.90 (m, 1H), 4.59-4.47 (m, 1H), 4.17-3.66 (m, 3H), 3.52-3.32 (m, 2H), 3.10-2.99 (m, 1H), 2.88-2.61 (m, 3H), 2.48-2.21 (m, 3H), 1.88-1.81 (m, 1H).

Example 251. (2S,4S)-4-fluoro-1-[2-[(3S)-3-(7-quinolylamino)pyrrolidin-1-yl]acetyl]pyrrolidine-2-carbonitrile The title compound (12.2 mg, 31.6%) was prepared in the same fashion as Example 28, except that (S)—N-(pyrrolidin-3-yl)quinolin-7-amine hydrochloride (25.6 mg, 0.12 mmol) prepared in Reference Example 130 was used instead of (S)—N-(pyrrolidin-3-yl)furo[3,2-c]pyridin-7-amine hydrochloride. $^1$H NMR (MeOD$_4$, 400 MHz) δ 8.56 (s, 1H), 8.07 (d, 1H), 7.62 (d, 1H), 7.16-7.13 (m, 1H), 7.05 (d, 1H), 6.84 (s, 1H), 5.49-4.95 (m, 2H), 4.19-3.71 (m, 3H), 3.59-3.37 (m, 2H), 3.05-2.95 (m, 2H), 2.81-2.35 (m, 5H), 1.87-1.78 (m, 1H).

Example 252. 5-[[(3S)-1-[2-oxo-2-[(2S,4S)-2-cyano-4-fluoro-pyrrolidin-1-yl]ethyl]pyrrolidin-3-yl]amino]quinoline-2-carbonitrile The title compound (3.8 mg, 9.2%) was prepared in the same fashion as Example 28, except that (S)-5-(pyrrolidin-3-ylamino)quinoline-2-carbonitrile hydrochloride (37.3 mg, 0.12 mmol) prepared in Reference Example 112 was used instead of (S)—N-(pyrrolidin-3-yl)furo[3,2-c]pyridin-7-amine hydrochloride. $^1$H NMR (MeOD$_4$, 400 MHz) δ 8.77-8.71 (m, 1H), 7.72-7.64 (m, 2H), 7.34 (d, 1H), 6.73 (d, 1H), 5.49-4.99 (m, 2H), 4.20-3.73 (m, 3H), 3.66-3.40 (m, 2H), 3.05-2.87 (m, 3H), 2.70- 2.39 (m, 4H), 1.94-1.86 (m, 1H).

Example 253. 5-[[(3S)-1-[2-oxo-2-[(2S,4S)-2-cyano-4-fluoro-pyrrolidin-1-yl]ethyl]pyrrolidin-3-yl]amino]quinoline-3-carbonitrile The title compound (4.4 mg, 10.7%) was prepared in the same fashion as Example 28, except that (S)-5-(pyrrolidin-3-ylamino)quinoline-3-carbonitrile hydrochloride (37.3 mg, 0.12 mmol) prepared in Reference Example 113 was used instead of (S)—N-(pyrrolidin-3-yl)furo[3,2-c]pyridin-7-amine hydrochloride. $^1$H NMR (MeOD$_4$, 400 MHz) δ 9.12 (d, 1H), 8.92 (s, 1H), 7.73 (t, 1H), 7.33 (d, 1H), 6.74 (d, 1H), 5.52-4.99 (m, 2H), 4.30-3.74 (m, 3H), 3.66-3.42 (m, 2H), 3.11-2.89 (m, 3H), 2.70- 2.37 (m, 4H), 1.97-1.89 (m, 1H).

Example 254. (2S,4S)-4-fluoro-1-[2-[(3S)-3-[(3-methoxy-5-quinolyl)amino]pyrrolidin-1-yl]acetyl]pyrrolidine-2-carbonitrile The title compound (2.3 mg, 5.4%) was prepared in the same fashion as Example 28, except that (S)-3-methoxy-N-(pyrrolidin-3-yl)quinolin-5-amine hydrochloride (37.9 mg, 0.12 mmol) prepared in Reference Example 114 was used instead of (S)—N-(pyrrolidin-3-yl)furo[3,2-c]pyridin-7-amine hydrochloride. $^1$H NMR (MeOD$_4$, 400 MHz) δ 8.51 (s, 1H), 7.97 (t, 1H), 7.43-7.28 (m, 2H), 6.76-6.68 (m, 1H), 5.50-4.99 (m, 2H), 4.30-3.92 (m, 5H), 3.82-3.42 (m, 4H), 3.14-2.91 (m, 2H), 2.70- 2.31 (m, 4H), 2.23-1.92 (m, 1H).

Example 255. (2S,4S)-4-fluoro-1-[2-[(3S)-3-[(3-fluoro-5-quinolyl)amino]pyrrolidin-1-yl]acetyl]pyrrolidine-2-carbonitrile The title compound (4.7 mg, 11.7%) was prepared in the same fashion as Example 28, except that (S)-3-fluoro-N-(pyrrolidin-3-yl)quinolin-5-amine hydrochloride (36.5 mg, 0.12 mmol) prepared in Reference Example 115 was used instead of (S)—N-(pyrrolidin-3-yl)furo[3,2-c]pyridin-7-amine hydrochloride. $^1$H NMR (MeOD$_4$, 400 MHz) δ 8.70 (d, 1H), 8.39-8.32 (m, 1H), 7.51 (t, 1H), 7.34 (d, 1H), 6.64 (d, 1H), 5.49-4.97 (m, 2H), 4.23-4.15 (m, 1H), 4.05-3.38 (m, 4H), 3.07-2.85 (m, 3H), 2.67-2.35 (m, 4H), 1.92-1.85 (m, 1H).

Example 256. (2S,4S)-4-fluoro-1-[2-[(3S)-3-[(3-chloro-5-quinolyl)amino]pyrrolidin-1-yl]acetyl]pyrrolidine-2-carbonitrile The title compound (4.9 mg, 11.8%) was prepared in the same fashion as Example 28, except that (S)-3-chloro-N-(pyrrolidin-3-yl)quinolin-5-amine hydrochloride (38.4 mg, 0.12 mmol) prepared in Reference Example 116 was used instead of (S)—N-(pyrrolidin-3-yl)furo[3,2-c]pyridin-7-amine hydrochloride. $^1$H NMR (MeOD$_4$, 400 MHz) δ 8.69-8.67 (m, 2H), 7.55 (t, 1H), 7.29 (d, 1H), 6.64 (d, 1H), 5.49-4.97 (m, 2H), 4.23-4.15 (m, 1H), 4.05-3.71 (m, 2H), 3.63-3.38 (m, 2H), 3.08-2.89 (m, 3H), 2.66-2.36 (m, 4H), 1.90-1.87 (m, 1H).

Example 257. (2S,4S)-4-fluoro-1-[2-[(3S)-3-[(7-methoxy-5-quinolyl)amino]pyrrolidin-1-yl]acetyl]pyrrolidine-2-carbonitrile The title compound (3.0 mg, 7.2%) was prepared in the same fashion as Example 28, except that (S)-7-methoxy-N-(pyrrolidin-3-yl)quinolin-5-amine hydrochloride (37.9 mg, 0.12 mmol) prepared in Reference Example 118 was used instead of (S)—N-(pyrrolidin-3-yl)furo[3,2-c]pyridin-7-amine hydrochloride. $^1$H NMR (MeOD$_4$, 400 MHz) δ 8.60 (d, 1H), 8.48-8.42 (m, 1H), 7.24 (q, 1H), 6.70 (s, 1H), 6.19 (s, 1H), 5.49-4.95 (m, 2H), 4.13-4.09 (m, 1H), 4.00-3.91 (dd, 1H), 3.89 (s, 3H), 3.81-3.66 (m, 1H), 3.61-3.36 (m, 2H), 3.04-2.88 (m, 3H), 2.60-2.32 (m, 4H), 1.88-1.85 (m, 1H).

Example 258. (2S,4S)-4-fluoro-1-[2-[(3S)-3-[[7-(trifluoromethyl)-5-quinolyl]amino]pyrrolidin-1-yl]acetyl]pyrrolidine-2-carbonitrile The title compound (3.5 mg, 7.7%) was prepared in the same fashion as Example 28, except that (S)—N-(pyrrolidin-3-yl)-7-(trifluoromethyl)quinolin-5-amine hydrochloride (42.5 mg, 0.12 mmol) prepared in Reference Example 119 was used instead of (S)—N-(pyrrolidin-3-yl)furo[3,2-c]pyridin-7-amine hydrochloride. $^1$H NMR (MeOD$_4$, 400 MHz) δ 8.87 (d, 1H), 8.74-8.67 (m, 1H), 7.58-7.55 (m, 2H), 6.68 (s, 1H), 5.51-4.99 (m, 2H), 4.29-4.24 (m, 1H), 4.07-3.98 (dd, 1H), 3.85-3.73 (m, 1H), 3.68-3.42 (m, 2H), 3.12-2.92 (m, 3H), 2.71-2.37 (m, 4H), 1.97-1.90 (m, 1H).

Example 259. (2S,4S)-4-fluoro-1-[2-[(3S)-3-[(6-methyl-5-quinolyl)amino]pyrrolidin-1-yl]acetyl]pyrrolidine-2-carbonitrile The title compound (5.3 mg, 13.3%) was prepared in the same fashion as Example 28, except that (S)-6-methyl-N-(pyrrolidin-3-yl)quinolin-5-amine hydrochloride (36.0 mg, 0.12 mmol) prepared in Reference Example 120 was used instead of (S)—N-(pyrrolidin-3-yl)furo[3,2-c]pyridin-7-amine hydrochloride. $^1$H NMR (MeOD$_4$, 400 MHz) δ 8.71 (d, 1H), 8.67-8.61 (m, 1H), 7.57 (q, 2H), 7.48 (q, 1H), 5.49-4.96 (m, 2H), 4.08-3.99 (m, 2H), 3.83-3.71 (m, 1H), 3.59-3.42 (m, 1H), 3.32-3.28 (m, 1H), 3.12-3.05 (m, 1H), 2.86-2.80 (m, 1H), 2.70-2.32 (m, 7H), 2.25-2.16 (m, 1H), 1.92-1.81 (m, 1H).

Example 260. (2S,4S)-4-fluoro-1-[2-[(3S)-3-[(6-methoxy-5-quinolyl)amino]pyrrolidin-1-yl]acetyl]pyrrolidine-2-carbonitrile The title compound (2.5 mg, 5.9%) was prepared in the same fashion as Example 28, except that (S)-6-methoxy-N-(pyrrolidin-3-yl)quinolin-5-amine hydrochloride (37.9 mg, 0.12 mmol) prepared in Reference Example 121 was used instead of (S)—N-(pyrrolidin-3-yl)furo[3,2-c]pyridin-7-amine hydrochloride. $^1$H NMR (MeOD$_4$, 400 MHz) δ 8.67 (d, 1H), 8.58-8.53 (m, 1H), 7.70 (d, 1H), 7.65-7.62 (m, 1H), 7.45 (dd, 1H), 5.49-4.96 (m, 2H), 4.12-4.00 (m, 5H), 3.87-3.75 (m, 1H), 3.62-3.32 (m, 2H), 3.04-2.99 (m, 1H), 2.85-2.36 (m, 5H), 2.23-2.09 (m, 1H), 1.95-1.76 (m, 1H).

Example 261. (2S,4S)-4-fluoro-1-[2-[(3S)-3-[(6-fluoro-5-quinolyl)amino]pyrrolidin-1-yl]acetyl]pyrrolidine-2-carbonitrile The title compound (4.6 mg, 11.3%) was prepared in the same fashion as Example 28, except that (S)-6-fluoro-N-(pyrrolidin-3-yl)quinolin-5-amine hydrochloride (36.5 mg, 0.12 mmol) prepared in Reference Example 122 was used instead of (S)—N-(pyrrolidin-3-yl)furo[3,2-c]pyridin-7-amine hydrochloride. $^1$H NMR (MeOD$_4$, 400 MHz) δ 8.75-8.64 (m, 2H), 7.54-7.50 (m, 3H), 5.49-4.98 (m, 2H), 4.35 (br s, 1H), 4.06-3.72 (m, 2H), 3.61-3.32 (m, 2H), 3.12-3.06 (m, 1H), 2.95-2.68 (m, 2H), 2.64-2.19 (m, 4H), 1.94-1.82 (m, 1H).

Example 262. (2S,4S)-4-fluoro-1-[2-[(3S)-3-[(8-methyl-5-quinolyl)amino]pyrrolidin-1-yl]acetyl]pyrrolidine-2-carbonitrile The title compound (8.6 mg, 21.6%) was prepared in the same fashion as Example 28, except that (S)-8-methyl-N-(pyrrolidin-3-yl)quinolin-5-amine hydrochloride (36.0 mg, 0.12 mmol) prepared in Reference Example 123 was used instead of (S)—N-(pyrrolidin-3-yl)furo[3,2-c]pyridin-7-amine hydrochloride. $^1$H NMR (MeOD$_4$, 400 MHz) δ 8.78 (s, 1H), 8.60-8.58 (m, 1H), 7.41 (br s, 2H), 6.56 (d, 1H), 5.49-4.96 (m, 2H), 4.17 (br s, 1H), 4.06-3.71 (m, 2H), 3.58-3.38 (m, 2H), 3.00-2.88 (m, 3H), 2.64-2.39 (m, 7H), 1.94-1.84 (m, 1H).

Example 263. (2S,4S)-4-fluoro-1-[2-[(3S)-3-[(8-methoxy-5-quinolyl)amino]pyrrolidin-1-yl]acetyl]pyrrolidine-2-carbonitrile The title compound (11.5 mg, 27.6%) was prepared in the same fashion as Example 28, except that (S)-8-methoxy-N-(pyrrolidin-3-yl)quinolin-5-amine hydrochloride (37.9 mg, 0.12 mmol) prepared in Reference Example 124 was used instead of (S)—N-(pyrrolidin-3-yl)furo[3,2-c]pyridin-7-amine hydrochloride. $^1$H-NMR (CDCl$_3$, 400 MHz) δ 8.93 (s, 1H), 8.29 (d, 1H), 7.43-7.40 (m, 1H), 6.95 (d, 1H), 6.52 (dd, 1H), 5.49-4.95 (m, 2H), 4.19-3.67 (m, 6H), 3.55-3.36 (m, 2H), 3.17-2.89 (m, 2H), 2.77-2.61 (m, 2H), 2.52-2.13 (m, 3H), 2.05-1.86 (m, 2H).

Example 264. (2S,4S)-4-fluoro-1-[2-[(3S)-3-[(8-fluoro-5-quinolyl)amino]pyrrolidin-1-yl]acetyl]pyrrolidine-2-carbonitrile The title compound (1.8 mg, 4.5%) was prepared in the same fashion as Example 28, except that (S)-8-fluoro-N-(pyrrolidin-3-yl)quinolin-5-amine hydrochloride (36.5 mg, 0.12 mmol) prepared in Reference Example 125 was used instead of (S)—N-(pyrrolidin-3-yl)furo[3,2-c]pyridin-7-amine hydrochloride. $^1$H NMR (MeOD$_4$, 400 MHz) δ 8.82 (d, 1H), 8.69-8.63 (m, 1H), 7.54 (dd, 1H), 7.33 (t, 1H), 6.57 (dd, 1H), 5.50-5.38 (m, 1H), 5.32-4.98 (m, 1H), 4.24-4.17 (m, 1H), 4.14-3.99 (m, 1H), 3.86-3.73 (m, 1H), 3.67-3.44 (m, 2H), 3.09-2.88 (m, 3H), 2.75-2.33 (m, 4H), 1.93-1.88 (m, 1H).

Example 265. (2S,4S)-4-fluoro-1-[2-[(3S)-3-[[8-(trifluoromethyl)-5-quinolyl]amino]pyrrolidin-1-yl]acetyl]pyrrolidine-2-carbonitrile The title compound (3.9 mg, 8.6%) was prepared in the same fashion as Example 28, except that (S)—N-(pyrrolidin-3-yl)-8-(trifluoromethyl)quinolin-5-amine hydrochloride (42.5 mg, 0.12 mmol) prepared in Reference Example 126 was used instead of (S)—N-(pyrrolidin-3-yl)furo[3,2-c]pyridin-7-amine hydrochloride. $^1$H NMR (MeOD$_4$, 400 MHz) δ 8.85 (d, 1H), 8.69-8.62 (m, 1H), 7.88 (d, 1H), 7.49 (dd, 1H), 6.58 (d, 1H), 5.49-4.98 (m, 2H), 4.24 (br s, 1H), 4.06-3.97 (m, 1H), 3.83-3.40 (m, 3H), 3.09-2.90 (m, 3H), 2.68-2.36 (m, 4H), 1.98-1.88 (m, 1H).

Example 266. (2S,4S)-4-fluoro-1-[2-[(3S)-3-[[8-(trifluoromethoxy)-5-quinolyl]amino]pyrrolidin-1-yl]acetyl]pyrrolidine-2-carbonitrile The title compound (5.5 mg, 11.7%) was prepared in the same fashion as Example 28, except that (S)—N-(pyrrolidin-3-yl)-8-(trifluoromethoxy)quinolin-5-amine hydrochloride (44.4 mg, 0.12 mmol) prepared in Reference Example 127 was used instead of (S)—N-(pyrrolidin-3-yl)furo[3,2-c]pyridin-7-amine hydrochloride. $^1$H NMR (MeOD$_4$, 400 MHz) δ 8.84 (d, 1H), 8.69-8.63 (m, 1H), 7.53-7.50 (m, 2H), 6.56 (d, 1H), 5.49-5.37 (m, 1H), 5.30-4.98 (m, 1H), 4.19 (br s, 1H), 4.06-3.97 (m, 1H), 3.83-3.72 (m, 1H), 3.66-3.40 (m, 2H), 3.08-2.88 (m, 3H), 2.69-2.36 (m, 4H), 1.91-1.88 (m, 1H).

Example 267. 5-[[(3S)-1-[2-oxo-2-[(2S,4S)-2-cyano-4-fluoro-pyrrolidin-1-yl]ethyl]pyrrolidin-3-yl]amino]quinoline-8-carbonitrile The title compound (2.6 mg, 6.3%) was prepared in the same fashion as Example 28, except that (S)-5-(pyrrolidin-3-ylamino)quinoline-8-carbonitrile hydrochloride (37.3 mg, 0.12 mmol) prepared in Reference Example 128 was used instead of (S)—N-(pyrrolidin-3-yl)furo[3,2-c]pyridin-7-amine hydrochloride. $^1$H NMR (MeOD$_4$, 400 MHz) δ 8.89 (d, 1H), 8.77-8.69 (m, 1H), 7.98 (d, 1H), 7.53 (dd, 1H), 6.68 (d, 1H), 5.50-5.38 (m, 1H), 5.31-5.00 (m, 1H), 4.38-4.30 (m, 1H), 4.09-4.00 (m, 1H), 3.86-3.43 (m, 3H), 3.13-2.92 (m, 3H), 2.72-2.41 (m, 4H), 2.02-1.96 (m, 1H).

Example 268. (2S,4S)-4-fluoro-1-[2-[(3S)-3-[(8-benzyloxy-5-quinolyl)amino]pyrrolidin-1-yl]acetyl]pyrrolidine-2-carbonitrile The title compound (3.2 mg, 6.4%) was prepared in the same fashion as Example 28, except that (S)-8-(benzyloxy)-N-(pyrrolidin-3-yl)quinolin-5-amine hydrochloride (47.1 mg, 0.12 mmol) prepared in Reference Example 129 was used instead of (S)—N-(pyrrolidin-3-yl)furo[3,2-c]pyridin-7-amine hydrochloride. $^1$H NMR (MeOD$_4$, 400 MHz) δ 8.78 (d, 1H), 8.58-8.53 (m, 1H), 7.51-7.45 (m, 3H), 7.35-7.25 (m, 3H), 7.03 (d, 1H), 6.47 (d, 1H), 5.49-5.25 (m, 3.2H), 4.95-4.93 (m, 0.8H), 4.04-3.64 (m, 3H), 3.58-3.29 (m, 2H), 2.97-2.80 (m, 3H), 2.58-2.28 (m, 4H), 1.87-1.80 (m, 1H).

Example 269. (2S,4S)-4-fluoro-1-[2-[(3S)-3-[(7-fluoro-5-quinolyl)amino]pyrrolidin-1-yl]acetyl]pyrrolidine-2-carbonitrile The title compound (7.2 mg, 15.9%) was prepared in the same fashion as Example 28, except that (S)-7-fluoro-N-(pyrrolidin-3-yl)quinolin-5-amine hydrochloride (36.5 mg, 0.12 mmol) prepared in Reference Example 117 was used instead of (S)—N-(pyrrolidin-3-yl)furo[3,2-c]pyridin-7-amine hydrochloride. $^1$H NMR (CDCl$_3$, 400 MHz) δ 8.79 (t, 1H), 8.30-8.22 (m, 1H), 7.26-7.23 (m, 1H), 7.04-7.00 (m, 1H), 6.28 (m, 1H), 5.71-5.46 (m, 1H), 5.38-5.25 (m, 1H), 4.89 (t, 1H), 4.15-3.44 (m, 3H), 3.34-3.26 (m, 1H), 3.17-2.94 (m, 2H), 2.73-2.22 (m, 6H), 2.03-1.91 (m, 1H).

Example 270. (2S)-1-[2-[(3S)-3-[[8-(trifluoromethyl)-4-quinolyl]amino]pyrrolidin-1-yl]acetyl]pyrrolidine-2-carbonitrile The title compound (12.2 mg, 24.3%) was prepared in the same fashion as Example 5, except that (S)—N-(pyrrolidin-3-yl)-8-(trifluoromethyl)quinolin-4-amine hydrochloride (42.5 mg, 0.12 mmol) prepared in Reference Example 131 was used instead of (S)—N-(pyrrolidin-3-yl)quinoline-4-amine hydrochloride. $^1$H NMR (CDCl$_3$, 400 MHz) δ 8.68 (t, 1H), 8.18 (dd, 1H), 8.00 (t, 1H), 7.47 (t, 1H), 6.45 (t, 1H), 6.21 (dd, 1H), 5.52-5.30 (m, 1H), 4.93 (dd, 1H), 4.26-3.54 (m, 4H), 3.45-3.02 (m, 3.5H), 2.78-2.26 (m, 4.5H), 2.10-1.88 (m, 1H).

Example 271. (2S,4S)-4-fluoro-1-[2-[(3S)-3-[[8-(trifluoromethyl)-4-quinolyl]amino]pyrrolidin-1-yl]acetyl]pyrrolidine-2-carbonitrile The title compound (8.0 mg, 15.4%) was prepared in the same fashion as Example 28, except that (S)—N-(pyrrolidin-3-yl)-8-(trifluoromethyl)quinolin-4-amine hydrochloride (42.5 mg, 0.12 mmol) prepared in Reference Example 131 was used instead of (S)—N-(pyrrolidin-3-yl)furo[3,2-c]pyridin-7-amine hydrochloride. $^1$H NMR (CDCl$_3$, 400 MHz) δ 8.68 (t, 1H), 8.22 (dd, 1H), 8.00 (t, 1H), 7.47 (dd, 1H), 6.47 (t, 1H), 6.42 (dd, 1H), 4.82-4.69 (m, 1H), 4.24 (d, 1H), 3.66-3.45 (m, 3H), 3.30-3.01 (m, 3H), 2.82-2.76 (m, 1H), 2.50-2.13 (m, 5H), 2.06-1.99 (m, 1H).

Example 272. (2S,4S)-4-fluoro-1-[2-[(3S)-3-(1,8-naphthyridin-3-ylamino)pyrrolidin-1-yl]acetyl]pyrrolidine-2-carbonitrile The title compound (67.7 mg, 26.6%) was prepared in the same fashion as Example 28, except that (S)—N-(pyrrolidin-3-yl)-1,8-naphthyridin-3-amine hydrochloride (196.7 mg, 0.69 mmol) prepared in Reference Example 132 was used instead of (S)—N-(pyrrolidin-3-yl)furo[3,2-c]pyridin-7-amine hydrochloride. $^1$H-NMR (CDCl$_3$, 600 MHz) δ 8.79 (d, 1H), 8.62 (s, 1H), 7.96 (d, 1H), 7.35 (t, 1H), 6.90 (s, 1H), 5.50-5.30 (m, 1H), 5.10-4.70 (m, 1H), 4.20-4.05 (m, 1H), 3.95-3.70 (m, 2H), 3.60- 3.35 (m, 2H), 3.15-3.00 (m, 2H), 2.90-2.65 (m, 3H), 2.50-2.25 (m, 3H), 1.95-1.80 (m, 1H)

Example 273. (2S,4S)-4-fluoro-1-[2-[(3S)-3-[(7-chloro-1,8-naphthyridin-3-yl)amino]pyrrolidin-1-yl]acetyl]pyrrolidine-2-carbonitrile The title compound (10.1 mg, 5.2%) was prepared in the same fashion as Example 28, except that (S)-7-chloro-N-(pyrrolidin-3-yl)-1,8-naphthyridin-3-amine hydrochloride (155.6 mg, 0.48 mmol) prepared in Reference Example 133 was used instead of (S)—N-(pyrrolidin-3-yl)furo[3,2-c]pyridin-7-amine hydrochloride. $^1$H-NMR (CDCl$_3$, 600 MHz) δ 8.58 (s, 1H), 7.90 (d, 1H), 7.34 (d, 1H), 6.90 (s, 1H), 5.50-5.30 (m, 1H), 5.10-4.90 (m, 1H), 4.20-4.00 (m, 2H), 4.00-3.65 (m, 1H), 3.60- 3.30 (m, 2H), 3.20-3.00 (m, 2H), 2.90-2.60 (m, 3H), 2.50-2.25 (m, 3H), 1.95-1.80 (m, 1H)

Example 274. (2S)-1-[2-[(3S)-3-[(8-ethoxy-5-quinolyl)amino]pyrrolidin-1-yl]acetyl]pyrrolidine-2-carbonitrile The title compound (3.4 mg, 7.5%) was prepared in the same fashion as Example 5, except that (S)-8-ethoxy-N-(pyrrolidin-3-yl)quinolin-5-amine hydrochloride (39.6 mg, 0.12 mmol) prepared in Reference Example 134 was used instead of (S)—N-(pyrrolidin-3-yl)quinoline-4-amine hydrochloride. $^1$H NMR (CDCl$_3$, 400 MHz) δ 8.93-8.91 (m, 1H), 8.31-8.24 (m, 1H), 7.39-7.35 (m, 1H), 6.94 (d, 1H), 6.49 (dd, 1H), 4.85-4.72 (m, 1H), 4.66-4.45 (m, 1H), 4.23 (q, 2H), 4.13-4.09 (m, 1H), 3.65-3.28 (m, 4H), 3.09-2.99 (m, 1H), 2.89-2.86 (m, 1H), 2.75-2.63 (m, 1H), 2.45-1.83 (m, 7H), 1.56 (t, 3H).

Example 275. (2S,4S)-4-fluoro-1-[2-[(3S)-3-[(8-ethoxy-5-quinolyl)amino]pyrrolidin-1-yl]acetyl]pyrrolidine-2-carbonitrile The title compound (3.5 mg, 8.0%) was prepared in the same fashion as Example 28, except that (S)-8-ethoxy-N-(pyrrolidin-3-yl)quinolin-5-amine hydrochloride (39.6 mg, 0.12 mmol) prepared in Reference Example 134 was used instead of (S)—N-(pyrrolidin-3-yl)furo[3,2-c]pyridin-7-amine hydrochloride. $^1$H NMR (CDCl$_3$, 400 MHz) δ 8.90 (t, 1H), 8.26 (d, 1H), 7.37-7.33 (m, 1H), 6.93 (d, 1H), 6.46 (dd, 1H), 5.41-5.17 (m, 1H), 5.07-4.84 (m, 1H), 4.54-4.39 (m, 1H), 4.20 (q, 2H), 4.13-3.99 (m, 1.5H), 3.89-3.58 (m, 1.5H), 3.50-3.25 (m, 2H), 3.09-2.81 (m, 2H), 2.72-2.08 (m, 5H), 1.98-1.80 (m, 1H), 1.54 (td, 3H).

Example 276. (2S,4S)-4-fluoro-1-[2-[(3S)-3-[(8-hydroxy-5-quinolyl)amino]pyrrolidin-1-yl]acetyl]pyrrolidine-2-carbonitrile The title compound (2.5 mg, 5.4%) was prepared in the same fashion as Example 28, except that (S)-5-(pyrrolidin-3-ylamino)quinolin-8-ol hydrochloride (36.2 mg, 0.12 mmol) prepared in Reference Example 135 was used instead of (S)—N-(pyrrolidin-3-yl)furo[3,2-c]pyridin-7-amine hydrochloride. $^1$H NMR (CDCl$_3$, 400 MHz) δ 8.78 (s, 1H), 8.31 (d, 1H), 7.69 (br s, 1H), 7.42 (dd, 1H), 7.06 (d, 1H), 6.53 (dd, 1H), 5.50-5.24 (m, 1H), 5.07-4.95 (m, 1H), 4.19-4.11 (m, 2H), 3.96-3.69 (m, 2H), 3.56-3.34 (m, 2H), 3.50-3.25 (m, 2H), 3.16-2.89 (m, 2H), 2.76-2.16 (m, 5H), 2.05-1.87 (m, 1H).

Example 277. (2S,4S)-4-fluoro-1-[2-[(3S)-3-[(8-methyl-6-quinolyl)amino]pyrrolidin-1-yl]acetyl]pyrrolidine-2-carbonitrile The title compound (122.9 mg, 40.3%) was prepared in the same fashion as Example 28, except that (S)-8-methyl-N-(pyrrolidin-3-yl)quinolin-6-amine hydrochloride (239.9 mg, 0.80 mmol) prepared in Reference Example 136 was used instead of (S)—N-(pyrrolidin-3-yl)furo[3,2-c]pyridin-7-amine hydrochloride. $^1$H-NMR (CDCl$_3$, 600 MHz) δ 8.63

(s, 1H), 7.88 (d, 1H), 7.27-7.24 (m, 1H), 6.95 (d, 1H), 6.50 (s, 1H), 5.50-5.25 (m, 1H), 5.20-4.90 (m, 1H), 4.20-4.05 (m, 2H), 4.00-3.70 (m, 1H), 3.55-3.30 (m, 2H), 3.15-3.00 (m, 2H), 2.95-2.75 (m, 2H), 2.71 (s, 3H), 2.71-2.60 (m, 1H), 2.50- 2.20 (m, 3H), 1.95-1.80 (m, 1H)

Example 278. (2S,4S)-4-fluoro-1-[2-[(3S)-3-[(8-fluoro-6-quinolyl)amino]pyrrolidin-1-yl]acetyl]pyrrolidine-2-carbonitrile The title compound (222.3 mg, 48.9%) was prepared in the same fashion as Example 28, except that (S)-8-fluoro-N-(pyrrolidin-3-yl)quinolin-6-amine hydrochloride (358.9 mg, 1.18 mmol) prepared in Reference Example 137 was used instead of (S)—N-(pyrrolidin-3-yl)furo[3,2-c]pyridin-7-amine hydrochloride. $^1$H-NMR (CDCl$_3$, 600 MHz) δ 8.62 (s, 1H), 7.89 (d, 1H), 7.29 (d, 1H), 6.80 (t, 1H), 6.44 (s, 1H), 5.50-5.35 (m, 1H), 5.10-4.90 (m, 1H), 4.20-4.05 (m, 2H), 3.95-3.70 (m, 1H), 3.60- 3.30 (m, 2H), 3.15-2.95 (m, 2H), 2.90-2.60 (m, 3H), 2.50-2.20 (m, 3H), 1.90-1.75 (m, 1H)

Example 279. (2S,4S)-4-fluoro-1-[2-[(3S)-3-[(8-chloro-6-quinolyl)amino]pyrrolidin-1-yl]acetyl]pyrrolidine-2-carbonitrile The title compound (314.5 mg, 86.0%) was prepared in the same fashion as Example 28, except that (S)-8-chloro-N-(pyrrolidin-3-yl)quinolin-6-amine hydrochloride (291.8 mg, 0.91 mmol) prepared in Reference Example 138 was used instead of (S)—N-(pyrrolidin-3-yl)furo[3,2-c]pyridin-7-amine hydrochloride. $^1$H-NMR (CDCl$_3$, 600 MHz) δ 8.68 (s, 1H), 7.88 (d, 1H), 7.29-7.22 (m, 2H), 6.54 (s, 1H), 5.50-5.25 (m, 1H), 5.10-4.85 (m, 1H), 4.20-4.00 (m, 2H), 3.95-3.65 (m, 1H), 3.55-3.25 (m, 2H), 3.10-2.90 (m, 2H), 2.90-2.55 (m, 3H), 2.45-2.20 (m, 3H), 1.90-1.75 (m, 1H)

Example 280. (2S,4S)-4-fluoro-1-[2-[(3S)-3-[[8-(trifluoromethyl)-6-quinolyl]amino]pyrrolidin-1-yl]acetyl]pyrrolidine-2-carbonitrile The title compound (72.1 mg, 27.3%) was prepared in the same fashion as Example 28, except that (S)—N-(pyrrolidin-3-yl)-8-(trifluoromethyl)quinolin-6-amine hydrochloride (215.7 mg, 0.61 mmol) prepared in Reference Example 139 was used instead of (S)—N-(pyrrolidin-3-yl)furo[3,2-c]pyridin-7-amine hydrochloride. $^1$H-NMR (CDCl$_3$, 600 MHz) δ 8.75 (s, 1H), 7.94 (d, 1H), 7.45 (d, 1H), 7.34 (t, 1H), 6.77 (s, 1H), 5.50-5.35 (m, 1H), 5.10-4.90 (m, 1H), 4.20-4.05 (m, 2H), 3.95-3.65 (m, 1H), 3.60-3.30 (m, 2H), 3.15-3.00 (m, 2H), 2.90-2.60 (m, 3H), 2.50-2.20 (m, 3H), 1.95-1.80 (m, 1H)

Example 281. N-methyl-5-[[(3S)-1-[2-oxo-2-[(2S,4S)-2-cyano-4-fluoro-pyrrolidin-1-yl]ethyl]pyrrolidin-3-yl]amino]quinoline-8-carboxamide The title compound (8.6 mg, 16.9%) was prepared in the same fashion as Example 28, except that (S)—N-methyl-5-(pyrrolidin-3-ylamino)quinoline-8-carboxamide hydrochloride (41.0 mg, 0.12 mmol) prepared in Reference Example 140 was used instead of (S)—N-(pyrrolidin-3-yl)furo[3,2-c]pyridin-7-amine hydrochloride. $^1$H NMR (CDCl$_3$, 400 MHz) δ 10.95 (t, 1H), 8.87-8.85 (m, 1H), 8.72 (dd, 1H), 8.42 (dd, 1H), 7.41-7.36 (m, 1H), 6.61 (dd, 1H), 5.93-5.62 (m, 1H), 5.53-5.27 (m, 1H), 4.94 (dd, 1H), 4.30-4.22 (m, 1H), 4.16-4.07 (m, 1H), 3.92-3.69 (m, 2H), 3.67-3.38 (m, 2H), 3.29-3.03 (m, 6H), 2.75-2.63 (m, 2H), 2.54-2.20 (m, 1H), 2.10-1.95 (m, 1H).

Example 282. N,N-dimethyl-5-[[(3S)-1-[2-oxo-2-[(2S,4S)-2-cyano-4-fluoro-pyrrolidin-1-yl]ethyl]pyrrolidin-3-yl]amino]quinoline-8-carboxamide The title compound (10.0 mg, 19.0%) was prepared in the same fashion as Example 28, except that (S)—N,N-dimethyl-5-(pyrrolidin-3-ylamino)quinoline-8-carboxamide hydrochloride (42.7 mg, 0.12 mmol) prepared in Reference Example 141 was used instead of (S)—N-(pyrrolidin-3-yl)furo[3,2-c]pyridin-7-amine hydrochloride. $^1$H NMR (CDCl$_3$, 400 MHz) δ 8.86-8.84 (m, 1H), 8.31-8.26 (m, 1H), 7.46 (d, 1H), 7.30-7.28 (m, 1H), 6.49-6.44 (m, 1H), 5.62-4.80 (m, 3H), 4.16-4.14 (m, 1H), 3.96-3.63 (m, 2H), 3.60-3.25 (m, 2H), 3.22 (d, 3H), 3.17-2.87 (m, 2H), 2.80 (d, 3H), 2.62-2.20 (m, 5H), 2.03-1.95 (m, 1H).

Example 283. N-phenyl-5-[[(3S)-1-[2-oxo-2-[(2S,4S)-2-cyano-4-fluoro-pyrrolidin-1-yl]ethyl]pyrrolidin-3-yl]amino]quinoline-8-carboxamide The title compound (12.0 mg, 21.2%) was prepared in the same fashion as Example 28, except that (S)—N-phenyl-5-(pyrrolidin-3-ylamino)quinoline-8-carboxamide hydrochloride (48.5 mg, 0.12 mmol) prepared in Reference Example 142 was used instead of (S)—N-(pyrrolidin-3-yl)furo[3,2-c]pyridin-7-amine hydrochloride. $^1$H NMR (CDCl$_3$, 400 MHz) δ 8.88 (t, 1H), 8.74-8.71 (m, 1H), 7.43 (d, 1H), 7.85 (d, 2H), 7.39-7.35 (m, 3H), 7.11-7.07 (m, 1H), 6.57 (dd, 1H), 6.28-5.81 (m, 1H), 5.43-5.24 (m, 1H), 4.91 (dd, 1H), 4.23-4.15 (m, 1H), 4.03-3.15 (m, 5H), 3.08-2.99 (m, 2H), 2.75-2.18 (m, 5H), 2.03-1.95 (m, 1H).

Example 284. N-methyl-N-phenyl-5-[[(3S)-1-[2-oxo-2-[(2S,4S)-2-cyano-4-fluoro-pyrrolidin-1-yl]ethyl]pyrrolidin-3-yl]amino]quinoline-8-carboxamide The title compound (17.6 mg, 28.6%) was prepared in the same fashion as Example 28, except that (S)—N-methyl-N-phenyl-5-(pyrrolidin-3-ylamino)quinoline-8-carboxamide hydrochloride (50.21 mg, 0.12 mmol) prepared in Reference Example 143 was used instead of (S)—N-(pyrrolidin-3-yl)furo[3,2-c]pyridin-7-amine hydrochloride. $^1$H NMR (CDCl$_3$, 400 MHz) δ 8.85-8.81 (m, 1H), 8.21-8.15 (m, 1H), 7.29-7.00 (m, 7H), 6.27-6.22 (m, 1H), 5.38-5.15 (m, 1H), 4.89 (dd, 1H), 4.02-3.66 (m, 2H), 3.59-3.50 (m, 2H), 3.42 (s, 3H), 3.35-3.22 (m, 2H), 3.06-2.79 (m, 2H), 2.61-1.98 (m, 5H), 1.89- 1.78 (m, 1H).

Example 285. N-benzyl-N-methyl-5-[[(3S)-1-[2-oxo-2-[(2S,4S)-2-cyano-4-fluoro-pyrrolidin-1-yl]ethyl]pyrrolidin-3-yl]amino]quinoline-8-carboxamide The title compound (11.0 mg, 17.8%) was prepared in the same fashion as Example 28, except that (S)—N-benzyl-N-methyl-5-(pyrrolidin-3-ylamino)quinoline-8-carboxamide hydrochloride (51.89 mg, 0.12 mmol) prepared in Reference Example 144 was used instead of (S)—N-(pyrrolidin-3-yl)furo[3,2-c]pyridin-7-amine hydrochloride. $^1$H NMR (CDCl$_3$, 400 MHz) δ 8.88-8.85 (m, 1H), 8.35-8.27 (m, 1H), 7.51 (t, 2H), 7.37 (t, 1H), 7.29-7.17 (m, 4H), 6.48-6.40 (m, 1H), 5.79-5.13 (m, 3H), 5.05-4.76 (m, 1H), 4.40-4.11 (m, 2H), 3.84-3.58 (m, 2H), 3.42 (s, 3H), 3.35-3.20 (m, 2H), 3.08 (s, 2H), 3.02-2.16 (m, 5H), 1.98-1.86 (m, 1H).

Example 286. N-methyl-5-[[(3S)-1-[2-oxo-2-[(2S)-2-cyanopyrrolidin-1-yl]ethyl]pyrrolidin-3-yl]amino]quinoline-8-carboxamide The title compound (10.1 mg, 29.7%) was prepared in the same fashion as Example 5, except that (S)—N-methyl-5-(pyrrolidin-3-ylamino)quinoline-8-carboxamide hydrochloride (29.0 mg, 0.084 mmol) prepared in Reference Example 140 was used instead of (S)—N-(pyrrolidin-3-yl)quinoline-4-amine hydrochloride. $^1$H NMR (CDCl$_3$, 400 MHz) δ 10.98-10.94 (m, 1H), 8.85-8.83 (m, 1H), 8.70 (dd, 1H), 8.48 (dd, 1H), 7.40-7.34 (m, 1H), 6.60 (dd, 1H), 6.39-5.65 (m, 1H), 4.78-4.73 (m, 1H), 4.27-4.24 (m, 1H), 3.66-3.42 (m, 3H), 3.29-3.01 (m, 5H), 2.79-2.70 (m, 1H), 2.49-2.36 (m, 1H), 2.33-1.96 (m, 7H)

Example 287. N-phenyl-5-[[(3S)-1-[2-oxo-2-[(2S)-2-cyanopyrrolidin-1-yl]ethyl]pyrrolidin-3-yl]amino]quinoline-8-carboxamide The title compound (4.4 mg, 12.1%) was prepared in the same fashion as Example 5, except that (S)—N-phenyl-5-(pyrrolidin-3-ylamino)quinoline-8-carboxamide hydrochloride (30.0 mg, 0.074 mmol) prepared in Reference Example 142 was used instead of (S)—N-(pyrrolidin-3-yl)quinoline-4-amine hydrochloride. $^1$H NMR (CDCl$_3$, 400 MHz) δ 8.88 (t, 1H), 8.72 (dd, 1H), 8.43 (dd, 1H), 7.85 (d, 2H), 7.39-7.35 (m, 3H), 7.09 (t, 1H), 6.57 (dd, 1H), 6.28-5.81 (m, 1H), 5.44-5.24 (m, 1H), 4.91 (dd, 1H), 4.23-4.15 (m, 1H), 4.04-3.17 (m, 5H), 3.08-2.99 (m, 2H), 2.75-2.60 (m, 2H), 2.39-2.18 (m, 2H), 2.05-1.93 (m, 1H)

Example 288. N-benzyl-N-methyl-5-[[(3S)-1-[2-oxo-2-[(2S)-2-cyanopyrrolidin-1-yl]ethyl]pyrrolidin-3-yl]amino]quinoline-8-carboxamide The title compound (6.89 mg, 11.5%) was prepared in the same fashion as Example 5, except that (S)—N-benzyl-N-methyl-5-(pyrrolidin-3-ylamino)quinoline-8-carboxamide hydrochloride (52.0 mg, 0.12 mmol) prepared in Reference Example 144 was used instead of (S)—N-(pyrrolidin-3-yl)quinoline-4-amine hydrochloride. $^1$H NMR (CDCl$_3$, 400 MHz) δ 8.91-8.88 (m, 1H), 8.33 (dt, 1H), 7.53 (dd, 2H), 7.40 (t, 1H), 7.33-7.25 (m, 2H), 7.23-7.19 (m, 2H), 6.52-6.43 (m, 1H), 5.80-5.32 (m, 1H), 4.99-4.74 (m, 1H), 4.38-4.32 (m, 1H), 4.22-4.13 (m, 1H), 3.63-3.43 (m, 4H), 3.10 (s, 3H), 2.99- 2.94 (m, 1H), 2.70-2.66 (m, 3H), 2.45-1.92 (m, 7H).

Example 289. N-methyl-N-phenyl-5-[[(3S)-1-[2-oxo-2-[(2S)-2-cyanopyrrolidin-1-yl]ethyl]pyrrolidin-3-yl]amino]quinoline-8-carboxamide The title compound (5.9 mg, 10.2%) was prepared in the same fashion as Example 5, except that (S)—N-methyl-N-phenyl-5-(pyrrolidin-3-ylamino)quinoline-8-carboxamide hydrochloride (50.3 mg, 0.12 mmol) prepared in Reference Example 143 was used instead of (S)—N-(pyrrolidin-3-yl)quinoline-4-amine hydrochloride. $^1$H NMR (CDCl$_3$, 400 MHz) δ 8.86-8.82 (dd, 1H), 8.38-8.28 (m, 2H), 7.29-7.25 (m, 2H), 7.05-7.00 (m, 4H), 6.18 (d, 1H), 4.76 (d, 1H), 4.09 (br s, 1H), 3.98-3.70 (m, 2H), 3.66-3.15 (m, 7H), 3.03 (br s, 1H), 2.32-2.07 (m, 4H), 2.02-1.96 (m, 1H).

Example 290. N-(3-pyridyl)-5-[[(3S)-1-[2-oxo-2-[(2S)-2-cyanopyrrolidin-1-yl]ethyl]pyrrolidin-3-yl]amino]quinoline-8-carboxamide The title compound (21.8 mg, 50.5%) was prepared in the same fashion as Example 5, except that (S)—N-(pyridin-3-yl)-5-(pyrrolidin-3-ylamino)quinoline-8-carboxamide hydrochloride (36.9 mg, 0.09 mmol) prepared in Reference Example 145 was used instead of (S)—N-(pyrrolidin-3-yl)quinoline-4-amine hydrochloride. $^1$H NMR (CDCl$_3$, 400 MHz) δ 8.91-8.88 (m, 1H), 8.86-8.84 (m, 1H), 8.75-8.71 (m, 1H), 8.67 (d, 0.7H), 8.46-8.44 (m, 1.3H), 8.31 (d, 1H), 7.44-7.39 (m, 1H), 7.31-7.28 (m, 1H), 6.87 (d, 0.7H), 6.62 (d, 1H), 5.95 (d, 0.3H), 4.78-4.70 (m, 1H), 4.24 (s, 1H), 3.67-3.40 (m, 3H), 3.17-3.11 (m, 2H), 2.81-2.69 (m, 1H), 2.49-2.12 (m, 8H), 2.04-1.97 (m, 1H).

Example 291. N-(4-pyridyl)-5-[[(3S)-1-[2-oxo-2-[(2S)-2-cyanopyrrolidin-1-yl]ethyl]pyrrolidin-3-yl]amino]quinoline-8-carboxamide The title compound (11.2 mg, 19.8%) was prepared in the same fashion as Example 5, except that (S)—N-(pyridin-4-yl)-5-(pyrrolidin-3-ylamino)quinoline-8-carboxamide hydrochloride (48.7 mg, 0.12 mmol) prepared in Reference Example 146 was used instead of (S)—N-(pyrrolidin-3-yl)quinoline-4-amine hydrochloride. $^1$H NMR (CDCl$_3$, 400 MHz) δ 8.91-8.87 (m, 1H), 8.74-8.67 (m, 1.7H), 8.49-8.44 (dd, 2.3H), 7.76 (d, 2H), 7.45-7.39 (m, 1H), 7.00 (d, 0.7H), 6.62 (d, 1H), 6.01 (d, 0.3H), 4.78-4.70 (m, 1H), 4.25 (s, 1H), 3.67-3.40 (m, 3H), 3.19-3.12 (m, 2H), 2.82-2.70 (m, 1H), 2.49-2.08 (m, 8H), 2.04-1.97 (m, 1H).

Example 292. N-(4-pyridyl)-5-[[(3S)-1-[2-oxo-2-[(2S,4S)-2-cyano-4-fluoro-pyrrolidin-1-yl]ethyl]pyrrolidin-3-yl]amino]quinoline-8-carboxamide The title compound (8.4 mg, 14.3%) was prepared in the same fashion as Example 28, except that (S)—N-(pyridin-4-yl)-5-(pyrrolidin-3-ylamino)quinoline-8-carboxamide hydrochloride (48.7 mg, 0.12 mmol) prepared in Reference Example 146 was used instead of (S)—N-(pyrrolidin-3-yl)furo[3,2-c]pyridin-7-amine hydrochloride. $^1$H NMR (CDCl$_3$, 400 MHz) δ 8.92-8.89 (m, 1H), 8.72 (t, 1H), 8.59-8.43 (m, 3H), 7.76-7.74 (m, 2H), 7.45-7.41 (m, 1H), 6.63 (d, 1H), 6.54 (d, 0.6H), 5.97 (d, 0.4H), 5.52-5.28 (m, 1H), 4.93 (dd, 1H), 4.30-4.25 (m, 1H), 4.01-3.39 (m, 4H), 3.29-3.06 (m, 3H), 2.79-2.65 (m, 2H), 2.53-2.24 (m, 2H), 2.11-1.99 (m, 1H).

Example 293. N-(2-pyridyl)-5-[[(3S)-1-[2-oxo-2-[(2S)-2-cyanopyrrolidin-1-yl]ethyl]pyrrolidin-3-yl]amino]quinoline-8-carboxamide The title compound (4.3 mg, 7.6%) was prepared in the same fashion as Example 5, except that (S)—N-(pyridin-2-yl)-5-(pyrrolidin-3-ylamino)quinoline-8-carboxamide hydrochloride (48.7 mg, 0.12 mmol) prepared in Reference Example 147 was used instead of (S)—N-(pyrrolidin-3-yl)quinoline-4-amine hydrochloride. $^1$H NMR (CDCl$_3$, 400 MHz) δ 9.06 (td, 1H), 8.80 (dd, 1H), 8.64 (dd, 0.6H), 8.54 (d, 1H), 8.44-8.40 (m, 1.4H), 7.76-7.71 (m, 1H), 7.48-7.41 (m, 1H), 7.04-7.00 (m, 1H), 6.74-6.65 (m, 1.6H), 5.85 (d, 0.4H), 4.81-4.70 (m, 1H), 4.30-4.28 (m, 1H), 3.68-3.43 (m, 4H), 3.28-3.04 (m, 3H), 2.82-2.76 (m, 1H), 2.51-2.11 (m, 6H), 2.03-2.00 (m, 1H).

Example 294. N-(2-pyridyl)-5-[[(3S)-1-[2-oxo-2-[(2S,4S)-2-cyano-4-fluoro-pyrrolidin-1-yl]ethyl]pyrrolidin-3-yl]amino]quinoline-8-carboxamide The title compound (1.7 mg, 2.9%) was prepared in the same fashion as Example 28, except that (S)—N-(pyridin-2-yl)-5-(pyrrolidin-3-ylamino)quinoline-8-carboxamide hydrochloride (48.7 mg, 0.12 mmol) prepared in Reference Example 147 was used instead of (S)—N-(pyrrolidin-3-yl)furo[3,2-c]pyridin-7-amine hydrochloride. $^1$H NMR (CDCl$_3$, 400 MHz) δ 9.06 (td, 1H), 8.79 (dd, 1H), 8.54-8.40 (m, 3H), 7.76-7.71 (m, 1H), 7.45-7.41 (m, 1H), 7.04-7.00 (m, 1H), 6.65 (t, 1H), 6.28 (d, 0.5H), 5.85 (d, 0.5H), 5.51-5.28 (m, 1H), 4.93 (dd, 1H), 4.32-4.26 (m, 1H), 4.13-3.39 (m, 4H), 3.29-3.05 (m, 3H), 2.78-2.64 (m, 2H), 2.57-2.21 (m, 3H), 2.12-1.97 (m, 1H).

Example 295. N-(3-pyridyl)-5-[[(3S)-1-[2-oxo-2-[(2S,4S)-2-cyano-4-fluoro-pyrrolidin-1-yl]ethyl]pyrrolidin-3-yl]amino]quinoline-8-carboxamide The title compound (2.6 mg, 5.5%) was prepared in the same fashion as Example 28, except that (S)—N-(pyridin-3-yl)-5-(pyrrolidin-3-ylamino)quinoline-8-carboxamide hydrochloride (36.9 mg, 0.09 mmol) prepared in Reference Example 145 was used instead of (S)—N-(pyrrolidin-3-yl)furo[3,2-c]pyridin-7-amine hydrochloride. $^1$H NMR (CDCl$_3$, 400 MHz) δ 8.96-8.95 (m, 1H), 8.86 (t, 1H), 8.80-8.77 (m, 1H), 8.59-8.45 (m, 2H), 8.33-8.32 (m, 1H), 7.49-7.44 (m, 1H), 7.34-7.30 (m, 1H), 6.67 (t, 1H), 6.38 (d, 0.5H), 5.89 (d, 0.5H), 5.54-5.30 (m, 1H), 4.94 (dd, 1H), 4.34-4.28 (m, 1H), 4.15-3.39 (m, 4H), 3.29-3.07 (m, 3H), 2.80-2.67 (m, 2H), 2.58-2.23 (m, 3H), 2.13-1.99 (m, 1H).

Example 296. N-[5-[[(3S)-1-[2-oxo-2-[(2S)-2-cyanopyrrolidin-1-yl]ethyl]pyrrolidin-3-yl]amino]-8-quinolyl]acetamide The title compound (5.9 mg, 12.2%) was prepared in the same fashion as Example 5, except that (S)—N-(5-(pyrrolidin-3-ylamino)quinolin-8-yl)acetamide hydrochloride (41.2 mg, 0.12 mmol) prepared in Reference Example 148 was used instead of (S)—N-(pyrrolidin-3-yl)quinoline-4-amine hydrochloride. $^1$H NMR (CDCl$_3$, 400 MHz) δ 9.47 (s, 1H), 8.76-8.74 (m, 1H), 8.59-8.57 (m, 1H), 8.39-8.28 (m, 1H), 7.40-7.36 (m, 1H), 6.52 (t, 1H), 4.79-4.72 (m, 1H), 4.17-4.09 (m, 1H), 3.64- 3.58 (m, 1H), 3.54-3.23 (m, 3H), 3.09-2.91 (m, 3H), 2.74-2.59 (m, 1H), 2.47-2.02 (m, 9H), 1.96-1.86 (m, 1H).

Example 297. N-[5-[[(3S)-1-[2-oxo-2-[(2S,4S)-2-cyano-4-fluoro-pyrrolidin-1-yl]ethyl]pyrrolidin-3-yl]amino]-8-quinolyl]acetamide The title compound (3.9 mg, 7.6%) was prepared in the same fashion as Example 28, except that (S)—N-(5-(pyrrolidin-3-ylamino)quinolin-8-yl)acetamide hydrochloride (41.2 mg, 0.12 mmol) prepared in Reference Example 148 was used instead of (S)—N-(pyrrolidin-3-yl)furo[3,2-c]pyridin-7-amine hydrochloride. $^1$H NMR (CDCl$_3$, 400 MHz) δ 9.47-9.46 (m, 1H), 8.77-8.74 (m, 1H), 8.56 (d, 1H), 8.33-8.29 (m, 1H), 7.39-7.36 (m, 1H), 6.52-6.48 (m, 1H), 5.45-5.21 (m, 1H), 5.01- 4.88 (m, 2H), 4.17-4.12 (m, 1H), 4.08-3.38 (m, 3H), 3.31-3.26 (m, 1H), 3.14-3.01 (m, 1H), 2.96-2.89 (m, 1H), 2.71-2.54 (m, 2H), 2.47-2.18 (m, 5H), 2.00-1.83 (m, 1H).

Example 298. N-[5-[[(3S)-1-[2-oxo-2-[(2S,4S)-2-cyano-4-fluoro-pyrrolidin-1-yl]ethyl]pyrrolidin-3-yl]amino]-8-quinolyl]benzamide The title compound (9.8 mg, 16.8%) was prepared in the same fashion as Example 28, except that (S)—N-(5-(pyrrolidin-3-ylamino)quinolin-8-yl)benzamide hydrochloride (48.5 mg, 0.12 mmol) prepared in Reference Example 149 was used instead of (S)—N-(pyrrolidin-3-yl)furo[3,2-c]pyridin-7-amine hydrochloride. $^1$H NMR (CDCl$_3$, 400 MHz) δ 10.46 (s, 1H), 8.83-8.78 (m, 2H), 8.36-8.33 (m, 1H), 8.06-8.02 (m, 2H), 7.60-7.48 (m, 3H), 7.43-7.40 (m, 1H), 6.59 (t, 1H), 5.47-5.23 (m, 1H), 5.02-4.91 (m, 2H), 4.22-4.18 (m, 1H), 4.15-3.55 (m, 3H), 3.48-3.13 (m, 1H), 3.10-2.93 (m, 2H), 2.75-2.59 (m, 2H), 2.53-2.16 (m, 2.5H), 2.05-1.88 (m, 1.5H).

Example 299. (2S,4S)-4-fluoro-1-[2-[(3S)-3-[(6-methoxy-4-quinolyl)oxy]pyrrolidin-1-yl]acetyl]pyrrolidine-2-carbonitrile (2S,4S)-1-(2-chloroacetyl)-4-fluoro-pyrrolidine-2-carbonitrile (152 mg, 0.80 mmol) prepared in Reference Example 2 was dissolved in anhydrous acetonitrile (4.0 mL). To the resulting solution, (S)-6-methoxy-4-(pyrrolidin-3-yloxy)quinoline hydrochloride (224 mg, 0.80 mmol) prepared in Reference Example 150, potassium carbonate (441 mg, 3.2 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=10/1, v/v) to give a title compound (76 mg, 24%). $^1$H NMR (CDCl$_3$, 600 MHz) δ 8.54 (d, 1H), 7.89 (d, 1H), 7.41 (s, 1H), 7.32 (d, 1H), 6.56 (d, 1H), 5.41-5.17 (m, 1.3H), 5.12-5.00 (m, 1H), 4.91 (d, 0.7H), 4.17-4.04 (m, 1H), 3.91 (s, 3H), 3.79-3.29 (m, 3H), 3.23-3.09 (m, 1H), 3.07-2.89 (m, 2H), 2.75-2.54 (m, 2H), 2.48-2.40 (m, 1H), 2.32-2.09 (m, 2H)

Example 300. (2S,4S)-4-fluoro-1-[2-[(3S)-3-[(6,7-dimethoxy-4-quinolyl)oxy]pyrrolidin-1-yl]acetyl]pyrrolidine-2-carbonitrile (2S,4S)-1-(2-chloroacetyl)-4-fluoro-pyrrolidine-2-carbonitrile (71 mg, 0.37 mmol) prepared in Reference Example 2 was dissolved in anhydrous acetonitrile (2.0 mL). To the resulting solution, (S)-6,7-dimethoxy-4-(pyrrolidin-3-yloxy)quinoline hydrochloride (114 mg, 0.37 mmol) prepared in Reference Example 151, potassium carbonate (204 mg, 1.5 mmol) were added. The reaction mixture was stirred overnight at room temperature. After the completion of the reaction, water was added to the reaction mixture. The aqueous layer of the reaction mixture was extracted with dichloromethane. The extracted organic layer was dried and filtered over anhydrous magnesium sulfate. The filtered solution was concentrated and then purified with silica gel column chromatography (dichloromethane/methanol=10/1, v/v) to give a title compound (40 mg, 25%). $^1$H NMR (CDCl$_3$, 600 MHz) δ 8.52 (d, 1H), 7.39 (s, 1H), 7.35 (s, 1H), 6.53 (d, 1H), 5.46-5.20 (m, 1.4H), 5.14-5.01 (m, 1H), 4.94 (d, 0.6H), 4.23-4.12 (m, 1H), 4.01 (d, 6H), 3.96-3.60 (m, 2H), 3.47-2.91 (m, 4H), 2.80-2.57 (m, 2H), 2.50-2.40 (m, 1H), 2.37-2.10 (m, 2H)

Example 301. N-[1-[2-oxo-2-[(2S)-2-cyanopyrrolidin-1-yl]ethyl]-4-piperidyl]quinoline-8-carboxamide The title compound (424.3 mg, 86.9%) was prepared in the same fashion as Example 110, except that N-(piperidin-4-yl)quinoline-8-carboxamide hydrochloride (409.7 mg, 1.25 mmol) prepared in Reference Example 152 was used instead of N-(piperidin-4-yl)quinoline-5-amine hydrochloride. $^1$H-NMR (CDCl$_3$, 400 MHz) δ 11.47 (s, 1H), 8.92 (d, 1H), 8.83 (d, 1H), 8.28 (d, 1H), 7.96 (d, 1H), 7.66 (t, 1H), 7.49 (t, 1H), 5.40-4.70 (m, 1H), 4.30-4.10 (m, 1H), 3.85-3.50 (m, 2H), 3.50-3.10 (m, 2H), 3.00-2.75 (m, 2H), 2.55-2.20 (m, 4H), 2.20-2.00 (m, 4H), 2.00-1.70 (m, 2H)

Example 302. (2S)-1-[2-[4-[ethyl(3-quinolyl)amino]-1-piperidyl]acetyl]pyrrolidine-2-carbonitrile The title compound (132.5 mg, 38.4%) was prepared in the same fashion as Example 121, except that N-ethyl-N-(piperidin-4-yl)quinolin-3-amine hydrochloride (230.4 mg, 0.88 mmol) prepared in Reference Example 153 was used instead of 3-methyl-N-(piperidin-4-yl)quinoline-5-amine hydrochloride. $^1$H NMR (CDCl$_3$, 400 MHz) δ 8.67 (d, 1H), 7.92-7.90 (m, 1H), 7.61-7.59 (m, 1H), 7.41-7.36 (m, 2H), 7.14 (d, 1H), 5.07-4.73 (m, 1H), 3.74-3.61 (m, 2H), 3.56-3.47 (m, 1H), 3.44-3.38 (m, 2H), 3.36-3.19 (m, 2H), 3.08-2.96 (m, 2H), 2.33-2.03 (m, 7H), 1.90-1.85 (m, 3H), 1.21 (t, 3H).

Example 303. (2S)-1-[2-[4-[ethyl(6-quinolyl)amino]-1-piperidyl]acetyl]pyrrolidine-2-carbonitrile The title compound (274.8 mg, 79.7%) was prepared in the same fashion as Example 121, except that N-ethyl-N-(piperidin-4-yl)quinolin-6-amine hydrochloride (230.4 mg, 0.88 mmol) prepared in Reference Example 154 was used instead of 3-methyl-N-(piperidin-4-yl)quinoline-5-amine hydrochloride. $^1$H NMR (CDCl$_3$, 400 MHz) δ 8.54 (dd, 1H), 7.90-7.86 (m, 2H), 7.30 (dd, 1H), 7.19 (q, 1H), 6.77 (d, 1H), 5.06-4.79 (m, 1H), 3.71-3.58 (m, 2H), 3.53-3.43 (m, 1H), 3.39-3.33 (m, 2H), 3.29-3.12 (m, 2H), 3.04-2.93 (m, 2H), 2.31-1.96 (m, 6H), 1.86-1.78 (m, 4H), 1.18 (t, 3H).

Example 304. (2S,4S)-1-[2-[4-[ethyl(3-quinolyl)amino]-1-piperidyl]acetyl]-4-fluoro-pyrrolidine-2-carbonitrile The title compound (12.4 mg, 27.5%) was prepared in the same fashion as Example 131, except that N-ethyl-N-(piperidin-4-yl)quinolin-3-amine hydrochloride (36.1 mg, 0.11 mmol) prepared in Reference Example 153 was used instead of 3-methyl-N-(piperidin-4-yl)quinoline-5-amine hydrochloride. $^1$H NMR (CDCl$_3$, 400 MHz) δ 8.69 (d, 1H), 7.95-7.92 (m, 1H), 7.63-7.61 (m, 1H), 7.44-7.40 (m, 2H), 7.17 (s, 1H), 5.51-4.94 (m, 2H), 4.21-4.12 (m, 1H), 4.02-3.71 (m, 2H), 3.47-3.40 (m, 3H), 3.30-3.19 (m, 2H), 3.12-2.99 (m, 2H), 2.80-2.64 (m, 1H), 2.50-2.24 (m, 3H), 1.89-1.88 (m, 3H), 1.23 (t, 3H).

Example 305. (2S,4S)-1-[2-[4-[ethyl(5-quinolyl)amino]-1-piperidyl]acetyl]-4-fluoro-pyrrolidine-2-carbonitrile The title compound (39.8 mg, 88.5%) was prepared in the same fashion as Example 131, except that N-ethyl-N-(piperidin-4-yl)quinolin-5-amine hydrochloride (36.1 mg, 0.11 mmol) prepared in Reference Example 155 was used instead of 3-methyl-N-(piperidin-4-yl)quinoline-5-amine hydrochloride. $^1$H NMR (CDCl$_3$, 400 MHz) δ 8.84 (d, 1H), 8.63 (m, 1H), 7.83 (d, 1H), 7.61 (t, 1H), 7.35 (q, 1H), 7.26 (d 1H), 5.44-4.83 (m, 2H), 4.10-3.83 (m, 1H), 3.79-3.66 (m, 1H), 3.37-3.06 (m, 4H), 2.99-2.94 (m, 1H), 2.90-2.76 (m, 2H), 2.69-2.20 (m, 2H), 2.07-2.00 (m, 2H), 1.81-1.59 (m, 4H), 0.86 (t, 3H).

Example 306. (2S,4S)-1-[2-[4-[ethyl(6-quinolyl)amino]-1-piperidyl]acetyl]-4-fluoro-pyrrolidine-2-carbonitrile The title compound (35.4 mg, 78.6%) was prepared in the same fashion as Example 131, except that N-ethyl-N-(piperidin-4-yl)quinolin-6-amine hydrochloride (36.1 mg, 0.11 mmol) prepared in Reference Example 154 was used instead of 3-methyl-N-(piperidin-4-yl)quinoline-5-amine hydrochloride. $^1$H NMR (CDCl$_3$, 400 MHz) δ 8.54 (dd, 1H), 7.90 (s, 1H), 7.87 (s, 1H), 7.32-7.29 (m, 1H), 7.20 (q, 1H), 6.78-6.77 (m, 1H), 5.44-4.87 (m, 2H), 4.13-4.04 (m, 1H), 3.95-3.64 (m, 2H), 3.39-3.34 (m, 2H), 3.26-3.13 (m, 2H), 3.06-2.94 (m, 2H), 2.36-2.22 (m, 3H), 1.86-1.82 (m, 4H), 1.18 (t, 3H).

Example 307. (2S)-1-[2-[4-[methyl(2-quinolyl)amino]-1-piperidyl]acetyl]pyrrolidine-2-carbonitrile The title compound (45.7 mg, 13.7%) was prepared in the same fashion as Example 121, except that N-methyl-N-(piperidin-4-yl)quinolin-2-amine hydrochloride (276.5 mg, 0.88 mmol) prepared in Reference Example 156 was used instead of 3-methyl-N-(piperidin-4-yl)quinoline-5-amine hydrochloride. $^1$H NMR (CDCl$_3$, 400 MHz) δ 7.86 (d, 1H), 7.67 (d, 1H), 7.58 (d, 1H), 7.51 (t, 1H), 7.17 (t, 1H), 6.88 (d, 1H), 5.19-4.71 (m, 2H), 3.81-3.73 (m, 2H), 3.59-3.55 (m, 1H), 3.42-3.22 (m, 2H), 3.08-3.04 (m, 4H), 2.39 (t, 2H), 2.29-2.11 (m, 4H), 1.96-1.90 (m, 2H), 1.76 (d, 2H).

Example 308. (2S)-1-[2-[4-[methyl(4-quinolyl)amino]-1-piperidyl]acetyl]pyrrolidine-2-carbonitrile The title compound (79.5 mg, 23.9%) was prepared in the same fashion as Example 121, except that N-methyl-N-(piperidin-4-yl)quinolin-4-amine hydrochloride (276.5 mg, 0.88 mmol) prepared in Reference Example 157 was used instead of 3-methyl-N-(piperidin-4-yl)quinoline-5-amine hydrochloride. $^1$H NMR (CDCl$_3$, 400 MHz) δ 8.67 (d, 1H), 8.04 (d, 1H), 7.94 (d, 1H), 7.65 (t, 1H), 7.46 (t, 1H), 6.85 (d, 1H), 5.09-4.75 (m, 1H), 3.70-3.48 (m, 3H), 3.31-3.12 (m, 4H), 2.89 (s, 3H), 2.29-2.01 (m, 8H), 1.80 (d, 2H).

Example 309. (2S)-1-[2-[4-[methyl(5-quinolyl)amino]-1-piperidyl]acetyl]pyrrolidine-2-carbonitrile The title compound (220.8 mg, 66.4%) was prepared in the same fashion as Example 121, except that N-methyl-N-(piperidin-4-yl)quinolin-5-amine hydrochloride (276.5 mg, 0.88 mmol) prepared in Reference Example 158 was used instead of 3-methyl-N-(piperidin-4-yl)quinoline-5-amine hydrochloride. $^1$H NMR (CDCl$_3$, 400 MHz) δ 8.88 (d, 1H), 8.51 (d, 1H), 7.80 (d, 1H), 7.62 (t, 1H), 7.38 (q, 1H), 7.20 (d, 1H), 5.18-4.72 (m, 1H), 3.72-3.48 (m, 2H), 3.33-3.02 (m, 3H), 2.95-2.81 (m, 5H), 2.34-2.06 (m, 6H), 2.01-1.80 (m, 4H).

Example 310. (2S)-1-[2-[4-[methyl(6-quinolyl)amino]-1-piperidyl]acetyl]pyrrolidine-2-carbonitrile The title compound (171.0 mg, 51.4%) was prepared in the same fashion as Example 121, except that N-methyl-N-

(piperidin-4-yl)quinolin-6-amine hydrochloride (276.5 mg, 0.88 mmol) prepared in Reference Example 159 was used instead of 3-methyl-N-(piperidin-4-yl)quinoline-5-amine hydrochloride. $^1$H NMR (CDCl$_3$, 400 MHz) δ 8.62 (d, 1H), 7.93 (d, 2H), 7.42 (d, 1H), 7.26 (q, 1H), 6.85 (d, 1H), 5.11-4.75 (m, 1H), 3.79-3.63 (m, 2H), 3.58-3.49 (m, 1H), 3.38-3.20 (m, 2H), 3.16- 2.97 (m, 2H), 3.29 (s, 3H), 2.35-2.08 (m, 7H), 1.99-1.88 (m, 1H), 1.78-1.75 (m, 2H).

Example 311. (2S)-1-[2-[4-[methyl(7-quinolyl)amino]-1-piperidyl]acetyl]pyrrolidine-2-carbonitrile The title compound (35.8 mg, 10.7%) was prepared in the same fashion as Example 121, except that N-methyl-N-(piperidin-4-yl)quinolin-7-amine hydrochloride (276.5 mg, 0.88 mmol) prepared in Reference Example 160 was used instead of 3-methyl-N-(piperidin-4-yl)quinoline-5-amine hydrochloride. $^1$H NMR (CDCl$_3$, 400 MHz) δ 8.73 (d, 1H), 7.96 (d, 1H), 7.64 (d, 1H), 7.22 (d, 2H), 7.10 (q, 1H), 5.14-4.77 (m, 1H), 3.86-3.55 (m, 3H), 3.39-3.00 (m, 4H), 2.94 (s, 3H), 2.45-2.09 (m, 6H), 2.03-1.89 (m, 2H), 1.81-1.78 (m, 2H).

Example 312. (2S)-1-[2-[4-[furo[3,2-c]pyridin-7-yl(methyl)amino]-1-piperidyl]acetyl]pyrrolidine-2-carbonitrile The title compound (139.4 mg, 43.1%) was prepared in the same fashion as Example 121, except that N-methyl-N-(piperidin-4-yl)furo[3,2-c]pyridin-7-amine hydrochloride (267.7 mg, 0.88 mmol) prepared in Reference Example 161 was used instead of 3-methyl-N-(piperidin-4-yl)quinoline-5-amine hydchloride. $^1$H NMR (CDCl$_3$, 400 MHz) δ 8.46 (s, 1H), 7.98 (s, 1H), 7.63 (s, 1H), 6.81 (s, 1H), 5.17-4.75 (m, 1H), 3.96-3.90 (m, 1H), 3.76-3.64 (m, 1H), 3.57-3.51 (m, 1H), 3.39-3.19 (m, 2H), 3.04-2.95 (m, 5H), 2.36-1.92 (m, 8H), 1.81-1.78 (m, 2H).

Example 313. (2S)-1-[2-[4-[5-isoquinolyl(methyl)amino]-1-piperidyl]acetyl]pyrrolidine-2-carbonitrile The title compound (28.4 mg, 8.5%) was prepared in the same fashion as Example 121, except that N-methyl-N-(piperidin-4-yl)isoquinolin-5-amine hydrochloride (267.7 mg, 0.88 mmol) prepared in Reference Example 162 was used instead of 3-methyl-N-(piperidin-4-yl)quinoline-5-amine hydochloride. $^1$H NMR (MeOD$_4$, 400 MHz) δ 9.18 (s, 1H), 8.42 (d, 1H), 8.06 (d, 1H), 7.75 (d, 1H), 7.64-7.51 (m, 2H), 4.74-4.64 (m, 1H), 3.73-3.50 (m, 2H), 3.26-2.85 (m, 8H), 2.22-2.09 (m, 6H), 1.95-1.80 (m, 4H).

Example 314. (2S)-1-(2-(4-(isoquinolin-6-yl(methyl)amino)piperidin-1-yl)acetyl)pyrrolidine-2-carbonitrile The title compound (146.1 mg, 44.0%) was prepared in the same fashion as Example 121, except that N-methyl-N-(piperidin-4-yl)isoquinolin-6-amine hydrochloride (267.7 mg, 0.88 mmol) prepared in Reference Example 163 was used instead of 3-methyl-N-(piperidin-4-yl)quinoline-5-amine hydrochloride. $^1$H NMR (MeOD$_4$, 400 MHz) δ 8.84 (s, 1H), 8.13 (d, 1H), 7.86 (d, 1H), 7.51 (d, 1H), 7.41-7.38 (m, 1H), 6.92 (s, 1H), 5.17-4.76 (m, 1H), 3.96-3.90 (m, 1H), 3.78-3.73 (m, 1H), 3.61- 3.53 (m, 1H), 3.45-3.22 (m, 3H), 3.10-3.08 (m, 2H), 2.96 (s, 3H), 2.39-2.33 (m, 2H), 2.28-2.12 (m, 4H), 2.05-1.96 (m, 1H), 1.74-1.71 (m, 2H).

Example 315. (2S,4S)-4-fluoro-1-[2-[4-[methyl(6-quinolyl)amino]-1-piperidyl]acetyl]pyrrolidine-2-carbonitrile The title compound (4.4 mg, 10.2%) was prepared in the same fashion as Example 131, except that N-methyl-N-(piperidin-4-yl)quinolin-6-amine hydrochloride (34.5 mg, 0.11 mmol) prepared in Reference Example 159 was used instead of 3-methyl-N-(piperidin-4-yl)quinoline-5-amine hydrochloride. $^1$H NMR (CDCl$_3$, 400 MHz) δ 8.62 (d, 1H), 7.94 (d, 2H), 7.41 (d, 1H), 7.27 (t, 1H), 6.85 (s, 1H), 5.49-4.93 (m, 2H), 4.21-3.91 (m, 1H), 3.87-3.75 (m, 2H), 3.46-3.18 (m, 2H), 3.11- 2.98 (m, 2H), 2.91 (s, 3H), 2.80-2.63 (m, 1H), 2.40-2.24 (m, 3H), 2.15-1.90 (m, 2H), 1.79-1.76 (m, 2H).

Example 316. (2S,4S)-4-fluoro-1-[2-[4-[methyl(3-quinolyl)amino]-1-piperidyl]acetyl]pyrrolidine-2-carbonitrile The title compound (12.0 mg, 27.5%) was prepared in the same fashion as Example 131, except that N-methyl-N-(piperidin-4-yl)quinolin-3-amine hydrochloride (34.5 mg, 0.11 mmol) prepared in Reference Example 164 was used instead of 3-methyl-N-(piperidin-4-yl)quinoline-5-amine hydrochloride. $^1$H NMR (CDCl$_3$, 400 MHz) δ 8.76 (d, 1H), 7.97-7.95 (m, 1H), 7.66-7.64 (m, 1H), 7.46-7.43 (m, 2H), 7.22 (d, 1H), 5.51-4.95 (m, 2H), 4.22-3.92 (m, 1H), 3.88-3.75 (m, 2H), 3.46- 3.19 (m, 2H), 3.12-3.00 (m, 2H), 2.92 (s, 3H), 2.81-2.65 (m, 1H), 2.41-2.24 (m, 3H), 2.18-1.79 (m, 4H).

Example 317. (2S,4S)-4-fluoro-1-[2-[4-[3-isoquinolyl(methyl)amino]-1-piperidyl]acetyl]pyrrolidine-2-carbonitrile The title compound (18.7 mg, 43.1%) was prepared in the same fashion as Example 131, except that N-methyl-N-(piperidin-4-yl)isoquinolin-3-amine hydrochloride (34.5 mg, 0.11 mmol) prepared in Reference Example 165 was used instead of 3-methyl-N-(piperidin-4-yl)quinoline-5-amine hydrochloride. $^1$H NMR (CDCl$_3$, 400 MHz) δ 8.75 (d, 1H), 7.95 (q, 1H), 7.65-7.63 (m, 1H), 7.43 (q, 2H), 7.21 (d, 1H), 5.49-4.93 (m, 2H), 4.20-3.91 (m, 1H), 3.87-3.73 (m, 2H), 3.45-3.17 (m, 2H), 3.11-2.99 (m, 2H), 2.91 (s, 3H), 2.76-2.63 (m, 1H), 2.40-2.24 (m, 3H), 2.13-1.77 (m, 4H).

Example 318. (2S,4S)-4-fluoro-1-[2-[4-[5-isoquinolyl(methyl)amino]-1-piperidyl]acetyl]pyrrolidine-2-carbonitrile The title compound (28.4 mg, 65.4%) was prepared in the same fashion as Example 131, except that N-methyl-N-(piperidin-4-yl)isoquinolin-5-amine hydrochloride (34.5 mg, 0.11 mmol) prepared in Reference Example 162 was used instead of 3-methyl-N-(piperidin-4-yl)quinoline-5-amine hydrochloride. $^1$H NMR (CDCl$_3$, 400 MHz) δ 9.21 (s, 1H), 8.51 (dd, 1H), 7.91 (d, 1H), 7.65 (d, 1H), 7.52 (t, 1H), 7.33 (d, 1H), 5.47-4.91 (m, 2H), 4.18-3.90 (m, 1H), 3.85-3.72 (m, 1H), 3.42-3.13 (m, 3H), 2.99-2.86 (m, 2H), 2.82 (s, 3H), 2.78-2.61 (m, 1H), 2.38-1.82 (m, 7H).

Example 319. (2S,4S)-4-fluoro-1-[2-[4-[7-isoquinolyl(methyl)amino]-1-piperidyl]acetyl]pyrrolidine-2-carbonitrile The title compound (14.0 mg, 32.1%) was prepared in the same fashion as Example 131, except that N-methyl-N-

(piperidin-4-yl)isoquinolin-7-amine hydrochloride (34.5 mg, 0.11 mmol) prepared in Reference Example 166 was used instead of 3-methyl-N-(piperidin-4-yl)quinoline-5-amine hydrochloride. $^1$H NMR (CDCl$_3$, 400 MHz) δ 9.06 (s, 1H), 8.27 (dd, 1H), 7.69 (d, 1H), 7.49 (d, 1H), 7.40 (d, 1H), 7.02 (s, 1H), 5.51-4.95 (m, 2H), 4.23-3.92 (m, 1H), 3.88-3.75 (m, 2H), 3.47-3.23 (m, 2H), 3.12-3.00 (m, 2H), 2.92 (s, 3H), 2.77-2.65 (m, 1H), 2.41-2.29 (m, 3H), 2.05-1.89 (m, 2H), 1.80-1.77 (m, 2H).

Example 320. (2S,4S)-4-fluoro-1-[2-[4-[8-isoquinolyl(methyl)amino]-1-piperidyl]acetyl]pyrrolidine-2-carbonitrile The title compound (20.4 mg, 46.9%) was prepared in the same fashion as Example 131, except that N-methyl-N-(piperidin-4-yl)isoquinolin-8-amine hydrochloride (34.5 mg, 0.11 mmol) prepared in Reference Example 166 was used instead of 3-methyl-N-(piperidin-4-yl)quinoline-5-amine hydrochloride. $^1$H NMR (CDCl$_3$, 400 MHz) δ 9.51 (s, 1H), 8.45 (dd, 1H), 7.59-7.43 (m, 3H), 7.17 (d, 1H), 5.45-4.87 (m, 2H), 4.11-3.70 (m, 2H), 3.47-3.09 (m, 3H), 2.92-2.89 (m, 2H), 2.82 (s, 3H), 2.74-2.57 (m, 2H), 2.37-2.22 (m, 2H), 2.09-2.03 (m, 2H), 1.88-1.81 (m, 2H).

Example 321. (2S)-1-[2-[4-[3-isoquinolyl(methyl)amino]-1-piperidyl]acetyl]pyrrolidine-2-carbonitrile The title compound (97.5 mg, 28.0%) was prepared in the same fashion as Example 121, except that N-methyl-N-(piperidin-4-yl)isoquinolin-3-amine hydrochloride (276.5 mg, 0.88 mmol) prepared in Reference Example 165 was used instead of 3-methyl-N-(piperidin-4-yl)quinoline-5-amine hydrochloride. $^1$H NMR (CDCl$_3$, 400 MHz) δ 8.75 (d, 1H), 7.96-7.93 (m, 1H), 7.65-7.63 (m, 1H), 7.44-7.42 (m, 2H), 7.20 (d, 1H), 5.10-4.76 (m, 1H), 3.79-3.65 (m, 2H), 3.57-3.51 (m, 1H), 3.38- 3.17 (m, 2H), 3.12-3.07 (m, 2H), 2.91 (s, 3H), 2.37-1.79 (m, 10H).

Example 322. (2S)-1-[2-[4-[methyl-(6-methyl-3-quinolyl)amino]-1-piperidyl]acetyl]pyrrolidine-2-carbonitrile The title compound (75.9 mg, 22.0%) was prepared in the same fashion as Example 121, except that N,6-dimethyl-N-(piperidin-4-yl)quinolin-3-amine hydrochloride (344.5 mg, 0.88 mmol) prepared in Reference Example 168 was used instead of 3-methyl-N-(piperidin-4-yl)quinoline-5-amine hydrochloride. $^1$H NMR (CDCl$_3$, 400 MHz) δ 8.65 (d, 1H), 7.82 (d, 1H), 7.39 (s, 1H), 7.24 (d, 1H), 7.11 (d, 1H), 5.09-4.75 (m, 1H), 4.21-3.96 (m, 2H), 3.67-3.50 (m, 3H), 3.33-3.18 (m, 2H), 3.06- 2.96 (m, 2H), 2.88 (s, 3H), 2.47 (s, 3H), 2.30-2.06 (m, 5H), 1.98-1.87 (m, 3H).

Example 323. (S)-1-(2-(4-((6-methoxyquinolin-3-yl)(methyl)amino)piperidin-1-yl)acetyl)pyrrolidine-2-carbonitrile The title compound (55.8 mg, 15.5%) was prepared in the same fashion as Example 121, except that 6-methoxy-N-methyl-N-(piperidin-4-yl)quinolin-3-amine hydrochloride (344.5 mg, 0.88 mmol) prepared in Reference Example 169 was used instead of 3-methyl-N-(piperidin-4-yl)quinoline-5-amine hydrochloride. $^1$H NMR (CDCl$_3$, 400 MHz) δ 8.54 (d, 1H), 7.80 (d, 1H), 7.09 (d, 1H), 7.04 (dd, 1H), 6.69 (d, 1H), 5.06-4.72 (m, 1H), 3.87 (s, 3H), 3.75-3.60 (m, 2H), 3.55-3.46 (m, 1H), 3.34-3.13 (m, 2H), 3.05-2.94 (m, 2H), 2.87 (s, 3H), 2.36-1.86 (m, 8H), 1.74 (d, 2H).

Example 324. (2S)-1-[2-[4-[(7-methoxy-3-quinolyl)-methyl-amino]-1-piperidyl]acetyl]pyrrolidine-2-carbonitrile The title compound (59.0 mg, 16.4%) was prepared in the same fashion as Example 121, except that 7-methoxy-N-methyl-N-(piperidin-4-yl)quinolin-3-amine hydrochloride (344.5 mg, 0.88 mmol) prepared in Reference Example 170 was used instead of 3-methyl-N-(piperidin-4-yl)quinoline-5-amine hydrochloride. $^1$H NMR (CDCl$_3$, 400 MHz) δ 8.68 (d, 1H), 7.55 (d, 1H), 7.32 (d, 1H), 7.24 (d, 1H), 7.13 (d, 1H), 5.13-4.78 (m, 1H), 4.15-3.96 (m, 1H), 3.92 (s, 3H), 3.71-3.49 (m, 3H), 3.35-3.17 (m, 2H), 3.07-2.97 (m, 2H), 2.88 (s, 3H), 2.47 (s, 3H), 2.33-1.87 (m, 10H).

Example 325. (2S)-1-[2-[4-[methyl-(8-methoxy-3-quinolyl)amino]-1-piperidyl]acetyl]pyrrolidine-2-carbonitrile The title compound (53.3 mg, 14.8%) was prepared in the same fashion as Example 121, except that 8-methoxy-N-methyl-N-(piperidin-4-yl)quinolin-3-amine hydrochloride (344.5 mg, 0.88 mmol) prepared in Reference Example 171 was used instead of 3-methyl-N-(piperidin-4-yl)quinoline-5-amine hydrochloride. $^1$H NMR (CDCl$_3$, 400 MHz) δ 8.65 (d, 1H), 7.27 (t, 1H), 7.14 (d, 1H), 7.10 (d, 1H), 6.71 (d, 1H), 5.02-4.67 (m, 1H), 3.97 (s, 3H), 3.71-3.40 (m, 3H), 3.29-3.08 (m, 2H), 3.00-2.90 (m, 2H), 2.83 (s, 3H), 2.31-1.97 (m, 6H), 1.92-1.82 (m, 2H), 1.71-1.68 (m, 2H).

Example 326. (2S,4S)-4-fluoro-1-[2-[4-[methyl-(6-methyl-3-quinolyl)amino]-1-piperidyl]acetyl]pyrrolidine-2-carbonitrile The title compound (13.0 mg, 28.9%) was prepared in the same fashion as Example 131, except that N,6-dimethyl-N-(piperidin-4-yl)quinolin-3-amine hydrochloride (36.1 mg, 0.11 mmol) prepared in Reference Example 168 was used instead of 3-methyl-N-(piperidin-4-yl)quinoline-5-amine hydrochloride. $^1$H NMR (CDCl$_3$, 400 MHz) δ 8.66 (d, 1H), 7.83 (d, 1H), 7.40 (s, 1H), 7.27-7.24 (m, 1H), 7.12 (d, 1H), 5.49-4.93 (m, 2H), 4.19-4.01 (m, 1H), 3.81-3.70 (m, 2H), 3.29-3.15 (m, 2H), 3.09-2.93 (m, 2H), 2.88 (s, 3H), 2.47 (s, 3H), 2.24-1.89 (m, 6H), 1.79-1.76 (m, 2H).

Example 327. (2S,4S)-4-fluoro-1-(2-(4-((6-methoxyquinolin-3-yl)(methyl)amino)piperidin-1-yl)acetyl)pyrrolidine-2-carbonitrile The title compound (7.3 mg, 15.5%) was prepared in the same fashion as Example 131, except that 6-methoxy-N-methyl-N-(piperidin-4-yl)quinolin-3-amine hydrochloride (37.8 mg, 0.11 mmol) prepared in Reference Example 169 was used instead of 3-methyl-N-(piperidin-4-yl)quinoline-5-amine hydrochloride. $^1$H NMR (CDCl$_3$, 400 MHz) δ 8.54 (d, 1H), 7.80 (d, 1H), 7.09 (d, 1H), 7.04 (dd, 1H), 6.90 (d, 1H), 5.46-5.24 (m, 2H), 4.14-3.90 (m, 1H), 3.87 (s, 3H), 3.84-3.68 (m, 2H), 3.40-3.13 (m, 2H), 3.07-2.92 (m, 2H), 2.86 (s, 3H), 2.75-2.57 (m, 1H), 2.37-2.20 (m, 3H), 2.10-1.84 (m, 2H), 1.76-1.63 (m, 2H).

Example 328. (2S,4S)-4-fluoro-1-(2-(4-((7-methoxyquinolin-3-yl)(methyl)amino)piperidin-1-yl)acetyl)pyrrolidine-2-carbonitrile The title compound (11.6 mg, 24.7%) was prepared in the same fashion as Example 131, except that 7-methoxy-N- methyl-N-(piperidin-4-yl)quinolin-3-amine hydrochloride (37.8 mg, 0.11 mmol) prepared in Reference Example 170 was used instead of 3-methyl-N-(piperidin-4-yl)quinoline-5-amine hydrochloride. $^1$H NMR (CDCl$_3$, 400 MHz) δ 8.68 (s, 1H), 7.55 (d, 1H), 7.32 (d, 1H), 7.24 (d, 1H), 7.13 (dd, 1H), 5.50-4.94 (m, 2H), 4.21-4.12 (m, 1H), 3.87 (s, 3H), 3.78-3.64 (m, 2H), 3.46-3.17 (m, 2H), 3.10-2.97 (m, 2H), 2.88 (s, 3H), 2.80-2.64 (m, 1H), 2.49-2.24 (m, 3H), 2.12-2.02 (m, 1H), 1.97-1.84 (m, 3H).

Example 329. (2S,4S)-4-fluoro-1-[2-[4-[(8-methoxy-3-quinolyl)-methyl-amino]-1-piperidyl]acetyl]pyrrolidine-2-carbonitrile The title compound (3.8 mg, 8.0%) was prepared in the same fashion as Example 131, except that 8-methoxy-N-methyl-N-(piperidin-4-yl)quinolin-3-amine hydrochloride (37.8 mg, 0.11 mmol) prepared in Reference Example 171 was used instead of 3-methyl-N-(piperidin-4-yl)quinoline-5-amine hydrochloride. $^1$H NMR (CDCl$_3$, 400 MHz) δ 8.72 (d, 1H), 7.35 (t, 1H), 7.22 (d, 1H), 7.18 (d, 1H), 6.80 (d, 1H), 5.50-4.94 (m, 2H), 4.21-4.12 (m, 1H), 4.06 (s, 3H), 3.88-3.73 (m, 2H), 3.46-3.21 (m, 2H), 3.11-2.96 (m, 2H), 2.91 (s, 3H), 2.80-2.65 (m, 1H), 2.50-2.22 (m, 3H), 2.15-1.86 (m, 2H), 1.81-1.78 (m, 3H).

Example 330. (2S,4S)-4-fluoro-1-[2-[4-[(8-fluoro-5-quinolyl)amino]-1-piperidyl]acetyl]pyrrolidine-2-carbonitrile (2S,4S)-1-(2-chloroacetyl)-4-fluoro-pyrrolidin-2-carbonitrile (90.4 mg, 0.47 mmol) prepared in Reference Example 2 was dissolved in anhydrous acetonitrile (4 ml). To the resulting solution, 8-fluoro-N-(piperidin-4-yl)quinolin-5-amine hydrochloride (151.0 mg, 0.47 mmol) prepared in Reference Example 172 and potassium carbonate (262.3 mg, 1.90 mmol) were added. The reaction mixture was stirred overnight at room temperature. After the completion of the reaction, water was added to the reaction mixture. The aqueous layer of the reaction mixture was extracted with ethyl acetate. The extracted organic layer was dried and filtered over anhydrous magnesium sulfate. The filtered solution was concentrated and then purified with silica gel column chromatography (dichloromethane/methanol=10/1, v/v) to give a title compound (76.2 mg, 40.2%). $^1$H-NMR (CD$_3$OD, 400 MHz) δ 8.94 (d, 1H), 8.18 (d, 1H), 7.42 (d, 1H), 7.30-7.26 (m, 1H), 6.55 (d, 1H), 5.50-5.30 (m, 1H), 5.10-4.80 (m, 1H), 4.30-4.15 (m, 1H), 4.05-3.85 (m, 1H), 3.85-3.70 (m, 2H), 3.55-3.15 (m, 2H), 3.05-2.85 (m, 2H), 2.80-2.60 (m, 1H), 2.50-2.30 (m, 2H), 2.20-2.05 (m, 2H), 1.90-1.55 (m, 3H).

Example 331. (2S,4S)-4-fluoro-1-[2-[4-[(8-methyl-5-quinolyl)amino]-1-piperidyl]acetyl]pyrrolidine-2-carbonitrile The title compound (46.7 mg, 24.9%) was prepared in the same fashion as Example 330, except that 8-methyl-N-(piperidin-4-yl)quinolin-5-amine hydrochloride (61.2 mg, 0.20 mmol) prepared in Reference Example 173 was used instead of 8-fluoro-N-(piperidin-4-yl)quinolin-5-amine hydrochloride. $^1$H-NMR (CDCl$_3$, 400 MHz) δ 8.93 (d, 1H), 8.17 (d, 1H), 7.42-7.33 (m, 2H), 6.60 (d, 1H), 5.55-5.30 (m, 1H), 5.05-4.90 (m, 1H), 4.30-4.10 (m, 1H), 4.05-3.65 (m, 2H), 3.55-3.16 (m, 3H), 3.05-2.85 (m, 2H), 2.80-2.68 (m, 1H), 2.68 (s, 3H), 2.50-2.25 (m, 2H), 2.25-2.05 (m, 2H), 1.95-1.50 (m, 3H).

Example 332. (2S,4S)-1-[2-[4-[(8-benzyloxy-5-quinolyl)amino]-1-piperidyl]acetyl]-4-fluoro-pyrrolidine-2-carbonitrile The title compound (109.7 mg, 47.4%) was prepared in the same fashion as Example 330, except that 8-(benzyloxy)-N-(piperidin-4-yl)quinolin-5-amine hydrochloride (134.2 mg, 0.33 mmol) prepared in Reference Example 174 was used instead of 8-fluoro-N-(piperidin-4-yl)quinolin-5-amine hydrochloride. $^1$H-NMR (CDCl$_3$, 400 MHz) δ 8.97 (d, 1H), 8.19 (d, 1H), 7.51-7.49 (m, 2H), 7.41-7.26 (m, 4H), 6.92 (d, 1H), 6.53 (d, 1H), 5.55-5.30 (m, 1H), 5.48 (s, 2H), 5.00-4.85 (m, 1H), 4.30-4.10 (m, 1H), 4.05-3.70 (m, 2H), 3.55-3.20 (m, 3H), 3.05-2.80 (m, 2H), 2.80-2.60 (m, 1H), 2.50-2.25 (m, 2H), 2.25-2.05 (m, 2H), 1.80-1.50 (m, 3H)

Example 333. (2S,4S)-1-[2-[4-[(3-chloro-5-quinolyl)amino]-1-piperidyl]acetyl]-4-fluoro-pyrrolidine-2-carbonitrile The title compound (191.7 mg, 97.1%) was prepared in the same fashion as Example 330, except that 3-chloro-N-(piperidin-4-yl)quinolin-5-amine hydrochloride (241.4 mg, 0.72 mmol) prepared in Reference Example 175 was used instead of 8-fluoro-N-(piperidin-4-yl)quinolin-5-amine hydrochloride. $^1$H-NMR (CDCl$_3$, 400 MHz) δ 8.80 (s, 1H), 8.13 (s, 1H), 7.55 (t, 1H), 7.45 (d, 1H), 6.68 (d, 1H), 5.50-5.30 (m, 1H), 5.00-4.85 (m, 1H), 4.30-4.15 (m, 1H), 4.10-3.70 (m, 2H), 3.60-3.10 (m, 3H), 3.10-2.85 (m, 2H), 2.85-2.60 (m, 1H), 2.50-2.30 (m, 2H), 2.30-2.10 (m, 2H), 1.90-1.50 (m, 3H)

Example 334. (2S,4S)-4-fluoro-1-[2-[4-[[8-(trifluoromethyl)-5-quinolyl]amino]-1-piperidyl]acetyl]pyrrolidine-2-carbonitrile The title compound (116.6 mg, 54.7%) was prepared in the same fashion as Example 330, except that N-(piperidin-4-yl)-8-(trifluoromethyl)quinolin-5-amine hydrochloride (137.5 mg, 0.37 mmol) prepared in Reference Example 176 was used instead of 8-fluoro-N-(piperidin-4-yl)quinolin-5-amine hydrochloride. $^1$H-NMR (CDCl$_3$, 400 MHz) δ 9.01 (d, 1H), 8.16 (d, 1H), 7.89 (d, 1H), 7.41 (t, 1H), 6.56 (d, 1H), 5.55-5.30 (m, 1H), 5.00-4.90 (m, 1H), 4.30-4.10 (m, 1H), 4.05-3.70 (m, 2H), 3.70-3.15 (m, 3H), 3.10-2.85 (m, 2H), 2.80-2.55 (m, 1H), 2.50-2.35 (m, 2H), 2.35-2.10 (m, 2H), 1.95-1.55 (m, 3H)

Example 335. 5-[[1-[2-oxo-2-[(2S,4S)-2-cyano-4-fluoro-pyrrolidin-1-yl]ethyl]-4-piperidyl]amino]quinoline-2-carbonitrile The title compound (42.1 mg, 21.8%) was prepared in the same fashion as Example 330, except that 5-(piperidin-4-ylamino)quinoline-2-carbonitrile hydrochloride (299.7 mg, 0.92 mmol) prepared in Reference Example 177 was used instead of 8-fluoro-N-(piperidin-4-yl)quinolin-5-amine hydrochloride. $^1$H-NMR (CDCl$_3$, 400 MHz) δ 8.29 (d, 1H), 7.68-7.59 (m, 2H), 7.50 (d, 1H), 6.76 (d, 1H), 5.60-5.30 (m, 1H), 5.00-4.90 (m, 1H), 4.30-4.10 (m, 1H), 4.10-3.70 (m, 2H), 3.60-3.20 (m, 3H), 3.10-2.90 (m, 2H), 2.80-2.60 (m, 1H), 2.50-2.30 (m, 2H), 2.30-2.10 (m, 2H), 1.90-1.55 (m, 3H)

Example 336. (2S,4S)-1-(2-(4-(benzo[b]thiophen-4-ylamino)piperidin-1-yl)acetyl)-4-fluoropyrrolidine-2-carbonitrile The title compound (239.9 mg, 93.6%) was prepared in the same fashion as Example 330, except that N-(benzo[b]

thiophen-4-yl)piperidin-4-amine hydrochloride (202.4 mg, 0.66 mmol) prepared in Reference Example 178 was used instead of 8-fluoro-N-(piperidin-4-yl)quinolin-5-amine hydrochloride. $^1$H-NMR (CDCl$_3$, 400 MHz) δ 7.31 (s, 1H), 7.31-7.17 (m, 3H), 6.52 (d, 1H), 5.50-5.25 (m, 1H), 4.95-4.85 (m, 1H), 4.25-4.15 (m, 1H), 4.15-3.70 (m, 2H), 3.55-3.10 (m, 3H), 3.00-2.80 (m, 2H), 2.75-2.60 (m, 1H), 2.40-2.25 (m, 2H), 2.20-2.05 (m, 2H), 1.85-1.50 (m, 3H)

Example 337. (2S,4S)-4-fluoro-1-[2-[4-[(6-fluoro-4-quinolyl)amino]-1-piperidyl]acetyl]pyrrolidine-2-carbonitrile The title compound (22.9 mg, 23.2%) was prepared in the same fashion as Example 330, except that 6-fluoro-N-(piperidin-4-yl)quinolin-4-amine hydrochloride (154.5 mg, 0.49 mmol) prepared in Reference Example 179 was used instead of 8-fluoro-N-(piperidin-4-yl)quinolin-5-amine hydrochloride. $^1$H-NMR (CDCl$_3$, 400 MHz) δ 8.53 (d, 1H), 7.97 (d, 1H), 7.40 (s, 1H), 7.33 (d, 1H), 6.46 (d, 1H), 5.55-5.35 (m, 1H), 5.05-4.95 (m, 1H), 4.30-4.10 (m, 1H), 3.90-3.50 (m, 3H), 3.50-3.10 (m, 2H), 3.05-2.90 (m, 2H), 2.85-2.70 (m, 1H), 2.50-2.35 (m, 2H), 2.25-2.10 (m, 2H), 1.80-1.60 (m, 3H)

Example 338. (2S,4S)-1-[2-[4-[(6-chloro-4-quinolyl)amino]-1-piperidyl]acetyl]-4-fluoro-pyrrolidine-2-carbonitrile The title compound (35.0 mg, 34.0%) was prepared in the same fashion as Example 330, except that 6-chloro-N-(piperidin-4-yl)quinolin-4-amine hydrochloride (194.2 mg, 0.58 mmol) prepared in Reference Example 180 was used instead of 8-fluoro-N-(piperidin-4-yl)quinolin-5-amine hydrochloride. $^1$H-NMR (CDCl$_3$, 400 MHz) δ 8.54 (d, 1H), 7.92 (d, 1H), 7.69 (s, 1H), 7.57 (d, 1H), 6.46 (d, 1H), 5.55-5.30 (m, 1H), 5.00-4.90 (m, 1H), 4.35-4.20 (m, 1H), 4.05-3.70 (m, 2H), 3.65-3.20 (m, 3H), 3.05-2.90 (m, 2H), 2.80-2.60 (m, 1H), 2.50-2.30 (m, 2H), 2.20-2.10 (m, 2H), 1.90-1.60 (m, 3H)

Example 339. (2S,4S)-4-fluoro-1-[2-[4-(4-isoquinolylamino)-1-piperidyl]acetyl]pyrrolidine-2-carbonitrile The title compound (180.2 mg, 40.5%) was prepared in the same fashion as Example 330, except that N-(piperidin-4-yl)isoquinolin-4-amine hydrochloride (350.0 mg, 1.17 mmol) prepared in Reference Example 181 was used instead of 8-fluoro-N-(piperidin-4-yl)quinolin-5-amine hydrochloride. $^1$H-NMR (CDCl$_3$, 400 MHz) δ 8.68 (s, 1H), 7.92-7.88 (m, 2H), 7.78 (d, 1H), 7.66 (t, 1H), 7.58 (t, 1H), 5.55-5.25 (m, 1H), 5.00-4.90 (m, 1H), 4.30-4.15 (m, 1H), 4.15-3.70 (m, 2H), 3.65- 3.20 (m, 3H), 3.10-2.85 (m, 2H), 2.80-2.60 (m, 1H), 2.50-2.30 (m, 2H), 2.30-2.15 (m, 2H), 1.90-1.65 (m, 3H)

Example 340. (2S,4S)-4-fluoro-1-[2-[4-(5-isoquinolylamino)-1-piperidyl]acetyl]pyrrolidine-2-carbonitrile The title compound (153.2 mg, 34.5%) was prepared in the same fashion as Example 330, except that N-(piperidin-4-yl)isoquinolin-5-amine hydrochloride (305.9 mg, 1.02 mmol) prepared in Reference Example 182 was used instead of 8-fluoro-N-(piperidin-4-yl)quinolin-5-amine hydrochloride. $^1$H-NMR (CDCl$_3$, 400 MHz) δ 9.15 (s, 1H), 8.47 (d, 1H), 7.54 (d, 1H), 7.45 (t, 1H), 7.31 (d, 1H), 6.78 (d, 1H), 5.55-5.25 (m, 1H), 5.00-4.85 (m, 1H), 4.30-4.15 (m, 1H), 4.10-3.70 (m, 2H), 3.60-3.15 (m, 3H), 3.05-2.85 (m, 2H), 2.80-2.60 (m, 1H), 2.50-2.30 (m, 2H), 2.30-2.10 (m, 2H), 1.90-1.55 (m, 3H)

Example 341. (2S,4S)-4-fluoro-1-[2-[4-(6-isoquinolylamino)-1-piperidyl]acetyl]pyrrolidine-2-carbonitrile The title compound (28.4 mg, 6.4%) was prepared in the same fashion as Example 330, except that N-(piperidin-4-yl)isoquinolin-6-amine hydrochloride (137.6 mg, 0.46 mmol) prepared in Reference Example 183 was used instead of 8-fluoro-N-(piperidin-4-yl)quinolin-5-amine hydrochloride. $^1$H-NMR (CDCl$_3$, 400 MHz) δ 8.93 (s, 1H), 8.31 (d, 1H), 7.71 (d, 1H), 7.37 (d, 1H), 6.89 (d, 1H), 6.65 (s, 1H), 5.55-5.25 (m, 1H), 5.00-4.85 (m, 1H), 4.35-4.15 (m, 1H), 4.15-3.70 (m, 2H), 3.55-3.15 (m, 3H), 3.05-2.85 (m, 2H), 2.80-2.60 (m, 1H), 2.50-2.30 (m, 2H), 2.25-2.05 (m, 2H), 1.75-1.50 (m, 3H)

Example 342. (2S,4S)-4-fluoro-1-[2-[4-(8-isoquinolylamino)-1-piperidyl]acetyl]pyrrolidine-2-carbonitrile The title compound (40.8 mg, 9.2%) was prepared in the same fashion as Example 330, except that N-(piperidin-4-yl)isoquinolin-8-amine hydrochloride (374.8 mg, 1.25 mmol) prepared in Reference Example 184 was used instead of 8-fluoro-N-(piperidin-4-yl)quinolin-5-amine hydrochloride. $^1$H-NMR (CDCl$_3$, 400 MHz) δ 9.32 (s, 1H), 8.45 (d, 1H), 7.57-7.50 (m, 2H), 7.12 (d, 1H), 6.68 (d, 1H), 5.60-5.25 (m, 1H), 5.00-4.90 (m, 1H), 4.30-4.15 (m, 1H), 4.05-3.70 (m, 2H), 3.60- 3.20 (m, 3H), 3.05-2.85 (m, 2H), 2.85-2.60 (m, 1H), 2.55-2.30 (m, 2H), 2.30-2.10 (m, 2H), 1.90-1.60 (m, 3H)

Example 343. (2S,4S)-4-fluoro-1-[2-[4-[(8-methyl-4-quinolyl)amino]-1-piperidyl]acetyl]pyrrolidine-2-carbonitrile The title compound (205.7 mg, 52.8%) was prepared in the same fashion as Example 330, except that 8-methyl-N-(piperidin-4-yl)quinolin-4-amine hydrochloride (309.6 mg, 0.99 mmol) prepared in Reference Example 185 was used instead of 8-fluoro-N-(piperidin-4-yl)quinolin-5-amine hydrochloride. $^1$H-NMR (CDCl$_3$, 400 MHz) δ 8.58 (d, 1H), 7.58 (d, 1H), 7.50 (d, 1H), 7.32 (t, 1H), 6.46 (d, 1H), 5.50-5.25 (m, 1H), 5.00-4.80 (m, 1H), 4.30-4.10 (m, 1H), 4.05-3.70 (m, 2H), 3.65-3.15 (m, 3H), 3.05-2.85 (m, 2H), 2.76 (s, 3H), 2.76-2.55 (m, 1H), 2.45-2.30 (m, 2H), 2.20-2.05 (m, 2H), 1.85-1.55 (m, 3H)

Example 344. (2S,4S)-1-[2-[4-[(8-chloro-4-quinolyl)amino]-1-piperidyl]acetyl]-4-fluoro-pyrrolidine-2-carbonitrile The title compound (16.6 mg, 4.1%) was prepared in the same fashion as Example 330, except that 8-chloro-N-(piperidin-4-yl)quinolin-4-amine hydrochloride (70.1 mg, 0.21 mmol) prepared in Reference Example 186 was used instead of 8-fluoro-N-(piperidin-4-yl)quinolin-5-amine hydrochloride. $^1$H-NMR (CDCl$_3$, 400 MHz) δ 8.54 (d, 1H), 7.46-7.37 (m, 3H), 6.71 (d, 1H), 5.70-5.20 (m, 1H), 5.05-4.85 (m, 1H), 4.30-4.10 (m, 1H), 4.05-3.70 (m, 2H), 3.60-

3.15 (m, 3H), 3.00-2.80 (m, 2H), 2.80-2.60 (m, 1H), 2.50-2.30 (m, 2H), 2.20-2.05 (m, 2H), 1.90-1.50 (m, 3H)

Example 345. (2S,4S)-4-fluoro-1-[2-[4-[(8-fluoro-4-quinolyl)amino]-1-piperidyl]acetyl]pyrrolidine-2-carbonitrile The title compound (18.7 mg, 4.8%) was prepared in the same fashion as Example 330, except that 8-fluoro-N-(piperidin-4-yl)quinolin-4-amine hydrochloride (192.9 mg, 0.61 mmol) prepared in Reference Example 187 was used instead of 8-fluoro-N-(piperidin-4-yl)quinolin-5-amine hydrochloride. $^1$H-NMR (CDCl$_3$, 400 MHz) δ 8.59 (d, 1H), 7.49 (d, 1H), 7.36-7.33 (m, 2H), 6.50 (d, 1H), 5.55-5.25 (m, 1H), 5.05-4.90 (m, 1H), 4.30-4.15 (m, 1H), 4.05-3.70 (m, 2H), 3.65-3.20 (m, 3H), 3.10-2.85 (m, 2H), 2.80-2.60 (m, 1H), 2.50-2.30 (m, 2H), 2.20-2.05 (m, 2H), 1.90-1.50 (m, 3H)

Example 346. (2S,4S)-4-fluoro-1-[2-[4-[[8-(trifluoromethyl)-4-quinolyl]amino]-1-piperidyl]acetyl]pyrrolidine-2-carbonitrile The title compound (347.4 mg, 78.5%) was prepared in the same fashion as Example 330, except that N-(piperidin-4-yl)-8-(trifluoromethyl)quinolin-4-amine hydrochloride (341.3 mg, 0.93 mmol) prepared in Reference Example 188 was used instead of 8-fluoro-N-(piperidin-4-yl)quinolin-5-amine hydrochloride. $^1$H-NMR (CDCl$_3$, 400 MHz) δ 8.65 (d, 1H), 7.99-7.95 (m, 2H), 7.44 (t, 1H), 6.51 (d, 1H), 5.50-5.20 (m, 1H), 5.10-4.85 (m, 1H), 4.30-4.10 (m, 1H), 4.00-3.65 (m, 2H), 3.60-3.10 (m, 3H), 3.05-2.80 (m, 2H), 2.75-2.55 (m, 1H), 2.50-2.25 (m, 2H), 2.25-2.05 (m, 2H), 1.90-1.55 (m, 3H)

Example 347. (2S,4S)-4-fluoro-1-[2-[4-[[8-(trifluoromethoxy)-5-quinolyl]amino]-1-piperidyl]acetyl]pyrrolidine-2-carbonitrile The title compound (125.5 mg, 82.2%) was prepared in the same fashion as Example 330, except that N-(piperidin-4-yl)-8-(trifluoromethoxy)quinolin-5-amine hydrochloride (408.2 mg, 1.06 mmol) prepared in Reference Example 189 was used instead of 8-fluoro-N-(piperidin-4-yl)quinolin-5-amine hydrochloride. $^1$H-NMR (CDCl$_3$, 400 MHz) δ 9.00 (d, 1H), 8.18 (d, 1H), 7.50 (d, 1H), 7.43 (t, 1H), 6.56 (d, 1H), 5.55-5.25 (m, 1H), 5.05-4.90 (m, 1H), 4.30-4.15 (m, 1H), 4.05-3.70 (m, 2H), 3.60- 3.20 (m, 3H), 3.10-2.90 (m, 2H), 2.80-2.60 (m, 1H), 2.50-2.35 (m, 2H), 2.35-2.10 (m, 2H), 1.90-1.60 (m, 3H)

Example 348. (2S,4S)-4-fluoro-1-[2-[4-[(3-methoxy-5-quinolyl)amino]-1-piperidyl]acetyl]pyrrolidine-2-carbonitrile The title compound (284.9 mg, 75.5%) was prepared in the same fashion as Example 330, except that 3-methoxy-N-(piperidin-4-yl)quinolin-5-amine hydrochloride (302.7 mg, 0.92 mmol) prepared in Reference Example 190 was used instead of 8-fluoro-N-(piperidin-4-yl)quinolin-5-amine hydrochloride. $^1$H-NMR (CDCl$_3$, 400 MHz) δ 8.65 (s, 1H), 7.47-7.38 (m, 2H), 7.34 (s, 1H), 6.68 (d, 1H), 5.50-5.20 (m, 1H), 5.00-4.85 (m, 1H), 4.30-4.15 (m, 1H), 3.90 (s, 3H), 4.10-3.70 (m, 2H), 3.55- 3.10 (m, 3H), 3.05-2.85 (m, 2H), 2.80-2.60 (m, 1H), 2.45-2.30 (m, 2H), 2.30-2.10 (m, 2H), 1.95-1.55 (m, 3H)

Example 349. (2S,4S)-4-fluoro-1-[2-[4-[(3-fluoro-5-quinolyl)amino]-1-piperidyl]acetyl]pyrrolidine-2-carbonitrile The title compound (147.1 mg, 37.0%) was prepared in the same fashion as Example 330, except that 3-fluoro-N-(piperidin-4-yl)quinolin-5-amine hydrochloride (316.6 mg, 1.00 mmol) prepared in Reference Example 191 was used instead of 8-fluoro-N-(piperidin-4-yl)quinolin-5-amine hydrochloride. $^1$H-NMR (CDCl$_3$, 400 MHz) δ 8.75 (s, 1H), 7.81 (d, 1H), 7.54-7.47 (m, 2H), 6.69 (d, 1H), 5.50-5.20 (m, 1H), 5.00-4.80 (m, 1H), 4.30-4.10 (m, 1H), 4.10-3.70 (m, 2H), 3.60-3.10 (m, 3H), 3.00-2.80 (m, 2H), 2.80-2.55 (m, 1H), 2.50-2.30 (m, 2H), 2.30-2.10 (m, 2H), 1.85-1.50 (m, 3H)

Example 350. (2S,4S)-4-fluoro-1-[2-[4-[furo[3,2-c]pyridin-7-yl(methyl)amino]-1-piperidyl]acetyl]pyrrolidine-2-carbonitrile The title compound (8.9 mg, 21.0%) was prepared in the same fashion as Example 131, except that N-methyl-N-(piperidin-4-yl)furo[3,2-c]pyridin-7-amine hydrochloride (33.4 mg, 0.11 mmol) prepared in Reference Example 161 was used instead of 3-methyl-N-(piperidin-4-yl)quinoline-5-amine hydrochloride. $^1$H NMR (MeOD$_4$, 400 MHz) δ 8.35 (s, 1H), 7.87 (d, 2H), 6.96 (d, 1H), 5.51-4.96 (m, 2H), 4.15-3.75 (m, 3H), 3.42-3.20 (m, 2H), 3.06-3.01 (m, 2H), 2.95 (s, 3H), 2.66-2.40 (m, 2H), 2.29-2.23 (m, 2H), 2.04-1.95 (m, 2H), 1.75-1.73 (m, 2H).

Example 351. (2S,4S)-1-[2-[4-[(1-chloro-5-isoquinolyl)amino]-1-piperidyl]acetyl]-4-fluoro-pyrrolidine-2-carbonitrile The title compound (34.6 mg, 60.8%) was prepared in the same fashion as Example 330, except that 1-chloro-N-(piperidin-4-yl)isoquinolin-5-amine hydrochloride (45.8 mg, 0.14 mmol) prepared in Reference Example 192 was used instead of 8-fluoro-N-(piperidin-4-yl)quinolin-5-amine hydrochloride. $^1$H-NMR (CDCl$_3$, 400 MHz) δ 8.21 (d, 1H), 8.06 (d, 1H), 7.88-7.49 (m, 2H), 6.83 (d, 1H), 5.55-5.25 (m, 1H), 5.00-4.85 (m, 1H), 4.30-4.15 (m, 1H), 4.15-3.70 (m, 2H), 3.60-3.20 (m, 3H), 3.05-2.85 (m, 2H), 2.80-2.60 (m, 1H), 2.50-2.30 (m, 2H), 2.30-2.10 (m, 2H), 1.85-1.55 (m, 3H)

Example 352. (2S,4S)-1-[2-[4-[(3-chloro-5-isoquinolyl)amino]-1-piperidyl]acetyl]-4-fluoro-pyrrolidine-2-carbonitrile The title compound (194.4 mg, 50.9%) was prepared in the same fashion as Example 330, except that 3-chloro-N-(piperidin-4-yl)isoquinolin-5-amine hydrochloride (307.2 mg, 0.92 mmol) prepared in Reference Example 193 was used instead of 8-fluoro-N-(piperidin-4-yl)quinolin-5-amine hydrochloride. $^1$H-NMR (CDCl$_3$, 400 MHz) δ 8.95 (s, 1H), 7.66 (s, 1H), 7.43 (t, 1H), 7.28 (d, 1H), 6.76 (d, 1H), 5.55-5.35 (m, 1H), 5.00-4.85 (m, 1H), 4.30-4.10 (m, 1H), 4.00-3.70 (m, 2H), 3.55-3.15 (m, 3H), 3.05-2.85 (m, 2H), 2.80-2.60 (m, 1H), 2.50-2.25 (m, 2H), 2.25-2.10 (m, 2H), 1.90-1.50 (m, 3H)

Example 353. (2S,4S)-1-[2-[4-[(8-chloro-5-isoquinolyl)amino]-1-piperidyl]acetyl]-4-fluoro-pyrrolidine-2-carbonitrile The title compound (193.7 mg, 63.6%) was prepared in the same fashion as Example 330, except that 8-chloro-N-

(piperidin-4-yl)isoquinolin-5-amine hydrochloride (245.2 mg, 0.73 mmol) prepared in Reference Example 194 was used instead of 8-fluoro-N-(piperidin-4-yl)quinolin-5-amine hydrochloride. ¹H-NMR (CDCl₃, 400 MHz) δ 9.58 (s, 1H), 8.57 (d, 1H), 7.54 (d, 1H), 7.45 (d, 1H), 6.67 (d, 1H), 5.55-5.25 (m, 1H), 5.00-4.90 (m, 1H), 4.30-4.10 (m, 1H), 4.00-3.65 (m, 2H), 3.60-3.20 (m, 3H), 3.10-2.85 (m, 2H), 2.85-2.60 (m, 1H), 2.50-2.30 (m, 2H), 2.30-2.10 (m, 2H), 1.90-1.55 (m, 3H)

Example 354. (2S,4S)-4-fluoro-1-[2-[4-[(4-methyl-5-isoquinolyl)amino]-1-piperidyl]acetyl]pyrrolidine-2-carbonitrile The title compound (307.2 mg, 93.3%) was prepared in the same fashion as Example 330, except that 4-methyl-N-(piperidin-4-yl)isoquinolin-5-amine hydrochloride (261.6 mg, 0.83 mmol) prepared in Reference Example 195 was used instead of 8-fluoro-N-(piperidin-4-yl)quinolin-5-amine hydrochloride. ¹H-NMR (CDCl₃, 400 MHz) δ 8.93 (s, 1H), 8.11 (s, 1H), 7.39 (t, 1H), 7.27-7.23 (m, 1H), 6.73 (d, 1H), 5.50-5.20 (m, 1H), 5.00-4.80 (m, 1H), 4.30-4.10 (m, 1H), 4.05-3.70 (m, 2H), 3.55- 3.15 (m, 3H), 2.91 (s, 3H), 2.91-2.80 (m, 2H), 2.80-2.60 (m, 1H), 2.55-2.30 (m, 2H), 2.30-2.10 (m, 2H), 1.85-1.50 (m, 3H)

Example 355. (2S,4S)-4-fluoro-1-[2-[4-[(3-methoxy-5-isoquinolyl)amino]-1-piperidyl]acetyl]pyrrolidine-2-carbonitrile The title compound (76.0 mg, 16.2%) was prepared in the same fashion as Example 330, except that 3-methoxy-N-(piperidin-4-yl)isoquinolin-5-amine hydrochloride (376.0 mg, 1.14 mmol) prepared in Reference Example 196 was used instead of 8-fluoro-N-(piperidin-4-yl)quinolin-5-amine hydrochloride. ¹H-NMR (CDCl₃, 400 MHz) δ 8.86 (s, 1H), 7.48-7.21 (m, 2H), 6.91 (s, 1H), 6.66 (d, 1H), 5.60-5.30 (m, 1H), 5.00-4.90 (m, 1H), 4.30-4.10 (m, 1H), 4.05 (s, 3H), 4.05-3.70 (m, 2H), 3.60- 3.20 (m, 3H), 3.10-2.90 (m, 2H), 2.80-2.60 (m, 1H), 2.60-2.30 (m, 2H), 2.30-2.10 (m, 2H), 1.85-1.50 (m, 3H)

Example 356. (2S,4S)-4-fluoro-1-[2-[4-[(8-nitro-5-isoquinolyl)amino]-1-piperidyl]acetyl]pyrrolidine-2-carbonitrile The title compound (95.6 mg, 19.7%) was prepared in the same fashion as Example 330, except that 8-nitro-N-(piperidin-4-yl)isoquinolin-5-amine hydrochloride (165.1 mg, 0.48 mmol) prepared in Reference Example 197 was used instead of 8-fluoro-N-(piperidin-4-yl)quinolin-5-amine hydrochloride. ¹H-NMR (CDCl₃, 400 MHz) δ 8.66 (d, 1H), 8.50 (d, 1H), 7.58 (d, 1H), 7.26 (s, 1H), 6.66 (d, 1H), 5.60-5.20 (m, 1H), 5.00-4.85 (m, 1H), 4.30-4.10 (m, 1H), 4.00-3.70 (m, 2H), 3.70-3.15 (m, 3H), 3.10-2.90 (m, 2H), 2.85-2.60 (m, 1H), 2.55-2.30 (m, 2H), 2.30-2.10 (m, 2H), 1.85-1.50 (m, 3H)

Example 357. (2S,4S)-4-fluoro-1-[2-[4-[(8-fluoro-5-isoquinolyl)amino]-1-piperidyl]acetyl]pyrrolidine-2-carbonitrile The title compound (225.9 mg, 49.7%) was prepared in the same fashion as Example 330, except that 8-fluoro-N-(piperidin-4-yl)isoquinolin-5-amine hydrochloride (348.2 mg, 1.09 mmol) prepared in Reference Example 198 was used instead of 8-fluoro-N-(piperidin-4-yl)quinolin-5-amine hydrochloride. ¹H-NMR (CDCl₃, 400 MHz) δ 9.45 (s, 1H), 8.56 (d, 1H), 7.57 (d, 1H), 7.10 (d, 1H), 6.66 (d, 1H), 5.55-5.25 (m, 1H), 5.00-4.85 (m, 1H), 4.30-4.10 (m, 1H), 4.05-3.70 (m, 2H), 3.55-3.15 (m, 3H), 3.05-2.85 (m, 2H), 2.80-2.60 (m, 1H), 2.55-2.30 (m, 2H), 2.25-2.05 (m, 2H), 1.85-1.55 (m, 3H)

Example 358. (2S)-1-[2-[4-[(2-chloro-6,7-dimethoxy-quinazolin-4-yl)amino]-1-piperidyl]acetyl]pyrrolidine-2-carbonitrile The title compound (210.7 mg, 95.2%) was prepared in the same fashion as Example 110, except that 2-chloro-6,7-dimethoxy-N-(piperidin-4-yl)quinazolin-4-amine hydrochloride (190.9 mg, 0.48 mmol) prepared in Reference Example 199 was used instead of N-(piperidin-4-yl)quinoline-5-amine hydrochloride. ¹H-NMR (CDCl₃, 400 MHz) δ 7.07-7.02 (m, 2H), 6.20-6.10 (m, 1H), 5.00-4.70 (m, 1H), 4.40-4.20 (m, 1H), 3.95 (s, 3H), 3.93 (s, 3H), 3.75-3.40 (m, 2H), 3.35-3.10 (m, 2H), 3.05-2.85 (m, 2H), 2.45-2.25 (m, 3H), 2.25-2.00 (m, 4H), 1.90-1.60 (m, 3H)

Example 359. (2S)-1-[2-[4-[(2-chloro-8-methyl-quinazolin-4-yl)amino]-1-piperidyl]acetyl]pyrrolidine-2-carbonitrile The title compound (148.0 mg, 74.3%) was prepared in the same fashion as Example 110, except that 2-chloro-8-methyl-N-(piperidin-4-yl)quinazolin-4-amine hydrochloride (128.7 mg, 0.37 mmol) prepared in Reference Example 200 was used instead of N-(piperidin-4-yl)quinoline-5-amine hydrochloride. ¹H-NMR (CDCl₃, 400 MHz) δ 7.59-7.54 (m, 2H), 7.34 (t, 1H), 5.90-5.75 (m, 1H), 5.10-4.70 (m, 1H), 4.40-4.20 (m, 1H), 3.80-3.50 (m, 2H), 3.40-3.10 (m, 2H), 3.10-2.85 (m, 2H), 2.64 (s, 3H), 2.50-2.20 (m, 3H), 2.20-2.00 (m, 4H), 1.90-1.60 (m, 3H)

Example 360. (2S,4S)-4-fluoro-1-[2-[4-(2,6-naphthyridin-4-ylamino)-1-piperidyl]acetyl]pyrrolidine-2-carbonitrile The title compound (55.6 mg, 42.1%) was prepared in the same fashion as Example 330, except that N-(piperidin-4-yl)-2,6-naphthyridin-4-amine hydrochloride (104.1 mg, 0.35 mmol) prepared in Reference Example 201 was used instead of 8-fluoro-N-(piperidin-4-yl)quinolin-5-amine hydrochloride. ¹H-NMR (CDCl₃, 400 MHz) δ 9.10 (s, 1H), 8.58 (d, 1H), 8.11 (d, 1H), 7.54 (s, 1H), 7.00 (s, 1H), 5.55-5.25 (m, 1H), 5.05-4.90 (m, 1H), 4.30-4.15 (m, 1H), 4.05-3.70 (m, 2H), 3.50-3.15 (m, 3H), 3.05-2.85 (m, 2H), 2.80-2.60 (m, 1H), 2.50-2.30 (m, 2H), 2.30-2.10 (m, 2H), 1.95-1.60 (m, 3H)

Example 361. (2S,4S)-1-[2-[4-[(8-chloro-4-isoquinolyl)amino]-1-piperidyl]acetyl]-4-fluoro-pyrrolidine-2-carbonitrile The title compound (91.6 mg, 63.7%) was prepared in the same fashion as Example 330, except that 8-chloro-N-(piperidin-4-yl)isoquinolin-4-amine hydrochloride (95.1 mg, 0.28 mmol) prepared in Reference Example 202 was used instead of 8-fluoro-N-(piperidin-4-yl)quinolin-5-amine hydrochloride. ¹H-NMR (CDCl₃, 400 MHz) δ 8.29 (d, 1H), 7.81-7.66 (m, 3H), 7.61 (s, 1H), 5.55-5.30 (m, 1H), 5.00-4.90 (m, 1H), 4.30-4.15 (m, 1H), 4.15-3.70 (m, 2H), 3.60-

3.20 (m, 3H), 3.10-2.90 (m, 2H), 2.85-2.65 (m, 1H), 2.50-2.35 (m, 2H), 2.35-2.15 (m, 2H), 1.90-1.60 (m, 3H)

Example 362. (2S,4S)-4-fluoro-1-[2-[4-(3-quinolylamino)-1-piperidyl]acetyl]pyrrolidine-2-carbonitrile The title compound (154.9 mg, 60.1%) was prepared in the same fashion as Example 330, except that N-(piperidin-4-yl)quinolin-3-amine hydrochloride (202.9 mg, 0.68 mmol) prepared in Reference Example 203 was used instead of 8-fluoro-N-(piperidin-4-yl)quinolin-5-amine hydrochloride. $^1$H-NMR (CDCl$_3$, 400 MHz) δ 8.44 (s, 1H), 7.95 (d, 1H), 7.62 (d, 1H), 7.44-7.43 (m, 2H), 7.03 (s, 1H), 5.50-5.30 (m, 1H), 5.00-4.90 (m, 1H), 4.30-4.15 (m, 1H), 4.15-3.70 (m, 2H), 3.55- 3.20 (m, 3H), 3.10-2.90 (m, 2H), 2.85-2.60 (m, 1H), 2.55-2.35 (m, 3H), 2.35-2.10 (m, 2H), 1.80-1.50 (m, 2H)

Example 363. (2S,4S)-4-fluoro-1-[2-[4-[(6-methyl-3-quinolyl)amino]-1-piperidyl]acetyl]pyrrolidine-2-carbonitrile The title compound (102.5 mg, 38.4%) was prepared in the same fashion as Example 330, except that 6-methyl-N-(piperidin-4-yl)quinolin-3-amine hydrochloride (131.9 mg, 0.42 mmol) prepared in Reference Example 204 was used instead of 8-fluoro-N-(piperidin-4-yl)quinolin-5-amine hydrochloride. $^1$H-NMR (CDCl$_3$, 400 MHz) δ 8.35 (s, 1H), 7.82 (d, 1H), 7.38 (s, 1H), 7.24 (d, 1H), 6.95 (s, 1H), 5.55-5.25 (m, 1H), 5.00-4.90 (m, 1H), 4.30-4.10 (m, 1H), 4.05-3.70 (m, 2H), 3.55-3.20 (m, 3H), 3.05-2.80 (m, 2H), 2.80-2.60 (m, 1H), 2.45 (s, 3H), 2.45-2.20 (m, 3H), 2.20-2.10 (m, 2H), 1.80-1.50 (m, 2H)

Example 364. (2S,4S)-4-fluoro-1-[2-[4-[(6-fluoro-3-quinolyl)amino]-1-piperidyl]acetyl]pyrrolidine-2-carbonitrile The title compound (167.9 mg, 62.2%) was prepared in the same fashion as Example 330, except that 6-fluoro-N-(piperidin-4-yl)quinolin-3-amine hydrochloride (201.1 mg, 0.63 mmol) prepared in Reference Example 205 was used instead of 8-fluoro-N-(piperidin-4-yl)quinolin-5-amine hydrochloride. $^1$H-NMR (CDCl$_3$, 400 MHz) δ 8.35 (s, 1H), 7.90 (d, 1H), 7.23-7.13 (m, 2H), 6.93 (s, 1H), 5.55-5.30 (m, 1H), 5.05-4.95 (m, 1H), 4.30-4.10 (m, 1H), 4.05-3.75 (m, 2H), 3.55-3.20 (m, 3H), 3.10-2.90 (m, 2H), 2.85-2.60 (m, 1H), 2.50-2.25 (m, 3H), 2.25-2.10 (m, 2H), 1.85-1.50 (m, 2H)

Example 365. (2S,4S)-4-fluoro-1-[2-[4-[(6-methoxy-3-quinolyl)amino]-1-piperidyl]acetyl]pyrrolidine-2-carbonitrile The title compound (85.7 mg, 30.8%) was prepared in the same fashion as Example 330, except that 6-methoxy-N-(piperidin-4-yl)quinolin-3-amine hydrochloride (179.4 mg, 0.54 mmol) prepared in Reference Example 206 was used instead of 8-fluoro-N-(piperidin-4-yl)quinolin-5-amine hydrochloride. $^1$H-NMR (CDCl$_3$, 400 MHz) δ 8.26 (s, 1H), 7.82 (d, 1H), 7.06 (d, 1H), 6.93 (s, 1H), 6.91 (s, 1H), 5.50-5.25 (m, 1H), 5.00-4.90 (m, 1H), 4.30-4.10 (m, 1H), 3.90 (s, 3H), 4.05-3.70 (m, 2H), 3.55-3.20 (m, 3H), 3.05-2.85 (m, 2H), 2.80-2.60 (m, 1H), 2.50-2.30 (m, 3H), 2.30-2.10 (m, 2H), 1.85-1.50 (m, 2H)

Example 366. (2S,4S)-4-fluoro-1-[2-[4-[(7-methoxy-3-quinolyl)amino]-1-piperidyl]acetyl]pyrrolidine-2-carbonitrile The title compound (39.6 mg, 14.2%) was prepared in the same fashion as Example 330, except that 7-methoxy-N-(piperidin-4-yl)quinolin-3-amine hydrochloride (61.0 mg, 0.19 mmol) prepared in Reference Example 207 was used instead of 8-fluoro-N-(piperidin-4-yl)quinolin-5-amine hydrochloride. $^1$H-NMR (CDCl$_3$, 400 MHz) δ 8.38 (s, 1H), 7.52 (d, 1H), 7.31 (s, 1H), 7.13 (d, 1H), 7.05 (s, 1H), 5.55-5.30 (m, 1H), 5.00-4.90 (m, 1H), 4.25-4.10 (m, 1H), 3.90 (s, 3H), 4.05-3.70 (m, 2H), 3.55-3.20 (m, 3H), 3.05-2.85 (m, 2H), 2.80-2.60 (m, 1H), 2.50-2.25 (m, 3H), 2.25-2.05 (m, 2H), 1.80-1.50 (m, 2H)

Example 367. (2S,4S)-4-fluoro-1-[2-[4-[(8-methoxy-3-quinolyl)amino]-1-piperidyl]acetyl]pyrrolidine-2-carbonitrile The title compound (29.5 mg, 10.6%) was prepared in the same fashion as Example 330, except that 8-methoxy-N-(piperidin-4-yl)quinolin-3-amine hydrochloride (72.5 mg, 0.22 mmol) prepared in Reference Example 208 was used instead of 8-fluoro-N-(piperidin-4-yl)quinolin-5-amine hydrochloride. $^1$H-NMR (CDCl$_3$, 400 MHz) δ 8.42 (s, 1H), 7.36 (t, 1H), 7.19 (d, 1H), 7.00 (s, 1H), 6.79 (d, 1H), 5.55-5.30 (m, 1H), 5.05-4.90 (m, 1H), 4.30-4.10 (m, 1H), 4.06 (s, 3H), 4.06-3.70 (m, 2H), 3.60-3.25 (m, 3H), 3.10-2.90 (m, 2H), 2.85-2.60 (m, 1H), 2.60-2.35 (m, 3H), 2.35-2.10 (m, 2H), 1.80-1.55 (m, 2H)

Example 368. (2S,4S)-4-fluoro-1-[2-[4-(1,8-naphthyridin-3-ylamino)-1-piperidyl]acetyl]pyrrolidine-2-carbonitrile The title compound (109.4 mg, 49.7%) was prepared in the same fashion as Example 330, except that N-(piperidin-4-yl)-1,8-naphthyridin-3-amine hydrochloride (173.4 mg, 0.58 mmol) prepared in Reference Example 209 was used instead of 8-fluoro-N-(piperidin-4-yl)quinolin-5-amine hydrochloride. $^1$H-NMR (CDCl$_3$, 600 MHz) δ 8.79 (d, 1H), 8.59 (s, 1H), 7.96 (d, 1H), 7.35 (t, 1H), 6.95 (s, 1H), 5.50-5.30 (m, 1H), 5.00-4.90 (m, 1H), 4.25-4.15 (m, 1H), 4.00-3.70 (m, 2H), 3.50-3.20 (m, 3H), 3.05-2.85 (m, 2H), 2.80-2.60 (m, 1H), 2.50-2.30 (m, 3H), 2.20-2.10 (m, 2H), 1.80-1.55 (m, 2H)

Example 369. (2S,4S)-1-[2-[4-[(7-chloro-1,8-naphthyridin-3-yl)amino]-1-piperidyl]acetyl]-4-fluoro-pyrrolidine-2-carbonitrile The title compound (13.8 mg, 20.6%) was prepared in the same fashion as Example 330, except that 7-chloro-N-(piperidin-4-yl)-1,8-naphthyridin-3-amine hydrochloride (53.6 mg, 0.16 mmol) prepared in Reference Example 210 was used instead of 8-fluoro-N-(piperidin-4-yl)quinolin-5-amine hydrochloride. $^1$H-NMR (CDCl$_3$, 600 MHz) δ 8.55 (s, 1H), 7.90 (d, 1H), 7.35 (d, 1H), 6.95 (s, 1H), 5.50-5.30 (m, 1H), 5.00-4.90 (m, 1H), 4.30-4.10 (m, 1H), 4.00-3.70 (m, 2H), 3.50-3.20 (m, 3H), 3.05-2.90 (m, 2H), 2.80-2.65 (m, 1H), 2.50-2.30 (m, 3H), 2.20-2.10 (m, 2H), 1.80-1.55 (m, 2H)

Example 370. (2S)-1-[2-[4-[(8-ethoxy-5-quinolyl)amino]-1-piperidyl]acetyl]pyrrolidine-2-carbonitrile The title compound (35.4 mg, 9.8%) was prepared in the same fashion as Example 121, except that 8-ethoxy-N-

(piperidin-4-yl)quinolin-5-amine hydrochloride (302.9 mg, 0.88 mmol) prepared in Reference Example 211 was used instead of 3-methyl-N-(piperidin-4-yl)quinoline-5-amine hydrochloride. 1H NMR (CDCl3, 400 MHz) δ 8.90 (dd, 1H), 8.18 (dd, 1H), 7.34 (q, 1H), 6.93 (d, 1H), 6.59 (d, 1H), 5.17-4.69 (m, 1H), 4.21 (q, 2H), 3.73-3.58 (m, 2H), 3.53-3.46 (m, 1H), 3.37-3.13 (m, 3H), 2.93-2.83 (m, 2H), 2.35-2.00 (m, 8H), 1.73-1.56 (m, 2H), 1.53 (t, 3H).

Example 371. (2S,4S)-1-[2-[4-[(8-ethoxy-5-quinolyl)amino]-1-piperidyl]acetyl]-4-fluoro-pyrrolidine-2-carbonitrile The title compound (2.4 mg, 5.0%) was prepared in the same fashion as Example 131, except that 8-ethoxy-N-(piperidin-4-yl)quinolin-5-amine hydrochloride (37.8 mg, 0.11 mmol) prepared in Reference Example 211 was used instead of 3-methyl-N-(piperidin-4-yl)quinoline-5-amine hydrochloride. 1H NMR (CDCl3, 400 MHz) δ 8.90 (dd, 1H), 8.18 (dd, 1H), 7.36 (q, 1H), 6.94 (d, 1H), 6.60 (d, 1H), 5.46-4.87 (m, 2H), 4.22 (q, 2H), 4.17-3.67 (m, 1H), 3.83-3.68 (m, 2H), 3.44-3.21 (m, 2H), 3.18 (s, 1H), 2.96-2.84 (m, 2H), 2.73-2.56 (m, 1H), 2.35-2.10 (m, 5H), 1.75-1.53 (m, 5H).

Example 372. (2S,4S)-1-[2-[4-(1,3-benzothiazol-7-ylamino)-1-piperidyl]acetyl]-4-fluoro-pyrrolidine-2-carbonitrile The title compound (266.8 mg, 61.2%) was prepared in the same fashion as Example 330, except that N-(piperidin-4-yl)benzo[d]thiazol-7-amine hydrochloride (344.8 mg, 1.13 mmol) prepared in Reference Example 212 was used instead of 8-fluoro-N-(piperidin-4-yl)quinolin-5-amine hydrochloride. $^1$H-NMR (CDCl$_3$, 600 MHz) δ 8.92 (s, 1H), 7.56 (d, 1H), 7.38 (t, 1H), 6.66 (d, 1H), 5.50-5.30 (m, 1H), 5.00-4.90 (m, 1H), 4.25-4.15 (m, 1H), 4.00-3.70 (m, 2H), 3.60-3.15 (m, 3H), 3.00- 2.80 (m, 2H), 2.80-2.60 (m, 1H), 2.50-2.20 (m, 3H), 2.20-2.10 (m, 2H), 1.85-1.50 (m, 2H)

Example 373. (2S,4S)-1-[2-[4-[(1-acetylindolin-4-yl)amino]-1-piperidyl]acetyl]-4-fluoro-pyrrolidine-2-carbonitrile The title compound (45.8 mg, 12.8%) was prepared in the same fashion as Example 330, except that 1-(4-(piperidin-4-ylamino)indolin-1-yl)ethan-1-one hydrochloride (286.8 mg, 0.86 mmol) prepared in Reference Example 213 was used instead of 8-fluoro-N-(piperidin-4-yl)quinolin-5-amine hydrochloride. $^1$H-NMR (CDCl$_3$, 400 MHz) δ 7.63 (d, 1H), 7.10 (t, 1H), 6.36 (d, 1H), 5.50-5.25 (m, 1H), 5.00-4.90 (m, 1H), 4.30-4.10 (m, 1H), 4.09 (t, 2H), 4.00-3.70 (m, 2H), 3.50-3.15 (m, 3H), 3.00- 2.80 (m, 4H), 2.80-2.60 (m, 1H), 2.45-2.25 (m, 3H), 2.21 (s, 3H), 2.20-2.00 (m, 2H), 1.75-1.45 (m, 2H)

Example 374. (2S,4S)-4-fluoro-1-[2-[4-[(8-methyl-6-quinolyl)amino]-1-piperidyl]acetyl]pyrrolidine-2-carbonitrile The title compound (149.1 mg, 65.6%) was prepared in the same fashion as Example 330, except that 8-methyl-N-(piperidin-4-yl)quinolin-6-amine hydrochloride (180.7 mg, 0.58 mmol) prepared in Reference Example 214 was used instead of 8-fluoro-N-(piperidin-4-yl)quinolin-5-amine hydrochloride. $^1$H-NMR (CDCl$_3$, 400 MHz) δ 8.64 (d, 1H), 7.88 (d, 1H), 7.28-7.24 (m, 1H), 6.94 (s, 1H), 6.57 (s, 1H), 5.50-5.25 (m, 1H), 5.00-4.90 (m, 1H), 4.30-4.15 (m, 1H), 4.05-3.70 (m, 2H), 3.50- 3.20 (m, 3H), 3.00-2.85 (m, 2H), 2.80-2.60 (m, 1H), 2.72 (s, 3H), 2.50-2.20 (m, 3H), 2.20-2.10 (m, 2H), 1.80-1.50 (m, 2H)

Example 375. (2S,4S)-4-fluoro-1-[2-[4-[(8-fluoro-6-quinolyl)amino]-1-piperidyl]acetyl]pyrrolidine-2-carbonitrile The title compound (305.3 mg, 83.1%) was prepared in the same fashion as Example 330, except that 8-fluoro-N-(piperidin-4-yl)quinolin-6-amine hydrochloride (292.4 mg, 0.92 mmol) prepared in Reference Example 215 was used instead of 8-fluoro-N-(piperidin-4-yl)quinolin-5-amine hydrochloride. $^1$H-NMR (CDCl$_3$, 400 MHz) δ 8.63 (s, 1H), 7.89 (d, 1H), 7.32-7.28 (m, 1H), 6.80 (d, 1H), 6.50 (s, 1H), 5.50-5.25 (m, 1H), 5.00-4.90 (m, 1H), 4.30-4.15 (m, 1H), 4.05-3.70 (m, 2H), 3.50- 3.20 (m, 3H), 3.05-2.85 (m, 2H), 2.80-2.60 (m, 1H), 2.50-2.20 (m, 3H), 2.20-2.05 (m, 2H), 1.80-1.50 (m, 2H)

Example 376. (2S,4S)-1-[2-[4-[(8-chloro-6-quinolyl)amino]-1-piperidyl]acetyl]-4-fluoro-pyrrolidine-2-carbonitrile The title compound (265.9 mg, 62.6%) was prepared in the same fashion as Example 330, except that 8-chloro-N-(piperidin-4-yl)quinolin-6-amine hydrochloride (341.7 mg, 1.02 mmol) prepared in Reference Example 216 was used instead of 8-fluoro-N-(piperidin-4-yl)quinolin-5-amine hydrochloride. $^1$H-NMR (CDCl$_3$, 400 MHz) δ 8.80 (d, 1H), 8.71 (d, 1H), 7.32 (t, 1H), 7.24 (s, 1H), 6.62 (s, 1H), 5.50-5.25 (m, 1H), 5.00-4.90 (m, 1H), 4.30-4.10 (m, 1H), 4.05-3.70 (m, 2H), 3.50-3.20 (m, 3H), 3.00-2.85 (m, 2H), 2.80-2.60 (m, 1H), 2.50-2.20 (m, 3H), 2.20-2.05 (m, 2H), 1.80-1.50 (m, 2H)

Example 377. (2S,4S)-4-fluoro-1-[2-[4-[[8-(trifluoromethyl)-6-quinolyl]amino]-1-piperidyl]acetyl]pyrrolidine-2-carbonitrile The title compound (270.6 mg, 83.7%) was prepared in the same fashion as Example 330, except that N-(piperidin-4-yl)-8-(trifluoromethyl)quinolin-6-amine hydrochloride (264.8 mg, 0.72 mmol) prepared in Reference Example 217 was used instead of 8-fluoro-N-(piperidin-4-yl)quinolin-5-amine hydrochloride. $^1$H-NMR (CDCl$_3$, 400 MHz) δ 8.75 (d, 1H), 7.95 (d, 1H), 7.44 (s, 1H), 7.35 (t, 1H), 6.83 (s, 1H), 5.50-5.30 (m, 1H), 5.00-4.90 (m, 1H), 4.30-4.10 (m, 1H), 4.05-3.70 (m, 2H), 3.55- 3.20 (m, 3H), 3.05-2.85 (m, 2H), 2.80-2.60 (m, 1H), 2.50-2.20 (m, 3H), 2.20-2.05 (m, 2H), 1.80-1.50 (m, 2H)

Example 378. (2S)-1-[2-[4-[(2-oxochromen-4-yl)amino]-1-piperidyl]acetyl]pyrrolidine-2-carbonitrile The title compound (25.9 mg, 72.0%) was prepared in the same fashion as Example 121, except that 4-(piperidin-4-ylamino)-2H-chromen-2-one hydrochloride (30.0 mg, 0.09 mmol) prepared in Reference Example 218 was used instead of 3-methyl-N-(piperidin-4-yl)quinoline-5-amine hydrochloride. $^1$H NMR (CDCl$_3$, 400 MHz) δ 7.55-7.47 (m, 2H), 7.33 (d, 1H), 7.28-7.24 (m, 1H), 5.34 (d, 1H), 5.22-5.15 (m, 1H), 5.03-4.75 (m, 1H), 3.75-3.63 (m, 1H), 3.60-3.42 (m, 2H), 3.32-3.17 (m, 2H), 3.04-2.91 (m, 2H), 2.39-2.06 (m, 8H), 1.92-1.66 (m, 2H).

Example 379. (2S,4S)-4-fluoro-1-[2-[4-[(2-oxochromen-4-yl)amino]-1-piperidyl]acetyl]pyrrolidine-2-carbonitrile The title compound (20.3 mg, 53.8%) was prepared in the same fashion as Example 131, except that 4-(piperidin-4-ylamino)-2H-chromen-2-one hydrochloride (30.0 mg, 0.09 mmol) prepared in Reference Example 218 was used instead of 3-methyl-N-(piperidin-4-yl)quinoline-5-amine hydrochloride. $^1$H NMR (CDCl$_3$, 400 MHz) δ 7.56-7.47 (m, 2H), 7.33 (d, 1H), 7.28-7.24 (m, 1H), 5.50-5.25 (m, 2.4H), 5.20-5.14 (m, 1H), 4.95 (d, 0.6H), 4.22-4.16 (m, 1.5H), 4.00-3.72 (m, 1.5H), 3.49-3.41 (m, 1H), 3.37-3.17 (m, 2H), 3.03-2.92 (m, 2H), 2.79-2.64 (m, 1H), 2.41-2.31 (m, 3H), 2.17- 2.07 (m, 2H), 1.94-1.64 (m, 2H).

Example 380. (2S,4S)-4-fluoro-1-[2-[4-(1,5-naphthyridin-4-ylamino)-1-piperidyl]acetyl]pyrrolidine-2-carbonitrile The title compound (4.3 mg, 10.2%) was prepared in the same fashion as Example 131, except that N-(piperidin-4-yl)-1,5-naphthyridin-4-amine hydrochloride (33.1 mg, 0.11 mmol) prepared in Reference Example 219 was used instead of 3-methyl-N-(piperidin-4-yl)quinoline-5-amine hydrochloride. $^1$H NMR (CDCl$_3$, 400 MHz) δ 8.69 (dd, 1H), 8.54 (d, 1H), 8.22 (dd, 1H), 7.57 (q, 1H), 6.65-6.62 (m, 1H), 6.53 (d, 1H), 5.51-4.94 (m, 2H), 4.26-3.93 (m, 1H), 3.90-3.73 (m, 1H), 3.59-3.26 (m, 2H), 3.25 (s, 1H), 3.03-2.90 (m, 2H), 2.80-2.64 (m, 1H), 2.49-2.16 (m, 4H), 1.89-1.67 (m, 3H).

Example 381. (2S,4S)-4-fluoro-1-[2-[4-[[2-(trifluoromethyl)-6-quinolyl]amino]-1-piperidyl]acetyl]pyrrolidine-2-carbonitrile The title compound (429.7 mg, 81.7%) was prepared in the same fashion as Example 330, except that N-(piperidin-4-yl)-2-(trifluoromethyl)quinolin-6-amine hydrochloride (430.8 mg, 1.17 mmol) prepared in Reference Example 220 was used instead of 8-fluoro-N-(piperidin-4-yl)quinolin-5-amine hydrochloride. $^1$H-NMR (CDCl$_3$, 400 MHz) δ 8.02 (d, 1H), 7.95 (d, 1H), 7.57 (d, 1H), 7.13 (d, 1H), 6.70 (s, 1H), 5.50-5.25 (m, 1H), 5.00-4.90 (m, 1H), 4.30-4.10 (m, 1H), 4.05-3.70 (m, 2H), 3.55- 3.20 (m, 3H), 3.05-2.85 (m, 2H), 2.80-2.60 (m, 1H), 2.50-2.20 (m, 3H), 2.20-2.10 (m, 2H), 1.85-1.55 (m, 2H)

Example 382. (2S,4S)-4-fluoro-1-[2-[4-[(4-methoxy-6-quinolyl)amino]-1-piperidyl]acetyl]pyrrolidine-2-carbonitrile The title compound (25.9 mg, 20.5%) was prepared in the same fashion as Example 330, except that 4-methoxy-N-(piperidin-4-yl)quinolin-6-amine hydrochloride (101.7 mg, 0.31 mmol) prepared in Reference Example 221 was used instead of 8-fluoro-N-(piperidin-4-yl)quinolin-5-amine hydrochloride. $^1$H-NMR (CDCl$_3$, 400 MHz) δ 8.49 (d, 1H), 7.83 (d, 1H), 7.08-7.03 (m, 2H), 6.66 (d, 1H), 5.50-5.25 (m, 1H), 5.00-4.90 (m, 1H), 4.30-4.15 (m, 1H), 4.03 (s, 3H), 4.00-3.70 (m, 2H), 3.55- 3.20 (m, 3H), 3.05-2.85 (m, 2H), 2.80-2.60 (m, 1H), 2.50-2.25 (m, 3H), 2.20-2.10 (m, 2H), 1.85-1.50 (m, 2H)

Example 383. (2S,4S)-1-[2-[4-[(2-bromo-4-pyridyl)amino]-1-piperidyl]acetyl]-4-fluoro-pyrrolidine-2-carbonitrile The title compound (65.4 mg, 22.1%) was prepared in the same fashion as Example 330, except that 2-bromo-N-(piperidin-4-yl)pyridin-4-amine hydrochloride (237.3 mg, 0.72 mmol) prepared in Reference Example 222 was used instead of 8-fluoro-N-(piperidin-4-yl)quinolin-5-amine hydrochloride. $^1$H-NMR (CDCl$_3$, 400 MHz) δ 7.91 (d, 1H), 6.59 (s, 1H), 6.36 (d, 1H), 5.50-5.25 (m, 1H), 5.00-4.90 (m, 1H), 4.25-4.10 (m, 1H), 4.05-3.70 (m, 2H), 3.45-3.15 (m, 3H), 3.05-2.80 (m, 2H), 2.80-2.60 (m, 1H), 2.50-2.25 (m, 3H), 2.05-2.00 (m, 2H), 1.80-1.50 (m, 2H)

Example 384. (2S,4S)-1-[2-[4-(3H-benzimidazol-4-ylamino)-1-piperidyl]acetyl]-4-fluoro-pyrrolidine-2-carbonitrile The title compound (363.5 mg, 97.2%) was prepared in the same fashion as Example 330, except that N-(piperidin-4-yl)-1H-benzo[d]imidazol-7-amine hydrochloride (292.1 mg, 1.01 mmol) prepared in Reference Example 223 was used instead of 8-fluoro-N-(piperidin-4-yl)quinolin-5-amine hydrochloride. $^1$H-NMR (MeOD, 400 MHz) δ 7.99 (s, 1H), 7.08 (t, 1H), 6.85 (d, 1H), 6.45 (d, 1H), 5.55-5.30 (m, 1H), 5.00-4.90 (m, 1H), 4.20-4.05 (m, 1H), 3.95-3.70 (m, 2H), 3.60-3.20 (m, 3H), 3.00- 2.90 (m, 2H), 2.70-2.55 (m, 1H), 2.55-2.30 (m, 3H), 2.20-2.05 (m, 2H), 1.85-1.60 (m, 2H)

Example 385. (2S,4S)-1-[2-[4-[(2-chloro-6-morpholino-4-pyridyl)amino]-1-piperidyl]acetyl]-4-fluoro-pyrrolidine-2-carbonitrile The title compound (157.9 mg, 29.9%) was prepared in the same fashion as Example 330, except that 2-chloro-6-morpholino-N-(piperidin-4-yl)pyridin-4-amine hydrochloride (431.5 mg, 1.17 mmol) prepared in Reference Example 224 was used instead of 8-fluoro-N-(piperidin-4-yl)quinolin-5-amine hydrochloride. $^1$H-NMR (CDCl$_3$, 400 MHz) δ 5.95 (s, 1H), 5.56 (s, 1H), 5.50-5.25 (m, 1H), 5.00-4.90 (m, 1H), 4.25-4.05 (m, 1H), 4.00-3.70 (m, 6H), 3.50-3.40 (m, 4H), 3.40-3.15 (m, 3H), 3.00- 2.80 (m, 2H), 2.80-2.60 (m, 1H), 2.50-2.20 (m, 3H), 2.10-1.95 (m, 2H), 1.70-1.45 (m, 2H)

Example 386. (2S,4S)-4-fluoro-1-[2-[4-[[3-(trifluoromethyl)-5-quinolyl]amino]-1-piperidyl]acetyl]pyrrolidine-2-carbonitrile The title compound (450.5 mg, 92.9%) was prepared in the same fashion as Example 330, except that N-(piperidin-4-yl)-3-(trifluoromethyl)quinolin-5-amine hydrochloride (397.5 mg, 1.08 mmol) prepared in Reference Example 225 was used instead of 8-fluoro-N-(piperidin-4-yl)quinolin-5-amine hydrochloride. $^1$H-NMR (CDCl$_3$, 400 MHz) δ 9.03 (s, 1H), 8.43 (s, 1H), 7.67 (t, 1H), 7.50 (d, 1H), 6.73 (d, 1H), 5.55-5.25 (m, 1H), 5.00-4.90 (m, 1H), 4.30-4.15 (m, 1H), 4.05-3.70 (m, 2H), 3.60- 3.20 (m, 3H), 3.10-2.90 (m, 2H), 2.80-2.60 (m, 1H), 2.50-2.25 (m, 3H), 2.25-2.10 (m, 2H), 1.90-1.60 (m, 2H)

Example 387. (2S)-1-[2-[4-[[3-(trifluoromethyl)-5-quinolyl]amino]-1-piperidyl]acetyl]pyrrolidine-2-carbonitrile The title compound (324.7 mg, 69.7%) was prepared in the same fashion as Example 110, except that N-(piperidin-4-yl)-3-(trifluoromethyl)quinolin-5-amine hydrochloride (397.5 mg, 1.08 mmol) prepared in Reference Example 225 was used instead of N-(piperidin-4-yl)quinoline-5-amine hydrochloride. $^1$H-NMR (CDCl$_3$, 400 MHz) δ 9.03 (s, 1H), 8.42 (s, 1H), 7.67 (t, 1H), 7.51 (d, 1H), 6.73 (d, 1H), 5.20-4.70 (m, 1H), 4.50-4.35 (m, 1H), 3.85-3.60 (m, 1H), 3.60-3.45 (m, 3H), 3.45-3.20 (m, 2H), 3.10-2.90 (m, 2H), 2.50-2.35 (m, 2H), 2.35-2.10 (m, 5H), 1.90-1.60 (m, 2H)

Example 388. 5-[[1-[2-oxo-2-[(2S,4S)-2-cyano-4-fluoro-pyrrolidin-1-yl]ethyl]-4-piperidyl]amino]-N-phenyl-quinoline-3-carboxamide The title compound (29.3 mg, 53.3%) was prepared in the same fashion as Example 131, except that N-phenyl-5-(piperidin-4-ylamino)quinoline-3-carboxamide hydrochloride (46.0 mg, 0.11 mmol) prepared in Reference Example 226 was used instead of 3-methyl-N-(piperidin-4-yl)quinoline-5-amine hydrochloride. 1H NMR (CDCl3, 400 MHz) δ 9.33 (d, 1H), 8.91 (d, 1H), 8.69 (d, 1H), 7.72-7.70 (m, 2H), 7.64-7.59 (m, 1H), 7.46-7.43 (m, 1H), 7.38 (q, 2H), 7.18 (q, 1H), 6.67-6.62 (m, 1H), 5.48-4.92 (m, 2H), 4.03-3.70 (m, 2H), 3.47-3.23 (m, 2H), 3.19 (d, 1H), 3.00-2.61 (m, 3H), 2.40-2.28 (m, 3H), 2.17-2.01 (m, 2H), 1.65-1.46 (m, 3H).

Example 389. N-benzyl-N-methyl-5-[[1-[2-oxo-2-[(2S,4S)-2-cyano-4-fluoro-pyrrolidin-1-yl]ethyl]-4-piperidyl]amino]quinoline-3-carboxamide The title compound (42.1 mg, 72.4%) was prepared in the same fashion as Example 131, except that N-benzyl-N-methyl-5-(piperidin-4-ylamino)quinoline-3-carboxamide hydrochloride (50.2 mg, 0.11 mmol) prepared in Reference Example 227 was used instead of 3-methyl-N-(piperidin-4-yl)quinoline-5-amine hydrochloride. $^1$H NMR (CDCl$_3$, 400 MHz) δ 8.90 (s, 1H), 8.37 (d, 1H), 7.55 (s, 1H), 7.36-7.19 (m, 6H), 6.60 (s, 1H), 5.45-4.89 (m, 2H), 4.76-3.73 (m, 5H), 3.44-2.88 (m, 8H), 2.73- 2.60 (m, 1H), 2.47-2.22 (m, 3H), 2.09-2.01 (m, 2H), 1.75-1.48 (m, 2H).

Example 390. N-methyl-5-[[1-[2-oxo-2-[(2S,4S)-2-cyano-4-fluoro-pyrrolidin-1-yl]ethyl]-4-piperidyl]amino]quinoline-8-carboxamide The title compound (11.7 mg, 24.4%) was prepared in the same fashion as Example 131, except that N-methyl-5-(piperidin-4-ylamino)quinoline-8-carboxamide hydrochloride (39.2 mg, 0.11 mmol) prepared in Reference Example 228 was used instead of 3-methyl-N-(piperidin-4-yl)quinoline-5-amine hydrochloride. $^1$H NMR (CDCl$_3$, 400 MHz) δ 10.92 (d, 1H), 8.83 (dd, 1H), 8.68 (d, 1H), 8.26 (d, 1H), 7.36-7.33 (m, 1H), 6.65 (dd, 1H), 5.47-4.91 (m, 2H), 4.89-4.85 (m, 1H), 4.21-3.71 (m, 2H), 3.60-3.50 (m, 1H), 3.42-3.16 (m, 3H), 3.09 (d, 3H), 3.00-2.89 (m, 2H), 2.74-2.60 (m, 1H), 2.40-1.58 (m, 6H).

Example 391. N,N-dimethyl-5-[[1-[2-oxo-2-[(2S,4S)-2-cyano-4-fluoro-pyrrolidin-1-yl]ethyl]-4-piperidyl]amino]quinoline-8-carboxamide The title compound (24.2 mg, 48.7%) was prepared in the same fashion as Example 131, except that N,N-dimethyl-5-(piperidin-4-ylamino)quinoline-8-carboxamide hydrochloride (40.7 mg, 0.11 mmol) prepared in Reference Example 229 was used instead of 3-methyl-N-(piperidin-4-yl)quinoline-5-amine hydrochloride. $^1$H NMR (CDCl$_3$, 400 MHz) δ 8.82 (dd, 1H), 8.16 (d, 1H), 7.45 (d, 1H), 7.27-7.23 (m, 1H), 6.54 (d, 1H), 5.44-4.86 (m, 2H), 4.63 (d, 1H), 4.19-3.71 (m, 2H), 3.46-3.47 (m, 3H), 3.28-3.13 (m, 4H), 2.91-2.86 (m, 2H), 2.78 (s, 3H), 2.70-2.54 (m, 1H), 2.74-2.60 (m, 1H), 2.46-2.02 (m, 5H).

Example 392. N-methyl-5-[[1-[2-oxo-2-[(2S,4S)-2-cyano-4-fluoro-pyrrolidin-1-yl]ethyl]-4-piperidyl]amino]-N-phenyl-quinoline-8-carboxamide The title compound (11.4 mg, 20.3%) was prepared in the same fashion as Example 131, except that N-methyl-N-phenyl-5-(piperidin-4-ylamino)quinoline-8-carboxamide hydrochloride (47.5 mg, 0.11 mmol) prepared in Reference Example 230 was used instead of 3-methyl-N-(piperidin-4-yl)quinoline-5-amine hydrochloride. $^1$H NMR (CDCl$_3$, 400 MHz) δ 8.84-8.83 (m, 1H), 8.04-8.02 (d, 1H), 7.27-6.99 (m, 7H), 6.34 (s, 1H), 5.41-5.20 (m, 2H), 4.48 (s, 1H), 4.14-3.82 (m, 1H), 3.80-3.65 (m, 1H), 3.63-3.41 (m, 3H), 3.37-3.21 (m, 2H), 3.17-3.10 (m, 1H), 2.91-2.79 (m, 2H), 2.66-2.51 (m, 1H), 2.36-2.00 (m, 5H), 1.74-1.51 (m, 2H).

Example 393. N-benzyl-N-methyl-5-[[1-[2-oxo-2-[(2S,4S)-2-cyano-4-fluoro-pyrrolidin-1-yl]ethyl]-4-piperidyl]amino]quinoline-8-carboxamide The title compound (12.5 mg, 21.5%) was prepared in the same fashion as Example 131, except that N-benzyl-N-methyl-5-(piperidin-4-ylamino)quinoline-8-carboxamide hydrochloride (49.1 mg, 0.11 mmol) prepared in Reference Example 231 was used instead of 3-methyl-N-(piperidin-4-yl)quinoline-5-amine hydrochloride. $^1$H NMR (CDCl$_3$, 400 MHz) δ 8.81 (s, 1H), 8.22-8.16 (m, 1H), 7.49 (t, 2H), 7.34 (t, 1H), 7.27-7.14 (m, 4H), 6.50 (q, 1H), 5.39-4.89 (m, 2H), 4.30 (q, 1H), 4.08-4.01 (m, 1H), 3.88-3.61 (m, 2H), 3.40-3.20 (m, 2H), 3.16-3.05 (m, 3H), 2.83-2.82 (m, 2H), 2.65-2.45 (m, 3H), 2.39-2.00 (m, 5H), 1.77-1.58 (m, 2H).

Example 394. 5-[[1-[2-oxo-2-[(2S,4S)-2-cyano-4-fluoro-pyrrolidin-1-yl]ethyl]-4-piperidyl]amino]-N-phenyl-quinoline-8-carboxamide The title compound (29.6 mg, 53.7%) was prepared in the same fashion as Example 131, except that N-phenyl-5-(piperidin-4-ylamino)quinoline-8-carboxamide hydrochloride (54.0 mg, 0.11 mmol) prepared in Reference Example 232 was used instead of 3-methyl-N-(piperidin-4-yl)quinoline-5-amine hydrochloride. $^1$H NMR (CDCl$_3$, 400 MHz) δ 13.47 (s, 1H), 8.87-8.85 (m, 1H), 8.71 (dd, 1H), 8.28 (dd, 1H), 7.83 (d, 2H), 7.38-7.32 (m, 3H), 7.09 (t, 1H), 6.64 (t, 1H), 5.42-4.88 (m, 3H), 4.14-3.86 (m, 1H), 3.84-3.65 (m, 1H), 3.58-3.47 (m, 1H), 3.34-3.12 (m, 2H), 2.99-2.87 (m, 2H), 2.69- 2.56 (m, 1H), 2.43-2.10 (m, 5H), 1.90-1.63 (m, 2H).

Example 395. N-methyl-5-[[1-[2-oxo-2-[(2S)-2-cyanopyrrolidin-1-yl]ethyl]-4-piperidyl]amino]quinoline-8-carboxamide The title compound (243.0 mg, 65.6%) was prepared in the same fashion as Example 121, except that N-methyl-5-(piperidin-4-ylamino)quinoline-8-carboxamide hydrochloride (313.6 mg, 0.88 mmol) prepared in Reference Example 228 was used instead of 3-methyl-N-(piperidin-4-yl)quinoline-5-amine hydrochloride. $^1$H NMR (CDCl$_3$, 400 MHz) δ 10.91 (d, 1H), 8.84 (dd, 1H), 8.70 (d, 1H), 8.25 (d, 1H), 7.37-7.34 (m, 1H), 6.67 (d, 1H), 5.10-4.74 (m, 2H), 3.76-3.49 (m, 3H), 3.37-3.17 (m, 2H), 3.09 (d, 3H), 3.01-2.89 (m, 2H), 2.42-2.07 (m, 8H), 1.88-1.63 (m, 2H)

Example 396. 5-[[1-[2-oxo-2-[(2S)-2-cyanopyrrolidin-1-yl]ethyl]-4-piperidyl]amino]-N-phenyl-quinoline-8-carboxamide The title compound (185.5 mg, 43.6%) was prepared in the same fashion as Example 121, except that N-phenyl-5-

(piperidin-4-ylamino)quinoline-8-carboxamide hydrochloride (369.0 mg, 0.88 mmol) prepared in Reference Example 232 was used instead of 3-methyl-N-(piperidin-4-yl)quinoline-5-amine hydrochloride. $^1$H NMR (CDCl$_3$, 400 MHz) δ 13.46 (s, 1H), 8.89 (d, 1H), 8.75 (d, 1H), 8.27 (d, 1H), 7.85 (d, 2H), 7.39-7.35 (m, 3H), 7.09 (t, 1H), 6.70-6.66 (m, 1H), 5.08-4.74 (m, 2H), 3.73-3.47 (m, 3H), 3.36-3.16 (m, 2H), 2.99-2.89 (m, 2H), 2.41-2.13 (m, 8H), 1.90-1.64 (m, 2H)

Example 397. N-benzyl-N-methyl-5-[[1-[2-oxo-2-[(2S)-2-cyanopyrrolidin-1-yl]ethyl]-4-piperidyl]amino]quinoline-8-carboxamide The title compound (256.2 mg, 57.0%) was prepared in the same fashion as Example 121, except that N-benzyl-N-methyl-5-(piperidin-4-ylamino)quinoline-8-carboxamide hydrochloride (393.7 mg, 0.88 mmol) prepared in Reference Example 231 was used instead of 3-methyl-N-(piperidin-4-yl)quinoline-5-amine hydrochloride. $^1$H NMR (CDCl$_3$, 400 MHz) δ 8.89-8.86 (m, 1H), 8.17-8.12 (m, 1H), 7.53 (d, 2H), 7.38 (t, 1H), 7.30-7.18 (m, 4H), 6.56 (dd, 1H), 5.17-4.73 (m, 2H), 4.56 (s, 1H), 4.34 (dd, 1H), 3.73-3.47 (m, 3H), 3.39-3.15 (m, 2H), 3.10 (s, 1.5H), 2.99-2.85 (m, 2H), 2.68 (s, 1.5H), 2.42-2.03 (m, 9H), 1.80-1.59 (m, 2H).

Example 398. N-methyl-5-[[1-[2-oxo-2-[(2S)-2-cyanopyrrolidin-1-yl]ethyl]-4-piperidyl]amino]-N-phenyl-quinoline-8-carboxamide The title compound (45.5 mg, 10.4%) was prepared in the same fashion as Example 121, except that N-methyl-N-phenyl-5-(piperidin-4-ylamino)quinoline-8-carboxamide hydrochloride (381.3 mg, 0.88 mmol) prepared in Reference Example 230 was used instead of 3-methyl-N-(piperidin-4-yl)quinoline-5-amine hydrochloride. $^1$H NMR (CDCl$_3$, 400 MHz) δ 8.88 (dd, 1H), 8.00 (d, 1H), 7.30-6.95 (m, 7H), 6.38 (s, 1H), 5.14-4.73 (m, 1H), 3.76-3.70 (m, 1H), 3.66-3.50 (m, 4H), 3.40-3.15 (m, 3H), 2.93-2.84 (m, 2H), 2.37-1.99 (m, 9H), 1.76-1.57 (m, 2H)

Example 399. 5-[[1-[2-oxo-2-[(2S)-2-cyanopyrrolidin-1-yl]ethyl]-4-piperidyl]amino]-N-(2-pyridyl)quinoline-8-carboxamide The title compound (340.4 mg, 80.0%) was prepared in the same fashion as Example 121, except that 5-(piperidin-4-ylamino)-N-(pyridin-2-yl)quinoline-8-carboxamide hydrochloride (369.9 mg, 0.88 mmol) prepared in Reference Example 233 was used instead of 3-methyl-N-(piperidin-4-yl)quinoline-5-amine hydrochloride. $^1$H NMR (CDCl$_3$, 400 MHz) δ 9.04 (d, 1H), 8.78 (d, 1H), 8.53 (d, 1H), 8.40 (d, 1H), 8.26 (d, 1H), 7.72 (t, 1H), 7.41 (q, 1H), 7.01 (dd, 1H), 6.72 (d, 1H), 5.09-4.75 (m, 2H), 3.76-3.51 (m, 3H), 3.38-3.18 (m, 2H), 3.02-2.88 (m, 2H), 2.45-2.35 (m, 2H), 2.31-2.07 (m, 6H), 1.75-1.65 (m, 2H).

Example 400. 5-[[1-[2-oxo-2-[(2S)-2-cyanopyrrolidin-1-yl]ethyl]-4-piperidyl]amino]-N-(3-pyridyl)quinoline-8-carboxamide The title compound (316.8 mg, 74.4%) was prepared in the same fashion as Example 121, except that 5-(piperidin-4-ylamino)-N-(pyridin-3-yl)quinoline-8-carboxamide hydrochloride (369.9 mg, 0.88 mmol) prepared in Reference Example 234 was used instead of 3-methyl-N-(piperidin-4-yl)quinoline-5-amine hydrochloride. $^1$H NMR (CDCl$_3$, 400 MHz) δ 8.92 (d, 1H), 8.84 (s, 1H), 8.84 (d, 1H), 8.46 (d, 1H), 8.31-8.29 (m, 2H), 7.41 (q, 1H), 7.29 (dd, 1H), 6.71 (dd, 1H), 5.07-4.74 (m, 2H), 3.76-3.49 (m, 3H), 3.37-3.18 (m, 2H), 3.01-2.91 (m, 2H), 2.44-2.35 (m, 2H), 2.31-2.07 (m, 6H), 1.91- 1.65 (m, 2H).

Example 401. 5-[[1-[2-oxo-2-[(2S)-2-cyanopyrrolidin-1-yl]ethyl]-4-piperidyl]amino]-N-(4-pyridyl)quinoline-8-carboxamide The title compound (85.1 mg, 20.0%) was prepared in the same fashion as Example 121, except that 5-(piperidin-4-ylamino)-N-(pyridin-4-yl)quinoline-8-carboxamide hydrochloride (369.9 mg, 0.88 mmol) prepared in Reference Example 235 was used instead of 3-methyl-N-(piperidin-4-yl)quinoline-5-amine hydrochloride. $^1$H NMR (CDCl$_3$, 400 MHz) δ 8.97 (dd, 1H), 8.78 (d, 1H), 8.52 (d, 2H), 8.29 (d, 1H), 7.78 (d, 2H), 7.47 (q, 1H), 6.76 (d, 1H), 5.06-4.77 (m, 2H), 3.78-3.50 (m, 3H), 3.39-3.21 (m, 2H), 3.07-2.94 (m, 2H), 2.47-2.37 (m, 2H), 2.34-2.09 (m, 6H), 1.94-1.76 (m, 2H).

Example 402. 5-[[1-[2-oxo-2-[(2S)-2-cyanopyrrolidin-1-yl]ethyl]-4-piperidyl]amino]-N-pyrimidin-2-yl-quinoline-8-carboxamide The title compound (324.4 mg, 76.0%) was prepared in the same fashion as Example 121, except that 5-(piperidin-4-ylamino)-N-(pyrimidin-2-yl)quinoline-8-carboxamide hydrochloride (370.7 mg, 0.88 mmol) prepared in Reference Example 236 was used instead of 3-methyl-N-(piperidin-4-yl)quinoline-5-amine hydrochloride. $^1$H NMR (CDCl$_3$, 400 MHz) δ 9.00 (t, 1H), 8.81 (d, 1H), 8.68 (dd, 2H), 8.29 (d, 1H), 7.41-7.39 (m, 1H), 6.98 (t, 1H), 6.70 (d, 1H), 5.09-4.99 (m, 1.4H), 5.76-4.75 (m, 0.6H), 3.72-3.51 (m, 3H), 3.48 (s, 1H), 3.34-3.17 (m, 2H), 3.00-2.87 (m, 2H), 2.43-2.34 (m, 2H), 2.30-2.08 (m, 6H), 1.75-1.65 (m, 2H).

Example 403. 5-[[1-[2-oxo-2-[(2S,4S)-2-cyano-4-fluoro-pyrrolidin-1-yl]ethyl]-4-piperidyl]amino]-N-pyrimidin-2-yl-quinoline-8-carboxamide The title compound (16.3 mg, 29.5%) was prepared in the same fashion as Example 131, except that 5-(piperidin-4-ylamino)-N-(pyrimidin-2-yl)quinoline-8-carboxamide hydrochloride (46.3 mg, 0.11 mmol) prepared in Reference Example 236 was used instead of 3-methyl-N-(piperidin-4-yl)quinoline-5-amine hydrochloride. $^1$H NMR (CDCl$_3$, 400 MHz) δ 8.99 (d, 1H), 8.79 (d, 1H), 8.68 (d, 2H), 8.32-8.29 (m, 1H), 7.39 (q, 1H), 6.98 (t, 1H), 6.70-6.67 (m, 1H), 5.48-5.27 (m, 1.4H), 5.09-4.92 (m, 1.6H), 4.20-3.72 (m, 2H), 3.62-3.56 (m, 1H), 3.48 (s, 1H), 3.43-3.17 (m, 2H), 3.01-2.87 (m, 2H), 2.49-1.83 (m, 6H), 1.75-1.55 (m, 2H).

Example 404. 5-[[1-[2-oxo-2-[(2S,4S)-2-cyano-4-fluoro-pyrrolidin-1-yl]ethyl]-4-piperidyl]amino]-N-(2-pyridyl)quinoline-8-carboxamide The title compound (45.5 mg, 82.6%) was prepared in the same fashion as Example 131, except that 5-(piperidin-4-ylamino)-N-(pyridin-2-yl)quinoline-8-carboxamide hydrochloride (46.3 mg, 0.11 mmol) prepared in Reference Example 233 was used instead of 3-methyl-N-(piperidin-4-yl)quinoline-5-amine hydrochloride. $^1$H NMR (CDCl$_3$, 400 MHz) δ 8.99 (d, 1H), 8.72 (d, 1H), 8.50 (d, 1H), 8.38 (d, 1H), 8.30-8.27 (m, 1H), 7.71 (t, 1H), 7.36 (q, 1H), 7.02-6.99 (m, 1H), 6.69-6.56 (m, 1H), 5.45-5.25 (m, 1.4H), 5.12-4.90

(m, 1.6H), 4.18-3.69 (m, 2H), 3.57-3.55 (m, 1H), 3.41-3.14 (m, 2H), 3.00-2.88 (m, 2H), 2.74-2.59 (m, 1H), 2.38-2.12 (m, 7H), 1.68-1.63 (m, 2H).

Example 405. 5-[[1-[2-oxo-2-[(2S,4S)-2-cyano-4-fluoro-pyrrolidin-1-yl]ethyl]-4-piperidyl]amino]-N-(3-pyridyl)quinoline-8-carboxamide The title compound (6.8 mg, 12.3%) was prepared in the same fashion as Example 131, except that 5-(piperidin-4-ylamino)-N-(pyridin-3-yl)quinoline-8-carboxamide hydrochloride (46.3 mg, 0.11 mmol) prepared in Reference Example 234 was used instead of 3-methyl-N-(piperidin-4-yl)quinoline-5-amine hydrochloride. $^1$H NMR (CDCl$_3$, 400 MHz) δ 8.92 (d, 1H), 8.85 (s, 1H), 8.44 (d, 1H), 8.31-8.29 (m, 2H), 7.41 (q, 1H), 7.30 (q, 1H), 6.72-6.68 (m, 1H), 5.49-5.29 (m, 1.4H), 5.06-4.93 (m, 1.6H), 4.23-4.13 (dd, 0.6H), 3.95-3.71 (m, 1.4H), 3.61-3.58 (m, 1H), 3.42-3.18 (m, 2H), 3.03-2.92 (m, 2H), 2.77-2.62 (m, 1H), 2.48-2.15 (m, 5H), 1.88-1.67 (m, 2H)

Example 406. 5-[[1-[2-oxo-2-[(2S,4S)-2-cyano-4-fluoro-pyrrolidin-1-yl]ethyl]-4-piperidyl]amino]-N-(4-pyridyl)quinoline-8-carboxamide The title compound (1.3 mg, 2.3%) was prepared in the same fashion as Example 131, except that 5-(piperidin-4-ylamino)-N-(pyridin-4-yl)quinoline-8-carboxamide hydrochloride (46.3 mg, 0.11 mmol) prepared in Reference Example 235 was used instead of 3-methyl-N-(piperidin-4-yl)quinoline-5-amine hydrochloride. $^1$H NMR (CDCl$_3$, 400 MHz) δ 8.98 (d, 1H), 8.80 (d, 1H), 8.53 (d, 2H), 8.28 (d, 1H), 7.78 (d, 1H), 7.48 (q, 1H), 6.77 (d, 1H), 5.50-5.30 (m, 1H), 5.29 (d, 0.4H), 4.97 (d, 0.6H), 4.86 (t, 1H), 4.23-3.66 (m, 3H), 3.44-3.21 (m, 2H), 3.06-2.95 (m, 2H), 2.81-2.66 (m, 1H), 2.49-2.23 (m, 5H), 2.05-2.00 (m, 1H) 1.94-1.67 (m, 1H).

Example 407. N-isoxazol-3-yl-5-[[1-[2-oxo-2-[(2S,4S)-2-cyano-4-fluoro-pyrrolidin-1-yl]ethyl]-4-piperidyl]amino]quinoline-8-carboxamide The title compound (20.4 mg, 37.7%) was prepared in the same fashion as Example 131, except that N-(isoxazol-3-yl)-5-(piperidin-4-ylamino)quinoline-8-carboxamide hydrochloride (45.3 mg, 0.11 mmol) prepared in Reference Example 237 was used instead of 3-methyl-N-(piperidin-4-yl)quinoline-5-amine hydrochloride. $^1$H NMR (CDCl$_3$, 400 MHz) δ 8.91 (d, 1H), 8.71 (d, 1H), 8.33 (s, 1H), 8.27 (d, 1H), 7.42-7.39 (m, 1H), 7.29 (s, 1H), 6.70 (d, 1H), 5.49-5.29 (m, 1.4H), 5.03 (t, 1H), 4.94 (d, 0.6H), 4.20 (dd, 0.5H), 4.00-3.72 (m, 1.5H), 3.62-3.61 (m, 1H), 3.44-3.19 (m, 2H), 2.98 (q, 2H), 2.78-2.63 (m, 1H), 2.48-2.16 (m, 4H), 1.80-1.66 (m, 4H)

Example 408. N-[5-[[1-[2-oxo-2-[(2S)-2-cyanopyrrolidin-1-yl]ethyl]-4-piperidyl]amino]-8-quinolyl]acetamide The title compound (33.6 mg, 9.0%) was prepared in the same fashion as Example 121, except that N-(5-(piperidin-4-ylamino)quinolin-8-yl)acetamide hydrochloride (314.4 mg, 0.88 mmol) prepared in Reference Example 238 was used instead of 3-methyl-N-(piperidin-4-yl)quinoline-5-amine hydrochloride. $^1$H NMR (CDCl$_3$, 400 MHz) δ 8.91 (d, 1H), 8.78 (dd, 1H), 8.60 (d, 1H), 8.20 (dd, 1H), 7.40 (q, 1H), 6.64 (d, 1H) 5.49-5.27 (m, 1.4H), 4.93 (d, 0.6H), 4.23-3.73 (m, 3H), 3.48-3.42 (m, 1.4H), 3.29-3.17 (m, 1.6H), 2.99-2.87 (m, 2H), 2.77-2.61 (m, 1H), 2.47-2.33 (m, 3H), 2.30 (s, 3H), 2.21-2.13 (m, 2.5H), 1.80-1.55 (m, 2.5H)

Example 409. N-[5-[[1-[2-oxo-2-[(2S,4S)-2-cyano-4-fluoro-pyrrolidin-1-yl]ethyl]-4-piperidyl]amino]-8-quinolyl]acetamide The title compound (3.7 mg, 7.7%) was prepared in the same fashion as Example 131, except that N-(5-(piperidin-4-ylamino)quinolin-8-yl)acetamide hydrochloride (39.3 mg, 0.11 mmol) prepared in Reference Example 238 was used instead of 3-methyl-N-(piperidin-4-yl)quinoline-5-amine hydrochloride. $^1$H NMR (CDCl$_3$, 400 MHz) δ 9.49 (s, 1H), 8.78 (dd, 1H), 8.60 (d, 1H), 8.20 (dd, 1H), 7.40 (q, 1H), 6.64 (d, 1H) 5.49-5.27 (m, 1.4H), 4.93 (d, 0.6H), 4.23-3.73 (m, 2.5H), 3.48-3.25 (m, 2.5H), 3.21 (d, 1H), 2.99-2.87 (m, 2H), 2.77-2.61 (m, 1H), 2.40-2.33 (m, 2.6H), 2.30 (s, 3H), 2.21-2.13 (m, 2H), 1.83-1.55 (m, 2.4H)

Example 410. (2S,4S)-4-fluoro-1-[2-[4-[(6-methyl-4-quinolyl)oxy]-1-piperidyl]acetyl]pyrrolidine-2-carbonitrile The title compound (190.9 mg, 38.8%) was prepared in the same fashion as Example 330, except that 6-methyl-4-(piperidin-4-yloxy)quinoline hydrochloride (346.3 mg, 1.24 mmol) prepared in Reference Example 239 was used instead of 8-fluoro-N-(piperidin-4-yl)quinolin-5-amine hydrochloride. $^1$H-NMR (CDCl$_3$, 400 MHz) δ 8.65 (d, 1H), 7.97 (s, 1H), 7.92 (d, 1H), 7.53 (d, 1H), 6.69 (d, 1H), 5.50-5.25 (m, 1H), 5.00-4.90 (m, 1H), 4.75-4.60 (m, 1H), 4.30-4.10 (m, 1H), 4.05-3.70 (m, 2H), 3.60-3.20 (m, 2H), 2.90-2.80 (m, 2H), 2.80-2.65 (m, 1H), 2.65-2.55 (m, 2H), 2.55 (s, 3H), 2.40-2.05 (m, 2H), 2.05-1.95 (m, 2H)

Example 411. (2S,4S)-4-fluoro-1-[2-[4-[[6-(trifluoromethyl)-4-quinolyl]oxy]-1-piperidyl]acetyl]pyrrolidine-2-carbonitrile The title compound (245.4 mg, 43.9%) was prepared in the same fashion as Example 330, except that 4-(piperidin-4-yloxy)-6-(trifluoromethyl)quinoline hydrochloride (413.3 mg, 1.24 mmol) prepared in Reference Example 240 was used instead of 8-fluoro-N-(piperidin-4-yl)quinolin-5-amine hydrochloride. $^1$H-NMR (CDCl$_3$, 400 MHz) δ 8.83 (d, 1H), 8.51 (s, 1H), 8.13 (d, 1H), 7.87 (d, 1H), 6.81 (d, 1H), 5.55-5.35 (m, 1H), 5.00-4.90 (m, 1H), 4.75-4.65 (m, 1H), 4.30-4.10 (m, 1H), 4.05-3.70 (m, 2H), 3.55-3.20 (m, 2H), 3.00-2.80 (m, 2H), 2.80-2.60 (m, 1H), 2.60-2.50 (m, 2H), 2.30-2.10 (m, 2H), 2.10-1.95 (m, 2H)

Example 412. (2S,4S)-4-fluoro-1-[2-[4-[[2-(trifluoromethyl)-4-quinolyl]oxy]-1-piperidyl]acetyl]pyrrolidine-2-carbonitrile The title compound (312.7 mg, 55.9%) was prepared in the same fashion as Example 330, except that 4-(piperidin-4-yloxy)-2-(trifluoromethyl)quinoline hydrochloride (291.3 mg, 0.88 mmol) prepared in Reference Example 241 was used instead of 8-fluoro-N-(piperidin-4-yl)quinolin-5-amine hydrochloride. $^1$H-NMR (CDCl$_3$, 400 MHz) δ 8.27 (d, 1H), 8.14 (d, 1H), 7.80 (t, 1H), 7.62 (t, 1H), 7.02 (s, 1H), 5.50-5.25 (m, 1H), 5.00-4.90 (m, 1H), 4.85-4.70 (m, 1H), 4.30-4.15 (m, 1H), 4.05-3.70 (m, 2H), 3.55-3.15 (m, 2H), 2.95-2.80 (m, 2H), 2.80-2.65 (m, 1H), 2.65-2.55 (m, 2H), 2.30-2.10 (m, 2H), 2.10-1.95 (m, 2H)

Example 413. (2S,4S)-4-fluoro-1-[2-[4-[[6-fluoro-2-(trifluoromethyl)-4-quinolyl]oxy]-1-piperidyl]acetyl]pyrrolidine-2-carbonitrile The title compound (243.7 mg, 41.9%) was prepared in the same fashion as Example 330, except that 6-fluoro-4-(piperidin-4-yloxy)-2-(trifluoromethyl)quinoline hydrochloride (255.6 mg, 0.73 mmol) prepared in Reference Example 242 was used instead of 8-fluoro-N-(piperidin-4-yl)quinolin-5-amine hydrochloride. $^1$H-NMR (CDCl$_3$, 400 MHz) δ 8.15 (d, 1H), 7.84 (d, 1H), 7.56 (s, 1H), 7.03 (s, 1H), 5.50-5.20 (m, 1H), 5.00-4.90 (m, 1H), 4.85-4.70 (m, 1H), 4.30-4.15 (m, 1H), 4.05-3.70 (m, 2H), 3.55-3.20 (m, 2H), 2.95-2.80 (m, 2H), 2.80-2.65 (m, 1H), 2.65-2.55 (m, 2H), 2.30-2.10 (m, 2H), 2.10- 1.95 (m, 2H)

Example 414. (2S,4S)-4-fluoro-1-[2-[4-[[6-methoxy-2-(trifluoromethyl)-4-quinolyl]oxy]-1-piperidyl]acetyl]pyrrolidine-2-carbonitrile The title compound (266.4 mg, 44.6%) was prepared in the same fashion as Example 330, except that 6-methoxy-4-(piperidin-4-yloxy)-2-(trifluoromethyl)quinoline hydrochloride (303.8 mg, 0.84 mmol) prepared in Reference Example 243 was used instead of 8-fluoro-N-(piperidin-4-yl)quinolin-5-amine hydrochloride. $^1$H-NMR (CDCl$_3$, 400 MHz) δ 8.04 (d, 1H), 7.48-7.42 (m, 2H), 7.00 (s, 1H), 5.55-5.25 (m, 1H), 5.00-4.90 (m, 1H), 4.85-4.70 (m, 1H), 4.35-4.20 (m, 1H), 3.98 (s, 3H), 3.98-3.70 (m, 2H), 3.50-3.20 (m, 2H), 2.95-2.85 (m, 2H), 2.85-2.60 (m, 1H), 2.70-2.55 (m, 2H), 2.30-2.10 (m, 2H), 2.10-2.00 (m, 2H)

Example 415. (2S,4S)-4-fluoro-1-[2-[4-[[8-methoxy-2-(trifluoromethyl)-4-quinolyl]oxy]-1-piperidyl]acetyl]pyrrolidine-2-carbonitrile The title compound (429.0 mg, 71.9%) was prepared in the same fashion as Example 330, except that 8-methoxy-4-(piperidin-4-yloxy)-2-(trifluoromethyl)quinoline hydrochloride (414.9 mg, 1.14 mmol) prepared in Reference Example 244 was used instead of 8-fluoro-N-(piperidin-4-yl)quinolin-5-amine hydrochloride. $^1$H-NMR (CDCl$_3$, 400 MHz) δ 7.81 (d, 1H), 7.54 (t, 1H), 7.14 (d, 1H), 7.05 (s, 1H), 5.55-5.35 (m, 1H), 5.00-4.90 (m, 1H), 4.85-4.70 (m, 1H), 4.30-4.15 (m, 1H), 4.09 (s, 3H), 4.05-3.70 (m, 2H), 3.55-3.20 (m, 2H), 2.90-2.80 (m, 2H), 2.80-2.70 (m, 1H), 2.70-2.55 (m, 2H), 2.35-2.10 (m, 2H), 2.10-2.00 (m, 2H)

Example 416. (2S,4S)-4-fluoro-1-[2-[4-[(3-fluoro-5-quinolyl)oxy]-1-piperidyl]acetyl]pyrrolidine-2-carbonitrile The title compound (179.0 mg, 36.0%) was prepared in the same fashion as Example 330, except that 3-fluoro-5-(piperidin-4-yloxy)quinoline hydrochloride (351.2 mg, 1.24 mmol) prepared in Reference Example 245 was used instead of 8-fluoro-N-(piperidin-4-yl)quinolin-5-amine hydrochloride. $^1$H-NMR (CDCl$_3$, 400 MHz) δ 8.79 (s, 1H), 8.17 (d, 1H), 7.68 (s, 1H), 7.56 (t, 1H), 6.91 (d, 1H), 5.55-5.30 (m, 1H), 5.05-4.85 (m, 1H), 4.70-4.50 (m, 1H), 4.30-4.10 (m, 1H), 4.00-3.70 (m, 2H), 3.55-3.20 (m, 2H), 2.90-2.75 (m, 2H), 2.75-2.60 (m, 1H), 2.60-2.50 (m, 2H), 2.35-2.10 (m, 2H), 2.10-1.90 (m, 2H)

Example 417. 5-[[1-[2-oxo-2-[(2S,4S)-2-cyano-4-fluoro-pyrrolidin-1-yl]ethyl]-4-piperidyl]oxy]quinoline-2-carbonitrile The title compound (70.2 mg, 13.9%) was prepared in the same fashion as Example 330, except that 5-(piperidin-4-yloxy)quinoline-2-carbonitrile hydrochloride (359.9 mg, 1.24 mmol) prepared in Reference Example 246 was used instead of 8-fluoro-N-(piperidin-4-yl)quinolin-5-amine hydrochloride. $^1$H-NMR (CDCl$_3$, 400 MHz) δ 8.73 (d, 1H), 7.73-7.64 (m, 3H), 6.99 (d, 1H), 5.55-5.35 (m, 1H), 5.00-4.90 (m, 1H), 4.70-4.55 (m, 1H), 4.30-4.15 (m, 1H), 4.05-3.70 (m, 2H), 3.55-3.20 (m, 2H), 2.90-2.80 (m, 2H), 2.80-2.65 (m, 1H), 2.65-2.50 (m, 2H), 2.35-2.05 (m, 2H), 2.05-1.95 (m, 2H)

Example 418. (2S,4S)-1-[2-[4-[(8-chloro-5-quinolyl)oxy]-1-piperidyl]acetyl]-4-fluoro-pyrrolidine-2-carbonitrile The title compound (304.0 mg, 58.7%) was prepared in the same fashion as Example 330, except that 8-chloro-5-(piperidin-4-yloxy)quinoline hydrochloride (371.7 mg, 1.24 mmol) prepared in Reference Example 247 was used instead of 8-fluoro-N-(piperidin-4-yl)quinolin-5-amine hydrochloride. $^1$H-NMR (CDCl$_3$, 400 MHz) δ 8.99 (d, 1H), 8.53 (d, 1H), 7.53-7.50 (m, 2H), 7.04 (d, 1H), 5.75-5.20 (m, 1H), 5.00-4.90 (m, 1H), 4.70-4.50 (m, 1H), 4.30-4.10 (m, 1H), 4.10-3.65 (m, 2H), 3.65-3.20 (m, 2H), 3.10-2.80 (m, 2H), 2.80-2.55 (m, 1H), 2.55-2.40 (m, 2H), 2.40-2.15 (m, 2H), 2.15- 1.90 (m, 2H)

Example 419. (2S,4S)-4-fluoro-1-[2-[4-(1-isoquinolyloxy)-1-piperidyl]acetyl]pyrrolidine-2-carbonitrile The title compound (156.9 mg, 86.5%) was prepared in the same fashion as Example 330, except that 1-(piperidin-4-yloxy)isoquinoline hydrochloride (125.6 mg, 0.47 mmol) prepared in Reference Example 248 was used instead of 8-fluoro-N-(piperidin-4-yl)quinolin-5-amine hydrochloride. $^1$H-NMR (CDCl$_3$, 400 MHz) δ 8.25 (d, 1H), 7.96 (d, 1H), 7.73 (d, 1H), 7.66 (t, 1H), 7.54 (t, 1H), 7.19 (d, 1H), 5.75-5.25 (m, 2H), 5.00-4.90 (m, 1H), 4.30-4.15 (m, 1H), 4.10-3.70 (m, 2H), 3.60-3.20 (m, 2H), 2.90-2.80 (m, 2H), 2.80-2.65 (m, 1H), 2.65-2.50 (m, 2H), 2.35-2.10 (m, 2H), 2.10-1.90 (m, 2H)

Example 420. (2S,4S)-4-fluoro-1-[2-[4-(4-isoquinolyloxy)-1-piperidyl]acetyl]pyrrolidine-2-carbonitrile The title compound (39.9 mg, 22.0%) was prepared in the same fashion as Example 330, except that 4-(piperidin-4-yloxy)isoquinoline hydrochloride (328.9 mg, 1.24 mmol) prepared in Reference Example 249 was used instead of 8-fluoro-N-(piperidin-4-yl)quinolin-5-amine hydrochloride. $^1$H-NMR (CDCl$_3$, 400 MHz) δ 8.90 (s, 1H), 8.22 (d, 1H), 8.10 (s, 1H), 7.94 (d, 1H), 7.71 (t, 1H), 7.63 (t, 1H), 5.60-5.25 (m, 1H), 5.00-4.90 (m, 1H), 4.80-4.60 (m, 1H), 4.30-4.15 (m, 1H), 4.05-3.70 (m, 2H), 3.60-3.15 (m, 2H), 2.95-2.80 (m, 2H), 2.80-2.60 (m, 1H), 2.60-2.50 (m, 2H), 2.30-2.10 (m, 2H), 2.10-1.90 (m, 2H)

Example 421. (2S,4S)-4-fluoro-1-[2-[4-(5-isoquinolyloxy)-1-piperidyl]acetyl]pyrrolidine-2-carbonitrile The title compound (107.7 mg, 59.4%) was prepared in the same fashion as Example 330, except that 5-(piperidin- 4-yloxy)isoquinoline hydrochloride (156.5 mg, 0.59 mmol) prepared in Reference Example 250 was used instead of 8-fluoro-N-(piperidin-4-yl)quinolin-5-amine hydrochloride. $^1$H-NMR (CDCl$_3$, 400 MHz) δ 9.20 (s, 1H), 8.53 (d, 1H), 8.03 (d, 1H), 7.55-7.47 (m, 2H), 7.02 (d, 1H), 5.55-5.20 (m, 1H), 5.00-4.85 (m, 1H), 4.70-4.50 (m, 1H), 4.30-4.15 (m, 1H), 4.05- 3.70 (m, 2H), 3.60-3.20 (m, 2H), 2.90-2.80 (m, 2H), 2.80-2.60 (m, 1H), 2.60-2.50 (m, 2H), 2.30-2.10 (m, 2H), 2.10-1.90 (m, 2H)

Example 422. (2S,4S)-4-fluoro-1-[2-[4-(6-isoquinolyloxy)-1-piperidyl]acetyl]pyrrolidine-2-carbonitrile The title compound (73.3 mg, 40.4%) was prepared in the same fashion as Example 330, except that 6-(piperidin-4-yloxy)isoquinoline hydrochloride (328.9 mg, 1.24 mmol) prepared in Reference Example 251 was used instead of 8-fluoro-N-(piperidin-4-yl)quinolin-5-amine hydrochloride. $^1$H-NMR (CDCl$_3$, 400 MHz) δ 9.10 (s, 1H), 8.43 (d, 1H), 7.87 (d, 1H), 7.52 (d, 1H), 7.23 (d, 1H), 7.06 (s, 1H), 5.55-5.25 (m, 1H), 5.00-4.90 (m, 1H), 4.65-4.50 (m, 1H), 4.30-4.15 (m, 1H), 4.05-3.70 (m, 2H), 3.60-3.15 (m, 2H), 2.90-2.80 (m, 2H), 2.80-2.60 (m, 1H), 2.60-2.45 (m, 2H), 2.30-2.10 (m, 2H), 2.00-1.80 (m, 2H)

Example 423. (2S,4S)-4-fluoro-1-[2-[4-(7-isoquinolyloxy)-1-piperidyl]acetyl]pyrrolidine-2-carbonitrile The title compound (140.7 mg, 77.6%) was prepared in the same fashion as Example 330, except that 7-(piperidin-4-yloxy)isoquinoline hydrochloride (328.9 mg, 1.24 mmol) prepared in Reference Example 252 was used instead of 8-fluoro-N-(piperidin-4-yl)quinolin-5-amine hydrochloride. $^1$H-NMR (CDCl$_3$, 400 MHz) δ 9.15 (s, 1H), 8.41 (d, 1H), 7.75 (d, 1H), 7.58 (d, 1H), 7.35 (d, 1H), 7.23 (s, 1H), 5.55-5.25 (m, 1H), 5.00-4.90 (m, 1H), 4.60-4.45 (m, 1H), 4.25-4.10 (m, 1H), 4.05-3.70 (m, 2H), 3.65-3.20 (m, 2H), 2.90-2.80 (m, 2H), 2.80-2.60 (m, 1H), 2.60-2.45 (m, 2H), 2.30-2.05 (m, 2H), 2.00-1.85 (m, 2H)

Example 424. (2S,4S)-4-fluoro-1-[2-[4-[(6-methoxy-2-methyl-4-quinolyl)oxy]-1-piperidyl]acetyl]pyrrolidine-2-carbonitrile The title compound (141.2 mg, 69.8%) was prepared in the same fashion as Example 330, except that 6-methoxy-2-methyl-4-(piperidin-4-yloxy)quinoline hydrochloride (383.6 mg, 1.24 mmol) prepared in Reference Example 253 was used instead of 8-fluoro-N-(piperidin-4-yl)quinolin-5-amine hydrochloride. $^1$H-NMR (CDCl$_3$, 400 MHz) δ 7.85 (d, 1H), 7.42 (s, 1H), 7.32 (d, 1H), 6.59 (s, 1H), 5.55-5.20 (m, 1H), 5.00-4.90 (m, 1H), 4.70-4.60 (m, 1H), 4.30-4.15 (m, 1H), 4.05-3.70 (m, 2H), 3.94 (s, 3H), 3.55-3.20 (m, 2H), 2.90-2.80 (m, 2H), 2.80-2.65 (m, 1H), 2.65 (s, 3H), 2.65-2.50 (m, 2H), 2.30-2.10 (m, 2H), 2.10-1.95 (m, 2H)

Example 425. (2S,4S)-4-fluoro-1-[2-[4-(5-quinolyloxy)-1-piperidyl]acetyl]pyrrolidine-2-carbonitrile The title compound (161.4 mg, 37.0%) was prepared in the same fashion as Example 330, except that 5-(piperidin-4-yloxy)quinoline hydrochloride (383.6 mg, 1.24 mmol) prepared in Reference Example 33 was used instead of 8-fluoro-N-(piperidin-4-yl)quinolin-5-amine hydrochloride. $^1$H-NMR (CDCl$_3$, 400 MHz) δ 8.91 (d, 1H), 8.60 (d, 1H), 7.69 (d, 1H), 7.60 (t, 1H), 7.40 (t, 1H), 6.89 (d, 1H), 5.55-5.25 (m, 1H), 5.00-4.90 (m, 1H), 4.80-4.70 (m, 1H), 4.30-4.15 (m, 1H), 4.05-3.70 (m, 2H), 3.55-3.20 (m, 2H), 2.95-2.80 (m, 2H), 2.80-2.65 (m, 1H), 2.65-2.50 (m, 2H), 2.30-2.10 (m, 2H), 2.10-1.95 (m, 2H)

Example 426. (2S)-1-[2-[4-[(6-methoxy-4-quinolyl)oxy]-1-piperidyl]acetyl]pyrrolidine-2-carbonitrile The title compound (127.1 mg, 25.9%) was prepared in the same fashion as Example 110, except that 6-methoxy-4-(piperidin-4-yloxy)quinoline hydrochloride (366.1 mg, 1.24 mmol) prepared in Reference Example 42 was used instead of N-(piperidin-4-yl)quinoline-5-amine hydrochloride. $^1$H-NMR (CDCl$_3$, 400 MHz) δ 8.59 (d, 1H), 7.93 (d, 1H), 7.47 (s, 1H), 7.34 (d, 1H), 6.70 (d, 1H), 5.20-4.70 (m, 1H), 4.70-4.60 (m, 1H), 3.95 (s, 3H), 3.80-3.60 (m, 1H), 3.60-3.50 (m, 1H), 3.45-3.20 (m, 2H), 2.95-2.75 (m, 2H), 2.70-2.50 (m, 2H), 2.40-2.10 (m, 6H), 2.10-1.95 (m, 2H)

Example 427. (2S)-1-[2-[4-[(6-fluoro-4-quinolyl)oxy]-1-piperidyl]acetyl]pyrrolidine-2-carbonitrile The title compound (51.1 mg, 10.8%) was prepared in the same fashion as Example 110, except that 6-fluoro-4-(piperidin-4-yloxy)quinoline hydrochloride (351.2 mg, 1.24 mmol) prepared in Reference Example 40 was used instead of N-(piperidin-4-yl)quinoline-5-amine hydrochloride. $^1$H-NMR (CDCl$_3$, 400 MHz) δ 8.69 (d, 1H), 8.02 (d, 1H), 7.81 (d, 1H), 7.46 (s, 1H), 6.74 (d, 1H), 5.20-4.75 (m, 1H), 4.75-4.60 (m, 1H), 3.80-3.60 (m, 1H), 3.60-3.50 (m, 1H), 3.50-3.20 (m, 2H), 2.95-2.75 (m, 2H), 2.70-2.50 (m, 2H), 2.40-2.10 (m, 6H), 2.10-1.95 (m, 2H)

Example 428. (2S)-1-[2-[4-[(7-chloro-4-quinolyl)oxy]-1-piperidyl]acetyl]pyrrolidine-2-carbonitrile The title compound (272.5 mg, 55.0%) was prepared in the same fashion as Example 110, except that 7-chloro-4-(piperidin-4-yloxy)quinoline hydrochloride (371.6 mg, 1.24 mmol) prepared in Reference Example 254 was used instead of N-(piperidin-4-yl)quinoline-5-amine hydrochloride. $^1$H-NMR (CDCl$_3$, 400 MHz) δ 8.70 (d, 1H), 8.14 (d, 1H), 8.00 (s, 1H), 7.43 (d, 1H), 6.70 (d, 1H), 5.20-4.75 (m, 1H), 4.75-4.60 (m, 1H), 3.80-3.60 (m, 1H), 3.60-3.50 (m, 1H), 3.45-3.15 (m, 2H), 2.90-2.75 (m, 2H), 2.70-2.50 (m, 2H), 2.40-2.10 (m, 6H), 2.10-1.95 (m, 2H)

Example 429. (2S)-1-[2-[4-[(3-fluoro-5-quinolyl)oxy]-1-piperidyl]acetyl]pyrrolidine-2-carbonitrile The title compound (419.4 mg, 88.3%) was prepared in the same fashion as Example 110, except that 3-fluoro-5-(piperidin-4-yloxy)quinoline hydrochloride (351.2 mg, 1.24 mmol) prepared in Reference Example 245 was used instead of N-(piperidin-4-yl)quinoline-5-amine hydrochloride. $^1$H-NMR (CDCl$_3$, 400 MHz) δ 8.79 (s, 1H), 8.19 (s, 1H), 7.68 (d, 1H), 7.55 (t, 1H), 6.91 (d, 1H), 5.25-4.70 (m, 1H), 4.65-4.55 (m, 1H), 3.80-3.60 (m, 1H), 3.60-3.50 (m, 1H), 3.50-3.10 (m, 2H), 2.90-2.75 (m, 2H), 2.65-2.50 (m, 2H), 2.45-2.10 (m, 6H), 2.10-1.95 (m, 2H)

Example 430. 5-[[1-[2-oxo-2-[(2S)-2-cyanopyrrolidin-1-yl]ethyl]-4-piperidyl]oxy]quinoline-2-carbonitrile The title compound (198.9 mg, 41.1%) was prepared in the same fashion as Example 110, except that 5-(piperidin- 4-yloxy)quinoline-2-carbonitrile hydrochloride (359.9 mg, 1.24 mmol) prepared in Reference Example 246 was used instead of N-(piperidin-4-yl)quinoline-5-amine hydrochloride. $^1$H-NMR (CDCl$_3$, 400 MHz) δ 8.74 (d, 1H), 7.72-7.66 (m, 3H), 7.01 (d, 1H), 5.20-4.75 (m, 1H), 4.70-4.60 (m, 1H), 3.80-3.60 (m, 1H), 3.60-3.50 (m, 1H), 3.45-3.20 (m, 2H), 2.90-2.80 (m, 2H), 2.70-2.50 (m, 2H), 2.40-2.10 (m, 6H), 2.10-1.95 (m, 2H)

Example 431. (2S)-1-[2-[4-[(8-chloro-5-quinolyl)oxy]-1-piperidyl]acetyl]pyrrolidine-2-carbonitrile The title compound (383.5 mg, 77.4%) was prepared in the same fashion as Example 110, except that 8-chloro-5-(piperidin-4-yloxy)quinoline hydrochloride (371.6 mg, 1.24 mmol) prepared in Reference Example 247 was used instead of N-(piperidin-4-yl)quinoline-5-amine hydrochloride. $^1$H-NMR (CDCl$_3$, 400 MHz) δ 9.00 (d, 1H), 8.54 (d, 1H), 7.56-7.51 (m, 2H), 7.05 (d, 1H), 5.45-4.70 (m, 1H), 4.65-4.55 (m, 1H), 3.85-3.65 (m, 1H), 3.65-3.55 (m, 1H), 3.55-3.20 (m, 2H), 3.05-2.85 (m, 2H), 2.60-2.40 (m, 2H), 2.40-2.00 (m, 8H)

Example 432. (2S,4S)-4-fluoro-1-[2-[4-[(7-methyl-4-quinolyl)oxy]-1-piperidyl]acetyl]pyrrolidine-2-carbonitrile The title compound (129.3 mg, 22.3%) was prepared in the same fashion as Example 330, except that 7-methyl-4-(piperidin-4-yloxy)quinoline hydrochloride (407.0 mg, 1.46 mmol) prepared in Reference Example 255 was used instead of 8-fluoro-N-(piperidin-4-yl)quinolin-5-amine hydrochloride. $^1$H-NMR (CDCl$_3$, 400 MHz) δ 8.68 (d, 1H), 8.11 (d, 1H), 7.80 (s, 1H), 7.34 (d, 1H), 6.67 (d, 1H), 5.50-5.25 (m, 1H), 5.00-4.90 (m, 1H), 4.75-4.65 (m, 1H), 4.30-4.15 (m, 1H), 4.05-3.70 (m, 2H), 3.55-3.20 (m, 2H), 2.95-2.75 (m, 2H), 2.75-2.65 (m, 1H), 2.65-2.56 (m, 2H), 2.56 (s, 3H), 2.30-2.10 (m, 2H), 2.10-1.95 (m, 2H)

Example 433. (2S,4S)-4-fluoro-1-[2-[4-[(7-fluoro-4-quinolyl)oxy]-1-piperidyl]acetyl]pyrrolidine-2-carbonitrile The title compound (239.1 mg, 40.9%) was prepared in the same fashion as Example 330, except that 7-fluoro-4-(piperidin-4-yloxy)quinoline hydrochloride (421.3 mg, 1.49 mmol) prepared in Reference Example 256 was used instead of 8-fluoro-N-(piperidin-4-yl)quinolin-5-amine hydrochloride. $^1$H-NMR (CDCl$_3$, 400 MHz) δ 8.71 (d, 1H), 8.22 (d, 1H), 7.64 (d, 1H), 7.27 (s, 1H), 6.69 (d, 1H), 5.50-5.25 (m, 1H), 5.00-4.90 (m, 1H), 4.75-4.65 (m, 1H), 4.30-4.15 (m, 1H), 4.05-3.70 (m, 2H), 3.50-3.20 (m, 2H), 2.95-2.80 (m, 2H), 2.80-2.65 (m, 1H), 2.65-2.50 (m, 2H), 2.30-2.10 (m, 2H), 2.10-1.95 (m, 2H)

Example 434. 4-[[1-[2-oxo-2-[(2S,4S)-2-cyano-4-fluoro-pyrrolidin-1-yl]ethyl]-4-piperidyl]oxy]quinoline-8-carbonitrile The title compound (277.0 mg, 46.6%) was prepared in the same fashion as Example 330, except that 4-(piperidin-4-yloxy)quinoline-8-carbonitrile hydrochloride (414.4 mg, 1.43 mmol) prepared in Reference Example 257 was used instead of 8-fluoro-N-(piperidin-4-yl)quinolin-5-amine hydrochloride. $^1$H-NMR (CDCl$_3$, 400 MHz) δ 8.87 (d, 1H), 8.46 (d, 1H), 8.09 (d, 1H), 7.54 (t, 1H), 6.84 (d, 1H), 5.55-5.25 (m, 1H), 5.00-4.90 (m, 1H), 4.80-4.65 (m, 1H), 4.30-4.15 (m, 1H), 4.00-3.70 (m, 2H), 3.50-3.20 (m, 2H), 2.90-2.80 (m, 2H), 2.80-2.65 (m, 1H), 2.65-2.50 (m, 2H), 2.30-2.10 (m, 2H), 2.10-1.95 (m, 2H)

Example 435. (2S,4S)-4-fluoro-1-[2-[4-[(8-fluoro-4-quinolyl)oxy]-1-piperidyl]acetyl]pyrrolidine-2-carbonitrile The title compound (301.2 mg, 50.5%) was prepared in the same fashion as Example 330, except that 8-fluoro-4-(piperidin-4-yloxy)quinoline hydrochloride (421.3 mg, 1.49 mmol) prepared in Reference Example 258 was used instead of 8-fluoro-N-(piperidin-4-yl)quinolin-5-amine hydrochloride. $^1$H-NMR (CDCl$_3$, 400 MHz) δ 8.77 (d, 1H), 8.00 (d, 1H), 7.44-7.37 (m, 2H), 6.78 (d, 1H), 5.55-5.25 (m, 1H), 5.00-4.90 (m, 1H), 4.80-4.65 (m, 1H), 4.30-4.15 (m, 1H), 4.05-3.70 (m, 2H), 3.55-3.20 (m, 2H), 2.95-2.75 (m, 2H), 2.75-2.65 (m, 1H), 2.65-2.50 (m, 2H), 2.30-2.10 (m, 2H), 2.10-1.95 (m, 2H)

Example 436. (2S,4S)-4-fluoro-1-[2-[4-[(2-methyl-4-quinolyl)oxy]-1-piperidyl]acetyl]pyrrolidine-2-carbonitrile The title compound (79.9 mg, 13.5%) was prepared in the same fashion as Example 330, except that 2-methyl-4-(piperidin-4-yloxy)quinoline hydrochloride (415.4 mg, 1.49 mmol) prepared in Reference Example 259 was used instead of 8-fluoro-N-(piperidin-4-yl)quinolin-5-amine hydrochloride. $^1$H-NMR (CDCl$_3$, 400 MHz) δ 8.16 (d, 1H), 7.94 (d, 1H), 7.66 (t, 1H), 7.44 (t, 1H), 6.61 (s, 1H), 5.50-5.25 (m, 1H), 5.00-4.90 (m, 1H), 4.75-4.65 (m, 1H), 4.30-4.15 (m, 1H), 4.05-3.70 (m, 2H), 3.55-3.20 (m, 2H), 2.95-2.80 (m, 2H), 2.80-2.69 (m, 1H), 2.69 (s, 3H), 2.69-2.55 (m, 2H), 2.30-2.10 (m, 2H), 2.10-1.95 (m, 2H)

Example 437. (2S,4S)-4-fluoro-1-[2-[4-[(6-fluoro-2-methyl-4-quinolyl)oxy]-1-piperidyl]acetyl]pyrrolidine-2-carbonitrile The title compound (403.6 mg, 65.4%) was prepared in the same fashion as Example 330, except that 6-fluoro-2-methyl-4-(piperidin-4-yloxy)quinoline hydrochloride (442.2 mg, 1.49 mmol) prepared in Reference Example 260 was used instead of 8-fluoro-N-(piperidin-4-yl)quinolin-5-amine hydrochloride. $^1$H-NMR (CDCl$_3$, 400 MHz) δ 7.90 (d, 1H), 7.72 (d, 1H), 7.39 (s, 1H), 6.60 (s, 1H), 5.50-5.25 (m, 1H), 5.00-4.90 (m, 1H), 4.70-4.60 (m, 1H), 4.30-4.15 (m, 1H), 4.05-3.70 (m, 2H), 3.50-3.20 (m, 2H), 2.90-2.75 (m, 2H), 2.75-2.65 (m, 1H), 2.65 (s, 3H), 2.65-2.55 (m, 2H), 2.30-2.10 (m, 2H), 2.10-1.95 (m, 2H)

Example 438. (2S,4S)-4-fluoro-1-[2-[4-[(8-methoxy-4-quinolyl)oxy]-1-piperidyl]acetyl]pyrrolidine-2-carbonitrile The title compound (65.9 mg, 10.7%) was prepared in the same fashion as Example 330, except that 8-methoxy-4-(piperidin-4-yloxy)quinoline hydrochloride (97.6 mg, 0.33 mmol) prepared in Reference Example 261 was used instead of 8-fluoro-N-(piperidin-4-yl)quinolin-5-amine hydrochloride. $^1$H-NMR (CDCl$_3$, 400 MHz) δ 8.74 (d, 1H), 7.79 (d, 1H), 7.43 (t, 1H), 7.06 (d, 1H), 6.76 (d, 1H), 5.50-5.25 (m, 1H), 5.00-4.90 (m, 1H), 4.75-4.65 (m, 1H), 4.30-4.15 (m, 1H), 4.08 (s, 3H), 4.08-3.70 (m, 2H), 3.55-3.20 (m, 2H), 2.90-2.75 (m, 2H), 2.75-2.65 (m, 1H), 2.65-2.55 (m, 2H), 2.30-2.10 (m, 2H), 2.10-1.95 (m, 2H)

Example 439. (2S,4S)-4-fluoro-1-[2-[4-[(8-methyl-4-quinolyl)oxy]-1-piperidyl]acetyl]pyrrolidine-2-carbonitrile The title compound (450.4 mg, 76.3%) was prepared in the same fashion as Example 330, except that 8-methyl-4-(piperidin-4-yloxy)quinoline hydrochloride (415.4 mg, 1.49 mmol) prepared in Reference Example 262 was used instead of 8-fluoro-N-(piperidin-4-yl)quinolin-5-amine hydrochloride. $^1$H-NMR (CDCl$_3$, 400 MHz) δ 8.75 (d, 1H), 8.08 (d, 1H), 7.54 (d, 1H), 7.38 (t, 1H), 6.72 (d, 1H), 5.50-5.25 (m, 1H), 5.00-4.90 (m, 1H), 4.75-4.65 (m, 1H), 4.25-4.10 (m, 1H), 4.05-3.70 (m, 2H), 3.50-3.20 (m, 2H), 2.90-2.78 (m, 2H), 2.78 (s, 3H), 2.78-2.60 (m, 1H), 2.60-2.50 (m, 2H), 2.30-2.10 (m, 2H), 2.10-1.95 (m, 2H)

Compound structures are provided in Table 1. Chemical names are as determined by ChemDraw.

TABLE 1

| Ex No. | Structure | Chemical Name |
|---|---|---|
| 1 | 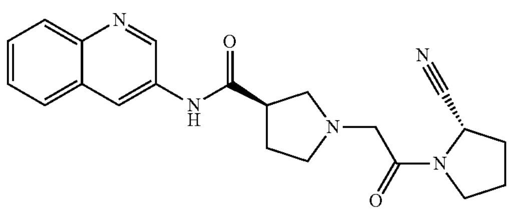 [SMILES: N#C[C@@H]1CCCN1C(=O)CN1CC[C@@H](C(=O)Nc2cnc3ccccc3c2)C1] | (R)-1-(2-((S)-2-cyanopyrrolidin-1-yl)-2-oxoethyl)-N-(quinolin-3-yl)pyrrolidine-3-carboxamide |
| 2 | 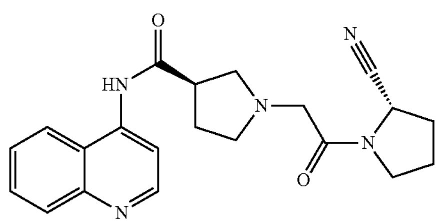 [SMILES: N#C[C@@H]1CCCN1C(=O)CN1CC[C@@H](C(=O)Nc2ccnc3ccccc23)C1] | (R)-1-(2-((S)-2-cyanopyrrolidin-1-yl)-2-oxoethyl)-N-(quinolin-4-yl)pyrrolidine-3-carboxamide |
| 3 | 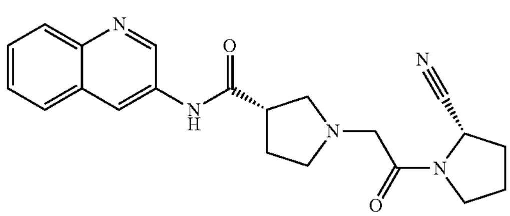 [SMILES: N#C[C@@H]1CCCN1C(=O)CN1CC[C@H](C(=O)Nc2cnc3ccccc3c2)C1] | (S)-1-(2-((S)-2-cyanopyrrolidin-1-yl)-2-oxoethyl)-N-(quinolin-3-yl)pyrrolidine-3-carboxamide |
| 4 | 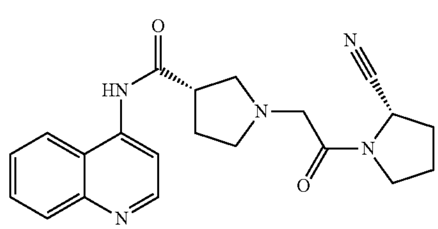 [SMILES: N#C[C@@H]1CCCN1C(=O)CN1CC[C@H](C(=O)Nc2ccnc3ccccc23)C1] | (S)-1-(2-((S)-2-cyanopyrrolidin-1-yl)-2-oxoethyl)-N-(quinolin-4-yl)pyrrolidine-3-carboxamide |
| 5 | 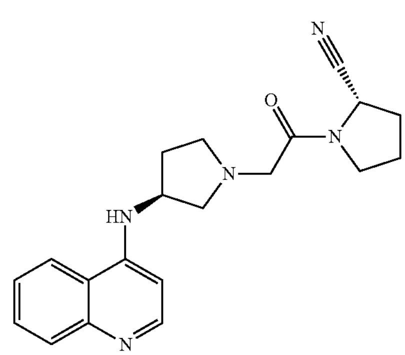 [SMILES: N#C[C@@H]1CCCN1C(=O)CN1CC[C@H](Nc2ccnc3ccccc23)C1] | (S)-1-(2-((S)-3-(quinolin-4-ylamino)pyrrolidin-1-yl)acetyl)pyrrolidine-2-carbonitrile |

TABLE 1-continued

| Ex No. | Structure | Chemical Name |
|---|---|---|
| 6 | 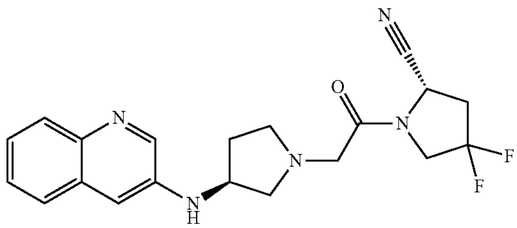 [SMILES: N#C[C@@H]1CC(F)(F)CN1C(=O)CN1CC[C@H](Nc2cnc3ccccc3c2)C1] | (S)-4,4-difluoro-1-(2-((S)-3-(quinolin-3-ylamino)pyrrolidin-1-yl)acetyl)pyrrolidine-2-carbonitrile |
| 7 | 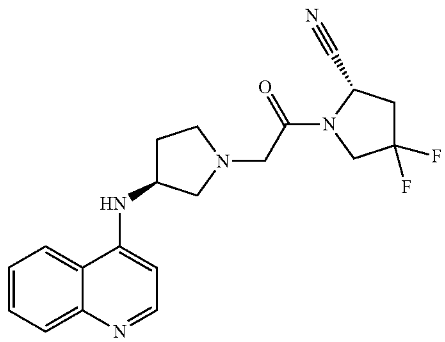 [SMILES: N#C[C@@H]1CC(F)(F)CN1C(=O)CN1CC[C@H](Nc2ccnc3ccccc23)C1] | (S)-4,4-difluoro-1-(2-((S)-3-(quinolin-4-ylamino)pyrrolidin-1-yl)acetyl)pyrrolidine-2-carbonitrile |
| 8 | 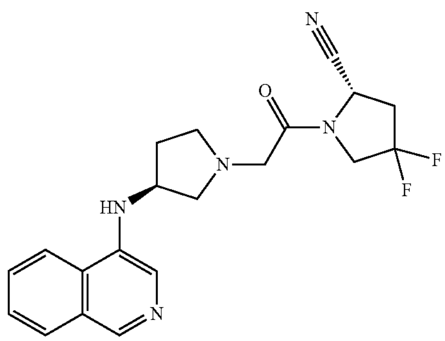 [SMILES: N#C[C@@H]1CC(F)(F)CN1C(=O)CN1CC[C@H](Nc2cncc3ccccc23)C1] | (S)-4,4-difluoro-1-(2-((S)-3-(isoquinolin-4-ylamino)pyrrolidin-1-yl)acetyl)pyrrolidine-2-carbonitrile |
| 9 | 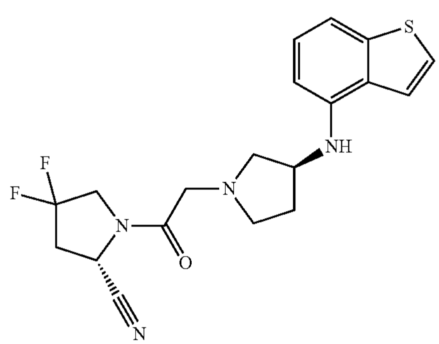 [SMILES: N#C[C@@H]1CC(F)(F)CN1C(=O)CN1CC[C@H](Nc2cccc3sccc23)C1] | (S)-1-(2-((S)-3-(benzo[b]thiophen-4-ylamino)pyrrolidin-1-yl)acetyl)-4,4-difluoropyrrolidine-2-carbonitrile |
| 10 | 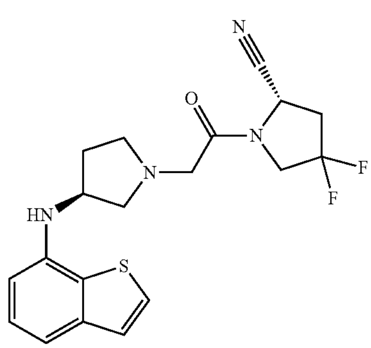 [SMILES: N#C[C@@H]1CC(F)(F)CN1C(=O)CN1CC[C@H](Nc2cccc3ccsc23)C1] | (S)-1-(2-((S)-3-(benzo[b]thiophen-7-ylamino)pyrrolidin-1-yl)acetyl)-4,4-difluoropyrrolidine-2-carbonitrile |

| Ex No. | Structure | Chemical Name |
| --- | --- | --- |
| 11 | 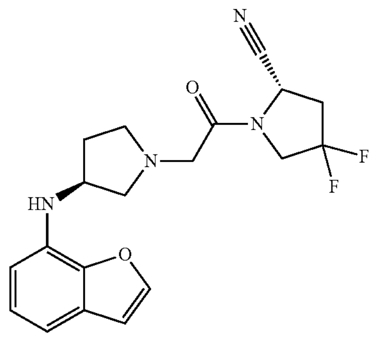 [SMILES: N#C[C@@H]1CC(F)(F)CN1C(=O)CN1CC[C@H](Nc2cccc3ccoc23)C1] | (S)-1-(2-((S)-3-(benzofuran-7-ylamino)pyrrolidin-1-yl)acetyl)-4,4-difluoropyrrolidine-2-carbonitrile |
| 12 | 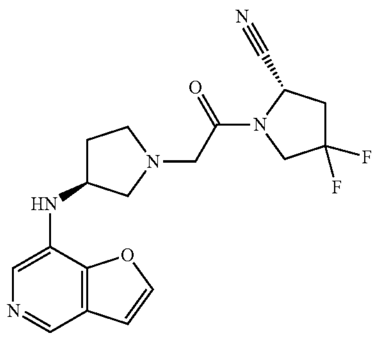 [SMILES: N#C[C@@H]1CC(F)(F)CN1C(=O)CN1CC[C@H](Nc2cncc3ccoc23)C1] | (S)-4,4-difluoro-1-(2-((S)-3-(furo[3,2-c]pyridin-7-ylamino)pyrrolidin-1-yl)acetyl)pyrrolidine-2-carbonitrile |
| 13 | 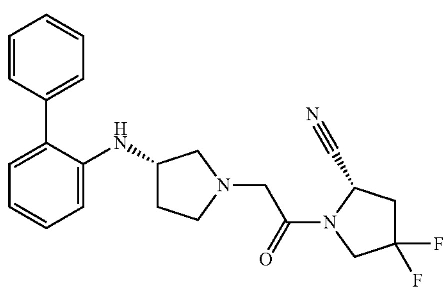 [SMILES: N#C[C@@H]1CC(F)(F)CN1C(=O)CN1CC[C@H](Nc2ccccc2-c2ccccc2)C1] | (S)-1-(2-((S)-3-([1,1'-biphenyl]-2-ylamino)pyrrolidin-1-yl)acetyl)-4,4-difluoropyrrolidine-2-carbonitrile |
| 14 | 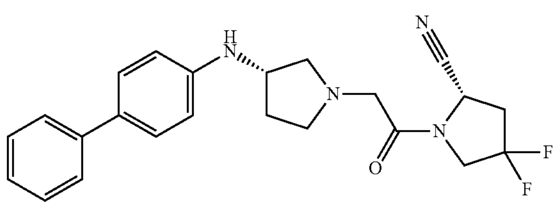 [SMILES: N#C[C@@H]1CC(F)(F)CN1C(=O)CN1CC[C@H](Nc2ccc(-c3ccccc3)cc2)C1] | (S)-1-(2-((S)-3-([1,1'-biphenyl]-4-ylamino)pyrrolidin-1-yl)acetyl)-4,4-difluoropyrrolidine-2-carbonitrile |
| 15 | 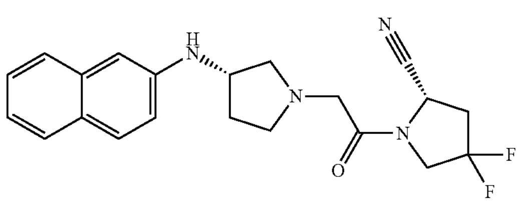 [SMILES: N#C[C@@H]1CC(F)(F)CN1C(=O)CN1CC[C@H](Nc2ccc3ccccc3c2)C1] | (S)-4,4-difluoro-1-(2-((S)-3-(naphthalen-2-ylamino)pyrrolidin-1-yl)acetyl)pyrrolidine-2-carbonitrile |
| 16 | 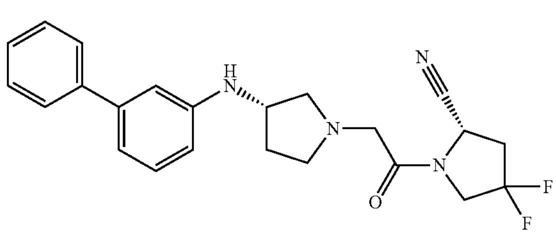 [SMILES: N#C[C@@H]1CC(F)(F)CN1C(=O)CN1CC[C@H](Nc2cccc(-c3ccccc3)c2)C1] | (S)-1-(2-((S)-3-([1,1'-biphenyl]-3-ylamino)pyrrolidin-1-yl)acetyl)-4,4-difluoropyrrolidine-2-carbonitrile |

TABLE 1-continued

| Ex No. | Structure | Chemical Name |
| --- | --- | --- |
| 17 | 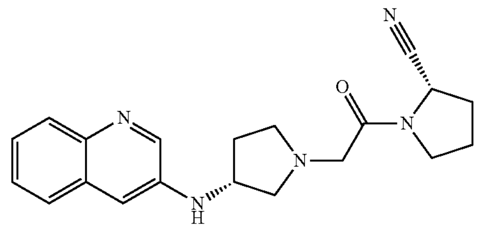 [SMILES: N#C[C@@H]1CCCN1C(=O)CN1CC[C@@H](Nc2cnc3ccccc3c2)C1] | (S)-1-(2-((R)-3-(quinolin-3-ylamino)pyrrolidin-1-yl)acetyl)pyrrolidine-2-carbonitrile |
| 18 | 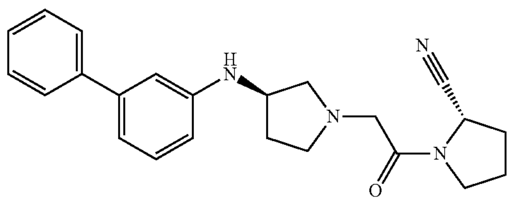 [SMILES: N#C[C@@H]1CCCN1C(=O)CN1CC[C@@H](Nc2cccc(-c3ccccc3)c2)C1] | (S)-1-(2-((R)-3-([1,1'-biphenyl]-3-ylamino)pyrrolidin-1-yl)acetyl)pyrrolidine-2-carbonitrile |
| 19 | 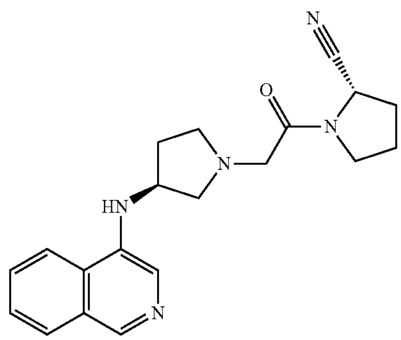 [SMILES: N#C[C@@H]1CCCN1C(=O)CN1CC[C@H](Nc2cncc3ccccc23)C1] | (S)-1-(2-((S)-3-(isoquinolin-4-ylamino)pyrrolidin-1-yl)acetyl)pyrrolidine-2-carbonitrile |
| 20 | 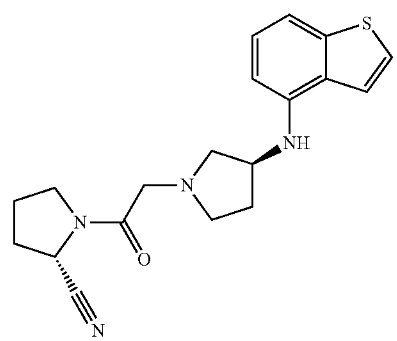 [SMILES: N#C[C@@H]1CCCN1C(=O)CN1CC[C@H](Nc2cccc3sccc23)C1] | (S)-1-(2-((S)-3-(benzo[b]thiophen-4-ylamino)pyrrolidin-1-yl)acetyl)pyrrolidine-2-carbonitrile |
| 21 | 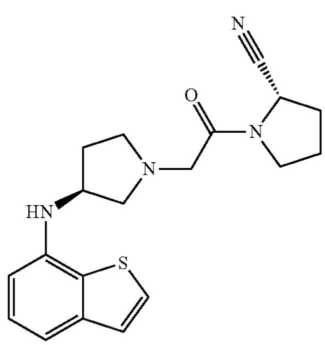 [SMILES: N#C[C@@H]1CCCN1C(=O)CN1CC[C@H](Nc2cccc3ccsc23)C1] | (S)-1-(2-((S)-3-(benzo[b]thiophen-7-ylamino)pyrrolidin-1-yl)acetyl)pyrrolidine-2-carbonitrile |

TABLE 1-continued

| Ex No. | Structure | Chemical Name |
| --- | --- | --- |
| 22 | 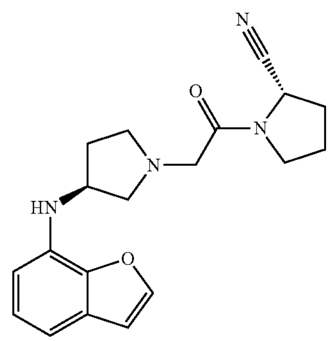 [SMILES: N#C[C@@H]1CCCN1C(=O)CN1CC[C@H](Nc2cccc3ccoc23)C1] | (S)-1-(2-((S)-3-(benzofuran-7-ylamino)pyrrolidin-1-yl)acetyl)pyrrolidine-2-carbonitrile |
| 23 | 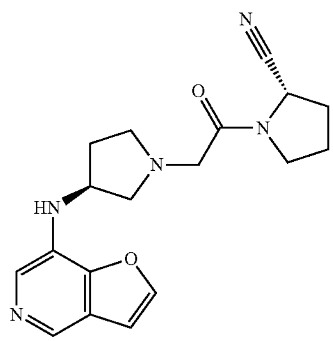 [SMILES: N#C[C@@H]1CCCN1C(=O)CN1CC[C@H](Nc2cncc3ccoc23)C1] | (S)-1-(2-((S)-3-(furo[3,2-c]pyridin-7-ylamino)pyrrolidin-1-yl)acetyl)pyrrolidine-2-carbonitrile |
| 24 | 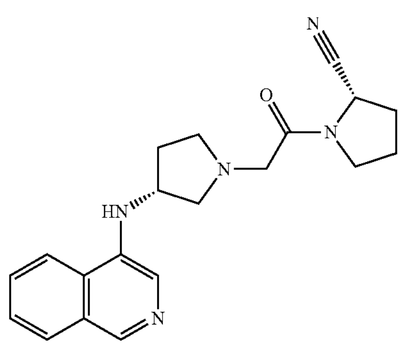 [SMILES: N#C[C@@H]1CCCN1C(=O)CN1CC[C@@H](Nc2cncc3ccccc23)C1] | (S)-1-(2-((R)-3-(isoquinolin-4-ylamino)pyrrolidin-1-yl)acetyl)pyrrolidine-2-carbonitrile |
| 25 | 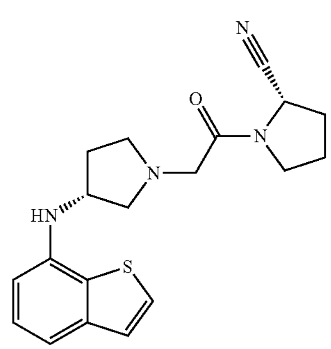 [SMILES: N#C[C@@H]1CCCN1C(=O)CN1CC[C@@H](Nc2cccc3ccsc23)C1] | (S)-1-(2-((R)-3-(benzo[b]thiophen-7-ylamino)pyrrolidin-1-yl)acetyl)pyrrolidine-2-carbonitrile |

TABLE 1-continued

| Ex No. | Structure | Chemical Name |
|---|---|---|
| 26 | 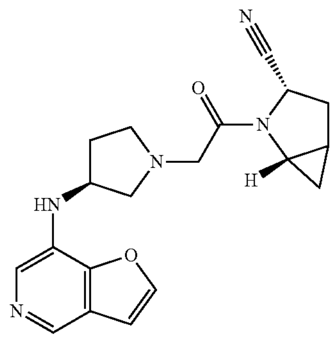 [SMILES: N#C[C@@H]1CC2C[C@@H]2N1C(=O)CN1CC[C@H](Nc2cncc3ccoc23)C1] | (1S,3S,5S)-2-(2-((S)-3-(furo[3,2-c]pyridin-7-ylamino)pyrrolidin-1-yl)acetyl)-2-azabicyclo[3.1.0]hexane-3-carbonitrile |
| 27 | 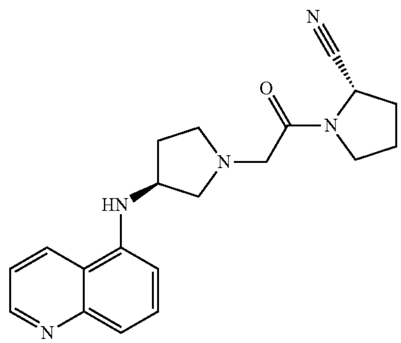 [SMILES: N#C[C@@H]1CCCN1C(=O)CN1CC[C@H](Nc2cccc3ncccc23)C1] | (S)-1-(2-((S)-3-(quinolin-5-ylamino)pyrrolidin-1-yl)acetyl)pyrrolidine-2-carbonitrile |
| 28 | 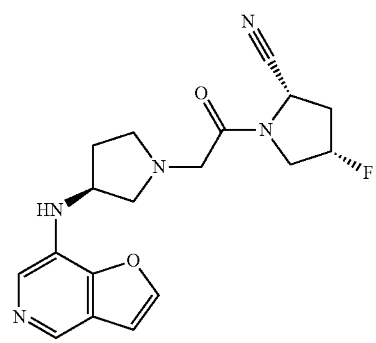 [SMILES: N#C[C@@H]1C[C@H](F)CN1C(=O)CN1CC[C@H](Nc2cncc3ccoc23)C1] | (2S,4S)-4-fluoro-1-(2-((S)-3-(furo[3,2-c]pyridin-7-ylamino)pyrrolidin-1-yl)acetyl)pyrrolidine-2-carbonitrile |
| 29 | 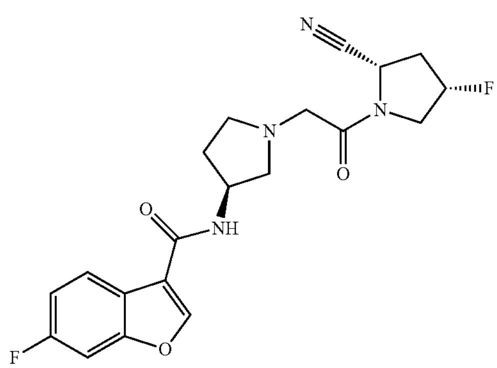 [SMILES: N#C[C@@H]1C[C@H](F)CN1C(=O)CN1CC[C@H](NC(=O)c2coc3cc(F)ccc23)C1] | N-((S)-1-(2-((2S,4S)-2-cyano-4-fluoropyrrolidin-1-yl)-2-oxoethyl)pyrrolidin-3-yl)-6-fluorobenzofuran-3-carboxamide |

TABLE 1-continued

| Ex No. | Structure | Chemical Name |
| --- | --- | --- |
| 30 | 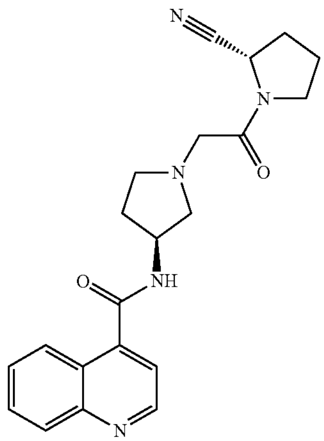 [SMILES: N#C[C@@H]1CCCN1C(=O)CN1CC[C@H](NC(=O)c2ccnc3ccccc23)C1] | N-((S)-1-(2-((S)-2-cyanopyrrolidin-1-yl)-2-oxoethyl)pyrrolidin-3-yl)quinoline-4-carboxamide |
| 31 | 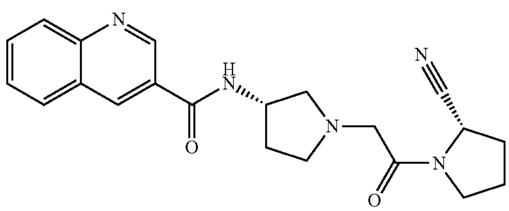 [SMILES: N#C[C@@H]1CCCN1C(=O)CN1CC[C@H](NC(=O)c2cnc3ccccc3c2)C1] | N-((S)-1-(2-((S)-2-cyanopyrrolidin-1-yl)-2-oxoethyl)pyrrolidin-3-yl)quinoline-3-carboxamide |
| 32 | 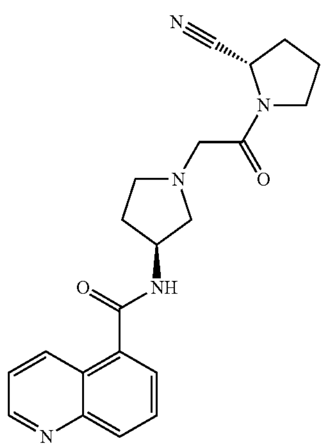 [SMILES: N#C[C@@H]1CCCN1C(=O)CN1CC[C@H](NC(=O)c2cccc3ncccc23)C1] | N-((S)-1-(2-((S)-2-cyanopyrrolidin-1-yl)-2-oxoethyl)pyrrolidin-3-yl)quinoline-5-carboxamide |
| 33 | 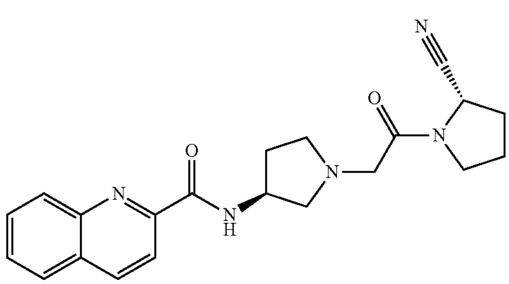 [SMILES: N#C[C@@H]1CCCN1C(=O)CN1CC[C@H](NC(=O)c2ccc3ccccc3n2)C1] | N-((S)-1-(2-((S)-2-cyanopyrrolidin-1-yl)-2-oxoethyl)pyrrolidin-3-yl)quinoline-2-carboxamide |

TABLE 1-continued

| Ex No. | Structure | Chemical Name |
|---|---|---|
| 34 | 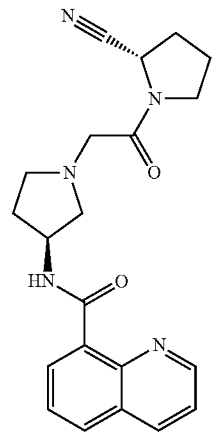 [SMILES: N#C[C@@H]1CCCN1C(=O)CN1CC[C@H](NC(=O)c2cccc3cccnc23)C1] | N-((S)-1-(2-((S)-2-cyanopyrrolidin-1-yl)-2-oxoethyl)pyrrolidin-3-yl)quinoline-8-carboxamide |
| 35 | 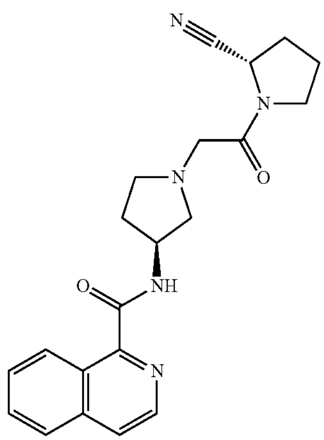 [SMILES: N#C[C@@H]1CCCN1C(=O)CN1CC[C@H](NC(=O)c2nccc3ccccc23)C1] | N-((S)-1-(2-((S)-2-cyanopyrrolidin-1-yl)-2-oxoethyl)pyrrolidin-3-yl)isoquinoline-1-carboxamide |
| 36 | 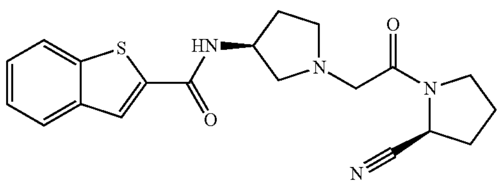 | N-((S)-1-(2-((S)-2-cyanopyrrolidin-1-yl)-2-oxoethyl)pyrrolidin-3-yl)benzo[b]thiophene-2-carboxamide |
| 37 | 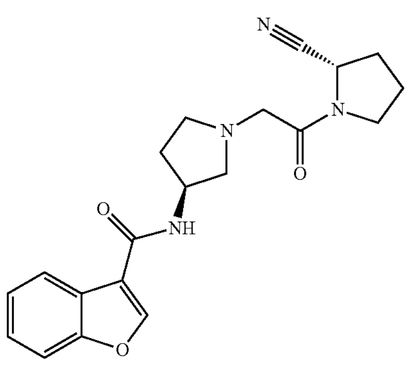 [SMILES: N#C[C@@H]1CCCN1C(=O)CN1CC[C@H](NC(=O)c2coc3ccccc23)C1] | N-((S)-1-(2-((S)-2-cyanopyrrolidin-1-yl)-2-oxoethyl)pyrrolidin-3-yl)benzofuran-3-carboxamide |

TABLE 1-continued

| Ex No. | Structure | Chemical Name |
| --- | --- | --- |
| 38 | 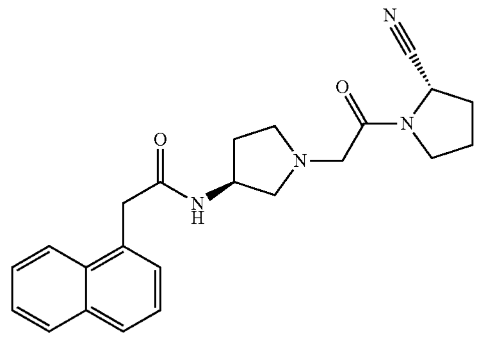 [SMILES: N#C[C@@H]1CCCN1C(=O)CN1CC[C@H](NC(=O)Cc2cccc3ccccc23)C1] | N-((S)-1-(2-((S)-2-cyanopyrrolidin-1-yl)-2-oxoethyl)pyrrolidin-3-yl)-2-(naphthalen-1-yl)acetamide |
| 39 | 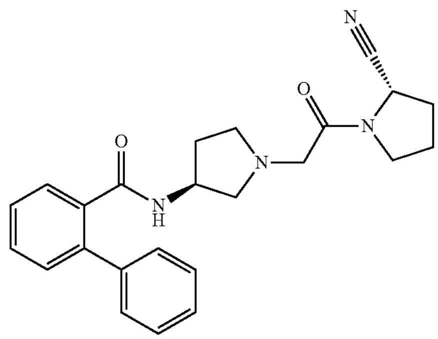 [SMILES: N#C[C@@H]1CCCN1C(=O)CN1CC[C@H](NC(=O)c2ccccc2-c2ccccc2)C1] | N-((S)-1-(2-((S)-2-cyanopyrrolidin-1-yl)-2-oxoethyl)pyrrolidin-3-yl)-[1,1'-biphenyl]-2-carboxamide |
| 40 | 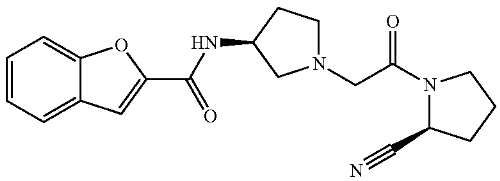 [SMILES: N#C[C@@H]1CCCN1C(=O)CN1CC[C@H](NC(=O)c2cc3ccccc3o2)C1] | N-((S)-1-(2-((S)-2-cyanopyrrolidin-1-yl)-2-oxoethyl)pyrrolidin-3-yl)benzofuran-2-carboxamide |
| 41 | 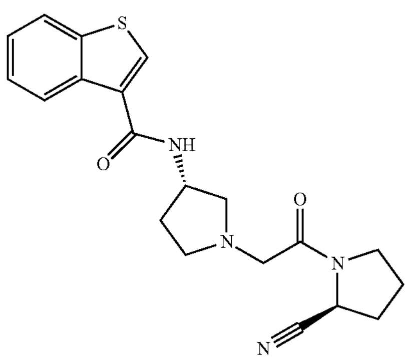 [SMILES: N#C[C@@H]1CCCN1C(=O)CN1CC[C@H](NC(=O)c2csc3ccccc23)C1] | N-((S)-1-(2-((S)-2-cyanopyrrolidin-1-yl)-2-oxoethyl)pyrrolidin-3-yl)benzo[b]thiophene-3-carboxamide |
| 42 | 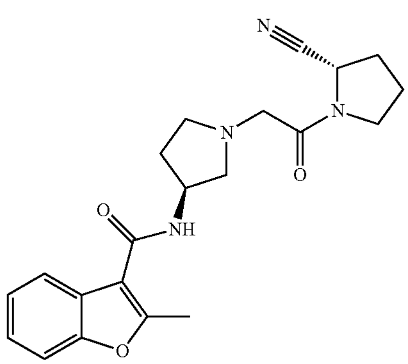 [SMILES: Cc1oc2ccccc2c1C(=O)N[C@H]1CCN(CC(=O)N2CCC[C@H]2C#N)C1] | N-((S)-1-(2-((S)-2-cyanopyrrolidin-1-yl)-2-oxoethyl)pyrrolidin-3-yl)-2-methylbenzofuran-3-carboxamide |

TABLE 1-continued

| Ex No. | Structure | Chemical Name |
| --- | --- | --- |
| 43 | 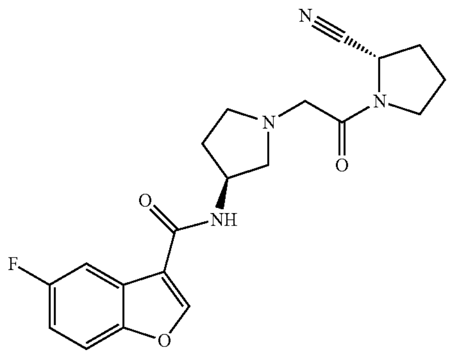 [SMILES: N#C[C@@H]1CCCN1C(=O)CN1CC[C@H](NC(=O)c2coc3ccc(F)cc23)C1] | N-((S)-1-(2-((S)-2-cyanopyrrolidin-1-yl)-2-oxoethyl)pyrrolidin-3-yl)-5-fluorobenzofuran-3-carboxamide |
| 44 | 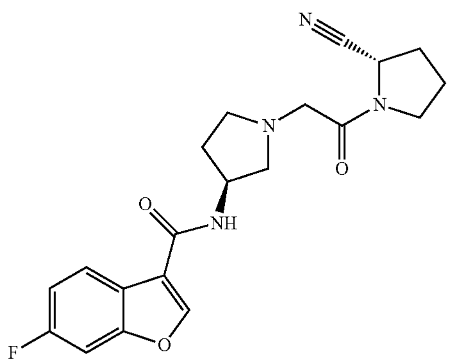 [SMILES: N#C[C@@H]1CCCN1C(=O)CN1CC[C@H](NC(=O)c2coc3cc(F)ccc23)C1] | N-((S)-1-(2-((S)-2-cyanopyrrolidin-1-yl)-2-oxoethyl)pyrrolidin-3-yl)-6-fluorobenzofuran-3-carboxamide |
| 45 | 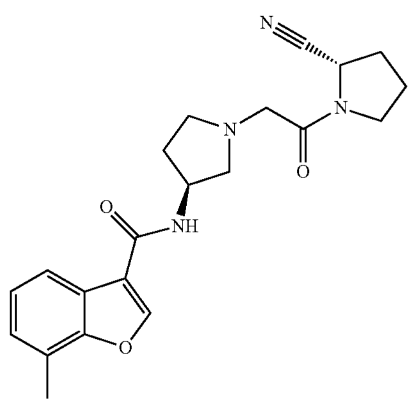 [SMILES: Cc1cccc2c(C(=O)N[C@H]3CCN(CC(=O)N4CCC[C@H]4C#N)C3)coc12] | N-((S)-1-(2-((S)-2-cyanopyrrolidin-1-yl)-2-oxoethyl)pyrrolidin-3-yl)-7-methylbenzofuran-3-carboxamide |
| 46 | 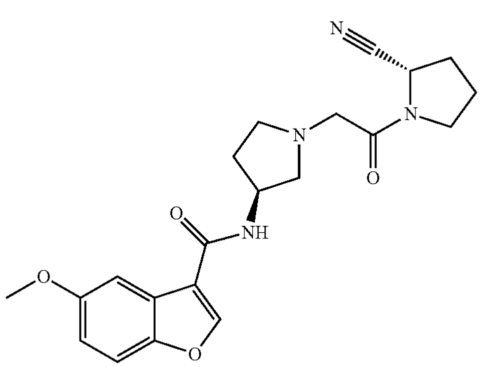 [SMILES: COc1ccc2occ(C(=O)N[C@H]3CCN(CC(=O)N4CCC[C@H]4C#N)C3)c2c1] | N-((S)-1-(2-((S)-2-cyanopyrrolidin-1-yl)-2-oxoethyl)pyrrolidin-3-yl)-5-methoxybenzofuran-3-carboxamide |

TABLE 1-continued

| Ex No. | Structure | Chemical Name |
|---|---|---|
| 47 | 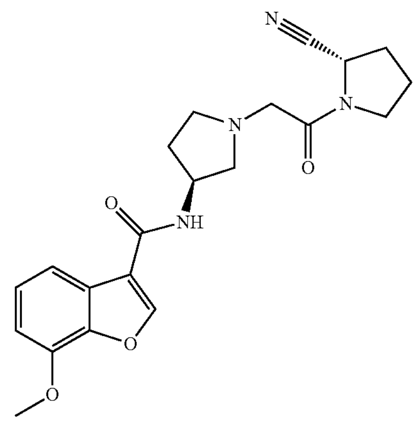 [SMILES: COc1cccc2c(C(=O)N[C@H]3CCN(CC(=O)N4CCC[C@H]4C#N)C3)coc12] | N-((S)-1-(2-((S)-2-cyanopyrrolidin-1-yl)-2-oxoethyl)pyrrolidin-3-yl)-7-methoxybenzofuran-3-carboxamide |
| 48 | 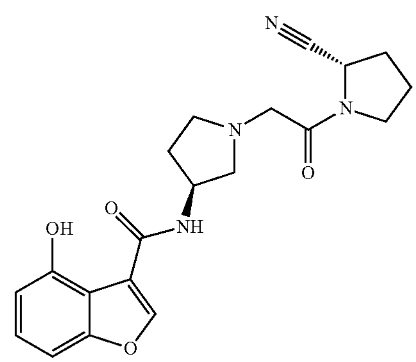 [SMILES: N#C[C@@H]1CCCN1C(=O)CN1CC[C@H](NC(=O)c2coc3cccc(O)c23)C1] | N-((S)-1-(2-((S)-2-cyanopyrrolidin-1-yl)-2-oxoethyl)pyrrolidin-3-yl)-4-hydroxybenzofuran-3-carboxamide |
| 49 | 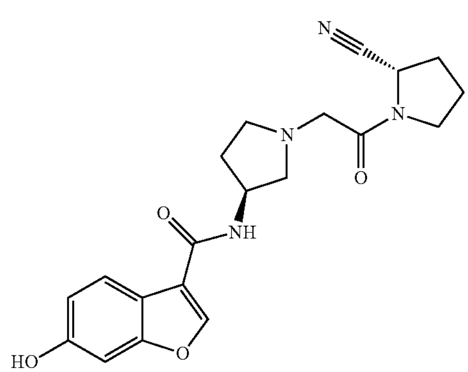 [SMILES: N#C[C@@H]1CCCN1C(=O)CN1CC[C@H](NC(=O)c2coc3cc(O)ccc23)C1] | N-((S)-1-(2-((S)-2-cyanopyrrolidin-1-yl)-2-oxoethyl)pyrrolidin-3-yl)-6-hydroxybenzofuran-3-carboxamide |
| 50 | 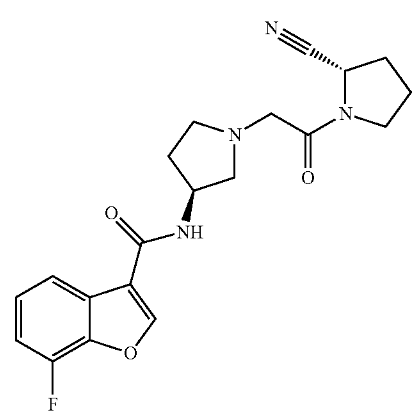 [SMILES: N#C[C@@H]1CCCN1C(=O)CN1CC[C@H](NC(=O)c2coc3c(F)cccc23)C1] | N-((S)-1-(2-((S)-2-cyanopyrrolidin-1-yl)-2-oxoethyl)pyrrolidin-3-yl)-7-fluorobenzofuran-3-carboxamide |

TABLE 1-continued

| Ex No. | Structure | Chemical Name |
|---|---|---|
| 51 | 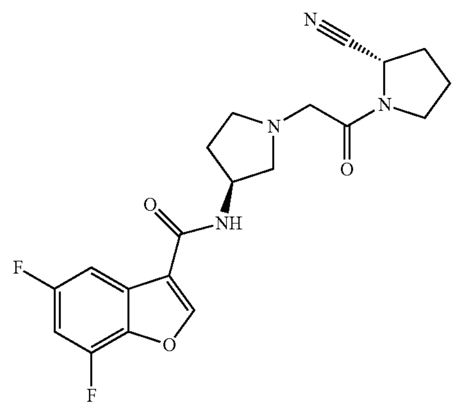 [SMILES: N#C[C@@H]1CCCN1C(=O)CN1CC[C@H](NC(=O)c2coc3c(F)cc(F)cc23)C1] | N-((S)-1-(2-((S)-2-cyanopyrrolidin-1-yl)-2-oxoethyl)pyrrolidin-3-yl)-5,7-difluorobenzofuran-3-carboxamide |
| 52 | 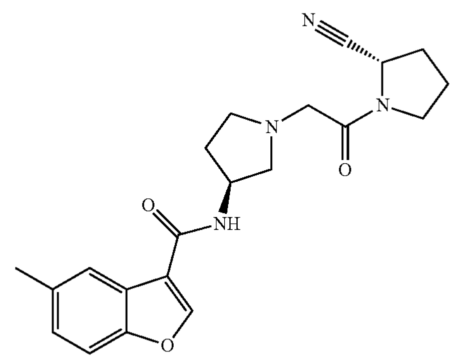 [SMILES: Cc1ccc2occ(C(=O)N[C@H]3CCN(CC(=O)N4CCC[C@H]4C#N)C3)c2c1] | N-((S)-1-(2-((S)-2-cyanopyrrolidin-1-yl)-2-oxoethyl)pyrrolidin-3-yl)-5-methylbenzofuran-3-carboxamide |
| 53 | 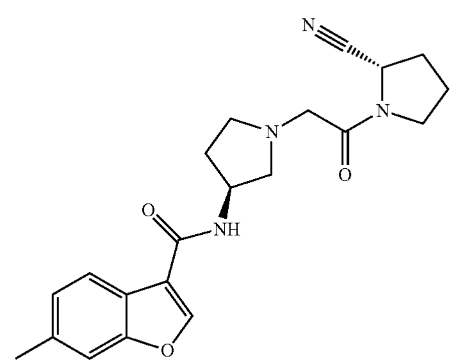 [SMILES: Cc1ccc2c(C(=O)N[C@H]3CCN(CC(=O)N4CCC[C@H]4C#N)C3)coc2c1] | N-((S)-1-(2-((S)-2-cyanopyrrolidin-1-yl)-2-oxoethyl)pyrrolidin-3-yl)-6-methylbenzofuran-3-carboxamide |
| 54 | 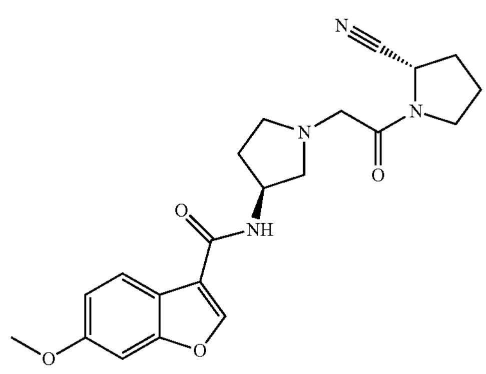 [SMILES: COc1ccc2c(C(=O)N[C@H]3CCN(CC(=O)N4CCC[C@H]4C#N)C3)coc2c1] | N-((S)-1-(2-((S)-2-cyanopyrrolidin-1-yl)-2-oxoethyl)pyrrolidin-3-yl)-6-methoxybenzofuran-3-carboxamide |

TABLE 1-continued

| Ex No. | Structure | Chemical Name |
| --- | --- | --- |
| 55 | 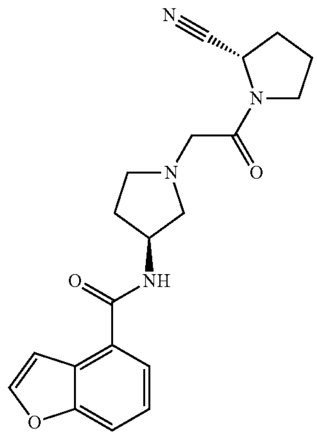 [SMILES: N#C[C@@H]1CCCN1C(=O)CN1CC[C@H](NC(=O)c2cccc3occc23)C1] | N-((S)-1-(2-((S)-2-cyanopyrrolidin-1-yl)-2-oxoethyl)pyrrolidin-3-yl)benzofuran-4-carboxamide |
| 56 | 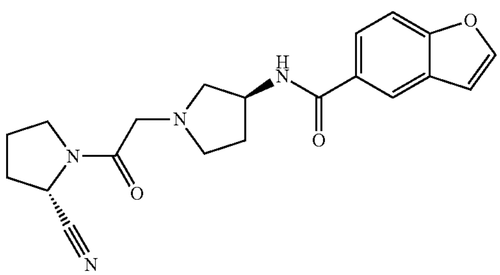 [SMILES: N#C[C@@H]1CCCN1C(=O)CN1CC[C@H](NC(=O)c2ccc3occc3c2)C1] | N-((S)-1-(2-((S)-2-cyanopyrrolidin-1-yl)-2-oxoethyl)pyrrolidin-3-yl)benzofuran-5-carboxamide |
| 57 | 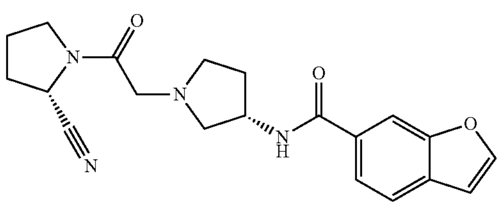 [SMILES: N#C[C@@H]1CCCN1C(=O)CN1CC[C@H](NC(=O)c2ccc3ccoc3c2)C1] | N-((S)-1-(2-((S)-2-cyanopyrrolidin-1-yl)-2-oxoethyl)pyrrolidin-3-yl)benzofuran-6-carboxamide |
| 58 | 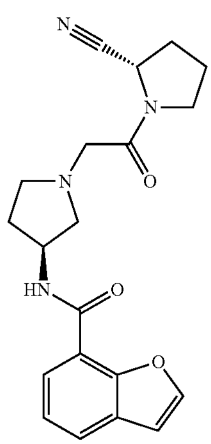 [SMILES: N#C[C@@H]1CCCN1C(=O)CN1CC[C@H](NC(=O)c2cccc3ccoc23)C1] | N-((S)-1-(2-((S)-2-cyanopyrrolidin-1-yl)-2-oxoethyl)pyrrolidin-3-yl)benzofuran-7-carboxamide |

TABLE 1-continued

| Ex No. | Structure | Chemical Name |
| --- | --- | --- |
| 59 | 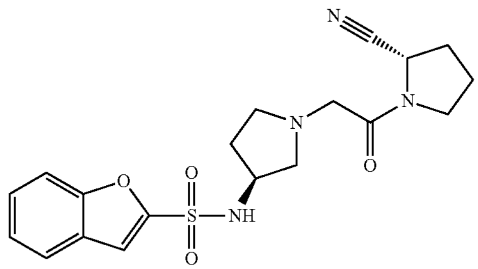 [SMILES: N#C[C@@H]1CCCN1C(=O)CN1CC[C@H](NS(=O)(=O)c2cc3ccccc3o2)C1] | N-((S)-1-(2-((S)-2-cyanopyrrolidin-1-yl)-2-oxoethyl)pyrrolidin-3-yl)benzofuran-2-sulfonamide |
| 60 | 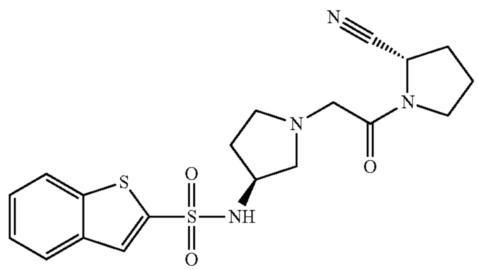 [SMILES: N#C[C@@H]1CCCN1C(=O)CN1CC[C@H](NS(=O)(=O)c2cc3ccccc3s2)C1] | N-((S)-1-(2-((S)-2-cyanopyrrolidin-1-yl)-2-oxoethyl)pyrrolidin-3-yl)benzo[b]thiophene-2-sulfonamide |
| 61 | 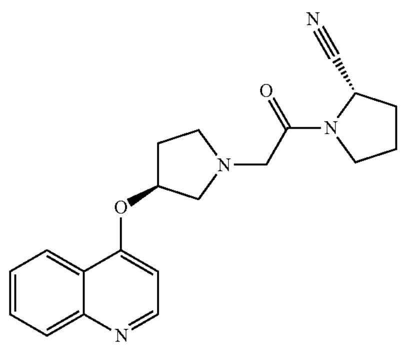 [SMILES: N#C[C@@H]1CCCN1C(=O)CN1CC[C@H](Oc2ccnc3ccccc23)C1] | (S)-1-(2-((S)-3-(quinolin-4-yloxy)pyrrolidin-1-yl)acetyl)pyrrolidine-2-carbonitrile |
| 62 | 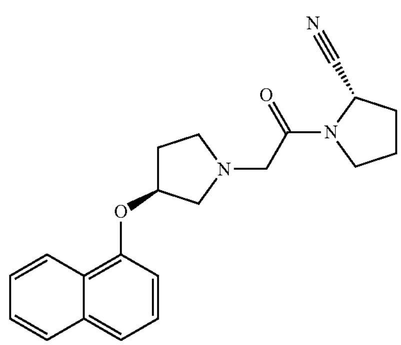 [SMILES: N#C[C@@H]1CCCN1C(=O)CN1CC[C@H](Oc2cccc3ccccc23)C1] | (S)-1-(2-((S)-3-(naphthalen-1-yloxy)pyrrolidin-1-yl)acetyl)pyrrolidine-2-carbonitrile |
| 63 | 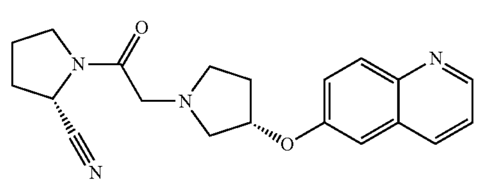 [SMILES: N#C[C@@H]1CCCN1C(=O)CN1CC[C@H](Oc2ccc3ncccc3c2)C1] | (S)-1-(2-((S)-3-(quinolin-6-yloxy)pyrrolidin-1-yl)acetyl)pyrrolidine-2-carbonitrile |

TABLE 1-continued

| Ex No. | Structure | Chemical Name |
|---|---|---|
| 64 | 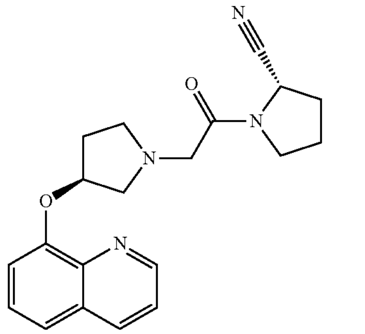 [SMILES: N#C[C@@H]1CCCN1C(=O)CN1CC[C@H](Oc2cccc3cccnc23)C1] | (S)-1-(2-((S)-3-(quinolin-8-yloxy)pyrrolidin-1-yl)acetyl)pyrrolidine-2-carbonitrile |
| 65 | 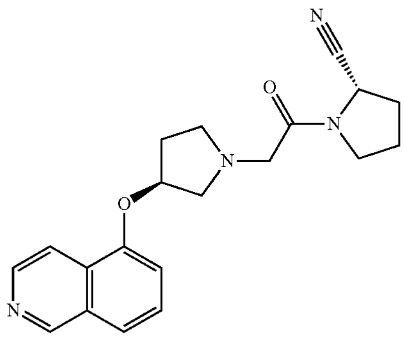 [SMILES: N#C[C@@H]1CCCN1C(=O)CN1CC[C@H](Oc2cccc3cnccc23)C1] | (S)-1-(2-((S)-3-(isoquinolin-5-yloxy)pyrrolidin-1-yl)acetyl)pyrrolidine-2-carbonitrile |
| 66 | 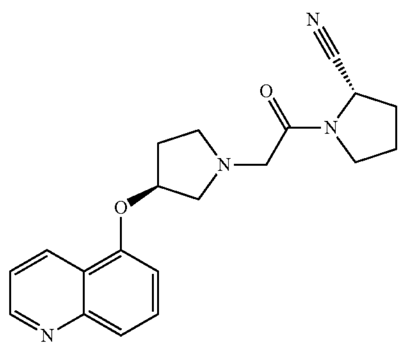 [SMILES: N#C[C@@H]1CCCN1C(=O)CN1CC[C@H](Oc2cccc3ncccc23)C1] | (S)-1-(2-((S)-3-(quinolin-5-yloxy)pyrrolidin-1-yl)acetyl)pyrrolidine-2-carbonitrile |
| 67 | 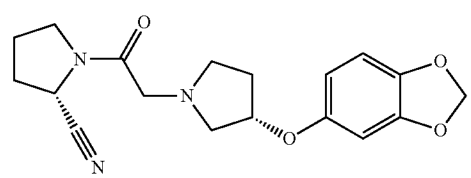 [SMILES: N#C[C@@H]1CCCN1C(=O)CN1CC[C@H](Oc2ccc3c(c2)OCO3)C1] | (S)-1-(2-((S)-3-(benzo[d][1,3]dioxol-5-yloxy)pyrrolidin-1-yl)acetyl)pyrrolidine-2-carbonitrile |
| 68 | 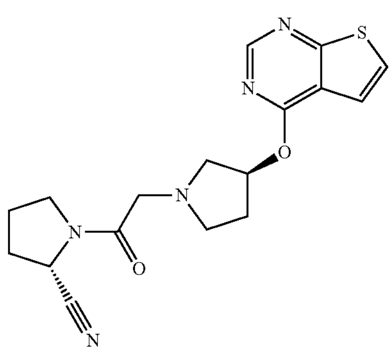 [SMILES: N#C[C@@H]1CCCN1C(=O)CN1CC[C@H](Oc2ncnc3sccc23)C1] | (S)-1-(2-((S)-3-(thieno[2,3-d]pyrimidin-4-yloxy)pyrrolidin-1-yl)acetyl)pyrrolidine-2-carbonitrile |

TABLE 1-continued

| Ex No. | Structure | Chemical Name |
| --- | --- | --- |
| 69 | 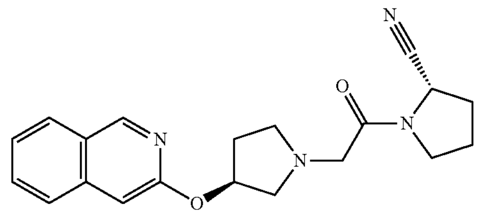 [SMILES: N#C[C@@H]1CCCN1C(=O)CN1CC[C@H](Oc2cc3ccccc3cn2)C1] | (S)-1-(2-((S)-3-(isoquinolin-3-yloxy)pyrrolidin-1-yl)acetyl)pyrrolidine-2-carbonitrile |
| 70 | 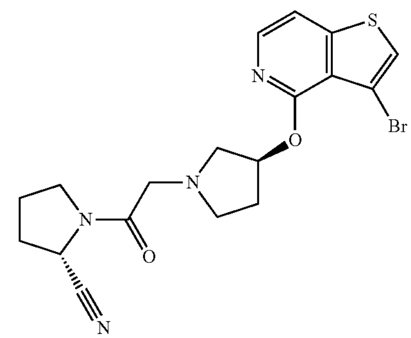 [SMILES: N#C[C@@H]1CCCN1C(=O)CN1CC[C@H](Oc2nccc3scc(Br)c23)C1] | (S)-1-(2-((S)-3-((3-bromothieno[3,2-c]pyridin-4-yl)oxy)pyrrolidin-1-yl)acetyl)pyrrolidine-2-carbonitrile |
| 71 | 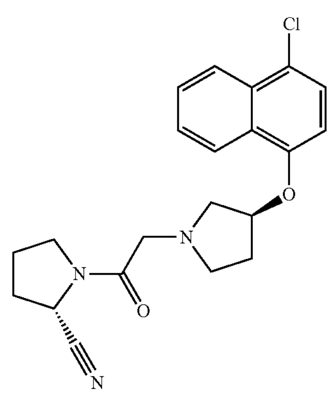 [SMILES: N#C[C@@H]1CCCN1C(=O)CN1CC[C@H](Oc2ccc(Cl)c3ccccc23)C1] | (S)-1-(2-((S)-3-((4-chloronaphthalen-1-yl)oxy)pyrrolidin-1-yl)acetyl)pyrrolidine-2-carbonitrile |
| 72 | 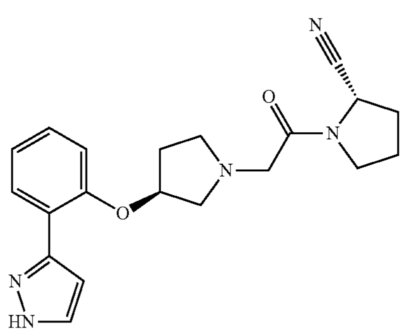 [SMILES: N#C[C@@H]1CCCN1C(=O)CN1CC[C@H](Oc2ccccc2-c2cc[nH]n2)C1] | (S)-1-(2-((S)-3-(2-(1H-pyrazol-3-yl)phenoxy)pyrrolidin-1-yl)acetyl)pyrrolidine-2-carbonitrile |

TABLE 1-continued

| Ex No. | Structure | Chemical Name |
|---|---|---|
| 73 | 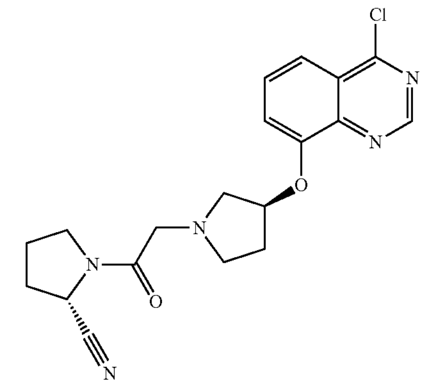 [SMILES: N#C[C@@H]1CCCN1C(=O)CN1CC[C@H](Oc2cccc3c(Cl)ncnc23)C1] | (S)-1-(2-((S)-3-((4-chloroquinazolin-8-yl)oxy)pyrrolidin-1-yl)acetyl)pyrrolidine-2-carbonitrile |
| 74 | 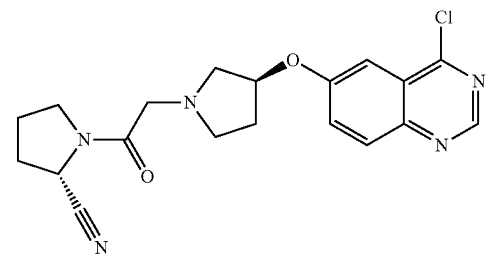 [SMILES: N#C[C@@H]1CCCN1C(=O)CN1CC[C@H](Oc2ccc3ncnc(Cl)c3c2)C1] | (S)-1-(2-((S)-3-((4-chloroquinazolin-6-yl)oxy)pyrrolidin-1-yl)acetyl)pyrrolidine-2-carbonitrile |
| 75 | 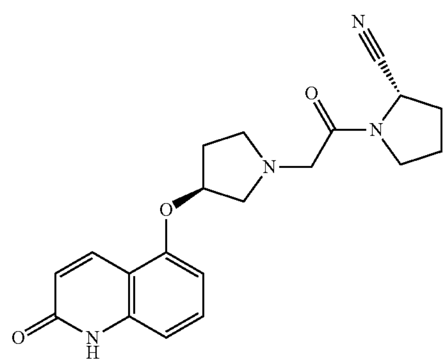 [SMILES: N#C[C@@H]1CCCN1C(=O)CN1CC[C@H](Oc2cccc3[nH]c(=O)ccc23)C1] | (S)-1-(2-((S)-3-((2-oxo-1,2-dihydroquinolin-5-yl)oxy)pyrrolidin-1-yl)acetyl)pyrrolidine-2-carbonitrile |
| 76 | 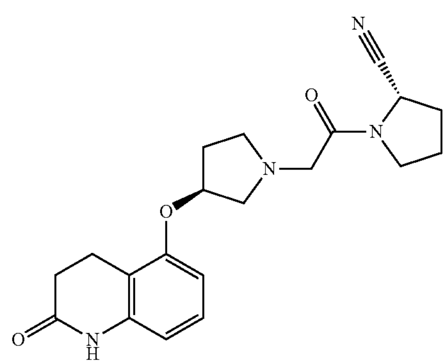 [SMILES: N#C[C@@H]1CCCN1C(=O)CN1CC[C@H](Oc2cccc3c2CCC(=O)N3)C1] | (S)-1-(2-((S)-3-((2-oxo-1,2,3,4-tetrahydroquinolin-5-yl)oxy)pyrrolidin-1-yl)acetyl)pyrrolidine-2-carbonitrile |
| 77 | 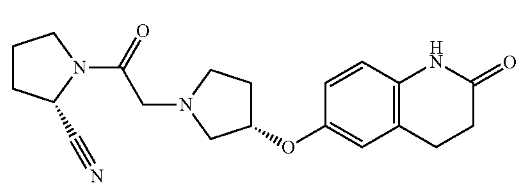 [SMILES: N#C[C@@H]1CCCN1C(=O)CN1CC[C@H](Oc2ccc3c(c2)CCC(=O)N3)C1] | (S)-1-(2-((S)-3-((2-oxo-1,2,3,4-tetrahydroquinolin-6-yl)oxy)pyrrolidin-1-yl)acetyl)pyrrolidine-2-carbonitrile |

TABLE 1-continued

| Ex No. | Structure | Chemical Name |
| --- | --- | --- |
| 78 | 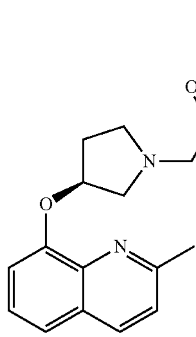 | (S)-1-(2-((S)-3-((2-methylquinolin-8-yl)oxy)pyrrolidin-1-yl)acetyl)pyrrolidine-2-carbonitrile |
| 79 | 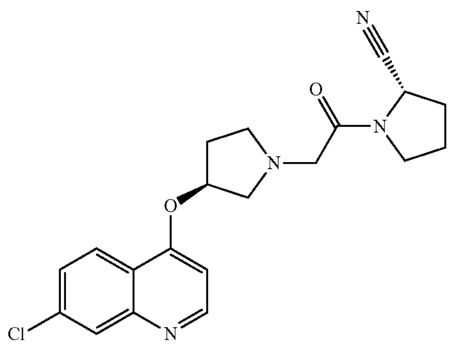 [SMILES: N#C[C@@H]1CCCN1C(=O)CN1CC[C@H](Oc2ccnc3cc(Cl)ccc23)C1] | (S)-1-(2-((S)-3-((7-chloroquinolin-4-yl)oxy)pyrrolidin-1-yl)acetyl)pyrrolidine-2-carbonitrile |
| 80 | 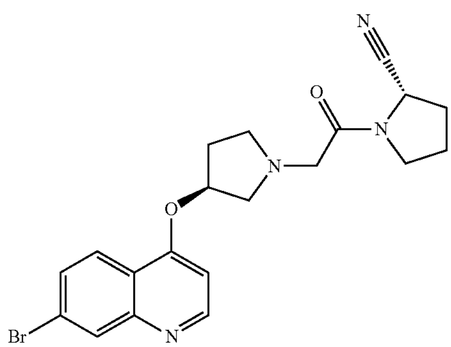 [SMILES: N#C[C@@H]1CCCN1C(=O)CN1CC[C@H](Oc2ccnc3cc(Br)ccc23)C1] | (S)-1-(2-((S)-3-((7-bromoquinolin-4-yl)oxy)pyrrolidin-1-yl)acetyl)pyrrolidine-2-carbonitrile |
| 81 | 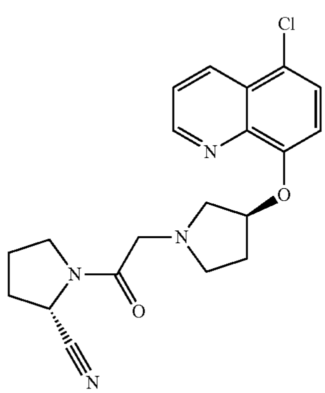 [SMILES: N#C[C@@H]1CCCN1C(=O)CN1CC[C@H](Oc2ccc(Cl)c3cccnc23)C1] | (S)-1-(2-((S)-3-((5-chloroquinolin-8-yl)oxy)pyrrolidin-1-yl)acetyl)pyrrolidine-2-carbonitrile |
| 82 | 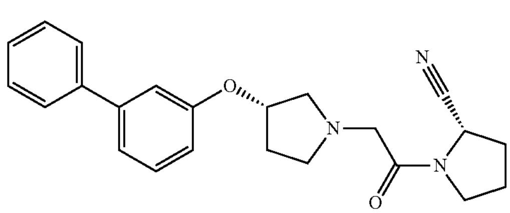 [SMILES: N#C[C@@H]1CCCN1C(=O)CN1CC[C@H](Oc2cccc(-c3ccccc3)c2)C1] | (S)-1-(2-((S)-3-([1,1'-biphenyl]-3-yloxy)pyrrolidin-1-yl)acetyl)pyrrolidine-2-carbonitrile |

TABLE 1-continued

| Ex No. | Structure | Chemical Name |
|---|---|---|
| 83 | 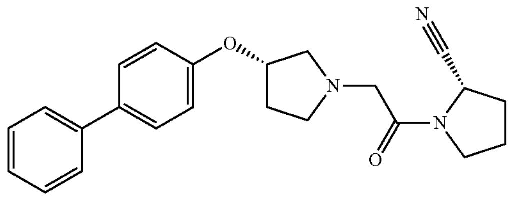 [SMILES: N#C[C@@H]1CCCN1C(=O)CN1CC[C@H](Oc2ccc(-c3ccccc3)cc2)C1] | (S)-1-(2-((S)-3-([1,1'-biphenyl]-4-yloxy)pyrrolidin-1-yl)acetyl)pyrrolidine-2-carbonitrile |
| 84 | 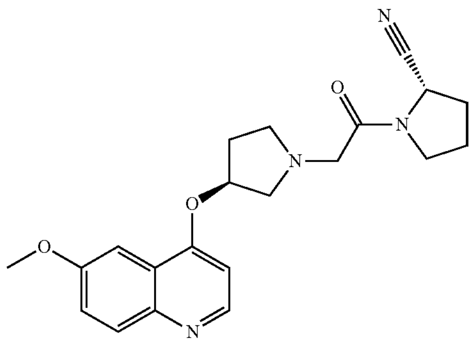 [SMILES: COc1ccc2nccc(O[C@H]3CCN(CC(=O)N4CCC[C@H]4C#N)C3)c2c1] | (S)-1-(2-((S)-3-((6-methoxyquinolin-4-yl)oxy)pyrrolidin-1-yl)acetyl)pyrrolidine-2-carbonitrile |
| 85 | 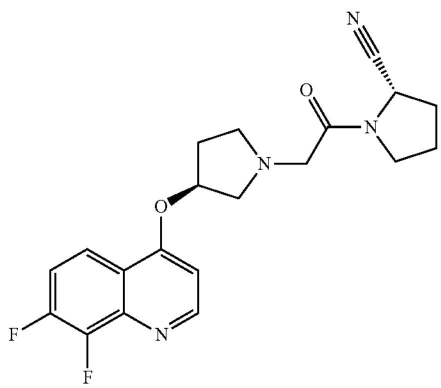 [SMILES: N#C[C@@H]1CCCN1C(=O)CN1CC[C@H](Oc2ccnc3c(F)c(F)ccc23)C1] | (S)-1-(2-((S)-3-((7,8-difluoroquinolin-4-yl)oxy)pyrrolidin-1-yl)acetyl)pyrrolidine-2-carbonitrile |
| 86 | 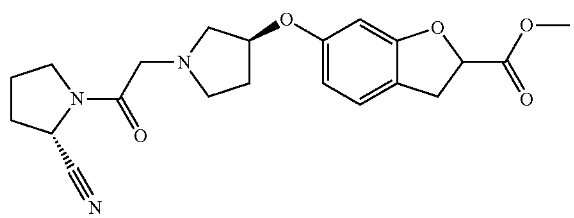 [SMILES: COC(=O)C1Cc2ccc(O[C@H]3CCN(CC(=O)N4CCC[C@H]4C#N)C3)cc2O1] | methyl 6-(((S)-1-(2-((S)-2-cyanopyrrolidin-1-yl)-2-oxoethyl)pyrrolidin-3-yl)oxy)-2,3-dihydrobenzofuran-2-carboxylate |
| 87 | 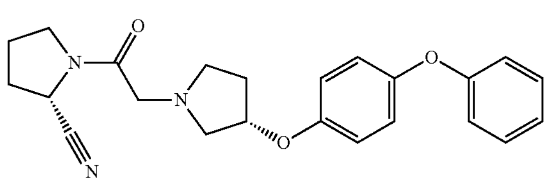 [SMILES: N#C[C@@H]1CCCN1C(=O)CN1CC[C@H](Oc2ccc(Oc3ccccc3)cc2)C1] | (S)-1-(2-((S)-3-(4-phenoxyphenoxy)pyrrolidin-1-yl)acetyl)pyrrolidine-2-carbonitrile |
| 88 | 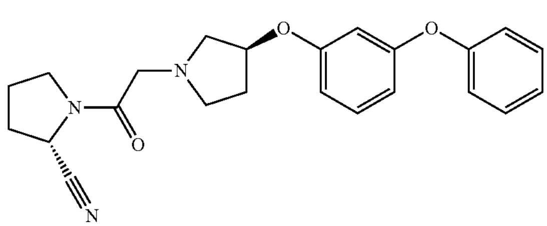 [SMILES: N#C[C@@H]1CCCN1C(=O)CN1CC[C@H](Oc2cccc(Oc3ccccc3)c2)C1] | (S)-1-(2-((S)-3-(3-phenoxyphenoxy)pyrrolidin-1-yl)acetyl)pyrrolidine-2-carbonitrile |

TABLE 1-continued

| Ex No. | Structure | Chemical Name |
| --- | --- | --- |
| 89 | 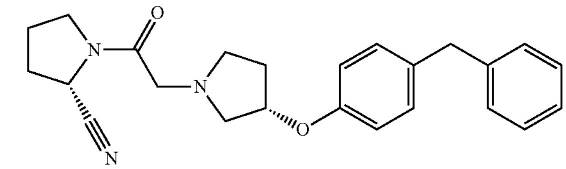 [SMILES: N#C[C@@H]1CCCN1C(=O)CN1CC[C@H](Oc2ccc(Cc3ccccc3)cc2)C1] | (S)-1-(2-((S)-3-(4-benzylphenoxy)pyrrolidin-1-yl)acetyl)pyrrolidine-2-carbonitrile |
| 90 | 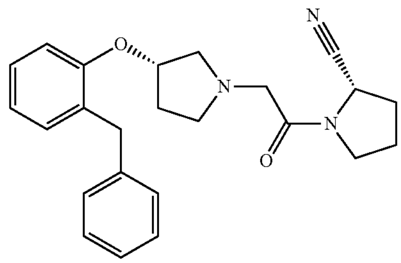 [SMILES: N#C[C@@H]1CCCN1C(=O)CN1CC[C@H](Oc2ccccc2Cc2ccccc2)C1] | (S)-1-(2-((S)-3-(2-benzylphenoxy)pyrrolidin-1-yl)acetyl)pyrrolidine-2-carbonitrile |
| 91 | 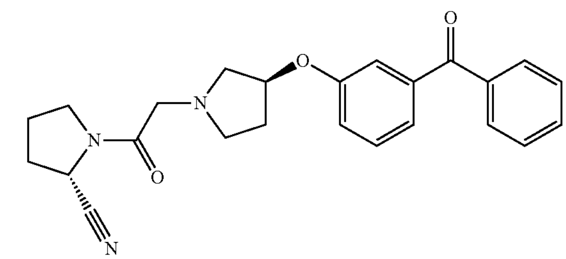 [SMILES: N#C[C@@H]1CCCN1C(=O)CN1CC[C@H](Oc2cccc(C(=O)c3ccccc3)c2)C1] | (S)-1-(2-((S)-3-(3-benzoylphenoxy)pyrrolidin-1-yl)acetyl)pyrrolidine-2-carbonitrile |
| 92 | 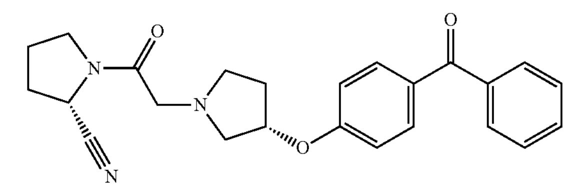 [SMILES: N#C[C@@H]1CCCN1C(=O)CN1CC[C@H](Oc2ccc(C(=O)c3ccccc3)cc2)C1] | (S)-1-(2-((S)-3-(4-benzoylphenoxy)pyrrolidin-1-yl)acetyl)pyrrolidine-2-carbonitrile |
| 93 | 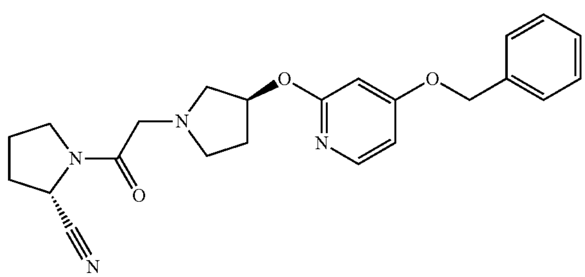 [SMILES: N#C[C@@H]1CCCN1C(=O)CN1CC[C@H](Oc2cc(OCc3ccccc3)ccn2)C1] | (S)-1-(2-((S)-3-((4-(benzyloxy)pyridin-2-yl)oxy)pyrrolidin-1-yl)acetyl)pyrrolidine-2-carbonitrile |
| 94 | 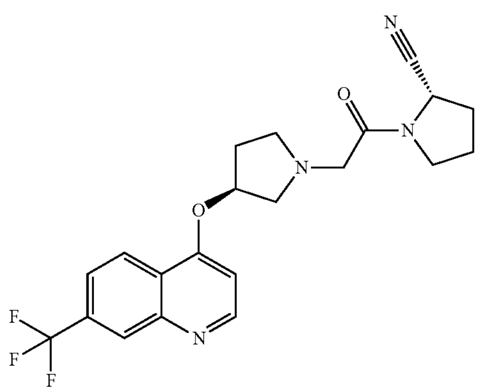 [SMILES: N#C[C@@H]1CCCN1C(=O)CN1CC[C@H](Oc2ccnc3cc(C(F)(F)F)ccc23)C1] | (S)-1-(2-((S)-3-((7-(trifluoromethyl)quinolin-4-yl)oxy)pyrrolidin-1-yl)acetyl)pyrrolidine-2-carbonitrile |

TABLE 1-continued

| Ex No. | Structure | Chemical Name |
| --- | --- | --- |
| 95 | 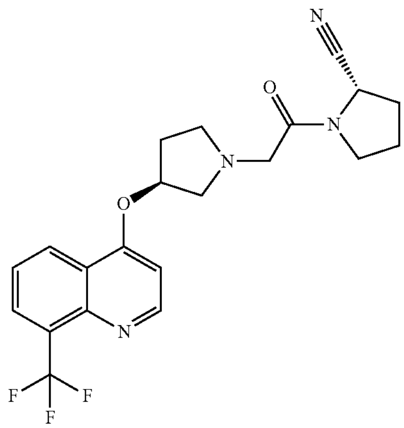 [SMILES: N#C[C@@H]1CCCN1C(=O)CN1CC[C@H](Oc2ccnc3c(C(F)(F)F)cccc23)C1] | (S)-1-(2-((S)-3-((8-(trifluoromethyl)quinolin-4-yl)oxy)pyrrolidin-1-yl)acetyl)pyrrolidine-2-carbonitrile |
| 96 | 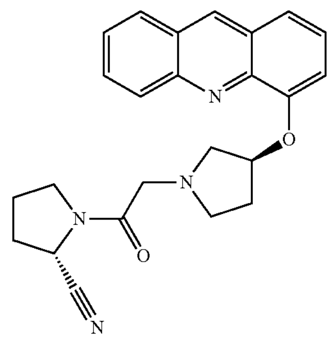 [SMILES: N#C[C@@H]1CCCN1C(=O)CN1CC[C@H](Oc2cccc3cc4ccccc4nc23)C1] | (S)-1-(2-((S)-3-(acridin-4-yloxy)pyrrolidin-1-yl)acetyl)pyrrolidine-2-carbonitrile |
| 97 | 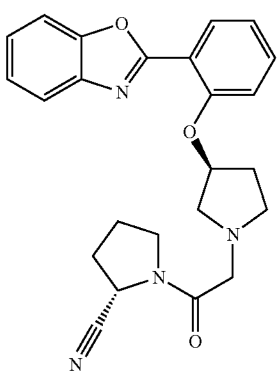 [SMILES: N#C[C@@H]1CCCN1C(=O)CN1CC[C@H](Oc2ccccc2-c2nc3ccccc3o2)C1] | (S)-1-(2-((S)-3-(2-(benzo[d]oxazol-2-yl)phenoxy)pyrrolidin-1-yl)acetyl)pyrrolidine-2-carbonitrile |
| 98 | 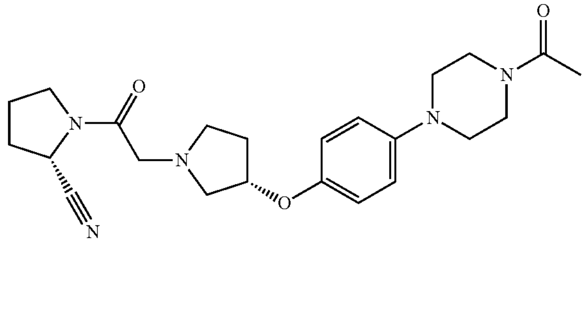 [SMILES: CC(=O)N1CCN(c2ccc(O[C@H]3CCN(CC(=O)N4CCC[C@H]4C#N)C3)cc2)CC1] | (S)-1-(2-((S)-3-(4-(4-acetylpiperazin-1-yl)phenoxy)pyrrolidin-1-yl)acetyl)pyrrolidine-2-carbonitrile |

TABLE 1-continued

| Ex No. | Structure | Chemical Name |
| --- | --- | --- |
| 99 | 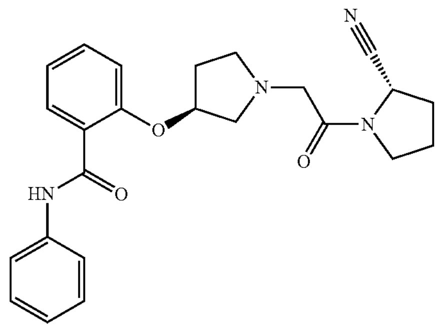 [SMILES: N#C[C@@H]1CCCN1C(=O)CN1CC[C@H](Oc2ccccc2C(=O)Nc2ccccc2)C1] | 2-(((S)-1-(2-((S)-2-cyanopyrrolidin-1-yl)-2-oxoethyl)pyrrolidin-3-yl)oxy)-N-phenylbenzamide |
| 100 | 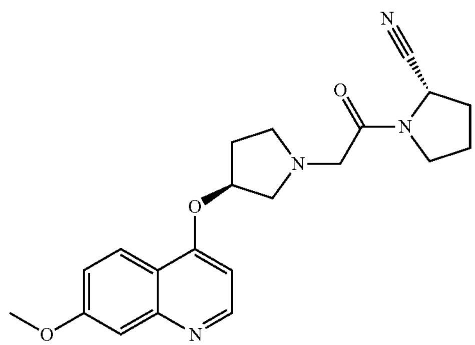 [SMILES: COc1ccc2c(O[C@H]3CCN(CC(=O)N4CCC[C@H]4C#N)C3)ccnc2c1] | (S)-1-(2-((S)-3-((7-methoxyquinolin-4-yl)oxy)pyrrolidin-1-yl)acetyl)pyrrolidine-2-carbonitrile |
| 101 | 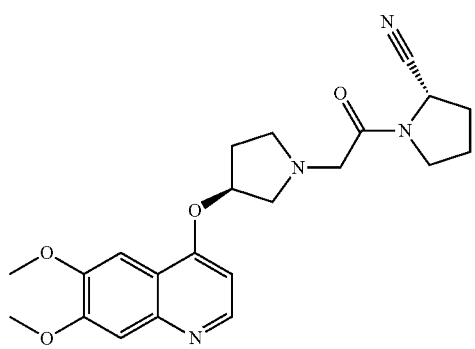 [SMILES: COc1cc2nccc(O[C@H]3CCN(CC(=O)N4CCC[C@H]4C#N)C3)c2cc1OC] | (S)-1-(2-((S)-3-((6,7-dimethoxyquinolin-4-yl)oxy)pyrrolidin-1-yl)acetyl)pyrrolidine-2-carbonitrile |
| 102 | 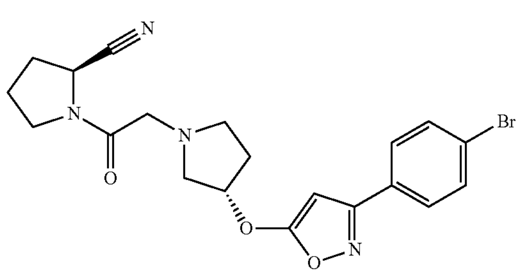 [SMILES: N#C[C@@H]1CCCN1C(=O)CN1CC[C@H](Oc2cc(-c3ccc(Br)cc3)no2)C1] | (S)-1-(2-((S)-3-((3-(4-bromophenyl)isoxazol-5-yl)oxy)pyrrolidin-1-yl)acetyl)pyrrolidine-2-carbonitrile |

TABLE 1-continued

| Ex No. | Structure | Chemical Name |
| --- | --- | --- |
| 103 | 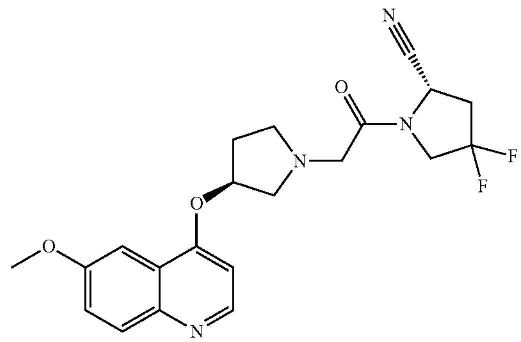 [SMILES: COc1ccc2nccc(O[C@H]3CCN(CC(=O)N4CC(F)(F)C[C@H]4C#N)C3)c2c1] | (S)-4,4-difluoro-1-(2-((S)-3-((6-methoxyquinolin-4-yl)oxy)pyrrolidin-1-yl)acetyl)pyrrolidine-2-carbonitrile |
| 104 | 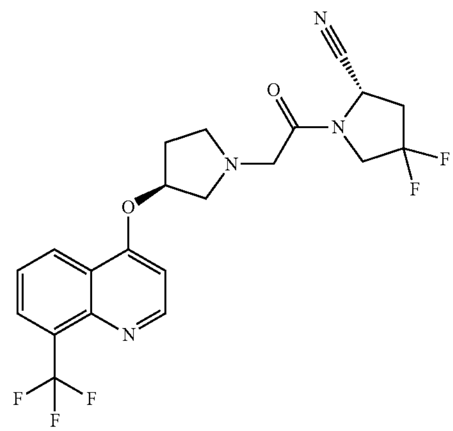 [SMILES: N#C[C@@H]1CC(F)(F)CN1C(=O)CN1CC[C@H](Oc2ccnc3c(C(F)(F)F)cccc23)C1] | (S)-4,4-difluoro-1-(2-((S)-3-((8-(trifluoromethyl)quinolin-4-yl)oxy)pyrrolidin-1-yl)acetyl)pyrrolidine-2-carbonitrile |
| 105 | 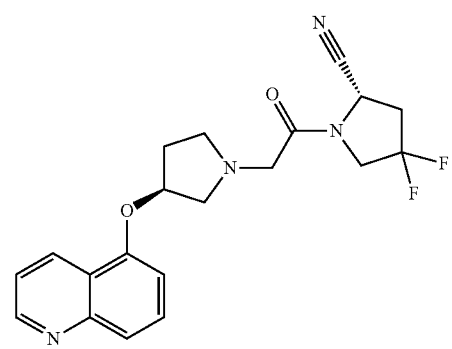 [SMILES: N#C[C@@H]1CC(F)(F)CN1C(=O)CN1CC[C@H](Oc2cccc3ncccc23)C1] | (S)-4,4-difluoro-1-(2-((S)-3-(quinolin-5-yloxy)pyrrolidin-1-yl)acetyl)pyrrolidine-2-carbonitrile |
| 106 | 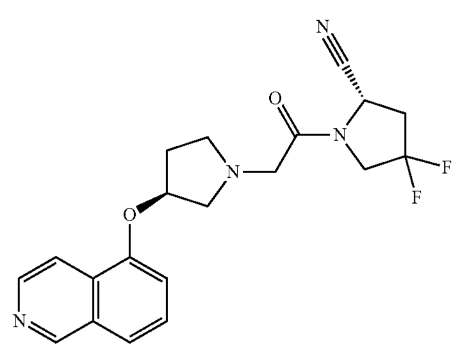 [SMILES: N#C[C@@H]1CC(F)(F)CN1C(=O)CN1CC[C@H](Oc2cccc3cnccc23)C1] | (S)-4,4-difluoro-1-(2-((S)-3-(isoquinolin-5-yloxy)pyrrolidin-1-yl)acetyl)pyrrolidine-2-carbonitrile |

TABLE 1-continued

| Ex No. | Structure | Chemical Name |
|---|---|---|
| 107 | 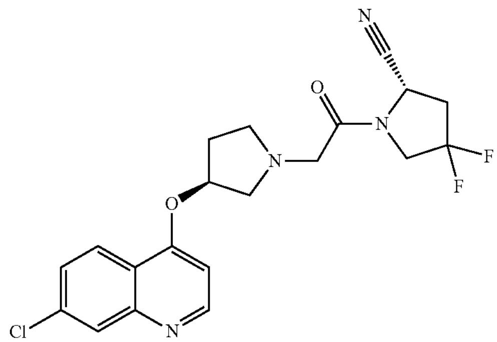 [SMILES: N#C[C@@H]1CC(F)(F)CN1C(=O)CN1CC[C@H](Oc2ccnc3cc(Cl)ccc23)C1] | (S)-1-(2-((S)-3-((7-chloroquinolin-4-yl)oxy)pyrrolidin-1-yl)acetyl)-4,4-difluoropyrrolidine-2-carbonitrile |
| 108 | 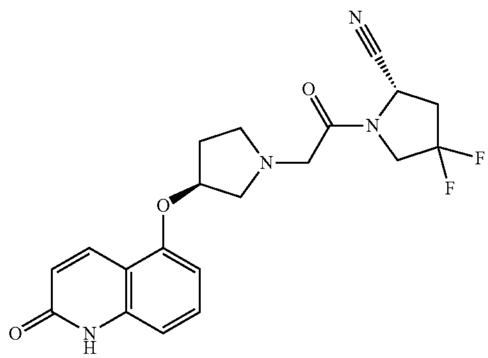 [SMILES: N#C[C@@H]1CC(F)(F)CN1C(=O)CN1CC[C@H](Oc2cccc3[nH]c(=O)ccc23)C1] | (S)-4,4-difluoro-1-(2-((S)-3-((2-oxo-1,2-dihydroquinolin-5-yl)oxy)pyrrolidin-1-yl)acetyl)pyrrolidine-2-carbonitrile |
| 109 | 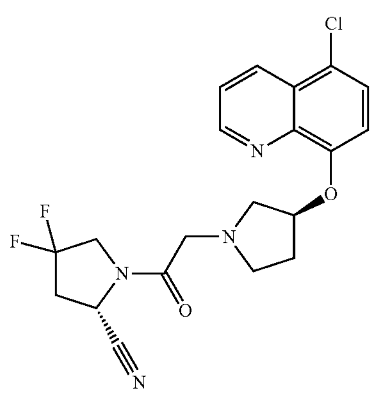 [SMILES: N#C[C@@H]1CC(F)(F)CN1C(=O)CN1CC[C@H](Oc2ccc(Cl)c3cccnc23)C1] | (S)-1-(2-((S)-3-((5-chloroquinolin-8-yl)oxy)pyrrolidin-1-yl)acetyl)-4,4-difluoropyrrolidine-2-carbonitrile |
| 110 | 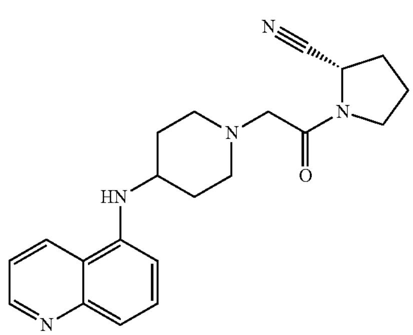 [SMILES: N#C[C@@H]1CCCN1C(=O)CN1CCC(Nc2cccc3ncccc23)CC1] | (S)-1-(2-(4-(quinolin-5-ylamino)piperidin-1-yl)acetyl)pyrrolidine-2-carbonitrile |

TABLE 1-continued

| Ex No. | Structure | Chemical Name |
| --- | --- | --- |
| 111 | 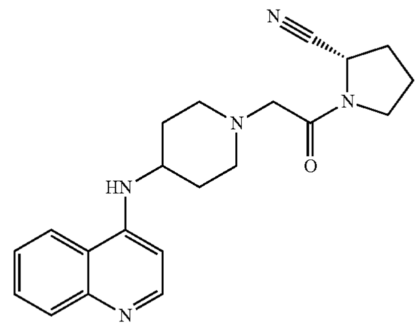 [SMILES: N#C[C@@H]1CCCN1C(=O)CN1CCC(Nc2ccnc3ccccc23)CC1] | (S)-1-(2-(4-(quinolin-4-ylamino)piperidin-1-yl)acetyl)pyrrolidine-2-carbonitrile |
| 112 | 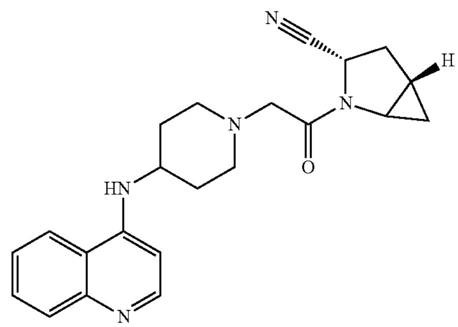 [SMILES: N#C[C@@H]1C[C@@H]2CC2N1C(=O)CN1CCC(Nc2ccnc3ccccc23)CC1] | (1S,3S,5S)-2-(2-(4-(quinolin-4-ylamino)piperidin-1-yl)acetyl)-2-azabicyclo[3.1.0]hexane-3-carbonitrile |
| 113 | 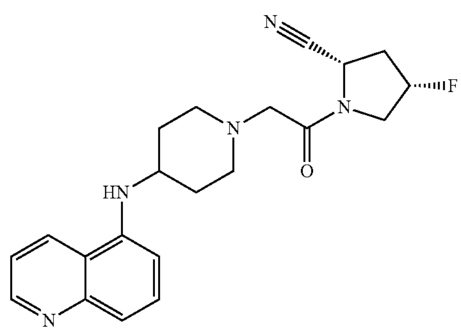 [SMILES: N#C[C@@H]1C[C@H](F)CN1C(=O)CN1CCC(Nc2cccc3ncccc23)CC1] | (2S,4S)-4-fluoro-1-(2-(4-(quinolin-5-ylamino)piperidin-1-yl)acetyl)pyrrolidine-2-carbonitrile |
| 114 | 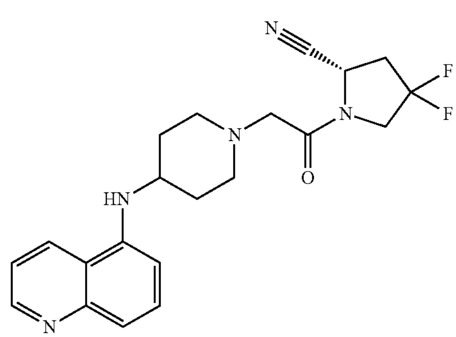 [SMILES: N#C[C@@H]1CC(F)(F)CN1C(=O)CN1CCC(Nc2cccc3ncccc23)CC1] | (S)-4,4-difluoro-1-(2-(4-(quinolin-5-ylamino)piperidin-1-yl)acetyl)pyrrolidine-2-carbonitrile |

TABLE 1-continued

| Ex No. | Structure | Chemical Name |
|---|---|---|
| 115 | 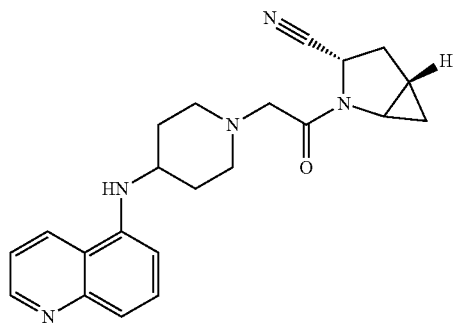 [SMILES: N#C[C@@H]1C[C@@H]2CC2N1C(=O)CN1CCC(Nc2cccc3ncccc23)CC1] | (1S,3S,5S)-2-(2-(4-(quinolin-5-ylamino)piperidin-1-yl)acetyl)-2-azabicyclo[3.1.0]hexane-3-carbonitrile |
| 116 | 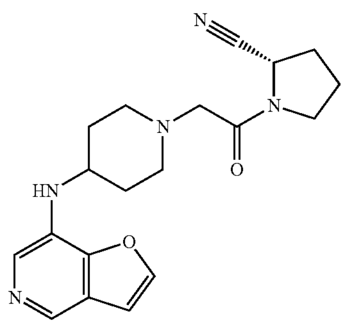 [SMILES: N#C[C@@H]1CCCN1C(=O)CN1CCC(Nc2cncc3ccoc23)CC1] | (S)-1-(2-(4-(furo[3,2-c]pyridin-7-ylamino)piperidin-1-yl)acetyl)pyrrolidine-2-carbonitrile |
| 117 | 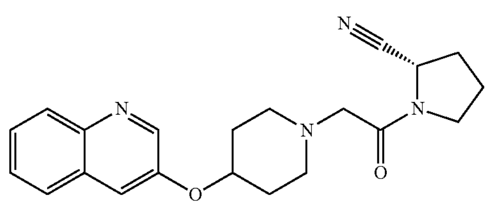 [SMILES: N#C[C@@H]1CCCN1C(=O)CN1CCC(Oc2cnc3ccccc3c2)CC1] | (S)-1-(2-(4-(quinolin-3-yloxy)piperidin-1-yl)acetyl)pyrrolidine-2-carbonitrile |
| 118 | 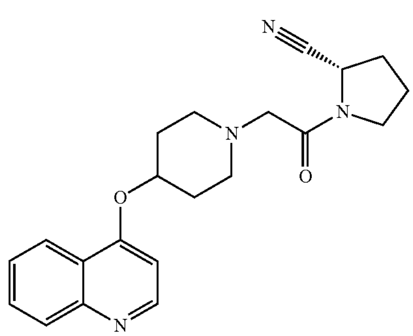 [SMILES: N#C[C@@H]1CCCN1C(=O)CN1CCC(Oc2ccnc3ccccc23)CC1] | (S)-1-(2-(4-(quinolin-4-yloxy)piperidin-1-yl)acetyl)pyrrolidine-2-carbonitrile |
| 119 | 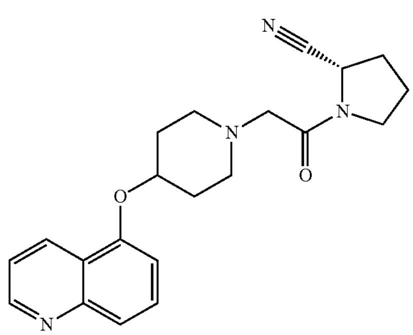 [SMILES: N#C[C@@H]1CCCN1C(=O)CN1CCC(Oc2cccc3ncccc23)CC1] | (S)-1-(2-(4-(quinolin-5-yloxy)piperidin-1-yl)acetyl)pyrrolidine-2-carbonitrile |

TABLE 1-continued

| Ex No. | Structure | Chemical Name |
|---|---|---|
| 120 | 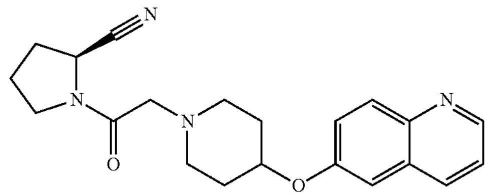 [SMILES: N#C[C@@H]1CCCN1C(=O)CN1CCC(Oc2ccc3ncccc3c2)CC1] | (S)-1-(2-(4-(quinolin-6-yloxy)piperidin-1-yl)acetyl)pyrrolidine-2-carbonitrile |
| 121 | 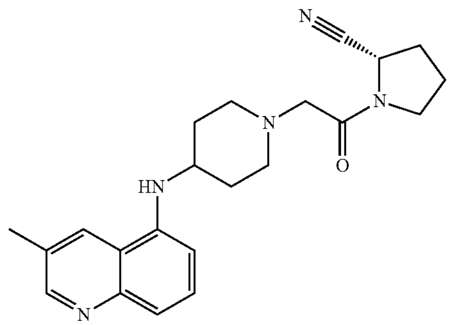 [SMILES: Cc1cnc2cccc(NC3CCN(CC(=O)N4CCC[C@H]4C#N)CC3)c2c1] | (S)-1-(2-(4-((3-methylquinolin-5-yl)amino)piperidin-1-yl)acetyl)pyrrolidine-2-carbonitrile |
| 122 | 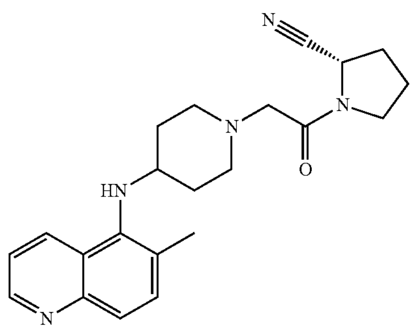 [SMILES: Cc1ccc2ncccc2c1NC1CCN(CC(=O)N2CCC[C@H]2C#N)CC1] | (S)-1-(2-(4-((6-methylquinolin-5-yl)amino)piperidin-1-yl)acetyl)pyrrolidine-2-carbonitrile |
| 123 | 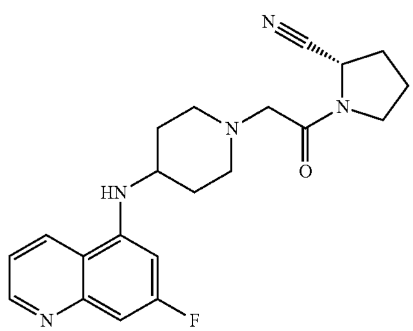 [SMILES: N#C[C@@H]1CCCN1C(=O)CN1CCC(Nc2cc(F)cc3ncccc23)CC1] | (S)-1-(2-(4-((7-fluoroquinolin-5-yl)amino)piperidin-1-yl)acetyl)pyrrolidine-2-carbonitrile |
| 124 | 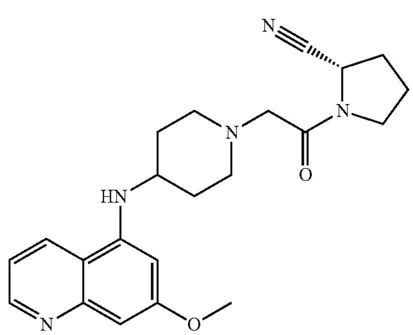 [SMILES: COc1cc(NC2CCN(CC(=O)N3CCC[C@H]3C#N)CC2)c2cccnc2c1] | (S)-1-(2-(4-((7-methoxyquinolin-5-yl)amino)piperidin-1-yl)acetyl)pyrrolidine-2-carbonitrile |

TABLE 1-continued

| Ex No. | Structure | Chemical Name |
|---|---|---|
| 125 | 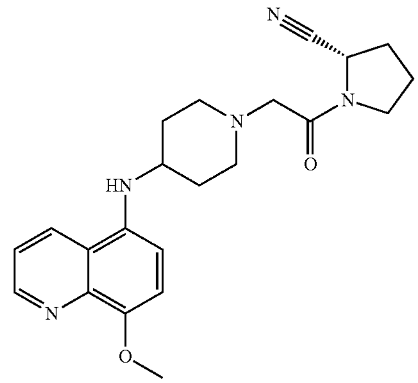 [SMILES: COc1ccc(NC2CCN(CC(=O)N3CCC[C@H]3C#N)CC2)c2cccnc12] | (S)-1-(2-(4-((8-methoxyquinolin-5-yl)amino)piperidin-1-yl)acetyl)pyrrolidine-2-carbonitrile |
| 126 | 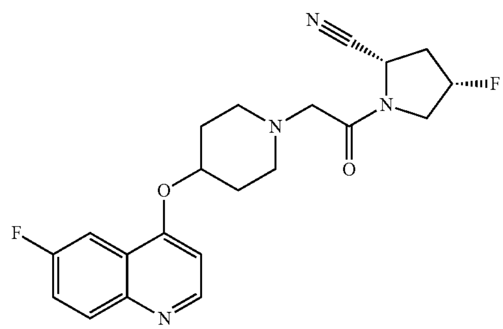 [SMILES: N#C[C@@H]1C[C@H](F)CN1C(=O)CN1CCC(Oc2ccnc3ccc(F)cc23)CC1] | (2S,4S)-4-fluoro-1-(2-(4-((6-fluoroquinolin-4-yl)oxy)piperidin-1-yl)acetyl)pyrrolidine-2-carbonitrile |
| 127 | 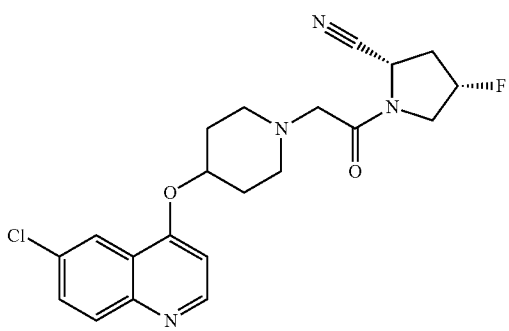 [SMILES: N#C[C@@H]1C[C@H](F)CN1C(=O)CN1CCC(Oc2ccnc3ccc(Cl)cc23)CC1] | (2S,4S)-1-(2-(4-((6-chloroquinolin-4-yl)oxy)piperidin-1-yl)acetyl)-4-fluoropyrrolidine-2-carbonitrile |
| 128 | 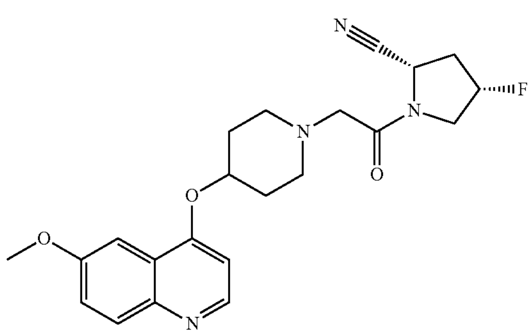 [SMILES: COc1ccc2nccc(OC3CCN(CC(=O)N4C[C@@H](F)C[C@H]4C#N)CC3)c2c1] | (2S,4S)-4-fluoro-1-(2-(4-((6-methoxyquinolin-4-yl)oxy)piperidin-1-yl)acetyl)pyrrolidine-2-carbonitrile |

TABLE 1-continued

| Ex No. | Structure | Chemical Name |
|---|---|---|
| 129 | 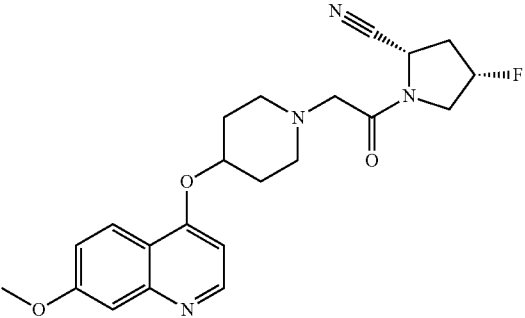 [SMILES: COc1ccc2c(OC3CCN(CC(=O)N4C[C@@H](F)C[C@H]4C#N)CC3)ccnc2c1] | (2S,4S)-4-fluoro-1-(2-(4-((7-methoxyquinolin-4-yl)oxy)piperidin-1-yl)acetyl)pyrrolidine-2-carbonitrile |
| 130 | 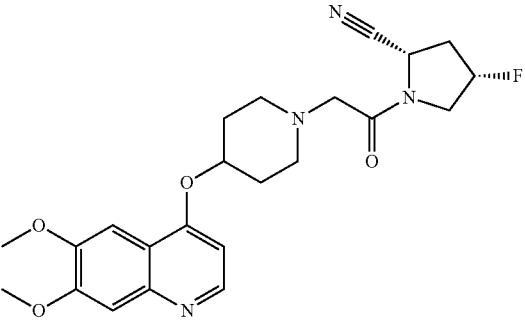 [SMILES: COc1cc2nccc(OC3CCN(CC(=O)N4C[C@@H](F)C[C@H]4C#N)CC3)c2cc1OC] | (2S,4S)-1-(2-(4-((6,7-dimethoxyquinolin-4-yl)oxy)piperidin-1-yl)acetyl)-4-fluoropyrrolidine-2-carbonitrile |
| 131 | 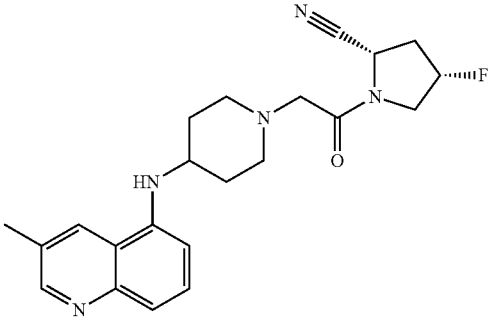 [SMILES: Cc1cnc2cccc(NC3CCN(CC(=O)N4C[C@@H](F)C[C@H]4C#N)CC3)c2c1] | (2S,4S)-4-fluoro-1-(2-(4-((3-methylquinolin-5-yl)amino)piperidin-1-yl)acetyl)pyrrolidine-2-carbonitrile |
| 132 | 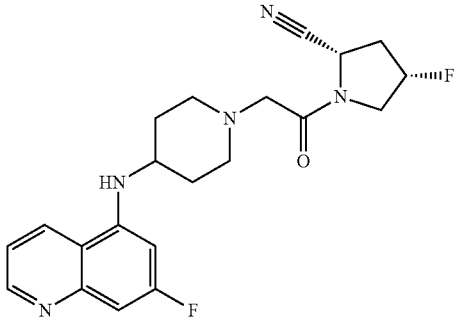 | (2S,4S)-4-fluoro-1-(2-(4-((7-fluoroquinolin-5-yl)amino)piperidin-1-yl)acetyl)pyrrolidine-2-carbonitrile |

TABLE 1-continued

| Ex No. | Structure | Chemical Name |
|---|---|---|
| 133 | 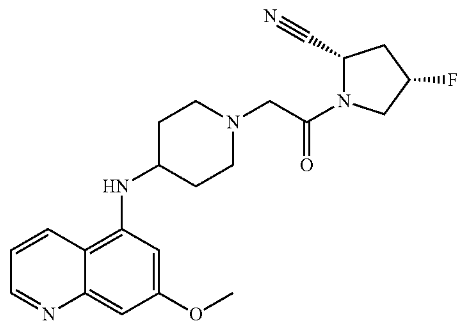 [SMILES: COc1cc(NC2CCN(CC(=O)N3C[C@@H](F)C[C@H]3C#N)CC2)c2cccnc2c1] | (2S,4S)-4-fluoro-1-(2-(4-((7-methoxyquinolin-5-yl)amino)piperidin-1-yl)acetyl)pyrrolidine-2-carbonitrile |
| 134 | 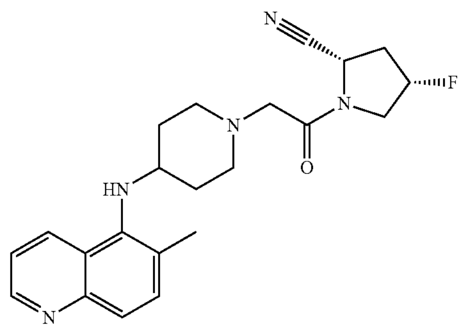 [SMILES: Cc1ccc2ncccc2c1NC1CCN(CC(=O)N2C[C@@H](F)C[C@H]2C#N)CC1] | (2S,4S)-4-fluoro-1-(2-(4-((6-methylquinolin-5-yl)amino)piperidin-1-yl)acetyl)pyrrolidine-2-carbonitrile |
| 135 | 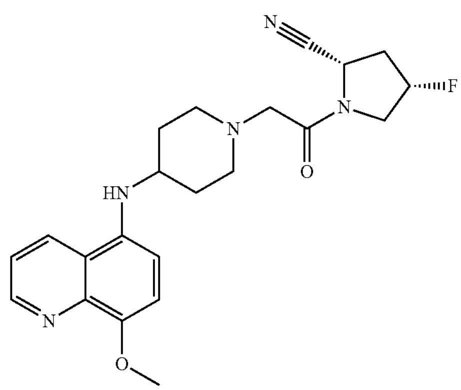 [SMILES: COc1ccc(NC2CCN(CC(=O)N3C[C@@H](F)C[C@H]3C#N)CC2)c2cccnc12] | (2S,4S)-4-fluoro-1-(2-(4-((8-methoxyquinolin-5-yl)amino)piperidin-1-yl)acetyl)pyrrolidine-2-carbonitrile |
| 136 | 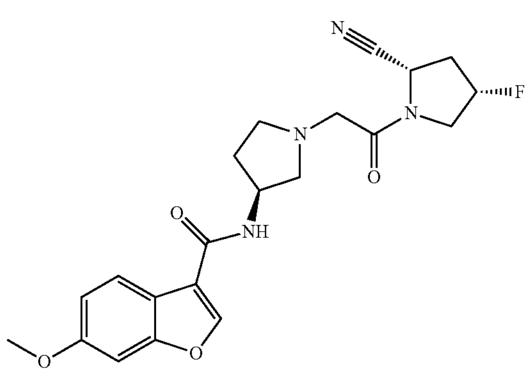 [SMILES: COc1ccc2c(C(=O)N[C@H]3CCN(CC(=O)N4C[C@@H](F)C[C@H]4C#N)C3)coc2c1] | 6-methoxy-N-[(3S)-1-[2-oxo-2-[(2S,4S)-2-cyano-4-fluoro-pyrrolidin-1-yl]ethyl]pyrrolidin-3-yl]benzofuran-3-carboxamide |
| 137 | 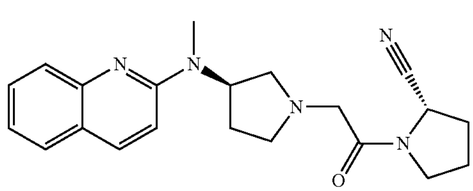 [SMILES: CN(c1ccc2ccccc2n1)[C@@H]1CCN(CC(=O)N2CCC[C@H]2C#N)C1] | (2S)-1-[2-[(3R)-3-[methyl(2-quinolyl)amino]pyrrolidin-1-yl]acetyl]pyrrolidine-2-carbonitrile |

TABLE 1-continued

| Ex No. | Structure | Chemical Name |
|---|---|---|
| 138 | 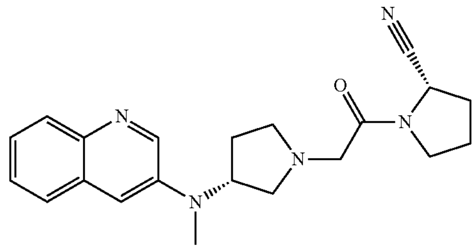 [SMILES: CN(c1cnc2ccccc2c1)[C@@H]1CCN(CC(=O)N2CCC[C@H]2C#N)C1] | (2S)-1-[2-[(3R)-3-[methyl(3-quinolyl)amino]pyrrolidin-1-yl]acetyl]pyrrolidine-2-carbonitrile |
| 139 | 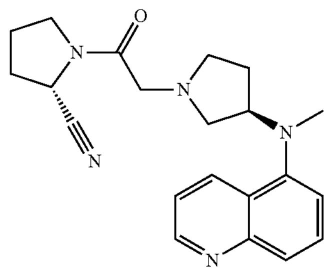 [SMILES: CN(c1cccc2ncccc12)[C@@H]1CCN(CC(=O)N2CCC[C@H]2C#N)C1] | (2S)-1-[2-[(3R)-3-[methyl(5-quinolyl)amino]pyrrolidin-1-yl]acetyl]pyrrolidine-2-carbonitrile |
| 140 | 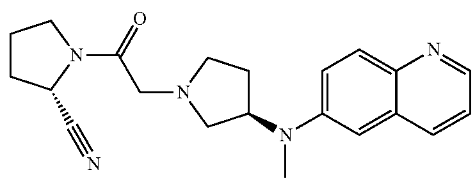 [SMILES: CN(c1ccc2ncccc2c1)[C@@H]1CCN(CC(=O)N2CCC[C@H]2C#N)C1] | (2S)-1-[2-[(3R)-3-[methyl(6-quinolyl)amino]pyrrolidin-1-yl]acetyl]pyrrolidine-2-carbonitrile |
| 141 | 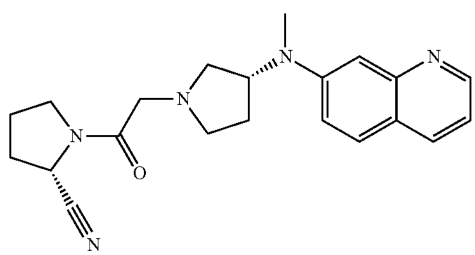 [SMILES: CN(c1ccc2cccnc2c1)[C@@H]1CCN(CC(=O)N2CCC[C@H]2C#N)C1] | (2S)-1-[2-[(3R)-3-[methyl(7-quinolyl)amino]pyrrolidin-1-yl]acetyl]pyrrolidine-2-carbonitrile |
| 142 | 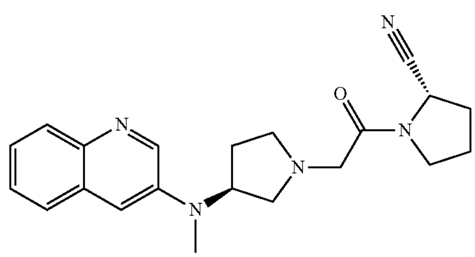 [SMILES: CN(c1cnc2ccccc2c1)[C@H]1CCN(CC(=O)N2CCC[C@H]2C#N)C1] | (2S)-1-[2-[(3S)-3-[methyl(3-quinolyl)amino]pyrrolidin-1-yl]acetyl]pyrrolidine-2-carbonitrile |
| 143 | 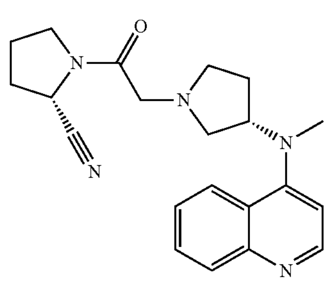 [SMILES: CN(c1ccnc2ccccc12)[C@H]1CCN(CC(=O)N2CCC[C@H]2C#N)C1] | (2S)-1-[2-[(3S)-3-[methyl(4-quinolyl)amino]pyrrolidin-1-yl]acetyl]pyrrolidine-2-carbonitrile |

TABLE 1-continued

| Ex No. | Structure | Chemical Name |
|---|---|---|
| 144 | 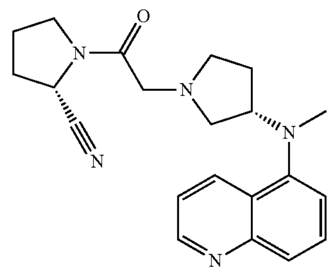 [SMILES: CN(c1cccc2ncccc12)[C@H]1CCN(CC(=O)N2CCC[C@H]2C#N)C1] | (2S)-1-[2-[(3S)-3-[methyl(5-quinolyl)amino]pyrrolidin-1-yl]acetyl]pyrrolidine-2-carbonitrile |
| 145 | 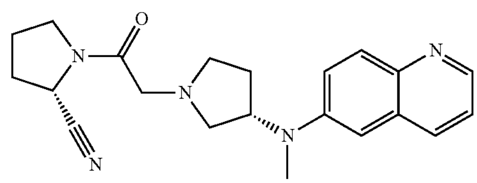 [SMILES: CN(c1ccc2ncccc2c1)[C@H]1CCN(CC(=O)N2CCC[C@H]2C#N)C1] | (2S)-1-[2-[(3S)-3-[methyl(6-quinolyl)amino]pyrrolidin-1-yl]acetyl]pyrrolidine-2-carbonitrile |
| 146 | 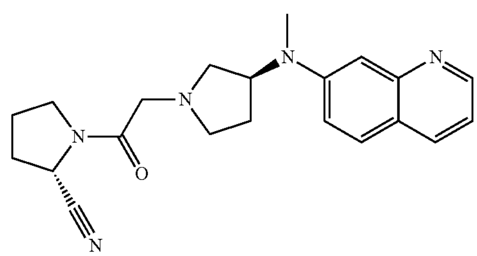 [SMILES: CN(c1ccc2cccnc2c1)[C@H]1CCN(CC(=O)N2CCC[C@H]2C#N)C1] | (2S)-1-[2-[(3S)-3-[methyl(7-quinolyl)amino]pyrrolidin-1-yl]acetyl]pyrrolidine-2-carbonitrile |
| 147 | 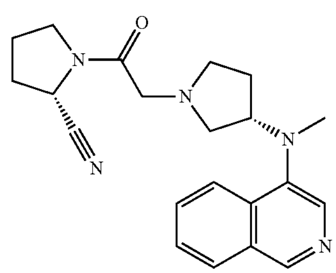 [SMILES: CN(c1cncc2ccccc12)[C@H]1CCN(CC(=O)N2CCC[C@H]2C#N)C1] | (2S)-1-[2-[(3S)-3-[4-isoquinolyl(methyl)amino]pyrrolidin-1-yl]acetyl]pyrrolidine-2-carbonitrile |
| 148 | 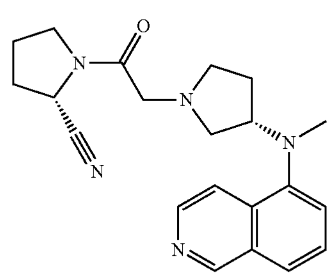 [SMILES: CN(c1cccc2cnccc12)[C@H]1CCN(CC(=O)N2CCC[C@H]2C#N)C1] | (2S)-1-[2-[(3S)-3-[5-isoquinolyl(methyl)amino]pyrrolidin-1-yl]acetyl]pyrrolidine-2-carbonitrile |
| 149 | 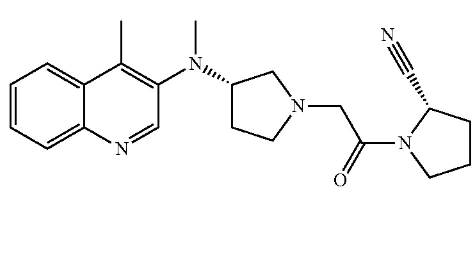 [SMILES: Cc1c(N(C)[C@H]2CCN(CC(=O)N3CCC[C@H]3C#N)C2)cnc2ccccc12] | (2S)-1-[2-[(3S)-3-[methyl-(4-methyl-3-quinolyl)amino]pyrrolidin-1-yl]acetyl]pyrrolidine-2-carbonitrile |

TABLE 1-continued

| Ex No. | Structure | Chemical Name |
| --- | --- | --- |
| 150 | 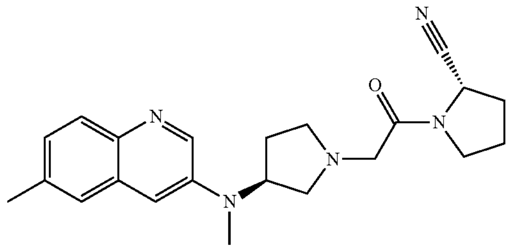 [SMILES: Cc1ccc2ncc(N(C)[C@H]3CCN(CC(=O)N4CCC[C@H]4C#N)C3)cc2c1] | (2S)-1-[2-[(3S)-3-[methyl-(6-methyl-3-quinolyl)amino]pyrrolidin-1-yl]acetyl]pyrrolidine-2-carbonitrile |
| 151 | 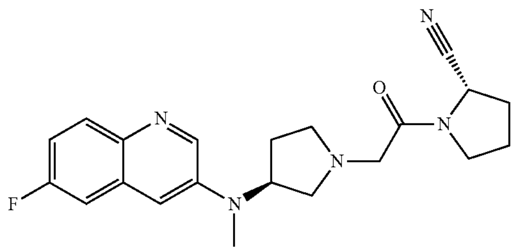 [SMILES: CN(c1cnc2ccc(F)cc2c1)[C@H]1CCN(CC(=O)N2CCC[C@H]2C#N)C1] | (S)-1-(2-((S)-3-((6-fluoroquinolin-3-yl)(methyl)amino)pyrrolidin-1-yl)acetyl)pyrrolidine-2-carbonitrile |
| 152 | 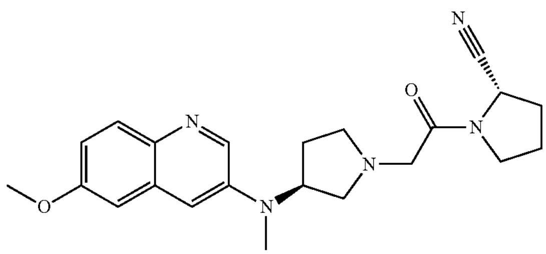 [SMILES: COc1ccc2ncc(N(C)[C@H]3CCN(CC(=O)N4CCC[C@H]4C#N)C3)cc2c1] | (S)-1-(2-((S)-3-((6-methoxyquinolin-3-yl)(methyl)amino)pyrrolidin-1-yl)acetyl)pyrrolidine-2-carbonitrile |
| 153 | 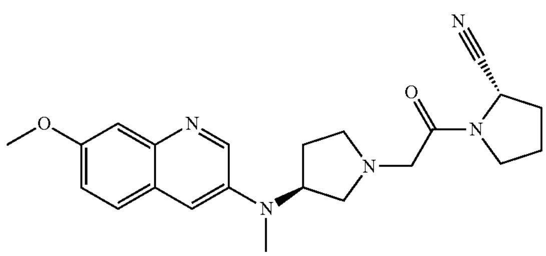 [SMILES: COc1ccc2cc(N(C)[C@H]3CCN(CC(=O)N4CCC[C@H]4C#N)C3)cnc2c1] | (S)-1-(2-((S)-3-((7-methoxyquinolin-3-yl)(methyl)amino)pyrrolidin-1-yl)acetyl)pyrrolidine-2-carbonitrile |
| 154 | 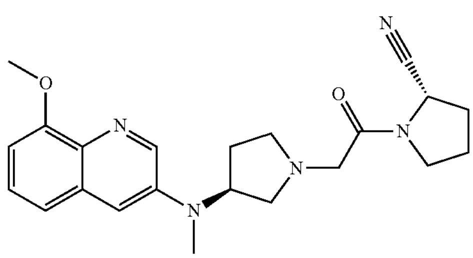 [SMILES: COc1cccc2cc(N(C)[C@H]3CCN(CC(=O)N4CCC[C@H]4C#N)C3)cnc12] | (S)-1-(2-((S)-3-((8-methoxyquinolin-3-yl)(methyl)amino)pyrrolidin-1-yl)acetyl)pyrrolidine-2-carbonitrile |
| 155 | 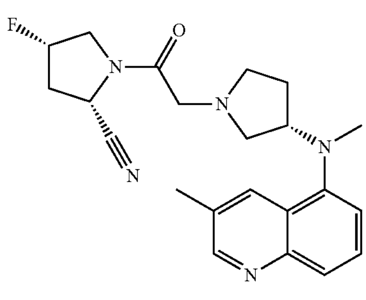 [SMILES: Cc1cnc2cccc(N(C)[C@H]3CCN(CC(=O)N4C[C@@H](F)C[C@H]4C#N)C3)c2c1] | (2S,4S)-4-fluoro-1-[2-[(3S)-3-[methyl-(3-methyl-5-quinolyl)amino]pyrrolidin-1-yl]acetyl]pyrrolidine-2-carbonitrile |

TABLE 1-continued

| Ex No. | Structure | Chemical Name |
|---|---|---|
| 156 | 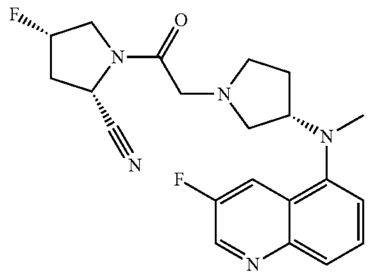 [SMILES: CN(c1cccc2ncc(F)cc12)[C@H]1CCN(CC(=O)N2C[C@@H](F)C[C@H]2C#N)C1] | (2S,4S)-4-fluoro-1-(2-((S)-3-((3-fluoroquinolin-5-yl)(methyl)amino)pyrrolidin-1-yl)acetyl)pyrrolidine-2-carbonitrile |
| 157 | 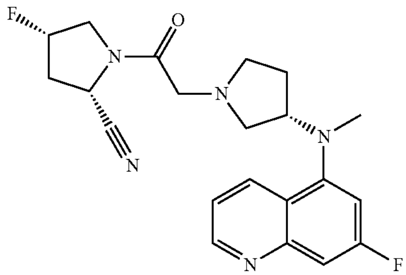 [SMILES: CN(c1cc(F)cc2ncccc12)[C@H]1CCN(CC(=O)N2C[C@@H](F)C[C@H]2C#N)C1] | (2S,4S)-4-fluoro-1-(2-((S)-3-((7-fluoroquinolin-5-yl)(methyl)amino)pyrrolidin-1-yl)acetyl)pyrrolidine-2-carbonitrile |
| 158 | 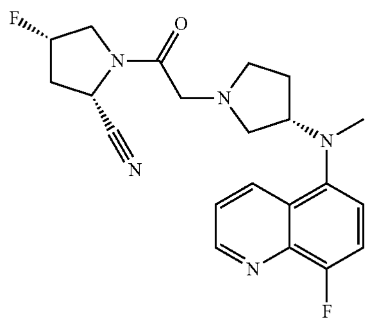 [SMILES: CN(c1ccc(F)c2ncccc12)[C@H]1CCN(CC(=O)N2C[C@@H](F)C[C@H]2C#N)C1] | (2S,4S)-4-fluoro-1-(2-((S)-3-((8-fluoroquinolin-5-yl)(methyl)amino)pyrrolidin-1-yl)acetyl)pyrrolidine-2-carbonitrile |
| 159 | 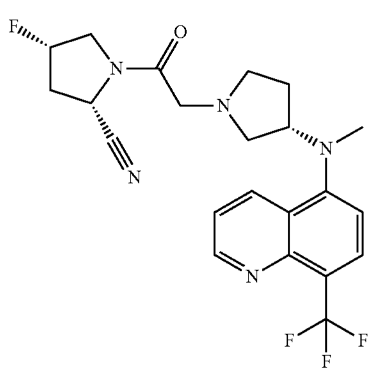 [SMILES: CN(c1ccc(C(F)(F)F)c2ncccc12)[C@H]1CCN(CC(=O)N2C[C@@H](F)C[C@H]2C#N)C1] | (2S,4S)-4-fluoro-1-[2-[(3S)-3-[methyl-[8-(trifluoromethyl)-5-quinolyl]amino]pyrrolidin-1-yl]acetyl]pyrrolidine-2-carbonitrile |

TABLE 1-continued

| Ex No. | Structure | Chemical Name |
|---|---|---|
| 160 | 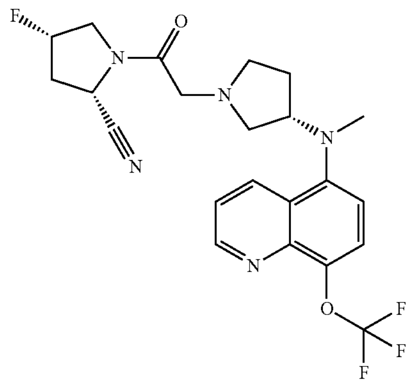 [SMILES: CN(c1ccc(OC(F)(F)F)c2ncccc12)[C@H]1CCN(CC(=O)N2C[C@@H](F)C[C@H]2C#N)C1] | (2S,4S)-4-fluoro-1-[2-[(3S)-3-[methyl-[8-(trifluoromethoxy)-5-quinolyl]amino]pyrrolidin-1-yl]acetyl]pyrrolidine-2-carbonitrile |
| 161 | 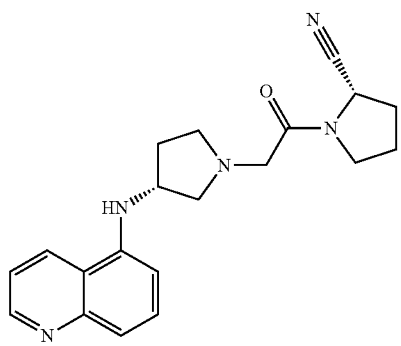 [SMILES: N#C[C@@H]1CCCN1C(=O)CN1CC[C@@H](Nc2cccc3ncccc23)C1] | (2S)-1-[2-[(3R)-3-(5-quinolylamino)pyrrolidin-1-yl]acetyl]pyrrolidine-2-carbonitrile |
| 162 | 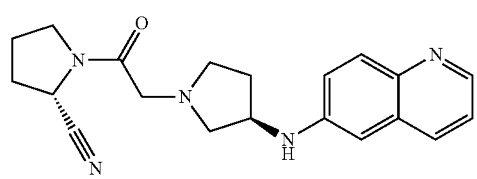 [SMILES: N#C[C@@H]1CCCN1C(=O)CN1CC[C@@H](Nc2ccc3ncccc3c2)C1] | (2S)-1-[2-[(3R)-3-(6-quinolylamino)pyrrolidin-1-yl]acetyl]pyrrolidine-2-carbonitrile |
| 163 | 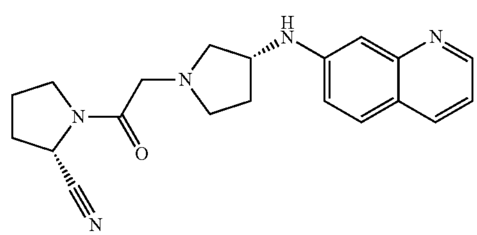 | (2S)-1-[2-[(3R)-3-(7-quinolylamino)pyrrolidin-1-yl]acetyl]pyrrolidine-2-carbonitrile |
| 164 | 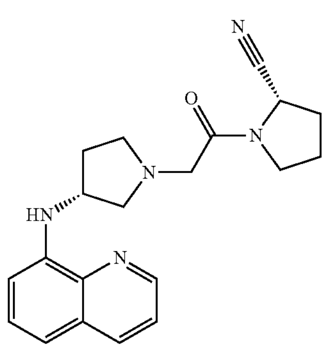 [SMILES: N#C[C@@H]1CCCN1C(=O)CN1CC[C@@H](Nc2cccc3cccnc23)C1] | (2S)-1-[2-[(3R)-3-(8-quinolylamino)pyrrolidin-1-yl]acetyl]pyrrolidine-2-carbonitrile |

TABLE 1-continued

| Ex No. | Structure | Chemical Name |
| --- | --- | --- |
| 165 | 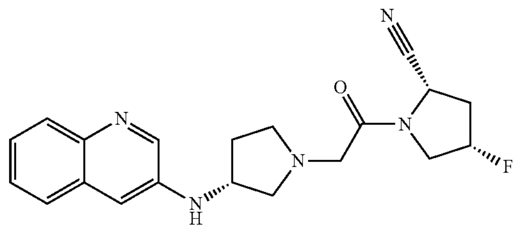 [SMILES: N#C[C@@H]1C[C@H](F)CN1C(=O)CN1CC[C@@H](Nc2cnc3ccccc3c2)C1] | (2S,4S)-4-fluoro-1-[2-[(3R)-3-(3-quinolylamino)pyrrolidin-1-yl]acetyl]pyrrolidine-2-carbonitrile |
| 166 | 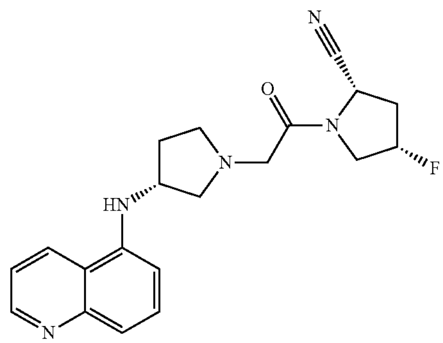 [SMILES: N#C[C@@H]1C[C@H](F)CN1C(=O)CN1CC[C@@H](Nc2cccc3ncccc23)C1] | (2S,4S)-4-fluoro-1-[2-[(3R)-3-(5-quinolylamino)pyrrolidin-1-yl]acetyl]pyrrolidine-2-carbonitrile |
| 167 | 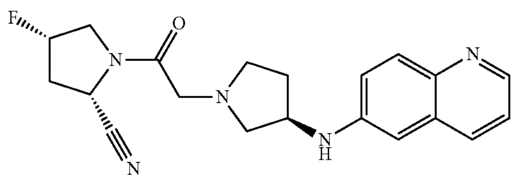 | (2S,4S)-4-fluoro-1-[2-[(3R)-3-(6-quinolylamino)pyrrolidin-1-yl]acetyl]pyrrolidine-2-carbonitrile |
| 168 | 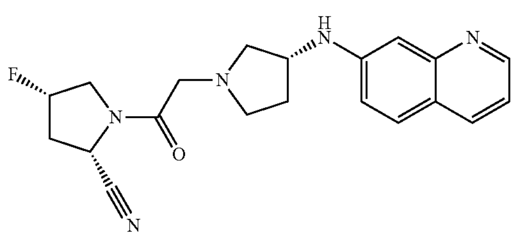 [SMILES: N#C[C@@H]1C[C@H](F)CN1C(=O)CN1CC[C@@H](Nc2ccc3cccnc3c2)C1] | (2S,4S)-4-fluoro-1-[2-[(3R)-3-(7-quinolylamino)pyrrolidin-1-yl]acetyl]pyrrolidine-2-carbonitrile |
| 169 | 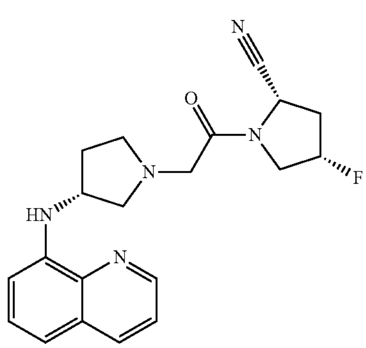 [SMILES: N#C[C@@H]1C[C@H](F)CN1C(=O)CN1CC[C@@H](Nc2cccc3cccnc23)C1] | (2S,4S)-4-fluoro-1-[2-[(3R)-3-(8-quinolylamino)pyrrolidin-1-yl]acetyl]pyrrolidine-2-carbonitrile |

TABLE 1-continued

| Ex No. | Structure | Chemical Name |
| --- | --- | --- |
| 170 | 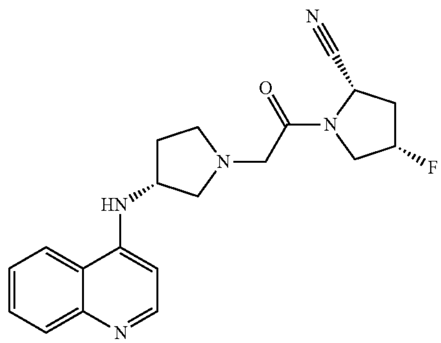 [SMILES: N#C[C@@H]1C[C@H](F)CN1C(=O)CN1CC[C@@H](Nc2ccnc3ccccc23)C1] | (2S,4S)-4-fluoro-1-[2-[(3R)-3-(4-quinolylamino)pyrrolidin-1-yl]acetyl]pyrrolidine-2-carbonitrile |
| 171 | 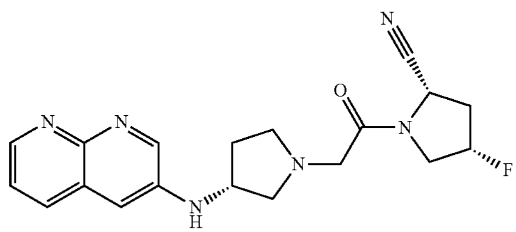 [SMILES: N#C[C@@H]1C[C@H](F)CN1C(=O)CN1CC[C@@H](Nc2cnc3ncccc3c2)C1] | (2S,4S)-4-fluoro-1-[2-[(3R)-3-(1,8-naphthyridin-3-ylamino)pyrrolidin-1-yl]acetyl]pyrrolidine-2-carbonitrile |
| 172 | 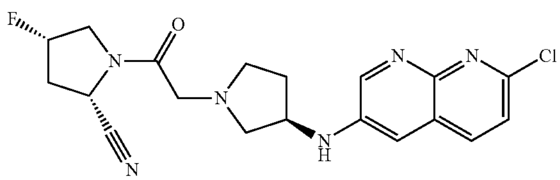 [SMILES: N#C[C@@H]1C[C@H](F)CN1C(=O)CN1CC[C@@H](Nc2cnc3nc(Cl)ccc3c2)C1] | (2S,4S)-4-fluoro-1-[2-[(3R)-3-[(7-chloro-1,8-naphthyridin-3-yl)amino]pyrrolidin-1-yl]acetyl]pyrrolidine-2-carbonitrile |
| 173 | 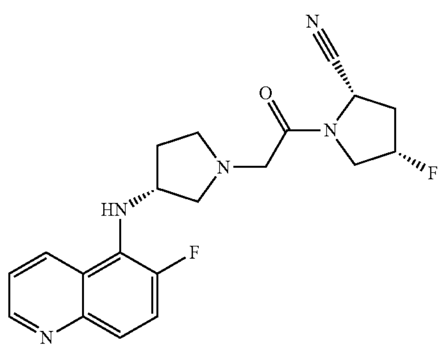 [SMILES: N#C[C@@H]1C[C@H](F)CN1C(=O)CN1CC[C@@H](Nc2c(F)ccc3ncccc23)C1] | (2S,4S)-4-fluoro-1-[2-[(3R)-3-[(6-fluoro-5-quinolyl)amino]pyrrolidin-1-yl]acetyl]pyrrolidine-2-carbonitrile |
| 174 | 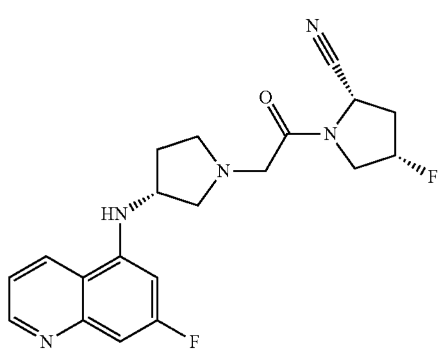 [SMILES: N#C[C@@H]1C[C@H](F)CN1C(=O)CN1CC[C@@H](Nc2cc(F)cc3ncccc23)C1] | (2S,4S)-4-fluoro-1-[2-[(3R)-3-[(7-fluoro-5-quinolyl)amino]pyrrolidin-1-yl]acetyl]pyrrolidine-2-carbonitrile |

| Ex No. | Structure | Chemical Name |
|---|---|---|
| 175 | 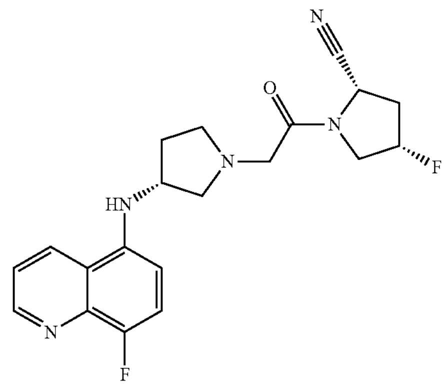 [SMILES: N#C[C@@H]1C[C@H](F)CN1C(=O)CN1CC[C@@H](Nc2ccc(F)c3ncccc23)C1] | (2S,4S)-4-fluoro-1-[2-[(3R)-3-[(8-fluoro-5-quinolyl)amino]pyrrolidin-1-yl]acetyl]pyrrolidine-2-carbonitrile |
| 176 | 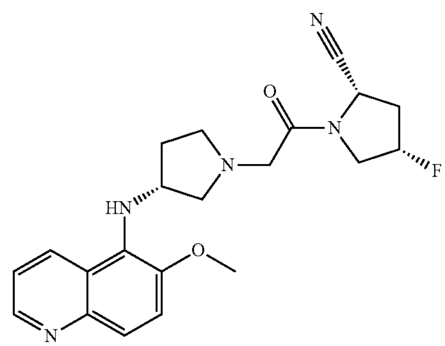 [SMILES: COc1ccc2ncccc2c1N[C@@H]1CCN(CC(=O)N2C[C@@H](F)C[C@H]2C#N)C1] | (2S,4S)-4-fluoro-1-[2-[(3R)-3-[(6-methoxy-5-quinolyl)amino]pyrrolidin-1-yl]acetyl]pyrrolidine-2-carbonitrile |
| 177 | 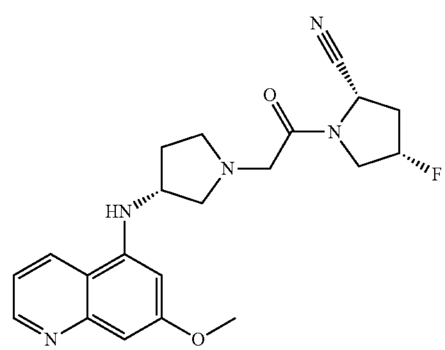 [SMILES: COc1cc(N[C@@H]2CCN(CC(=O)N3C[C@@H](F)C[C@H]3C#N)C2)c2cccnc2c1] | (2S,4S)-4-fluoro-1-[2-[(3R)-3-[(7-methoxy-5-quinolyl)amino]pyrrolidin-1-yl]acetyl]pyrrolidine-2-carbonitrile |
| 178 | 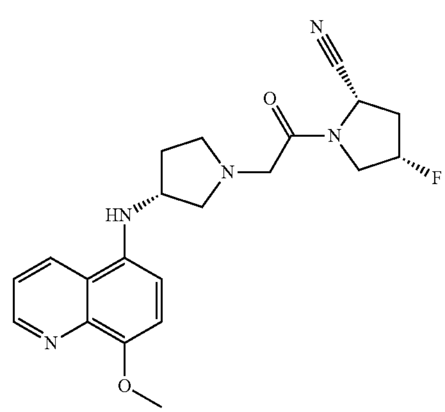 [SMILES: COc1ccc(N[C@@H]2CCN(CC(=O)N3C[C@@H](F)C[C@H]3C#N)C2)c2cccnc12] | (2S,4S)-4-fluoro-1-[2-[(3R)-3-[(8-methoxy-5-quinolyl)amino]pyrrolidin-1-yl]acetyl]pyrrolidine-2-carbonitrile |

TABLE 1-continued

| Ex No. | Structure | Chemical Name |
| --- | --- | --- |
| 179 | 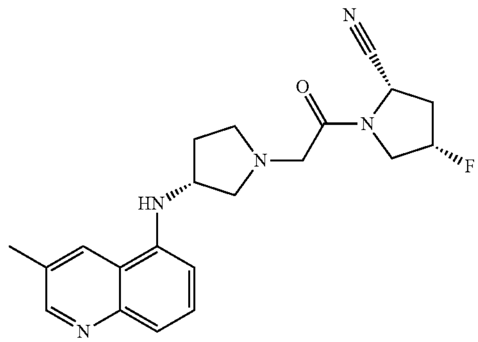 [SMILES: Cc1cnc2cccc(N[C@@H]3CCN(CC(=O)N4C[C@@H](F)C[C@H]4C#N)C3)c2c1] | (2S,4S)-4-fluoro-1-[2-[(3R)-3-[(3-methyl-5-quinolyl)amino]pyrrolidin-1-yl]acetyl]pyrrolidine-2-carbonitrile |
| 180 | 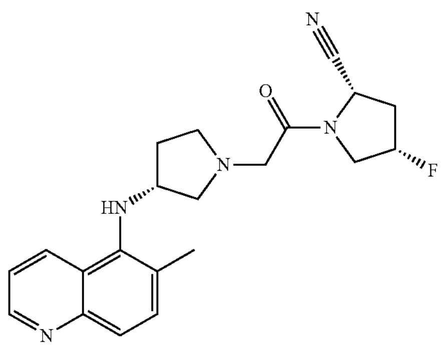 | (2S,4S)-4-fluoro-1-[2-[(3R)-3-[(6-methyl-5-quinolyl)amino]pyrrolidin-1-yl]acetyl]pyrrolidine-2-carbonitrile |
| 181 | 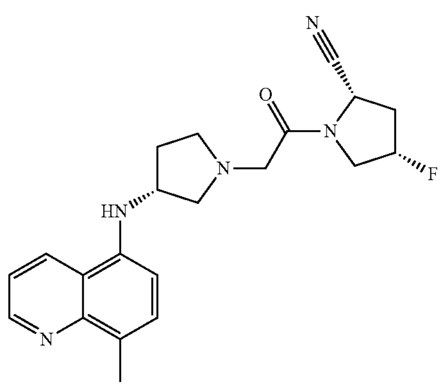 [SMILES: Cc1ccc(N[C@@H]2CCN(CC(=O)N3C[C@@H](F)C[C@H]3C#N)C2)c2cccnc12] | (2S,4S)-4-fluoro-1-[2-[(3R)-3-[(8-methyl-5-quinolyl)amino]pyrrolidin-1-yl]acetyl]pyrrolidine-2-carbonitrile |
| 182 | 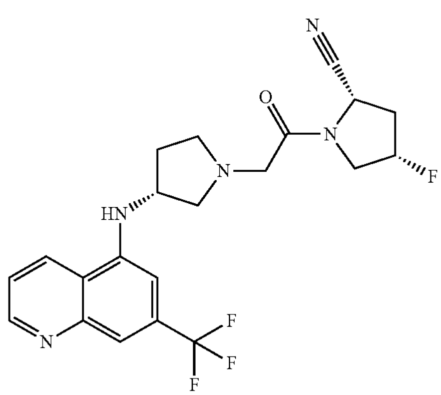 [SMILES: N#C[C@@H]1C[C@H](F)CN1C(=O)CN1CC[C@@H](Nc2cc(C(F)(F)F)cc3ncccc23)C1] | (2S,4S)-4-fluoro-1-[2-[(3R)-3-[[7-(trifluoromethyl)-5-quinolyl]amino]pyrrolidin-1-yl]acetyl]pyrrolidine-2-carbonitrile |

TABLE 1-continued

| Ex No. | Structure | Chemical Name |
|---|---|---|
| 183 | 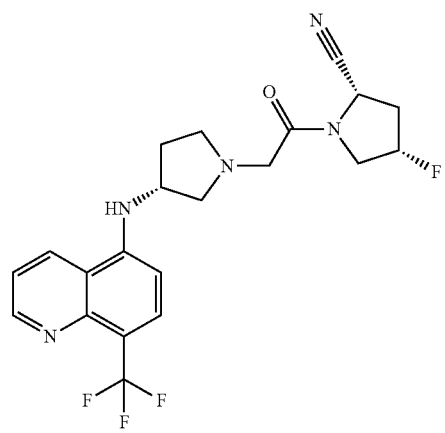 [SMILES: N#C[C@@H]1C[C@H](F)CN1C(=O)CN1CC[C@@H](Nc2ccc(C(F)(F)F)c3ncccc23)C1] | (2S,4S)-4-fluoro-1-[2-[(3R)-3-[[8-(trifluoromethyl)-5-quinolyl]amino]pyrrolidin-1-yl]acetyl]pyrrolidine-2-carbonitrile |
| 184 | 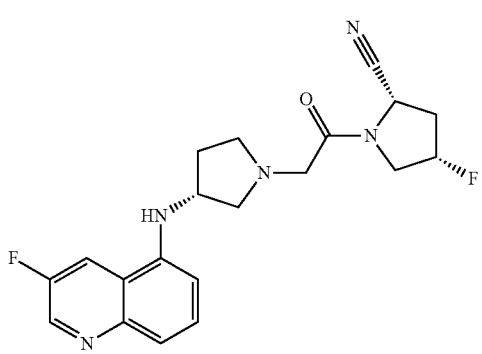 [SMILES: N#C[C@@H]1C[C@H](F)CN1C(=O)CN1CC[C@@H](Nc2cccc3ncc(F)cc23)C1] | (2S,4S)-4-fluoro-1-[2-[(3R)-3-[(3-fluoro-5-quinolyl)amino]pyrrolidin-1-yl]acetyl]pyrrolidine-2-carbonitrile |
| 185 | 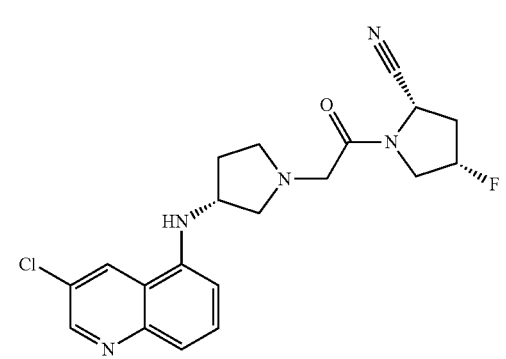 [SMILES: N#C[C@@H]1C[C@H](F)CN1C(=O)CN1CC[C@@H](Nc2cccc3ncc(Cl)cc23)C1] | (2S,4S)-4-fluoro-1-[2-[(3R)-3-[(3-chloro-5-quinolyl)amino]pyrrolidin-1-yl]acetyl]pyrrolidine-2-carbonitrile |
| 186 | 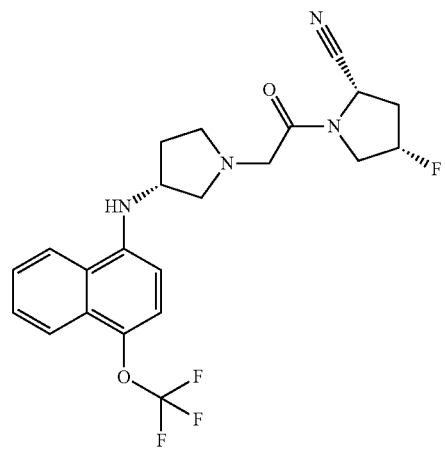 [SMILES: N#C[C@@H]1C[C@H](F)CN1C(=O)CN1CC[C@@H](Nc2ccc(OC(F)(F)F)c3ccccc23)C1] | (2S,4S)-4-fluoro-1-[2-[(3R)-3-[[8-(trifluoromethoxy)-5-quinolyl]amino]pyrrolidin-1-yl]acetyl]pyrrolidine-2-carbonitrile |

TABLE 1-continued

| Ex No. | Structure | Chemical Name |
|---|---|---|
| 187 | 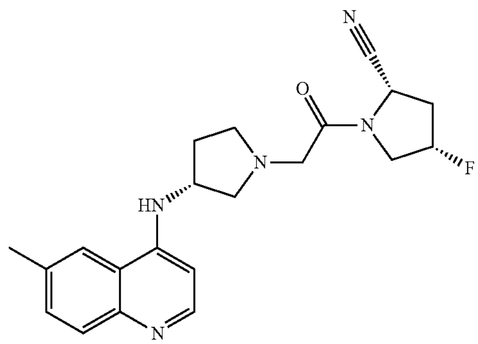 [SMILES: Cc1ccc2nccc(N[C@@H]3CCN(CC(=O)N4C[C@@H](F)C[C@H]4C#N)C3)c2c1] | (2S,4S)-4-fluoro-1-[2-[(3R)-3-[(6-methyl-4-quinolyl)amino]pyrrolidin-1-yl]acetyl]pyrrolidine-2-carbonitrile |
| 188 | 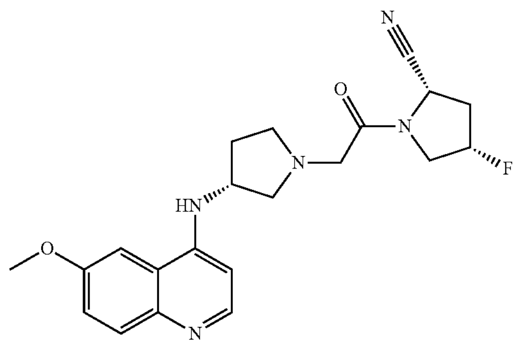 [SMILES: COc1ccc2nccc(N[C@@H]3CCN(CC(=O)N4C[C@@H](F)C[C@H]4C#N)C3)c2c1] | (2S,4S)-4-fluoro-1-[2-[(3R)-3-[(6-methoxy-4-quinolyl)amino]pyrrolidin-1-yl]acetyl]pyrrolidine-2-carbonitrile |
| 189 | 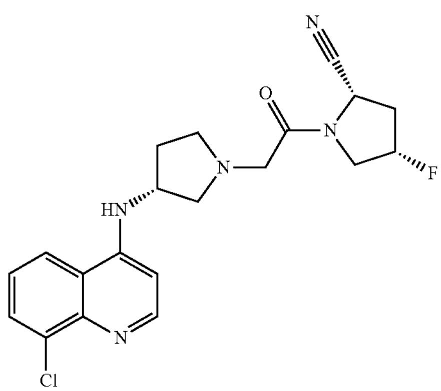 [SMILES: N#C[C@@H]1C[C@H](F)CN1C(=O)CN1CC[C@@H](Nc2ccnc3c(Cl)cccc23)C1] | (2S,4S)-4-fluoro-1-[2-[(3R)-3-[(8-chloro-4-quinolyl)amino]pyrrolidin-1-yl]acetyl]pyrrolidine-2-carbonitrile |
| 190 | 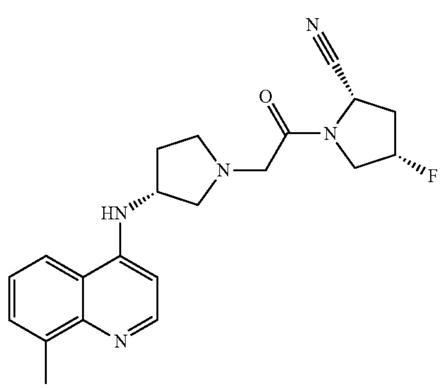 [SMILES: Cc1cccc2c(N[C@@H]3CCN(CC(=O)N4C[C@@H](F)C[C@H]4C#N)C3)ccnc12] | (2S,4S)-4-fluoro-1-[2-[(3R)-3-[(8-methyl-4-quinolyl)amino]pyrrolidin-1-yl]acetyl]pyrrolidine-2-carbonitrile |

TABLE 1-continued

| Ex No. | Structure | Chemical Name |
| --- | --- | --- |
| 191 | 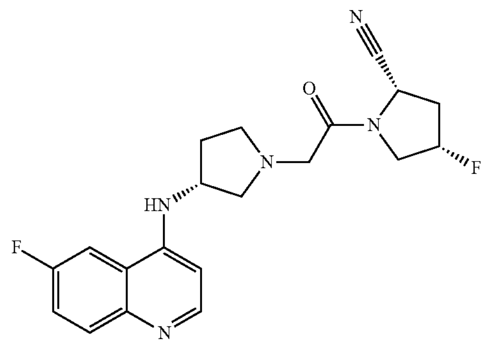 [SMILES: N#C[C@@H]1C[C@H](F)CN1C(=O)CN1CC[C@@H](Nc2ccnc3ccc(F)cc23)C1] | (2S,4S)-4-fluoro-1-[2-[(3R)-3-[(6-fluoro-4-quinolyl)amino]pyrrolidin-1-yl]acetyl]pyrrolidine-2-carbonitrile |
| 192 | 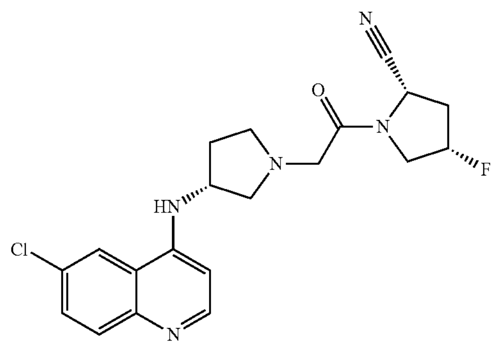 [SMILES: N#C[C@@H]1C[C@H](F)CN1C(=O)CN1CC[C@@H](Nc2ccnc3ccc(Cl)cc23)C1] | (2S,4S)-4-fluoro-1-[2-[(3R)-3-[(6-chloro-4-quinolyl)amino]pyrrolidin-1-yl]acetyl]pyrrolidine-2-carbonitrile |
| 193 | 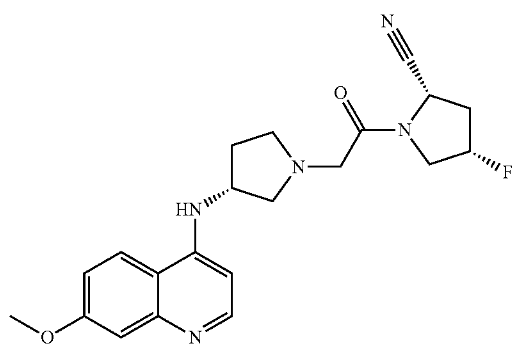 [SMILES: COc1ccc2c(N[C@@H]3CCN(CC(=O)N4C[C@@H](F)C[C@H]4C#N)C3)ccnc2c1] | (2S,4S)-4-fluoro-1-[2-[(3R)-3-[(7-methoxy-4-quinolyl)amino]pyrrolidin-1-yl]acetyl]pyrrolidine-2-carbonitrile |
| 194 | 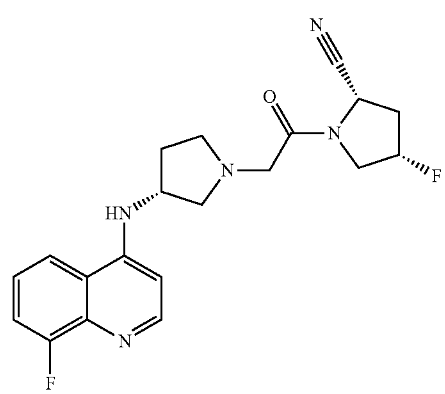 | (2S,4S)-4-fluoro-1-[2-[(3R)-3-[(8-fluoro-4-quinolyl)amino]pyrrolidin-1-yl]acetyl]pyrrolidine-2-carbonitrile |

TABLE 1-continued

| Ex No. | Structure | Chemical Name |
|---|---|---|
| 195 | 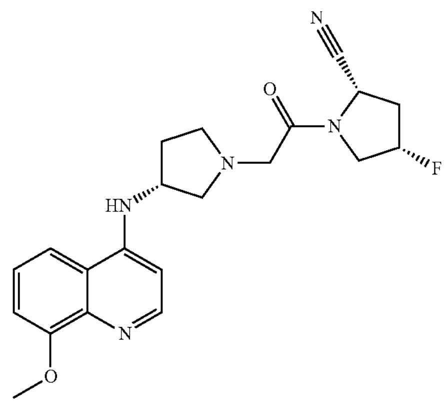 [SMILES: COc1cccc2c(N[C@@H]3CCN(CC(=O)N4C[C@@H](F)C[C@H]4C#N)C3)ccnc12] | (2S,4S)-4-fluoro-1-[2-[(3R)-3-[(8-methoxy-4-quinolyl)amino]pyrrolidin-1-yl]acetyl]pyrrolidine-2-carbonitrile |
| 196 | 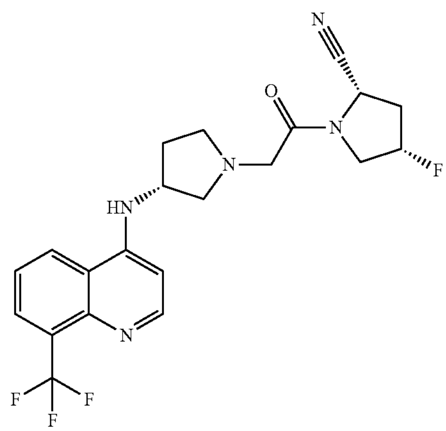 [SMILES: N#C[C@@H]1C[C@H](F)CN1C(=O)CN1CC[C@@H](Nc2ccnc3c(C(F)(F)F)cccc23)C1] | (2S,4S)-4-fluoro-1-[2-[(3R)-3-[[8-(trifluoromethyl)-4-quinolyl]amino]pyrrolidin-1-yl]acetyl]pyrrolidine-2-carbonitrile |
| 197 | 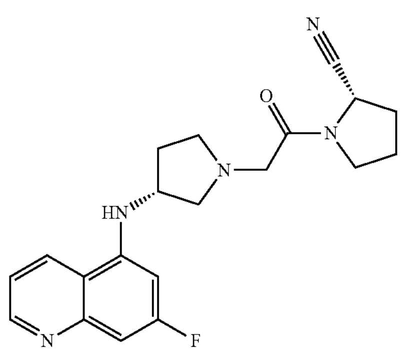 [SMILES: N#C[C@@H]1CCCN1C(=O)CN1CC[C@@H](Nc2cc(F)cc3ncccc23)C1] | (2S)-1-[2-[(3R)-3-[(7-fluoro-5-quinolyl)amino]pyrrolidin-1-yl]acetyl]pyrrolidine-2-carbonitrile |
| 198 | 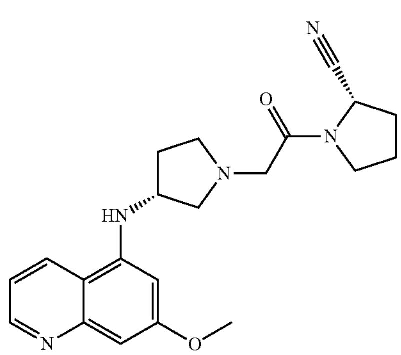 [SMILES: COc1cc(N[C@@H]2CCN(CC(=O)N3CCC[C@H]3C#N)C2)c2cccnc2c1] | (2S)-1-[2-[(3R)-3-[(7-methoxy-5-quinolyl)amino]pyrrolidin-1-yl]acetyl]pyrrolidine-2-carbonitrile |

TABLE 1-continued
| Ex No. | Structure | Chemical Name |
| --- | --- | --- |
| 199 | 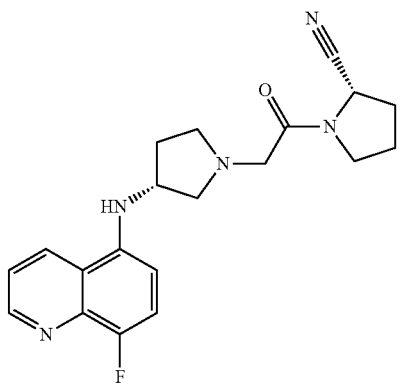 [SMILES: N#C[C@@H]1CCCN1C(=O)CN1CC[C@@H](Nc2ccc(F)c3ncccc23)C1] | (2S)-1-[2-[(3R)-3-[(8-fluoro-5-quinolyl)amino]pyrrolidin-1-yl]acetyl]pyrrolidine-2-carbonitrile |
| 200 | 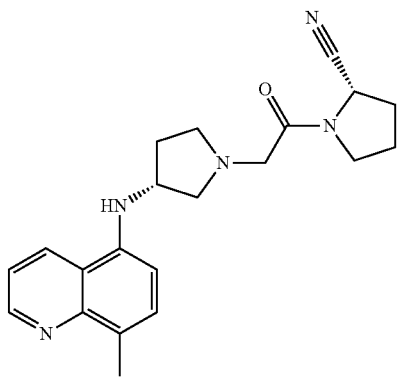 [SMILES: Cc1ccc(N[C@@H]2CCN(CC(=O)N3CCC[C@H]3C#N)C2)c2cccnc12] | (2S)-1-[2-[(3R)-3-[(8-methyl-5-quinolyl)amino]pyrrolidin-1-yl]acetyl]pyrrolidine-2-carbonitrile |
| 201 | 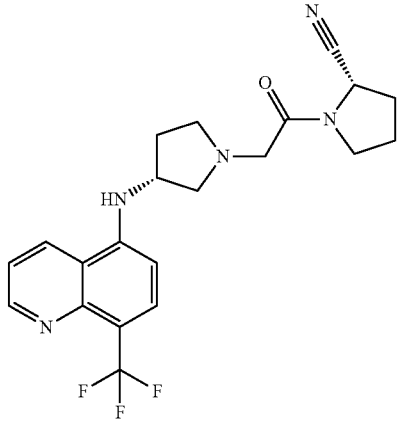 [SMILES: N#C[C@@H]1CCCN1C(=O)CN1CC[C@@H](Nc2ccc(C(F)(F)F)c3ncccc23)C1] | (2S)-1-[2-[(3R)-3-[[8-(trifluoromethyl)-5-quinolyl]amino]pyrrolidin-1-yl]acetyl]pyrrolidine-2-carbonitrile |

TABLE 1-continued

| Ex No. | Structure | Chemical Name |
|---|---|---|
| 202 | 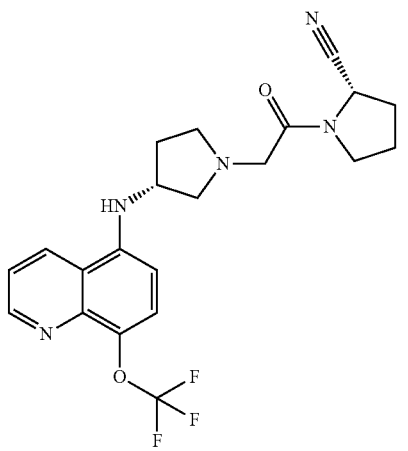 [SMILES: N#C[C@@H]1CCCN1C(=O)CN1CC[C@@H](Nc2ccc(OC(F)(F)F)c3ncccc23)C1] | (2S)-1-[2-[(3R)-3-[[8-(trifluoromethoxy)-5-quinolyl]amino]pyrrolidin-1-yl]acetyl]pyrrolidine-2-carbonitrile |
| 203 | 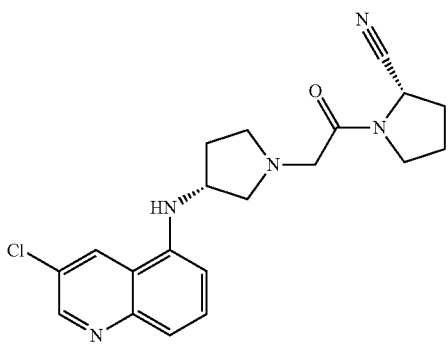 [SMILES: N#C[C@@H]1CCCN1C(=O)CN1CC[C@@H](Nc2cccc3ncc(Cl)cc23)C1] | (2S)-1-[2-[(3R)-3-[(3-chloro-5-quinolyl)amino]pyrrolidin-1-yl]acetyl]pyrrolidine-2-carbonitrile |
| 204 | 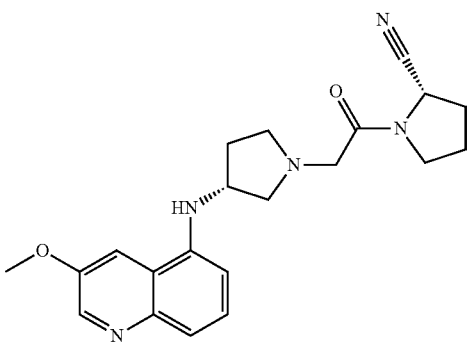 [SMILES: COc1cnc2cccc(N[C@@H]3CCN(CC(=O)N4CCC[C@H]4C#N)C3)c2c1] | (2S)-1-[2-[(3R)-3-[(3-methoxy-5-quinolyl)amino]pyrrolidin-1-yl]acetyl]pyrrolidine-2-carbonitrile |
| 205 | 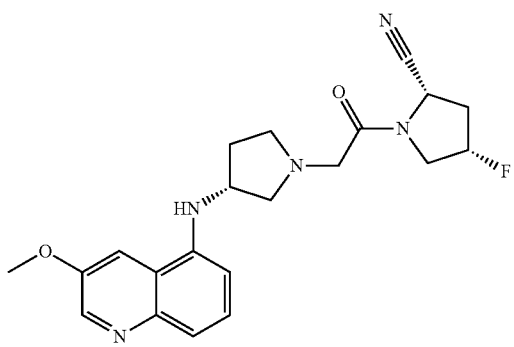 [SMILES: COc1cnc2cccc(N[C@@H]3CCN(CC(=O)N4C[C@@H](F)C[C@H]4C#N)C3)c2c1] | (2S,4S)-4-fluoro-1-[2-[(3R)-3-[(3-methoxy-5-quinolyl)amino]pyrrolidin-1-yl]acetyl]pyrrolidine-2-carbonitrile |

TABLE 1-continued

| Ex No. | Structure | Chemical Name |
|---|---|---|
| 206 | 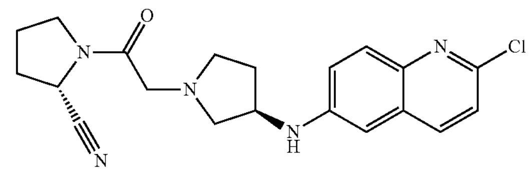 [SMILES: N#C[C@@H]1CCCN1C(=O)CN1CC[C@@H](Nc2ccc3nc(Cl)ccc3c2)C1] | (2S)-1-[2-[(3R)-3-[(2-chloro-6-quinolyl)amino]pyrrolidin-1-yl]acetyl]pyrrolidine-2-carbonitrile |
| 207 | 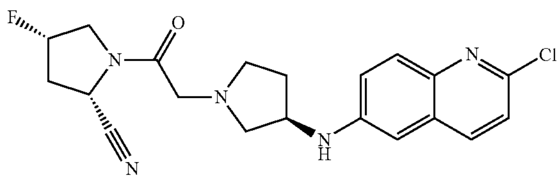 [SMILES: N#C[C@@H]1C[C@H](F)CN1C(=O)CN1CC[C@@H](Nc2ccc3nc(Cl)ccc3c2)C1] | (2S,4S)-4-fluoro-1-[2-[(3R)-3-[(2-chloro-6-quinolyl)amino]pyrrolidin-1-yl]acetyl]pyrrolidine-2-carbonitrile |
| 208 | 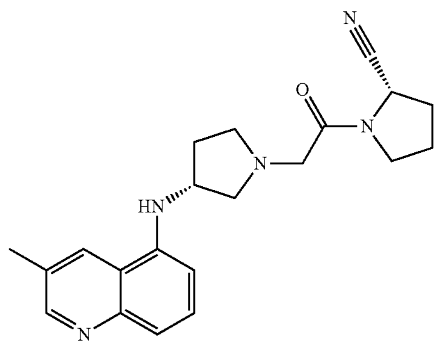 [SMILES: Cc1cnc2cccc(N[C@@H]3CCN(CC(=O)N4CCC[C@H]4C#N)C3)c2c1] | (2S)-1-[2-[(3R)-3-[(3-methyl-5-quinolyl)amino]pyrrolidin-1-yl]acetyl]pyrrolidine-2-carbonitrile |
| 209 | 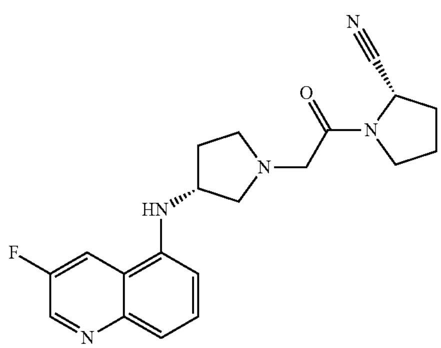 [SMILES: N#C[C@@H]1CCCN1C(=O)CN1CC[C@@H](Nc2cccc3ncc(F)cc23)C1] | (2S)-1-[2-[(3R)-3-[(3-fluoro-5-quinolyl)amino]pyrrolidin-1-yl]acetyl]pyrrolidine-2-carbonitrile |
| 210 | 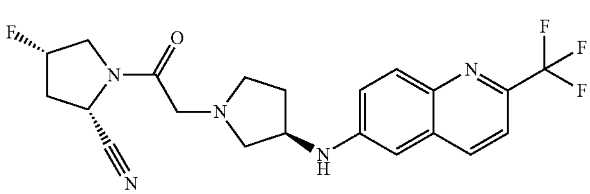 [SMILES: N#C[C@@H]1C[C@H](F)CN1C(=O)CN1CC[C@@H](Nc2ccc3nc(C(F)(F)F)ccc3c2)C1] | (2S,4S)-4-fluoro-1-[2-[(3R)-3-[[2-(trifluoromethyl)-6-quinolyl]amino]pyrrolidin-1-yl]acetyl]pyrrolidine-2-carbonitrile |
| 211 | 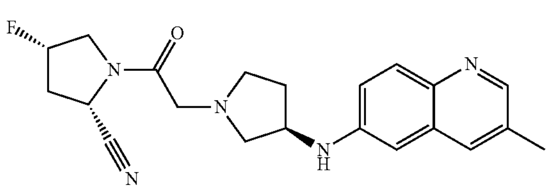 [SMILES: Cc1cnc2ccc(N[C@@H]3CCN(CC(=O)N4C[C@@H](F)C[C@H]4C#N)C3)cc2c1] | (2S,4S)-4-fluoro-1-[2-[(3R)-3-[(3-methyl-6-quinolyl)amino]pyrrolidin-1-yl]acetyl]pyrrolidine-2-carbonitrile |

TABLE 1-continued

| Ex No. | Structure | Chemical Name |
|---|---|---|
| 212 | 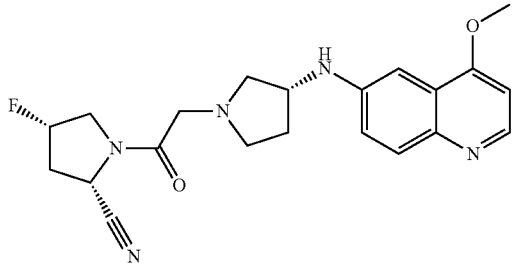 [SMILES: COc1ccnc2ccc(N[C@@H]3CCN(CC(=O)N4C[C@@H](F)C[C@H]4C#N)C3)cc12] | (2S,4S)-4-fluoro-1-[2-[(3R)-3-[(4-methoxy-6-quinolyl)amino]pyrrolidin-1-yl]acetyl]pyrrolidine-2-carbonitrile |
| 213 | 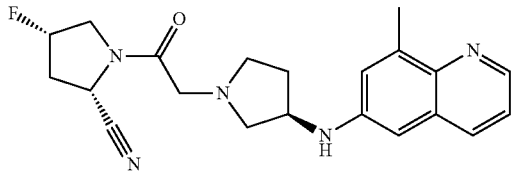 | (2S,4S)-4-fluoro-1-[2-[(3R)-3-[(8-methyl-6-quinolyl)amino]pyrrolidin-1-yl]acetyl]pyrrolidine-2-carbonitrile |
| 214 | 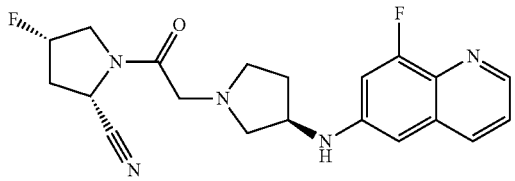 [SMILES: N#C[C@@H]1C[C@H](F)CN1C(=O)CN1CC[C@@H](Nc2cc(F)c3ncccc3c2)C1] | (2S,4S)-4-fluoro-1-[2-[(3R)-3-[(8-fluoro-6-quinolyl)amino]pyrrolidin-1-yl]acetyl]pyrrolidine-2-carbonitrile |
| 215 | 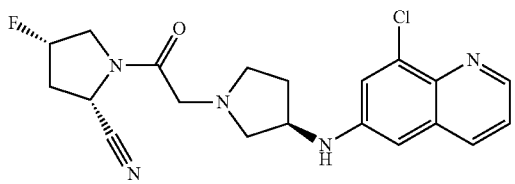 [SMILES: N#C[C@@H]1C[C@H](F)CN1C(=O)CN1CC[C@@H](Nc2cc(Cl)c3ncccc3c2)C1] | (2S,4S)-4-fluoro-1-[2-[(3R)-3-[(8-chloro-6-quinolyl)amino]pyrrolidin-1-yl]acetyl]pyrrolidine-2-carbonitrile |
| 216 | 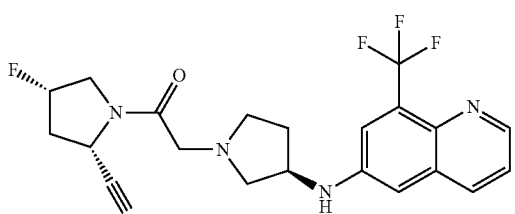 | (2S,4S)-4-fluoro-1-[2-[(3R)-3-[[8-(trifluoromethyl)-6-quinolyl]amino]pyrrolidin-1-yl]acetyl]pyrrolidine-2-carbonitrile |
| 217 | 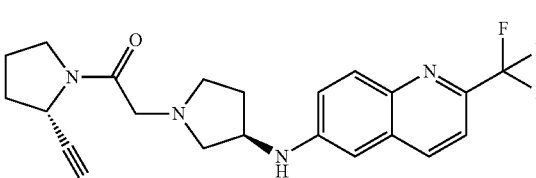 | (2S)-1-[2-[(3R)-3-[[2-(trifluoromethyl)-6-quinolyl]amino]pyrrolidin-1-yl]acetyl]pyrrolidine-2-carbonitrile |
| 218 | 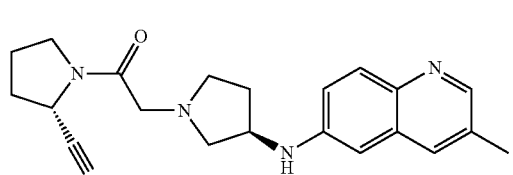 | (2S)-1-[2-[(3R)-3-[(3-methyl-6-quinolyl)amino]pyrrolidin-1-yl]acetyl]pyrrolidine-2-carbonitrile |

| Ex No. | Structure | Chemical Name |
|---|---|---|
| 219 | 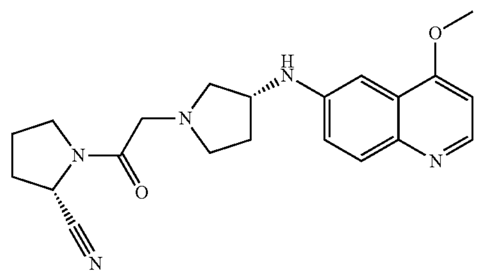 [SMILES: COc1ccnc2ccc(N[C@@H]3CCN(CC(=O)N4CCC[C@H]4C#N)C3)cc12] | (2S)-1-[2-[(3R)-3-[(4-methoxy-6-quinolyl)amino]pyrrolidin-1-yl]acetyl]pyrrolidine-2-carbonitrile |
| 220 | 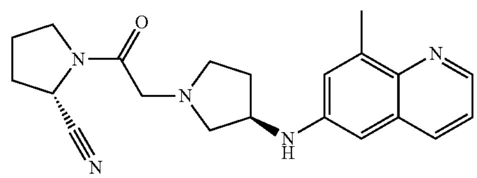 [SMILES: Cc1cc(N[C@@H]2CCN(CC(=O)N3CCC[C@H]3C#N)C2)cc2cccnc12] | (2S)-1-[2-[(3R)-3-[(8-methyl-6-quinolyl)amino]pyrrolidin-1-yl]acetyl]pyrrolidine-2-carbonitrile |
| 221 | 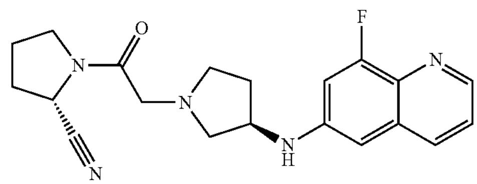 [SMILES: N#C[C@@H]1CCCN1C(=O)CN1CC[C@@H](Nc2cc(F)c3ncccc3c2)C1] | (2S)-1-[2-[(3R)-3-[(8-fluoro-6-quinolyl)amino]pyrrolidin-1-yl]acetyl]pyrrolidine-2-carbonitrile |
| 222 | 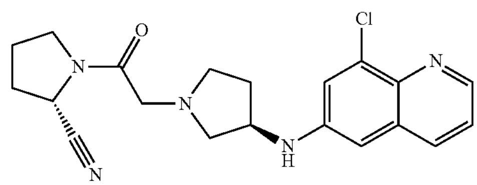 [SMILES: N#C[C@@H]1CCCN1C(=O)CN1CC[C@@H](Nc2cc(Cl)c3ncccc3c2)C1] | (2S)-1-[2-[(3R)-3-[(8-chloro-6-quinolyl)amino]pyrrolidin-1-yl]acetyl]pyrrolidine-2-carbonitrile |
| 223 | 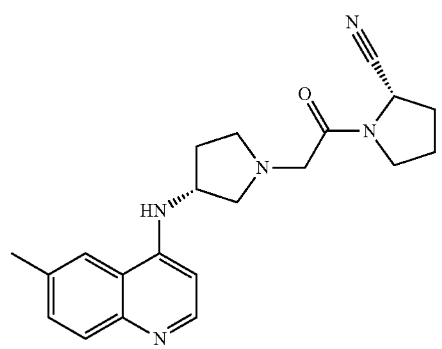 [SMILES: Cc1ccc2nccc(N[C@@H]3CCN(CC(=O)N4CCC[C@H]4C#N)C3)c2c1] | (2S)-1-[2-[(3R)-3-[(6-methyl-4-quinolyl)amino]pyrrolidin-1-yl]acetyl]pyrrolidine-2-carbonitrile |
| 224 | 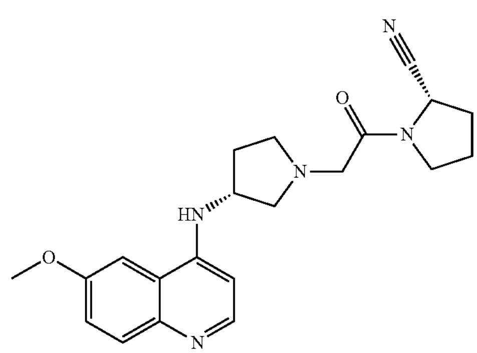 [SMILES: COc1ccc2nccc(N[C@@H]3CCN(CC(=O)N4CCC[C@H]4C#N)C3)c2c1] | (2S)-1-[2-[(3R)-3-[(6-methoxy-4-quinolyl)amino]pyrrolidin-1-yl]acetyl]pyrrolidine-2-carbonitrile |

TABLE 1-continued

| Ex No. | Structure | Chemical Name |
|---|---|---|
| 225 | 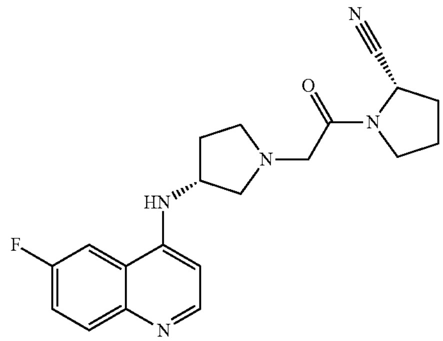 [SMILES: N#C[C@@H]1CCCN1C(=O)CN1CC[C@@H](Nc2ccnc3ccc(F)cc23)C1] | (2S)-1-[2-[(3R)-3-[(6-fluoro-4-quinolyl)amino]pyrrolidin-1-yl]acetyl]pyrrolidine-2-carbonitrile |
| 226 | 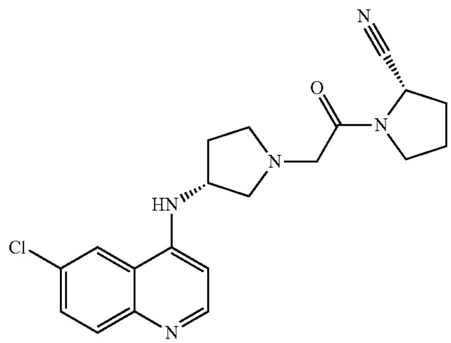 [SMILES: N#C[C@@H]1CCCN1C(=O)CN1CC[C@@H](Nc2ccnc3ccc(Cl)cc23)C1] | (2S)-1-[2-[(3R)-3-[(6-chloro-4-quinolyl)amino]pyrrolidin-1-yl]acetyl]pyrrolidine-2-carbonitrile |
| 227 | 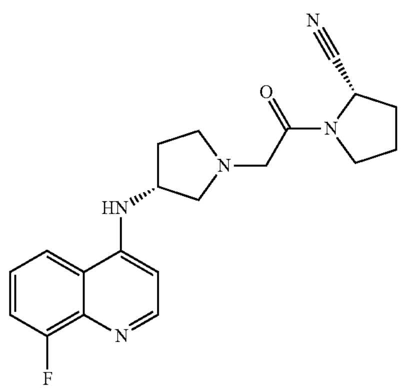 [SMILES: N#C[C@@H]1CCCN1C(=O)CN1CC[C@@H](Nc2ccnc3c(F)cccc23)C1] | (2S)-1-[2-[(3R)-3-[(8-fluoro-4-quinolyl)amino]pyrrolidin-1-yl]acetyl]pyrrolidine-2-carbonitrile |
| 228 | 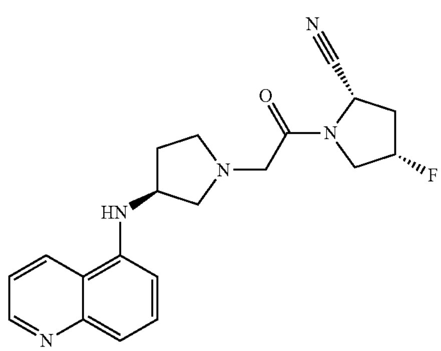 [SMILES: N#C[C@@H]1C[C@H](F)CN1C(=O)CN1CC[C@H](Nc2cccc3ncccc23)C1] | (2S,4S)-4-fluoro-1-[2-[(3S)-3-(5-quinolylamino)pyrrolidin-1-yl]acetyl]pyrrolidine-2-carbonitrile |

TABLE 1-continued

| Ex No. | Structure | Chemical Name |
|---|---|---|
| 229 | 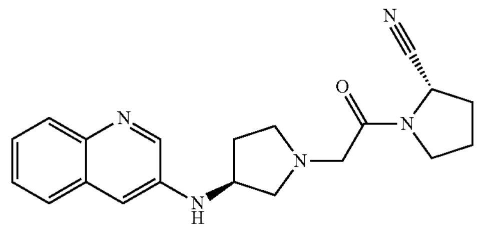 [SMILES: N#C[C@@H]1CCCN1C(=O)CN1CC[C@H](Nc2cnc3ccccc3c2)C1] | (2S)-1-[2-[(3S)-3-(3-quinolylamino)pyrrolidin-1-yl]acetyl]pyrrolidine-2-carbonitrile |
| 230 | 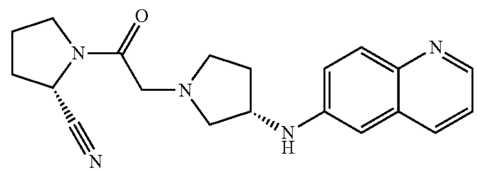 | (2S)-1-[2-[(3S)-3-(6-quinolylamino)pyrrolidin-1-yl]acetyl]pyrrolidine-2-carbonitrile |
| 231 | 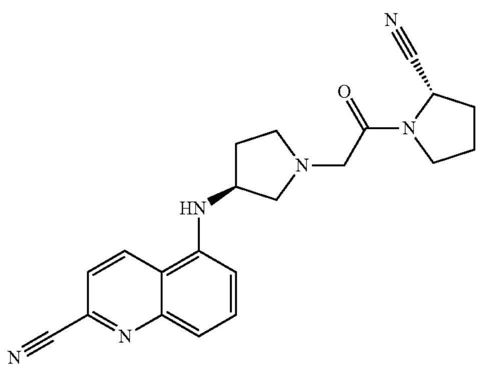 [SMILES: N#Cc1ccc2c(N[C@H]3CCN(CC(=O)N4CCC[C@H]4C#N)C3)cccc2n1] | 5-[[(3S)-1-[2-oxo-2-[(2S)-2-cyanopyrrolidin-1-yl]ethyl]pyrrolidin-3-yl]amino]quinoline-2-carbonitrile |
| 232 | 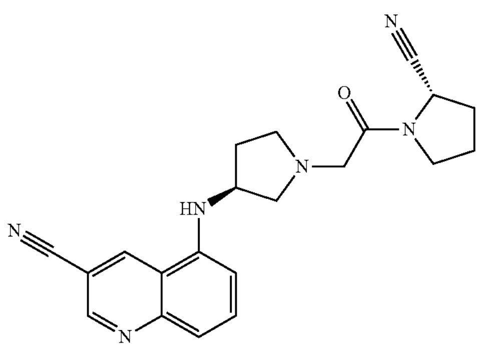 [SMILES: N#Cc1cnc2cccc(N[C@H]3CCN(CC(=O)N4CCC[C@H]4C#N)C3)c2c1] | 5-[[(3S)-1-[2-oxo-2-[(2S)-2-cyanopyrrolidin-1-yl]ethyl]pyrrolidin-3-yl]amino]quinoline-3-carbonitrile |
| 233 | 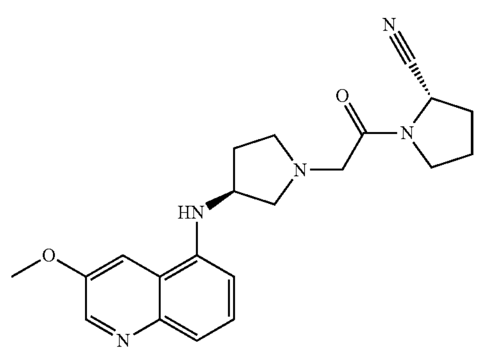 [SMILES: COc1cnc2cccc(N[C@H]3CCN(CC(=O)N4CCC[C@H]4C#N)C3)c2c1] | (2S)-1-[2-[(3S)-3-[(3-methoxy-5-quinolyl)amino]pyrrolidin-1-yl]acetyl]pyrrolidine-2-carbonitrile |

TABLE 1-continued
| Ex No. | Structure | Chemical Name |
|---|---|---|
| 234 | 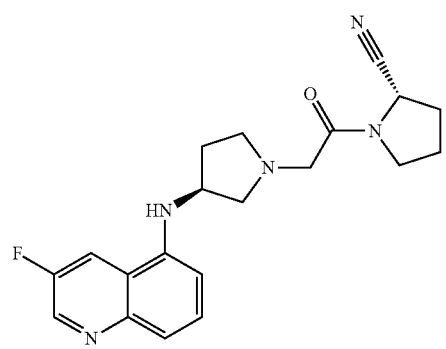 [SMILES: N#C[C@@H]1CCCN1C(=O)CN1CC[C@H](Nc2cccc3ncc(F)cc23)C1] | (2S)-1-[2-[(3S)-3-[(3-fluoro-5-quinolyl)amino]pyrrolidin-1-yl]acetyl]pyrrolidine-2-carbonitrile |
| 235 | 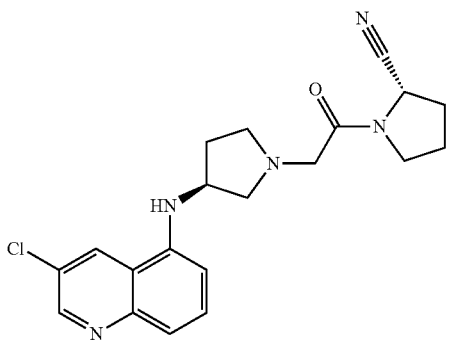 [SMILES: N#C[C@@H]1CCCN1C(=O)CN1CC[C@H](Nc2cccc3ncc(Cl)cc23)C1] | (2S)-1-[2-[(3S)-3-[(3-chloro-5-quinolyl)amino]pyrrolidin-1-yl]acetyl]pyrrolidine-2-carbonitrile |
| 236 | 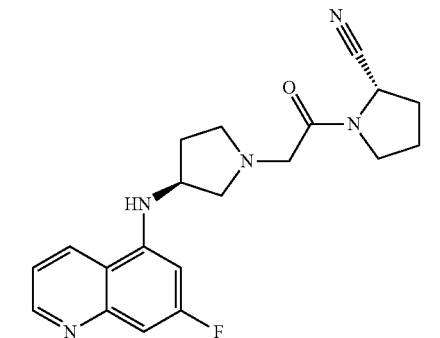 [SMILES: N#C[C@@H]1CCCN1C(=O)CN1CC[C@H](Nc2cc(F)cc3ncccc23)C1] | (2S)-1-[2-[(3S)-3-[(7-fluoro-5-quinolyl)amino]pyrrolidin-1-yl]acetyl]pyrrolidine-2-carbonitrile |
| 237 | 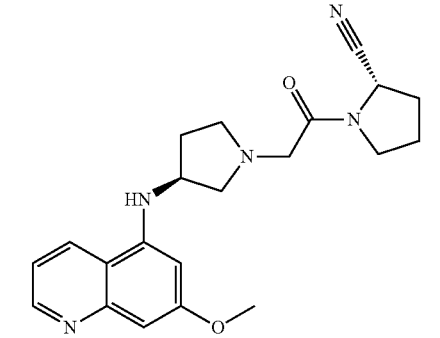 [SMILES: COc1cc(N[C@H]2CCN(CC(=O)N3CCC[C@H]3C#N)C2)c2cccnc2c1] | (2S)-1-[2-[(3S)-3-[(7-methoxy-5-quinolyl)amino]pyrrolidin-1-yl]acetyl]pyrrolidine-2-carbonitrile |

TABLE 1-continued

| Ex No. | Structure | Chemical Name |
|---|---|---|
| 238 | 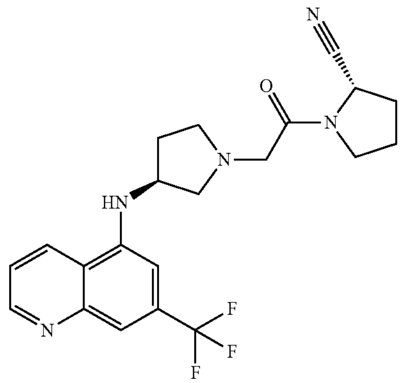 [SMILES: N#C[C@@H]1CCCN1C(=O)CN1CC[C@H](Nc2cc(C(F)(F)F)cc3ncccc23)C1] | (2S)-1-[2-[(3S)-3-[[7-(trifluoromethyl)-5-quinolyl]amino]pyrrolidin-1-yl]acetyl]pyrrolidine-2-carbonitrile |
| 239 | 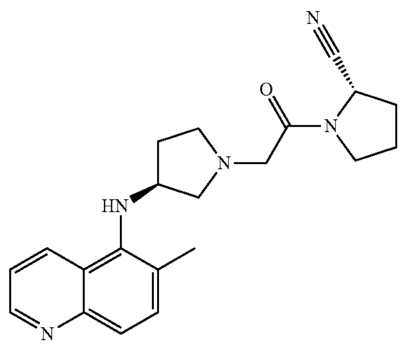 [SMILES: Cc1ccc2ncccc2c1N[C@H]1CCN(CC(=O)N2CCC[C@H]2C#N)C1] | (2S)-1-[2-[(3S)-3-[(6-methyl-5-quinolyl)amino]pyrrolidin-1-yl]acetyl]pyrrolidine-2-carbonitrile |
| 240 | 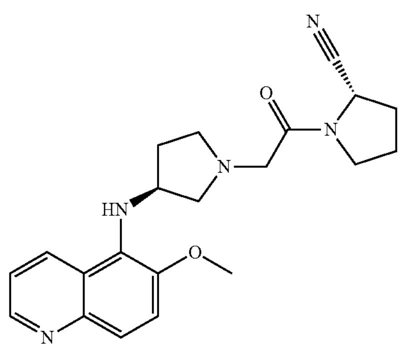 [SMILES: COc1ccc2ncccc2c1N[C@H]1CCN(CC(=O)N2CCC[C@H]2C#N)C1] | (2S)-1-[2-[(3S)-3-[(6-methoxy-5-quinolyl)amino]pyrrolidin-1-yl]acetyl]pyrrolidine-2-carbonitrile |
| 241 | 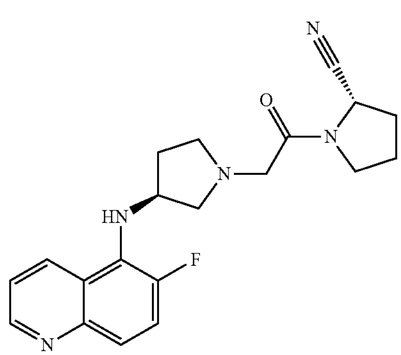 [SMILES: N#C[C@@H]1CCCN1C(=O)CN1CC[C@H](Nc2c(F)ccc3ncccc23)C1] | (2S)-1-[2-[(3S)-3-[(6-fluoro-5-quinolyl)amino]pyrrolidin-1-yl]acetyl]pyrrolidine-2-carbonitrile |

| Ex No. | Structure | Chemical Name |
| --- | --- | --- |
| 242 | 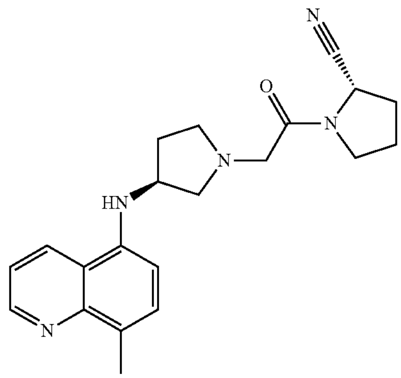 [SMILES: Cc1ccc(N[C@H]2CCN(CC(=O)N3CCC[C@H]3C#N)C2)c2cccnc12] | (2S)-1-[2-[(3S)-3-[(8-methyl-5-quinolyl)amino]pyrrolidin-1-yl]acetyl]pyrrolidine-2-carbonitrile |
| 243 | 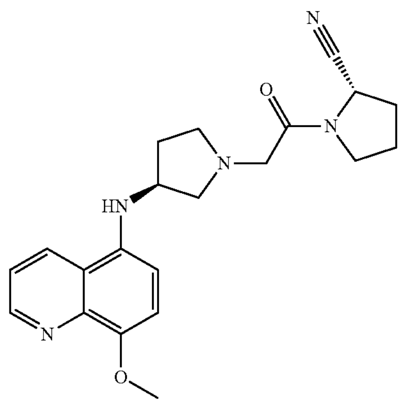 [SMILES: COc1ccc(N[C@H]2CCN(CC(=O)N3CCC[C@H]3C#N)C2)c2cccnc12] | (2S)-1-[2-[(3S)-3-[(8-methoxy-5-quinolyl)amino]pyrrolidin-1-yl]acetyl]pyrrolidine-2-carbonitrile |
| 244 | 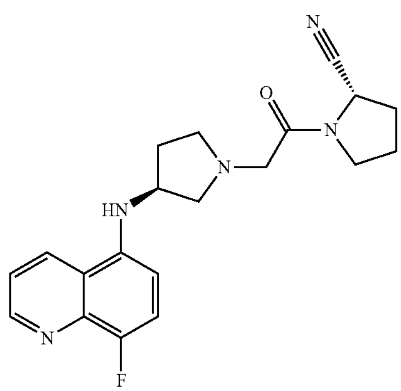 [SMILES: N#C[C@@H]1CCCN1C(=O)CN1CC[C@H](Nc2ccc(F)c3ncccc23)C1] | (2S)-1-[2-[(3S)-3-[(8-fluoro-5-quinolyl)amino]pyrrolidin-1-yl]acetyl]pyrrolidine-2-carbonitrile |
| 245 | 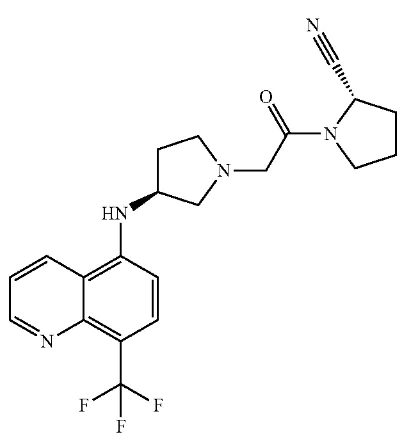 [SMILES: N#C[C@@H]1CCCN1C(=O)CN1CC[C@H](Nc2ccc(C(F)(F)F)c3ncccc23)C1] | (2S)-1-[2-[(3S)-3-[[8-(trifluoromethyl)-5-quinolyl]amino]pyrrolidin-1-yl]acetyl]pyrrolidine-2-carbonitrile |

TABLE 1-continued

| Ex No. | Structure | Chemical Name |
|---|---|---|
| 246 | 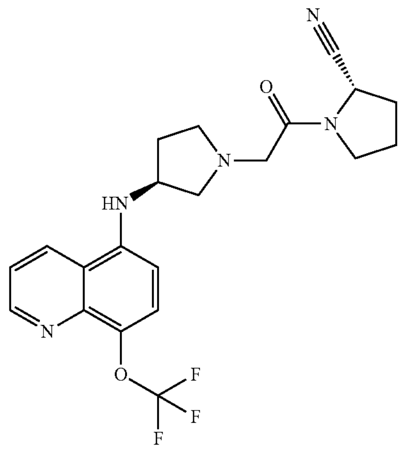 [SMILES: N#C[C@@H]1CCCN1C(=O)CN1CC[C@H](Nc2ccc(OC(F)(F)F)c3ncccc23)C1] | (2S)-1-[2-[(3S)-3-[[8-(trifluoromethoxy)-5-quinolyl]amino]pyrrolidin-1-yl]acetyl]pyrrolidine-2-carbonitrile |
| 247 | 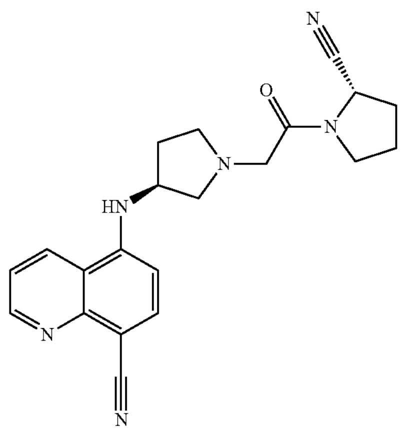 [SMILES: N#Cc1ccc(N[C@H]2CCN(CC(=O)N3CCC[C@H]3C#N)C2)c2cccnc12] | 5-[[(3S)-1-[2-oxo-2-[(2S)-2-cyanopyrrolidin-1-yl]ethyl]pyrrolidin-3-yl]amino]quinoline-8-carbonitrile |
| 248 | 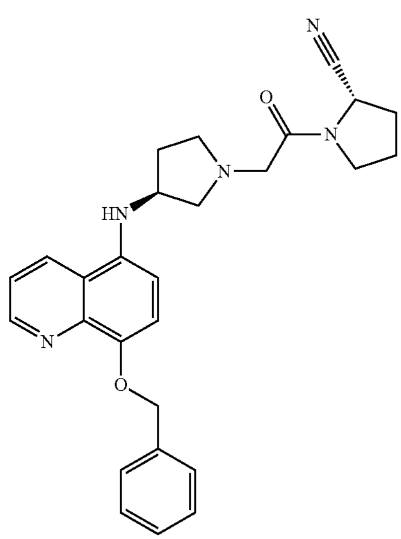 [SMILES: N#C[C@@H]1CCCN1C(=O)CN1CC[C@H](Nc2ccc(OCc3ccccc3)c3ncccc23)C1] | (2S)-1-[2-[(3S)-3-[(8-benzyloxy-5-quinolyl)amino]pyrrolidin-1-yl]acetyl]pyrrolidine-2-carbonitrile |

TABLE 1-continued

| Ex No. | Structure | Chemical Name |
| --- | --- | --- |
| 249 | 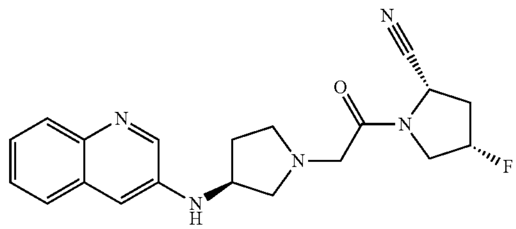 [SMILES: N#C[C@@H]1C[C@H](F)CN1C(=O)CN1CC[C@H](Nc2cnc3ccccc3c2)C1] | (2S,4S)-4-fluoro-1-[2-[(3S)-3-(3-quinolylamino)pyrrolidin-1-yl]acetyl]pyrrolidine-2-carbonitrile |
| 250 | 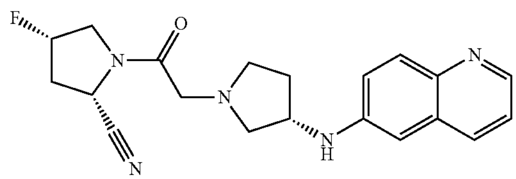 [SMILES: N#C[C@@H]1C[C@H](F)CN1C(=O)CN1CC[C@H](Nc2ccc3ncccc3c2)C1] | (2S,4S)-4-fluoro-1-[2-[(3S)-3-(6-quinolylamino)pyrrolidin-1-yl]acetyl]pyrrolidine-2-carbonitrile |
| 251 | 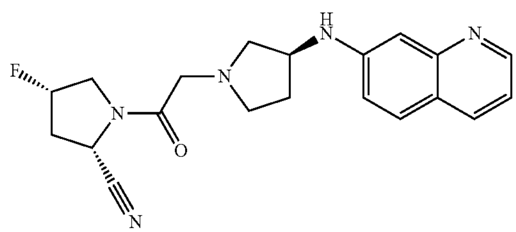 [SMILES: N#C[C@@H]1C[C@H](F)CN1C(=O)CN1CC[C@H](Nc2ccc3cccnc3c2)C1] | (2S,4S)-4-fluoro-1-[2-[(3S)-3-(7-quinolylamino)pyrrolidin-1-yl]acetyl]pyrrolidine-2-carbonitrile |
| 252 | 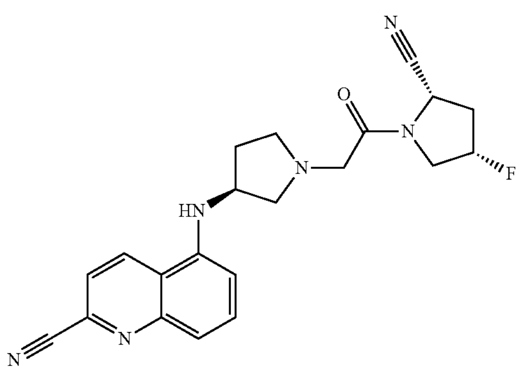 [SMILES: N#Cc1ccc2c(N[C@H]3CCN(CC(=O)N4C[C@@H](F)C[C@H]4C#N)C3)cccc2n1] | 5-[[(3S)-1-[2-oxo-2-[(2S,4S)-2-cyano-4-fluoro-pyrrolidin-1-yl]ethyl]pyrrolidin-3-yl]amino]quinoline-2-carbonitrile |
| 253 | 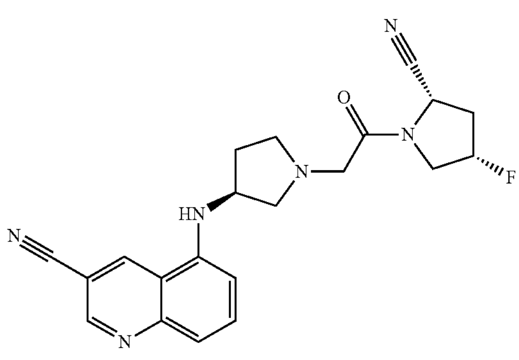 [SMILES: N#Cc1cnc2cccc(N[C@H]3CCN(CC(=O)N4C[C@@H](F)C[C@H]4C#N)C3)c2c1] | 5-[[(3S)-1-[2-oxo-2-[(2S,4S)-2-cyano-4-fluoro-pyrrolidin-1-yl]ethyl]pyrrolidin-3-yl]amino]quinoline-3-carbonitrile |

TABLE 1-continued

| Ex No. | Structure | Chemical Name |
|---|---|---|
| 254 | 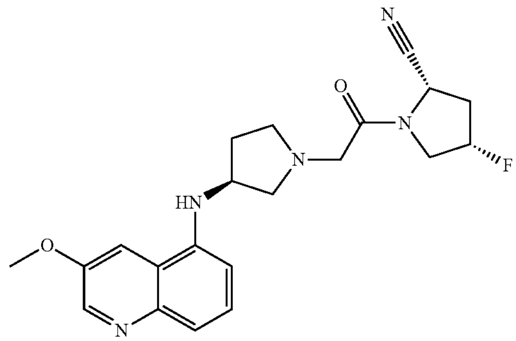 [SMILES: COc1cnc2cccc(N[C@H]3CCN(CC(=O)N4C[C@@H](F)C[C@H]4C#N)C3)c2c1] | (2S,4S)-4-fluoro-1-[2-[(3S)-3-[(3-methoxy-5-quinolyl)amino]pyrrolidin-1-yl]acetyl]pyrrolidine-2-carbonitrile |
| 255 | 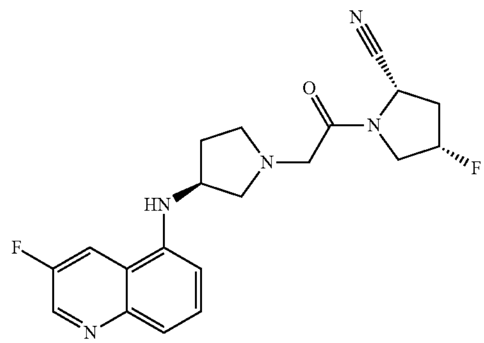 [SMILES: N#C[C@@H]1C[C@H](F)CN1C(=O)CN1CC[C@H](Nc2cccc3ncc(F)cc23)C1] | (2S,4S)-4-fluoro-1-[2-[(3S)-3-[(3-fluoro-5-quinolyl)amino]pyrrolidin-1-yl]acetyl]pyrrolidine-2-carbonitrile |
| 256 | 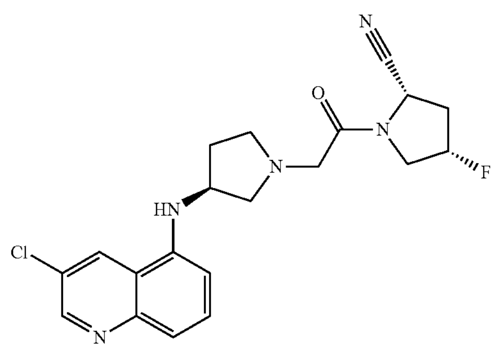 [SMILES: N#C[C@@H]1C[C@H](F)CN1C(=O)CN1CC[C@H](Nc2cccc3ncc(Cl)cc23)C1] | (2S,4S)-4-fluoro-1-[2-[(3S)-3-[(3-chloro-5-quinolyl)amino]pyrrolidin-1-yl]acetyl]pyrrolidine-2-carbonitrile |
| 257 | 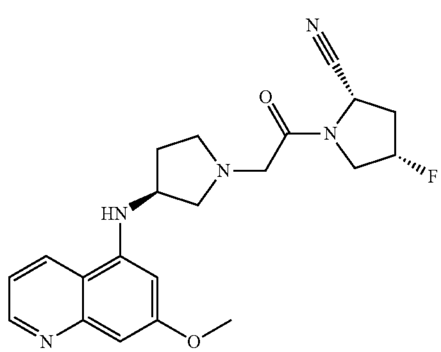 [SMILES: COc1cc(N[C@H]2CCN(CC(=O)N3C[C@@H](F)C[C@H]3C#N)C2)c2cccnc2c1] | (2S,4S)-4-fluoro-1-[2-[(3S)-3-[(7-methoxy-5-quinolyl)amino]pyrrolidin-1-yl]acetyl]pyrrolidine-2-carbonitrile |

TABLE 1-continued

| Ex No. | Structure | Chemical Name |
|---|---|---|
| 258 | 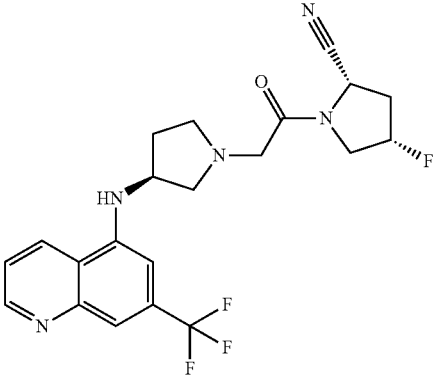 [SMILES: N#C[C@@H]1C[C@H](F)CN1C(=O)CN1CC[C@H](Nc2cc(C(F)(F)F)cc3ncccc23)C1] | (2S,4S)-4-fluoro-1-[2-[(3S)-3-[[7-(trifluoromethyl)-5-quinolyl]amino]pyrrolidin-1-yl]acetyl]pyrrolidine-2-carbonitrile |
| 259 | 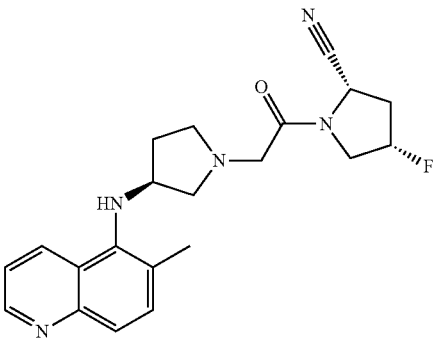 [SMILES: Cc1ccc2ncccc2c1N[C@H]1CCN(CC(=O)N2C[C@@H](F)C[C@H]2C#N)C1] | (2S,4S)-4-fluoro-1-[2-[(3S)-3-[(6-methyl-5-quinolyl)amino]pyrrolidin-1-yl]acetyl]pyrrolidine-2-carbonitrile |
| 260 | 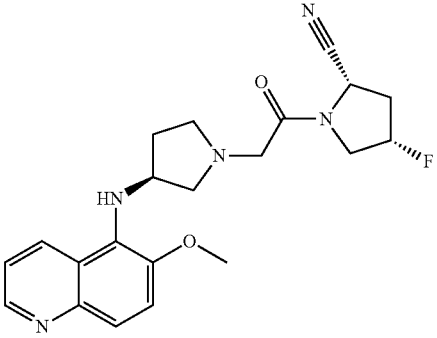 [SMILES: COc1ccc2ncccc2c1N[C@H]1CCN(CC(=O)N2C[C@@H](F)C[C@H]2C#N)C1] | (2S,4S)-4-fluoro-1-[2-[(3S)-3-[(6-methoxy-5-quinolyl)amino]pyrrolidin-1-yl]acetyl]pyrrolidine-2-carbonitrile |
| 261 | 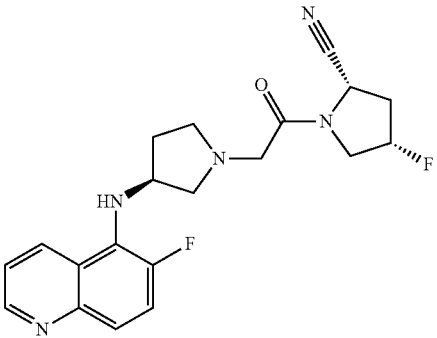 [SMILES: N#C[C@@H]1C[C@H](F)CN1C(=O)CN1CC[C@H](Nc2c(F)ccc3ncccc23)C1] | (2S,4S)-4-fluoro-1-[2-[(3S)-3-[(6-fluoro-5-quinolyl)amino]pyrrolidin-1-yl]acetyl]pyrrolidine-2-carbonitrile |

TABLE 1-continued

| Ex No. | Structure | Chemical Name |
|---|---|---|
| 262 | 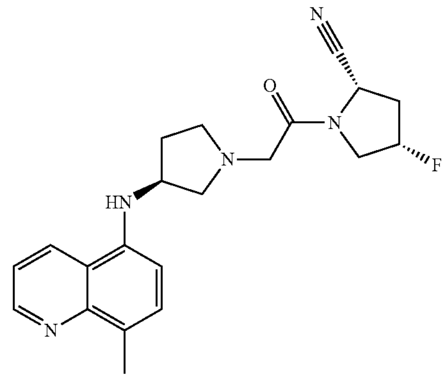 [SMILES: Cc1ccc(N[C@H]2CCN(CC(=O)N3C[C@@H](F)C[C@H]3C#N)C2)c2cccnc12] | (2S,4S)-4-fluoro-1-[2-[(3S)-3-[(8-methyl-5-quinolyl)amino]pyrrolidin-1-yl]acetyl]pyrrolidine-2-carbonitrile |
| 263 | 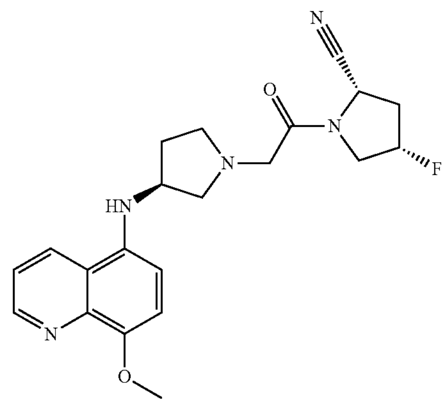 [SMILES: COc1ccc(N[C@H]2CCN(CC(=O)N3C[C@@H](F)C[C@H]3C#N)C2)c2cccnc12] | (2S,4S)-4-fluoro-1-[2-[(3S)-3-[(8-methoxy-5-quinolyl)amino]pyrrolidin-1-yl]acetyl]pyrrolidine-2-carbonitrile |
| 264 | 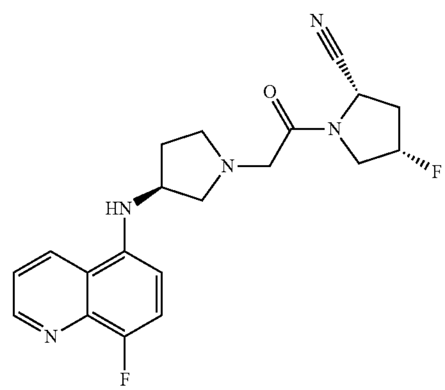 [SMILES: N#C[C@@H]1C[C@H](F)CN1C(=O)CN1CC[C@H](Nc2ccc(F)c3ncccc23)C1] | (2S,4S)-4-fluoro-1-[2-[(3S)-3-[(8-fluoro-5-quinolyl)amino]pyrrolidin-1-yl]acetyl]pyrrolidine-2-carbonitrile |
| 265 | 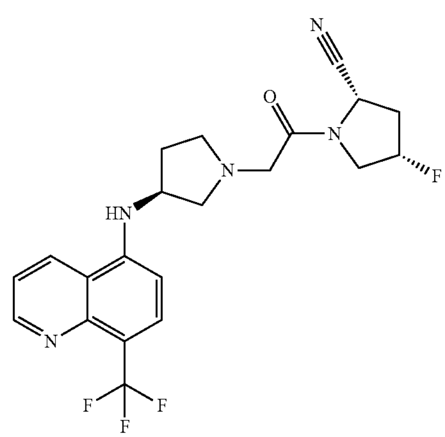 [SMILES: N#C[C@@H]1C[C@H](F)CN1C(=O)CN1CC[C@H](Nc2ccc(C(F)(F)F)c3ncccc23)C1] | (2S,4S)-4-fluoro-1-[2-[(3S)-3-[[8-(trifluoromethyl)-5-quinolyl]amino]pyrrolidin-1-yl]acetyl]pyrrolidine-2-carbonitrile |

TABLE 1-continued
| Ex No. | Structure | Chemical Name |
|---|---|---|
| 266 | 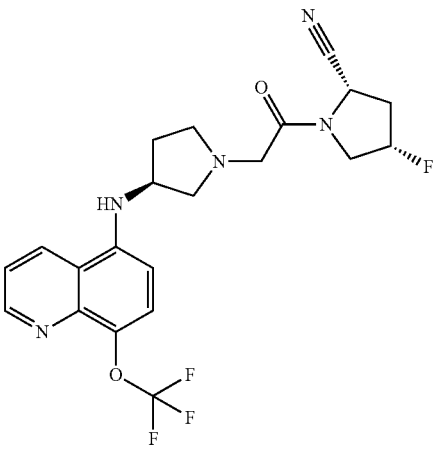 [SMILES: N#C[C@@H]1C[C@H](F)CN1C(=O)CN1CC[C@H](Nc2ccc(OC(F)(F)F)c3ncccc23)C1] | (2S,4S)-4-fluoro-1-[2-[(3S)-3-[[8-(trifluoromethoxy)-5-quinolyl]amino]pyrrolidin-1-yl]acetyl]pyrrolidine-2-carbonitrile |
| 267 | 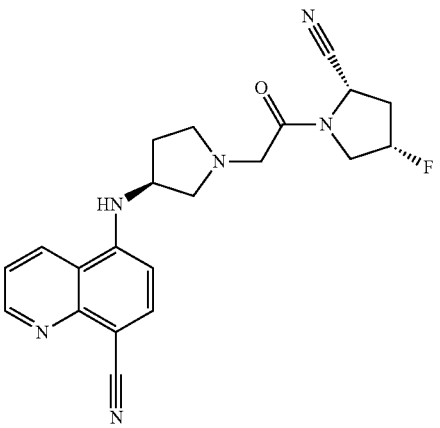 [SMILES: N#Cc1ccc(N[C@H]2CCN(CC(=O)N3C[C@@H](F)C[C@H]3C#N)C2)c2cccnc12] | 5-[[(3S)-1-[2-oxo-2-[(2S,4S)-2-cyano-4-fluoro-pyrrolidin-1-yl]ethyl]pyrrolidin-3-yl]amino]quinoline-8-carbonitrile |
| 268 | 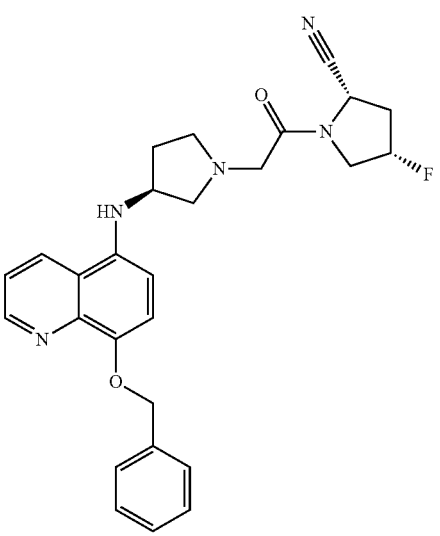 [SMILES: N#C[C@@H]1C[C@H](F)CN1C(=O)CN1CC[C@H](Nc2ccc(OCc3ccccc3)c3ncccc23)C1] | (2S,4S)-4-fluoro-1-[2-[(3S)-3-[(8-benzyloxy-5-quinolyl)amino]pyrrolidin-1-yl]acetyl]pyrrolidine-2-carbonitrile |

TABLE 1-continued

| Ex No. | Structure | Chemical Name |
| --- | --- | --- |
| 269 | 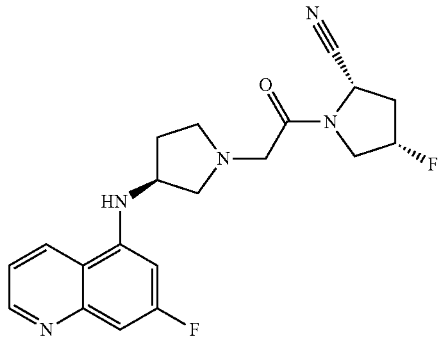 [SMILES: N#C[C@@H]1C[C@H](F)CN1C(=O)CN1CC[C@H](Nc2cc(F)cc3ncccc23)C1] | (2S,4S)-4-fluoro-1-[2-[(3S)-3-[(7-fluoro-5-quinolyl)amino]pyrrolidin-1-yl]acetyl]pyrrolidine-2-carbonitrile |
| 270 | 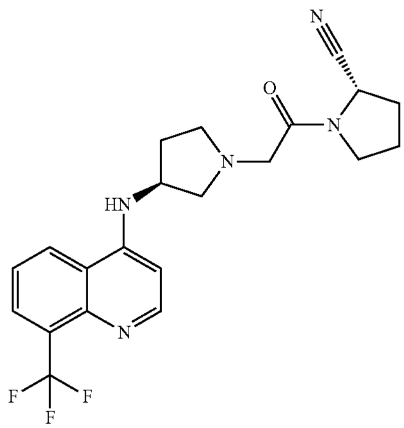 [SMILES: N#C[C@@H]1CCCN1C(=O)CN1CC[C@H](Nc2ccnc3c(C(F)(F)F)cccc23)C1] | (2S)-1-[2-[(3S)-3-[[8-(trifluoromethyl)-4-quinolyl]amino]pyrrolidin-1-yl]acetyl]pyrrolidine-2-carbonitrile |
| 271 | 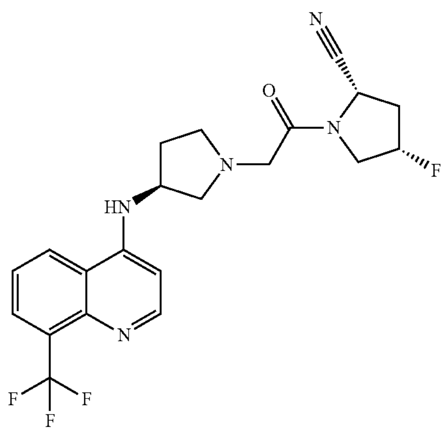 [SMILES: N#C[C@@H]1C[C@H](F)CN1C(=O)CN1CC[C@H](Nc2ccnc3c(C(F)(F)F)cccc23)C1] | (2S,4S)-4-fluoro-1-[2-[(3S)-3-[[8-(trifluoromethyl)-4-quinolyl]amino]pyrrolidin-1-yl]acetyl]pyrrolidine-2-carbonitrile |
| 272 | 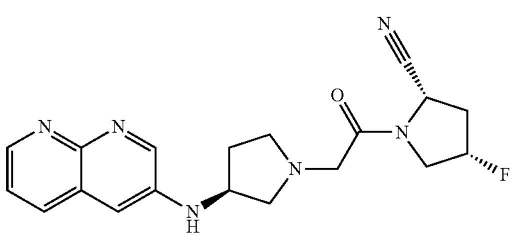 [SMILES: N#C[C@@H]1C[C@H](F)CN1C(=O)CN1CC[C@H](Nc2cnc3ncccc3c2)C1] | (2S,4S)-4-fluoro-1-[2-[(3S)-3-(1,8-naphthyridin-3-ylamino)pyrrolidin-1-yl]acetyl]pyrrolidine-2-carbonitrile |
| 273 | 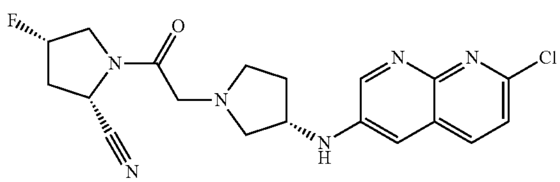 [SMILES: N#C[C@@H]1C[C@H](F)CN1C(=O)CN1CC[C@H](Nc2cnc3nc(Cl)ccc3c2)C1] | (2S,4S)-4-fluoro-1-[2-[(3S)-3-[(7-chloro-1,8-naphthyridin-3-yl)amino]pyrrolidin-1-yl]acetyl]pyrrolidine-2-carbonitrile |

TABLE 1-continued

| Ex No. | Structure | Chemical Name |
| --- | --- | --- |
| 274 | 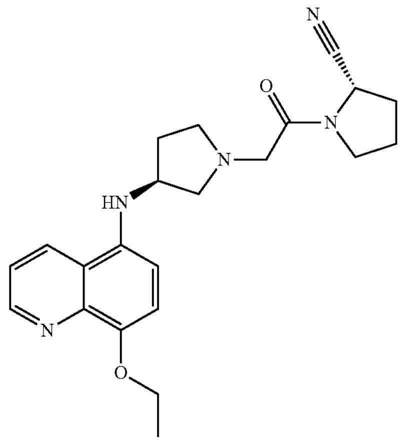 [SMILES: CCOc1ccc(N[C@H]2CCN(CC(=O)N3CCC[C@H]3C#N)C2)c2cccnc12] | (2S)-1-[2-[(3S)-3-[(8-ethoxy-5-quinolyl)amino]pyrrolidin-1-yl]acetyl]pyrrolidine-2-carbonitrile |
| 275 | 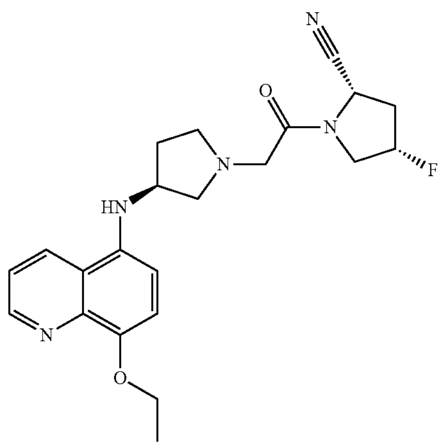 [SMILES: CCOc1ccc(N[C@H]2CCN(CC(=O)N3C[C@@H](F)C[C@H]3C#N)C2)c2cccnc12] | (2S,4S)-4-fluoro-1-[2-[(3S)-3-[(8-ethoxy-5-quinolyl)amino]pyrrolidin-1-yl]acetyl]pyrrolidine-2-carbonitrile |
| 276 | 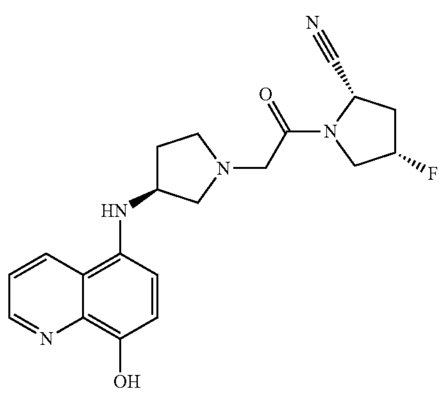 [SMILES: N#C[C@@H]1C[C@H](F)CN1C(=O)CN1CC[C@H](Nc2ccc(O)c3ncccc23)C1] | (2S,4S)-4-fluoro-1-[2-[(3S)-3-[(8-hydroxy-5-quinolyl)amino]pyrrolidin-1-yl]acetyl]pyrrolidine-2-carbonitrile |
| 277 | 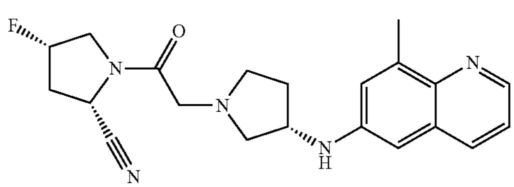 [SMILES: Cc1cc(N[C@H]2CCN(CC(=O)N3C[C@@H](F)C[C@H]3C#N)C2)cc2cccnc12] | (2S,4S)-4-fluoro-1-[2-[(3S)-3-[(8-methyl-6-quinolyl)amino]pyrrolidin-1-yl]acetyl]pyrrolidine-2-carbonitrile |

TABLE 1-continued

| Ex No. | Structure | Chemical Name |
| --- | --- | --- |
| 278 | 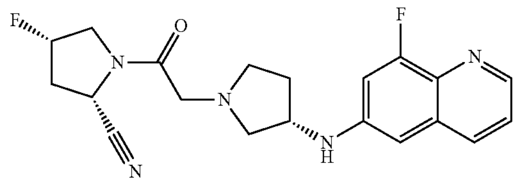 [SMILES: N#C[C@@H]1C[C@H](F)CN1C(=O)CN1CC[C@H](Nc2cc(F)c3ncccc3c2)C1] | (2S,4S)-4-fluoro-1-[2-[(3S)-3-[(8-fluoro-6-quinolyl)amino]pyrrolidin-1-yl]acetyl]pyrrolidine-2-carbonitrile |
| 279 | 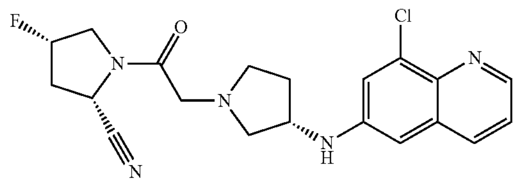 [SMILES: N#C[C@@H]1C[C@H](F)CN1C(=O)CN1CC[C@H](Nc2cc(Cl)c3ncccc3c2)C1] | (2S,4S)-4-fluoro-1-[2-[(3S)-3-[(8-chloro-6-quinolyl)amino]pyrrolidin-1-yl]acetyl]pyrrolidine-2-carbonitrile |
| 280 | 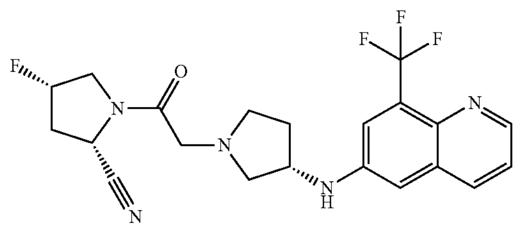 [SMILES: N#C[C@@H]1C[C@H](F)CN1C(=O)CN1CC[C@H](Nc2cc(C(F)(F)F)c3ncccc3c2)C1] | (2S,4S)-4-fluoro-1-[2-[(3S)-3-[[8-(trifluoromethyl)-6-quinolyl]amino]pyrrolidin-1-yl]acetyl]pyrrolidine-2-carbonitrile |
| 281 | 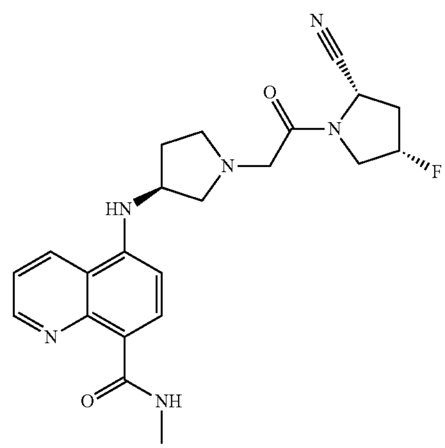 [SMILES: CNC(=O)c1ccc(N[C@H]2CCN(CC(=O)N3C[C@@H](F)C[C@H]3C#N)C2)c2cccnc12] | N-methyl-5-[[(3S)-1-[2-oxo-2-[(2S,4S)-2-cyano-4-fluoro-pyrrolidin-1-yl]ethyl]pyrrolidin-3-yl]amino]quinoline-8-carboxamide |
| 282 | 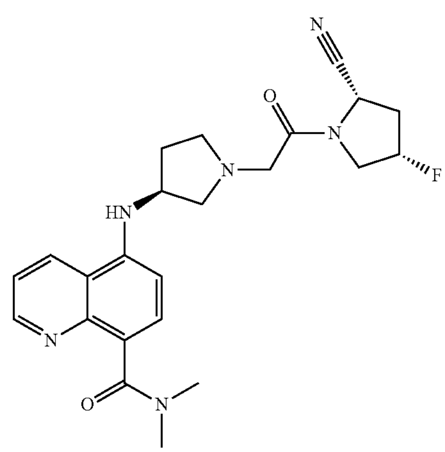 [SMILES: CN(C)C(=O)c1ccc(N[C@H]2CCN(CC(=O)N3C[C@@H](F)C[C@H]3C#N)C2)c2cccnc12] | N,N-dimethyl-5-[[(3S)-1-[2-oxo-2-[(2S,4S)-2-cyano-4-fluoro-pyrrolidin-1-yl]ethyl]pyrrolidin-3-yl]amino]quinoline-8-carboxamide |

| Ex No. | Structure | Chemical Name |
|---|---|---|
| 283 | 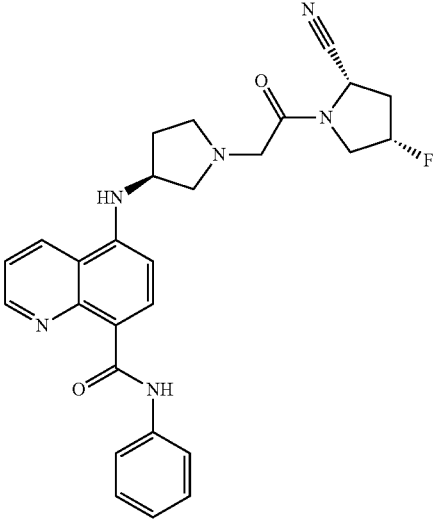 [SMILES: N#C[C@@H]1C[C@H](F)CN1C(=O)CN1CC[C@H](Nc2ccc(C(=O)Nc3ccccc3)c3ncccc23)C1] | N-phenyl-5-[[(3S)-1-[2-oxo-2-[(2S,4S)-2-cyano-4-fluoro-pyrrolidin-1-yl]ethyl]pyrrolidin-3-yl]amino]quinoline-8-carboxamide |
| 284 | 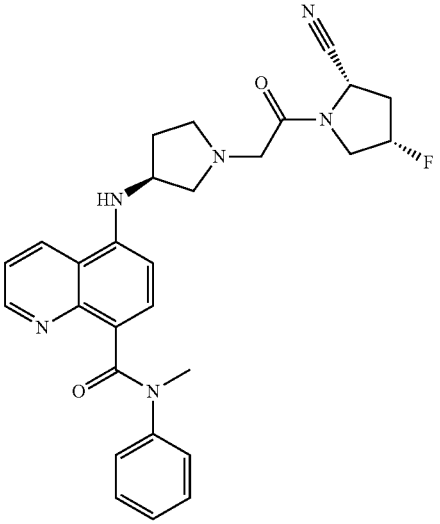 [SMILES: CN(C(=O)c1ccc(N[C@H]2CCN(CC(=O)N3C[C@@H](F)C[C@H]3C#N)C2)c2cccnc12)c1ccccc1] | N-methyl-N-phenyl-5-[[(3S)-1-[2-oxo-2-[(2S,4S)-2-cyano-4-fluoro-pyrrolidin-1-yl]ethyl]pyrrolidin-3-yl]amino]quinoline-8-carboxamide |
| 285 | 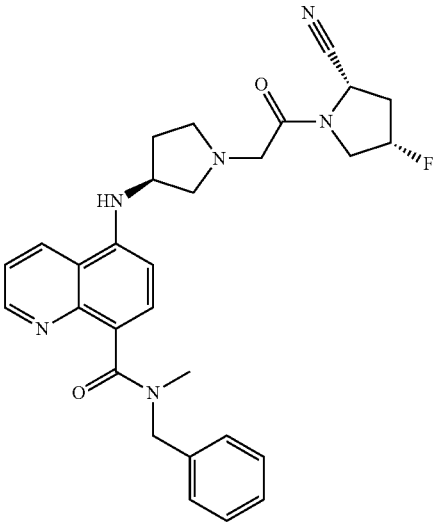 [SMILES: CN(Cc1ccccc1)C(=O)c1ccc(N[C@H]2CCN(CC(=O)N3C[C@@H](F)C[C@H]3C#N)C2)c2cccnc12] | N-benzyl-N-methyl-5-[[(3S)-1-[2-oxo-2-[(2S,4S)-2-cyano-4-fluoro-pyrrolidin-1-yl]ethyl]pyrrolidin-3-yl]amino]quinoline-8-carboxamide |

TABLE 1-continued
| Ex No. | Structure | Chemical Name |
|---|---|---|
| 286 | 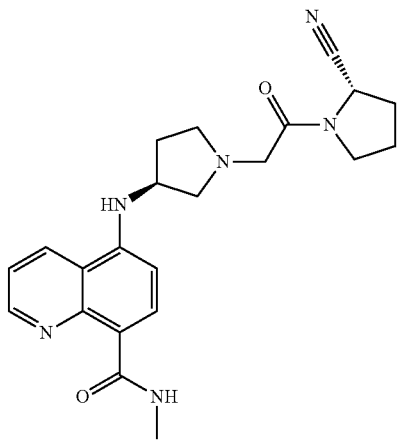 [SMILES: CNC(=O)c1ccc(N[C@H]2CCN(CC(=O)N3CCC[C@H]3C#N)C2)c2cccnc12] | N-methyl-5-[[(3S)-1-[2-oxo-2-[(2S)-2-cyanopyrrolidin-1-yl]ethyl]pyrrolidin-3-yl]amino]quinoline-8-carboxamide |
| 287 | 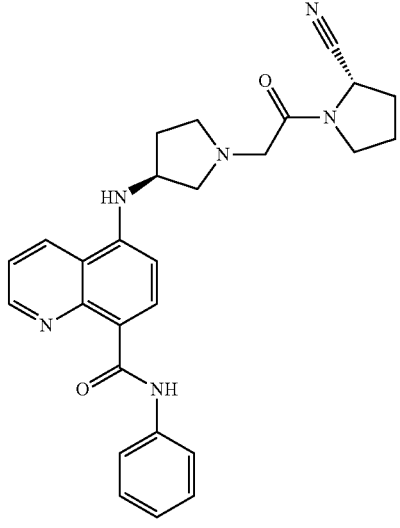 [SMILES: N#C[C@@H]1CCCN1C(=O)CN1CC[C@H](Nc2ccc(C(=O)Nc3ccccc3)c3ncccc23)C1] | N-phenyl-5-[[(3S)-1-[2-oxo-2-[(2S)-2-cyanopyrrolidin-1-yl]ethyl]pyrrolidin-3-yl]amino]quinoline-8-carboxamide |
| 288 | 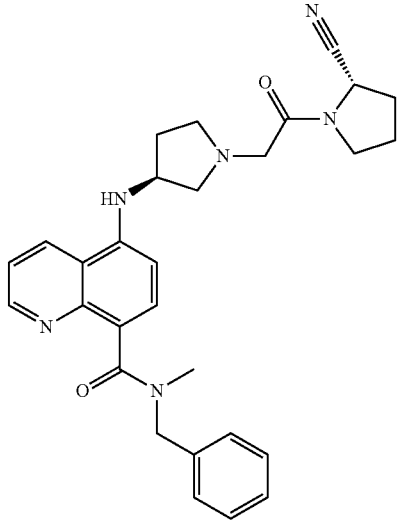 [SMILES: CN(Cc1ccccc1)C(=O)c1ccc(N[C@H]2CCN(CC(=O)N3CCC[C@H]3C#N)C2)c2cccnc12] | N-benzyl-N-methyl-5-[[(3S)-1-[2-oxo-2-[(2S)-2-cyanopyrrolidin-1-yl]ethyl]pyrrolidin-3-yl]amino]quinoline-8-carboxamide |

TABLE 1-continued
| Ex No. | Structure | Chemical Name |
|---|---|---|
| 289 | 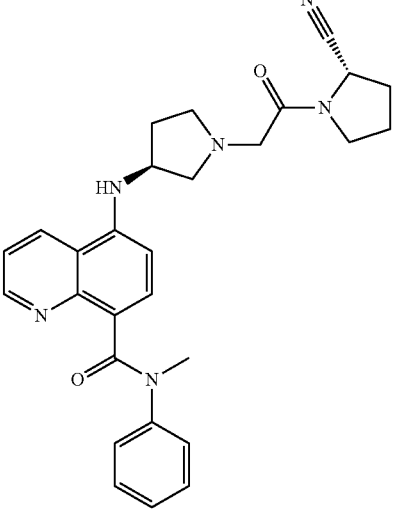 | N-methyl-N-phenyl-5-[[(3S)-1-[2-oxo-2-[(2S)-2-cyanopyrrolidin-1-yl]ethyl]pyrrolidin-3-yl]amino]quinoline-8-carboxamide |
| 290 | 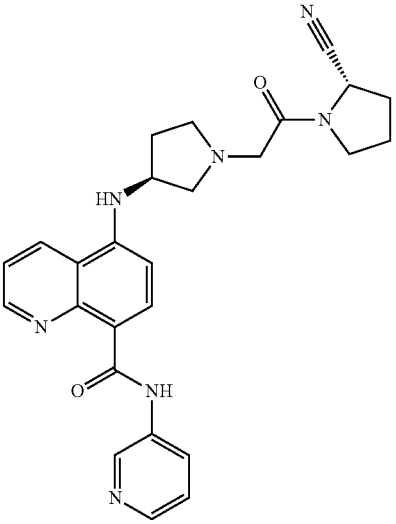 [SMILES: N#C[C@@H]1CCCN1C(=O)CN1CC[C@H](Nc2ccc(C(=O)Nc3cccnc3)c3ncccc23)C1] | N-(3-pyridyl)-5-[[(3S)-1-[2-oxo-2-[(2S)-2-cyanopyrrolidin-1-yl]ethyl]pyrrolidin-3-yl]amino]quinoline-8-carboxamide |
| 291 | 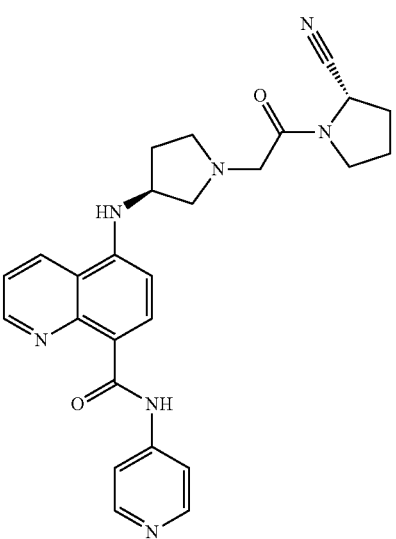 [SMILES: N#C[C@@H]1CCCN1C(=O)CN1CC[C@H](Nc2ccc(C(=O)Nc3ccncc3)c3ncccc23)C1] | N-(4-pyridyl)-5-[[(3S)-1-[2-oxo-2-[(2S)-2-cyanopyrrolidin-1-yl]ethyl]pyrrolidin-3-yl]amino]quinoline-8-carboxamide |

TABLE 1-continued
| Ex No. | Structure | Chemical Name |
|---|---|---|
| 292 | 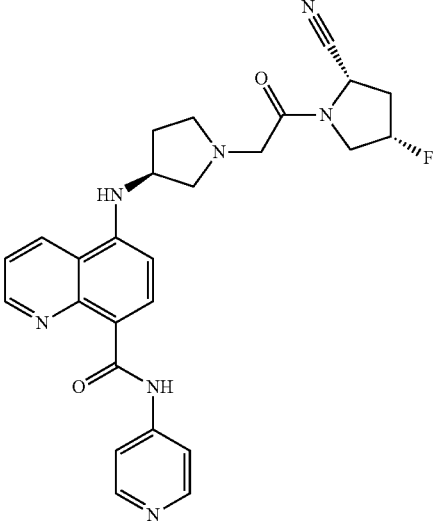 [SMILES: N#C[C@@H]1C[C@H](F)CN1C(=O)CN1CC[C@H](Nc2ccc(C(=O)Nc3ccncc3)c3ncccc23)C1] | N-(4-pyridyl)-5-[[(3S)-1-[2-oxo-2-[(2S,4S)-2-cyano-4-fluoro-pyrrolidin-1-yl]ethyl]pyrrolidin-3-yl]amino]quinoline-8-carboxamide |
| 293 | 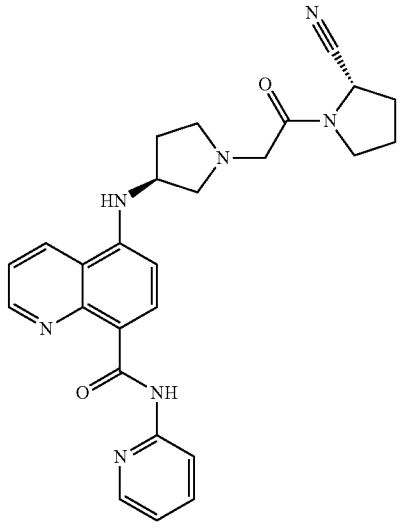 [SMILES: N#C[C@@H]1CCCN1C(=O)CN1CC[C@H](Nc2ccc(C(=O)Nc3ccccn3)c3ncccc23)C1] | N-(2-pyridyl)-5-[[(3S)-1-[2-oxo-2-[(2S)-2-cyanopyrrolidin-1-yl]ethyl]pyrrolidin-3-yl]amino]quinoline-8-carboxamide |
| 294 | 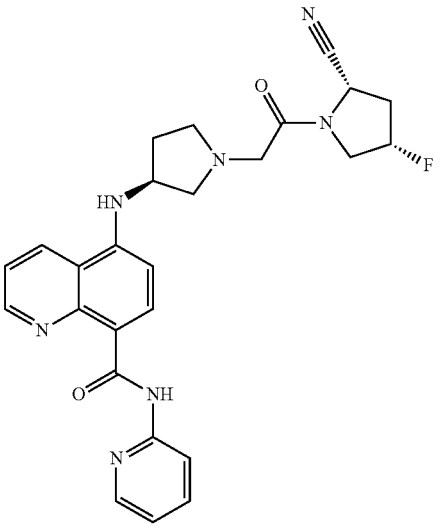 [SMILES: N#C[C@@H]1C[C@H](F)CN1C(=O)CN1CC[C@H](Nc2ccc(C(=O)Nc3ccccn3)c3ncccc23)C1] | N-(2-pyridyl)-5-[[(3S)-1-[2-oxo-2-[(2S,4S)-2-cyano-4-fluoro-pyrrolidin-1-yl]ethyl]pyrrolidin-3-yl]amino]quinoline-8-carboxamide |

TABLE 1-continued

| Ex No. | Structure | Chemical Name |
| --- | --- | --- |
| 295 | 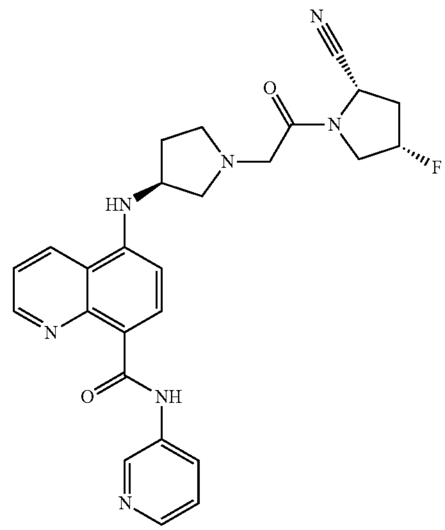 [SMILES: N#C[C@@H]1C[C@H](F)CN1C(=O)CN1CC[C@H](Nc2ccc(C(=O)Nc3cccnc3)c3ncccc23)C1] | N-(3-pyridyl)-5-[[(3S)-1-[2-oxo-2-[(2S,4S)-2-cyano-4-fluoro-pyrrolidin-1-yl]ethyl]pyrrolidin-3-yl]amino]quinoline-8-carboxamide |
| 296 | 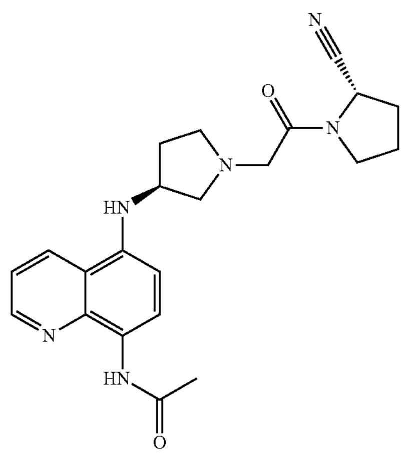 [SMILES: CC(=O)Nc1ccc(N[C@H]2CCN(CC(=O)N3CCC[C@H]3C#N)C2)c2cccnc12] | N-[5-[[(3S)-1-[2-oxo-2-[(2S)-2-cyanopyrrolidin-1-yl]ethyl]pyrrolidin-3-yl]amino]-8-quinolyl]acetamide |
| 297 | 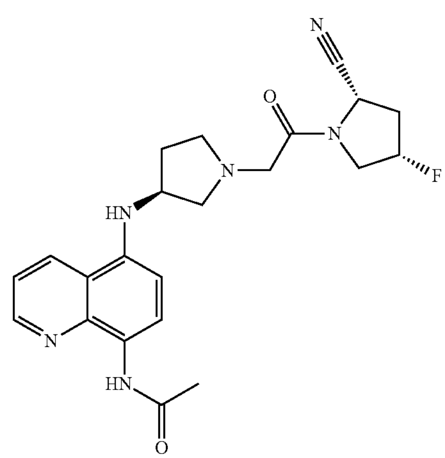 [SMILES: CC(=O)Nc1ccc(N[C@H]2CCN(CC(=O)N3C[C@@H](F)C[C@H]3C#N)C2)c2cccnc12] | N-[5-[[(3S)-1-[2-oxo-2-[(2S,4S)-2-cyano-4-fluoro-pyrrolidin-1-yl]ethyl]pyrrolidin-3-yl]amino]-8-quinolyl]acetamide |

TABLE 1-continued

| Ex No. | Structure | Chemical Name |
| --- | --- | --- |
| 298 | 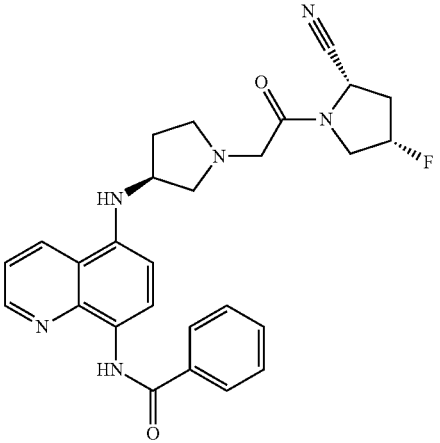 [SMILES: N#C[C@@H]1C[C@H](F)CN1C(=O)CN1CC[C@H](Nc2ccc(NC(=O)c3ccccc3)c3ncccc23)C1] | N-[5-[[(3S)-1-[2-oxo-2-[(2S,4S)-2-cyano-4-fluoro-pyrrolidin-1-yl]ethyl]pyrrolidin-3-yl]amino]-8-quinolyl]benzamide |
| 299 | 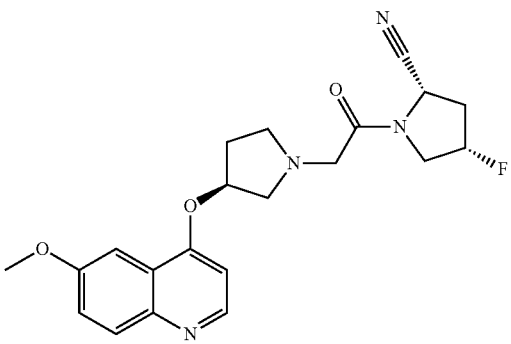 [SMILES: COc1ccc2nccc(O[C@H]3CCN(CC(=O)N4C[C@@H](F)C[C@H]4C#N)C3)c2c1] | (2S,4S)-4-fluoro-1-[2-[(3S)-3-[(6-methoxy-4-quinolyl)oxy]pyrrolidin-1-yl]acetyl]pyrrolidine-2-carbonitrile |
| 300 | 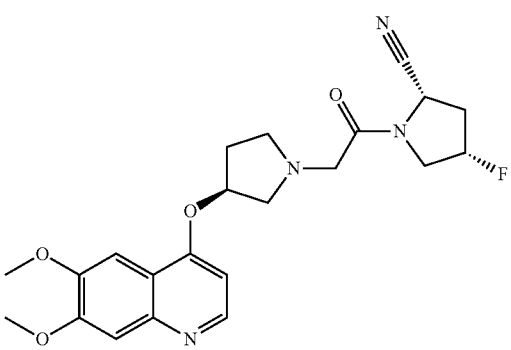 [SMILES: COc1cc2nccc(O[C@H]3CCN(CC(=O)N4C[C@@H](F)C[C@H]4C#N)C3)c2cc1OC] | (2S,4S)-4-fluoro-1-[2-[(3S)-3-[(6,7-dimethoxy-4-quinolyl)oxy]pyrrolidin-1-yl]acetyl]pyrrolidine-2-carbonitrile |
| 301 | 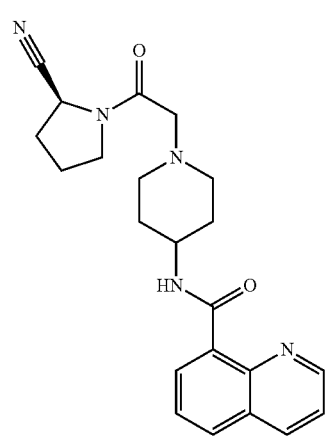 [SMILES: N#C[C@@H]1CCCN1C(=O)CN1CCC(NC(=O)c2cccc3cccnc23)CC1] | N-[1-[2-oxo-2-[(2S)-2-cyanopyrrolidin-1-yl]ethyl]-4-piperidyl]quinoline-8-carboxamide |

TABLE 1-continued

| Ex No. | Structure | Chemical Name |
|---|---|---|
| 302 | 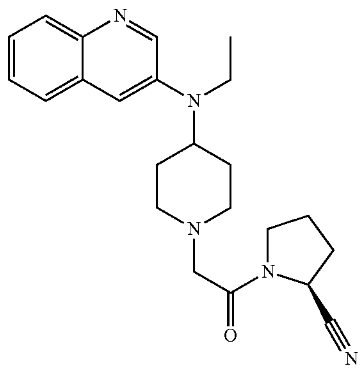 [SMILES: CCN(c1cnc2ccccc2c1)C1CCN(CC(=O)N2CCC[C@H]2C#N)CC1] | (2S)-1-[2-[4-[ethyl(3-quinolyl)amino]-1-piperidyl]acetyl]pyrrolidine-2-carbonitrile |
| 303 | 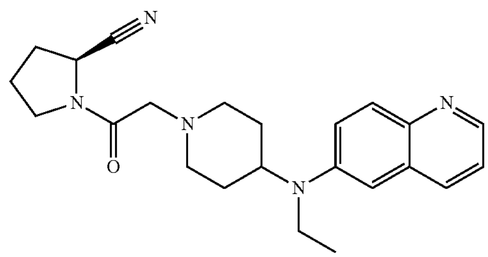 [SMILES: CCN(c1ccc2ncccc2c1)C1CCN(CC(=O)N2CCC[C@H]2C#N)CC1] | (2S)-1-[2-[4-[ethyl(6-quinolyl)amino]-1-piperidyl]acetyl]pyrrolidine-2-carbonitrile |
| 304 | 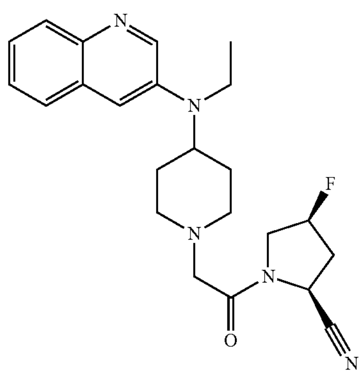 [SMILES: CCN(c1cnc2ccccc2c1)C1CCN(CC(=O)N2C[C@@H](F)C[C@H]2C#N)CC1] | (2S,4S)-1-[2-[4-[ethyl(3-quinolyl)amino]-1-piperidyl]acetyl]-4-fluoro-pyrrolidine-2-carbonitrile |
| 305 | 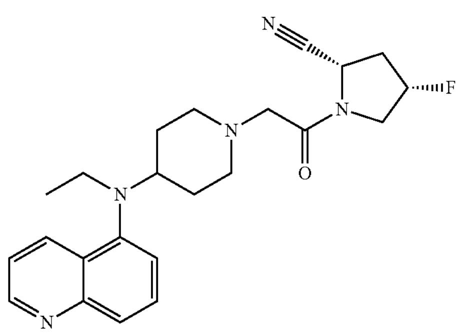 [SMILES: CCN(c1cccc2ncccc12)C1CCN(CC(=O)N2C[C@@H](F)C[C@H]2C#N)CC1] | (2S,4S)-1-[2-[4-[ethyl(5-quinolyl)amino]-1-piperidyl]acetyl]-4-fluoro-pyrrolidine-2-carbonitrile |
| 306 | 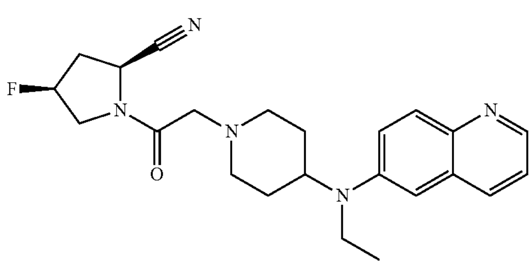 [SMILES: CCN(c1ccc2ncccc2c1)C1CCN(CC(=O)N2C[C@@H](F)C[C@H]2C#N)CC1] | (2S,4S)-1-[2-[4-[ethyl(6-quinolyl)amino]-1-piperidyl]acetyl]-4-fluoro-pyrrolidine-2-carbonitrile |

TABLE 1-continued

| Ex No. | Structure | Chemical Name |
|---|---|---|
| 307 | 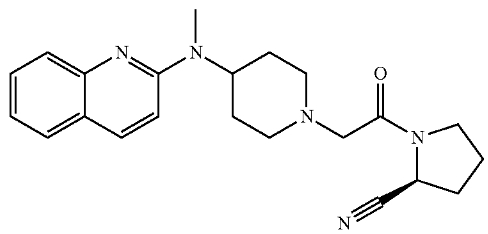 [SMILES: CN(c1ccc2ccccc2n1)C1CCN(CC(=O)N2CCC[C@H]2C#N)CC1] | (2S)-1-[2-[4-[methyl(2-quinolyl)amino]-1-piperidyl]acetyl]pyrrolidine-2-carbonitrile |
| 308 | 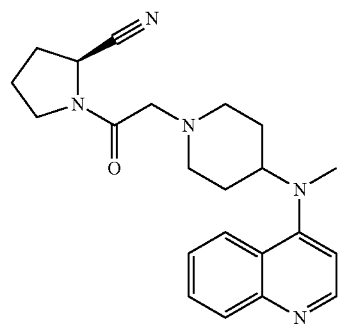 [SMILES: CN(c1ccnc2ccccc12)C1CCN(CC(=O)N2CCC[C@H]2C#N)CC1] | (2S)-1-[2-[4-[methyl(4-quinolyl)amino]-1-piperidyl]acetyl]pyrrolidine-2-carbonitrile |
| 309 | 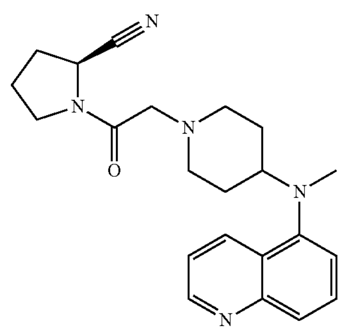 [SMILES: CN(c1cccc2ncccc12)C1CCN(CC(=O)N2CCC[C@H]2C#N)CC1] | (2S)-1-[2-[4-[methyl(5-quinolyl)amino]-1-piperidyl]acetyl]pyrrolidine-2-carbonitrile |
| 310 | 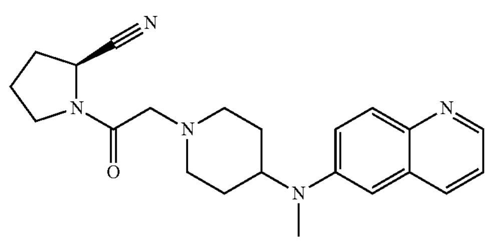 [SMILES: CN(c1ccc2ncccc2c1)C1CCN(CC(=O)N2CCC[C@H]2C#N)CC1] | (2S)-1-[2-[4-[methyl(6-quinolyl)amino]-1-piperidyl]acetyl]pyrrolidine-2-carbonitrile |
| 311 | 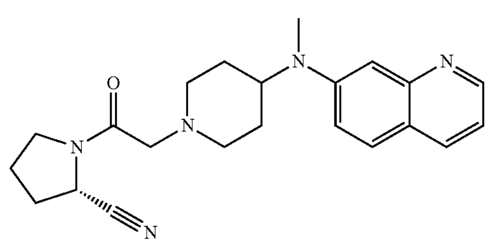 [SMILES: CN(c1ccc2cccnc2c1)C1CCN(CC(=O)N2CCC[C@H]2C#N)CC1] | (2S)-1-[2-[4-[methyl(7-quinolyl)amino]-1-piperidyl]acetyl]pyrrolidine-2-carbonitrile |

TABLE 1-continued

| Ex No. | Structure | Chemical Name |
| --- | --- | --- |
| 312 | 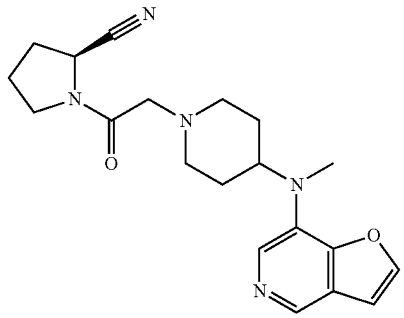 [SMILES: CN(c1cncc2ccoc12)C1CCN(CC(=O)N2CCC[C@H]2C#N)CC1] | (2S)-1-[2-[4-[furo[3,2-c]pyridin-7-yl(methyl)amino]-1-piperidyl]acetyl]pyrrolidine-2-carbonitrile |
| 313 | 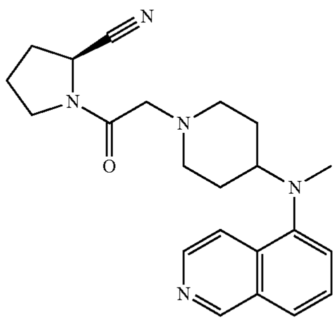 [SMILES: CN(c1cccc2cnccc12)C1CCN(CC(=O)N2CCC[C@H]2C#N)CC1] | (2S)-1-[2-[4-[5-isoquinolyl(methyl)amino]-1-piperidyl]acetyl]pyrrolidine-2-carbonitrile |
| 314 | 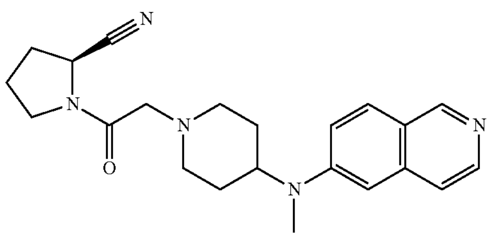 [SMILES: CN(c1ccc2cnccc2c1)C1CCN(CC(=O)N2CCC[C@H]2C#N)CC1] | (2S)-1-(2-(4-(isoquinolin-6-yl(methyl)amino)piperidin-1-yl)acetyl)pyrrolidine-2-carbonitrile |
| 315 | 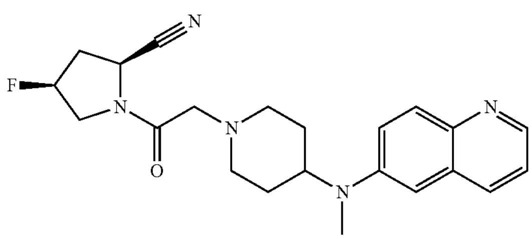 [SMILES: CN(c1ccc2ncccc2c1)C1CCN(CC(=O)N2C[C@@H](F)C[C@H]2C#N)CC1] | (2S,4S)-4-fluoro-1-[2-[4-[methyl(6-quinolyl)amino]-1-piperidyl]acetyl]pyrrolidine-2-carbonitrile |
| 316 | 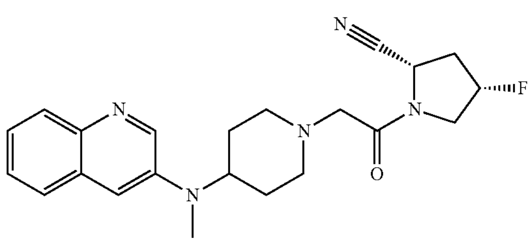 [SMILES: CN(c1cnc2ccccc2c1)C1CCN(CC(=O)N2C[C@@H](F)C[C@H]2C#N)CC1] | (2S,4S)-4-fluoro-1-[2-[4-[methyl(3-quinolyl)amino]-1-piperidyl]acetyl]pyrrolidine-2-carbonitrile |
| 317 | 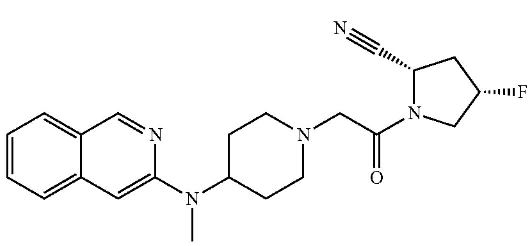 [SMILES: CN(c1cc2ccccc2cn1)C1CCN(CC(=O)N2C[C@@H](F)C[C@H]2C#N)CC1] | (2S,4S)-4-fluoro-1-[2-[4-[3-isoquinolyl(methyl)amino]-1-piperidyl]acetyl]pyrrolidine-2-carbonitrile |

TABLE 1-continued

| Ex No. | Structure | Chemical Name |
|---|---|---|
| 318 | 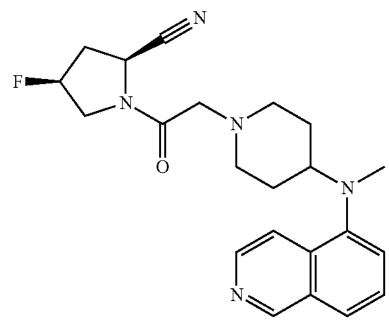 [SMILES: CN(c1cccc2cnccc12)C1CCN(CC(=O)N2C[C@@H](F)C[C@H]2C#N)CC1] | (2S,4S)-4-fluoro-1-[2-[4-[5-isoquinolyl(methyl)amino]-1-piperidyl]acetyl]pyrrolidine-2-carbonitrile |
| 319 | 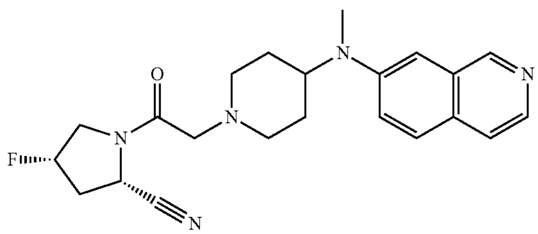 [SMILES: CN(c1ccc2ccncc2c1)C1CCN(CC(=O)N2C[C@@H](F)C[C@H]2C#N)CC1] | (2S,4S)-4-fluoro-1-[2-[4-[7-isoquinolyl(methyl)amino]-1-piperidyl]acetyl]pyrrolidine-2-carbonitrile |
| 320 | 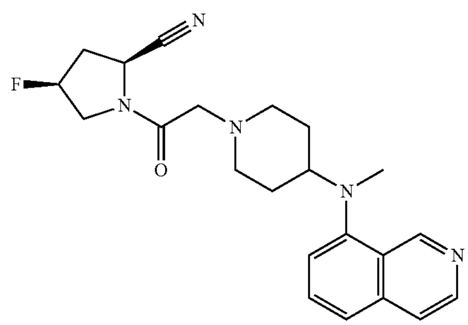 [SMILES: CN(c1cccc2ccncc12)C1CCN(CC(=O)N2C[C@@H](F)C[C@H]2C#N)CC1] | (2S,4S)-4-fluoro-1-[2-[4-[8-isoquinolyl(methyl)amino]-1-piperidyl]acetyl]pyrrolidine-2-carbonitrile |
| 321 | 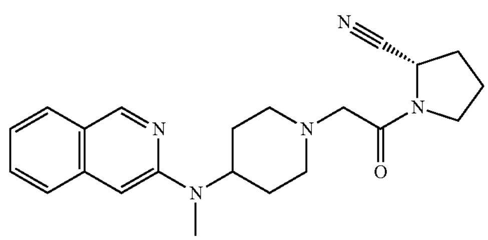 [SMILES: CN(c1cc2ccccc2cn1)C1CCN(CC(=O)N2CCC[C@H]2C#N)CC1] | (2S)-1-[2-[4-[3-isoquinolyl(methyl)amino]-1-piperidyl]acetyl]pyrrolidine-2-carbonitrile |
| 322 | 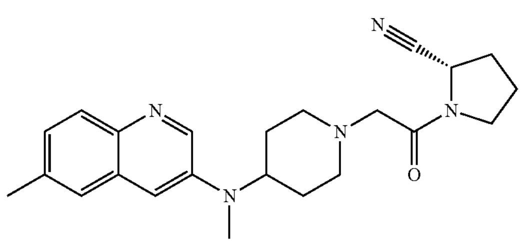 [SMILES: Cc1ccc2ncc(N(C)C3CCN(CC(=O)N4CCC[C@H]4C#N)CC3)cc2c1] | (2S)-1-[2-[4-[methyl-(6-methyl-3-quinolyl)amino]-1-piperidyl]acetyl]pyrrolidine-2-carbonitrile |
| 323 | 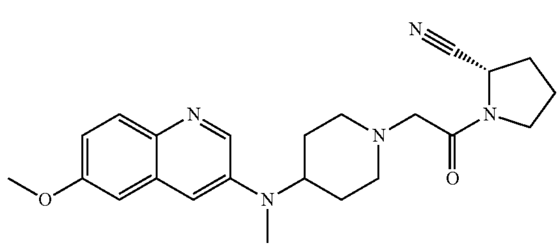 [SMILES: COc1ccc2ncc(N(C)C3CCN(CC(=O)N4CCC[C@H]4C#N)CC3)cc2c1] | (S)-1-(2-(4-((6-methoxyquinolin-3-yl)(methyl)amino)piperidin-1-yl)acetyl)pyrrolidine-2-carbonitrile |

TABLE 1-continued

| Ex No. | Structure | Chemical Name |
| --- | --- | --- |
| 324 | 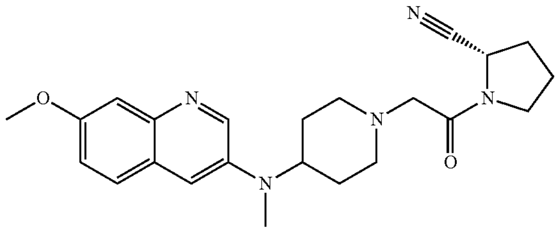 [SMILES: COc1ccc2cc(N(C)C3CCN(CC(=O)N4CCC[C@H]4C#N)CC3)cnc2c1] | (2S)-1-[2-[4-[(7-methoxy-3-quinolyl)-methyl-amino]-1-piperidyl]acetyl]pyrrolidine-2-carbonitrile |
| 325 | 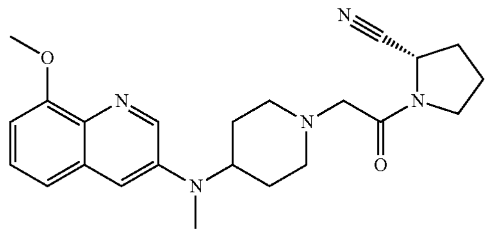 [SMILES: COc1cccc2cc(N(C)C3CCN(CC(=O)N4CCC[C@H]4C#N)CC3)cnc12] | (2S)-1-[2-[4-[(8-methoxy-3-quinolyl)-methyl-amino]-1-piperidyl]acetyl]pyrrolidine-2-carbonitrile |
| 326 | 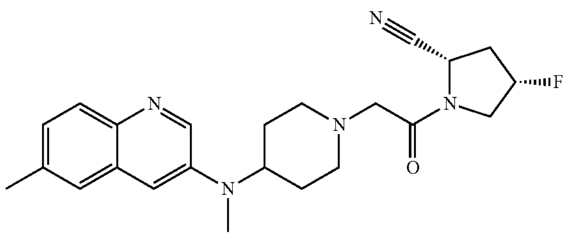 [SMILES: Cc1ccc2ncc(N(C)C3CCN(CC(=O)N4C[C@@H](F)C[C@H]4C#N)CC3)cc2c1] | (2S,4S)-4-fluoro-1-[2-[4-[methyl-(6-methyl-3-quinolyl)amino]-1-piperidyl]acetyl]pyrrolidine-2-carbonitrile |
| 327 | 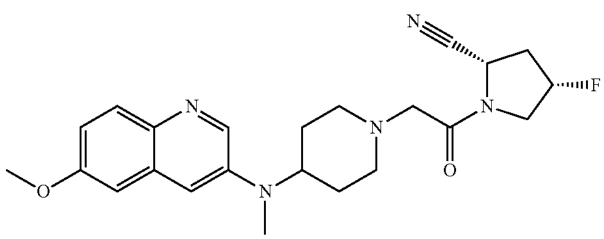 [SMILES: COc1ccc2ncc(N(C)C3CCN(CC(=O)N4C[C@@H](F)C[C@H]4C#N)CC3)cc2c1] | (2S,4S)-4-fluoro-1-(2-(4-((6-methoxyquinolin-3-yl)(methyl)amino)piperidin-1-yl)acetyl)pyrrolidine-2-carbonitrile |
| 328 | 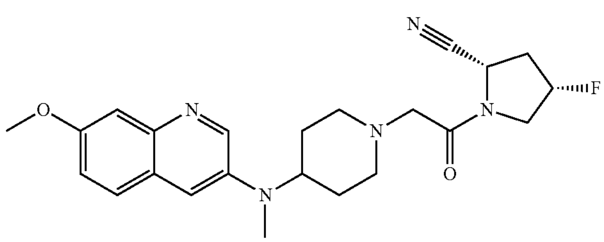 [SMILES: COc1ccc2cc(N(C)C3CCN(CC(=O)N4C[C@@H](F)C[C@H]4C#N)CC3)cnc2c1] | (2S,4S)-4-fluoro-1-(2-(4-((7-methoxyquinolin-3-yl)(methyl)amino)piperidin-1-yl)acetyl)pyrrolidine-2-carbonitrile |
| 329 | 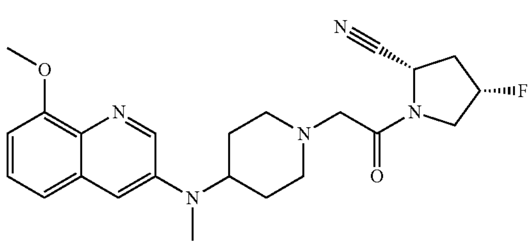 [SMILES: COc1cccc2cc(N(C)C3CCN(CC(=O)N4C[C@@H](F)C[C@H]4C#N)CC3)cnc12] | (2S,4S)-4-fluoro-1-[2-[4-[(8-methoxy-3-quinolyl)-methyl-amino]-1-piperidyl]acetyl]pyrrolidine-2-carbonitrile |

| Ex No. | Structure | Chemical Name |
|---|---|---|
| 330 | 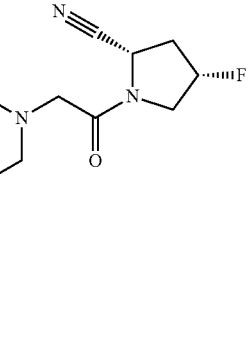 | (2S,4S)-4-fluoro-1-[2-[4-[(8-fluoro-5-quinolyl)amino]-1-piperidyl]acetyl]pyrrolidine-2-carbonitrile |
| 331 | 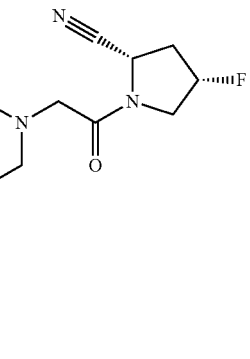 | (2S,4S)-4-fluoro-1-[2-[4-[(8-methyl-5-quinolyl)amino]-1-piperidyl]acetyl]pyrrolidine-2-carbonitrile |
| 332 | 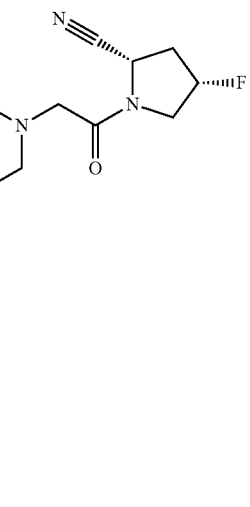 | (2S,4S)-1-[2-[4-[(8-benzyloxy-5-quinolyl)amino]-1-piperidyl]acetyl]-4-fluoro-pyrrolidine-2-carbonitrile |
| 333 | 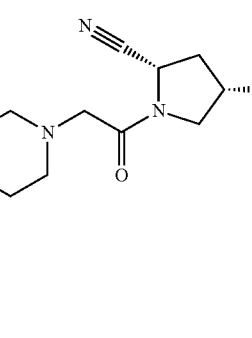 | (2S,4S)-1-[2-[4-[(3-chloro-5-quinolyl)amino]-1-piperidyl]acetyl]-4-fluoro-pyrrolidine-2-carbonitrile |

TABLE 1-continued

| Ex No. | Structure | Chemical Name |
|---|---|---|
| 334 | 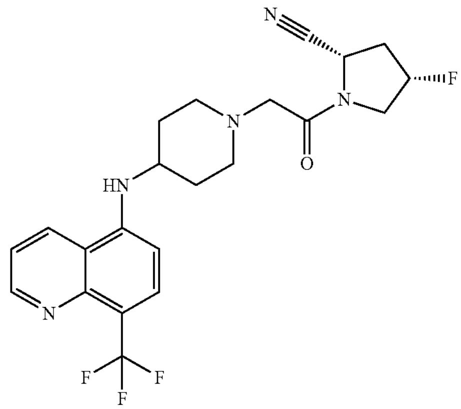 [SMILES: N#C[C@@H]1C[C@H](F)CN1C(=O)CN1CCC(Nc2ccc(C(F)(F)F)c3ncccc23)CC1] | (2S,4S)-4-fluoro-1-[2-[4-[[8-(trifluoromethyl)-5-quinolyl]amino]-1-piperidyl]acetyl]pyrrolidine-2-carbonitrile |
| 335 | 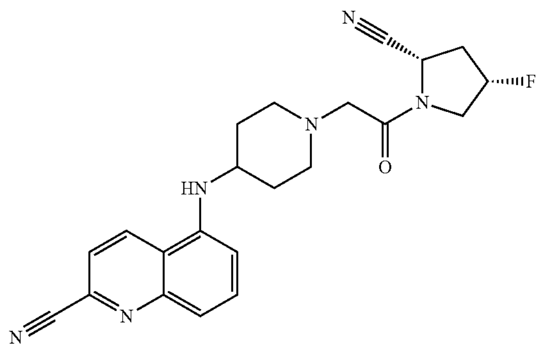 [SMILES: N#Cc1ccc2c(NC3CCN(CC(=O)N4C[C@@H](F)C[C@H]4C#N)CC3)cccc2n1] | 5-[[1-[2-oxo-2-[(2S,4S)-2-cyano-4-fluoro-pyrrolidin-1-yl]ethyl]-4-piperidyl]amino]quinoline-2-carbonitrile |
| 336 | 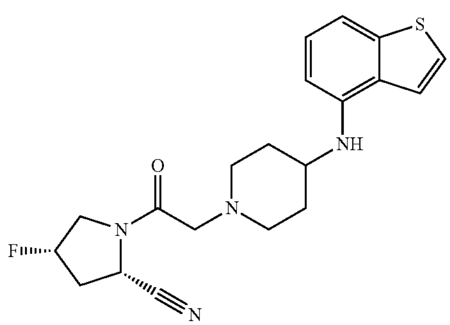 [SMILES: N#C[C@@H]1C[C@H](F)CN1C(=O)CN1CCC(Nc2cccc3sccc23)CC1] | (2S,4S)-1-(2-(4-(benzo[b]thiophen-4-ylamino)piperidin-1-yl)acetyl)-4-fluoropyrrolidine-2-carbonitrile |
| 337 | 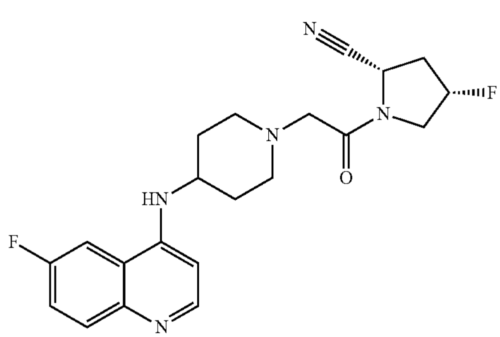 [SMILES: N#C[C@@H]1C[C@H](F)CN1C(=O)CN1CCC(Nc2ccnc3ccc(F)cc23)CC1] | (2S,4S)-4-fluoro-1-[2-[4-[(6-fluoro-4-quinolyl)amino]-1-piperidyl]acetyl]pyrrolidine-2-carbonitrile |

TABLE 1-continued

| Ex No. | Structure | Chemical Name |
|---|---|---|
| 338 | 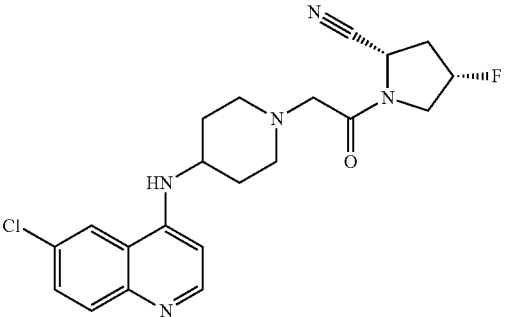 [SMILES: N#C[C@@H]1C[C@H](F)CN1C(=O)CN1CCC(Nc2ccnc3ccc(Cl)cc23)CC1] | (2S,4S)-1-[2-[4-[(6-chloro-4-quinolyl)amino]-1-piperidyl]acetyl]-4-fluoro-pyrrolidine-2-carbonitrile |
| 339 | 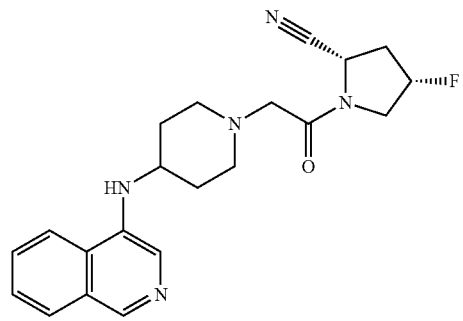 [SMILES: N#C[C@@H]1C[C@H](F)CN1C(=O)CN1CCC(Nc2cncc3ccccc23)CC1] | (2S,4S)-4-fluoro-1-[2-[4-(4-isoquinolylamino)-1-piperidyl]acetyl]pyrrolidine-2-carbonitrile |
| 340 | 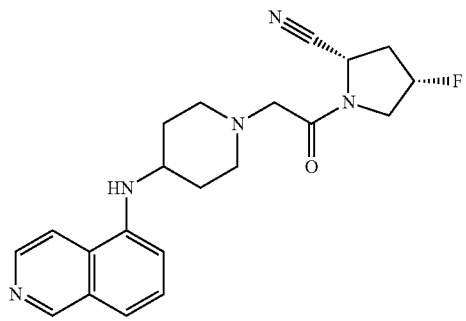 [SMILES: N#C[C@@H]1C[C@H](F)CN1C(=O)CN1CCC(Nc2cccc3cnccc23)CC1] | (2S,4S)-4-fluoro-1-[2-[4-(5-isoquinolylamino)-1-piperidyl]acetyl]pyrrolidine-2-carbonitrile |
| 341 | 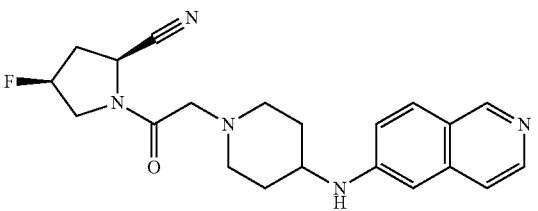 [SMILES: N#C[C@@H]1C[C@H](F)CN1C(=O)CN1CCC(Nc2ccc3cnccc3c2)CC1] | (2S,4S)-4-fluoro-1-[2-[4-(6-isoquinolylamino)-1-piperidyl]acetyl]pyrrolidine-2-carbonitrile |
| 342 | 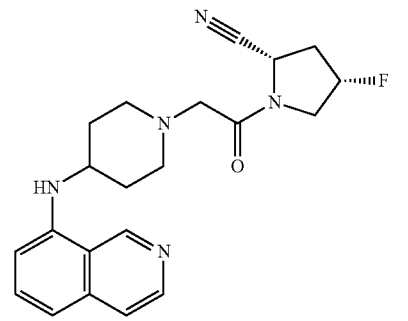 [SMILES: N#C[C@@H]1C[C@H](F)CN1C(=O)CN1CCC(Nc2cccc3ccncc23)CC1] | (2S,4S)-4-fluoro-1-[2-[4-(8-isoquinolylamino)-1-piperidyl]acetyl]pyrrolidine-2-carbonitrile |

TABLE 1-continued

| Ex No. | Structure | Chemical Name |
|---|---|---|
| 343 | 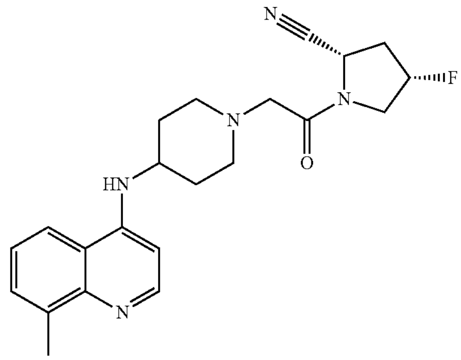 [SMILES: Cc1cccc2c(NC3CCN(CC(=O)N4C[C@@H](F)C[C@H]4C#N)CC3)ccnc12] | (2S,4S)-4-fluoro-1-[2-[4-[(8-methyl-4-quinolyl)amino]-1-piperidyl]acetyl]pyrrolidine-2-carbonitrile |
| 344 | 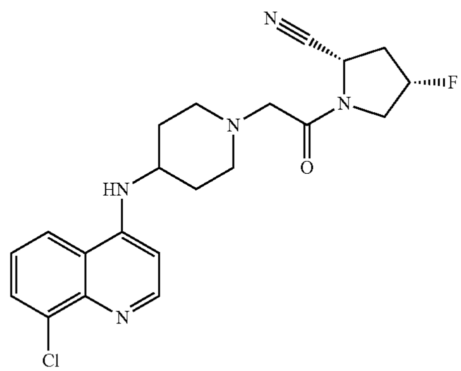 [SMILES: N#C[C@@H]1C[C@H](F)CN1C(=O)CN1CCC(Nc2ccnc3c(Cl)cccc23)CC1] | (2S,4S)-1-[2-[4-[(8-chloro-4-quinolyl)amino]-1-piperidyl]acetyl]-4-fluoro-pyrrolidine-2-carbonitrile |
| 345 | 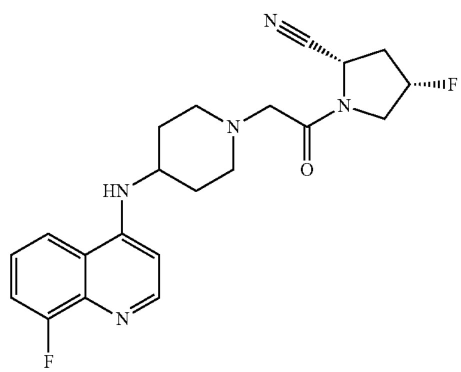 [SMILES: N#C[C@@H]1C[C@H](F)CN1C(=O)CN1CCC(Nc2ccnc3c(F)cccc23)CC1] | (2S,4S)-4-fluoro-1-[2-[4-[(8-fluoro-4-quinolyl)amino]-1-piperidyl]acetyl]pyrrolidine-2-carbonitrile |
| 346 | 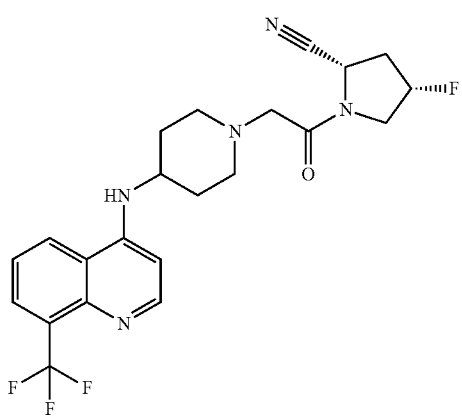 [SMILES: N#C[C@@H]1C[C@H](F)CN1C(=O)CN1CCC(Nc2ccnc3c(C(F)(F)F)cccc23)CC1] | (2S,4S)-4-fluoro-1-[2-[4-[[8-(trifluoromethyl)-4-quinolyl]amino]-1-piperidyl]acetyl]pyrrolidine-2-carbonitrile |

TABLE 1-continued

| Ex No. | Structure | Chemical Name |
|---|---|---|
| 347 | 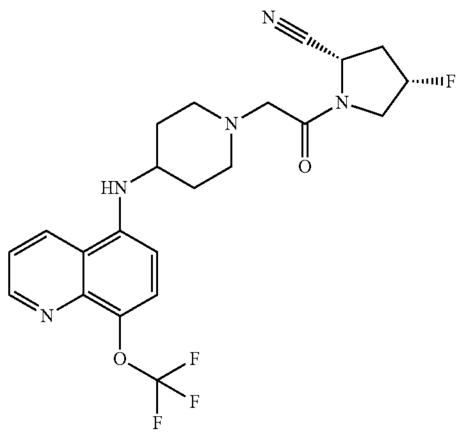 [SMILES: N#C[C@@H]1C[C@H](F)CN1C(=O)CN1CCC(Nc2ccc(OC(F)(F)F)c3ncccc23)CC1] | (2S,4S)-4-fluoro-1-[2-[4-[[8-(trifluoromethoxy)-5-quinolyl]amino]-1-piperidyl]acetyl]pyrrolidine-2-carbonitrile |
| 348 | 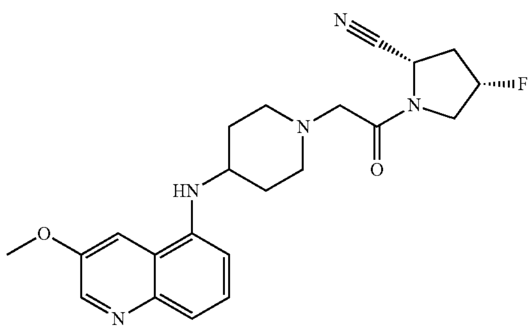 [SMILES: COc1cnc2cccc(NC3CCN(CC(=O)N4C[C@@H](F)C[C@H]4C#N)CC3)c2c1] | (2S,4S)-4-fluoro-1-[2-[4-[(3-methoxy-5-quinolyl)amino]-1-piperidyl]acetyl]pyrrolidine-2-carbonitrile |
| 349 | 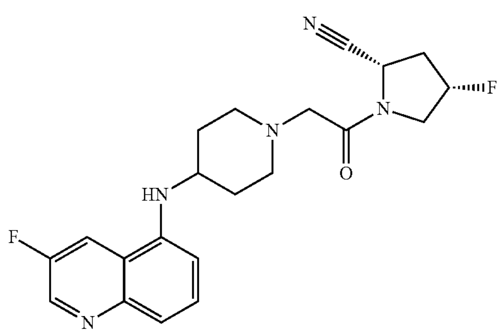 [SMILES: N#C[C@@H]1C[C@H](F)CN1C(=O)CN1CCC(Nc2cccc3ncc(F)cc23)CC1] | (2S,4S)-4-fluoro-1-[2-[4-[(3-fluoro-5-quinolyl)amino]-1-piperidyl]acetyl]pyrrolidine-2-carbonitrile |
| 350 | 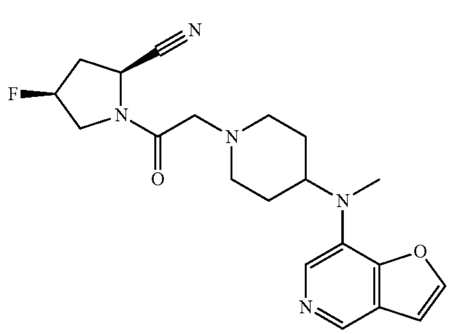 [SMILES: CN(c1cncc2ccoc12)C1CCN(CC(=O)N2C[C@@H](F)C[C@H]2C#N)CC1] | (2S,4S)-4-fluoro-1-[2-[4-[furo[3,2-c]pyridin-7-yl(methyl)amino]-1-piperidyl]acetyl]pyrrolidine-2-carbonitrile |

TABLE 1-continued

| Ex No. | Structure | Chemical Name |
|---|---|---|
| 351 | 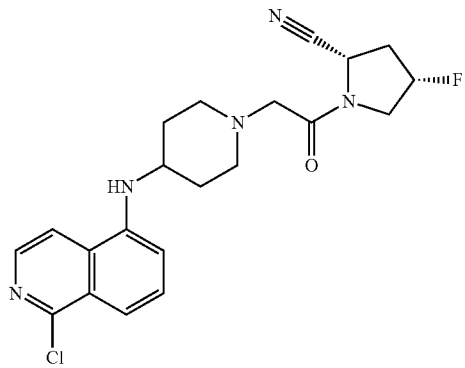 [SMILES: N#C[C@@H]1C[C@H](F)CN1C(=O)CN1CCC(Nc2cccc3c(Cl)nccc23)CC1] | (2S,4S)-1-[2-[4-[(1-chloro-5-isoquinolyl)amino]-1-piperidyl]acetyl]-4-fluoro-pyrrolidine-2-carbonitrile |
| 352 | 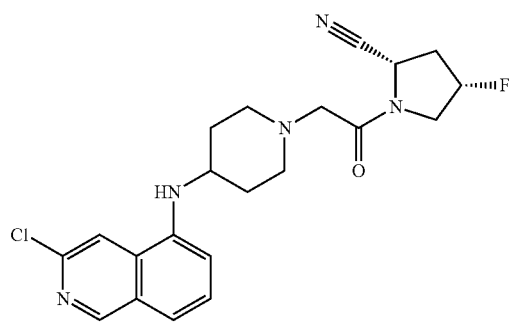 [SMILES: N#C[C@@H]1C[C@H](F)CN1C(=O)CN1CCC(Nc2cccc3cnc(Cl)cc23)CC1] | (2S,4S)-1-[2-[4-[(3-chloro-5-isoquinolyl)amino]-1-piperidyl]acetyl]-4-fluoro-pyrrolidine-2-carbonitrile |
| 353 | 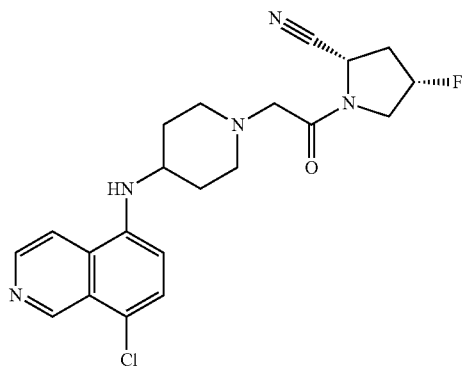 | (2S,4S)-1-[2-[4-[(8-chloro-5-isoquinolyl)amino]-1-piperidyl]acetyl]-4-fluoro-pyrrolidine-2-carbonitrile |
| 354 | 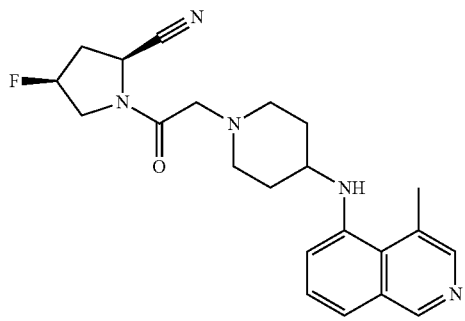 [SMILES: Cc1cncc2cccc(NC3CCN(CC(=O)N4C[C@@H](F)C[C@H]4C#N)CC3)c12] | (2S,4S)-4-fluoro-1-[2-[4-[(4-methyl-5-isoquinolyl)amino]-1-piperidyl]acetyl]pyrrolidine-2-carbonitrile |

TABLE 1-continued

| Ex No. | Structure | Chemical Name |
|---|---|---|
| 355 | 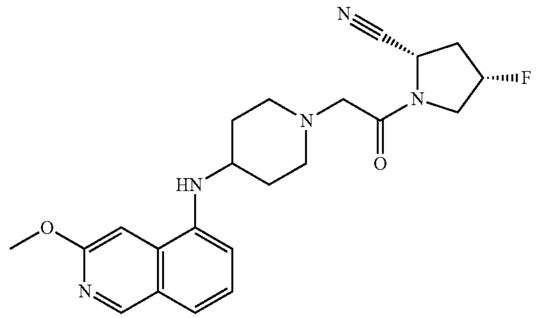 [SMILES: COc1cc2c(NC3CCN(CC(=O)N4C[C@@H](F)C[C@H]4C#N)CC3)cccc2cn1] | (2S,4S)-4-fluoro-1-[2-[4-[(3-methoxy-5-isoquinolyl)amino]-1-piperidyl]acetyl]pyrrolidine-2-carbonitrile |
| 356 | 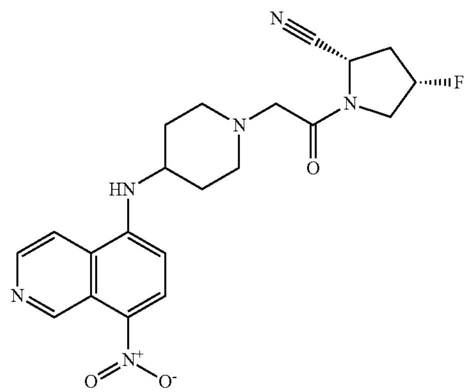 [SMILES: N#C[C@@H]1C[C@H](F)CN1C(=O)CN1CCC(Nc2ccc([N+](=O)[O-])c3cnccc23)CC1] | (2S,4S)-4-fluoro-1-[2-[4-[(8-nitro-5-isoquinolyl)amino]-1-piperidyl]acetyl]pyrrolidine-2-carbonitrile |
| 357 | 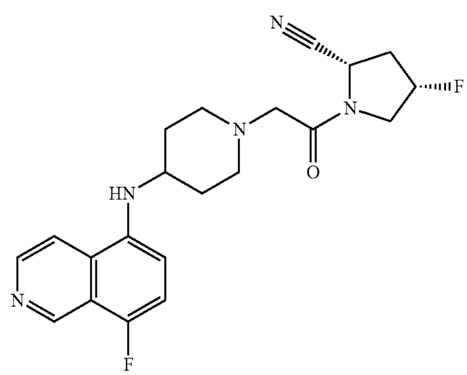 [SMILES: N#C[C@@H]1C[C@H](F)CN1C(=O)CN1CCC(Nc2ccc(F)c3cnccc23)CC1] | (2S,4S)-4-fluoro-1-[2-[4-[(8-fluoro-5-isoquinolyl)amino]-1-piperidyl]acetyl]pyrrolidine-2-carbonitrile |
| 358 | 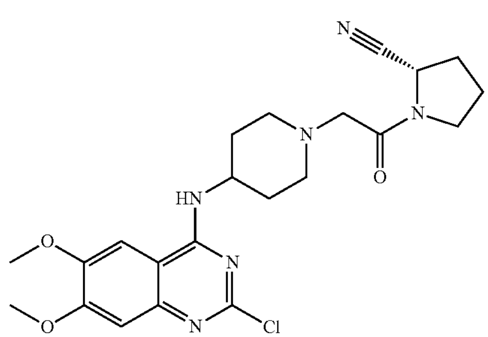 [SMILES: COc1cc2nc(Cl)nc(NC3CCN(CC(=O)N4CCC[C@H]4C#N)CC3)c2cc1OC] | (2S)-1-[2-[4-[(2-chloro-6,7-dimethoxy-quinazolin-4-yl)amino]-1-piperidyl]acetyl]pyrrolidine-2-carbonitrile |

TABLE 1-continued

| Ex No. | Structure | Chemical Name |
|---|---|---|
| 359 | 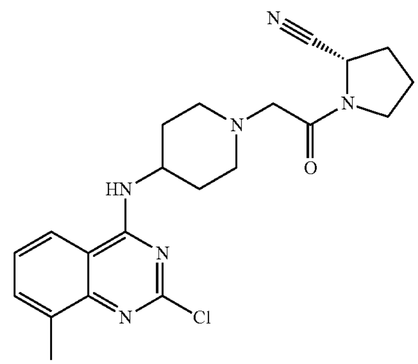 [SMILES: Cc1cccc2c(NC3CCN(CC(=O)N4CCC[C@H]4C#N)CC3)nc(Cl)nc12] | (2S)-1-[2-[4-[(2-chloro-8-methyl-quinazolin-4-yl)amino]-1-piperidyl]acetyl]pyrrolidine-2-carbonitrile |
| 360 | 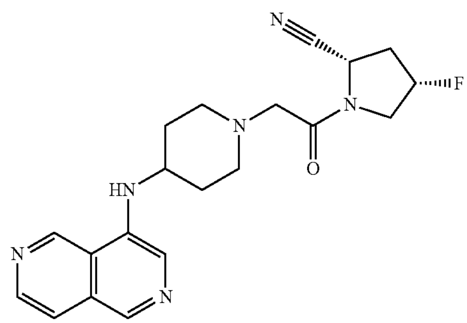 [SMILES: N#C[C@@H]1C[C@H](F)CN1C(=O)CN1CCC(Nc2cncc3ccncc23)CC1] | (2S,4S)-4-fluoro-1-[2-[4-(2,6-naphthyridin-4-ylamino)-1-piperidyl]acetyl]pyrrolidine-2-carbonitrile |
| 361 | 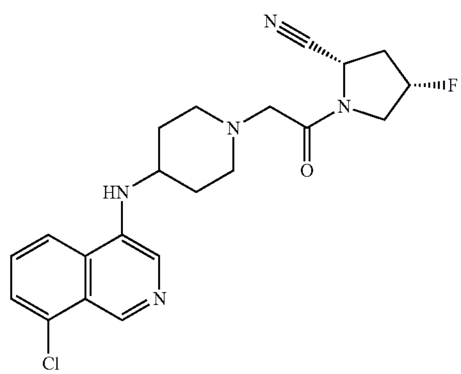 [SMILES: N#C[C@@H]1C[C@H](F)CN1C(=O)CN1CCC(Nc2cncc3c(Cl)cccc23)CC1] | (2S,4S)-1-[2-[4-[(8-chloro-4-isoquinolyl)amino]-1-piperidyl]acetyl]-4-fluoro-pyrrolidine-2-carbonitrile |
| 362 | 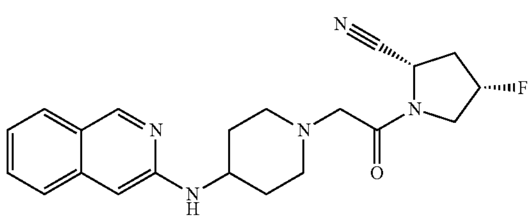 [SMILES: N#C[C@@H]1C[C@H](F)CN1C(=O)CN1CCC(Nc2cc3ccccc3cn2)CC1] | (2S,4S)-4-fluoro-1-[2-[4-(3-quinolylamino)-1-piperidyl]acetyl]pyrrolidine-2-carbonitrile |
| 363 | 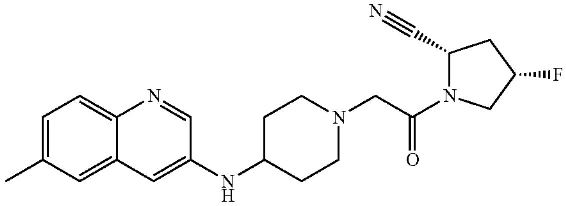 [SMILES: Cc1ccc2ncc(NC3CCN(CC(=O)N4C[C@@H](F)C[C@H]4C#N)CC3)cc2c1] | (2S,4S)-4-fluoro-1-[2-[4-[(6-methyl-3-quinolyl)amino]-1-piperidyl]acetyl]pyrrolidine-2-carbonitrile |

TABLE 1-continued

| Ex No. | Structure | Chemical Name |
|---|---|---|
| 364 | 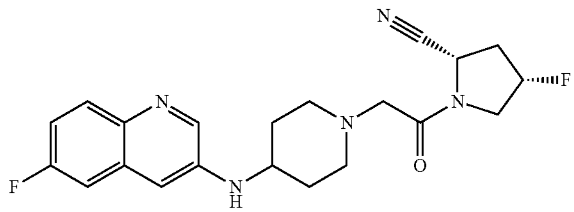 [SMILES: N#C[C@@H]1C[C@H](F)CN1C(=O)CN1CCC(Nc2cnc3ccc(F)cc3c2)CC1] | (2S,4S)-4-fluoro-1-[2-[4-[(6-fluoro-3-quinolyl)amino]-1-piperidyl]acetyl]pyrrolidine-2-carbonitrile |
| 365 | 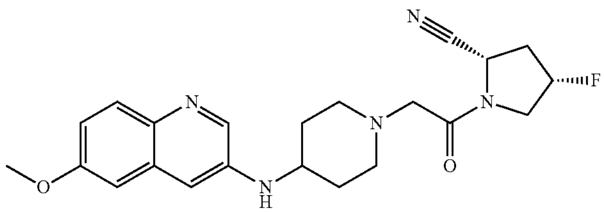 [SMILES: COc1ccc2ncc(NC3CCN(CC(=O)N4C[C@@H](F)C[C@H]4C#N)CC3)cc2c1] | (2S,4S)-4-fluoro-1-[2-[4-[(6-methoxy-3-quinolyl)amino]-1-piperidyl]acetyl]pyrrolidine-2-carbonitrile |
| 366 | 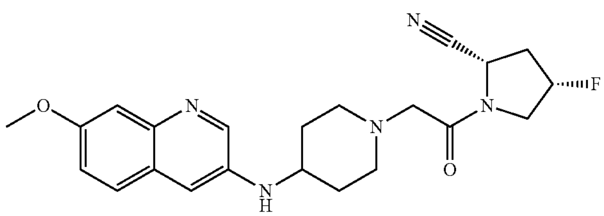 [SMILES: COc1ccc2cc(NC3CCN(CC(=O)N4C[C@@H](F)C[C@H]4C#N)CC3)cnc2c1] | (2S,4S)-4-fluoro-1-[2-[4-[(7-methoxy-3-quinolyl)amino]-1-piperidyl]acetyl]pyrrolidine-2-carbonitrile |
| 367 | 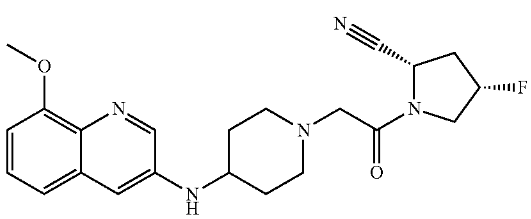 [SMILES: COc1cccc2cc(NC3CCN(CC(=O)N4C[C@@H](F)C[C@H]4C#N)CC3)cnc12] | (2S,4S)-4-fluoro-1-[2-[4-[(8-methoxy-3-quinolyl)amino]-1-piperidyl]acetyl]pyrrolidine-2-carbonitrile |
| 368 | 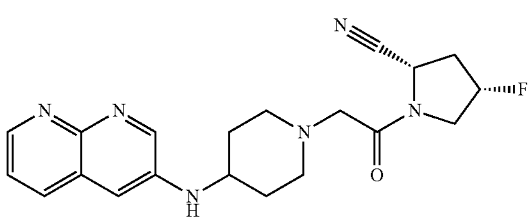 [SMILES: N#C[C@@H]1C[C@H](F)CN1C(=O)CN1CCC(Nc2cnc3ncccc3c2)CC1] | (2S,4S)-4-fluoro-1-[2-[4-(1,8-naphthyridin-3-ylamino)-1-piperidyl]acetyl]pyrrolidine-2-carbonitrile |
| 369 | 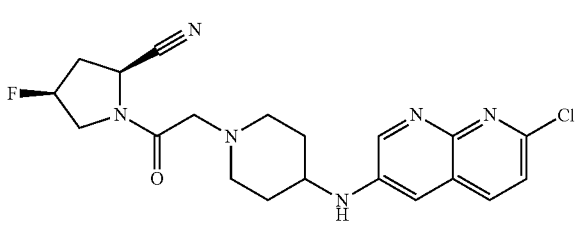 [SMILES: N#C[C@@H]1C[C@H](F)CN1C(=O)CN1CCC(Nc2cnc3nc(Cl)ccc3c2)CC1] | (2S,4S)-1-[2-[4-[(7-chloro-1,8-naphthyridin-3-yl)amino]-1-piperidyl]acetyl]-4-fluoro-pyrrolidine-2-carbonitrile |

TABLE 1-continued

| Ex No. | Structure | Chemical Name |
|---|---|---|
| 370 | 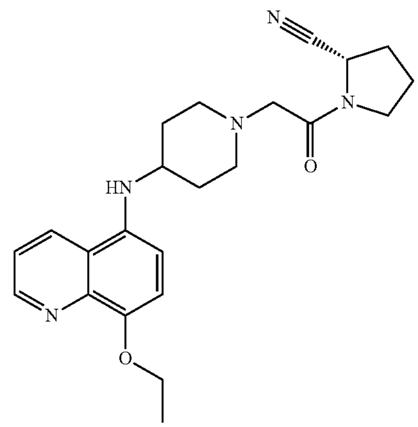 [SMILES: CCOc1ccc(NC2CCN(CC(=O)N3CCC[C@H]3C#N)CC2)c2cccnc12] | (2S)-1-[2-[4-[(8-ethoxy-5-quinolyl)amino]-1-piperidyl]acetyl]pyrrolidine-2-carbonitrile |
| 371 | 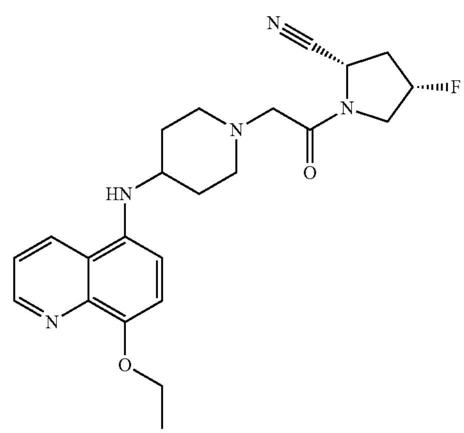 [SMILES: CCOc1ccc(NC2CCN(CC(=O)N3C[C@@H](F)C[C@H]3C#N)CC2)c2cccnc12] | (2S,4S)-1-[2-[4-[(8-ethoxy-5-quinolyl)amino]-1-piperidyl]acetyl]-4-fluoro-pyrrolidine-2-carbonitrile |
| 372 | 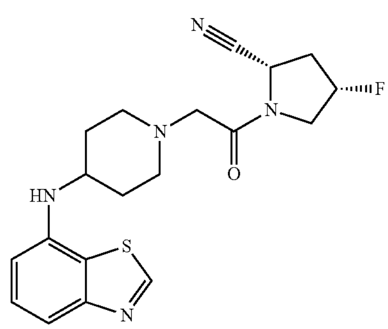 [SMILES: N#C[C@@H]1C[C@H](F)CN1C(=O)CN1CCC(Nc2cccc3ncsc23)CC1] | (2S,4S)-1-[2-[4-(1,3-benzothiazol-7-ylamino)-1-piperidyl]acetyl]-4-fluoro-pyrrolidine-2-carbonitrile |
| 373 | 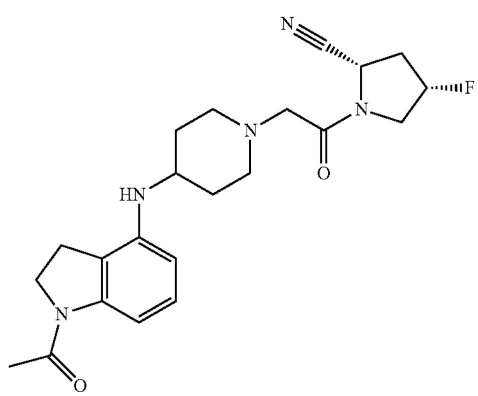 [SMILES: CC(=O)N1CCc2c(NC3CCN(CC(=O)N4C[C@@H](F)C[C@H]4C#N)CC3)cccc21] | (2S,4S)-1-[2-[4-[(1-acetylindolin-4-yl)amino]-1-piperidyl]acetyl]-4-fluoro-pyrrolidine-2-carbonitrile |

TABLE 1-continued

| Ex No. | Structure | Chemical Name |
|---|---|---|
| 374 | 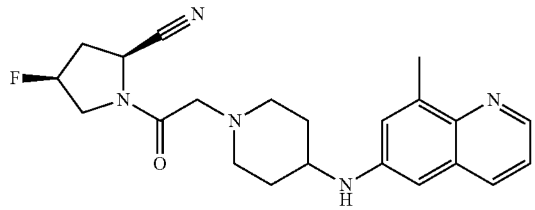 [SMILES: Cc1cc(NC2CCN(CC(=O)N3C[C@@H](F)C[C@H]3C#N)CC2)cc2cccnc12] | (2S,4S)-4-fluoro-1-[2-[4-[(8-methyl-6-quinolyl)amino]-1-piperidyl]acetyl]pyrrolidine-2-carbonitrile |
| 375 | 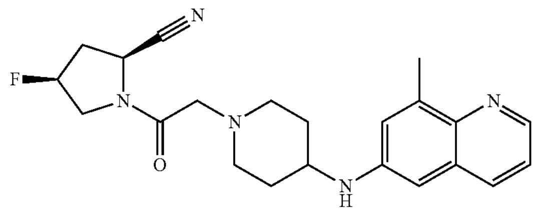 [SMILES: Cc1cc(NC2CCN(CC(=O)N3C[C@@H](F)C[C@H]3C#N)CC2)cc2cccnc12] | (2S,4S)-4-fluoro-1-[2-[4-[(8-fluoro-6-quinolyl)amino]-1-piperidyl]acetyl]pyrrolidine-2-carbonitrile |
| 376 | 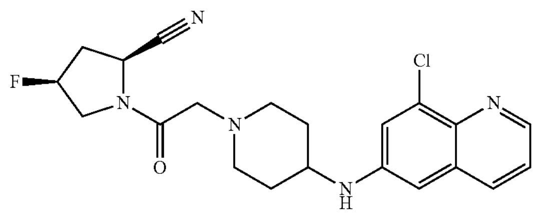 [SMILES: N#C[C@@H]1C[C@H](F)CN1C(=O)CN1CCC(Nc2cc(Cl)c3ncccc3c2)CC1] | (2S,4S)-1-[2-[4-[(8-chloro-6-quinolyl)amino]-1-piperidyl]acetyl]-4-fluoro-pyrrolidine-2-carbonitrile |
| 377 | 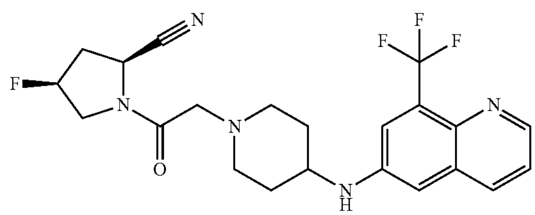 [SMILES: N#C[C@@H]1C[C@H](F)CN1C(=O)CN1CCC(Nc2cc(C(F)(F)F)c3ncccc3c2)CC1] | (2S,4S)-4-fluoro-1-[2-[4-[[8-(trifluoromethyl)-6-quinolyl]amino]-1-piperidyl]acetyl]pyrrolidine-2-carbonitrile |
| 378 | 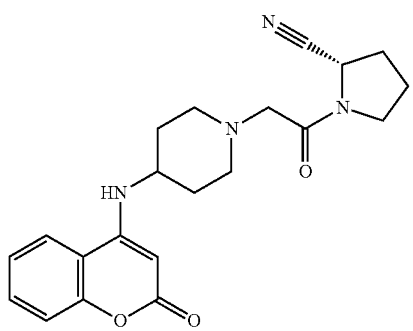 [SMILES: N#C[C@@H]1CCCN1C(=O)CN1CCC(Nc2cc(=O)oc3ccccc23)CC1] | (2S)-1-[2-[4-[(2-oxochromen-4-yl)amino]-1-piperidyl]acetyl]pyrrolidine-2-carbonitrile |
| 379 | 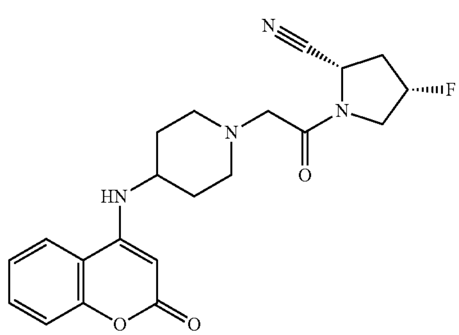 [SMILES: N#C[C@@H]1C[C@H](F)CN1C(=O)CN1CCC(Nc2cc(=O)oc3ccccc23)CC1] | (2S,4S)-4-fluoro-1-[2-[4-[(2-oxochromen-4-yl)amino]-1-piperidyl]acetyl]pyrrolidine-2-carbonitrile |

TABLE 1-continued

| Ex No. | Structure | Chemical Name |
|---|---|---|
| 380 | 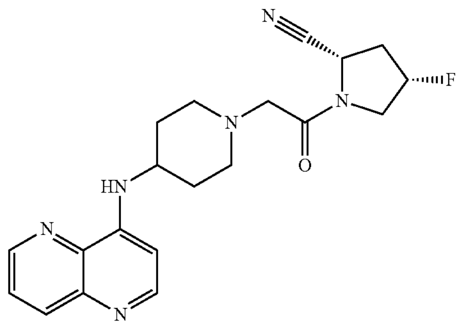 [SMILES: N#C[C@@H]1C[C@H](F)CN1C(=O)CN1CCC(Nc2ccnc3cccnc23)CC1] | (2S,4S)-4-fluoro-1-[2-[4-(1,5-naphthyridin-4-ylamino)-1-piperidyl]acetyl]pyrrolidine-2-carbonitrile |
| 381 | 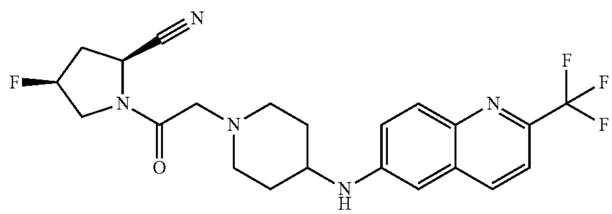 [SMILES: N#C[C@@H]1C[C@H](F)CN1C(=O)CN1CCC(Nc2ccc3nc(C(F)(F)F)ccc3c2)CC1] | (2S,4S)-4-fluoro-1-[2-[4-[[2-(trifluoromethyl)-6-quinolyl]amino]-1-piperidyl]acetyl]pyrrolidine-2-carbonitrile |
| 382 | 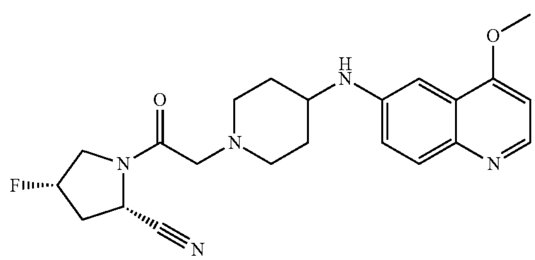 [SMILES: COc1ccnc2ccc(NC3CCN(CC(=O)N4C[C@@H](F)C[C@H]4C#N)CC3)cc12] | (2S,4S)-4-fluoro-1-[2-[4-[(4-methoxy-6-quinolyl)amino]-1-piperidyl]acetyl]pyrrolidine-2-carbonitrile |
| 383 | 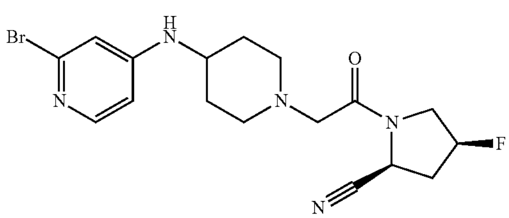 [SMILES: N#C[C@@H]1C[C@H](F)CN1C(=O)CN1CCC(Nc2ccnc(Br)c2)CC1] | (2S,4S)-1-[2-[4-[(2-bromo-4-pyridyl)amino]-1-piperidyl]acetyl]-4-fluoro-pyrrolidine-2-carbonitrile |
| 384 | 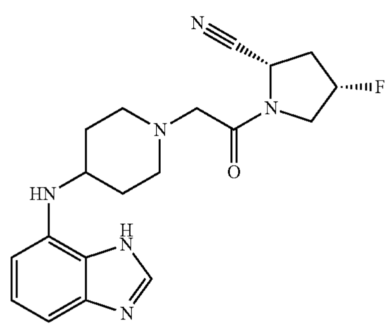 [SMILES: N#C[C@@H]1C[C@H](F)CN1C(=O)CN1CCC(Nc2cccc3nc[nH]c23)CC1] | (2S,4S)-1-[2-[4-(3H-benzimidazol-4-ylamino)-1-piperidyl]acetyl]-4-fluoro-pyrrolidine-2-carbonitrile |
| 385 | 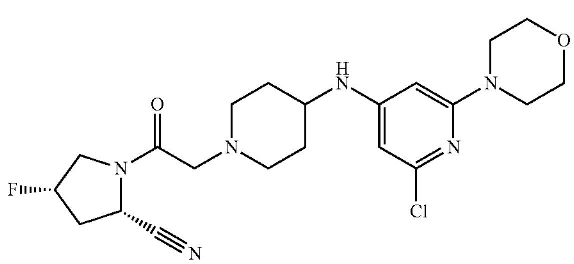 [SMILES: N#C[C@@H]1C[C@H](F)CN1C(=O)CN1CCC(Nc2cc(Cl)nc(N3CCOCC3)c2)CC1] | (2S,4S)-1-[2-[4-[(2-chloro-6-morpholino-4-pyridyl)amino]-1-piperidyl]acetyl]-4-fluoro-pyrrolidine-2-carbonitrile |

TABLE 1-continued

| Ex No. | Structure | Chemical Name |
| --- | --- | --- |
| 386 | 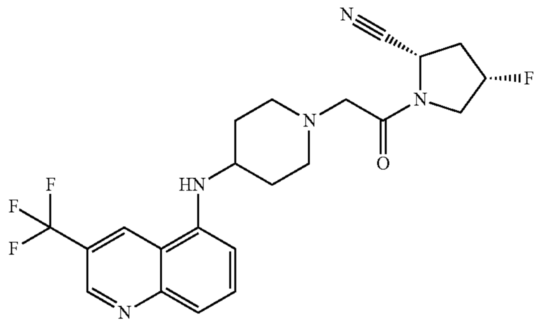 [SMILES: N#C[C@@H]1C[C@H](F)CN1C(=O)CN1CCC(Nc2cccc3ncc(C(F)(F)F)cc23)CC1] | (2S,4S)-4-fluoro-1-[2-[4-[[3-(trifluoromethyl)-5-quinolyl]amino]-1-piperidyl]acetyl]pyrrolidine-2-carbonitrile |
| 387 | 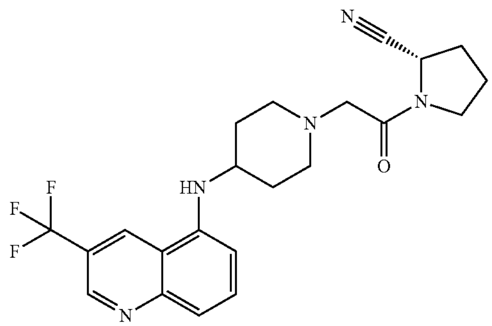 [SMILES: N#C[C@@H]1CCCN1C(=O)CN1CCC(Nc2cccc3ncc(C(F)(F)F)cc23)CC1] | (2S)-1-[2-[4-[[3-(trifluoromethyl)-5-quinolyl]amino]-1-piperidyl]acetyl]pyrrolidine-2-carbonitrile |
| 388 | 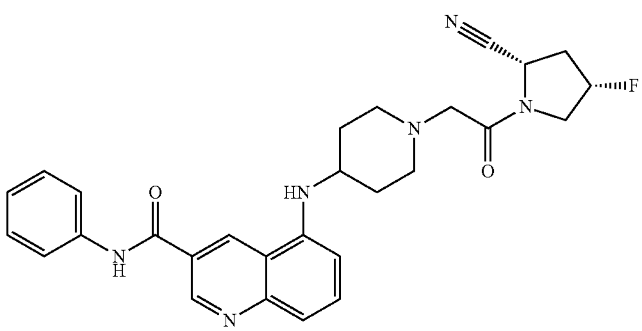 [SMILES: N#C[C@@H]1C[C@H](F)CN1C(=O)CN1CCC(Nc2cccc3ncc(C(=O)Nc4ccccc4)cc23)CC1] | 5-[[1-[2-oxo-2-[(2S,4S)-2-cyano-4-fluoro-pyrrolidin-1-yl]ethyl]-4-piperidyl]amino]-N-phenyl-quinoline-3-carboxamide |
| 389 | 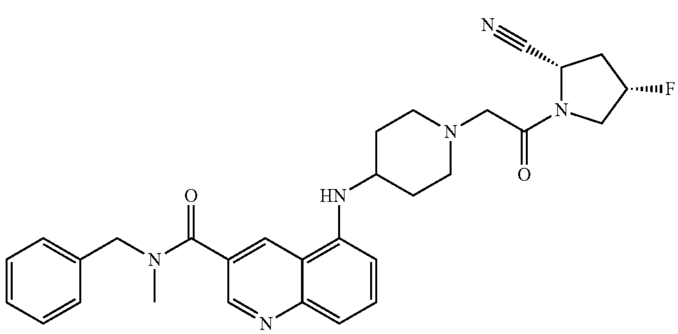 [SMILES: CN(Cc1ccccc1)C(=O)c1cnc2cccc(NC3CCN(CC(=O)N4C[C@@H](F)C[C@H]4C#N)CC3)c2c1] | N-benzyl-N-methyl-5-[[1-[2-oxo-2-[(2S,4S)-2-cyano-4-fluoro-pyrrolidin-1-yl]ethyl]-4-piperidyl]amino]quinoline-3-carboxamide |

TABLE 1-continued
| Ex No. | Structure | Chemical Name |
| --- | --- | --- |
| 390 | 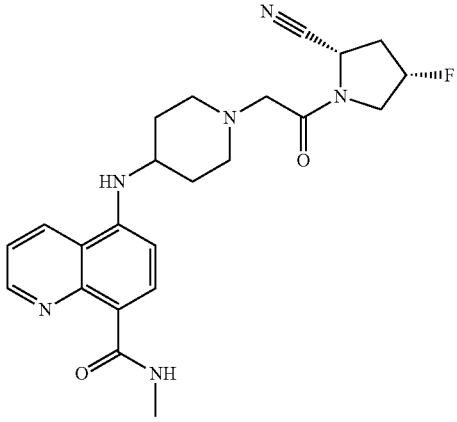 [SMILES: CNC(=O)c1ccc(NC2CCN(CC(=O)N3C[C@@H](F)C[C@H]3C#N)CC2)c2cccnc12] | N-methyl-5-[[1-[2-oxo-2-[(2S,4S)-2-cyano-4-fluoro-pyrrolidin-1-yl]ethyl]-4-piperidyl]amino]quinoline-8-carboxamide |
| 391 | 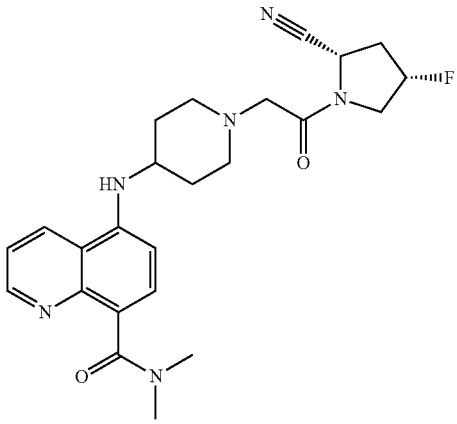 [SMILES: CN(C)C(=O)c1ccc(NC2CCN(CC(=O)N3C[C@@H](F)C[C@H]3C#N)CC2)c2cccnc12] | N,N-dimethyl-5-[[1-[2-oxo-2-[(2S,4S)-2-cyano-4-fluoro-pyrrolidin-1-yl]ethyl]-4-piperidyl]amino]quinoline-8-carboxamide |
| 392 | 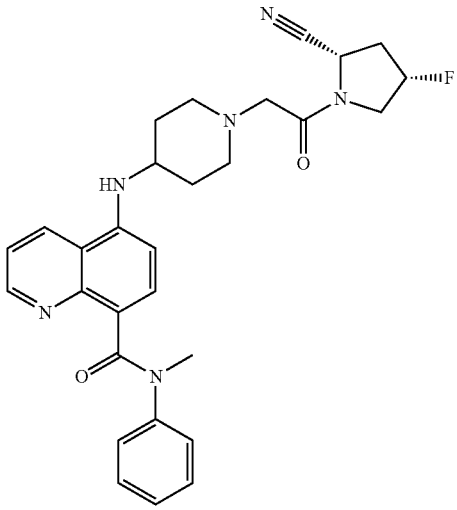 [SMILES: CN(C(=O)c1ccc(NC2CCN(CC(=O)N3C[C@@H](F)C[C@H]3C#N)CC2)c2cccnc12)c1ccccc1] | N-methyl-5-[[1-[2-oxo-2-[(2S,4S)-2-cyano-4-fluoro-pyrrolidin-1-yl]ethyl]-4-piperidyl]amino]-N-phenyl-quinoline-8-carboxamide |

TABLE 1-continued
| Ex No. | Structure | Chemical Name |
| --- | --- | --- |
| 393 | 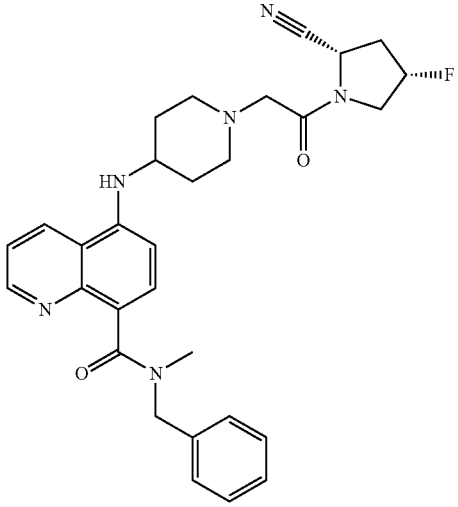 [SMILES: CN(Cc1ccccc1)C(=O)c1ccc(NC2CCN(CC(=O)N3C[C@@H](F)C[C@H]3C#N)CC2)c2cccnc12] | N-benzyl-N-methyl-5-[[1-[2-oxo-2-[(2S,4S)-2-cyano-4-fluoro-pyrrolidin-1-yl]ethyl]-4-piperidyl]amino]quinoline-8-carboxamide |
| 394 | 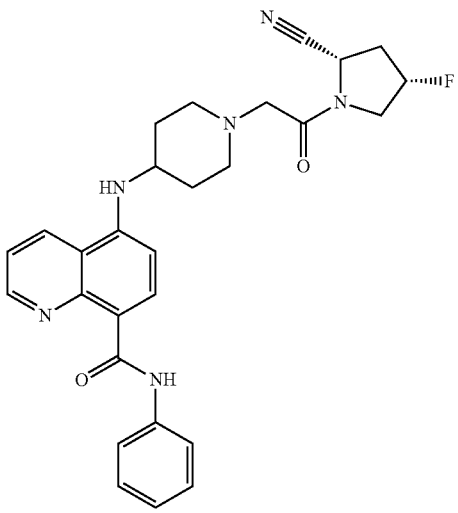 [SMILES: N#C[C@@H]1C[C@H](F)CN1C(=O)CN1CCC(Nc2ccc(C(=O)Nc3ccccc3)c3ncccc23)CC1] | 5-[[1-[2-oxo-2-[(2S,4S)-2-cyano-4-fluoro-pyrrolidin-1-yl]ethyl]-4-piperidyl]amino]-N-phenyl-quinoline-8-carboxamide |
| 395 | 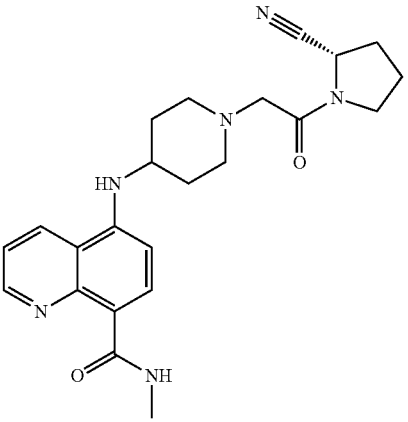 [SMILES: CNC(=O)c1ccc(NC2CCN(CC(=O)N3CCC[C@H]3C#N)CC2)c2cccnc12] | N-methyl-5-[[1-[2-oxo-2-[(2S)-2-cyanopyrrolidin-1-yl]ethyl]-4-piperidyl]amino]quinoline-8-carboxamide |

| Ex No. | Structure | Chemical Name |
|---|---|---|
| 396 | 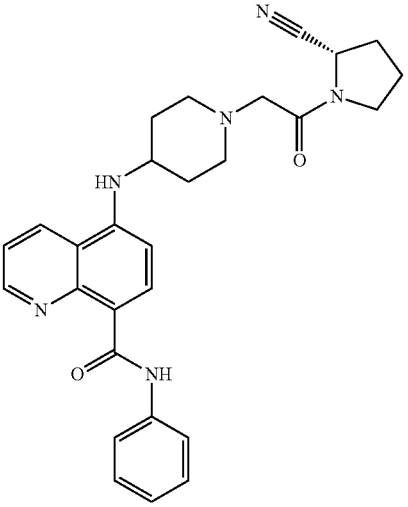 [SMILES: N#C[C@@H]1CCCN1C(=O)CN1CCC(Nc2ccc(C(=O)Nc3ccccc3)c3ncccc23)CC1] | 5-[[1-[2-oxo-2-[(2S)-2-cyanopyrrolidin-1-yl]ethyl]-4-piperidyl]amino]-N-phenyl-quinoline-8-carboxamide |
| 397 | 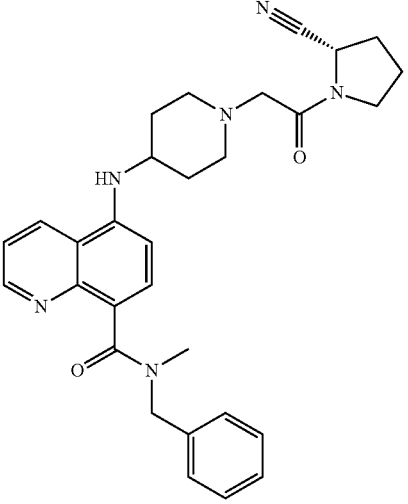 [SMILES: CN(Cc1ccccc1)C(=O)c1ccc(NC2CCN(CC(=O)N3CCC[C@H]3C#N)CC2)c2cccnc12] | N-benzyl-N-methyl-5-[[1-[2-oxo-2-[(2S)-2-cyanopyrrolidin-1-yl]ethyl]-4-piperidyl]amino]quinoline-8-carboxamide |
| 398 | 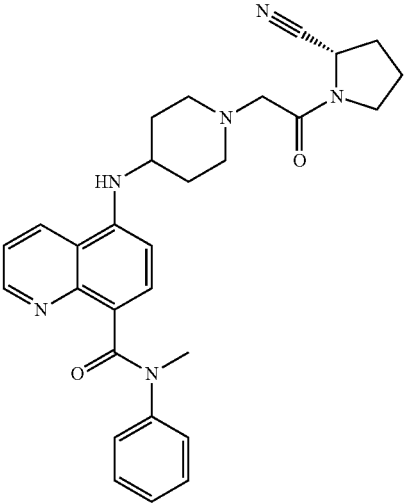 [SMILES: CN(C(=O)c1ccc(NC2CCN(CC(=O)N3CCC[C@H]3C#N)CC2)c2cccnc12)c1ccccc1] | N-methyl-5-[[1-[2-oxo-2-[(2S)-2-cyanopyrrolidin-1-yl]ethyl]-4-piperidyl]amino]-N-phenyl-quinoline-8-carboxamide |

TABLE 1-continued
| Ex No. | Structure | Chemical Name |
|---|---|---|
| 399 | 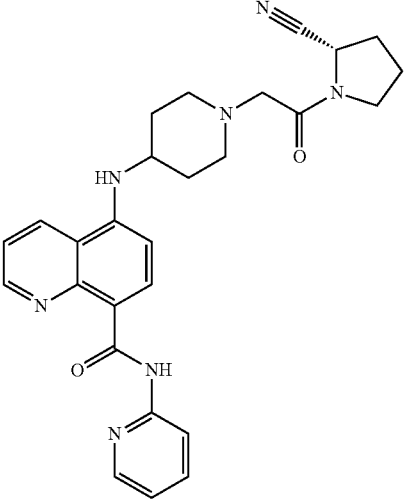 [SMILES: N#C[C@@H]1CCCN1C(=O)CN1CCC(Nc2ccc(C(=O)Nc3ccccn3)c3ncccc23)CC1] | 5-[[1-[2-oxo-2-[(2S)-2-cyanopyrrolidin-1-yl]ethyl]-4-piperidyl]amino]-N-(2-pyridyl)quinoline-8-carboxamide |
| 400 | 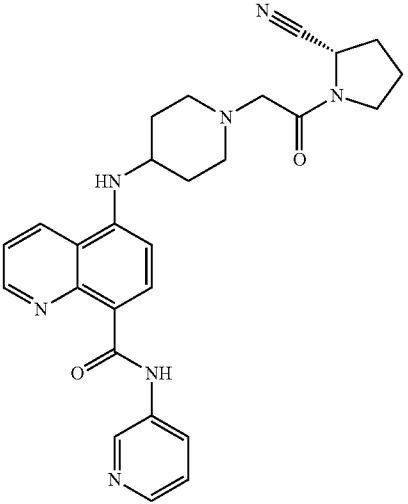 [SMILES: N#C[C@@H]1CCCN1C(=O)CN1CCC(Nc2ccc(C(=O)Nc3cccnc3)c3ncccc23)CC1] | 5-[[1-[2-oxo-2-[(2S)-2-cyanopyrrolidin-1-yl]ethyl]-4-piperidyl]amino]-N-(3-pyridyl)quinoline-8-carboxamide |
| 401 | 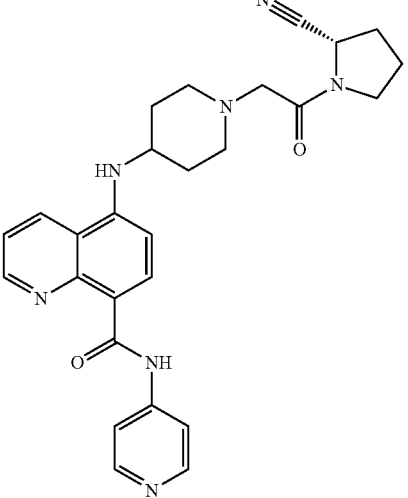 | 5-[[1-[2-oxo-2-[(2S)-2-cyanopyrrolidin-1-yl]ethyl]-4-piperidyl]amino]-N-(4-pyridyl)quinoline-8-carboxamide |

TABLE 1-continued
| Ex No. | Structure | Chemical Name |
|---|---|---|
| 402 | 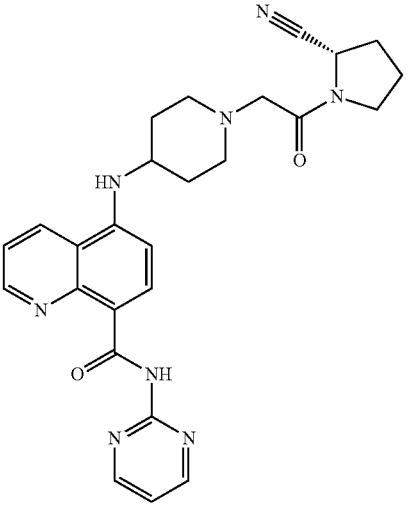 [SMILES: N#C[C@@H]1CCCN1C(=O)CN1CCC(Nc2ccc(C(=O)Nc3ncccn3)c3ncccc23)CC1] | 5-[[1-[2-oxo-2-[(2S)-2-cyanopyrrolidin-1-yl]ethyl]-4-piperidyl]amino]-N-pyrimidin-2-yl-quinoline-8-carboxamide |
| 403 | 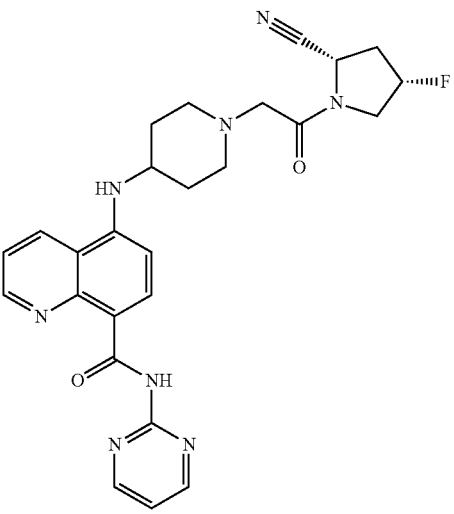 [SMILES: N#C[C@@H]1C[C@H](F)CN1C(=O)CN1CCC(Nc2ccc(C(=O)Nc3ncccn3)c3ncccc23)CC1] | 5-[[1-[2-oxo-2-[(2S,4S)-2-cyano-4-fluoro-pyrrolidin-1-yl]ethyl]-4-piperidyl]amino]-N-pyrimidin-2-yl-quinoline-8-carboxamide |
| 404 | 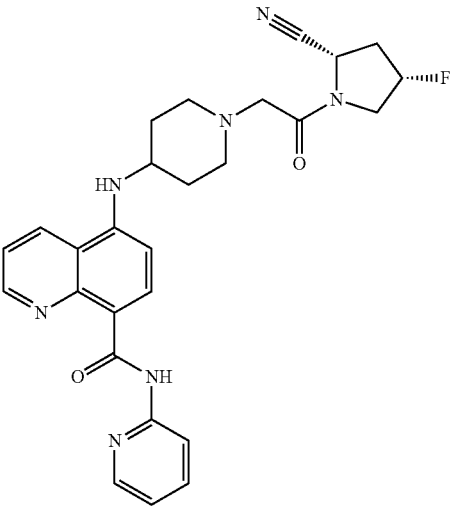 [SMILES: N#C[C@@H]1C[C@H](F)CN1C(=O)CN1CCC(Nc2ccc(C(=O)Nc3ccccn3)c3ncccc23)CC1] | 5-[[1-[2-oxo-2-[(2S,4S)-2-cyano-4-fluoro-pyrrolidin-1-yl]ethyl]-4-piperidyl]amino]-N-(2-pyridyl)quinoline-8-carboxamide |

TABLE 1-continued
| Ex No. | Structure | Chemical Name |
|---|---|---|
| 405 | 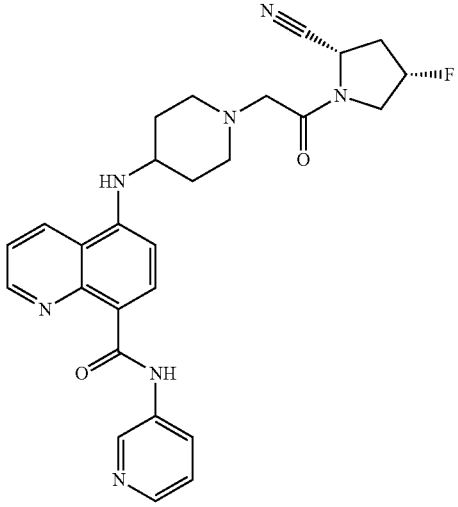 [SMILES: N#C[C@@H]1C[C@H](F)CN1C(=O)CN1CCC(Nc2ccc(C(=O)Nc3cccnc3)c3ncccc23)CC1] | 5-[[1-[2-oxo-2-[(2S,4S)-2-cyano-4-fluoro-pyrrolidin-1-yl]ethyl]-4-piperidyl]amino]-N-(3-pyridyl)quinoline-8-carboxamide |
| 406 | 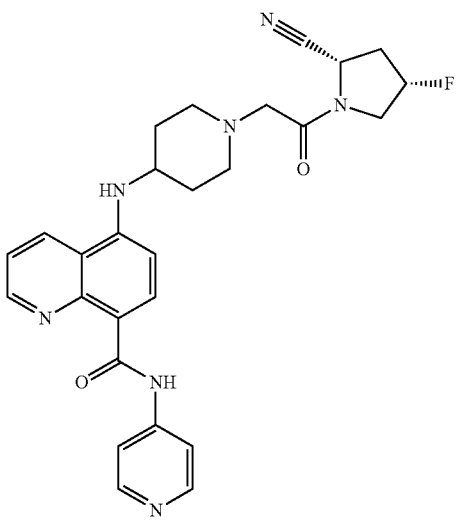 [SMILES: N#C[C@@H]1C[C@H](F)CN1C(=O)CN1CCC(Nc2ccc(C(=O)Nc3ccncc3)c3ncccc23)CC1] | 5-[[1-[2-oxo-2-[(2S,4S)-2-cyano-4-fluoro-pyrrolidin-1-yl]ethyl]-4-piperidyl]amino]-N-(4-pyridyl)quinoline-8-carboxamide |
| 407 | 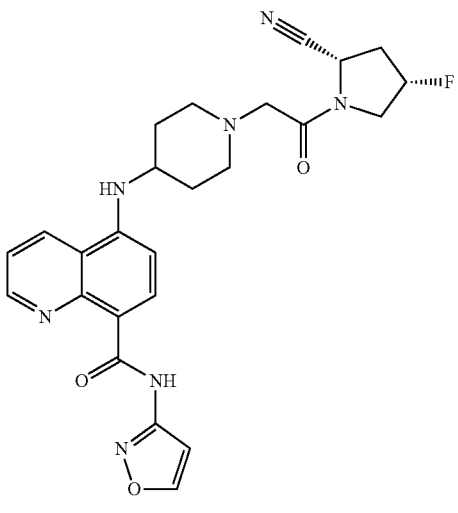 [SMILES: N#C[C@@H]1C[C@H](F)CN1C(=O)CN1CCC(Nc2ccc(C(=O)Nc3ccon3)c3ncccc23)CC1] | N-isoxazol-3-yl-5-[[1-[2-oxo-2-[(2S,4S)-2-cyano-4-fluoro-pyrrolidin-1-yl]ethyl]-4-piperidyl]amino]quinoline-8-carboxamide |

TABLE 1-continued

| Ex No. | Structure | Chemical Name |
| --- | --- | --- |
| 408 | 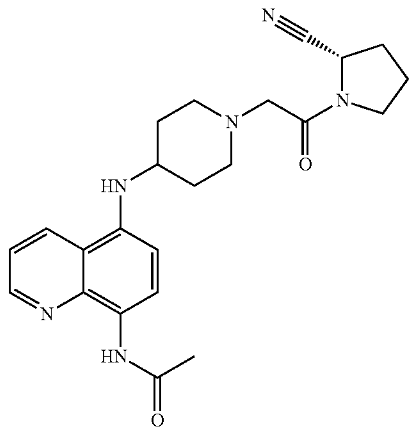 [SMILES: CC(=O)Nc1ccc(NC2CCN(CC(=O)N3CCC[C@H]3C#N)CC2)c2cccnc12] | N-[5-[[1-[2-oxo-2-[(2S)-2-cyanopyrrolidin-1-yl]ethyl]-4-piperidyl]amino]-8-quinolyl]acetamide |
| 409 | 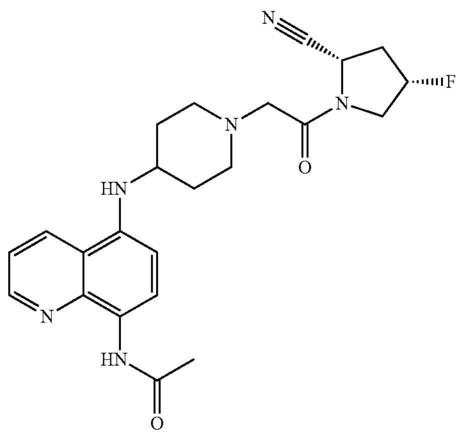 [SMILES: CC(=O)Nc1ccc(NC2CCN(CC(=O)N3C[C@@H](F)C[C@H]3C#N)CC2)c2cccnc12] | N-[5-[[1-[2-oxo-2-[(2S,4S)-2-cyano-4-fluoro-pyrrolidin-1-yl]ethyl]-4-piperidyl]amino]-8-quinolyl]acetamide |
| 410 | 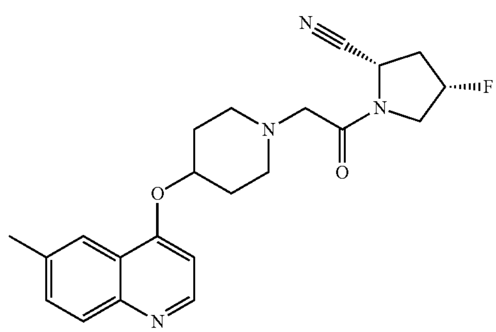 [SMILES: Cc1ccc2nccc(OC3CCN(CC(=O)N4C[C@@H](F)C[C@H]4C#N)CC3)c2c1] | (2S,4S)-4-fluoro-1-[2-[4-[(6-methyl-4-quinolyl)oxy]-1-piperidyl]acetyl]pyrrolidine-2-carbonitrile |
| 411 | 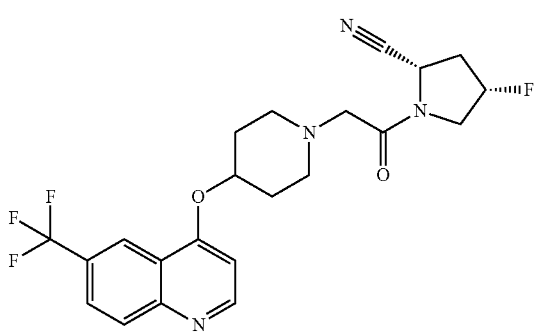 [SMILES: N#C[C@@H]1C[C@H](F)CN1C(=O)CN1CCC(Oc2ccnc3ccc(C(F)(F)F)cc23)CC1] | (2S,4S)-4-fluoro-1-[2-[4-[[6-(trifluoromethyl)-4-quinolyl]oxy]-1-piperidyl]acetyl]pyrrolidine-2-carbonitrile |

TABLE 1-continued

| Ex No. | Structure | Chemical Name |
|---|---|---|
| 412 | 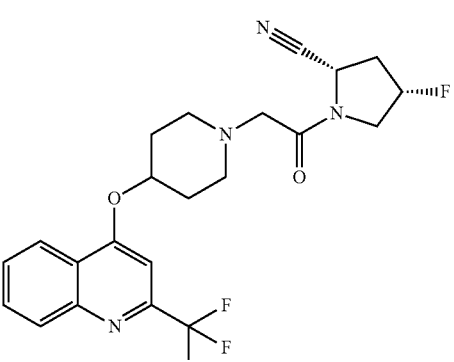 | (2S,4S)-4-fluoro-1-[2-[4-[[2-(trifluoromethyl)-4-quinolyl]oxy]-1-piperidyl]acetyl]pyrrolidine-2-carbonitrile |
| 413 | 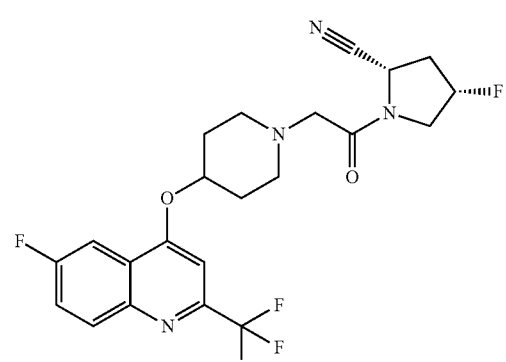 | (2S,4S)-4-fluoro-1-[2-[4-[[6-fluoro-2-(trifluoromethyl)-4-quinolyl]oxy]-1-piperidyl]acetyl]pyrrolidine-2-carbonitrile |
| 414 | 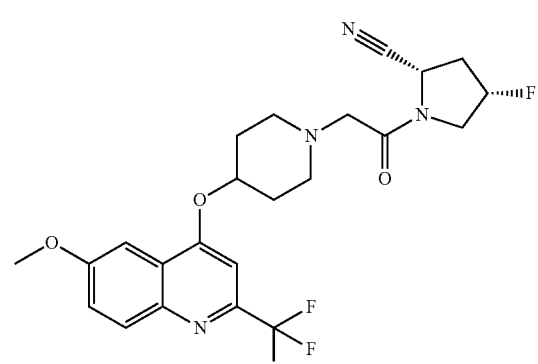 | (2S,4S)-4-fluoro-1-[2-[4-[[6-methoxy-2-(trifluoromethyl)-4-quinolyl]oxy]-1-piperidyl]acetyl]pyrrolidine-2-carbonitrile |
| 415 | 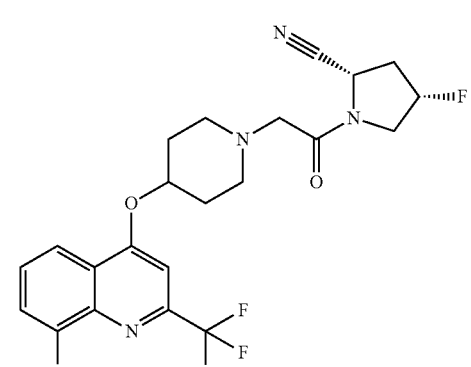 | (2S,4S)-4-fluoro-1-[2-[4-[[8-methoxy-2-(trifluoromethyl)-4-quinolyl]oxy]-1-piperidyl]acetyl]pyrrolidine-2-carbonitrile |

TABLE 1-continued

| Ex No. | Structure | Chemical Name |
| --- | --- | --- |
| 416 | 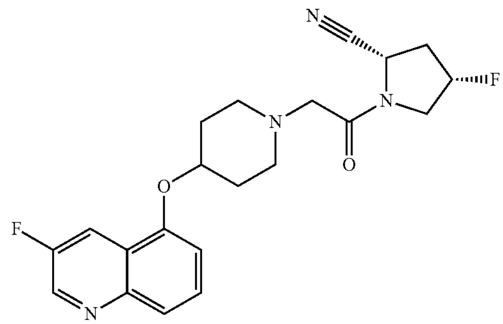 [SMILES: N#C[C@@H]1C[C@H](F)CN1C(=O)CN1CCC(Oc2cccc3ncc(F)cc23)CC1] | (2S,4S)-4-fluoro-1-[2-[4-[(3-fluoro-5-quinolyl)oxy]-1-piperidyl]acetyl]pyrrolidine-2-carbonitrile |
| 417 | 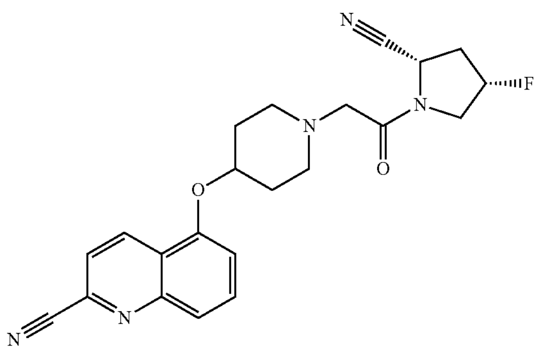 [SMILES: N#Cc1ccc2c(OC3CCN(CC(=O)N4C[C@@H](F)C[C@H]4C#N)CC3)cccc2n1] | 5-[[1-[2-oxo-2-[(2S,4S)-2-cyano-4-fluoro-pyrrolidin-1-yl]ethyl]-4-piperidyl]oxy]quinoline-2-carbonitrile |
| 418 | 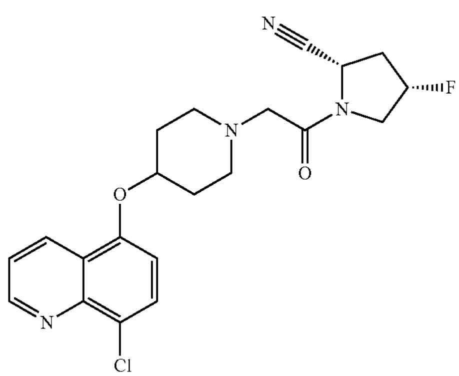 [SMILES: N#C[C@@H]1C[C@H](F)CN1C(=O)CN1CCC(Oc2ccc(Cl)c3ncccc23)CC1] | (2S,4S)-1-[2-[4-[(8-chloro-5-quinolyl)oxy]-1-piperidyl]acetyl]-4-fluoro-pyrrolidine-2-carbonitrile |
| 419 | 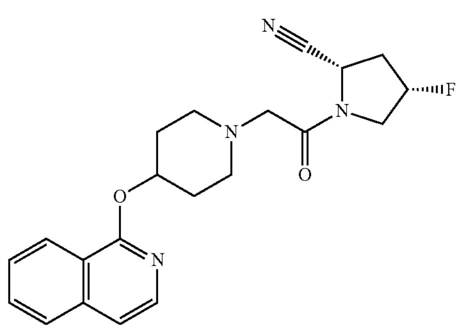 [SMILES: N#C[C@@H]1C[C@H](F)CN1C(=O)CN1CCC(Oc2nccc3ccccc23)CC1] | (2S,4S)-4-fluoro-1-[2-[4-(1-isoquinolyloxy)-1-piperidyl]acetyl]pyrrolidine-2-carbonitrile |

TABLE 1-continued

| Ex No. | Structure | Chemical Name |
| --- | --- | --- |
| 420 | 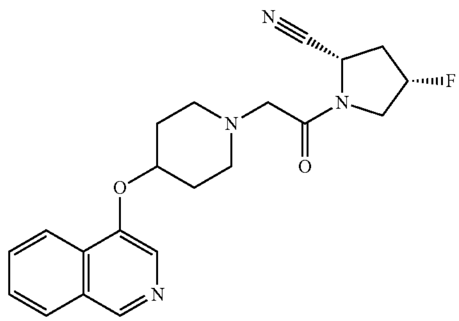 [SMILES: N#C[C@@H]1C[C@H](F)CN1C(=O)CN1CCC(Oc2cncc3ccccc23)CC1] | (2S,4S)-4-fluoro-1-[2-[4-(4-isoquinolyloxy)-1-piperidyl]acetyl]pyrrolidine-2-carbonitrile |
| 421 | 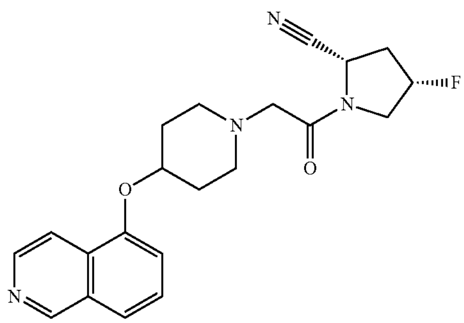 [SMILES: N#C[C@@H]1C[C@H](F)CN1C(=O)CN1CCC(Oc2cccc3cnccc23)CC1] | (2S,4S)-4-fluoro-1-[2-[4-(5-isoquinolyloxy)-1-piperidyl]acetyl]pyrrolidine-2-carbonitrile |
| 422 | 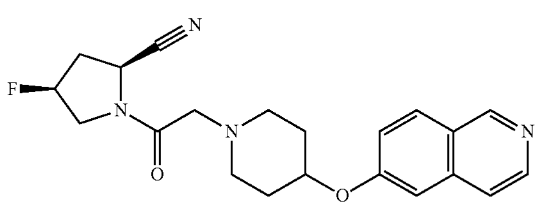 [SMILES: N#C[C@@H]1C[C@H](F)CN1C(=O)CN1CCC(Oc2ccc3cnccc3c2)CC1] | (2S,4S)-4-fluoro-1-[2-[4-(6-isoquinolyloxy)-1-piperidyl]acetyl]pyrrolidine-2-carbonitrile |
| 423 | 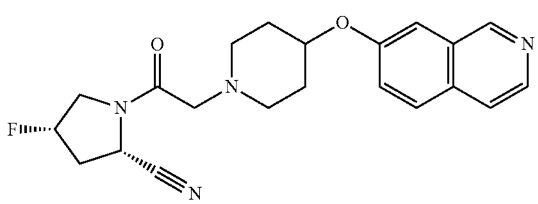 [SMILES: N#C[C@@H]1C[C@H](F)CN1C(=O)CN1CCC(Oc2ccc3ccncc3c2)CC1] | (2S,4S)-4-fluoro-1-[2-[4-(7-isoquinolyloxy)-1-piperidyl]acetyl]pyrrolidine-2-carbonitrile |
| 424 | 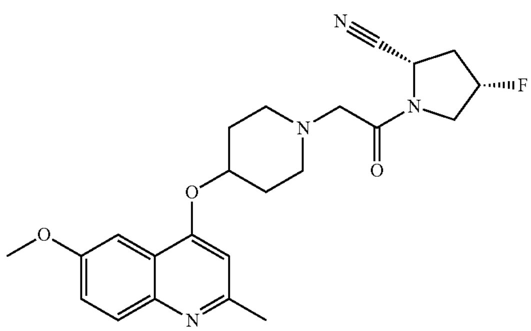 [SMILES: COc1ccc2nc(C)cc(OC3CCN(CC(=O)N4C[C@@H](F)C[C@H]4C#N)CC3)c2c1] | (2S,4S)-4-fluoro-1-[2-[4-[(6-methoxy-2-methyl-4-quinolyl)oxy]-1-piperidyl]acetyl]pyrrolidine-2-carbonitrile |

TABLE 1-continued

| Ex No. | Structure | Chemical Name |
|---|---|---|
| 425 | 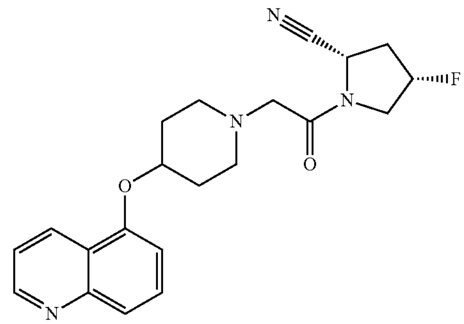 [SMILES: N#C[C@@H]1C[C@H](F)CN1C(=O)CN1CCC(Oc2cccc3ncccc23)CC1] | (2S,4S)-4-fluoro-1-[2-[4-(5-quinolyloxy)-1-piperidyl]acetyl]pyrrolidine-2-carbonitrile |
| 426 | 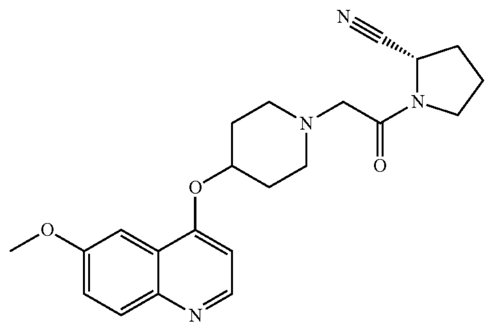 [SMILES: COc1ccc2nccc(OC3CCN(CC(=O)N4CCC[C@H]4C#N)CC3)c2c1] | (2S)-1-[2-[4-[(6-methoxy-4-quinolyl)oxy]-1-piperidyl]acetyl]pyrrolidine-2-carbonitrile |
| 427 | 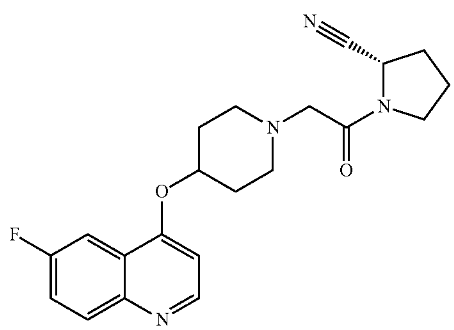 [SMILES: N#C[C@@H]1CCCN1C(=O)CN1CCC(Oc2ccnc3ccc(F)cc23)CC1] | (2S)-1-[2-[4-[(6-fluoro-4-quinolyl)oxy]-1-piperidyl]acetyl]pyrrolidine-2-carbonitrile |
| 428 | 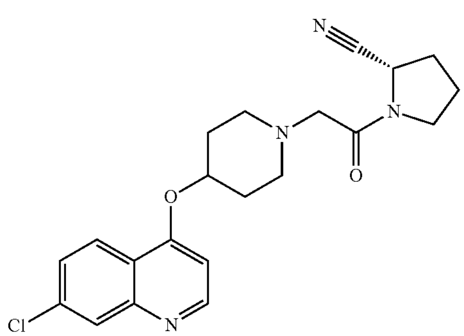 [SMILES: N#C[C@@H]1CCCN1C(=O)CN1CCC(Oc2ccnc3cc(Cl)ccc23)CC1] | (2S)-1-[2-[4-[(7-chloro-4-quinolyl)oxy]-1-piperidyl]acetyl]pyrrolidine-2-carbonitrile |

TABLE 1-continued
| Ex No. | Structure | Chemical Name |
|---|---|---|
| 429 | 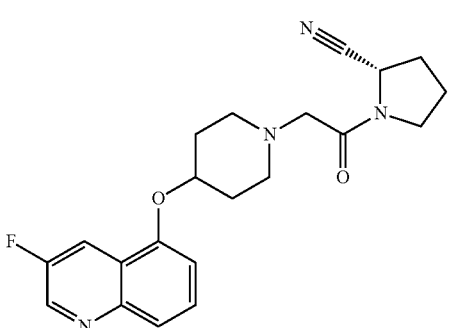 | (2S)-1-[2-[4-[(3-fluoro-5-quinolyl)oxy]-1-piperidyl]acetyl]pyrrolidine-2-carbonitrile |
| 430 | 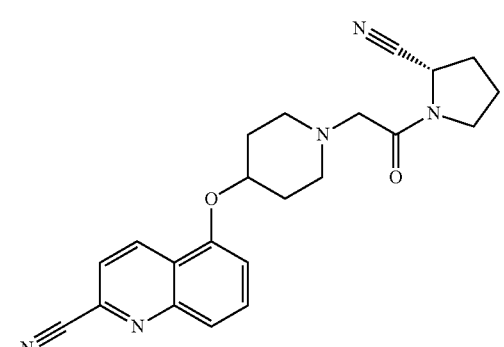 | 5-[[1-[2-oxo-2-[(2S)-2-cyanopyrrolidin-1-yl]ethyl]-4-piperidyl]oxy]quinoline-2-carbonitrile |
| 431 | 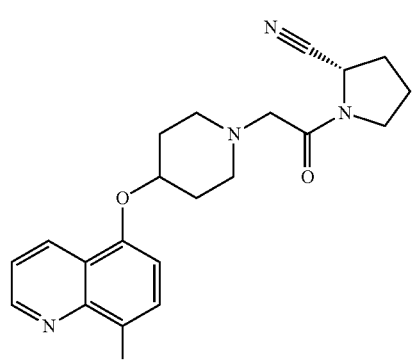 | (2S)-1-[2-[4-[(8-chloro-5-quinolyl)oxy]-1-piperidyl]acetyl]pyrrolidine-2-carbonitrile |
| 432 | 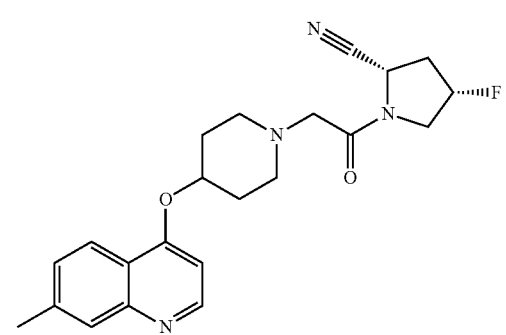 [SMILES: Cc1ccc2c(OC3CCN(CC(=O)N4C[C@@H](F)C[C@H]4C#N)CC3)ccnc2c1] | (2S,4S)-4-fluoro-1-[2-[4-[(7-methyl-4-quinolyl)oxy]-1-piperidyl]acetyl]pyrrolidine-2-carbonitrile |

TABLE 1-continued
| Ex No. | Structure | Chemical Name |
|---|---|---|
| 433 | 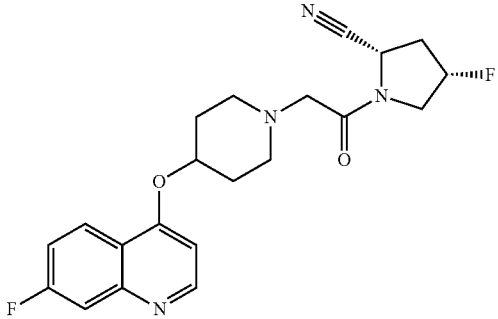 [SMILES: N#C[C@@H]1C[C@H](F)CN1C(=O)CN1CCC(Oc2ccnc3cc(F)ccc23)CC1] | (2S,4S)-4-fluoro-1-[2-[4-[(7-fluoro-4-quinolyl)oxy]-1-piperidyl]acetyl]pyrrolidine-2-carbonitrile |
| 434 | 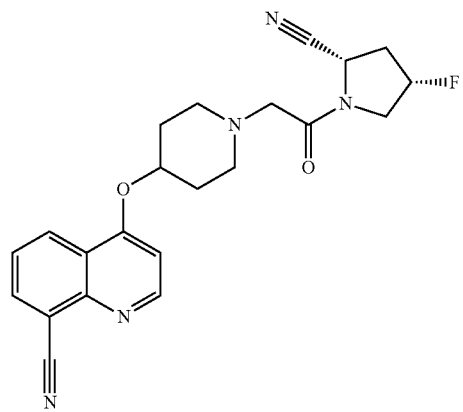 [SMILES: N#Cc1cccc2c(OC3CCN(CC(=O)N4C[C@@H](F)C[C@H]4C#N)CC3)ccnc12] | 4-[[1-[2-oxo-2-[(2S,4S)-2-cyano-4-fluoro-pyrrolidin-1-yl]ethyl]-4-piperidyl]oxy]quinoline-8-carbonitrile |
| 435 | 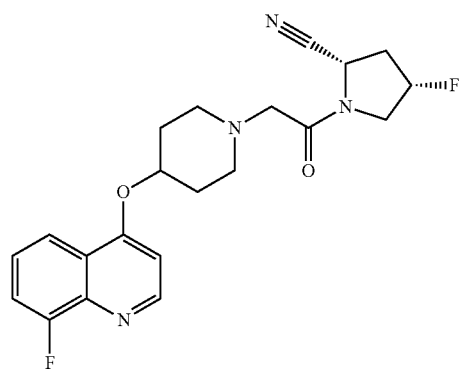 [SMILES: N#C[C@@H]1C[C@H](F)CN1C(=O)CN1CCC(Oc2ccnc3c(F)cccc23)CC1] | (2S,4S)-4-fluoro-1-[2-[4-[(8-fluoro-4-quinolyl)oxy]-1-piperidyl]acetyl]pyrrolidine-2-carbonitrile |
| 436 | 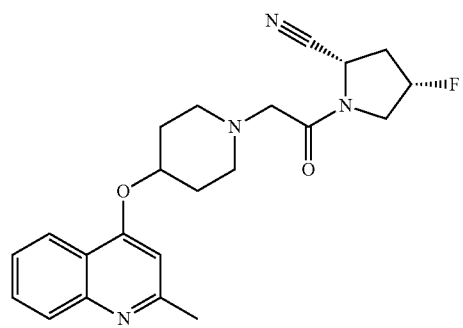 [SMILES: Cc1cc(OC2CCN(CC(=O)N3C[C@@H](F)C[C@H]3C#N)CC2)c2ccccc2n1] | (2S,4S)-4-fluoro-1-[2-[4-[(2-methyl-4-quinolyl)oxy]-1-piperidyl]acetyl]pyrrolidine-2-carbonitrile |

TABLE 1-continued

| Ex No. | Structure | Chemical Name |
|---|---|---|
| 437 | 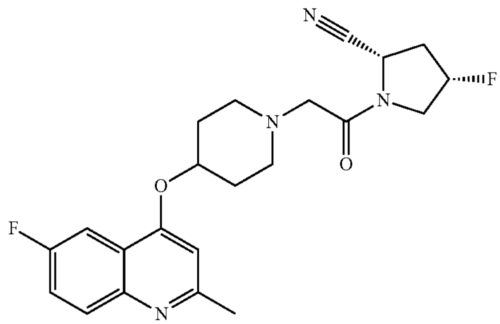 [SMILES: Cc1cc(OC2CCN(CC(=O)N3C[C@@H](F)C[C@H]3C#N)CC2)c2cc(F)ccc2n1] | (2S,4S)-4-fluoro-1-[2-[4-[(6-fluoro-2-methyl-4-quinolyl)oxy]-1-piperidyl]acetyl]pyrrolidine-2-carbonitrile |
| 438 | 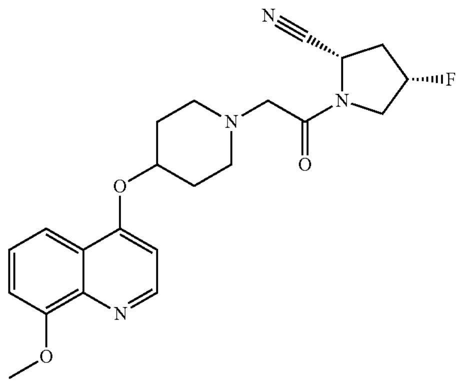 [SMILES: COc1cccc2c(OC3CCN(CC(=O)N4C[C@@H](F)C[C@H]4C#N)CC3)ccnc12] | (2S,4S)-4-fluoro-1-[2-[4-[(8-methoxy-4-quinolyl)oxy]-1-piperidyl]acetyl]pyrrolidine-2-carbonitrile |
| 439 | 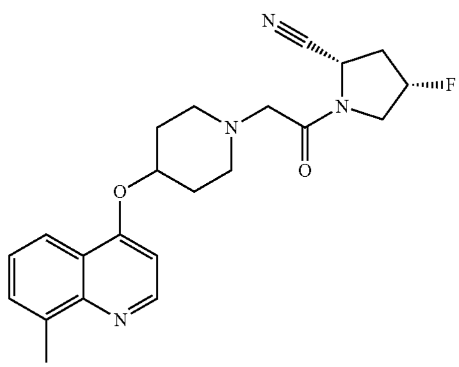 [SMILES: Cc1cccc2c(OC3CCN(CC(=O)N4C[C@@H](F)C[C@H]4C#N)CC3)ccnc12] | (2S,4S)-4-fluoro-1-[2-[4-[(8-methyl-4-quinoly)oxy]-1-piperidyl]acetyl]pyrrolidine-2-carbonitrile |

Experimental Example 1: Evaluation of the Inhibitory Effect on the Activity of Dipeptidyl Peptidases Including FAP The compounds according to the present technology were evaluated in terms of the inhibitory effect on the activity of dipeptidyl peptidases including FAP by using a substrate producing fluorescent substances upon enzymatic decomposition. The test was conducted at 25° C. to get a final reaction volume of 100 μL in a 96 black well plate. Each of the dipeptidyl peptidases was reacted with test compounds (compounds according to the present technology) or Talabostat for 10 minutes and then decomposed by enzymes for 10 minutes to measure the level of the fluorescent substances released therefrom. Briefly, the test compounds were dissolved in dimethyl sulfoxide (DMSO) at a concentration of 20 mM and then subjected to serial dilution, thereby creating an 8 point curve. As for the control group, a 6 point curve created by serial dilution of Talabostat in the same buffer solution was used. Fluorescence intensity was measured using a microplate reader (Flexstation3, Molecular Devices) under the wavelength condition exciting at 380 nm and reading the emission at 460 nm. The inhibitory effect of the test compounds was measured as a decrease (%) in the signal rate as compared to the control group without any inhibitor. Data was fixed to a logistic model with four variables and $IC_{50}$ value was calculated using GraphPad Prism program.

Recombinant human FAP (R&D systems) was diluted with 50 mM tris (pH 7.5) buffer comprising 1 M of sodium chloride and 1 mg/ml of bovine serum albumin (BSA) to be 10 ng per final reaction. The test compounds were subjected to serial dilution in a buffer under the condition containing up to 0.1% of DMSO. Z-Gly-Pro-AMC (Bachem) was used as a substrate. By dissolving in DMSO and then diluting in the same buffer, the substrate was added to be 50 m per final reaction.

As for recombinant human DPP4 (R&D Systems), 25 mM tris (pH 8.0) buffer as a buffer solution and H-Gly-Pro-AMC (Bachem) as a substrate were used. As for recombinant human DPP7 (R&D Systems), 25 mM MES (pH 6.0)

buffer as a buffer solution and Lys-Pro-AMC (Bachem) as a substrate were used. As for recombinant human DPP8 (PBS Bioscience), as a buffer solution, a 10 mM tris (pH 7.4) buffer comprising 10 mM of magnesium chloride and 0.05% of Tween 20, and Z-Ala-Pro-AMC (BPS Bioscience) as a substrate were used. As for recombinant human DPP9 (R&D Systems), a 25 mM tris (pH 8.0) buffer as a buffer solution and H-Gly-Pro-AMC (Bachem) as a substrate were used. As for recombinant human PREP (R&D System), as a buffer solution, a 25 mM tris (pH 7.5) buffer comprising 250 mM sodium chloride and 2.5 mM DTT (Dithiolthreitol), and Z-Gly-Pro-AMC (Bachem) as a substrate were used. The evaluation was made by using 10 ng of DPP4, PDD7, and PREP, 20 ng of DPP8, and 50 ng of DPP9 based on the final reaction. In the evaluation of DPP4, the test compounds were subjected to serial dilution in a buffer under the condition containing up to 0.1% of DMSO. In the evaluation of DPP7, DPP8, DPP9, and PREP, the test compounds were subjected to serial dilution in each buffer under the condition containing up to 0.5% of DMSO.

For the FAP FRET assay, recombinant human FAP (R&D systems) was diluted with 50 mM HEPES (pH 7.2) buffer comprising 150 mM of sodium chloride, 0.1 mg/ml of bovine serum albumin (BSA) and 1 mM EDTA to be 10 ng per final reaction. The test compounds were subjected to serial dilution in a buffer under the condition containing up to 0.1% of DMSO. FRET peptides containing human FGF21 sequence (VGPSQGK) conjugated with HyLite Fluor 488 and dark quencher QXL 520 (Anaspec) was used as a substrate. By dissolving in DMSO and then diluting in the same buffer, the substrate was added to be 6 μM per final reaction. All reactions of FRET assay was conducted at 37° C.

The results obtained by evaluating the inhibitory effect on the activity of dipeptidyl peptidase including FAP as above are shown in Tables 2-8 below.

TABLE 2

| | Inhibitory Activity (IC$_{50}$, nM) | | | | | |
|---|---|---|---|---|---|---|
| Example | hFAP | hDPP4 | DPP7 | DPP8 | DPP9 | PREP |
| 1 | 163.30 | 4.4%** | | | | |
| 2 | 84.52 | 14.6%** | | | | |
| 3 | 174.80 | 4.2%** | | | | |
| 4 | 99.15 | 15.1%** | | | | |
| 5 | 2.60 | >1000 | 293.7 | >100000 | >100000 | >100000 |
| 6 | 1.83 | >1000 | 46.2 | 7888.0 | 5710.0 | >100000 |
| 7 | 0.46 | >1000 | <30.0* | 97587.0 | 12770.0 | >100000 |
| 8 | 1.096 | >1000 | <30.0* | 5787.0 | 487.7 | >100000 |
| 9 | 1.1 | >1000 | 75.1 | 213.2 | 12296.0 | >100000 |
| 10 | 3.2 | >1000 | 75.0 | 143.0 | 9977.0 | >100000 |
| 11 | 1.3 | >1000 | 95.6 | 227.9 | 17060.0 | >100000 |
| 12 | 0.5 | >1000 | <30.0* | 371 | 17708.0 | >100000 |
| 13 | 24.6 | >1000 | 243.0 | 163.2 | 56482.0 | >100000 |
| 14 | 18.7 | >1000 | 126.5 | 676.2 | 11064.0 | >100000 |
| 15 | 12.3 | 9.7%** | 195.6 | 253.1 | 48800.0 | >100000 |
| 16 | 2.6 | 11.0%** | 84.7 | 557.0 | 13718.0 | >100000 |
| 17 | 6.24 | >1000 | 1611.0 | >10000 | >100000 | 6961.0 |
| 18 | 25.27 | No inhibition** | | | | |
| 19 | 5.74 | >1000 | 206.0 | 45207.0 | 44016.0 | 11786.0 |
| 20 | 4.53 | >1000 | 2121.0 | 23095.0 | 69069.0 | 7231.0 |
| 21 | 34.12 | 3.6%** | | | | |
| 22 | 9.03 | 4.2%** | | | | |
| 23 | 3.08 | >1000 | 950.6 | >100000.0 | 78611.0 | 10216.0 |
| 24 | 2.12 | >1000 | 524.0 | 77261.0 | 67959.0 | 5462.0 |
| 25 | 57.62 | 2.9%** | | | | |
| 26 | 93.7%** | 0.4%** | | | | |

*IC$_{50}$ value is between 1 and 30 nM.;
**is inhibition % at 1 μM

TABLE 3

| | Inhibitory Activity (IC$_{50}$, nM) | | | | | |
|---|---|---|---|---|---|---|
| Example | hFAP | hDPP4 | DPP7 | DPP8 | DPP9 | PREP |
| 27 | 1.62 | 5.4%** | 1218.0 | 20717.0 | 27434.0 | 12135.0 |
| 28 | 1.82 | 2633.0 | 345.5 | 18622.0 | 8237.0 | 6601.0 |
| 29 | 6.22 | >100000.0 | 728.2 | 28748.0 | 17465.0 | 6172.0 |
| 30 | 145.2 | No inhibition** | | | | |
| 31 | 163.8 | 5.4%** | | | | |
| 32 | 70.44 | 2.0%** | | | | |
| 33 | 66.1%** | No inhibition** | | | | |
| 34 | 190.7 | No inhibition** | | | | |
| 35 | 76.1%** | No inhibition** | | | | |
| 36 | 32.73 | >1000.0 | 3552.0 | 21788.0 | >100000.0 | 6447.0 |
| 37 | 11.81 | >1000.0 | 5171.0 | 72771.0 | >100000.0 | 8260.0 |
| 38 | 170.1 | No inhibition** | | | | |
| 39 | 68.1%** | 0.4%** | | | | |

TABLE 3-continued

| | Inhibitory Activity (IC$_{50}$, nM) | | | | | |
|---|---|---|---|---|---|---|
| Example | hFAP | hDPP4 | DPP7 | DPP8 | DPP9 | PREP |
| 40 | 38.35 | 3.2%** | | | | |
| 41 | 3.699 | >1000.0 | 4129.0 | 62127.0 | >100000.0 | 3187.0 |
| 42 | 84.6%** | 1.4%** | | | | |
| 43 | 9.94 | 0.2%** | 3372.0 | 44668.0 | >100000.0 | 8353.0 |
| 44 | 5.07 | 1.4%** | 1720.0 | 46154.0 | >100000.0 | 12149.0 |
| 45 | 30.1 | 1.2%** | | | | |
| 46 | 7.70 | 1.4%** | 2198.0 | 23107.0 | >100000.0 | 9849.0 |
| 47 | 18.82 | 3.7%** | | | | |
| 48 | 2.23 | 3.6%** | 761.8 | 12050.0 | >100000.0 | 6753.0 |
| 49 | 4.42 | 0.6%** | 4373.0 | 12259.0 | 92633.0 | 8361.0 |
| 50 | 16.42 | No inhibition** | | | | |
| 51 | 10.88 | 0.6%** | 3321.0 | 38886.0 | >100000.0 | 13365.0 |
| 52 | 13.65 | 0.5%** | | | | |

*IC$_{50}$ value is between 1 and 30 nM.;
**is inhibition % at 1 μM

TABLE 4

| | Inhibitory Activity (IC$_{50}$, nM) | | | | | |
|---|---|---|---|---|---|---|
| Example | hFAP | hDPP4 | DPP7 | DPP8 | DPP9 | PREP |
| 53 | 17.67 | 1.3%** | | | | |
| 54 | 8.48 | 2.0%** | 2389.0 | 23166.0 | >100000.0 | 5504.0 |
| 55 | 20.0 | 1.1%** | | | | |
| 56 | 45.22 | 2.4%** | | | | |
| 57 | 25.07 | 0.6%** | 499.5 | 6005.0 | 26478.0 | 10182.0 |
| 58 | 62.45 | No inhibition** | | | | |
| 59 | 33.4%** | No inhibition** | | | | |
| 60 | 44.2%** | No inhibition** | | | | |
| 61 | 21.49 | >1000.0 | 1149.0 | >100000.0 | >100000.0 | 83276.0 |
| 62 | 75.09 | No inhibition** | | | | |
| 63 | 130.0 | No inhibition** | | | | |
| 64 | 19.01 | >1000.0 | 3561.0 | >100000 | 15734.0 | 84015.0 |
| 65 | 6.77 | >1000.0 | 3402.0 | >100000 | 70583.0 | 85686.0 |
| 66 | 5.48 | >1000.0 | 6390.0 | >100000 | 82687.0 | 93140.0 |
| 67 | 64.0%** | No inhibition** | | | | |
| 68 | 7.96 | >1000.0 | 3732.0 | >100000.0 | >100000.0 | >100000.0 |
| 69 | 64.31 | 8.0%** | | | | |
| 70 | 31.87 | 22.6%** | | | | |
| 71 | 42.61 | No inhibition** | | | | |
| 72 | 101.4 | 0.8%** | | | | |
| 73 | 97.1%** | 1.2%** | | | | |
| 74 | 92.3%** | No inhibition** | | | | |
| 75 | 9.838 | >1000.0 | 813.9 | 93204.0 | >100000.0 | 5253.0 |
| 76 | 53.62 | No inhibition** | | | | |
| 77 | 82.33 | 0.4%** | | | | |
| 78 | 22.49 | No inhibition** | | | | |

*IC$_{50}$ value is between 1 and 30 nM.;
**is inhibition % at 1 μM

TABLE 5

| | Inhibitory Activity (IC$_{50}$, nM) | | | | | |
|---|---|---|---|---|---|---|
| Example | hFAP | hDPP4 | DPP7 | DPP8 | DPP9 | PREP |
| 79 | 17.9 | 4.6%** | | | | |
| 80 | 20.5 | 5.1%** | | | | |
| 81 | 7.6 | >1000.0 | 5940.0 | 27448.0 | 84923.0 | 3927.0 |
| 82 | 72.6%** | 6.5%** | | | | |
| 83 | 68.1%** | 6.3%** | | | | |
| 84 | 1.0 | >1000.0 | 9459.0 | >100000.0 | >100000.0 | 5403.0 |
| 85 | 19.9 | 5.9%** | | | | |
| 86 | 70.7%** | 6.8%** | | | | |
| 87 | 51.9%** | 6.9%** | | | | |
| 88 | 57.9%** | 6.1%** | | | | |

TABLE 5-continued

| | Inhibitory Activity (IC$_{50}$, nM) | | | | | |
|---|---|---|---|---|---|---|
| Example | hFAP | hDPP4 | DPP7 | DPP8 | DPP9 | PREP |
| 89 | 56.8%** | 7.9%** | | | | |
| 90 | 52.9%** | 7.7%** | | | | |
| 91 | 59.2%** | 9.1%** | | | | |
| 92 | 56.4%** | 10.2%** | | | | |
| 93 | 69.6 | 11.6%** | | | | |
| 94 | 63.3 | 6.9%** | | | | |
| 95 | 3.3 | >1000 | 4740 | >100000 | No inhibition** | 4119 |
| 96 | 270.0 | 11.5%** | | | | |
| 97 | 36.3%** | 8.3%** | | | | |
| 98 | 63.2%** | 9.1%** | | | | |
| 99 | 18.2%** | 10.9%** | | | | |
| 100 | 13.5 | >1000.0 | 1153.0 | 73824.0 | >100000.0 | 2487.0 |
| 101 | 0.57 | >1000.0 | 626.3 | >100000.0 | >100000.0 | 3024.0 |
| 102 | 52.4%** | 6.2%** | | | | |
| 103 | 0.68 | >1000.0 | 174.3 | 7679.0 | 4754.0 | 5674.0 |
| 104 | 1.14 | >1000.0 | 83.4 | 16168.0 | 22202.0 | 3080.0 |

*IC$_{50}$ value is between 1 and 30 nM.;
**is inhibition % at 1 μM

TABLE 6

| | Inhibitory Activity (IC$_{50}$, nM) | | | | | |
|---|---|---|---|---|---|---|
| Example | hFAP | hDPP4 | DPP7 | DPP8 | DPP9 | PREP |
| 105 | 1.21 | >1000.0 | 63.5 | 11808.0 | 12460.0 | 5230.0 |
| 106 | 1.88 | >1000.0 | 41.6 | 8275.0 | 10320.0 | 4310.0 |
| 107 | 3.67 | >1000.0 | 18.7 | 9893.0 | 13456.0 | 6496.0 |
| 108 | 2.15 | >1000.0 | 7.6 | 6681.0 | 6300.0 | 3148.0 |
| 109 | 1.80 | >1000.0 | 38.3 | 2173.0 | 4429.0 | 4140.0 |
| 110 | 2.20 | >1000.0 | 499.5 | 6005.0 | 26478.0 | 10182.0 |
| 111 | 8.28 | No inhibition** | 502.8 | 31901.0 | 21112.0 | 4175.0 |
| 112 | 18.84 | No inhibition** | | | | |
| 113 | 1.65 | 20.0%** | 341.7 | 2406.0 | 3972.0 | 2931.0 |
| 114 | 0.94 | 15.7%** | <30.0 | 1532.0 | 3398.0 | 31004.0 |
| 115 | 5.64 | 1.4%** | 5737.0 | 52080.0 | 45087.0 | >100000.0 |
| 116 | 82.4%** | No inhibition** | | | | |
| 117 | 22.89 | No inhibition** | | | | |
| 118 | 2.34 | No inhibition** | 10161.0 | 85429.0 | >100000.0 | 1042.0 |
| 119 | 1.45 | No inhibition** | 2349.0 | 60390.0 | >100000.0 | 3755.0 |
| 120 | 11.82 | No inhibition** | | | | |
| 121 | 1.84 | >10000.0 | 1743.0 | 48115.0 | 46857.0 | 73693.0 |
| 122 | 444.7 | >10000.0 | >100000.0 | >100000.0 | >100000.0 | 23747.0 |
| 123 | 2.41 | >10000.0 | 1281.0 | >30000.0 | 44852.0 | 20126.0 |
| 124 | 3.81 | >10000.0 | 518.4 | 46846.0 | 82682 | 16105.0 |
| 125 | 5.50 | >10000.0 | 5552.0 | 33709.0 | >100000.0 | 28901.0 |
| 126 | 0.84 | 7956.0 | 10411.0 | 16392.0 | 11048.0 | 1125.0 |
| 127 | 0.65 | >10000.0 | 9235.0 | 8726.0 | 23709.0 | 620.9 |
| 128 | 0.78 | >10000.0 | 5904.0 | 9791.0 | 11275.0 | 2460.0 |
| 129 | 2.66 | >10000.0 | 642.3 | 9838.0 | 4849.0 | 160.5 |
| 130 | 1.25 | >10000.0 | 904.5 | 10371.0 | 5974.0 | 2340.0 |

*IC$_{50}$ value is between 1 and 30 nM.;
**is inhibition % at 1 μM

TABLE 7

| | Inhibitory Activity (IC$_{50}$, nM) | | | | | |
|---|---|---|---|---|---|---|
| Example | hFAP | hDPP4 | DPP7 | DPP8 | DPP9 | PREP |
| 131 | 2.73 | 3451.0 | 610.0 | 8258.0 | 2776.0 | 7920.0 |
| 132 | 2.17 | 7426.0 | 491.9 | 13866.0 | 3640.0 | 2816.0 |
| 133 | 2.37 | 6016.0 | 152.8 | 6476.0 | 6000.0 | 2600.0 |
| 134 | 342.7 | 8013.0 | | | | |
| 135 | 3.47 | 4144.0 | 1016.0 | 5784.0 | 3437.0 | 4986.0 |
| 136 | 12.3 | 9034 | 1954 | 22335 | 14521 | 5154 |
| 137 | 86.1 | | | | | |
| 138 | 24.8 | | 3698 | 100000 | 100000 | 7969 |
| 139 | 16.7 | | 12996 | 100000 | 89005 | 5016 |
| 140 | 15.7 | | 1399 | 100000 | 32555 | 4257 |
| 141 | 34.1 | | | | | |
| 142 | 2.6 | | 4990 | 100000 | 70954 | 4515 |
| 143 | 55.4 | | | | | |
| 144 | 6 | | 19288 | 85005 | 23808 | 3361 |
| 145 | 2.7 | | 2027 | 19086 | 16818 | 2690 |
| 146 | 6.6 | | 916.4 | 100000 | 100000 | 4585 |
| 147 | 14.7 | | | | | |
| 148 | 7.3 | | 10832 | 86638 | 29301 | 3811 |

TABLE 7-continued

| Example | hFAP | hDPP4 | DPP7 | DPP8 | DPP9 | PREP |
|---|---|---|---|---|---|---|
| 149 | 9.9 | | 3965 | 100000 | 49114 | 1616 |
| 150 | 1.1 | | 1835 | 100000 | 39617 | 2642 |
| 151 | 1.6 | | 2548 | 12304 | 23881 | 3088 |
| 152 | 2.5 | | 1663 | 100000 | 29007 | 4131 |
| 153 | 3.4 | | 3116 | 100000 | 48066 | 2330 |
| 154 | 5.2 | | 3306 | 22049 | 41711 | 970.1 |

TABLE 8

Inhibitory Activity (IC$_{50}$, nM)

| Example | hFAP | hDPP4 | DPP7 | DPP8 | DPP9 | PREP | hFAP FRET |
|---|---|---|---|---|---|---|---|
| 155 | | 1851 | 2898 | 9848 | 5717 | 2545 | 2.4 |
| 156 | | 736.2 | 5064 | 11984 | 6786 | 1021 | 2.7 |
| 157 | | 2158 | | | | | 20.2 |
| 158 | | 2090 | 4899 | 8617 | 3365 | 1721 | 4 |
| 159 | | 1864 | 61 | 7593 | 3704 | 429.8 | 6.7 |
| 160 | | 1780 | 77.8 | | 2819 | 1076 | 4.9 |
| 161 | 1.4 | | 5450 | 41473 | 25410 | 4248 | |
| 162 | 5.2 | | 2342 | 100000 | 14868 | 2609 | |
| 163 | 29 | | | | | | |
| 164 | 56.8 | | | | | | |
| 165 | 2.3 | | 1154 | 100000 | 7550 | 3973 | |
| 166 | 2.1 | | 958 | 6158 | 1826 | 769.4 | |
| 167 | 1.4 | | 2038 | 6285 | 2556 | 5858 | |
| 168 | 11.5 | | | | | | |
| 169 | 35.4 | | | | | | |
| 170 | 3.5 | | 302 | 14013 | 2703 | 7976 | |
| 171 | | 2195 | 2793 | | 9356 | 3425 | 8.2 |
| 172 | | 1872 | 4899 | | 5398 | 4240 | 9.3 |
| 173 | | 1124 | 11143 | | 2952 | 1866 | 5.3 |
| 174 | | 3020 | 846.3 | | 1994 | 2435 | 2.6 |
| 175 | | 1692 | 4237 | | 1630 | 3515 | 3.5 |
| 176 | | 1510 | | | | | 22.2 |
| 177 | | 3425 | 46.9 | | 1175 | 2925 | 2.6 |
| 178 | | 1364 | 5964 | | 2569 | 2346 | 10.1 |
| 179 | | 1945 | 400.7 | | 2558 | 2926 | 3.6 |
| 180 | | 1018 | 6790 | | 3176 | 1556 | 6.2 |
| 181 | | 1061 | 215.1 | | 4621 | 4669 | 2.6 |
| 182 | | 4067 | 818.9 | | 6693 | 5360 | 3.3 |
| 183 | | 1837 | 1367 | | 6774 | 3374 | 2.2 |
| 184 | | 1290 | 2760 | 2429 | 5151 | 3154 | 3.2 |
| 185 | | 995.3 | 1299 | | 2750 | 3553 | 2.1 |
| 186 | | 2223 | 2018 | | 4406 | 3595 | 2.7 |
| 187 | | 17617 | | | | | 23.9 |
| 188 | | 15205 | | | | | 21.5 |
| 189 | | 3504 | 2575 | | 1505 | 1154 | 10 |
| 190 | | 12498 | 63.7 | | 1390 | 1247 | 16.7 |
| 191 | | 3220 | | | | | 19.4 |
| 192 | | 5559 | | | | | 15.6 |
| 193 | | 9092 | | | | | 24.4 |
| 194 | | 19559 | | | | | 10.9 |
| 195 | | 14094 | | | | | 21.7 |
| 196 | | 3836 | | | | | 7.4 |
| 197 | | 13391 | 4119 | | 23841 | 14719 | 5.2 |
| 198 | | 9457 | 900.6 | | 14899 | 2917 | 8.6 |
| 199 | | 2619 | 8006 | 8228 | 10888 | 7251 | 2.3 |
| 200 | | 5514 | 1696 | ND | 27262 | 6087 | 6.3 |
| 201 | | 26311 | 3914 | ND | | 9150 | 1.3 |
| 202 | | 12128 | 6813 | 14204 | 13109 | 8082 | 2.3 |
| 203 | | 4657 | 3257 | | 11212 | 12187 | 0.9 |
| 204 | | 6204 | 3867 | | 16219 | 11515 | 2.1 |
| 205 | | 795.8 | 1762 | | 3038 | 7502 | 2.6 |
| 206 | | ND | | | | | 32.8 |
| 207 | | ND | | | | | 17.9 |
| 208 | | 6508 | 1366 | | 19165 | 12009 | 1.7 |
| 209 | | 4427 | 7011 | 39107 | 32393 | 12842 | 1.7 |
| 210 | | 2703 | 281 | | 1296 | 1477 | 3.5 |
| 211 | | 1801 | 368.6 | | 657.1 | 2736 | 5.2 |
| 212 | | 1958 | 206.1 | | 1160 | 5229 | 8 |
| 213 | | 1740 | 392.7 | | 1394 | 3020 | 3.5 |
| 214 | | 1288 | 764 | | 970.1 | 3030 | 3.8 |
| 215 | | 1161 | 543.8 | | 631.1 | 3149 | 1.5 |
| 216 | | 1352 | 398.6 | | 822.1 | 2557 | 1.7 |
| 217 | | 28960 | | | | | 8.8 |

TABLE 8-continued

| | Inhibitory Activity (IC$_{50}$, nM) | | | | | | |
|---|---|---|---|---|---|---|---|
| Example | hFAP | hDPP4 | DPP7 | DPP8 | DPP9 | PREP | hFAP FRET |
| 218 | | 17275 | | | | | 26.6 |
| 219 | | 13042 | | | | | 16.8 |
| 220 | | 13236 | | | | | 5.7 |
| 221 | | 11064 | | | | | 7.5 |
| 222 | | 11826 | | | | | 2.1 |
| 223 | | 92550 | | | | | 13.1 |
| 224 | | 54167 | | | | | 10 |
| 225 | | 34247 | | | | | 7.2 |
| 226 | | 37856 | | | | | 4.8 |
| 227 | | 31659 | | | | | 7.2 |
| 228 | 1.209 | >100000.0 | 387.4 | 10751 | 7485 | 4291 | 3 |
| 229 | 16.8 | >10000.0 | 1155 | >100000.0 | 36273 | 4842 | |
| 230 | 9.3 | >10000.0 | 1363 | >100000.0 | 17576 | 8771 | |
| 231 | 1 | >10000.0 | 1513 | 12554 | 21586 | 11457 | |
| 232 | 1.3 | >10000.0 | 7148 | >100000.0 | 28970 | 13679 | 1.8 |
| 233 | 0.7 | 37790 | 1067 | 28144 | 21246 | 11501 | 0.7 |
| 234 | 1.3 | 63644 | 6082 | 57822 | 12259 | 18129 | 1.6 |
| 235 | 0.7 | >10000.0 | 2788 | 23438 | 17616 | 8456 | |
| 236 | 1.5 | >10000.0 | 3467 | >100000.0 | 18837 | 8898 | |
| 237 | 1.5 | 9287 | 746 | 22628 | 34556 | 6601 | |
| 238 | 1.4 | >10000.0 | 2205 | >100000.0 | 29251 | 3928 | |
| 239 | 6 | >10000.0 | 7283 | 74254 | 43856 | 9983 | |
| 240 | 20 | >10000.0 | | | | | |
| 241 | 4.5 | >10000.0 | 17032 | 77288 | 47962 | 12978 | |
| 242 | 1.7 | >10000.0 | 1705 | 11020 | 19302 | 8439 | |
| 243 | 2.6 | 16851 | 3243 | 23726 | 16549/ | 10368/ | 4 |
| 244 | 2.2 | >10000.0 | 9140 | 32680 | 31936 | 11101 | 5.6 |
| 245 | 1 | >10000.0 | 3751 | >100000.0 | >100000.0 | 9467 | 1.2 |
| 246 | 0.9 | >10000.0 | 2558 | >30000.0 | 21037 | 11250 | |
| 247 | 1.3 | >10000.0 | >50000.0 | >100000.0 | >100000.0 | >10000.0 | 2 |
| 248 | 3.1 | 7066 | 810.2 | 5338 | 3681 | 6162 | |
| 249 | 6 | 1450 | 488.8 | >3000.0 | 5766 | 1052 | |
| 250 | 3.4 | 963.8 | 654 | 2277 | 3687 | 2164 | |
| 251 | 3.1 | 2312 | 199.4 | >3000.0 | 7385 | 10474 | |
| 252 | 0.8 | 1630 | 308.3 | 2484 | 4926 | 3319 | |
| 253 | 0.9 | 2311 | 2186 | 2672 | 5361 | 2221 | |
| 254 | 2.1 | 4707 | 1401 | 12177 | 13109 | 275.2 | |
| 255 | 1 | 2407 | 1853 | 5099 | 7359 | 2213 | 1 |
| 256 | 0.8 | 1883 | 1789 | 3346 | 6962 | 603.1 | |
| 257 | 0.9 | 694.4 | 289 | 4538 | 6558 | 1530 | |
| 258 | 1 | 1830 | 1390 | >100000.0 | 7974 | 1285 | |
| 259 | 2.6 | 1272 | 3313 | 18559 | 8428 | 2471 | |
| 260 | 5.8 | 740.6 | 8283 | 20772 | 7710 | 6495 | |
| 261 | 2 | 1170 | 6569 | 20772 | 9424 | 3938 | |
| 262 | 1.2 | 1355 | 452 | 3005 | 3559 | 1851 | |
| 263 | 1.1 | 791.8 | 553.8 | 3565 | 3829 | 3469 | 1.9 |
| 264 | 1.3 | 1039 | 2274 | 3602 | 5329 | 2255 | 2.4 |
| 265 | 0.8 | 1239 | 1128 | >100000.0 | 5425 | 1732 | |
| 266 | 0.8 | 1306 | 1070 | >10000.0 | 4378 | 3169 | 1.2 |
| 267 | | 2574 | 3161 | | | 834.8 | 1.5 |
| 268 | 1 | 574.3 | 510.7 | 1109 | 877.4 | 3523 | 0.7 |
| 269 | 1.2 | 2838 | 812.2 | 7179 | 4916 | 2310 | |
| 270 | 1.3 | >10000.0 | 591.4 | 44035 | 19201 | 10866.0? | |
| 271 | 1.4 | 3787 | 212.6 | 7985 | 4406 | 3737 | |
| 272 | | 2802 | | | | | 16.3 |
| 273 | | 529.7 | | | | | 19 |
| 274 | | 10982 | 959.7 | | 5548 | 14876 | 4.4 |
| 275 | | 1429 | 90.4 | | 1591 | 6123 | 1.7 |
| 276 | | 977.4 | 3485 | | 5329 | 3035 | 14 |
| 277 | | 1038 | 192.7 | | 740 | 1231 | 3 |
| 278 | | 609.6 | 614.6 | | 592.9 | 1279 | 3.5 |
| 279 | | 253.5 | 397.5 | | 613.5 | 637.1 | 1.5 |
| 280 | | 839.1 | 184 | | 674.5 | 970 | 2.1 |
| 281 | | 2750 | 1131 | 4448 | 2602 | 2454 | 3.4 |
| 282 | | 3467 | 241.2 | | 4846 | 5057 | 5.8 |
| 283 | | 1215 | 74.3 | | 778 | 577.1 | 1 |
| 284 | | 2390 | 932.3 | | 1639 | 574.3 | 10.6 |
| 285 | | 2502 | 333.4 | | 1084 | 2454 | 3.9 |
| 286 | | 10890 | 3099 | 19782 | 32153 | 6301 | 9.3 |
| 287 | | 7578 | 904 | | 5850 | 3422 | 1.2 |
| 288 | | 18549 | 676.6 | | 1211 | 11419 | 14 |
| 289 | | 14216 | | | | | 36.3 |
| 290 | | 925.8 | 121.2 | | 566.7 | 429.3 | 1.1 |
| 291 | | 12852 | 173.1 | | 2837 | 2113 | 4.4 |
| 292 | | 5178 | 163.3 | | 371 | 1466 | 1.3 |
| 293 | | 2666 | 122 | | 1254 | 422.4 | 0.8 |

TABLE 8-continued

| | Inhibitory Activity (IC$_{50}$, nM) | | | | | | |
|---|---|---|---|---|---|---|---|
| Example | hFAP | hDPP4 | DPP7 | DPP8 | DPP9 | PREP | hFAP FRET |
| 294 | | 439.5 | 16.6 | | 92.9 | 128 | 0.6 |
| 295 | | 864.8 | 64.1 | | 87.8 | 723.9 | 0.7 |
| 296 | | 15634 | 142.4 | | 10602 | 6445 | 4.7 |
| 297 | | 2805 | 13.5 | | 4204 | 4746 | 2.9 |
| 298 | | 1863 | 256.9 | | 3069 | 6524 | 2.1 |
| 299 | 1.7 | >10000.0 | 9839 | 13076 | 8188 | 1410 | |
| 300 | 1.9 | >10000.0 | 2926 | 17834 | 12149 | 4893 | |
| 301 | 69.5 | 8133 | 1563.0?? | >100000.0 | >100000.0 | 36032 | |
| 302 | | 100000 | 7354 | | 100000 | 350.4 | 22.2 |
| 303 | | 100000 | 1940 | | 100000 | 482.8 | 9.2 |
| 304 | | 18773 | 1051 | | 7597 | 117.3 | 8 |
| 305 | | 2076 | | | | | 50.7 |
| 306 | | 24258 | 477.1 | | 13150 | 129.2 | 4.4 |
| 307 | 47.1 | >10000.0 | | | | | |
| 308 | 96.8 | >10000.0 | | | | | |
| 309 | 68.3 | >10000.0 | | | | | |
| 310 | 5.3 | >10000.0 | 4327 | >100000.0 | 66443 | 739.9 | |
| 311 | 14 | >10000.0 | 2486 | >100000.0 | 96860 | 4347 | |
| 312 | 31.8 | >10000.0 | | | | | |
| 313 | 73.9 | >10000.0 | >100000.0 | >100000.0 | 13711 | 9364 | |
| 314 | 8.7 | >10000.0 | 2467 | >100000.0 | 34933 | 530.6 | |
| 315 | 1.7 | 9152 | 1051 | >10000.0 | 5771 | 133.5 | |
| 316 | 3.1 | >10000.0 | 1872.0?? | >100000.0 | 8198.0?? | 500.2 | |
| 317 | 2.7 | >10000.0 | 1848.0?? | >100000.0 | 7066.0?? | 299.4 | |
| 318 | 18.2 | >10000.0 | | | | | |
| 319 | 1.8 | >10000.0 | 1317.0?? | 3820.0?? | 5037.0?? | 502.6 | |
| 320 | 46.2 | 409.7 | | | | | |
| 321 | 8.8 | >10000.0 | 10450 | >100000.0 | 59793 | 2467 | |
| 322 | | 100000 | | | | | 10.3 |
| 323 | | 100000 | | | | | 5.8 |
| 324 | | 100000 | | | | | 25 |
| 325 | | 100000 | | | | | 8.9 |
| 326 | | 50592 | | | | | 8.8 |
| 327 | | 31538 | | | | | 3.1 |
| 328 | | 21409 | | | | | 6 |
| 329 | | 26272 | | | | | 7.5 |
| 330 | 2.8 | 3289 | | | | | 6.3 |
| 331 | 3.8 | 5112 | | | | | 6.5 |
| 332 | 5.5 | 6196 | | | | | |
| 333 | 2.6 | 7540 | | | | | |
| 334 | 4 | 7761 | 404.2 | | 1092 | 2296/2782 | 2.6 |
| 335 | 5.9 | 7328 | | | | | |
| 336 | 59.3 | 7395 | 1192 | 11531 | 6516 | 8500 | |
| 337 | 7.8 | 8175 | 570.8 | 7882 | 2290 | 2543 | |
| 338 | 6.5 | 6886 | 809 | 8328 | 2945 | 1451 | |
| 339 | 11.4 | 8790 | 554.7 | >10000.0 | >30000.0 | 3590 | |
| 340 | 5.1 | 6497 | 523.4 | 2396 | 5305 | 7854 | |
| 341 | 22.7 | >10000.0 | | | | | |
| 342 | 14 | 3258 | 316 | 39561 | 5329 | 6646 | |
| 343 | | 17406 | | | | | 30.7 |
| 344 | | 100000 | 4613 | | 100000 | 5792 | 6 |
| 345 | | 6475 | | | | | 19.3 |
| 346 | 2.7 | 2346 | 338.9 | 5962 | 3262 | 637.1 | |
| 347 | 2.2 | 2656 | 1009 | 2619 | 2955 | 4582 | 5.7 |
| 348 | 2.1 | 3603 | 611.7 | 2442 | 6200 | 10004 | 3.9 |
| 349 | 1.6 | 1885 | 1985 | 2900 | 5056 | 5204 | 4 |
| 350 | 8.2 | 7895 | 9080 | 17498 | 27531 | 625.3 | |
| 351 | 3.4 | 6726 | 842.2 | 2814 | 4529 | 3282 | |
| 352 | 2.7 | >10000.0 | 2935 | >10000.0 | 9771 | 10708 | 2.5 |
| 353 | 4.5 | 5891 | 1063 | >10000.0 | 2877 | 3567 | |
| 354 | 8.9 | 2075 | 428 | 1776 | 4941 | 2817 | |
| 355 | 2.7 | 5248 | 845.6 | >100000.0 | 9860 | 14191 | 2.5 |
| 356 | 3.7 | 4023 | 2053 | 953.1 | 740.8 | 4983 | |
| 357 | 3.8 | 4710 | 1640 | 3598 | 2801 | 4831 | |
| 358 | 3.7 | >10000.0 | 1438.0?? | 30013.0?? | 64649.0?? | 11796 | |
| 359 | 2.3 | >10000.0 | 971.0?? | 8224.0?? | 31285.0?? | 5995 | |
| 360 | 1.9 | | 1340 | 100000 | 7354 | 16427 | |
| 361 | 2.7 | | 314.2 | 100000 | 4575 | 408.9 | |
| 362 | | 10000 | | | | | 27.6 |
| 363 | | 10000 | | | | | 30.6 |
| 364 | | 9126 | | | | | 17.2 |
| 365 | | 10000 | | | | | 22.3 |
| 366 | | 10000 | | | | | 36 |
| 367 | | 10000 | | | | | 28.1 |
| 368 | | 10000 | | | | | 36.7 |
| 369 | | 10000 | | | | | 62.1 |

TABLE 8-continued

| | Inhibitory Activity (IC$_{50}$, nM) | | | | | | |
|---|---|---|---|---|---|---|---|
| Example | hFAP | hDPP4 | DPP7 | DPP8 | DPP9 | PREP | hFAP FRET |
| 370 | | 36806 | | | | | 11 |
| 371 | | 4568 | 306.8 | | 5202 | 4912 | 7 |
| 372 | | 1648 | 645.1 | | 944.6 | 1999 | 51.6 |
| 373 | | 2762 | | | | | 92.4 |
| 374 | | 5670 | | | | | 31.6 |
| 375 | | 6961 | | | | | 22.9 |
| 376 | | 3512 | 226.2 | | 4374 | 869.6 | 7 |
| 377 | | 6609 | 178.2 | | ND | 1398 | 12.4 |
| 378 | | 24472 | | | | | 99.2 |
| 379 | | 3382 | | | | | 47.4 |
| 380 | | 8160 | | | | | 77.1 |
| 381 | | 10639 | | | | | 14.3 |
| 382 | | 3148 | | | | | 80 |
| 383 | | 2804 | | | | | 39.3 |
| 384 | | | | | | | 74.9 |
| 385 | | | | | | | 77.4 |
| 386 | | | | | | | 19.8 |
| 387 | | | | | | | 32.4 |
| 388 | | 6889 | | | | | 70.2 |
| 389 | | 3891 | | | | | 67.5 |
| 390 | | 1520 | 358.1 | | 1315 | 1418 | 5.9 |
| 391 | | 3497 | | | | | 27.5 |
| 392 | | 2072 | | | | | 50.6 |
| 393 | | 3312 | | | | | 43.8 |
| 394 | | 2545 | 360.8 | | 1088 | 420.6 | 1.3 |
| 395 | | 6045 | | | | | 18.6 |
| 396 | | 16432 | 874.7 | | 7419 | 1772 | 3.1 |
| 397 | | 28517 | | | | | 38.9 |
| 398 | | 13984 | | | | | 98.6 |
| 399 | | 17432 | 1009 | 1202 | 3332 | 627.1 | 1.5 |
| 400 | | 17401 | 961.3 | 970.7 | 2013 | 1956 | 2.3 |
| 401 | | 15177 | 775 | 266 | 1608 | 1196 | 5.9 |
| 402 | | 12436 | 1155 | 1517 | 7831 | 359.1 | 3.7 |
| 403 | | 2079 | 404.8 | 251.2 | 557.6 | 60.2 | 1.8 |
| 404 | | 4730 | 633.7 | 595.9 | 681.5 | 78.3 | 1.8 |
| 405 | | 2164 | 392.2 | 66.7 | 398.4 | 597.3 | 1.9 |
| 406 | | 2700 | 402.1 | 23.3 | 218.2 | 535.2 | 4.2 |
| 407 | | 1820 | 394.7 | 313.6 | 756 | <30 | 3.4 |
| 408 | | 8186 | | | | | 12.8 |
| 409 | | 1318 | 62.6 | | 1859 | 1627 | 7.5 |
| 410 | 1.2 | >10000.0 | 4729 | 10705 | 17734 | 3173 | 1.5 |
| 411 | 2.5 | >10000.0 | 3150 | 9916 | 29436 | 10565 | |
| 412 | 5.9 | >10000.0 | 10709 | 12000 | 69771 | 1277 | |
| 413 | 3 | >10000.0 | >100000.0 | 18162 | >100000.0 | 26471 | |
| 414 | 4.3 | >10000.0 | 8737 | 43973 | >100000.0 | 57487 | |
| 415 | 6.4 | >10000.0 | 13454 | 16492 | 39369 | 1413 | |
| 416 | 2.3 | 6838 | | | | | |
| 417 | 3.3 | 5473 | | | | | 6.5 |
| 418 | 3.7 | 4672 | | | | | |
| 419 | 8.1 | >10000.0 | 2022 | 9392 | 23023 | 1102 | |
| 420 | 7 | >10000.0 | 2076 | 8593 | 22135 | 1742 | |
| 421 | 2.5 | 7528 | >100000.0 | 1576 | 4165 | 2608 | |
| 422 | 11.4 | >10000.0 | 1221 | 6420 | 10317 | 1412 | |
| 423 | 9.3 | 8990 | 2046 | 3464 | 9332 | 990.1 | |
| 424 | 2.3 | >10000.0 | 3887 | 13107 | 48932 | FA | |
| 425 | | 7237 | 2151 | | 33818 | 1326 | 7 |
| 426 | | 54844.7 | 9397 | | 100000 | 10819 | 3.9 |
| 427 | | 37172.7 | 15848 | 36625 | 100000 | 5005 | 5.6 |
| 428 | | 32568.2 | | | | | 17.3 |
| 429 | | 37236.9 | 3972 | | 100000 | 25324 | 6.9 |
| 430 | | 29397 | | | | | 24.5 |
| 431 | | 19327.5 | 6343 | | 100000 | 3503 | 12.2 |
| 432 | | 6577 | | | | | 19.8 |
| 433 | | 5676 | 3068 | 3065 | 3894 | 98 | 5.1 |
| 434 | | 2441 | 4312 | 2742 | 4513 | 394.7 | 3.6 |
| 435 | | 4835 | 6556 | 2768 | 4028 | 178.9 | 3.2 |
| 436 | | 9042 | 8505 | 11738 | 18228 | 555.3 | 11.1 |
| 437 | | 4490 | 6262 | 4145 | 17424 | 454.3 | 1.8 |
| 438 | | 5671 | 3580 | 3377 | 5967 | 155.8 | 7.7 |
| 439 | | 6307 | 3111 | 2700 | 5459 | 75 | 3.7 |

What is claimed is:

1. A compound of Formula 1:

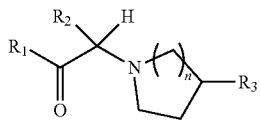

(Formula 1)

or a stereoisomer, a mixture of stereoisomers, or a pharmaceutically acceptable salt thereof, wherein:

n is 1 or 2;

$R_1$ is selected from the group consisting of Formulas I, II, III, IV, and V:

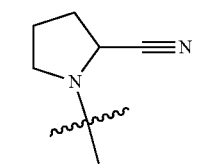

I

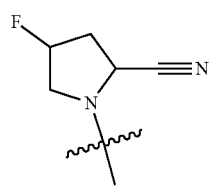

II

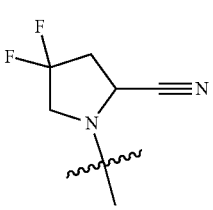

III

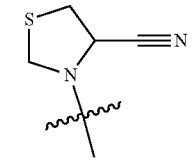

IV

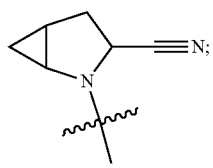

V $R_2$ is a hydrogen or a $C_{1-3}$alkyl;

$R_3$ is: a 5- to 12-membered heteroaryl, wherein said heteroaryl contains 1 to 3 heteroatoms independently selected from O, N, and S and is optionally substituted by 1 to 3 Z, a 3- to 12-membered non-aromatic heterocycle, wherein said heterocycle contains 1 to 3 heteroatoms independently selected from O, N, and S and is optionally substituted by 1 to 3 Z, —$NR_4R_5$, —$OR_4$, —$C(O)NHR_4$, —$NHC(O)(CH_2)_mR_4$, —$NHS(O)_2R_4$, —$(CH_2)_mCH_2R_4$, or —$(CH_2)_mNHR_4$, wherein m is 0 or 1;

$R_4$ is: a phenyl substituted with 1 to 3 Z, a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl, wherein said heterocycle is optionally substituted with 1 to 3 Z, a naphthyl optionally substituted with 1 to 3 Z, or a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z;

$R_5$ is a hydrogen or a $C_{1-3}$alkyl;

each Z is independently selected from the group consisting of hydroxy, amino, halogen, cyano, nitro, carboxylic acid, $C_{1-5}$alkyl optionally substituted by 1 to 3 $Z^1$, $C_{2-6}$alkenyl optionally substituted by $Z^1$, $C_{2-6}$alkynyl optionally substituted by $Z^1$, $C_{1-5}$alkoxy optionally substituted by 1 to 3 $Z^1$, $C_{1-5}$alkylthio optionally substituted by $Z^1$, mono- or di-$C_{1-5}$ alkylamino optionally substituted by $Z^1$, piperazinyl optionally substituted by $Z^1$, $C_{1-5}$ alkylsulfonylamino optionally substituted by $Z^1$, $C_{1-5}$alkylcarbonylamino optionally substituted by $Z^1$, aminosulfonyl optionally substituted by $Z^1$, aminocarbonyl optionally substituted by $Z^1$, $C_{1-5}$alkylaminocarbonyl optionally substituted by $Z^1$, phenyl optionally substituted by $Z^1$, phenoxy optionally substituted by $Z^1$, benzyl optionally substituted by $Z^1$, benzoyl optionally substituted by $Z^1$, phenylaminocarbonyl optionally substituted by $Z^1$, pyrazolyl optionally substituted by $Z^1$, benzoxazolyl optionally substituted by $Z^1$, $C_{1-5}$ alkoxycarbonyl optionally substituted by $Z^1$, benzyloxy optionally substituted by $Z^1$, $C_{1-5}$ alkylsulfonyl optionally substituted by $Z^1$, acetyl, morpholinyl optionally substituted by $Z^1$, —$NR_6C(O)R_7$, and —$C(O)NR_6R_7$;

wherein each $Z^1$ is independently selected from halogen, hydroxyl, amino, $C_{1-5}$ alkylamino, cyano, acetyl, $C_{1-5}$ alkyl, $C_{1-5}$ haloalkyl, $C_{3-6}$ carbocycle, and $C_{3-6}$ heterocycle, wherein said $C_{3-6}$ carbocycle and said $C_{3-6}$ heterocycle are optionally substituted with halogen, hydroxyl, $C_{1-5}$alkyl, or $C_{1-5}$ haloalkyl;

$R_6$ is hydrogen or a $C_{1-3}$alkyl group;

$R_7$ is: a $C_{1-3}$alkyl group optionally substituted with phenyl, a phenyl optionally substituted with 1 to 3 $Z^2$, or a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]

pyridinyl, isoxazolyl, acridinyl, and naphthyridinyl, wherein said heteroaryl is optionally substituted with 1 to 3 $Z^2$; and each $Z^2$ is independently selected from the group consisting of hydroxy, amino, halogen, cyano, nitro, hydroxycarbonyl, $C_{1-5}$alkyl optionally substituted by 1 to 3 $Z^3$, $C_{2-6}$alkenyl, $C_{2-6}$alkynyl, $C_{1-5}$alkoxy optionally substituted by 1 to 3 $Z^3$, $C_{1-5}$alkylthio, mono- or di-$C_{1-5}$alkylamino, piperazinyl optionally substituted by $Z^3$, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl;

wherein each $Z^3$ is independently selected from halogen, amino, and acetyl.

2. The compound according to claim 1, or a stereoisomer, a mixture of stereoisomers, or a pharmaceutically acceptable salt thereof, wherein $R_1$ is selected from the group consisting of Formulas Ia, IIa, IIIa, IVa, and Va:

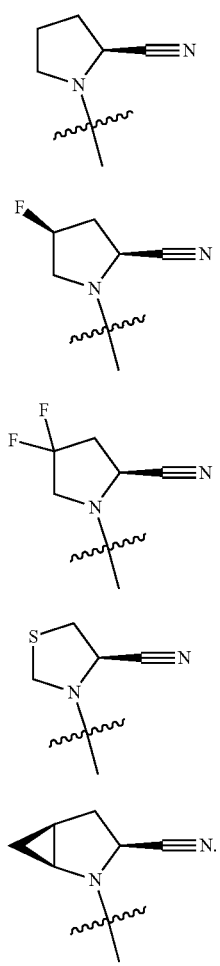

3. The compound according to claim 1, or a stereoisomer, a mixture of stereoisomers, or a pharmaceutically acceptable salt thereof, having a structure of Formula 1a:

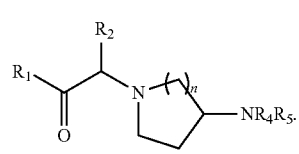

(Formula 1a)

4. The compound according to claim 3, or a stereoisomer, a mixture of stereoisomers, or a pharmaceutically acceptable salt thereof, wherein $R_5$ is hydrogen.

5. The compound according to claim 3, or a stereoisomer, a mixture of stereoisomers, or a pharmaceutically acceptable salt thereof, wherein $R_5$ is a $C_{1-3}$alkyl.

6. The compound according to claim 1, or a stereoisomer, a mixture of stereoisomers, or a pharmaceutically acceptable salt thereof, having a structure of Formula 1b:

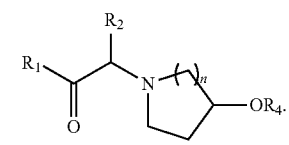

(Formula 1b)

7. The compound according to claim 1, or a stereoisomer, a mixture of stereoisomers, or a pharmaceutically acceptable salt thereof, having a structure of Formula 1c:

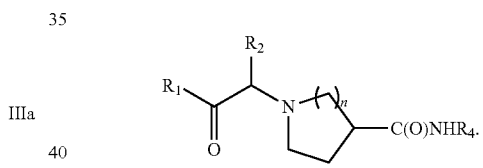

(Formula 1c)

8. The compound according to claim 1, or a stereoisomer, a mixture of stereoisomers, or a pharmaceutically acceptable salt thereof, having a structure of Formula 1d:

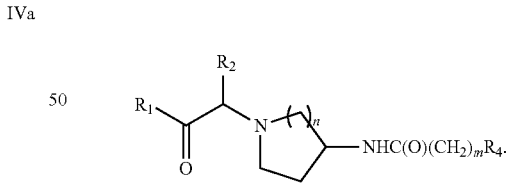

(Formula 1d)

9. The compound according to claim 8, or a stereoisomer, a mixture of stereoisomers, or a pharmaceutically acceptable salt thereof, wherein m is 0.

10. The compound according to claim 8, or a stereoisomer, a mixture of stereoisomers, or a pharmaceutically acceptable salt thereof, wherein m is 1.

11. The compound according to claim 1, or a stereoisomer, a mixture of stereoisomers, or a pharmaceutically acceptable salt thereof, having a structure of Formula 1e:

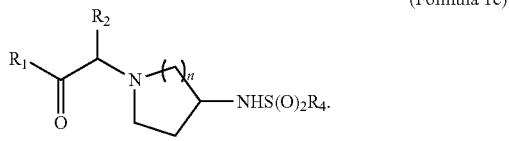

(Formula 1e)

12. The compound according to claim 1, or a stereoisomer, a mixture of stereoisomers, or a pharmaceutically acceptable salt thereof, wherein $R_3$ is selected from the group consisting of —$NR_4R_5$, —$OR_4$, —$C(O)NHR_4$, —$NHC(O)(CH_2)_mR_4$, and —$NHS(O)_2R_4$.

13. The compound according to claim 1, or a stereoisomer, a mixture of stereoisomers, or a pharmaceutically acceptable salt thereof, wherein $R_4$ is a phenyl substituted with 1 to 3 Z, wherein each Z is independently selected from the group consisting of hydroxy, amino, halogen, cyano, nitro, carboxylic acid, $C_{1-5}$alkyl optionally substituted with 1 to 3 halogens or amino, $C_{2-6}$alkenyl, $C_{2-6}$alkynyl, $C_{1-5}$alkoxy, $C_{1-5}$alkylthio, mono- or di-$C_{1-5}$alkylamino, piperazinyl optionally substituted with acetyl, $C_{1-5}$alkylsulfonylamino, $C_{1-5}$alkylcarbonylamino, aminosulfonyl, aminocarbonyl, $C_{1-5}$alkylaminocarbonyl, phenyl, phenoxy, benzyl, benzoyl, phenylaminocarbonyl, pyrazolyl, and benzoxazolyl.

14. The compound according to claim 1, or a stereoisomer, a mixture of stereoisomers, or a pharmaceutically acceptable salt thereof, wherein $R_4$ is a heterocycle selected from the group consisting of benzo[d][1,3]dioxolyl, dihydrobenzo[1,4]dioxinyl, 2,3-dihydrobenzofuranyl, 2-oxo-1,2-dihydroquinolinyl, and 2-oxo-1,2,3,4-tetrahydroquinolinyl, wherein said heterocycle is optionally substituted with 1 to 3 Z.

15. The compound according to claim 1, or a stereoisomer, a mixture of stereoisomers, or a pharmaceutically acceptable salt thereof, wherein $R_4$ is a naphthyl optionally substituted with 1 halogen.

16. The compound according to claim 1, or a stereoisomer, a mixture of stereoisomers, or a pharmaceutically acceptable salt thereof, wherein $R_4$ is a heteroaryl selected from the group consisting of pyridinyl, pyrimidinyl, pyrazinyl, imidazolyl, pyrazolyl, triazolyl, oxazolyl, thiazolyl, furanyl, pyrrolyl, thiophenyl, quinolinyl, isoquinolinyl, chromenonyl, quinazolinyl, benzoxazolyl, benzofuranyl, benzothiophenyl, indolyl, indolinyl, benzimidazolyl, benzoxazolyl, benzothiazolyl, indazolyl, furo[3,2-c]pyridinyl, thieno[2,3-d]pyrimidinyl, thieno[3,2-c]pyridinyl, isoxazolyl, acridinyl, and naphthyridinyl, wherein said heteroaryl is optionally substituted with 1 to 3 Z, wherein each Z is independently selected from the group consisting of hydroxy, amino, di-$C_{1-5}$alkylamino, cyano, nitro, halogen, $C_{1-5}$alkyl optionally substituted with 1 to 3 halogens, $C_{1-5}$alkoxy optionally substituted with 1 to 3 halogens, $C_{1-5}$ alkoxycarbonyl, benzyloxy, phenyl optionally substituted with halogen, acetyl, $C_{1-5}$ alkylsulfonyl, morpholinyl, —$NR_6C(O)R_7$, and —$C(O)NR_6R_7$.

17. The compound according to claim 1, or a stereoisomer, a mixture of stereoisomers, or a pharmaceutically acceptable salt thereof, wherein $R_3$ is a 5- to 12-membered heteroaryl optionally substituted by 1 to 3 Z.

18. The compound according to claim 1, or a stereoisomer, a mixture of stereoisomers, or a pharmaceutically acceptable salt thereof, wherein $R_3$ is a 3- to 12-membered non-aromatic heterocycle containing nitrogen, wherein said heterocycle is optionally substituted by 1 to 3 Z.

19. The compound according to claim 1, or a stereoisomer, a mixture of stereoisomers, or a pharmaceutically acceptable salt thereof, wherein n is 1.

20. The compound according to claim 1, or a stereoisomer, a mixture of stereoisomers, or a pharmaceutically acceptable salt thereof, wherein n is 2.

21. A compound selected from the group consisting of:

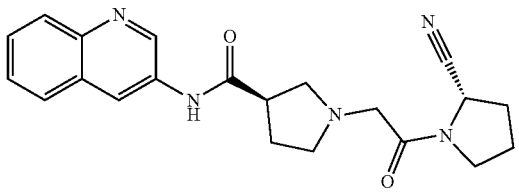 [SMILES: N#C[C@@H]1CCCN1C(=O)CN1CC[C@@H](C(=O)Nc2cnc3ccccc3c2)C1]

(R)-1-(2-((S)-2-cyanopyrrolidin-1-yl)-2-oxoethyl)-N-(quinolin-3-yl)pyrrolidine-3-carboxamide

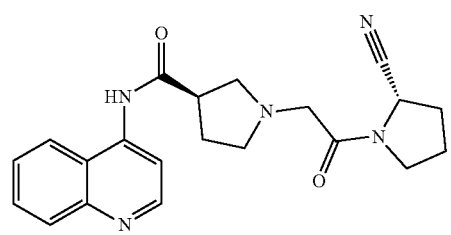 [SMILES: N#C[C@@H]1CCCN1C(=O)CN1CC[C@@H](C(=O)Nc2ccnc3ccccc23)C1]

(R)-1-(2-((S)-2-cyanopyrrolidin-1-yl)-2-oxoethyl)-N-(quinolin-4-yl)pyrrolidine-3-carboxamide

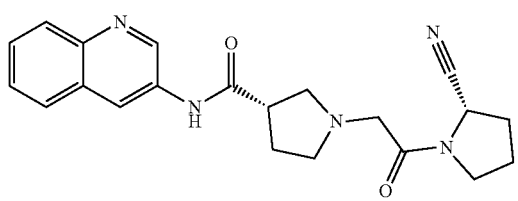 [SMILES: N#C[C@@H]1CCCN1C(=O)CN1CC[C@H](C(=O)Nc2cnc3ccccc3c2)C1]

(S)-1-(2-((S)-2-cyanopyrrolidin-1-yl)-2-oxoethyl)-N-(quinolin-3-yl)pyrrolidine-3-carboxamide -continued

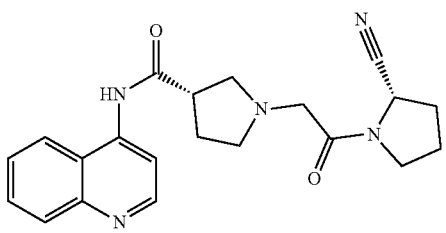 [SMILES: N#C[C@@H]1CCCN1C(=O)CN1CC[C@H](C(=O)Nc2ccnc3ccccc23)C1]

(S)-1-(2-((S)-2-cyanopyrrolidin-1-yl)-2-oxoethyl)-N-(quinolin-4-yl)pyrrolidine-3-carboxamide

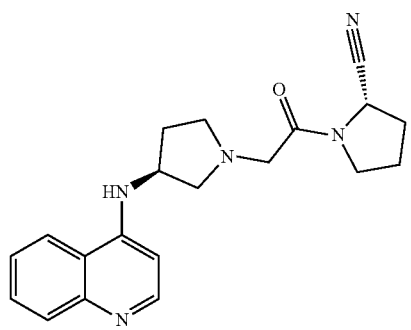 [SMILES: N#C[C@@H]1CCCN1C(=O)CN1CC[C@H](Nc2ccnc3ccccc23)C1]

(S)-1-(2-((S)-3-(quinolin-4-ylamino)pyrrolidin-1-yl)acetyl)pyrrolidine-2-carbonitrile

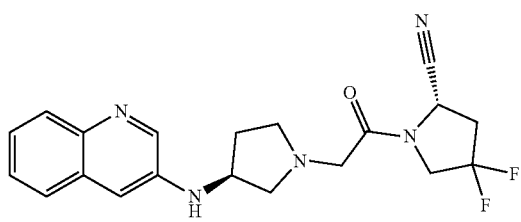 [SMILES: N#C[C@@H]1CC(F)(F)CN1C(=O)CN1CC[C@H](Nc2cnc3ccccc3c2)C1]

(S)-4,4-difluoro-1-(2-((S)-3-(quinolin-3-ylamino)pyrrolidin-1-yl)acetyl)pyrrolidine-2-carbonitrile

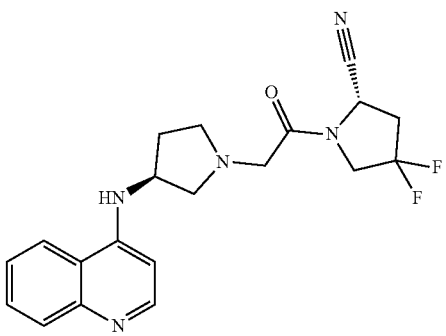 [SMILES: N#C[C@@H]1CC(F)(F)CN1C(=O)CN1CC[C@H](Nc2ccnc3ccccc23)C1]

(S)-4,4-difluoro-1-(2-((S)-3-(quinolin-4-ylamino)pyrrolidin-1-yl)acetyl)pyrrolidine-2-carbonitrile

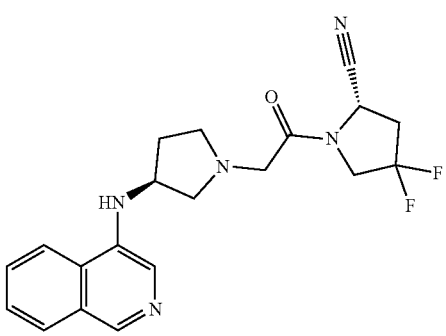 [SMILES: N#C[C@@H]1CC(F)(F)CN1C(=O)CN1CC[C@H](Nc2cncc3ccccc23)C1]

(S)-4,4-difluoro-1-(2-((S)-3-(isoquinolin-4-ylamino)pyrrolidin-1-yl)acetyl)pyrrolidine-2-carbonitrile -continued

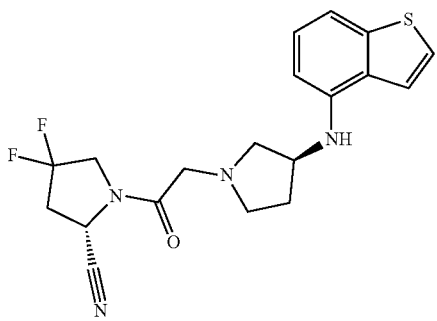 [SMILES: N#C[C@@H]1CC(F)(F)CN1C(=O)CN1CC[C@H](Nc2cccc3sccc23)C1]

(S)-1-(2-((S)-3-(benzo[b]thiophen-4-ylamino)
pyrrolidin-1-yl)acetyl)-4,4-difluoropyrrolidine-
2-carbonitrile

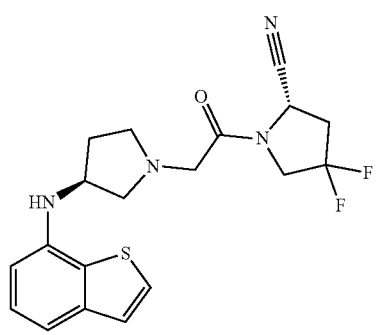 [SMILES: N#C[C@@H]1CC(F)(F)CN1C(=O)CN1CC[C@H](Nc2cccc3ccsc23)C1]

(S)-1-(2-((S)-3-(benzo[b]thiophen-7-ylamino)
pyrrolidin-1-yl)acetyl)-4,4-difluoropyrrolidine-
2-carbonitrile

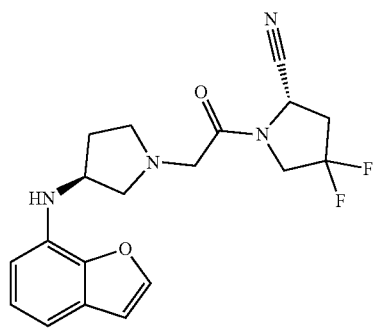 [SMILES: N#C[C@@H]1CC(F)(F)CN1C(=O)CN1CC[C@H](Nc2cccc3ccoc23)C1]

(S)-1-(2-((S)-3-(benzofuran-7-ylamino)
pyrrolidin-1-yl)acetyl)-4,4-difluoropyrrolidine-
2-carbonitrile

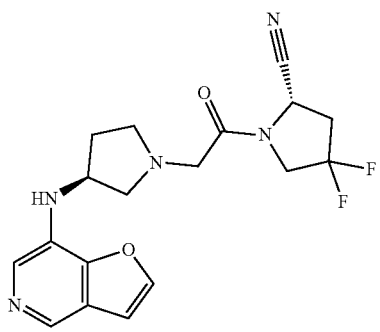 [SMILES: N#C[C@@H]1CC(F)(F)CN1C(=O)CN1CC[C@H](Nc2cncc3ccoc23)C1]

(S)-4,4-difluoro-1-(2-((S)-3-(furo[3,2-c]pyridin-
7-ylamino)pyrrolidin-1-yl)acetyl)pyrrolidine-
2-carbonitrile

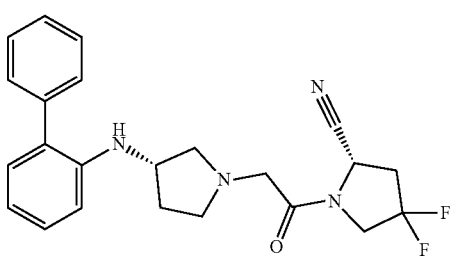 [SMILES: N#C[C@@H]1CC(F)(F)CN1C(=O)CN1CC[C@H](Nc2ccccc2-c2ccccc2)C1]

(S)-1-(2-((S)-3-([1,1'-biphenyl]-2-ylamino)
pyrrolidin-1-yl)acetyl)-4,4-difluoropyrrolidine-
2-carbonitrile

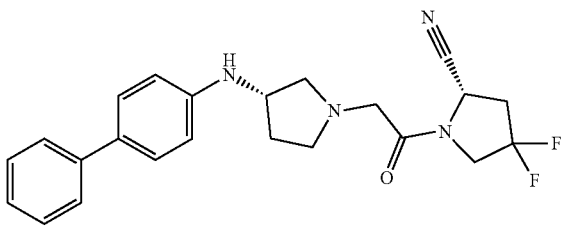 [SMILES: N#C[C@@H]1CC(F)(F)CN1C(=O)CN1CC[C@H](Nc2ccc(-c3ccccc3)cc2)C1]

(S)-1-(2-((S)-3-([1,1'-biphenyl]-4-ylamino)pyrrolidin-1-yl)acetyl)-4,4-difluoropyrrolidine-2-carbonitrile

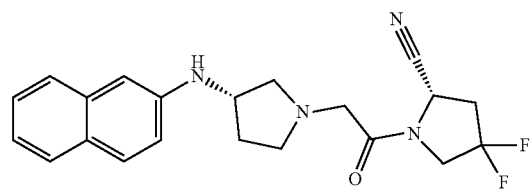 [SMILES: N#C[C@@H]1CC(F)(F)CN1C(=O)CN1CC[C@H](Nc2ccc3ccccc3c2)C1]

(S)-4,4-difluoro-1-(2-((S)-3-(naphthalen-2-ylamino)pyrrolidin-1-yl)acetyl)pyrrolidine-2-carbonitrile

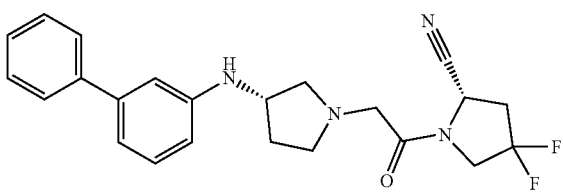 [SMILES: N#C[C@@H]1CC(F)(F)CN1C(=O)CN1CC[C@H](Nc2cccc(-c3ccccc3)c2)C1]

(S)-1-(2-((S)-3-([1,1'-biphenyl]-3-ylamino)pyrrolidin-1-yl)acetyl)-4,4-difluoropyrrolidine-2-carbonitrile

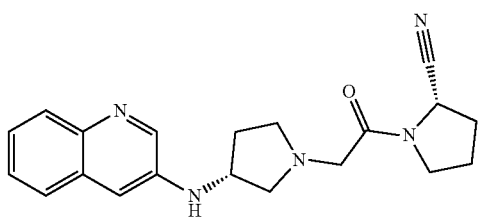 [SMILES: N#C[C@@H]1CCCN1C(=O)CN1CC[C@@H](Nc2cnc3ccccc3c2)C1]

(S)-1-(2-((R)-3-(quinolin-3-ylamino)pyrrolidin-1-yl)acetyl)pyrrolidine-2-carbonitrile

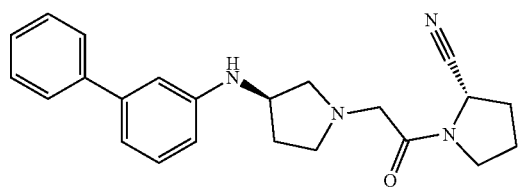 [SMILES: N#C[C@@H]1CCCN1C(=O)CN1CC[C@@H](Nc2cccc(-c3ccccc3)c2)C1]

(S)-1-(2-((R)-3-([1,1'-biphenyl]-3-ylamino)pyrrolidin-1-yl)acetyl)pyrrolidine-2-carbonitrile

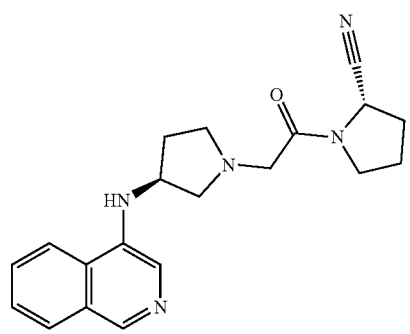 [SMILES: N#C[C@@H]1CCCN1C(=O)CN1CC[C@H](Nc2cncc3ccccc23)C1]

(S)-1-(2-((S)-3-(isoquinolin-4-ylamino)pyrrolidin-1-yl)acetyl)pyrrolidine-2-carbonitrile -continued

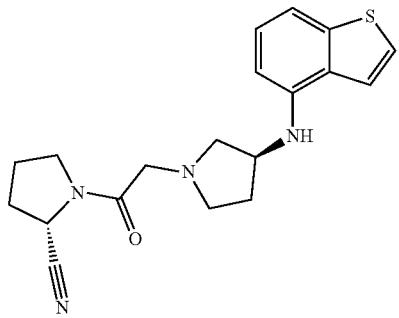 [SMILES: N#C[C@@H]1CCCN1C(=O)CN1CC[C@H](Nc2cccc3sccc23)C1]
(S)-1-(2-((S)-3-(benzo[b]thiophen-4-ylamino)pyrrolidin-1-yl)acetyl)pyrrolidine-2-carbonitrile

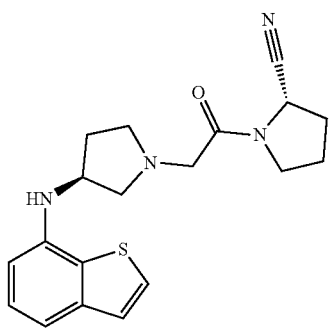 [SMILES: N#C[C@@H]1CCCN1C(=O)CN1CC[C@H](Nc2cccc3ccoc23)C1]
(S)-1-(2-((S)-3-(benzo[b]thiophen-7-ylamino)pyrrolidin-1-yl)acetyl)pyrrolidine-2-carbonitrile

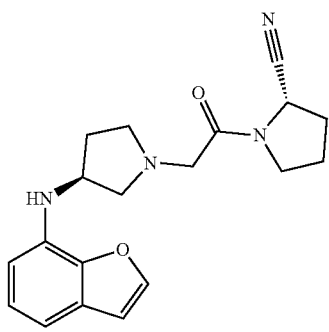
(S)-1-(2-((S)-3-(benzofuran-7-ylamino)pyrrolidin-1-yl)acetyl)pyrrolidine-2-carbonitrile

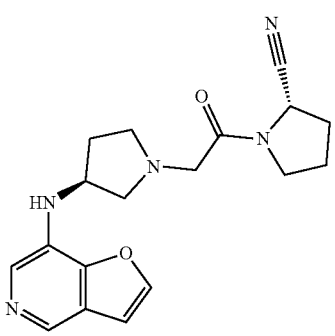 [SMILES: N#C[C@@H]1CCCN1C(=O)CN1CC[C@H](Nc2cncc3ccoc23)C1]
(S)-1-(2-((S)-3-(furo[3,2-c]pyridin-7-ylamino)pyrrolidin-1-yl)acetyl)pyrrolidine-2-carbonitrile

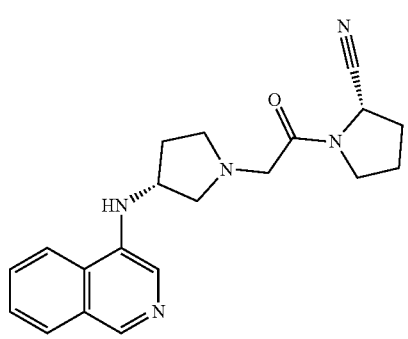 [SMILES: N#C[C@@H]1CCCN1C(=O)CN1CC[C@@H](Nc2cncc3ccccc23)C1]
(S)-1-(2-((R)-3-(isoquinolin-4-ylamino)pyrrolidin-1-yl)acetyl)pyrrolidine-2-carbonitrile

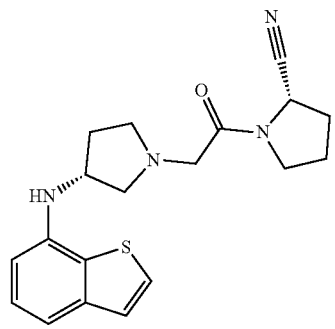 [SMILES: N#C[C@@H]1CCCN1C(=O)CN1CC[C@@H](Nc2cccc3ccsc23)C1]
(S)-1-(2-((R)-3-(benzo[b]thiophen-7-ylamino)pyrrolidin-1-yl)acetyl)pyrrolidine-2-carbonitrile
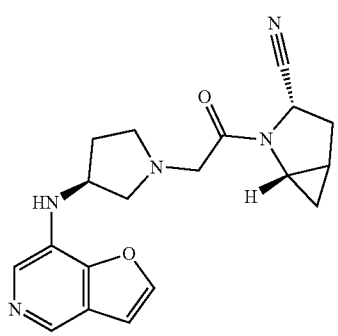 [SMILES: N#C[C@@H]1CC2C[C@@H]2N1C(=O)CN1CC[C@H](Nc2cncc3ccoc23)C1]
(1S,3S,5S)-2-(2-((S)-3-(furo[3,2-c]pyridin-7-ylamino)pyrrolidin-1-yl)acetyl)-2-azabicyclo[3.1.0]hexane-3-carbonitrile
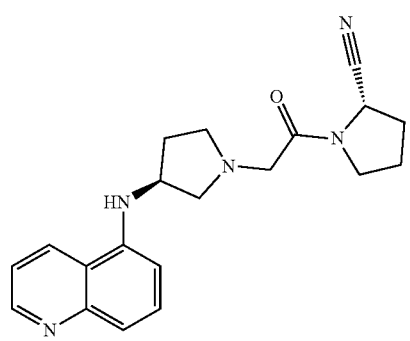 [SMILES: N#C[C@@H]1CCCN1C(=O)CN1CC[C@H](Nc2cccc3ncccc23)C1]
(S)-1-(2-((S)-3-(quinolin-5-ylamino)pyrrolidin-1-yl)acetyl)pyrrolidine-2-carbonitrile
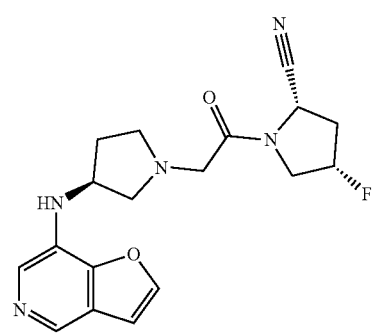 [SMILES: N#C[C@@H]1C[C@H](F)CN1C(=O)CN1CC[C@H](Nc2cncc3ccoc23)C1]
(2S,4S)-4-fluoro-1-(2-((S)-3-(furo[3,2-c]pyridin-7-ylamino)pyrrolidin-1-yl)acetyl)pyrrolidine-2-carbonitrile -continued

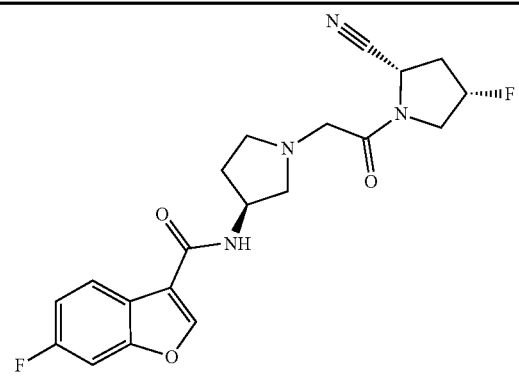

N-((S)-1-(2-((2S,4S)-2-cyano-4-fluoropyrrolidin-1-yl)-2-oxoethyl)pyrrolidin-3-yl)-6-fluorobenzofuran-3-carboxamide

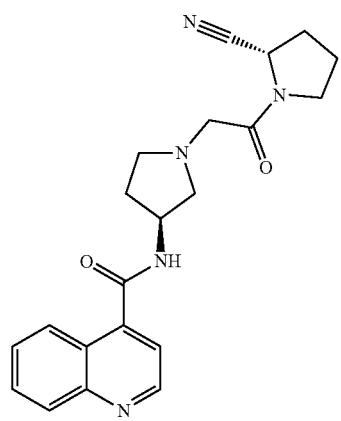 [SMILES: N#C[C@@H]1CCCN1C(=O)CN1CC[C@H](NC(=O)c2ccnc3ccccc23)C1]

N-((S)-1-(2-((S)-2-cyanopyrrolidin-1-yl)-2-oxoethyl)pyrrolidin-3-yl)quinoline-4-carboxamide

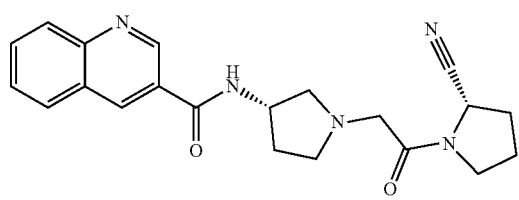 [SMILES: N#C[C@@H]1CCCN1C(=O)CN1CC[C@H](NC(=O)c2cnc3ccccc3c2)C1]

N-((S)-1-(2-((S)-2-cyanopyrrolidin-1-yl)-2-oxoethyl)pyrrolidin-3-yl)quinoline-3-carboxamide

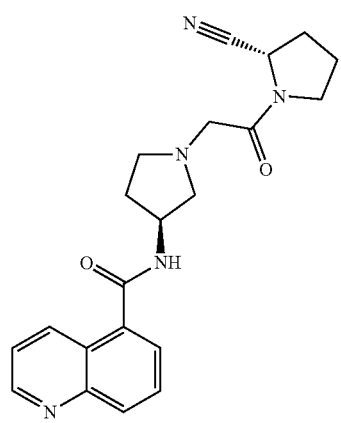 [SMILES: N#C[C@@H]1CCCN1C(=O)CN1CC[C@H](NC(=O)c2cccc3ncccc23)C1]

N-((S)-1-(2-((S)-2-cyanopyrrolidin-1-yl)-2-oxoethyl)pyrrolidin-3-yl)quinoline-5-carboxamide

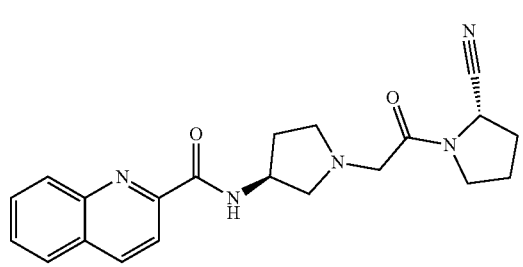 [SMILES: N#C[C@@H]1CCCN1C(=O)CN1CC[C@H](NC(=O)c2ccc3ccccc3n2)C1]

N-((S)-1-(2-((S)-2-cyanopyrrolidin-1-yl)-2-oxoethyl)pyrrolidin-3-yl)quinoline-2-carboxamide

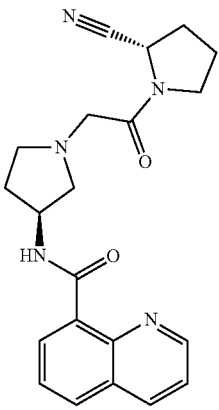 [SMILES: N#C[C@@H]1CCCN1C(=O)CN1CC[C@H](NC(=O)c2cccc3cccnc23)C1] N-((S)-1-(2-((S)-2-cyanopyrrolidin-1-yl)-2-oxoethyl)pyrrolidin-3-yl)quinoline-8-carboxamide
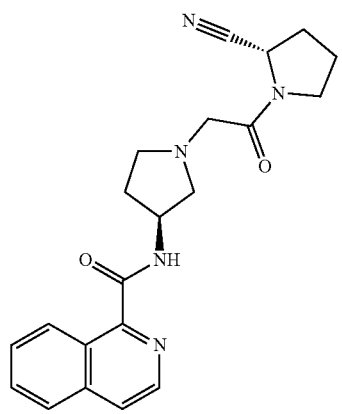 [SMILES: N#C[C@@H]1CCCN1C(=O)CN1CC[C@H](NC(=O)c2nccc3ccccc23)C1] N-((S)-1-(2-((S)-2-cyanopyrrolidin-1-yl)-2-oxoethyl)pyrrolidin-3-yl)isoquinoline-1-carboxamide
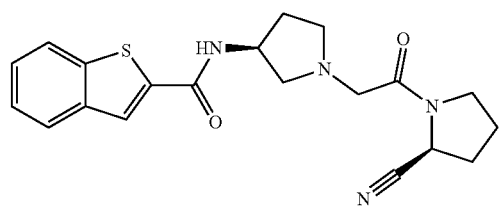 [SMILES: N#C[C@@H]1CCCN1C(=O)CN1CC[C@H](NC(=O)c2cc3ccccc3s2)C1] N-((S)-1-(2-((S)-2-cyanopyrrolidin-1-yl)-2-oxoethyl)pyrrolidin-3-yl)benzo[b]thiophene-2-carboxamide
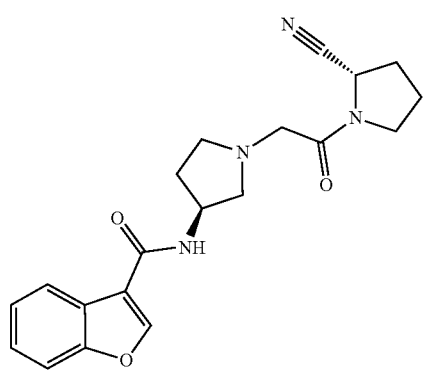 [SMILES: N#C[C@@H]1CCCN1C(=O)CN1CC[C@H](NC(=O)c2coc3ccccc23)C1] N-((S)-1-(2-((S)-2-cyanopyrrolidin-1-yl)-2-oxoethyl)pyrrolidin-3-yl)benzofuran-3-carboxamide

| | |
|---|---|
| 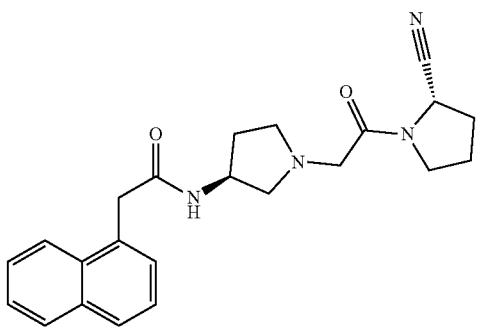 [SMILES: N#C[C@@H]1CCCN1C(=O)CN1CC[C@H](NC(=O)Cc2cccc3ccccc23)C1] | N-((S)-1-(2-((S)-2-cyanopyrrolidin-1-yl)-2-oxoethyl)pyrrolidin-3-yl)-2-(naphthalen-1-yl)acetamide |
| 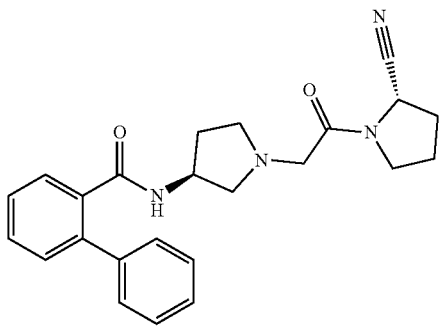 [SMILES: N#C[C@@H]1CCCN1C(=O)CN1CC[C@H](NC(=O)c2ccccc2-c2ccccc2)C1] | N-((S)-1-(2-((S)-2-cyanopyrrolidin-1-yl)-2-oxoethyl)pyrrolidin-3-yl)-(1,1'-biphenyl]-2-carboxamide |
| 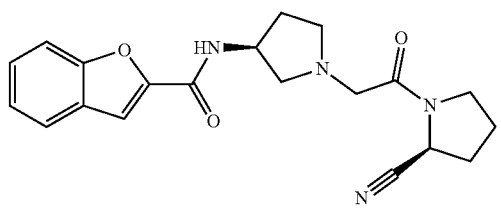 [SMILES: N#C[C@@H]1CCCN1C(=O)CN1CC[C@H](NC(=O)c2cc3ccccc3o2)C1] | N-((S)-1-(2-((S)-2-cyanopyrrolidin-1-yl)-2-oxoethyl)pyrrolidin-3-yl)benzofuran-2-carboxamide |
| 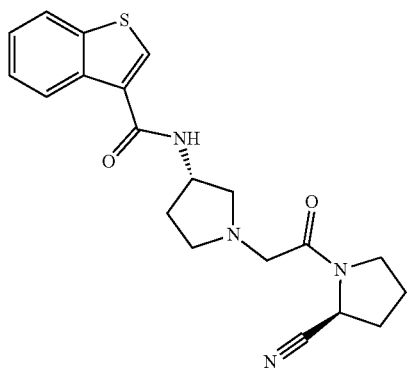 [SMILES: N#C[C@@H]1CCCN1C(=O)CN1CC[C@H](NC(=O)c2csc3ccccc23)C1] | N-((S)-1-(2-((S)-2-cyanopyrrolidin-1-yl)-2-oxoethyl)pyrrolidin-3-yl)benzo[b]thiophene-3-carboxamide |
| 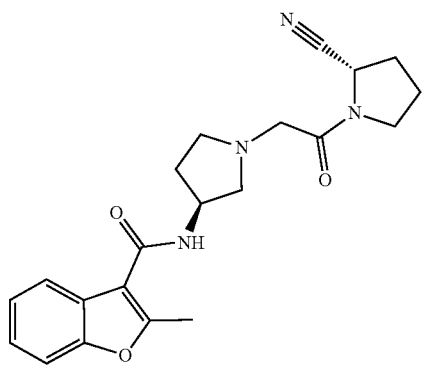 [SMILES: Cc1oc2ccccc2c1C(=O)N[C@H]1CCN(CC(=O)N2CCC[C@H]2C#N)C1] | N-((S)-1-(2-((S)-2-cyanopyrrolidin-1-yl)-2-oxoethyl)pyrrolidin-3-yl)-2-methylbenzofuran-3-carboxamide |

-continued
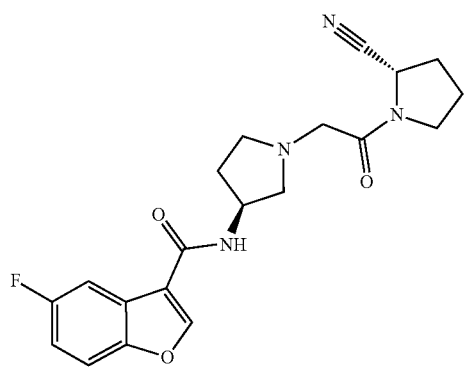 [SMILES: N#C[C@@H]1CCCN1C(=O)CN1CC[C@H](NC(=O)c2coc3ccc(F)cc23)C1]
N-((S)-1-(2-((S)-2-cyanopyrrolidin-1-yl)-2-oxoethyl)pyrrolidin-3-yl)-5-fluorobenzofuran-3-carboxamide
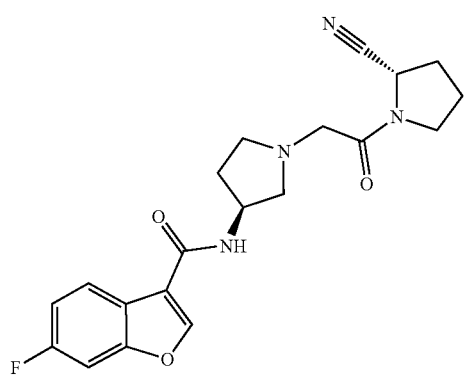 [SMILES: N#C[C@@H]1CCCN1C(=O)CN1CC[C@H](NC(=O)c2coc3cc(F)ccc23)C1]
N-((S)-1-(2-((S)-2-cyanopyrrolidin-1-yl)-2-oxoethyl)pyrrolidin-3-yl)-6-fluorobenzofuran-3-carboxamide
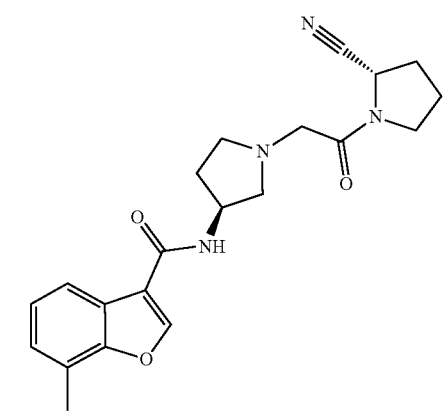 [SMILES: Cc1cccc2c(C(=O)N[C@H]3CCN(CC(=O)N4CCC[C@H]4C#N)C3)coc12]
N-((S)-1-(2-((S)-2-cyanopyrrolidin-1-yl)-2-oxoethyl)pyrrolidin-3-yl)-7-methylbenzofuran-3-carboxamide
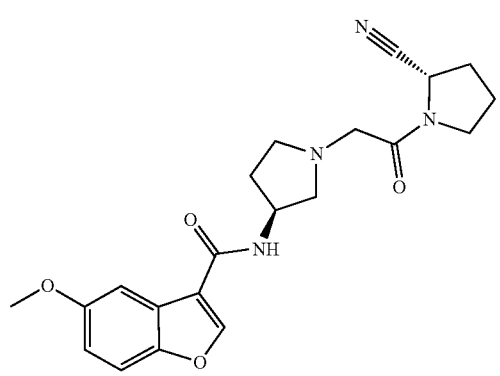 [SMILES: COc1ccc2occ(C(=O)N[C@H]3CCN(CC(=O)N4CCC[C@H]4C#N)C3)c2c1]
N-((S)-1-(2-((S)-2-cyanopyrrolidin-1-yl)-2-oxoethyl)pyrrolidin-3-yl)-5-methoxybenzofuran-3-carboxamide

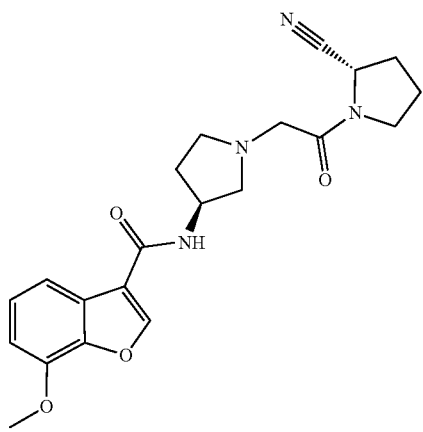 [SMILES: COc1cccc2c(C(=O)N[C@H]3CCN(CC(=O)N4CCC[C@H]4C#N)C3)coc12] N-((S)-1-(2-((S)-2-cyanopyrrolidin-1-yl)-2-oxoethyl)pyrrolidin-3-yl)-7-methoxybenzofuran-3-carboxamide
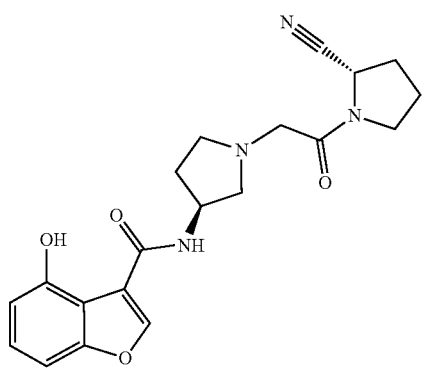 [SMILES: N#C[C@@H]1CCCN1C(=O)CN1CC[C@H](NC(=O)c2coc3cccc(O)c23)C1] N-((S)-1-(2-((S)-2-cyanopyrrolidin-1-yl)-2-oxoethyl)pyrrolidin-3-yl)-4-hydroxybenzofuran-3-carboxamide
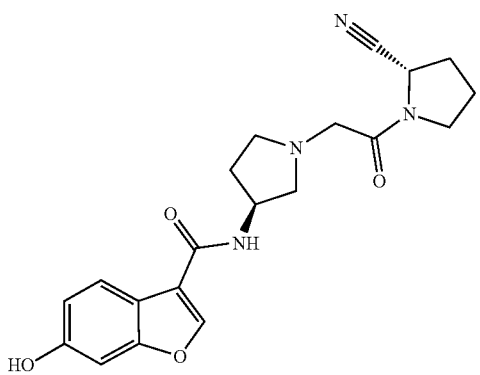 [SMILES: N#C[C@@H]1CCCN1C(=O)CN1CC[C@H](NC(=O)c2coc3cc(O)ccc23)C1] N-((S)-1-(2-((S)-2-cyanopyrrolidin-1-yl)-2-oxoethyl)pyrrolidin-3-yl)-6-hydroxybenzofuran-3-carboxamide
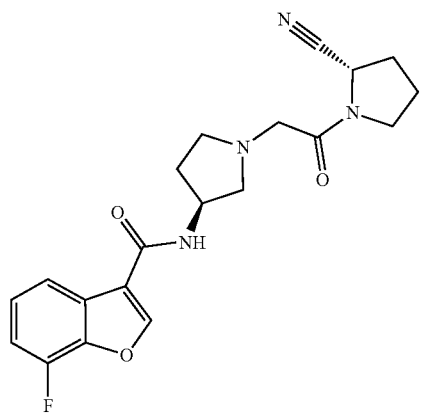 [SMILES: N#C[C@@H]1CCCN1C(=O)CN1CC[C@H](NC(=O)c2coc3c(F)cccc23)C1] N-((S)-1-(2-((S)-2-cyanopyrrolidin-1-yl)-2-oxoethyl)pyrrolidin-3-yl)-7-fluorobenzofuran-3-carboxamide

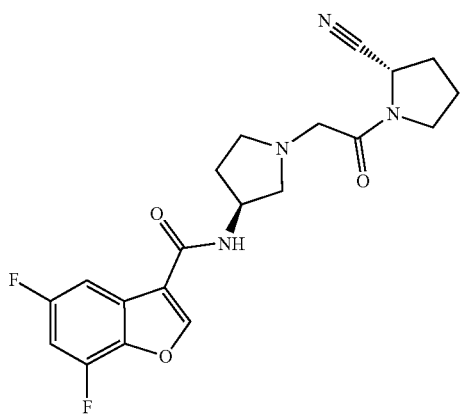 [SMILES: N#C[C@@H]1CCCN1C(=O)CN1CC[C@H](NC(=O)c2coc3c(F)cc(F)cc23)C1]
N-((S)-1-(2-((S)-2-cyanopyrrolidin-1-yl)-2-oxoethyl)pyrrolidin-3-yl)-5,7-difluorobenzofuran-3-carboxamide
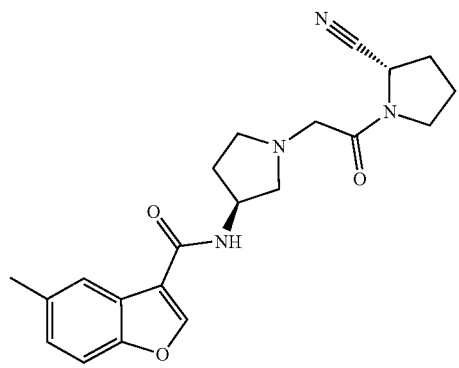 [SMILES: Cc1ccc2occ(C(=O)N[C@H]3CCN(CC(=O)N4CCC[C@H]4C#N)C3)c2c1]
N-((S)-1-(2-((S)-2-cyanopyrrolidin-1-yl)-2-oxoethyl)pyrrolidin-3-yl)-5-methylbenzofuran-3-carboxamide
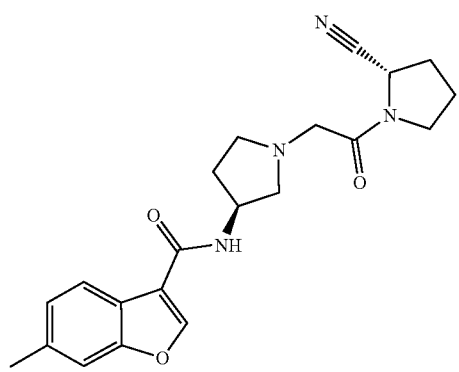 [SMILES: Cc1ccc2c(C(=O)N[C@H]3CCN(CC(=O)N4CCC[C@H]4C#N)C3)coc2c1]
N-((S)-1-(2-((S)-2-cyanopyrrolidin-1-yl)-2-oxoethyl)pyrrolidin-3-yl)-6-methylbenzofuran-3-carboxamide
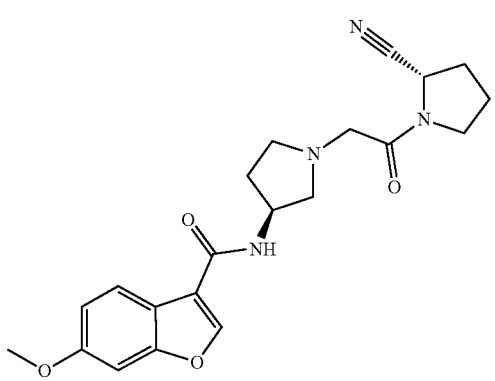 [SMILES: COc1ccc2c(C(=O)N[C@H]3CCN(CC(=O)N4CCC[C@H]4C#N)C3)coc2c1]
N-((S)-1-(2-((S)-2-cyanopyrrolidin-1-yl)-2-oxoethyl)pyrrolidin-3-yl)-6-methoxybenzofuran-3-carboxamide

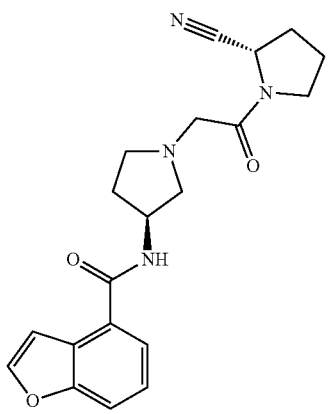 [SMILES: N#C[C@@H]1CCCN1C(=O)CN1CC[C@H](NC(=O)c2cccc3occc23)C1]
N-((S)-1-(2-((S)-2-cyanopyrrolidin-1-yl)-2-oxoethyl)pyrrolidin-3-yl)benzofuran-4-carboxamide

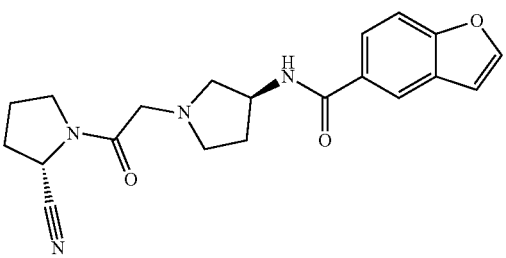 [SMILES: N#C[C@@H]1CCCN1C(=O)CN1CC[C@H](NC(=O)c2ccc3occc3c2)C1]
N-((S)-1-(2-((S)-2-cyanopyrrolidin-1-yl)-2-oxoethyl)pyrrolidin-3-yl)benzofuran-5-carboxamide

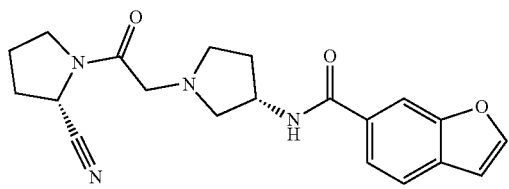 [SMILES: N#C[C@@H]1CCCN1C(=O)CN1CC[C@H](NC(=O)c2ccc3ccoc3c2)C1]
N-((S)-1-(2-((S)-2-cyanopyrrolidin-1-yl)-2-oxoethyl)pyrrolidin-3-yl)benzofuran-6-carboxamide

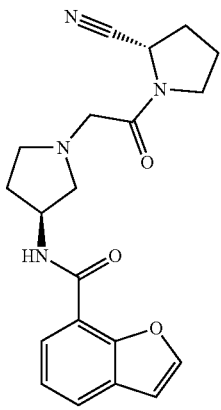 [SMILES: N#C[C@@H]1CCCN1C(=O)CN1CC[C@H](NC(=O)c2cccc3ccoc23)C1]
N-((S)-1-(2-((S)-2-cyanopyrrolidin-1-yl)-2-oxoethyl)pyrrolidin-3-yl)benzofuran-7-carboxamide

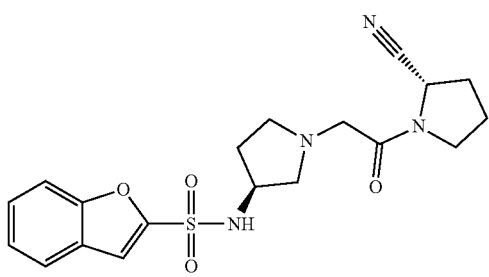 [SMILES: N#C[C@@H]1CCCN1C(=O)CN1CC[C@H](NS(=O)(=O)c2cc3ccccc3o2)C1]
N-((S)-1-(2-((S)-2-cyanopyrrolidin-1-yl)-2-oxoethyl)pyrrolidin-3-yl)benzofuran-2-sulfonamide -continued

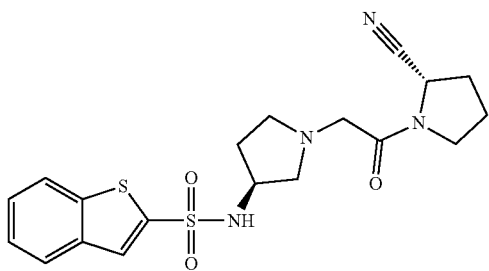

N-((S)-1-(2-((S)-2-cyanopyrrolidin-1-yl)-2-oxoethyl)pyrrolidin-3-yl)benzo[b]thiophene-2-sulfonamide

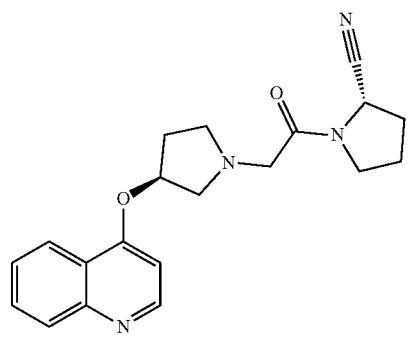 [SMILES: N#C[C@@H]1CCCN1C(=O)CN1CC[C@H](Oc2ccnc3ccccc23)C1]

(S)-1-(2-((S)-3-(quinolin-4-yloxy)pyrrolidin-1-yl)acetyl)pyrrolidine-2-carbonitrile

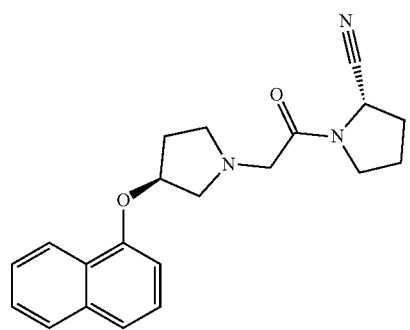 [SMILES: N#C[C@@H]1CCCN1C(=O)CN1CC[C@H](Oc2cccc3ccccc23)C1]

(S)-1-(2-((S)-3-(naphthalen-1-yloxy)pyrrolidin-1-yl)acetyl)pyrrolidine-2-carbonitrile

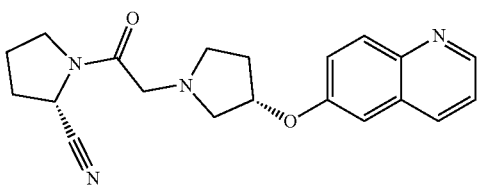 [SMILES: N#C[C@@H]1CCCN1C(=O)CN1CC[C@H](Oc2ccc3ncccc3c2)C1]

(S)-1-(2-((S)-3-(quinolin-6-yloxy)pyrrolidin-1-yl)acetyl)pyrrolidine-2-carbonitrile

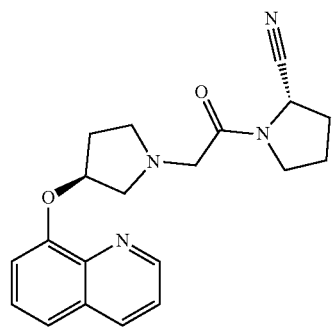 [SMILES: N#C[C@@H]1CCCN1C(=O)CN1CC[C@H](Oc2cccc3cccnc23)C1]

(S)-1-(2-((S)-3-(quinolin-8-yloxy)pyrrolidin-1-yl)acetyl)pyrrolidine-2-carbonitrile -continued

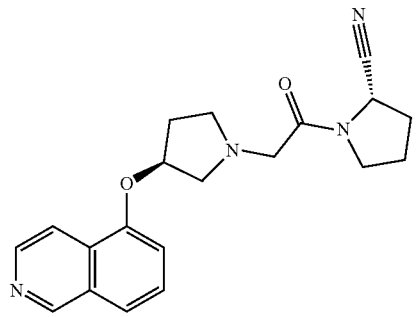 [SMILES: N#C[C@@H]1CCCN1C(=O)CN1CC[C@H](Oc2cccc3cnccc23)C1]

(S)-1-(2-((S)-3-(isoquinolin-5-yloxy)
pyrrolidin-1-yl)acetyl)pyrrolidine-2-carbonitrile

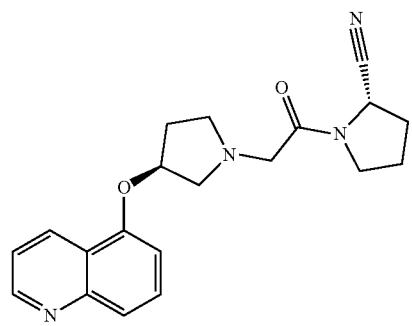 [SMILES: N#C[C@@H]1CCCN1C(=O)CN1CC[C@H](Oc2cccc3ncccc23)C1]

(S)-1-(2-((S)-3-(quinolin-5-yloxy)pyrrolidin-
1-yl)acetyl)pyrrolidine-2-carbonitrile

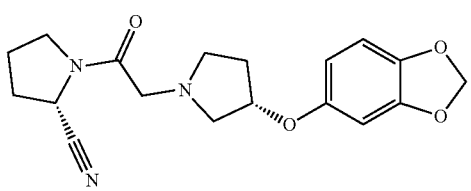 [SMILES: N#C[C@@H]1CCCN1C(=O)CN1CC[C@H](Oc2ccc3c(c2)OCO3)C1]

(S)-1-(2-((S)-3-(benzo[d][1,3]dioxol-5-yloxy)
pyrrolidin-1-yl)acetyl)pyrrolidine-2-carbonitrile

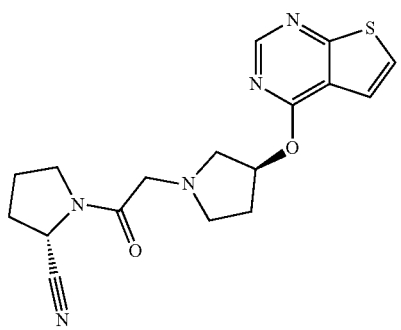 [SMILES: N#C[C@@H]1CCCN1C(=O)CN1CC[C@H](Oc2ncnc3sccc23)C1]

(S)-1-(2-((S)-3-(thieno[2,3-d]pyrimidin-4-
yloxy)pyrrolidin-1-yl)acetyl)pyrrolidine-2-
carbonitrile

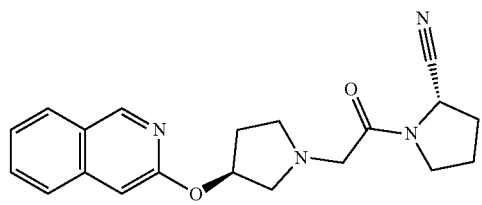 [SMILES: N#C[C@@H]1CCCN1C(=O)CN1CC[C@H](Oc2cc3ccccc3cn2)C1]

(S)-1-(2-((S)-3-(isoquinolin-3-yloxy)pyrrolidin-
1-yl)acetyl)pyrrolidine-2-carbonitrile

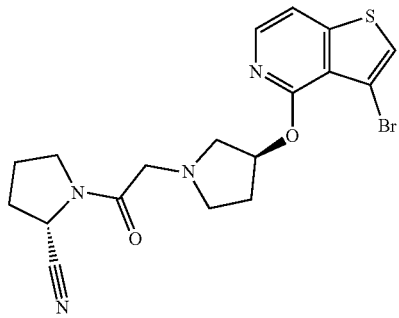 [SMILES: N#C[C@@H]1CCCN1C(=O)CN1CC[C@H](Oc2nccc3scc(Br)c23)C1]

(S)-1-(2-((S)-3-((3-bromothieno[3,2-c]pyridin-4-yl)oxy)pyrrolidin-1-yl)acetyl)pyrrolidine-2-carbonitrile

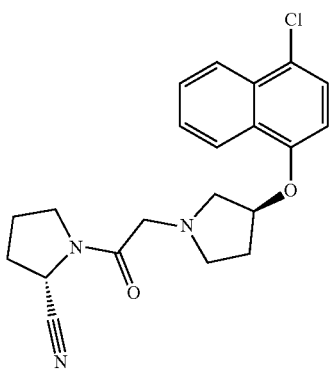 [SMILES: N#C[C@@H]1CCCN1C(=O)CN1CC[C@H](Oc2ccc(Cl)c3ccccc23)C1]

(S)-1-(2-((S)-3-((4-chloronaphthalen-1-yl)oxy)pyrrolidin-1-yl)acetyl)pyrrolidine-2-carbonitrile

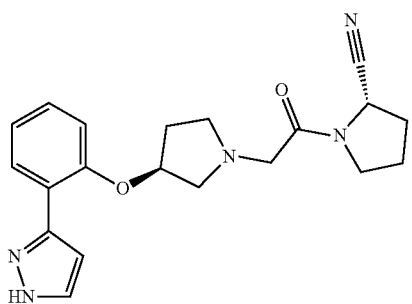 [SMILES: N#C[C@@H]1CCCN1C(=O)CN1CC[C@H](Oc2ccccc2-c2cc[nH]n2)C1]

(S)-1-(2-((S)-3-(2-(1H-pyrazol-3-yl)phenoxy)pyrrolidin-1-yl)acetyl)pyrrolidine-2-carbonitrile

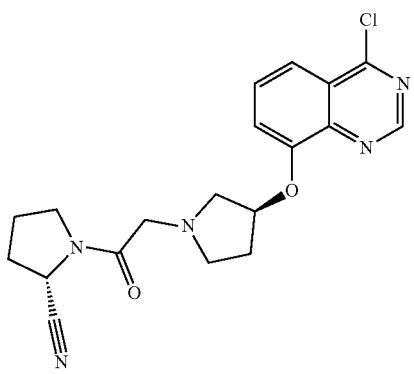 [SMILES: N#C[C@@H]1CCCN1C(=O)CN1CC[C@H](Oc2cccc3c(Cl)ncnc23)C1]

(S)-1-(2-((S)-3-(4-chloroquinazolin-8-yl)oxy)pyrrolidin-1-yl)acetyl)pyrrolidine-2-carbonitrile

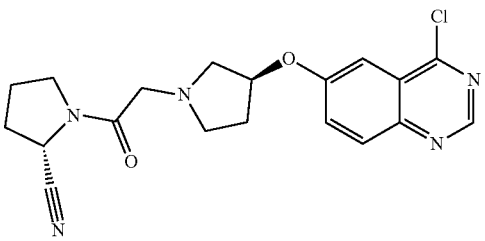 [SMILES: N#C[C@@H]1CCCN1C(=O)CN1CC[C@H](Oc2ccc3ncnc(Cl)c3c2)C1]

(S)-1-(2-((S)-3-((4-chloroquinazolin-6-yl)oxy)pyrrolidin-1-yl)acetyl)pyrrolidine-2-carbonitrile -continued

| | |
|---|---|
| 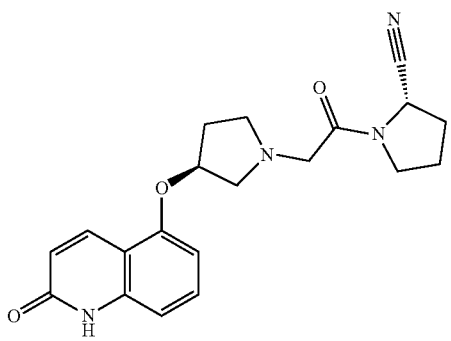 [SMILES: N#C[C@@H]1CCCN1C(=O)CN1CC[C@H](Oc2cccc3[nH]c(=O)ccc23)C1] | (S)-1-(2-((S)-3-(2-oxo-1,2-dihydroquinolin-5-yl)oxy)pyrrolidin-1-yl)acetyl)pyrrolidine-2-carbonitrile |
| 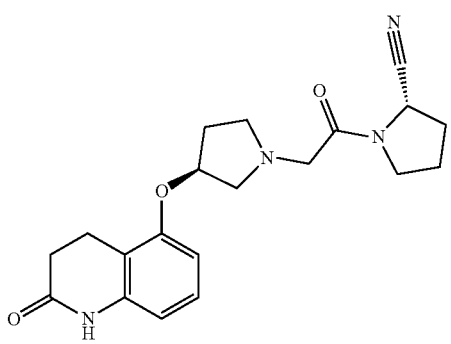 | (S)-1-(2-((S)-3-((2-oxo-1,2,3,4-tetrahydroquinolin-5-yl)oxy)pyrrolidin-1-yl)acetyl)pyrrolidine-2-carbonitrile |
| 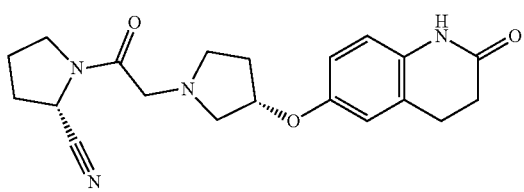 [SMILES: N#C[C@@H]1CCCN1C(=O)CN1CC[C@H](Oc2ccc3c(c2)CCC(=O)N3)C1] | (S)-1-(2-((S)-3-((2-oxo-1,2,3,4-tetrahydroquinolin-6-yl)oxy)pyrrolidin-1-yl)acetyl)pyrrolidine-2-carbonitrile |
| 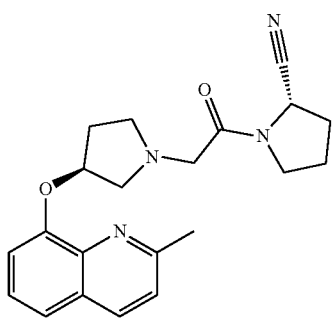 [SMILES: Cc1ccc2cccc(O[C@H]3CCN(CC(=O)N4CCC[C@H]4C#N)C3)c2n1] | (S)-1-(2-((S)-3-((2-methylquinolin-8-yl)oxy)pyrrolidin-1-yl)acetyl)pyrrolidine-2-carbonitrile |
| 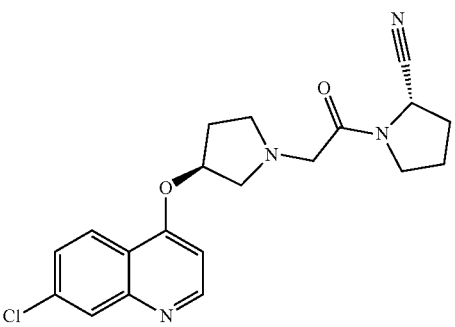 [SMILES: N#C[C@@H]1CCCN1C(=O)CN1CC[C@H](Oc2ccnc3cc(Cl)ccc23)C1] | (S)-1-(2-((S)-3-((7-chloroquinolin-4-yl)oxy)pyrrolidin-1-yl)acetyl)pyrrolidine-2-carbonitrile |

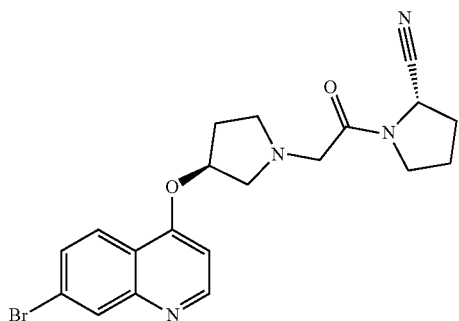

(S)-1-(2-((S)-3-((7-bromoquinolin-4-yl)oxy)
pyrrolidin-1-yl)acetyl)pyrrolidine-2-carbonitrile

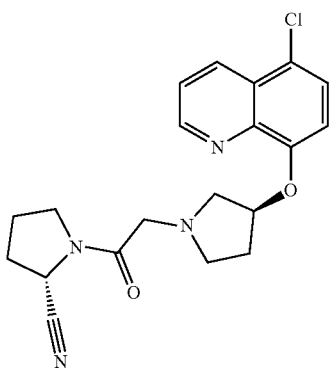 [SMILES: N#C[C@@H]1CCCN1C(=O)CN1CC[C@H](Oc2ccc(Cl)c3cccnc23)C1]

(S)-1-(2-((S)-3-((5-chloroquinolin-8-yl)oxy)
pyrrolidin-1-yl)acetyl)pyrrolidine-2-carbonitrile

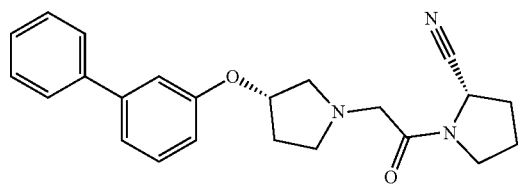 [SMILES: N#C[C@@H]1CCCN1C(=O)CN1CC[C@H](Oc2cccc(-c3ccccc3)c2)C1]

(S)-1-(2-((S)-3-([1,1'-biphenyl]-3-yloxy)
pyrrolidin-1-yl)acetyl)pyrrolidine-2-carbonitrile

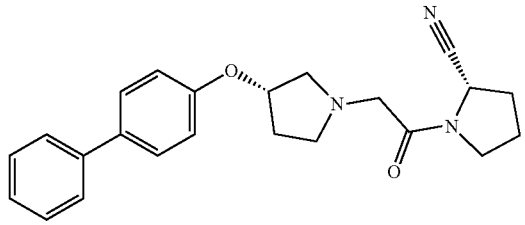 [SMILES: N#C[C@@H]1CCCN1C(=O)CN1CC[C@H](Oc2ccc(-c3ccccc3)cc2)C1]

(S)-1-(2-((S)-3-([1,1'-biphenyl]-4-yloxy)
pyrrolidin-1-yl)acetyl)pyrrolidine-2-carbonitrile

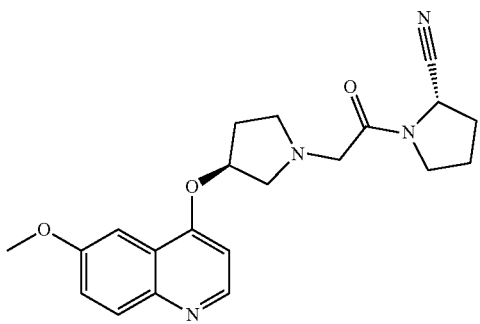 [SMILES: COc1ccc2nccc(O[C@H]3CCN(CC(=O)N4CCC[C@H]4C#N)C3)c2c1]

(S)-1-(2-((S)-3-((6-methoxyquinolin-4-yl)
oxy)pyrrolidin-1-yl)acetyl)pyrrolidine-2-carbonitrile

| | |
|---|---|
| 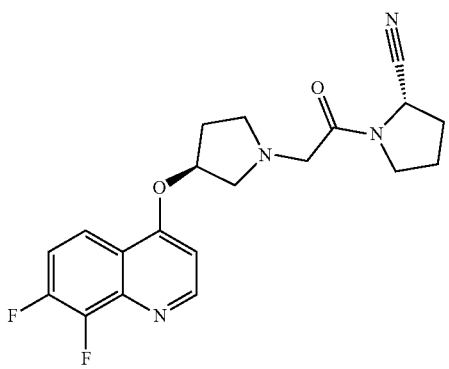 [SMILES: N#C[C@@H]1CCCN1C(=O)CN1CC[C@H](Oc2ccnc3c(F)c(F)ccc23)C1] | (S)-1-(2-((S)-3-((7,8-difluoroquinolin-4-yl)oxy)pyrrolidin-1-yl)acetyl)pyrrolidine-2-carbonitrile |
| 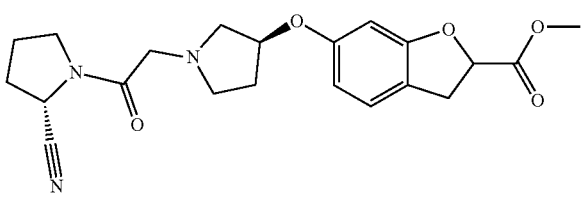 [SMILES: COC(=O)C1Cc2ccc(O[C@H]3CCN(CC(=O)N4CCC[C@H]4C#N)C3)cc2O1] | methyl 6-(((S)-1-(2-((S)-2-cyanopyrrolidin-1-yl)-2-oxoethyl)pyrrolidin-3-yl)oxy)-2,3-dihydrobenzofuran-2-carboxylate |
| 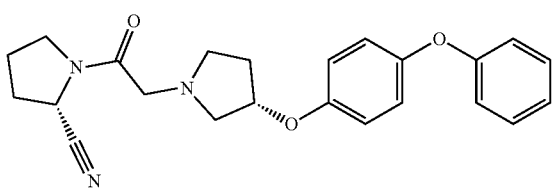 | (S)-1-(2-((S)-3-(4-phenoxyphenoxy)pyrrolidin-1-yl)acetyl)pyrrolidine-2-carbonitrile |
| 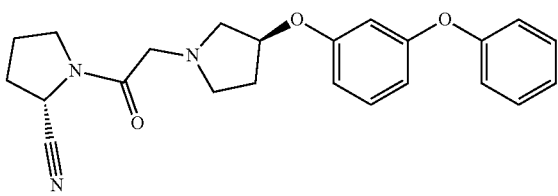 [SMILES: N#C[C@@H]1CCCN1C(=O)CN1CC[C@H](Oc2cccc(Oc3ccccc3)c2)C1] | (S)-1-(2-((S)-3-(3-phenoxyphenoxy)pyrrolidin-1-yl)acetyl)pyrrolidine-2-carbonitrile |
| 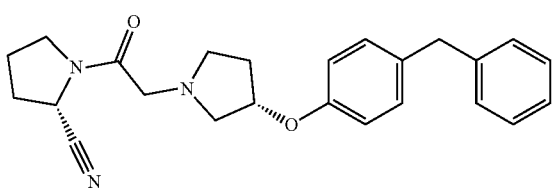 [SMILES: N#C[C@@H]1CCCN1C(=O)CN1CC[C@H](Oc2ccc(Cc3ccccc3)cc2)C1] | (S)-1-(2-((S)-3-(4-benzylphenoxy)pyrrolidin-1-yl)acetyl)pyrrolidine-2-carbonitrile |
| 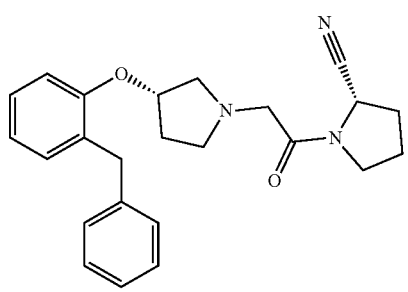 [SMILES: N#C[C@@H]1CCCN1C(=O)CN1CC[C@H](Oc2ccccc2Cc2ccccc2)C1] | (S)-1-(2-((S)-3-(2-benzylphenoxy)pyrrolidin-1-yl)acetyl)pyrrolidine-2-carbonitrile |

-continued

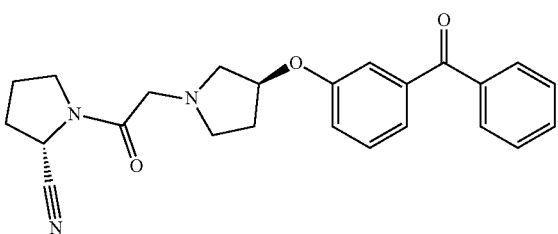 [SMILES: N#C[C@@H]1CCCN1C(=O)CN1CC[C@H](Oc2cccc(C(=O)c3ccccc3)c2)C1]

(S)-1-(2-((S)-3-(3-benzoylphenoxy)pyrrolidin-1-yl)acetyl)pyrrolidine-2-carbonitrile

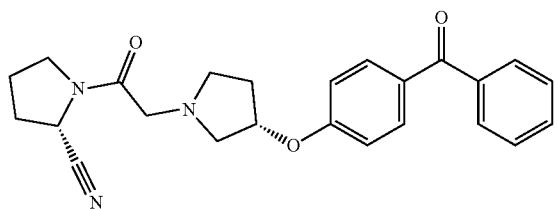 [SMILES: N#C[C@@H]1CCCN1C(=O)CN1CC[C@H](Oc2ccc(C(=O)c3ccccc3)cc2)C1]

(S)-1-(2-((S)-3-(4-benzoylphenoxy)pyrrolidin-1-yl)acetyl)pyrrolidine-2-carbonitrile

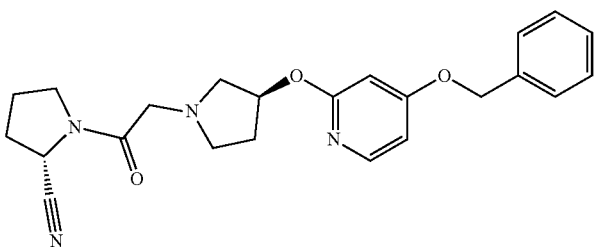 [SMILES: N#C[C@@H]1CCCN1C(=O)CN1CC[C@H](Oc2cc(OCc3ccccc3)ccn2)C1]

(S)-1-(2-((S)-3-((4-(benzyloxy)pyridin-2-yl)oxy)pyrrolidin-1-yl)acetyl)pyrrolidine-2-carbonitrile

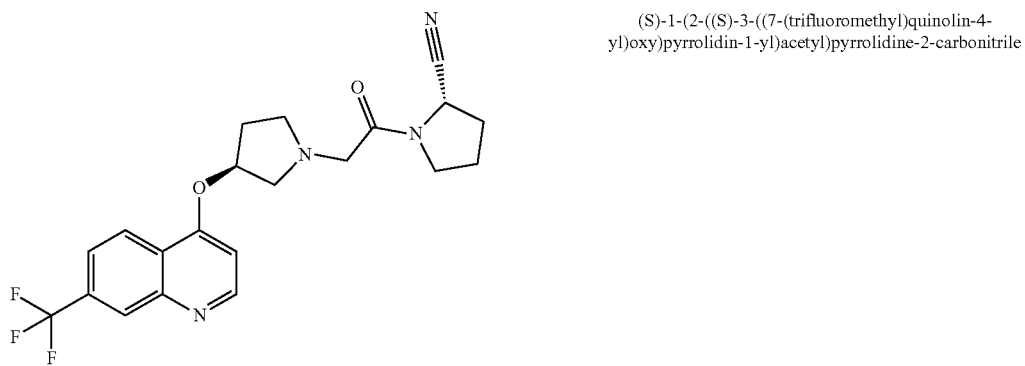

(S)-1-(2-((S)-3-((7-(trifluoromethyl)quinolin-4-yl)oxy)pyrrolidin-1-yl)acetyl)pyrrolidine-2-carbonitrile

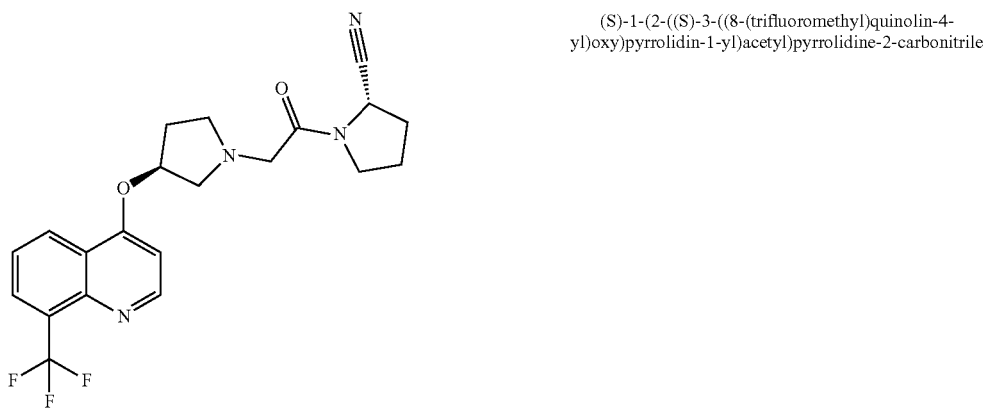

(S)-1-(2-((S)-3-((8-(trifluoromethyl)quinolin-4-yl)oxy)pyrrolidin-1-yl)acetyl)pyrrolidine-2-carbonitrile

| | |
|---|---|
| 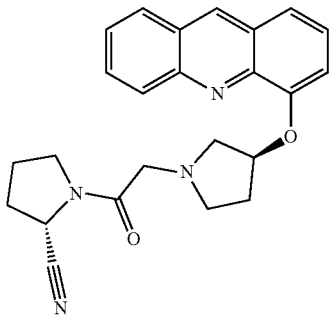 [SMILES: N#C[C@@H]1CCCN1C(=O)CN1CC[C@H](Oc2cccc3cc4ccccc4nc23)C1] | (S)-1-(2-((S)-3-(acridin-4-yloxy)pyrrolidin-1-yl)acetyl)pyrrolidine-2-carbonitrile |
| 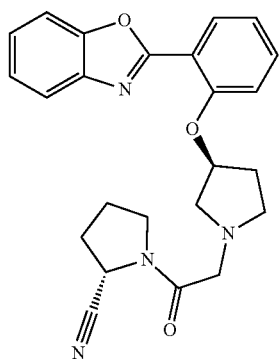 [SMILES: N#C[C@@H]1CCCN1C(=O)CN1CC[C@H](Oc2ccccc2-c2nc3ccccc3o2)C1] | (S)-1-(2-((S)-3-(2-(benzo[d]oxazol-2-yl)phenoxy)pyrrolidin-1-yl)acetyl)pyrrolidine-2-carbonitrile |
| 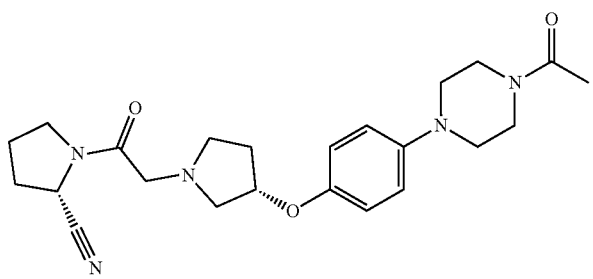 [SMILES: CC(=O)N1CCN(c2ccc(O[C@H]3CCN(CC(=O)N4CCC[C@H]4C#N)C3)cc2)CC1] | (S)-1-(2-((S)-3-(4-(4-acetylpiperazin-1-yl)phenoxy)pyrrolidin-1-yl)acetyl)pyrrolidine-2-carbonitrile |
| 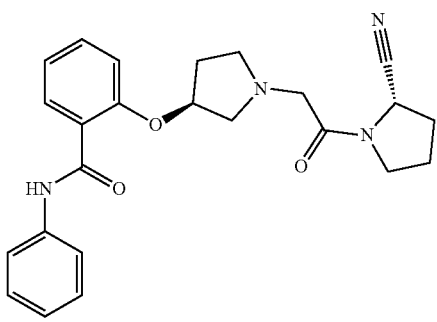 [SMILES: N#C[C@@H]1CCCN1C(=O)CN1CC[C@H](Oc2ccccc2C(=O)Nc2ccccc2)C1] | 2-(((S)-1-(2-((S)-2-cyanopyrrolidin-1-yl)-2-oxoethyl)pyrrolidin-3-yl)oxy)-N-phenylbenzamide |
| 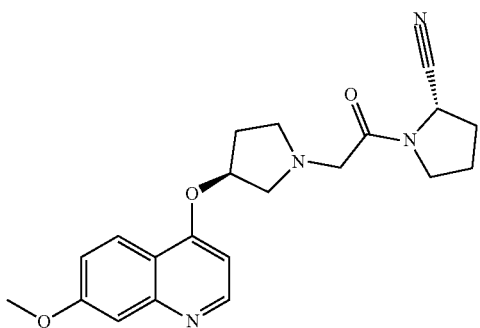 | (S)-1-(2-((S)-3-((7-methoxyquinolin-4-yl)oxy)pyrrolidin-1-yl)acetyl)pyrrolidine-2-carbonitrile |

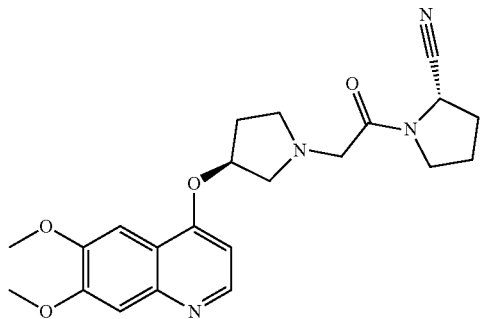 [SMILES: COc1cc2nccc(O[C@H]3CCN(CC(=O)N4CCC[C@H]4C#N)C3)c2cc1OC]
(S)-1-(2-((S)-3-((6,7-dimethoxyquinolin-4-yl)oxy)pyrrolidin-1-yl)acetyl)pyrrolidine-2-carbonitrile
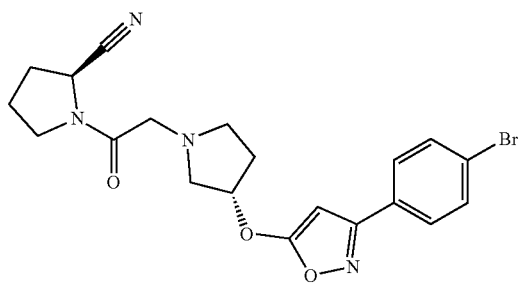 [SMILES: N#C[C@@H]1CCCN1C(=O)CN1CC[C@H](Oc2cc(-c3ccc(Br)cc3)no2)C1]
(S)-1-(2-((S)-3-((3-(4-bromophenyl)isoxazol-5-yl)oxy)pyrrolidin-1-yl)acetyl)pyrrolidine-2-carbonitrile
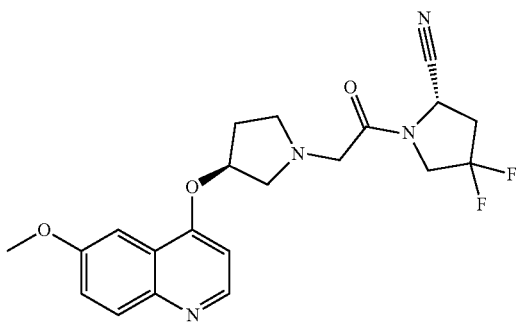 [SMILES: COc1ccc2nccc(O[C@H]3CCN(CC(=O)N4CC(F)(F)C[C@H]4C#N)C3)c2c1]
(S)-4,4-difluoro-1-(2-((S)-3-((6-methoxyquinolin-4-yl)oxy)pyrrolidin-1-yl)acetyl)pyrrolidine-2-carbonitrile
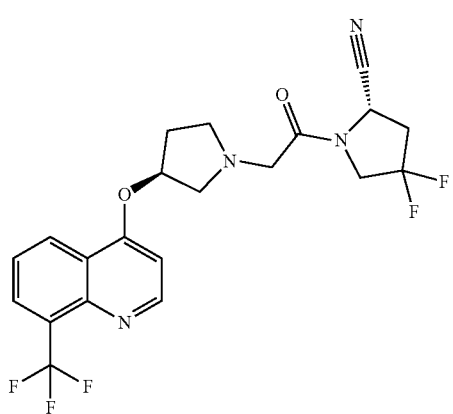 [SMILES: N#C[C@@H]1CC(F)(F)CN1C(=O)CN1CC[C@H](Oc2ccnc3c(C(F)(F)F)cccc23)C1]
(S)-4,4-difluoro-1-(2-((S)-3-((8-(trifluoromethyl)quinolin-4-yl)oxy)pyrrolidin-1-yl)acetyl)pyrrolidine-2-carbonitrile

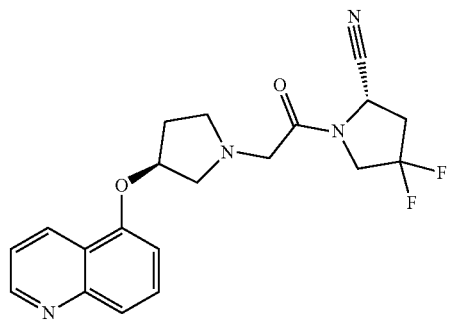 [SMILES: N#C[C@@H]1CC(F)(F)CN1C(=O)CN1CC[C@H](Oc2cccc3ncccc23)C1]
(S)-4,4-difluoro-1-(2-((S)-3-(quinolin-5-yloxy)
pyrrolidin-1-yl)acetyl)pyrrolidine-2-carbonitrile
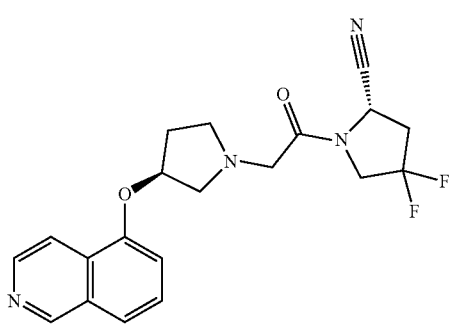 [SMILES: N#C[C@@H]1CC(F)(F)CN1C(=O)CN1CC[C@H](Oc2cccc3cnccc23)C1]
(S)-4,4-difluoro-1-(2-((S)-3-(isoquinolin-5-yloxy)
pyrrolidin-1-yl)acetyl)pyrrolidine-2-carbonitrile
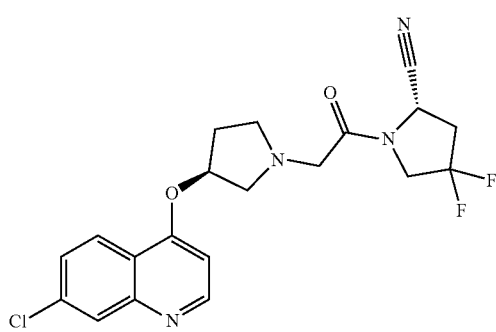 [SMILES: N#C[C@@H]1CC(F)(F)CN1C(=O)CN1CC[C@H](Oc2ccnc3cc(Cl)ccc23)C1]
(S)-1-(2-((S)-3-((7-chloroquinolin-4-yl)
oxy)pyrrolidin-1-yl)acetyl)-4,4-difluoropyrrolidine-
2-carbonitrile
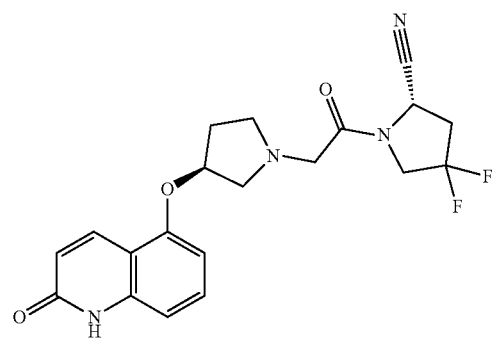 [SMILES: N#C[C@@H]1CC(F)(F)CN1C(=O)CN1CC[C@H](Oc2cccc3[nH]c(=O)ccc23)C1]
(S)-4,4-difluoro-1-(2-((S)-3-((2-oxo-1,2-
dihydroquinolin-5-yl)oxy)pyrrolidin-1-yl)
acetyl)pyrrolidine-2-carbonitrile

| | |
|---|---|
| 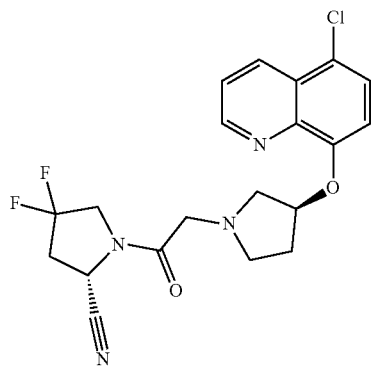 [SMILES: N#C[C@@H]1CC(F)(F)CN1C(=O)CN1CC[C@H](Oc2ccc(Cl)c3cccnc23)C1] | (S)-1-(2-((S)-3-((5-chloroquinolin-8-yl)oxy)pyrrolidin-1-yl)acetyl)-4,4-difluoropyrrolidine-2-carbonitrile |
| 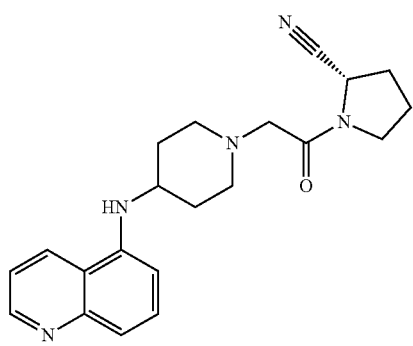 | (S)-1-(2-(4-(quinolin-5-ylamino)piperidin-1-yl)acetyl)pyrrolidine-2-carbonitrile |
| 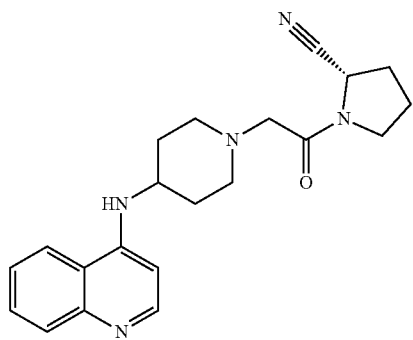 | (S)-1-(2-(4-(quinolin-4-ylamino)piperidin-1-yl)acetyl)pyrrolidine-2-carbonitrile |
| 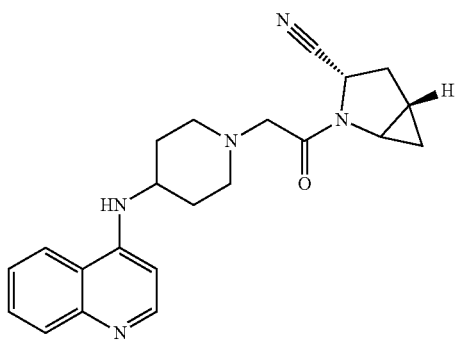 [SMILES: N#C[C@@H]1C[C@@H]2CC2N1C(=O)CN1CCC(Nc2ccnc3ccccc23)CC1] | (1S,3S,5S)-2-(2-(4-(quinolin-4-ylamino)piperidin-1-yl)acetyl)-2-azabicyclo[3.1.0]hexane-3-carbonitrile |

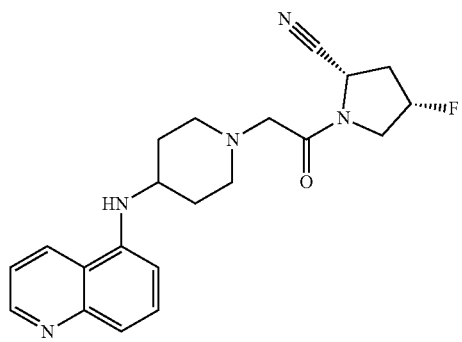 [SMILES: N#C[C@@H]1C[C@H](F)CN1C(=O)CN1CCC(Nc2cccc3ncccc23)CC1]

(2S,4S)-4-fluoro-1-(2-(4-(quinolin-5-ylamino)piperidin-1-yl)acetyl)pyrrolidine-2-carbonitrile

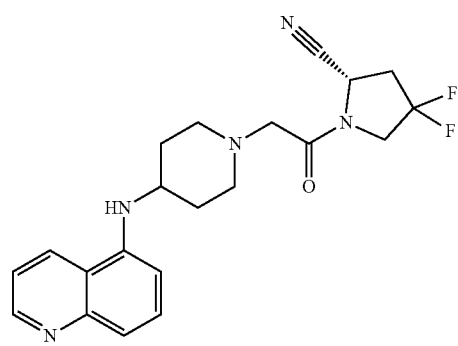 [SMILES: N#C[C@@H]1CC(F)(F)CN1C(=O)CN1CCC(Nc2cccc3ncccc23)CC1]

(S)-4,4-difluoro-1-(2-(4-(quinolin-5-ylamino)piperidin-1-yl)acetyl)pyrrolidine-2-carbonitrile

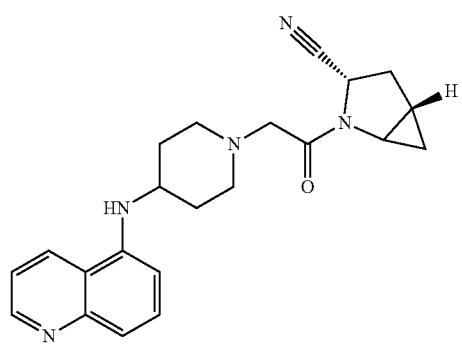 [SMILES: N#C[C@@H]1C[C@@H]2CC2N1C(=O)CN1CCC(Nc2cccc3ncccc23)CC1]

(1S,3S,5S)-2-(2-(4-(quinolin-5-ylamino)piperidin-1-yl)acetyl)-2-azabicyclo[3.1.0]hexane-3-carbonitrile

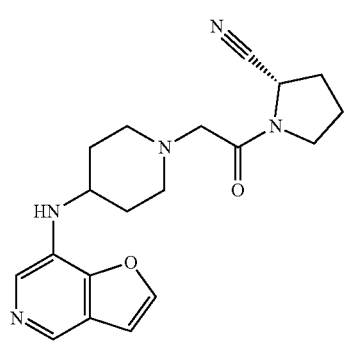 [SMILES: N#C[C@@H]1CCCN1C(=O)CN1CCC(Nc2cncc3ccoc23)CC1]

(S)-1-(2-(4-(furo[3,2-c]pyridin-7-ylamino)piperidin-1-yl)acetyl)pyrrolidine-2-carbonitrile

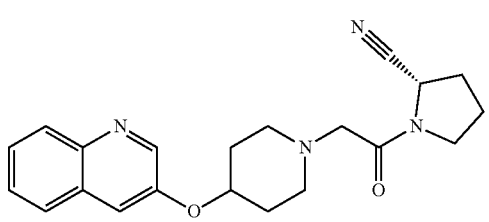 [SMILES: N#C[C@@H]1CCCN1C(=O)CN1CCC(Oc2cnc3ccccc3c2)CC1]

(S)-1-(2-(4-(quinolin-3-yloxy)piperidin-1-yl)acetyl)pyrrolidine-2-carbonitrile

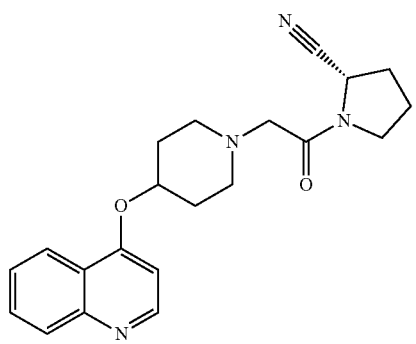 [SMILES: N#C[C@@H]1CCCN1C(=O)CN1CCC(Oc2ccnc3ccccc23)CC1] (S)-1-(2-(4-(quinolin-4-yloxy)piperidin-1-yl)acetyl)pyrrolidine-2-carbonitrile
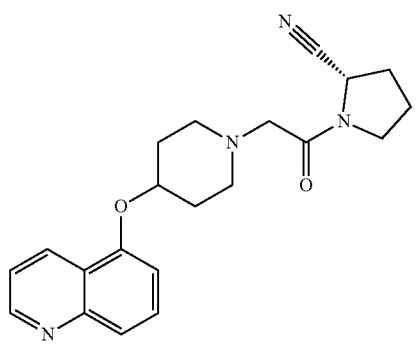 [SMILES: N#C[C@@H]1CCCN1C(=O)CN1CCC(Oc2cccc3ncccc23)CC1] (S)-1-(2-(4-(quinolin-5-yloxy)piperidin-1-yl)acetyl)pyrrolidine-2-carbonitrile
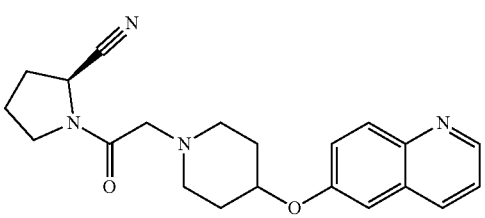 [SMILES: N#C[C@@H]1CCCN1C(=O)CN1CCC(Oc2ccc3ncccc3c2)CC1] (S)-1-(2-(4-(quinolin-6-yloxy)piperidin-1-yl)acetyl)pyrrolidine-2-carbonitrile
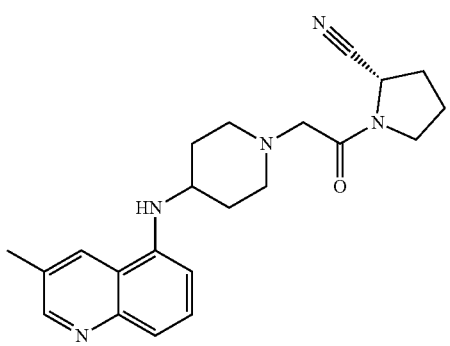 [SMILES: Cc1cnc2cccc(NC3CCN(CC(=O)N4CCC[C@H]4C#N)CC3)c2c1] (S)-1-(2-(4-((3-methylquinolin-5-yl)amino)piperidin-1-yl)acetyl)pyrrolidine-2-carbonitrile
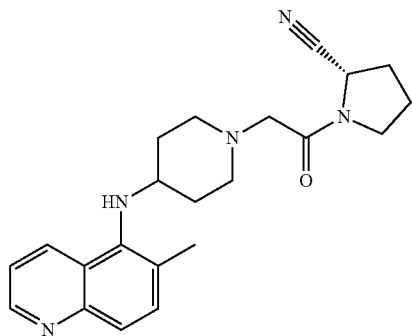 [SMILES: Cc1ccc2ncccc2c1NC1CCN(CC(=O)N2CCC[C@H]2C#N)CC1] (S)-1-(2-(4-((6-methylquinolin-5-yl)amino)piperidin-1-yl)acetyl)pyrrolidine-2-carbonitrile

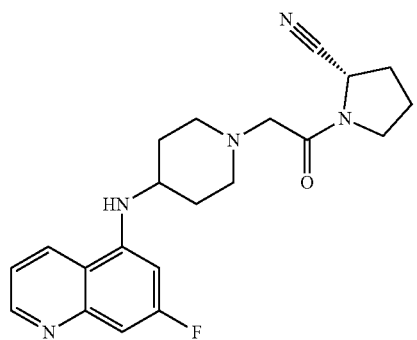 [SMILES: N#C[C@@H]1CCCN1C(=O)CN1CCC(Nc2cc(F)cc3ncccc23)CC1]
(S)-1-(2-(4-((7-fluoroquinolin-5-yl)amino)piperidin-1-yl)acetyl)pyrrolidine-2-carbonitrile
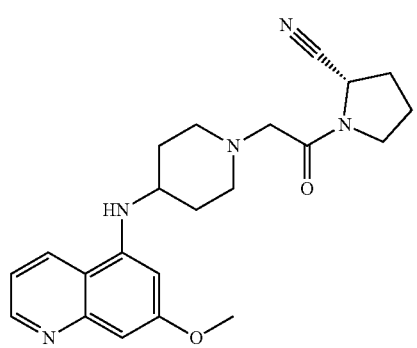 [SMILES: COc1cc(NC2CCN(CC(=O)N3CCC[C@H]3C#N)CC2)c2cccnc2c1]
(S)-1-(2-(4-((7-methoxyquinolin-5-yl)amino)piperidin-1-yl)acetyl)pyrrolidine-2-carbonitrile
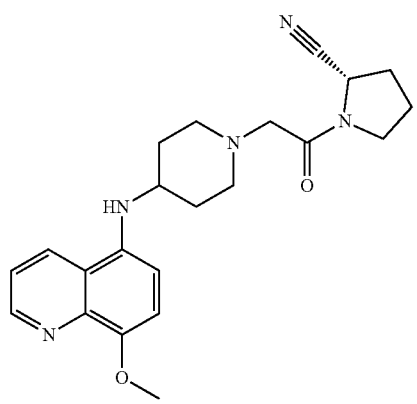 [SMILES: COc1ccc(NC2CCN(CC(=O)N3CCC[C@H]3C#N)CC2)c2cccnc12]
(S)-1-(2-(4-((8-methoxyquinolin-5-yl)amino)piperidin-1-yl)acetyl)pyrrolidine-2-carbonitrile
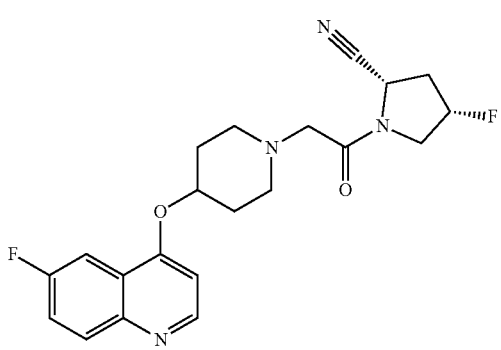 [SMILES: N#C[C@@H]1C[C@H](F)CN1C(=O)CN1CCC(Oc2ccnc3ccc(F)cc23)CC1]
(2S,4S)-4-fluoro-1-(2-(4-((6-fluoroquinolin-4-yl)oxy)piperidin-1-yl)acetyl)pyrrolidine-2-carbonitrile

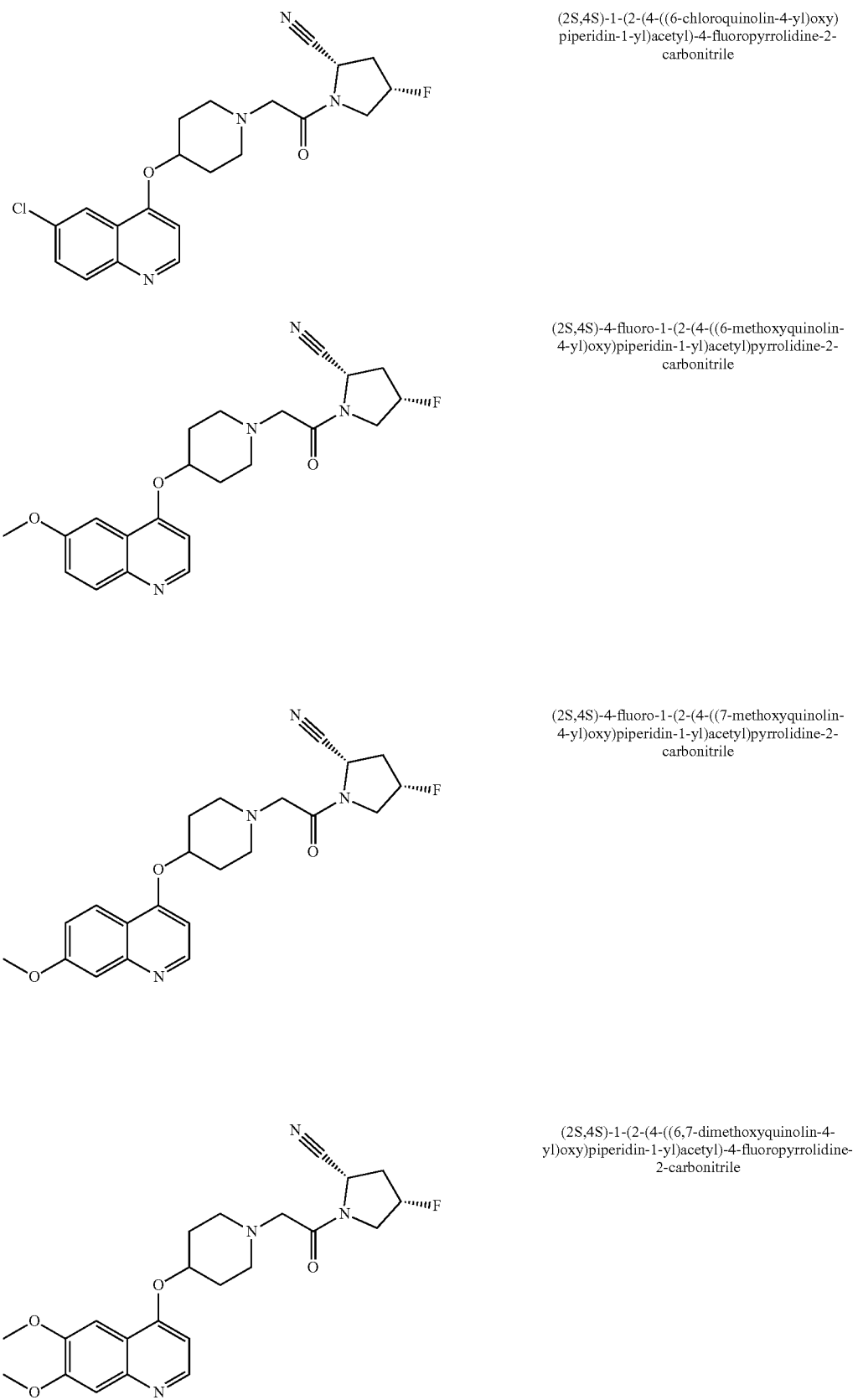
(2S,4S)-1-(2-(4-((6-chloroquinolin-4-yl)oxy)piperidin-1-yl)acetyl)-4-fluoropyrrolidine-2-carbonitrile
(2S,4S)-4-fluoro-1-(2-(4-((6-methoxyquinolin-4-yl)oxy)piperidin-1-yl)acetyl)pyrrolidine-2-carbonitrile
(2S,4S)-4-fluoro-1-(2-(4-((7-methoxyquinolin-4-yl)oxy)piperidin-1-yl)acetyl)pyrrolidine-2-carbonitrile
(2S,4S)-1-(2-(4-((6,7-dimethoxyquinolin-4-yl)oxy)piperidin-1-yl)acetyl)-4-fluoropyrrolidine-2-carbonitrile

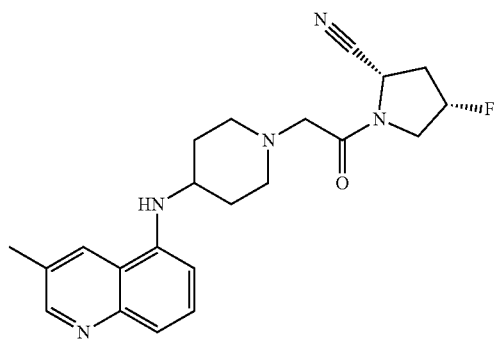 [SMILES: Cc1cnc2cccc(NC3CCN(CC(=O)N4C[C@@H](F)C[C@H]4C#N)CC3)c2c1]
(2S,4S)-4-fluoro-1-(2-(4-((3-methylquinolin-5-yl)amino)piperidin-1-yl)acetyl)pyrrolidine-2-carbonitrile
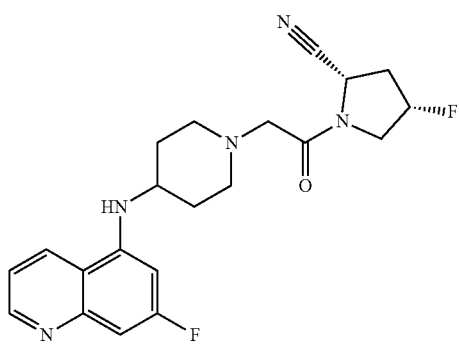 [SMILES: N#C[C@@H]1C[C@H](F)CN1C(=O)CN1CCC(Nc2cc(F)cc3ncccc23)CC1]
(2S,4S)-4-fluoro-1-(2-(4-((7-fluoroquinolin-5-yl)amino)piperidin-1-yl)acetyl)pyrrolidine-2-carbonitrile
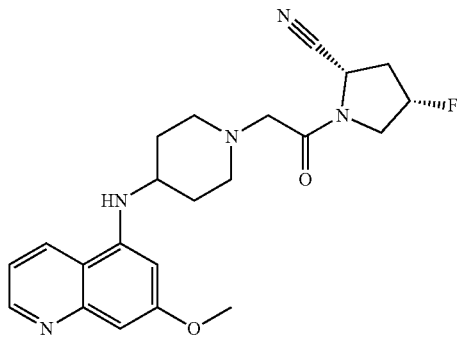 [SMILES: COc1cc(NC2CCN(CC(=O)N3C[C@@H](F)C[C@H]3C#N)CC2)c2cccnc2c1]
(2S,4S)-4-fluoro-1-(2-(4-((7-methoxyquinolin-5-yl)amino)piperidin-1-yl)acetyl)pyrrolidine-2-carbonitrile
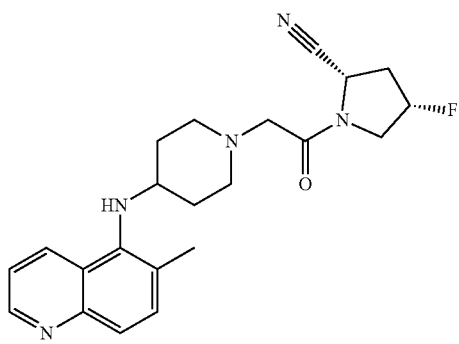 [SMILES: Cc1ccc2ncccc2c1NC1CCN(CC(=O)N2C[C@@H](F)C[C@H]2C#N)CC1]
(2S,4S)-4-fluoro-1-(2-(4-((6-methylquinolin-5-yl)amino)piperidin-1-yl)acetyl)pyrrolidine-2-carbonitrile

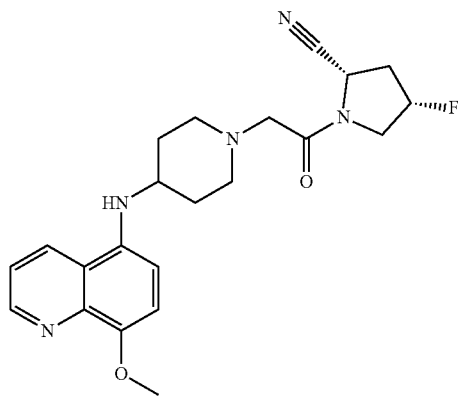 [SMILES: COc1ccc(NC2CCN(CC(=O)N3C[C@@H](F)C[C@H]3C#N)CC2)c2cccnc12]

(2S,4S)-4-fluoro-1-(2-(4-((8-methoxyquinolin-5-yl)amino)piperidin-1-yl)acetyl)pyrrolidine-2-carbonitrile

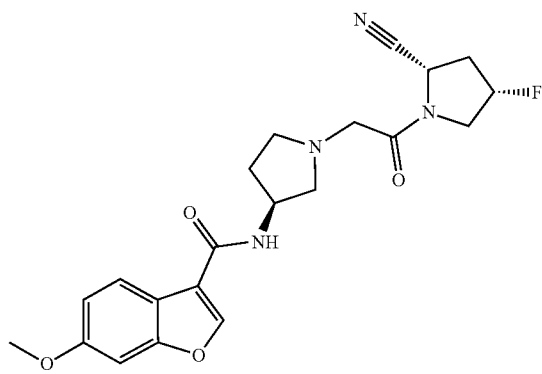 [SMILES: COc1ccc2c(C(=O)N[C@H]3CCN(CC(=O)N4C[C@@H](F)C[C@H]4C#N)C3)coc2c1]

6-methoxy-N-[(3S)-1-[2-oxo-2-[(2S,4S)-2-cyano-4-fluoro-pyrrolidin-1-yl]ethyl]pyrrolidin-3-yl]benzofuran-3-carboxamide

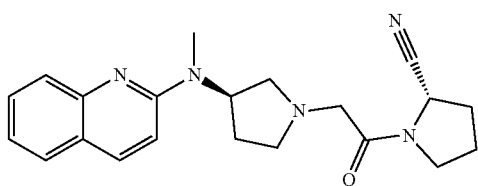 [SMILES: CN(c1ccc2ccccc2n1)[C@@H]1CCN(CC(=O)N2CCC[C@H]2C#N)C1]

(2S)-1-[2-[(3R)-3-[methyl(2-quinoyl)amino]pyrrolidin-1-yl]acetyl]pyrrolidine-2-carbonitrile

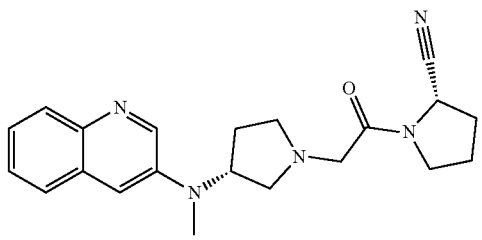 [SMILES: CN(c1cnc2ccccc2c1)[C@@H]1CCN(CC(=O)N2CCC[C@H]2C#N)C1]

(2S)-1-[2-[(3R)-3-[methyl(3-quinolyl)amino]pyrrolidin-1-yl]acetyl]pyrrolidine-2-carbonitrile

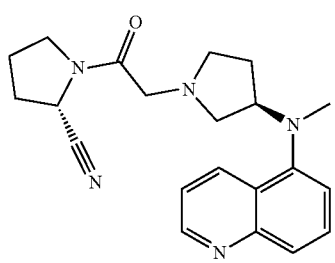 [SMILES: CN(c1cccc2ncccc12)[C@@H]1CCN(CC(=O)N2CCC[C@H]2C#N)C1]

(2S)-1-[2-[(3R)-3-[methyl(5-quinolyl)amino]pyrrolidin-1-yl]acetyl]pyrrolidine-2-carbonitrile -continued

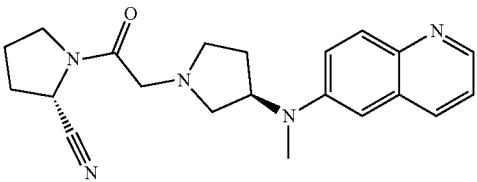 [SMILES: CN(c1ccc2ncccc2c1)[C@@H]1CCN(CC(=O)N2CCC[C@H]2C#N)C1]
(2S)-1-[2-[(3R)-3-[methyl(6-quinolyl)amino]pyrrolidin-1-yl]acetyl]pyrrolidine-2-carbonitrile

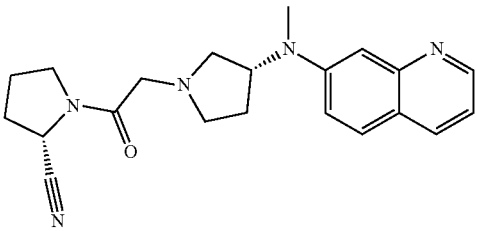 [SMILES: CN(c1ccc2cccnc2c1)[C@@H]1CCN(CC(=O)N2CCC[C@H]2C#N)C1]
(2S)-1-[2-[(3R)-3-[methyl(7-quinolyl)amino]pyrrolidin-1-yl]acetyl]pyrrolidine-2-carbonitrile

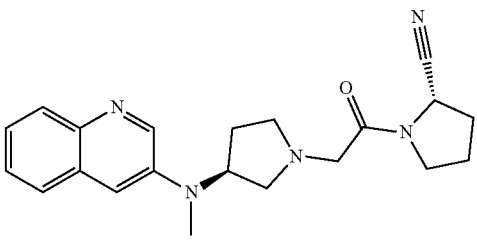 [SMILES: CN(c1cnc2ccccc2c1)[C@H]1CCN(CC(=O)N2CCC[C@H]2C#N)C1]
(2S)-1-[2-[(3S)-3-[methyl(3-quinolyl)amino]pyrrolidin-1-yl]acetyl]pyrrolidine-2-carbonitrile

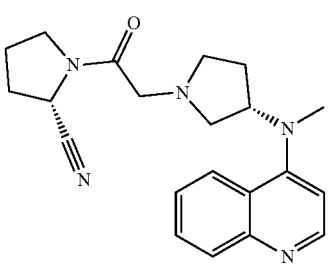 [SMILES: CN(c1ccnc2ccccc12)[C@H]1CCN(CC(=O)N2CCC[C@H]2C#N)C1]
(2S)-1-[2-[(3S)-3-[methyl(4-quinolyl)amino]pyrrolidin-1-yl]acetyl]pyrrolidine-2-carbonitrile

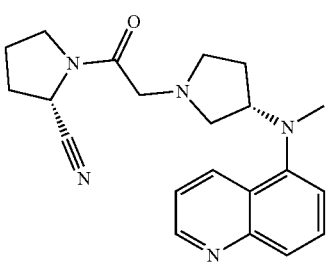 [SMILES: CN(c1cccc2ncccc12)[C@H]1CCN(CC(=O)N2CCC[C@H]2C#N)C1]
(2S)-1-[2-[(3S)-3-[methyl(5-quinolyl)amino]pyrrolidin-1-yl]acetyl]pyrrolidine-2-carbonitrile

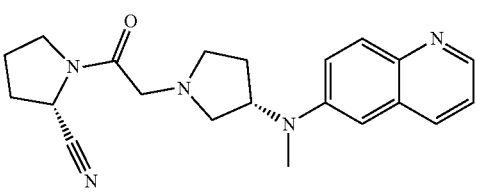 [SMILES: CN(c1ccc2ncccc2c1)[C@H]1CCN(CC(=O)N2CCC[C@H]2C#N)C1]
(2S)-1-[2-[(3S)-3-[methyl(6-quinolyl)amino]pyrrolidin-1-yl]acetyl]pyrrolidine-2-carbonitrile

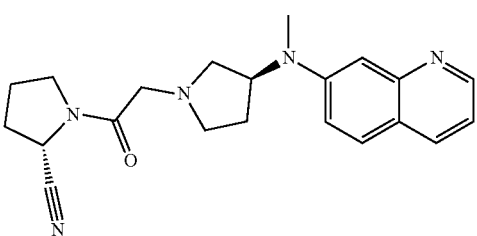 [SMILES: CN(c1ccc2cccnc2c1)[C@H]1CCN(CC(=O)N2CCC[C@H]2C#N)C1]
(2S)-1-[2-[(3S)-3-[methyl(7-quinolyl)amino]pyrrolidin-1-yl]acetyl]pyrrolidine-2-carbonitrile

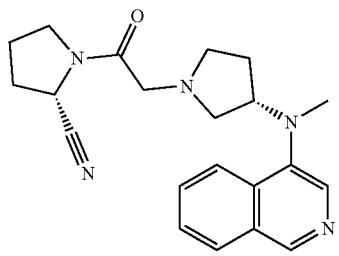 [SMILES: CN(c1cncc2ccccc12)[C@H]1CCN(CC(=O)N2CCC[C@H]2C#N)C1]

(2S)-1-[2-[(3S)-3-[4-isoquinolyl(methyl)amino]pyrrolidin-1-yl]acetyl]pyrrolidine-2-carbonitrile

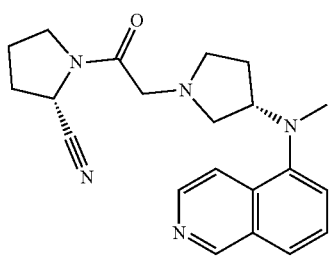 [SMILES: CN(c1cccc2cnccc12)[C@H]1CCN(CC(=O)N2CCC[C@H]2C#N)C1]

(2S)-1-[2-[(3S)-3-(5-isoquinolyl(methyl)amino]pyrrolidin-1-yl]acetyl]pyrrolidine-2-carbonitrile

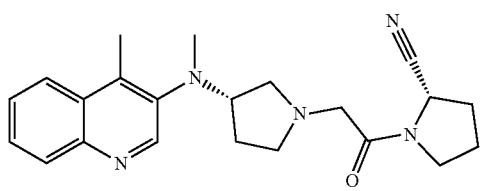 [SMILES: Cc1c(N(C)[C@H]2CCN(CC(=O)N3CCC[C@H]3C#N)C2)cnc2ccccc12]

(2S)-1-[2-[(3S)-3-[methyl-(4-methyl-3-quinolyl)amino]pyrrolidin-1-yl]acetyl]pyrrolidine-2-carbonitrile

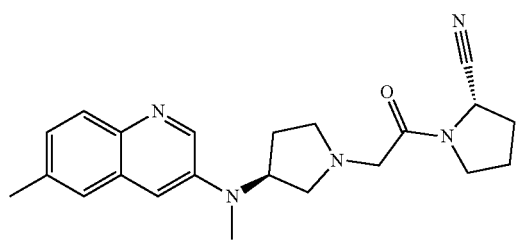 [SMILES: Cc1ccc2ncc(N(C)[C@H]3CCN(CC(=O)N4CCC[C@H]4C#N)C3)cc2c1]

(2S)-1-[2-[(3S)-3-[methyl-(6-methyl-3-quinolyl)amino]pyrrolidin-1-yl]acetyl]pyrrolidine-2-carbonitrile

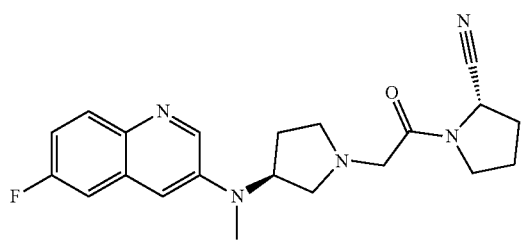 [SMILES: CN(c1cnc2ccc(F)cc2c1)[C@H]1CCN(CC(=O)N2CCC[C@H]2C#N)C1]

(S)-1-(2-((S)-3-((6-fluoroquinolin-3-yl)(methyl)amino)pyrrolidin-1-yl)acetyl)pyrrolidine-2-carbonitrile

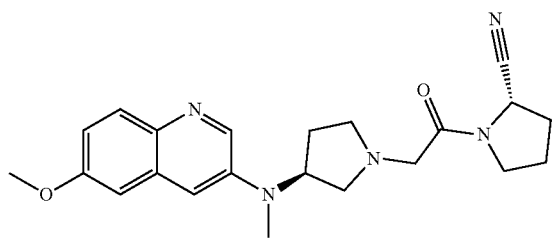 [SMILES: COc1ccc2ncc(N(C)[C@H]3CCN(CC(=O)N4CCC[C@H]4C#N)C3)cc2c1]

(S)-1-(2-((S)-3-((6-methoxyquinolin-3-yl)(methyl)amino)pyrrolidin-1-yl)acetyl)pyrrolidine-2-carbonitrile -continued

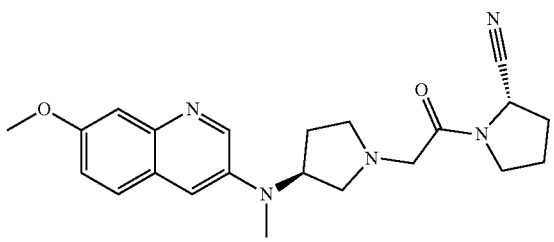 [SMILES: COc1ccc2cc(N(C)[C@H]3CCN(CC(=O)N4CCC[C@H]4C#N)C3)cnc2c1]
(S)-1-(2-((S)-3-((7-methoxyquinolin-3-yl)(methyl)amino)pyrrolidin-1-yl)acetyl)pyrrolidine-2-carbonitrile

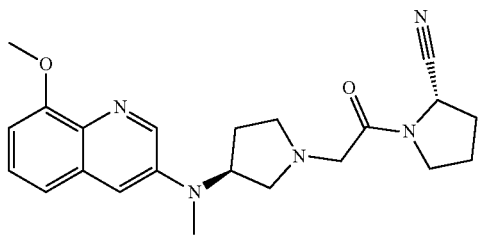 [SMILES: COc1cccc2cc(N(C)[C@H]3CCN(CC(=O)N4CCC[C@H]4C#N)C3)cnc12]
(S)-1-(2-((S)-3-((8-methoxyquinolin-3-yl)(methyl)amino)pyrrolidin-1-yl)acetyl)pyrrolidine-2-carbonitrile

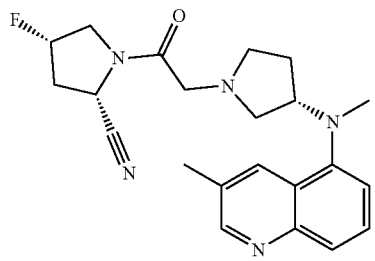 [SMILES: Cc1cnc2cccc(N(C)[C@H]3CCN(CC(=O)N4C[C@@H](F)C[C@H]4C#N)C3)c2c1]
(2S,4S)-4-fluoro-1-[2-[(3S)-3-[methyl-(3-methyl-5-quinolyl)amino]pyrrolidin-1-yl]acetyl]pyrrolidine-2-carbonitrile

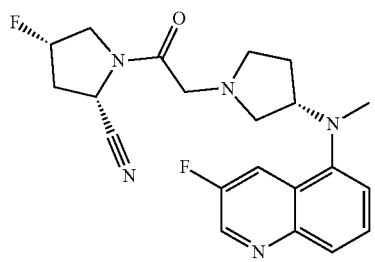 [SMILES: CN(c1cccc2ncc(F)cc12)[C@H]1CCN(CC(=O)N2C[C@@H](F)C[C@H]2C#N)C1]
(2S,4S)-4-fluoro-1-(2-((S)-3-((3-fluoroquinolin-5-yl)(methyl)amino)pyrrolidin-1-yl)acetyl)pyrrolidine-2-carbonitrile

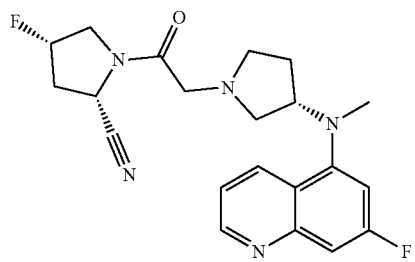 [SMILES: CN(c1cc(F)cc2ncccc12)[C@H]1CCN(CC(=O)N2C[C@@H](F)C[C@H]2C#N)C1]
(2S,4S)-4-fluoro-1-(2-((S)-3-((7-fluoroquinolin-5-yl)(methyl)amino)pyrrolidin-1-yl)acetyl)pyrrolidine-2-carbonitrile

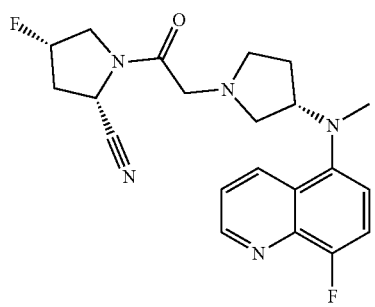 [SMILES: CN(c1ccc(F)c2ncccc12)[C@H]1CCN(CC(=O)N2C[C@@H](F)C[C@H]2C#N)C1]
(2S,4S)-4-fluoro-1-(2-((S)-3-((8-fluoroquinolin-5-yl)(methyl)amino)pyrrolidin-1-yl)acetyl)pyrrolidine-2-carbonitrile

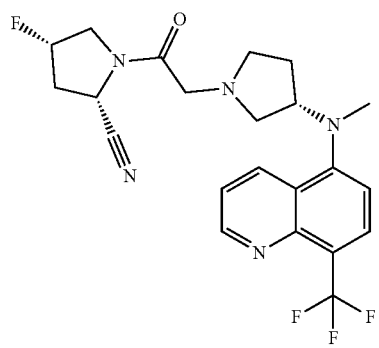 [SMILES: CN(c1ccc(C(F)(F)F)c2ncccc12)[C@H]1CCN(CC(=O)N2C[C@@H](F)C[C@H]2C#N)C1]

(2S,4S)-4-fluoro-1-[2-[(3S)-3-[methyl-[8-(trifluoromethyl)-5-quinolyl]amino]pyrrolidin-1-yl]acetyl]pyrrolidine-2-carbonitrile

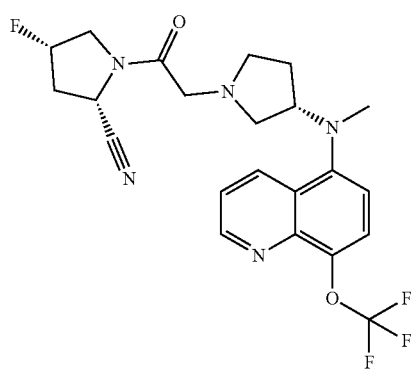 [SMILES: CN(c1ccc(OC(F)(F)F)c2ncccc12)[C@H]1CCN(CC(=O)N2C[C@@H](F)C[C@H]2C#N)C1]

(2S,4S)-4-fluoro-1-[2-[(3S)-3-[methyl-[8-(trifluoromethoxy)-5-quinolyl]amino]pyrrolidin-1-yl]acetyl]pyrrolidine-2-carbonitrile

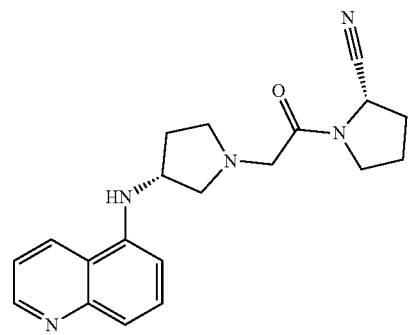 [SMILES: N#C[C@@H]1CCCN1C(=O)CN1CC[C@@H](Nc2cccc3ncccc23)C1]

(2S)-1-[2-[(3R)-3-(5-quinolylamino)pyrrolidin-1-yl]acetyl]pyrrolidine-2-carbonitrile

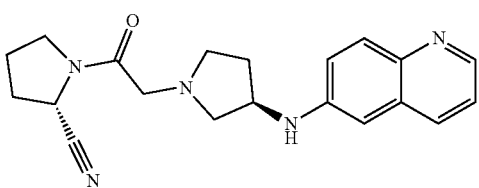 [SMILES: N#C[C@@H]1CCCN1C(=O)CN1CC[C@@H](Nc2ccc3ncccc3c2)C1]

(2S)-1-[2-[(3R)-3-(6-quinolylamino)pyrrolidin-1-yl]acetyl]pyrrolidine-2-carbonitrile

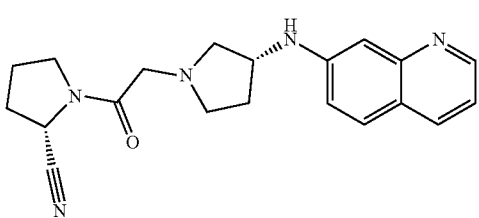 [SMILES: N#C[C@@H]1CCCN1C(=O)CN1CC[C@@H](Nc2ccc3cccnc3c2)C1]

(2S)-1-[2-[(3R)-3-(7-quinolylamino)pyrrolidin-1-yl]acetyl]pyrrolidine-2-carbonitrile -continued

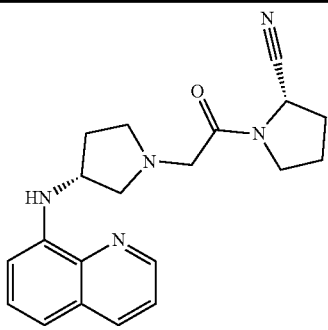

(2S)-1-[2-[(3R)-3-(8-quinolylamino)pyrrolidin-1-yl]acetyl]pyrrolidine-2-carbonitrile

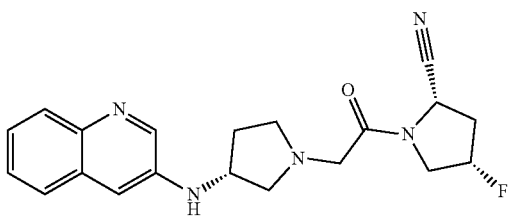 [SMILES: N#C[C@@H]1C[C@H](F)CN1C(=O)CN1CC[C@@H](Nc2cnc3ccccc3c2)C1]

(2S,4S)-4-fluoro-1-[2-[(3R)-3-(3-quinolylamino)pyrrolidin-1-yl]acetyl]pyrrolidine-2-carbonitrile

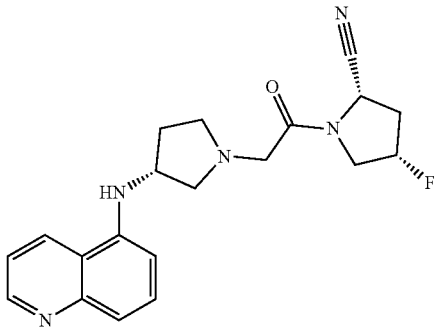 [SMILES: N#C[C@@H]1C[C@H](F)CN1C(=O)CN1CC[C@@H](Nc2cccc3ncccc23)C1]

(2S,4S)-4-fluoro-1-[2-[(3R)-3-(5-quinolylamino)pyrrolidin-1-yl]acetyl]pyrrolidine-2-carbonitrile

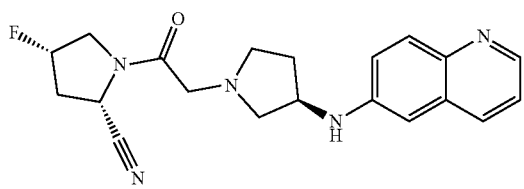 [SMILES: N#C[C@@H]1C[C@H](F)CN1C(=O)CN1CC[C@@H](Nc2ccc3ncccc3c2)C1]

(2S,4S)-4-fluoro-1-(2-[(3R)-3-(6-quinolylamino)pyrrolidin-1-yl]acetyl]pyrrolidine-2-carbonitrile

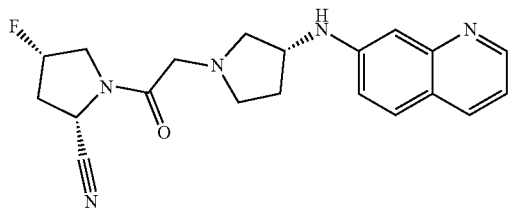 [SMILES: N#C[C@@H]1C[C@H](F)CN1C(=O)CN1CC[C@@H](Nc2ccc3cccnc3c2)C1]

(2S,4S)-4-fluoro-1-[2-[(3R)-3-(7-quinolylamino)pyrrolidin-1-yl]acetyl]pyrrolidine-2-carbonitrile

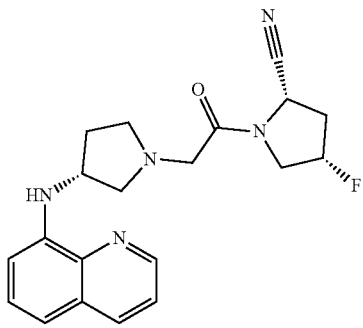 [SMILES: N#C[C@@H]1C[C@H](F)CN1C(=O)CN1CC[C@@H](Nc2cccc3cccnc23)C1]

(2S,4S)-4-fluoro-1-[2-[(3R)-3-(8-quinolylamino)pyrrolidin-1-yl]acetyl]pyrrolidine-2-carbonitrile

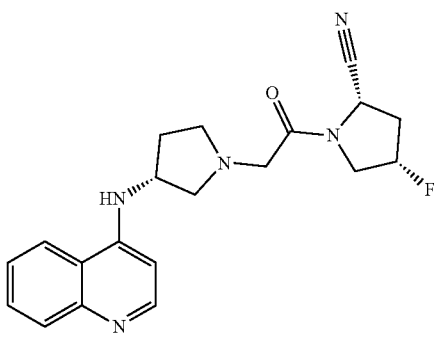 [SMILES: N#C[C@@H]1C[C@H](F)CN1C(=O)CN1CC[C@@H](Nc2ccnc3ccccc23)C1]

(2S,4S)-4-fluoro-1-[2-[(3R)-3-(4-quinolylamino)pyrrolidin-1-yl]acetyl]pyrrolidine-2-carbonitrile

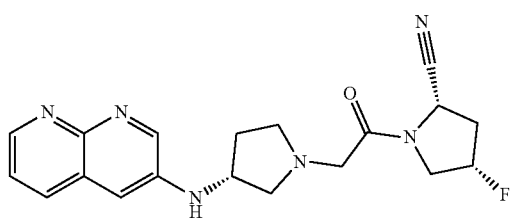 [SMILES: N#C[C@@H]1C[C@H](F)CN1C(=O)CN1CC[C@@H](Nc2cnc3ncccc3c2)C1]

(2S,4S)-4-fluoro-1-[2-[(3R)-3-(1,8-naphthyridin-3-ylamino)pyrrolidin-1-yl]acetyl]pyrrolidine-2-carbonitrile

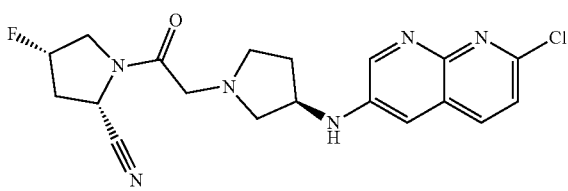 [SMILES: N#C[C@@H]1C[C@H](F)CN1C(=O)CN1CC[C@@H](Nc2cnc3nc(Cl)ccc3c2)C1]

(2S,4S)-4-fluoro-1-[2-[(3R)-3-[(7-chloro-1,8-naphthyridin-3-yl)amino]pyrrolidin-1-yl]acetyl]pyrrolidine-2-carbonitrile

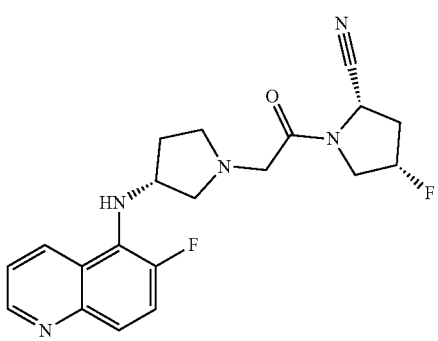

(2S,4S)-4-fluoro-1-[2-[(3R)-3-[(6-fluoro-5-quinolyl)amino]pyrrolidin-1-yl]acetyl]pyrrolidine-2-carbonitrile

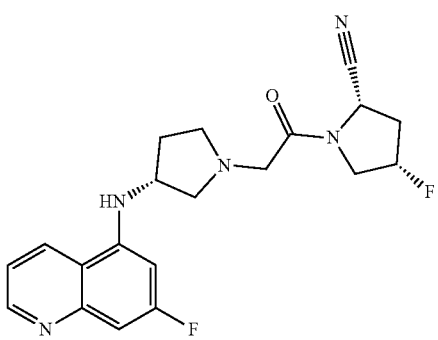 [SMILES: N#C[C@@H]1C[C@H](F)CN1C(=O)CN1CC[C@@H](Nc2cc(F)cc3ncccc23)C1]

(2S,4S)-4-fluoro-1-[2-[(3R)-3-[(7-fluoro-5-quinolyl)amino]pyrrolidin-1-yl]acetyl]pyrrolidine-2-carbonitrile

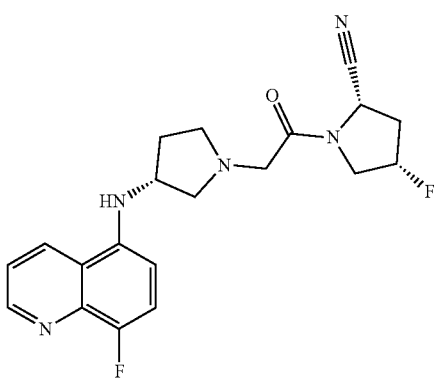 [SMILES: N#C[C@@H]1C[C@H](F)CN1C(=O)CN1CC[C@@H](Nc2ccc(F)c3ncccc23)C1]
(2S,4S)-4-fluoro-1-[2-[(3R)-3-[(8-fluoro-5-quinolyl)amino]pyrrolidin-1-yl]acetyl]pyrrolidine-2-carbonitrile
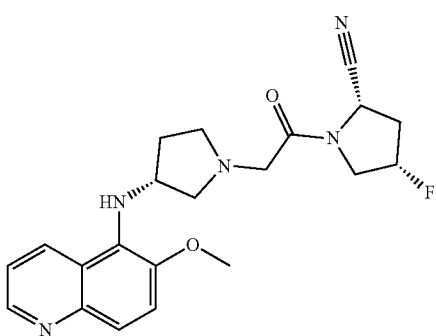 [SMILES: COc1ccc2ncccc2c1N[C@@H]1CCN(CC(=O)N2C[C@@H](F)C[C@H]2C#N)C1]
(2S,4S)-4-fluoro-1-(2-[(3R)-3-[(6-methoxy-5-quinolyl)amino]pyrrolidin-1-yl]acetyl]pyrrolidine-2-carbonitrile
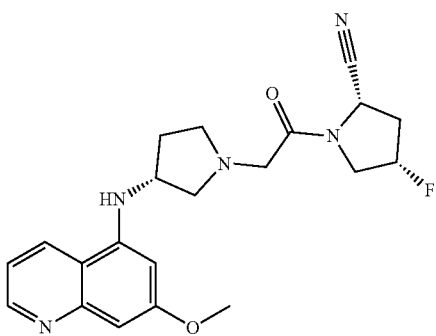 [SMILES: COc1cc(N[C@@H]2CCN(CC(=O)N3C[C@@H](F)C[C@H]3C#N)C2)c2cccnc2c1]
(2S,4S)-4-fluoro-1-[2-[(3R)-3-[(7-methoxy-5-quinolyl)amino]pyrrolidin-1-yl]acetyl]pyrrolidine-2-carbonitrile
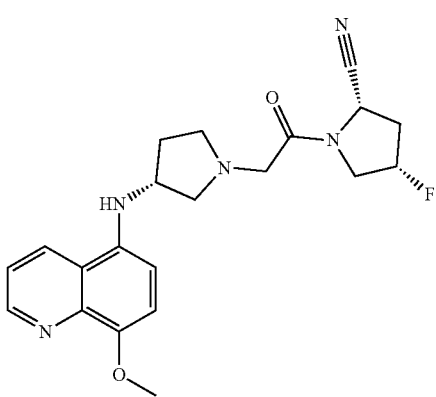 [SMILES: COc1ccc(N[C@@H]2CCN(CC(=O)N3C[C@@H](F)C[C@H]3C#N)C2)c2cccnc12]
(2S,4S)-4-fluoro-1-[2-[(3R)-3-[(8-methoxy-5-quinolyl)amino]pyrrolidin-1-yl]acetyl]pyrrolidine-2-carbonitrile

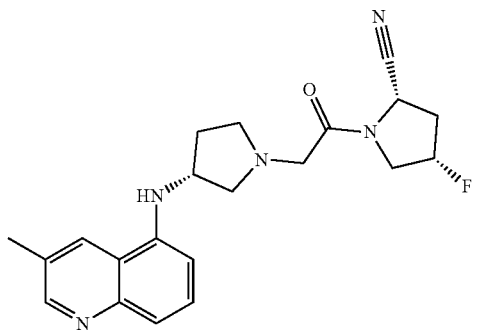 [SMILES: Cc1cnc2cccc(N[C@@H]3CCN(CC(=O)N4C[C@@H](F)C[C@H]4C#N)C3)c2c1]
(2S,4S)-4-fluoro-1-[2-[(3R)-3-[(3-methyl-5-quinolyl)amino]pyrrolidin-1-yl]acetyl]pyrrolidine-2-carbonitrile
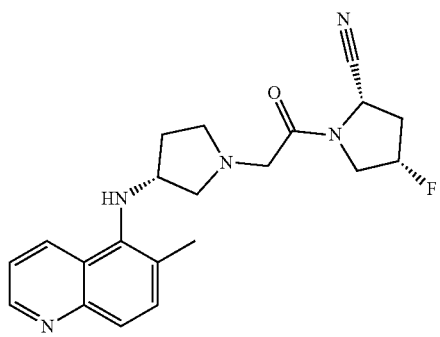 [SMILES: Cc1ccc2ncccc2c1N[C@@H]1CCN(CC(=O)N2C[C@@H](F)C[C@H]2C#N)C1]
(2S,4S)-4-fluoro-1-[2-[(3R)-3-[(6-methyl-5-quinolyl)amino]pyrrolidin-1-yl]acetyl]pyrrolidine-2-carbonitrile
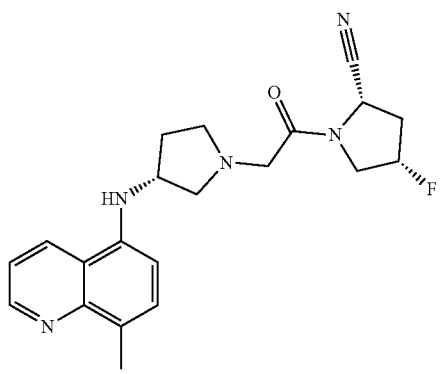 [SMILES: Cc1ccc(N[C@@H]2CCN(CC(=O)N3C[C@@H](F)C[C@H]3C#N)C2)c2cccnc12]
(2S,4S)-4-fluoro-1-[2-[(3R)-3-[(8-methyl-5-quinolyl)amino]pyrrolidin-1-yl]acetyl]pyrrolidine-2-carbonitrile
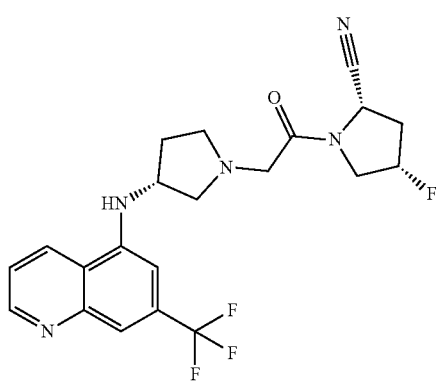 [SMILES: N#C[C@@H]1C[C@H](F)CN1C(=O)CN1CC[C@@H](Nc2cc(C(F)(F)F)cc3ncccc23)C1]
(2S,4S)-4-fluoro-1-(2-[(3R)-3-[[7-(trifluoromethyl)-5-quinolyl]amino]pyrrolidin-1-yl]acetyl]pyrrolidine-2-carbonitrile

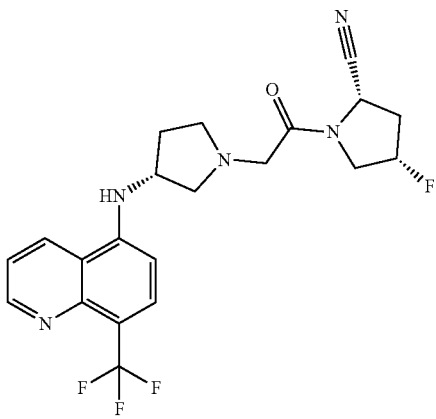 [SMILES: N#C[C@@H]1C[C@H](F)CN1C(=O)CN1CC[C@@H](Nc2ccc(C(F)(F)F)c3ncccc23)C1]
(2S,4S)-4-fluoro-1-[2-[(3R)-3-[[8-(trifluoromethyl)-5-quinolyl]amino]pyrrolidin-1-yl]acetyl]pyrrolidine-2-carbonitrile
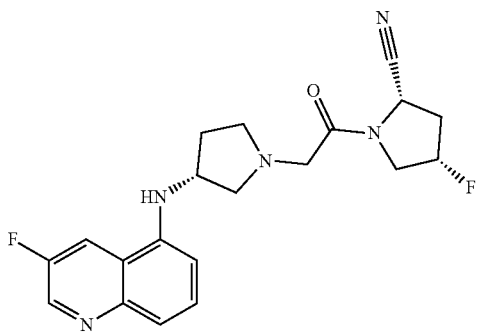 [SMILES: N#C[C@@H]1C[C@H](F)CN1C(=O)CN1CC[C@@H](Nc2cccc3ncc(F)cc23)C1]
(2S,4S)-4-fluoro-1-[2-[(3R)-3-[(3-fluoro-5-quinolyl)amino]pyrrolidin-1-yl]acetyl]pyrrolidine-2-carbonitrile
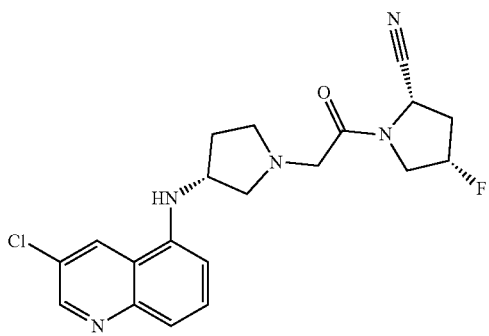 [SMILES: N#C[C@@H]1C[C@H](F)CN1C(=O)CN1CC[C@@H](Nc2cccc3ncc(Cl)cc23)C1]
(2S,4S)-4-fluoro-1-[2-[(3R)-3-[(3-chloro-5-quinolyl)amino]pyrrolidin-1-yl]acetyl]pyrrolidine-2-carbonitrile
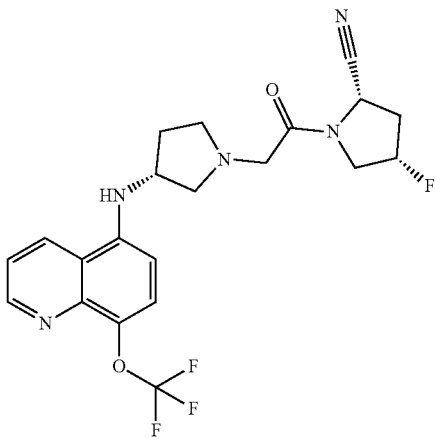 [SMILES: N#C[C@@H]1C[C@H](F)CN1C(=O)CN1CC[C@@H](Nc2ccc(OC(F)(F)F)c3ncccc23)C1]
(2S,4S)-4-fluoro-1-[2-[(3R)-3-[[8-(trifluoromethoxy)-5-quinolyl]amino]pyrrolidin-1-yl]acetyl]pyrrolidine-2-carbonitrile

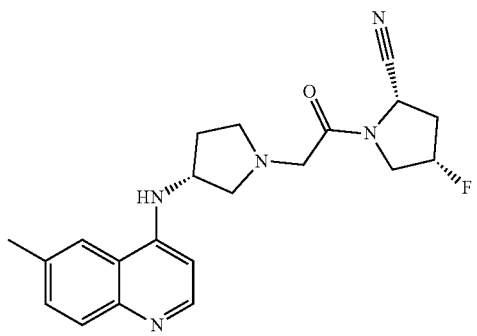 [SMILES: Cc1ccc2nccc(N[C@@H]3CCN(CC(=O)N4C[C@@H](F)C[C@H]4C#N)C3)c2c1]
(2S,4S)-4-fluoro-1-[2-[(3R)-3-[(6-methyl-4-quinolyl)amino]pyrrolidin-1-yl]acetyl]pyrrolidine-2-carbonitrile
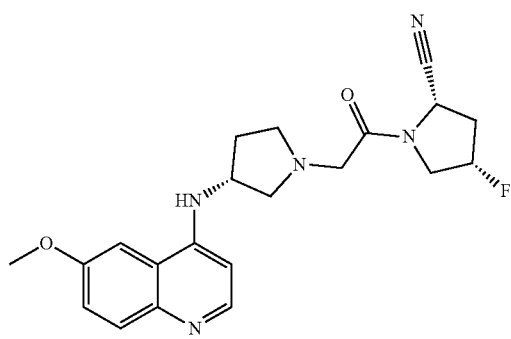 [SMILES: COc1ccc2nccc(N[C@@H]3CCN(CC(=O)N4C[C@@H](F)C[C@H]4C#N)C3)c2c1]
(2S,4S)-4-fluoro-1-[2-[(3R)-3-[(6-methoxy-4-quinolyl)amino]pyrrolidin-1-yl]acetyl]pyrrolidine-2-carbonitrile
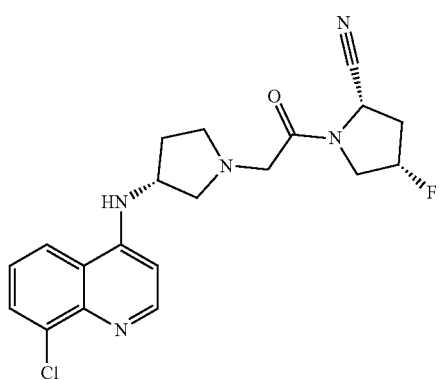 [SMILES: N#C[C@@H]1C[C@H](F)CN1C(=O)CN1CC[C@@H](Nc2ccnc3c(Cl)cccc23)C1]
(2S,4S)-4-fluoro-1-[2-[(3R)-3-[(8-chloro-4-quinolyl)amino]pyrrolidin-1-yl]acetyl]pyrrolidine-2-carbonitrile
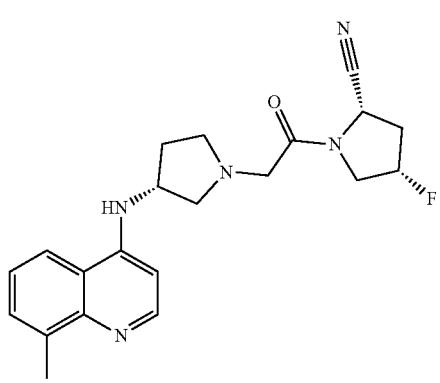 [SMILES: Cc1cccc2c(N[C@@H]3CCN(CC(=O)N4C[C@@H](F)C[C@H]4C#N)C3)ccnc12]
(2S,4S)-4-fluoro-1-[2-[(3R)-3-[(8-methyl-4-quinolyl)amino]pyrrolidin-1-yl]acetyl]pyrrolidine-2-carbonitrile

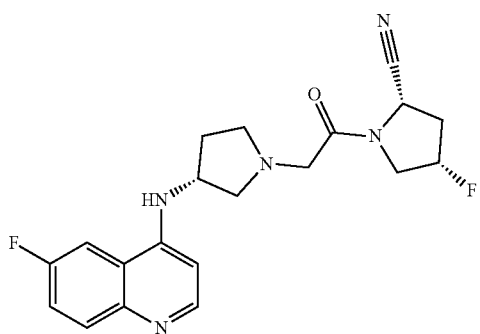 [SMILES: N#C[C@@H]1C[C@H](F)CN1C(=O)CN1CC[C@@H](Nc2ccnc3ccc(F)cc23)C1]
(2S,4S)-4-fluoro-1-[2-[(3R)-3-[(6-fluoro-4-quinolyl)amino]pyrrolidin-1-yl]acetyl]pyrrolidine-2-carbonitrile
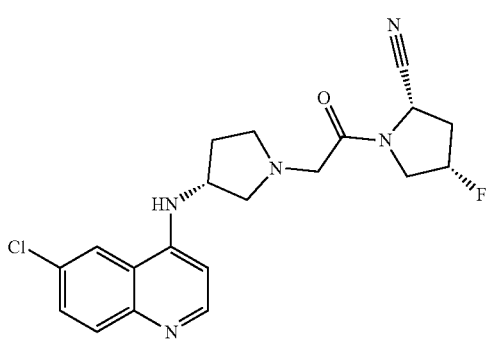 [SMILES: N#C[C@@H]1C[C@H](F)CN1C(=O)CN1CC[C@@H](Nc2ccnc3ccc(Cl)cc23)C1]
(2S,4S)-4-fluoro-1-[2-[(3R)-3-[(6-chloro-4-quinolyl)amino]pyrrolidin-1-yl]acetyl]pyrrolidine-2-carbonitrile
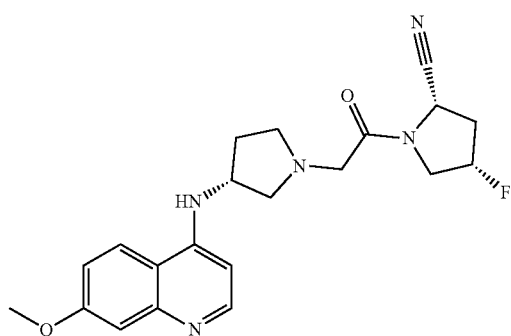 [SMILES: COc1ccc2c(N[C@@H]3CCN(CC(=O)N4C[C@@H](F)C[C@H]4C#N)C3)ccnc2c1]
(2S,4S)-4-fluoro-1-[2-[(3R)-3-[(7-methoxy-4-quinolyl)amino]pyrrolidin-1-yl]acetyl]pyrrolidine-2-carbonitrile
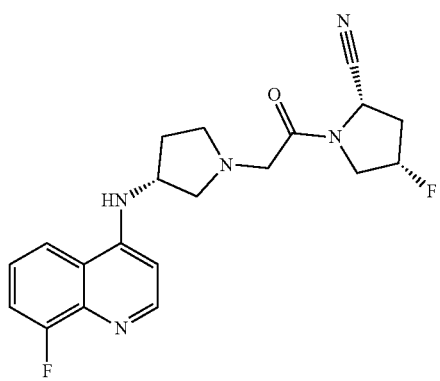 [SMILES: N#C[C@@H]1C[C@H](F)CN1C(=O)CN1CC[C@@H](Nc2ccnc3c(F)cccc23)C1]
(2S,4S)-4-fluoro-1-[2-[(3R)-3-[(8-fluoro-4-quinolyl)amino]pyrrolidin-1-yl]acetyl]pyrrolidine-2-carbonitrile

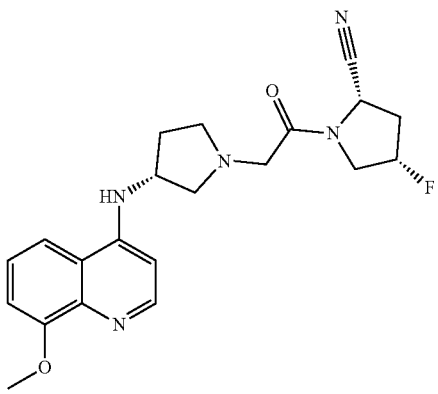 [SMILES: COc1cccc2c(N[C@@H]3CCN(CC(=O)N4C[C@@H](F)C[C@H]4C#N)C3)ccnc12]
(2S,4S)-4-fluoro-1-[2-[(3R)-3-[(8-methoxy-4-quinolyl)amino]pyrrolidin-1-yl]acetyl]pyrrolidine-2-carbonitrile
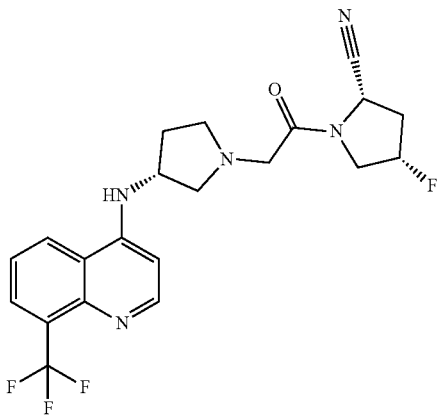 [SMILES: N#C[C@@H]1C[C@H](F)CN1C(=O)CN1CC[C@@H](Nc2ccnc3c(C(F)(F)F)cccc23)C1]
(2S,4S)-4-fluoro-1-[2-[(3R)-3-[[8-(trifluoromethyl)-4-quinolyl]amino]pyrrolidin-1-yl]acetyl]pyrrolidine-2-carbonitrile
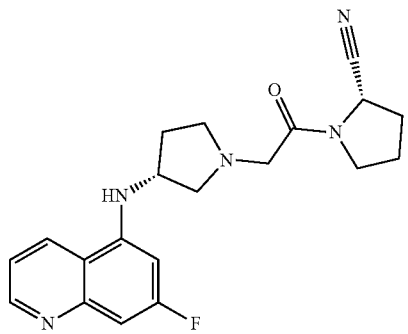 [SMILES: N#C[C@@H]1CCCN1C(=O)CN1CC[C@@H](Nc2cc(F)cc3ncccc23)C1]
(2S)-1-[2-[(3R)-3-[(7-fluoro-5-quinolyl)amino]pyrrolidin-1-yl]acetyl]pyrrolidine-2-carbonitrile
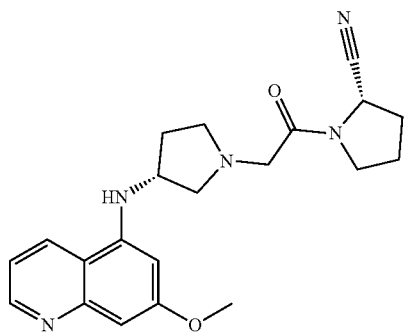 [SMILES: COc1cc(N[C@@H]2CCN(CC(=O)N3CCC[C@H]3C#N)C2)c2cccnc2c1]
(2S)-1-[2-[(3R)-3-[(7-methoxy-5-quinolyl)amino]pyrrolidin-1-yl]acetyl]pyrrolidine-2-carbonitrile

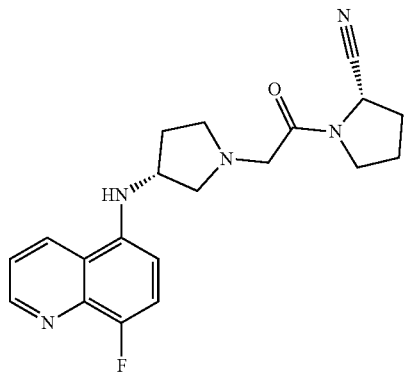 [SMILES: N#C[C@@H]1CCCN1C(=O)CN1CC[C@@H](Nc2ccc(F)c3ncccc23)C1]
(2S)-1-[2-[(3R)-3-[(8-fluoro-5-quinolyl)amino]pyrrolidin-1-yl]acetyl]pyrrolidine-2-carbonitrile
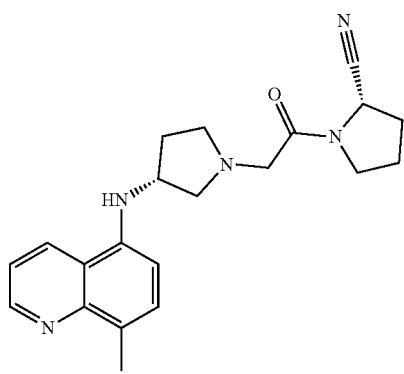 [SMILES: Cc1ccc(N[C@@H]2CCN(CC(=O)N3CCC[C@H]3C#N)C2)c2cccnc12]
(2S)-1-[2-[(3R)-3-[(8-methyl-5-quinolyl)amino]pyrrolidin-1-yl]acetyl]pyrrolidine-2-carbonitrile
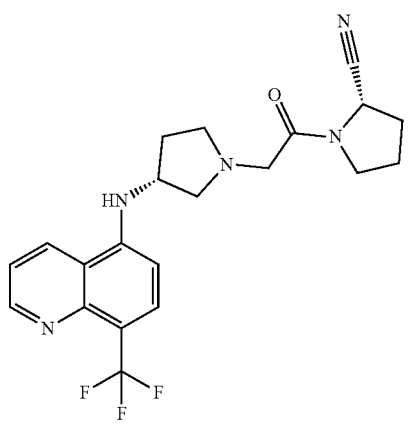 [SMILES: N#C[C@@H]1CCCN1C(=O)CN1CC[C@@H](Nc2ccc(C(F)(F)F)c3ncccc23)C1]
(2S)-1-[2-[(3R)-3-[[8-(trifluoromethyl)-5-quinolyl]amino]pyrrolidin-1-yl]acetyl]pyrrolidine-2-carbonitrile
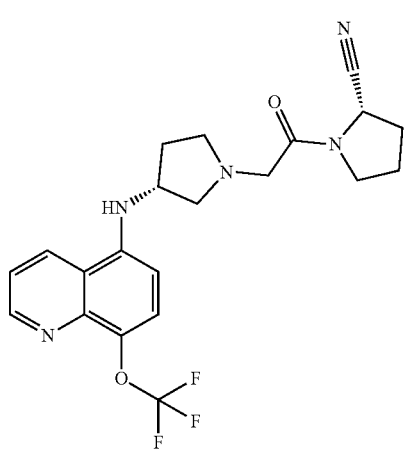 [SMILES: N#C[C@@H]1CCCN1C(=O)CN1CC[C@@H](Nc2ccc(OC(F)(F)F)c3ncccc23)C1]
(2S)-1-[2-[(3R)-3-[[8-(trifluoromethoxy)-5-quinolyl]amino]pyrrolidin-1-yl]acetyl]pyrrolidine-2-carbonitrile

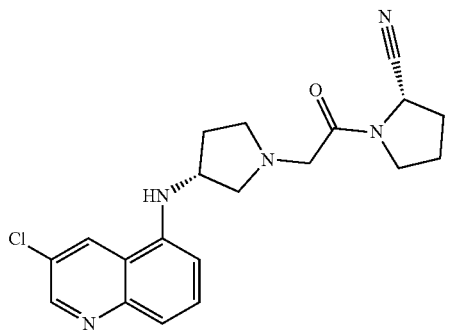 [SMILES: N#C[C@@H]1CCCN1C(=O)CN1CC[C@@H](Nc2cccc3ncc(Cl)cc23)C1]

(2S)-1-[2-[(3R)-3-[(3-chloro-5-quinolyl)amino]pyrrolidin-1-yl]acetyl]pyrrolidine-2-carbonitrile

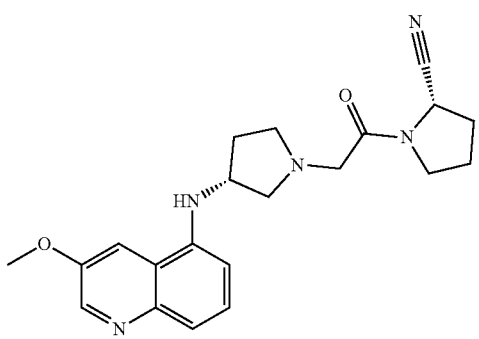 [SMILES: COc1cnc2cccc(N[C@@H]3CCN(CC(=O)N4CCC[C@H]4C#N)C3)c2c1]

(2S)-1-[2-[(3R)-3-[(3-methoxy-5-quinolyl)amino]pyrrolidin-1-yl]acetyl]pyrrolidine-2-carbonitrile

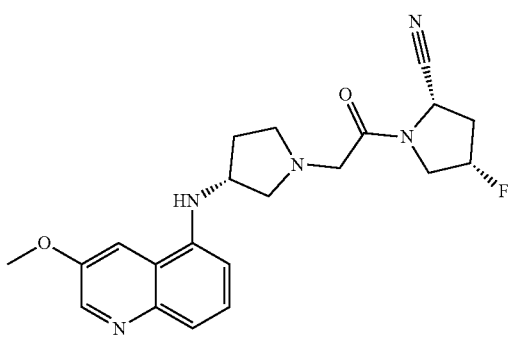 [SMILES: COc1cnc2cccc(N[C@@H]3CCN(CC(=O)N4C[C@@H](F)C[C@H]4C#N)C3)c2c1]

(2S,4S)-4-fluoro-1-[2-[(3R)-3-[(3-methoxy-5-quinolyl)amino]pyrrolidin-1-yl]acetyl]pyrrolidine-2-carbonitrile

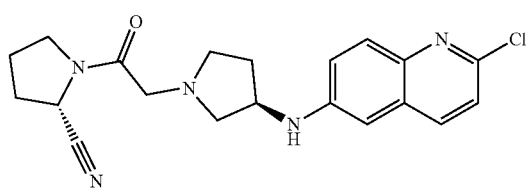 [SMILES: N#C[C@@H]1CCCN1C(=O)CN1CC[C@@H](Nc2ccc3nc(Cl)ccc3c2)C1]

(2S)-1-[2-[(3R)-3-[(2-chloro-6-quinolyl)amino]pyrrolidin-1-yl]acetyl]pyrrolidine-2-carbonitrile

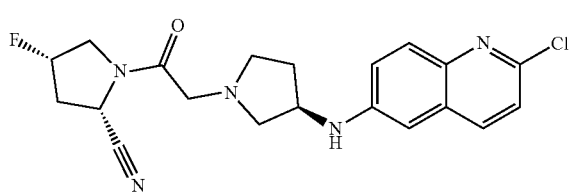 [SMILES: N#C[C@@H]1C[C@H](F)CN1C(=O)CN1CC[C@@H](Nc2ccc3nc(Cl)ccc3c2)C1]

(2S,4S)-4-fluoro-1-[2-[(3R)-3-[(2-chloro-6-quinolyl)amino]pyrrolidin-1-yl]acetyl]pyrrolidine-2-carbonitrile -continued

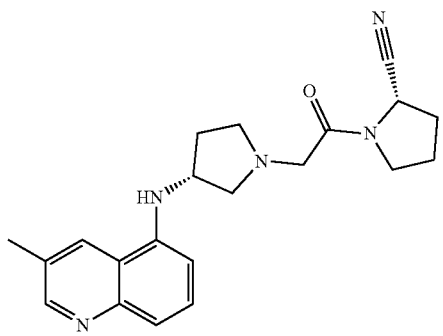 [SMILES: Cc1cnc2cccc(N[C@@H]3CCN(CC(=O)N4CCC[C@H]4C#N)C3)c2c1]

(2S)-1-[2-[(3R)-3-[(3-methyl-5-quinolyl)amino]pyrrolidin-1-yl]acetyl]pyrrolidine-2-carbonitrile

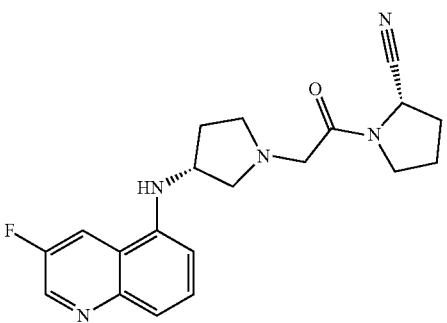 [SMILES: N#C[C@@H]1CCCN1C(=O)CN1CC[C@@H](Nc2cccc3ncc(F)cc23)C1]

(2S)-1-[2-[(3R)-3-[(3-fluoro-5-quinolyl)amino]pyrrolidin-1-yl]acetyl]pyrrolidine-2-carbonitrile

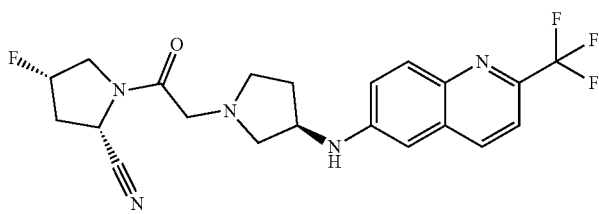 [SMILES: N#C[C@@H]1C[C@H](F)CN1C(=O)CN1CC[C@@H](Nc2ccc3nc(C(F)(F)F)ccc3c2)C1]

(2S,4S)-4-fluoro-1-(2-[(3R)-3-[[2-(trifluoromethyl)-6-quinolyl]amino]pyrrolidin-1-yl]acetyl]pyrrolidine-2-carbonitrile

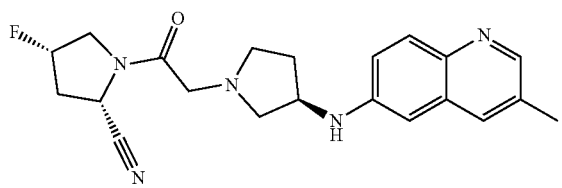 [SMILES: Cc1cnc2ccc(N[C@@H]3CCN(CC(=O)N4C[C@@H](F)C[C@H]4C#N)C3)cc2c1]

(2S,4S)-4-fluoro-1-[2-[(3R)-3-[(3-methyl-6-quinolyl)amino]pyrrolidin-1-yl]acetyl]pyrrolidine-2-carbonitrile

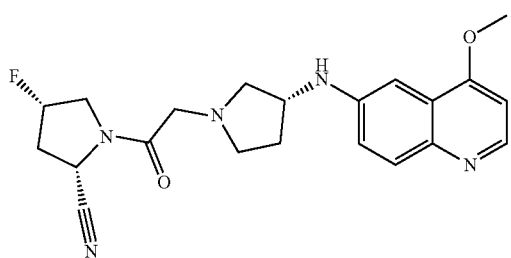 [SMILES: COc1ccnc2ccc(N[C@@H]3CCN(CC(=O)N4C[C@@H](F)C[C@H]4C#N)C3)cc12]

(2S,4S)-4-fluoro-1-[2-[(3R)-3-[(4-methoxy-6-quinolyl)amino]pyrrolidin-1-yl]acetyl]pyrrolidine-2-carbonitrile

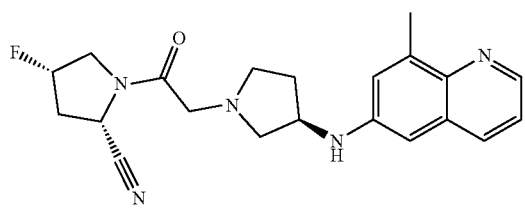 [SMILES: Cc1cc(N[C@@H]2CCN(CC(=O)N3C[C@@H](F)C[C@H]3C#N)C2)cc2cccnc12]

(2S,4S)-4-fluoro-1-[2-[(3R)-3-[(8-methyl-6-quinolyl)amino]pyrrolidin-1-yl]acetyl]pyrrolidine-2-carbonitrile -continued

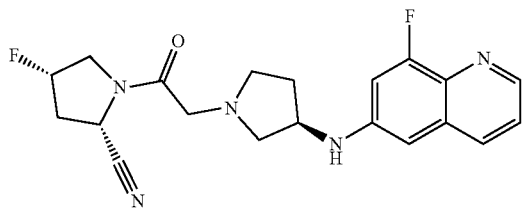 [SMILES: N#C[C@@H]1C[C@H](F)CN1C(=O)CN1CC[C@@H](Nc2cc(F)c3ncccc3c2)C1]
(2S,4S)-4-fluoro-1-[2-[(3R)-3-[(8-fluoro-6-quinolyl)amino]pyrrolidin-1-yl]acetyl]pyrrolidine-2-carbonitrile

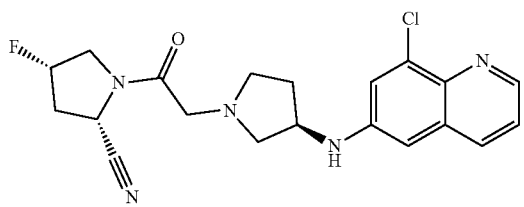 [SMILES: N#C[C@@H]1C[C@H](F)CN1C(=O)CN1CC[C@@H](Nc2cc(Cl)c3ncccc3c2)C1]
(2S,4S)-4-fluoro-1-[2-[(3R)-3-[(8-chloro-6-quinolyl)amino]pyrrolidin-1-yl]acetyl]pyrrolidine-2-carbonitrile

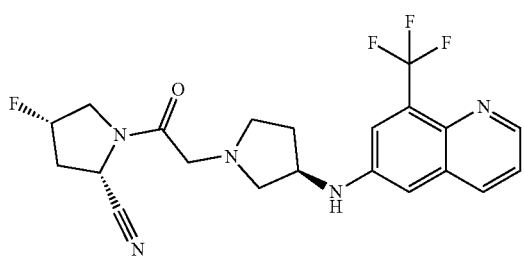 [SMILES: N#C[C@@H]1C[C@H](F)CN1C(=O)CN1CC[C@@H](Nc2cc(C(F)(F)F)c3ncccc3c2)C1]
(2S,4S)-4-fluoro-1-(2-[(3R)-3-[[8-(trifluoromethyl)-6-quinolyl]amino]pyrrolidin-1-yl]acetyl]pyrrolidine-2-carbonitrile

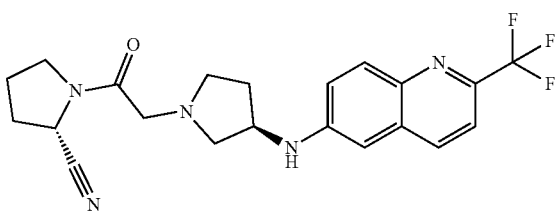 [SMILES: N#C[C@@H]1CCCN1C(=O)CN1CC[C@@H](Nc2ccc3nc(C(F)(F)F)ccc3c2)C1]
(2S)-1-[2-[(3R)-3-[[2-(trifluoromethyl)-6-quinolyl]amino]pyrrolidin-1-yl]acetyl]pyrrolidine-2-carbonitrile

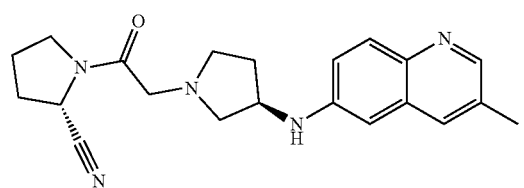 [SMILES: Cc1cnc2ccc(N[C@@H]3CCN(CC(=O)N4CCC[C@H]4C#N)C3)cc2c1]
(2S)-1-[2-[(3R)-3-[(3-methyl-6-quinolyl)amino]pyrrolidin-1-yl]acetyl]pyrrolidine-2-carbonitrile

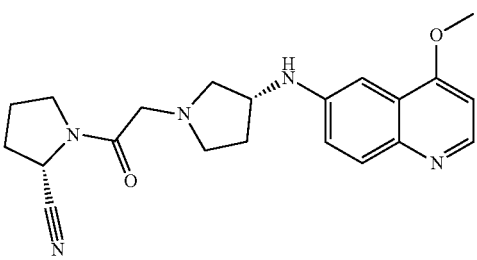 [SMILES: COc1ccnc2ccc(N[C@@H]3CCN(CC(=O)N4CCC[C@H]4C#N)C3)cc12]
(2S)-1-[2-[(3R)-3-[(4-methoxy-6-quinolyl)amino]pyrrolidin-1-yl]acetyl]pyrrolidine-2-carbonitrile

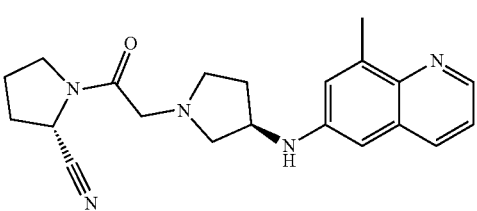 [SMILES: Cc1cc(N[C@@H]2CCN(CC(=O)N3CCC[C@H]3C#N)C2)cc2cccnc12]
(2S)-1-[2-[(3R)-3-[(8-methyl-6-quinolyl)amino]pyrrolidin-1-yl]acetyl]pyrrolidine-2-carbonitrile

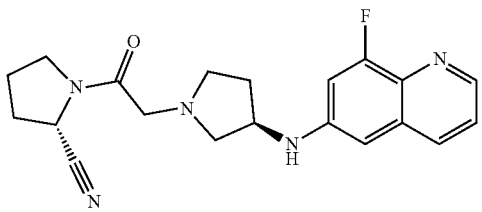 [SMILES: N#C[C@@H]1CCCN1C(=O)CN1CC[C@@H](Nc2cc(F)c3ncccc3c2)C1] (2S)-1-[2-[(3R)-3-[(8-fluoro-6-quinolyl)amino]pyrrolidin-1-yl]acetyl]pyrrolidine-2-carbonitrile

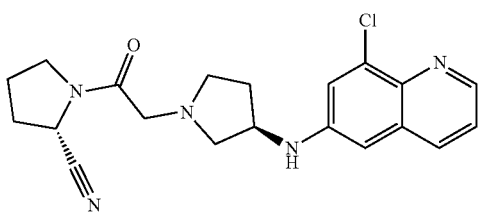 [SMILES: N#C[C@@H]1CCCN1C(=O)CN1CC[C@@H](Nc2cc(Cl)c3ncccc3c2)C1] (2S)-1-[2-[(3R)-3-[(8-chloro-6-quinolyl)amino]pyrrolidin-1-yl]acetyl]pyrrolidine-2-carbonitrile

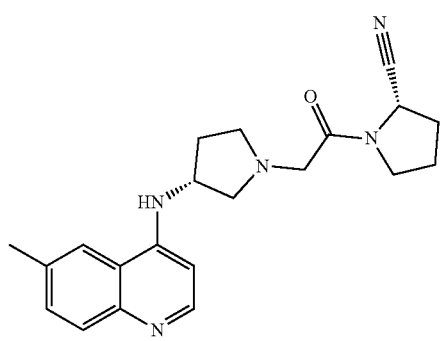 [SMILES: Cc1ccc2nccc(N[C@@H]3CCN(CC(=O)N4CCC[C@H]4C#N)C3)c2c1] (2S)-1-[2-[(3R)-3-[(6-methyl-4-quinolyl)amino]pyrrolidin-1-yl]acetyl]pyrrolidine-2-carbonitrile

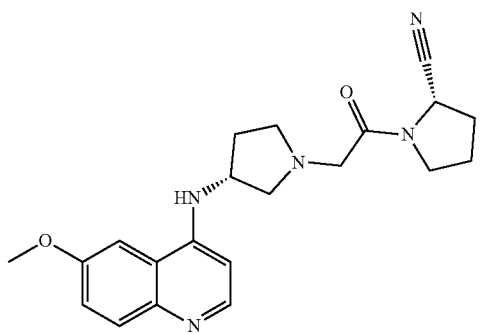 [SMILES: COc1ccc2nccc(N[C@@H]3CCN(CC(=O)N4CCC[C@H]4C#N)C3)c2c1] (2S)-1-[2-[(3R)-3-[(6-methoxy-4-quinolyl)amino]pyrrolidin-1-yl]acetyl]pyrrolidine-2-carbonitrile

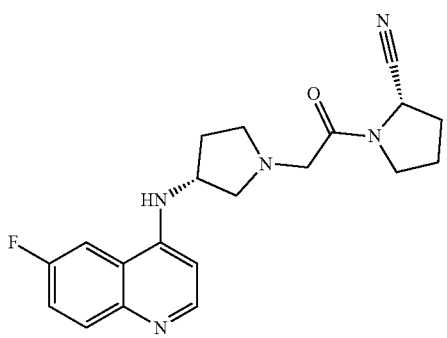 [SMILES: N#C[C@@H]1CCCN1C(=O)CN1CC[C@@H](Nc2ccnc3ccc(F)cc23)C1] (2S)-1-[2-[(3R)-3-[(6-fluoro-4-quinolyl)amino]pyrrolidin-1-yl]acetyl]pyrrolidine-2-carbonitrile -continued

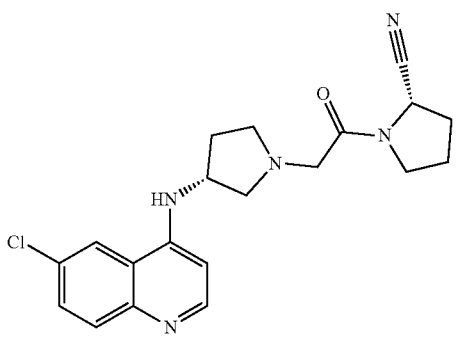 [SMILES: N#C[C@@H]1CCCN1C(=O)CN1CC[C@@H](Nc2ccnc3ccc(Cl)cc23)C1]

(2S)-1-[2-[(3R)-3-[(6-chloro-4-quinolyl)amino]pyrrolidin-1-yl]acetyl]pyrrolidine-2-carbonitrile

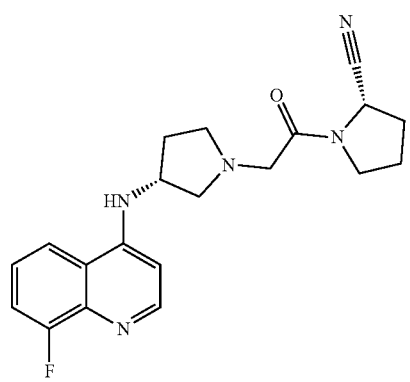 [SMILES: N#C[C@@H]1CCCN1C(=O)CN1CC[C@@H](Nc2ccnc3c(F)cccc23)C1]

(2S)-1-[2-[(3R)-3-[(8-fluoro-4-quinolyl)amino]pyrrolidin-1-yl]acetyl]pyrrolidine-2-carbonitrile

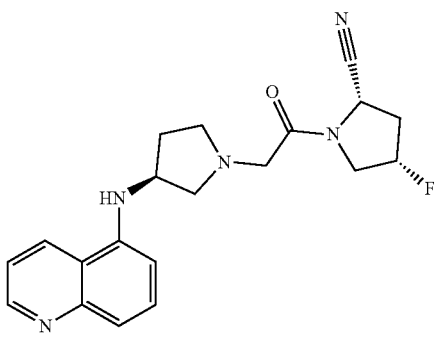 [SMILES: N#C[C@@H]1C[C@H](F)CN1C(=O)CN1CC[C@H](Nc2cccc3ncccc23)C1]

(2S,4S)-4-fluoro-1-[2-[(3S)-3-(5-quinolylamino)pyrrolidin-1-yl]acetyl]pyrrolidine-2-carbonitrile

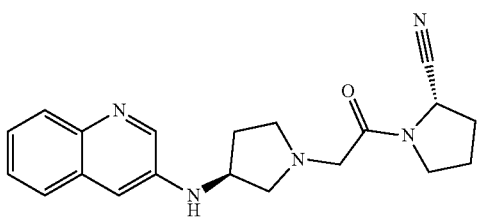 [SMILES: N#C[C@@H]1CCCN1C(=O)CN1CC[C@H](Nc2cnc3ccccc3c2)C1]

(2S)-1-[2-[(3S)-3-(3-quinolylamino)pyrrolidin-1-yl]acetyl]pyrrolidine-2-carbonitrile

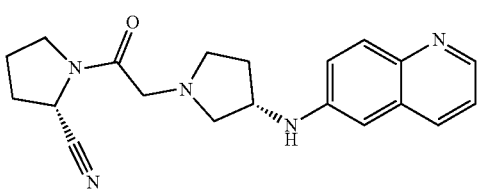 [SMILES: N#C[C@@H]1CCCN1C(=O)CN1CC[C@H](Nc2ccc3ncccc3c2)C1]

(2S)-1-[2-[(3S)-3-(6-quinolylamino)pyrrolidin-1-yl]acetyl]pyrrolidine-2-carbonitrile

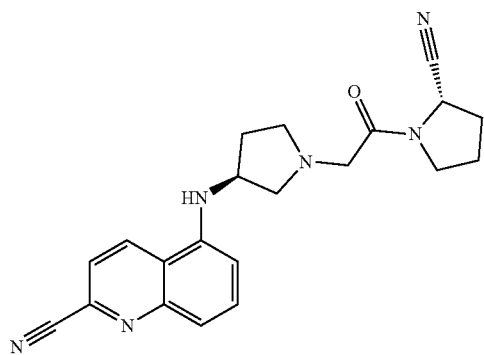 [SMILES: N#Cc1ccc2c(N[C@H]3CCN(CC(=O)N4CCC[C@H]4C#N)C3)cccc2n1]
5-[[(3S)-1-[2-oxo-2-[(2S)-2-cyanopyrrolidin-1-yl]ethyl]pyrrolidin-3-yl]amino]quinoline-2-carbonitrile
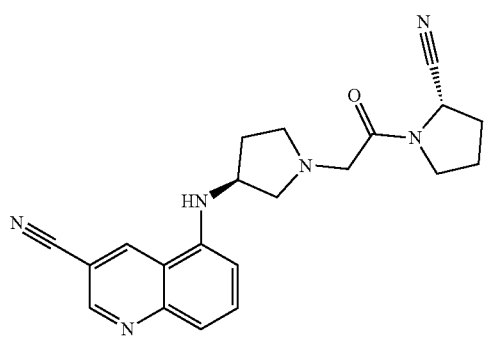 [SMILES: N#Cc1cnc2cccc(N[C@H]3CCN(CC(=O)N4CCC[C@H]4C#N)C3)c2c1]
5-[[(3S)-1-[2-oxo-2-[(2S)-2-cyanopyrrolidin-1-yl]ethyl]pyrrolidin-3-yl]amino]quinoline-3-carbonitrile
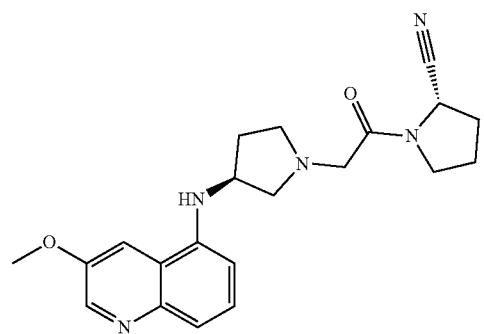 [SMILES: COc1cnc2cccc(N[C@H]3CCN(CC(=O)N4CCC[C@H]4C#N)C3)c2c1]
(2S)-1-[2-[(3S)-3-[(3-methoxy-5-quinolyl)amino]pyrrolidin-1-yl]acetyl]pyrrolidine-2-carbonitrile
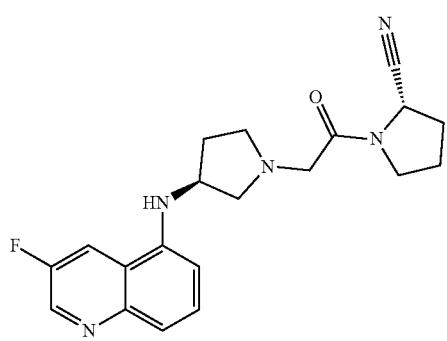 [SMILES: N#C[C@@H]1CCCN1C(=O)CN1CC[C@H](Nc2cccc3ncc(F)cc23)C1]
(2S)-1-[2-[(3S)-3-[(3-fluoro-5-quinolyl)amino]pyrrolidin-1-yl]acetyl]pyrrolidine-2-carbonitrile

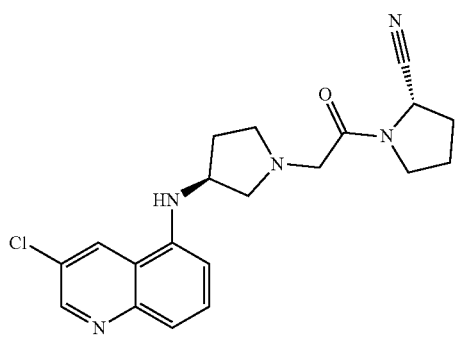 [SMILES: N#C[C@@H]1CCCN1C(=O)CN1CC[C@H](Nc2cccc3ncc(Cl)cc23)C1]
(2S)-1-[2-[(3S)-3-[(3-chloro-5-quinolyl)amino]pyrrolidin-1-yl]acetyl]pyrrolidine-2-carbonitrile
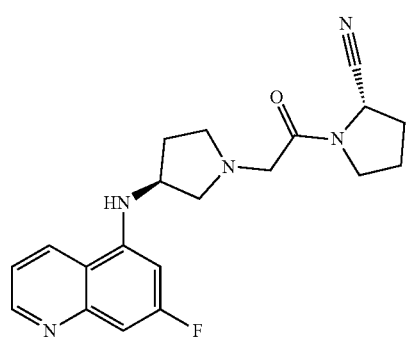 [SMILES: N#C[C@@H]1CCCN1C(=O)CN1CC[C@H](Nc2cc(F)cc3ncccc23)C1]
(2S)-1-[2-[(3S)-3-[(7-fluoro-5-quinolyl)amino]pyrrolidin-1-yl]acetyl]pyrrolidine-2-carbonitrile
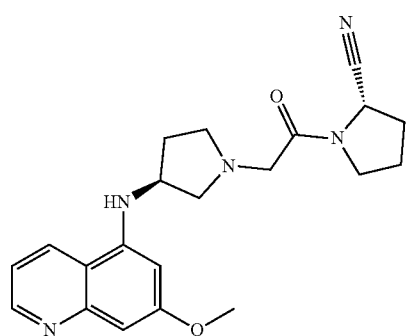 [SMILES: COc1cc(N[C@H]2CCN(CC(=O)N3CCC[C@H]3C#N)C2)c2cccnc2c1]
(2S)-1-[2-[(3S)-3-[(7-methoxy-5-quinolyl)amino]pyrrolidin-1-yl]acetyl]pyrrolidine-2-carbonitrile
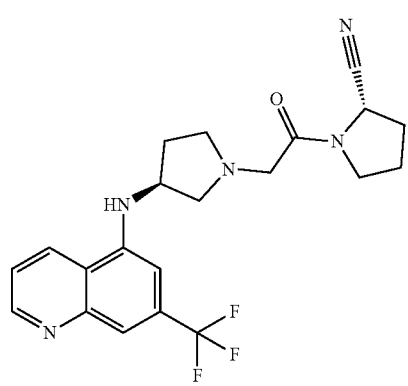 [SMILES: N#C[C@@H]1CCCN1C(=O)CN1CC[C@H](Nc2cc(C(F)(F)F)cc3ncccc23)C1]
(2S)-1-[2-[(3S)-3-[[7-(trifluoromethyl)-5-quinolyl]amino]pyrrolidin-1-yl]acetyl]pyrrolidine-2-carbonitrile -continued
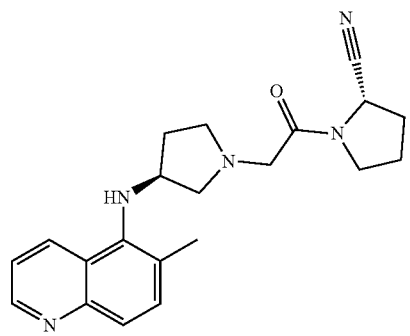 [SMILES: Cc1ccc2ncccc2c1N[C@H]1CCN(CC(=O)N2CCC[C@H]2C#N)C1]
(2S)-1-[2-[(3S)-3-[(6-methyl-5-quinolyl)amino]pyrrolidin-1-yl]acetyl]pyrrolidine-2-carbonitrile
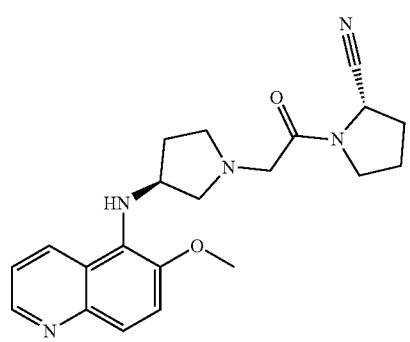 [SMILES: COc1ccc2ncccc2c1N[C@H]1CCN(CC(=O)N2CCC[C@H]2C#N)C1]
(2S)-1-[2-[(3S)-3-[(6-methoxy-5-quinolyl)amino]pyrrolidin-1-yl]acetyl]pyrrolidine-2-carbonitrile
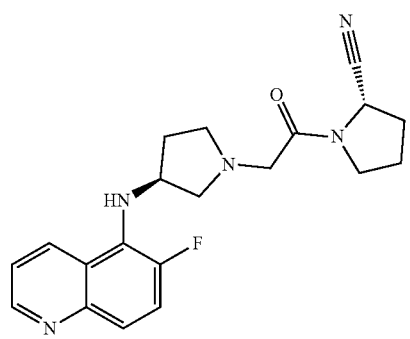
(2S)-1-[2-[(3S)-3-[(6-fluoro-5-quinolyl)amino]pyrrolidin-1-yl]acetyl]pyrrolidine-2-carbonitrile
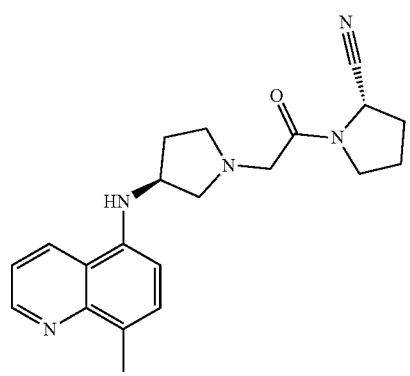 [SMILES: Cc1ccc(N[C@H]2CCN(CC(=O)N3CCC[C@H]3C#N)C2)c2cccnc12]
(2S)-1-[2-[(3S)-3-[(8-methyl-5-quinolyl)amino]pyrrolidin-1-yl]acetyl]pyrrolidine-2-carbonitrile

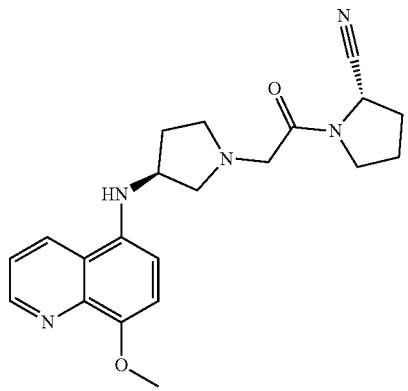 [SMILES: COc1ccc(N[C@H]2CCN(CC(=O)N3CCC[C@H]3C#N)C2)c2cccnc12]
(2S)-1-[2-[(3S)-3-[(8-methoxy-5-quinolyl)amino]pyrrolidin-1-yl]acetyl]pyrrolidine-2-carbonitrile
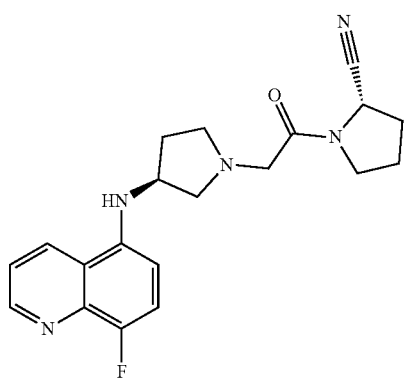 [SMILES: N#C[C@@H]1CCCN1C(=O)CN1CC[C@H](Nc2ccc(F)c3ncccc23)C1]
(2S)-1-[2-[(3S)-3-[(8-fluoro-5-quinolyl)amino]pyrrolidin-1-yl]acetyl]pyrrolidine-2-carbonitrile
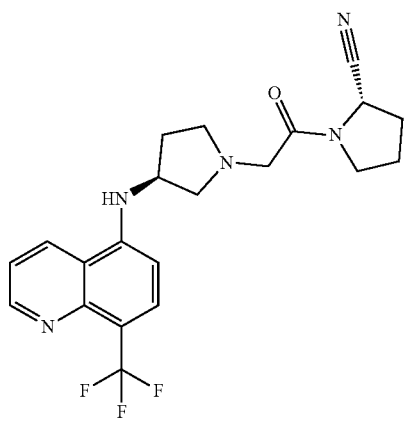 [SMILES: N#C[C@@H]1CCCN1C(=O)CN1CC[C@H](Nc2ccc(C(F)(F)F)c3ncccc23)C1]
(2S)-1-[2-[(3S)-3-[[8-(trifluoromethyl)-5-quinolyl]amino]pyrrolidin-1-yl]acetyl]pyrrolidine-2-carbonitrile
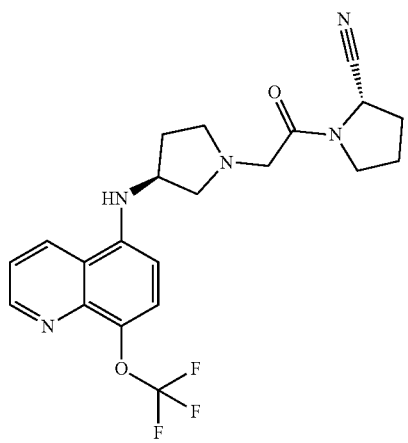 [SMILES: N#C[C@@H]1CCCN1C(=O)CN1CC[C@H](Nc2ccc(OC(F)(F)F)c3ncccc23)C1]
(2S)-1-[2-[(3S)-3-[[8-(trifluoromethoxy)-5-quinolyl]amino]pyrrolidin-1-yl]acetyl]pyrrolidine-2-carbonitrile

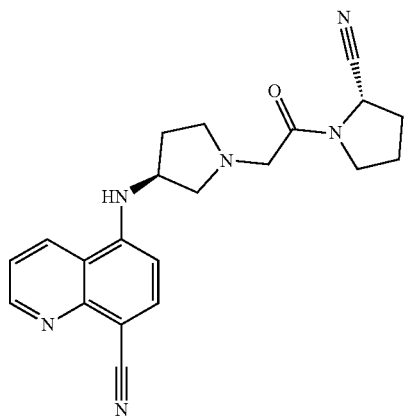 [SMILES: N#Cc1ccc(N[C@H]2CCN(CC(=O)N3CCC[C@H]3C#N)C2)c2cccnc12]

5-[[(3S)-1-[2-oxo-2-[(2S)-2-cyanopyrrolidin-1-yl]ethyl]pyrrolidin-3-yl]amino]quinoline-8-carbonitrile

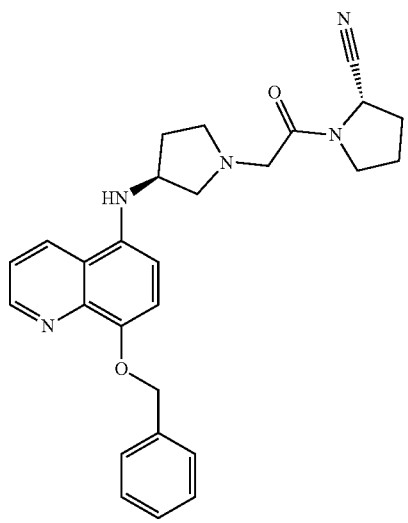 [SMILES: N#C[C@@H]1CCCN1C(=O)CN1CC[C@H](Nc2ccc(OCc3ccccc3)c3ncccc23)C1]

(2S)-1-[2-[(3S)-3-[(8-benzyloxy-5-quinolyl)amino]pyrrolidin-1-yl]acetyl]pyrrolidine-2-carbonitrile

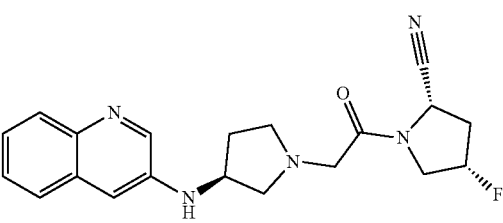 [SMILES: N#C[C@@H]1C[C@H](F)CN1C(=O)CN1CC[C@H](Nc2cnc3ccccc3c2)C1]

(2S,4S)-4-fluoro-1-[2-[(3S)-3-(3-quinolylamino)pyrrolidin-1-yl]acetyl]pyrrolidine-2-carbonitrile

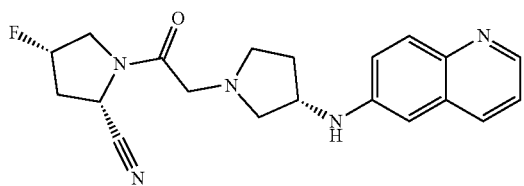 [SMILES: N#C[C@@H]1C[C@H](F)CN1C(=O)CN1CC[C@H](Nc2ccc3ncccc3c2)C1]

(2S,4S)-4-fluoro-1-(2-[(3S)-3-(6-quinolylamino)pyrrolidin-1-yl]acetyl]pyrrolidine-2-carbonitrile

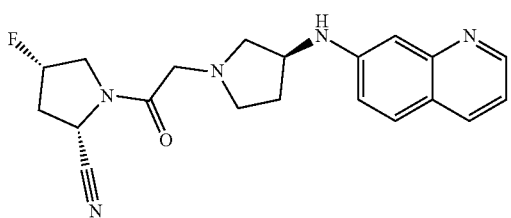 [SMILES: N#C[C@@H]1C[C@H](F)CN1C(=O)CN1CC[C@H](Nc2ccc3cccnc3c2)C1]

(2S,4S)-4-fluoro-1-[2-[(3S)-3-(7-quinolylamino)pyrrolidin-1-yl]acetyl]pyrrolidine-2-carbonitrile -continued
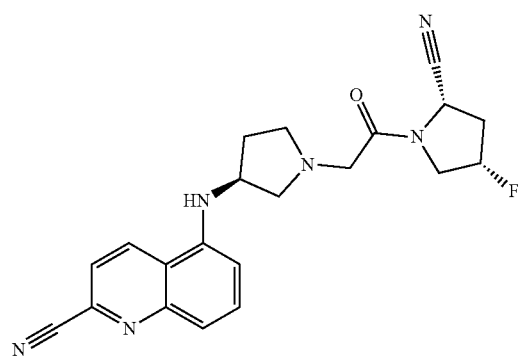 [SMILES: N#Cc1ccc2c(N[C@H]3CCN(CC(=O)N4C[C@@H](F)C[C@H]4C#N)C3)cccc2n1]
5-[[(3S)-1-[2-oxo-2-[(2S,4S)-2-cyano-4-fluoro-pyrrolidin-1-yl]ethyl]pyrrolidin-3-yl]amino]quinoline-2-carbonitrile
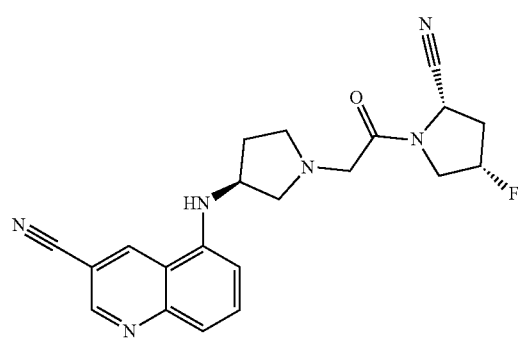 [SMILES: N#Cc1cnc2cccc(N[C@H]3CCN(CC(=O)N4C[C@@H](F)C[C@H]4C#N)C3)c2c1]
5-[[(3S)-1-[2-oxo-2-[(2S,4S)-2-cyano-4-fluoro-pyrrolidin-1-yl]ethyl]pyrrolidin-3-yl]amino]quinoline-3-carbonitrile
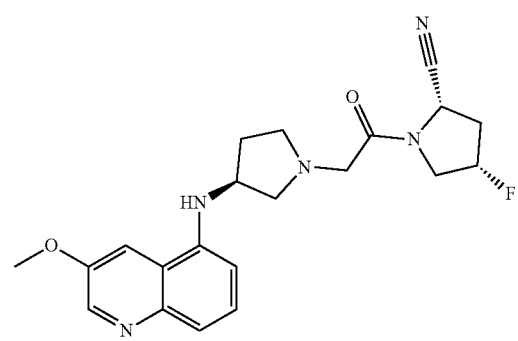 [SMILES: COc1cnc2cccc(N[C@H]3CCN(CC(=O)N4C[C@@H](F)C[C@H]4C#N)C3)c2c1]
(2S,4S)-4-fluoro-1-(2-[(3S)-3-[(3-methoxy-5-quinolyl)amino]pyrrolidin-1-yl]acetyl]pyrrolidine-2-carbonitrile
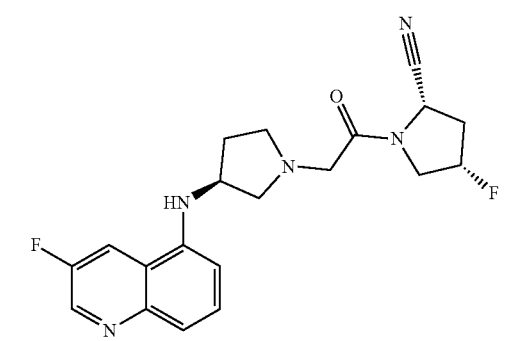 [SMILES: N#C[C@@H]1C[C@H](F)CN1C(=O)CN1CC[C@H](Nc2cccc3ncc(F)cc23)C1]
(2S,4S)-4-fluoro-1-[2-[(3S)-3-[(3-fluoro-5-quinolyl)amino]pyrrolidin-1-yl]acetyl]pyrrolidine-2-carbonitrile

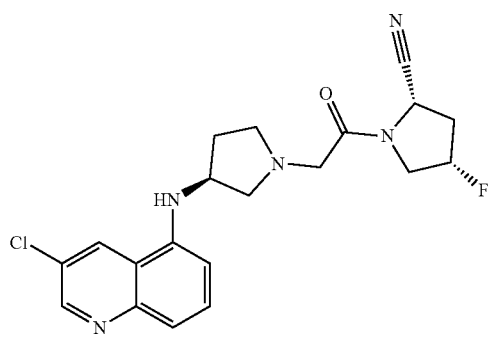 [SMILES: N#C[C@@H]1C[C@H](F)CN1C(=O)CN1CC[C@H](Nc2cccc3ncc(Cl)cc23)C1]
(2S,4S)-4-fluoro-1-[2-[(3S)-3-[(3-chloro-5-quinolyl)amino]pyrrolidin-1-yl]acetyl]pyrrolidine-2-carbonitrile
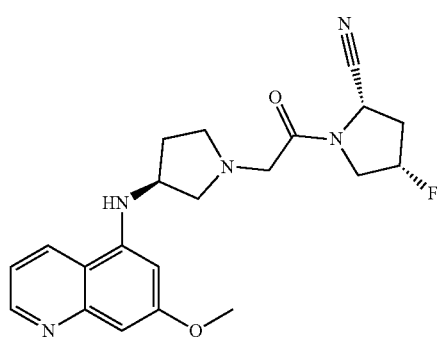 [SMILES: COc1cc(N[C@H]2CCN(CC(=O)N3C[C@@H](F)C[C@H]3C#N)C2)c2cccnc2c1]
(2S,4S)-4-fluoro-1-[2-[(3S)-3-[(7-methoxy-5-quinolyl)amino]pyrrolidin-1-yl]acetyl]pyrrolidine-2-carbonitrile
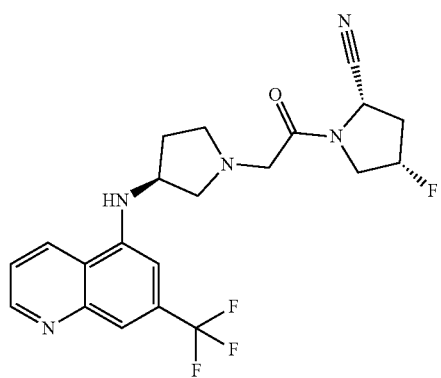 [SMILES: N#C[C@@H]1C[C@H](F)CN1C(=O)CN1CC[C@H](Nc2cc(C(F)(F)F)cc3ncccc23)C1]
(2S,4S)-4-fluoro-1-[2-[(3S)-3-[[7-(trifluoromethyl)-5-quinolyl]amino]pyrrolidin-1-yl]acetyl]pyrrolidine-2-carbonitrile
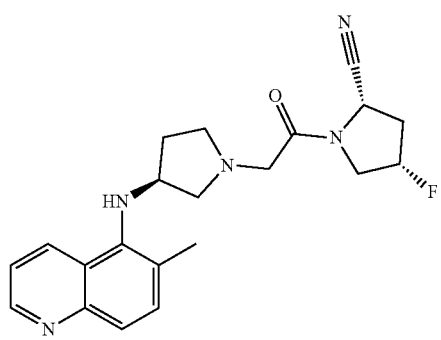 [SMILES: Cc1ccc2ncccc2c1N[C@H]1CCN(CC(=O)N2C[C@@H](F)C[C@H]2C#N)C1]
(2S,4S)-4-fluoro-1-[2-[(3S)-3-[(6-methyl-5-quinolyl)amino]pyrrolidin-1-yl]acetyl]pyrrolidine-2-carbonitrile -continued
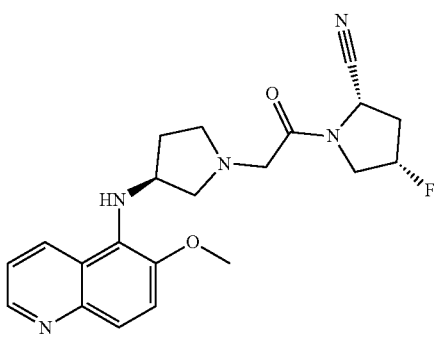 [SMILES: COc1ccc2ncccc2c1N[C@H]1CCN(CC(=O)N2C[C@@H](F)C[C@H]2C#N)C1]
(2S,4S)-4-fluoro-1-[2-[(3S)-3-[(6-methoxy-5-quinolyl)amino]pyrrolidin-1-yl]acetyl]pyrrolidine-2-carbonitrile
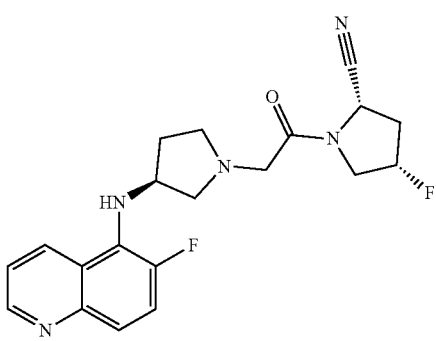 [SMILES: N#C[C@@H]1C[C@H](F)CN1C(=O)CN1CC[C@H](Nc2c(F)ccc3ncccc23)C1]
(2S,4S)-4-fluoro-1-[2-[(3S)-3-[(6-fluoro-5-quinolyl)amino]pyrrolidin-1-yl]acetyl]pyrrolidine-2-carbonitrile
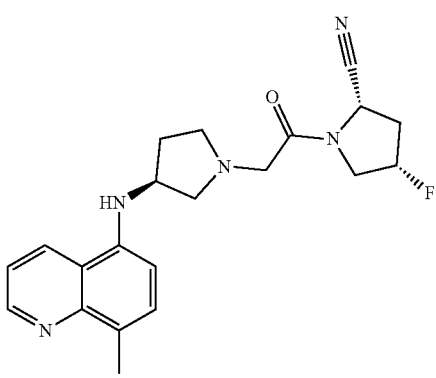 [SMILES: Cc1ccc(N[C@H]2CCN(CC(=O)N3C[C@@H](F)C[C@H]3C#N)C2)c2cccnc12]
(2S,4S)-4-fluoro-1-[2-[(3S)-3-[(8-methyl-5-quinolyl)amino]pyrrolidin-1-yl]acetyl]pyrrolidine-2-carbonitrile
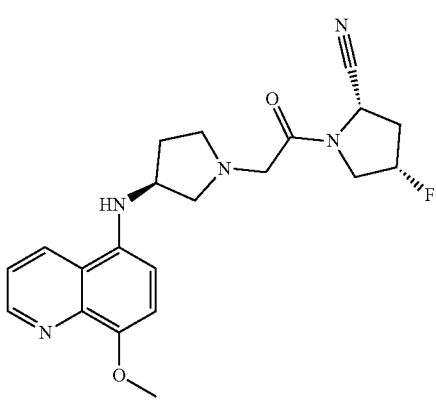 [SMILES: COc1ccc(N[C@H]2CCN(CC(=O)N3C[C@@H](F)C[C@H]3C#N)C2)c2cccnc12]
(2S,4S)-4-fluoro-1-[2-[(3S)-3-[(8-methoxy-5-quinolyl)amino]pyrrolidin-1-yl]acetyl]pyrrolidine-2-carbonitrile

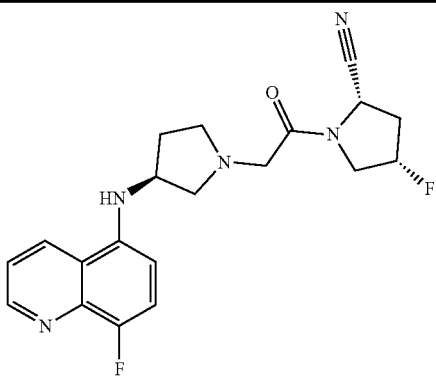
(2S,4S)-4-fluoro-1-[2-[(3S)-3-[(8-fluoro-5-quinolyl)amino]pyrrolidin-1-yl]acetyl]pyrrolidine-2-carbonitrile
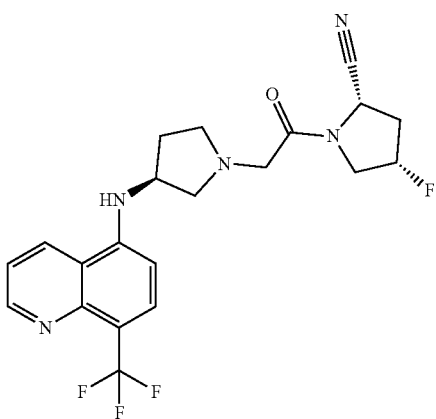 [SMILES: N#C[C@@H]1C[C@H](F)CN1C(=O)CN1CC[C@H](Nc2ccc(C(F)(F)F)c3ncccc23)C1]
(2S,4S)-4-fluoro-1-[2-[(3S)-3-[[8-(trifluoromethyl)-5-quinolyl]amino]pyrrolidin-1-yl]acetyl]pyrrolidine-2-carbonitrile
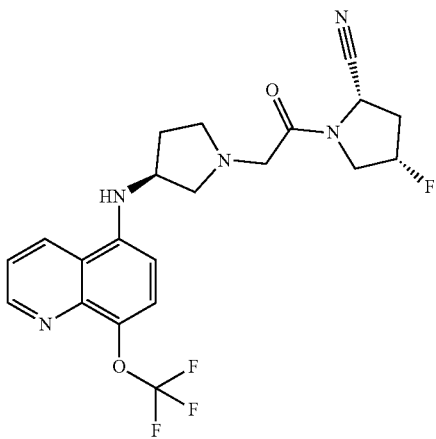 [SMILES: N#C[C@@H]1C[C@H](F)CN1C(=O)CN1CC[C@H](Nc2ccc(OC(F)(F)F)c3ncccc23)C1]
(2S,4S)-4-fluoro-1-[2-[(3S)-3-[[8-(trifluoromethoxy)-5-quinolyl]amino]pyrrolidin-1-yl]acetyl]pyrrolidine-2-carbonitrile
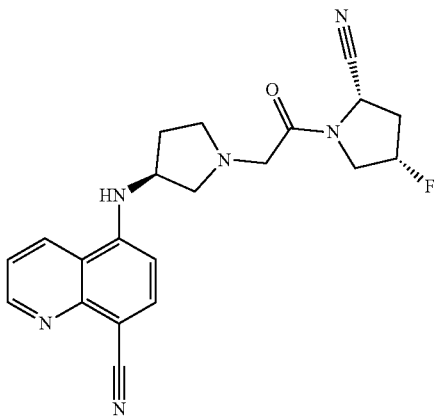 [SMILES: N#Cc1ccc(N[C@H]2CCN(CC(=O)N3C[C@@H](F)C[C@H]3C#N)C2)c2cccnc12]
5-[[(3S)-1-[2-oxo-2-[(2S,4S)-2-cyano-4-fluoro-pyrrolidin-1-yl]ethyl]pyrrolidin-3-yl]amino]quinoline-8-carbonitrile

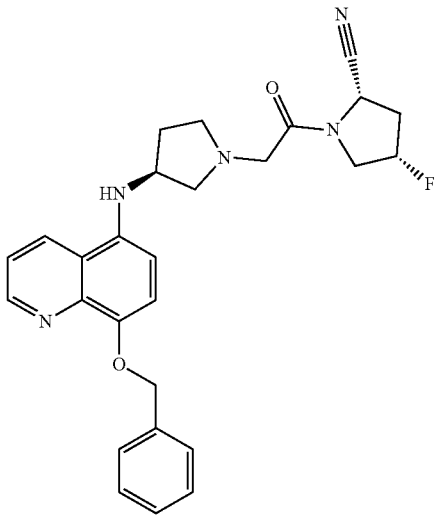 [SMILES: N#C[C@@H]1C[C@H](F)CN1C(=O)CN1CC[C@H](Nc2ccc(OCc3ccccc3)c3ncccc23)C1]
(2S,4S)-4-fluoro-1-[2-[(3S)-3-[(8-benzyloxy-5-quinolyl)amino]pyrrolidin-1-yl]acetyl]pyrrolidine-2-carbonitrile
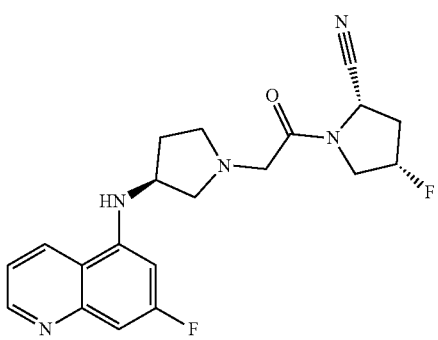 [SMILES: N#C[C@@H]1C[C@H](F)CN1C(=O)CN1CC[C@H](Nc2cc(F)cc3ncccc23)C1]
(2S,4S)-4-fluoro-1-[2-[(3S)-3-[(7-fluoro-5-quinolyl)amino]pyrrolidin-1-yl]acetyl]pyrrolidine-2-carbonitrile
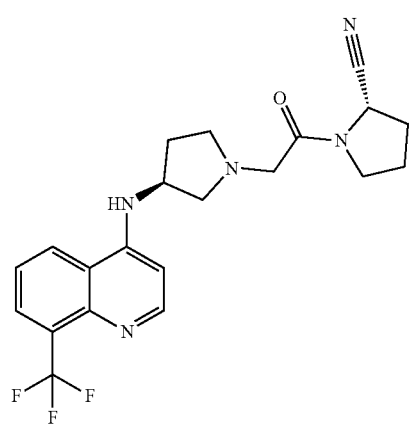 [SMILES: N#C[C@@H]1CCCN1C(=O)CN1CC[C@H](Nc2ccnc3c(C(F)(F)F)cccc23)C1]
(2S)-1-[2-[(3S)-3-[[8-(trifluoromethyl)-4-quinolyl]amino]pyrrolidin-1-yl]acetyl]pyrrolidine-2-carbonitrile

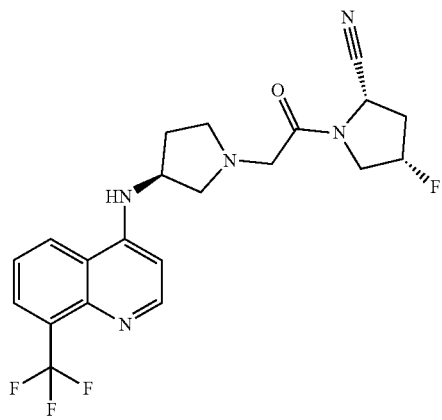 [SMILES: N#C[C@@H]1C[C@H](F)CN1C(=O)CN1CC[C@H](Nc2ccnc3c(C(F)(F)F)cccc23)C1]
(2S,4S)-4-fluoro-1-[2-[(3S)-3-[[8-(trifluoromethyl)-4-quinolyl]amino]pyrrolidin-1-yl]acetyl]pyrrolidine-2-carbonitrile
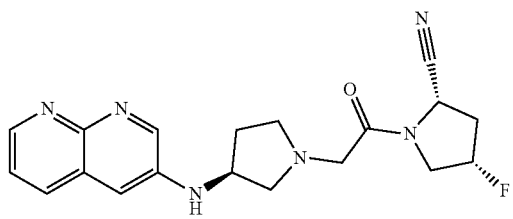 [SMILES: N#C[C@@H]1C[C@H](F)CN1C(=O)CN1CC[C@H](Nc2cnc3ncccc3c2)C1]
(2S,4S)-4-fluoro-1-[2-[(3S)-3-(1,8-naphthyridin-3-ylamino)pyrrolidin-1-yl]acetyl]pyrrolidine-2-carbonitrile
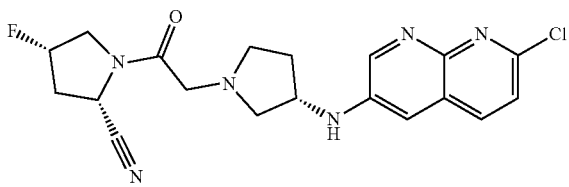 [SMILES: N#C[C@@H]1C[C@H](F)CN1C(=O)CN1CC[C@H](Nc2cnc3nc(Cl)ccc3c2)C1]
(2S,4S)-4-fluoro-1-[2-[(3S)-3-[(7-chloro-1,8-naphthyridin-3-yl)amino]pyrrolidin-1-yl]acetyl]pyrrolidine-2-carbonitrile
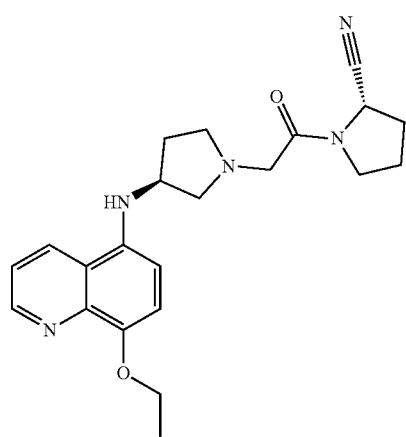 [SMILES: CCOc1ccc(N[C@H]2CCN(CC(=O)N3CCC[C@H]3C#N)C2)c2cccnc12]
(2S)-1-[2-[(3S)-3-[(8-ethoxy-5-quinolyl)amino]pyrrolidin-1-yl]acetyl]pyrrolidine-2-carbonitrile -continued

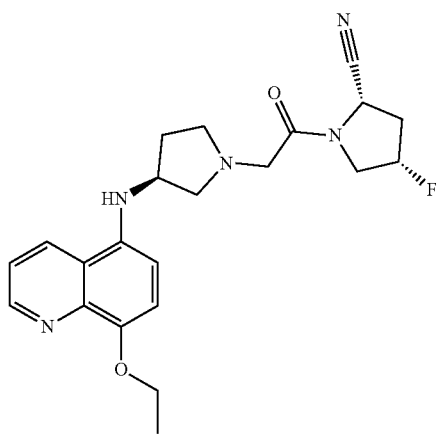 [SMILES: CCOc1ccc(N[C@H]2CCN(CC(=O)N3C[C@@H](F)C[C@H]3C#N)C2)c2cccnc12]

(2S,4S)-4-fluoro-1-[2-[(3S)-3-[(8-ethoxy-5-quinolyl)amino]pyrrolidin-1-yl]acetyl]pyrrolidine-2-carbonitrile

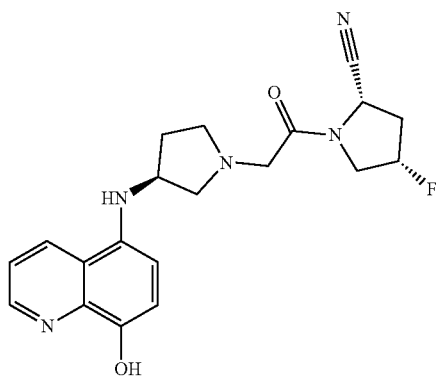 [SMILES: N#C[C@@H]1C[C@H](F)CN1C(=O)CN1CC[C@H](Nc2ccc(O)c3ncccc23)C1]

(2S,4S)-4-fluoro-1-[2-[(3S)-3-[(8-hydroxy-5-quinolyl)amino]pyrrolidin-1-yl]acetyl]pyrrolidine-2-carbonitrile

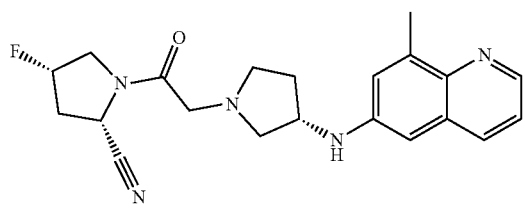 [SMILES: Cc1cc(N[C@H]2CCN(CC(=O)N3C[C@@H](F)C[C@H]3C#N)C2)cc2cccnc12]

(2S,4S)-4-fluoro-1-[2-[(3S)-3-[(8-methyl-6-quinolyl)amino]pyrrolidin-1-yl]acetyl]pyrrolidine-2-carbonitrile

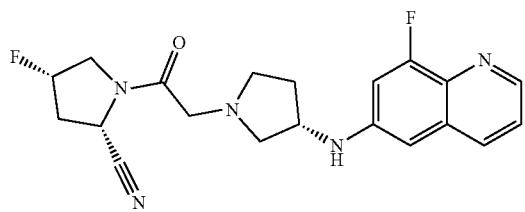 [SMILES: N#C[C@@H]1C[C@H](F)CN1C(=O)CN1CC[C@H](Nc2cc(F)c3ncccc3c2)C1]

(2S,4S)-4-fluoro-1-(2-[(3S)-3-[(8-fluoro-6-quinolyl)amino]pyrrolidin-1-yl]acetyl]pyrrolidine-2-carbonitrile

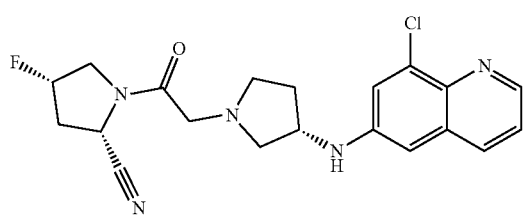 [SMILES: N#C[C@@H]1C[C@H](F)CN1C(=O)CN1CC[C@H](Nc2cc(Cl)c3ncccc3c2)C1]

(2S,4S)-4-fluoro-1-[2-[(3S)-3-[(8-chloro-6-quinolyl)amino]pyrrolidin-1-yl]acetyl]pyrrolidine-2-carbonitrile -continued

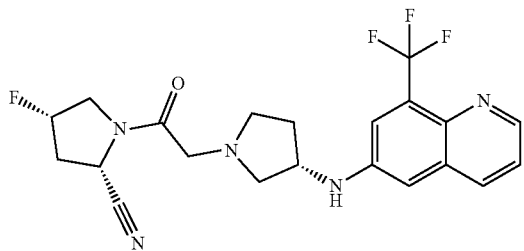 [SMILES: N#C[C@@H]1C[C@H](F)CN1C(=O)CN1CC[C@H](Nc2cc(C(F)(F)F)c3ncccc3c2)C1]

(2S,4S)-4-fluoro-1-[2-[(3S)-3-[[8-(trifluoromethyl)-6-quinolyl]amino]pyrrolidin-1-yl]acetyl]pyrrolidine-2-carbonitrile

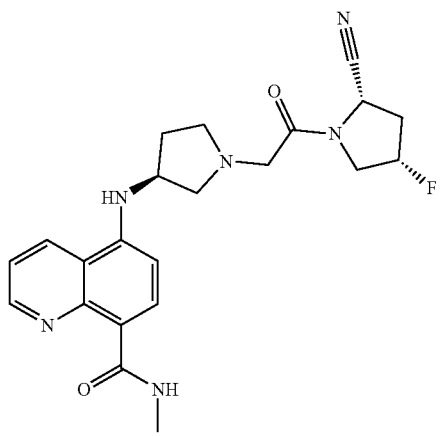 [SMILES: CNC(=O)c1ccc(N[C@H]2CCN(CC(=O)N3C[C@@H](F)C[C@H]3C#N)C2)c2cccnc12]

N-methyl-5-[[(3S)-1-[2-oxo-2-[(2S,4S)-2-cyano-4-fluoro-pyrrolidin-1-yl]ethyl]pyrrolidin-3-yl]amino]quinoline-8-carboxamide

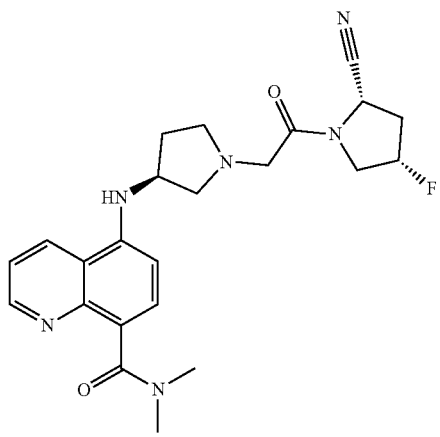 [SMILES: CN(C)C(=O)c1ccc(N[C@H]2CCN(CC(=O)N3C[C@@H](F)C[C@H]3C#N)C2)c2cccnc12]

N,N-dimethyl-5-[[(3S)-1-[2-oxo-2-[(2S,4S)-2-cyano-4-fluoro-pyrrolidin-1-yl]ethyl]pyrrolidin-3-yl]amino]quinoline-8-carboxamide

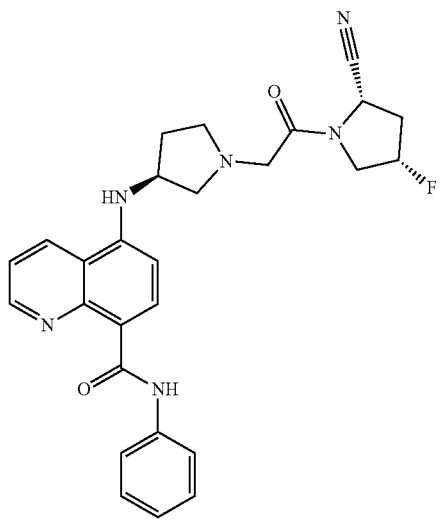 [SMILES: N#C[C@@H]1C[C@H](F)CN1C(=O)CN1CC[C@H](Nc2ccc(C(=O)Nc3ccccc3)c3ncccc23)C1]

N-phenyl-5-[[(3S)-1-(2-oxo-2-[(2S,4S)-2-cyano-4-fluoro-pyrrolidin-1-yl]ethyl]pyrrolidin-3-yl]amino]quinoline-8-carboxamide

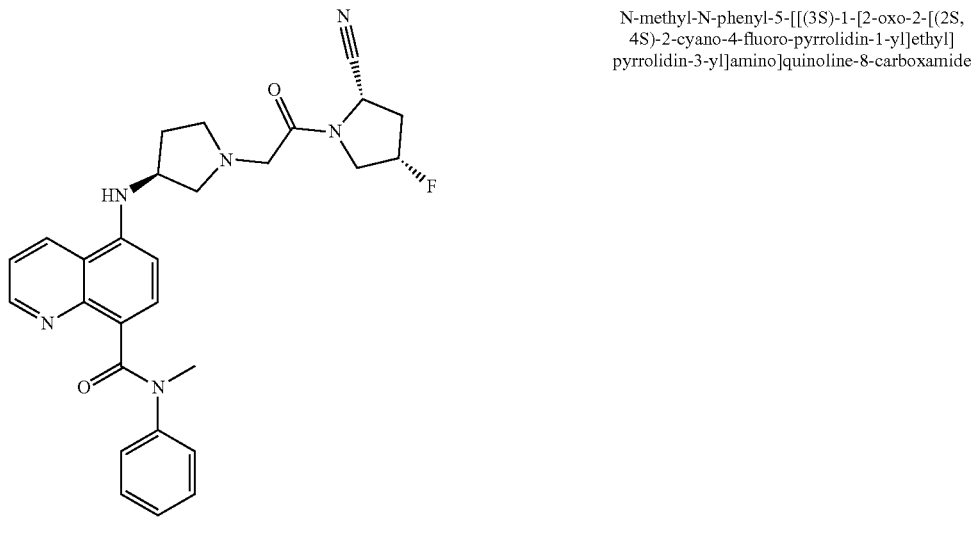
N-methyl-N-phenyl-5-[[(3S)-1-[2-oxo-2-[(2S,4S)-2-cyano-4-fluoro-pyrrolidin-1-yl]ethyl]pyrrolidin-3-yl]amino]quinoline-8-carboxamide
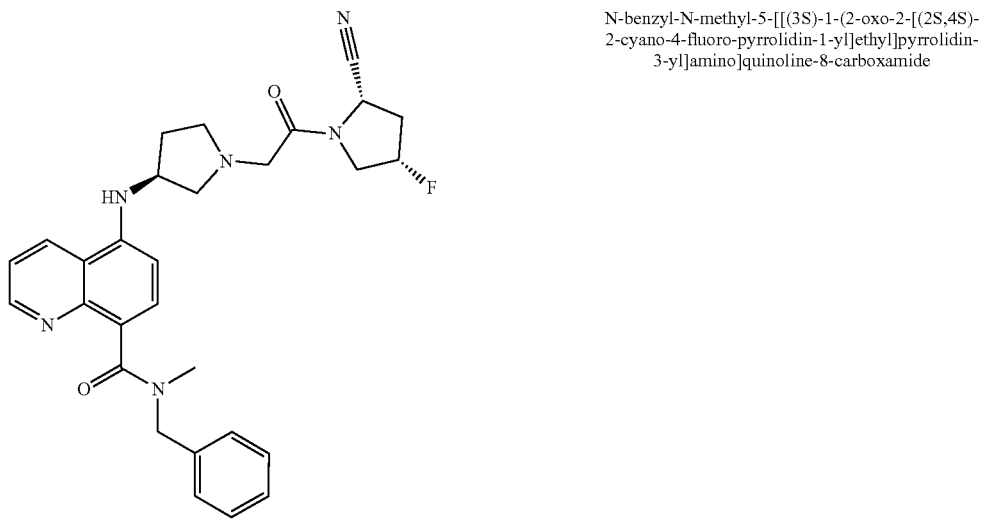
N-benzyl-N-methyl-5-[[(3S)-1-(2-oxo-2-[(2S,4S)-2-cyano-4-fluoro-pyrrolidin-1-yl]ethyl]pyrrolidin-3-yl]amino]quinoline-8-carboxamide
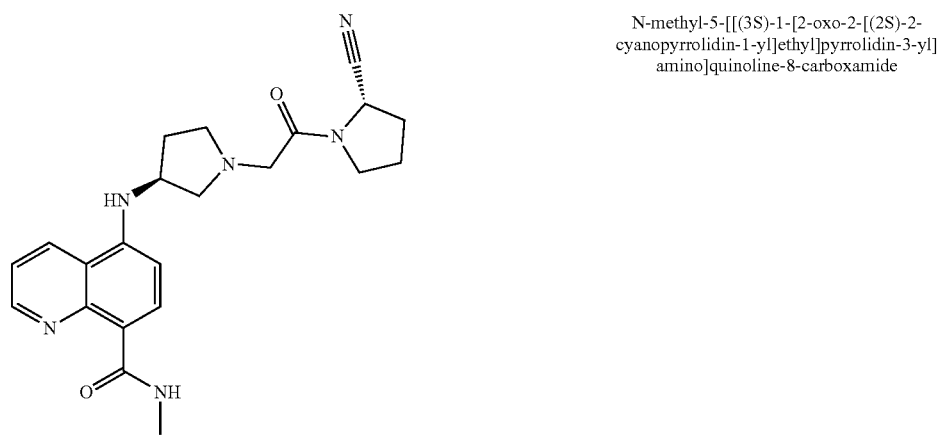
N-methyl-5-[[(3S)-1-[2-oxo-2-[(2S)-2-cyanopyrrolidin-1-yl]ethyl]pyrrolidin-3-yl]amino]quinoline-8-carboxamide

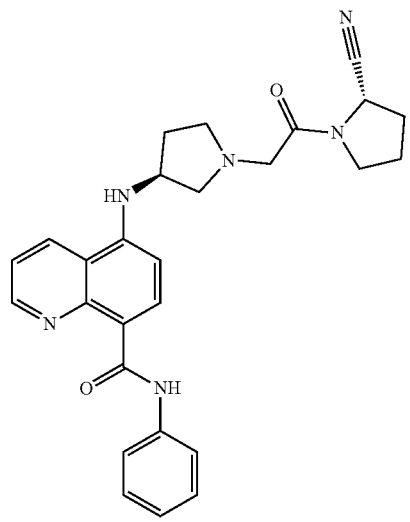 [SMILES: N#C[C@@H]1CCCN1C(=O)CN1CC[C@H](Nc2ccc(C(=O)Nc3ccccc3)c3ncccc23)C1]
N-phenyl-5-[[(3S)-1-[2-oxo-2-[(2S)-2-cyanopyrrolidin-1-yl]ethyl]pyrrolidin-3-yl]amino]quinoline-8-carboxamide
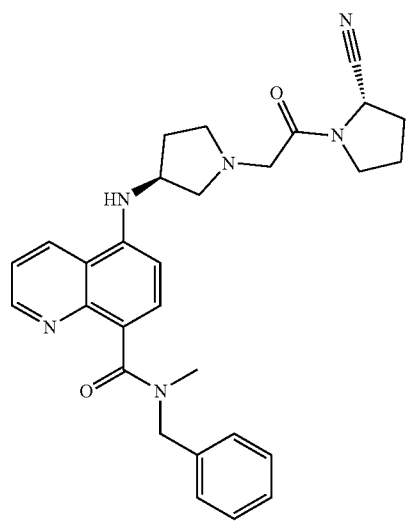 [SMILES: CN(Cc1ccccc1)C(=O)c1ccc(N[C@H]2CCN(CC(=O)N3CCC[C@H]3C#N)C2)c2cccnc12]
N-benzyl-N-methyl-5-[[(3S)-1-[2-oxo-2-[(2S)-2-cyanopyrrolidin-1-yl]ethyl]pyrrolidin-3-yl]amino]quinoline-8-carboxamide
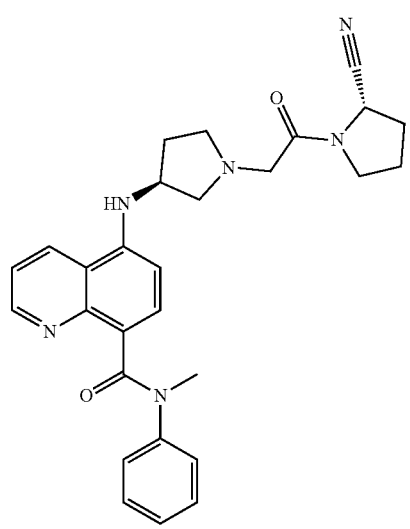 [SMILES: CN(C(=O)c1ccc(N[C@H]2CCN(CC(=O)N3CCC[C@H]3C#N)C2)c2cccnc12)c1ccccc1]
N-methyl-N-phenyl-5-[[(3S)-1-[2-oxo-2-[(2S)-2-cyanopyrrolidin-1-yl]ethyl]pyrrolidin-3-yl]amino]quinoline-8-carboxamide

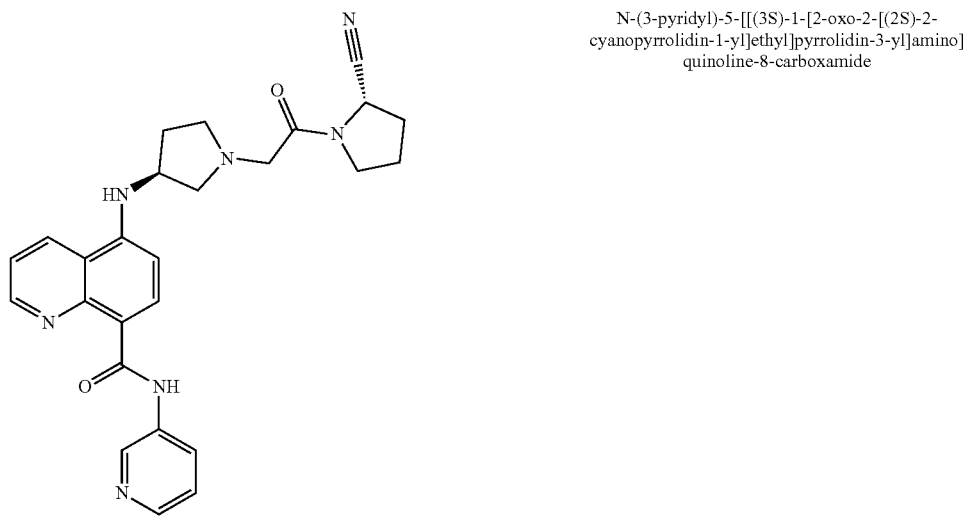
N-(3-pyridyl)-5-[[(3S)-1-[2-oxo-2-[(2S)-2-cyanopyrrolidin-1-yl]ethyl]pyrrolidin-3-yl]amino]quinoline-8-carboxamide
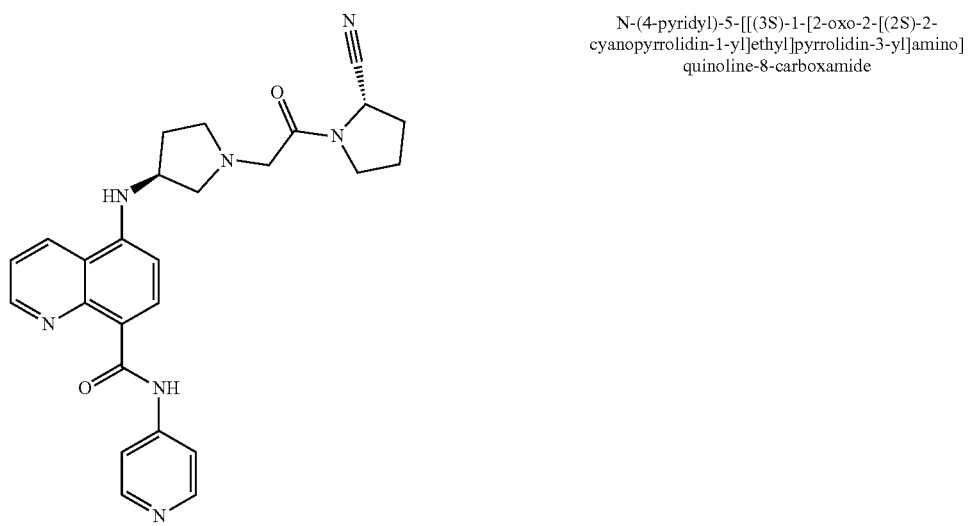
N-(4-pyridyl)-5-[[(3S)-1-[2-oxo-2-[(2S)-2-cyanopyrrolidin-1-yl]ethyl]pyrrolidin-3-yl]amino]quinoline-8-carboxamide
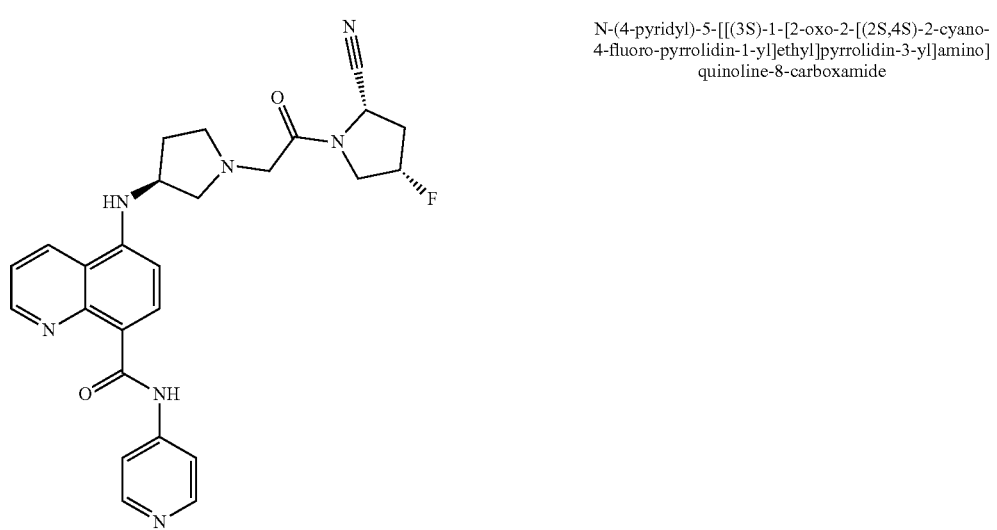
N-(4-pyridyl)-5-[[(3S)-1-[2-oxo-2-[(2S,4S)-2-cyano-4-fluoro-pyrrolidin-1-yl]ethyl]pyrrolidin-3-yl]amino]quinoline-8-carboxamide

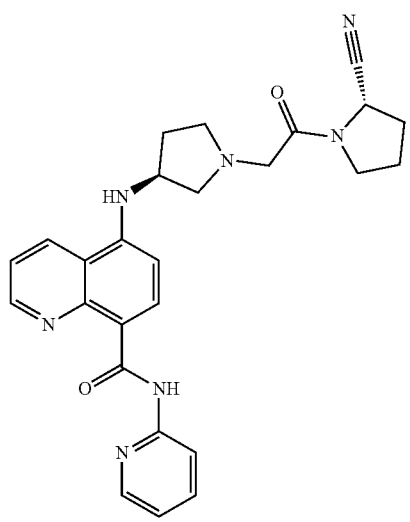 [SMILES: N#C[C@@H]1CCCN1C(=O)CN1CC[C@H](Nc2ccc(C(=O)Nc3ccccn3)c3ncccc23)C1]
N-(2-pyridyl)-5-[[(3S)-1-[2-oxo-2-[(2S)-2-cyanopyrrolidin-1-yl]ethyl]pyrrolidin-3-yl]amino]quinoline-8-carboxamide
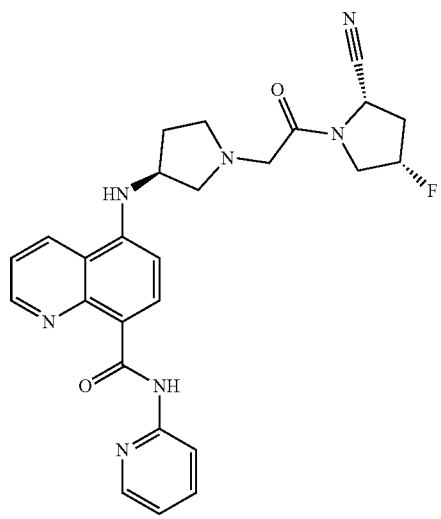 [SMILES: N#C[C@@H]1C[C@H](F)CN1C(=O)CN1CC[C@H](Nc2ccc(C(=O)Nc3ccccn3)c3ncccc23)C1]
N-(2-pyridyl)-5-[[(3S)-1-[2-oxo-2-[(2S,4S)-2-cyano-4-fluoro-pyrrolidin-1-yl]ethyl]pyrrolidin-3-yl]amino]quinoline-8-carboxamide
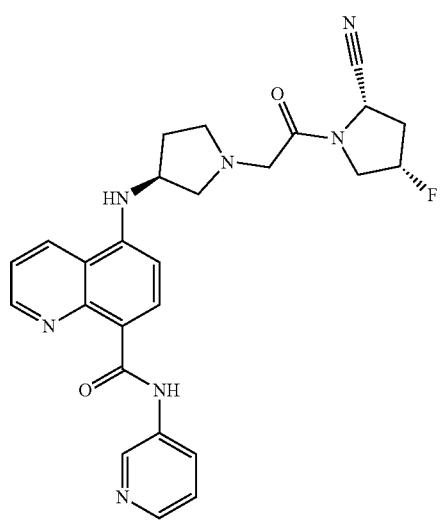 [SMILES: N#C[C@@H]1C[C@H](F)CN1C(=O)CN1CC[C@H](Nc2ccc(C(=O)Nc3cccnc3)c3ncccc23)C1]
N-(3-pyridyl)-5-[[(3S)-1-[2-oxo-2-[(2S,4S)-2-cyano-4-fluoro-pyrrolidin-1-yl]ethyl]pyrrolidin-3-yl]amino]quinoline-8-carboxamide -continued
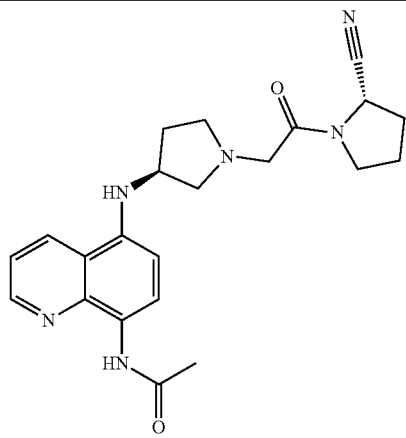
N-[5-[[(3S)-1-[2-oxo-2-[(2S)-2-cyanopyrrolidin-1-yl]ethyl]pyrrolidin-3-yl]amino]-8-quinolyl]acetamide
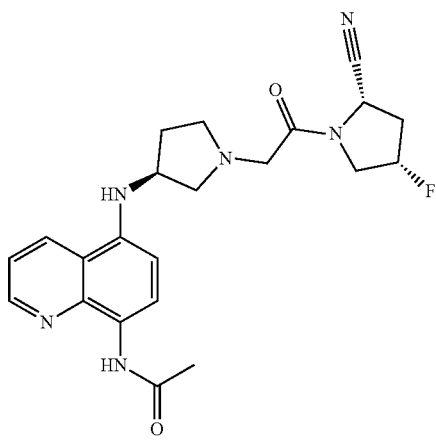 [SMILES: CC(=O)Nc1ccc(N[C@H]2CCN(CC(=O)N3C[C@@H](F)C[C@H]3C#N)C2)c2cccnc12]
N-[5-[[(3S)-1-[2-oxo-2-[(2S,4S)-2-cyano-4-fluoro-pyrrolidin-1-yl]ethyl]pyrrolidin-3-yl]amino]-8-quinolyl]acetamide
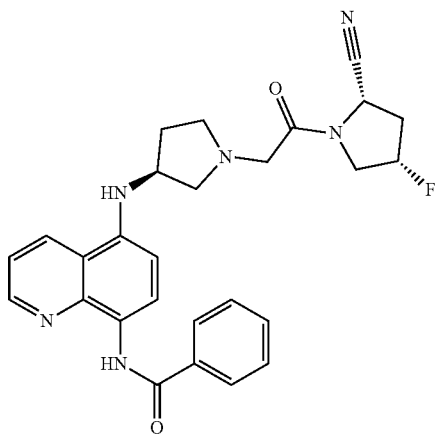 [SMILES: N#C[C@@H]1C[C@H](F)CN1C(=O)CN1CC[C@H](Nc2ccc(NC(=O)c3ccccc3)c3ncccc23)C1]
N-[5-[[(3S)-1-[2-oxo-2-[(2S,4S)-2-cyano-4-fluoro-pyrrolidin-1-yl]ethyl]pyrrolidin-3-yl]amino]-8-quinolyl]benzamide
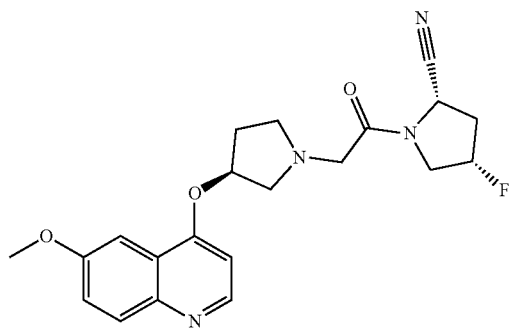 [SMILES: COc1ccc2nccc(O[C@H]3CCN(CC(=O)N4C[C@@H](F)C[C@H]4C#N)C3)c2c1]
(2S,4S)-4-fluoro-1-(2-[(3S)-3-[(6-methoxy-4-quinolyl)oxy]pyrrolidin-1-yl]acetyl]pyrrolidine-2-carbonitrile

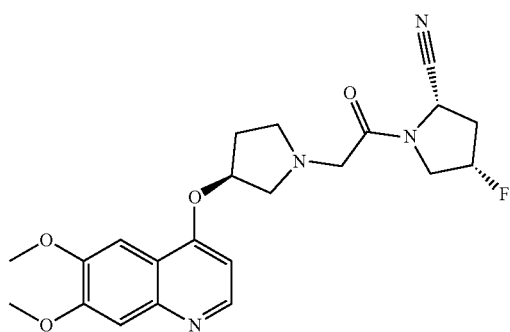 [SMILES: COc1cc2nccc(O[C@H]3CCN(CC(=O)N4C[C@@H](F)C[C@H]4C#N)C3)c2cc1OC]
(2S,4S)-4-fluoro-1-[2-[(3S)-3-[(6,7-dimethoxy-4-quinolyl)oxy]pyrrolidin-1-yl]acetyl]pyrrolidine-2-carbonitrile
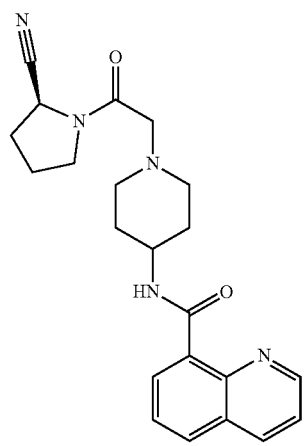 [SMILES: N#C[C@@H]1CCCN1C(=O)CN1CCC(NC(=O)c2cccc3cccnc23)CC1]
N-[1-[2-oxo-2-[(2S)-2-cyanopyrrolidin-1-yl]ethyl]-4-piperidyl]quinoline-8-carboxamide
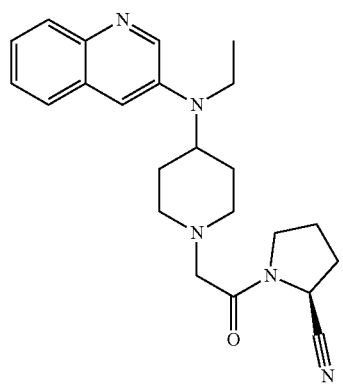 [SMILES: CCN(c1cnc2ccccc2c1)C1CCN(CC(=O)N2CCC[C@H]2C#N)CC1]
(2S)-1-[2-[4-[ethyl(3-quinolyl)amino]-1-piperidyl]acetyl]pyrrolidine-2-carbonitrile
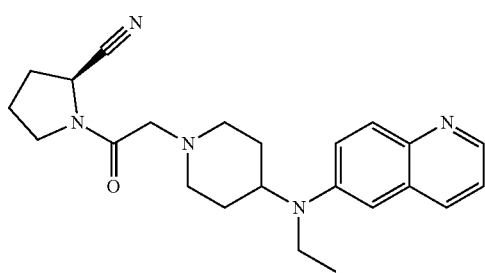 [SMILES: CCN(c1ccc2ncccc2c1)C1CCN(CC(=O)N2CCC[C@H]2C#N)CC1]
(2S)-1-[2-[4-[ethyl(6-quinolyl)amino]-1-piperidyl]acetyl]pyrrolidine-2-carbonitrile -continued

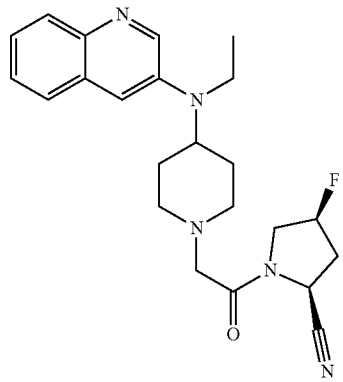 [SMILES: CCN(c1cnc2ccccc2c1)C1CCN(CC(=O)N2C[C@@H](F)C[C@H]2C#N)CC1]

(2S,4S)-1-[2-[4-[ethyl(3-quinolyl)amino]-1-piperidyl]acetyl]-4-fluoro-pyrrolidine-2-carbonitrile

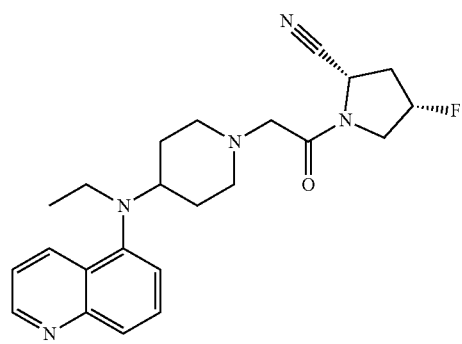 [SMILES: CCN(c1cccc2ncccc12)C1CCN(CC(=O)N2C[C@@H](F)C[C@H]2C#N)CC1]

(2S,4S)-1-[2-[4-[ethyl(5-quinolyl)amino]-1-piperidyl]acetyl]-4-fluoro-pyrrolidine-2-carbonitrile

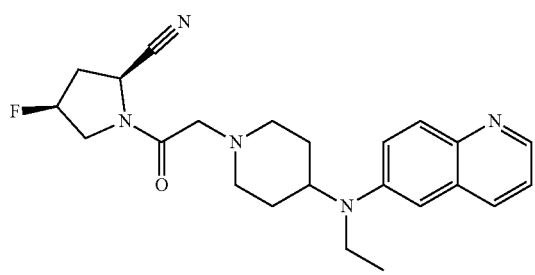 [SMILES: CCN(c1ccc2ncccc2c1)C1CCN(CC(=O)N2C[C@@H](F)C[C@H]2C#N)CC1]

(2S,4S)-1-[2-[4-[ethyl(6-quinolyl)amino]-1-piperidyl]acetyl]-4-fluoro-pyrrolidine-2-carbonitrile

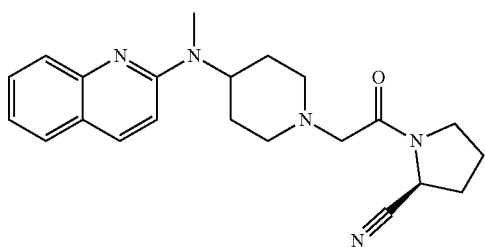 [SMILES: CN(c1ccc2ccccc2n1)C1CCN(CC(=O)N2CCC[C@H]2C#N)CC1]

(2S)-1-[2-[4-[methyl(2-quinolyl)amino]-1-piperidyl]acetyl]pyrrolidine-2-carbonitrile

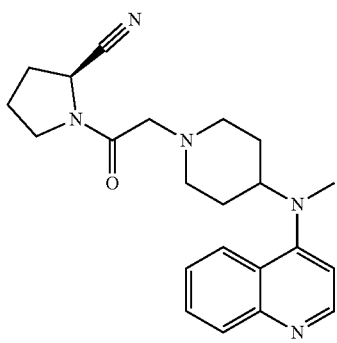 [SMILES: CN(c1ccnc2ccccc12)C1CCN(CC(=O)N2CCC[C@H]2C#N)CC1]

(2S)-1-[2-[4-[methyl(4-quinolyl)amino]-1-piperidyl]acetyl]pyrrolidine-2-carbonitrile

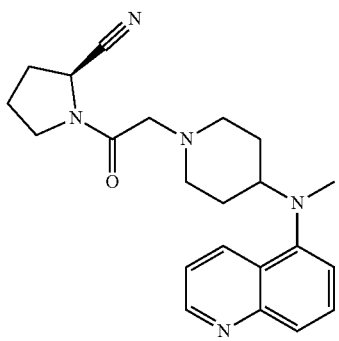 [SMILES: CN(c1cccc2ncccc12)C1CCN(CC(=O)N2CCC[C@H]2C#N)CC1]
(2S)-1-[2-[4-[methyl(5-quinolyl)amino]-1-piperidyl]acetyl]pyrrolidine-2-carbonitrile
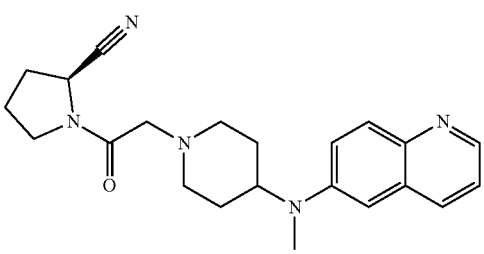 [SMILES: CN(c1ccc2ncccc2c1)C1CCN(CC(=O)N2CCC[C@H]2C#N)CC1]
(2S)-1-[2-[4-[methyl(6-quinolyl)amino]-1-piperidyl]acetyl]pyrrolidine-2-carbonitrile
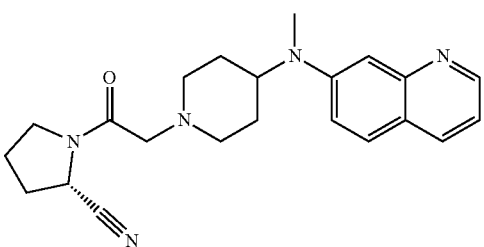 [SMILES: CN(c1ccc2cccnc2c1)C1CCN(CC(=O)N2CCC[C@H]2C#N)CC1]
(2S)-1-[2-[4-[methyl(7-quinolyl)amino]-1-piperidyl]acetyl]pyrrolidine-2-carbonitrile
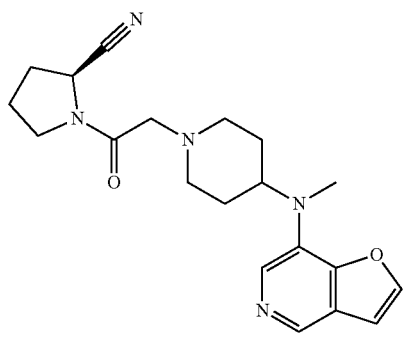 [SMILES: CN(c1cncc2ccoc12)C1CCN(CC(=O)N2CCC[C@H]2C#N)CC1]
(2S)-1-[2-[4-[furo[3,2-c]pyridin-7-yl(methyl)amino]-1-piperidyl]acetyl]pyrrolidine-2-carbonitrile
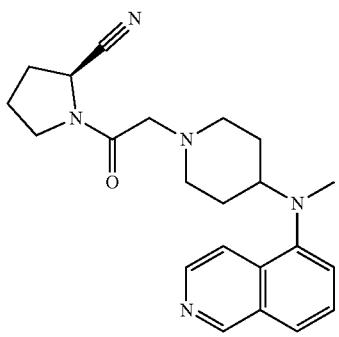 [SMILES: CN(c1cccc2cnccc12)C1CCN(CC(=O)N2CCC[C@H]2C#N)CC1]
(2S)-1-[2-[4-[5-isoquinolyl(methyl)amino]-1-piperidyl]acetyl]pyrrolidine-2-carbonitrile -continued

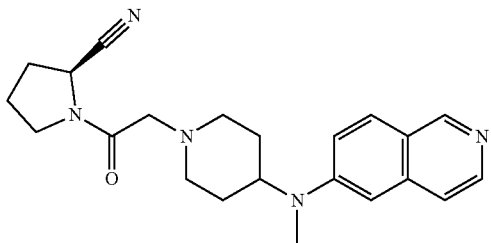 [SMILES: CN(c1ccc2cnccc2c1)C1CCN(CC(=O)N2CCC[C@H]2C#N)CC1]

(2S)-1-(2-[4-(isoquinolin-6-yl(methyl)amino)piperidin-1-yl)acetyl)pyrrolidine-2-carbonitrile

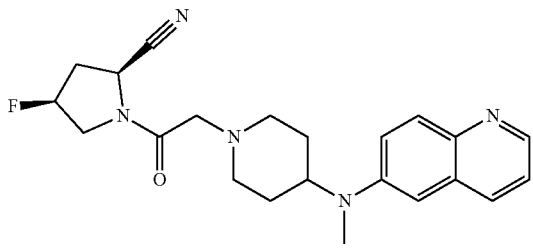 [SMILES: CN(c1ccc2ncccc2c1)C1CCN(CC(=O)N2C[C@@H](F)C[C@H]2C#N)CC1]

(2S,4S)-4-fluoro-1-[2-[4-[methyl(6-quinolyl)amino]-1-piperidyl]acetyl]pyrrolidine-2-carbonitrile

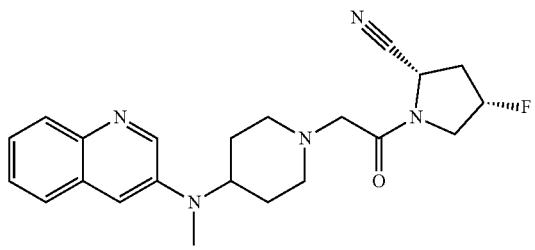 [SMILES: CN(c1cnc2ccccc2c1)C1CCN(CC(=O)N2C[C@@H](F)C[C@H]2C#N)CC1]

(2S,4S)-4-fluoro-1-[2-[4-[methyl(3-quinolyl)amino]-1-piperidyl]acetyl]pyrrolidine-2-carbonitrile

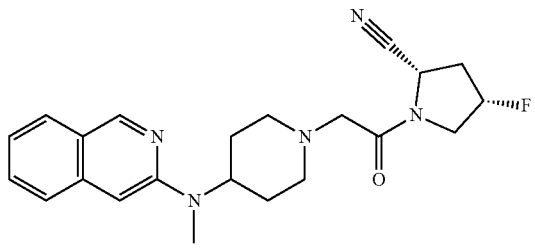 [SMILES: CN(c1cc2ccccc2cn1)C1CCN(CC(=O)N2C[C@@H](F)C[C@H]2C#N)CC1]

(2S,4S)-4-fluoro-1-[2-[4-[3-isoquinolyl(methyl)amino]-1-piperidyl]acetyl]pyrrolidine-2-carbonitrile

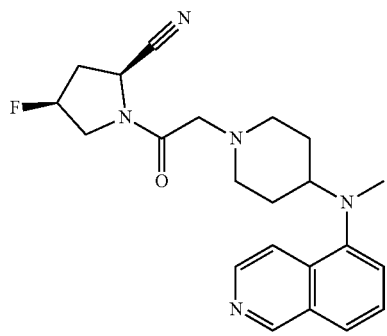 [SMILES: CN(c1cccc2cnccc12)C1CCN(CC(=O)N2C[C@@H](F)C[C@H]2C#N)CC1]

(2S,4S)-4-fluoro-1-[2-[4-(5-isoquinolyl(methyl)amino]-1-piperidyl]acetyl]pyrrolidine-2-carbonitrile

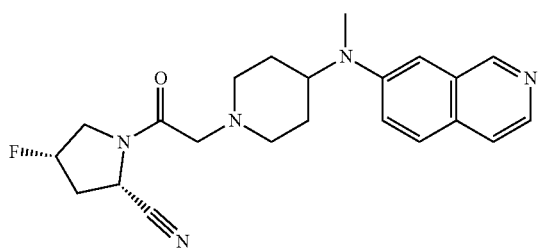 [SMILES: CN(c1ccc2ccncc2c1)C1CCN(CC(=O)N2C[C@@H](F)C[C@H]2C#N)CC1]

(2S,4S)-4-fluoro-1-[2-[4-(7-isoquinolyl(methyl)amino]-1-piperidyl]acetyl]pyrrolidine-2-carbonitrile

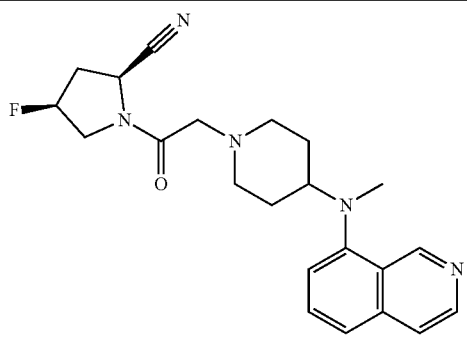

(2S,4S)-4-fluoro-1-[2-[4-[8-isoquinolyl(methyl)amino]-1-piperidyl]acetyl]pyrrolidine-2-carbonitrile

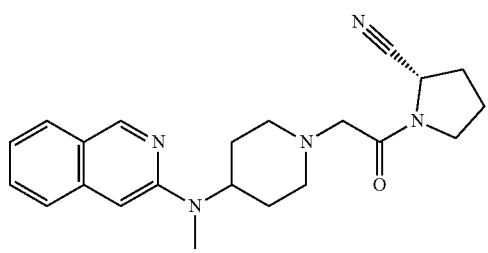 [SMILES: CN(c1cc2ccccc2cn1)C1CCN(CC(=O)N2CCC[C@H]2C#N)CC1]

(2S)-1-[2-[4-[3-isoquinolyl(methyl)amino]-1-piperidyl]acetyl]pyrrolidine-2-carbonitrile

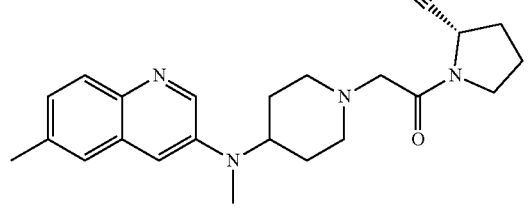

(2S)-1-[2-[4-[methyl-(6-methyl-3-quinolyl)amino]-1-piperidyl]acetyl]pyrrolidine-2-carbonitrile

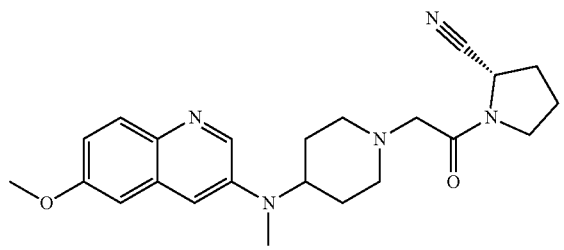 [SMILES: COc1ccc2ncc(N(C)C3CCN(CC(=O)N4CCC[C@H]4C#N)CC3)cc2c1]

(S)-1-[2-[4-((6-methoxyquinolin-3-yl)(methyl)amino)piperidin-1-yl)acetyl)pyrrolidine-2-carbonitrile

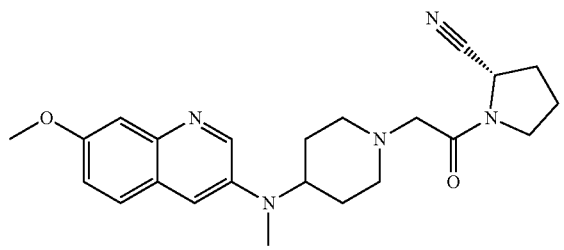 [SMILES: COc1ccc2cc(N(C)C3CCN(CC(=O)N4CCC[C@H]4C#N)CC3)cnc2c1]

(2S)-1-[2-[4-[(7-methoxy-3-quinolyl)-methyl-amino]-1-piperidyl]acetyl]pyrrolidine-2-carbonitrile

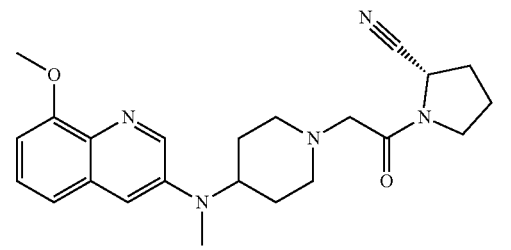 [SMILES: COc1cccc2cc(N(C)C3CCN(CC(=O)N4CCC[C@H]4C#N)CC3)cnc12]

(2S)-1-[2-[4-[(8-methoxy-3-quinolyl)-methyl-amino]-1-piperidyl]acetyl]pyrrolidine-2-carbonitrile

| | |
|---|---|
| 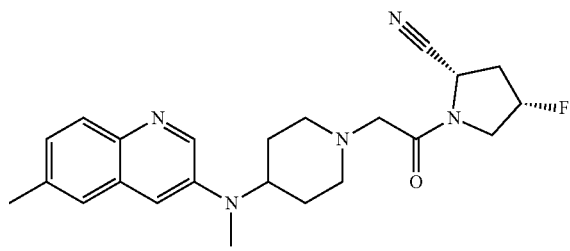 [SMILES: Cc1ccc2ncc(N(C)C3CCN(CC(=O)N4C[C@@H](F)C[C@H]4C#N)CC3)cc2c1] | (2S,4S)-4-fluoro-1-[2-[4-[methyl-(6-methyl-3-quinolyl)amino]-1-piperidyl]acetyl]pyrrolidine-2-carbonitrile |
| 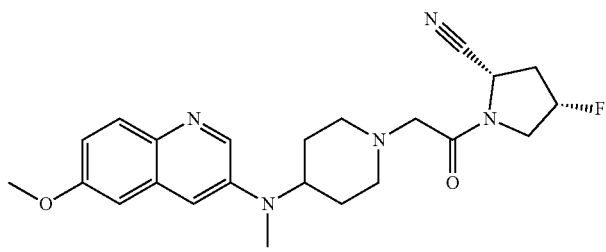 [SMILES: COc1ccc2ncc(N(C)C3CCN(CC(=O)N4C[C@@H](F)C[C@H]4C#N)CC3)cc2c1] | (2S,4S)-4-fluoro-1-(2-(4-((6-methoxyquinolin-3-yl)(methyl)amino)piperidin-1-yl)acetyl)pyrrolidine-2-carbonitrile |
| 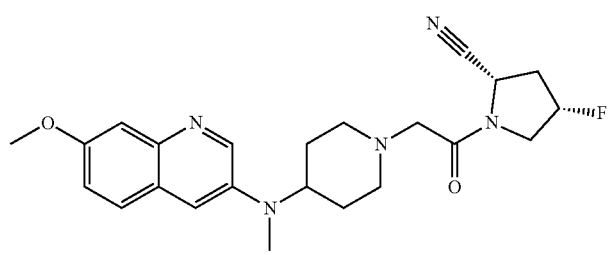 [SMILES: COc1ccc2cc(N(C)C3CCN(CC(=O)N4C[C@@H](F)C[C@H]4C#N)CC3)cnc2c1] | (2S,4S)-4-fluoro-1-(2-(4-((7-methoxyquinolin-3-yl)(methyl)amino)piperidin-1-yl)acetyl)pyrrolidine-2-carbonitrile |
| 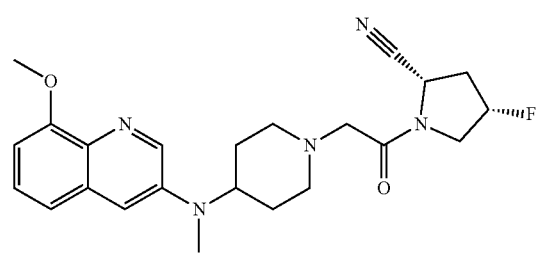 [SMILES: COc1cccc2cc(N(C)C3CCN(CC(=O)N4C[C@@H](F)C[C@H]4C#N)CC3)cnc12] | (2S,4S)-4-fluoro-1-[2-[4-[(8-methoxy-3-quinolyl)-methyl-amino]-1-piperidyl]acetyl]pyrrolidine-2-carbonitrile |
| 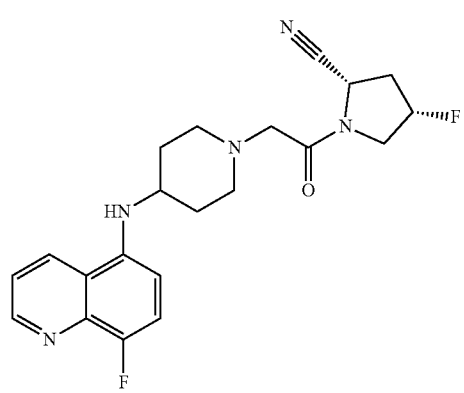 [SMILES: N#C[C@@H]1C[C@H](F)CN1C(=O)CN1CCC(Nc2ccc(F)c3ncccc23)CC1] | (2S,4S)-4-fluoro-1-[2-[4-[(8-fluoro-5-quinolyl)amino]-1-piperidyl]acetyl]pyrrolidine-2-carbonitrile |

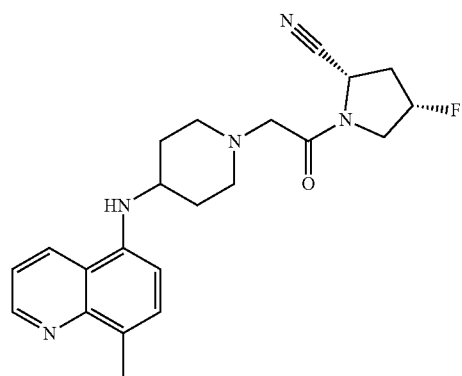 [SMILES: Cc1ccc(NC2CCN(CC(=O)N3C[C@@H](F)C[C@H]3C#N)CC2)c2cccnc12]
(2S,4S)-4-fluoro-1-[2-[4-[(8-methyl-5-quinolyl)amino]-1-piperidyl]acetyl]pyrrolidine-2-carbonitrile
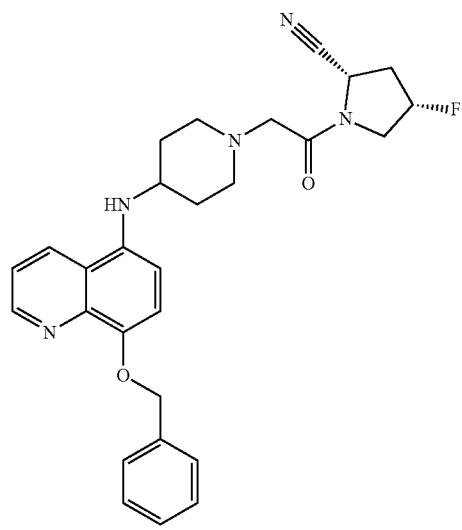 [SMILES: N#C[C@@H]1C[C@H](F)CN1C(=O)CN1CCC(Nc2ccc(OCc3ccccc3)c3ncccc23)CC1]
(2S,4S)-1-[2-[4-[(8-benzyloxy-5-quinolyl)amino]-1-piperidyl]acetyl]-4-fluoro-pyrrolidine-2-carbonitrile
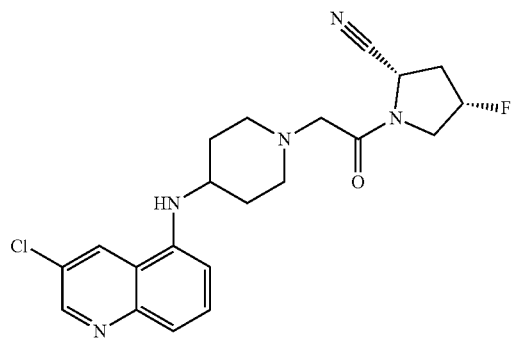 [SMILES: N#C[C@@H]1C[C@H](F)CN1C(=O)CN1CCC(Nc2cccc3ncc(Cl)cc23)CC1]
(2S,4S)-1-[2-[4-[(3-chloro-5-quinolyl)amino]-1-piperidyl]acetyl]-4-fluoro-pyrrolidine-2-carbonitrile

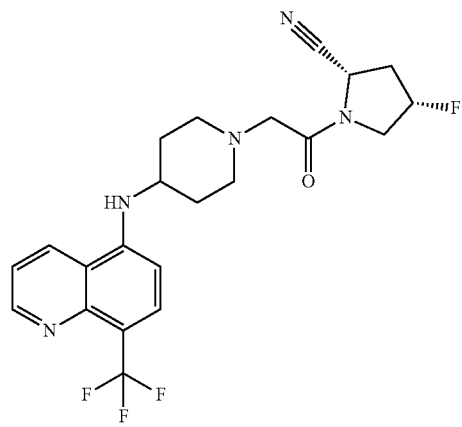 [SMILES: N#C[C@@H]1C[C@H](F)CN1C(=O)CN1CCC(Nc2ccc(C(F)(F)F)c3ncccc23)CC1]
(2S,4S)-4-fluoro-1-[2-[4-[[8-(trifluoromethyl)-5-quinolyl]amino]-1-piperidyl]acetyl]pyrrolidine-2-carbonitrile
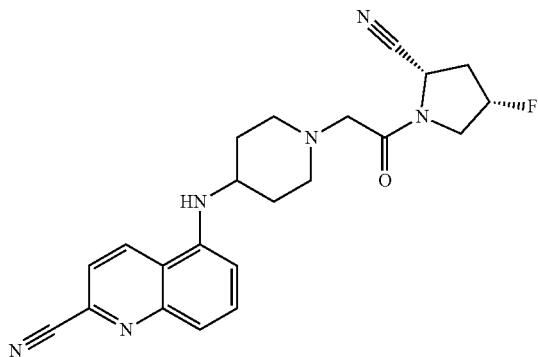 [SMILES: N#Cc1ccc2c(NC3CCN(CC(=O)N4C[C@@H](F)C[C@H]4C#N)CC3)cccc2n1]
5-[[1-[2-oxo-2-[(2S,4S)-2-cyano-4-fluoro-pyrrolidin-1-yl]ethyl]-4-piperidyl]amino]quinoline-2-carbonitrile
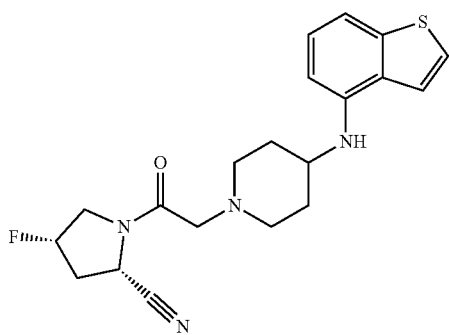 [SMILES: N#C[C@@H]1C[C@H](F)CN1C(=O)CN1CCC(Nc2cccc3sccc23)CC1]
(2S,4S)-1-(2-(4-(benzo[b]thiophen-4-ylamino)piperidin-1-yl)acetyl)-4-fluoropyrrolidine-2-carbonitrile
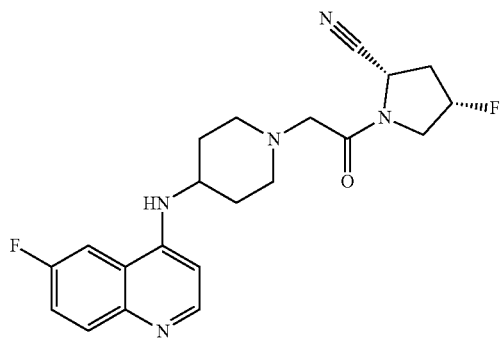 [SMILES: N#C[C@@H]1C[C@H](F)CN1C(=O)CN1CCC(Nc2ccnc3ccc(F)cc23)CC1]
(2S,4S)-4-fluoro-1-[2-[4-[(6-fluoro-4-quinolyl)amino]-1-piperidyl]acetyl]pyrrolidine-2-carbonitrile

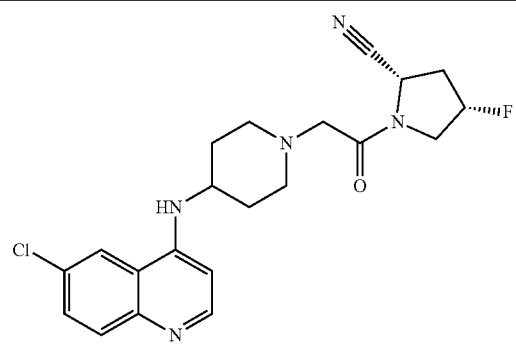

(2S,4S)-1-[2-[4-[(6-chloro-4-quinolyl)amino]-1-piperidyl]acetyl]-4-fluoro-pyrrolidine-2-carbonitrile

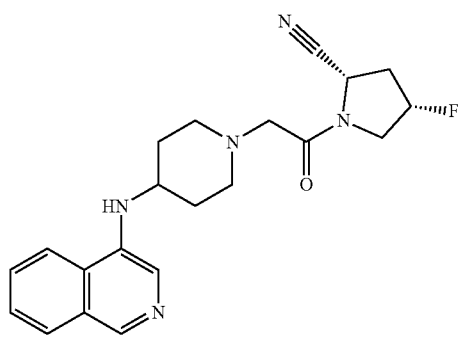 [SMILES: N#C[C@@H]1C[C@H](F)CN1C(=O)CN1CCC(Nc2cncc3ccccc23)CC1]

(2S,4S)-4-fluoro-1-[2-[4-(4-isoquinolylamino)-1-piperidyl]acetyl]pyrrolidine-2-carbonitrile

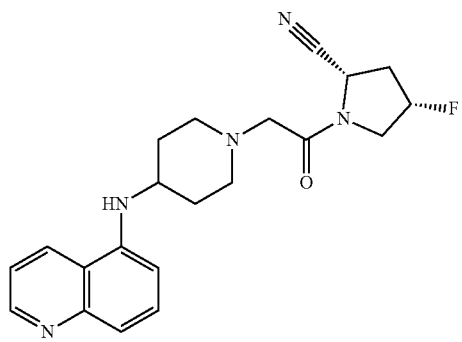 [SMILES: N#C[C@@H]1C[C@H](F)CN1C(=O)CN1CCC(Nc2cccc3ncccc23)CC1]

(2S,4S)-4-fluoro-1-[2-[4-(5-isoquinolylamino)-1-piperidyl]acetyl]pyrrolidine-2-carbonitrile

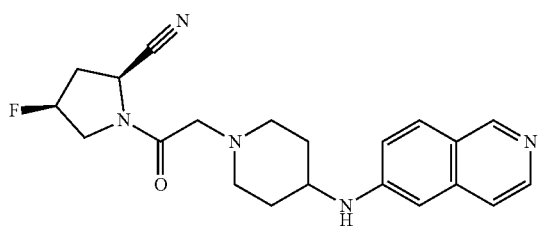 [SMILES: N#C[C@@H]1C[C@H](F)CN1C(=O)CN1CCC(Nc2ccc3cnccc3c2)CC1]

(2S,4S)-4-fluoro-1-[2-[4-(6-isoquinolylamino)-1-piperidyl]acetyl]pyrrolidine-2-carbonitrile

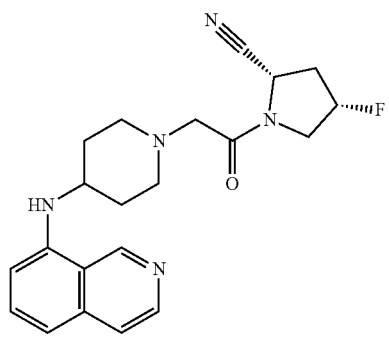 [SMILES: N#C[C@@H]1C[C@H](F)CN1C(=O)CN1CCC(Nc2cccc3ccncc23)CC1]

(2S,4S)-4-fluoro-1-[2-[4-(8-isoquinolylamino)-1-piperidyl]acetyl]pyrrolidine-2-carbonitrile

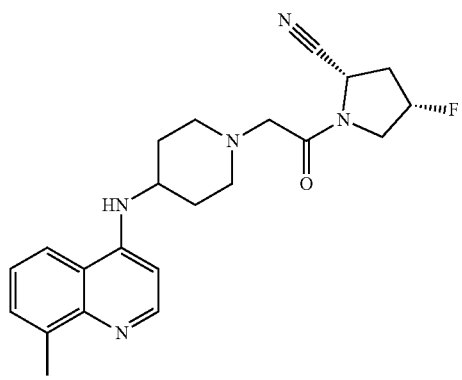 [SMILES: Cc1cccc2c(NC3CCN(CC(=O)N4C[C@@H](F)C[C@H]4C#N)CC3)ccnc12]
(2S,4S)-4-fluoro-1-[2-[4-[(8-methyl-4-quinolyl)amino]-1-piperidyl]acetyl]pyrrolidine-2-carbonitrile
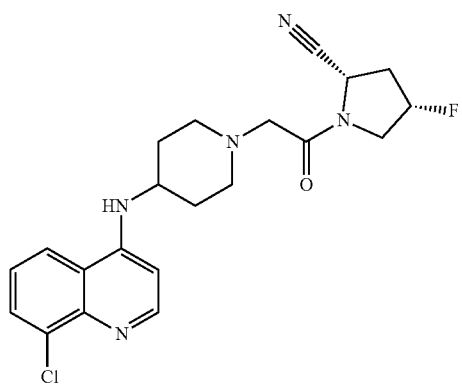
(2S,4S)-1-[2-[4-[(8-chloro-4-quinolyl)amino]-1-piperidyl]acetyl]-4-fluoro-pyrrolidine-2-carbonitrile
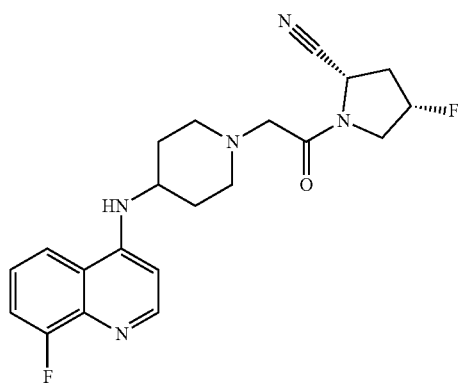 [SMILES: N#C[C@@H]1C[C@H](F)CN1C(=O)CN1CCC(Nc2ccnc3c(F)cccc23)CC1]
(2S,4S)-4-fluoro-1-[2-[4-[(8-fluoro-4-quinolyl)amino]-1-piperidyl]acetyl]pyrrolidine-2-carbonitrile
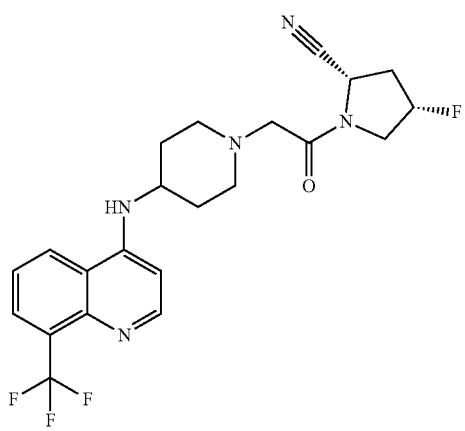 [SMILES: N#C[C@@H]1C[C@H](F)CN1C(=O)CN1CCC(Nc2ccnc3c(C(F)(F)F)cccc23)CC1]
(2S,4S)-4-fluoro-1-[2-[4-[[8-(trifluoromethyl)-4-quinolyl]amino]-1-piperidyl]acetyl]pyrrolidine-2-carbonitrile

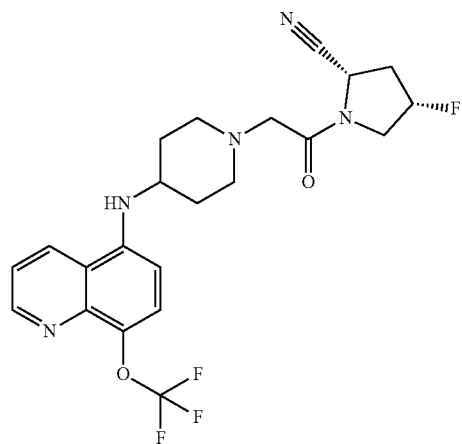 [SMILES: N#C[C@@H]1C[C@H](F)CN1C(=O)CN1CCC(Nc2ccc(OC(F)(F)F)c3ncccc23)CC1]
(2S,4S)-4-fluoro-1-[2-[4-[[8-(trifluoromethoxy)-5-quinolyl]amino]-1-piperidyl]acetyl]pyrrolidine-2-carbonitrile
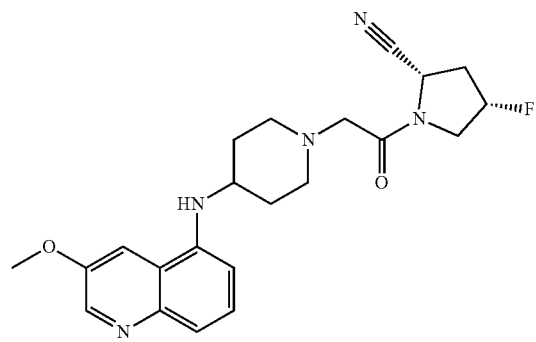 [SMILES: COc1cnc2cccc(NC3CCN(CC(=O)N4C[C@@H](F)C[C@H]4C#N)CC3)c2c1]
(2S,4S)-4-fluoro-1-[2-[4-[(3-methoxy-5-quinolyl)amino]-1-piperidyl]acetyl]pyrrolidine-2-carbonitrile
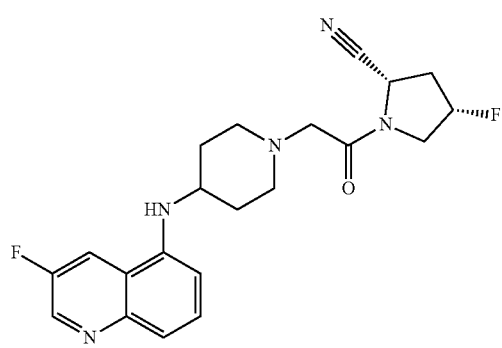 [SMILES: N#C[C@@H]1C[C@H](F)CN1C(=O)CN1CCC(Nc2cccc3ncc(F)cc23)CC1]
(2S,4S)-4-fluoro-1-[2-[4-[(3-fluoro-5-quinolyl)amino]-1-piperidyl]acetyl]pyrrolidine-2-carbonitrile
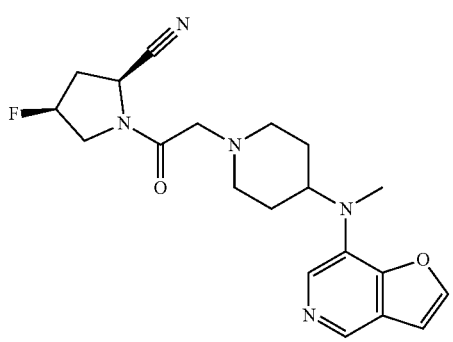 [SMILES: CN(c1cncc2ccoc12)C1CCN(CC(=O)N2C[C@@H](F)C[C@H]2C#N)CC1]
(2S,4S)-4-fluoro-1-[2-[4-[furo[3,2-c]pyridin-7-yl(methyl)amino]-1-piperidyl]acetyl]pyrrolidine-2-carbonitrile

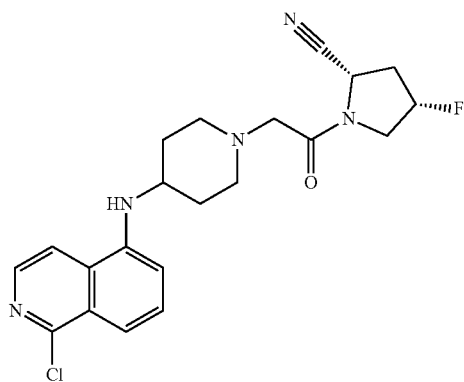 [SMILES: N#C[C@@H]1C[C@H](F)CN1C(=O)CN1CCC(Nc2cccc3c(Cl)nccc23)CC1]
(2S,4S)-1-[2-[4-[(1-chloro-5-isoquinolyl)amino]-1-piperidyl]acetyl]-4-fluoro-pyrrolidine-2-carbonitrile
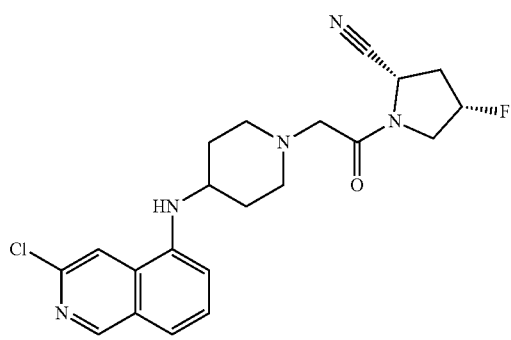 [SMILES: N#C[C@@H]1C[C@H](F)CN1C(=O)CN1CCC(Nc2cccc3cnc(Cl)cc23)CC1]
(2S,4S)-1-[2-[4-[(3-chloro-5-isoquinolyl)amino]-1-piperidyl]acetyl]-4-fluoro-pyrrolidine-2-carbonitrile
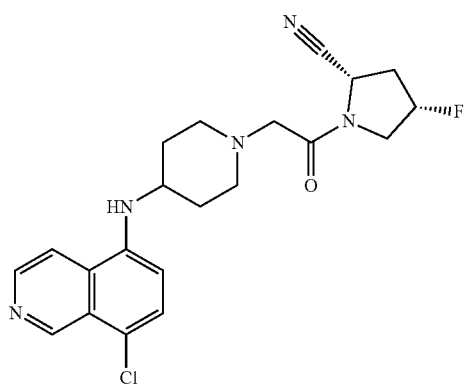 [SMILES: N#C[C@@H]1C[C@H](F)CN1C(=O)CN1CCC(Nc2ccc(Cl)c3cnccc23)CC1]
(2S,4S)-1-[2-[4-[(8-chloro-5-isoquinolyl)amino]-1-piperidyl]acetyl]-4-fluoro-pyrrolidine-2-carbonitrile
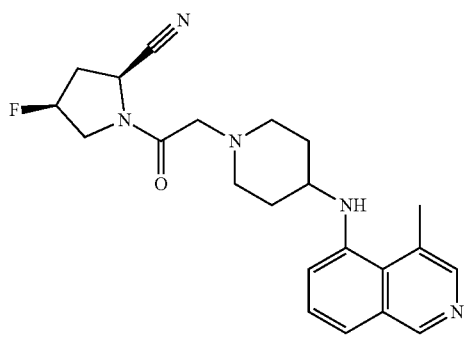 [SMILES: Cc1cncc2cccc(NC3CCN(CC(=O)N4C[C@@H](F)C[C@H]4C#N)CC3)c12]
(2S,4S)-4-fluoro-1-[2-[4-[(4-methyl-5-isoquinolyl)amino]-1-piperidyl]acetyl]pyrrolidine-2-carbonitrile

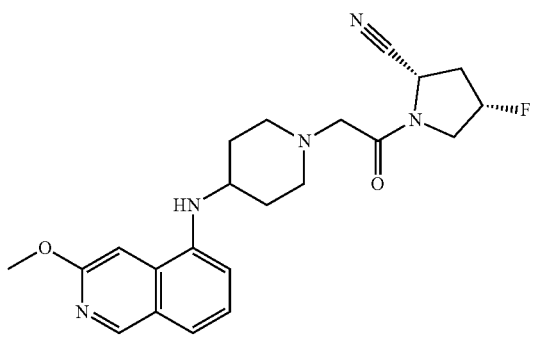 [SMILES: COc1cc2c(NC3CCN(CC(=O)N4C[C@@H](F)C[C@H]4C#N)CC3)cccc2cn1]
(2S,4S)-4-fluoro-1-[2-[4-[(3-methoxy-5-isoquinolyl)amino]-1-piperidyl]acetyl]pyrrolidine-2-carbonitrile
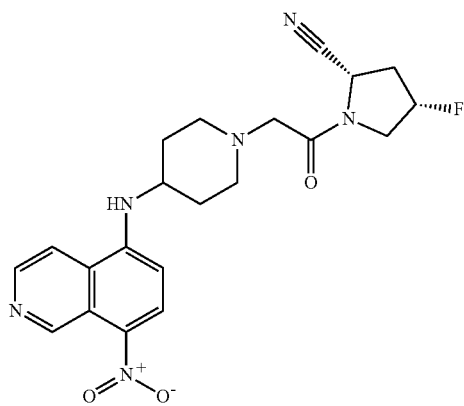
(2S,4S)-4-fluoro-1-[2-[4-[(8-nitro-5-isoquinolyl)amino]-1-piperidyl]acetyl]pyrrolidine-2-carbonitrile
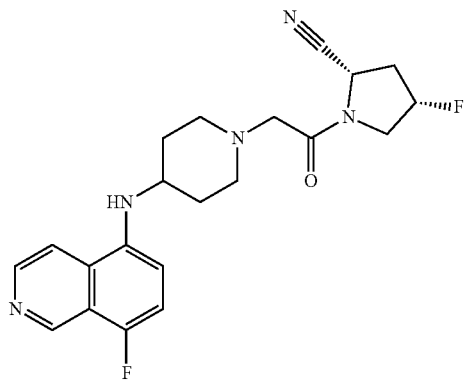 [SMILES: N#C[C@@H]1C[C@H](F)CN1C(=O)CN1CCC(Nc2ccc(F)c3cnccc23)CC1]
(2S,4S)-4-fluoro-1-[2-[4-[(8-fluoro-5-isoquinolyl)amino]-1-piperidyl]acetyl]pyrrolidine-2-carbonitrile
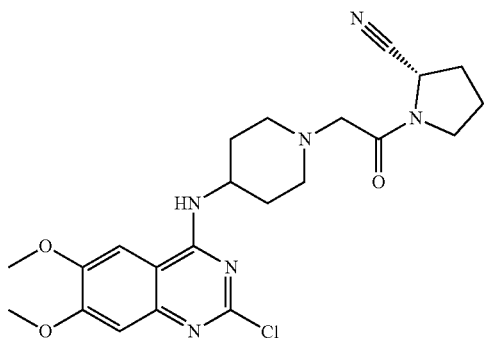 [SMILES: COc1cc2nc(Cl)nc(NC3CCN(CC(=O)N4CCC[C@H]4C#N)CC3)c2cc1OC]
(2S)-1-[2-[4-[(2-chloro-6,7-dimethoxy-quinazolin-4-yl)amino]-1-piperidyl]acetyl]pyrrolidine-2-carbonitrile

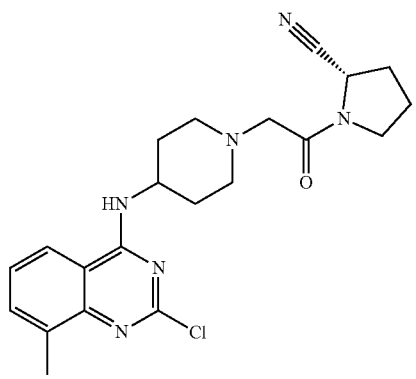 [SMILES: Cc1cccc2c(NC3CCN(CC(=O)N4CCC[C@H]4C#N)CC3)nc(Cl)nc12]

(2S)-1-[2-[4-[(2-chloro-8-methyl-quinazolin-4-yl)amino]-1-piperidyl]acetyl]pyrrolidine-2-carbonitrile

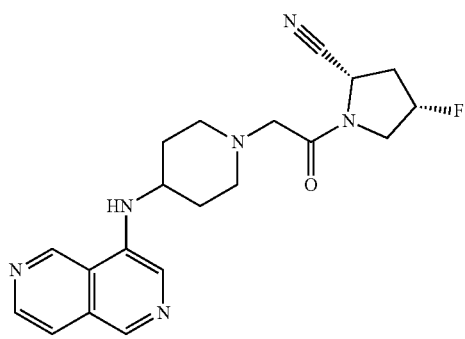 [SMILES: N#C[C@@H]1C[C@H](F)CN1C(=O)CN1CCC(Nc2cncc3ccncc23)CC1]

(2S,4S)-4-fluoro-1-[2-[4-(2,6-naphthyridin-4-ylamino)-1-piperidyl]acetyl]pyrrolidine-2-carbonitrile

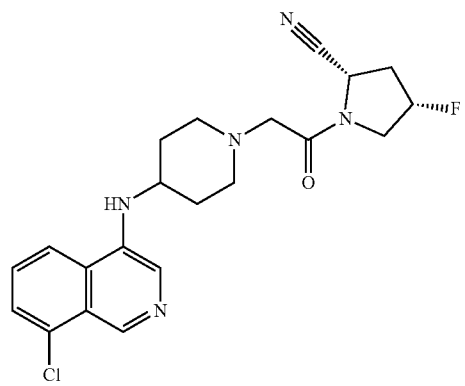 [SMILES: N#C[C@@H]1C[C@H](F)CN1C(=O)CN1CCC(Nc2cncc3c(Cl)cccc23)CC1]

(2S,4S)-1-[2-[4-[(8-chloro-4-isoquinolyl)amino]-1-piperidyl]acetyl]-4-fluoro-pyrrolidine-2-carbonitrile

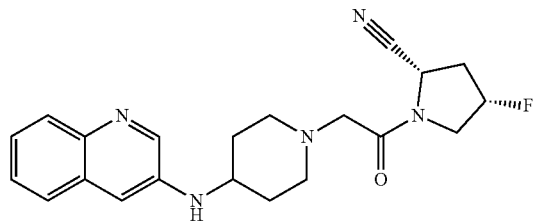 [SMILES: N#C[C@@H]1C[C@H](F)CN1C(=O)CN1CCC(Nc2cnc3ccccc3c2)CC1]

(2S,4S)-4-fluoro-1-[2-[4-(3-quinolylamino)-1-piperidyl]acetyl]pyrrolidine-2-carbonitrile

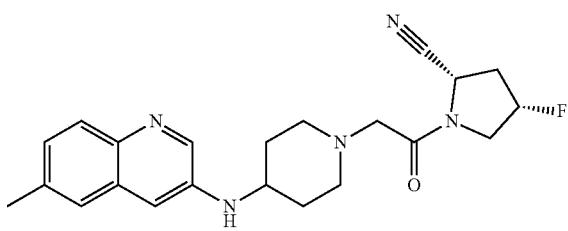 [SMILES: Cc1ccc2ncc(NC3CCN(CC(=O)N4C[C@@H](F)C[C@H]4C#N)CC3)cc2c1]

(2S,4S)-4-fluoro-1-[2-[4-[(6-methyl-3-quinolyl)amino]-1-piperidyl]acetyl]pyrrolidine-2-carbonitrile -continued

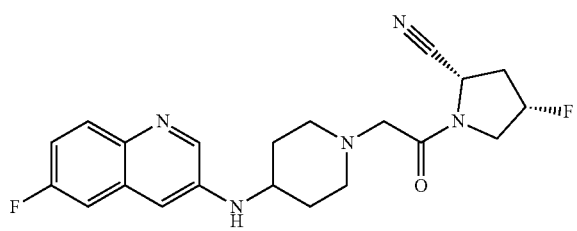 [SMILES: N#C[C@@H]1C[C@H](F)CN1C(=O)CN1CCC(Nc2cnc3ccc(F)cc3c2)CC1]

(2S,4S)-4-fluoro-1-[2-[4-[(6-fluoro-3-quinolyl)amino]-1-piperidyl]acetyl]pyrrolidine-2-carbonitrile

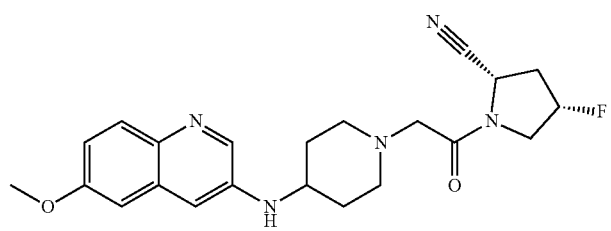 [SMILES: COc1ccc2ncc(NC3CCN(CC(=O)N4C[C@@H](F)C[C@H]4C#N)CC3)cc2c1]

(2S,4S)-4-fluoro-1-[2-[4-[(6-methoxy-3-quinolyl)amino]-1-piperidyl]acetyl]pyrrolidine-2-carbonitrile

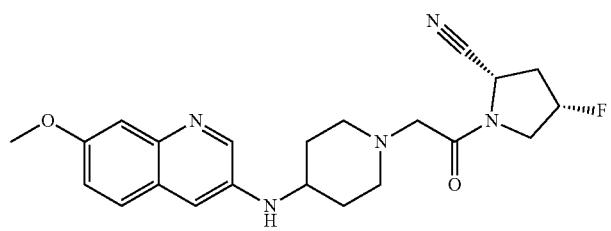 [SMILES: COc1ccc2cc(NC3CCN(CC(=O)N4C[C@@H](F)C[C@H]4C#N)CC3)cnc2c1]

(2S,4S)-4-fluoro-1-[2-[4-[(7-methoxy-3-quinolyl)amino]-1-piperidyl]acetyl]pyrrolidine-2-carbonitrile

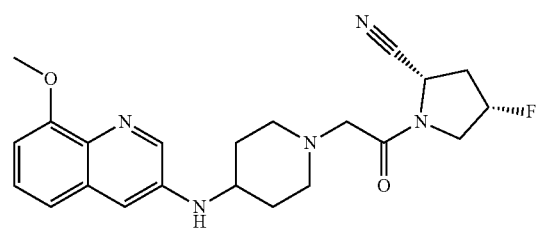 [SMILES: COc1cccc2cc(NC3CCN(CC(=O)N4C[C@@H](F)C[C@H]4C#N)CC3)cnc12]

(2S,4S)-4-fluoro-1-[2-[4-[(8-methoxy-3-quinolyl)amino]-1-piperidyl]acetyl]pyrrolidine-2-carbonitrile

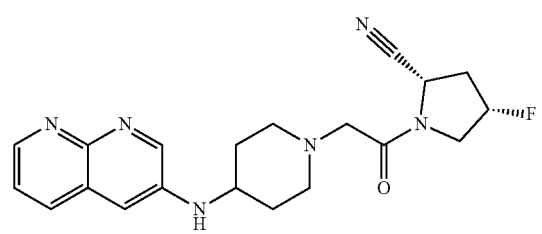 [SMILES: N#C[C@@H]1C[C@H](F)CN1C(=O)CN1CCC(Nc2cnc3ncccc3c2)CC1]

(2S,4S)-4-fluoro-1-[2-[4-(1,8-naphthyridin-3-ylamino)-1-piperidyl]acetyl]pyrrolidine-2-carbonitrile

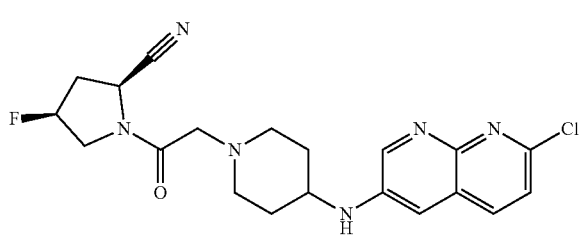 [SMILES: N#C[C@@H]1C[C@H](F)CN1C(=O)CN1CCC(Nc2cnc3nc(Cl)ccc3c2)CC1]

(2S,4S)-1-[2-[4-[(7-chloro-1,8-naphthyridin-3-yl)amino]-1-piperidyl]acetyl]-4-fluoro-pyrrolidine-2-carbonitrile -continued
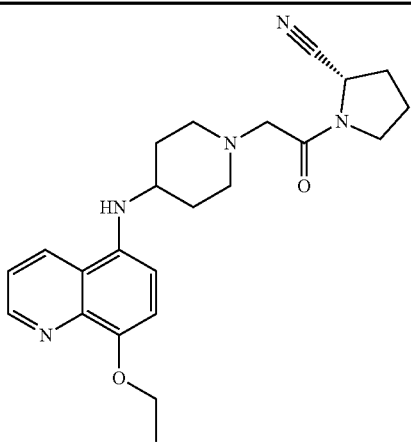
(2S)-1-[2-[4-[(8-ethoxy-5-quinolyl)amino]-1-piperidyl]acetyl]pyrrolidine-2-carbonitrile
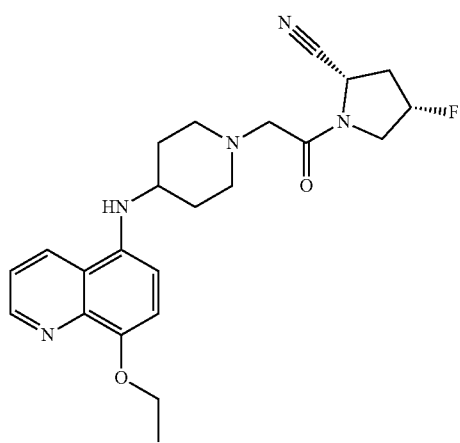 [SMILES: CCOc1ccc(NC2CCN(CC(=O)N3C[C@@H](F)C[C@H]3C#N)CC2)c2cccnc12]
(2S,4S)-1-[2-[4-[(8-ethoxy-5-quinolyl)amino]-1-piperidyl]acetyl]-4-fluoro-pyrrolidine-2-carbonitrile
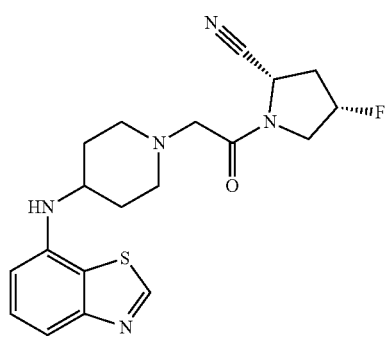 [SMILES: N#C[C@@H]1C[C@H](F)CN1C(=O)CN1CCC(Nc2cccc3ncsc23)CC1]
(2S,4S)-1-[2-[4-(1,3-benzothiazol-7-ylamino)-1-piperidyl]acetyl]-4-fluoro-pyrrolidine-2-carbonitrile
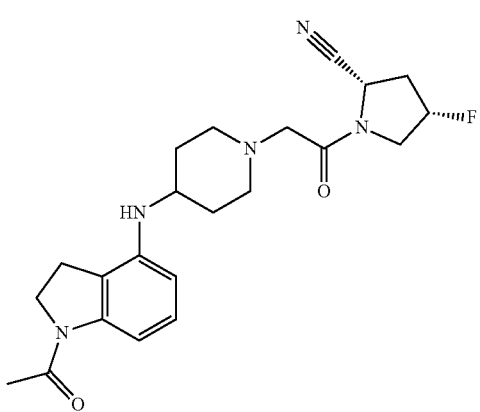 [SMILES: CC(=O)N1CCc2c(NC3CCN(CC(=O)N4C[C@@H](F)C[C@H]4C#N)CC3)cccc21]
(2S,4S)-1-[2-[4-[(1-acetylindolin-4-yl)amino]-1-piperidyl]acetyl]-4-fluoro-pyrrolidine-2-carbonitrile -continued

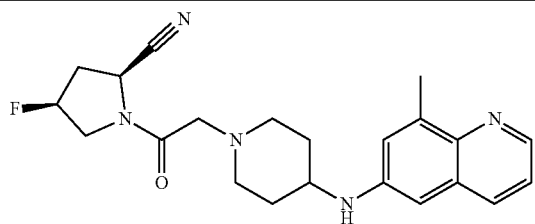

(2S,4S)-4-fluoro-1-[2-[4-[(8-methyl-6-quinolyl)amino]-1-piperidyl]acetyl]pyrrolidine-2-carbonitrile

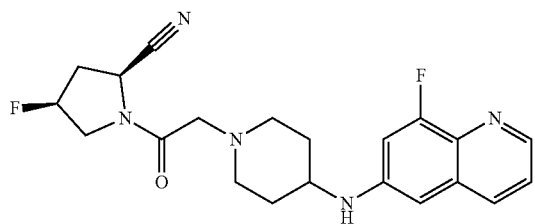 [SMILES: N#C[C@@H]1C[C@H](F)CN1C(=O)CN1CCC(Nc2cc(F)c3ncccc3c2)CC1]

(2S,4S)-4-fluoro-1-[2-[4-[(8-fluoro-6-quinolyl)amino]-1-piperidyl]acetyl]pyrrolidine-2-carbonitrile

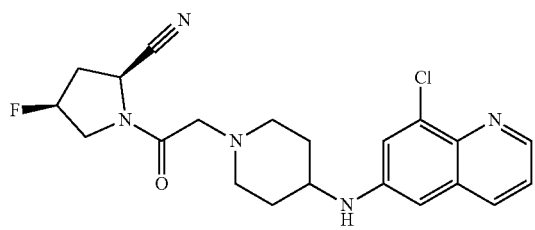 [SMILES: N#C[C@@H]1C[C@H](F)CN1C(=O)CN1CCC(Nc2cc(Cl)c3ncccc3c2)CC1]

(2S,4S)-1-[2-[4-[(8-chloro-6-quinolyl)amino]-1-piperidyl]acetyl]-4-fluoro-pyrrolidine-2-carbonitrile

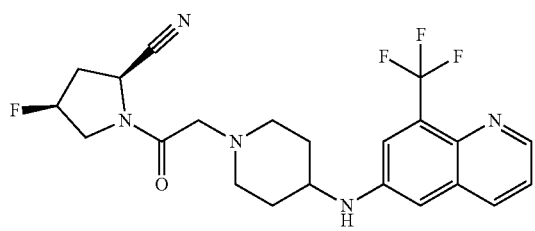 [SMILES: N#C[C@@H]1C[C@H](F)CN1C(=O)CN1CCC(Nc2cc(C(F)(F)F)c3ncccc3c2)CC1]

(2S,4S)-4-fluoro-1-[2-[4-[[8-(trifluoromethyl)-6-quinolyl]amino]-1-piperidyl]acetyl]pyrrolidine-2-carbonitrile

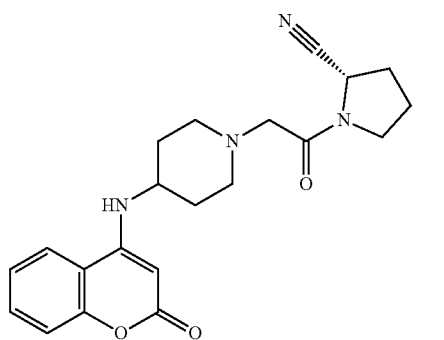 [SMILES: N#C[C@@H]1CCCN1C(=O)CN1CCC(Nc2cc(=O)oc3ccccc23)CC1]

(2S)-1-[2-[4-[(2-oxochromen-4-yl)amino]-1-piperidyl]acetyl]pyrrolidine-2-carbonitrile

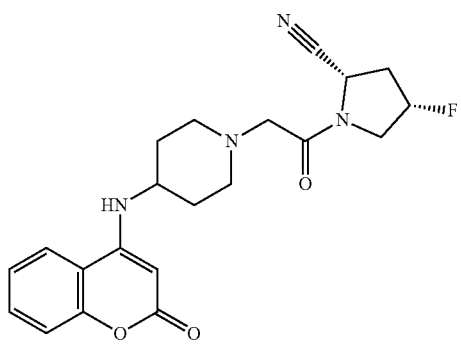 [SMILES: N#C[C@@H]1C[C@H](F)CN1C(=O)CN1CCC(Nc2cc(=O)oc3ccccc23)CC1]

(2S,4S)-4-fluoro-1-[2-[4-[(2-oxochromen-4-yl)amino]-1-piperidyl]acetyl]pyrrolidine-2-carbonitrile

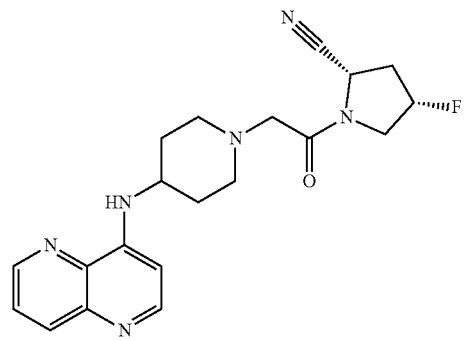 [SMILES: N#C[C@@H]1C[C@H](F)CN1C(=O)CN1CCC(Nc2ccnc3cccnc23)CC1]

(2S,4S)-4-fluoro-1-[2-[4-(1,5-naphthyridin-4-ylamino)-1-piperidyl]acetyl]pyrrolidine-2-carbonitrile

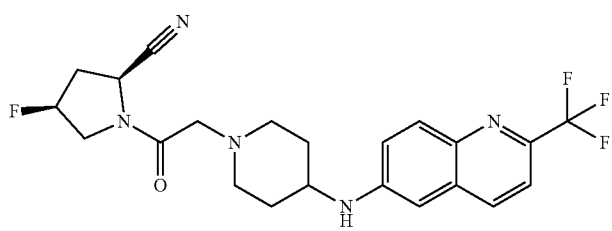 [SMILES: N#C[C@@H]1C[C@H](F)CN1C(=O)CN1CCC(Nc2ccc3nc(C(F)(F)F)ccc3c2)CC1]

(2S,4S)-4-fluoro-1-[2-[4-[[2-(trifluoromethyl)-6-quinolyl]amino]-1-piperidyl]acetyl]pyrrolidine-2-carbonitrile

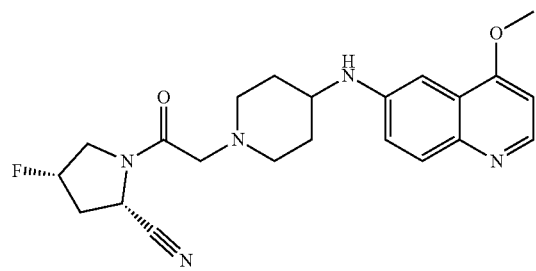 [SMILES: COc1ccnc2ccc(NC3CCN(CC(=O)N4C[C@@H](F)C[C@H]4C#N)CC3)cc12]

(2S,4S)-4-fluoro-1-[2-[4-[(4-methoxy-6-quinolyl)amino]-1-piperidyl]acetyl]pyrrolidine-2-carbonitrile

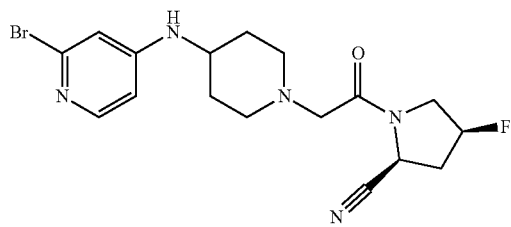 [SMILES: N#C[C@@H]1C[C@H](F)CN1C(=O)CN1CCC(Nc2ccnc(Br)c2)CC1]

(2S,4S)-1-[2-[4-[(2-bromo-4-pyridyl)amino]-1-piperidyl]acetyl]-4-fluoro-pyrrolidine-2-carbonitrile

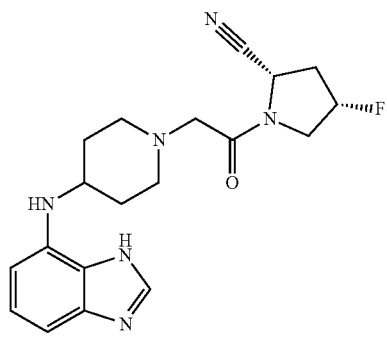 [SMILES: N#C[C@@H]1C[C@H](F)CN1C(=O)CN1CCC(Nc2cccc3nc[nH]c23)CC1]

(2S,4S)-1-[2-[4-(3H-benzimidazol-4-ylamino)-1-piperidyl]acetyl]-4-fluoro-pyrrolidine-2-carbonitrile -continued

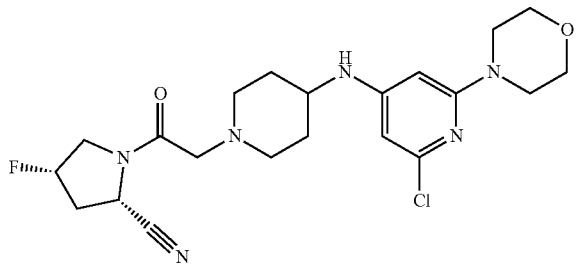 [SMILES: N#C[C@@H]1C[C@H](F)CN1C(=O)CN1CCC(Nc2cc(Cl)nc(N3CCOCC3)c2)CC1]

(2S,4S)-1-[2-[4-[(2-chloro-6-morpholino-4-pyridyl)amino]-1-piperidyl]acetyl]-4-fluoro-pyrrolidine-2-carbonitrile

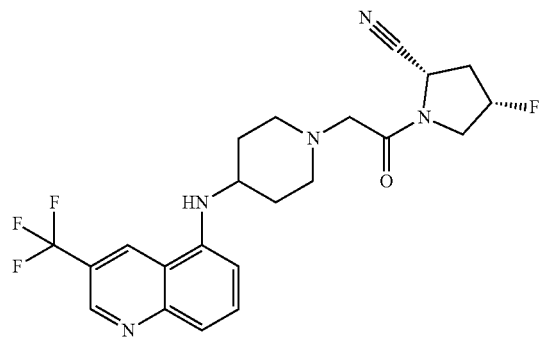 [SMILES: N#C[C@@H]1C[C@H](F)CN1C(=O)CN1CCC(Nc2cccc3ncc(C(F)(F)F)cc23)CC1]

(2S,4S)-4-fluoro-1-[2-[4-[[3-(trifluoromethyl)-5-quinolyl]amino]-1-piperidyl]acetyl]pyrrolidine-2-carbonitrile

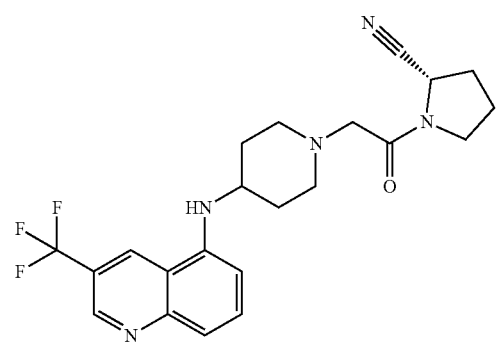 [SMILES: N#C[C@@H]1CCCN1C(=O)CN1CCC(Nc2cccc3ncc(C(F)(F)F)cc23)CC1]

(2S)-1-[2-[4-[[3-(trifluoromethyl)-5-quinolyl]amino]-1-piperidyl]acetyl]pyrrolidine-2-carbonitrile

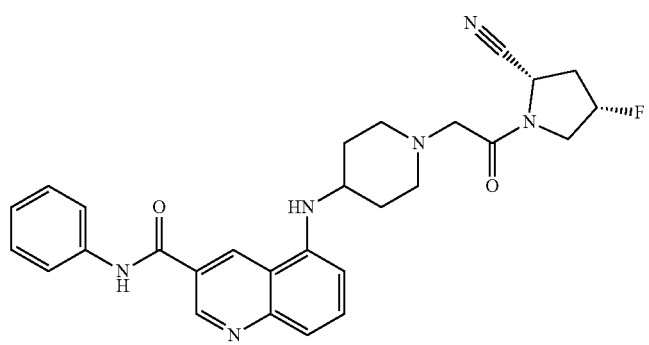 [SMILES: N#C[C@@H]1C[C@H](F)CN1C(=O)CN1CCC(Nc2cccc3ncc(C(=O)Nc4ccccc4)cc23)CC1]

5-[[1-[2-oxo-2-[(2S,4S)-2-cyano-4-fluoro-pyrrolidin-1-yl]ethyl]-4-piperidyl]amino]-N-phenyl-quinoline-3-carboxamide

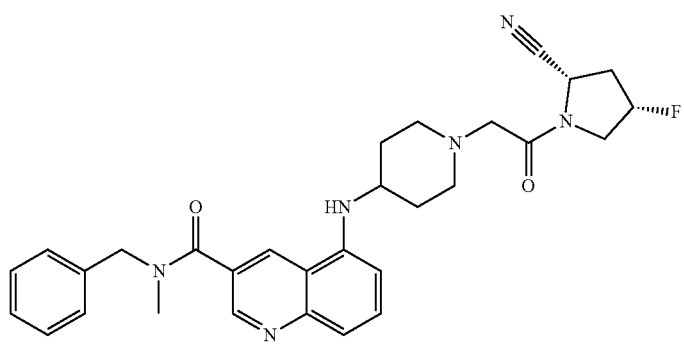 [SMILES: CN(Cc1ccccc1)C(=O)c1cnc2cccc(NC3CCN(CC(=O)N4C[C@@H](F)C[C@H]4C#N)CC3)c2c1]

N-benzyl-N-methyl-5-[[1-[2-oxo-2-[(2S,4S)-2-cyano-4-fluoro-pyrrolidin-1-yl]ethyl]-4-piperidyl]amino]quinoline-3-carboxamide

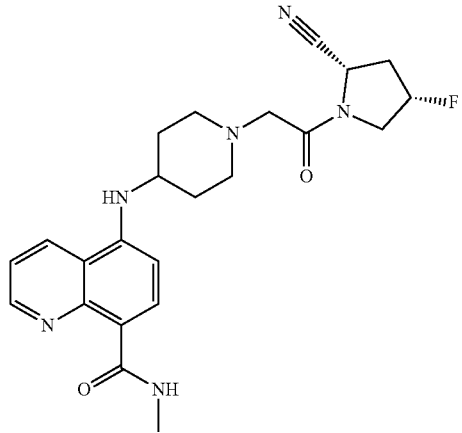 [SMILES: CNC(=O)c1ccc(NC2CCN(CC(=O)N3C[C@@H](F)C[C@H]3C#N)CC2)c2cccnc12]
N-methyl-5-[[1-[2-oxo-2-[(2S,4S)-2-cyano-4-fluoro-pyrrolidin-1-yl]ethyl]-4-piperidyl]amino]quinoline-8-carboxamide
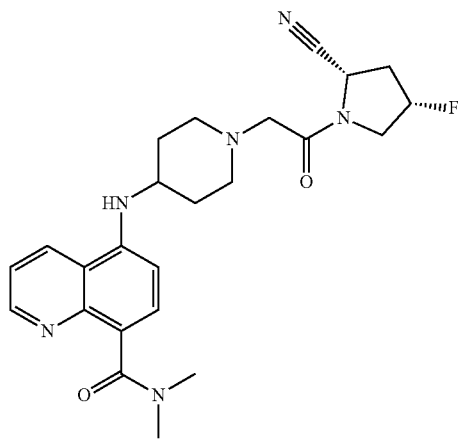 [SMILES: CN(C)C(=O)c1ccc(NC2CCN(CC(=O)N3C[C@@H](F)C[C@H]3C#N)CC2)c2cccnc12]
N,N-dimethyl-5-[[1-[2-oxo-2-[(2S,4S)-2-cyano-4-fluoro-pyrrolidin-1-yl]ethyl]-4-piperidyl]amino]quinoline-8-carboxamide
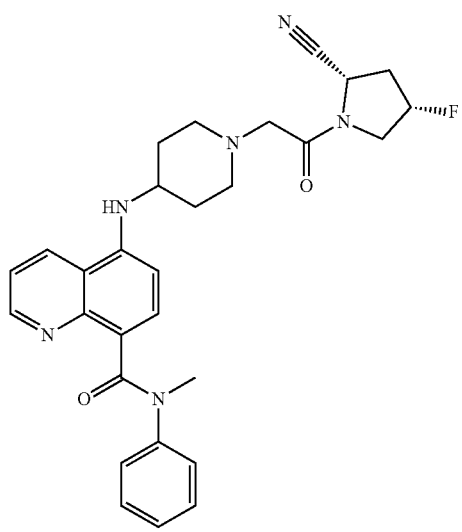 [SMILES: CN(C(=O)c1ccc(NC2CCN(CC(=O)N3C[C@@H](F)C[C@H]3C#N)CC2)c2cccnc12)c1ccccc1]
N-methyl-5-[[1-[2-oxo-2-[(2S,4S)-2-cyano-4-fluoro-pyrrolidin-1-yl]ethyl]-4-piperidyl]amino]-N-phenyl-quinoline-8-carboxamide

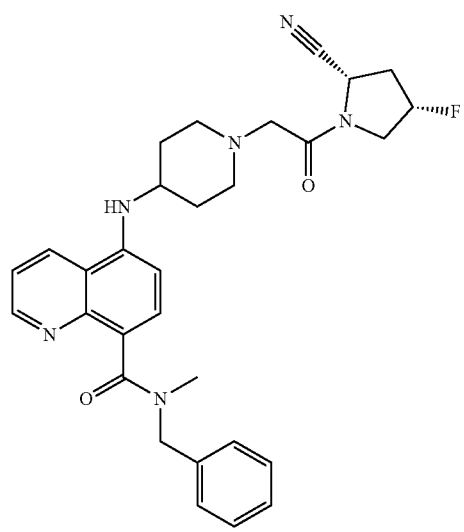 [SMILES: CN(Cc1ccccc1)C(=O)c1ccc(NC2CCN(CC(=O)N3C[C@@H](F)C[C@H]3C#N)CC2)c2cccnc12]
N-benzyl-N-methyl-5-[[1-[2-oxo-2-[(2S,4S)-2-cyano-4-fluoro-pyrrolidin-1-yl]ethyl]-4-piperidyl]amino]quinoline-8-carboxamide
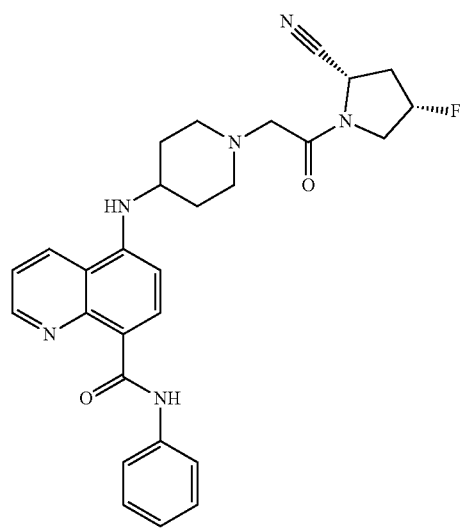 [SMILES: N#C[C@@H]1C[C@H](F)CN1C(=O)CN1CCC(Nc2ccc(C(=O)Nc3ccccc3)c3ncccc23)CC1]
5-[[1-[2-oxo-2-[(2S,4S)-2-cyano-4-fluoro-pyrrolidin-1-yl]ethyl]-4-piperidyl]amino]-N-phenyl-quinoline-8-carboxamide
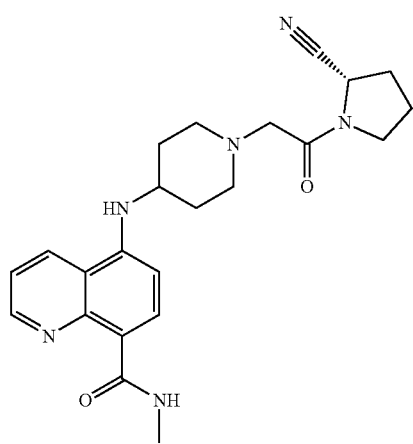 [SMILES: CNC(=O)c1ccc(NC2CCN(CC(=O)N3CCC[C@H]3C#N)CC2)c2cccnc12]
N-methyl-5-[[1-[2-oxo-2-[(2S)-2-cyanopyrrolidin-1-yl]ethyl]-4-piperidyl]amino]quinoline-8-carboxamide

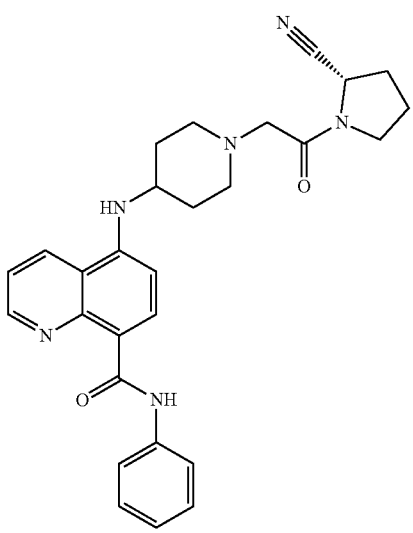 [SMILES: N#C[C@@H]1CCCN1C(=O)CN1CCC(Nc2ccc(C(=O)Nc3ccccc3)c3ncccc23)CC1]
5-[[1-[2-oxo-2-[(2S)-2-cyanopyrrolidin-1-yl]ethyl]-4-piperidyl]amino]-N-phenyl-quinoline-8-carboxamide
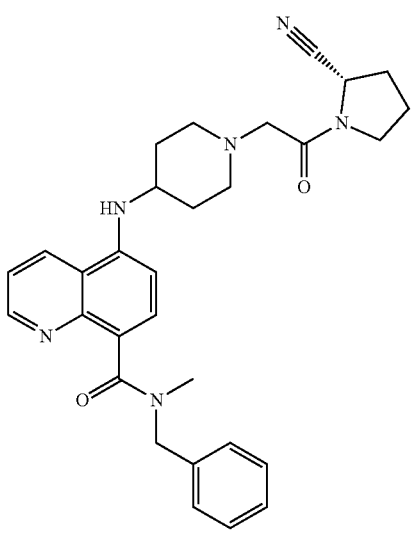 [SMILES: CN(Cc1ccccc1)C(=O)c1ccc(NC2CCN(CC(=O)N3CCC[C@H]3C#N)CC2)c2cccnc12]
N-benzyl-N-methyl-5-[[1-[2-oxo-2-[(2S)-2-cyanopyrrolidin-1-yl]ethyl]-4-piperidyl]amino]quinoline-8-carboxamide
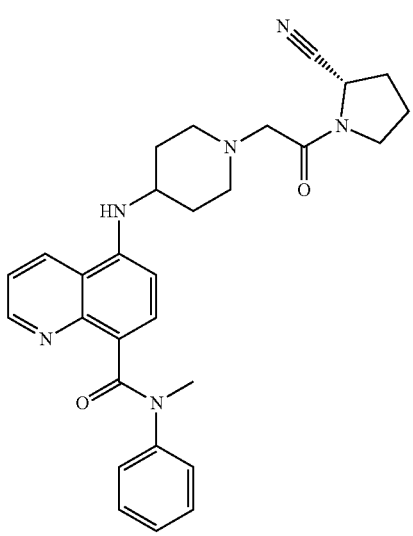 [SMILES: CN(C(=O)c1ccc(NC2CCN(CC(=O)N3CCC[C@H]3C#N)CC2)c2cccnc12)c1ccccc1]
N-methyl-5-[[1-[2-oxo-2-[(2S)-2-cyanopyrrolidin-1-yl]ethyl]-4-piperidyl]amino]-N-phenyl-quinoline-8-carboxamide

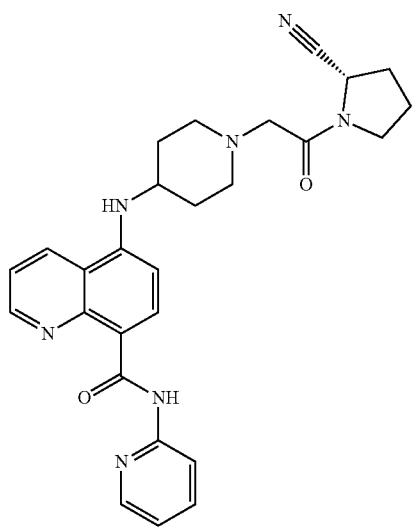 [SMILES: N#C[C@@H]1CCCN1C(=O)CN1CCC(Nc2ccc(C(=O)Nc3ccccn3)c3ncccc23)CC1]
5-[[1-[2-oxo-2-[(2S)-2-cyanopyrrolidin-1-yl]ethyl]-4-piperidyl]amino]-N-(2-pyridyl)quinoline-8-carboxamide
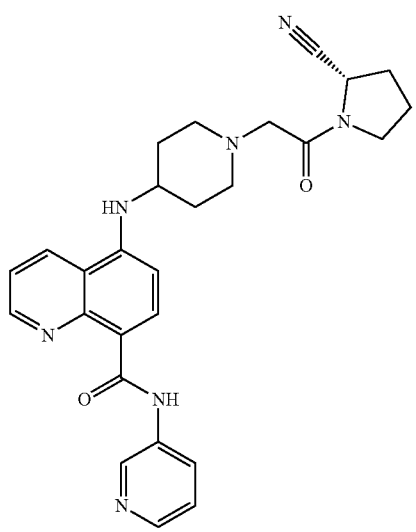 [SMILES: N#C[C@@H]1CCCN1C(=O)CN1CCC(Nc2ccc(C(=O)Nc3cccnc3)c3ncccc23)CC1]
5-[[1-[2-oxo-2-[(2S)-2-cyanopyrrolidin-1-yl]ethyl]-4-piperidyl]amino]-N-(3-pyridyl)quinoline-8-carboxamide
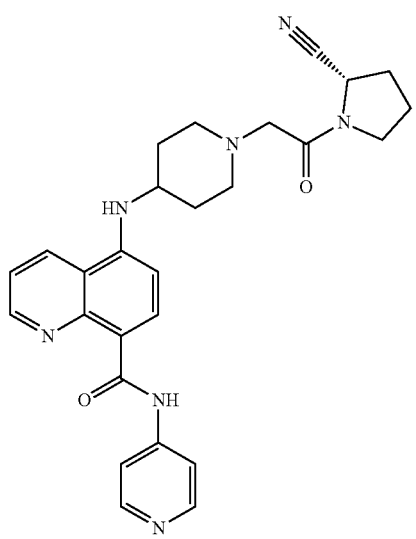 [SMILES: N#C[C@@H]1CCCN1C(=O)CN1CCC(Nc2ccc(C(=O)Nc3ccncc3)c3ncccc23)CC1]
5-[[1-[2-oxo-2-[(2S)-2-cyanopyrrolidin-1-yl]ethyl]-4-piperidyl]amino]-N-(4-pyridyl)quinoline-8-carboxamide

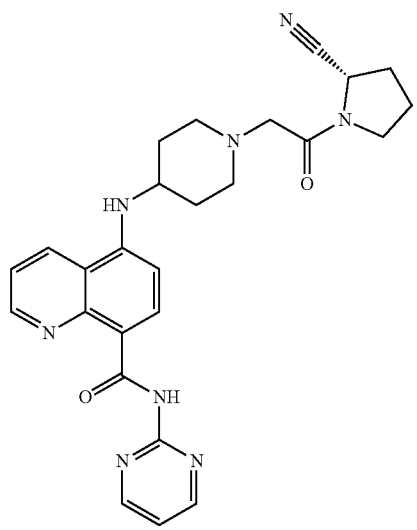 [SMILES: N#C[C@@H]1CCCN1C(=O)CN1CCC(Nc2ccc(C(=O)Nc3ncccn3)c3ncccc23)CC1]
5-[[1-[2-oxo-2-[(2S)-2-cyanopyrrolidin-1-yl]ethyl]-4-piperidyl]amino]-N-pyrimidin-2-yl-quinoline-8-carboxamide
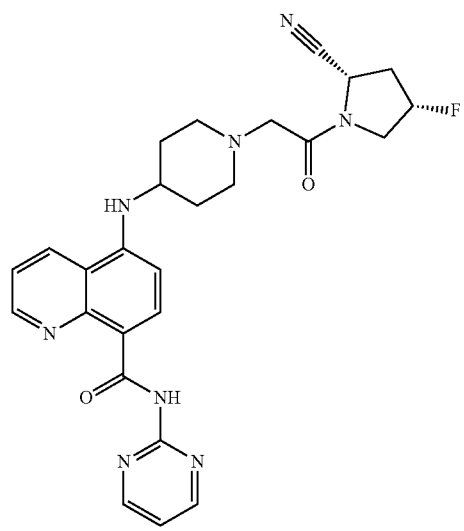 [SMILES: N#C[C@@H]1C[C@H](F)CN1C(=O)CN1CCC(Nc2ccc(C(=O)Nc3ncccn3)c3ncccc23)CC1]
5-[[1-[2-oxo-2-[(2S,4S)-2-cyano-4-fluoro-pyrrolidin-1-yl]ethyl]-4-piperidyl]amino]-N-pyrimidin-2-yl-quinoline-8-carboxamide
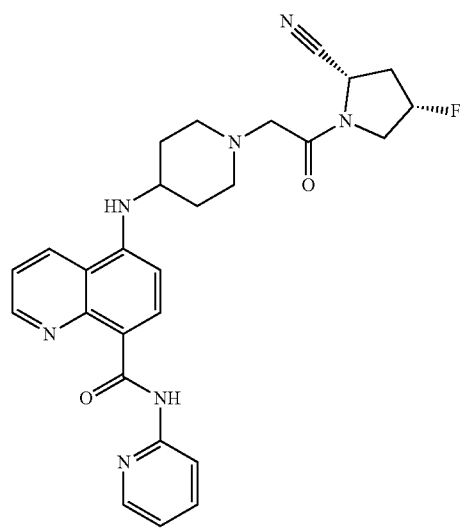 [SMILES: N#C[C@@H]1C[C@H](F)CN1C(=O)CN1CCC(Nc2ccc(C(=O)Nc3ccccn3)c3ncccc23)CC1]
5-[[1-[2-oxo-2-[(2S,4S)-2-cyano-4-fluoro-pyrrolidin-1-yl]ethyl]-4-piperidyl]amino]-N-(2-pyridyl)quinoline-8-carboxamide -continued
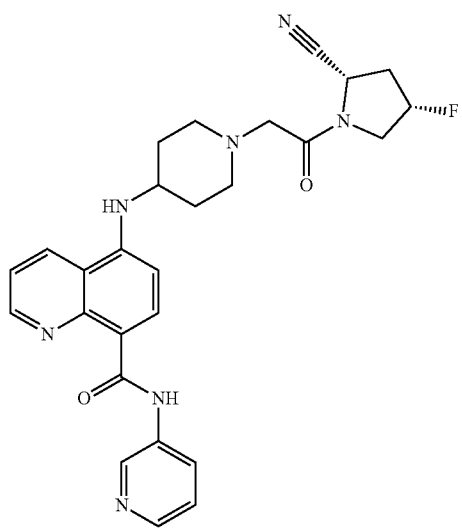 [SMILES: N#C[C@@H]1C[C@H](F)CN1C(=O)CN1CCC(Nc2ccc(C(=O)Nc3cccnc3)c3ncccc23)CC1]
5-[[1-[2-oxo-2-[(2S,4S)-2-cyano-4-fluoro-pyrrolidin-1-yl]ethyl]-4-piperidyl]amino]-N-(3-pyridyl)quinoline-8-carboxamide
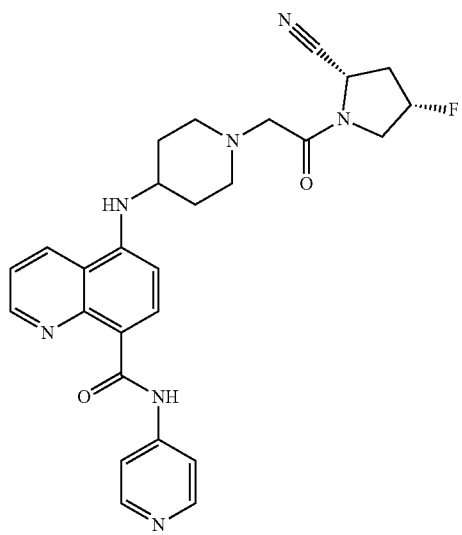 [SMILES: N#C[C@@H]1C[C@H](F)CN1C(=O)CN1CCC(Nc2ccc(C(=O)Nc3ccncc3)c3ncccc23)CC1]
5-[[1-[2-oxo-2-[(2S,4S)-2-cyano-4-fluoro-pyrrolidin-1-yl]ethyl]-4-piperidyl]amino]-N-(4-pyridyl)quinoline-8-carboxamide
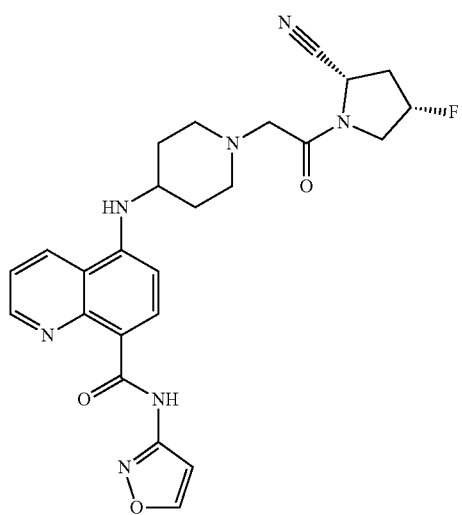 [SMILES: N#C[C@@H]1C[C@H](F)CN1C(=O)CN1CCC(Nc2ccc(C(=O)Nc3ccon3)c3ncccc23)CC1]
N-isoxazol-3-yl-5-[[1-[2-oxo-2-[(2S,4S)-2-cyano-4-fluoro-pyrrolidin-1-yl]ethyl]-4-piperidyl]amino]quinoline-8-carboxamide

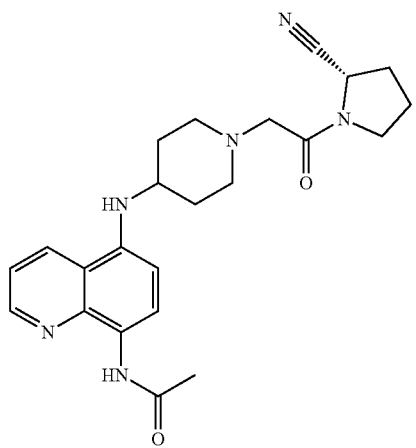 [SMILES: CC(=O)Nc1ccc(NC2CCN(CC(=O)N3CCC[C@H]3C#N)CC2)c2cccnc12]
N-[5-[[1-[2-oxo-2-[(2S)-2-cyanopyrrolidin-1-yl]ethyl]-4-piperidyl]amino]-8-quinolyl]acetamide
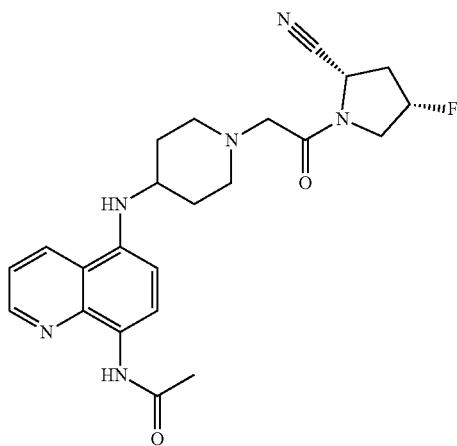 [SMILES: CC(=O)Nc1ccc(NC2CCN(CC(=O)N3C[C@@H](F)C[C@H]3C#N)CC2)c2cccnc12]
N-[5-[[1-[2-oxo-2-[(2S,4S)-2-cyano-4-fluoropyrrolidin-1-yl]ethyl]-4-piperidyl]amino]-8-quinolyl]acetamide
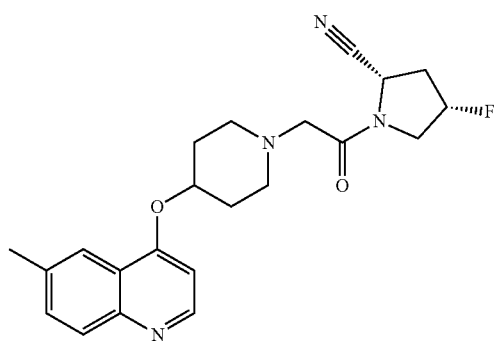 [SMILES: Cc1ccc2nccc(OC3CCN(CC(=O)N4C[C@@H](F)C[C@H]4C#N)CC3)c2c1]
(2S,4S)-4-fluoro-1-[2-[4-[(6-methyl-4-quinolyl)oxy]-1-piperidyl]acetyl]pyrrolidine-2-carbonitrile
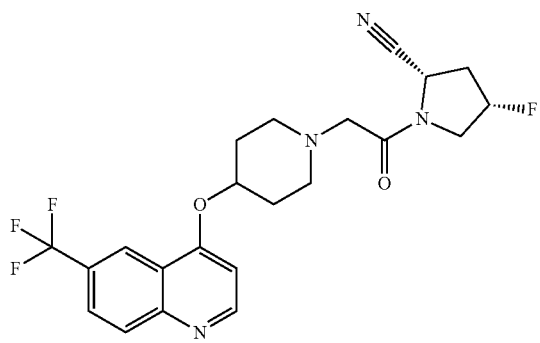 [SMILES: N#C[C@@H]1C[C@H](F)CN1C(=O)CN1CCC(Oc2ccnc3ccc(C(F)(F)F)cc23)CC1]
(2S,4S)-4-fluoro-1-[2-[4-[[6-(trifluoromethyl)-4-quinolyl]oxy]-1-piperidyl]acetyl]pyrrolidine-2-carbonitrile

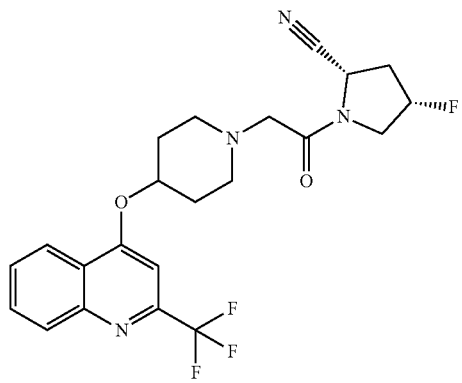 [SMILES: N#C[C@@H]1C[C@H](F)CN1C(=O)CN1CCC(Oc2cc(C(F)(F)F)nc3ccccc23)CC1]

(2S,4S)-4-fluoro-1-[2-[4-[[2-(trifluoromethyl)-4-quinolyl]oxy]-1-piperidyl]acetyl]pyrrolidine-2-carbonitrile

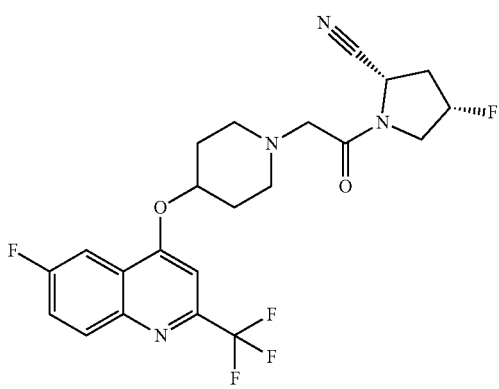 [SMILES: N#C[C@@H]1C[C@H](F)CN1C(=O)CN1CCC(Oc2cc(C(F)(F)F)nc3ccc(F)cc23)CC1]

(2S,4S)-4-fluoro-1-[2-[4-[[6-fluoro-2-(trifluoromethyl)-4-quinolyl]oxy]-1-piperidyl]acetyl]pyrrolidine-2-carbonitrile

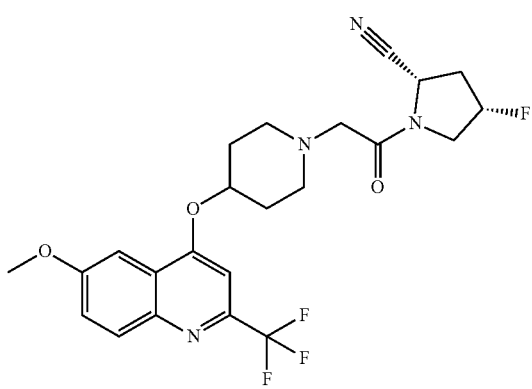 [SMILES: COc1ccc2nc(C(F)(F)F)cc(OC3CCN(CC(=O)N4C[C@@H](F)C[C@H]4C#N)CC3)c2c1]

(2S,4S)-4-fluoro-1-[2-[4-[[6-methoxy-2-(trifluoromethyl)-4-quinolyl]oxy]-1-piperidyl]acetyl]pyrrolidine-2-carbonitrile

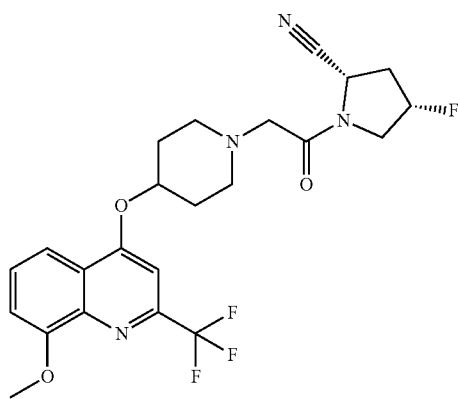 [SMILES: COc1cccc2c(OC3CCN(CC(=O)N4C[C@@H](F)C[C@H]4C#N)CC3)cc(C(F)(F)F)nc12]

(2S,4S)-4-fluoro-1-[2-[4-[[8-methoxy-2-(trifluoromethyl)-4-quinolyl]oxy]-1-piperidyl]acetyl]pyrrolidine-2-carbonitrile

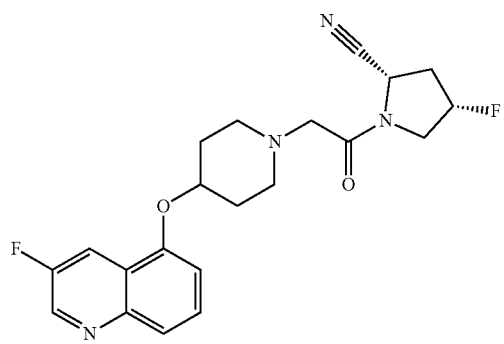 [SMILES: N#C[C@@H]1C[C@H](F)CN1C(=O)CN1CCC(Oc2cccc3ncc(F)cc23)CC1] (2S,4S)-4-fluoro-1-[2-[4-[(3-fluoro-5-quinolyl)oxy]-1-piperidyl]acetyl]pyrrolidine-2-carbonitrile
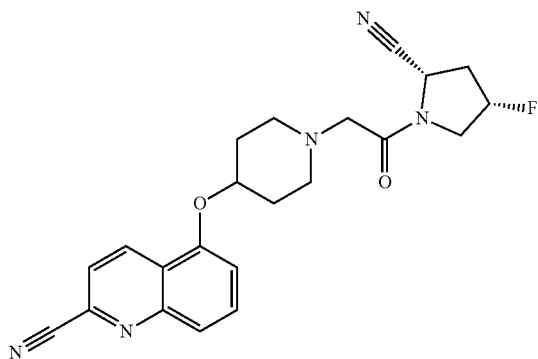 [SMILES: N#Cc1ccc2c(OC3CCN(CC(=O)N4C[C@@H](F)C[C@H]4C#N)CC3)cccc2n1] 5-[[1-(2-oxo-2-[(2S,4S)-2-cyano-4-fluoro-pyrrolidin-1-yl]ethyl]-4-piperidyl]oxy]quinoline-2-carbonitrile
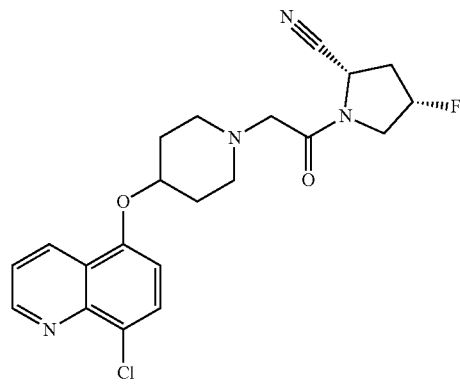 [SMILES: N#C[C@@H]1C[C@H](F)CN1C(=O)CN1CCC(Oc2ccc(Cl)c3ncccc23)CC1] (2S,4S)-1-[2-[4-[(8-chloro-5-quinolyl)oxy]-1-piperidyl]acetyl]-4-fluoro-pyrrolidine-2-carbonitrile
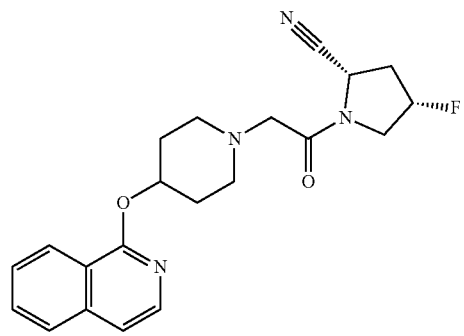 [SMILES: N#C[C@@H]1C[C@H](F)CN1C(=O)CN1CCC(Oc2nccc3ccccc23)CC1] (2S,4S)-4-fluoro-1-[2-(4-(1-isoquinolyloxy)-1-piperidyl]acetyl]pyrrolidine-2-carbonitrile

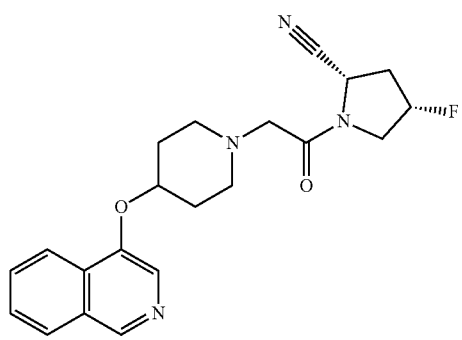 [SMILES: N#C[C@@H]1C[C@H](F)CN1C(=O)CN1CCC(Oc2cncc3ccccc23)CC1]
(2S,4S)-4-fluoro-1-[2-[4-[4-isoquinolyloxy)-1-piperidyl]acetyl]pyrrolidine-2-carbonitrile

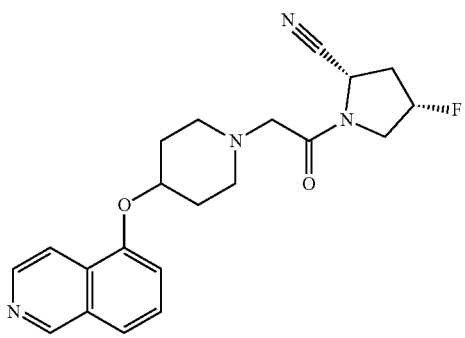 [SMILES: N#C[C@@H]1C[C@H](F)CN1C(=O)CN1CCC(Oc2cccc3cnccc23)CC1]
(2S,4S)-4-fluoro-1-[2-[4-(5-isoquinolyloxy)-1-piperidyl]acetyl]pyrrolidine-2-carbonitrile

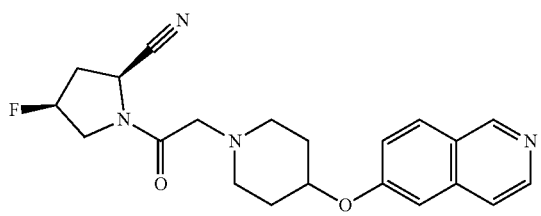 [SMILES: N#C[C@@H]1C[C@H](F)CN1C(=O)CN1CCC(Oc2ccc3cnccc3c2)CC1]
(2S,4S)-4-fluoro-1-[2-[4-(6-isoquinolyloxy)-1-piperidyl]acetyl]pyrrolidine-2-carbonitrile

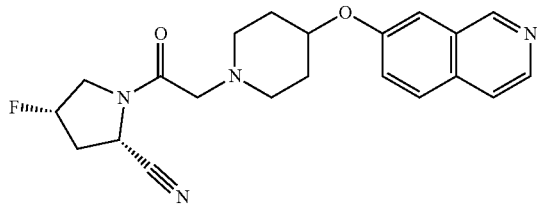 [SMILES: N#C[C@@H]1C[C@H](F)CN1C(=O)CN1CCC(Oc2ccc3ccncc3c2)CC1]
(2S,4S)-4-fluoro-1-[2-[4-(7-isoquinolyloxy)-1-piperidyl]acetyl]pyrrolidine-2-carbonitrile

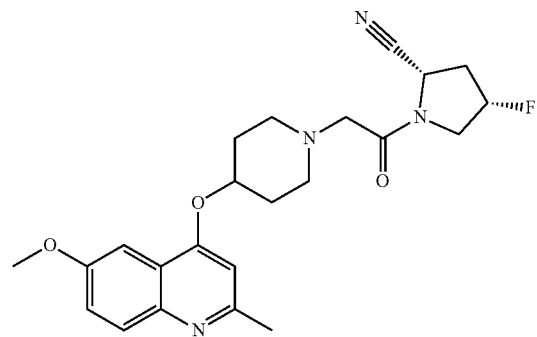 [SMILES: COc1ccc2nc(C)cc(OC3CCN(CC(=O)N4C[C@@H](F)C[C@H]4C#N)CC3)c2c1]
(2S,4S)-4-fluoro-1-[2-[4-[(6-methoxy-2-methyl-4-quinolyl)oxy]-1-piperidyl]acetyl]pyrrolidine-2-carbonitrile

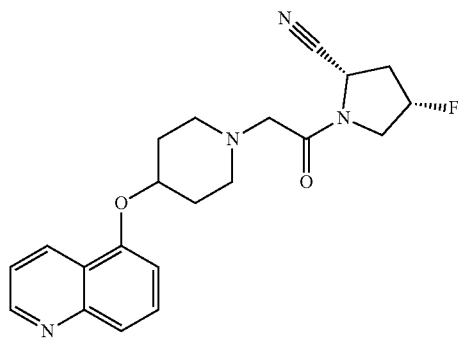 [SMILES: N#C[C@@H]1C[C@H](F)CN1C(=O)CN1CCC(Oc2cccc3ncccc23)CC1]
(2S,4S)-4-fluoro-1-[2-[4-(5-quinolyloxy)-1-piperidyl]acetyl]pyrrolidine-2-carbonitrile
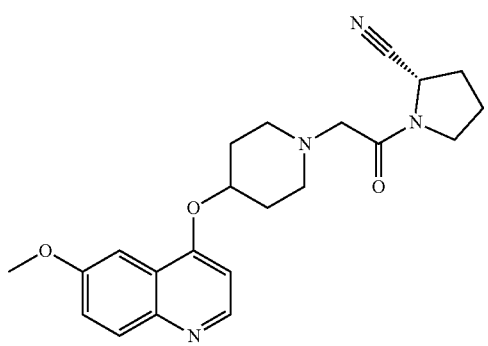 [SMILES: COc1ccc2nccc(OC3CCN(CC(=O)N4CCC[C@H]4C#N)CC3)c2c1]
(2S)-1-[2-[4-[(6-methoxy-4-quinolyl)oxy]-1-piperidyl]acetyl]pyrrolidine-2-carbonitrile
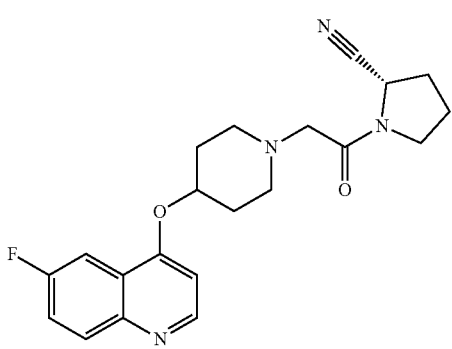 [SMILES: N#C[C@@H]1CCCN1C(=O)CN1CCC(Oc2ccnc3ccc(F)cc23)CC1]
(2S)-1-[2-[4-[(6-fluoro-4-quinolyl)oxy]-1-piperidyl]acetyl]pyrrolidine-2-carbonitrile
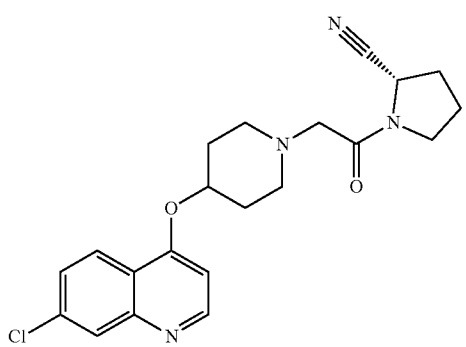 [SMILES: N#C[C@@H]1CCCN1C(=O)CN1CCC(Oc2ccnc3cc(Cl)ccc23)CC1]
(2S)-1-[2-[4-[(7-chloro-4-quinolyl)oxy]-1-piperidyl]acetyl]pyrrolidine-2-carbonitrile -continued
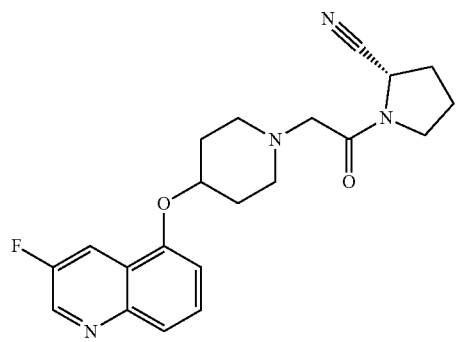 [SMILES: N#C[C@@H]1CCCN1C(=O)CN1CCC(Oc2cccc3ncc(F)cc23)CC1]
(2S)-1-[2-[4-[(3-fluoro-5-quinolyl)oxy]-1-piperidyl]acetyl]pyrrolidine-2-carbonitrile
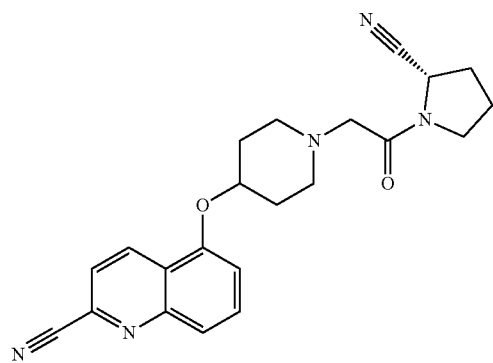 [SMILES: N#Cc1ccc2c(OC3CCN(CC(=O)N4CCC[C@H]4C#N)CC3)cccc2n1]
5-[[1-[2-oxo-2-[(2S)-2-cyanopyrrolidin-1-yl]ethyl]-4-piperidyl]oxy]quinoline-2-carbonitrile
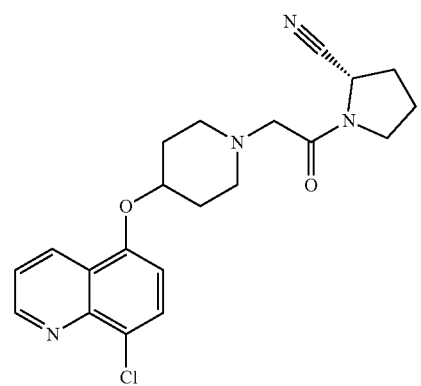 [SMILES: N#C[C@@H]1CCCN1C(=O)CN1CCC(Oc2ccc(Cl)c3ncccc23)CC1]
(2S)-1-[2-[4-[(8-chloro-5-quinolyl)oxy]-1-piperidyl]acetyl]pyrrolidine-2-carbonitrile
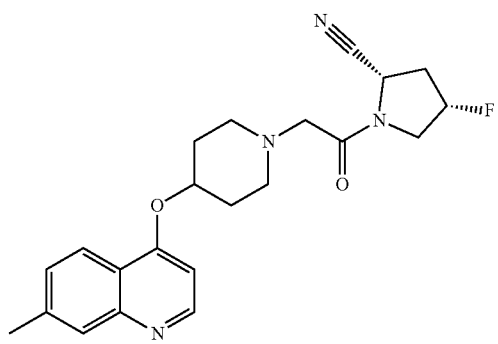 [SMILES: Cc1ccc2c(OC3CCN(CC(=O)N4C[C@@H](F)C[C@H]4C#N)CC3)ccnc2c1]
(2S,4S)-4-fluoro-1-[2-[4-[(7-methyl-4-quinolyl)oxy]-1-piperidyl]acetyl]pyrrolidine-2-carbonitrile -continued
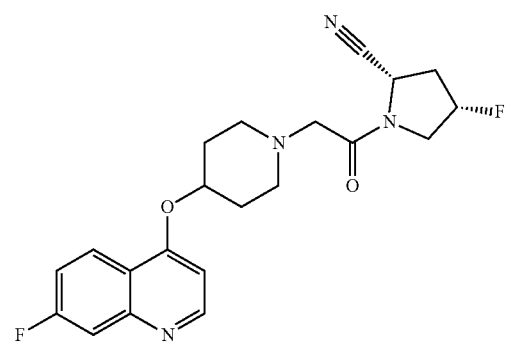 [SMILES: N#C[C@@H]1C[C@H](F)CN1C(=O)CN1CCC(Oc2ccnc3cc(F)ccc23)CC1]
(2S,4S)-4-fluoro-1-[2-[4-[(7-fluoro-4-quinolyl)oxy]-1-piperidyl]acetyl]pyrrolidine-2-carbonitrile
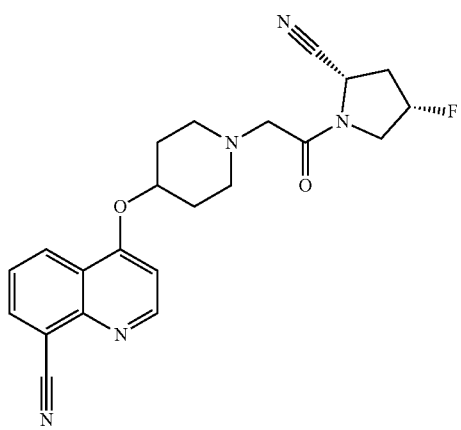 [SMILES: N#Cc1cccc2c(OC3CCN(CC(=O)N4C[C@@H](F)C[C@H]4C#N)CC3)ccnc12]
4-[[1-[2-oxo-2-[(2S,4S)-2-cyano-4-fluoropyrrolidin-1-yl]ethyl]-4-piperidyl]oxy]quinoline-8-carbonitrile
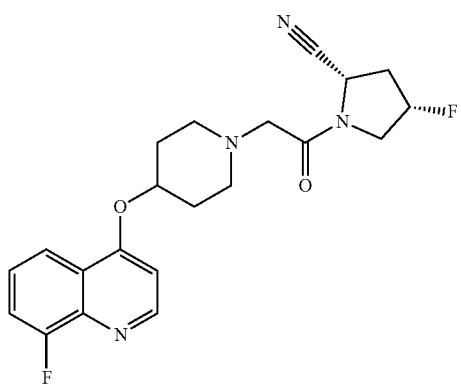 [SMILES: N#C[C@@H]1C[C@H](F)CN1C(=O)CN1CCC(Oc2ccnc3c(F)cccc23)CC1]
(2S,4S)-4-fluoro-1-[2-[4-[(8-fluoro-4-quinolyl)oxy]-1-piperidyl]acetyl]pyrrolidine-2-carbonitrile
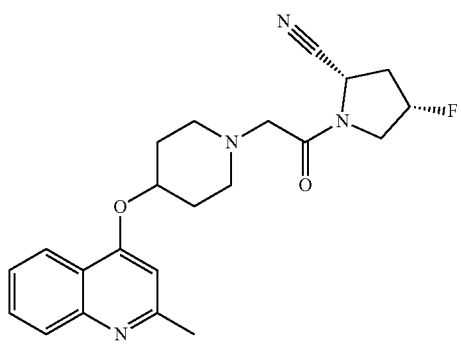 [SMILES: Cc1cc(OC2CCN(CC(=O)N3C[C@@H](F)C[C@H]3C#N)CC2)c2ccccc2n1]
(2S,4S)-4-fluoro-1-[2-[4-[(2-methyl-4-quinolyl)oxy]-1-piperidyl]acetyl]pyrrolidine-2-carbonitrile

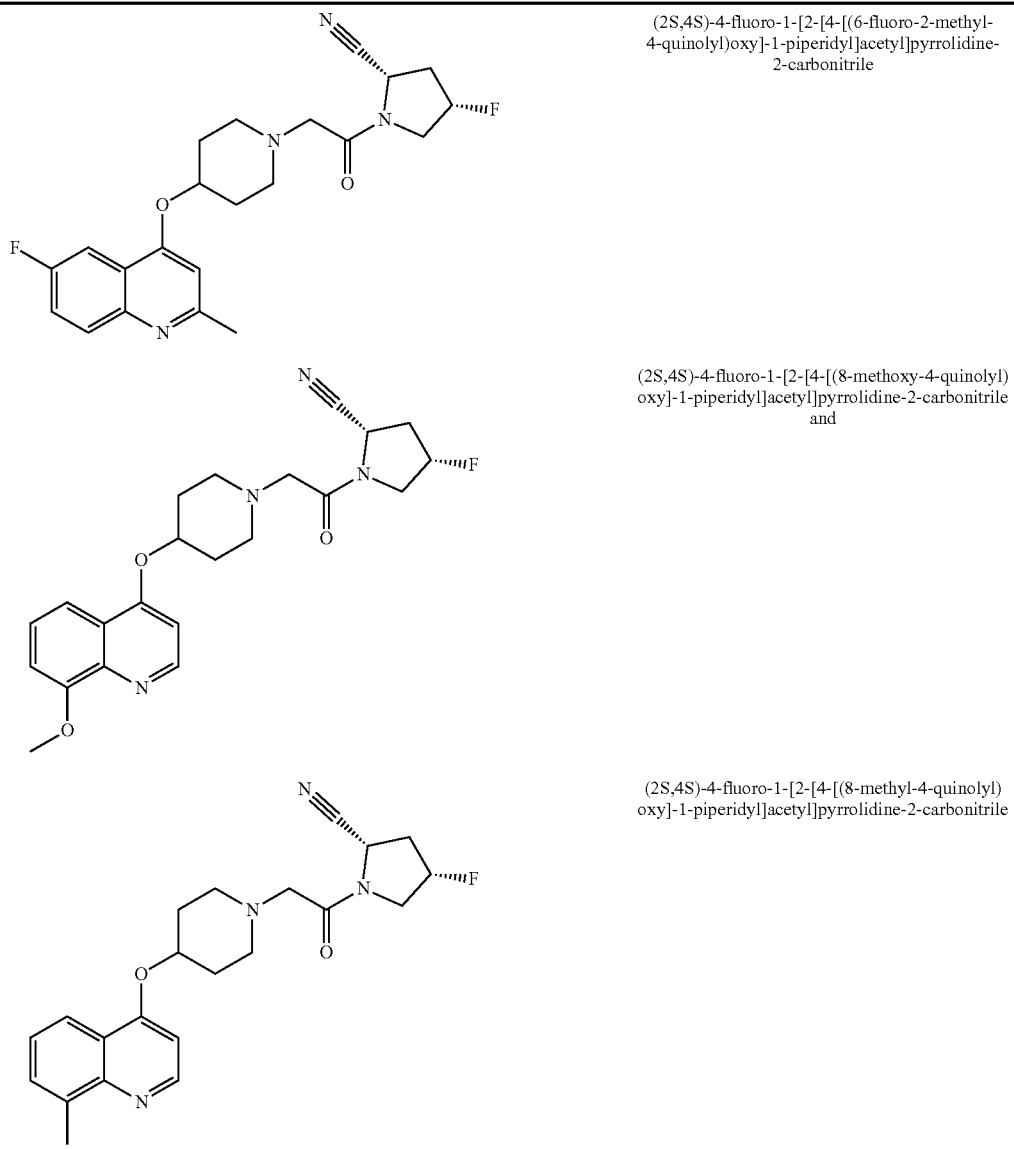

or a stereoisomer, a mixture of stereoisomers, or a pharmaceutically acceptable salt thereof.

22. A pharmaceutical composition comprising the compound according to claim 1, or a stereoisomer, a mixture of stereoisomers, or a pharmaceutically acceptable salt thereof, and at least one pharmaceutically acceptable excipient.

23. A method of inhibiting fibroblast activation protein in a mammal, comprising administering, to the mammal, a therapeutically effective amount of the compound according to claim 1, or a stereoisomer, a mixture of stereoisomers, or a pharmaceutically acceptable salt thereof.

24. A method of treating nonalcoholic hepatosteatosis (NASH) in a subject in need thereof, the method comprising administering to the subject a therapeutically effective amount of the compound according to claim 1, or a stereoisomer, a mixture of stereoisomers, or a pharmaceutically acceptable salt thereof.

25. A method of treating a disease mediated by fibroblast activation protein in a subject in need thereof, the method comprising administering to the subject a therapeutically effective amount of the compound according to claim 1, or a stereoisomer, a mixture of stereoisomers, or a pharmaceutically acceptable salt thereof.

26. The method according to claim 25, wherein the disease mediated by fibroblast activation protein is selected from the group consisting of a lipid disorder, lipoprotein disorder, condition, or disease which results from chronic fatty and fibrotic degeneration of organs due to accumulated lipid and triglyceride accumulation and subsequent activation of a profibrotic pathway, Type I Diabetes, Type II Diabetes, a clinical complication of Type I and Type II Diabetes, chronic intrahepatic cholestatic condition, extrahepatic cholestatic condition, liver fibrosis, acute intrahepatic cholestatic condition, obstructive or chronic inflammatory disorder that arises out of improper bile composition, gastrointestinal condition with a reduced uptake of dietary fat and fat-soluble dietary vitamin, inflammatory bowel disease, obesity, metabolic syndrome, combined conditions of dyslipidemia, diabetes, and abnormally high body-mass index, persistent infection by intracellular bacteria or parasitic protozoae, non-malignant hyperproliferative disorder, malignant hyperproliferative disorder, colon adenocarcinomas hepatocellular carcinoma, liver steatosis or an associated syndrome, Hepatitis B infection, Hepatitis C infection, cholestatic and fibrotic effects that are associated with alcohol-induced cirrhosis or with viral-borne forms of hepatitis, liver failure or liver malfunction as an outcome of chronic liver disease or of surgical liver resection, acute myocardial infarction, acute stroke, thrombosis which occurs as an endpoint of chronic obstructive atherosclerosis, osteoarthritis, rheumatoid arthritis, psoriasis, and cerebral infarction, or a combination thereof.

27. A method of treating cancer in a subject in need thereof, the method comprising administering to the subject a therapeutically effective amount of the compound according to claim 1, or a stereoisomer, a mixture of stereoisomers, or a pharmaceutically acceptable salt thereof.

28. A method of inhibiting degradation of fibroblast growth factor-21 in a subject, the method comprising administering to the subject, a therapeutically effective amount of the compound according to claim 1, or a stereoisomer, a mixture of stereoisomers, or a pharmaceutically acceptable salt thereof.

* * * * *

UNITED STATES PATENT AND TRADEMARK OFFICE
CERTIFICATE OF CORRECTION

PATENT NO. : 11,655,235 B2
APPLICATION NO. : 17/090552
DATED : May 23, 2023
INVENTOR(S) : Tae Han Dong et al.

Page 1 of 4

It is certified that error appears in the above-identified patent and that said Letters Patent is hereby corrected as shown below:

On the Title Page

In Item (72), please replace "Jun Chui Park, Yongin-si (KR);" with --Jun Chul Park, Yongin-si (KR)--.

In the Specification

In Table 1, Column 351, Ex no. 186, please replace

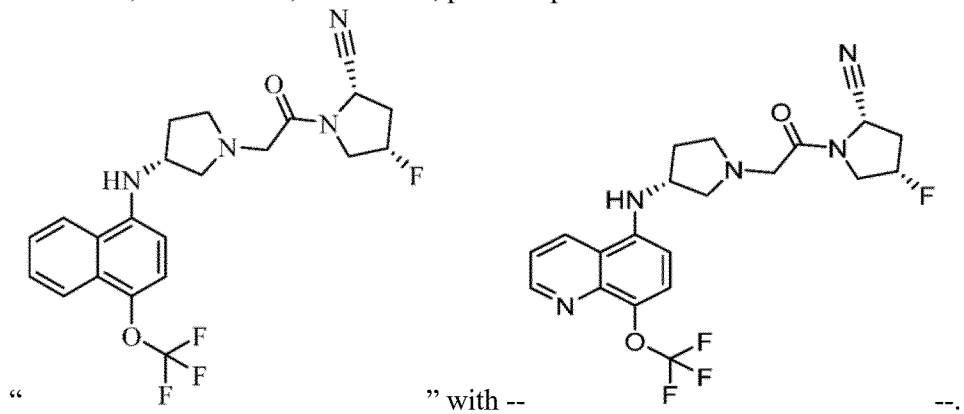

" with -- --.

In Table 1, Column 433, Ex no. 362, please replace

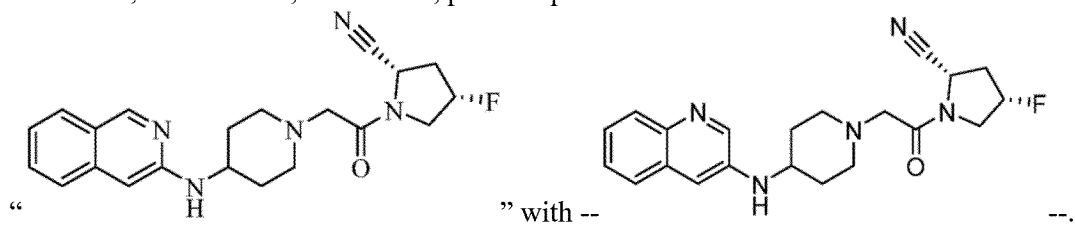

" with -- --.

Signed and Sealed this
Thirty-first Day of December, 2024

Derrick Brent
*Acting Director of the United States Patent and Trademark Office*

CERTIFICATE OF CORRECTION (continued)  
U.S. Pat. No. 11,655,235 B2

In Table 1, Column 439, Ex no. 375, please replace

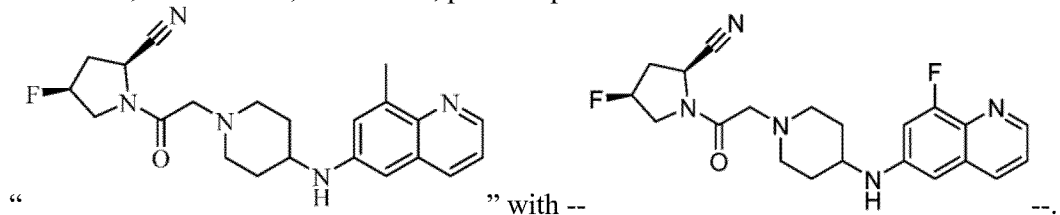

" " with -- --.

In the Claims

In Claim 2, Column 489, Lines 54 to 61, please replace

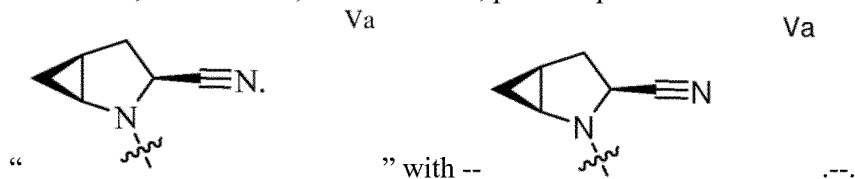

" " with -- --.

In Claim 3, Column 490, Lines 2 to 9, please replace (Formula 1a)

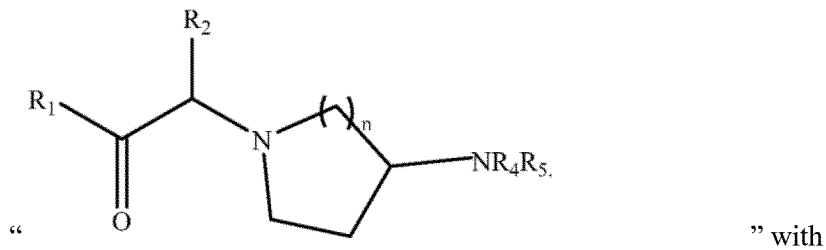

" " with (Formula 1a)

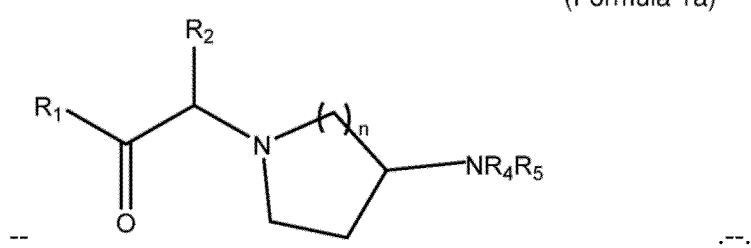

-- --.

In Claim 6, Column 490, Lines 21 to 29, please replace (Formula 1b)

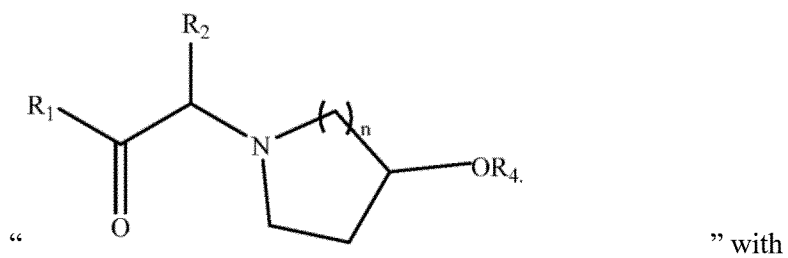

" " with

CERTIFICATE OF CORRECTION (continued)
U.S. Pat. No. 11,655,235 B2

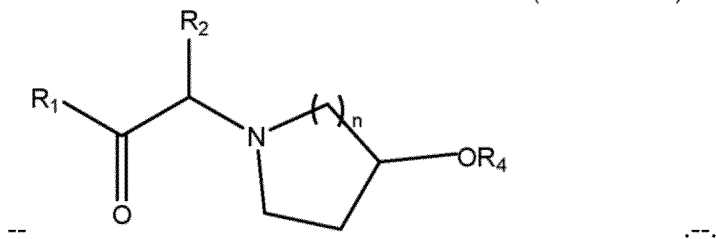

(Formula 1b)

-- .--.

In Claim 7, Column 490, Lines 34 to 42, please replace

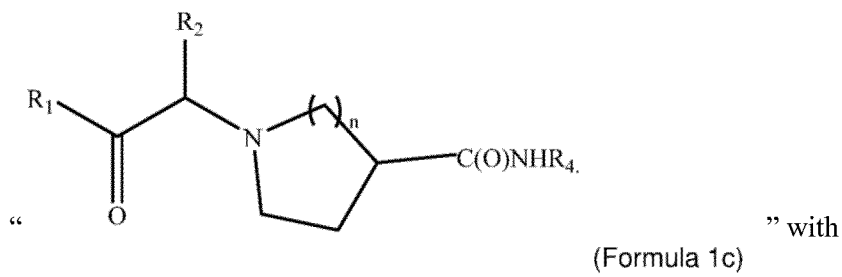

(Formula 1c)

" with

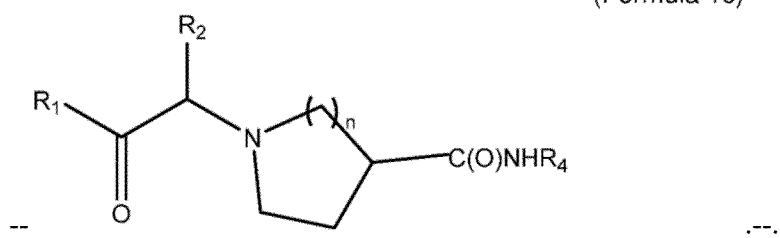

(Formula 1c)

-- .--.

In Claim 8, Column 490, Lines 46 to 55, please replace

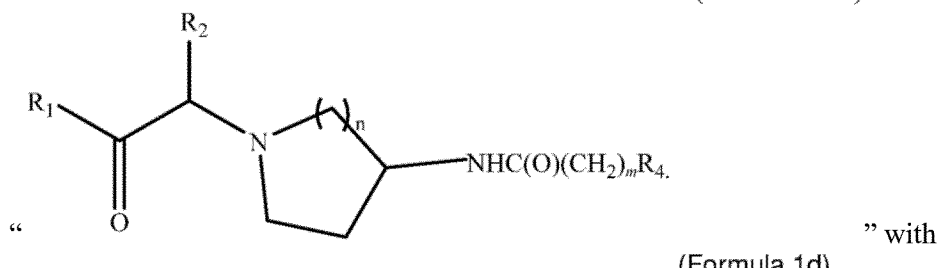

(Formula 1d)

" with

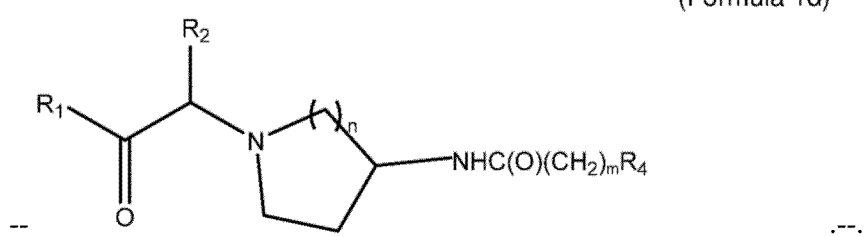

(Formula 1d)

-- .--.

In Claim 11, Column 491, Lines 2 to 8, please replace

CERTIFICATE OF CORRECTION (continued)
U.S. Pat. No. 11,655,235 B2

(Formula 1e)

" 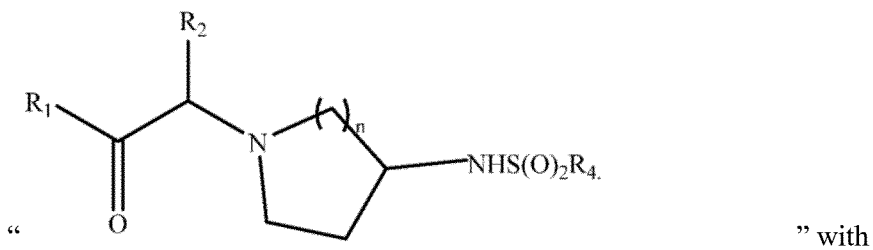 " with (Formula 1e)

-- 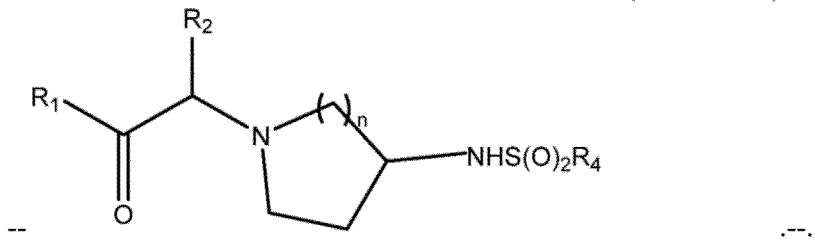 --.

In Claim 21, Column 639, the third row, counting from the top, please replace

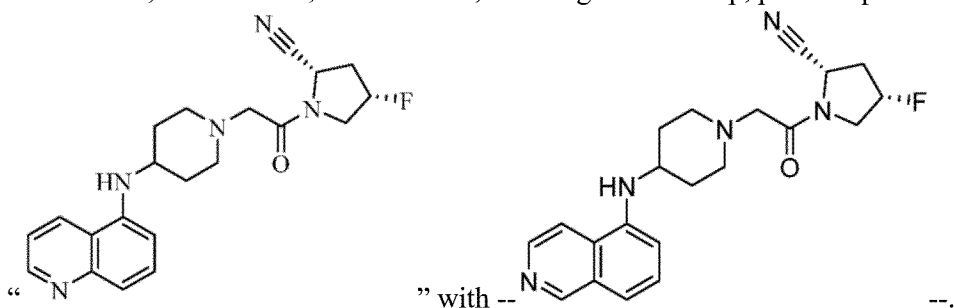

" " with -- --.

In Claim 26, Column 689, Lines 4 to 5, please replace "adenocarcino-mas heptatocellular" with --adenocarcinoma, hepatocellular--.